US012622972B2

(12) United States Patent
Saulnier et al.

(10) Patent No.: US 12,622,972 B2
(45) Date of Patent: *May 12, 2026

(54) ASGPR-BINDING COMPOUNDS FOR THE DEGRADATION OF EXTRACELLULAR PROTEINS

(71) Applicant: AVILAR THERAPEUTICS, INC., Waltham, MA (US)

(72) Inventors: Mark George Saulnier, Higganum, CT (US); Jesse Jingyang Chen, Lexington, MA (US); Srinivasa Karra, Pembroke, MA (US); Kevin Tyler Sprott, Needham, MA (US); Jason Allan Wiles, Madison, CT (US); Soumya Ray, Quincy, MA (US)

(73) Assignee: AVILAR THERAPEUTICS, INC., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/081,876

(22) Filed: Mar. 17, 2025

(65) Prior Publication Data

US 2025/0213699 A1 Jul. 3, 2025

Related U.S. Application Data

(63) Continuation of application No. 18/653,655, filed on May 2, 2024, now Pat. No. 12,280,116, which is a continuation of application No. 18/220,708, filed on Jul. 11, 2023, now Pat. No. 12,076,408, which is a continuation of application No. 17/877,538, filed on Jul. 29, 2022, now Pat. No. 11,819,551, which is a continuation of application No. PCT/US2021/015939, filed on Jan. 29, 2021.

(60) Provisional application No. 63/063,015, filed on Aug. 7, 2020, provisional application No. 62/968,802, filed on Jan. 31, 2020.

(51) Int. Cl.

| | |
|---|---|
| ***A61K 47/54*** | (2017.01) |
| ***A61K 47/62*** | (2017.01) |
| ***C07H 5/06*** | (2006.01) |
| ***C07H 7/02*** | (2006.01) |
| ***C07H 9/02*** | (2006.01) |
| ***C07H 9/04*** | (2006.01) |
| ***C07H 15/203*** | (2006.01) |
| ***C07H 17/00*** | (2006.01) |
| ***C07H 17/02*** | (2006.01) |
| ***C07H 19/02*** | (2006.01) |
| ***C07H 19/044*** | (2006.01) |
| ***H03L 7/081*** | (2006.01) |
| ***H03L 7/099*** | (2006.01) |

(52) U.S. Cl.

CPC ............ *A61K 47/549* (2017.08); *A61K 47/62* (2017.08); *C07H 5/06* (2013.01); *C07H 7/02* (2013.01); *C07H 9/02* (2013.01); *C07H 9/04* (2013.01); *C07H 15/203* (2013.01); *C07H 17/00* (2013.01); *C07H 17/02* (2013.01); *C07H 19/02* (2013.01); *C07H 19/044* (2013.01); *H03L 7/0814* (2013.01); *H03L 7/0818* (2013.01); *H03L 7/0998* (2013.01)

(58) Field of Classification Search

None

See application file for complete search history.

(56) References Cited

U.S. PATENT DOCUMENTS

| | | | | |
|---|---|---|---|---|
| 4,344,894 | A | 8/1982 | Laidler et al. | |
| 5,047,518 | A | 9/1991 | Furneaux et al. | |
| 5,554,386 | A | 9/1996 | Groman et al. | |
| 5,571,796 | A | 11/1996 | Srivastava | |
| 5,624,896 | A | 4/1997 | Axworthy et al. | |
| 5,958,408 | A | 9/1999 | Griffiths et al. | |
| 5,985,826 | A | 11/1999 | Theodore et al. | |
| 6,172,045 | B1 | 1/2001 | Theodore et al. | |
| 6,294,521 | B1 | 9/2001 | Cowden | |
| 7,737,287 | B2 | 6/2010 | Meutermans et al. | |
| 7,989,422 | B2 | 8/2011 | Meutermans et al. | |
| 9,340,553 | B2 | 5/2016 | Liras et al. | |
| 9,617,293 | B2 | 4/2017 | Liras et al. | |
| 10,039,778 | B2 | 8/2018 | Liras et al. | |
| 10,376,531 | B2 | 8/2019 | Liras et al. | |
| 10,813,942 | B2 | 10/2020 | Liras et al. | |
| 10,821,157 | B2 | 11/2020 | Hubbell et al. | |
| 11,819,551 | B2 * | 11/2023 | Saulnier | C07K 14/495 |
| 2009/0317381 | A1 | 12/2009 | Plaut et al. | |

(Continued)

FOREIGN PATENT DOCUMENTS

| | | | |
|---|---|---|---|
| EP | 2191849 | A1 | 6/2010 |
| WO | WO 89/10140 | A1 | 11/1989 |

(Continued)

OTHER PUBLICATIONS

Baenziger, J. U. "Galactose and N-Acetylgalactosamine-Specific Endocytosis of Glycopeptides by Isolated Rat Hepatocytes" Cell, 22, 611-620, Nov. 1980.

(Continued)

*Primary Examiner* — Jeffrey S Lundgren

*Assistant Examiner* — Michael J Schmitt

(74) *Attorney, Agent, or Firm* — Knowles Intellectual Property Strategies, LLC

(57) ABSTRACT

Compounds and compositions that have an asialoglycoprotein receptor (ASGPR) binding ligand bound to an extracellular protein binding ligand for the selective degradation of the target extracellular protein in vivo to treat disorders mediated by the extracellular protein are described.

30 Claims, 138 Drawing Sheets

Specification includes a Sequence Listing.

(56) References Cited

U.S. PATENT DOCUMENTS

| | | | |
|---|---|---|---|
| 2015/0299313 | A1 | 10/2015 | Igawa et al. |
| 2016/0058872 | A1 | 3/2016 | Crew et al. |
| 2016/0082112 | A1 | 3/2016 | Spiegel et al. |
| 2016/0136299 | A1 | 5/2016 | Avila et al. |
| 2017/0137801 | A1 | 5/2017 | Liras et al. |
| 2019/0321382 | A1 | 10/2019 | Liras et al. |
| 2023/0083388 | A1 | 3/2023 | Spiegel et al. |
| 2023/0087994 | A1 | 3/2023 | Spiegel et al. |
| 2023/0090282 | A1 | 3/2023 | Spiegel et al. |
| 2023/0097887 | A1 | 3/2023 | Spiegel et al. |
| 2023/0233689 | A1 | 7/2023 | Spiegel et al. |
| 2023/0346951 | A1 | 11/2023 | Caianiello et al. |
| 2023/0416377 | A1 | 12/2023 | Bertozzi et al. |
| 2024/0050578 | A1 | 2/2024 | Spiegel et al. |
| 2024/0083859 | A1 | 3/2024 | Spiegel et al. |

FOREIGN PATENT DOCUMENTS

| | | | |
|---|---|---|---|
| WO | WO 1993/25240 | A2 | 12/1993 |
| WO | WO 2002/032915 | A1 | 4/2002 |
| WO | WO 2003/082846 | A1 | 10/2003 |
| WO | WO 2007/070947 | A1 | 6/2007 |
| WO | WO 2011/036457 | A1 | 3/2011 |
| WO | WO 2014/025805 | A1 | 2/2014 |
| WO | WO 2015/140648 | A2 | 9/2015 |
| WO | WO 2015/143091 | A2 | 9/2015 |
| WO | WO 2015/160845 | A1 | 10/2015 |
| WO | WO 2015/177668 | A1 | 11/2015 |
| WO | WO 2015/179693 | A1 | 11/2015 |
| WO | WO-2015/197652 | A1 | 12/2015 |
| WO | WO 2016/057769 | A2 | 4/2016 |
| WO | WO 2017/083368 | A1 | 5/2017 |
| WO | WO 2017/212019 | A1 | 12/2017 |
| WO | WO 2018/146199 | A1 | 8/2018 |
| WO | WO 2018/223056 | A1 | 12/2018 |
| WO | WO 2018/223073 | A1 | 12/2018 |
| WO | WO 2018/223081 | A1 | 12/2018 |
| WO | WO 2019/075357 | A1 | 4/2019 |
| WO | WO 2019/199621 | A1 | 10/2019 |
| WO | WO 2019/199634 | A1 | 10/2019 |
| WO | WO 2020/132100 | A1 | 6/2020 |
| WO | WO 2021/072269 | A1 | 4/2021 |
| WO | WO 2021/142377 | A2 | 7/2021 |
| WO | WO 2021/156792 | A1 | 8/2021 |
| WO | WO 2021/219077 | A1 | 11/2021 |
| WO | WO 2021/234459 | A2 | 11/2021 |
| WO | WO 2021/263060 | A1 | 12/2021 |
| WO | WO 2021/263061 | A2 | 12/2021 |
| WO | WO 2022/084331 | A2 | 4/2022 |
| WO | WO 2023/288033 | A1 | 1/2023 |

OTHER PUBLICATIONS

Bagshawe, K.D. et al. "Antibody directed enzyme prodrug therapy (ADEPT)" Annals of Oncology 5: 879-891, Dec. 1994.
Banik, Steven M. et al. "Lysosome-targeting chimaeras for degradation of extracellular proteins" Nature 584, 291-297, Jul. 29, 2020.
Banik, Steven M. et al. "Lysosome targeting chimaeras (LYTACs) for degradation of secreted and membrane proteins" Chemrxiv, Mar. 29, 2019.
Baynes, John W. et al. "Effect of glycosylation on the in vivo circulating half-life of ribonuclease" The Journal of Biological Chemistry, vol. 251, No. 19, pp. 6016-6024, Issue of Oct. 10, 1976.
Bergeron, J. J. M. et al. "Subcellular Biochemistry, vol. 19, Endocytic Components: Identification and Characterization" ISBN 978-1-4615-3026-8, Springer Science, 1993.
Bernini, Franco et al. "Lactosaminated fab fragments specific for low density lipoproteins/hepatocyte targeting and hypolipoproteinemic activity" Arteriosclerosis, vol. 8, No. 6, Nov./Dec. 1988.
Bernini, Franco et al. "Enhanced catabolismof low density lipoproteins in rat by lactosaminated fab fragment" The Journal of Biological Chemistry, vol. 261, No. 20, pp. 9294-9299, Issue of Jul. 15, 1986.
Bider, M.D. et al. "Ligand-induced endocytosis of the asialoglycoprotein receptor: evidence for heterogeneity in subunit oligomerization" FEBS Letters, 434, 37-41, 1998.
Biessen, Erick A.L. et al. "The cholesterol derivative of a triantennary galactoside with high affinity for the hepatic asialoglycoprotein receptor: a potent cholesterol lowering agent" J Med. Chem., 38, 1846-1852, 1995.
Biessen, Erick A.L. et al. "Induction of hepatic uptake of lipoprotein(a) by cholesterol-derivatized cluster galactosides" Arterioscler Thromb Vasc Biol., vol. 16, No. 12, 1552-1558, Dec. 1996.
Biessen, Erick A.L. et al. "Cholesterol derivative of a new triantennary cluster galactoside directs low- and high-density lipoproteins to the parenchymal liver cell" Biochem. J. 302, 283-289, 1994.
Biessen, Erick A.L. et al. "Synthesis of cluster galactoside with high affinity for the hepatic asialoglycoprotein receptor" J. Med. Chem., 38, 1538-1546, 1995.
Bijsterbosch, Martin K. et al. "Enhanced Hepatic Update and Processing of Cholesterol Esters From Low Density Lipoprotein by Specific Lactosaminated Fab Fragments, Ateriosclerosis and Thrombosis" vol. 11, No. 6, 1806-1813, Nov./Dec. 1991.
Blakey, D.C. "Antibody-directed enzyme prodrug therapy (ADEPT) for treatment of major solid tumor disease" Biochemical Society Transactions Therapeutic Monoclonals, vol. 23, 1047-1050, Nov. 1, 1995.
Bon, Charlotte et al. "Capacity limits of asialoglycoprotein receptor-mediated liver targeting" vol. 9, No. 8, 1360-1369, Nov. 23, 2017.
Brown, William R. et al. "The liver and IgA: Immunological, cell biological and clinical implications" Hepatology, vol. 9, No. 5, pp. 763-784, 1989.
Buckley, Dennis L. et al. "Targeting the von Hippel-Lindau E3 Ubiquitin Ligase Using Small Molecules to Disrupt the VHL/HIF-1α Interaction"; J. Am. Chem. Soc. 134, 4465-4468; Feb. 27, 2012.
Connolly, Daniel T. et al. "Binding and endocytosis of cluster glycosides by rabbit hepatocytes; Evidence for short-circuit pathway that does not lead to degradation" The Journal of Biological Chemistry, vol. 257, No. 2, pp. 939-945, Issue of Jan. 25, 1982.
D'Souza, Anisha A. et al. "Asialogycoprotein receptor mediated hepatocyte targeting—strategies and applications" Journal of Controlled Release, 203, 126-139, Feb. 18, 2015.
Dalpiaz, A. et al. "Molecular mechanism involved in the transport of a prodrug dopamine gycosyl conjugate, International Journal of Pharmaceutics" 336; 133-139; May 4, 2007.
Dancygier, Henryk et al. Clinical Hepatology, Chapter 6 "Hepatic Metabolism" Springer Berlin, Heidelberg, pp. 75-102, Oct. 27, 2009.
Day, James F. et al. "Carbohydrate-mediated clearance of antibody—antigen complexes from the circulation" The Journal of Biological Chemistry, vol. 255, No. 6, pp. 2360-2368, Issue of Mar. 25, 1980.
Eldeeb, Mohamed A. et al. "Extracellular protein degradation via the lysosome" Communications Chemistry, 3:149, Oct. 30, 2020.
Goetze, et al. "High-mannose glycans on the Fc region of therapeutic lgG antibodies increase serum clearance in humans" Glycobiology 21.7, 949-959, 2011.
Gregoriadis, G. et al. "Catabolismof Desialylated Ceruloplasmin in the Liver" J. Biol. Chem. 245(21), 5833-5837, Nov. 10, 1970.
Harford, J. et al. "Intracellular Dissociation of Receptor-Bound Asialoglycoproteins in Cultured Hepatocytes" J. Biol. Chem. 258(5) 3191-3197, Mar. 10, 1983.
Huang, Xiangang et al. "Well-Defined Multivalent Ligands for Hepatocytes Targeting via Asialoglycoprotein Receptor" Bioconjugate Chem. 2017, 28, 283-295, Dec. 14, 2016.
International Search Report and Written Opinion for PCT/US2021/015939, 11 pages, dated Jun. 4, 2021.
Inamoto, Takashi et al. "IgG is associated with the asialoglycoprotein receptor in the human liver" Hepatology vol. 14(6), 1070-1075, Dec. 1991.
Iobst, Susanne et al. "Selective sugar binding to the carbohydrate recognition domains of the rat hepatic and macrophage asialoglycoprotein receptors" The Journal of Biological Chemistry, vol. 271, No. 12, pp. 6686-6693, Issue of Mar. 22, 1996.
Janas, Maja M. et al. "The nonclinical safety profile of GalNAc-conjugated RNAi therapeutics in subacute studies: Toxicologic Pathology" vol. 46(7) 735-745, Aug. 23, 2018.

(56) References Cited

OTHER PUBLICATIONS

Kempen, Herman J. et al. "Effect of infusion of "tris-galactosyl-cholesterol" on plasma cholesterol, clearance of lipoprotein cholesteryl esters, and biliary secretion in the rat" Journal of Lipid Research, vol. 28, 659-666, 1987.
Kempen, Herman J. et al. "A Water-soluble cholesteryl-containing trisgalactoside: synthesis, properties, and use in directing lipid-containing particles to the liver" J. Med. Chem. 27, 1306-1312, 1984.
Kolset, S.O. et al. "The Effects of Colchicine and Cytochalasin B on Uptake and Degradation of Asialo-Glycoproteins in Isolated Rat Hepatocytes" Exp Cell Res, 159-167, 1979.
Kudo, Masatoshi et al. "Quantitative assessment of hepatocellular function through in vivo radiorespector imaging with technetium 99m galactosyl human serum albumin" Hepatology vol. 17, No. 5, 814-819, May 17, 1993.
Li, Yan et al. "Targeted delivery of macromolecular drugs: Asialoglycoprotein Receptor (ASGPR) Expression by Selected Hepatoma Cell Lines used in Antiviral Drug Development" Current Drug Delivery, 5, 299-302, Sep. 30, 2008.
Lu, Jing et al. "Hijacking the E3 Ubiquitin Ligase Cereblon to Efficiently Target BRD4" Chem. Biol. 22(6): 755-763; Jun. 18, 2015.
Mamidyala, Sreeman K. et al. "Glycomimetric ligands for the human asialoglycoprotein receptor" Journal of the American Chemical Society, 134, 1978-1981, Jan. 24, 2012.
Meir, Markus et al. "Crystal Structure of the Carbohydrate Recognition Domain of the H1 Subunit of the Asialoglycoprotein Receptor" J. Mol. Biol., 300, 857-865, Jul. 21, 2000.
Miki, Kenji et al. "Receptor measurements via Tc-GSA Kinetic Modeling are Proportional to Functional Hepatocellular Mass" J Nucl Med 2001; 42:733-737; Japan, Jan. 10, 2001.
Morell, Anatol G. et al. "The Role of Sialic Acid in Determining the Survival of Glycoproteins in the Circulation" The Journal of Biological Chemistry, vol. 246, No. 5, pp. 1461-1467, Issue of Mar. 10, 1971.
Nalawansha, Dhanusha et al. "Targeted protein internalization and degradation by ENDosome TArgeting Chimeras (ENDTACs)" ACS Central Science 5, 1079-1084, May 9, 2019.
Nandakumar, Kutty Selva et al. "Therapeutic cleavage of IgG: new avenues for treating inflammation" Cell Press, 173, Trends in Immunology vol. 29 No. 4, 2008.
Nandakumar, Kutty Selva "Targeting IgG in arthritis: Disease pathways and therapeutic avenues" International Journal of Molecular Sciences, 19, 677, 2018.
Napier, M.P. et al. "Antibody-directed enzyme prodrug therapy: efficacy and mechanism of action in colorectal carcinoma" Clinical Cancer Research vol. 6, 765-772, Mar. 2000.
Nioi, P. et al. "Variant ASGR1 Associated with a Reduced Risk of Coronary Artery Disease" The New England Journal of Medicine, 374:2131-41, May 18, 2016.
Oka, J. A. et al. "Microtubule-Depolymerizing Agents Inhibit Asialo-Orosomucoid Delivery to Lysosomes but Not Its Endocytosis or Degradation in Isolated Rat Hepatocytes" Biochim Biophys Acta 763, 368-378, Dec. 19, 1983.
Ong, Gaik Lin et al. "Galactose-conjugated antibodies in cancer therapy: properties and principles of action" Cancer Research, 51:1619-1626. Published online Mar. 1, 1991.
Park, Jung-Hyun et al. "Detection of surface asialoglycoprotein receptor expression in hepatic and extra-hepatic cells using a novel monoclonal antibody" Biotechnol Lett 28:1061-1069, Jun. 24, 2006.
Petrov, Rostislav A. et al. "Synthesis and biological evaluation of novel mono- and bivalent ASGP-R-targeted drug-conjugates" Bioorganic and Medicinal Chemistry Letters 28, 382-387, Dec. 14, 2017.
Pimstone, Neville R. et al. "Evaluation of Hepatocellular Function by Way of Receptor-mediated Uptake of a Technetium-99m-labeled Asialoglycoprotein Analog" Symposium on Bile Acids. Hepatology, 917-923, Oct. 1994.
PrabhuDas, Mercy R. et al. "A Consensus Definitive Classification of Scavenger Receptors and Their Roles in Health and Disease" The Journal of Immunology 198(10) 3775-3789, May 15, 2017.
Pubchem CID 28862057 Create Date: Dec. 5, 2007; Date Accessed May 20, 2021.
Rensen, Patrick C.N. et al. "Determination of the upper size limit for uptake and processing of ligands by the asialoglycoprotein receptor on hepatocytes in vitro and in vivo" The Journal of Biological Chemistry, vol. 276, No. 40, pp. 37577-37584, Issue of Oct. 5, 2001.
Rensen, Patrick C.N. et al. "Design and Synthesis of Novel N-Acetylgalactosamine-Terminated Glycolipids for Targeting of Lipoproteins to the Hepatic Asialoglycoprotein Receptor" J. Med. Chem., 47, 5798-5808, Oct. 6, 2004.
Rensen, Patrick C.N. "Stimulation of liver-directed cholesterol flux in mice by novel N-acetylgalactosamine-Terminated Glycolipds with high affinity for the asialoglycoprotein receptor" Arterioscler Thromb Vasc Biol., 26, 169-175, Jan. 2006.
Roelen, Harlof C.P.F. et al. "Water-soluble cholesteryl-containing phosphorothioate monogalactosides: synthesis, properties, and use in lowering blood cholesterol by directing plasma lipoproteins to the liver" J. Med. Chem. 34, 1036-1042, 1991.
Rogers, G.T. et al. "Plasma clearance of an antibody—enzyme conjugate in ADEPT by monoclonal anti-enzyme: its effect on prodrug activation in vivo" British Journal of Cancer 72, 1357-1363, Dec. 1, 1995.
Rogers, John C. et al. "Hepatic uptake of proteins coupled to fetuin glycopeptide" Biochemical and biophysical research communications, vol. 45, No. 3, 1971.
Roggenbuck, Dirk et al. "Asialoglycoprotein receptor (ASGPR): a peculiar target of liver-specific autoimmunity" Autoimmun Highlights 3:119-125, Oct. 30, 2012.
Roy, Marc et al. "Characterization of Asialoglycoprotein Receptor (ASGPR) directed hepatocellular delivery using a Pfizer developed targeting ligand PF-06853291" The FASEB Journal, 31: 938. 7-938. 7, Oct. 3, 2018.
Sanhueza, Carlos A. et al. "Efficient Liver Targeting by Polyvalent Display of a Compact Ligand for the Asialoglycoprotein Receptor" JACS, 2017, 139, 3528, Feb. 23, 2017.
Schmidt, Karsten et al. "Characterizing the effect of GalNAc and phosphorothioate backbone on binding of antisense obligonucleotides to the asalogycoprotein receptor" Nucleic Acids Research, vol. 45(5) 2294-2306, Feb. 3, 2017.
Seymour, Leonard W. et al. "Hepatic drug targeting: phase I evaluation of polymer-bound doxorubicin" J. Clin. Oncol. 20(6): 1668-76; Mar. 15, 2002.
Sharma, Surinder K. "Galactosylated Antibodies and Antibody-enzyme conjugates in antibody-directed enzyme prodrug therapy" Cancer Supplemental vol. 73, No. 3, 1114-1120, Feb. 1, 1994.
Sliedregt, Leo A. J. et al. "Design and synthesis of novel amphiphilic dendritic galactosides for selective targeting of liposomes to the hepatic asialoglycoprotein receptor" J. Med. Chem., 42, 609-618, Feb. 5, 1999.
Sockolosky, Jonathan T. et al. "Fusion of a short peptide that binds immunoglobulin G to a recombinant protein substantially increases its plasma half-life in mice" PLos One, 1-16, Jul. 24, 2014.
Spiess, M. "The Asialoglycoprotein Receptor: A Model for Endocytic Transport Receptors" Biochemistry, 29(43), 10009-10018, Oct. 30, 1990.
Springer, Aaron D. et al. "GalNAc-siRNA Conjugates: Leading the Way for Delivery of RNAi Therapeutics" Nucleic Acid Therapeutics vol. 28(3) 109-118, May 24, 2018.
Stockert, Richard J. et al. "Hepatic binding protein: The protective role of its sialic acid residues" Science, vol. 197, 667-668, Aug. 12, 1977.
Stokmaier, Daniela, et al. "Design, synthesis and evaluation of monovalent ligands for the asialoglycoprotein receptor (ASGP-R)" Bioorganic & Medicinal Chemistry, 7254-7264, 17, vol. 17920), Aug. 29, 2009.
Thornburg, Robert W. et al. "Carbohydrate-mediated clearance of immune complexes from the circulation" The Journal of Biological Chemistry vol. 255, No. 14, pp. 6820-6825, Issue of Jul. 25, 1980.

(56) References Cited

OTHER PUBLICATIONS

Tolleshaug, H. et al. "Uptake and Degradation of 125-I Labeled Asialo-Fetuin by Isolated Rat Hepatocytes" Biochim. Biophys. Acta, 499, 73-84, Aug. 25, 1977.
Toure et al. "Small-Molecule Protacs: New Approaches to Protein Degradation" Angew. Chem. Int. Ed. 2016, 55(6), 2-10, Jan. 12, 2016.
Van Berkel, Theo J.C. et al. "The effect of a water-soluble tris tris-galactoside-terminated cholesterol derivative on the fate of low-density lipoproteins and liposomes" The Journal of Biological Chemistry, vol. 260, No. 5, pp. 2694-2699, Issue of Mar. 10, 1985.
Winter et al. "Drug Development. Phthalimide Conjugation as a Strategy for in Vivo Targeted Protein Degradation" Science, 348, issue 6241, 1376-1381, May 21, 2015.
Weigel, P. H. "Rat Hepatocytes Bind to Syawnthetic Galactoside Surfaces Via a Patch of Asialoglycoprotein Receptors" J. Cell Biol. 87(3), 855-861, Dec. 1, 1980.
Wong, Ting Chi et al. "Synthesis of D-Galactosamine derivatives and binding studies using isolated rat hepatocytes" Carbohydrate Research, 170, 27-46, 1987.
Yoo, Barney, et al. "N-Acetylgalactosamino dendrons as clearing agents to enhance liver targeting of model antibody-fusion protein" Bioconjugate Chemistry, 24, 2088-2103, 2013.
U.S. Pat. No. 11/819,551, B2, U.S. Appl. No. 17/877,538, Saulnier et al., Nov. 21, 2023.
U.S. Pat. No. 12,076,408, B2, U.S. Appl. No. 18/220,708, Saulnier et al., Sep. 3, 2024.
U.S. Pat. No. 12,091,402, B2, U.S. Appl. No. 18/220,737, Wiles et al., Sep. 17, 2024.
U.S. Pat. No. 12,128,106, B2, U.S. Appl. No. 18/584,914, Saulnier et al., Oct. 29, 2024.
2024/0279209, A1, U.S. Appl. No. 18/590,713, Wiles et al., Aug. 22, 2024.
2024/0424108, A1, U.S. Appl. No. 18/653,610, Saulnier et al., Dec. 26, 2024.
U.S. Pat. No. 12,280,116-B2, Apr. 22, 2025, Saulnier et al., U.S. Appl. No. 18/653,655.
U.S. Pat. No. 12,290,568-B2, May 6, 2025, Saulnier et al., U.S. Appl. No. 18/653,610.
U.S. Pat. No. 12,312,340-B2, May 27, 2025, Wiles et al., U.S. Appl. No. 18/590,713.
US-2024/0239828-A1, Jul. 18, 2024, Wiles et al., U.S. Appl. No. 18/586,086.
US-2025/0223280-A1, Jul. 10, 2025, Wiles et al., U.S. Appl. No. 19/081,912.
US-2025/0339541-A1, Nov. 6, 2025, Saulnier et al., U.S. Appl. No. 19/192,108.
U.S. Appl. No. 19/179,878, Wiles et al., filed Apr. 15, 2025.

* cited by examiner

4PEGhexynamide

4PEGAmine

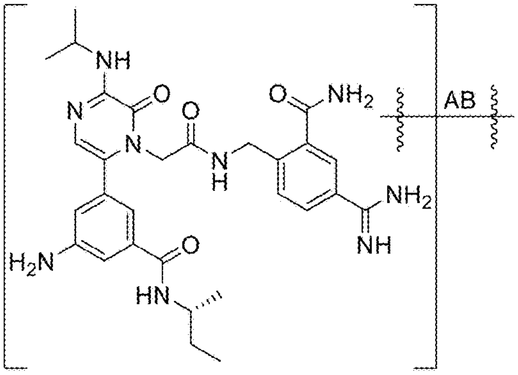
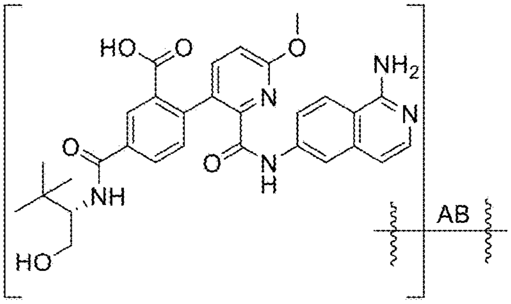
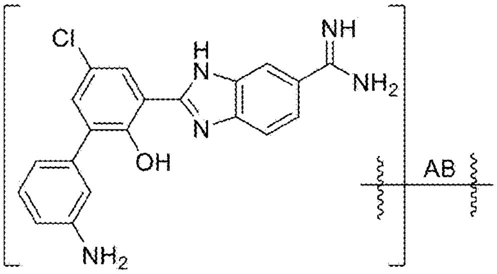
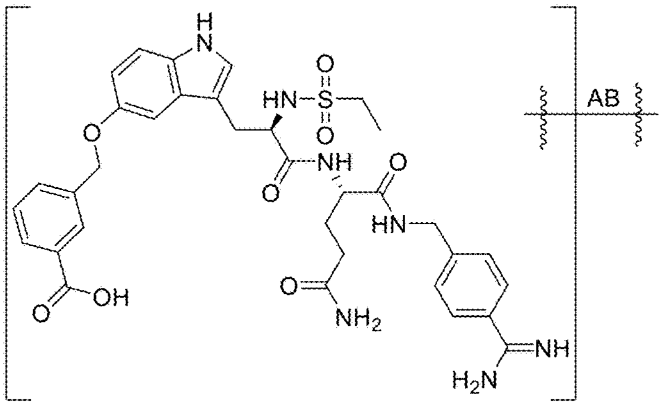
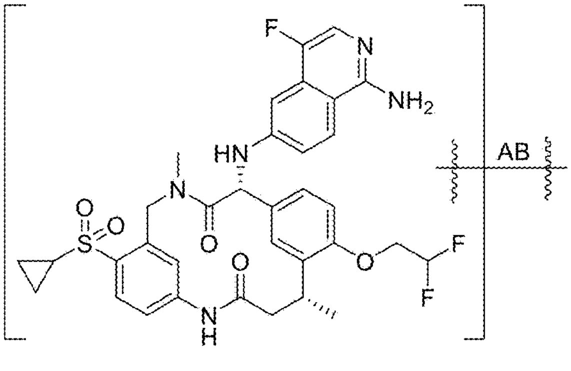
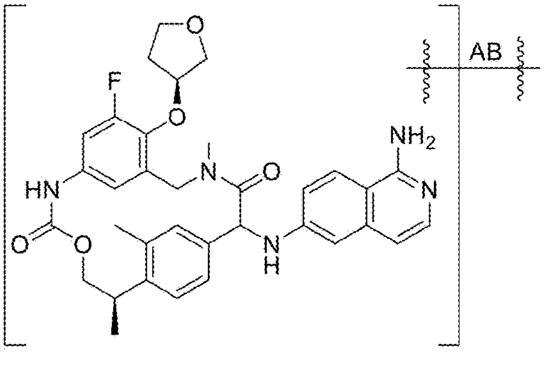
FIG. 1AAA

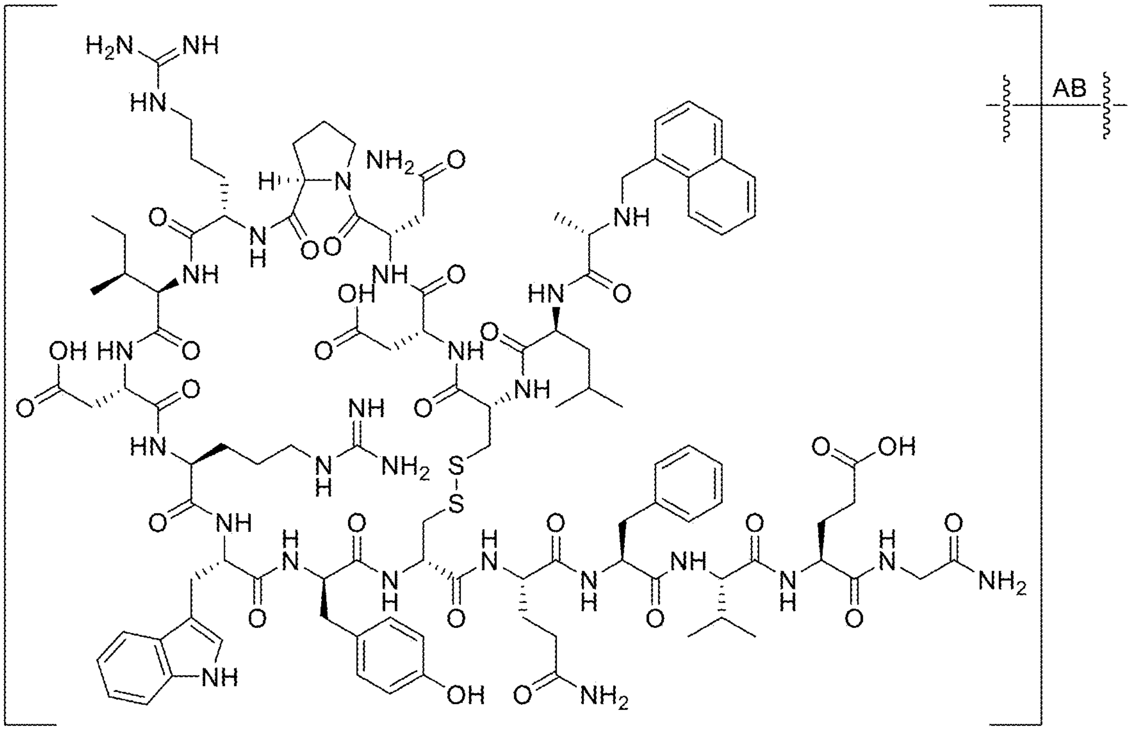
FIG. 1BBB
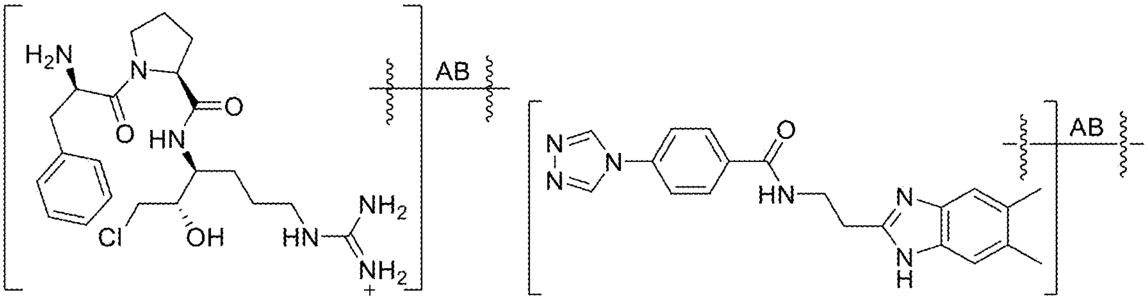
FIG. 1CCC

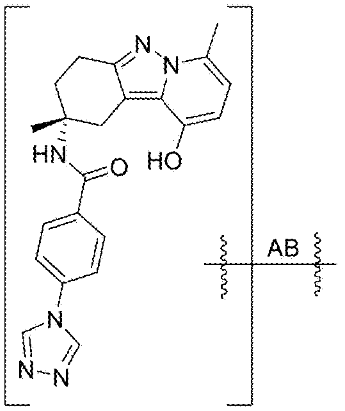
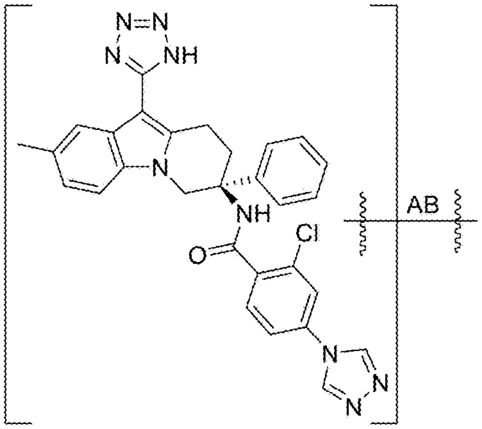
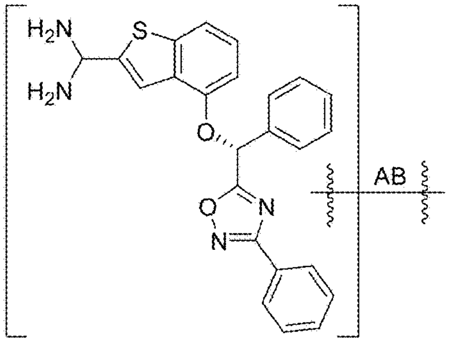
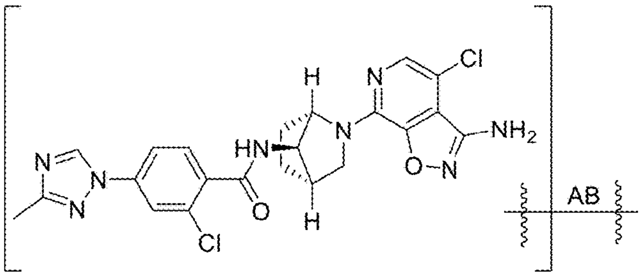
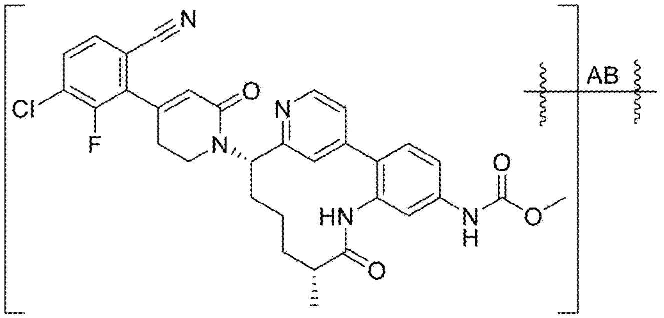
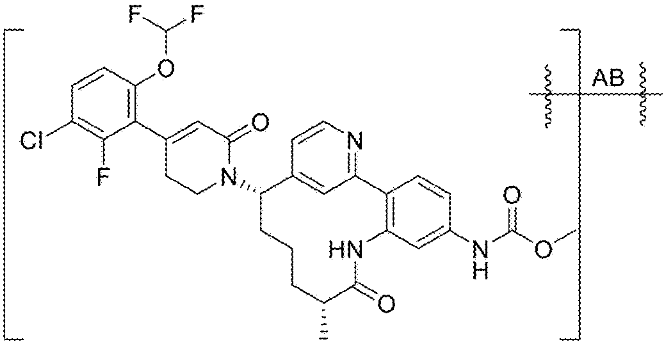
FIG. 1DDD

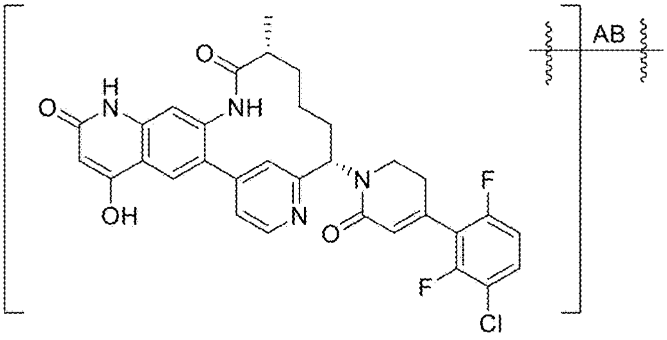
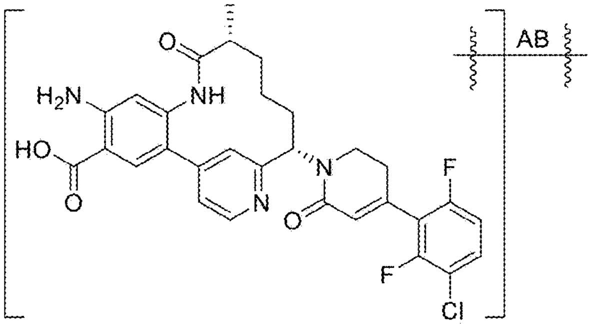
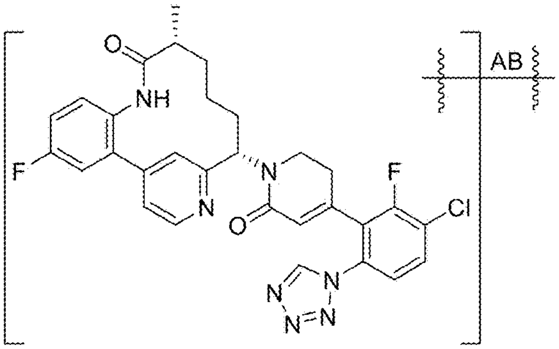
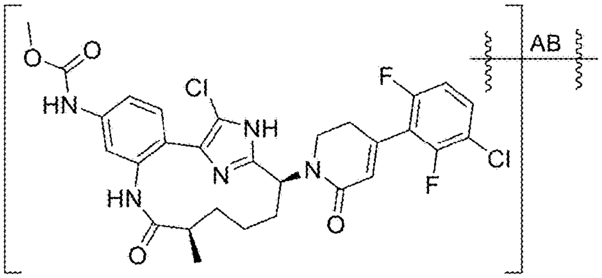
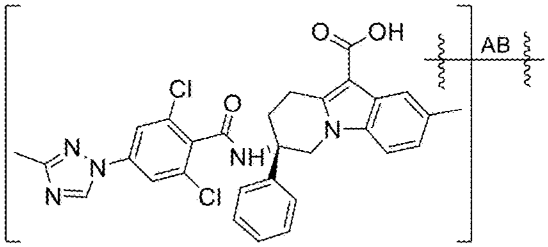
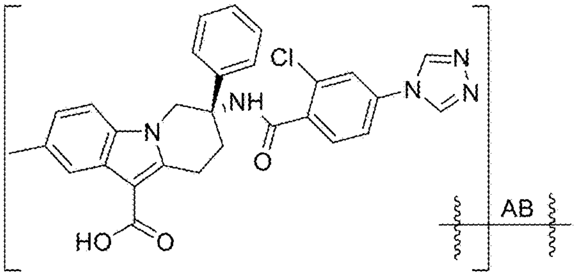
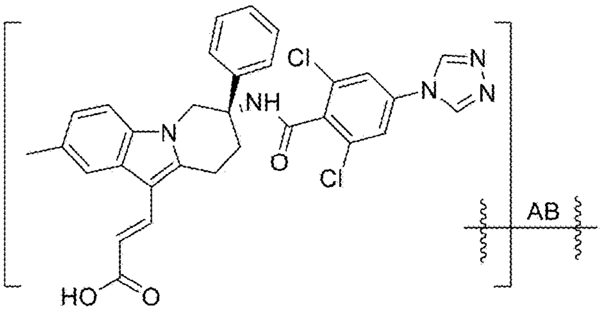
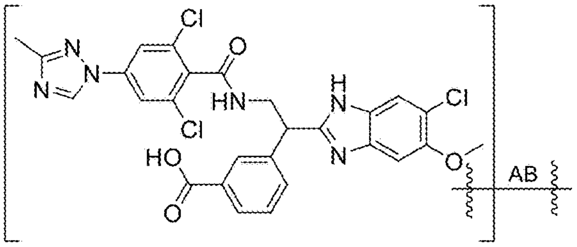
FIG. 1EEE

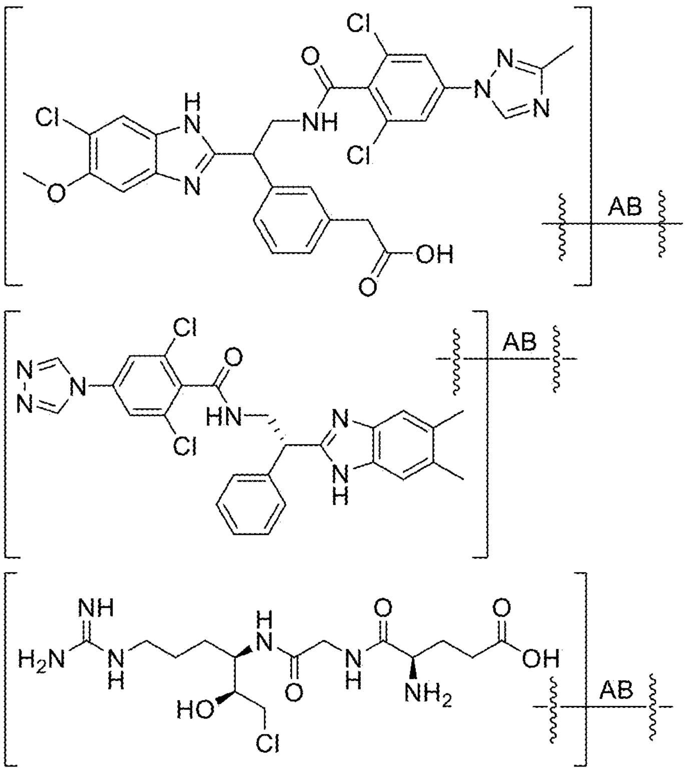
FIG. 1FFF
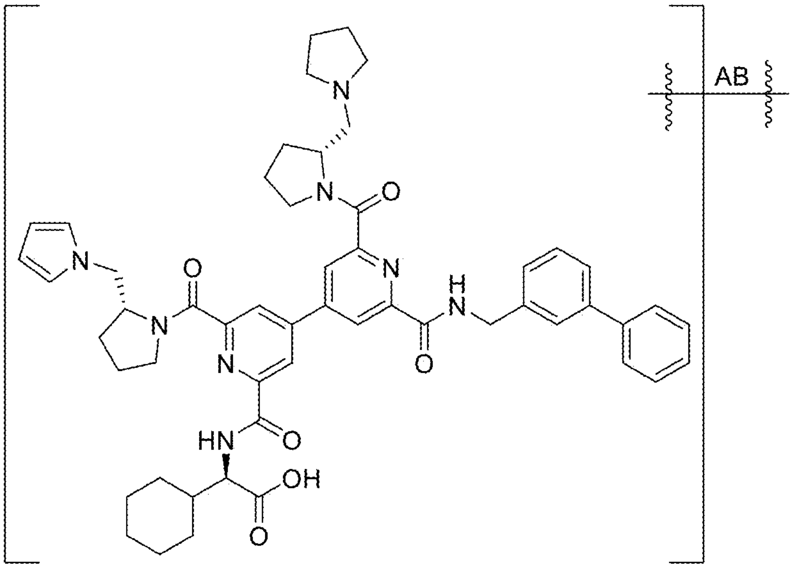
FIG. 1GGG

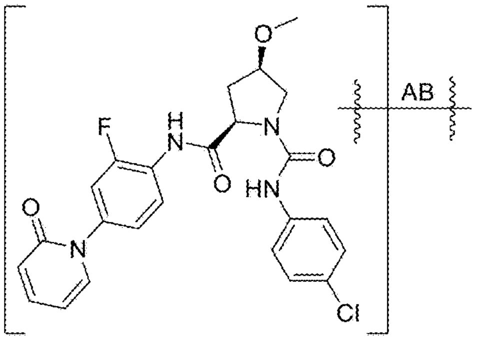
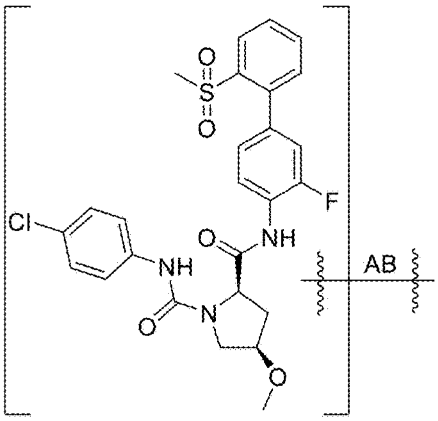
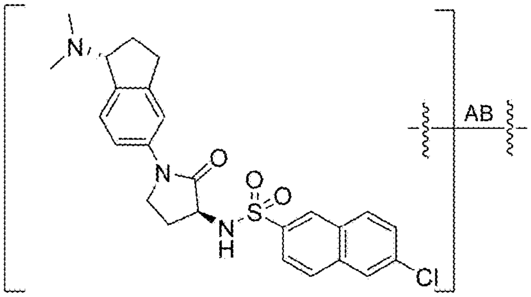
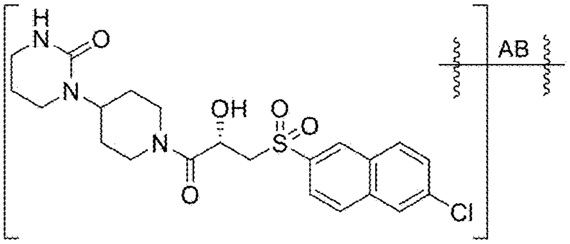
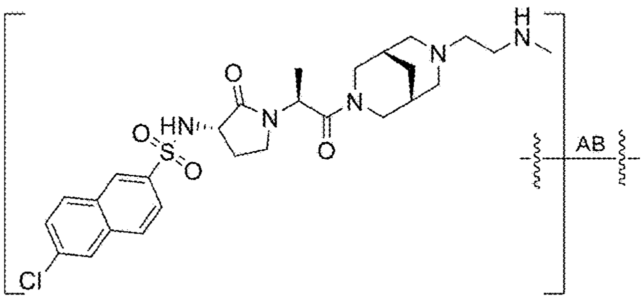
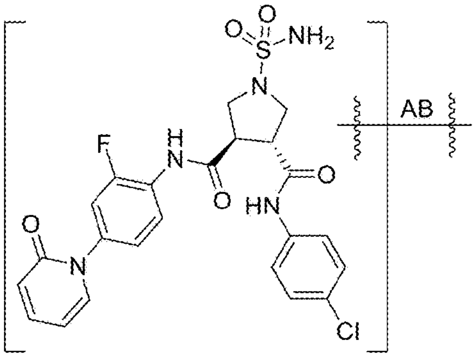
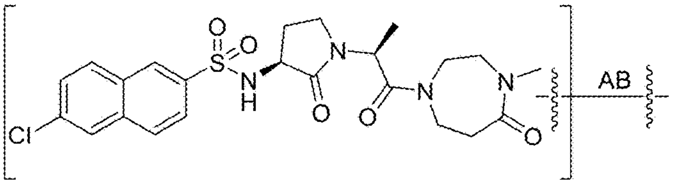
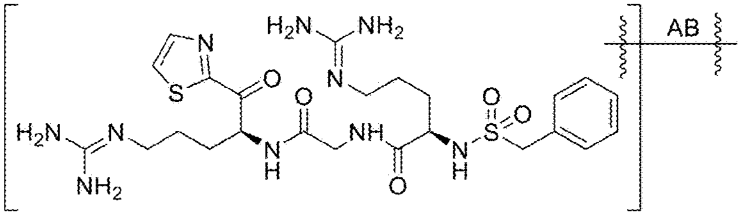
FIG. 1HHH

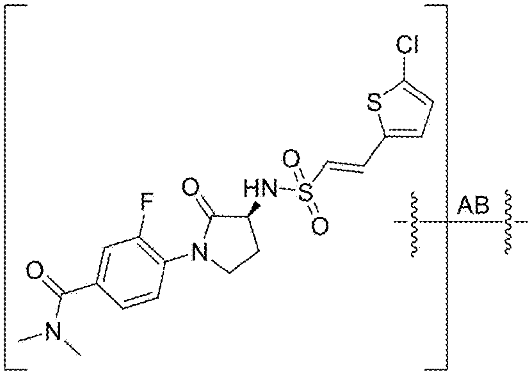
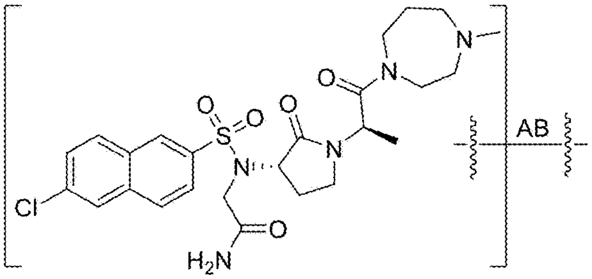
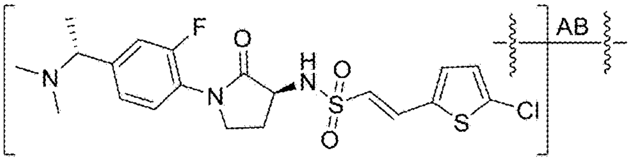
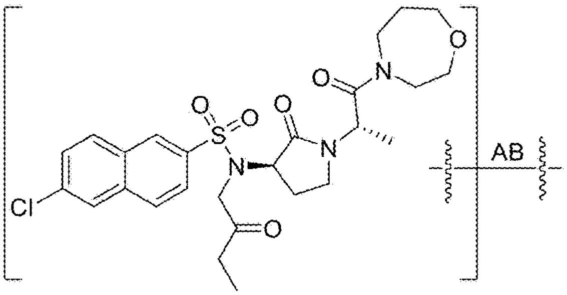
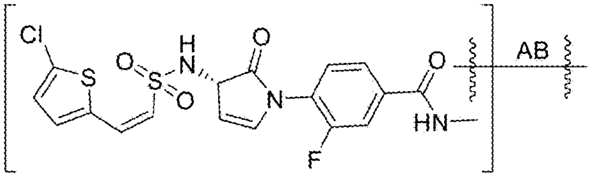
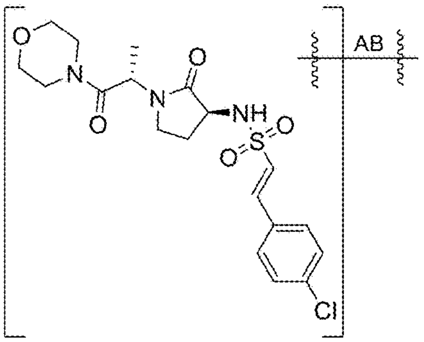
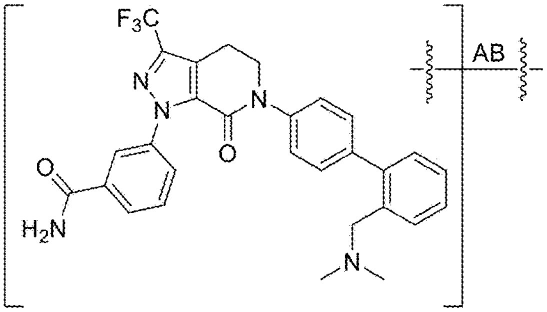
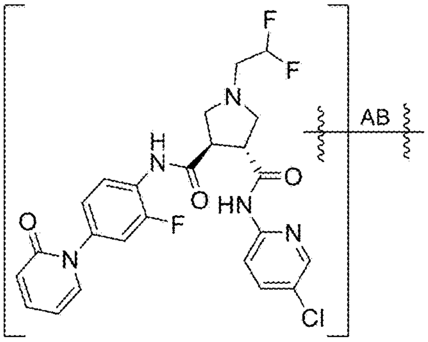
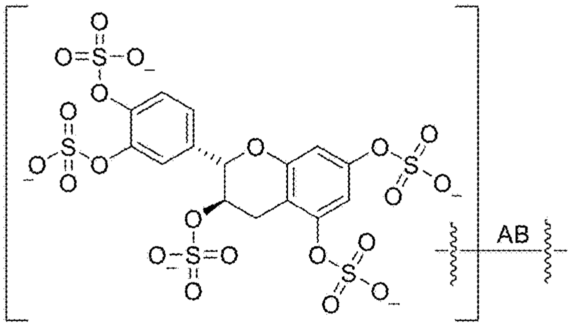
FIG. 1III

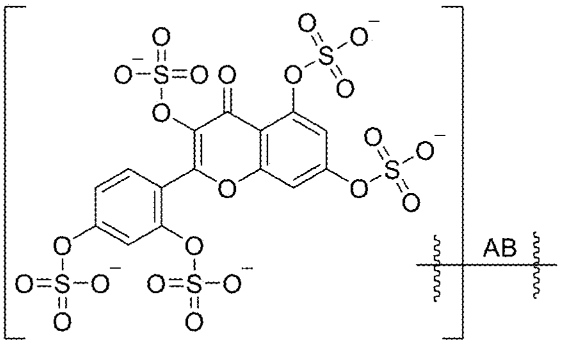
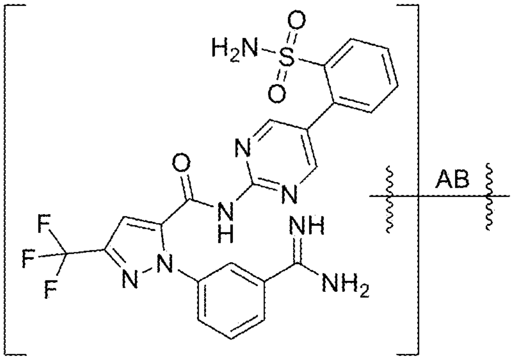
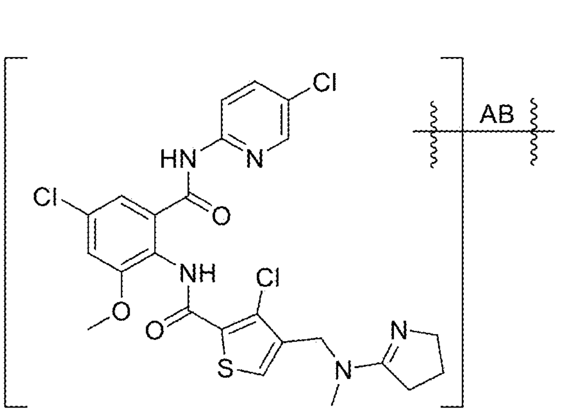
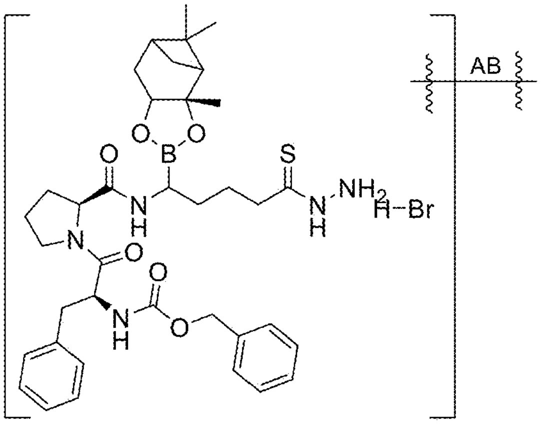
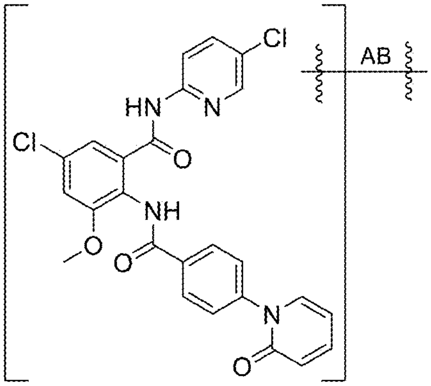
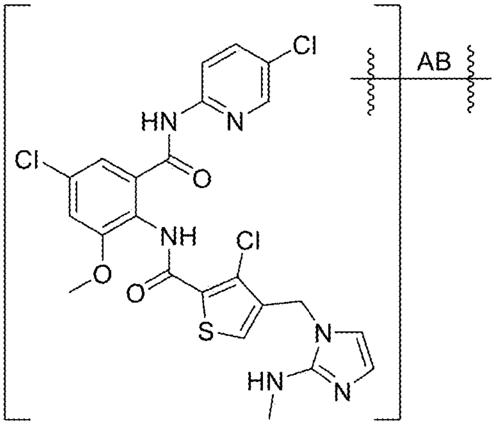
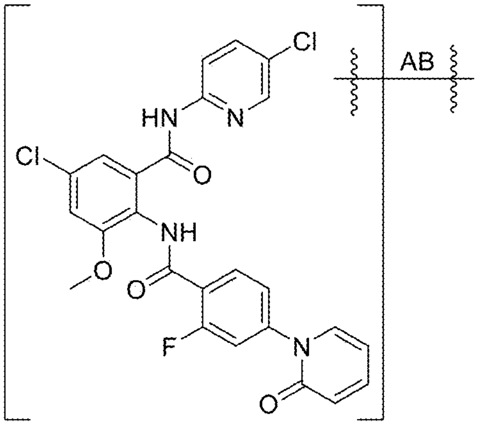
FIG. 1JJJ

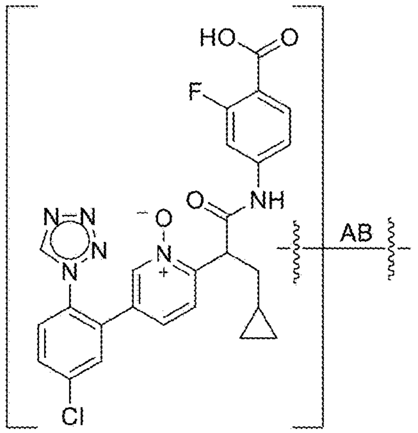
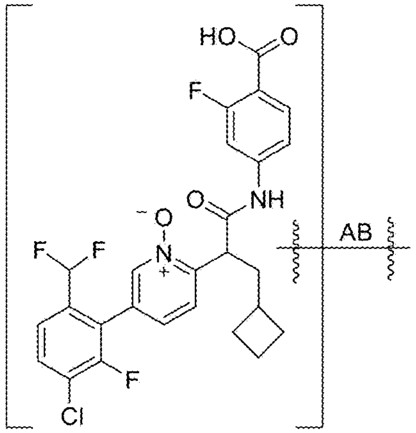
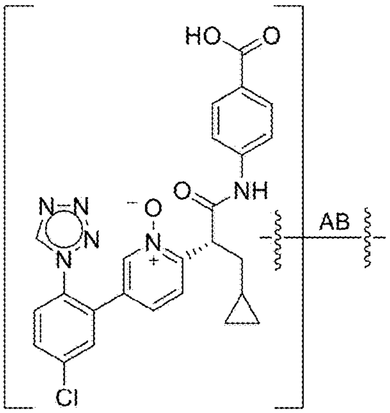
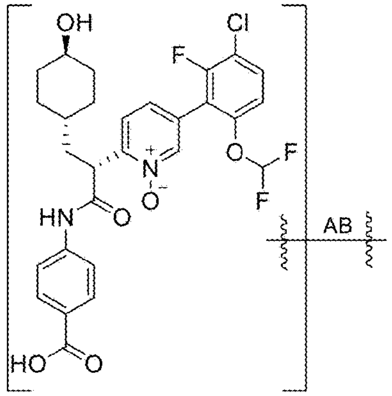
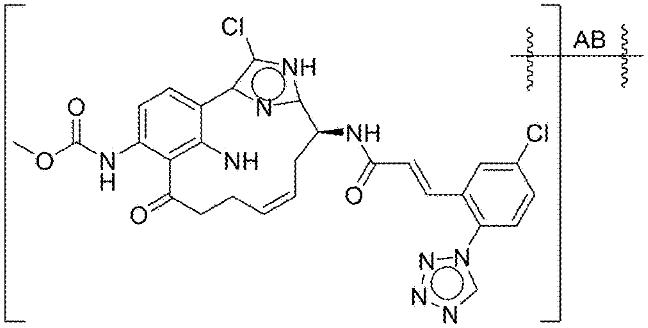
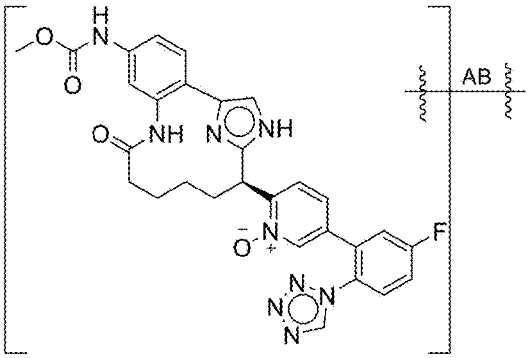
FIG. 1KKK

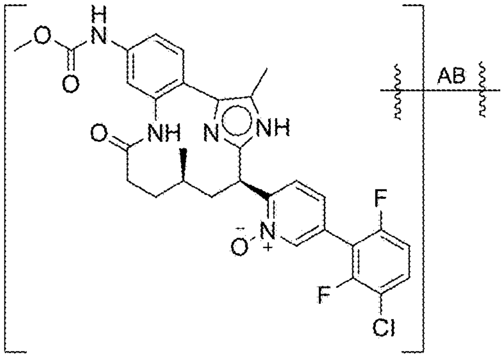
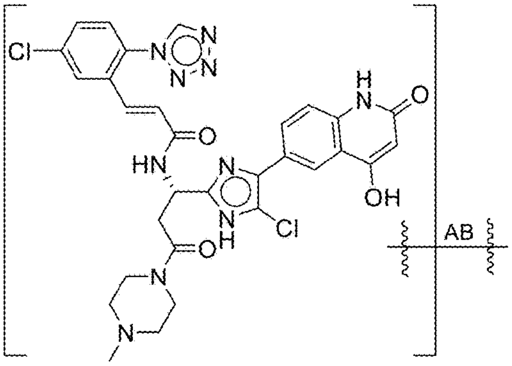
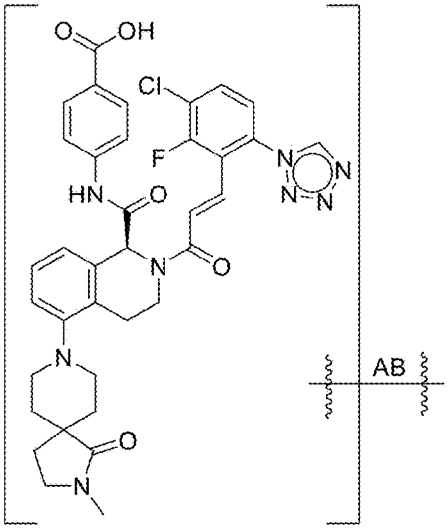
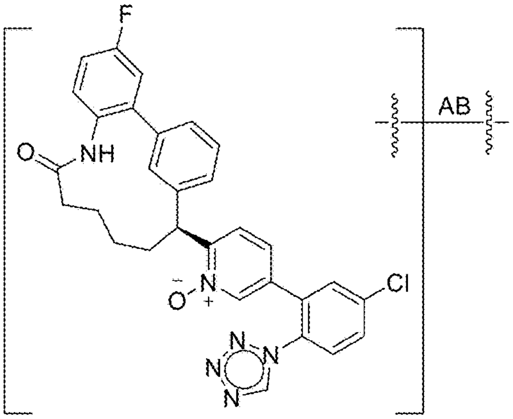
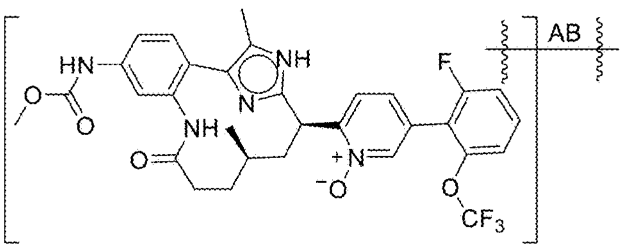
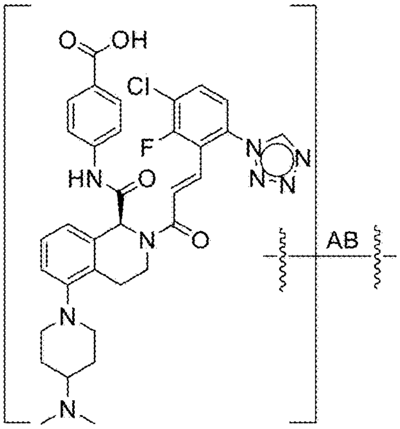
FIG. 1LLL

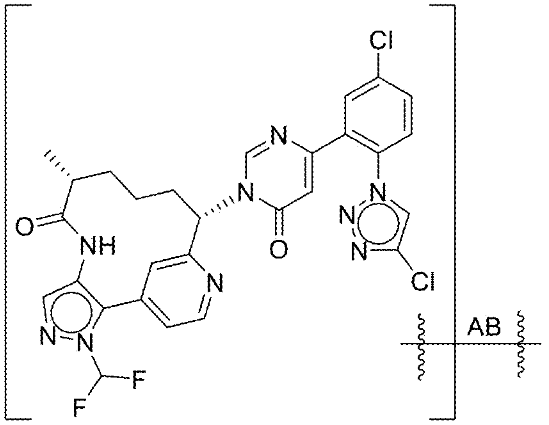
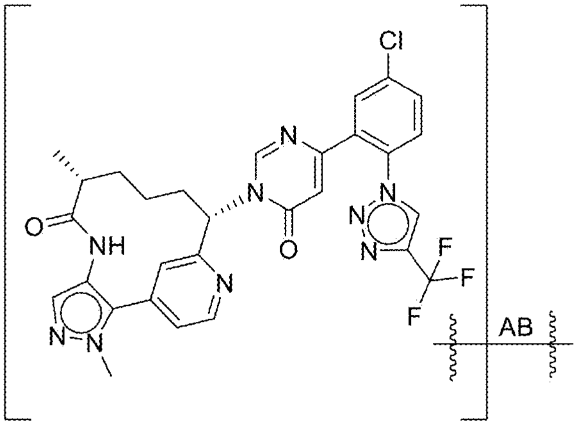
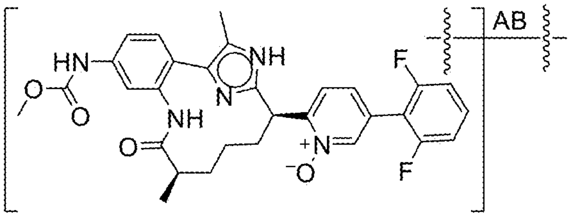
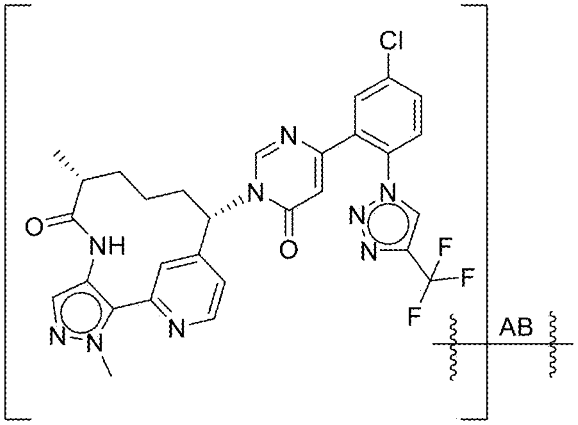
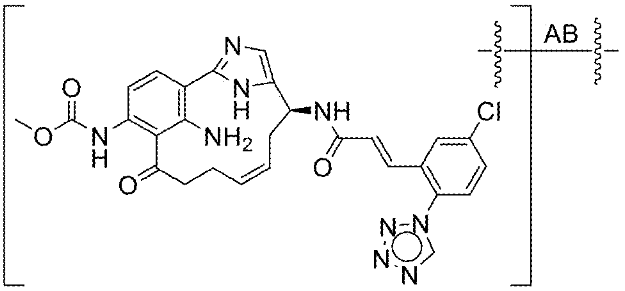
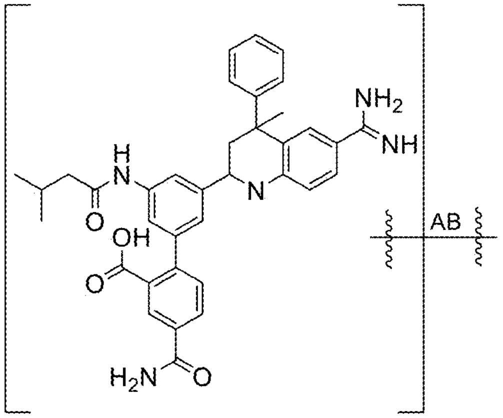
FIG. 1MMM

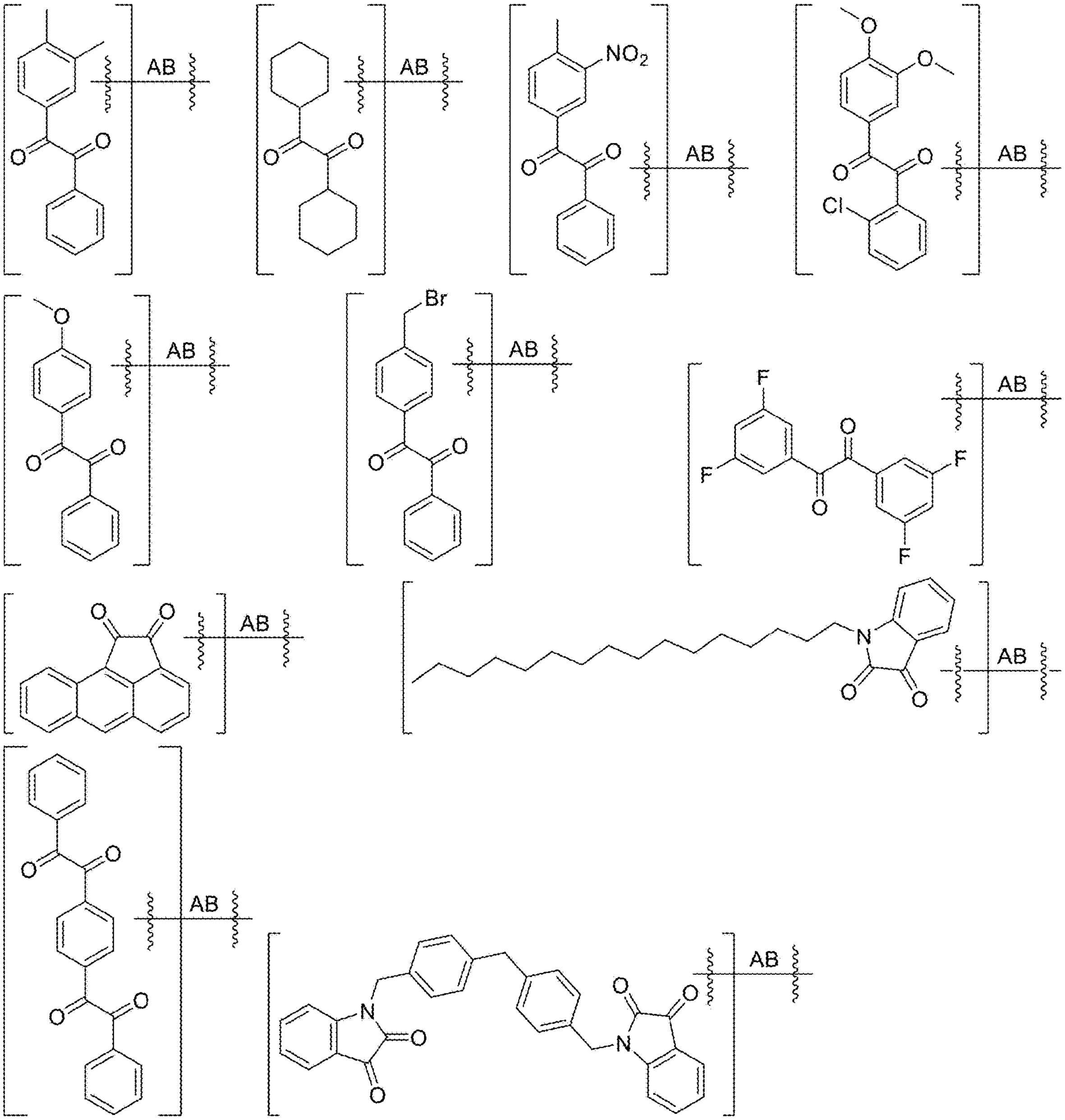
FIG. 1NNN

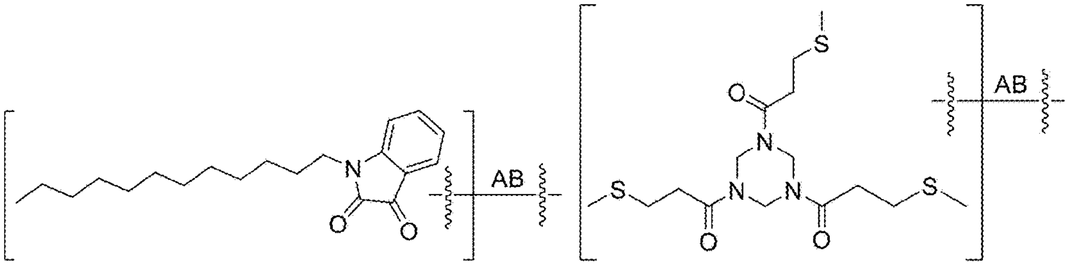
FIG. 1OOO
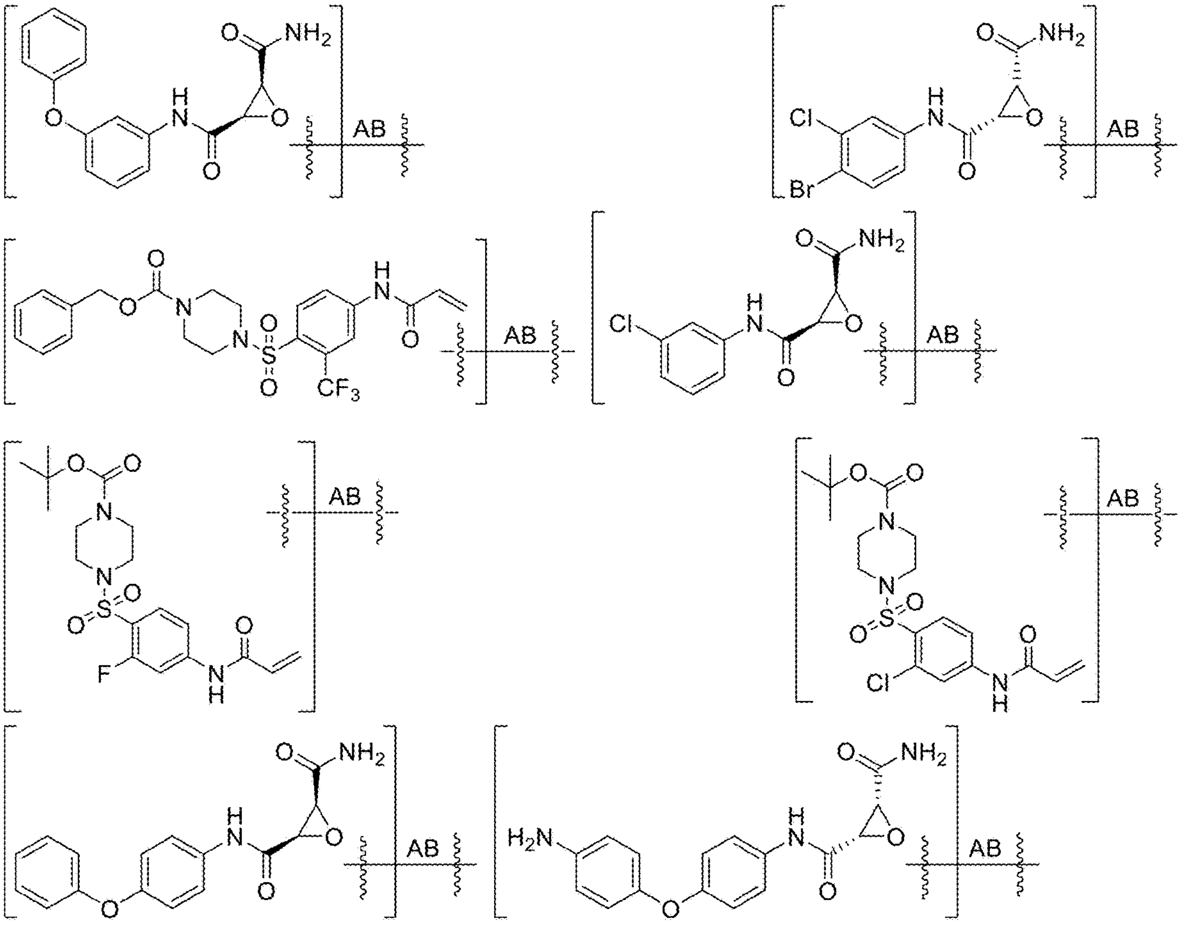
FIG. 1PPP

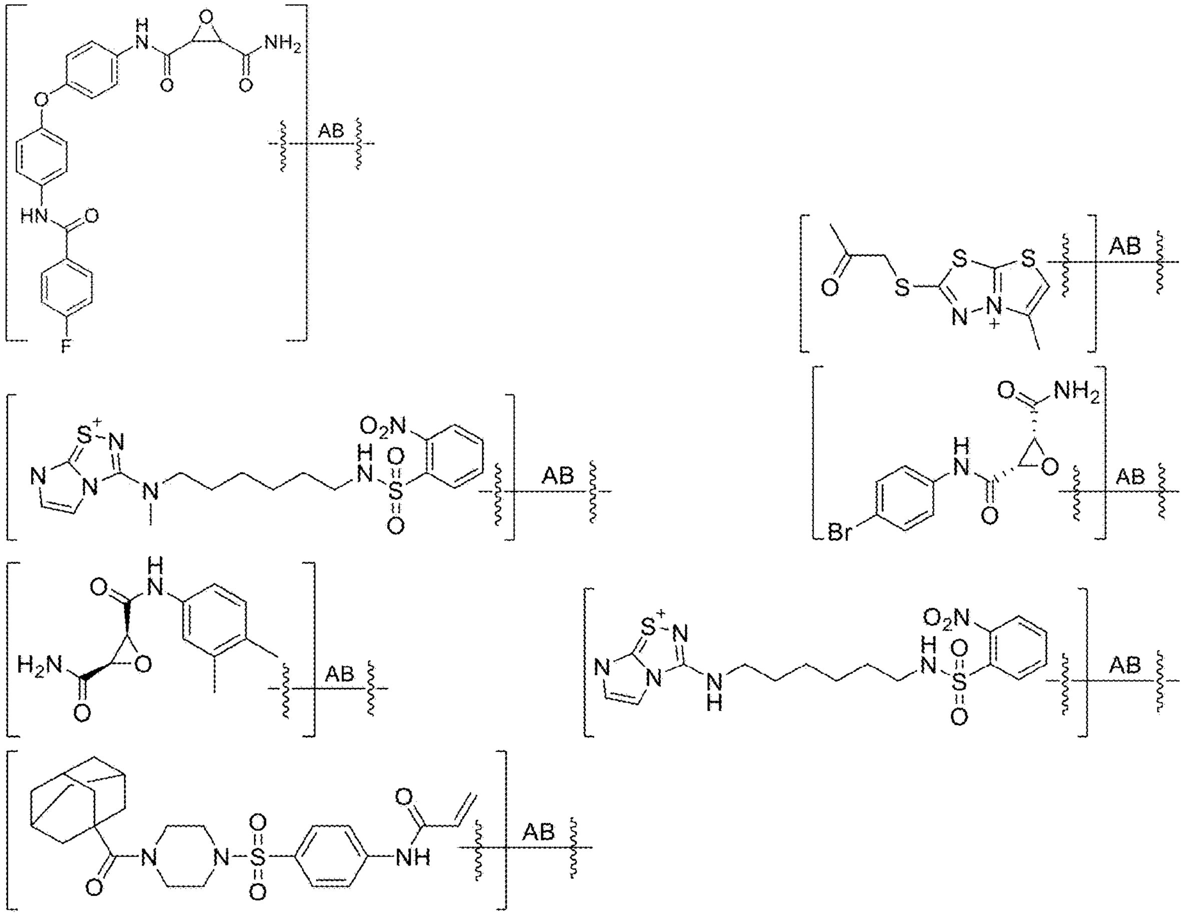
FIG. 1QQQ
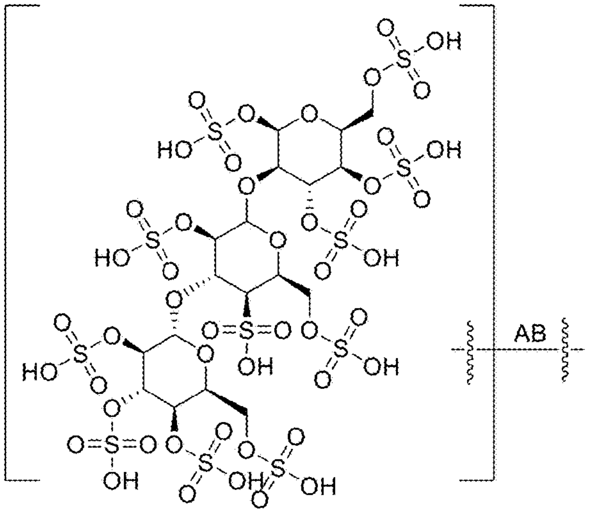
FIG. 1RRR

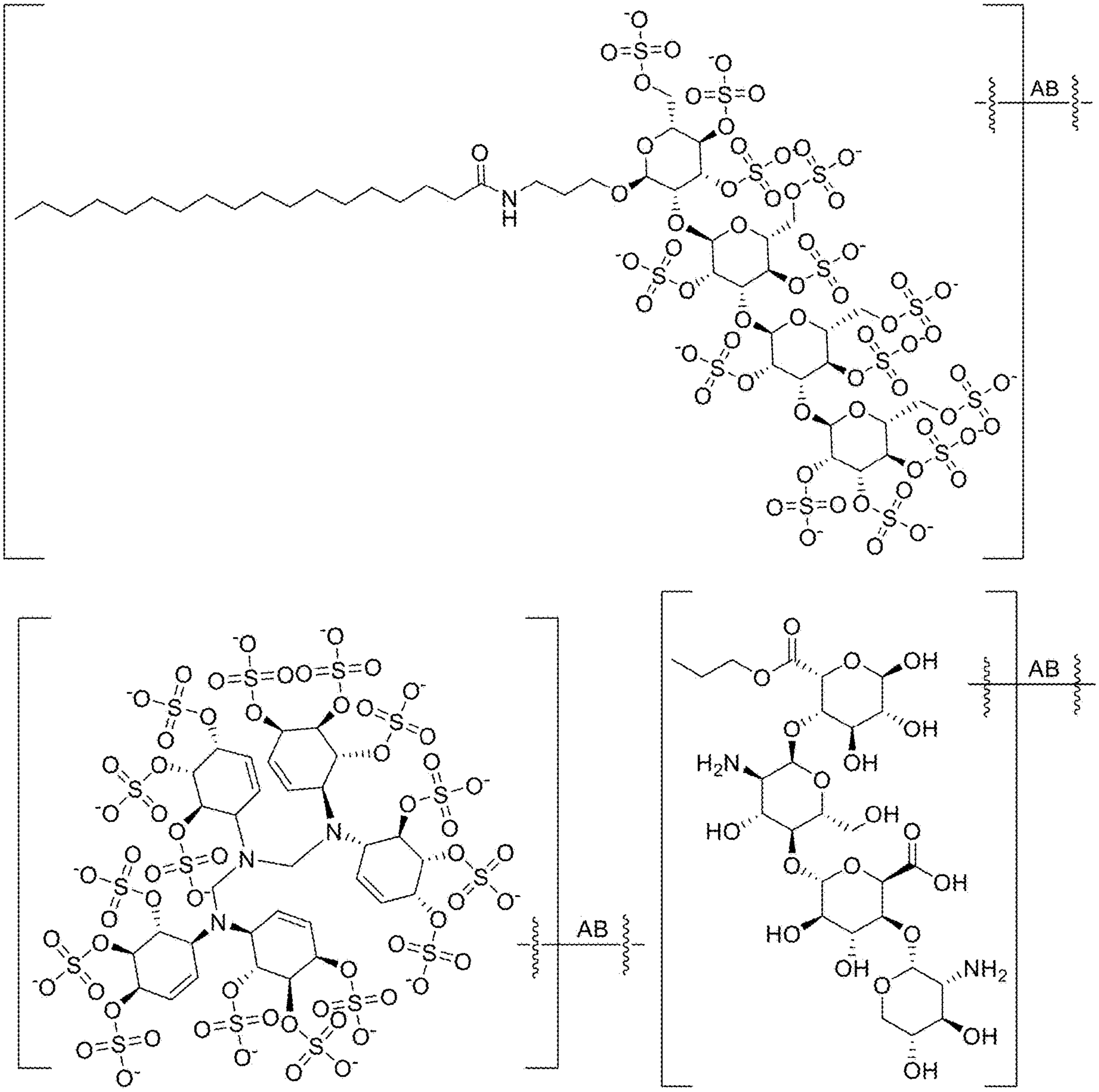
FIG. 1SSS

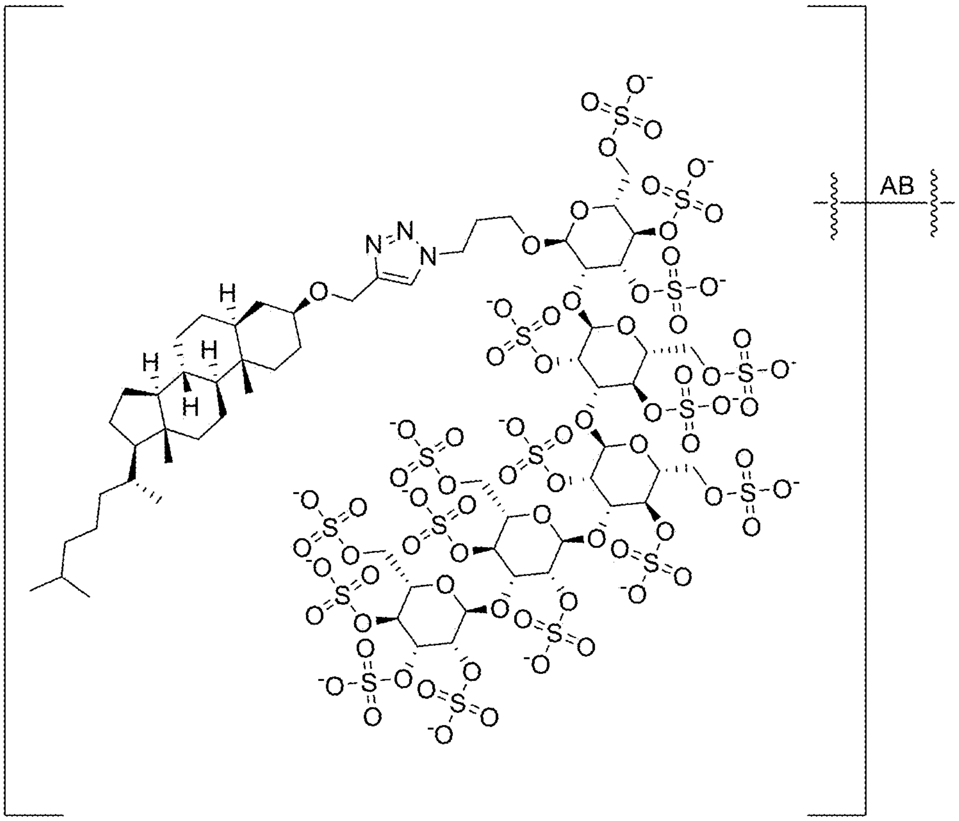
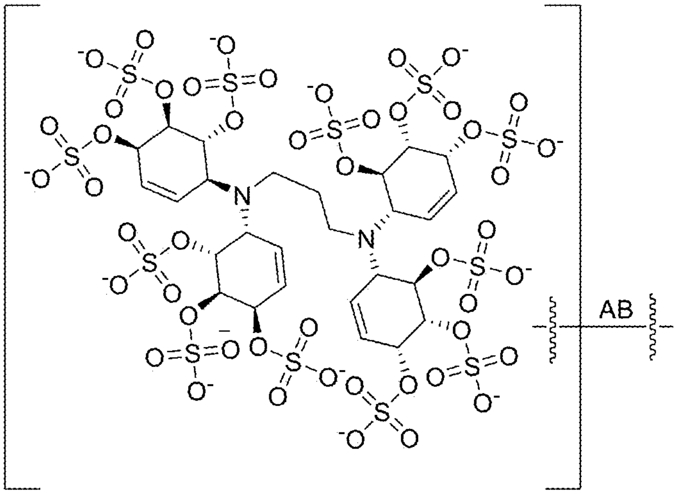
FIG. 1TTT

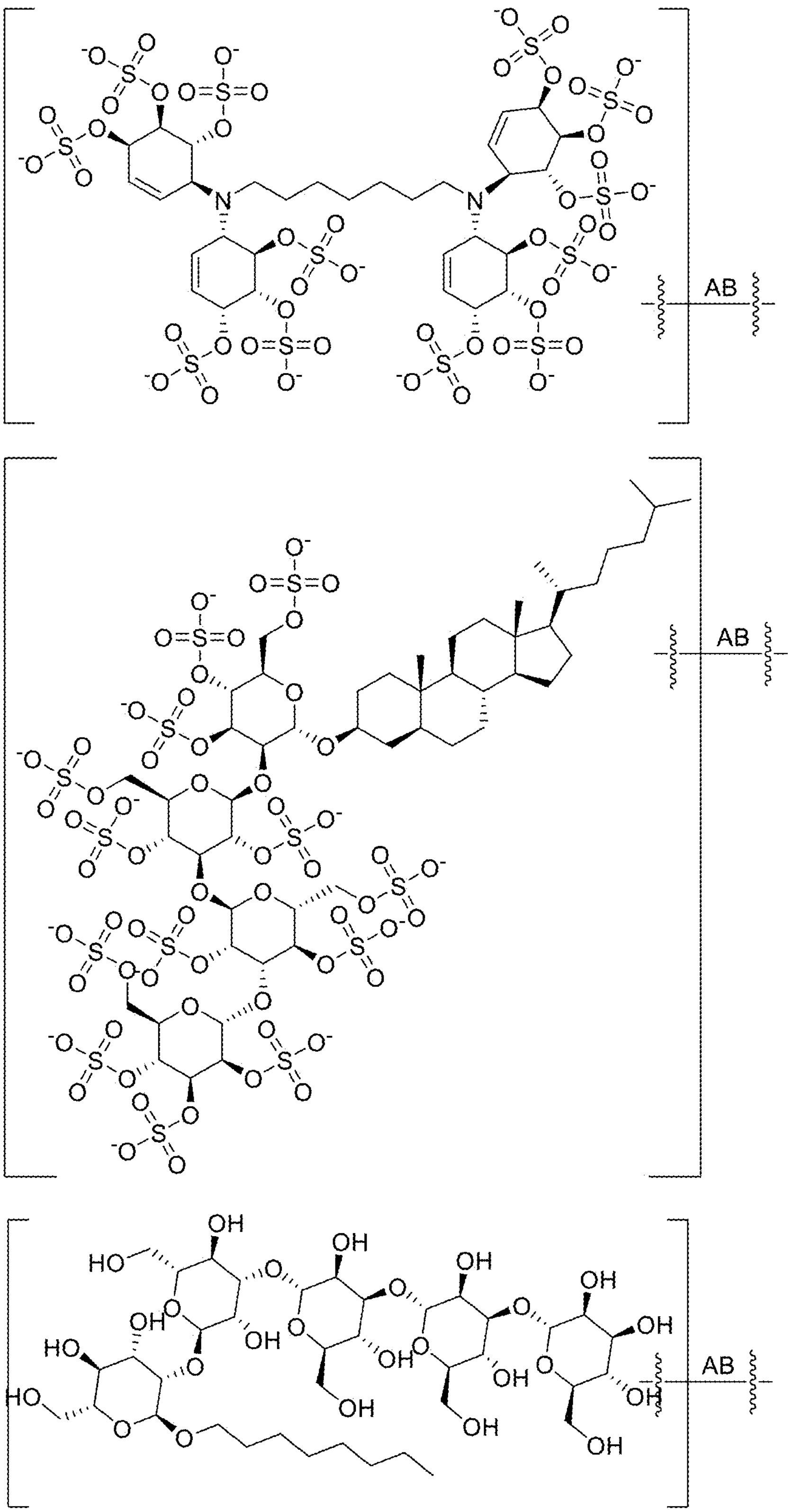
FIG. 1UUU

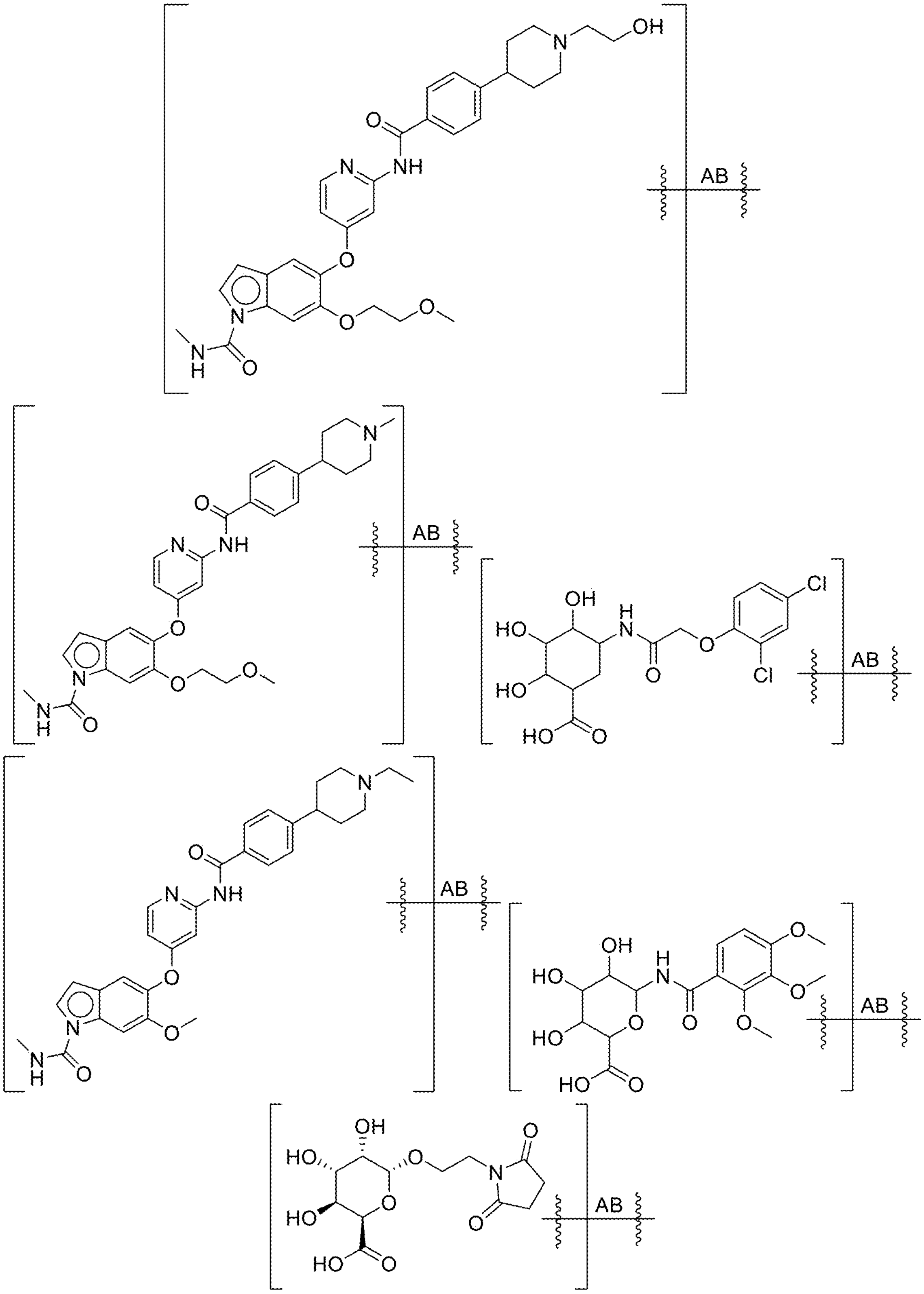
FIG. 1VVV

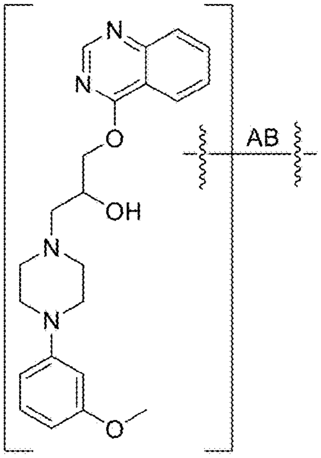
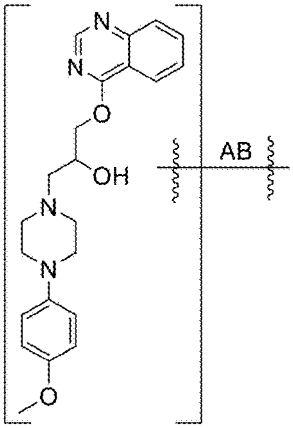
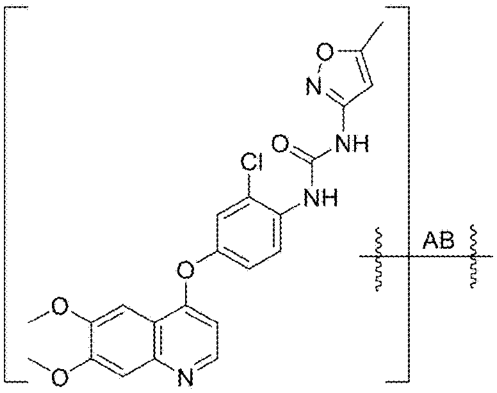
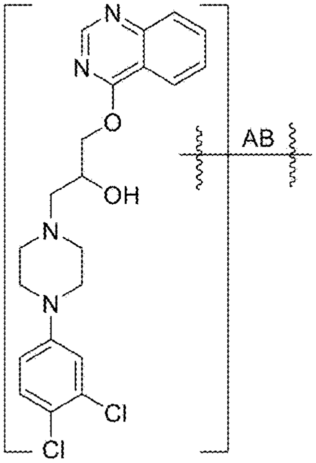
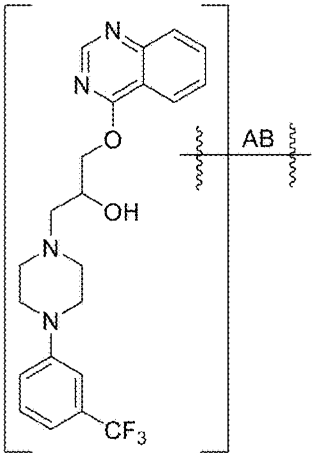
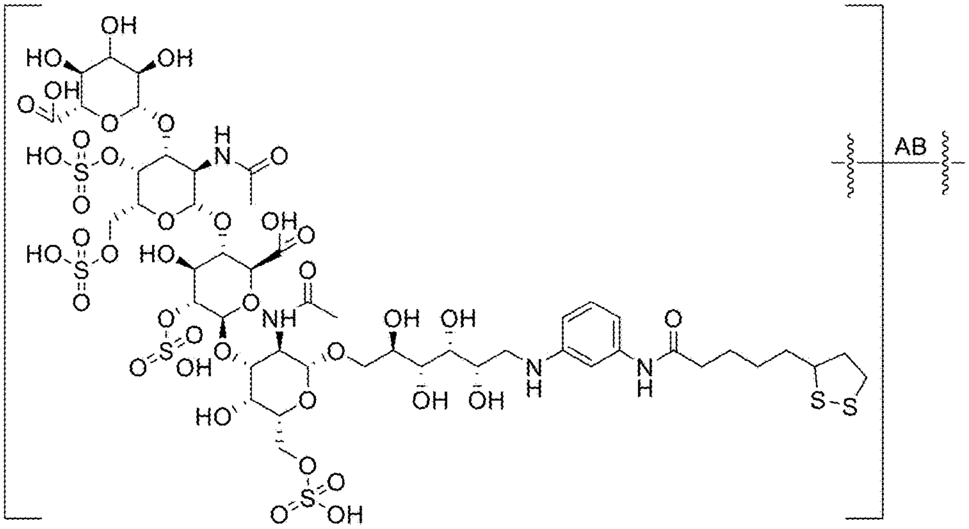
FIG. 1WWW

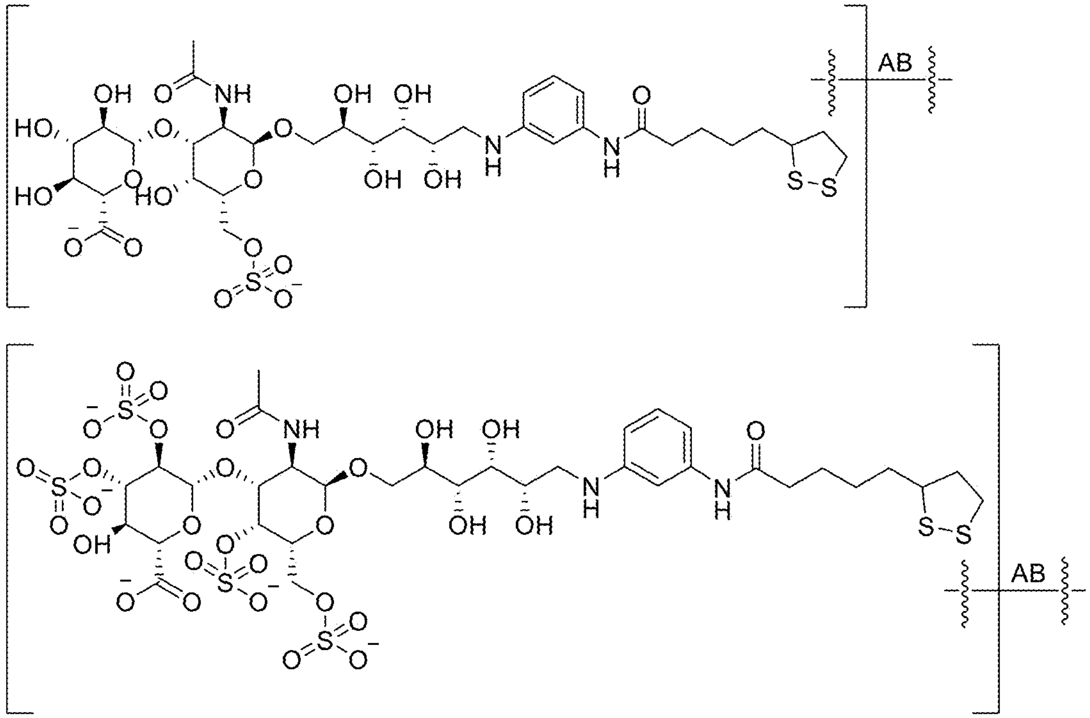
FIG. 1XXX
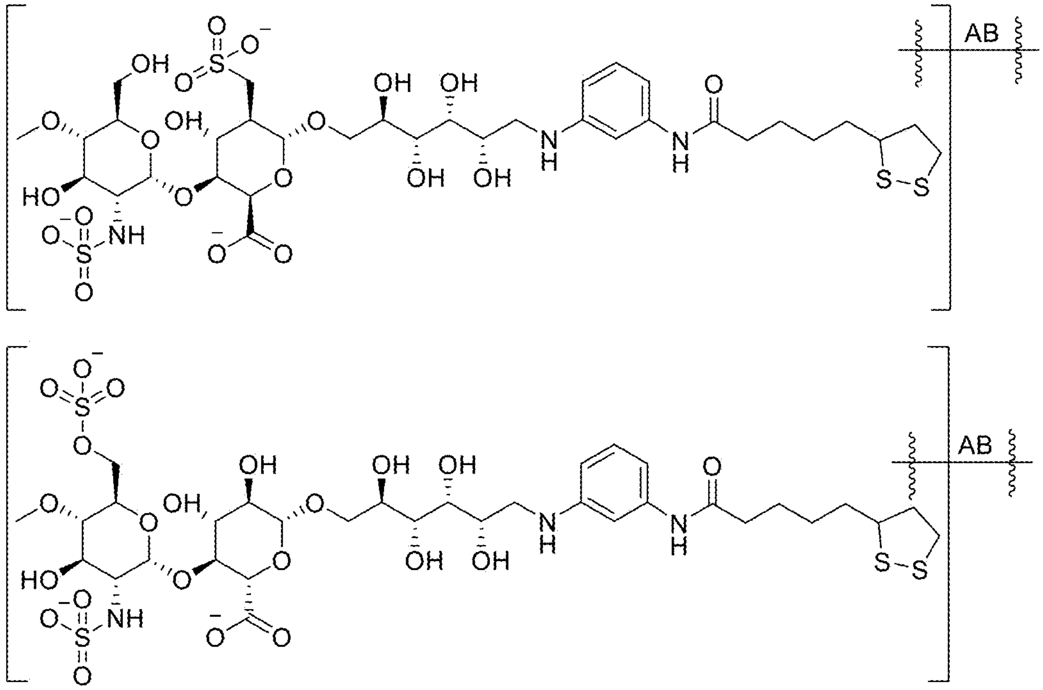
FIG. 1YYY

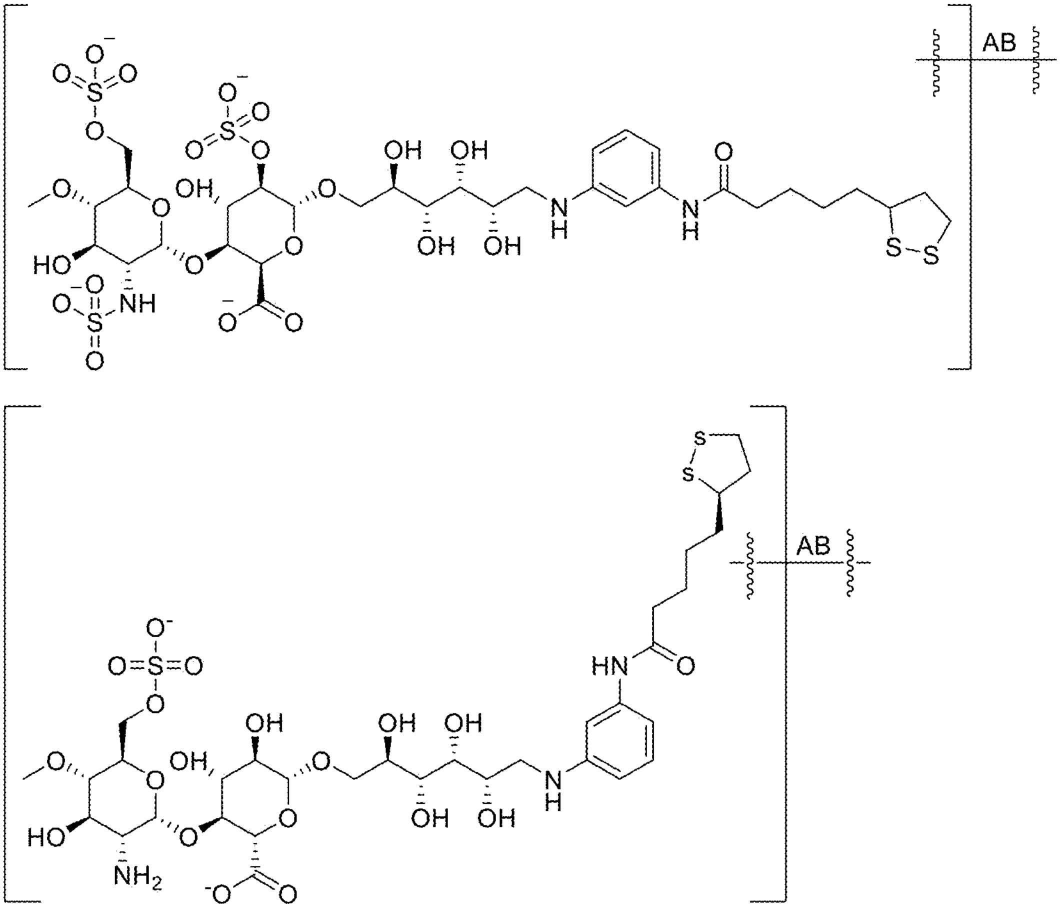
FIG. 1ZZZ
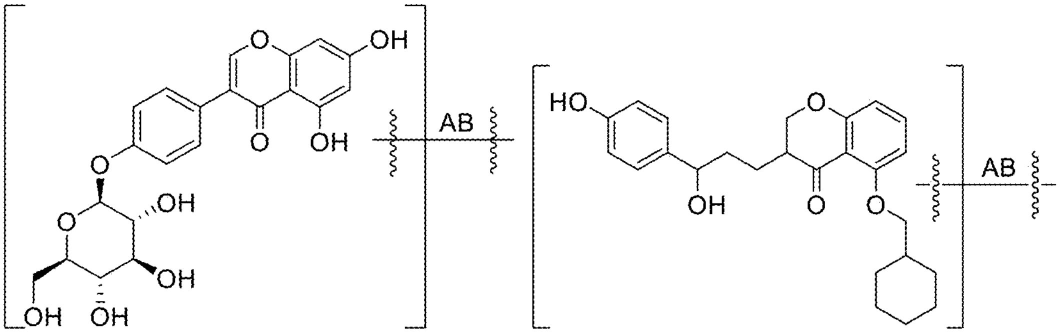
FIG. 1AAAA

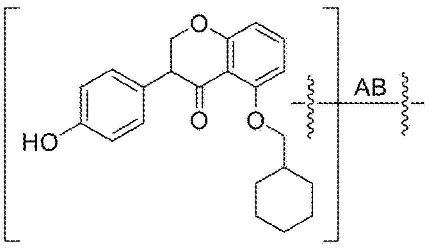
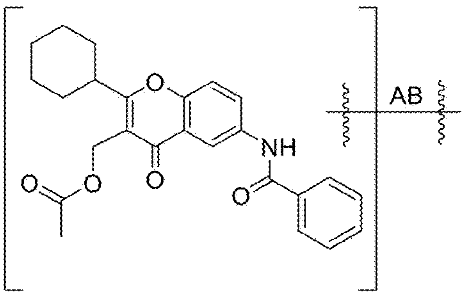
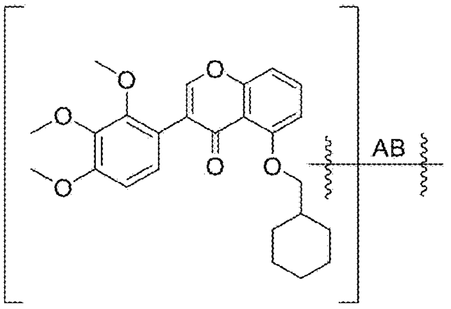
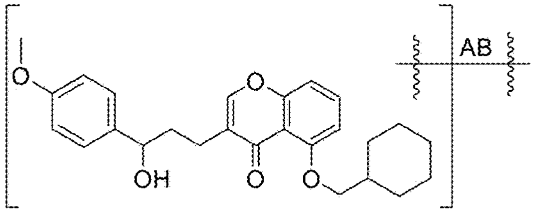
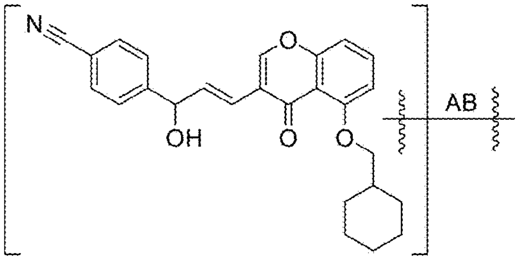
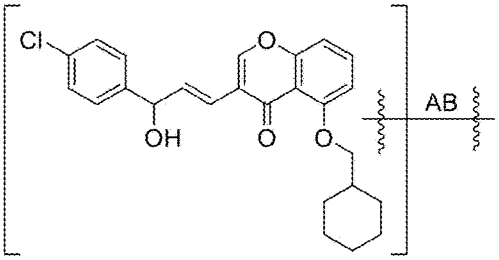
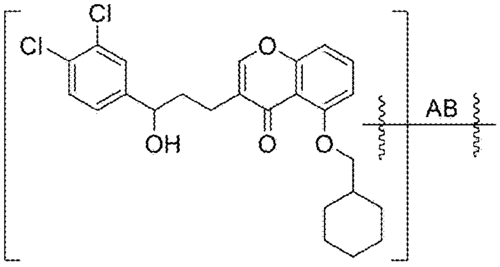
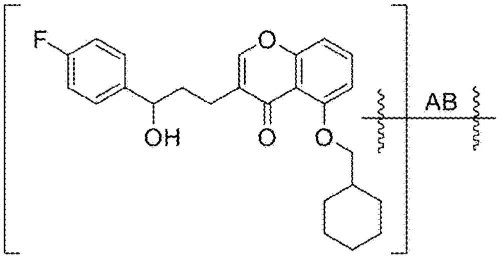
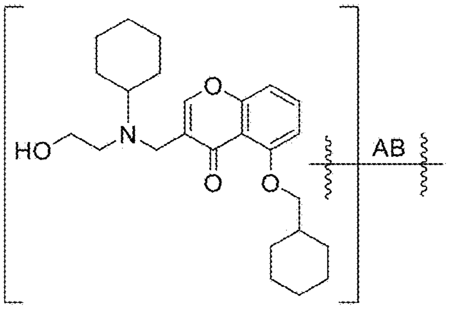
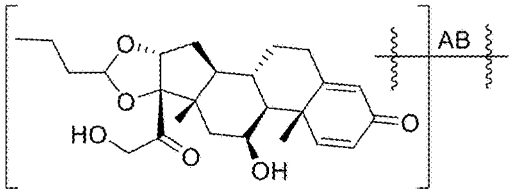
FIG. 1BBBB

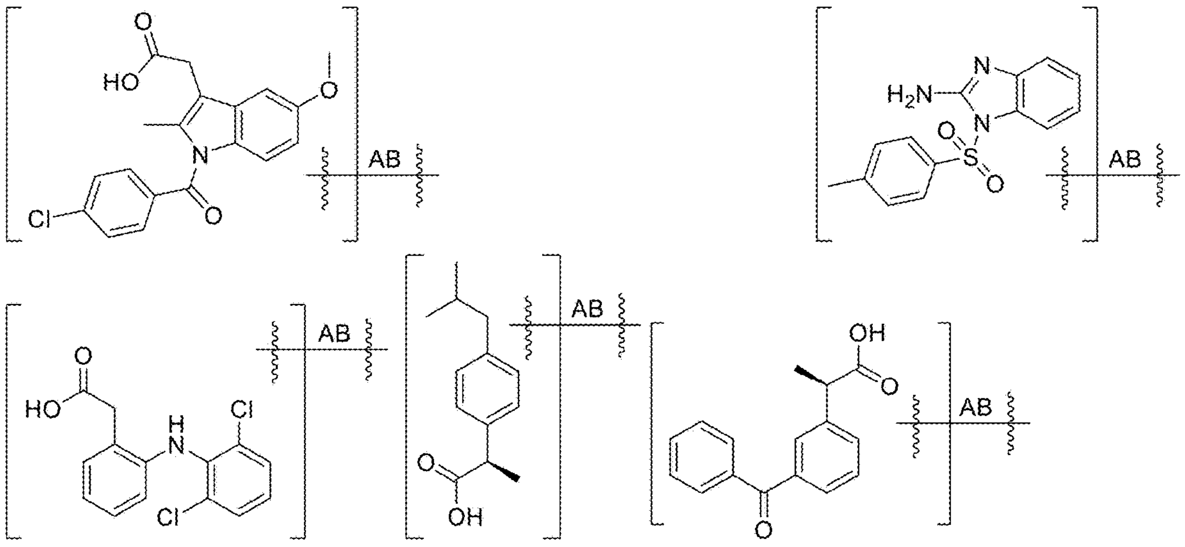
FIG. 1CCCC
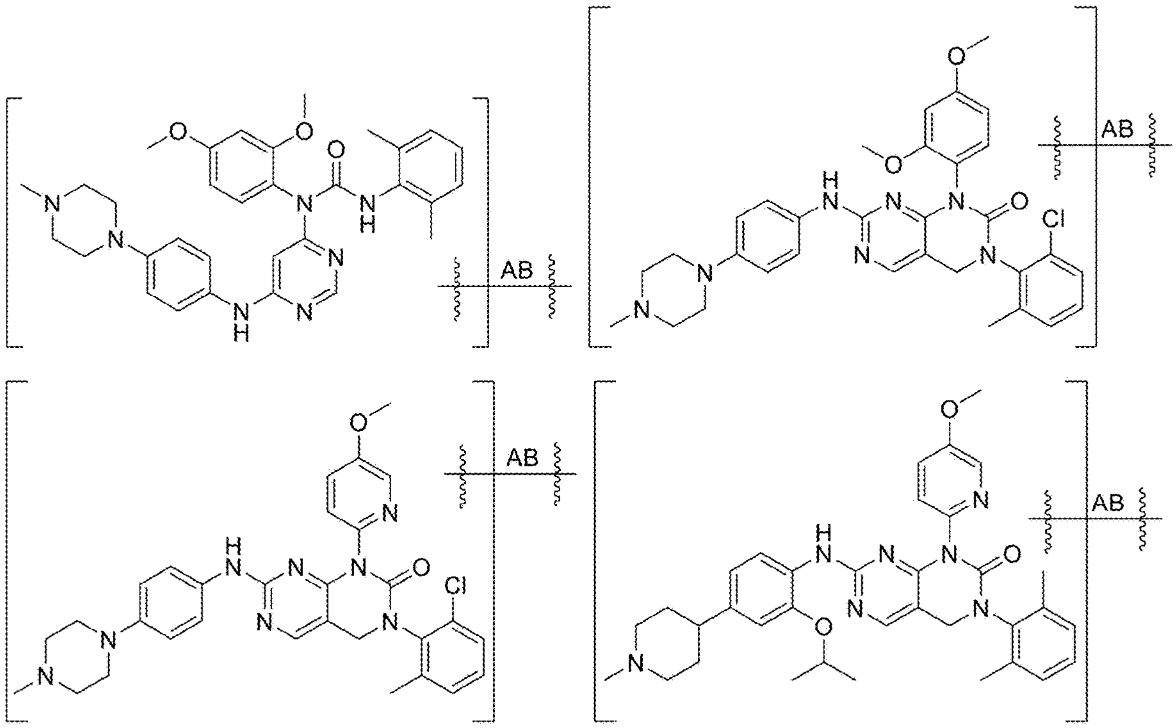
FIG. 1DDDD

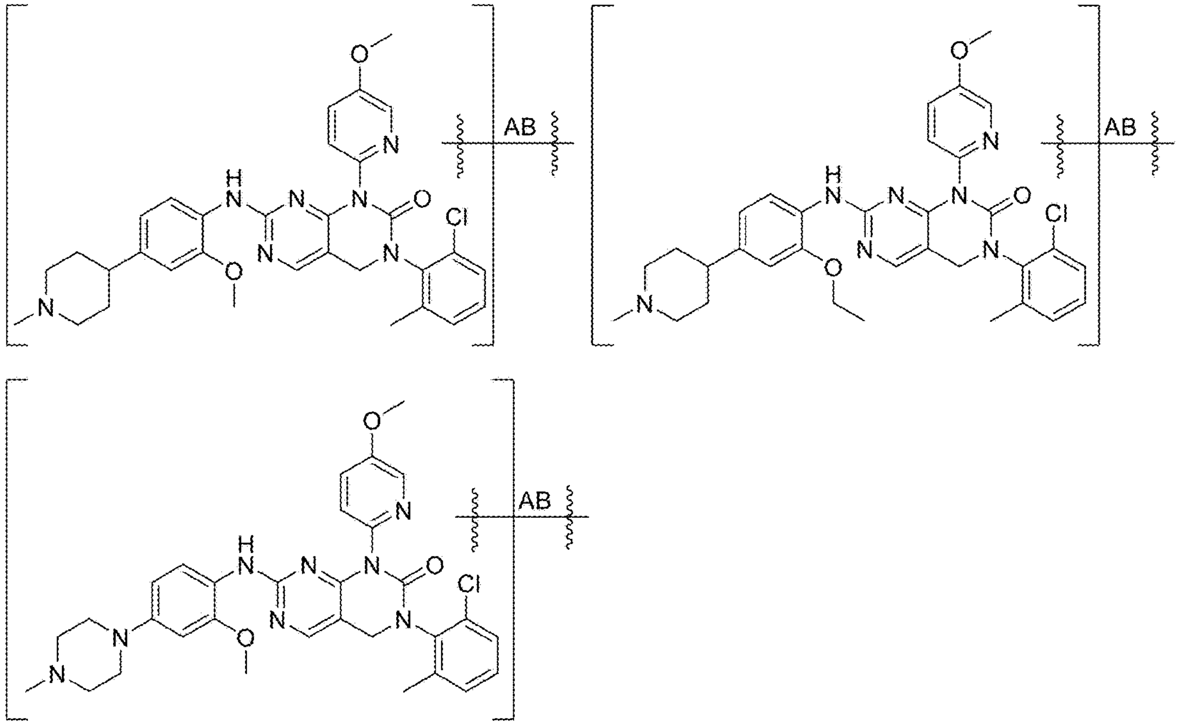
FIG. 1EEEE
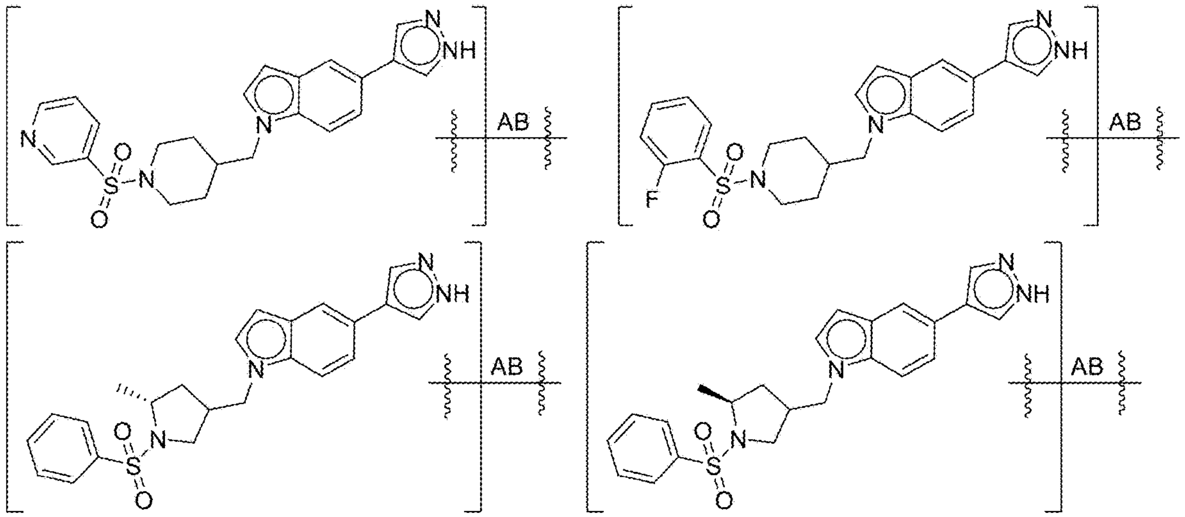
FIG. 1FFFF

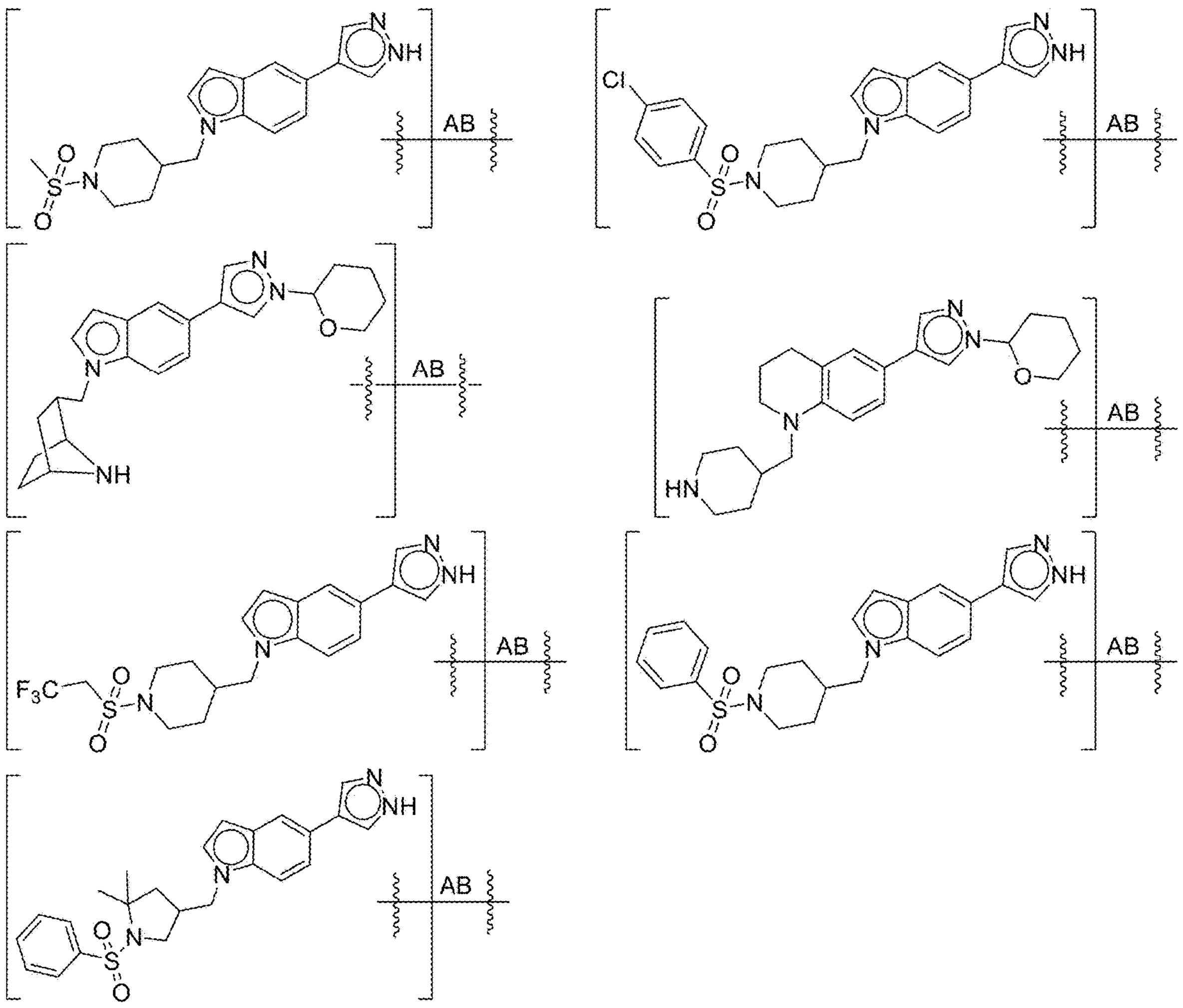
FIG. 1GGGG
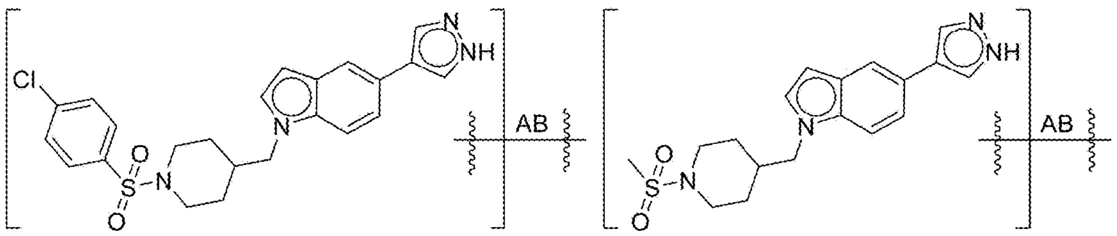
FIG. 1HHHH

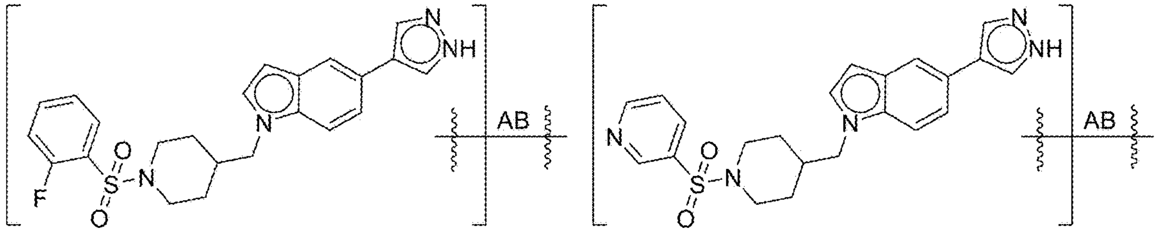
FIG 1IIII
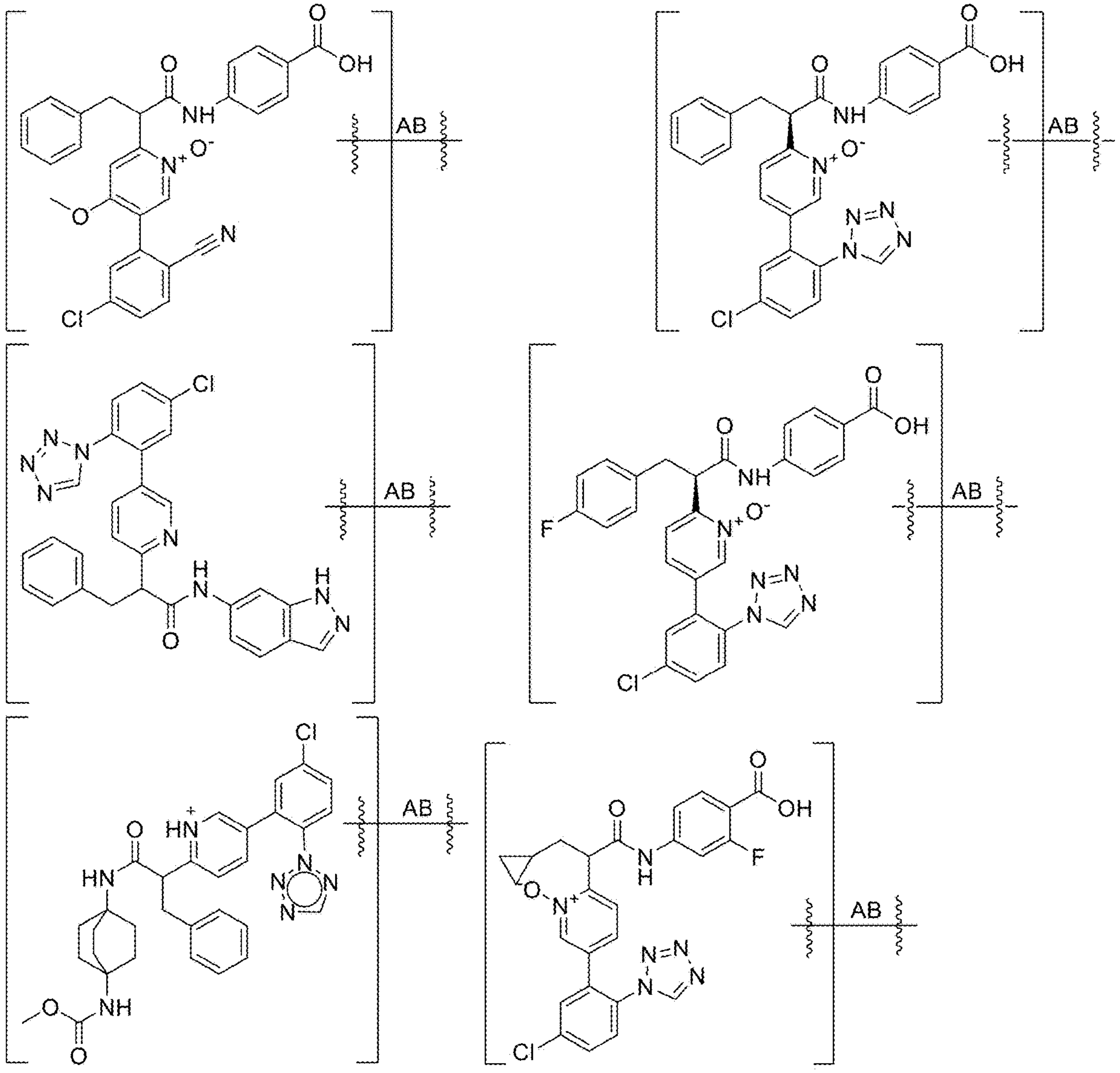
FIG. 1JJJJ

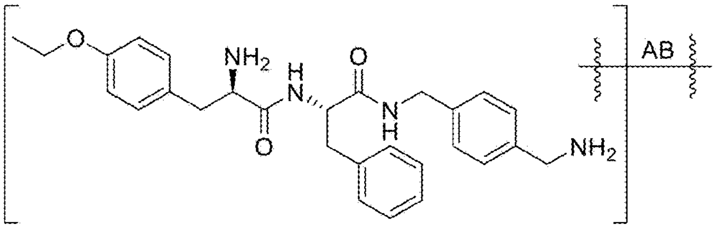
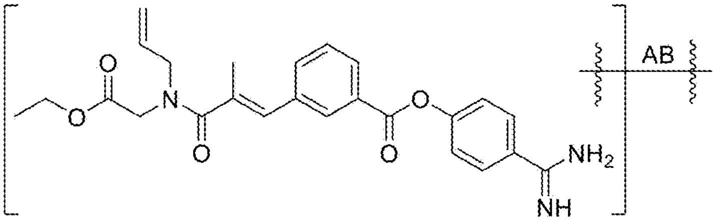
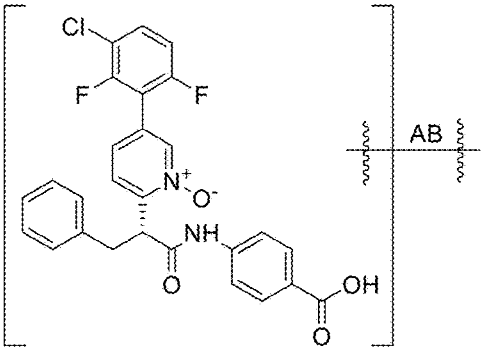
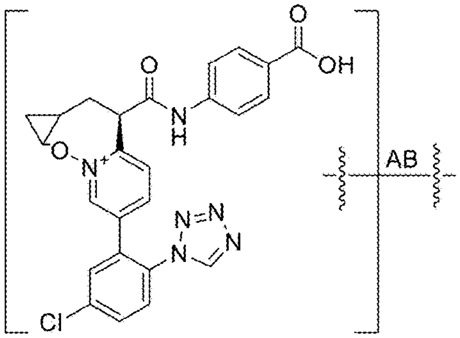
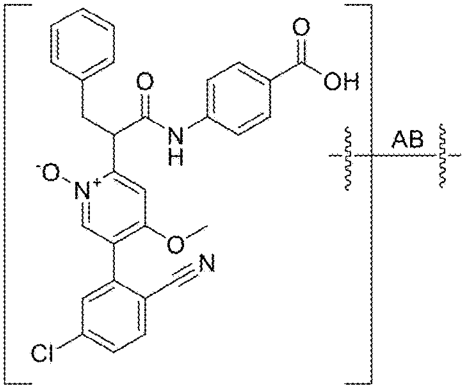
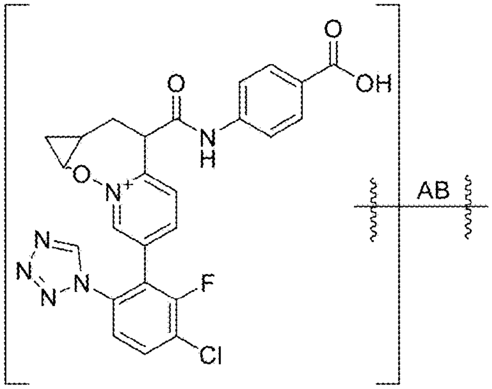
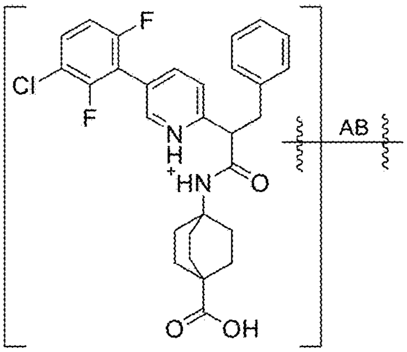
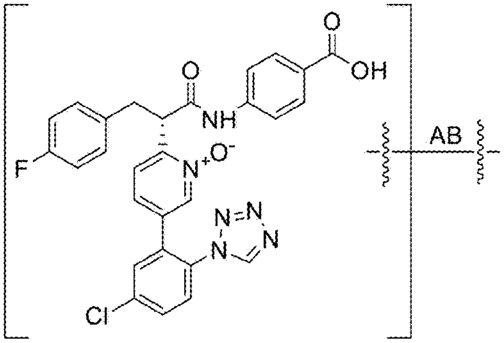
FIG. 1KKKK

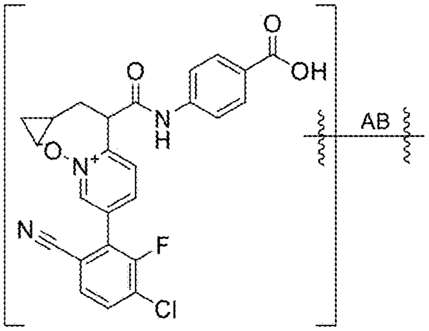
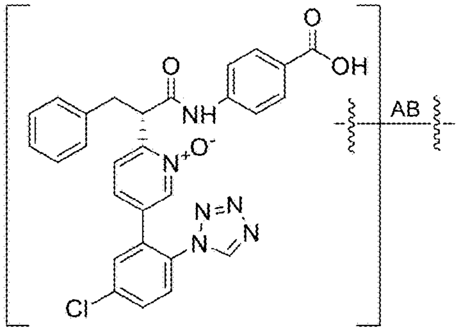
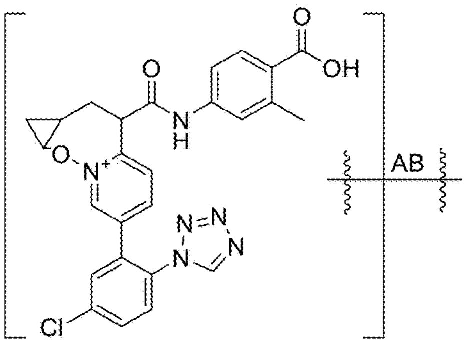
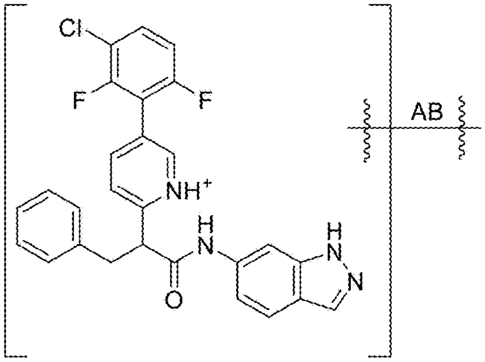
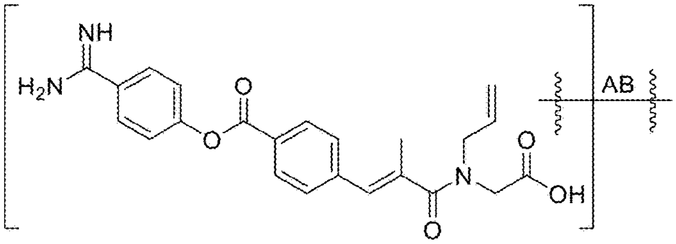
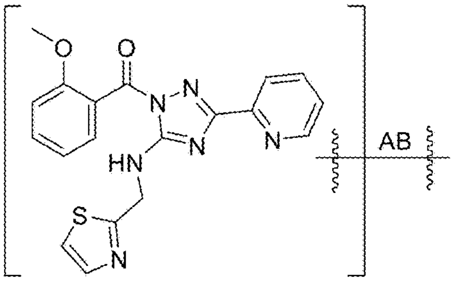
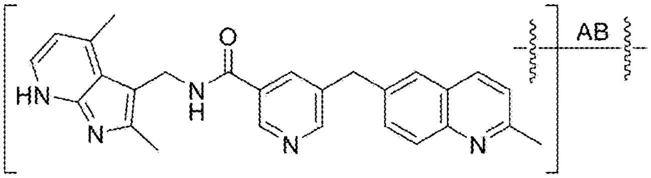
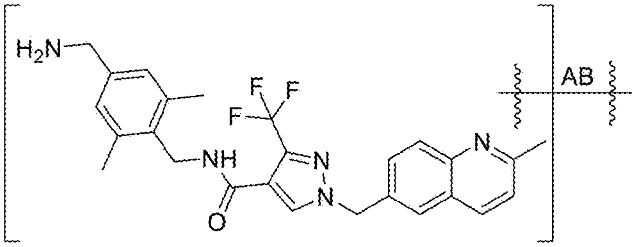
FIG. 1LLLL

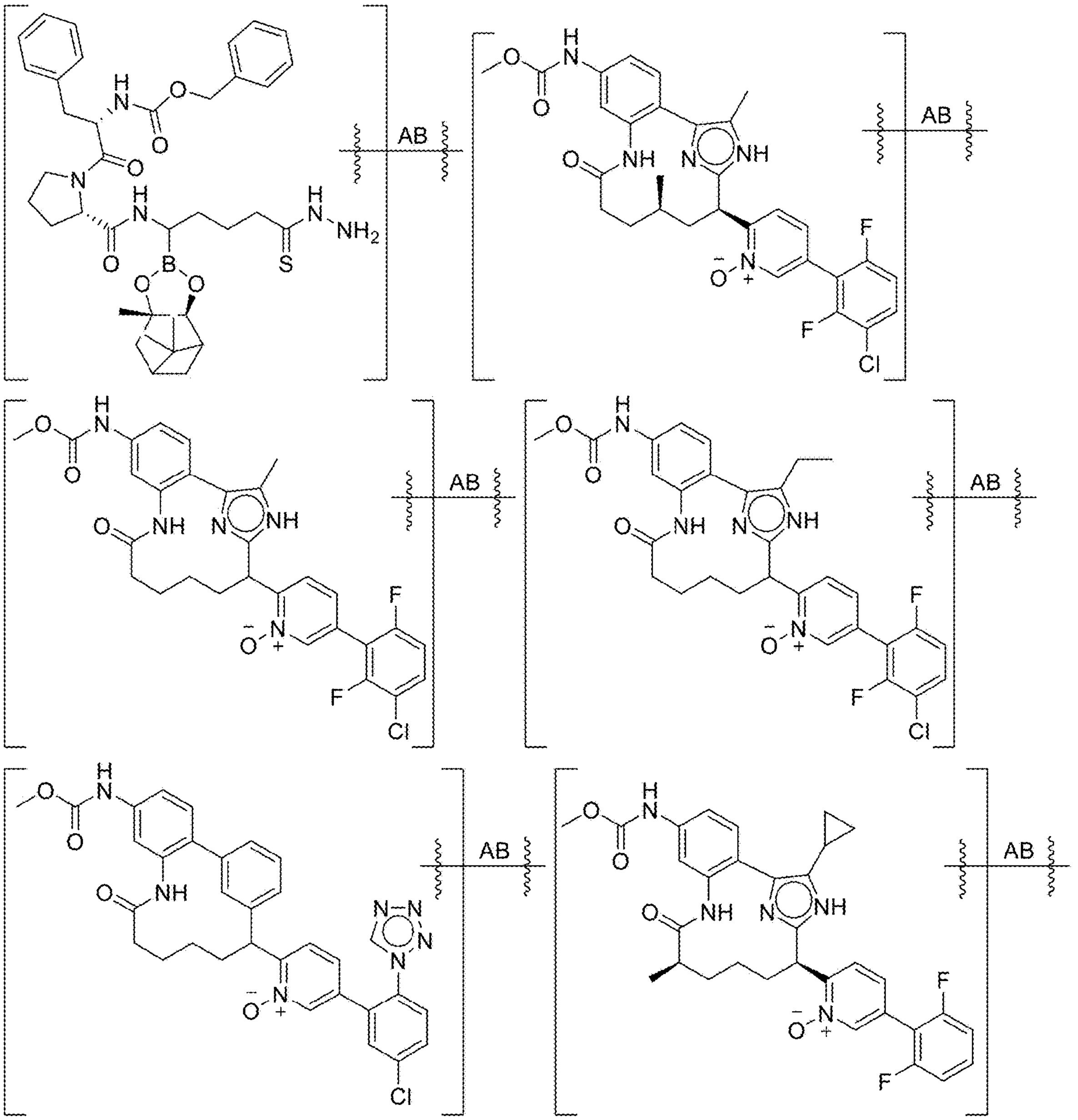
FIG. 1MMMMM

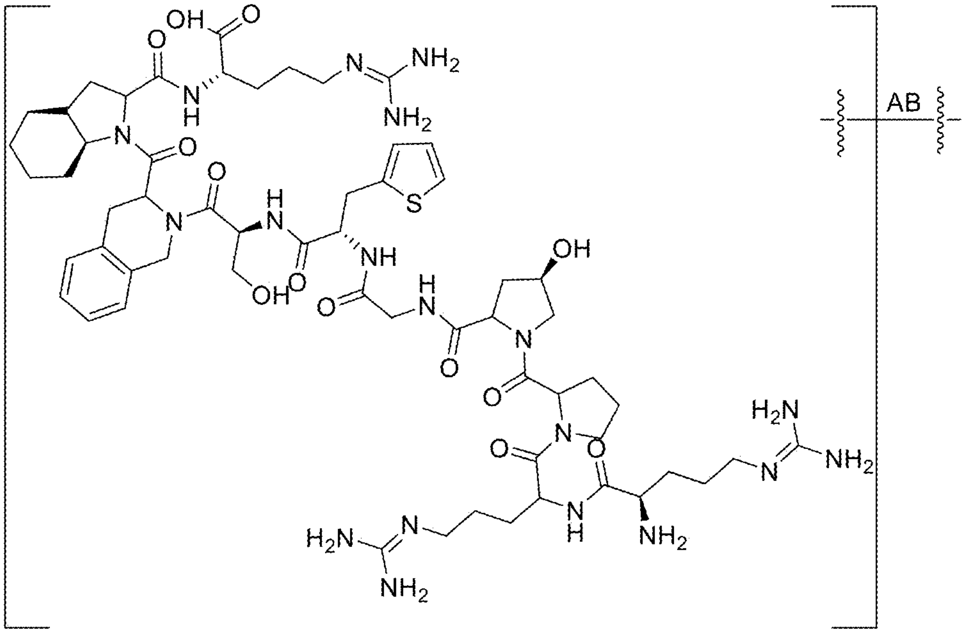
FIG. 1NNNN
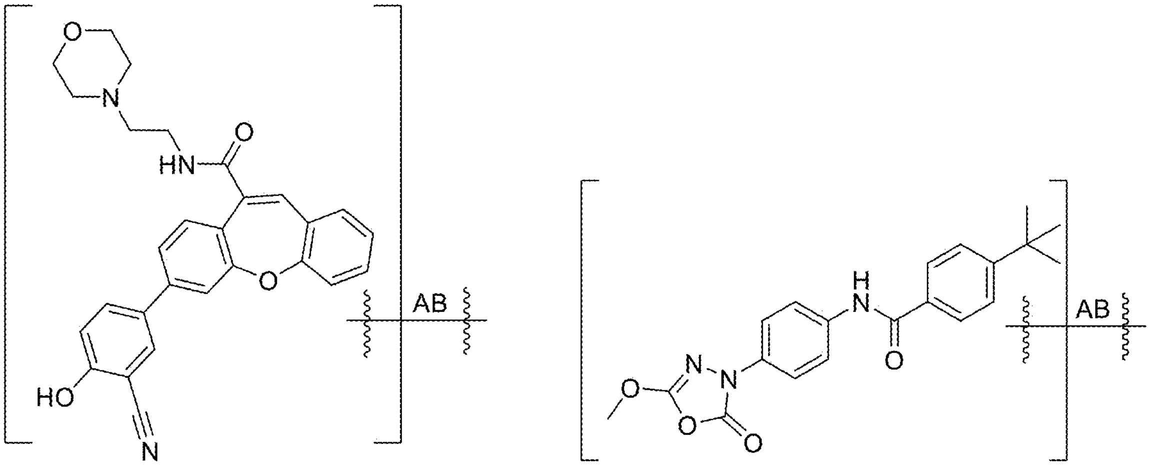
FIG 1OOOO

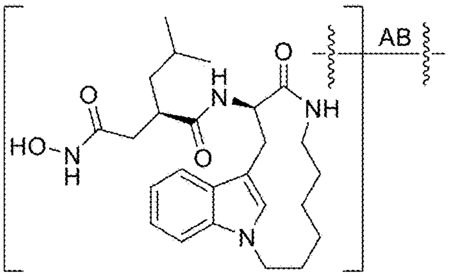
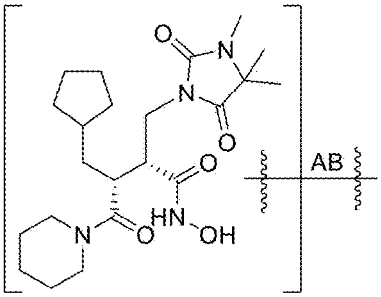
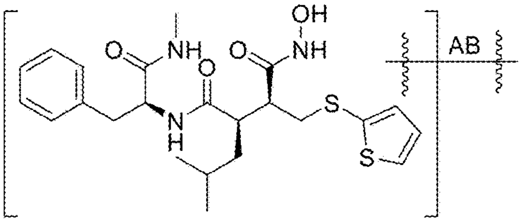
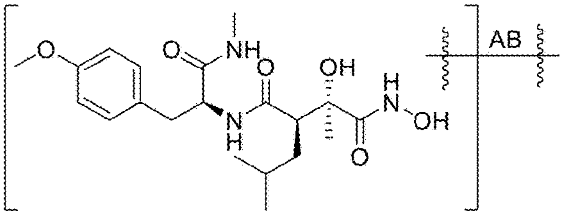
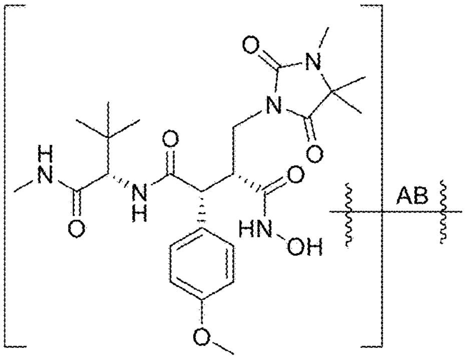
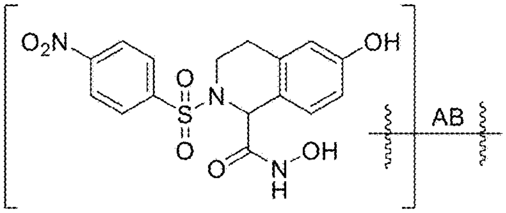
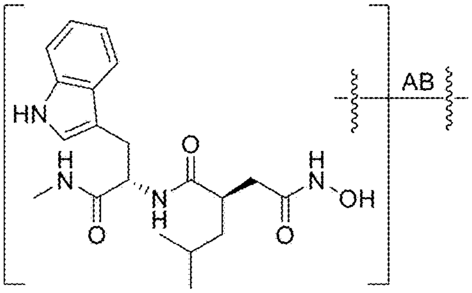
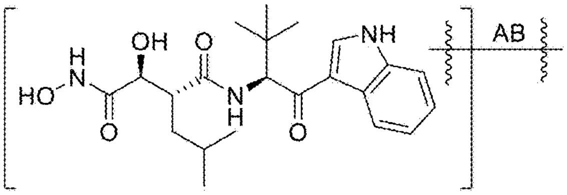
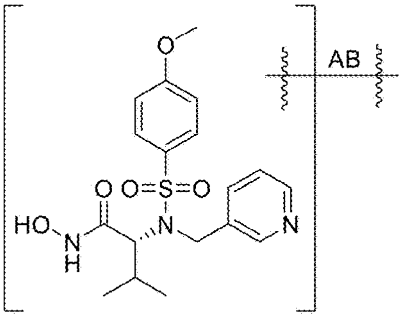
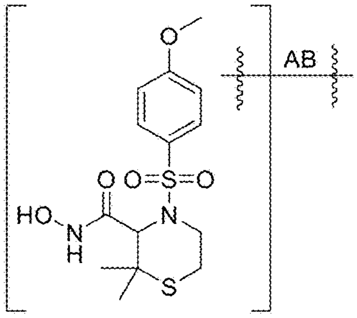
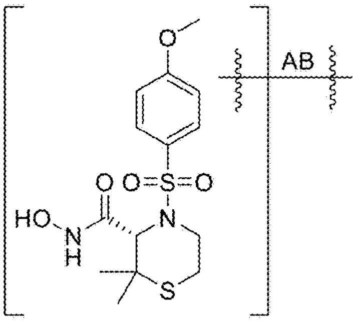
FIG. 1PPPP

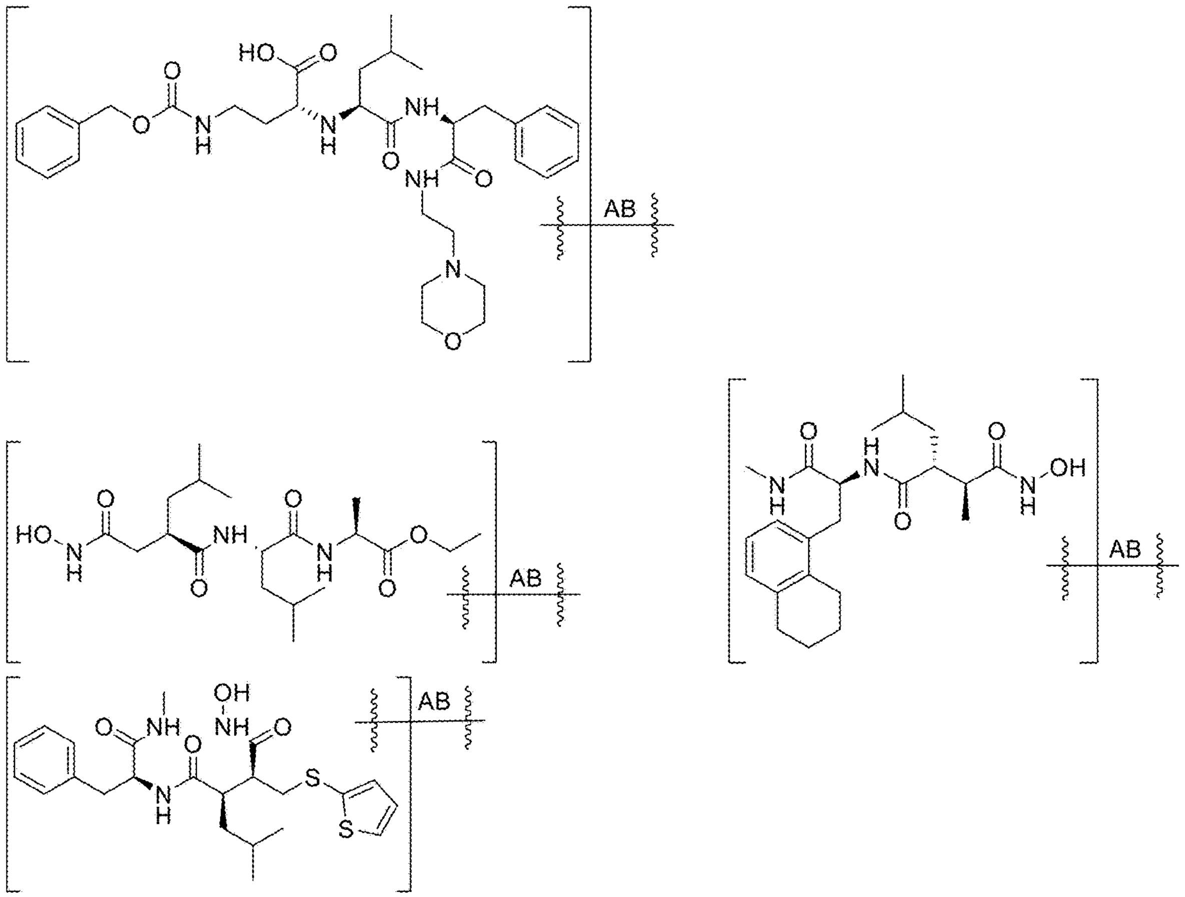
FIG. 1QQQQ
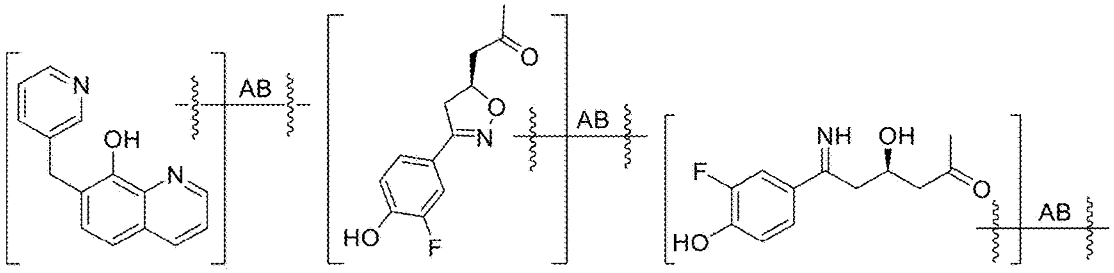
FIG. 1RRRR

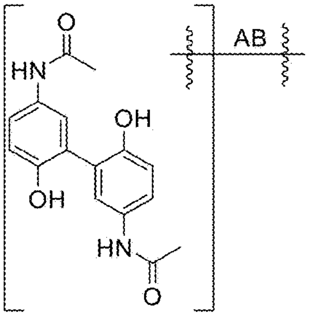
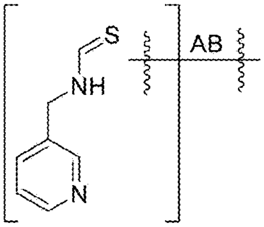
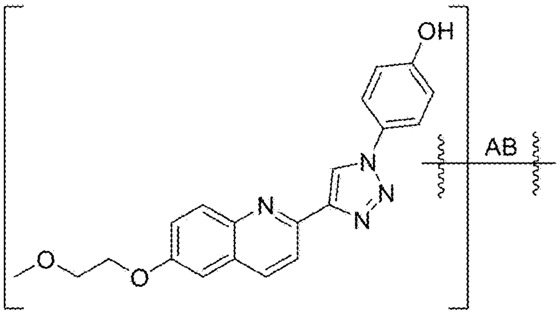
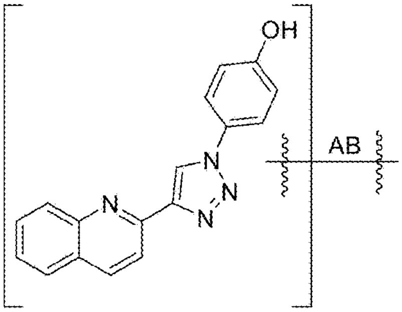
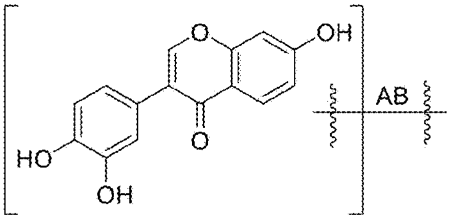
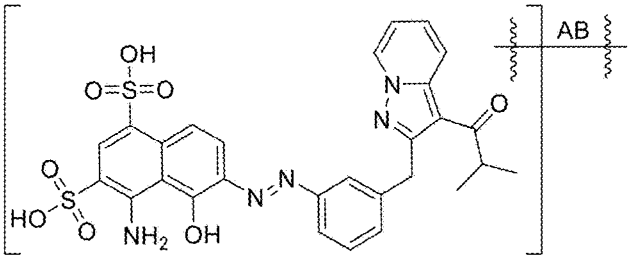
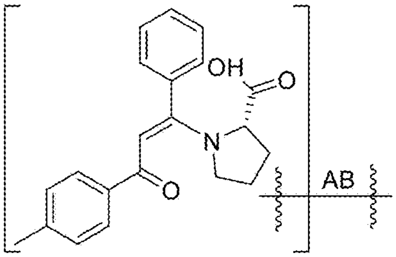
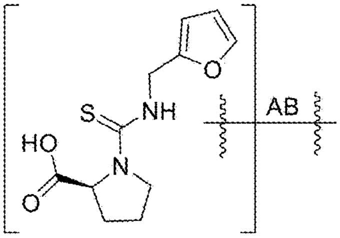
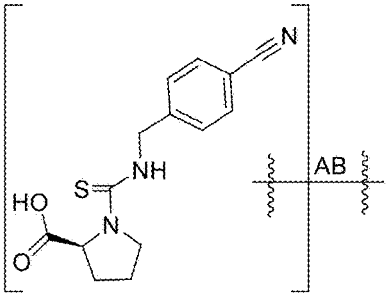
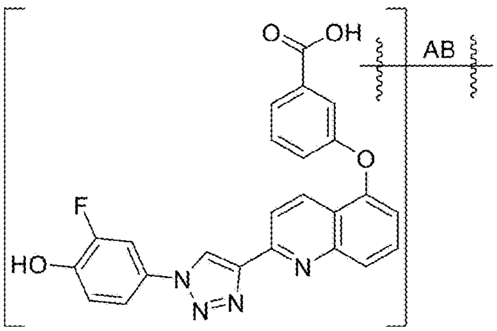
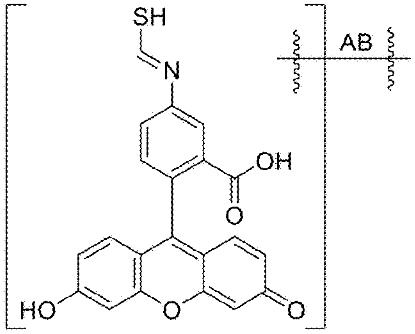
FIG. 1SSSS

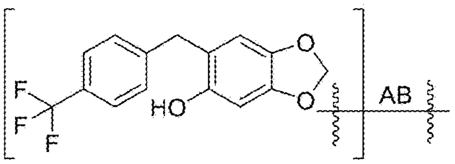
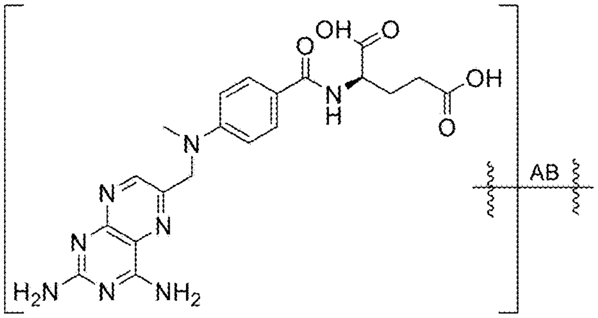
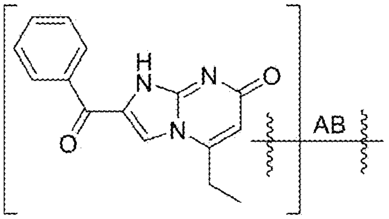
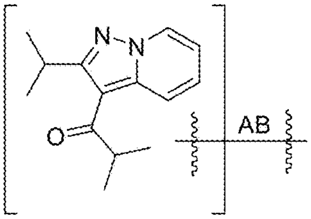
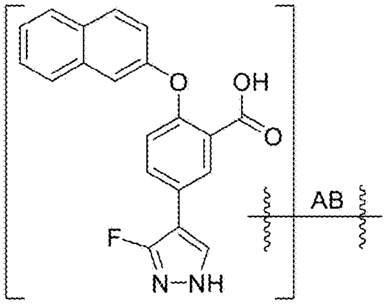
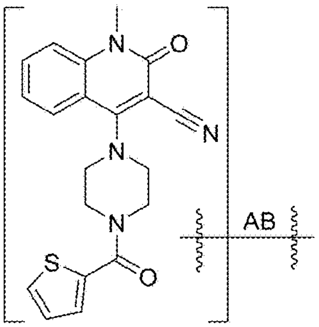
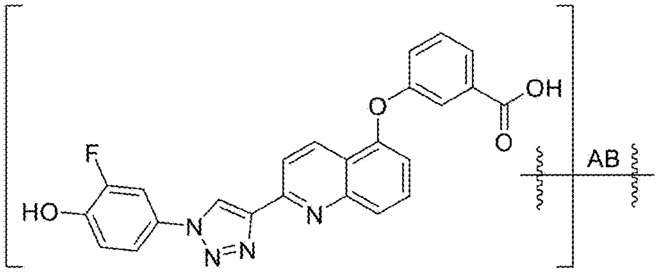
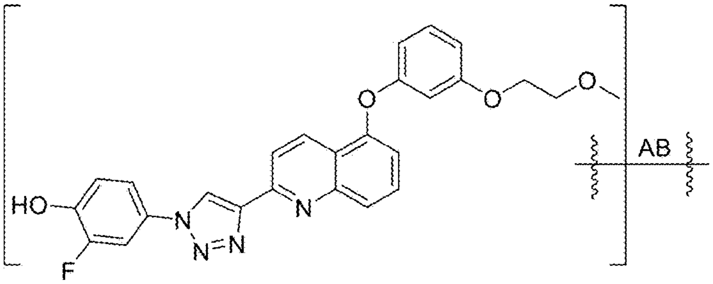
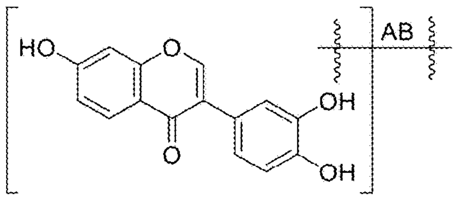
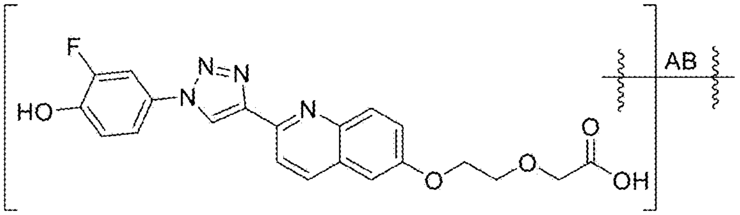
FIG. 1TTTT

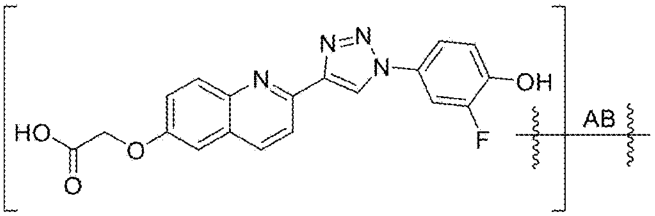
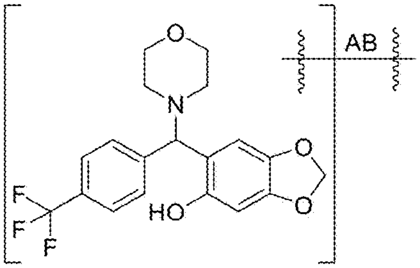
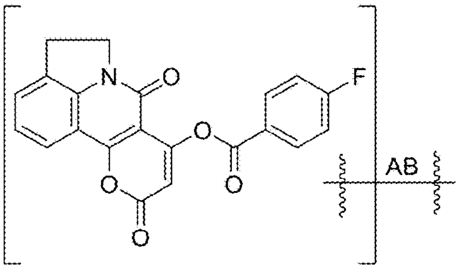
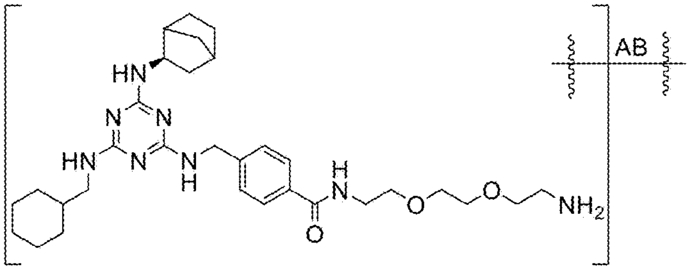
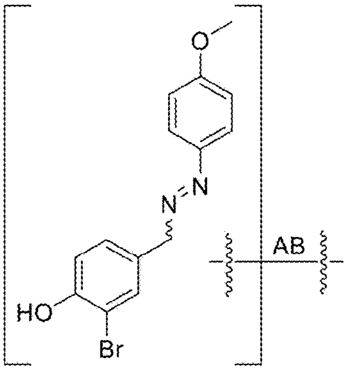
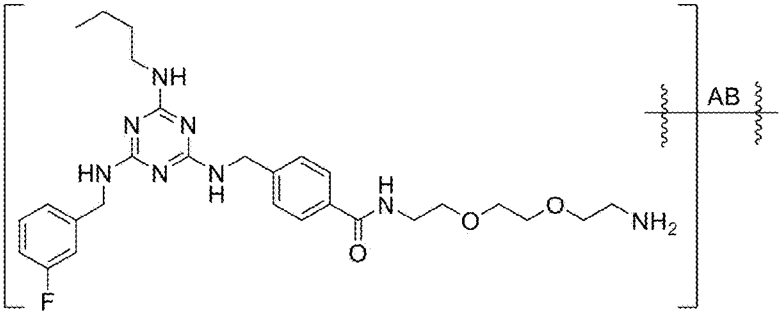
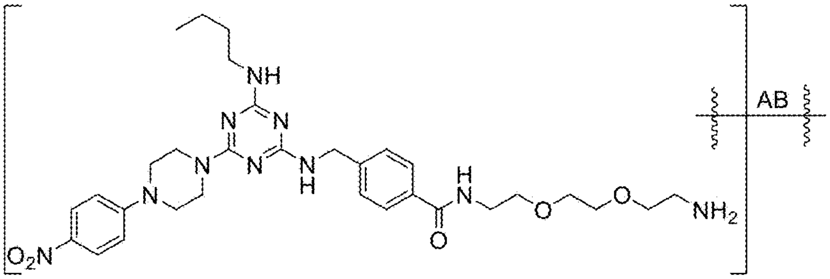
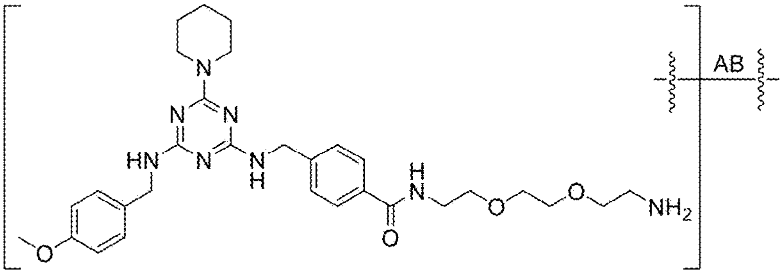
FIG. 1UUUU

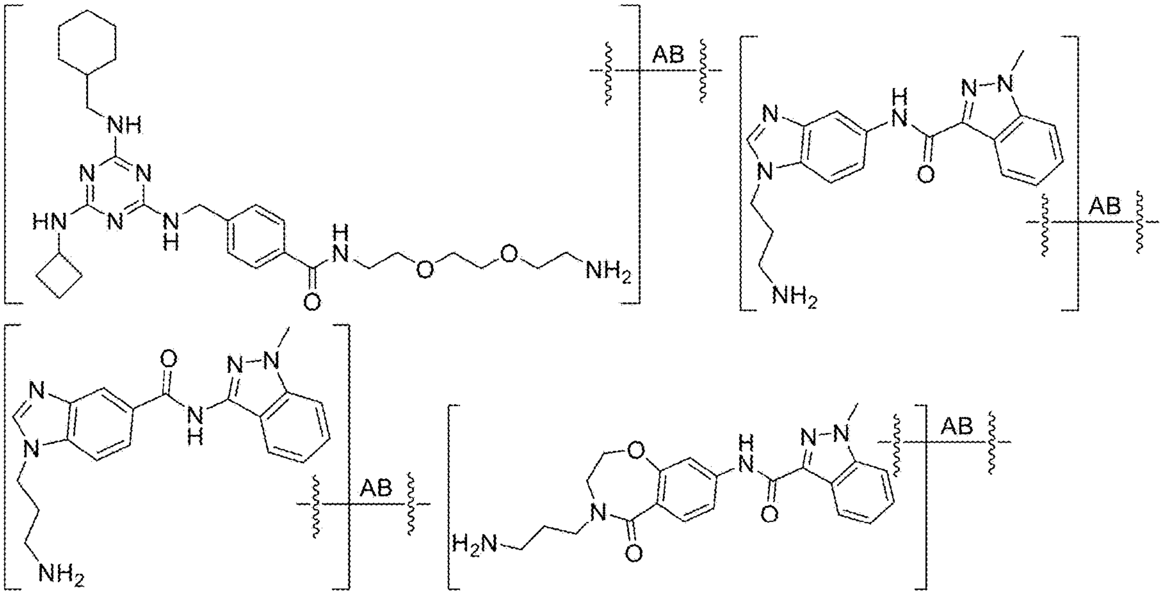
FIG. 1VVVV
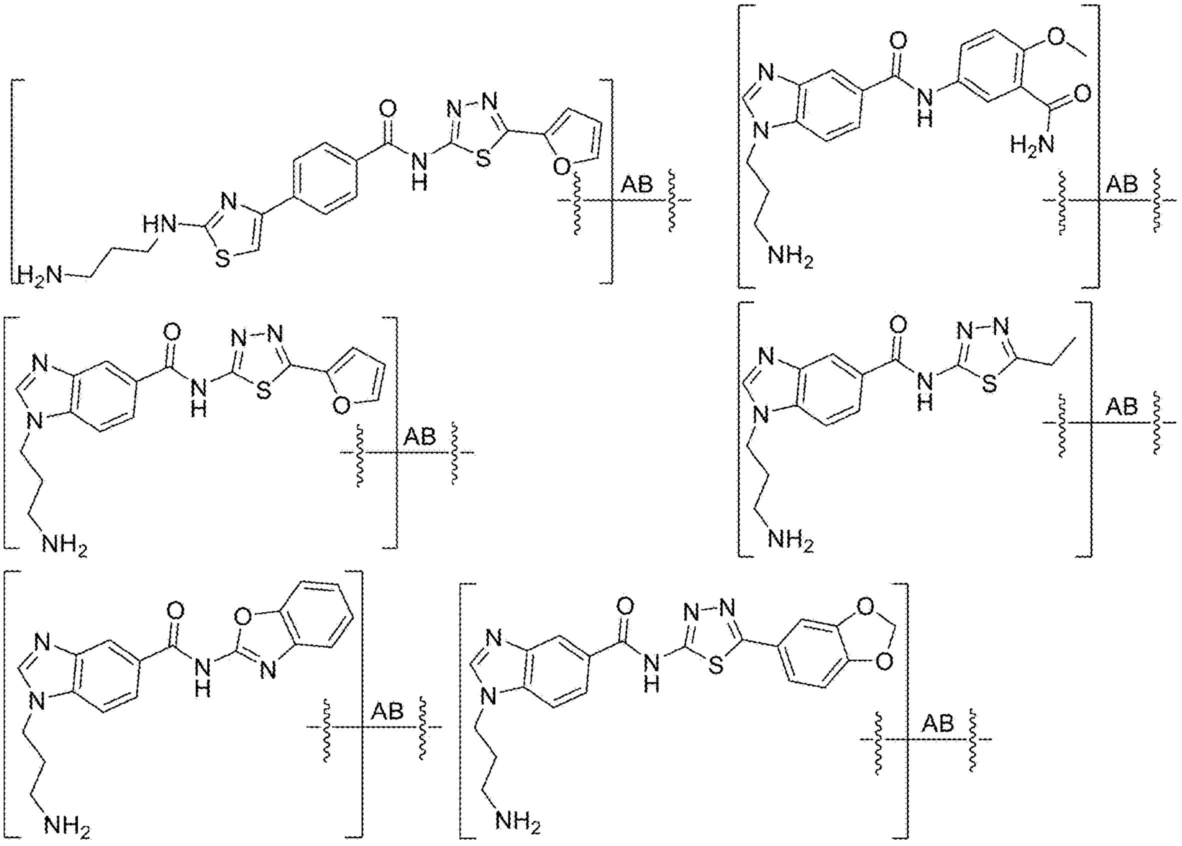
FIG. 1WWWW

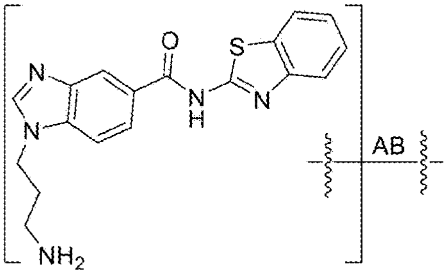
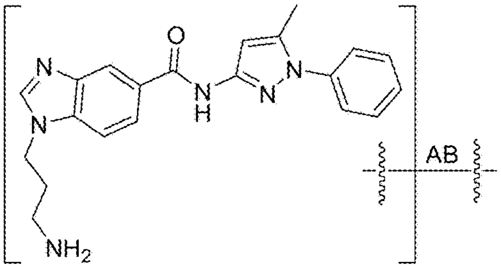
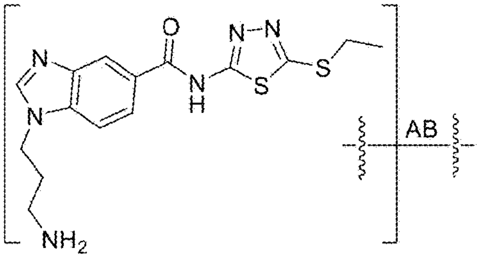
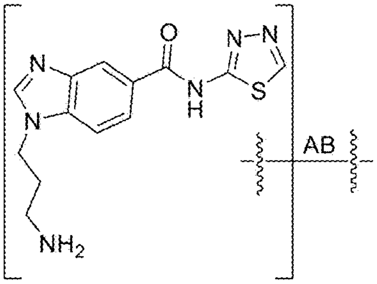
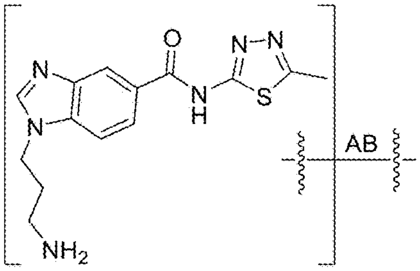
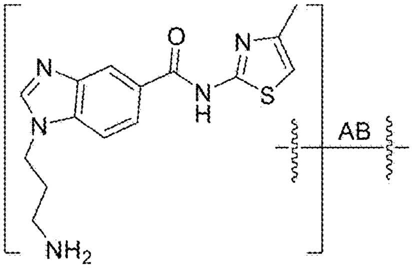
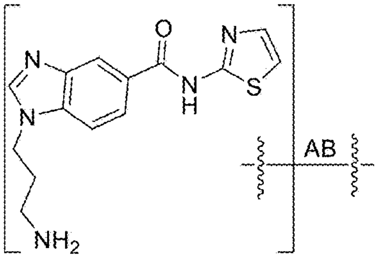
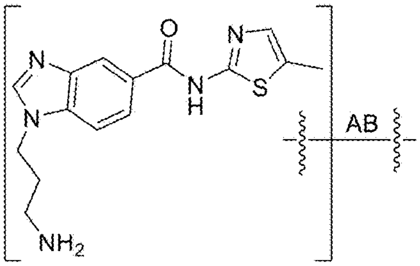
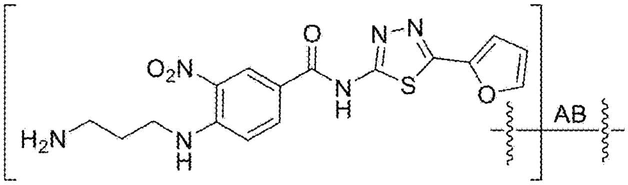
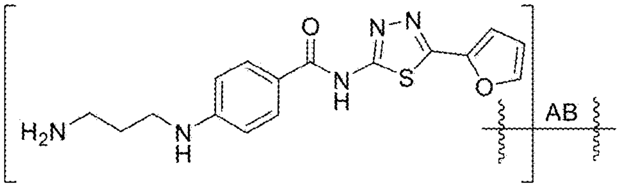
FIG. 1XXXX

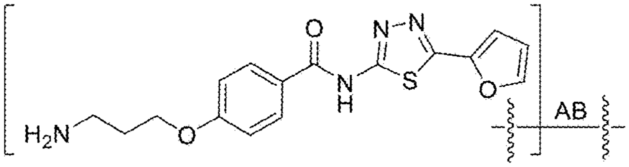
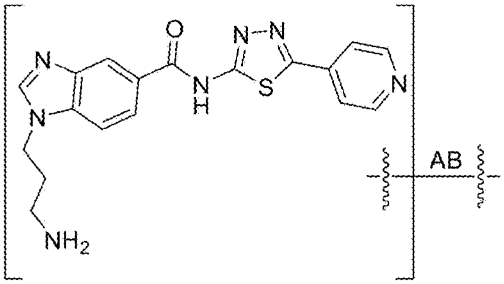
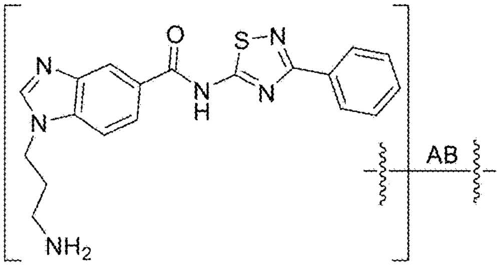
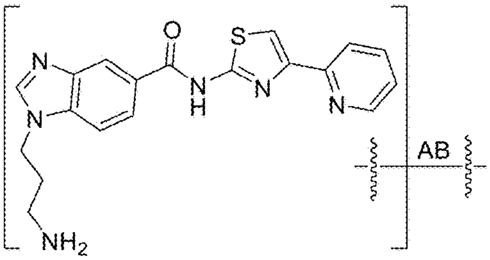
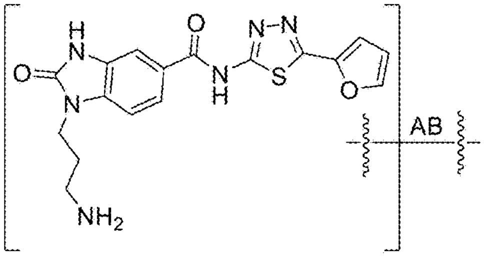
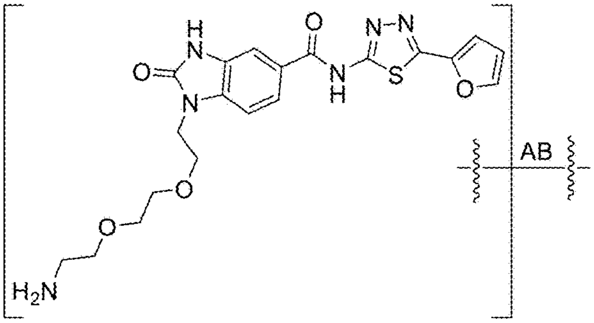
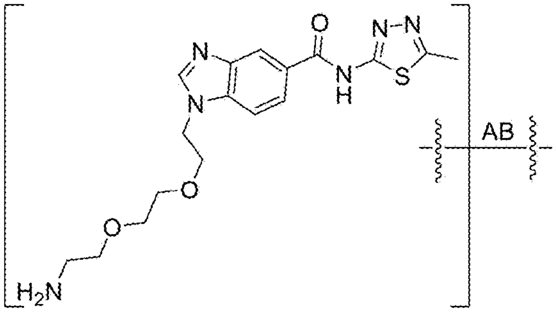
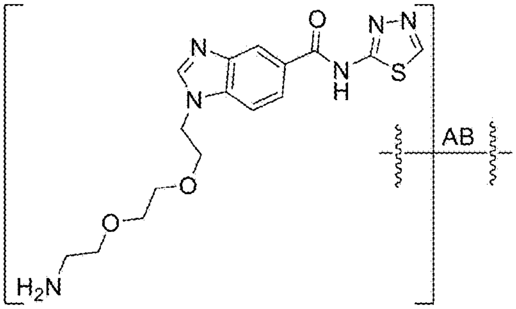
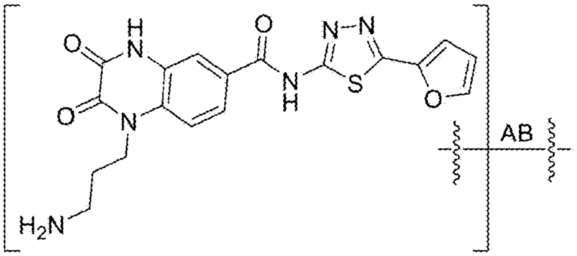
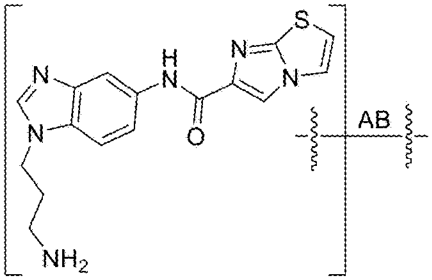
FIG. 1YYYY

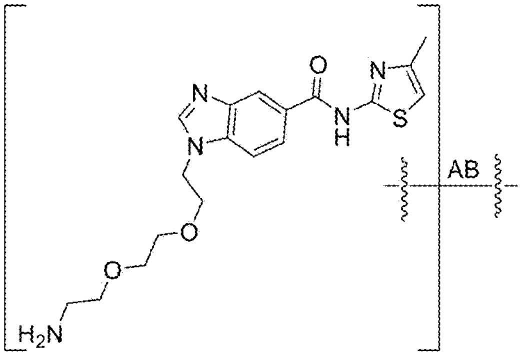
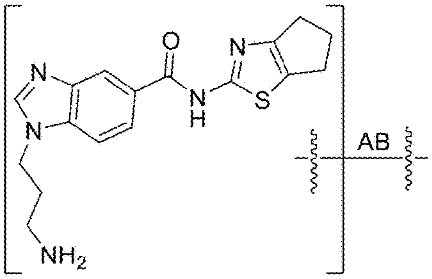
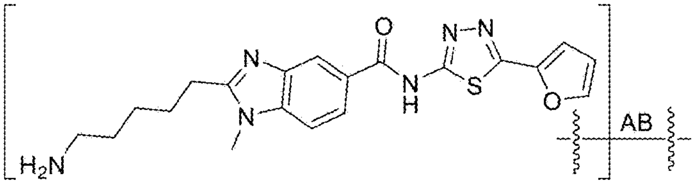
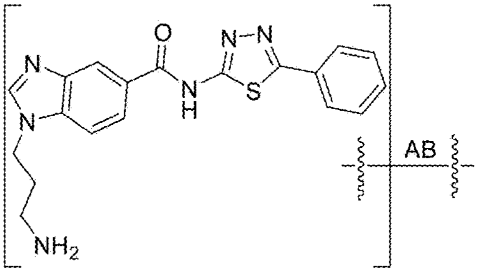
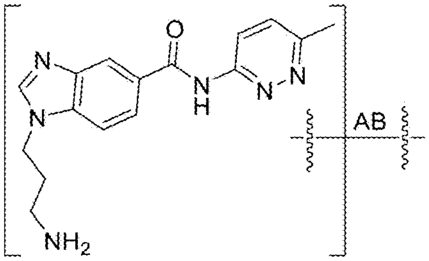
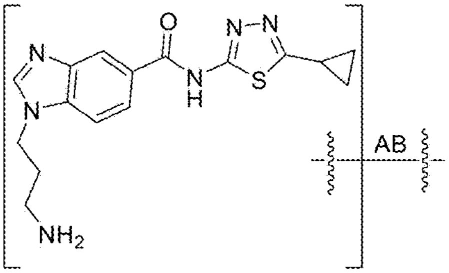
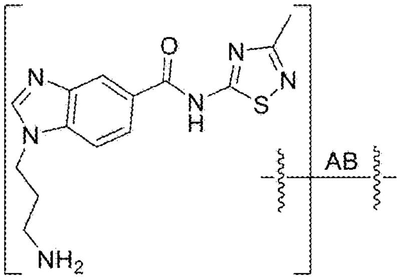
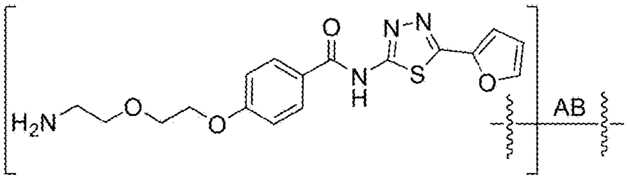
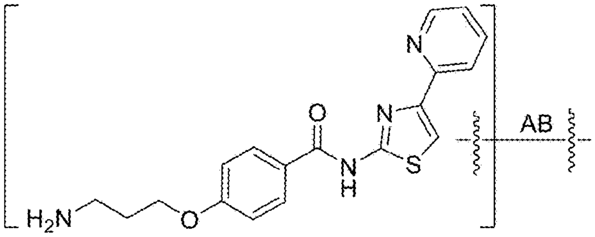
FIG. 1ZZZZ

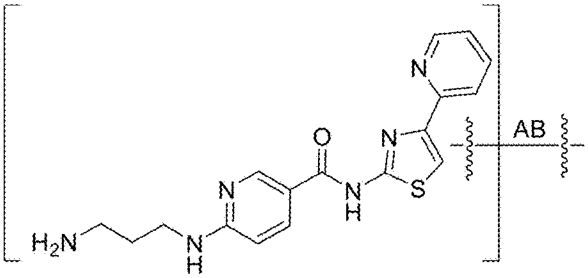
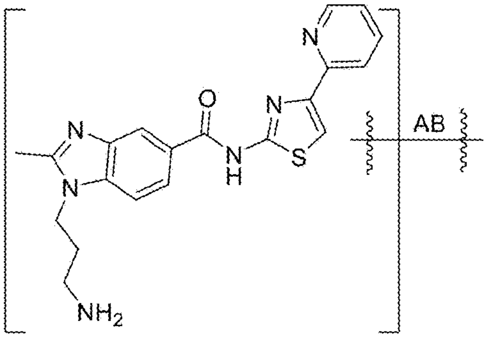
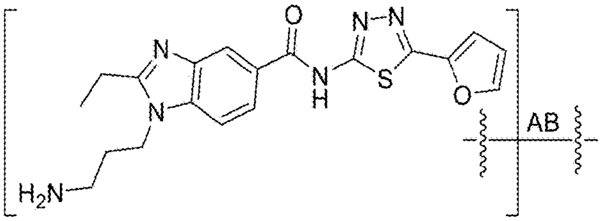
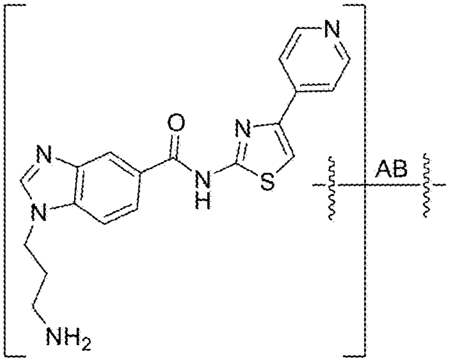
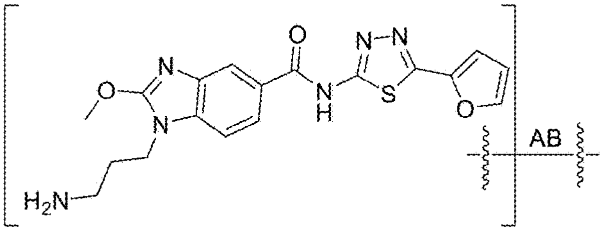
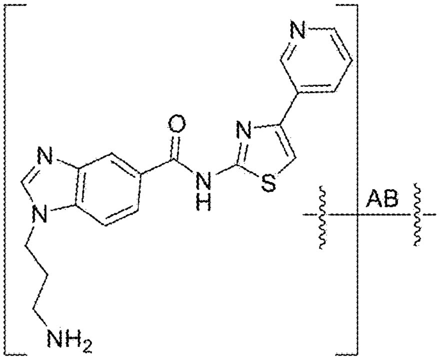
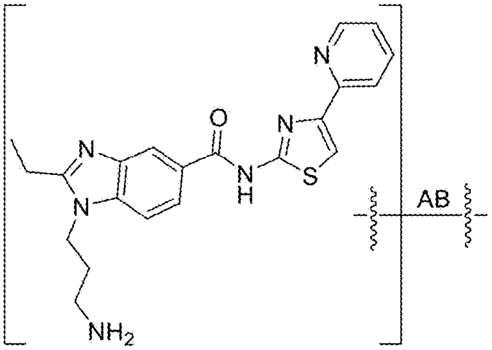
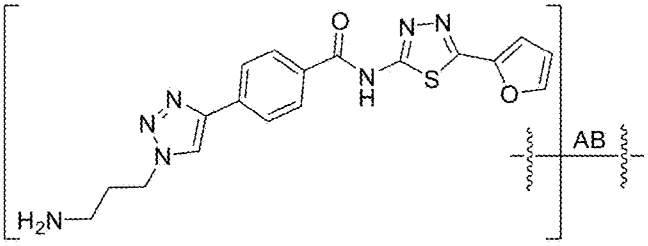
FIG. 1AAAAA

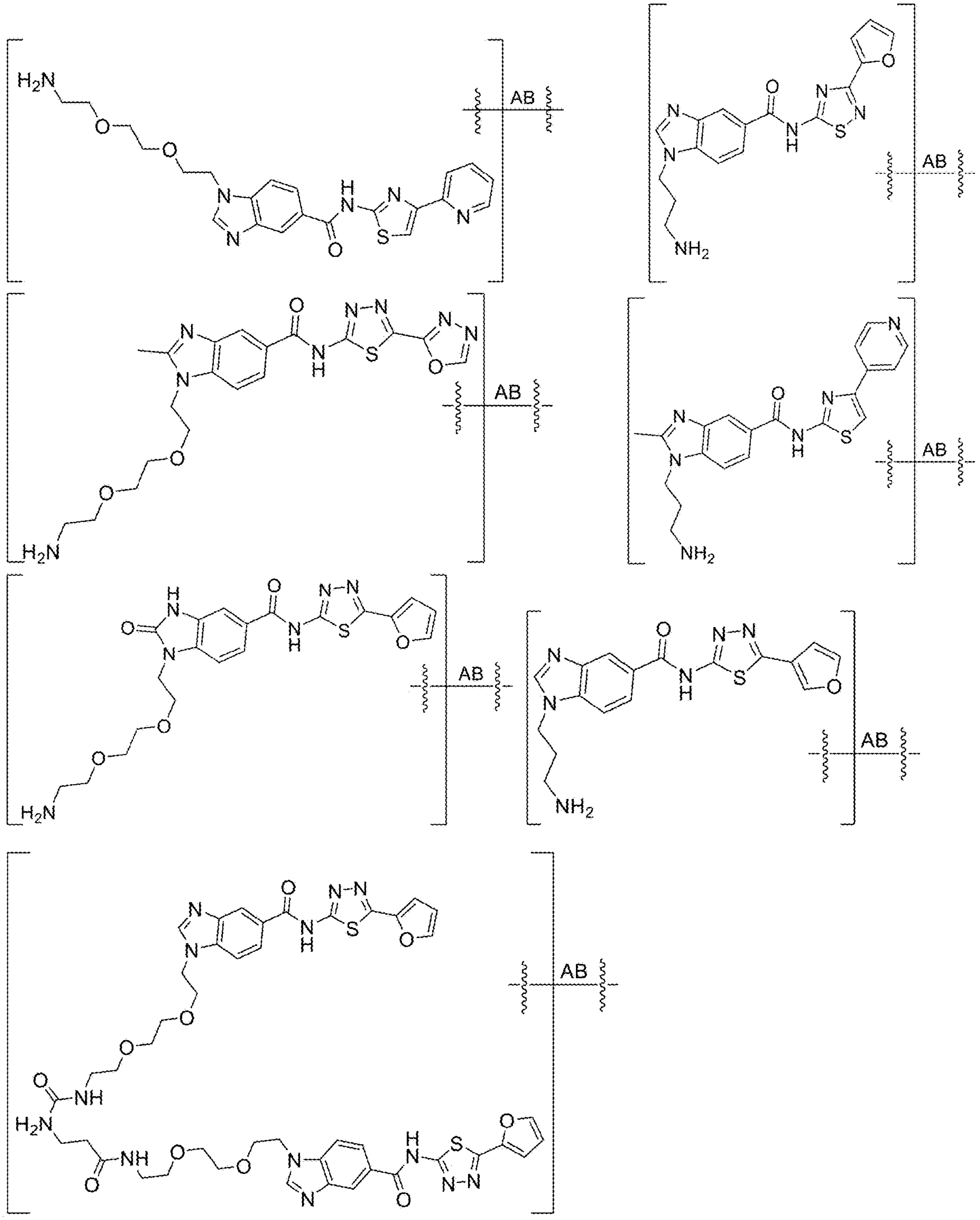
FIG. 1BBBBBB

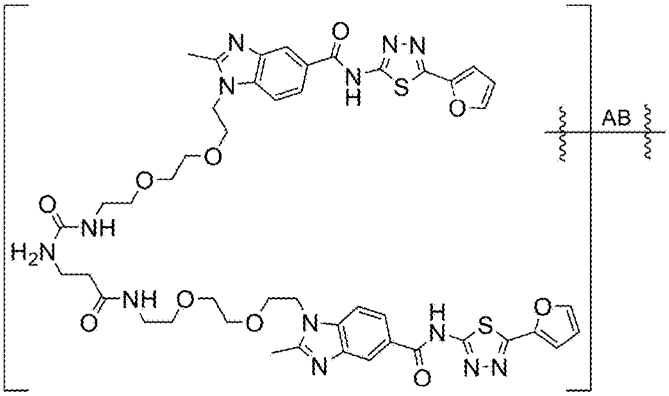
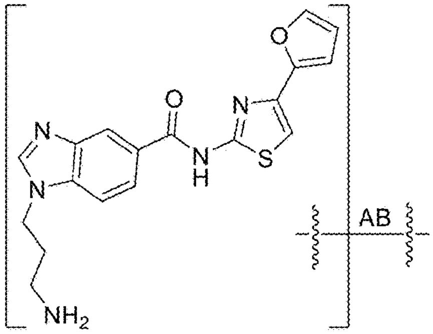
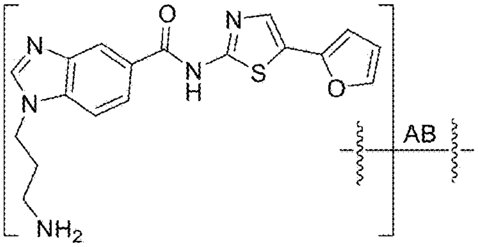
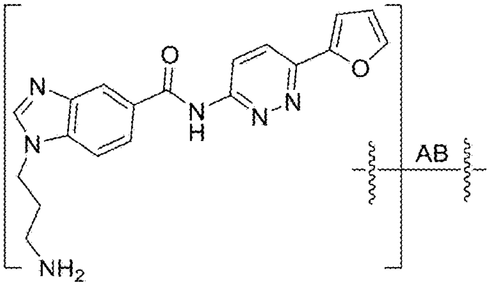
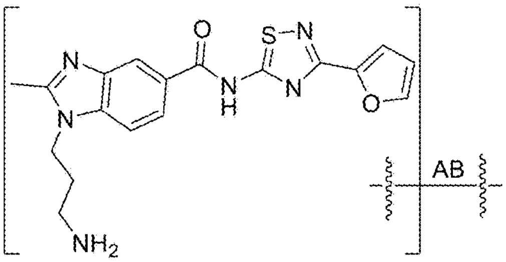
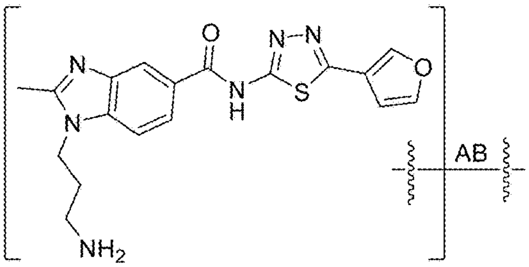
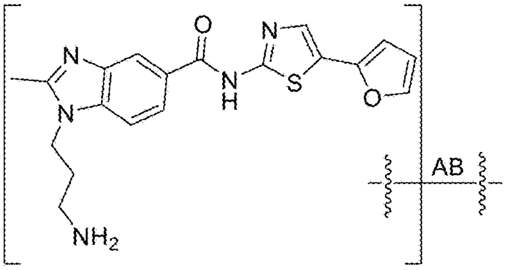
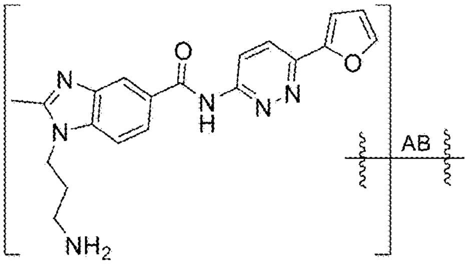
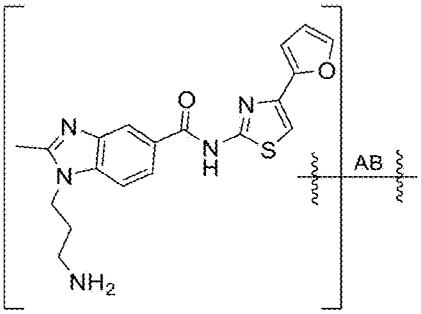
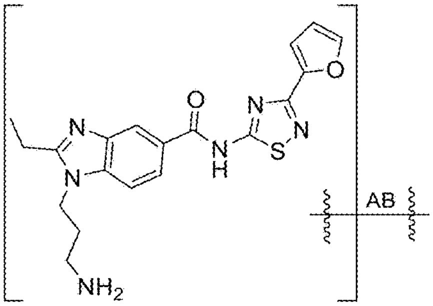
FIG. 1CCCCC

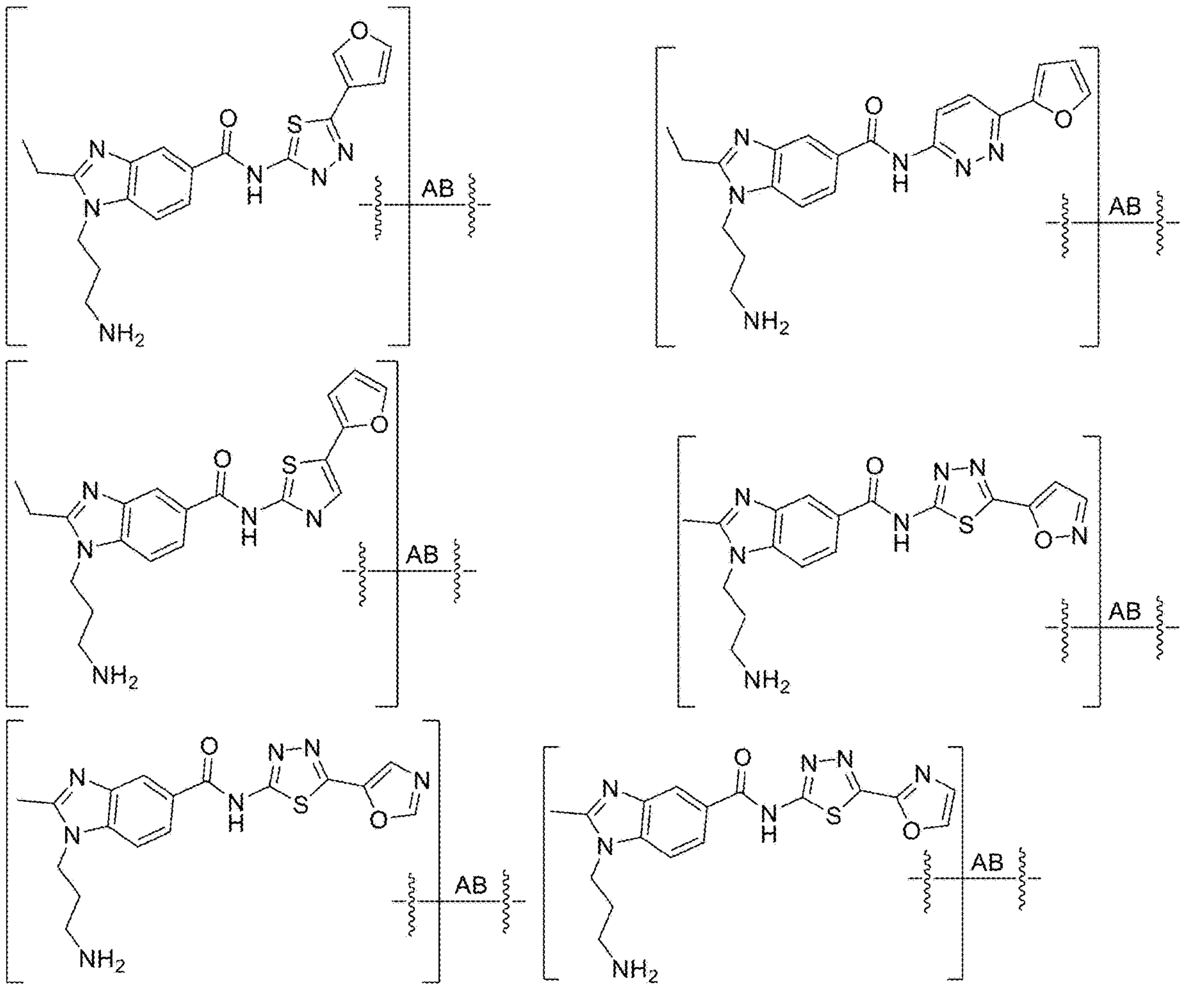
FIG. 1DDDDD

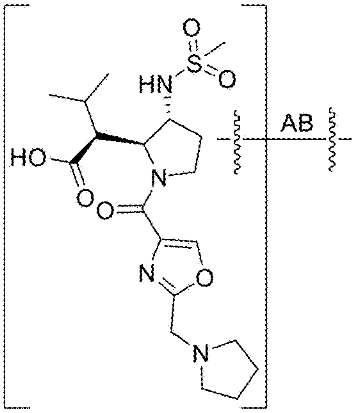
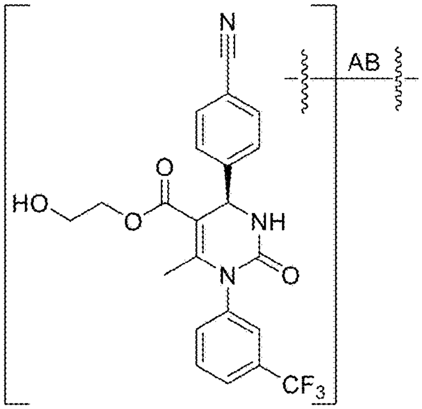
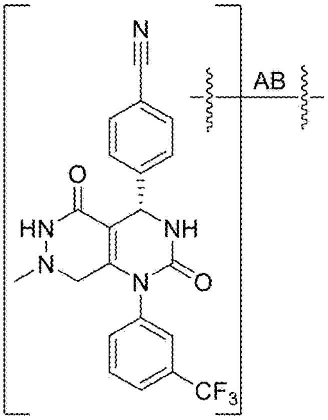
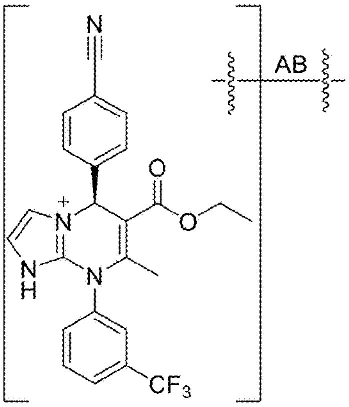
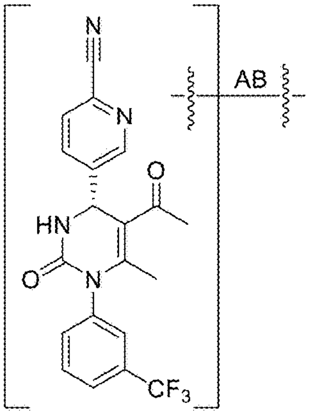
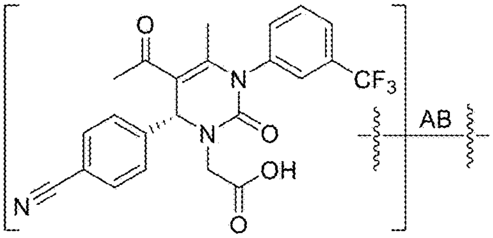
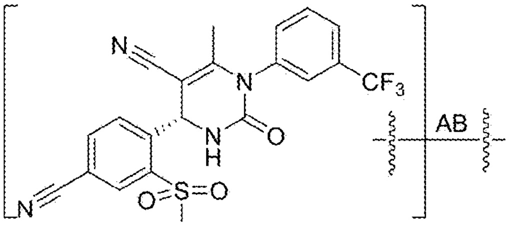
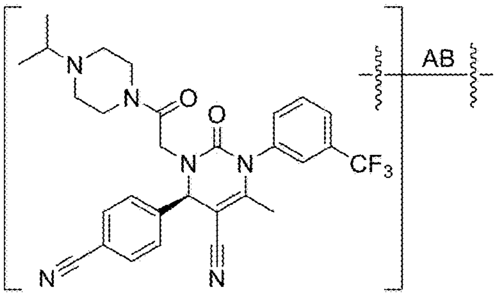
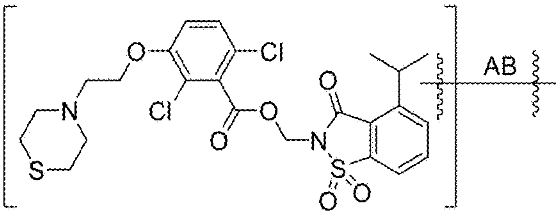
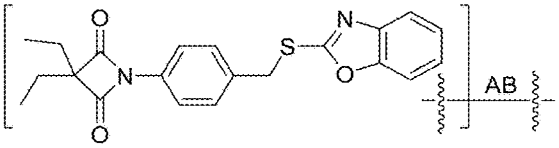
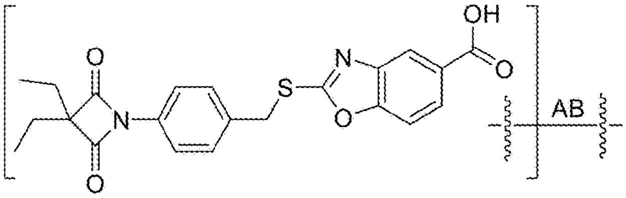
FIG. 1EEEEE

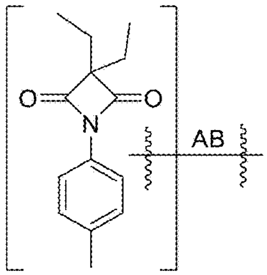
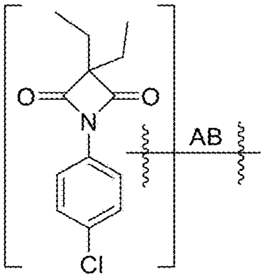
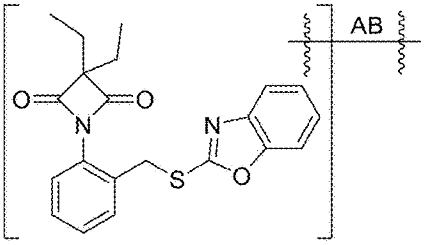
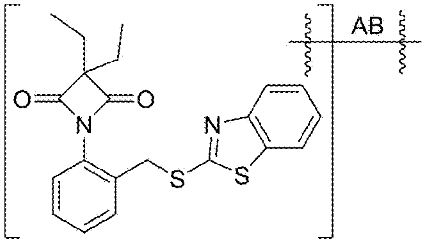
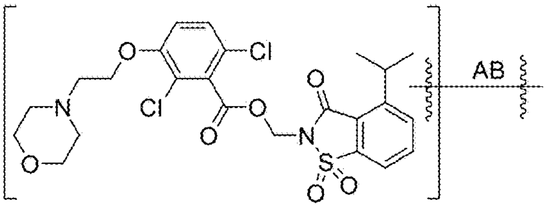
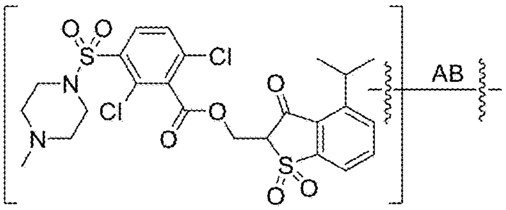
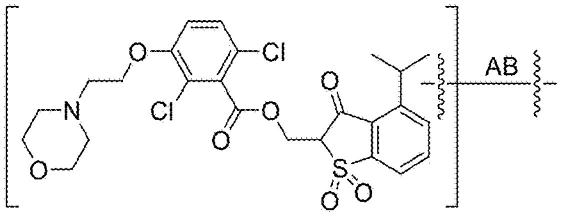
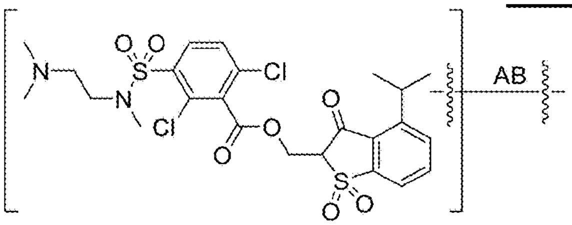
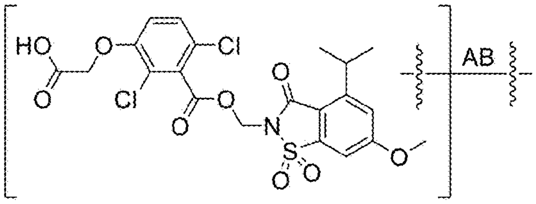
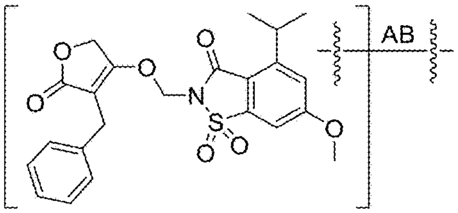
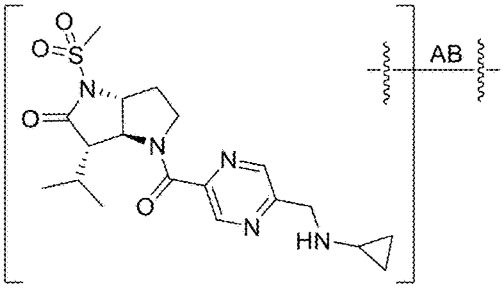
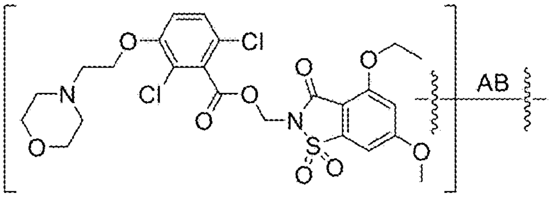
FIG. 1FFFFF

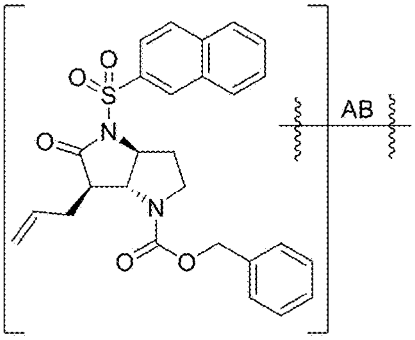
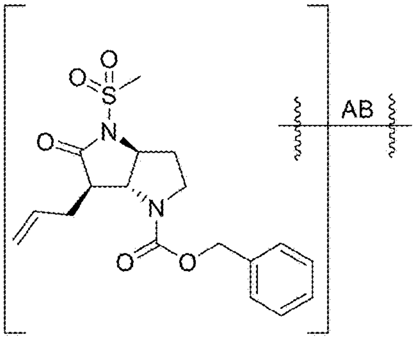
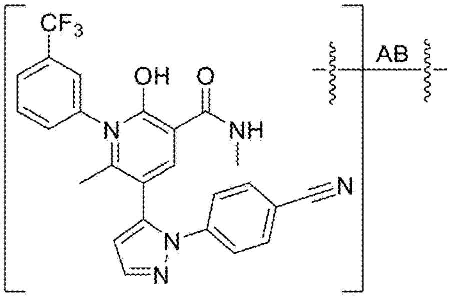
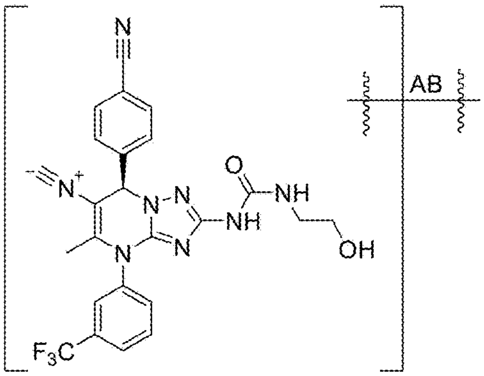
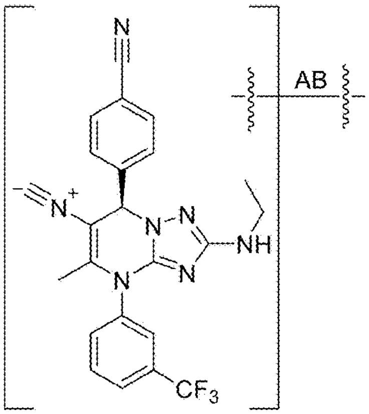
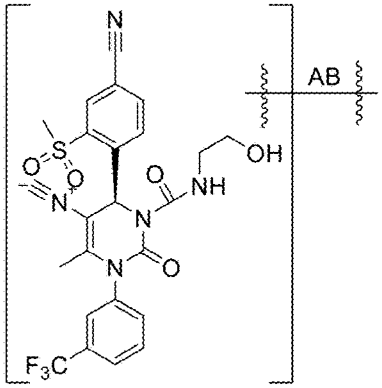
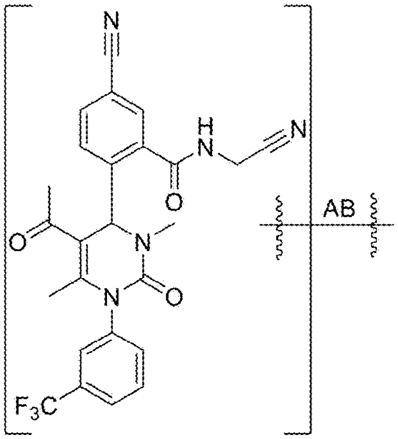
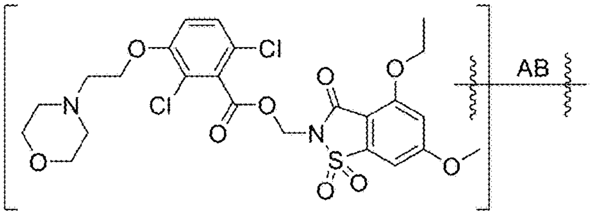
FIG. 1GGGGG

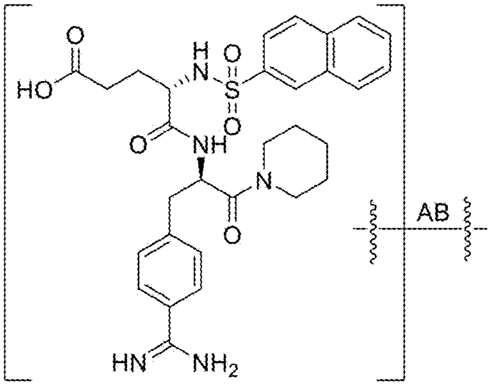
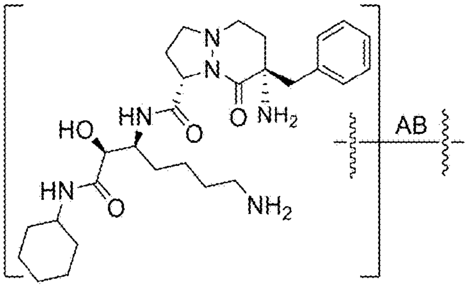
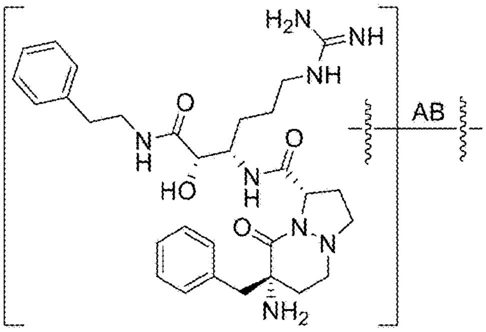
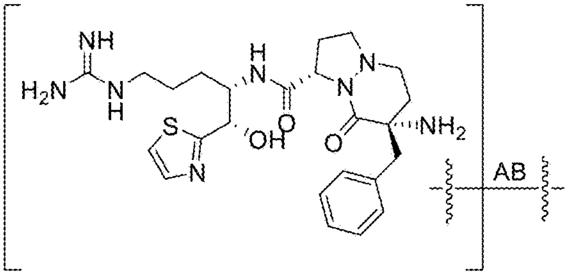
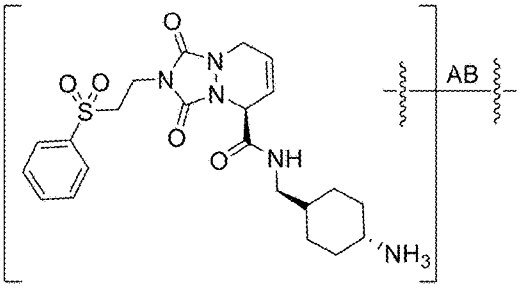
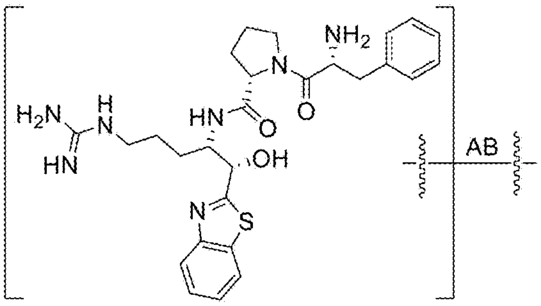
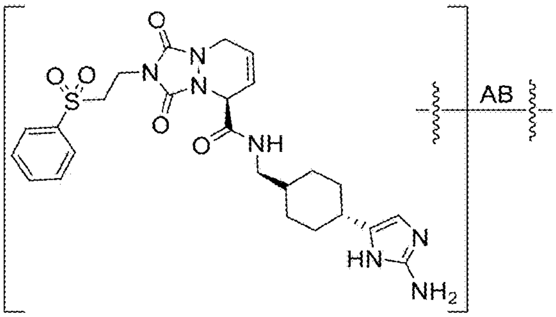
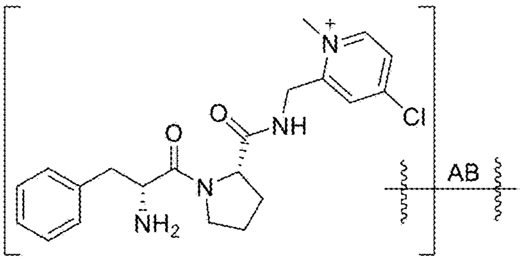
FIG. 1HHHHH

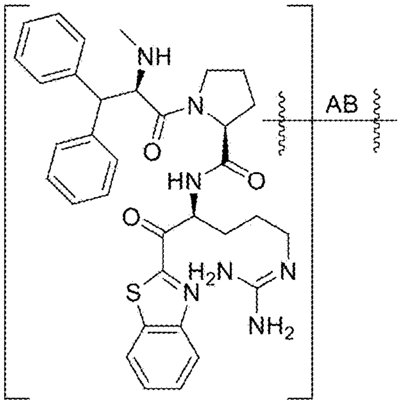
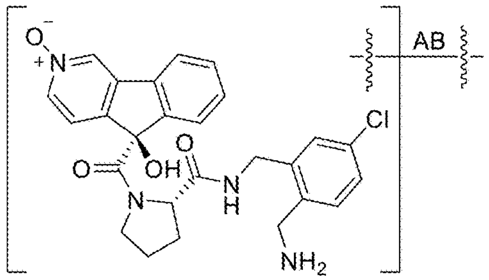
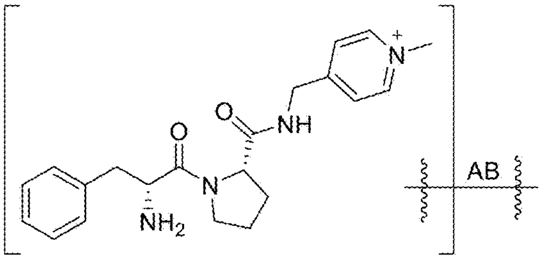
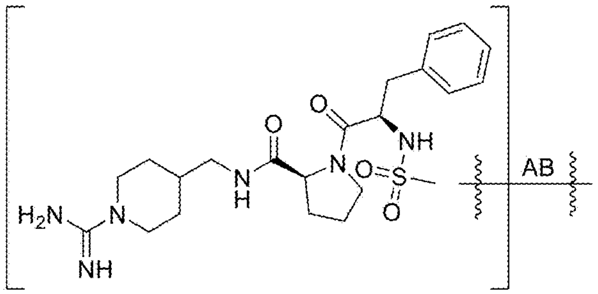
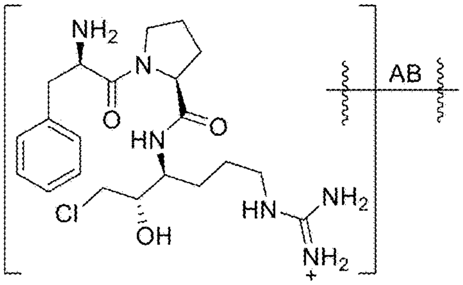
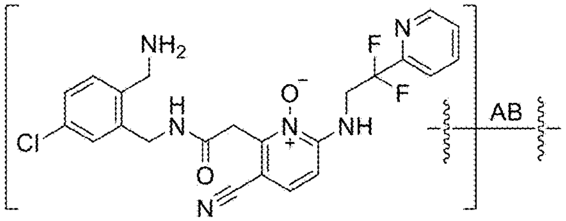
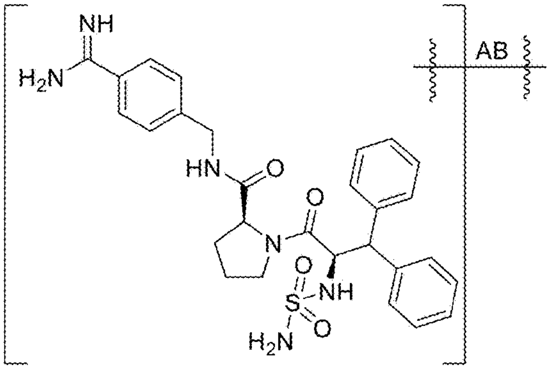
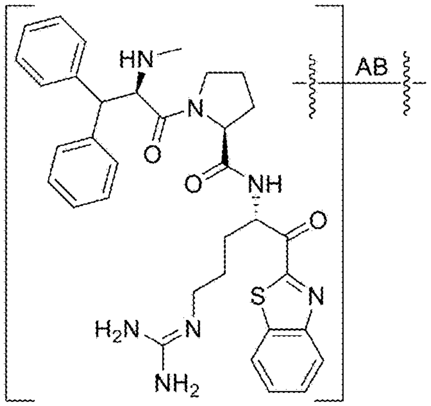
FIG. 1IIIII

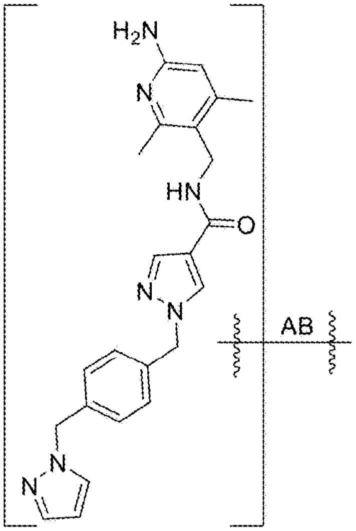
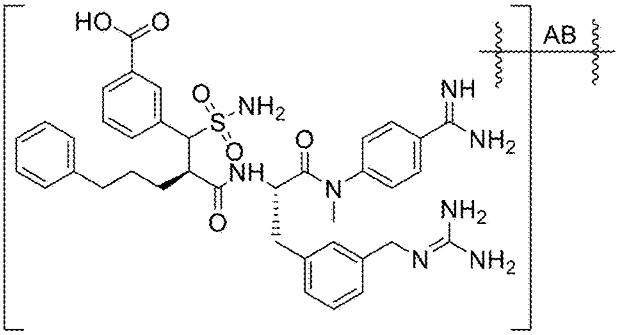
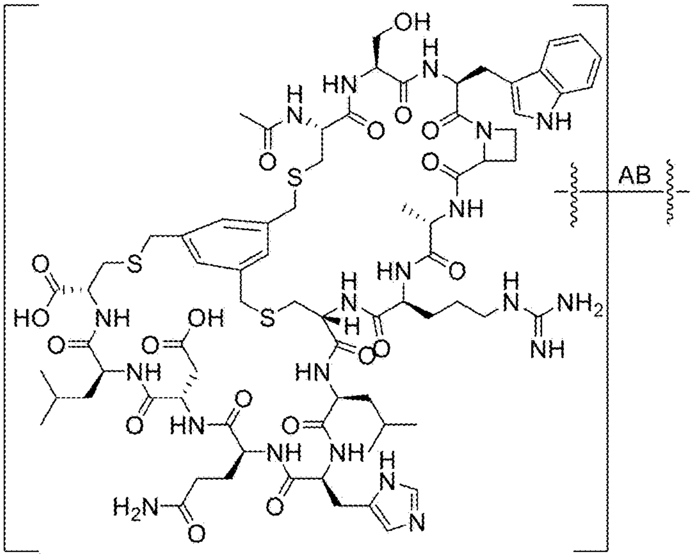
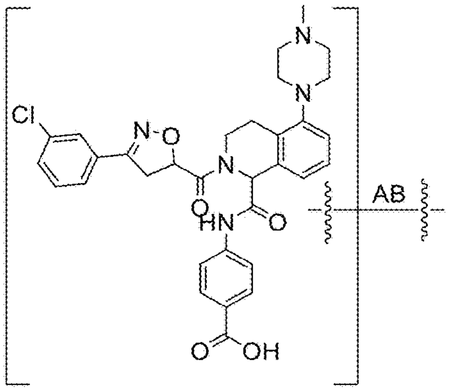
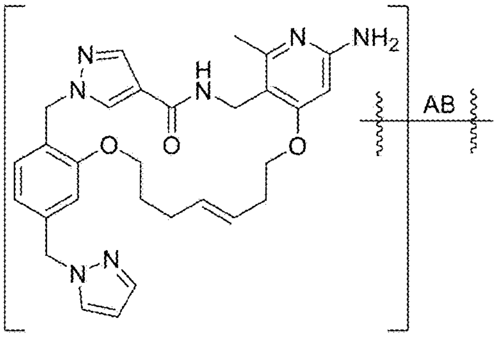
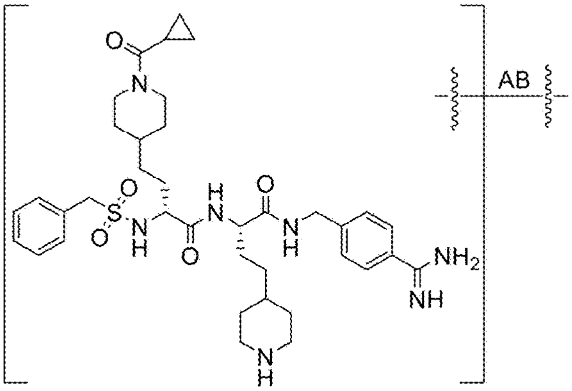
FIG. 1JJJJJ

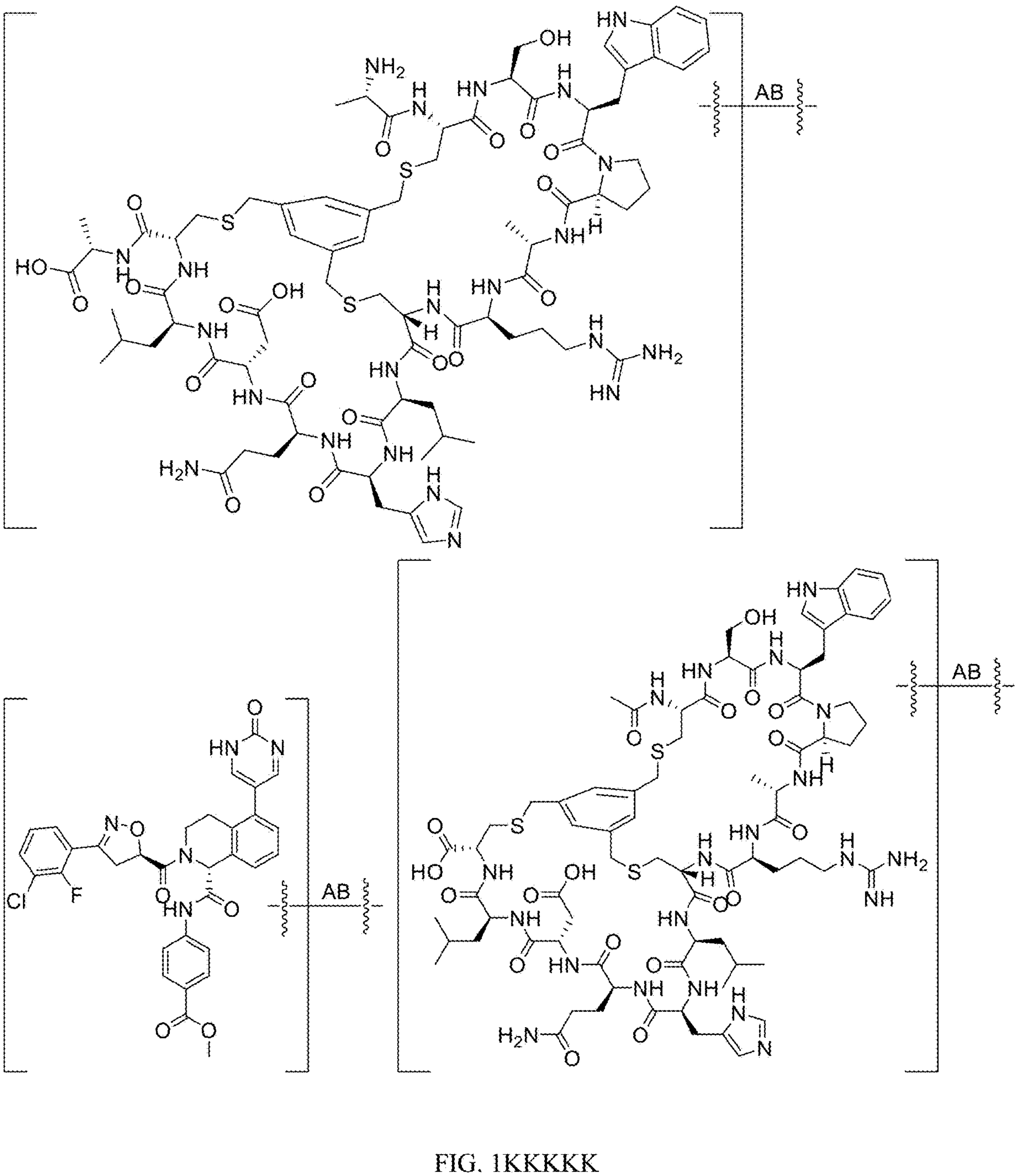
FIG. 1KKKKK

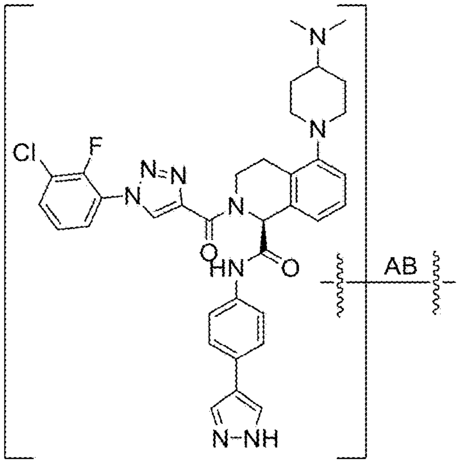
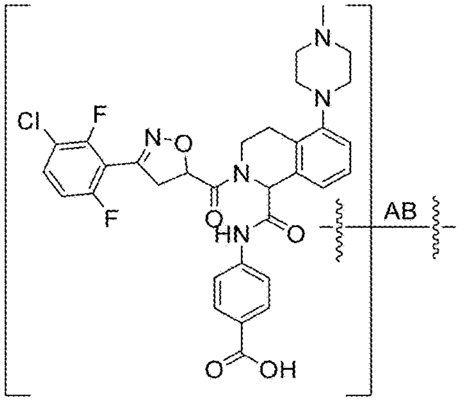
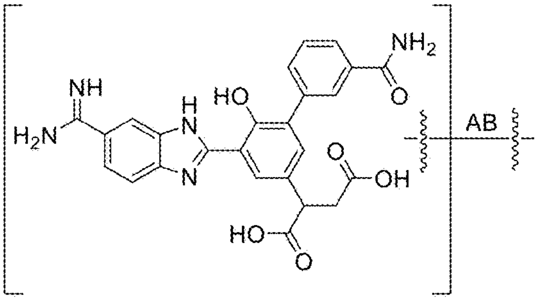
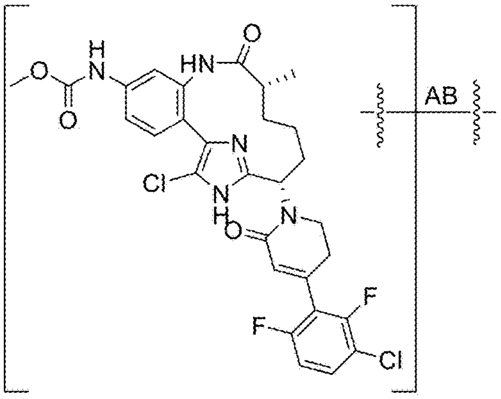
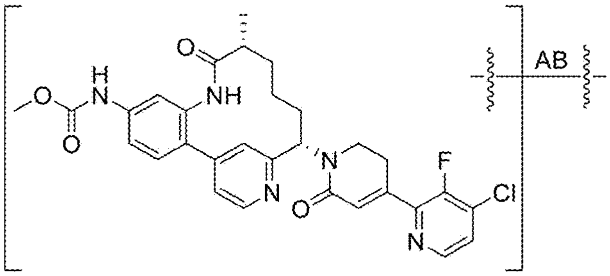
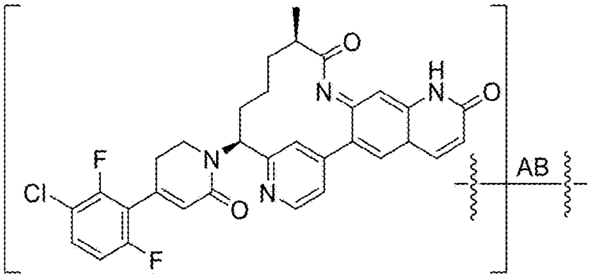
FIG. 1LLLLL

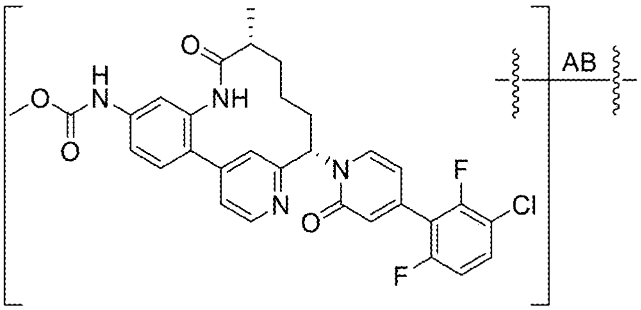
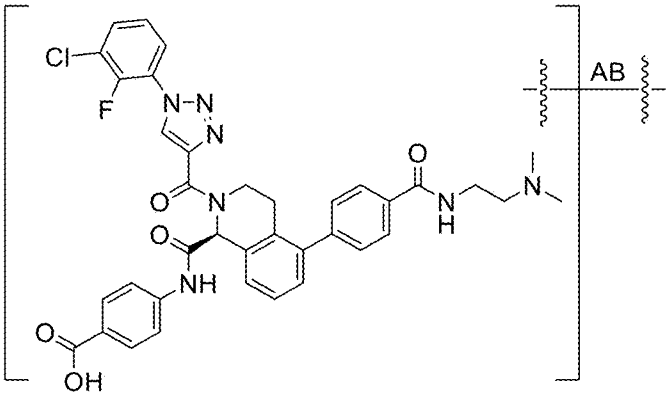
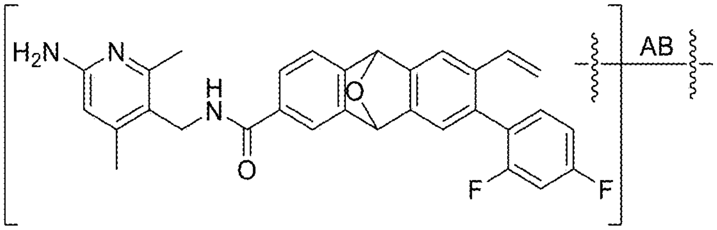
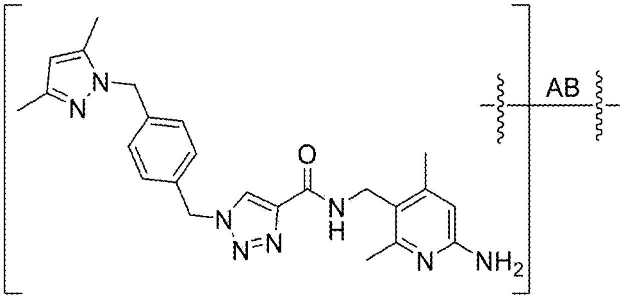
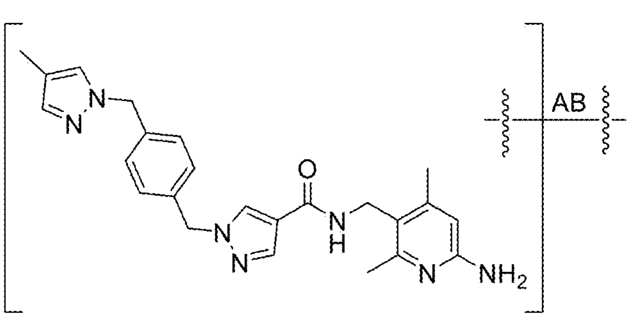
FIG. 1MMMMM

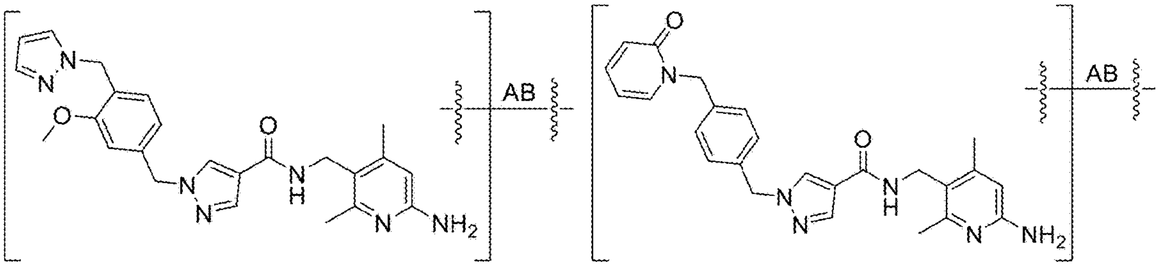
FIG. 1NNNNN
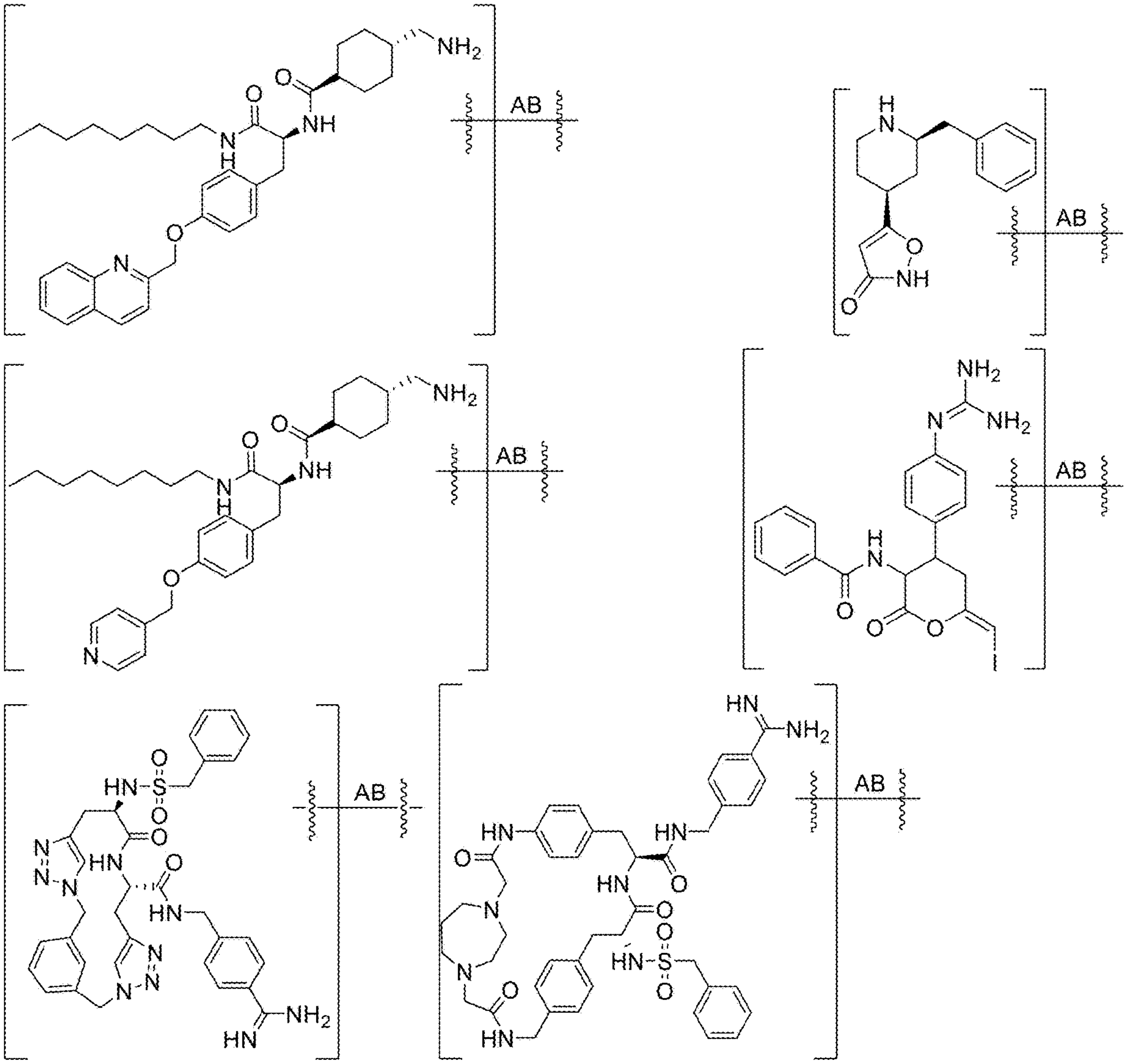
FIG. 1OOOOO

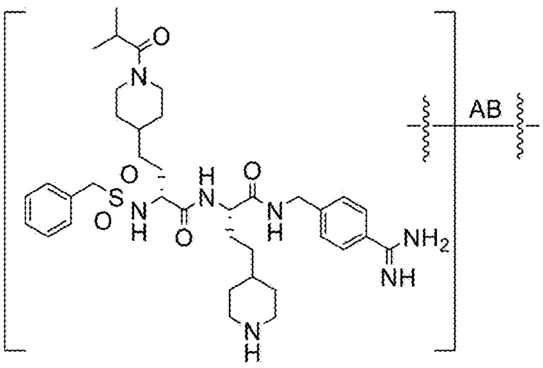
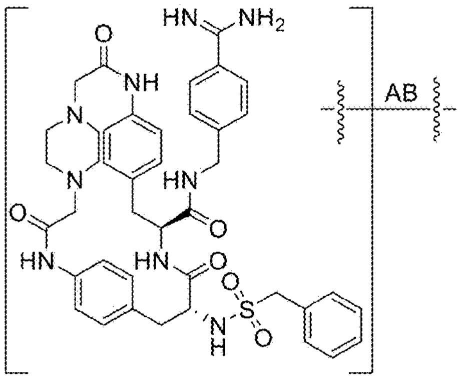
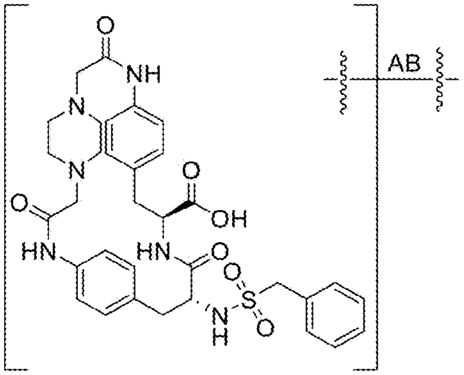
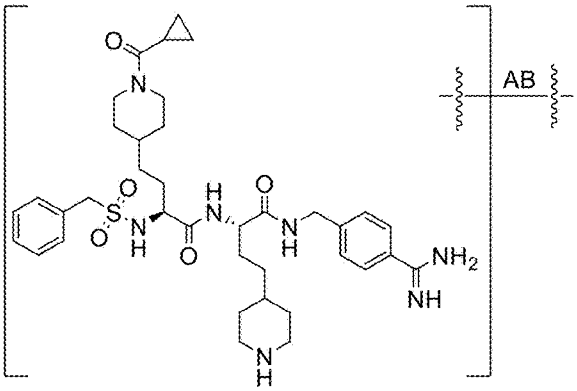
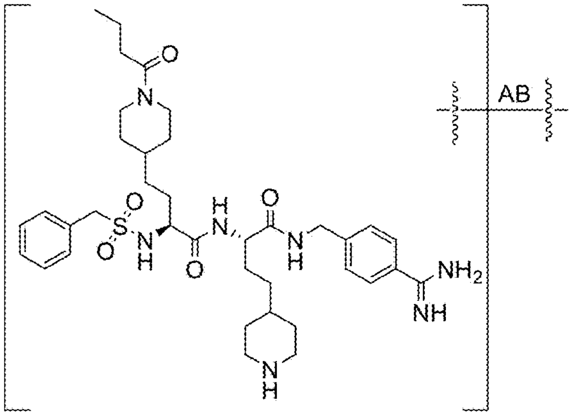
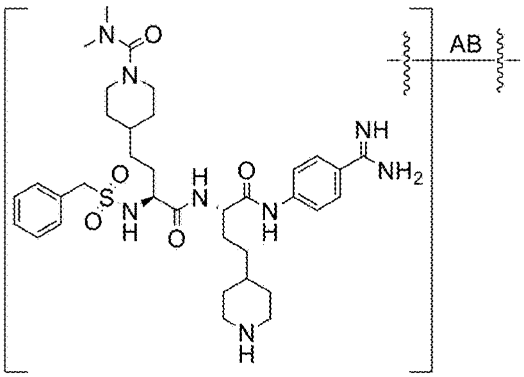
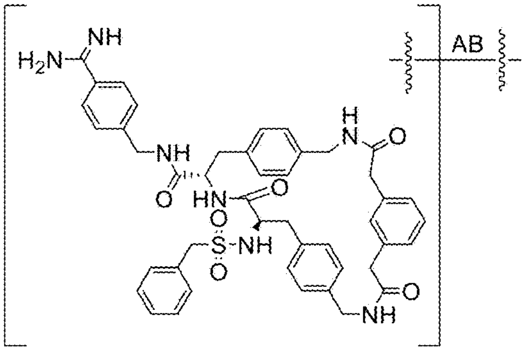
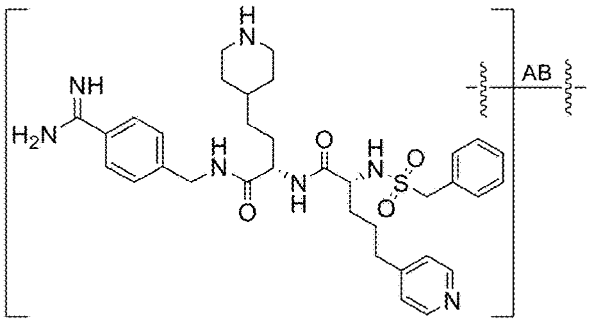
FIG. 1PPPPP

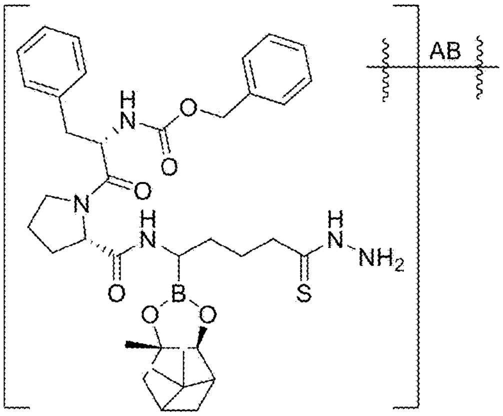
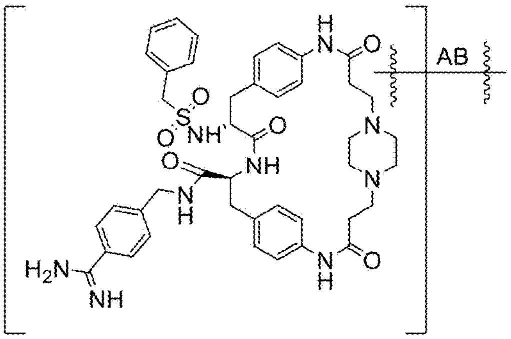
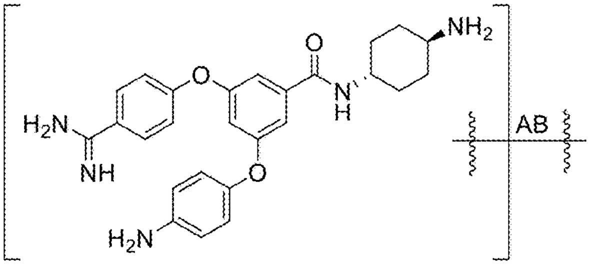
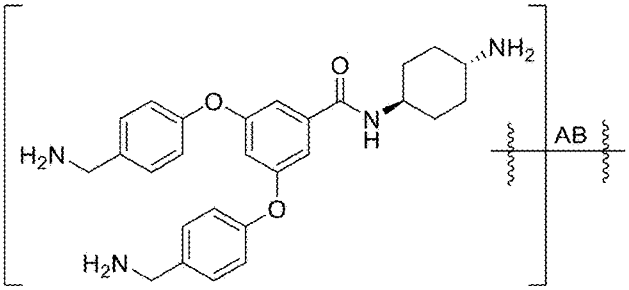
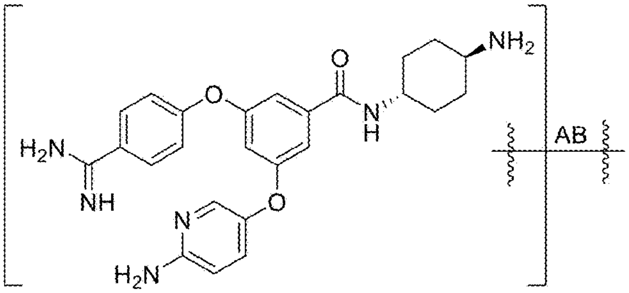
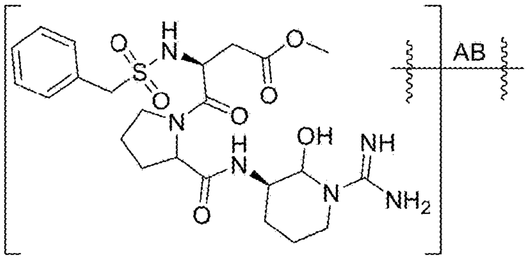
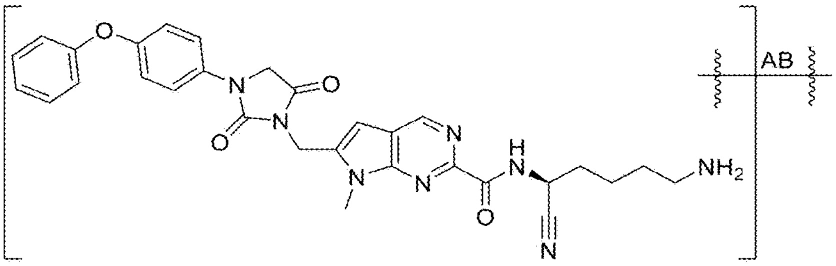
FIG. 1QQQQQ

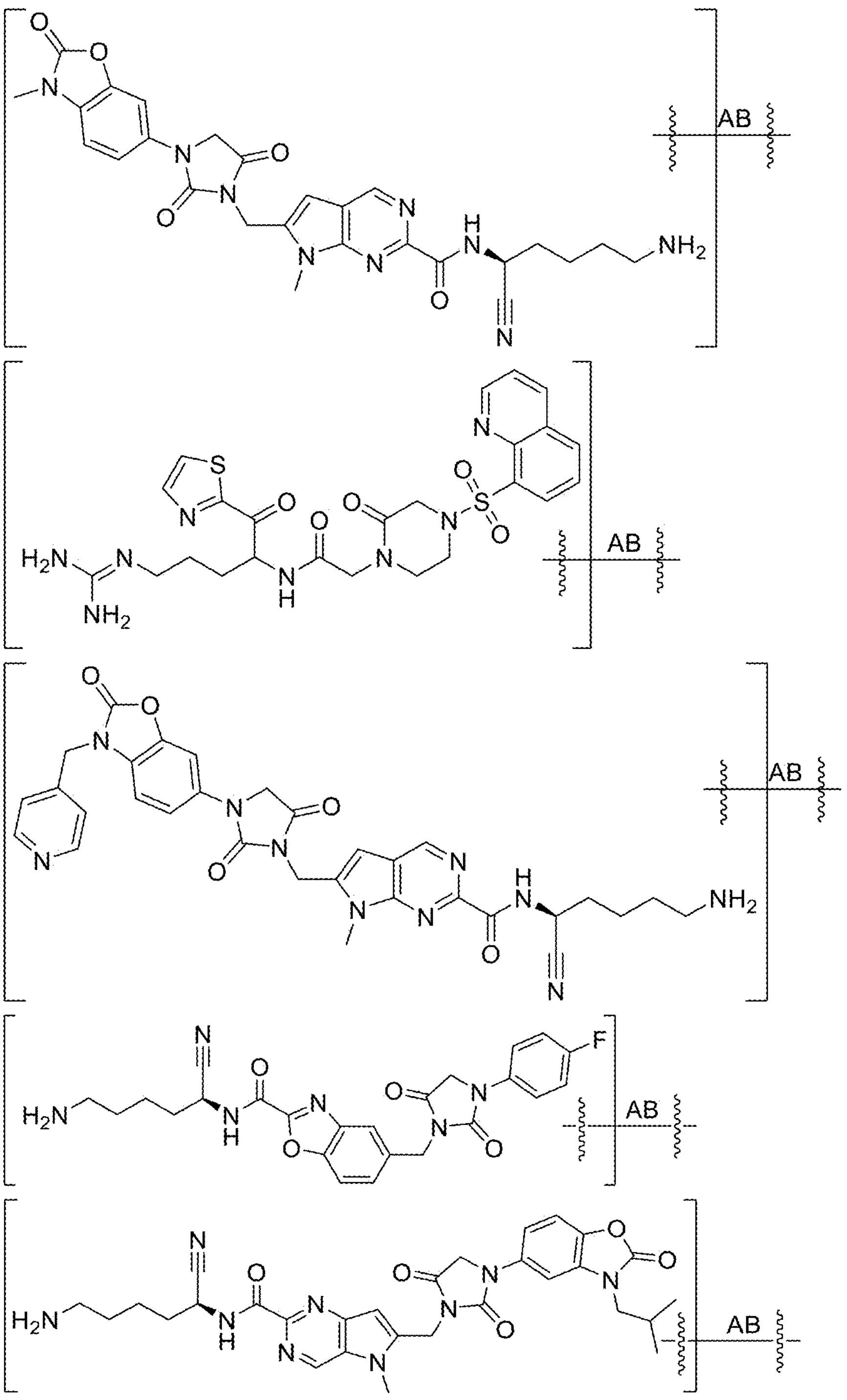
FIG. 1RRRRR

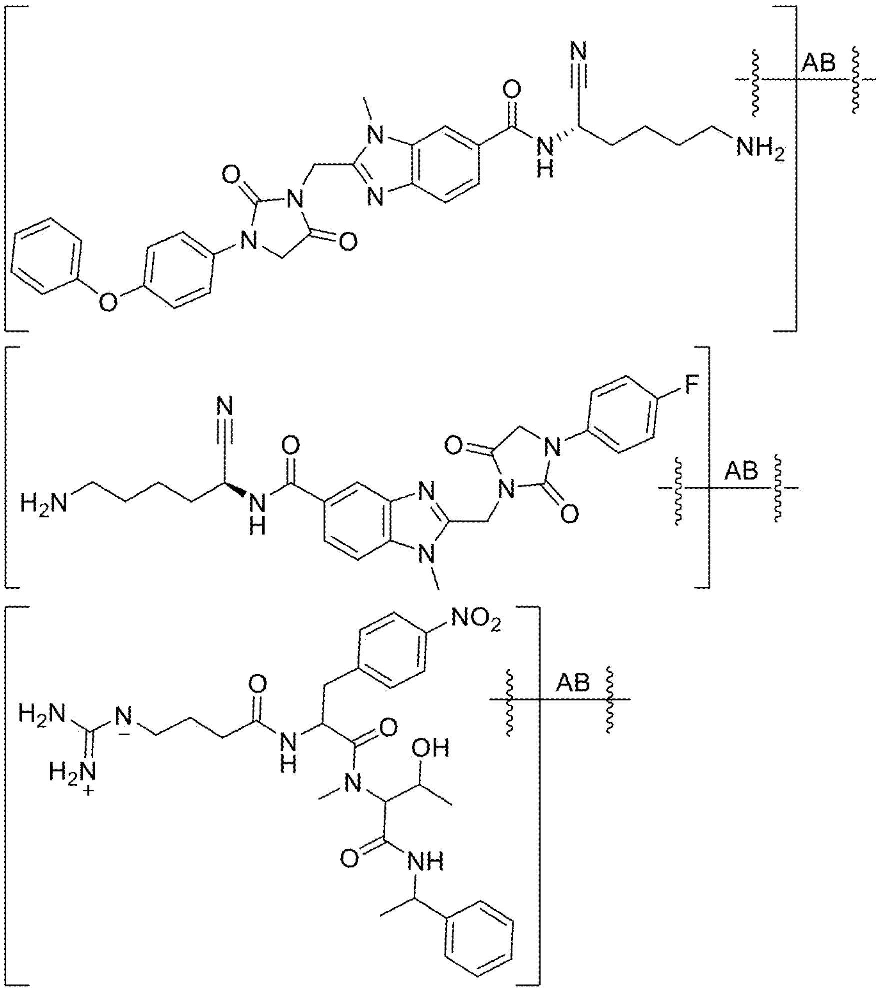
FIG. 1SSSSS
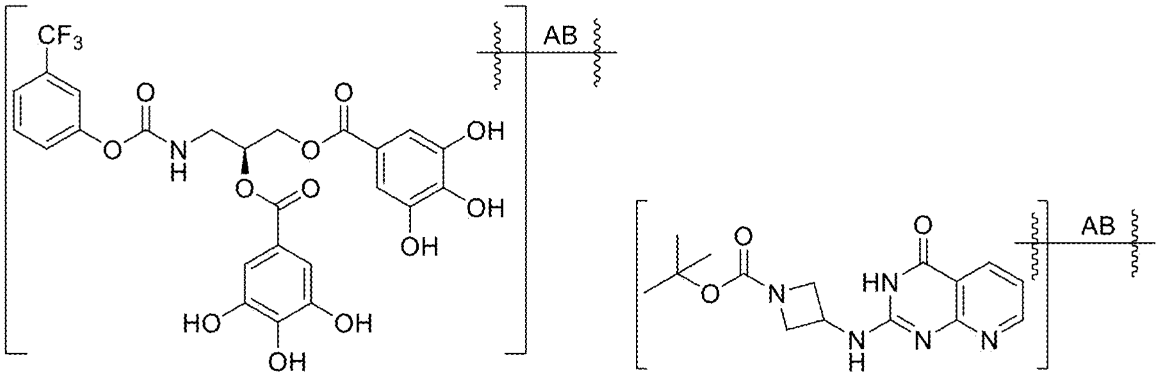
FIG. 1TTTTT

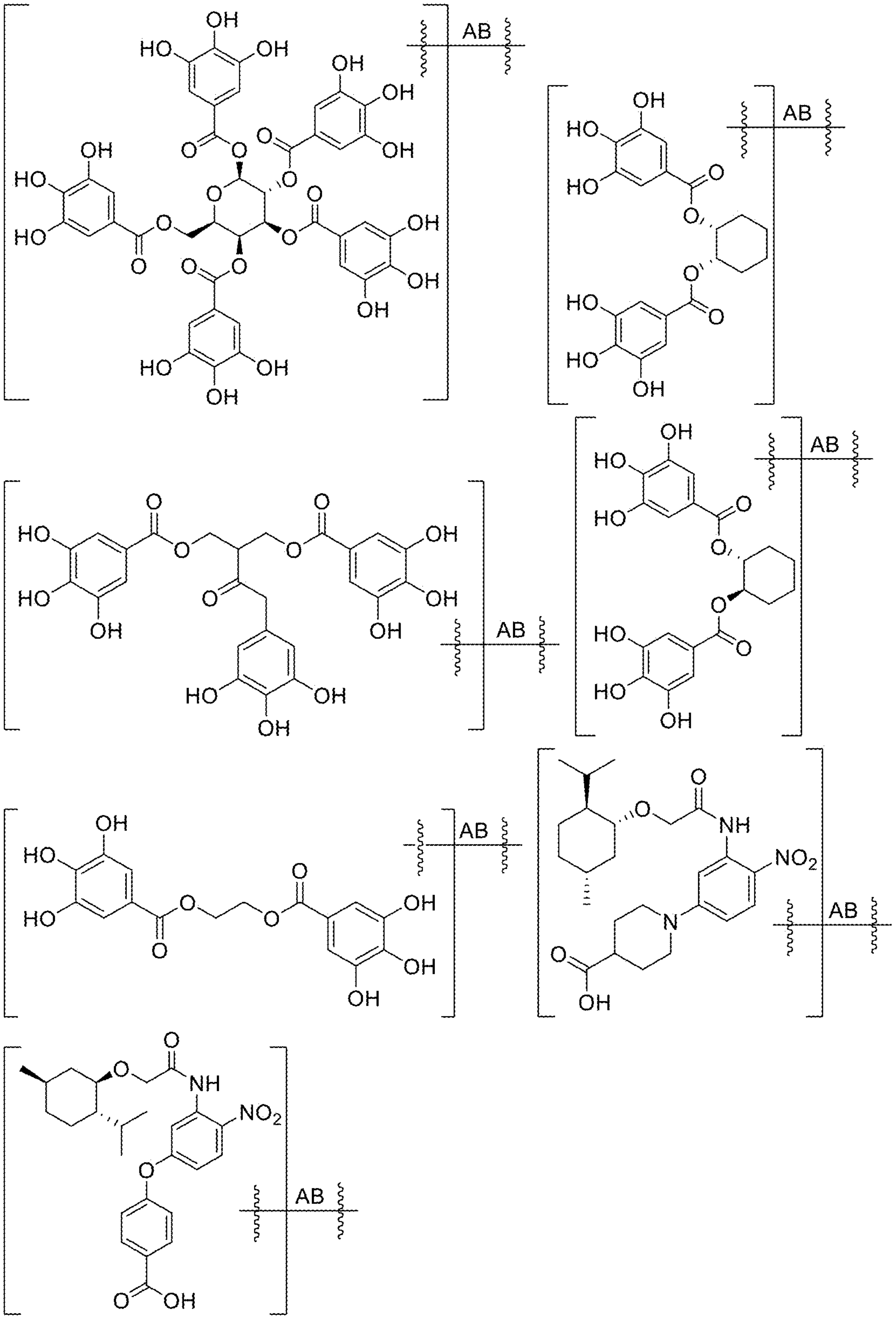
FIG. 1UUUUU

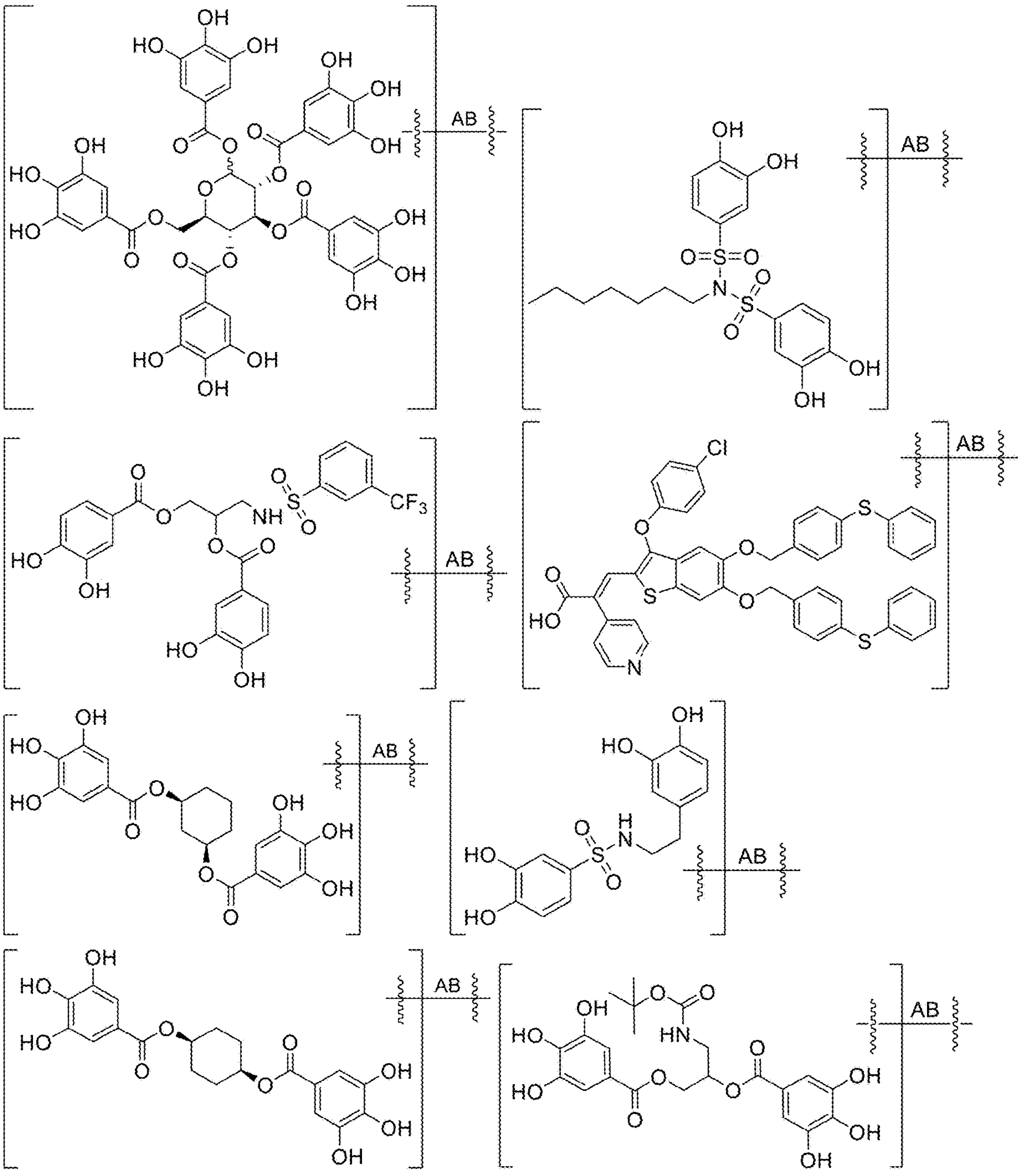
FIG. 1VVVVV

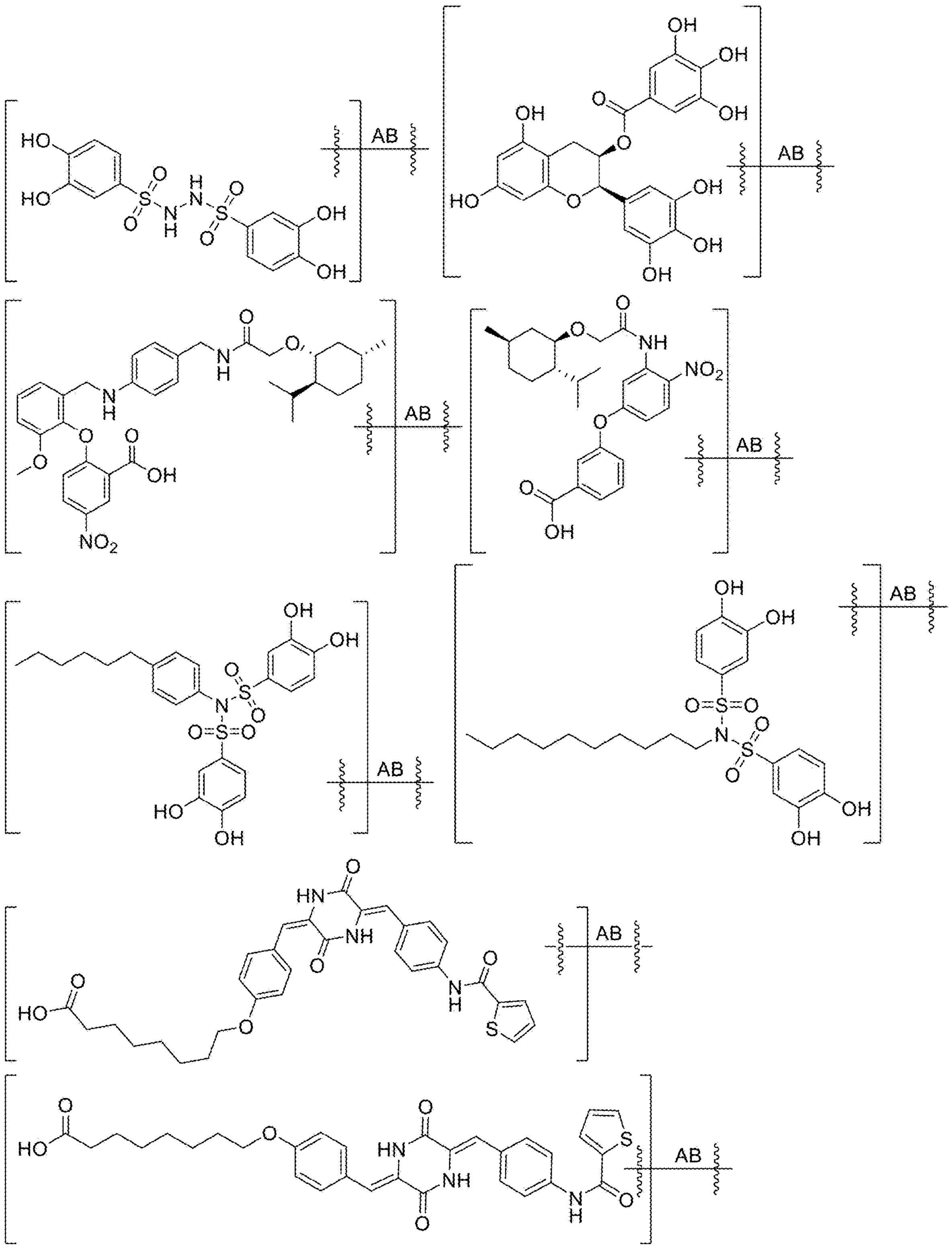
FIG. 1WWWWWW

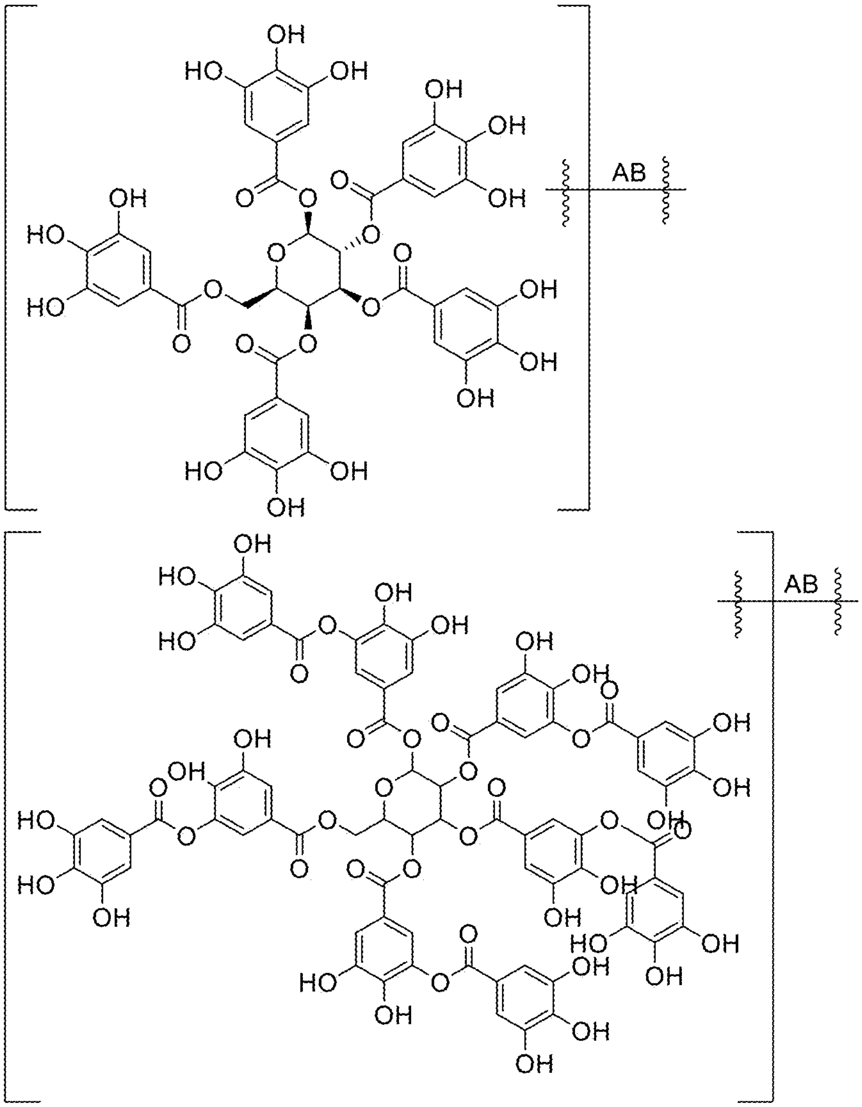
FIG. 1XXXXX
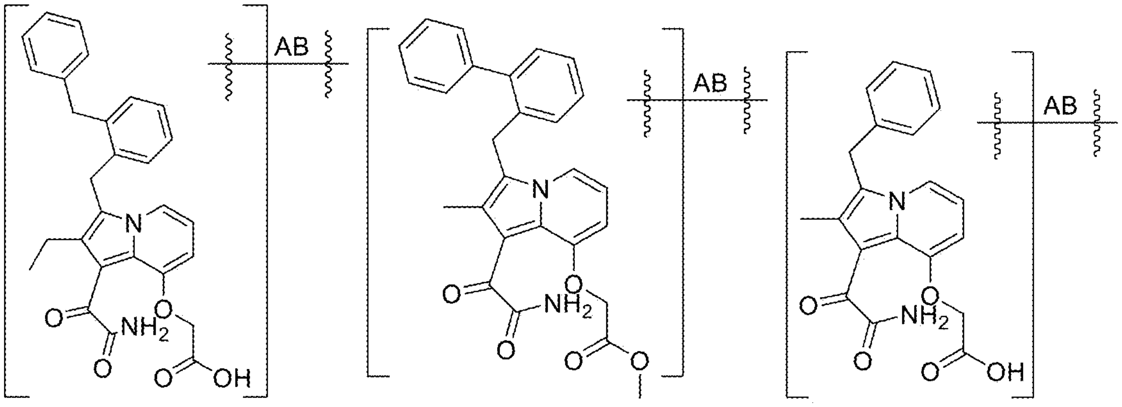
FIG. 1YYYYY

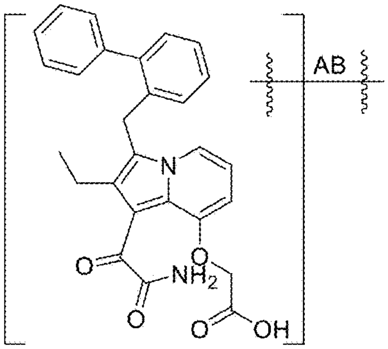
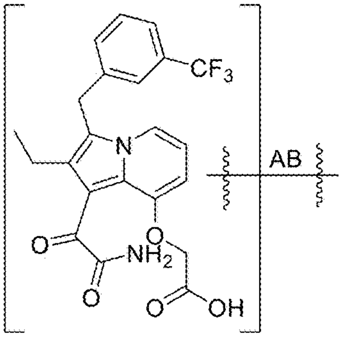
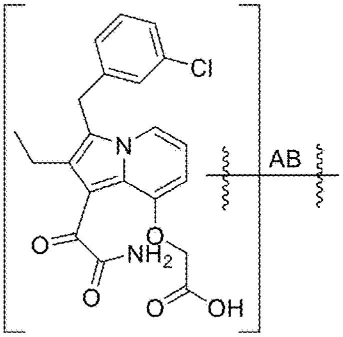
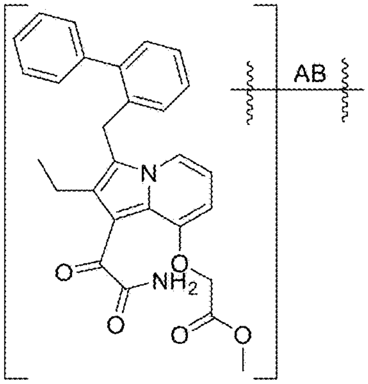
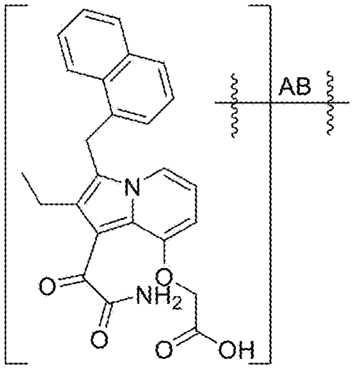
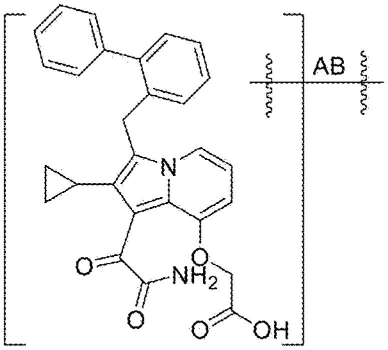
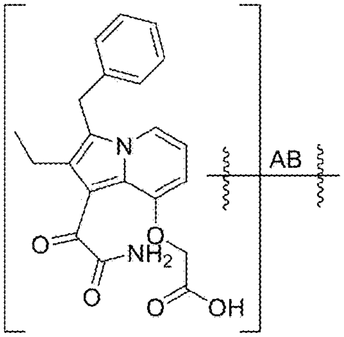
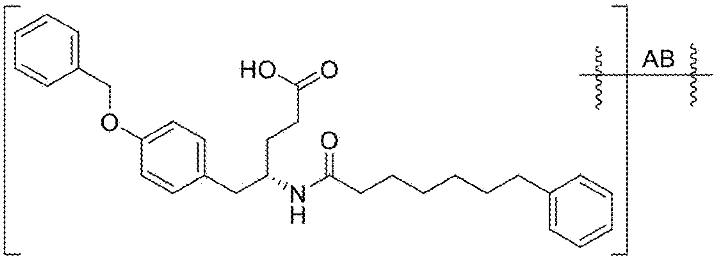
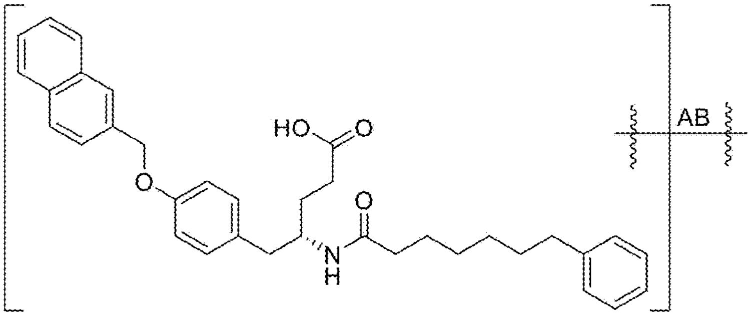
FIG. 1ZZZZZ

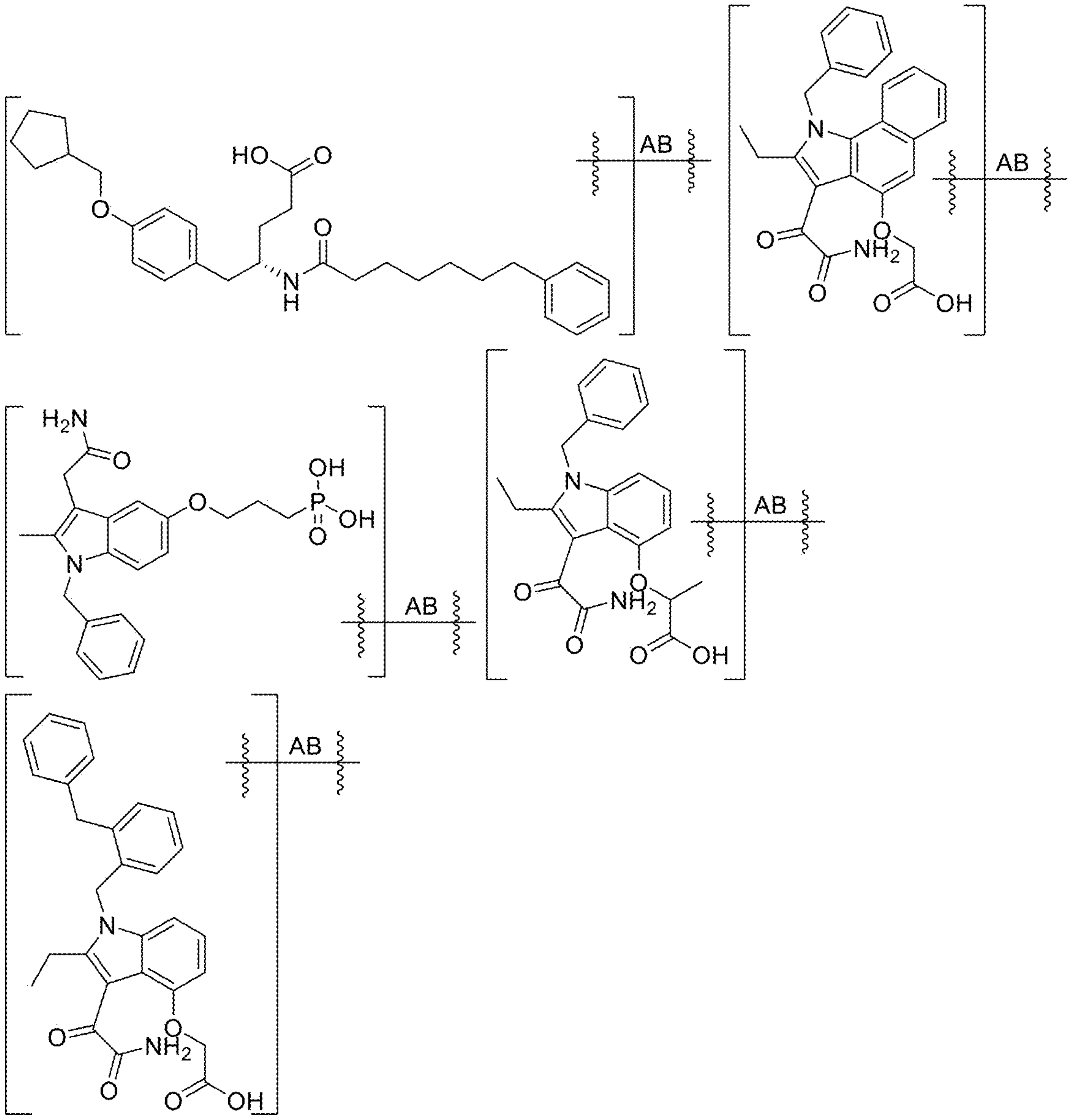
FIG. 1AAAAAA

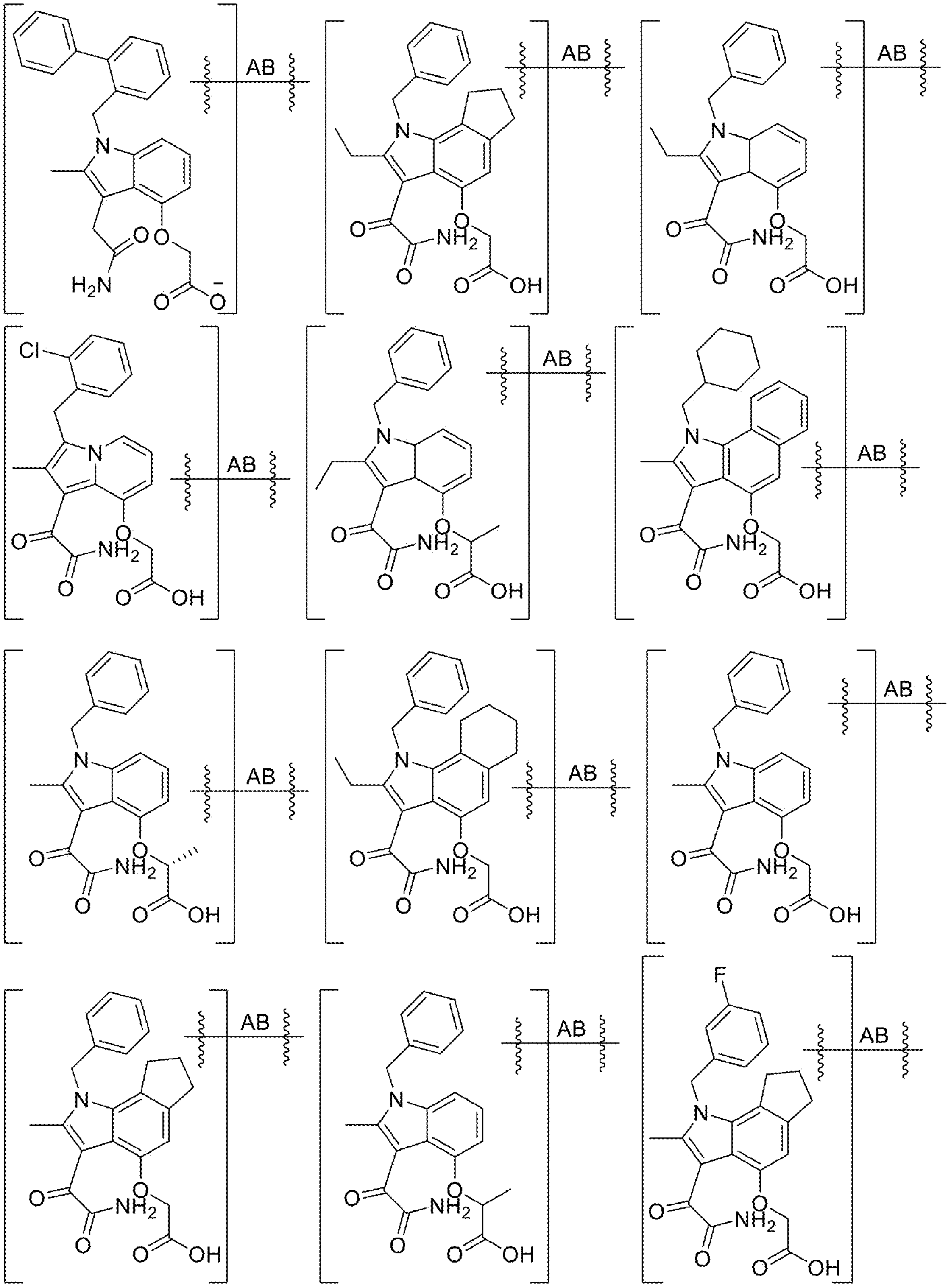
FIG. 1BBBBBB

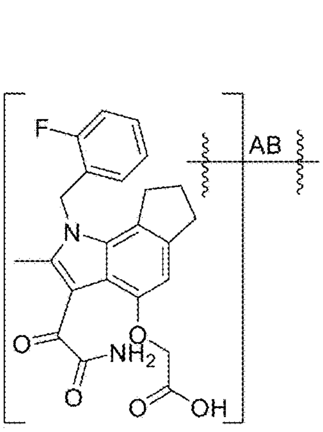
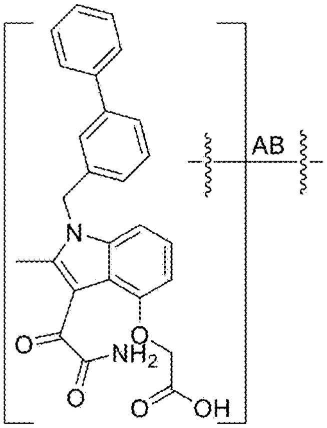
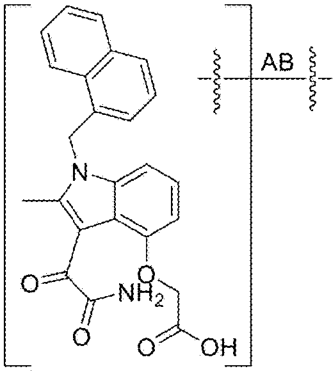
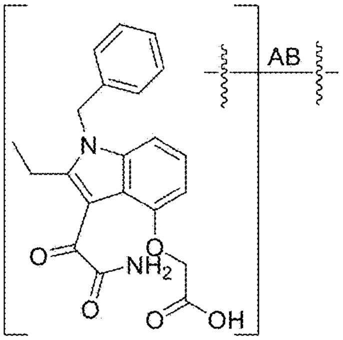
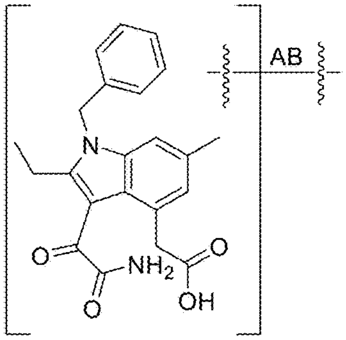
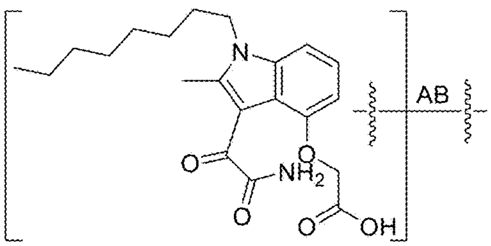
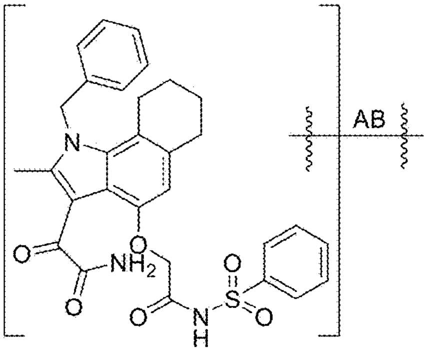
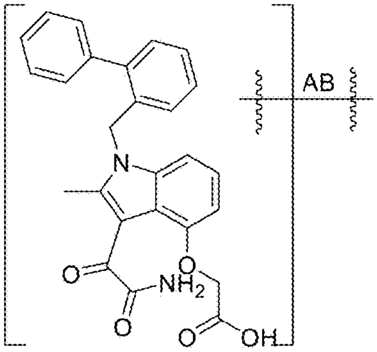
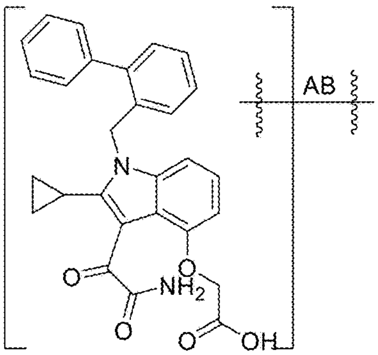
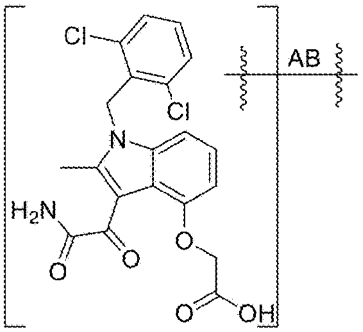
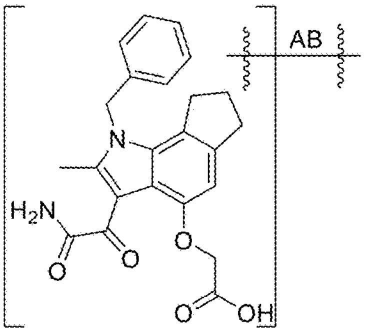
FIG. 1CCCCCC

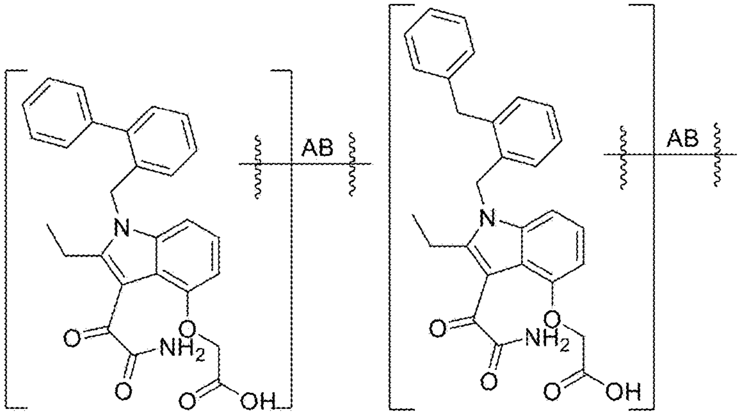
FIG. 1DDDDDD
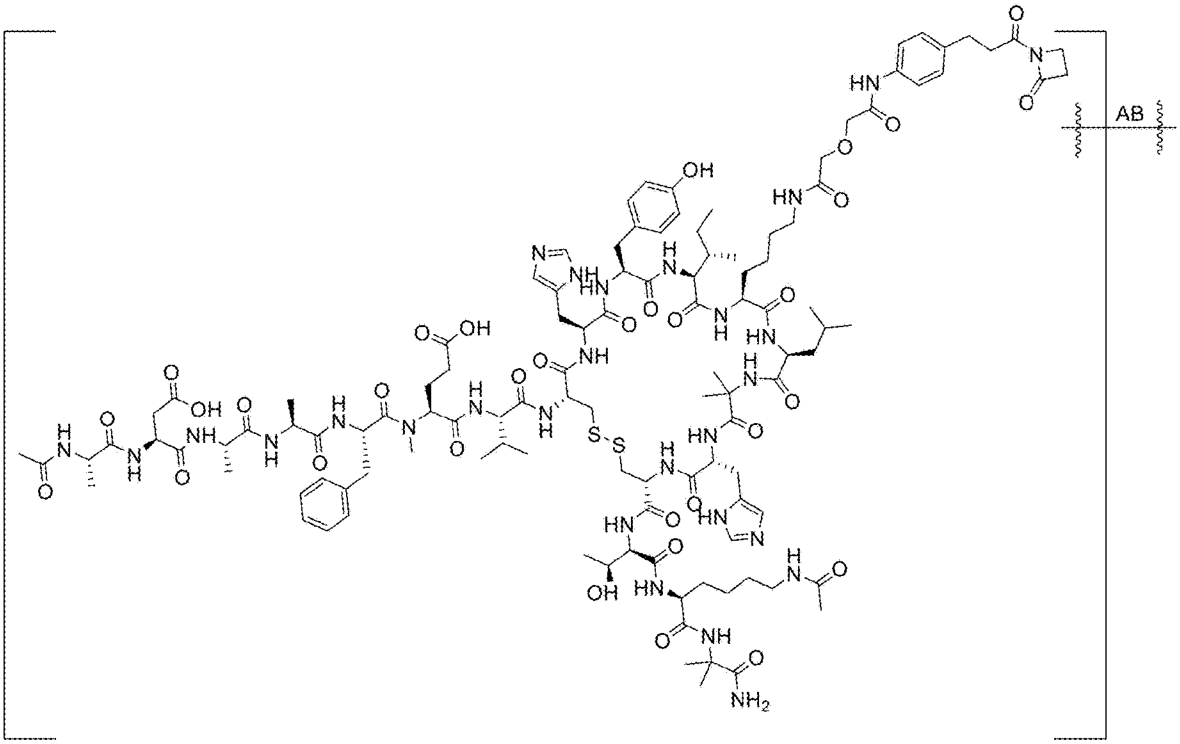
FIG. 1EEEEEE

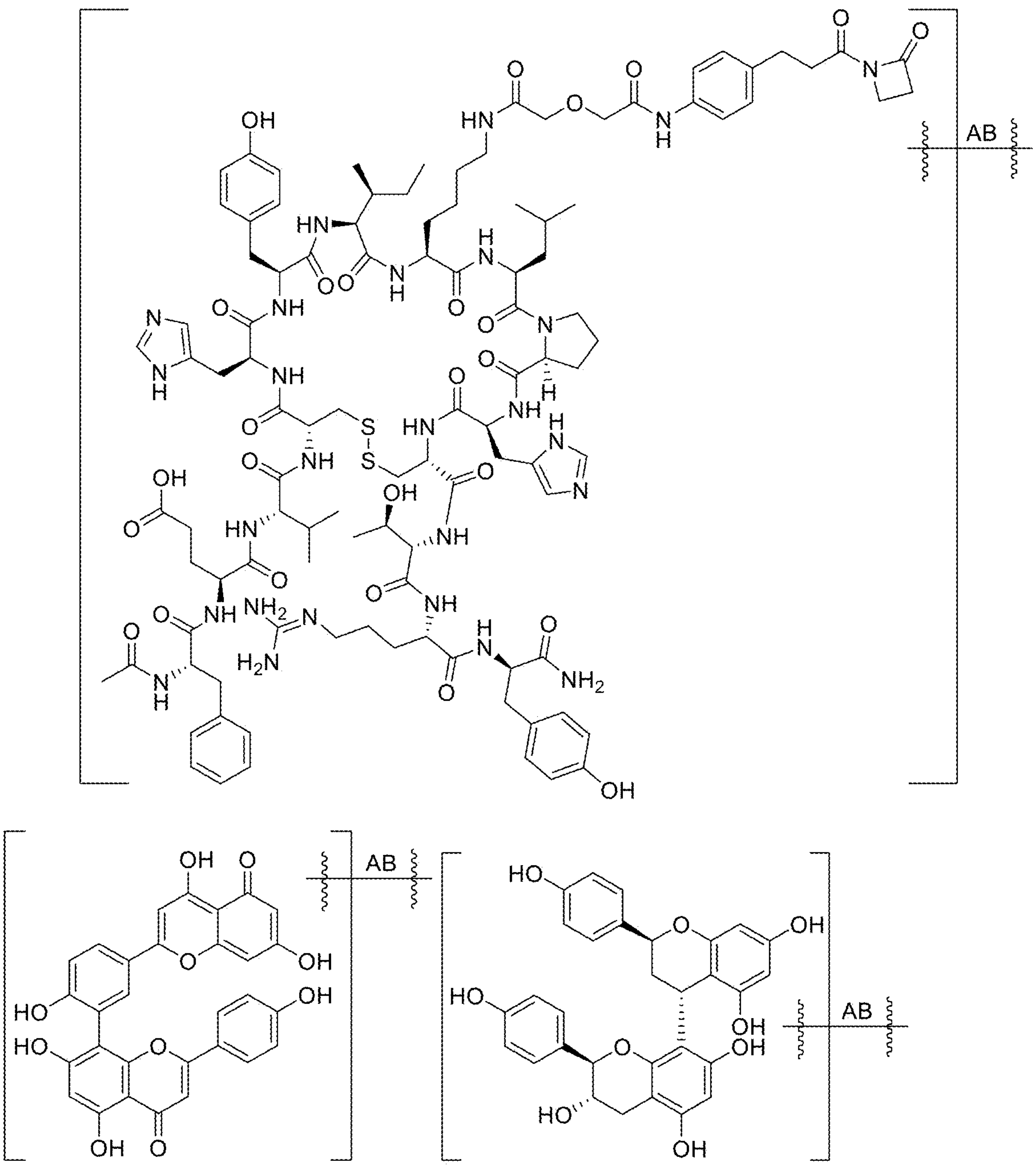
FIG. 1FFFFFF

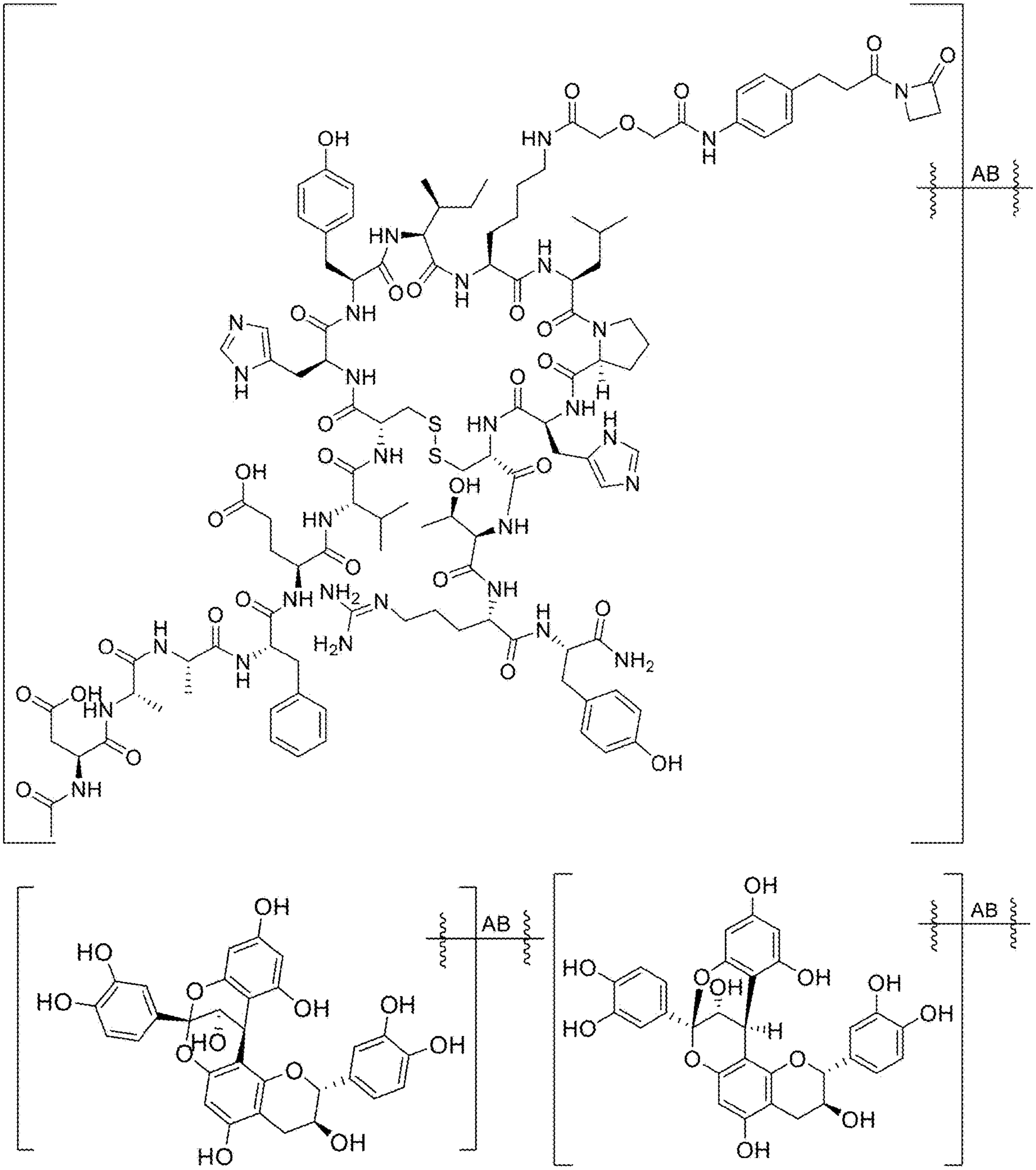
FIG. 1GGGGGG

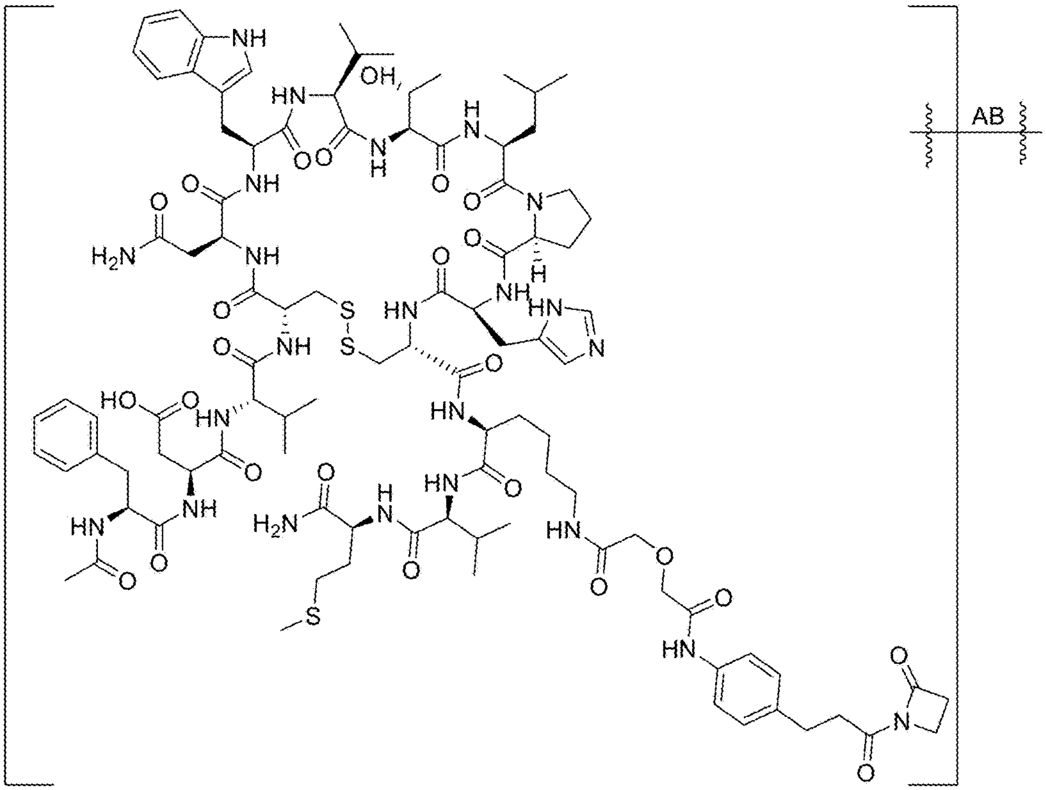
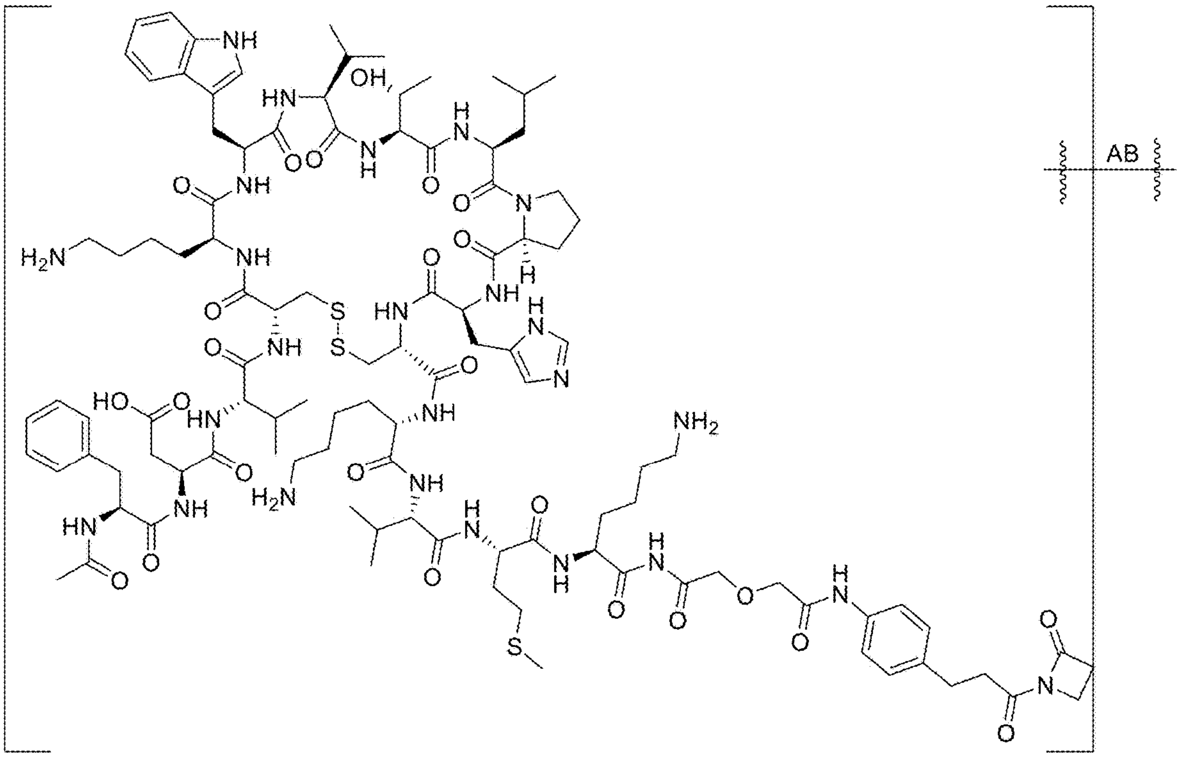
FIG. 1HHHHHH

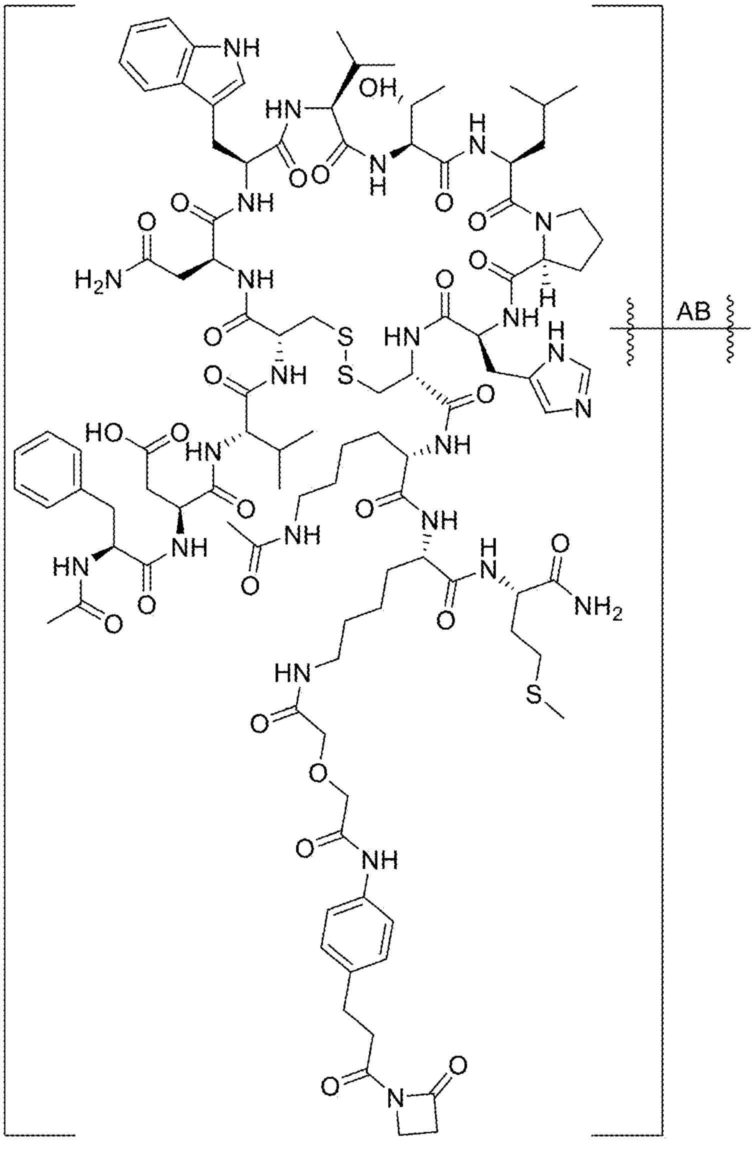
FIG. 1IIIIII

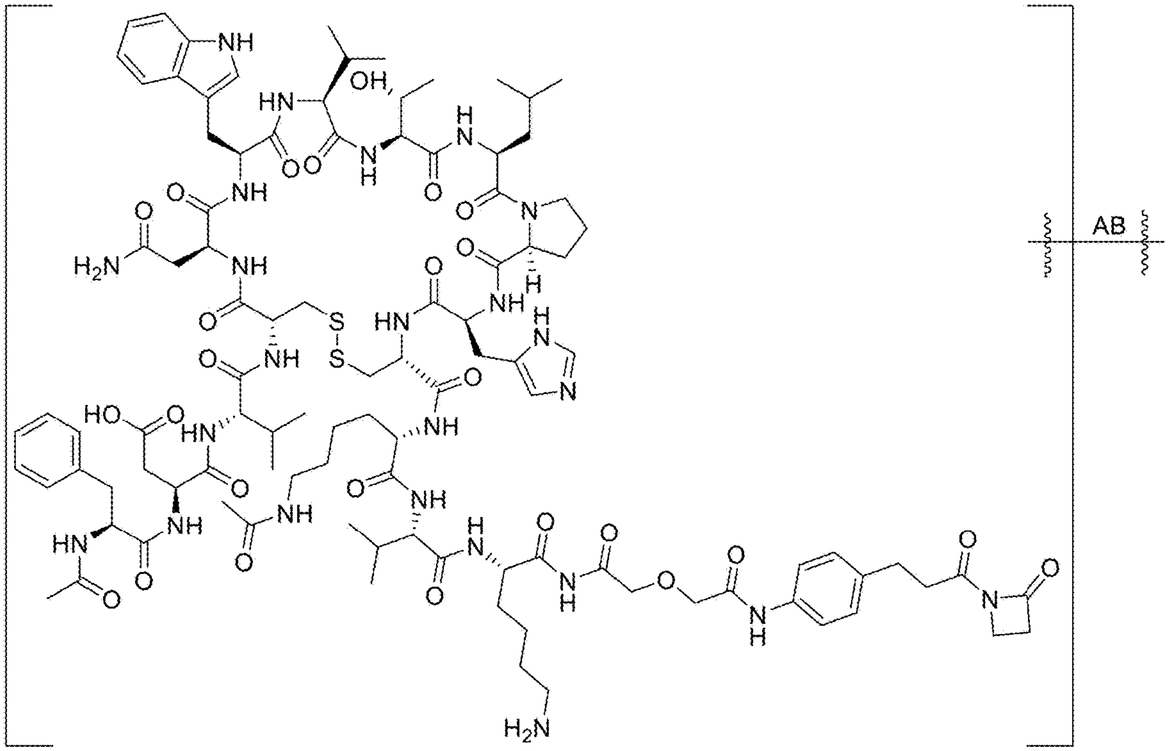
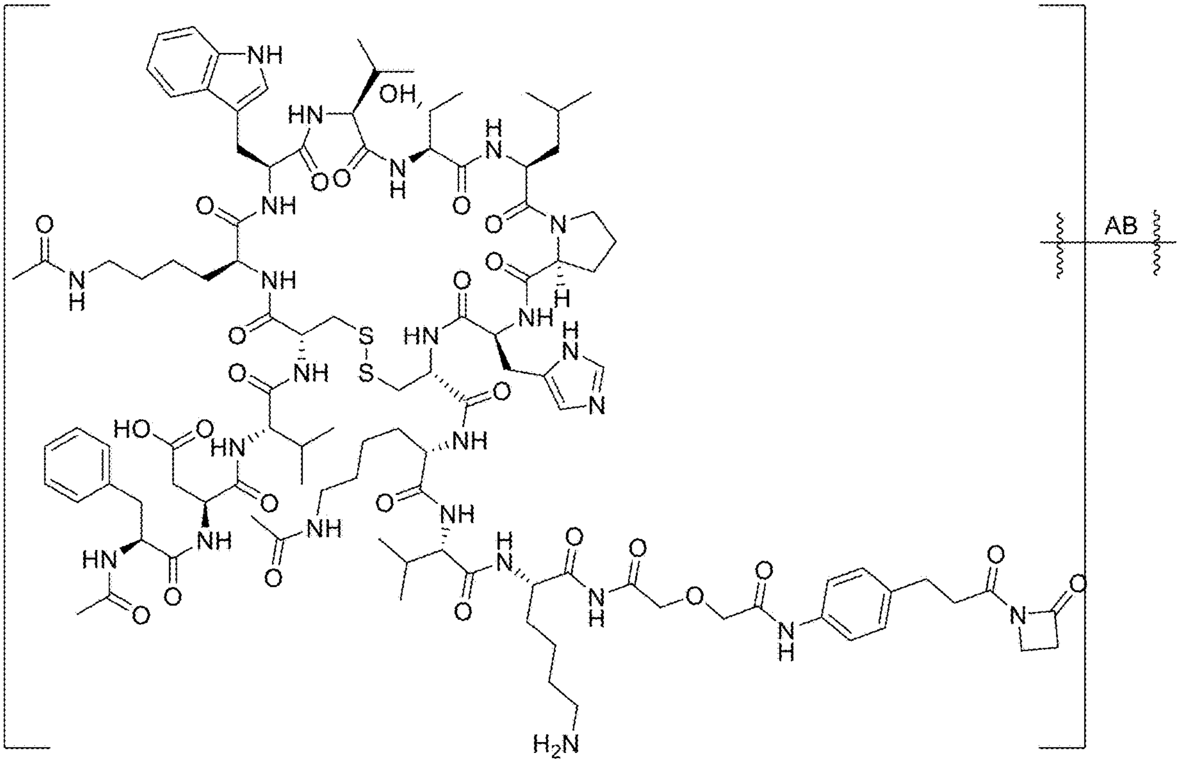
FIG. 1JJJJJJ

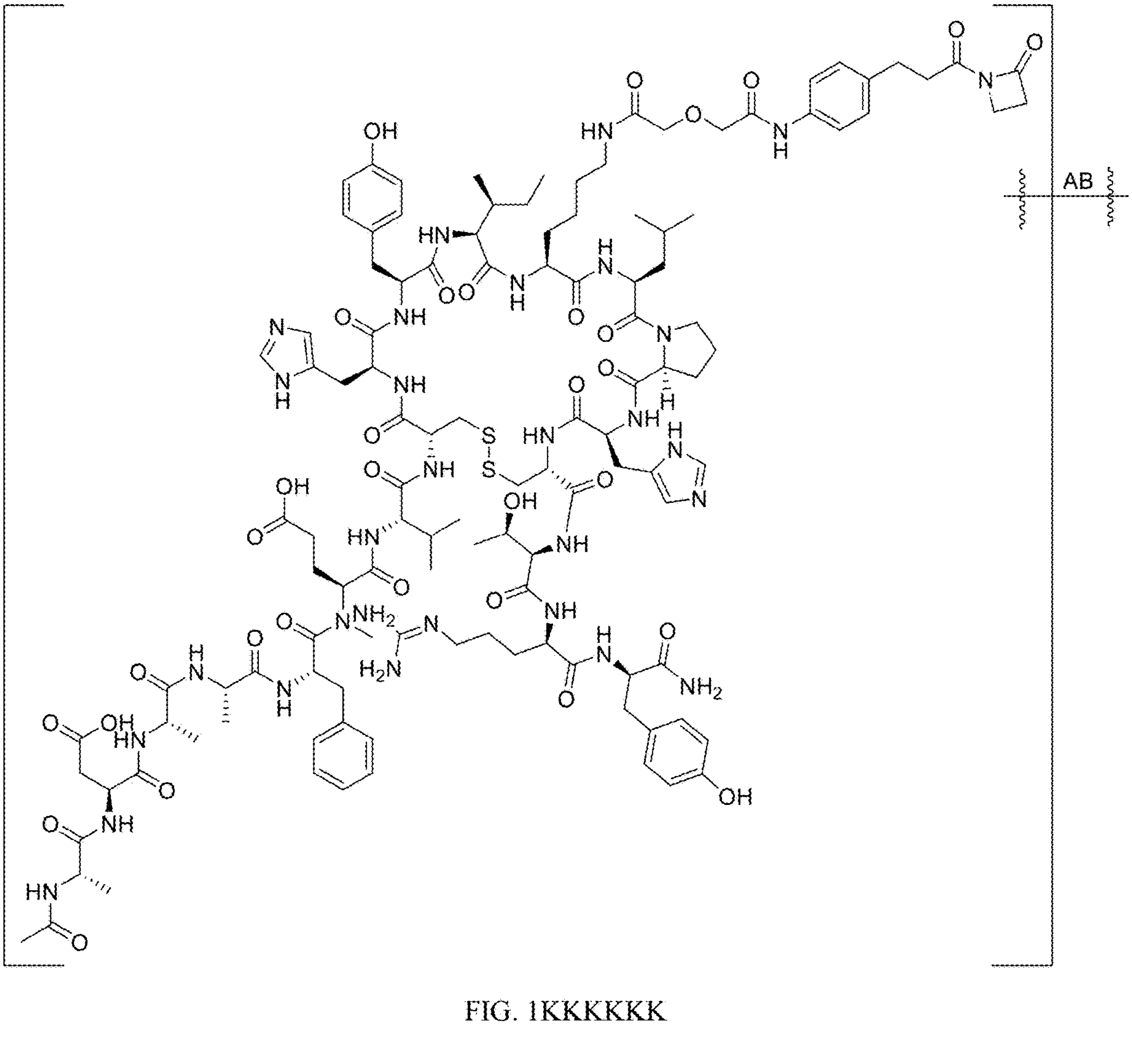
FIG. 1KKKKKK

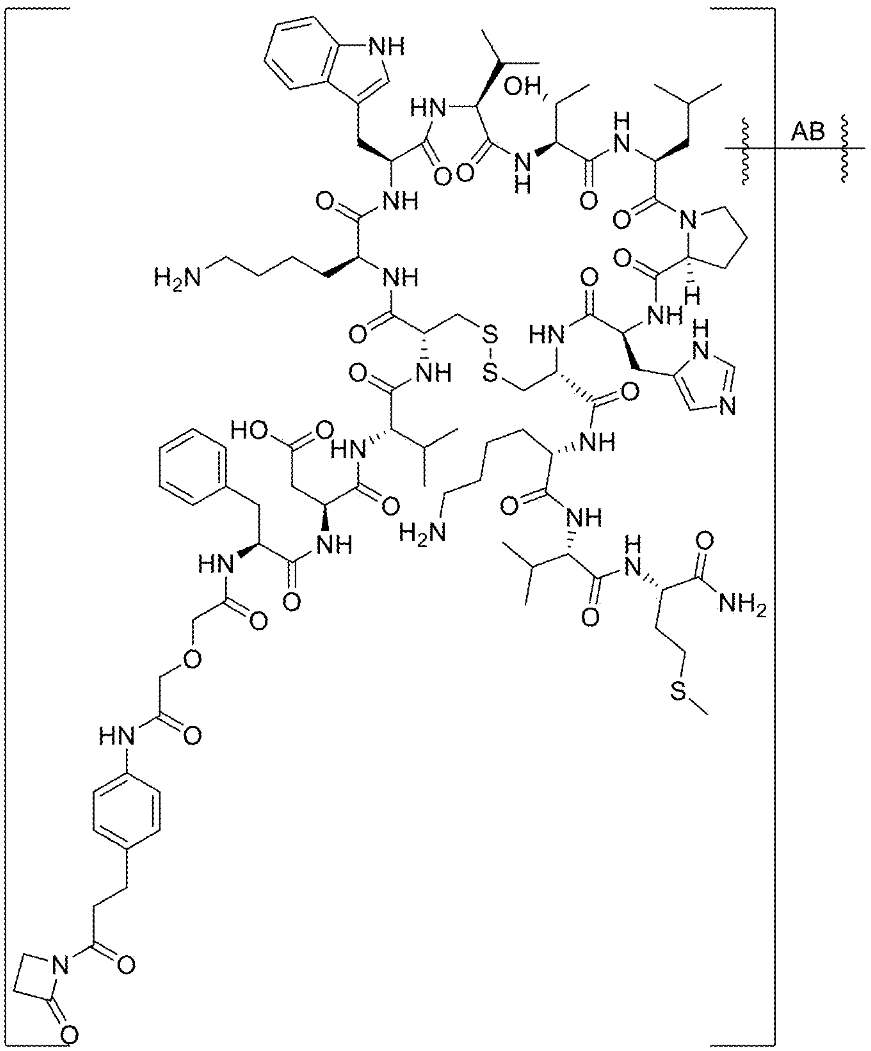
FIG. 1LLLLLL

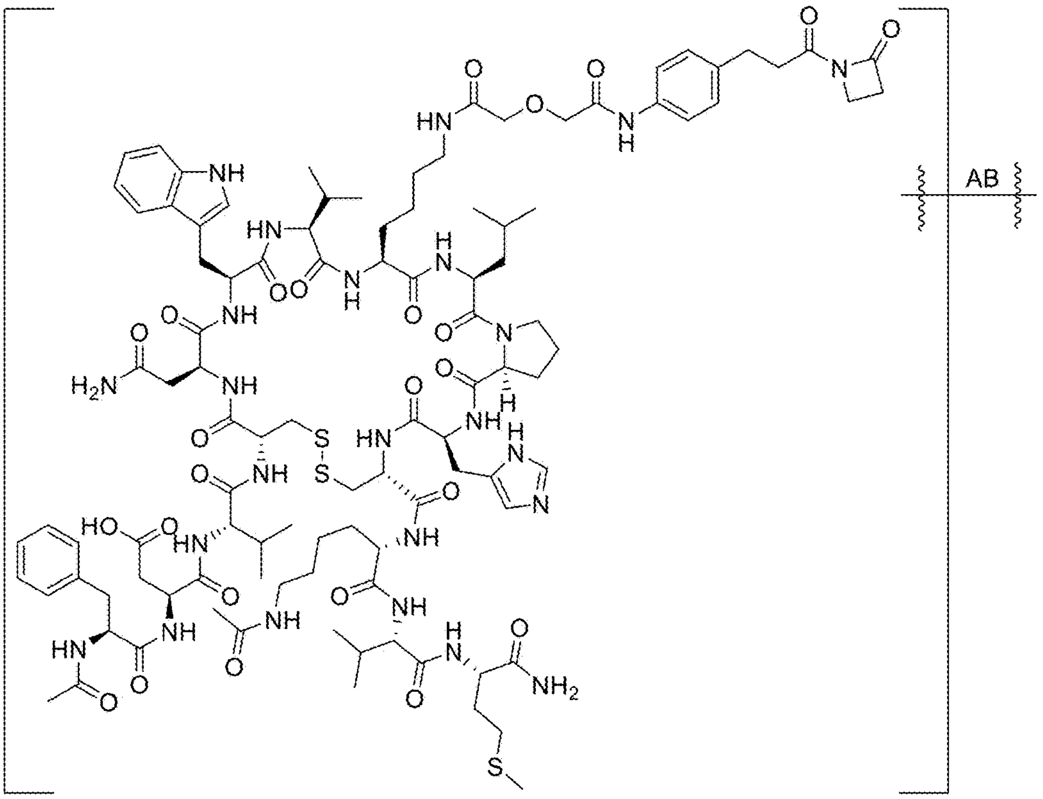
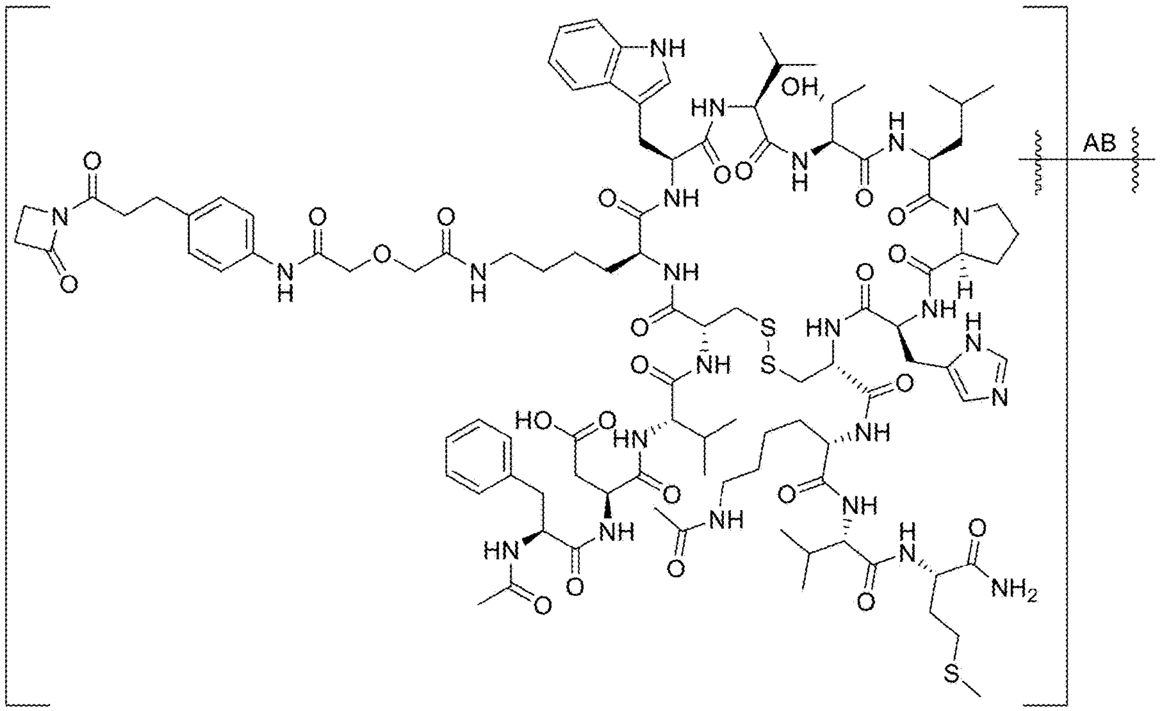
FIG. 1MMMMMMM

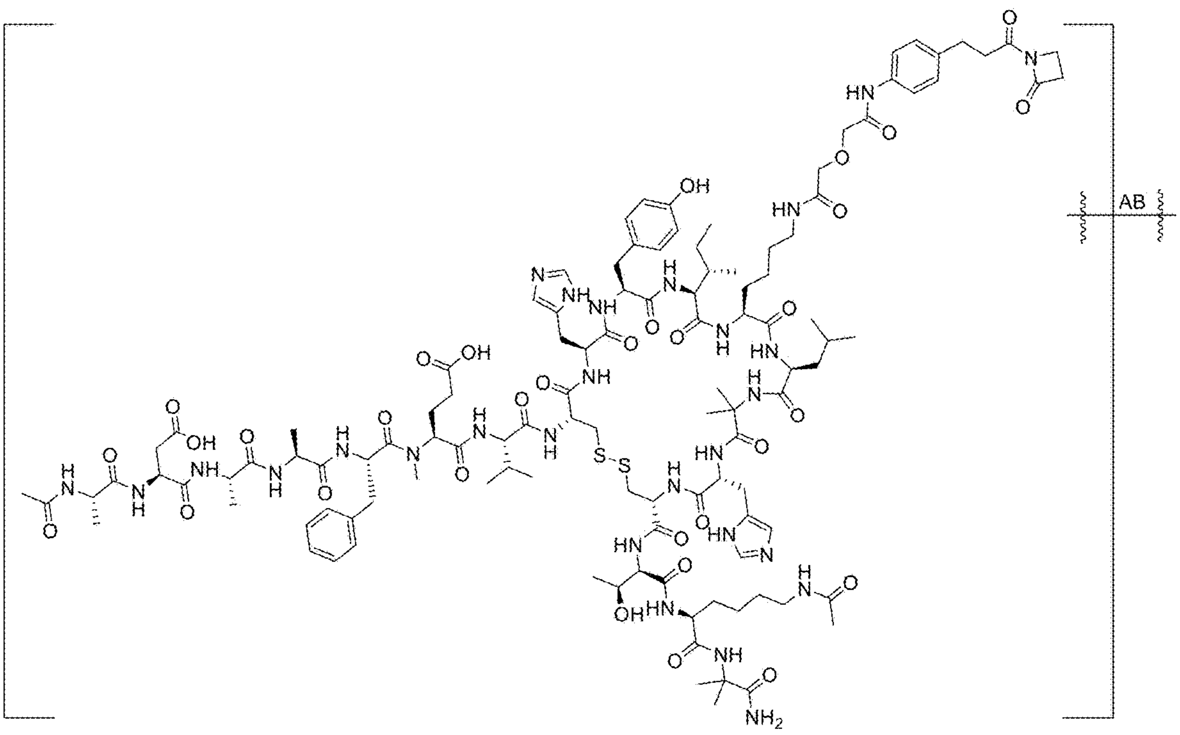
FIG. 1NNNNNNN

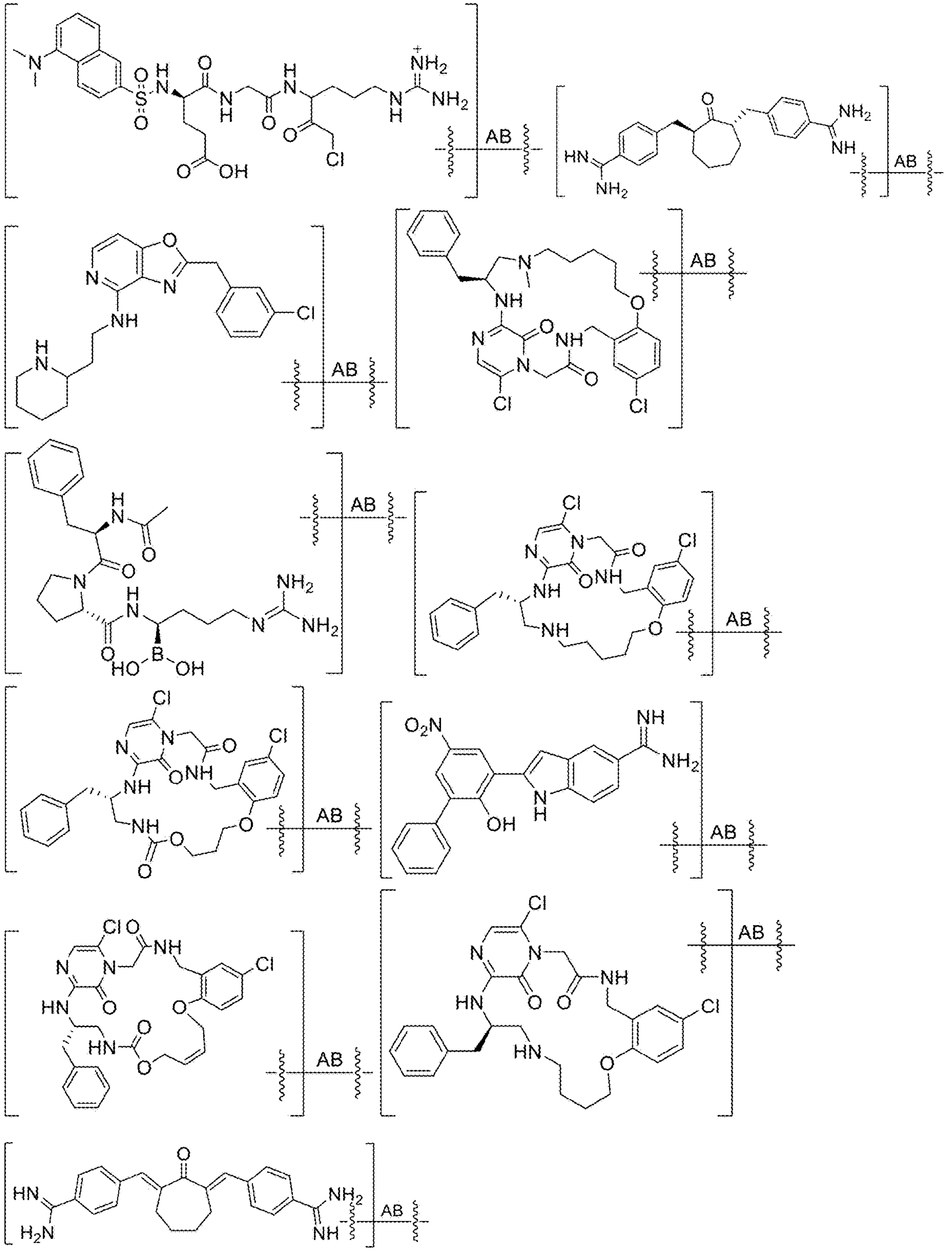
FIG. 1OOOOOO

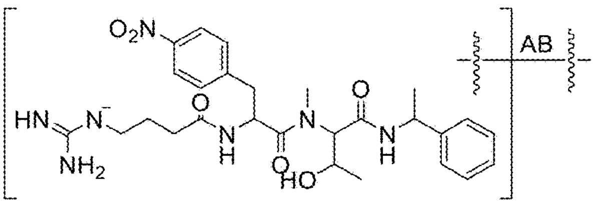
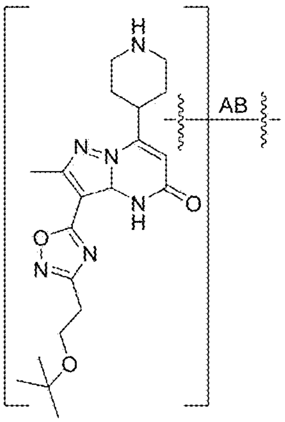
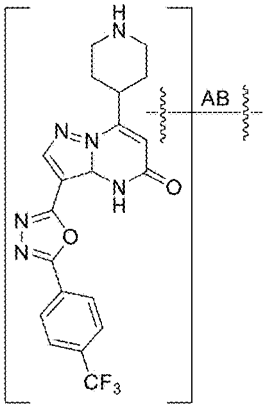
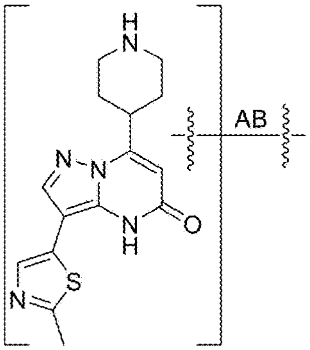
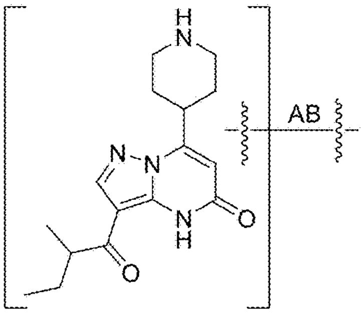
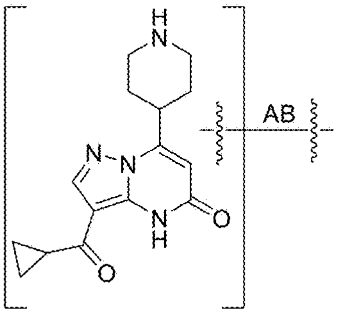
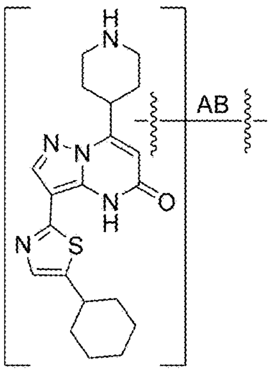
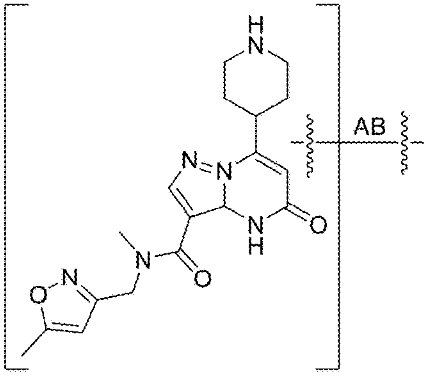
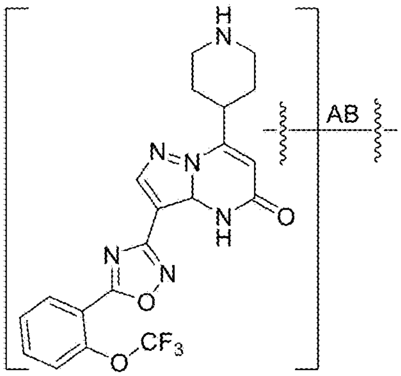
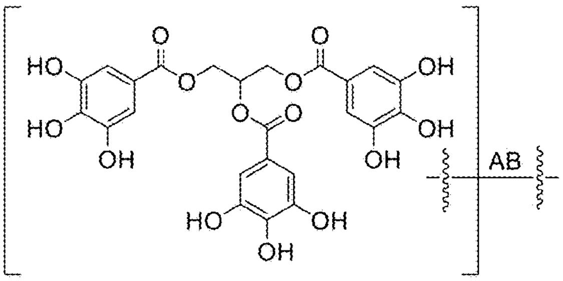
FIG. 1PPPPPP

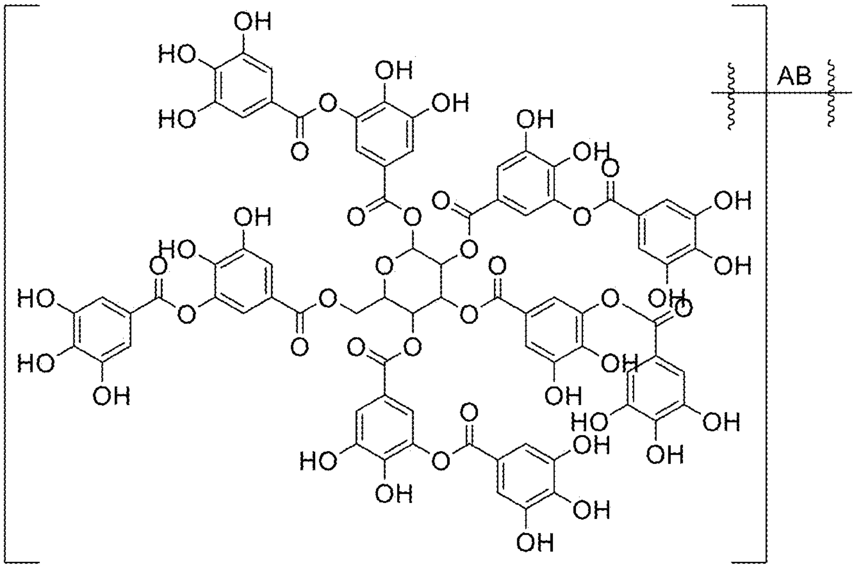
FIG. 1QQQQQQ
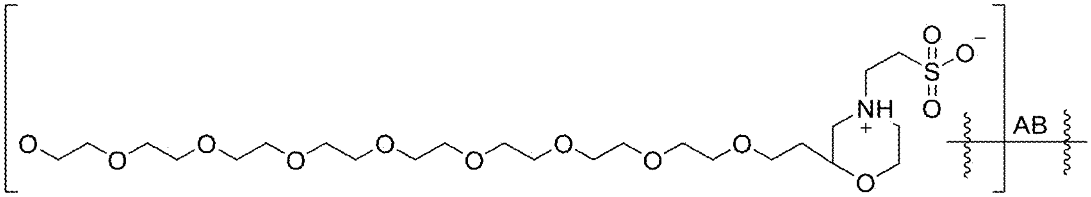
FIG. 1RRRRRR
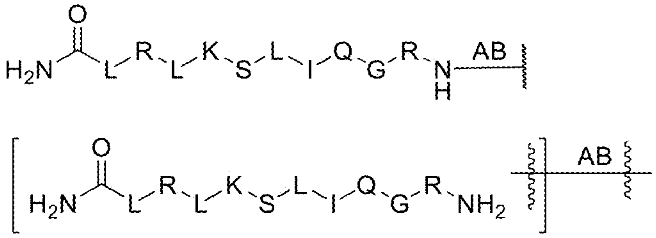
FIG. 1SSSSSS

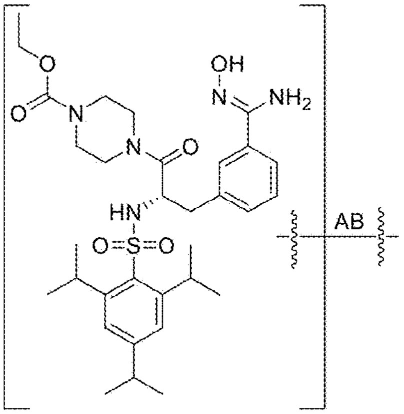
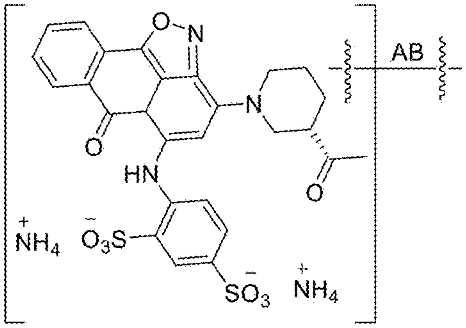
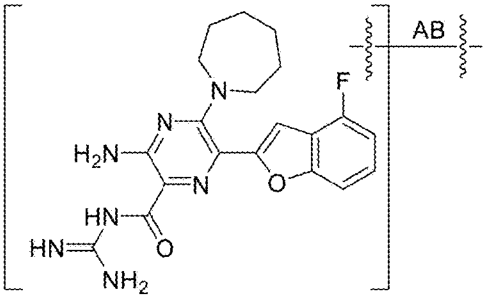
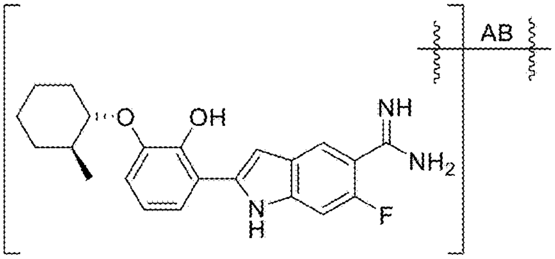
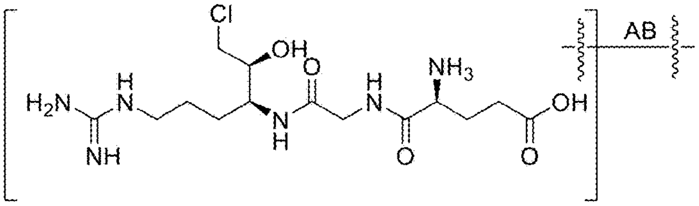
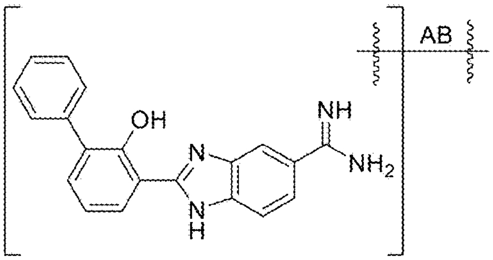
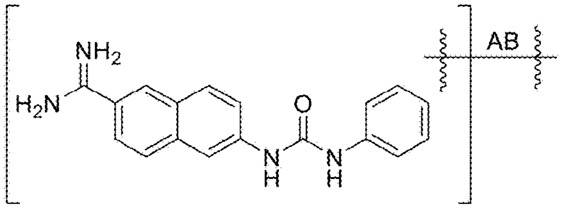
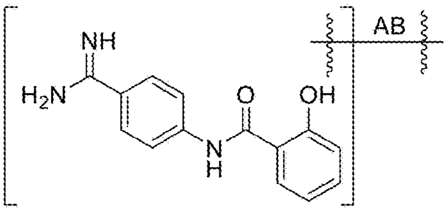
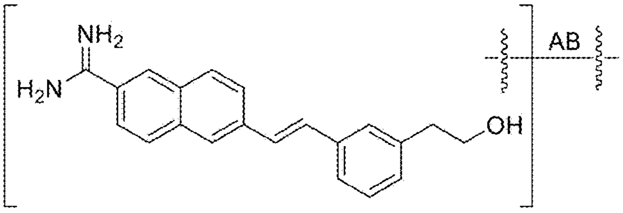
FIG. 1TTTTTTT

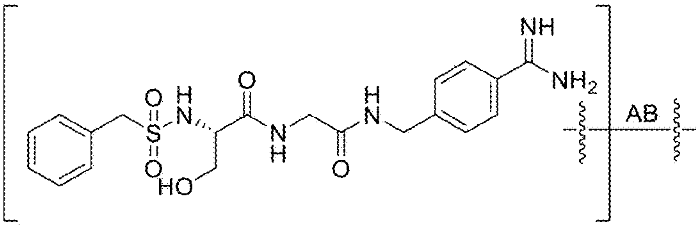
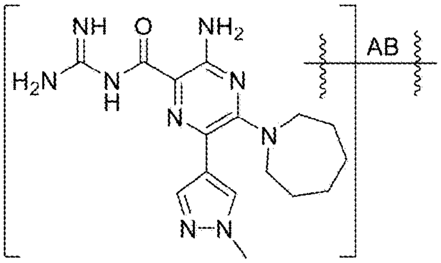
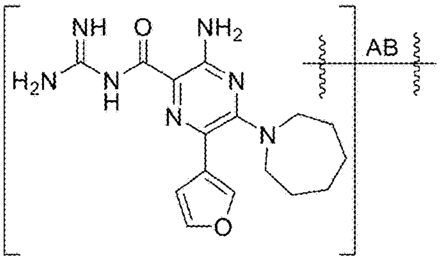
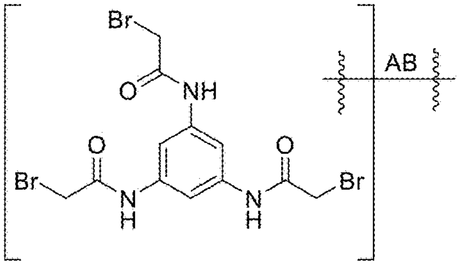
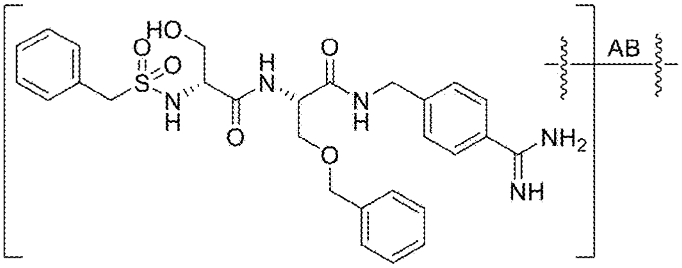
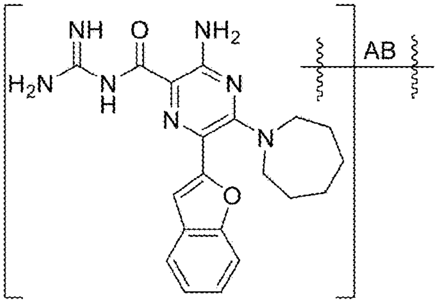
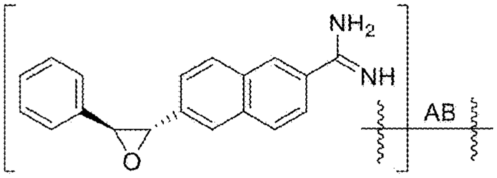
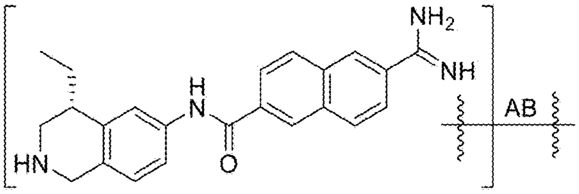
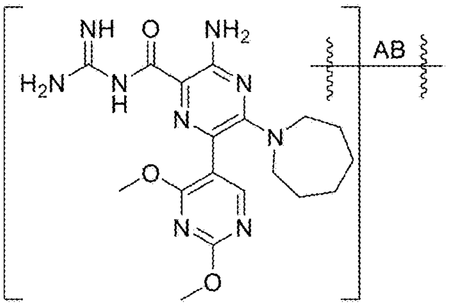
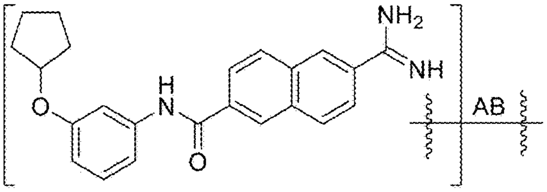
FIG. 1UUUUUU

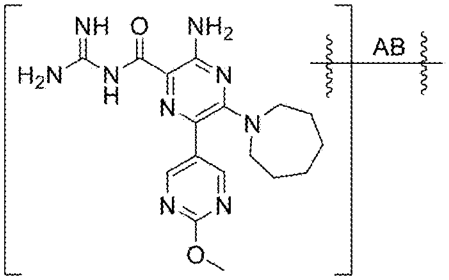
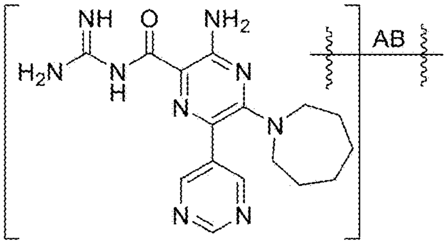
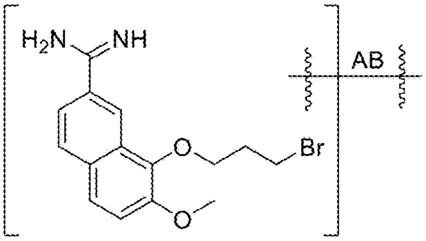
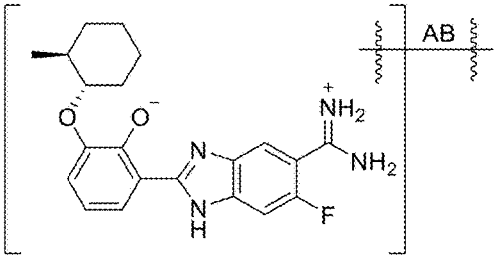
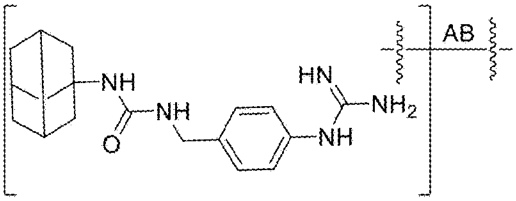
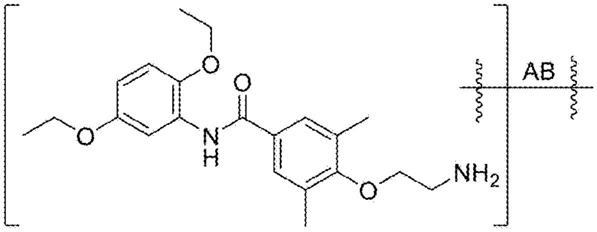
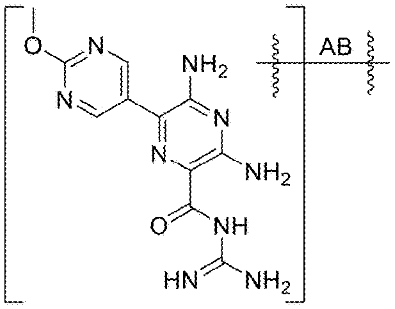
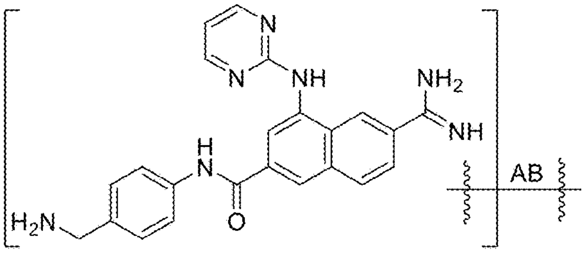
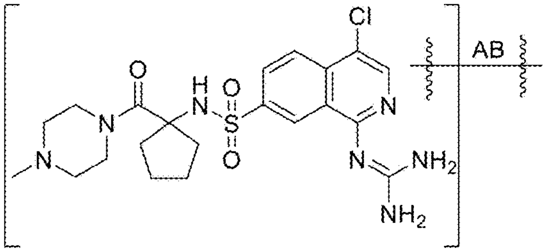
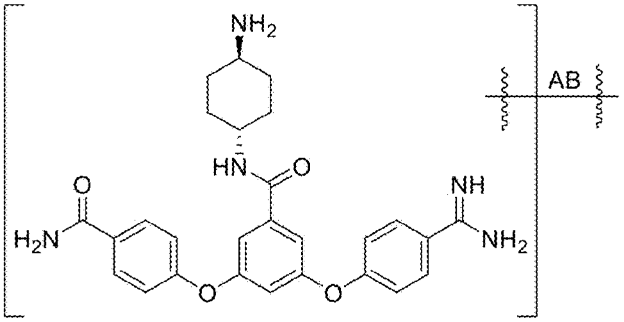
FIG. 1VVVVVV

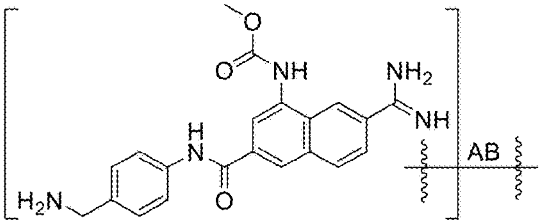
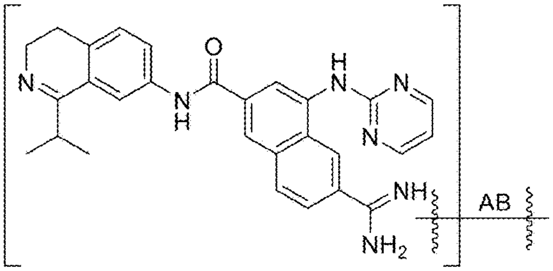
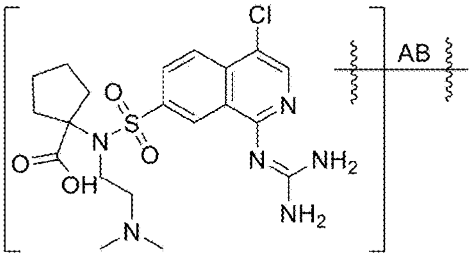
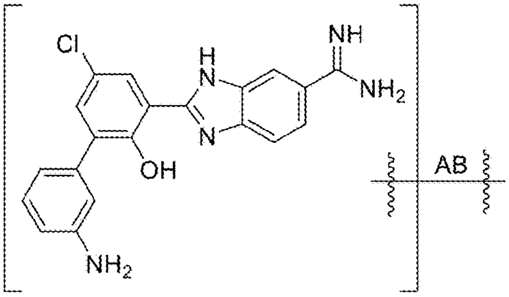
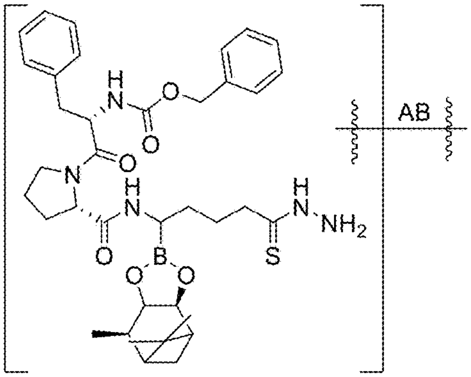
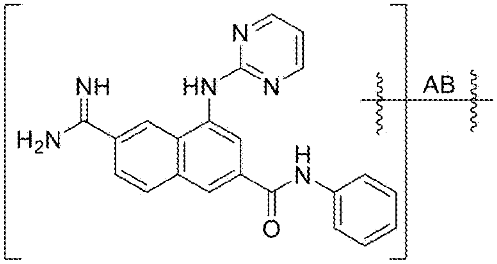
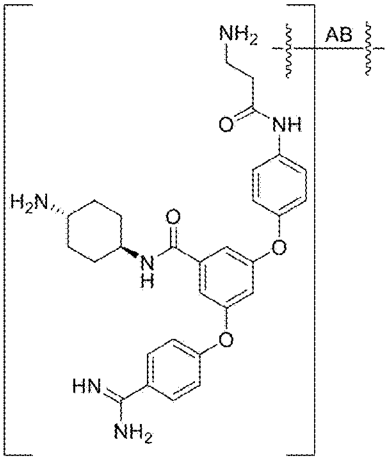
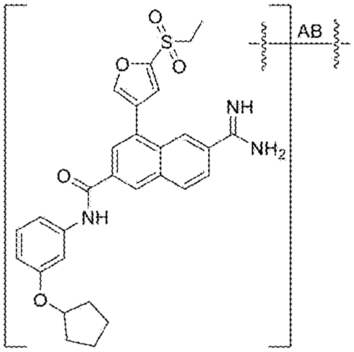
FIG. 1WWWWWWW

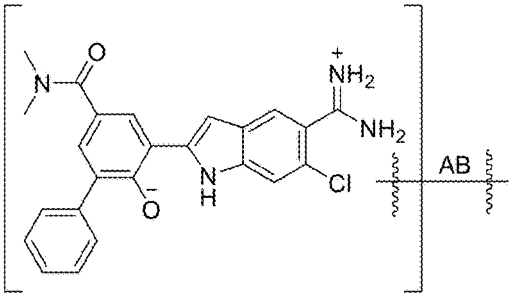
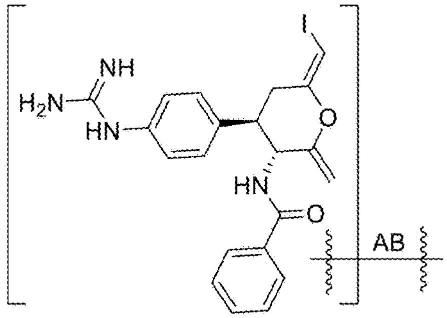
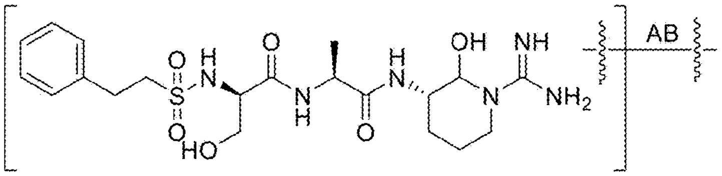
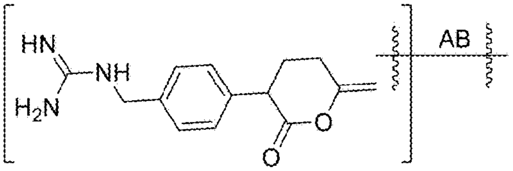
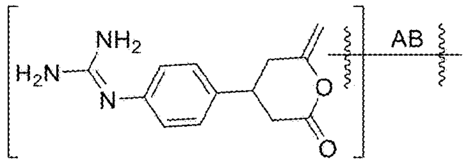
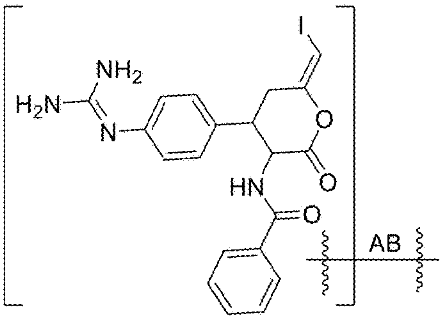
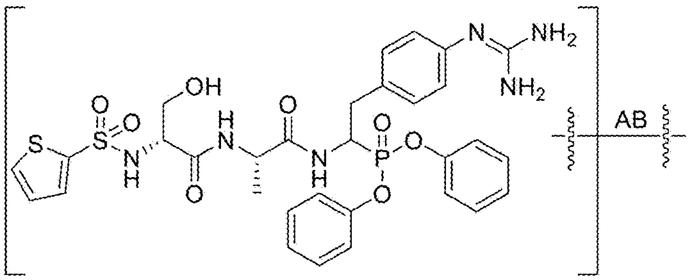
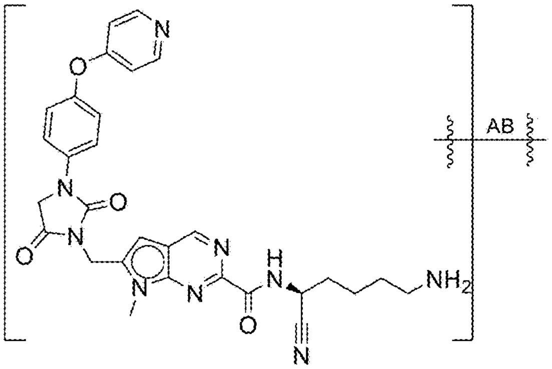
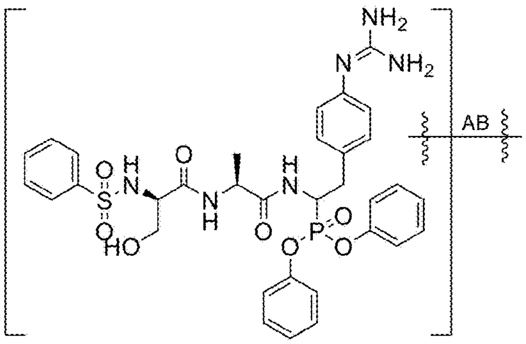
FIG. 1XXXXXX

ASGPR-BINDING COMPOUNDS FOR THE DEGRADATION OF EXTRACELLULAR PROTEINS

CROSS-REFERENCE TO RELATED APPLICATIONS

This application is a continuation of U.S. patent application Ser. No. 18/653,655, filed May 2, 2024, which is a continuation of U.S. patent application Ser. No. 18/220,708, filed Jul. 11, 2023, which is a continuation of U.S. patent application Ser. No. 17/877,538, filed Jul. 29, 2022, which is a continuation of International Patent Application No. PCT/US2021/015939, filed in the U.S. Receiving Office on Jan. 29, 2021, which claims the benefit of U.S. Provisional Patent Application No. 62/968,802, filed Jan. 31, 2020, and U.S. Provisional Patent Application No. 63/063,015, filed Aug. 7, 2020. The entirety of each of these applications is hereby incorporated by reference herein for all purposes.

INCORPORATION BY REFERENCE

The contents of the XML file named "19121-001WO1US2_SequenceListing_ST26.2" which was created on Sep. 19, 2023, and is 79.3 KB in size, are hereby incorporated by reference in their entirety.

FIELD OF THE INVENTION

This invention provides compounds and compositions that have an asialoglycoprotein receptor (ASGPR) binding ligand bound to an extracellular protein binding ligand for the selective degradation of the target extracellular protein in vivo to treat disorders mediated by the extracellular protein.

BACKGROUND OF THE INVENTION

Historically, therapeutic strategies for the inhibition of proteins employed small molecule inhibitors which bound in an enzymatic pocket or at an allosteric position. Those proteins which were not enzymes were difficult to control, and some were considered "not druggable."

Intracellular protein degradation is a natural and highly regulated, essential process that maintains cellular homeostasis. The selective identification and removal of damaged, misfolded, or excess proteins within the cell is achieved via the ubiquitin-proteasome pathway (UPP). The UPP is central to the regulation of almost all intracellular processes. A number of companies and institutions have designed intracellular protein degrading molecules that take advantage of this natural process to degrade disease-mediating proteins intracellularly by linking a ligand to the protein to be degraded to a protein in the UPP. Examples are found in U.S. 2014/0356322 assigned to Yale University, GlaxoSmithKline, and Cambridge EntA122-1 erprise Limited University of Cambridge; Buckley et al. (*J. Am. Chem. Soc.* 2012, 134, 4465-4468) titled "Targeting the Von Hippel-Lindau E3 Ubiquitin Ligase Using Small Molecules to Disrupt the Vhl/Hif-1 alpha Interaction"; WO 2015/160845 assigned to Arvinas Inc. titled "Imide Based Modulators of Proteolysis and Associated Methods of Use"; Lu et al. (*Chem. Biol.* 2015, 22, 755-763) titled "Hijacking the E3 Ubiquitin Ligase Cereblon to Efficiently Target Brd4"; Bondeson et al. (*Nat. Chem. Biol.* 2015, 11, 611-617) titled "Catalytic in Vivo Protein Knockdown by Small-Molecule Protacs"; Gustafson et al. (*Angewandte Chemie, International Edition in English* 2015, 54, 9659-9662) titled "Small-Molecule-Mediated Degradation of the Androgen Receptor through Hydrophobic Tagging"; Lai et al. (*Angewandte Chemie, International Edition in English* 2016, 55, 807-810) titled "Modular Protac Design for the Degradation of Oncogenic Bcr-Abl"; Toure et al. (*Angew. Chem. Int. Ed.* 2016, 55, 1966-1973) titled "Small-Molecule Protacs: New Approaches to Protein Degradation"; Winter et al. (*Science* 2015, 348, 1376-1381) titled "Drug Development. Phthalimide Conjugation as a Strategy for in Vivo Targeted Protein Degradation"; U.S. 2016/0058872 assigned to Arvinas, Inc. titled "Imide Based Modulators of Proteolysis and Associated Methods of Use" and U.S. 2016/0045607 assigned to Arvinas Inc. titled "Estrogen-related Receptor Alpha Based PROTAC Compounds and Associated Methods of Use".

The highjacking of the UPP intracellular process to degrade difficult or undruggable proteins, however, is not available to degrade extracellular proteins. Nonlimiting examples of extracellular proteins include immunoglobulins and cytokines, which can play a strong role in creating or exacerbating serious diseases. Immunoglobulins include IgA, IgG, IgD, IgE, and IgM. Cytokines are cell signaling peptides secreted into the bloodstream which cannot cross the lipid bilayer of cells to enter the cytoplasm, for example, interferons, interleukins, chemokines, lymphokines, MIP, and tumor necrosis factors. Cytokines are involved in autocrine, paracrine and endocrine signaling. They mediate immunity, inflammation and hematopoiesis. Cytokines are produced by immune cells (macrophages, B-cells, T-cells and mast cells), endothelial cells, fibroblasts and stromal cells.

The asialoglycoprotein receptor (ASGPR) is a $Ca^{2+}$-dependent lectin that is primarily expressed in parenchymal hepatocyte cells. The main role of ASGPRs is to help regulate serum glycoprotein levels by mediating endocytosis of desialylated glycoproteins (as depicted below). The receptor binds ligands with a terminal galactose or N-acetylgalactosamine. The $C^3$—and $C^4$-hydroxyl groups bind to $Ca^{2+}$. The $C^2$N-acetyl position has also been considered important to binding activity.

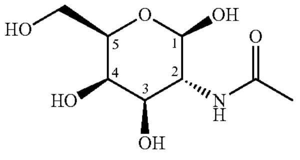

N-acetyl galactosamine

Asialoglycoproteins bind to ASGPRs and are then cleared by receptor-mediated endocytosis. The receptor and the protein are dissociated in the acidic endosomal compartment and the protein is eventually degraded by lysosomes. The receptor is endocytosed and recycled constitutively from the endosome back to the plasma membrane about every 15 minutes regardless of whether or not a glycoprotein is bound. However, it has been shown that the internalization rate of the receptor is dependent on the presence of ligand. In a 1998 study, the internalization rate of the protein without ligand was less than one-third of the rate of internalization of the ligand-receptor complex (Bider et al. *FEBS Letters,* 1998, 434, 37).

The ASGPR is comprised of two homologous subunits with 58% sequence identity known as H1 and H2. Various ratios of H1 and H2 form functional homo- and hetero-oligomers with different conformations, but the most abundant conformation is a trimer composed of two H1 and one H2 subunits. The ASGPR is composed of a cytoplasmic domain, a transmembrane domain, a stalk region, and a carbohydrate recognition domain (CRD). Both the H1 and H2 subunit are required to form the CRD, and therefore, co-expression of both subunits is a requirement for endocytosis of asialoglycoproteins. In 2000, the crystal structure of the CRD region was published, revealing three $Ca^{2+}$ binding sites (Meier et al. *J. Mol. Biol.* 2000, 300, 857).

A number of publications describe ligands that are thought to bind to the CRD region of ASGPRs. For example, Stokmaier et al. (*Bioorg. Med. Chem.,* 2009, 17, 7254) describes the synthesis of a series of D-GalNAc derivatives where the anomeric OH group is removed and the acetamido group is replaced with a 4-substituted 1,2,3-triazole moiety. The most potent compound is twice as potent as D-GalNAc in competitive NMR binding experiments. Mamidyala et al. (*JACS,* 2012, 134, 1978) describes compounds derived from 2-azidogalactosyl analogs where the anomeric position is occupied by either a β-methyl or a β-4-methoxy-phenyl group and the azide group is replaced with an amide or a triazole. The ligands were tested for binding activity by surface plasmon resonance and many exhibited more potent $K_d$ values than that of the parent N-acetylgalactosamine.

Studies have also shown that the receptor affinity for a ligand may be influenced by the ligand's valency. For example, Lee et al. (*J. Biol. Chem.,* 1983, 258, 199) showed that the $IC_{50}$ ranged from approximately 1 mM for monoantennary oligosaccharides to approximately 1 nM for triantennary oligosaccharides in an assay studying the binding ability of certain analogs to rabbit hepatocytes.

ASGPRs are primarily expressed on hepatocytes and are minimally found on cells outside of the liver. Hepatocytes exhibit a high exposition of ASGPR binding cites (approximately 100,000-500,000 binding sites per cell).

U.S. Pat. No. 5,985,826 to NeoRx Corporation describes the use of hepatic-directed systems that include a therapeutic agent with activity against a liver disease or disorder that is bound to a director moiety. The director moiety, which in one embodiment is a galactose or galactose derivative, directs the active agent to the liver, where the active agent acts as a therapeutic agent that is then removed from circulation with assistance from the director moiety.

U.S. Pat. Nos. 9,340,553; 9,617,293; 10,039,778; 10,376,531, and 10,813,942 assigned to Pfizer Inc. describe certain bicyclic, bridged ketal derivatives of GalNAc as targeting agents for the ASGPR receptor that in one embodiment are bound to a linker and/or a therapeutic agent such as a small molecule, an amino acid sequence, a nucleic acid sequence, an antibody, or a fluorescent probe. The linker of the drug delivery system can be monovalent, divalent, or trivalent. The disclosure also includes a method for the treatment of a liver disease or condition comprising administering the targeted drug delivery system. Several monovalent, divalent, and trivalent bicyclic bridged GalNAc-derived ASGPR targeting agents linked to fluorescence probes are disclosed in Sanhueza et al. (*JACS,* 2017, 139, 3528). One trivalent conjugate in particular exhibited selective hepatocyte targeting in an in vivo biodistribution study in mice.

Pfizer Inc. and the Regents of the University of California jointly disclosed the use of targeted drug delivery systems comprising certain ASPGR targeting ligands covalently bound to a ribonucleoprotein or an endonuclease in US 2017/0137801 for use in CRISPR gene editing.

Pfizer also developed PK2, a targeted drug delivery system wherein doxorubicin is linked via a lysosomally degradable tetrapeptide sequence to N-(2-hydroxypropyl) methacrylamide copolymers bearing galactosamine as the targeting agent. In a Phase 1 clinical trial to determine the selectivity, toxicity, and pharmacokinetic profile, it was demonstrated that the drug targeted primary hepatocellular tumors in patients with primary or metastatic liver cancer (Seymour et al. *J. Clin. Oncol.* 2002, 20, 1668).

Conjugates of paclitaxel covalently bound to one, two, or three units of GalNAc via a short linker are described in Petrov et al. (*Bioorganic and Medicinal Chemistry Letters,* 2018, 28, 382). The analogs were cytotoxic against human hepatocellular carcinoma cells and showed high affinity for ASGPR via surface plasmon resonance.

Pfizer Inc. and Wave Life Sciences Ltd. jointly disclosed the use of selected ASGPR ligands attached to oligonucleotides in PCT Applications WO 2018/223073 and WO2018/223081. The '073 application describes the use of APOC3 oligonucleotides attached to an ASGPR targeting ligand for selective delivery to the liver and the '081 application describes the use of PNPLA3 oligonucleotides attached to an ASGPR targeting ligand. PCT Application WO 2018/223056 assigned to Wave Sciences Ltd. describes compositions comprising oligonucleotides for RNA interference and in one embodiment, the oligonucleotide is attached to an ASGPR targeting ligand.

The targeted delivery of antisense oligonucleotides (ASOs), which bind and modulate complementary RNA, to hepatocytes via an ASGPR targeting ligand was studied in Schmidt et al. (*Nucleic Acids Research,* 2017, 45, 2294). Mono, di, and trivalent GalNAc were conjugated to single stranded and duplexed ASOs and it was found that di- and trivalent GalNAc-conjugated ASO systems were bind to ASGPR with the strongest affinity.

Examples of ASGPR-targeted therapy using modified glycoproteins as the target agents are reviewed in Huang et al. (*Bioconjugate Chem.* 2017, 28, 283). A number of multivalent ligands that have been developed are discussed in addition to certain properties for drug delivery, including linker length and spatial geometry of the scaffold.

Yale University has filed two PCT Applications, WO 2019/199621 and WO 2019/199634, which describe the use of certain ASGPR targeting ligands covalently bound to a circulating protein binding moiety. Once the circulating protein binding moiety binds the circulating protein, the complex passes to the liver where it is recognized by ASGPR and degraded via the endo-lysosomal pathway. The '621 application describes circulating protein binding moieties that are capable of targeting macrophage migration inhibitory factor (MIF) and/or immunoglobulin G (IgG). The '634 application describes the targeting of numerous circulating proteins including CD40L, TNF-α, PCSK9, VEGF, TGF-β, uPAR, PSMA, IL-2, GP120, TSP-1, and CXCL-2 using a drug delivery system comprising a circulating protein binding moiety covalently bound to a targeting ligand, which is a ASGPR targeting ligand.

The Board of Trustees of the Leland Stanford Junior University has filed a PCT application, WO2020/132100, which describes the use of compounds that bind a lysosomal targeting molecule such as ASGPR to degrade a cell surface molecule or extracellular molecule. Compounds related to the WO2020/132100 disclosure are described in an article by Banik et al. (*Nature,* 2020, 584, 291). Related work from the Bertozzi group was published in a preprint article titled "Lysosome Targeting Chimeras (LYTACs) That Engage a Liver-Specific Asialoglycoprotein Receptor for Targeted Protein Degradation," online on ChemRxiv in July 2020.

While some progress has been made in the area of targeted degradation of disease-mediating extracellular proteins, much is left to be accomplished. There remains an unmet need for additional chemical compounds and approaches to treat medical disorders mediated by extracellular proteins.

SUMMARY OF THE INVENTION

Novel compounds and their pharmaceutically acceptable salts and compositions thereof that degrade disease-mediating extracellular proteins, as well as starting materials and intermediates for such compounds and their methods of use and processes of manufacture are provided. This invention focuses on novel modifications of the $C^2$-position of the ASGPR ligand, referred to herein as $R^2$. These modifications include molecules with the $C^2$ substituent in the "down" configuration which correspond to the stereochemistry of galactose as well as molecules with the $C^2$ substituent in the "up" configuration which corresponds to the stereochemistry of talose. It has been discovered that advantageous extracellular protein degrader molecules are provided when ASGPR ligands with $R^2$ groups as specified herein that have either galactose or talose stereochemistry are incorporated into the structure.

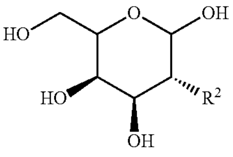

Galactose Stereochemistry

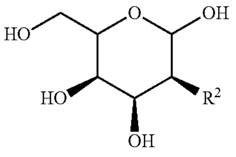

Talose Stereochemistry

The extracellular protein degrading compounds described herein can be used to degrade a selected extracellular protein by attaching a ligand for the extracellular protein to a selected ASGPR ligand, through a covalent bond or a covalent linking group. Extracellular proteins that can be targeted according the present invention include but are not limited to immunoglobulins such as IgA, IgG, IgD, IgE, and IgM, and derivatives thereof which retain the same basic function, and cytokines such as interferons, interleukins, chemokines, lymphokines, MIP, and tumor necrosis factors. In certain embodiments, the extracellular protein is selected from IgA, IgG, IgE, TNF (α or β), IL-1b, IL-2, IFN-γ, IL-6, VGEF, TGF-b1 and PCSK-9. In other nonlimiting embodiments, proteins of the complement system are targeted for degradation, including Factor B, Factor D, Factor H and CC5.

Galactose-Based Molecules

It has been discovered that sugars in the galactose stereochemistry with new $C^2$ substituents are useful ligands for ASGPR. These molecules can be used as ASGPR ligands or linked to an extracellular protein targeting ligand to recruit extracellular protein and degrade it in the liver.

In particular, a compound of Formula I, Formula II, Formula III, Formula IV, Formula V, Formula VI, Formula VII, or Formula VIII is provided:

(I)

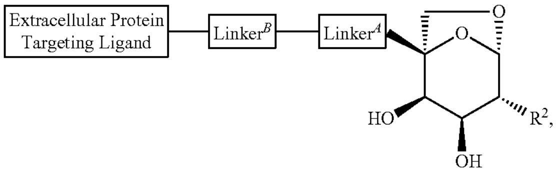

, (II)

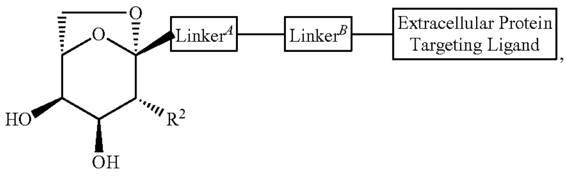

, (III)

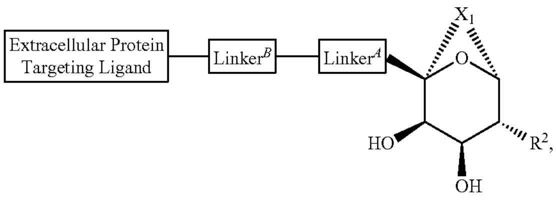

, (IV)

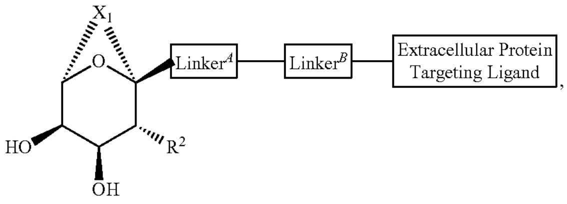

, (V)

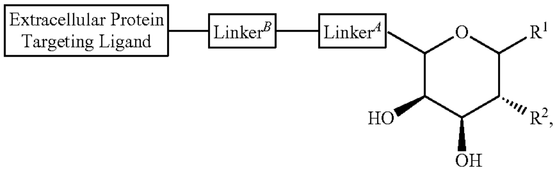

, (VI)

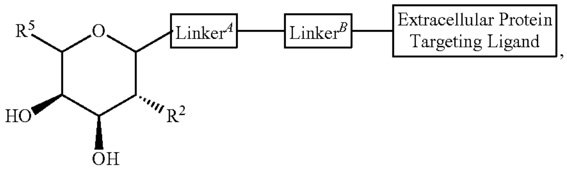

, (VII)

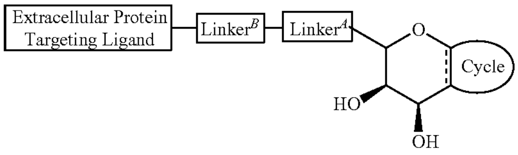

, or

-continued (VIII)

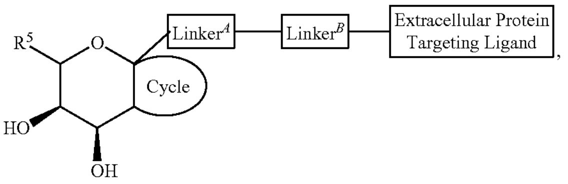

or a pharmaceutically acceptable salt thereof;

wherein:

$X^1$ is 1 to 5 contiguous atoms independently selected from O, S, $N(R^6)$, and $C(R^4)(R^4)$, wherein if $X^1$ is 1 atom then $X^1$ is O, S, $N(R^6)$, or $C(R^4)(R^4)$, if $X^1$ is 2 atoms then no more than 1 atom of $X^1$ is O, S, or $N(R^6)$, if $X^1$ is 3, 4, or 5 atoms then no more than 2 atoms of $X^1$ are O, S, or $N(R^6)$;

$R^2$ is selected from (i) aryl, heterocycle, and heteroaryl containing 1 or 2 heteroatoms independently selected from N, O, and S, each of which aryl, heterocycle, and heteroaryl is optionally substituted with 1, 2, 3, or 4 substituents;

(ii)

(ii)

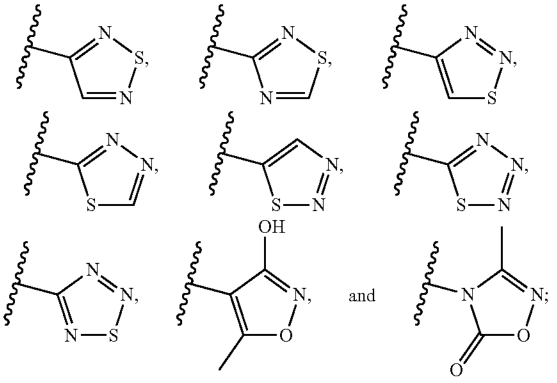

and (iii) —$NR^8$—S(O)—$R^3$, —$NR^8$—C(S)—$R^3$, —$NR^8$—S(O)($NR^6$)—$R^3$, —N═S(O)$(R^3)_2$, —$NR^8$C(O)$NR^9$S$(O)_2R^3$, —$NR^8$—$S(O)_2$—$R^{10}$, and —$NR^8$—C($NR^6$)—$R^3$ each of which is optionally substituted with 1, 2, 3, or 4 substituents; and (iv) hydrogen, $R^{10}$, alkyl-C(O)—$R^3$, —C(O)—$R^3$, alkyl, haloalkyl, —OC(O)$R^3$, and —$NR^8$—C(O)$R^{10}$;

$R^{10}$ is selected from alkenyl, allyl, alkynyl, —$NR^6$-alkenyl, —O-alkenyl, —$NR^6$-alkynyl, —$NR^6$— heteroaryl, —$NR^6$-aryl, —O-heteroaryl, —O-aryl, and —O-alkynyl, each of which $R^{10}$ is optionally substituted with 1, 2, 3, or 4 substituents;

or $R^{10}$ is selected from aryl, alkyl-$NR^8$—C(O)—$R^3$, alkyl-aryl, alkyl-heteroaryl with 1, 2, or 4 heteroatoms, alkyl-cyano, alkyl-$OR^6$, alkyl-$NR^6R^8$, $NR^8$—$NR^6$—C(O)$R^3$, $NR^8$—$S(O)_2$—$R^3$, alkenyl, allyl, alkynyl, —$NR^6$-alkenyl, —O-alkenyl, —$NR^6$-alkynyl, —$NR^6$-heteroaryl, —$NR^6$-aryl, —O-heteroaryl, —O-aryl, and —O-alkynyl, each of which $R^{10}$ is optionally substituted with 1, 2, 3, or 4 substituents;

in certain embodiments $R^{10}$ is selected from

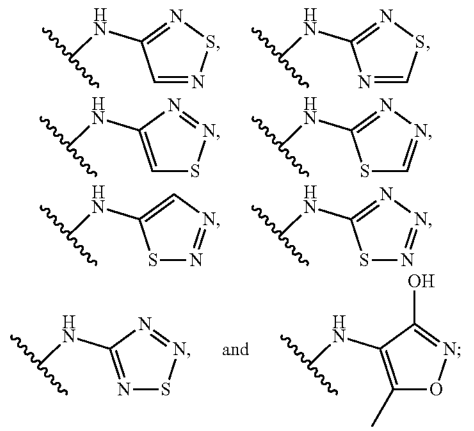

and in certain embodiments $R^{10}$ is selected from

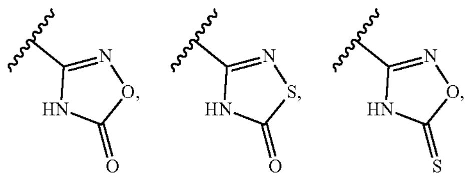

and

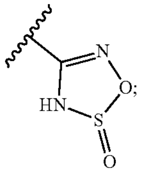

$R^1$ and $R^5$ are independently selected from hydrogen, heteroalkyl, $C_0$-$C_6$ alkyl-cyano, alkyl, alkenyl, alkynyl, haloalkyl, F, Cl, Br, I, aryl, arylalkyl, heteroaryl, heteroarylalkyl, heterocycle, heterocycloalkyl, haloalkoxy, —O-alkenyl, —O-alkynyl, $C_0$-$C_6$ alkyl-$OR^6$, $C_0$-$C_6$ alkyl-$SR^6$, $C_0$-$C_6$ alkyl-$NR^6R^7$, $C_0$-$C_6$ alkyl-C(O)$R^3$, $C_0$-$C_6$ alkyl-S(O)$R^3$, $C_0$-$C_6$ alkyl-C(S)$R^3$, $C_0$-$C_6$ alkyl-$S(O)_2R^3$, $C_0$-$C_6$ alkyl-N($R^8$—C(O)$R^3$, $C_0$-$C_6$ alkyl-N($R^8$)—S(O)$R^3$, $C_0$-$C_6$ alkyl-N($R^8$)—C(S)$R^3$, $C_0$-$C_6$ alkyl-N(R')—$S(O)_2R^3$, $C_0$-$C_6$ alkyl-O—C(O)$R^3$, $C_0$-$C_6$ alkyl-O—S(O)$R^3$, $C_0$-$C_6$ alkyl-O—C(S)$R^3$, —N═S(O)$(R^3)_2$, $C_0$-$C_6$ alkyl$N_3$, and $C_0$-$C_6$ alkyl-O—$S(O)_2R^3$, each of which is optionally substituted with 1, 2, 3, or 4 substituents;

$R^3$ at each occurrence is independently selected from hydrogen, alkyl, heteroalkyl, haloalkyl (including —$CF_3$, —$CHF_2$, —$CH_2F$, —$CH_2CF_3$, —$CH_2CH_2F$, and —$CF_2CF_3$), arylalkyl, heteroarylalkyl, alkenyl, alkynyl, aryl, heteroaryl, heterocycle, —$OR^8$, and —$NR^8R^9$;

$R^4$ is independently selected at each occurrence from hydrogen, heteroalkyl, alkyl, haloalkyl, arylalkyl, heteroarylalkyl, alkenyl, alkynyl, aryl, heteroaryl, heterocycle, —$OR^6$, —$NR^6R^7$, C(O)$R^3$, S(O)$R^3$, C(S)$R^3$, and $S(O)_2R^3$;

$R^6$ and $R^7$ are independently selected at each occurrence from hydrogen, heteroalkyl, alkyl, arylalkyl, heteroarylalkyl, alkenyl, alkynyl, aryl, haloalkyl, heteroaryl, heterocycle, -alkyl-$OR^8$, -alkyl-$NR^8R^9$, C(O)$R^3$, S(O)$R^3$, C(S)$R^3$, and $S(O)_2R^3$;

$R^8$ and $R^9$ are independently selected at each occurrence from hydrogen, heteroalkyl, alkyl, arylalkyl, heteroarylalkyl, alkenyl, alkynyl, aryl, heteroaryl, and heterocycle;

Cycle is a 3-8 membered fused cyclic group optionally substituted with 1, 2, 3, or 4 substituents; exemplary Cycle groups include carbocycle (e.g. cyclopropane, cyclohexane, or cyclohexene), heterocycle (e.g. oxetane, piperazine), aryl (e.g. phenyl), or a heteroaryl group (e.g. pyridine, furan, or pyrrole) as appropriate and allowed by valence;

each Linker$^A$ is a bond or a moiety that covalently links the ASGPR ligand to Linker$^B$;

Linker$^B$ is a bond or a moiety that covalently links Linker$^A$ to an Extracellular Protein Targeting Ligand;

Extracellular Protein Targeting Ligand is a chemical moiety that binds to the targeted disease-modifying extracellular protein; and when a compound is "optionally substituted" it may be substituted as allowed by valence by one or more groups selected from alkyl (including $C_1$-$C_4$ alkyl), alkenyl (including $C_2$-$C_4$ alkenyl), alkynyl (including $C_2$-$C_4$alkynyl), haloalkyl (including $C_1$-$C_4$ haloalkyl), —$OR^6$, F, Cl, Br, I, —$NR^6R^7$, heteroalkyl, cyano, nitro, $C(O)R^3$,

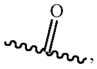, 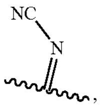, 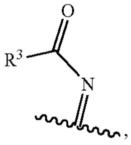, and 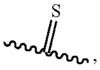, wherein the optional substituent is selected such that a stable compound results.

In an alternative embodiment when a compounds is "optionally substituted" it may be substituted as allowed by valence with one or more groups selected from alkyl (including $C_1$-$C_4$ alkyl), alkenyl (including $C_2$-$C_4$ alkenyl), alkynyl (including $C_2$-$C_4$alkynyl), haloalkyl (including $C_1$-$C_4$ haloalkyl), —$OR^6$, F, Cl, Br, I, —$NR^6R^7$, heteroalkyl, heterocycle, heteroaryl, aryl, cyano, nitro, hydroxyl, azide, amide, —$SR^3$, —$S(O)(NR^6)R^3$, —$NR^8C(O)R^3$, —$C(O)NR^6R^7$, —$C(O)OR^3$, —$C(O)R^3$, —$SF_5$,

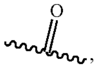, 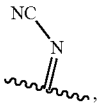, 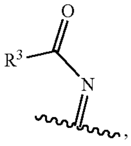, and 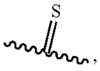, wherein the optional substituent is selected such that a stable compound results.

In one embodiment the Extracellular Protein Targeting Ligand is not an oligomer.

In another embodiment neither the Extracellular Protein nor the Extracellular Protein Targeting Ligand directly mediates intracellular gene editing such as CRISPR.

In an alternative embodiment of the invention, when $R^2$ is $NR^6$-alkenyl, —$NR^6$-alkynyl, —$NR^8$—$C(O)R^{10}$, —$NR^8$—$S(O)_2$-alkenyl, —$NR^8$—$S(O)_2$-alkynyl, —$NR^6$-heteroaryl, or —$NR^6$-aryl, then Extracellular Protein Targeting Ligand does not comprise an oligonucleotide. In certain embodiment of the invention, when $R^2$ is $R^{10}$, $NR^6$-alkenyl, —$NR^6$-alkynyl, —$NR^8$—$C(O)R^{10}$, —$NR^8$—$S(O)_2$-alkenyl, —$NR^8$—$S(O)_2$-alkynyl, —$NR^6$-heteroaryl, or —$NR^6$-aryl, then Extracellular Protein Targeting Ligand does not comprise an oligonucleotide.

A compound of Formula I-Bi, Formula II-Bi, Formula III-Bi, Formula IV-Bi, Formula V-Bi, Formula VI-Bi, Formula VII-Bi, or Formula VIII-Bi is provided:

(I-Bi)

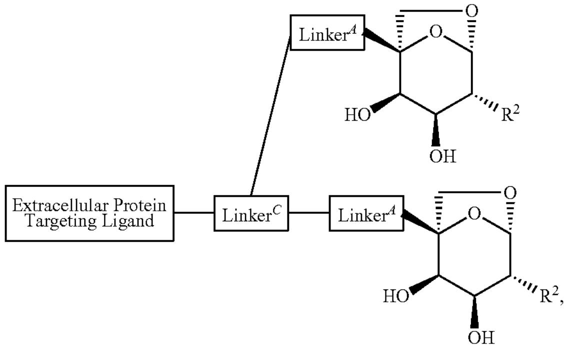

(II-Bi)

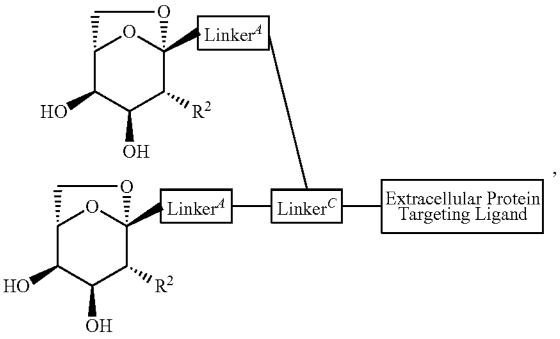

(III-Bi)

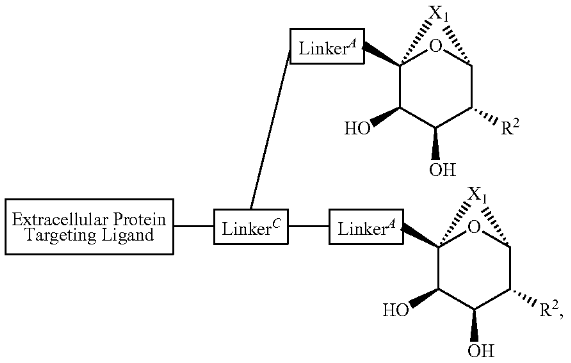

-continued (IV-Bi)

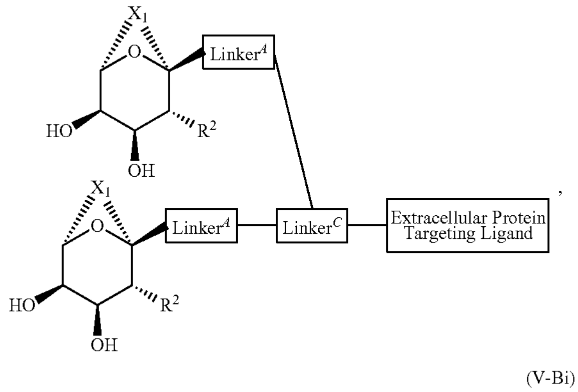

, (V-Bi)

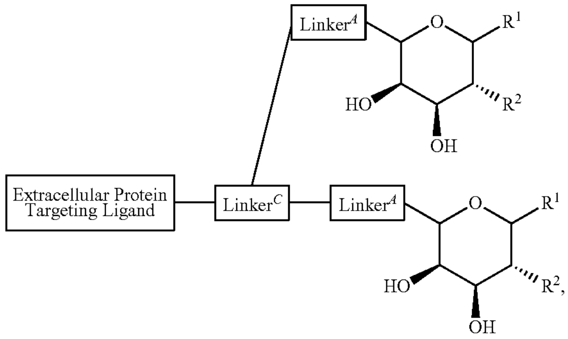

(VI-Bi)

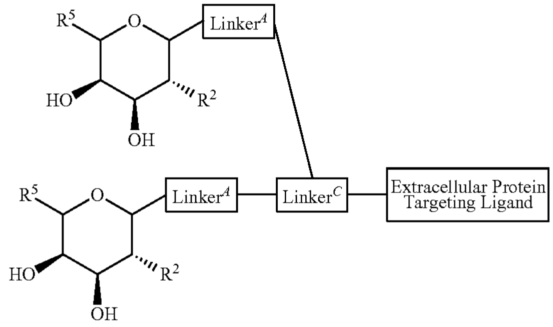

, (VII-Bi)

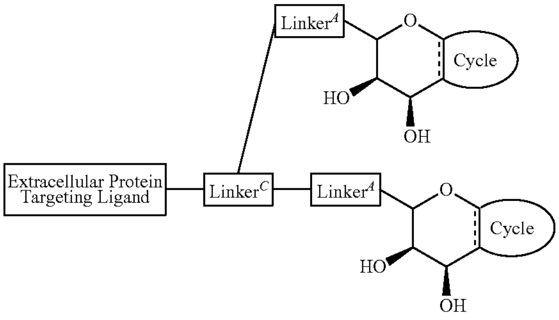

,

-continued (VIII-Bi)

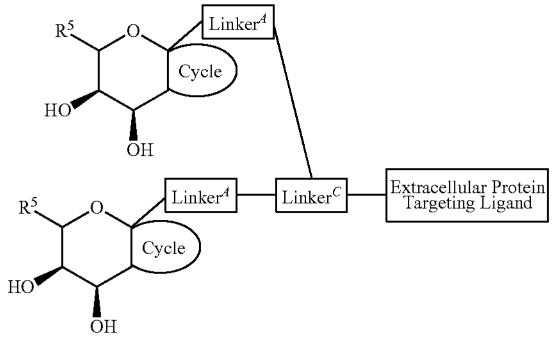

, or a pharmaceutically acceptable salt thereof;

wherein:

$Linker^C$ is a chemical group that links each $Linker^A$ to the Extracellular Protein Targeting Ligand; and all other variables are as defined herein.

A compound of Formula I-Tri, Formula II-Tri, Formula III-Tri, Formula IV-Tri, Formula V-Tri, Formula VI-Tri, Formula VII-Tri, or Formula VIII-Tri is also provided:

(I-Tri)

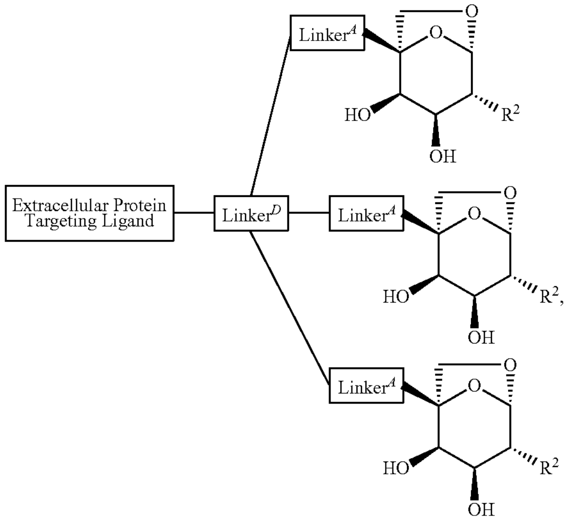

-continued
(II-Tri)
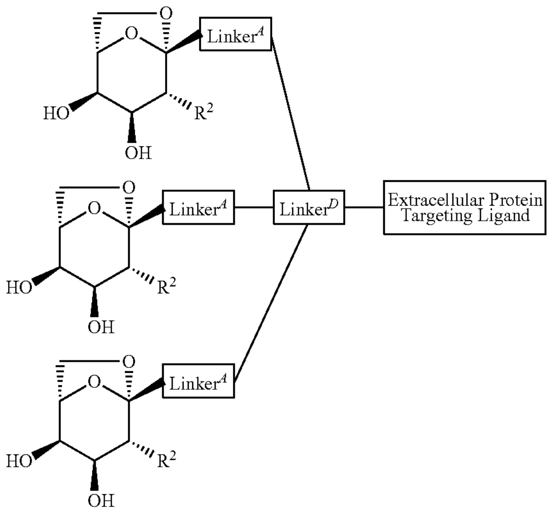
,
(III-Tri)
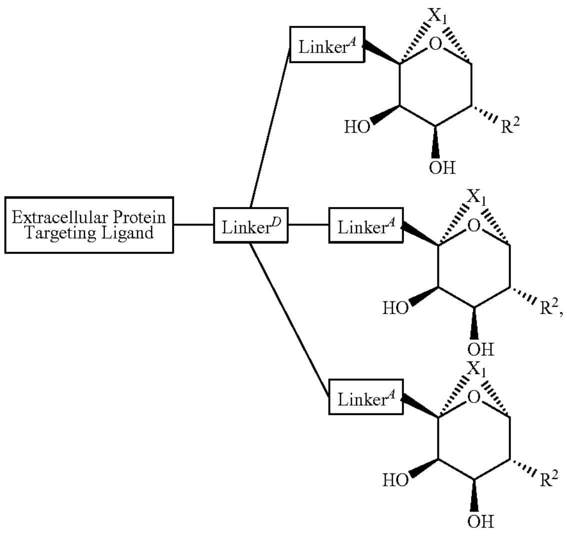
(IV-Tri)
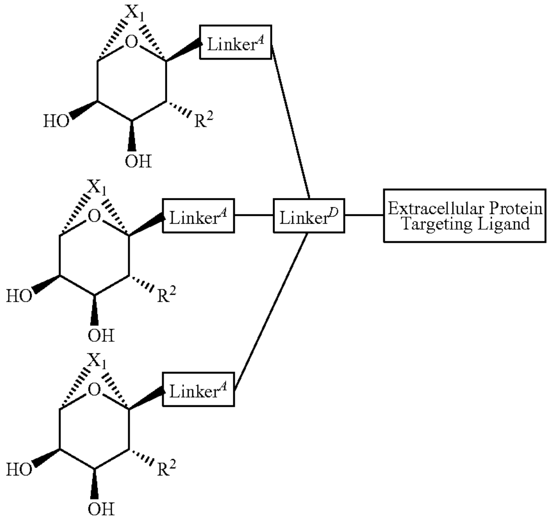
,
-continued
(V-Tri)
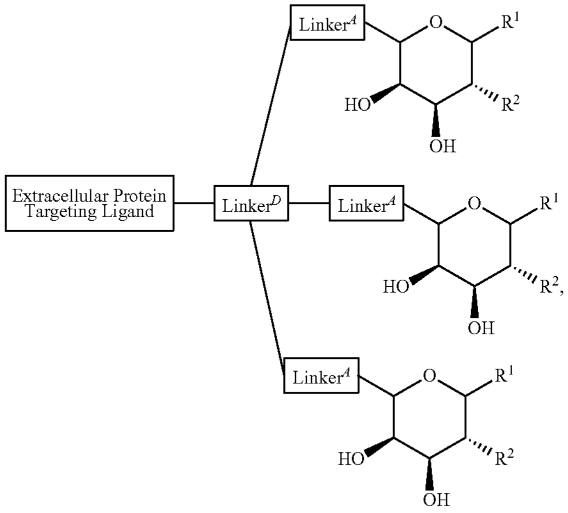
(VI-Tri)
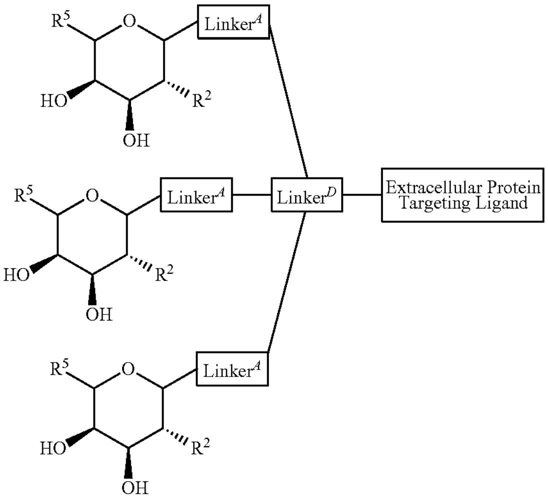
,
(VII-Tri)
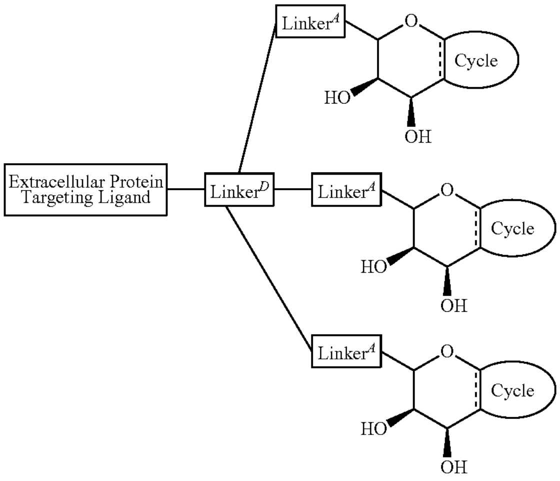
, -continued (VIII-Tri)

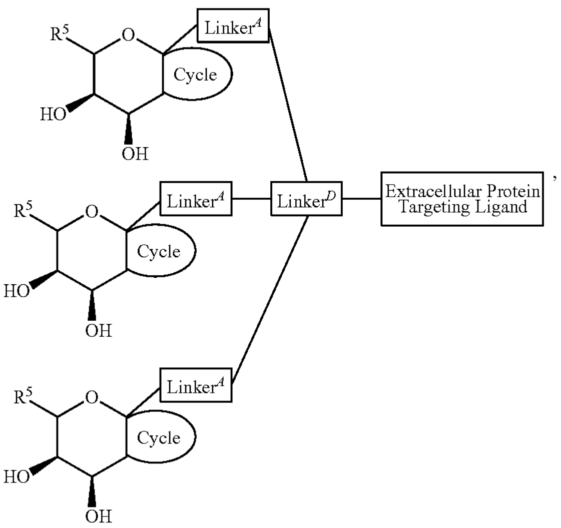

or a pharmaceutically acceptable salt thereof;

wherein:

Linker$^D$ is a chemical group that links each Linker$^A$ to the Extracellular Protein Targeting Ligand; and all other variables are as defined herein.

As used herein, Anchor Bond is defined as the chemical bond between the Extracellular Protein Targeting Ligand and either Linker$^B$, Linker$^C$ or Linker$^D$, as appropriate.

A compound of Formula IX, Formula X, Formula XI, Formula XII, or Formula XIII is provided:

(IX)

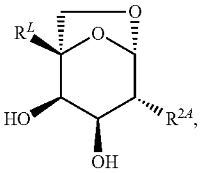

(X)

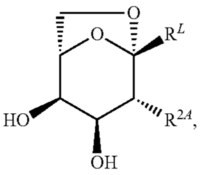

(XI)

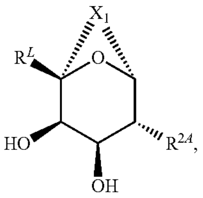

(XII)

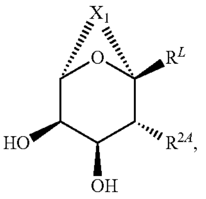

-continued (XIII)

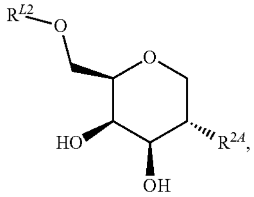

(XIV)

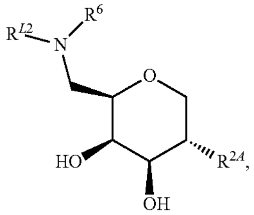

(XV)

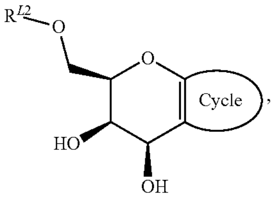

(XVI)

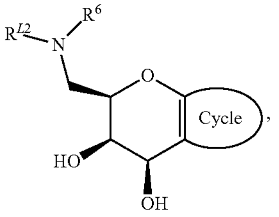

or a pharmaceutically acceptable salt thereof;

wherein:

$R^L$ is selected from $R^5$ and Linker$^E$;

$R^{L2}$ is selected from $R^6$ and Linker$^E$;

$X^1$ is 1 to 5 contiguous atoms independently selected from O, S, N($R^6$), and C($R^4$)($R^4$), wherein if $X^1$ is 1 atom then $X^1$ is O, S, N($R^6$), or C($R^4$)($R^4$), if $X^1$ is 2 atoms then no more than 1 atom of $X^1$ is O, S, or N($R^6$), if $X^1$ is 3, 4, or 5 atoms then no more than 2 atoms of $X^1$ are O, S, or N($R^6$);

$R^{2A}$ is selected from (i) aryl, heterocycle, and heteroaryl containing 1 or 2 heteroatoms independently selected from N, O, and S, each of which aryl, heterocycle, and heteroaryl is optionally substituted with 1, 2, 3, or 4 substituents;

(ii)

(ii)

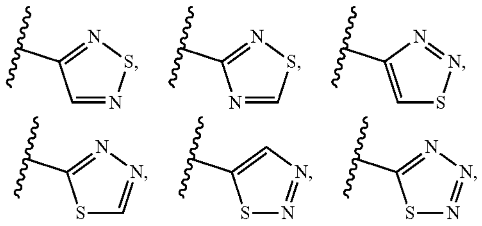

-continued

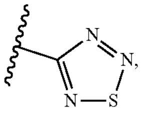, 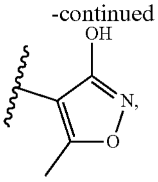, and 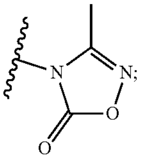;

and (iii) —NH—S(O)—$R^3$, —$NR^8$—C(S)—$R^3$, —NH—S(O)($NR^6$)—$R^3$, and —N═S(O)($R^3$)—$NR^6R^7$ each of which is optionally substituted with 1, 2, 3, or 4 substituents;

In an alternative embodiment $R^{2A}$ is selected from

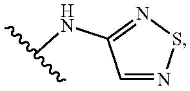, 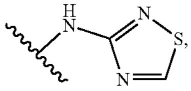,

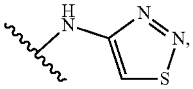, 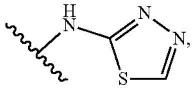,

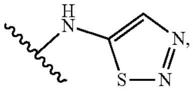, 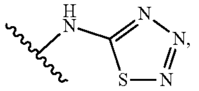,

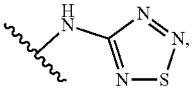 and 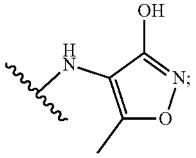;

In an alternative embodiment $R^{2A}$ is selected from $R^{10}$;

$R^1$ and $R^5$ are independently selected from hydrogen, heteroalkyl, $C_0$-$C_6$ alkyl-cyano, alkyl, alkenyl, alkynyl, haloalkyl, F, Cl, Br, I, aryl, arylalkyl, heteroaryl, heteroarylalkyl, heterocycle, heterocycloalkyl, haloalkoxy, —O-alkenyl, —O-alkynyl, $C_0$-$C_6$ alkyl-$OR^6$, $C_0$-$C_6$ alkyl-$SR^6$, $C_0$-$C_6$ alkyl-$NR^6R^7$, $C_0$-$C_6$ alkyl-C(O)$R^3$, $C_0$-$C_6$ alkyl-S(O)$R^3$, $C_0$-$C_6$ alkyl-C(S)$R^3$, $C_0$-$C_6$ alkyl-$S(O)_2R^3$, $C_0$-$C_6$ alkyl-N($R^8$)—C(O)$R^3$, $C_0$-$C_6$ alkyl-N(R')—S(O)$R^3$, $C_0$-$C_6$ alkyl-N($R^8$)—C(S)$R^3$, $C_0$-$C_6$ alkyl-N(R')—$S(O)_2R^3$, $C_0$-$C_6$ alkyl-O—C(O)$R^3$, $C_0$-$C_6$ alkyl-O—S(O)$R^3$, $C_0$-$C_6$ alkyl-O—C(S)$R^3$, —N═S(O)$(R^3)_2$, $C_0$-$C_6$ alkyl$N_3$, and $C_0$-$C_6$ alkyl-O—$S(O)_2R^3$, each of which is optionally substituted with 1, 2, 3, or 4 substituents;

$R^3$ at each occurrence is independently selected from hydrogen, alkyl, heteroalkyl, haloalkyl, arylalkyl, heteroarylalkyl, alkenyl, alkynyl, aryl, heteroaryl, heterocycle, —$OR^8$, or —$NR^8R^9$;

$R^4$ is independently selected at each occurrence from hydrogen, heteroalkyl, alkyl, haloalkyl, arylalkyl, heteroarylalkyl, alkenyl, alkynyl, aryl, heteroaryl, heterocycle, —$OR^6$, —$NR^6R^7$, C(O)$R^3$, S(O)$R^3$, C(S)$R^3$, and $S(O)_2R^3$;

$R^6$ and $R^7$ are independently selected at each occurrence from hydrogen, heteroalkyl, alkyl, arylalkyl, heteroarylalkyl, alkenyl, alkynyl, aryl, haloalkyl, heteroaryl, heterocycle, -alkyl-$OR^8$, -alkyl-$NR^8R^9$, C(O)$R^3$, S(O)$R^3$, C(S)$R^3$, and $S(O)_2R^3$;

$R^8$ and $R^9$ are independently selected at each occurrence from hydrogen, heteroalkyl, alkyl, arylalkyl, heteroarylalkyl, alkenyl, alkynyl, aryl, heteroaryl, and heterocycle;

Cycle is a 3-8 membered fused cyclic group optionally substituted with 1, 2, 3, or 4 substituents; exemplary Cycle groups include carbocycle (e.g. cyclopropane, cyclohexane, or cyclohexene), heterocycle (e.g. oxetane, of piperazine), aryl (e.g. phenyl), or a heteroaryl group (e.g. pyridine, furan, or pyrrole) as appropriate and allowed by valence;

$Linker^E$ is

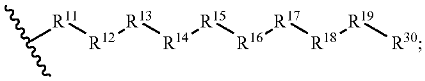;

$R^{30}$ is selected from Cl, Br, I, —$NR^6$H, —OH, —$N_3$, —SH,

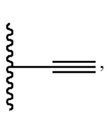, 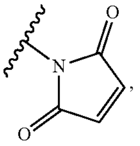,

—C(O)N($CH_3$)$OCH_3$, —B($OR^6$)($OR^7$), heterocycle, —$NR^6COR^3$, —$OCOR^3$ and —$COR^3$, $R^{11}$, $R^{12}$, $R^{13}$, $R^{14}$, $R^{15}$, $R^{16}$, $R^{17}$, $R^{18}$, and $R^{19}$ are independently at each occurrence selected from the group consisting of a bond, alkyl, —C(O)—, —C(O)O—, —OC(O)—, —$SO_2$—, —S(O)—, —C(S)—, —C(O)$NR^6$—, —$NR^6$C(O)—, —O—, —S—, —NR—, —C($R^{21}R^{21}$)—, —P(O)($OR^6$)O—, —P(O)($OR^6$)—, —P(O)($NR^6R^7$)$NR^6$—, —P(O)($NR^6R^7$)—, amino acid, alkenyl, alkynyl, haloalkyl, alkoxy, aryl, heterocycle, heteroaryl, —[—$(CH_2)_2$—O—$]_n$—, —[O—$(CH_2)_2]_n$—, —[O—CH($CH_3$)C(O)$]_n$—, —[C(O)—CH($CH_3$)—O$]_n$—, —[O—$CH_2$C(O)$]_n$—, —[C(O)—$CH_2$—O$]_n$—, fatty acid, unsaturated acid, each of which is optionally substituted with 1, 2, 3, or 4 substituents independently selected from $R^{21}$;

n is independently selected at each instance from 0, 1, 2, 3, 4, 5, 6, 7, 8, 9, or 10;

$R^{21}$ is independently at each occurrence selected from the group consisting of hydrogen, alkyl, alkenyl, alkynyl, F, Cl, Br, I, hydroxyl, alkoxy, azide, amino, cyano, —$NR^6R^7$, —$NR^8SO_2R^3$, —$NR^8$S(O)$R^3$, haloalkyl, heteroalkyl, aryl, heteroaryl, and heterocycle; or or $R^{21}$ is independently at each occurrence selected from the group consisting of hydrogen, alkyl, alkenyl, alkynyl, F, Cl, Br, I, hydroxyl, alkoxy, azide, amino, cyano, —$NR^6R^7$, —$NR^8SO_2R^3$, —$NR^8$S(O)$R^3$, haloalkyl, heteroalkyl, aryl, heteroaryl, heterocyclyl, —$SR^3$, —C(O)$OR^3$, —C(O)$NR^6NR^7$, —$OR^3$,

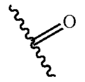

and heterocycle.

Talose-Based Molecules

It has also been discovered that sugars in the talose stereochemistry with specific $C^2$ substituents are useful ligands for ASGPR. These molecules can be used as ASGPR ligands or linked to an extracellular protein targeting ligand to recruit extracellular protein and degrade it in the liver.

In particular, a compound of Formula I-d, Formula II-d, Formula III-d, Formula IV-d, Formula V-d, or Formula VI-d is provided:

(I-d)

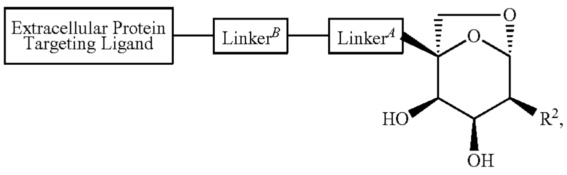

(II-d)

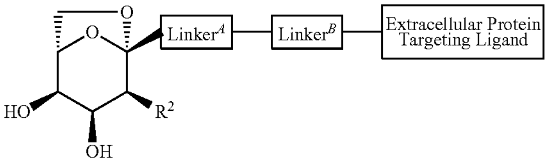

, (III-d)

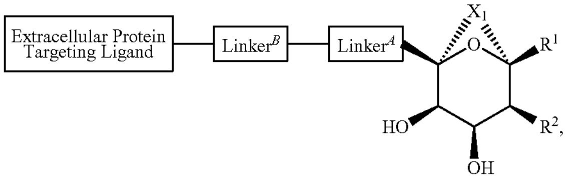

(IV-d)

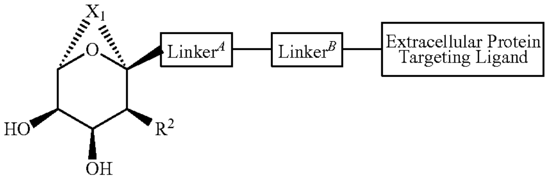

, (V-d)

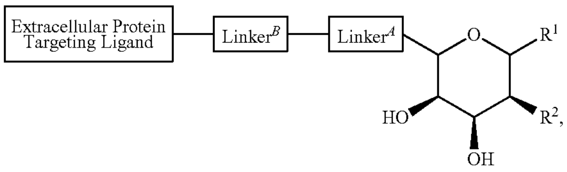

(VI-d)

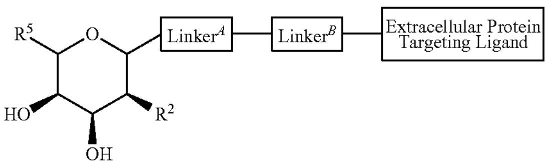

, or a pharmaceutically acceptable salt thereof, wherein for compounds of Formula I-d, II-d, III-d, IV-d, V-d, and VI-d $R^2$ is selected from:

(i) aryl, heterocycle, and heteroaryl containing 1 or 2 heteroatoms independently selected from N, O, and S, each of which aryl, heterocycle, and heteroaryl is optionally substituted with 1, 2, 3, or 4 substituents;

(ii)

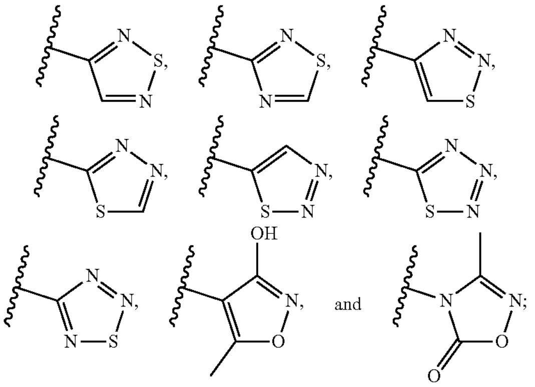

(iii) —$NR^8$—S(O)—$R^3$, —$NR^8$—C(S)—$R^3$, —$NR^8$—S(O)($NR^6$)—$R^3$, —N═S(O)$(R^3)_2$, —$NR^8C(O)NR^9S(O)_2R^3$, —$NR^8$—$S(O)_2$—$R^{10}$, and —$NR^8$—C($NR^6$)—$R^3$ each of which is optionally substituted with 1, 2, 3, or 4 substituents; and (iv) hydrogen, $R^{10}$, alkyl-C(O)—$R^3$, —C(O)—$R^3$, alkyl, haloalkyl, —OC(O)$R^3$, and —$NR^8$—C(O)$R^{10}$; and (v) $R^{200}$;

$R^{200}$ is —$NR^8$—C(O)—$R^3$;

or $R^{200}$ is —$NR^8$—C(O)—$R^3$, —$NR^6$-alkyl, —$OR^8$, heteroaryl (including for example triazole and tetrazole), $NR^8$—$S(O)_2$—$R^3$, or —$NR^6$-heteroalkyl, each of which $R^{200}$ substituents is optionally substituted with 1, 2, 3, or 4 substituents;

when compounds are "optionally substituted" they may be substituted as allowed by valence by groups selected from alkyl (including $C_1$-$C_4$ alkyl), alkenyl (including $C_2$-$C_4$ alkenyl), alkynyl (including $C_2$-$C_4$alkynyl), haloalkyl (including $C_1$-$C_4$ haloalkyl), —$OR^6$, F, Cl, Br, I, —$NR^6R^7$, heteroalkyl, cyano, nitro, C(O)$R^3$,

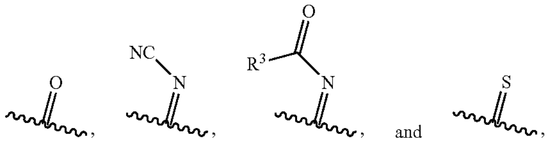

wherein the optional substituent is selected such that a stable compound results.

In an alternative embodiment when compounds are "optionally substituted" they may be substituted as allowed by valence by groups selected from alkyl (including $C_1$-$C_4$ alkyl), alkenyl (including $C_2$-$C_4$ alkenyl), alkynyl (including $C_2$-$C_4$alkynyl), haloalkyl (including $C_1$-$C_4$ haloalkyl), —$OR^6$, F, Cl, Br, I, —$NR^6R^7$, heteroalkyl, heterocycle, heteroaryl, aryl, cyano, nitro, hydroxyl, azide, amide, —$SR^3$, —S(O)($NR^6$)$R^3$, —$NR^8C(O)R^3$, —C(O)$NR^6R^7$, —C(O)$OR^3$, —C(O)$R^3$, —$SF_5$,

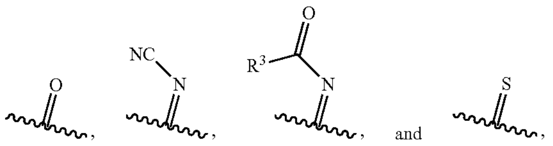

wherein the optional substituent is selected such that a stable compound results; and all other variables are as defined herein.

In certain embodiments, a mixture of the galactose and talose-based stereochemistry are used in medical therapy, including but not limited to an equal mixture. For example, a compound Formula I and a corresponding compound of Formula I-d may be used in any mixture that provides the desired therapeutic results. More generally, any mixture of any of the Formulas I through XVI and Formulas I-d through XVI-d (any of which can be in the mono, bi, or tri framework).

A compound of Formula I-d-Bi, Formula II-d-Bi, Formula III-d-Bi, Formula IV-d-Bi, Formula V-d-Bi, or Formula VI-d-Bi is provided:

(I-d-Bi)

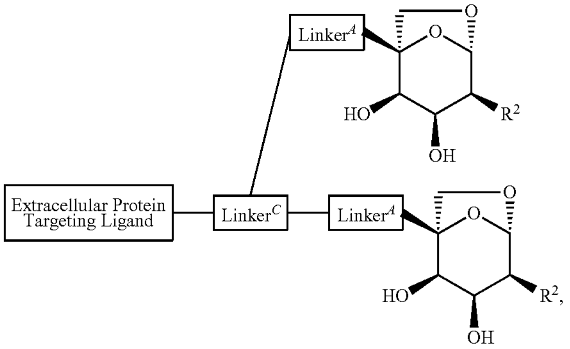

(II-d-Bi)

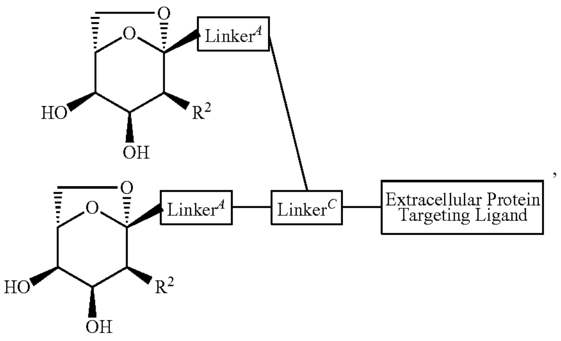

(III-d-Bi)

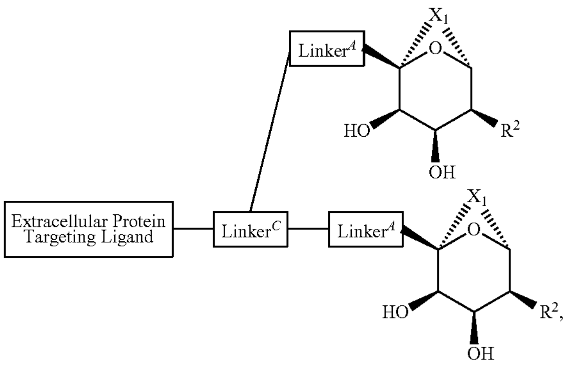

-continued (IV-d-Bi)

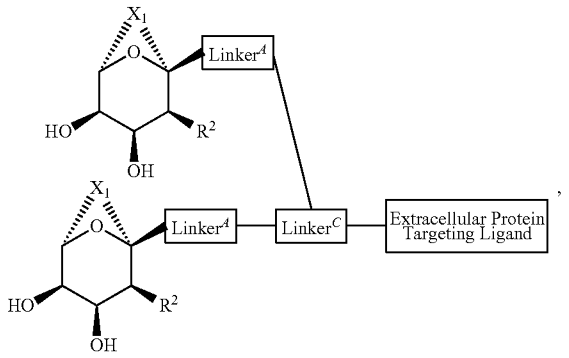

(V-d-Bi)

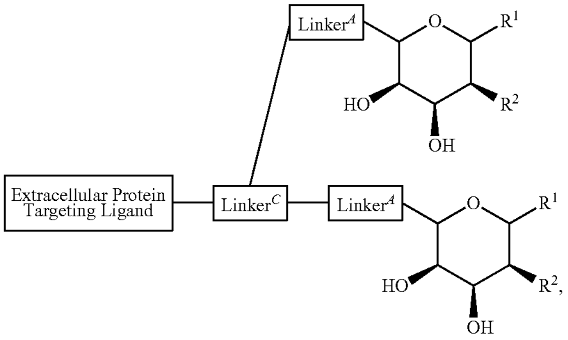

(VI-d-Bi)

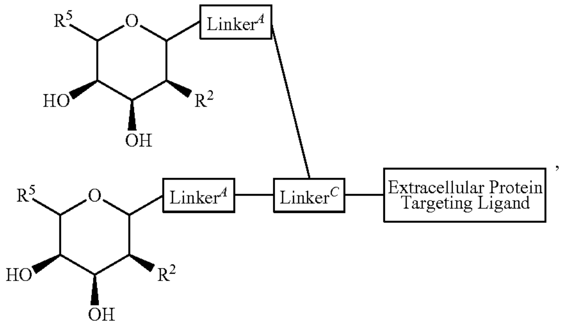

wherein for compounds of Formula I-d-Bi, II-d-Bi, III-d-Bi, IV-d-Bi, V-d-Bi, and VI-d-Bi, $R^2$ is selected from:

(i) aryl, heterocycle, and heteroaryl containing 1 or 2 heteroatoms independently selected from N, O, and S, each of which aryl, heterocycle, and heteroaryl is optionally substituted with 1, 2, 3, or 4 substituents;

(ii)

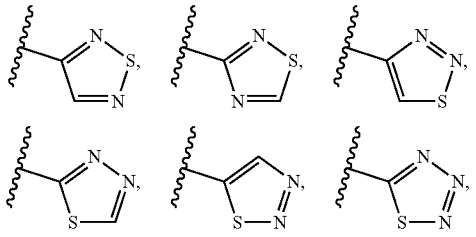

-continued

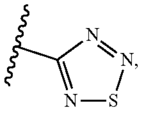

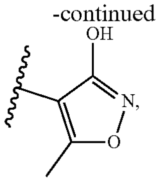

and

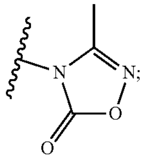

(iii) $-NR^8-S(O)-R^3$, $-NR^8-C(S)-R^3$, $-NR^8-S(O)(NR^6)-R^3$, $-N{=}S(O)(R^3)_2$, $-NR^8C(O)NR^9S(O)_2R^3$, $-NR^8-S(O)_2-R^{10}$, and $-NR^8-C(NR^6)-R^3$ each of which is optionally substituted with 1, 2, 3, or 4 substituents; and (iv) hydrogen, $R^{10}$, alkyl-C(O)$-R^3$, $-C(O)-R^3$, alkyl, haloalkyl, $-OC(O)R^3$, and $-NR^8-C(O)R^{10}$; and (v) $R^{200}$;

$R^{200}$ is $-NR^8-C(O)-R^3$; and all other variables are as defined herein.

A compound of Formula I-d-Tri, Formula II-d-Tri, Formula III-d-Tri, Formula IV-d-Tri, Formula V-d-Tri, or Formula VI-d-Tri, is provided:

(I-d-Tri)

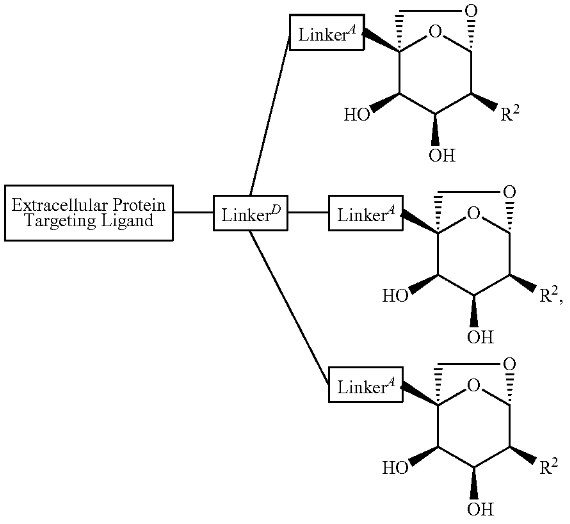

(II-d-Tri)

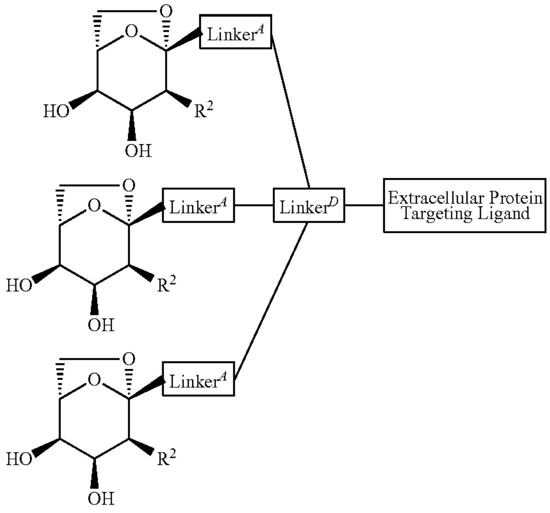

,

-continued (III-d-Tri)

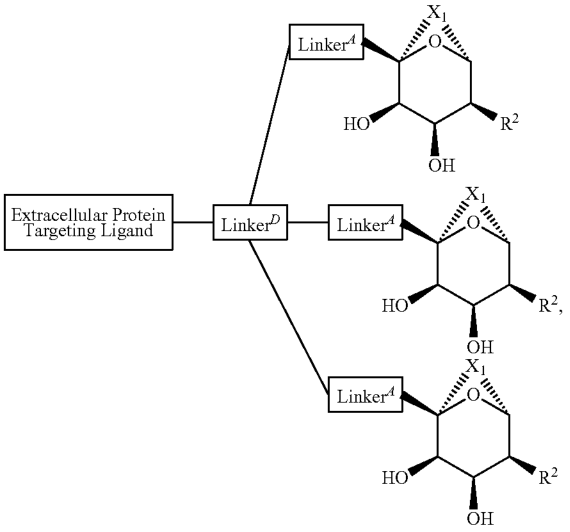

(IV-d-Tri)

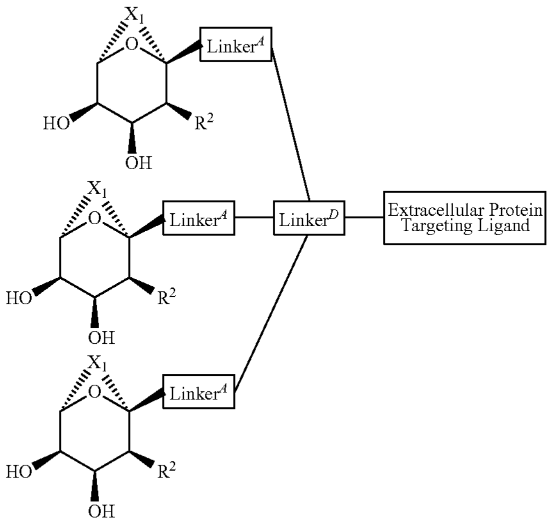

, (V-d-Tri)

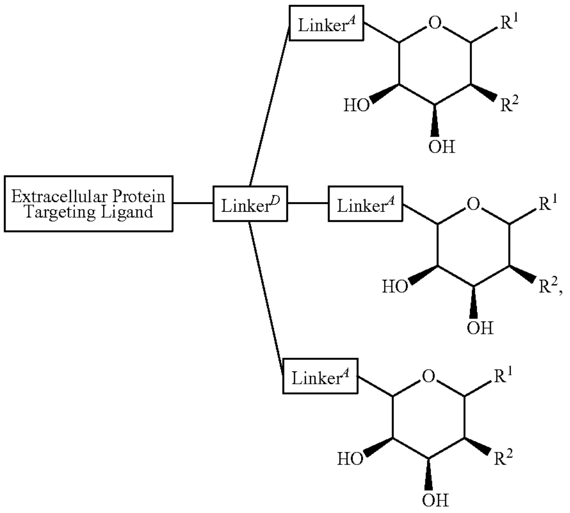

-continued (VI-d-Tri)

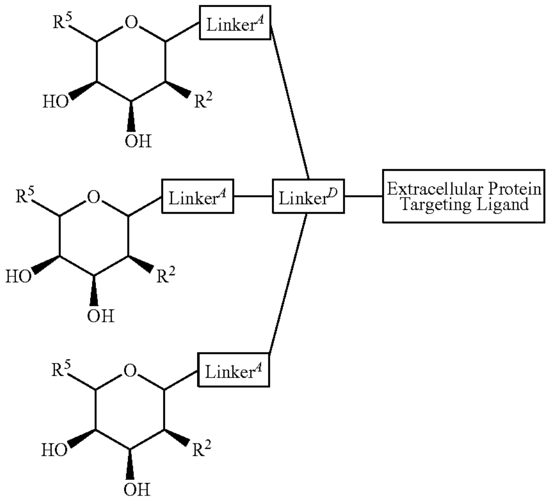

or a pharmaceutically acceptable salt thereof, wherein for compounds of Formula I-d-Tri, II-d-Tri, III-d-Tri, IV-d-Tri, V-d-Tri, and VI-d-Tri $R^2$ is selected from:

(i) aryl, heterocycle, and heteroaryl containing 1 or 2 heteroatoms independently selected from N, O, and S, each of which aryl, heterocycle, and heteroaryl is optionally substituted with 1, 2, 3, or 4 substituents;

(ii)

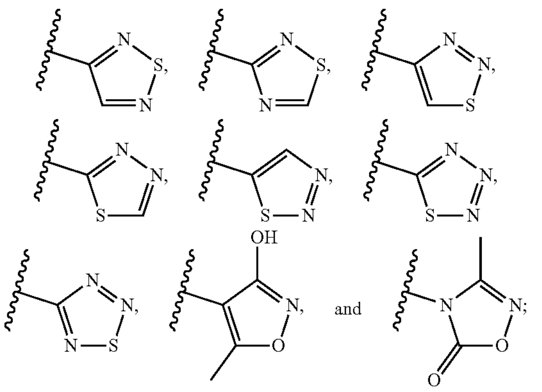

and (iii) $-NR^8-S(O)-R^3$, $-NR^8-C(S)-R^3$, $-NR^8-S(O)(NR^6)-R^3$, $-N{=}S(O)(R^3)_2$, $-NR^8C(O)NR^9S(O)_2R^3$, $-NR^8-S(O)_2-R^{10}$, and $-NR^8-C(NR^6)-R^3$ each of which is optionally substituted with 1, 2, 3, or 4 substituents; and (iv) hydrogen, $R^{10}$, alkyl-C(O)—$R^3$, —C(O)—$R^3$, alkyl, haloalkyl, —OC(O)$R^3$, and $-NR^8-C(O)R^{10}$; and (v) $R^{200}$.

$R^{200}$ is $-NR^8-C(O)-R^3$; and all other variables are as defined herein.

A compound of Formula IX-d, X-d, XI-d, XII-d, XIII-d, XIV-d is provided.

(IX-d)

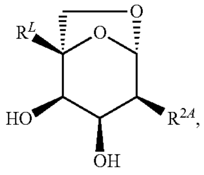

(X-d)

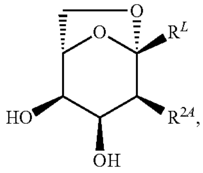

(XI-d)

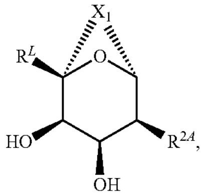

(XII-d)

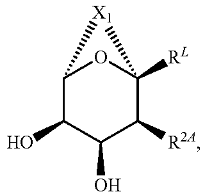

(XIII-d)

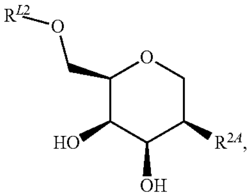

(XIV-d)

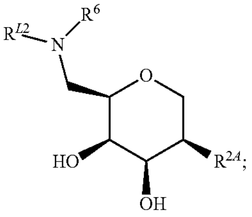

or a pharmaceutically acceptable salt thereof.

In an embodiment of the invention, the Extracellular Protein Targeting Ligand is a small organic molecule (i.e., a non-biologic) that adequately binds to the protein in such a manner that it is able to transport it to the liver, the residue of a pharmaceutically active compound that binds to the target extracellular protein (for example but not limited to a compound of the sort that would be reviewed as a drug by CDER of the FDA, or an approved or clinical stage drug) or a peptide, protein or biologic or a binding fragment thereof that adequately binds to the protein in such a manner that it is able to transport it to the liver, and in some embodiments, that does not comprise an oligonucleotide or aptamer. A plethora of illustrative nonlimiting examples of extracellular protein targeting ligands is provided in FIG. 1. The present invention focuses on the degradation of circulating extracellular proteins that mediate diseases, for example, involving immunity, inflammation, hematopoiesis/blood disorders (including those caused or exacerbated by blood vessel formation) and abnormal cellular proliferation such as tumors and cancer. In a typical embodiment of the invention, neither the Extracellular Protein nor the Extracellular Protein Targeting Ligand directly mediates intracellular gene editing such as CRISPR.

In one embodiment of the invention, when $R^2$ is $NR^6$-alkenyl, —$NR^6$-alkynyl, —$NR^8$—$C(O)R^{10}$, —$NR^8$—$S(O)_2$-alkenyl, —$NR^8$—$S(O)_2$-alkynyl, —$NR^6$-heteroaryl, or —$NR^6$-aryl, then Extracellular Protein Targeting Ligand does not comprise an oligonucleotide or aptamer.

The ASGPR-binding Extracellular Protein degraders of the present invention can be administered in any manner that allows the degrader to bind to the Extracellular Protein, typically in the blood stream, and carry it to the ASGPR-bearing hepatocyte cells on the liver for endocytosis and degradation. As such, examples of methods to deliver the degraders of the present invention include, but are not limited to, oral, intravenous, buccal, sublingual, subcutaneous and transnasal.

BRIEF DESCRIPTION OF FIGURES

FIG. 1BB-1KK provides a non-limiting list of Extracellular Protein Targeting Ligands that target Vascular endothelial growth factor (VEGF).

FIG. 1LL provides a non-limiting list of Extracellular Protein Targeting Ligands that target Transforming growth factor beta (TGF-β1).

FIG. 1MM-1PP provides a non-limiting list of Extracellular Protein Targeting Ligands that target proprotein convertase subtilisin kexin 9 (PCSK-9).

FIG. 1QQ-1SS provides a non-limiting list of Extracellular Protein Targeting Ligands that target Carboxypeptidase B2 (CPB2).

FIG. 1TT-1UU provides a non-limiting list of Extracellular Protein Targeting Ligands that target Cholinesterase (ChE).

FIG. 1VV-1WW provides a non-limiting list of Extracellular Protein Targeting Ligands that target C—C Motif Chemokine Ligand 2 (CCL2).

FIG. 1XX-1BBB provides a non-limiting list of Extracellular Protein Targeting Ligands that target coagulation factor VII (Factor VII).

FIG. 1CCC-1FFF provides a non-limiting list of Extracellular Protein Targeting Ligands that target coagulation factor IX (Factor IX).

FIG. 1GGG provides a non-limiting list of Extracellular Protein Targeting Ligands that target CD40 Ligand (CD40L).

FIG. 1HHH-1JJJ provides a non-limiting list of Extracellular Protein Targeting Ligands that target coagulation factor Xa (Factor Xa).

FIG. 1KKK-1MMM provides a non-limiting list of Extracellular Protein Targeting Ligands that target coagulation factor XI (Factor XI).

FIGS. 1NNN and 1OOO provides a non-limiting list of Extracellular Protein Targeting Ligands that target coagulation factor XII (Factor XII).

FIGS. 1PPP and 1QQQ provides a non-limiting list of Extracellular Protein Targeting Ligands that target coagulation factor XIII (Factor XIII).

FIG. 1RRR-1UUU provides a non-limiting list of Extracellular Protein Targeting Ligands that target fibroblast growth factor 1 (FGF1).

FIG. 1VVV-1XXX provides a non-limiting list of Extracellular Protein Targeting Ligands that target fibroblast growth factor 2 (FGF2).

FIGS. 1AAAA and 1BBBB provides a non-limiting list of Extracellular Protein Targeting Ligands that target Interleukin-5 (TL-5).

FIG. 1CCCC provides a non-limiting list of Extracellular Protein Targeting Ligands that target Interleukin-8 (IL-8).

FIGS. 1DDDD and 1EEEE provides a non-limiting list of Extracellular Protein Targeting Ligands that target Interleukin-10 (IL-10).

FIGS. 1FFFF and 1GGGG provides a non-limiting list of Extracellular Protein Targeting Ligands that target Interleukin-21 (IL-21).

FIGS. 1HHHH and 1IIII provides a non-limiting list of Extracellular Protein Targeting Ligands that target Interleukin-22 (IL-22).

FIG. 1JJJJ-1NNNN provides a non-limiting list of Extracellular Protein Targeting Ligands that target Kallikrein 1.

FIG. 1OOOO provides a non-limiting list of Extracellular Protein Targeting Ligands that target lipoprotein lipase (LPL).

FIGS. 1PPPP and 1QQQQ provides a non-limiting list of Extracellular Protein Targeting Ligands that target matrix metalloproteinase-1 (MMP1).

FIG. 1RRRR-1DDDDD provides a non-limiting list of Extracellular Protein Targeting Ligands that target Macrophage migration inhibitory factor (MIF), also known as glycosylation-inhibiting factor (GIF), L-dopachrome isomerase, or phenylpyruvate tautomerase.

FIG. 1EEEEE-1GGGGG provides a non-limiting list of Extracellular Protein Targeting Ligands that target neutrophil elastase (NE).

FIGS. 1HHHHH and 1IIIII provides a non-limiting list of Extracellular Protein Targeting Ligands that target Prothrombin.

FIG. 1JJJJJ-1NNNNN provides a non-limiting list of Extracellular Protein Targeting Ligands that target Plasma kallikrein (KLKB1).

FIG. 1OOOOO-1SSSSS provides a non-limiting list of Extracellular Protein Targeting Ligands that target plasminogen (PLG).

FIG. 1TTTTT-1XXXXX provides a non-limiting list of Extracellular Protein Targeting Ligands that target Plasminogen activator inhibitor-1 (PAI-1), endothelial plasminogen activator inhibitor or serpin E1.

FIG. 1YYYYY-1AAAAAA provides a non-limiting list of Extracellular Protein Targeting Ligands that target phospholipases A2, for example type 1B or group 1B (PLA2, PA21B, PLA2G1B, PLA2-IB).

FIG. 1BBBBBB-1DDDDDD provides a non-limiting list of Extracellular Protein Targeting Ligands that target phospholipases A2, for example type IIA or group IIA (PLA2, PLA2A, PA2IIA, PLA2G2A, PLA2-IIA).

FIG. 1EEEEEE-1NNNNNN provides a non-limiting list of Extracellular Protein Targeting Ligands that target placental growth factor (PGF).

FIG. 1OOOOOO-1QQQQQQ provides a non-limiting list of Extracellular Protein Targeting Ligands that target plasminogen activator, tissue type (tPA, PLAT).

FIG. 1RRRRRR provides a non-limiting list of Extracellular Protein Targeting Ligands that target Transforming growth factor beta 2 (TGF-β2, TGFB2).

FIG. 1SSSSSS provides a non-limiting list of Extracellular Protein Targeting Ligands that target thrombospondin 1 (TSP1, TSP-1, THBS1).

FIG. 1TTTTTT-1XXXXXX provides a non-limiting list of Extracellular Protein Targeting Ligands that target Urokinase or Urokinase-type plasminogen activator (UPA, uPA).

DETAILED DESCRIPTION OF THE INVENTION

Figure 1A:
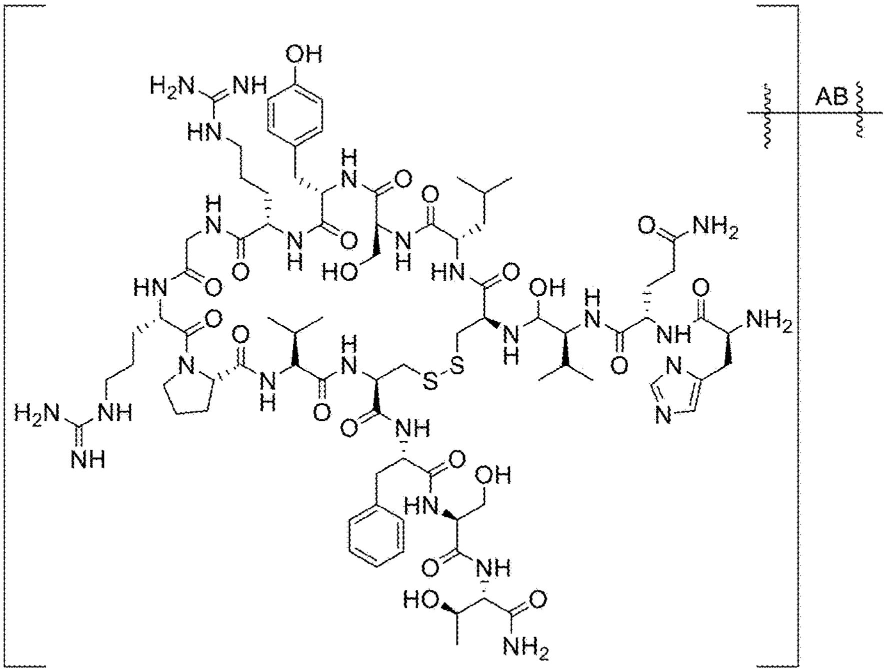
FIG. 1A provides a non-limiting list of Extracellular Protein Targeting Ligands that target Immunoglobulin A (IgA).
Figure 1A:
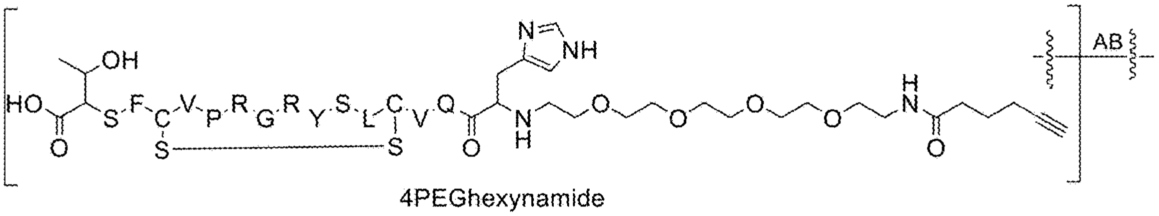
Figure 1A:
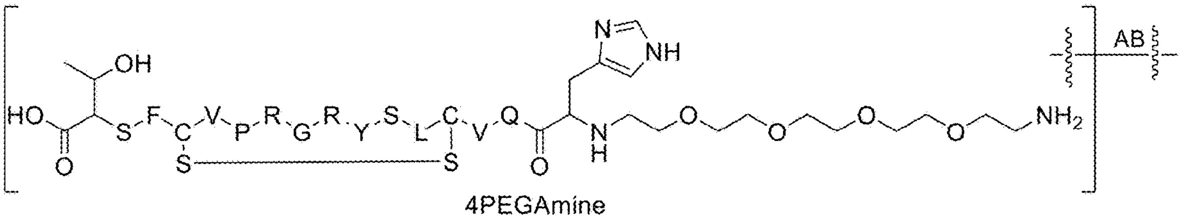
Figure 1B:
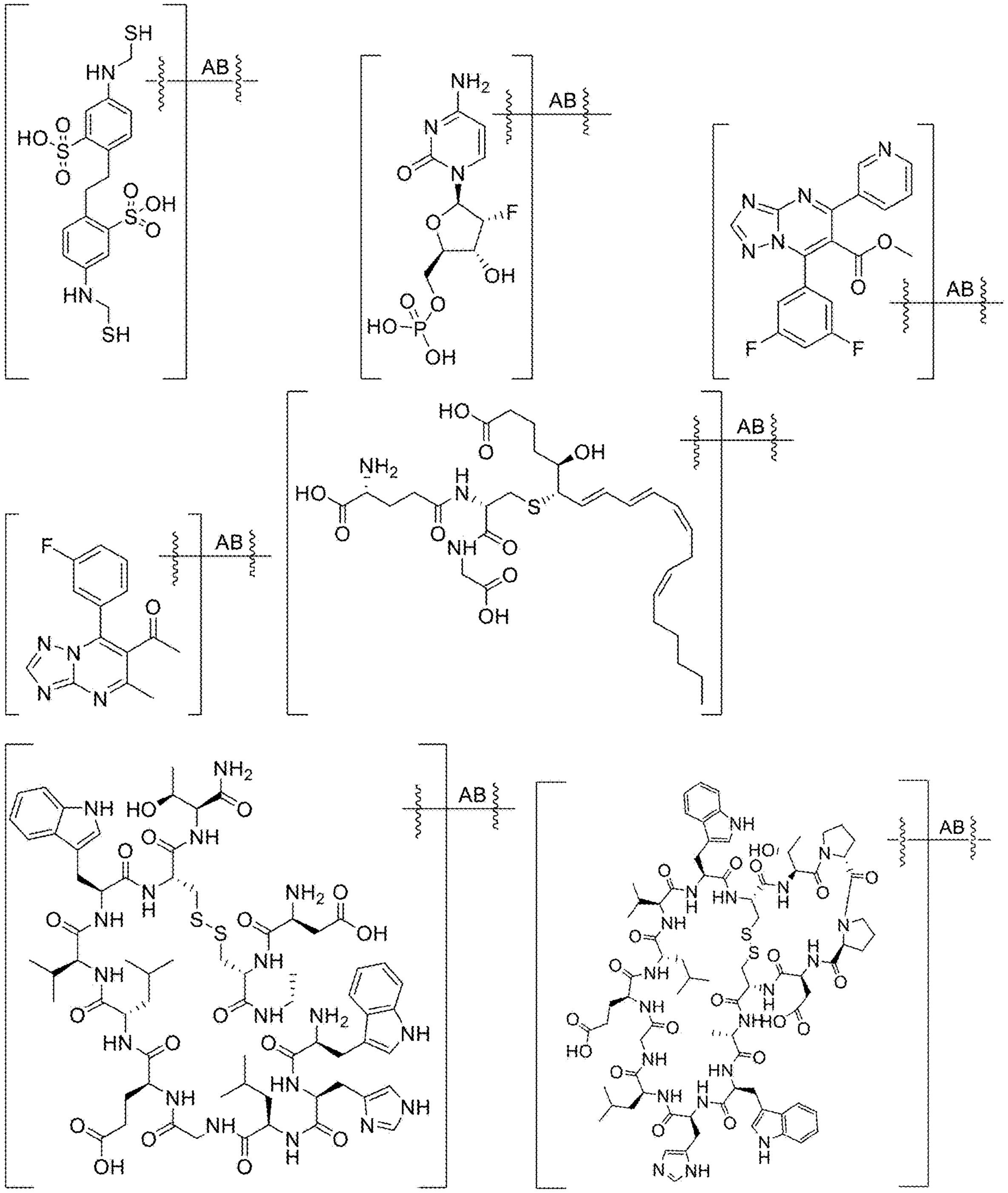
FIG. 1B provides a non-limiting list of Extracellular Protein Targeting Ligands that target Immunoglobulin G (IgG).
Figure 1C:
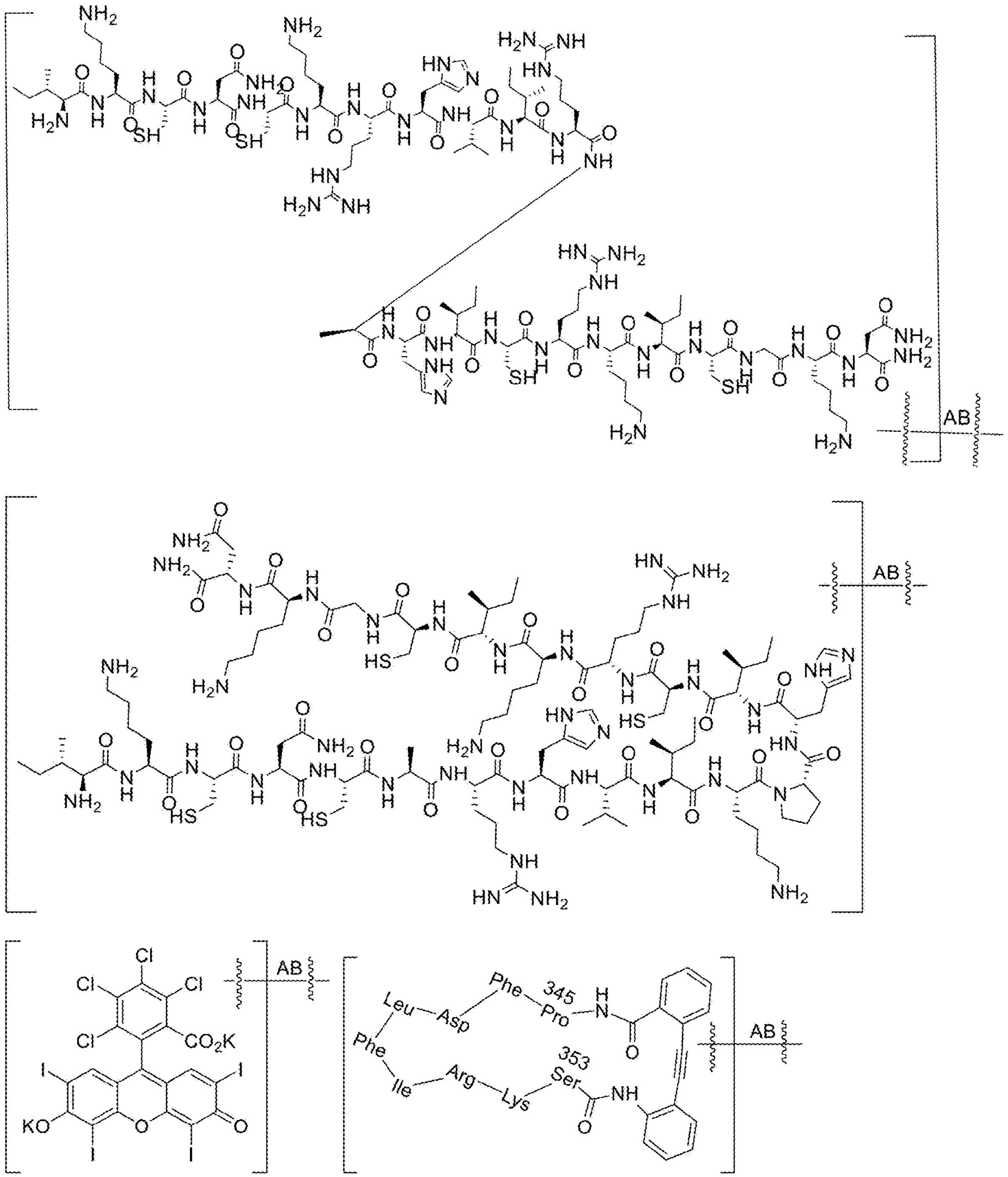
FIG. 1C-1G provides a non-limiting list of Extracellular Protein Targeting Ligands that target Immunoglobulin E (IgE).
Figure 1D:
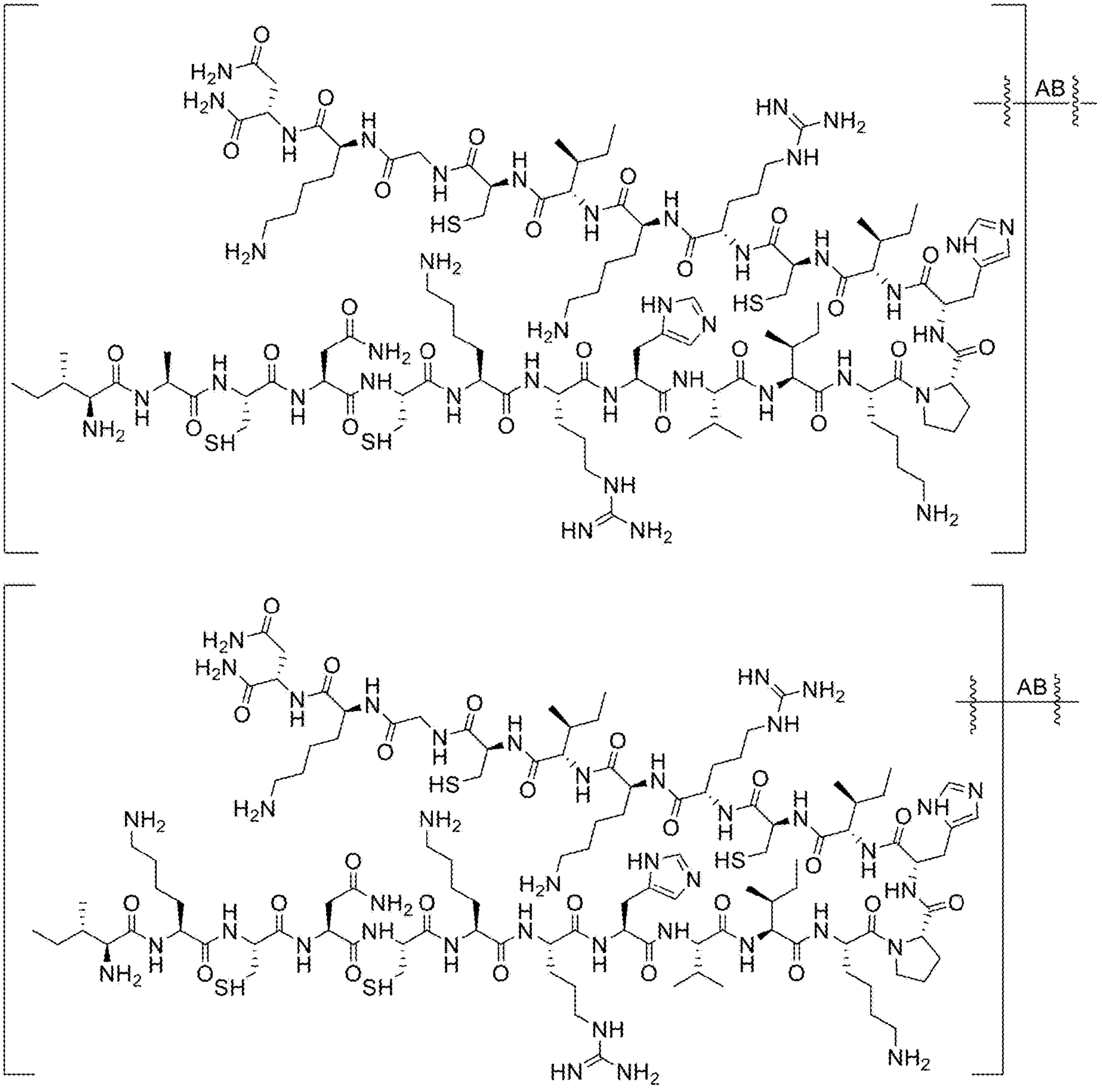
Figure 1E:
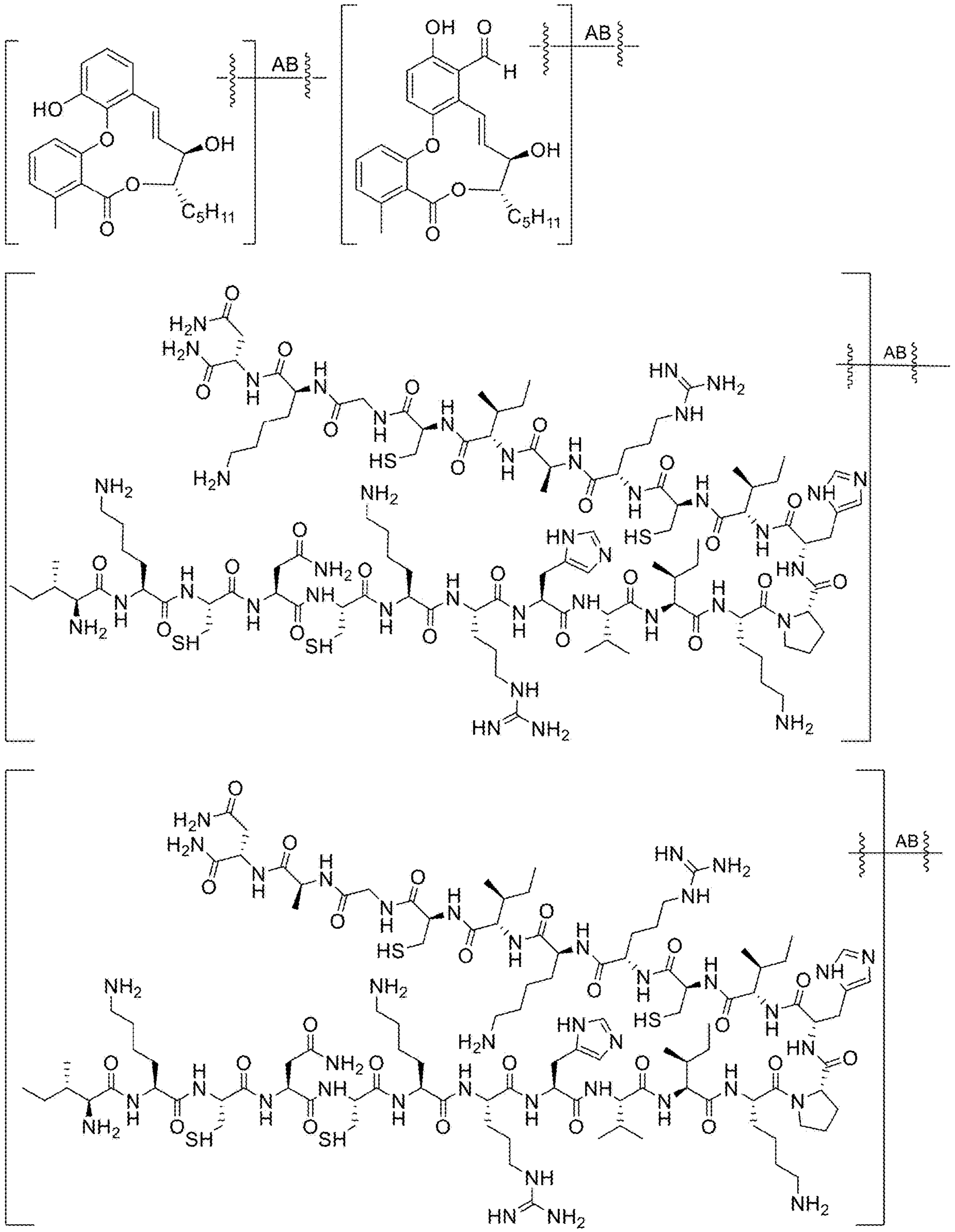
Figure 1F:
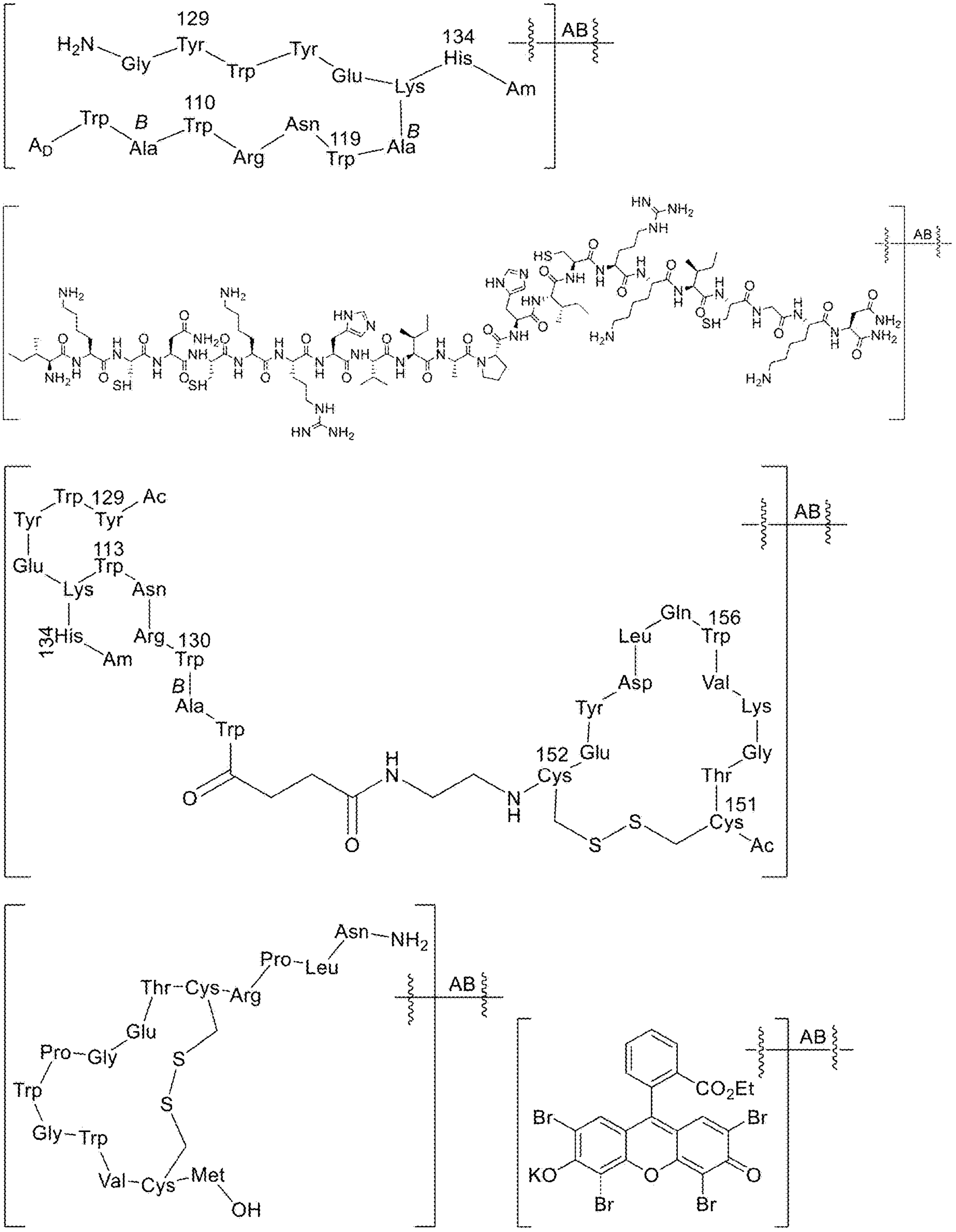
Figure 1G:
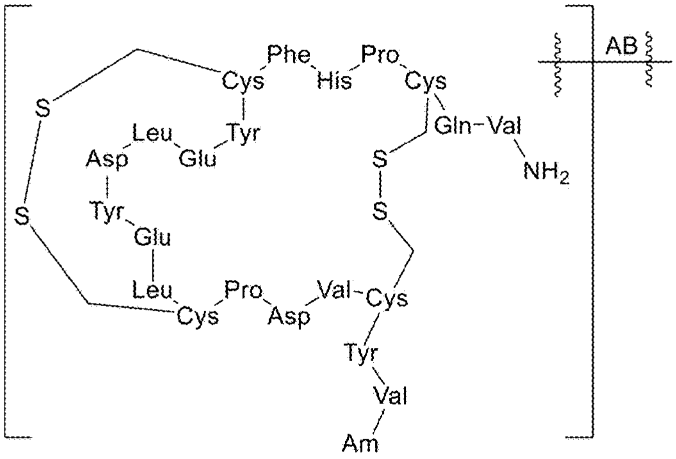
Figure 1G:
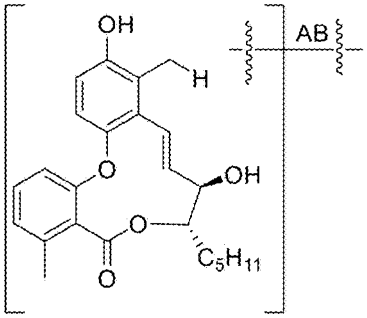
Figure 1G:
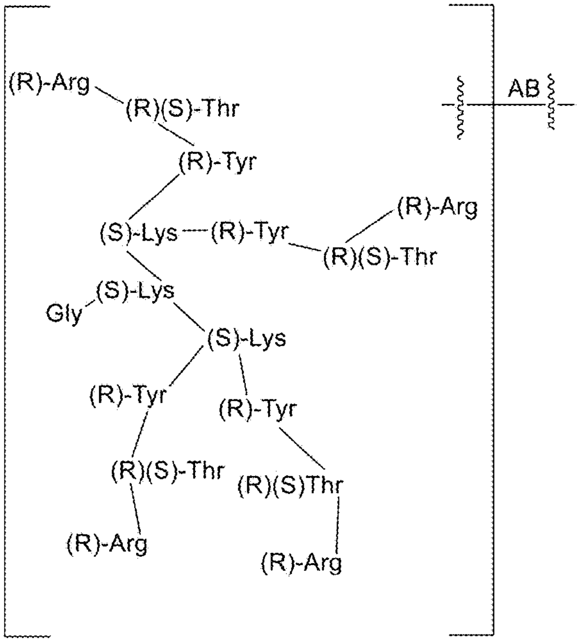
Figure 1G:
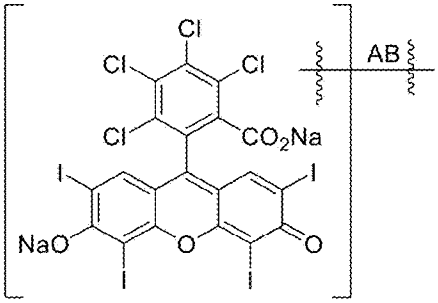
Figure 1H:
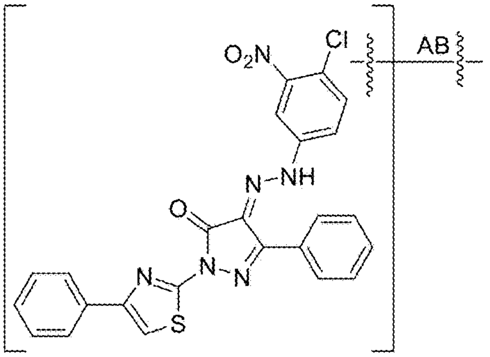
FIG. 1H-1M provides a non-limiting list of Extracellular Protein Targeting Ligands that target Tumor Necrosis Factor alpha (TNF-α).
Figure 1H:
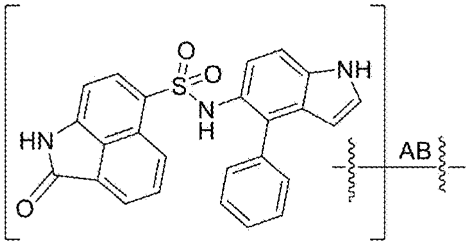
Figure 1H:
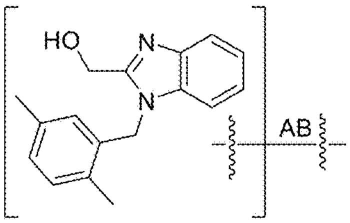
Figure 1H:
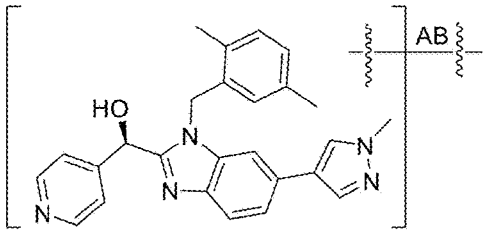
Figure 1H:
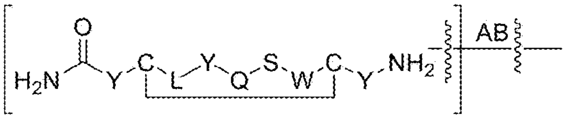
Figure 1H:
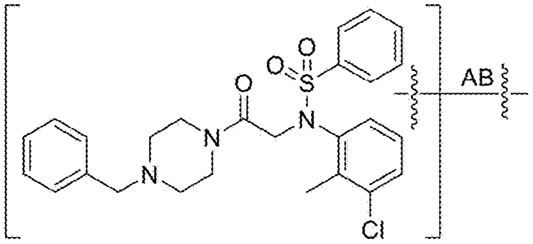
Figure 1H:
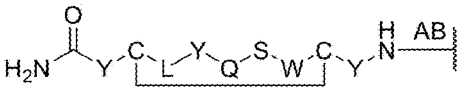
Figure 1H:
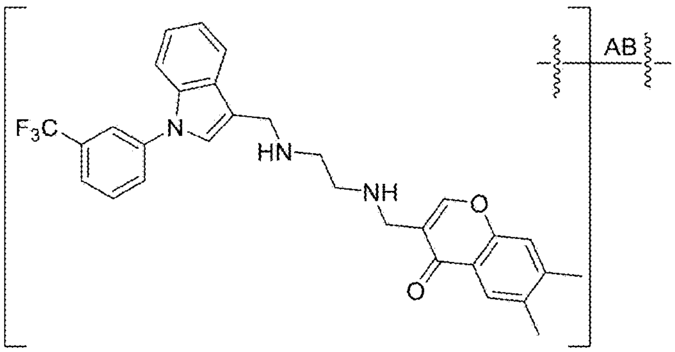
Figure 1H:
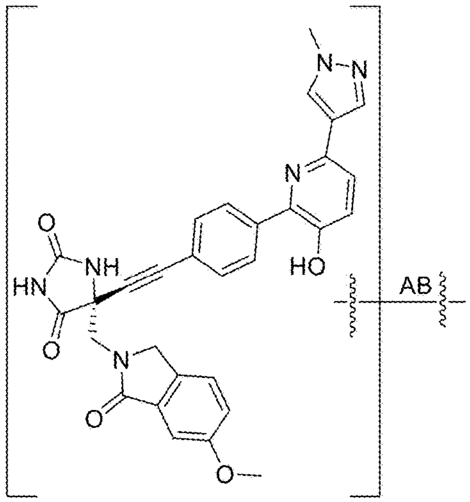
Figure 1I:
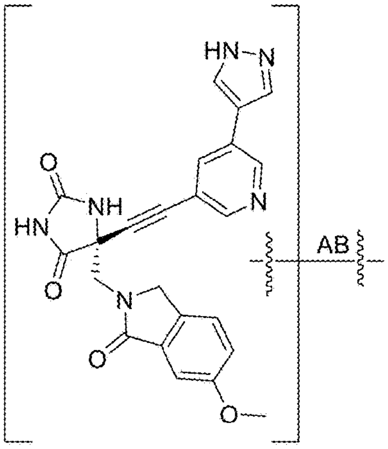
Figure 1I:
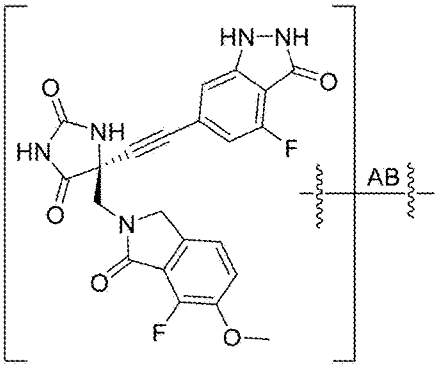
Figure 1I:
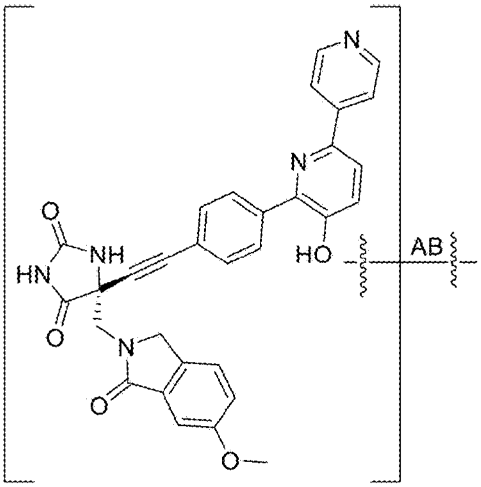
Figure 1I:
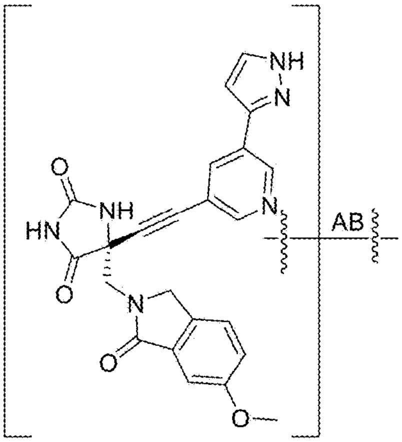
Figure 1I:
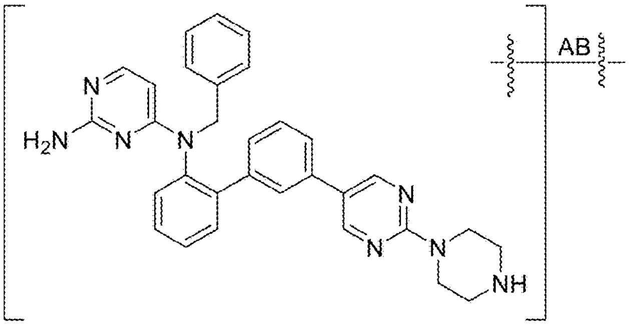
Figure 1I:
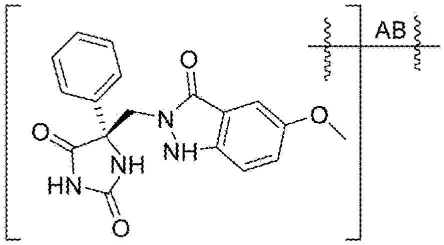
Figure 1J:
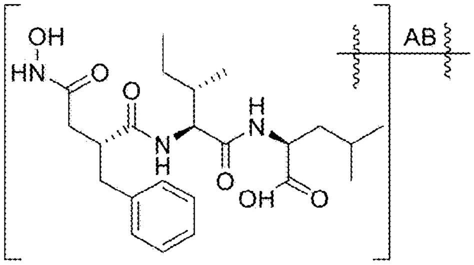
Figure 1J:
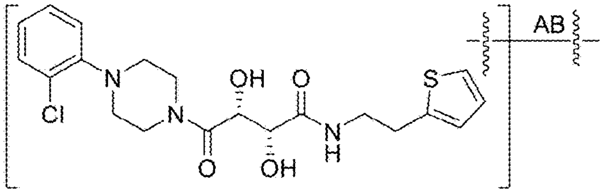
Figure 1J:
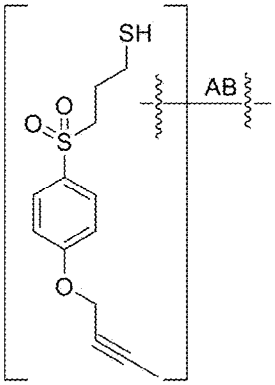
Figure 1J:
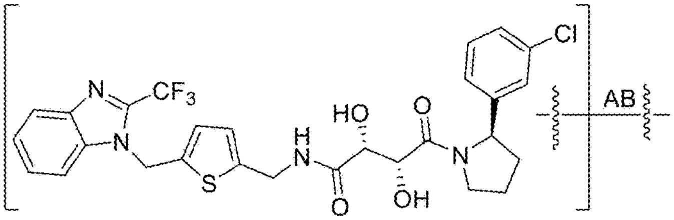
Figure 1J:
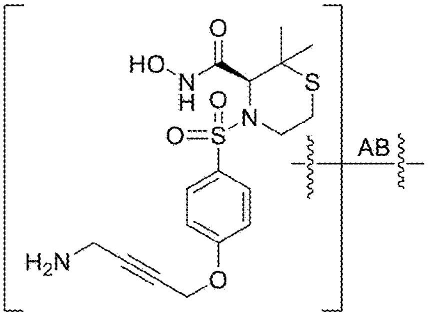
Figure 1J:
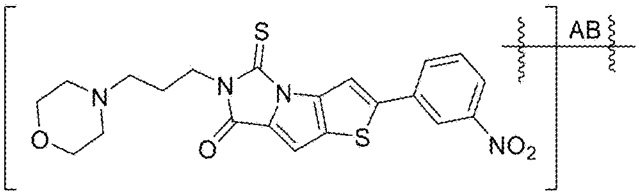
Figure 1J:
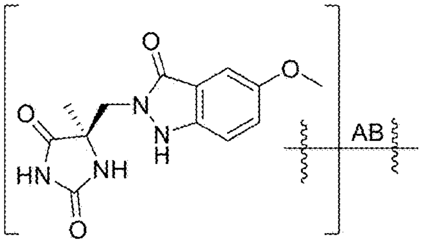
Figure 1J:
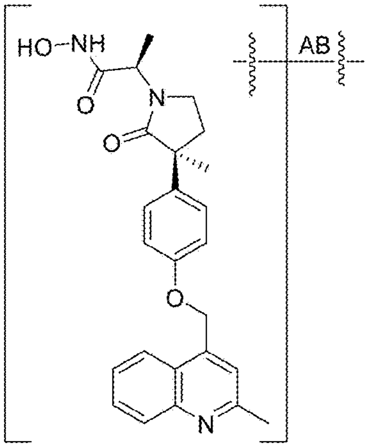
Figure 1J:
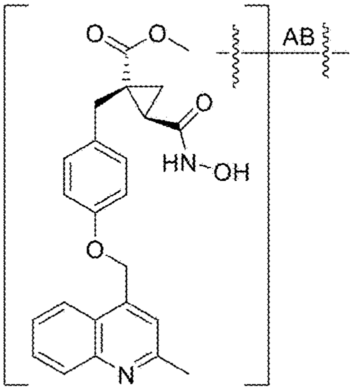
Figure 1K:
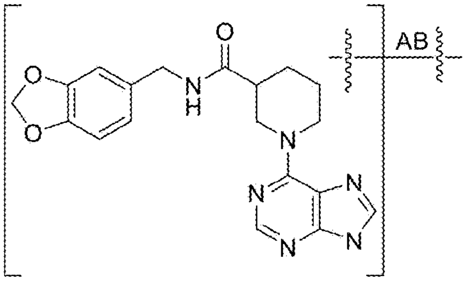
Figure 1K:
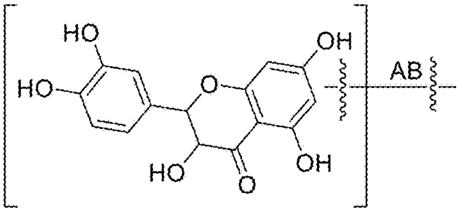
Figure 1K:
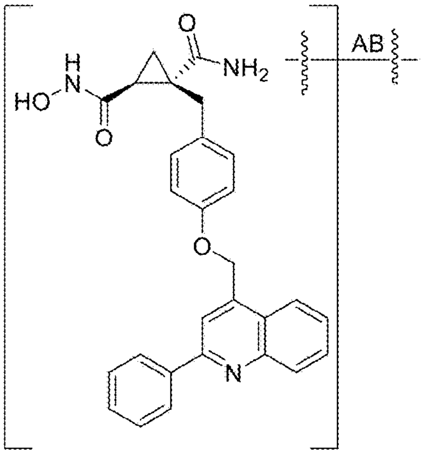
Figure 1K:
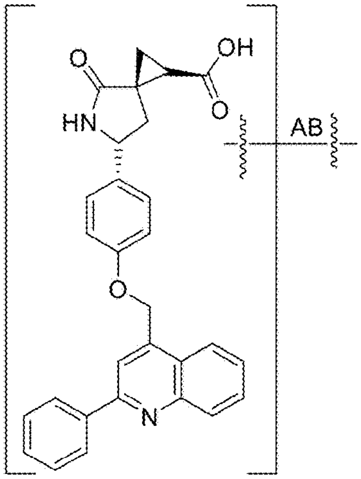
Figure 1K:
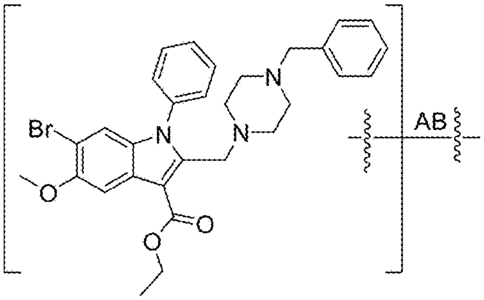
Figure 1K:
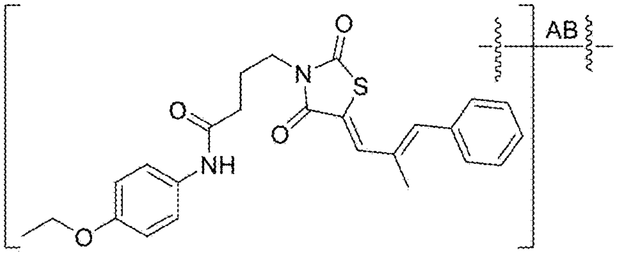
Figure 1K:
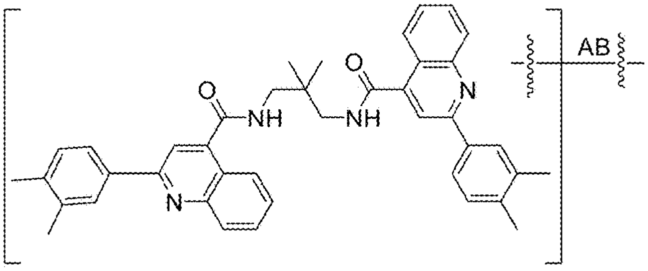
Figure 1K:
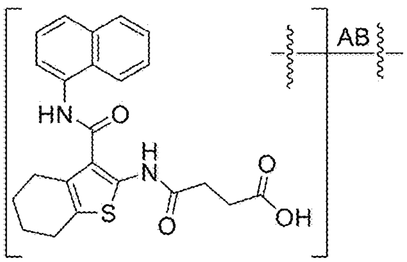
Figure 1L:
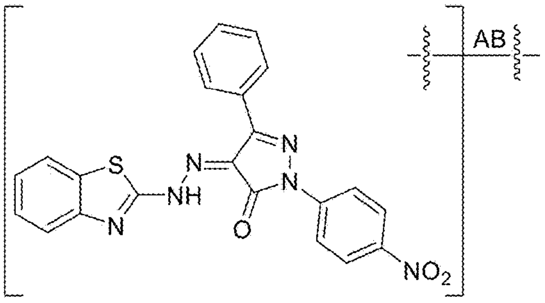
Figure 1L:
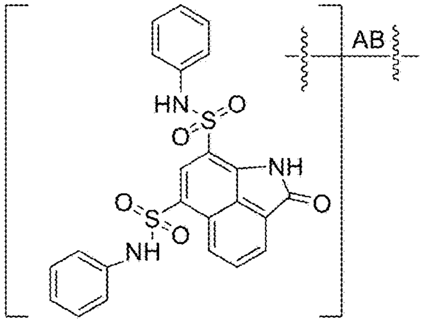
Figure 1L:
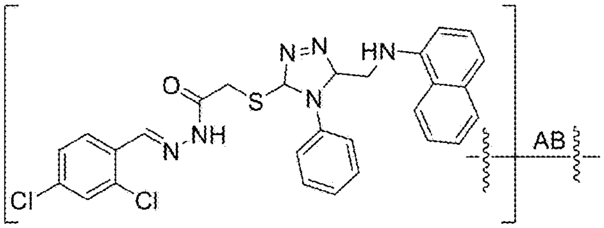
Figure 1L:
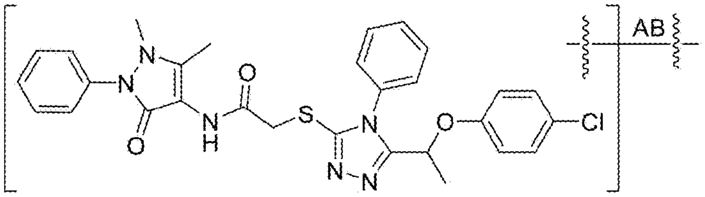
Figure 1L:
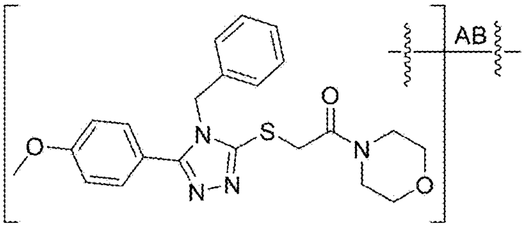
Figure 1L:
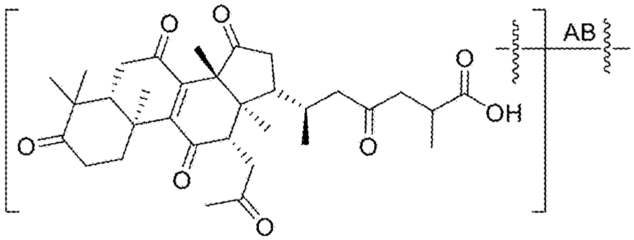
Figure 1L:
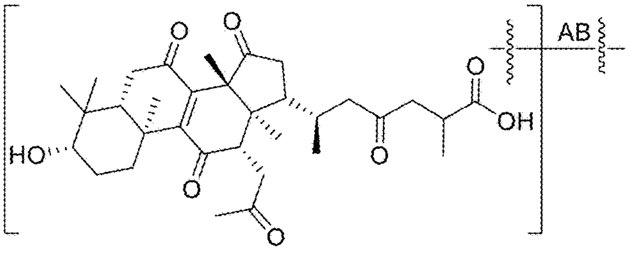
Figure 1M:
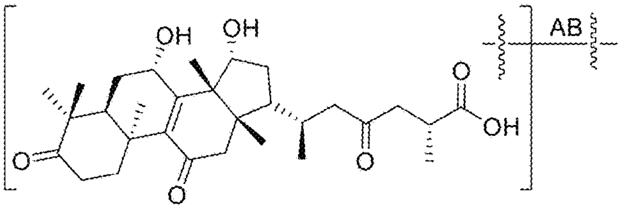
Figure 1M:
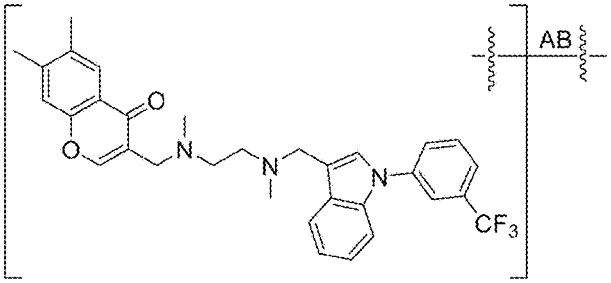
Figure 1M:
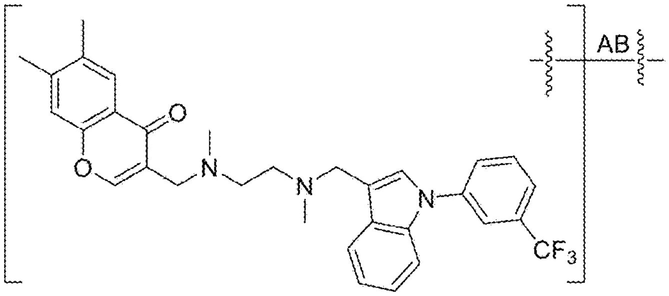
Figure 1M:
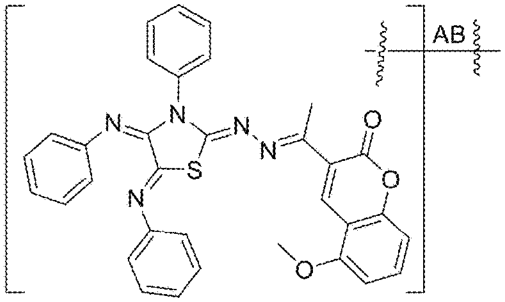
Figure 1N:
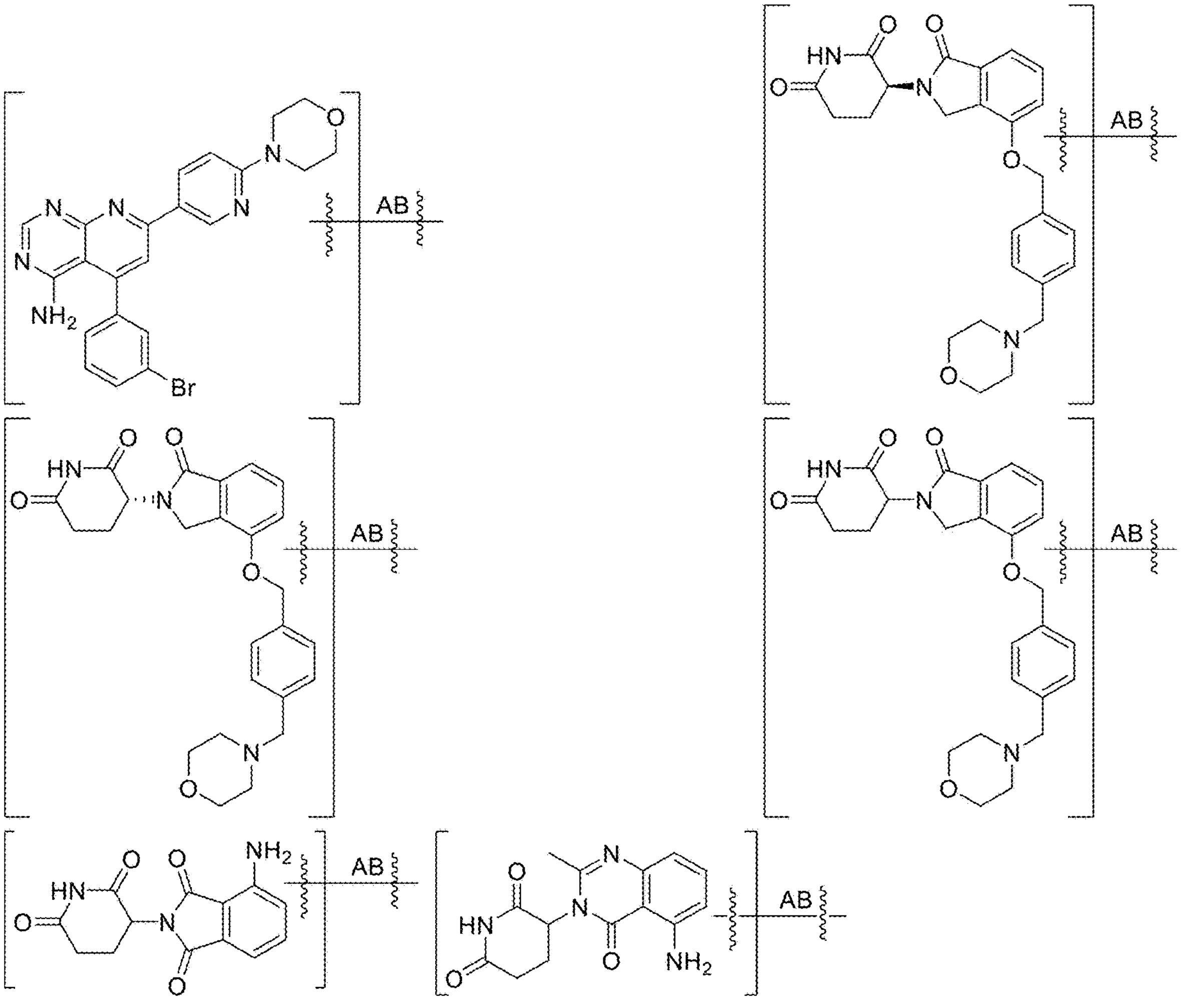
FIG. 1N provides a non-limiting list of Extracellular Protein Targeting Ligands that target Interleukin-1 (IL-1).
Figure 1O:
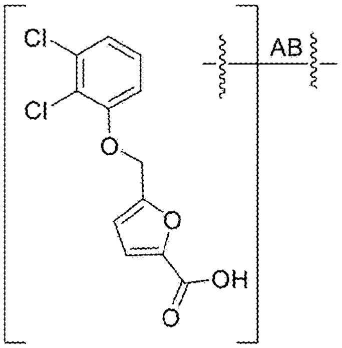
FIG. 1O-1S provides a non-limiting list of Extracellular Protein Targeting Ligands that target Interleukin-2 (IL-2).
Figure 1O:
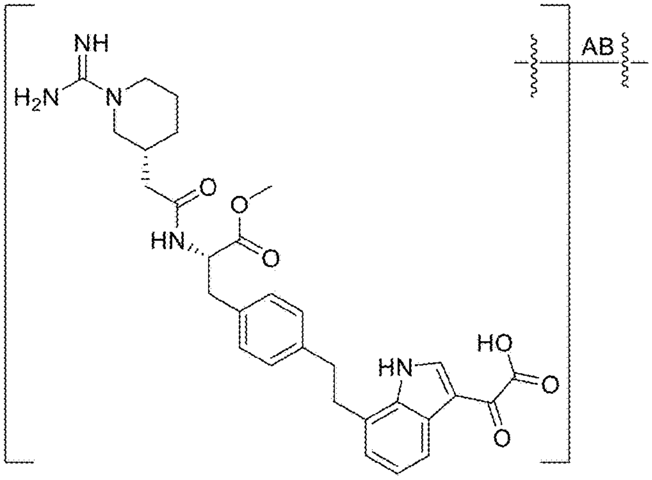
Figure 1O:
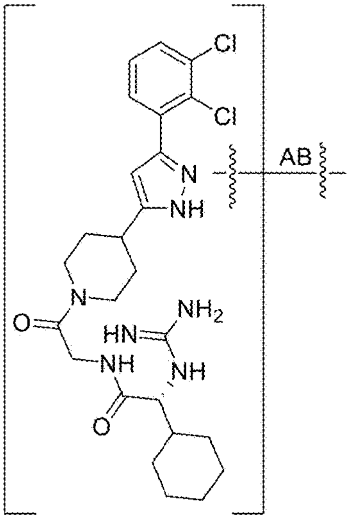
Figure 1O:
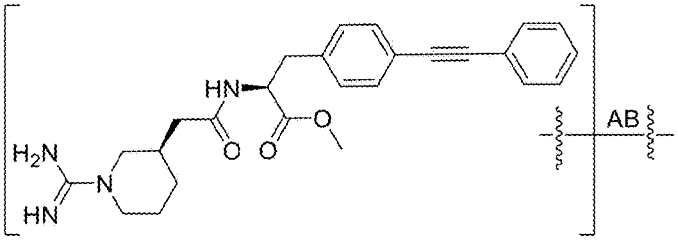
Figure 1O:
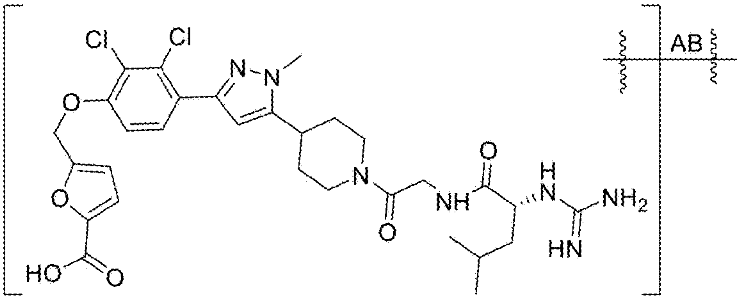
Figure 1O:
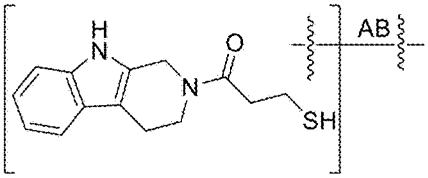
Figure 1O:
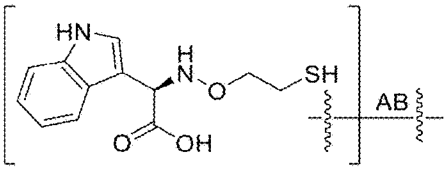
Figure 1P:
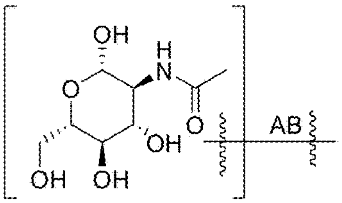
Figure 1P:
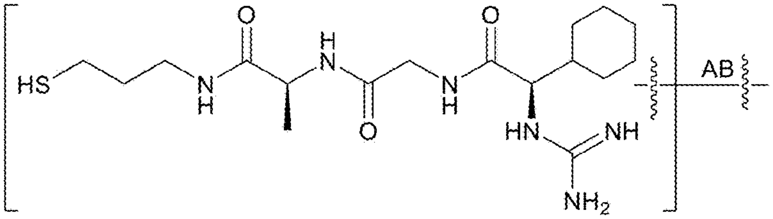
Figure 1P:
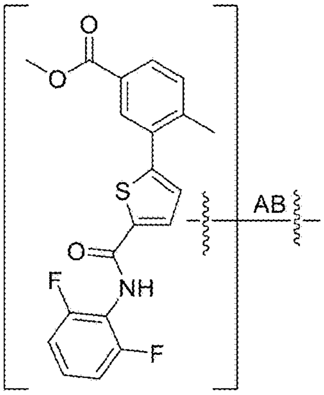
Figure 1P:
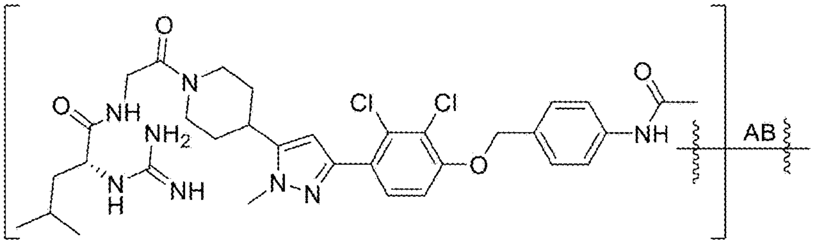
Figure 1P:
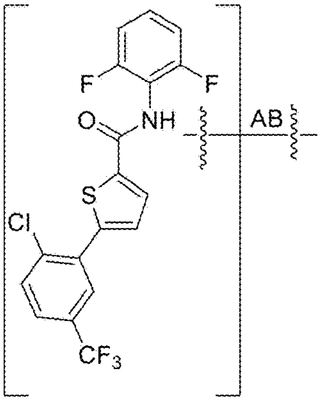
Figure 1P:
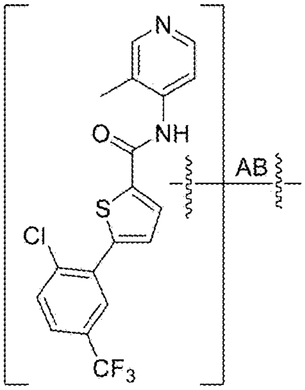
Figure 1P:
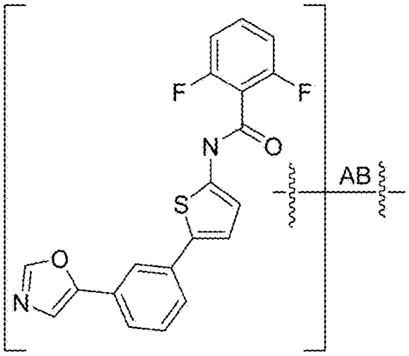
Figure 1P:
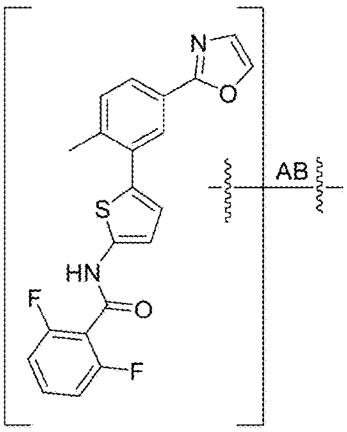
Figure 1P:
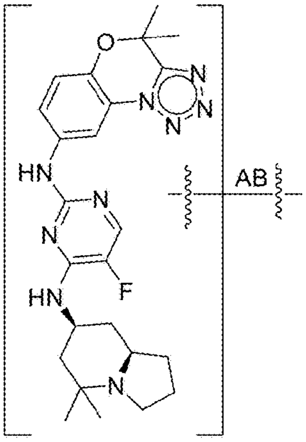
Figure 1P:
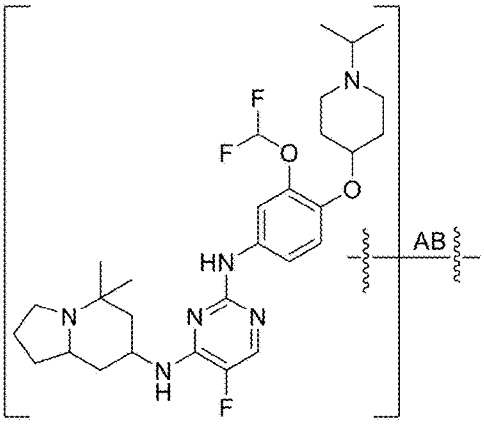
Figure 1Q:
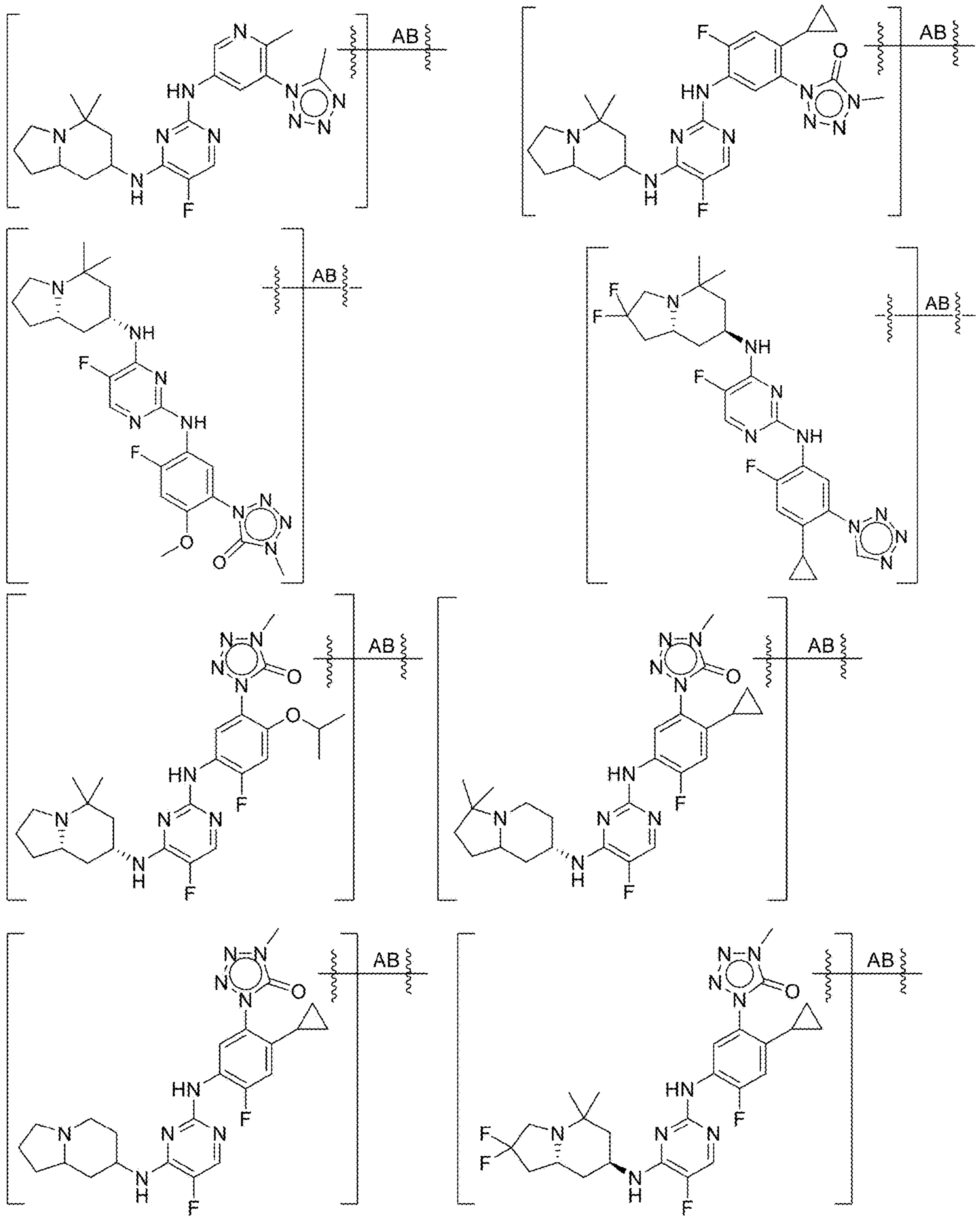
Figure 1R:
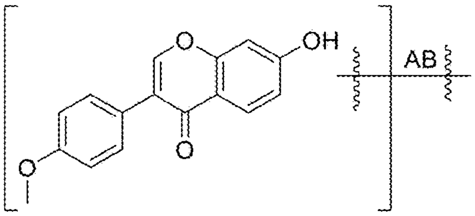
Figure 1R:
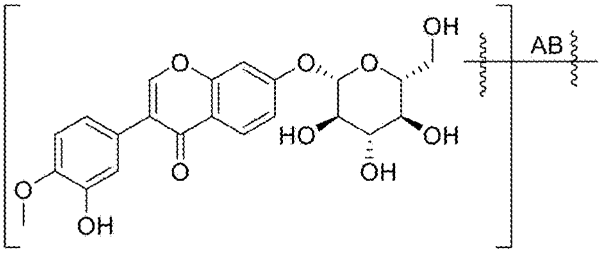
Figure 1R:
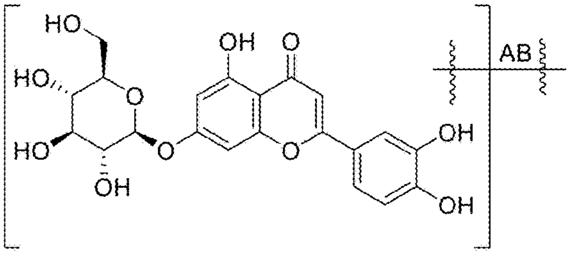
Figure 1R:
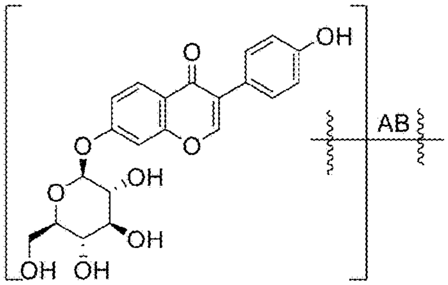
Figure 1R:
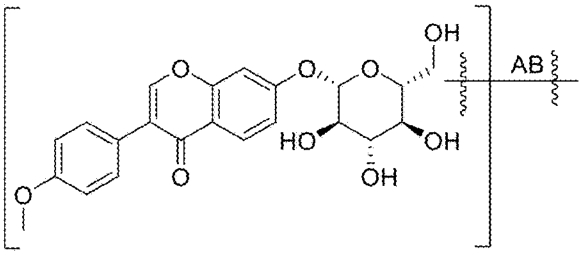
Figure 1R:
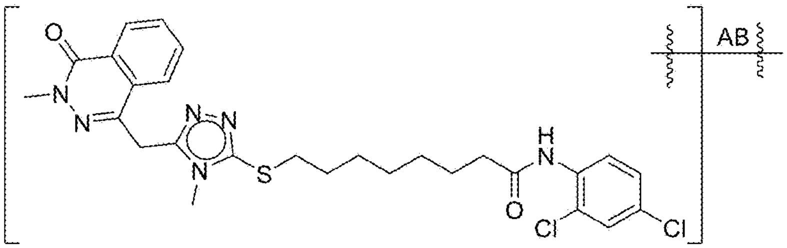
Figure 1R:
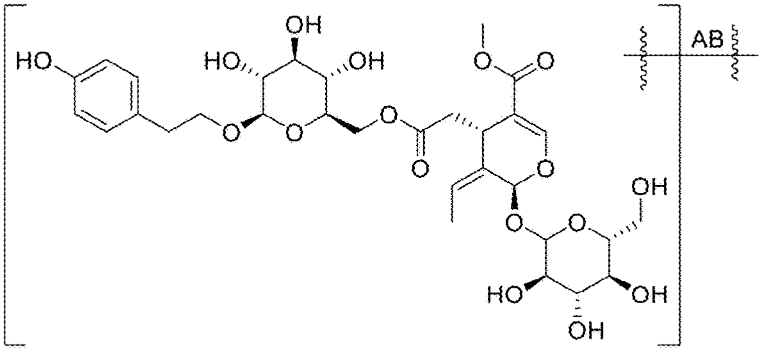
Figure 1S:
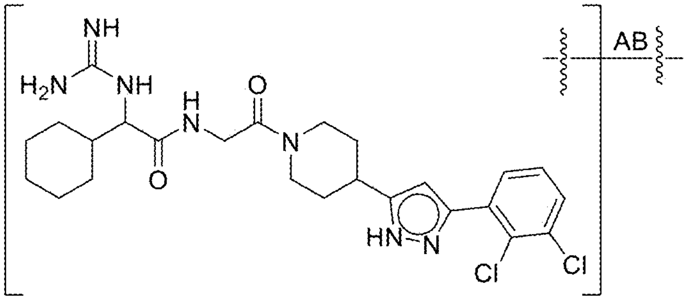
Figure 1S:
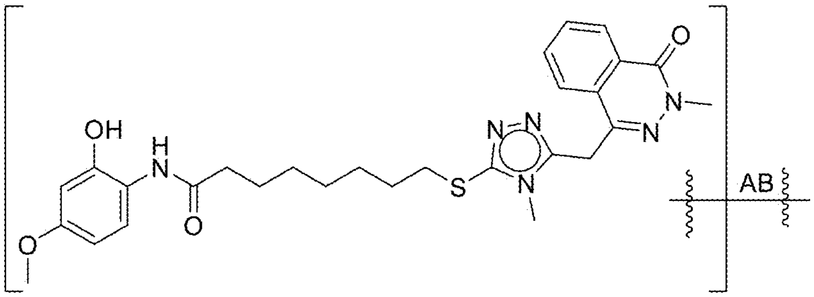
Figure 1S:
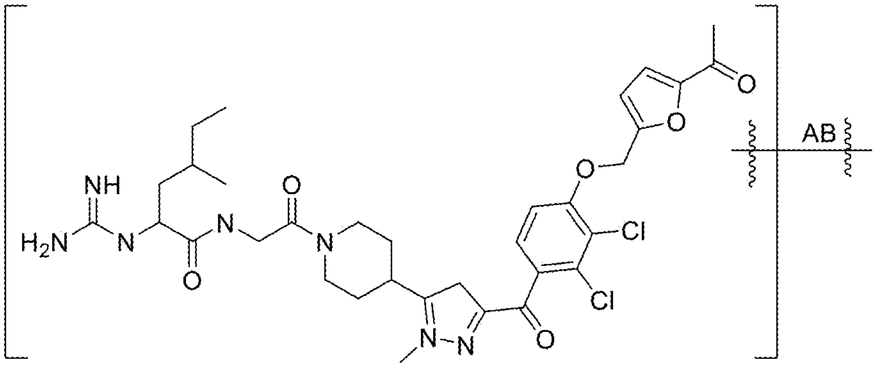
Figure 1S:
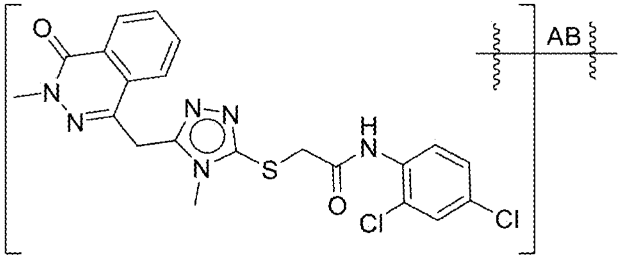
Figure 1S:
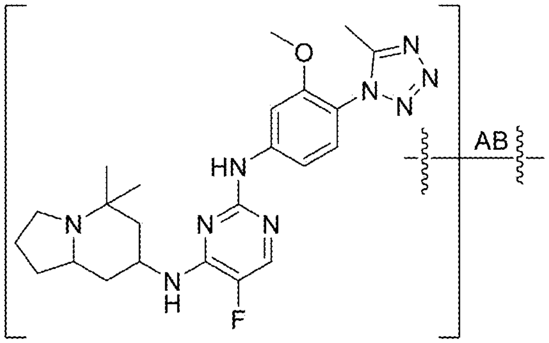
Figure 1T:
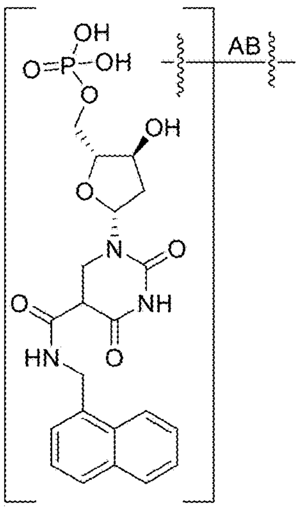
FIG. 1T-1W provides a non-limiting list of Extracellular Protein Targeting Ligands that target Interleukin-6 (IL-6).
Figure 1T:
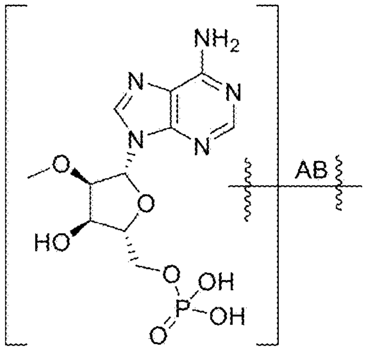
Figure 1T:
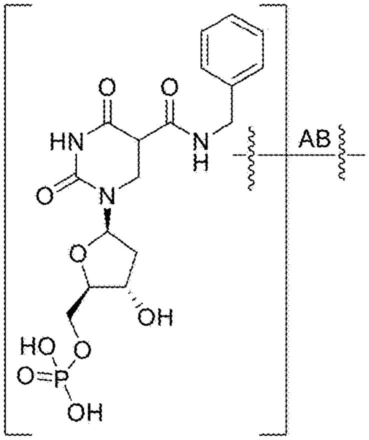
Figure 1T:
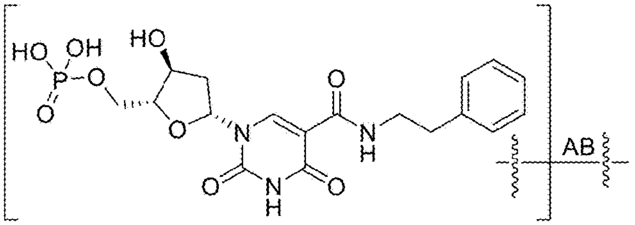
Figure 1T:
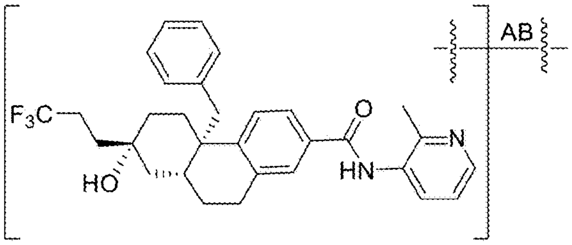
Figure 1T:
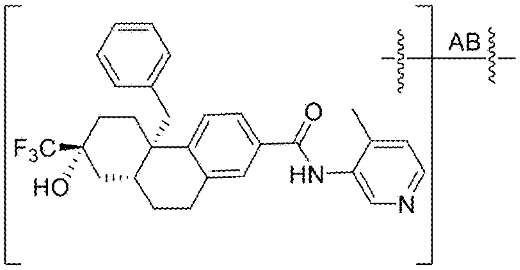
Figure 1T:
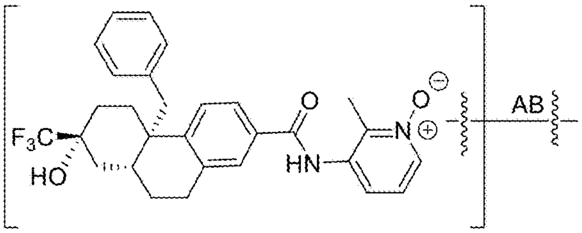
Figure 1T:
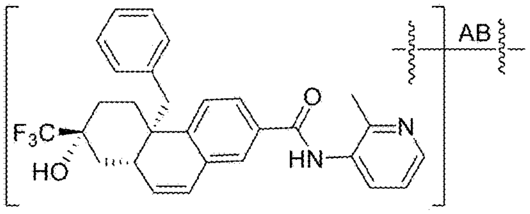
Figure 1T:
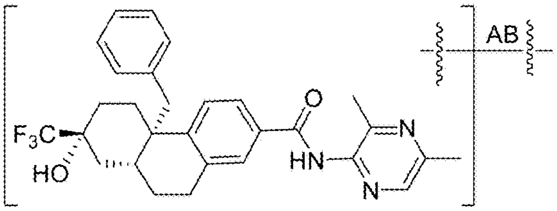
Figure 1T:
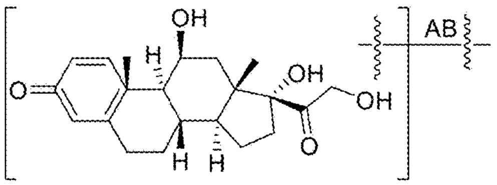
Figure 1U:
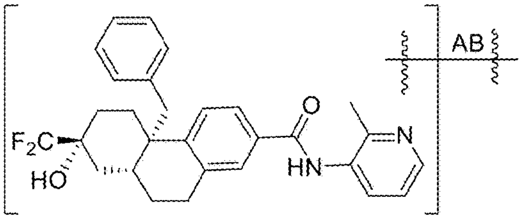
Figure 1U:
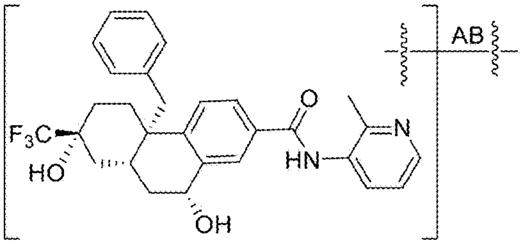
Figure 1U:
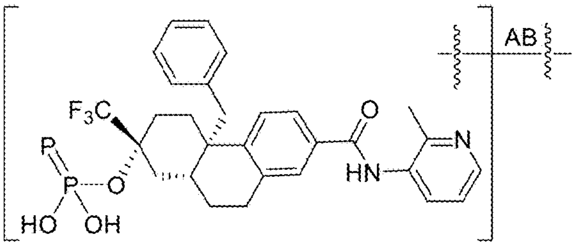
Figure 1U:
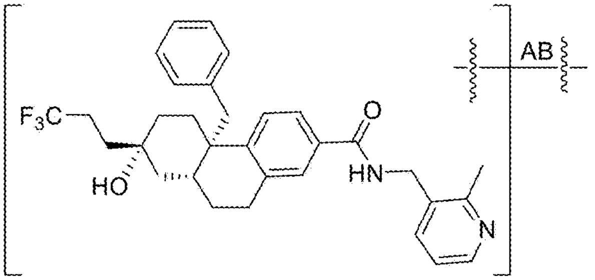
Figure 1U:
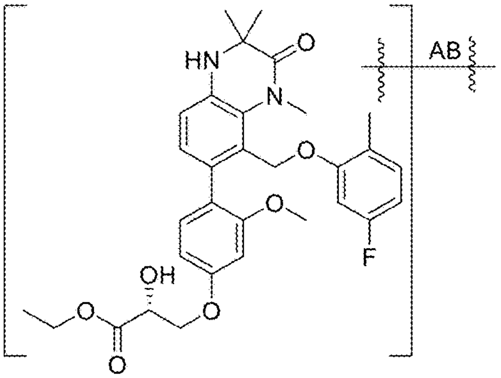
Figure 1U:
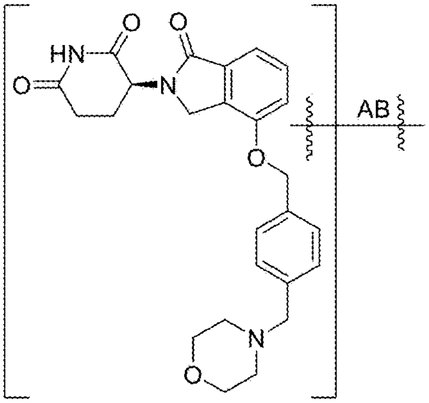
Figure 1U:
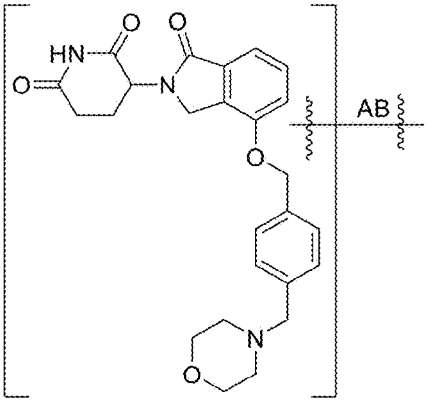
Figure 1U:
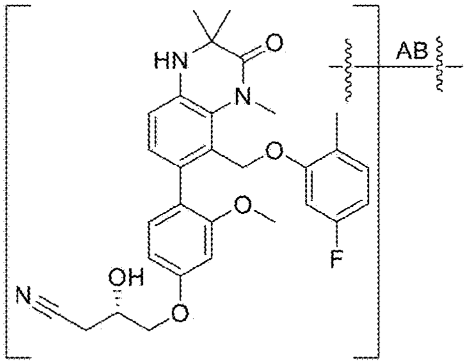
Figure 1V:
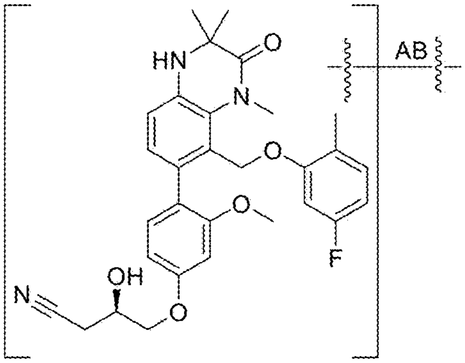
Figure 1V:
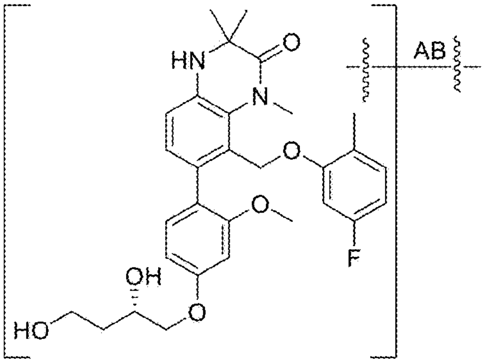
Figure 1V:
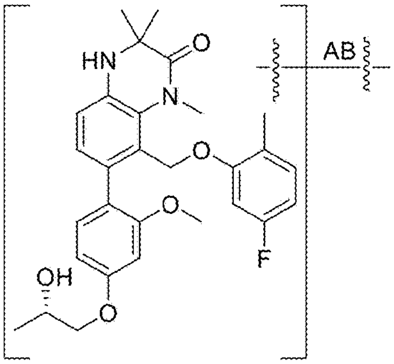
Figure 1V:
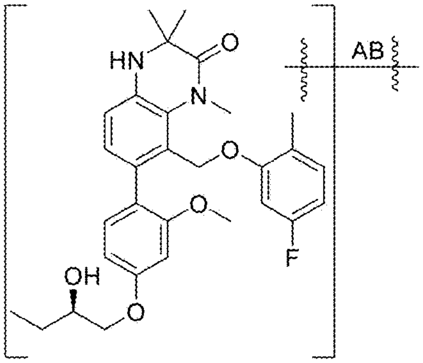
Figure 1V:
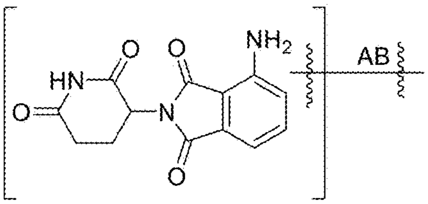
Figure 1V:
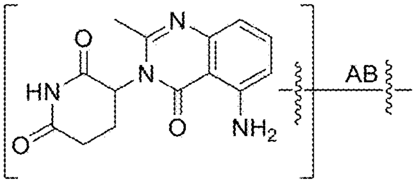
Figure 1V:
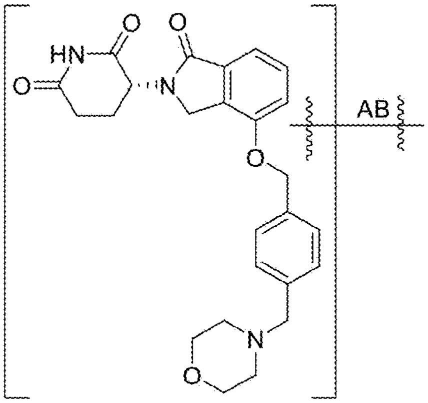
Figure 1V:
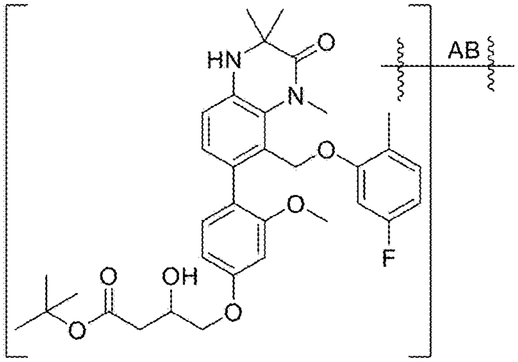
Figure 1W:
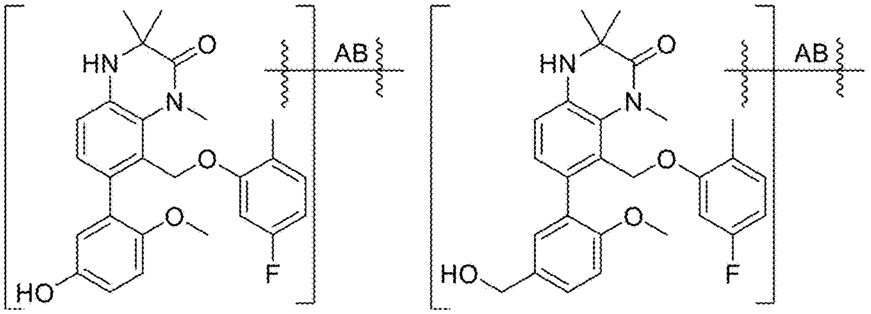
Figure 1X:
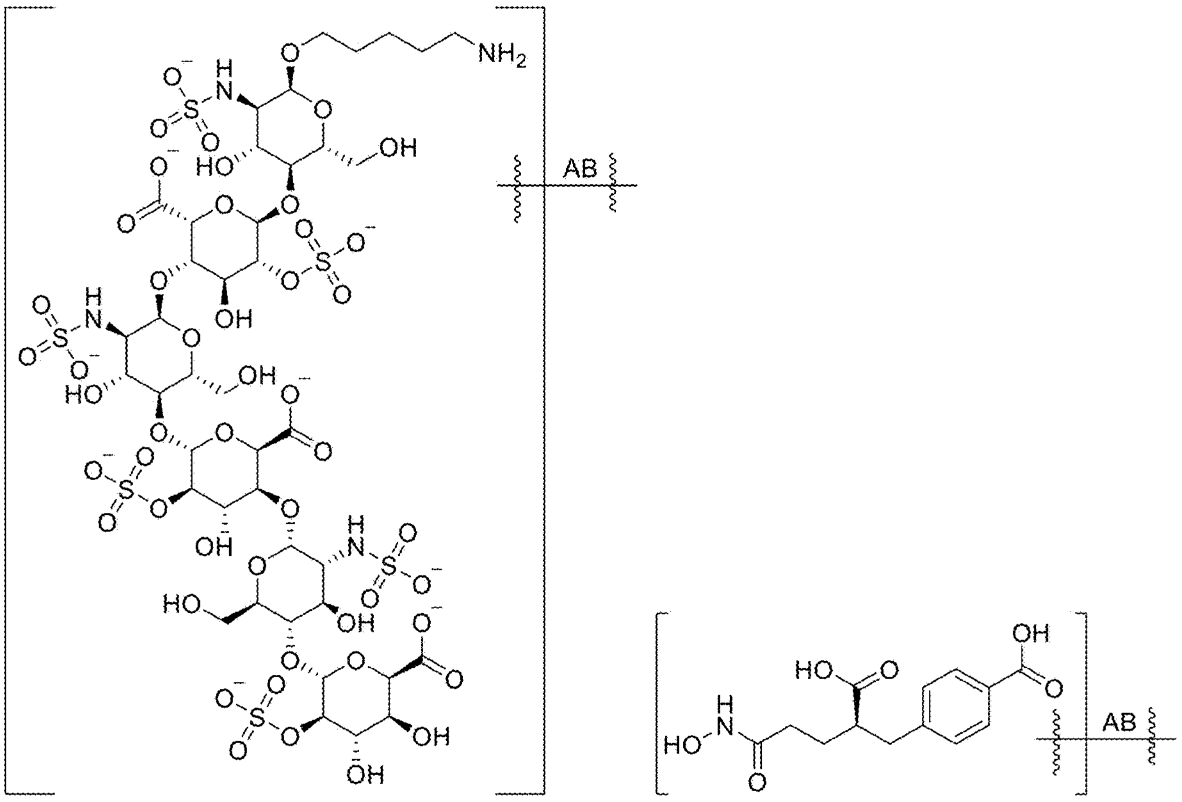
FIG. 1X-IAA provides a non-limiting list of Extracellular Protein Targeting Ligands that target Interferon gamma (IFN-γ).
Figure 1Y:
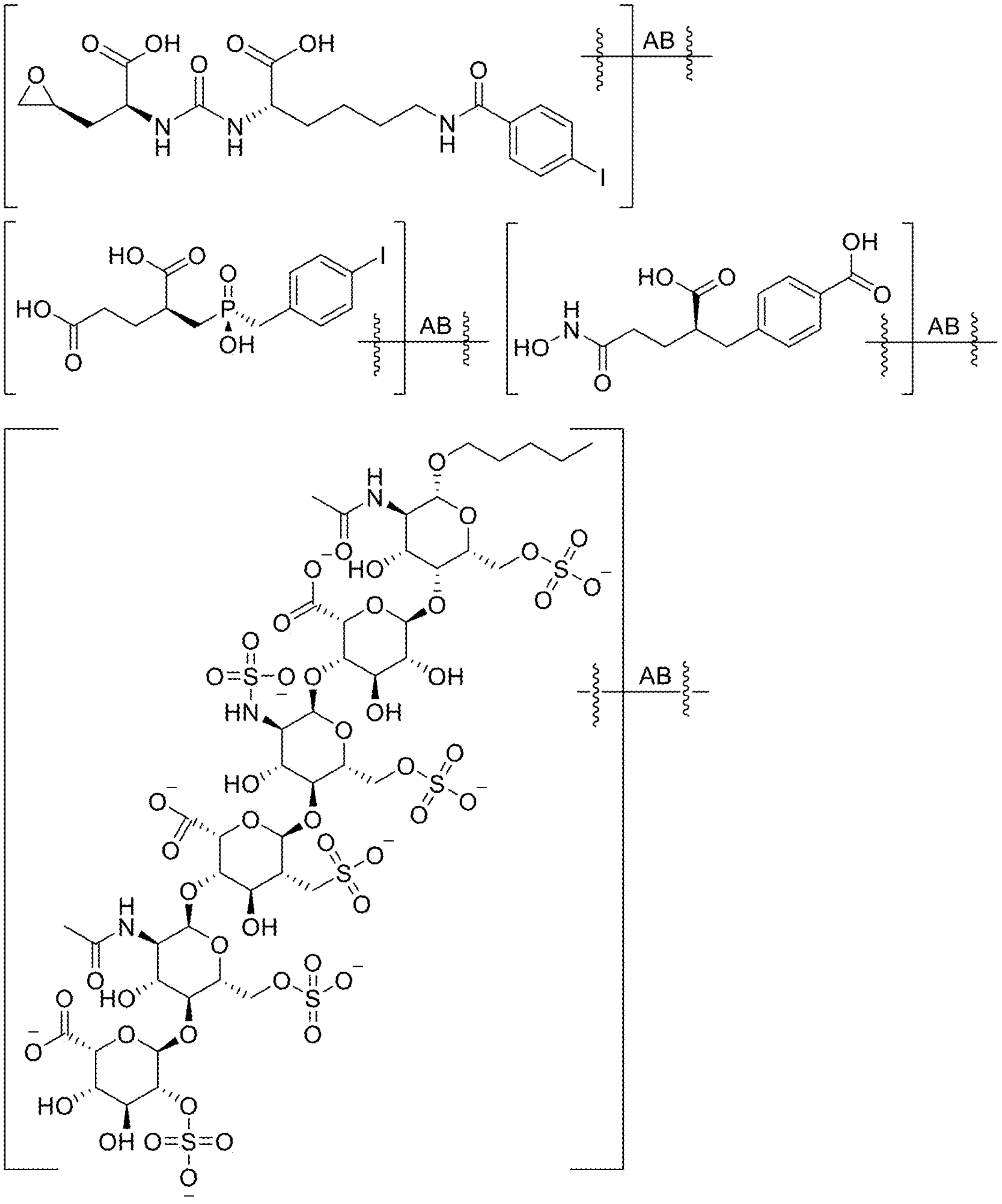
FIGS. 1YYY and 1ZZZ provides a non-limiting list of Extracellular Protein Targeting Ligands that target fibronectin (FN1).
Figure 1Z:
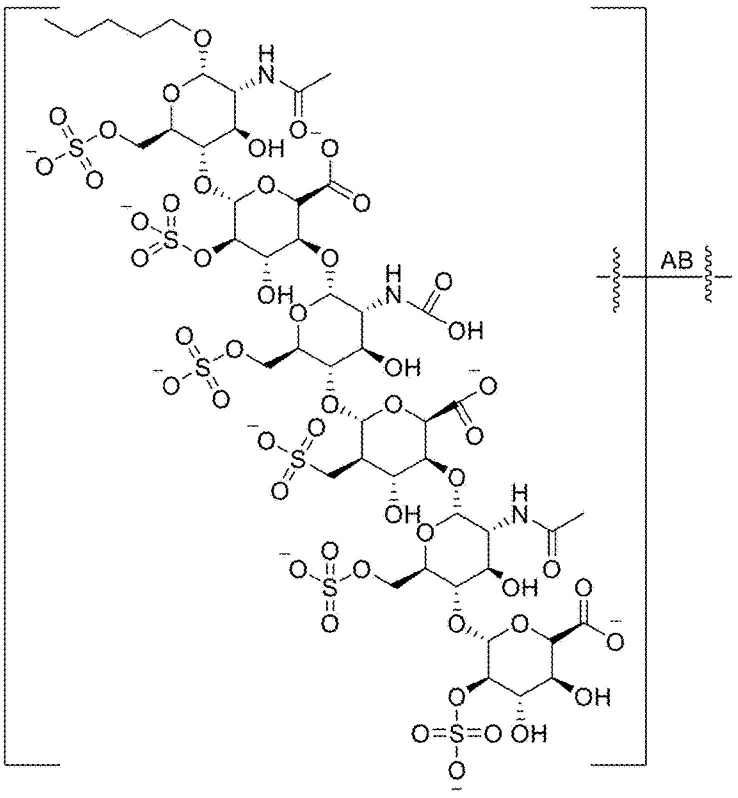
Figure 1Z:
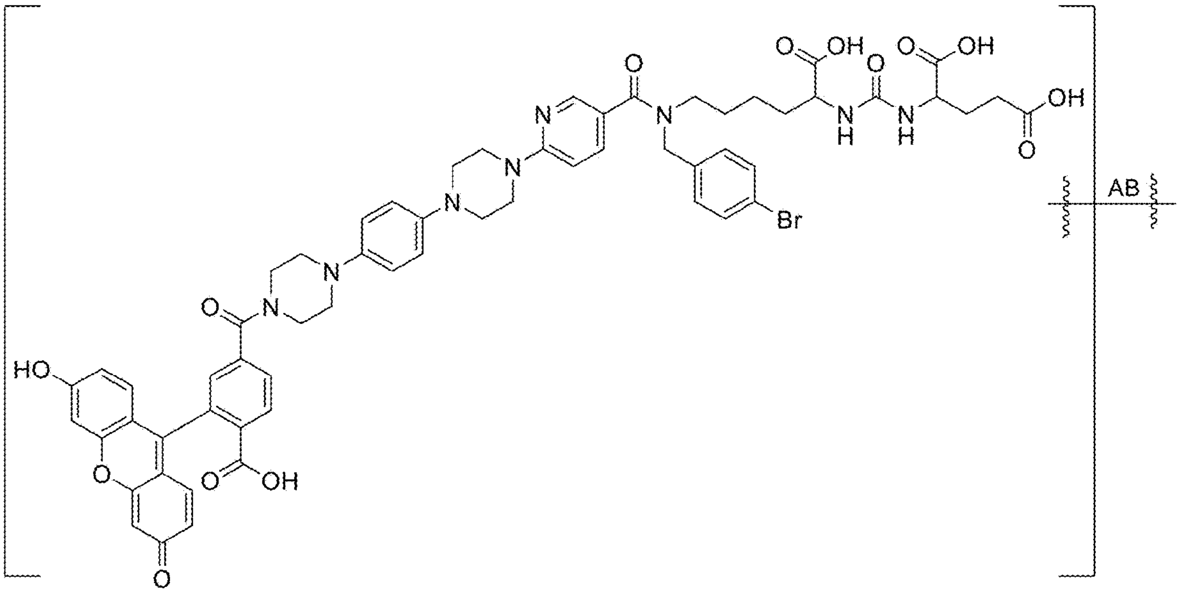
Figure 1A:
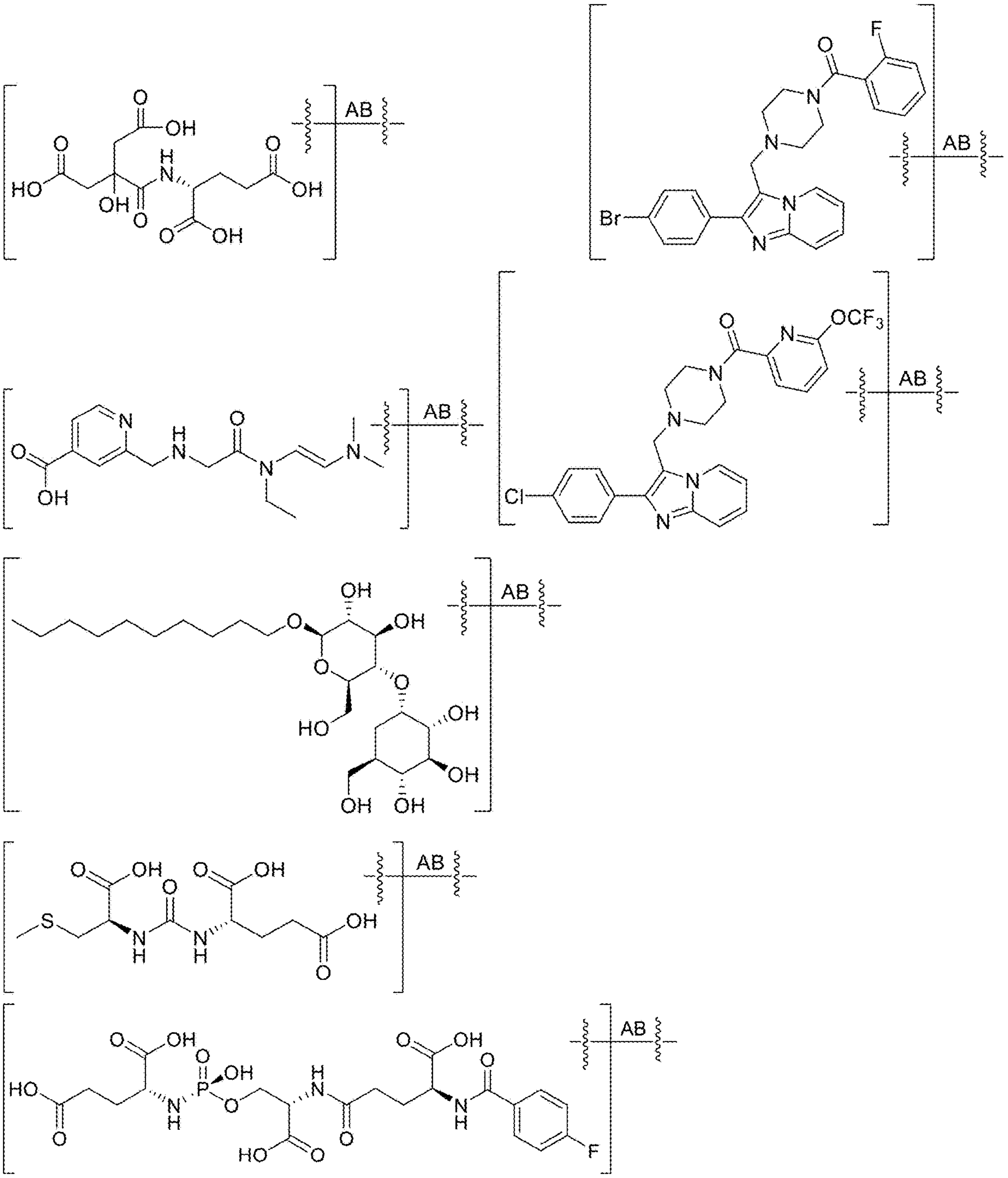
Figure 1B:
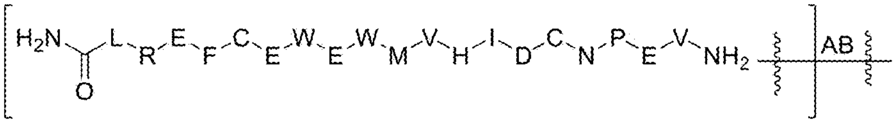
Figure 1B:
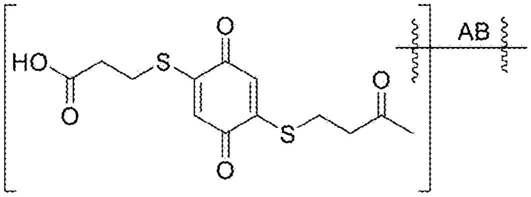
Figure 1B:
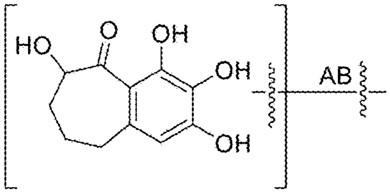
Figure 1B:
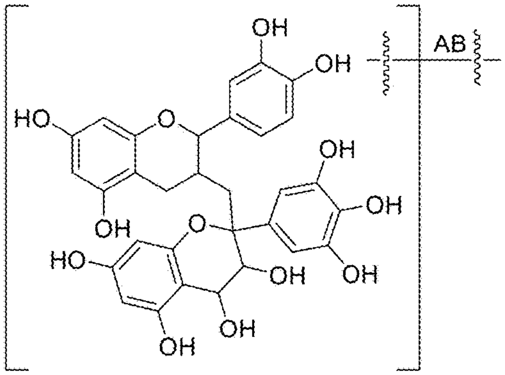
Figure 1B:
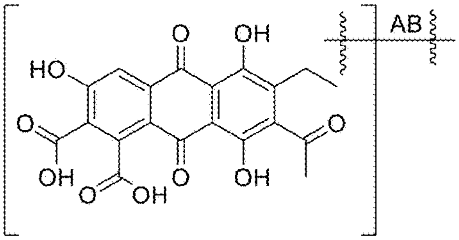
Figure 1B:
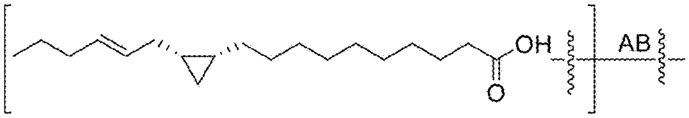
Figure 1B:
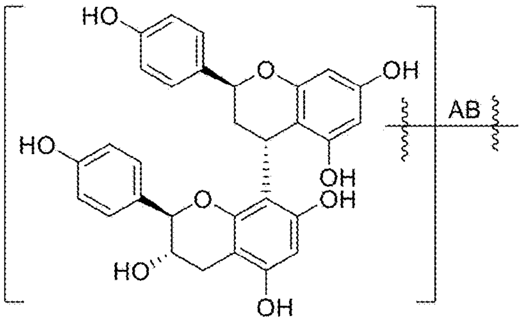
Figure 1B:
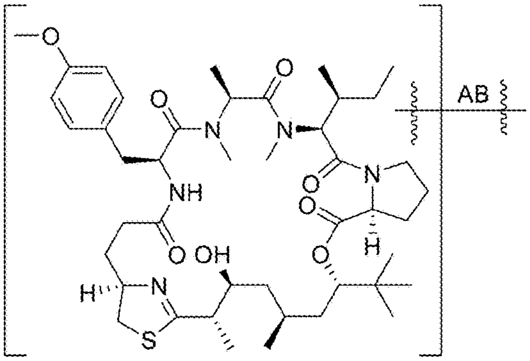
Figure 1B:
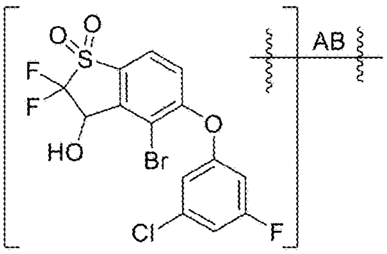
Figure 1B:
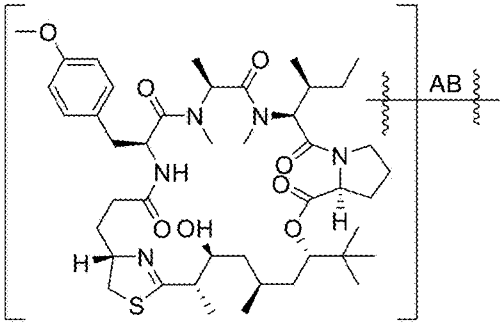
Figure 1C:
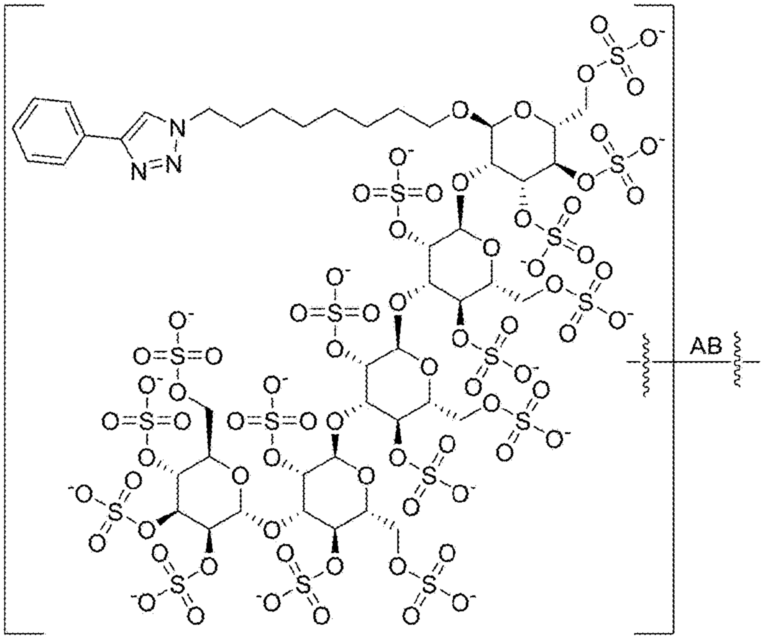
Figure 1C:
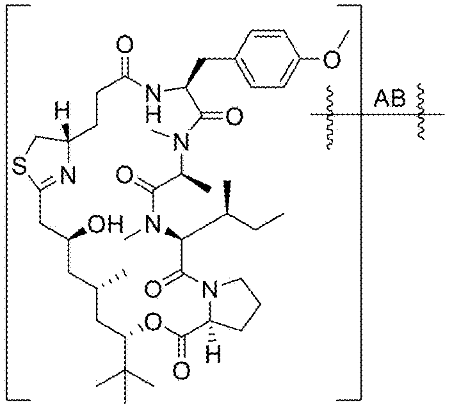
Figure 1C:
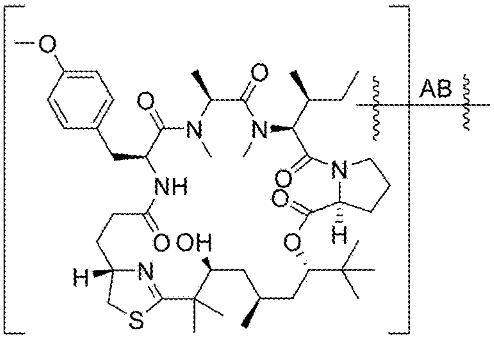
Figure 1C:
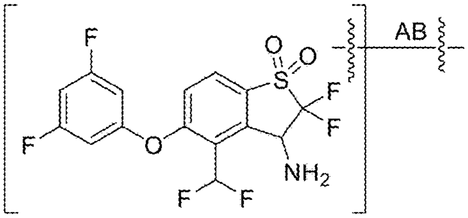
Figure 1C:
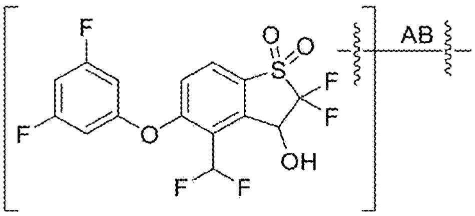
Figure 1C:
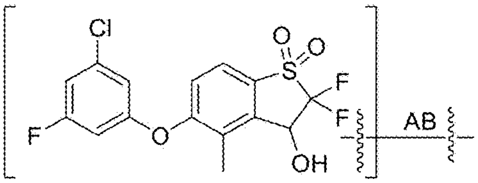
Figure 1D:
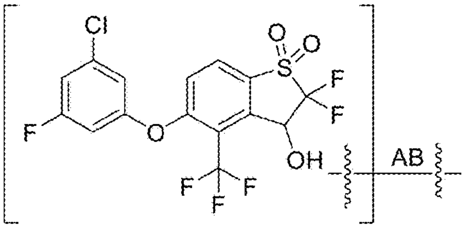
Figure 1D:
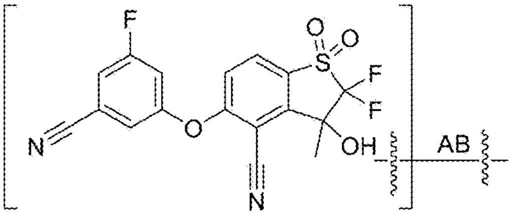
Figure 1D:
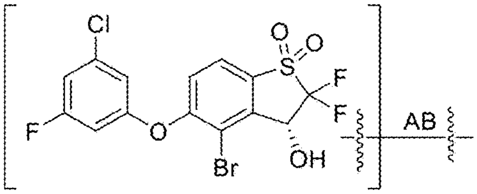
Figure 1D:
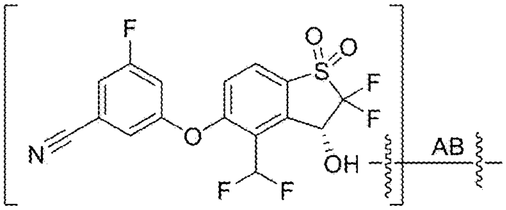
Figure 1D:
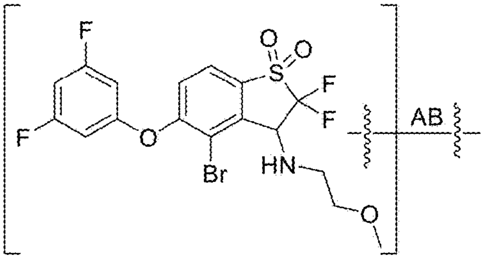
Figure 1D:
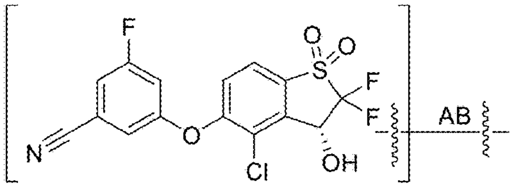
Figure 1D:
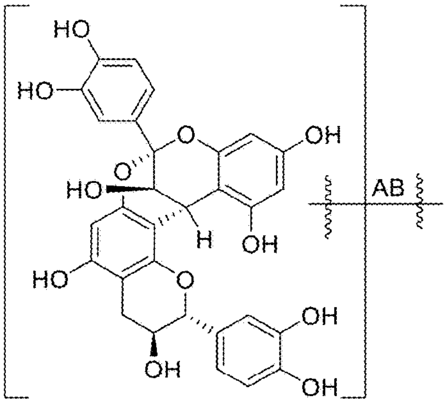
Figure 1D:
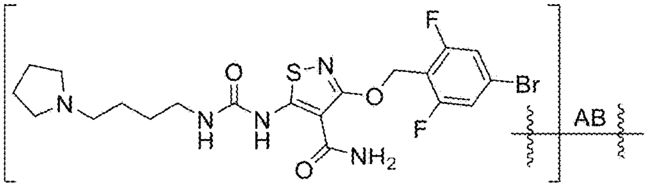
Figure 1D:
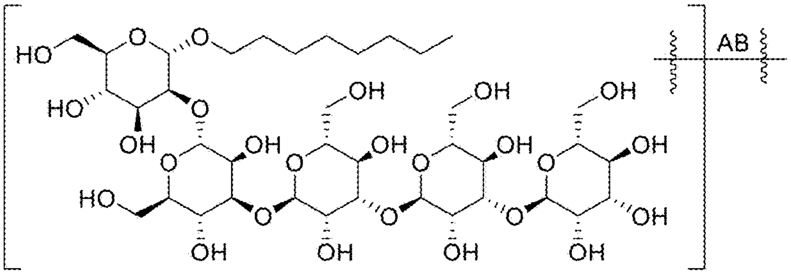
Figure 1D:
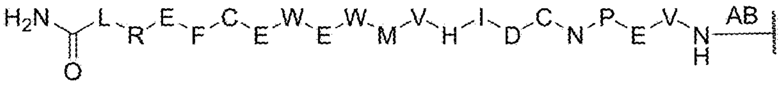
Figure 1E:
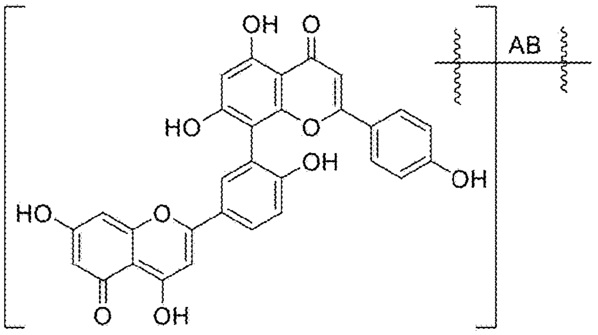
Figure 1E:
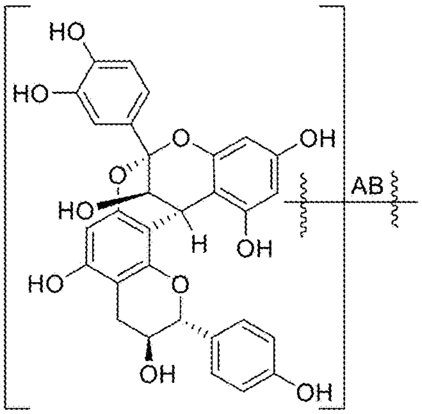
Figure 1E:
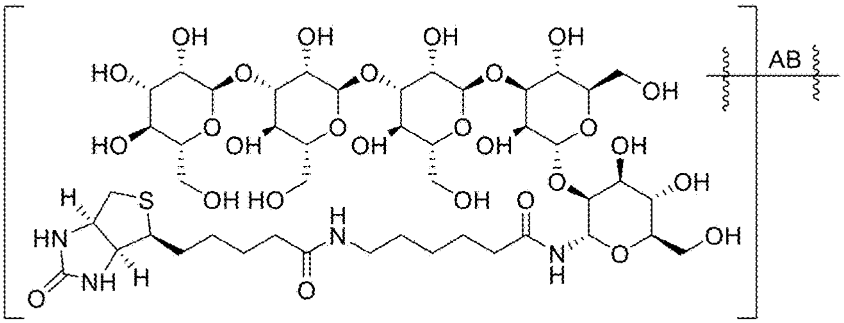
Figure 1E:
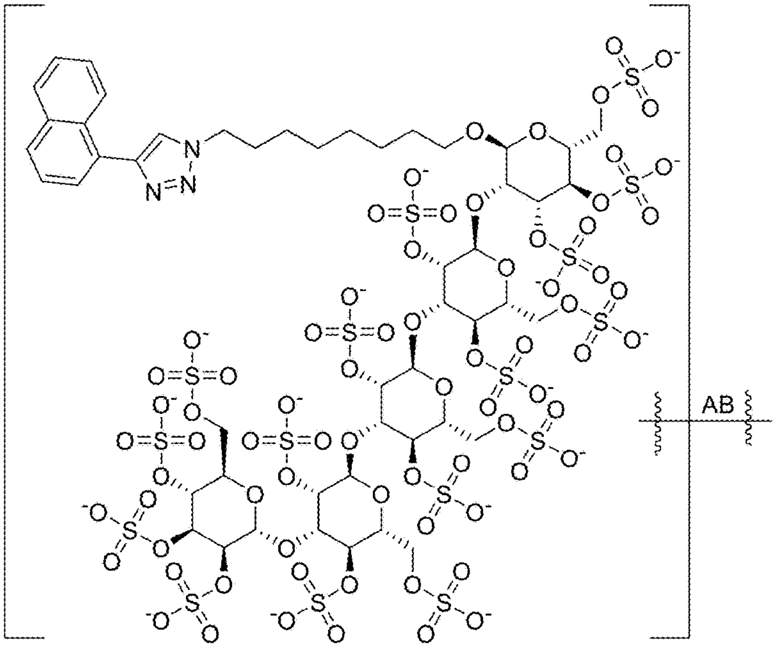
Figure 1F:
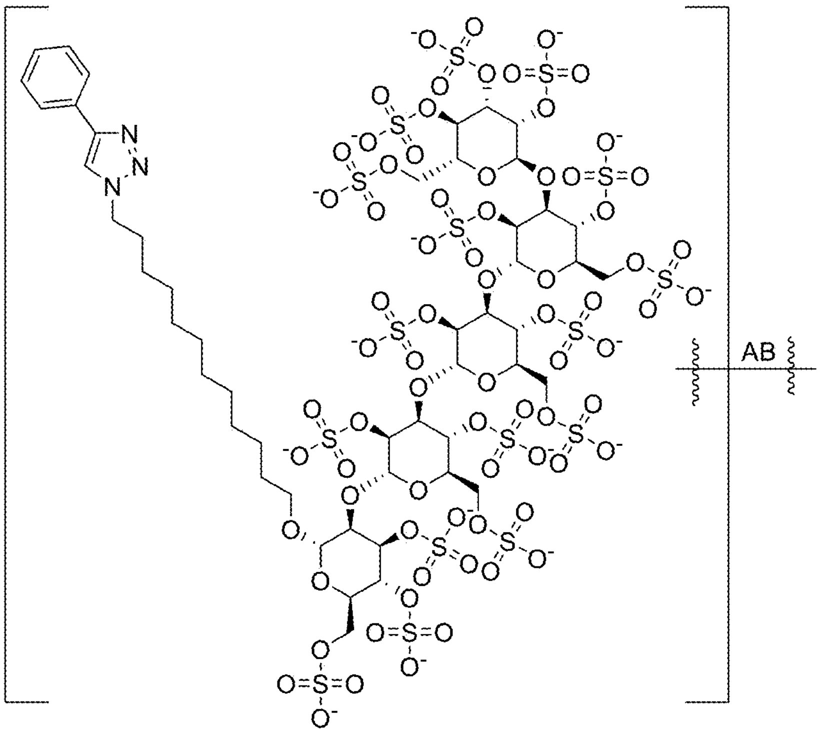
Figure 1F:
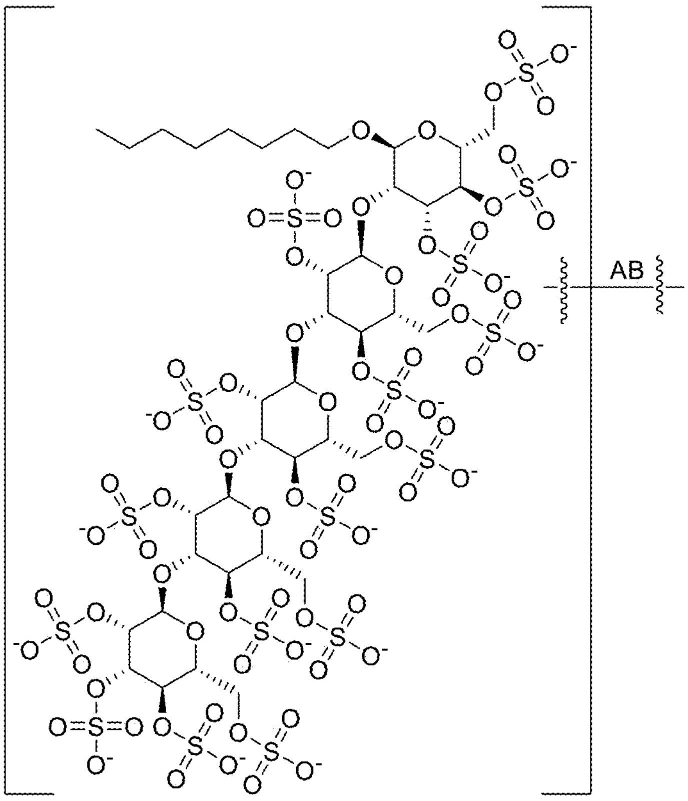
Figure 1G:
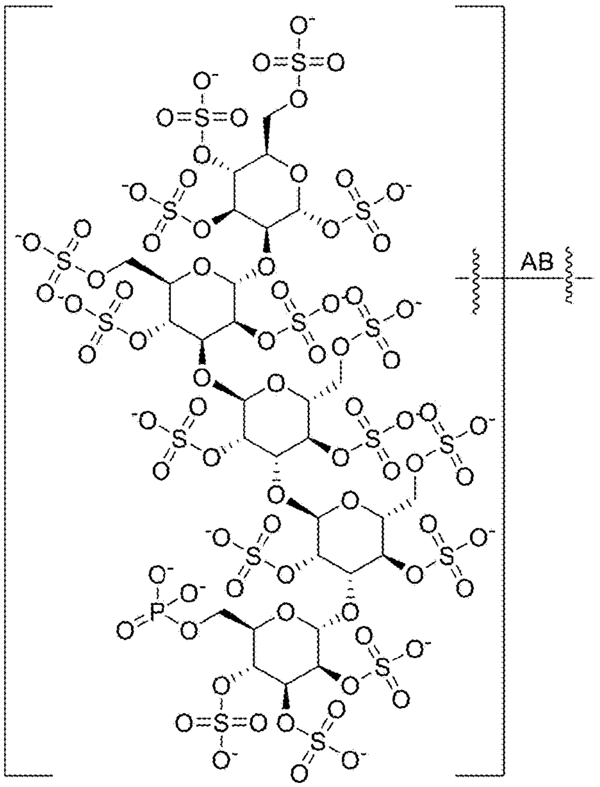
Figure 1G:
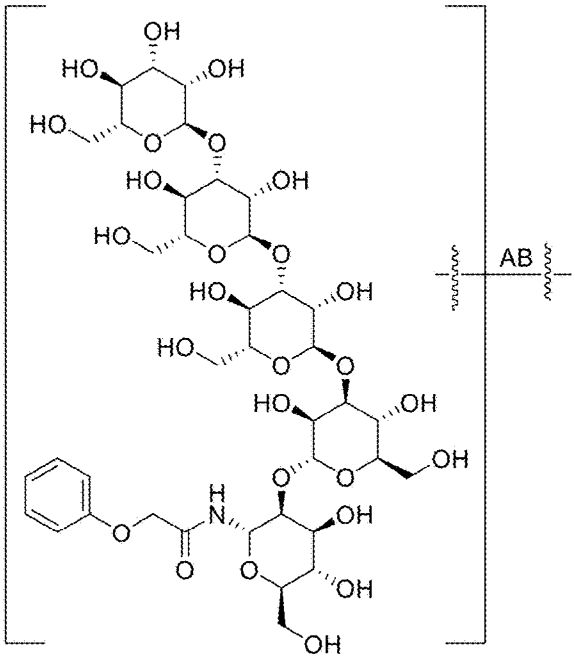
Figure 1G:
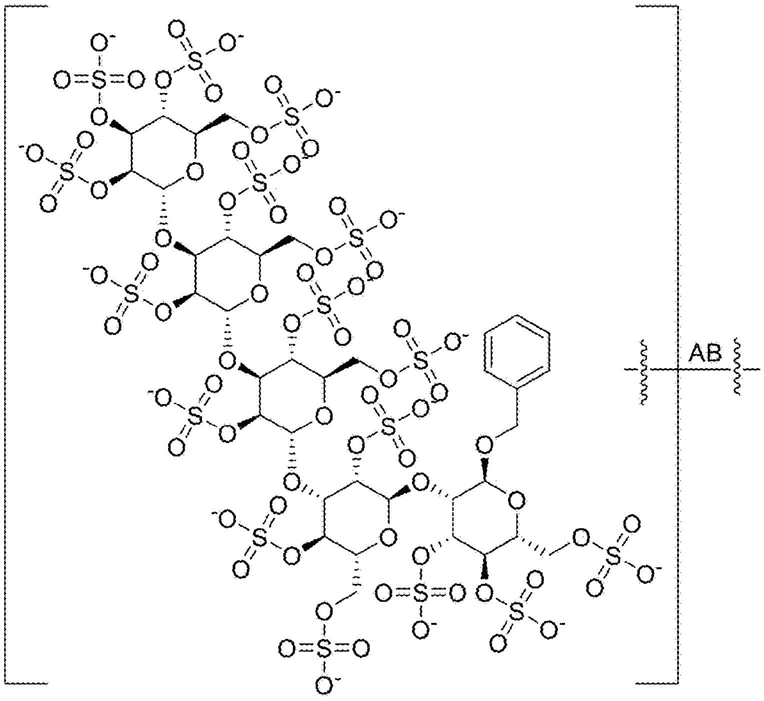
Figure 1H:
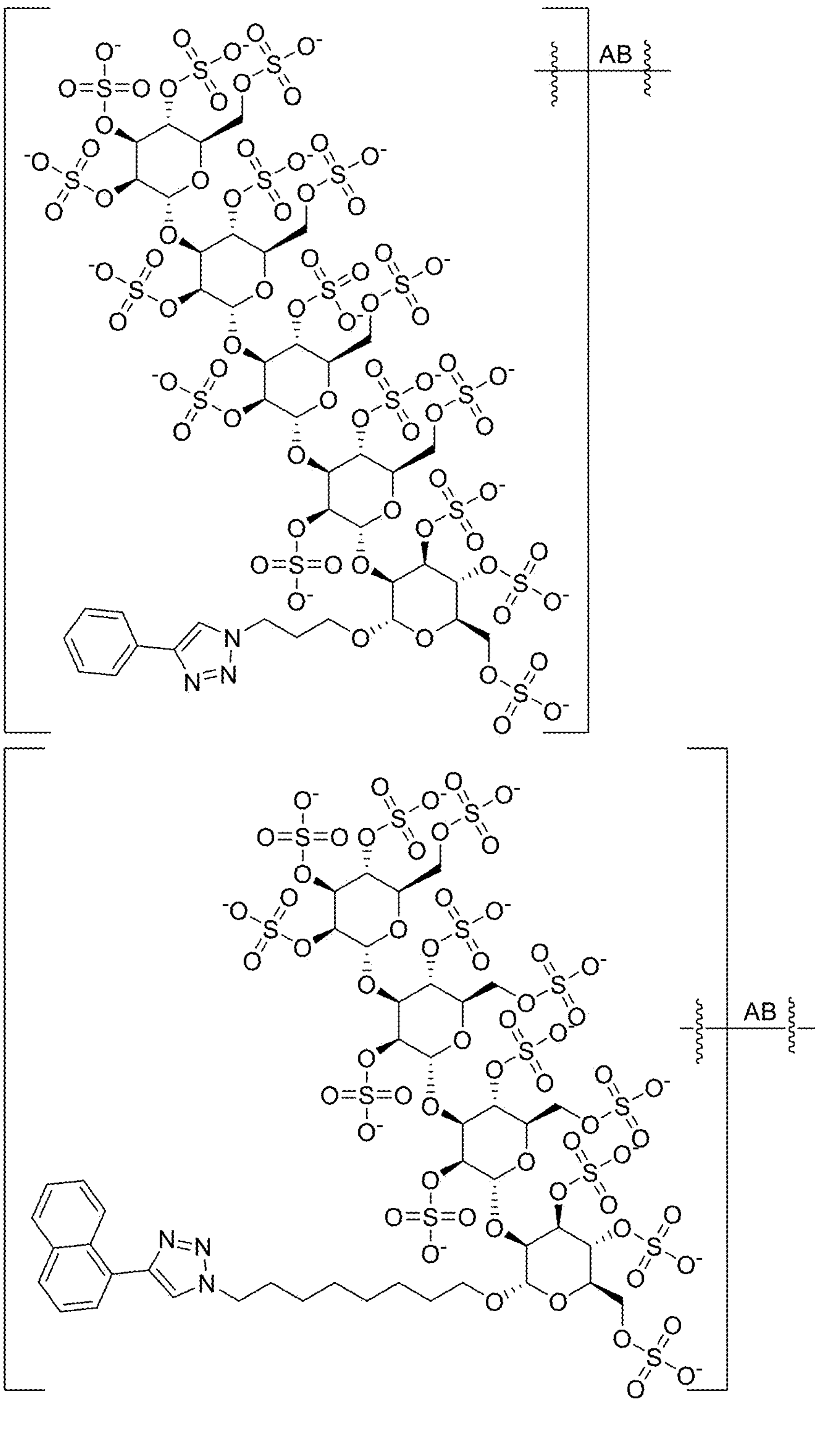
Figure 1I:
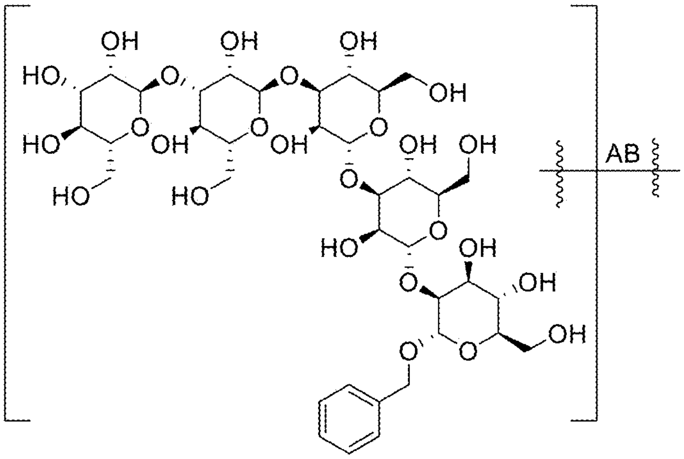
Figure 1I:
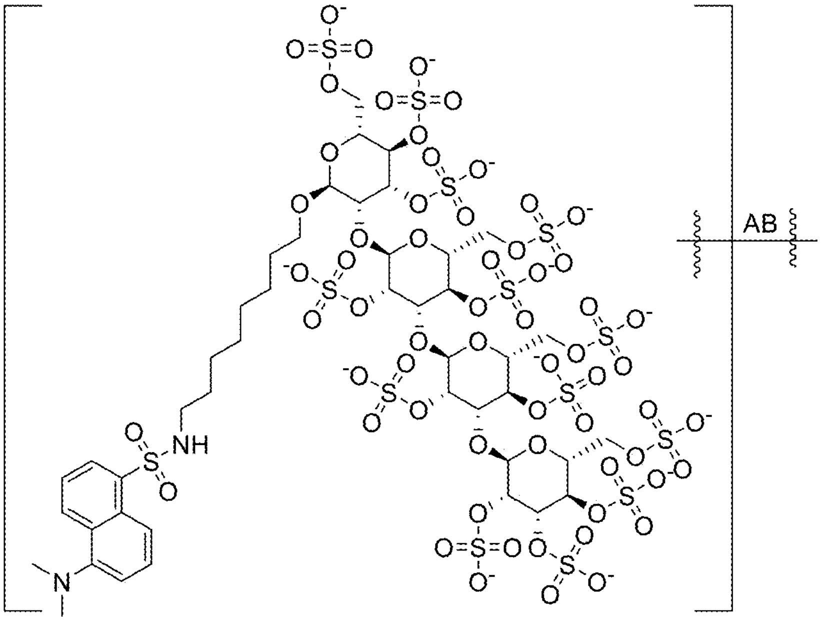
Figure 1J:
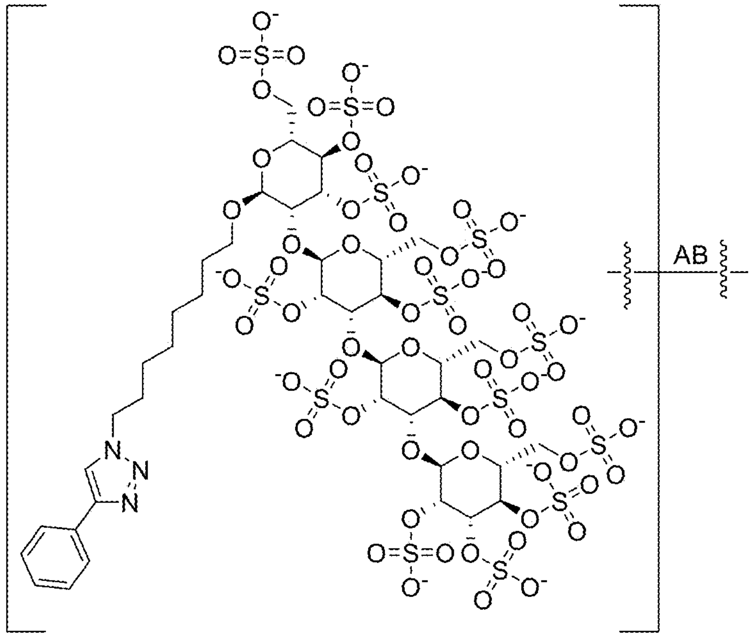
Figure 1J:
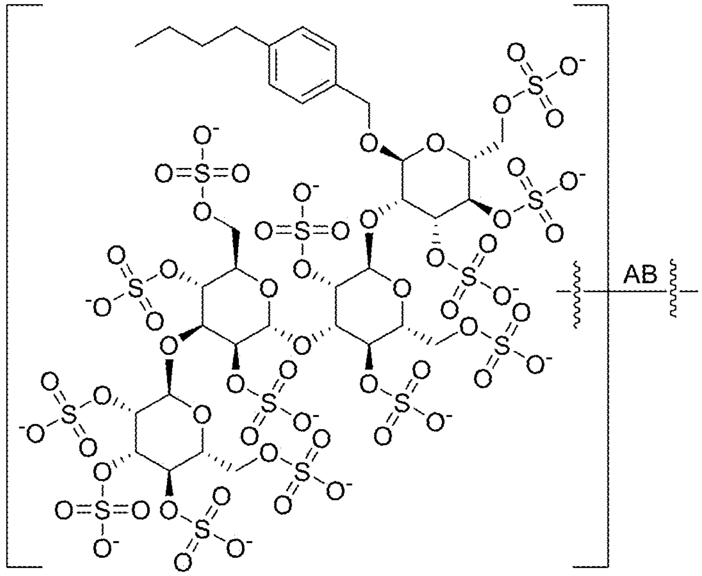
Figure 1K:
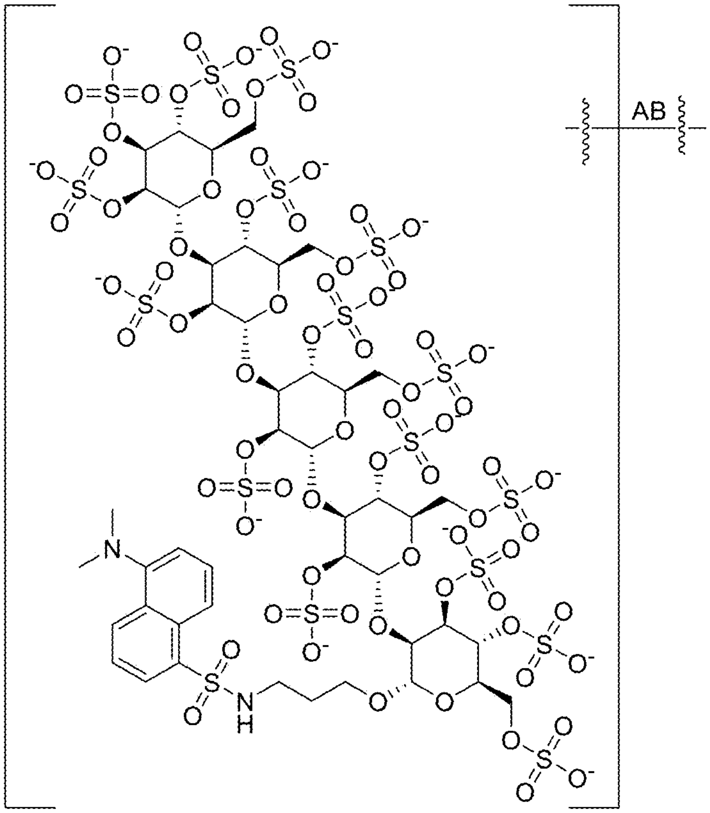
Figure 1L:
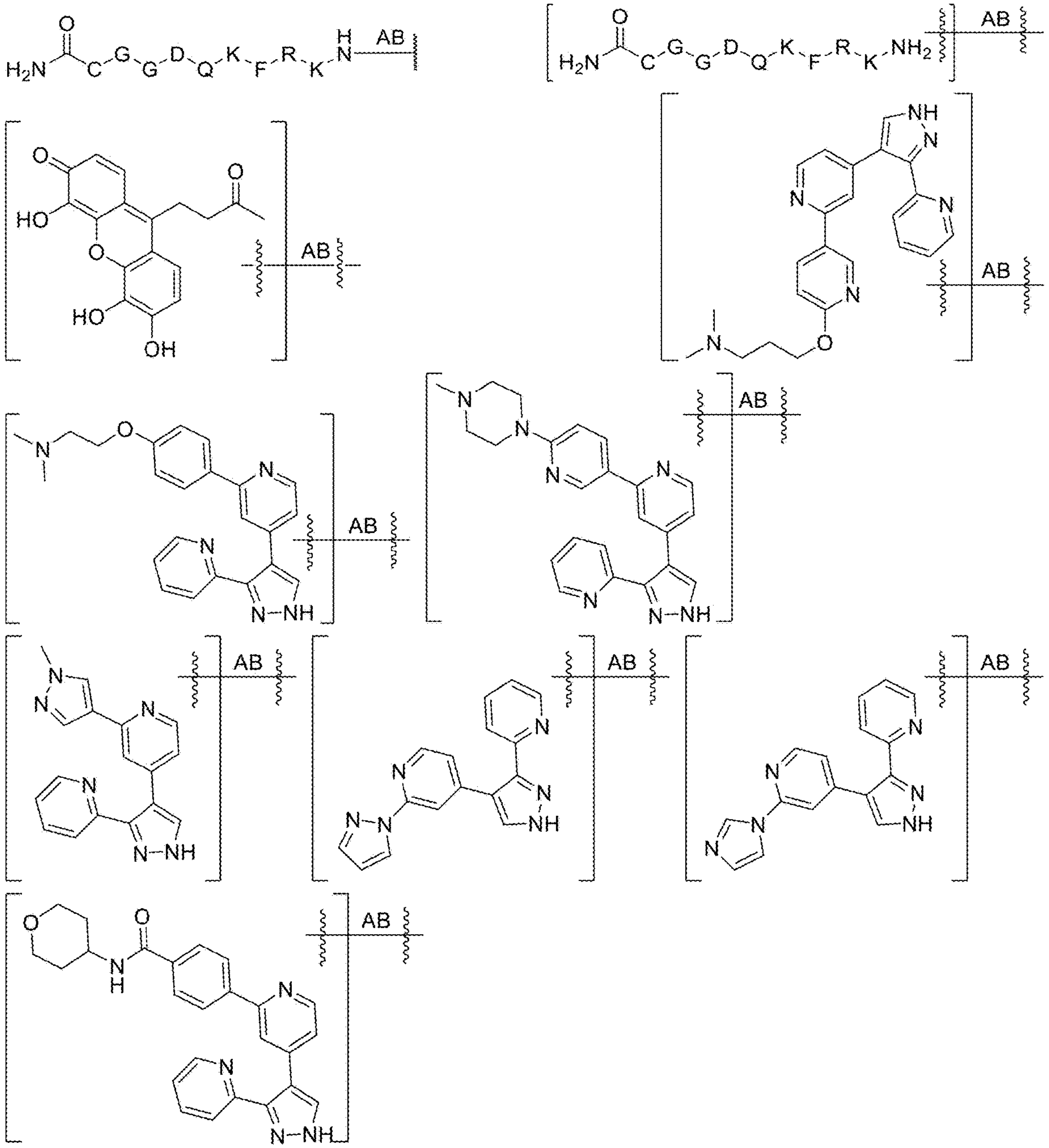
Figure 1M:
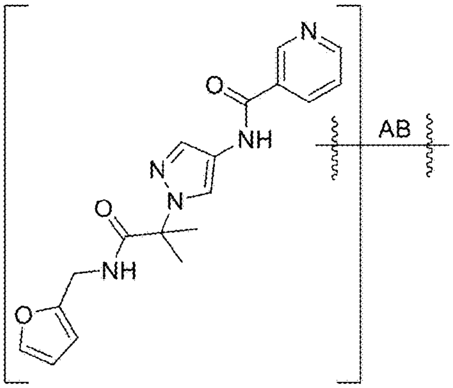
Figure 1M:
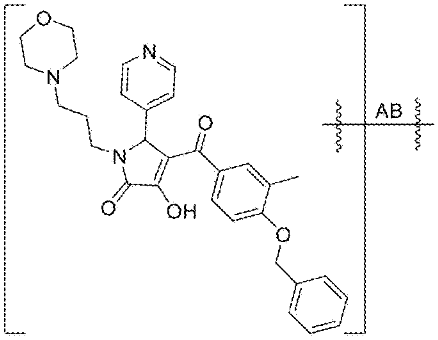
Figure 1M:
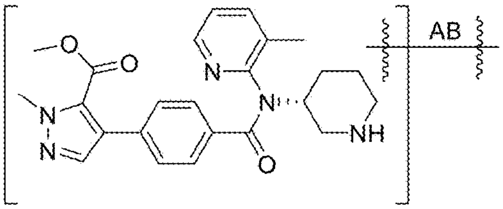
Figure 1M:
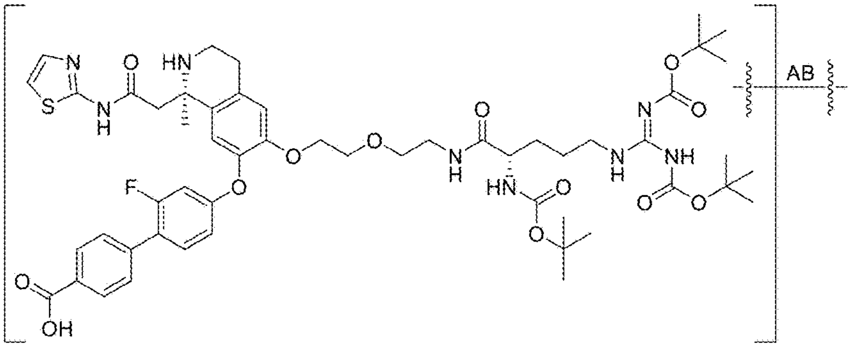
Figure 1M:
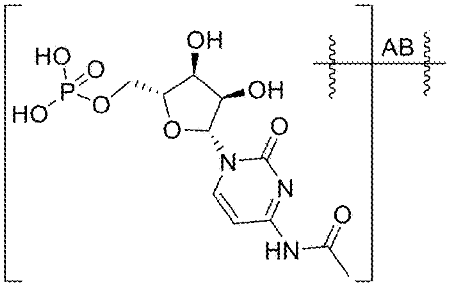
Figure 1M:
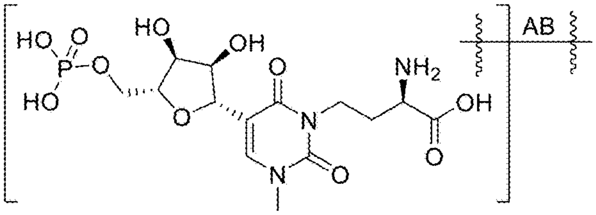
Figure 1M:
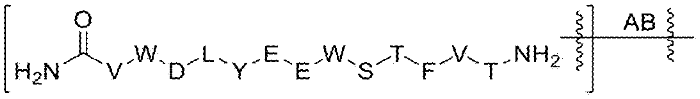
Figure 1M:
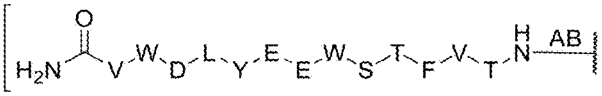
Figure 1N:
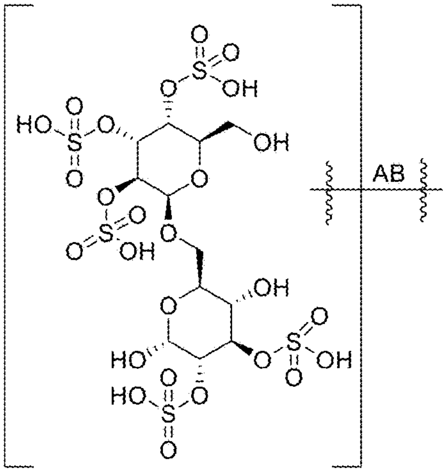
Figure 1N:
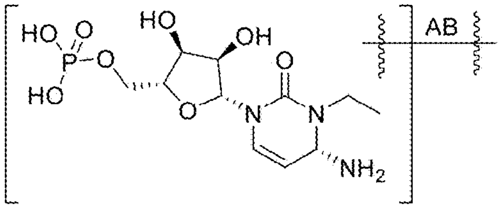
Figure 1N:
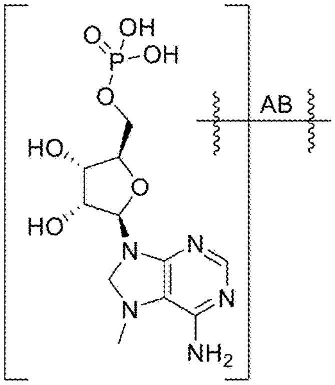
Figure 1N:
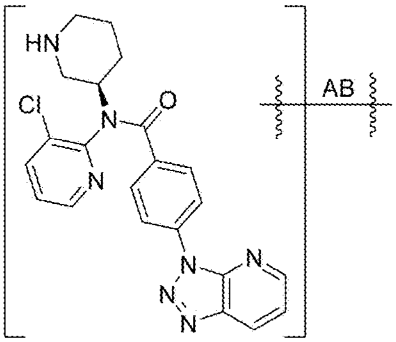
Figure 1N:
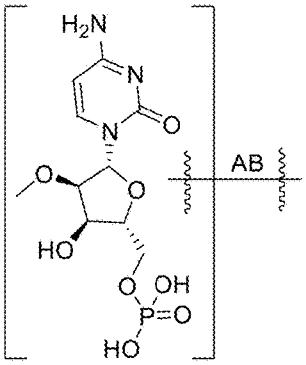
Figure 1N:
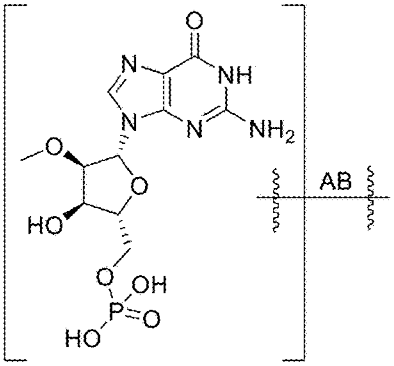
Figure 1N:
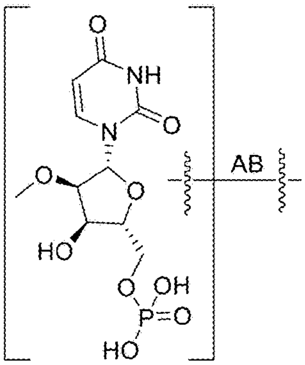
Figure 1N:
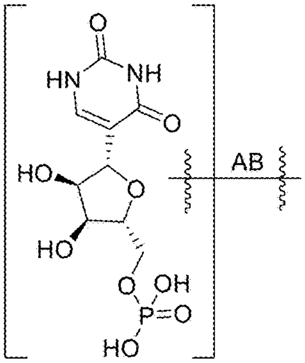
Figure 1N:
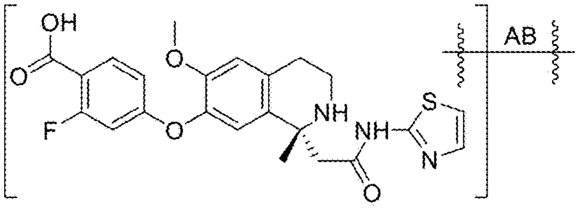
Figure 1N:
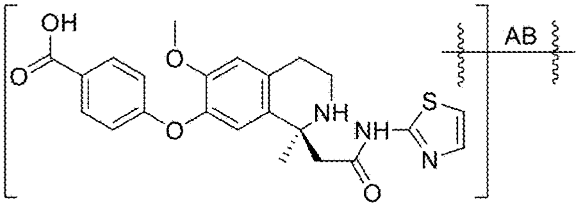
Figure 1O:
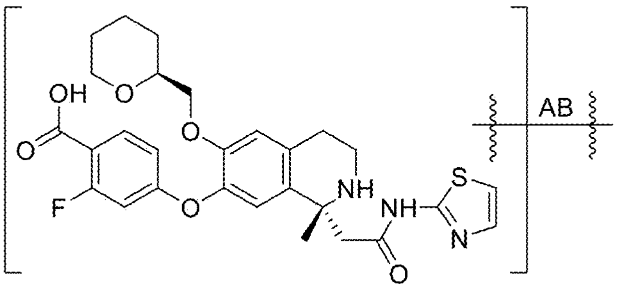
Figure 1O:
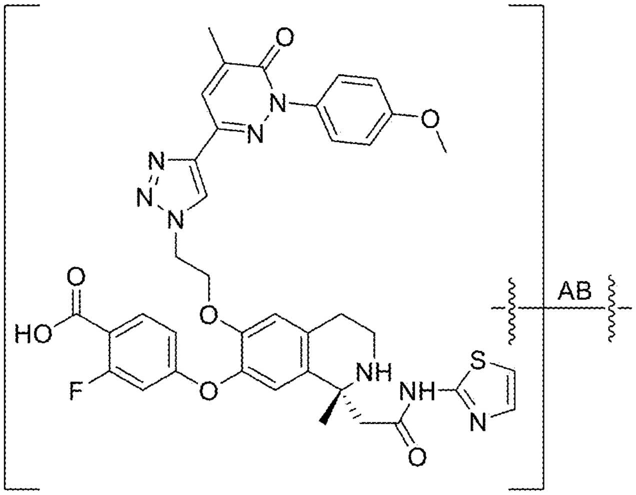
Figure 1O:
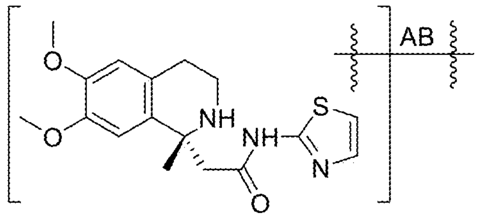
Figure 1O:
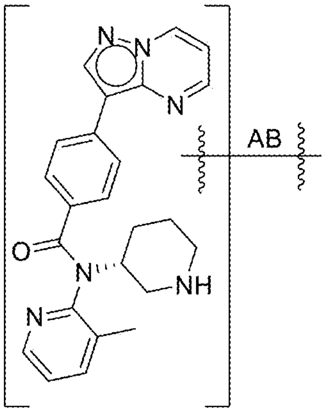
Figure 1O:
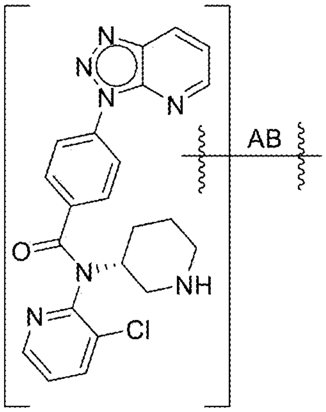
Figure 1O:
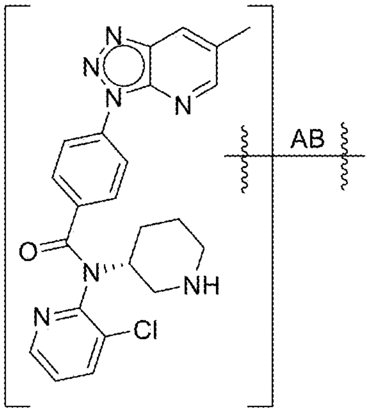
Figure 1O:
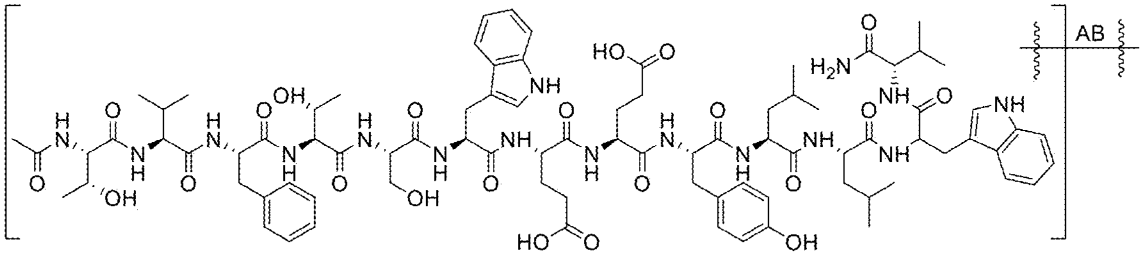
Figure 1P:
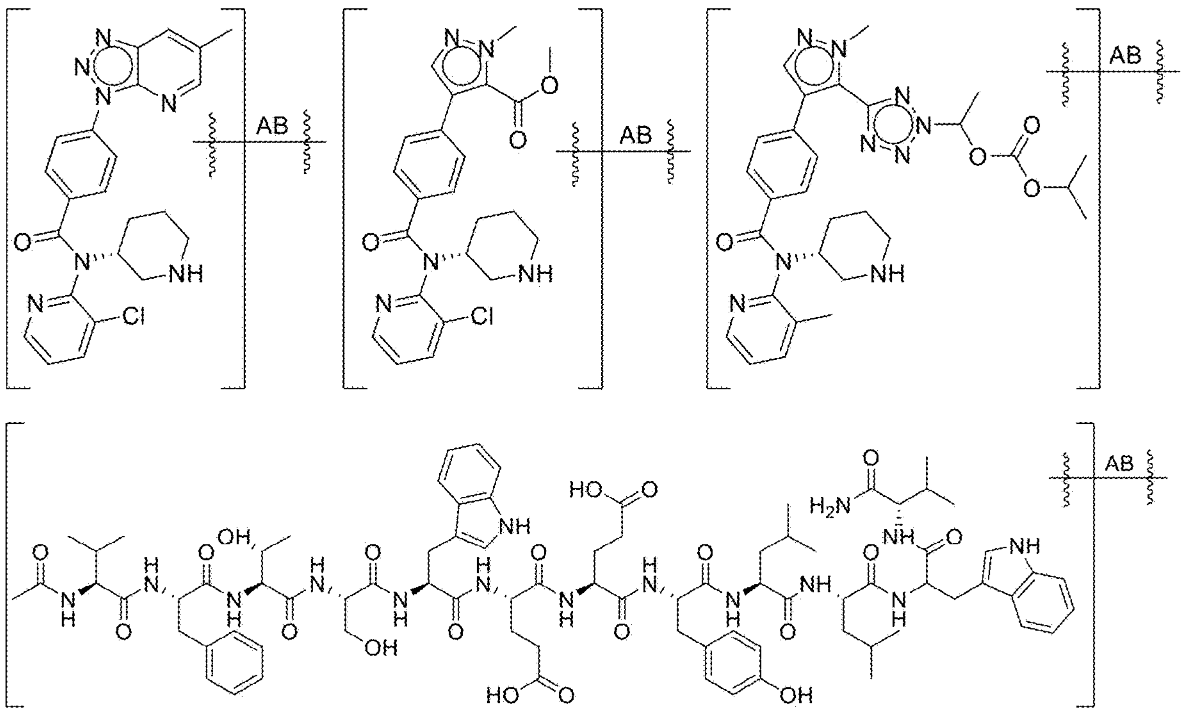
Figure 1Q:
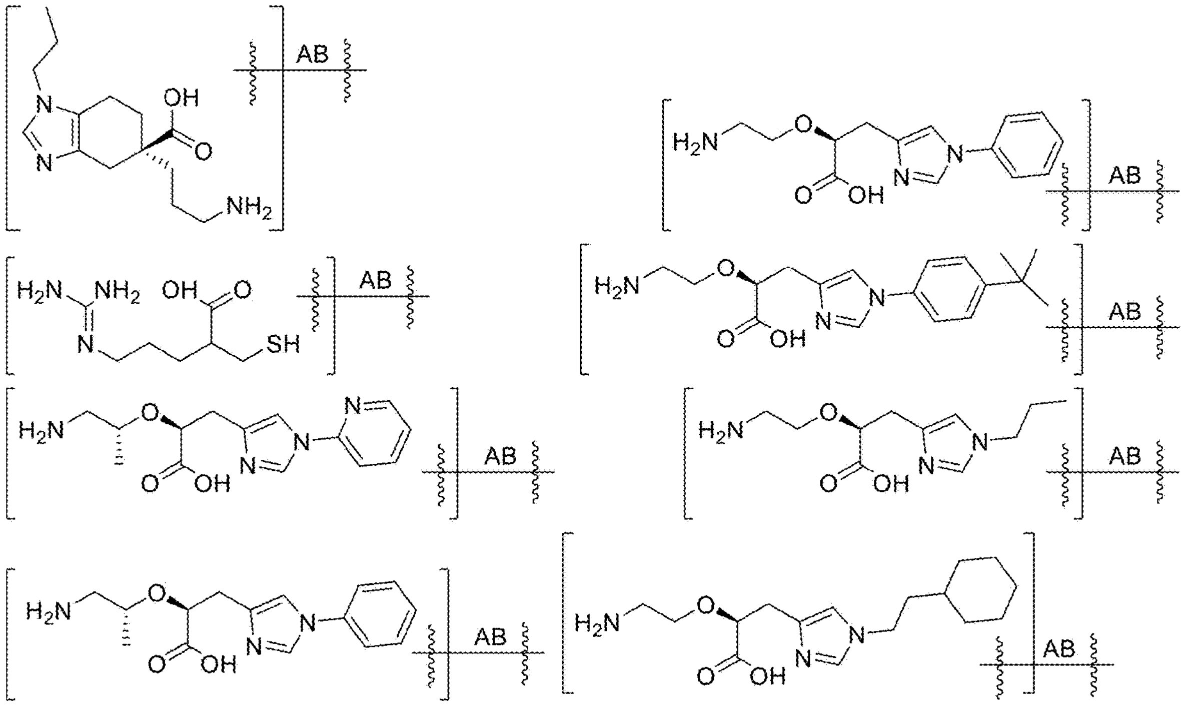
Figure 1R:
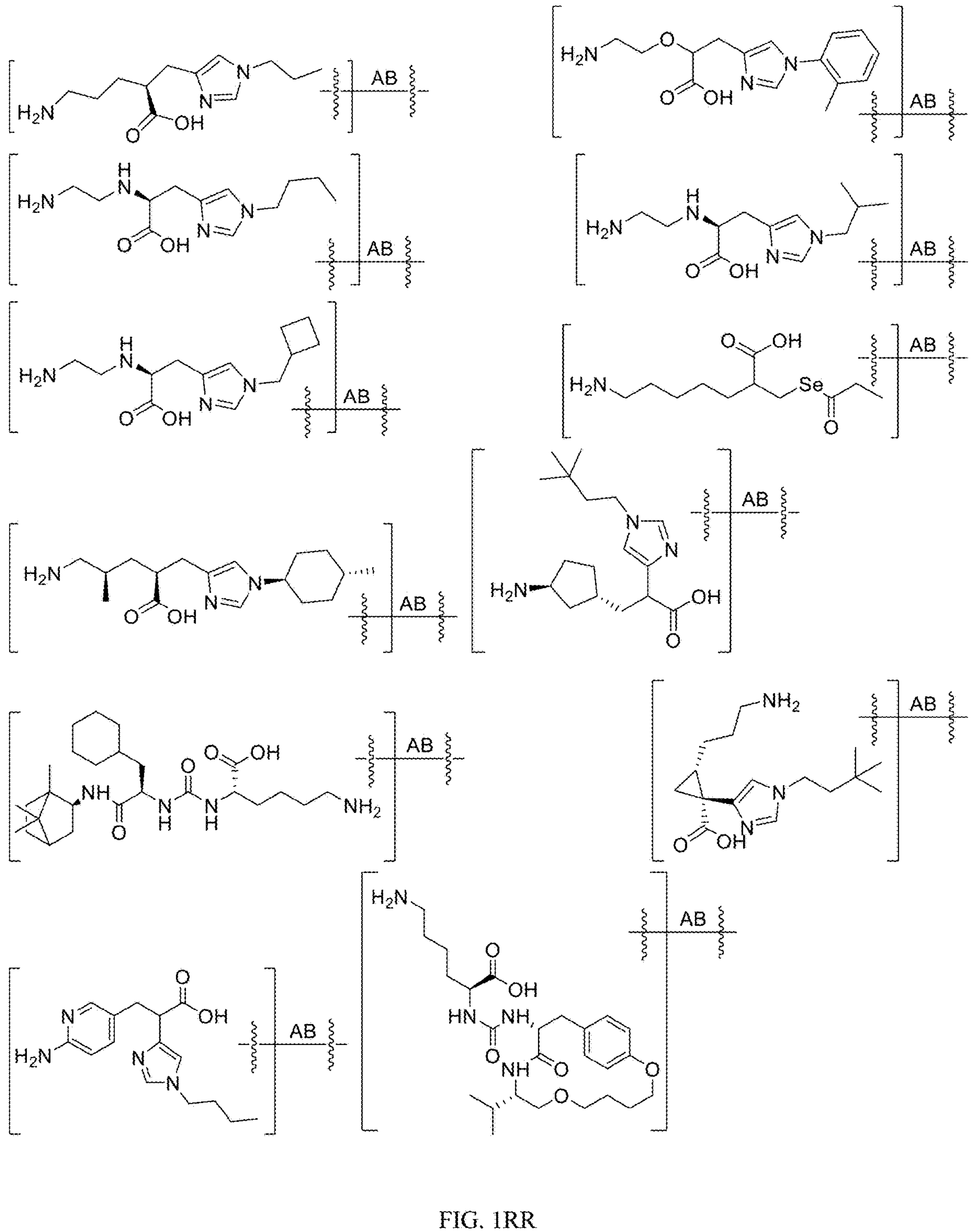
Figure 1S:
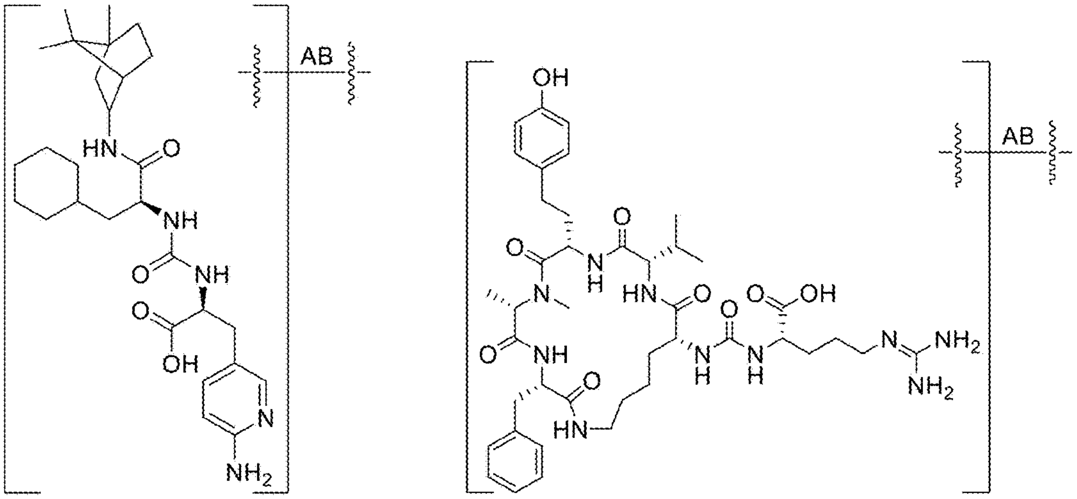
Figure 1T:
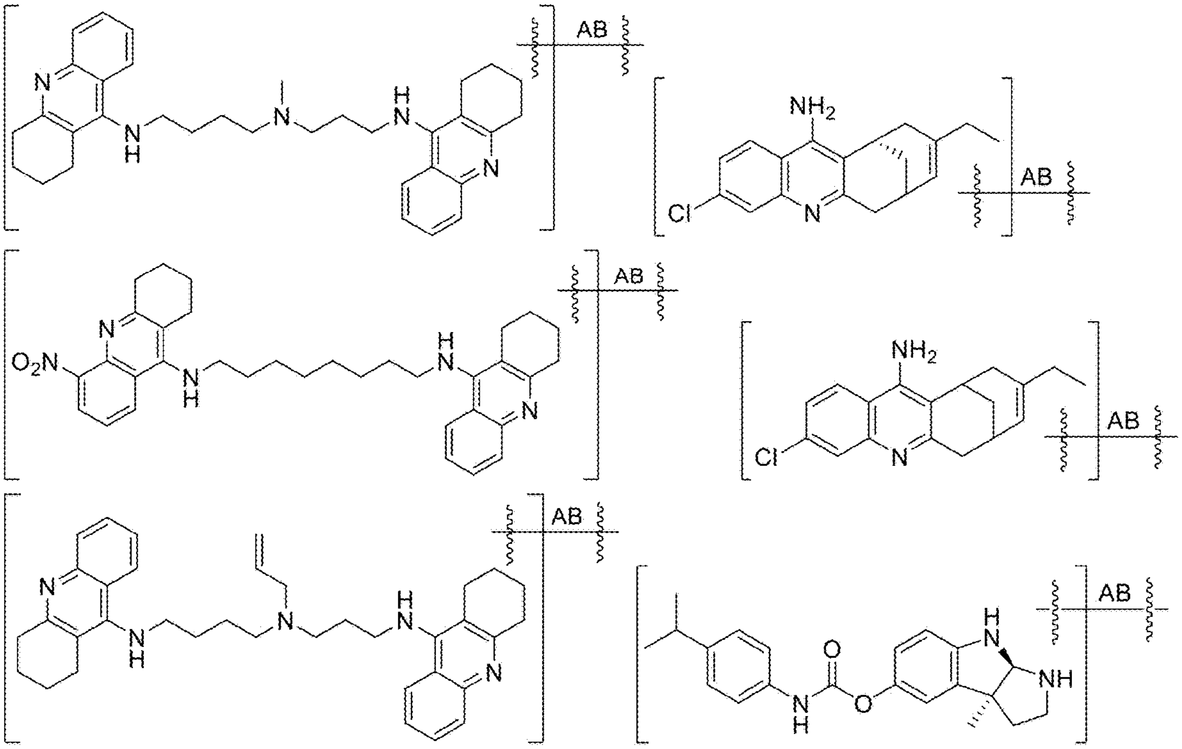
Figure 1U:
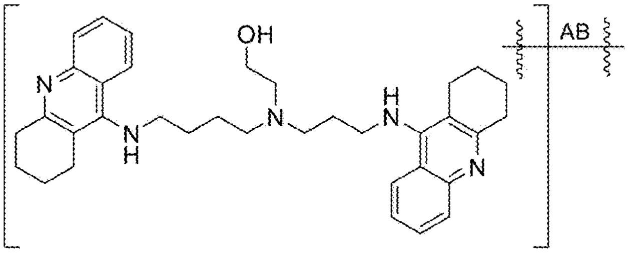
Figure 1U:
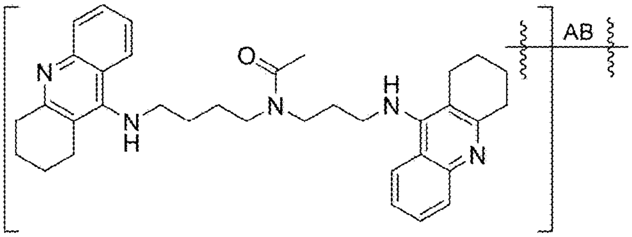
Figure 1U:
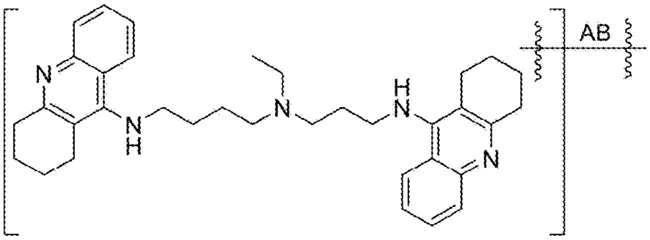
Figure 1U:
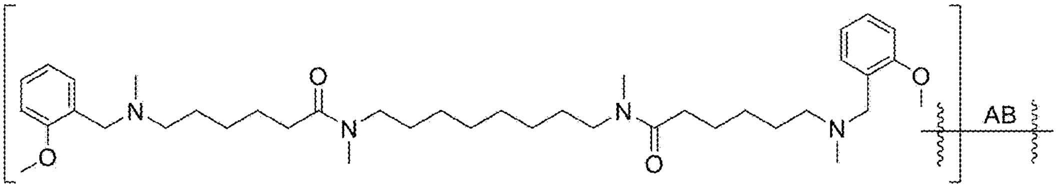
Figure 1U:
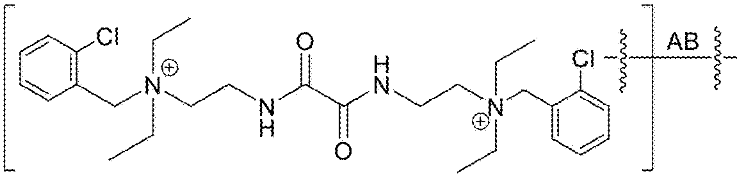
Figure 1U:
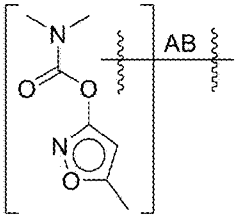
Figure 1U:
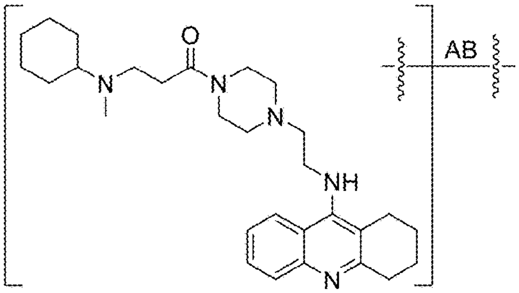
Figure 1U:
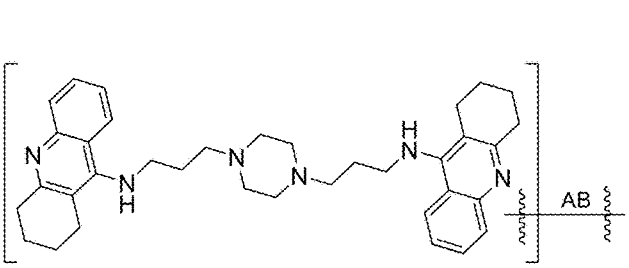
Figure 1V:
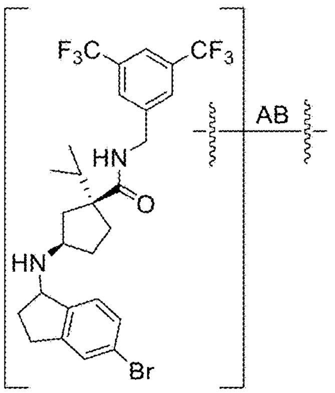
Figure 1V:
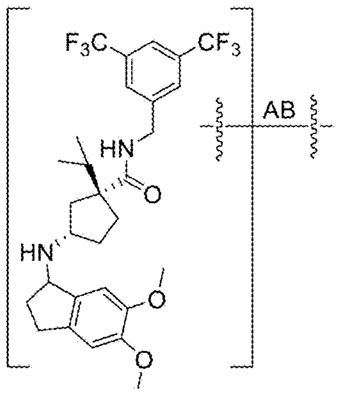
Figure 1V:
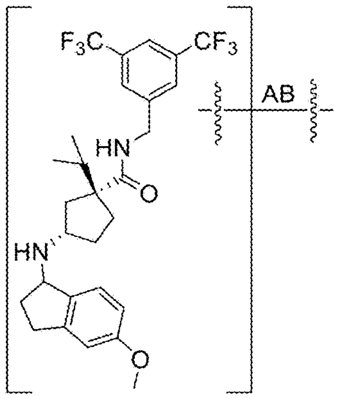
Figure 1V:
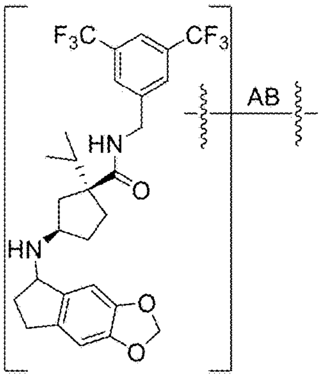
Figure 1V:
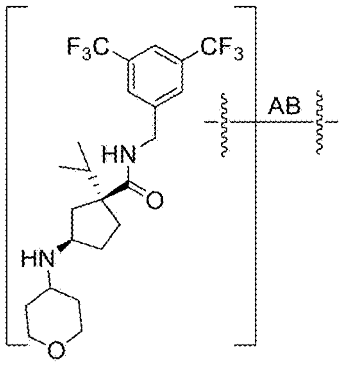
Figure 1V:
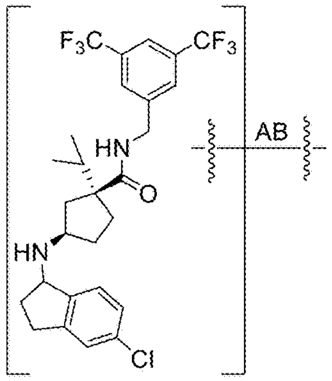
Figure 1V:
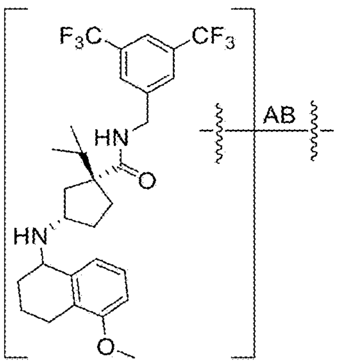
Figure 1V:
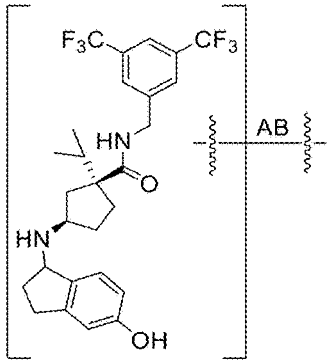
Figure 1V:
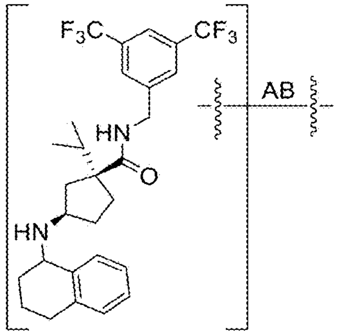
Figure 1V:
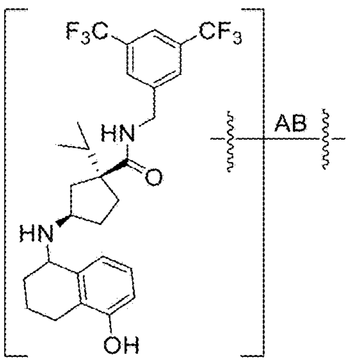
Figure 1V:
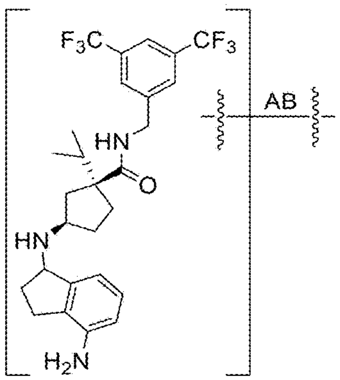
Figure 1V:
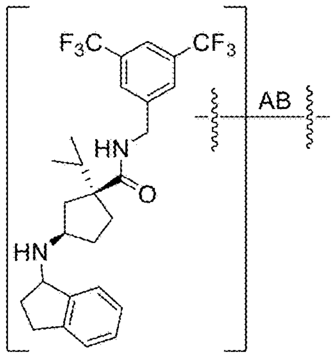
Figure 1W:
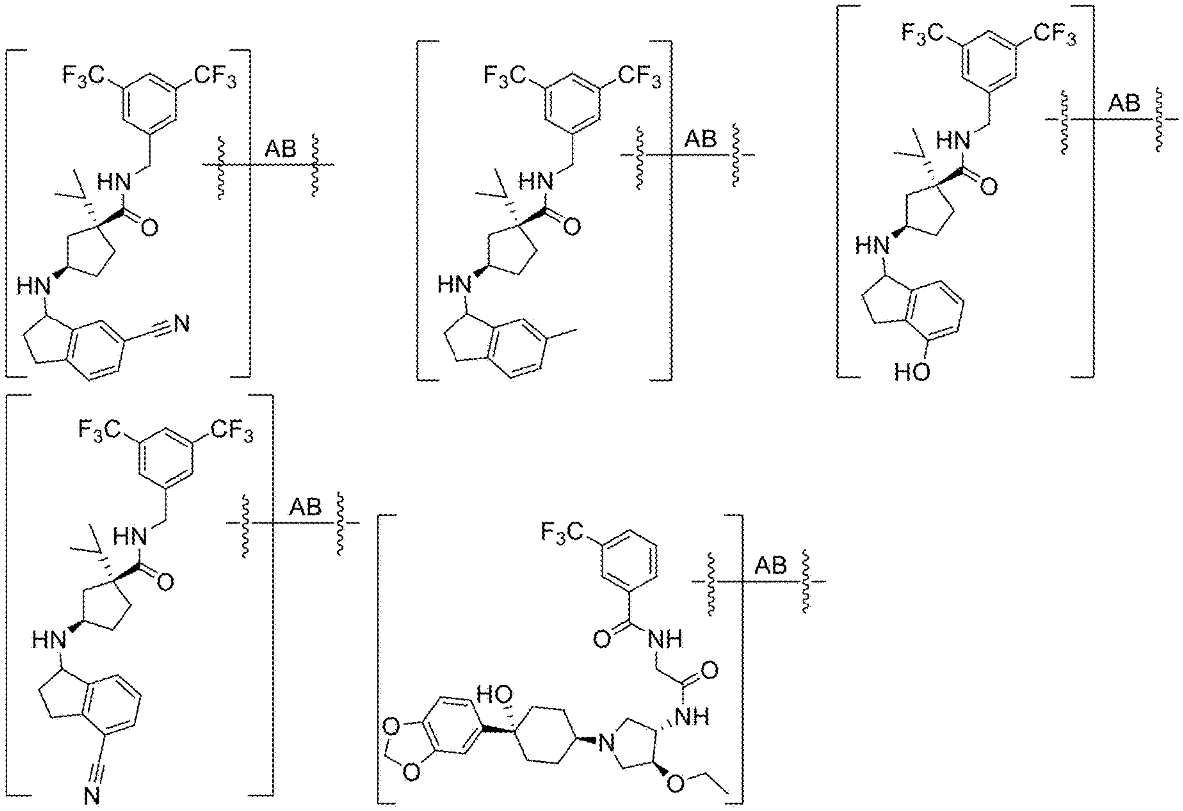
Figure 1X:
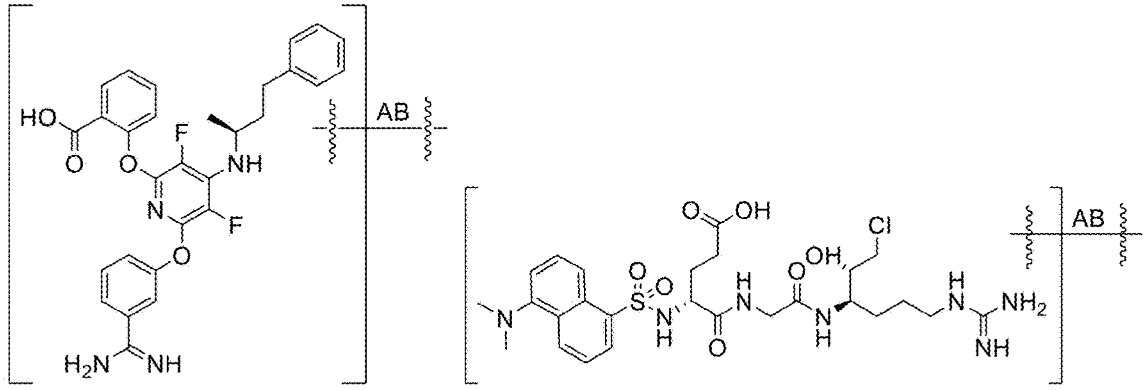
Figure 1Y:
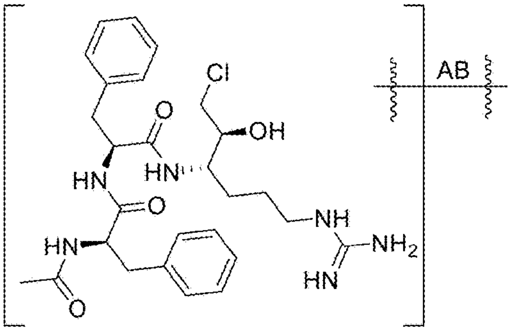
Figure 1Y:
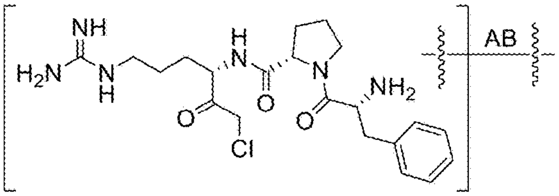
Figure 1Y:
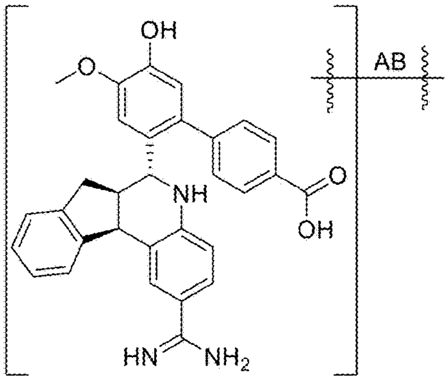
Figure 1Y:
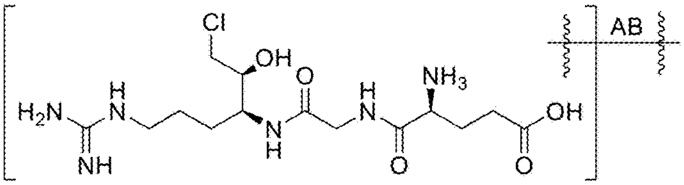
Figure 1Y:
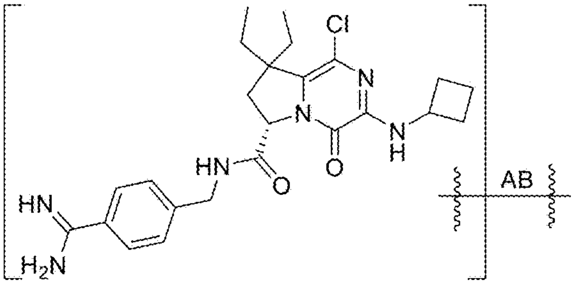
Figure 1Y:
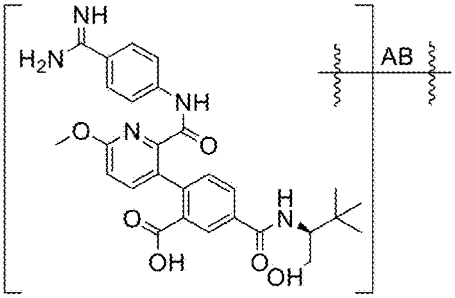
Figure 1Y:
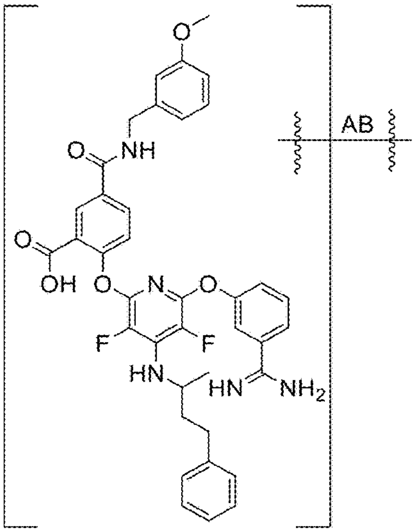
Figure 1Y:
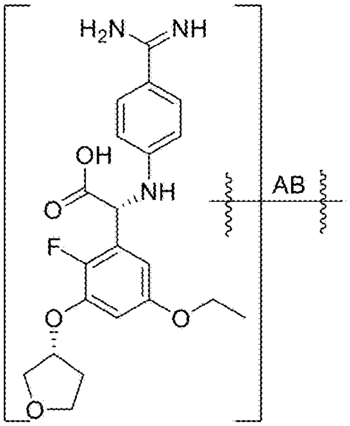
Figure 1Z:
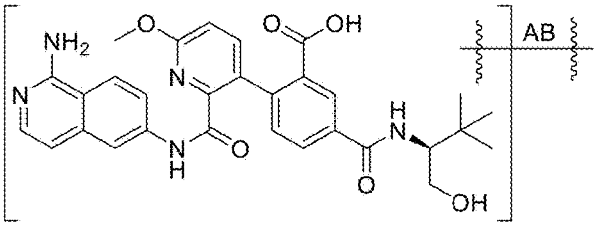
Figure 1Z:
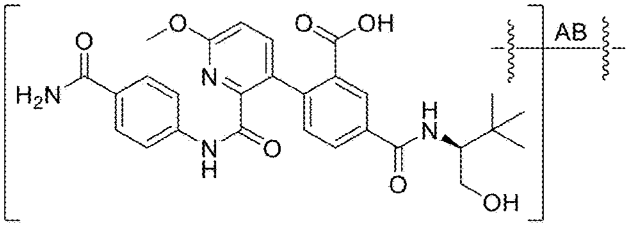
Figure 1Z:
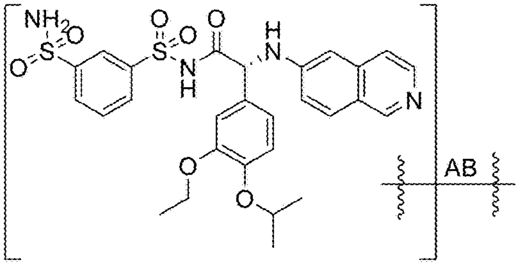
Figure 1Z:
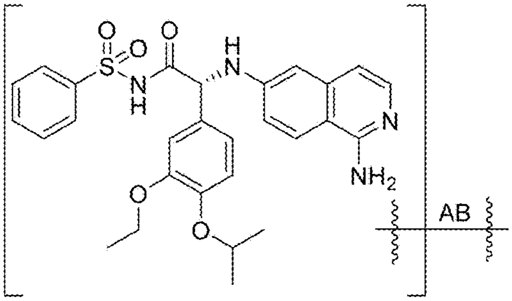
Figure 1Z:
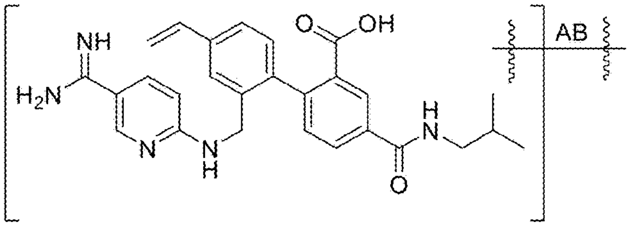
Figure 1Z:
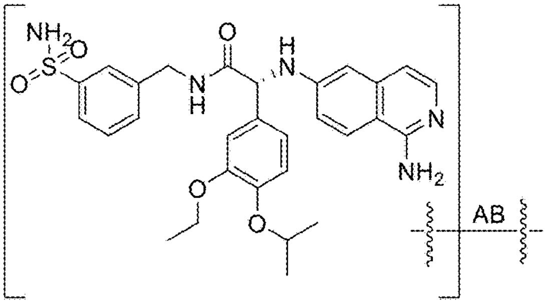
Figure 1Z:
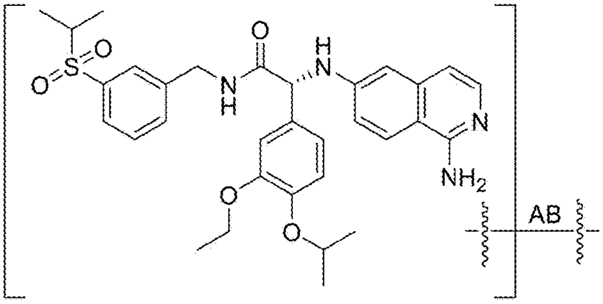
Figure 1Z:
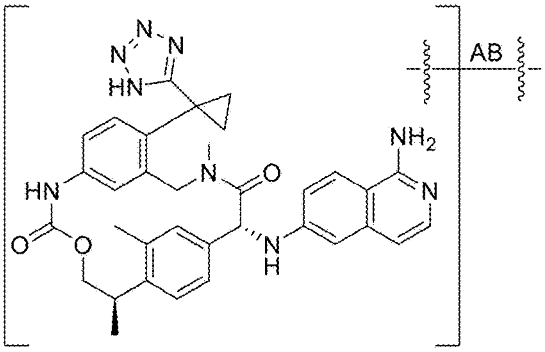
Figure 1Z:
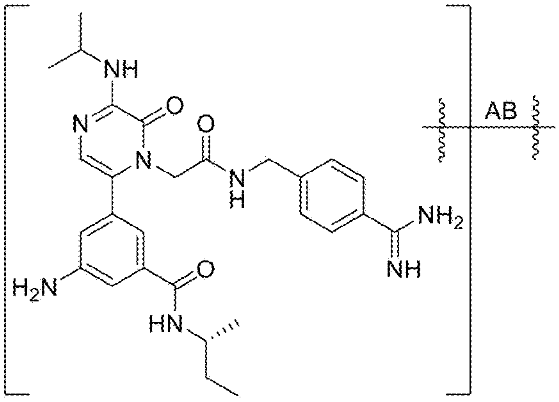
Figure 2:
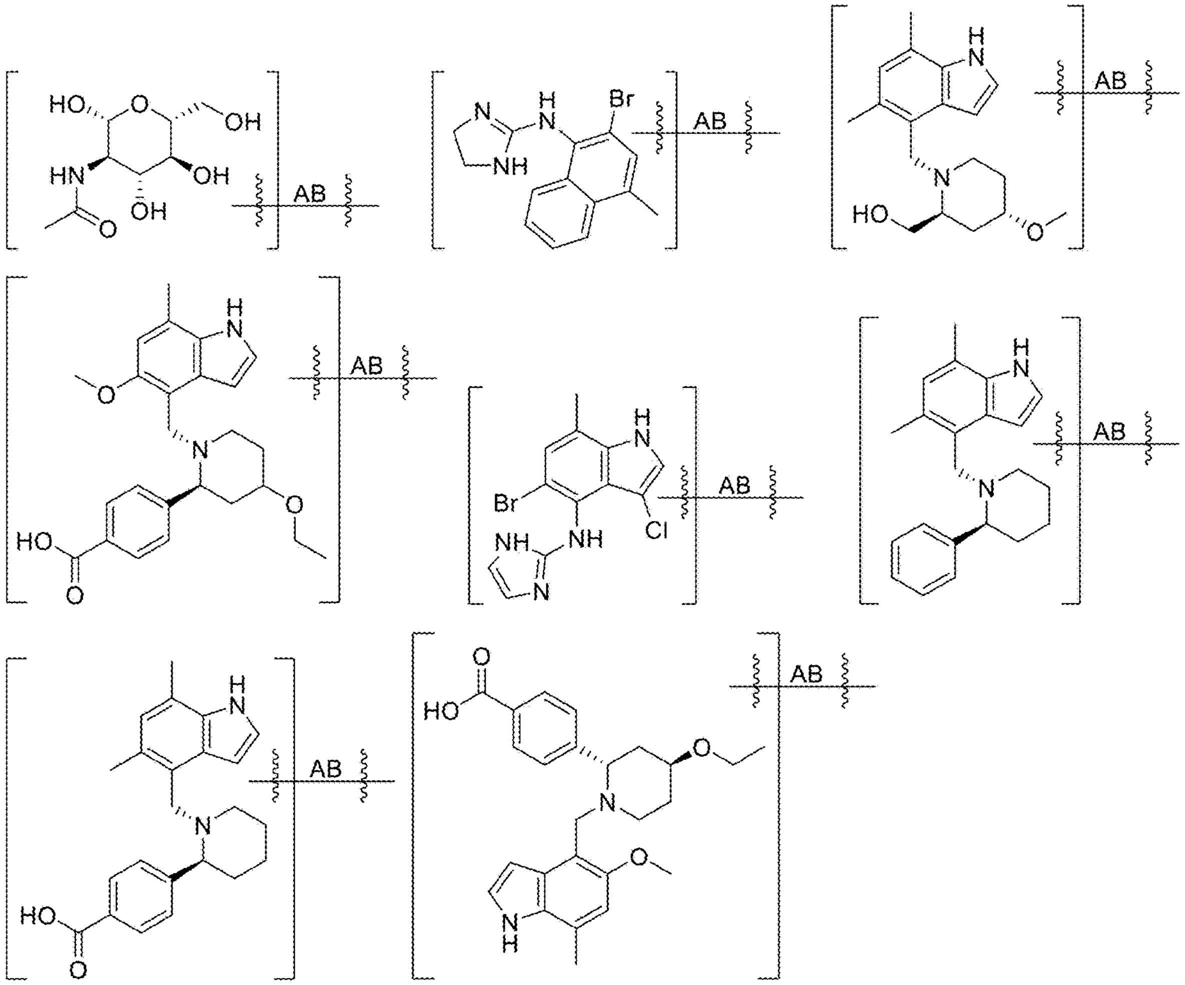
FIG. 2 provides a non-limiting list of exemplary Extracellular Protein Targeting Ligands that target complement factor B.
Figure 3A:
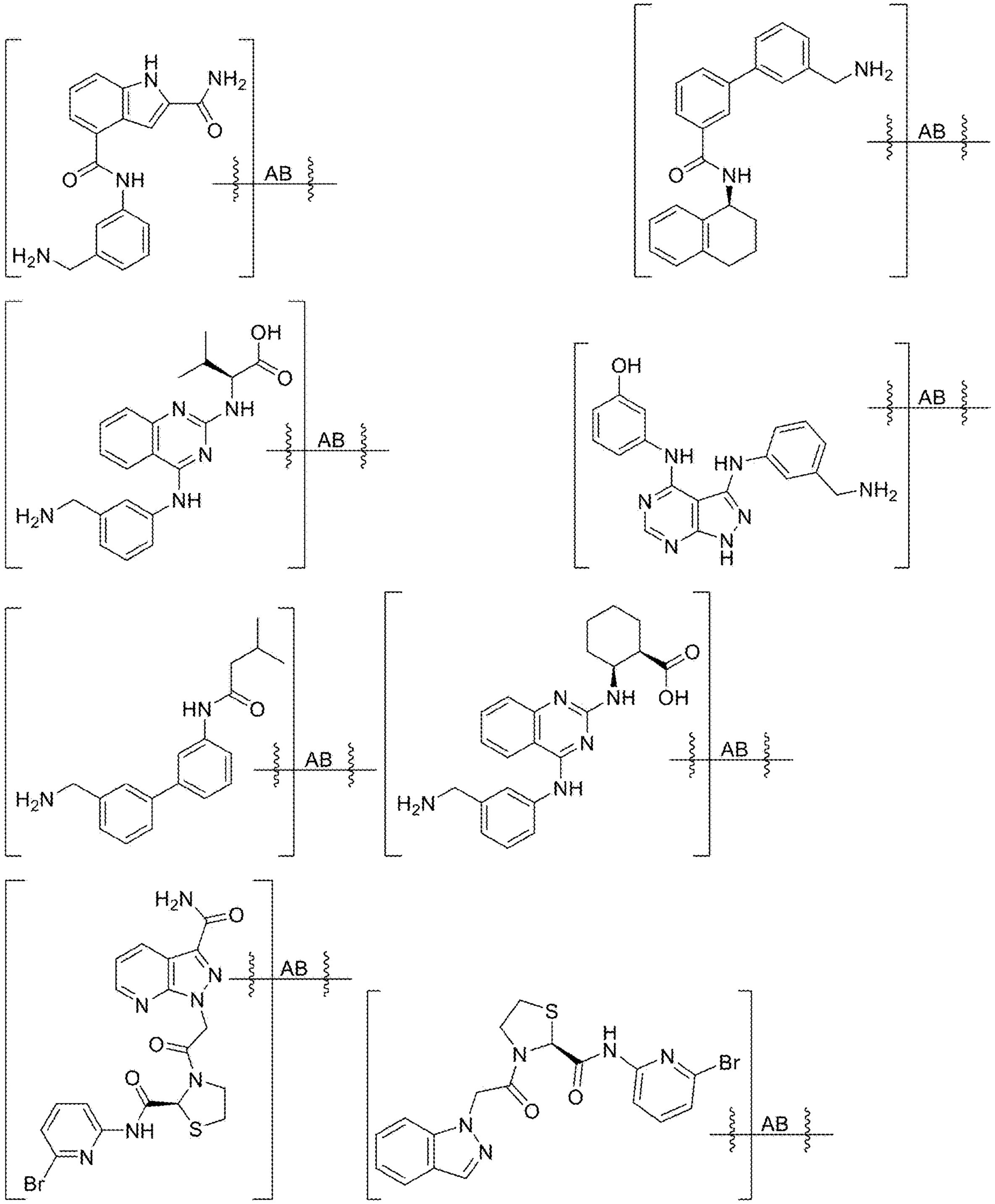
FIGS. 3A and 3B provides a non-limiting list of exemplary Extracellular Protein Targeting Ligands that target complement factor D.
Figure 3B:
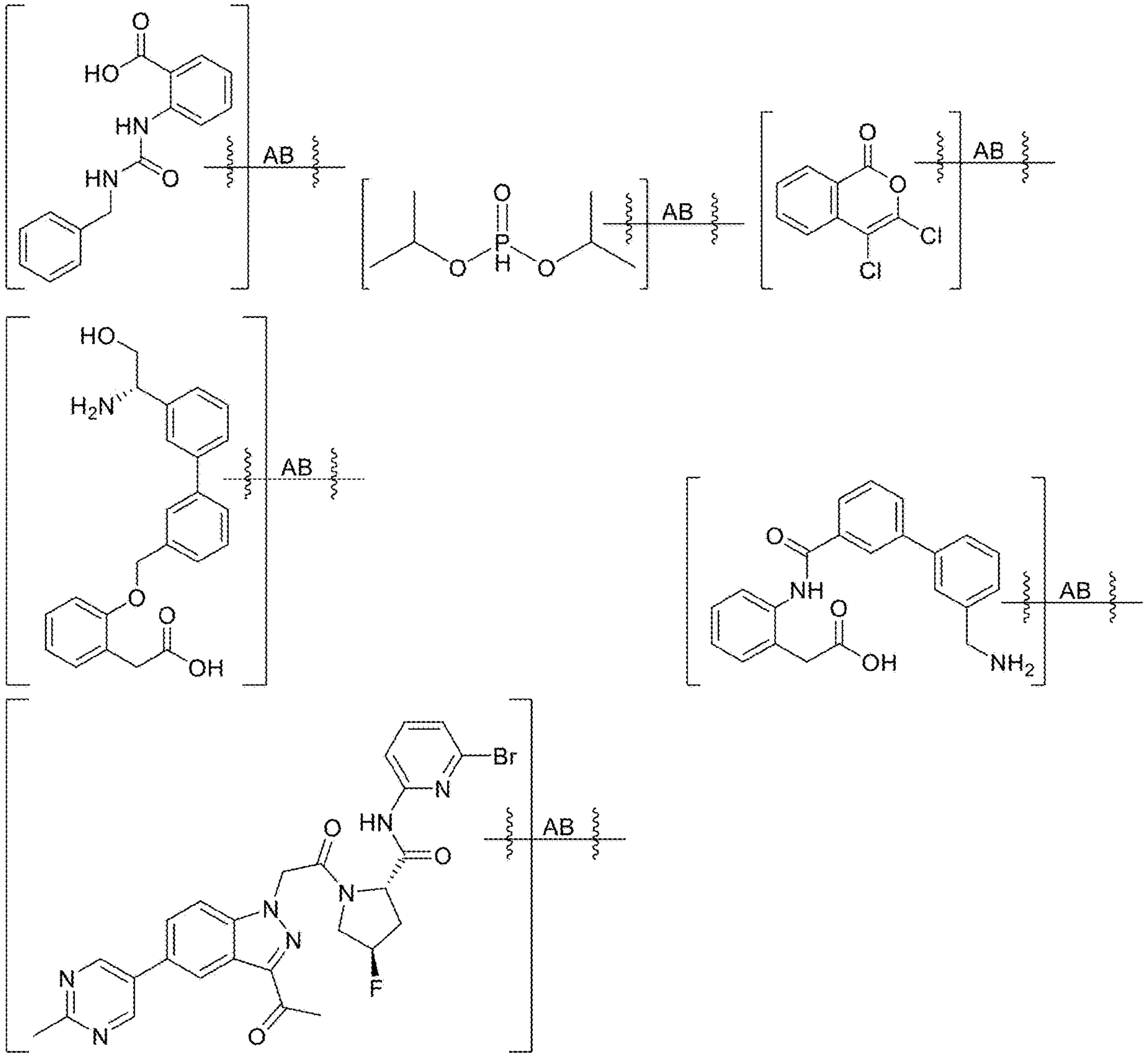
Figure 4:
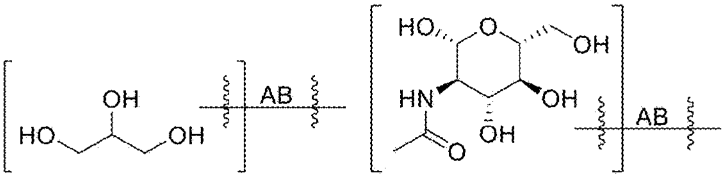
FIG. 4 provides a non-limiting list of exemplary Extracellular Protein Targeting Ligands that target complement factor H.

Novel compounds and their pharmaceutically acceptable salts and compositions thereof that degrade disease-mediating extracellular proteins, as well as starting materials and intermediates for such compounds and their methods of use and processes of manufacture are provided. This invention focuses on novel modifications of the C-position of the ASGPR ligand, referred to herein as $R^2$. These modifications include molecules with the $C^2$ substituent in the "down" configuration which correspond to the stereochemistry of galactose as well as molecules with the $C^2$ substituent in the "up" configuration which corresponds to the stereochemistry of talose. It has been discovered that advantageous extracellular protein degrader molecules are provided when ASGPR ligands with $R^2$ groups as specified herein that have either galactose or talose stereochemistry are incorporated into the structure.

I. Galactose-Based ASGPR-Binding Extracellular Protein Degraders of the Present Invention As used in the embodiments here, xx is independently selected from 0, 1, 2, 3, 4, 5, 6, 7, 8, 9, 10, 11, 12, 13, 14, 15, 16, 17, 18, 19, 20, 21, 22, 23, 24, and 25.

As used in the embodiments here, yy is independently selected from 0, 1, 2, 3, 4, 5, 6, 7, 8, 9, 10, 11, 12, 13, 14, 15, 16, 17, 18, 19, 20, 21, 22, 23, 24, and 25.

As used in the embodiments here, zz is independently selected from 0, 1, 2, 3, 4, 5, 6, 7, 8, 9, 10, 11, 12, 13, 14, 15, 16, 17, 18, 19, 20, 21, 22, 23, 24, and 25.

In certain embodiments the compound of the present invention is selected from:

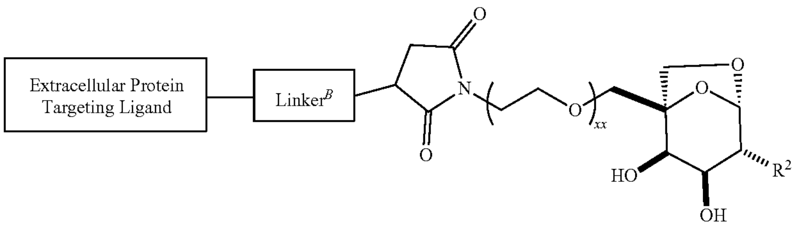

In certain embodiments the compound of the present invention is selected from:
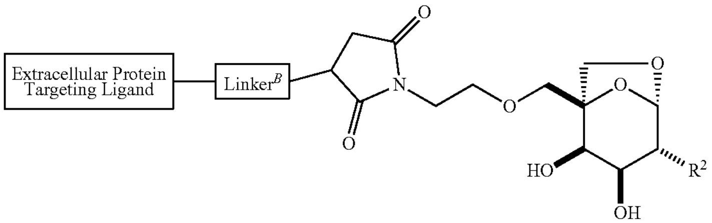
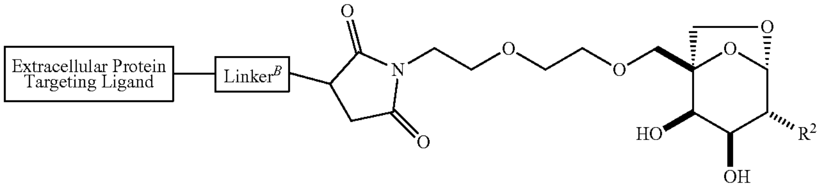
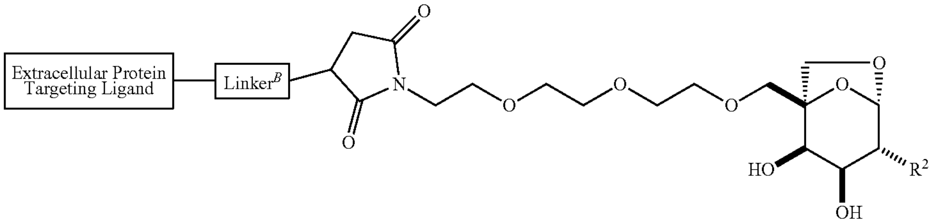
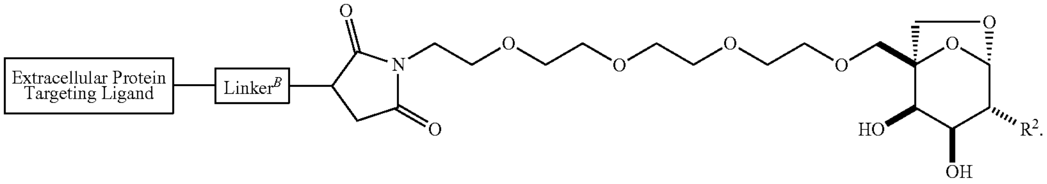
In certain embodiments the compound of the present invention is selected from:
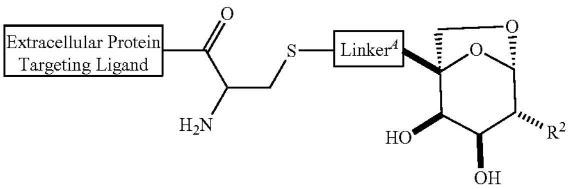
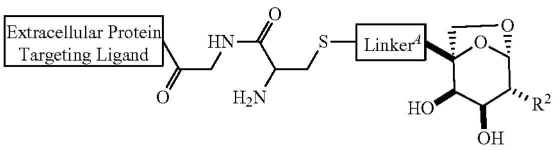
In certain embodiments the compound of the present invention is selected from:
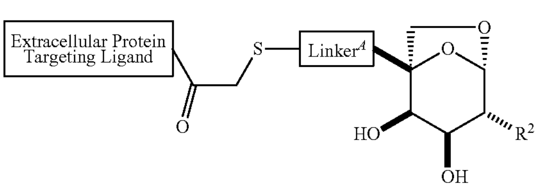
-continued
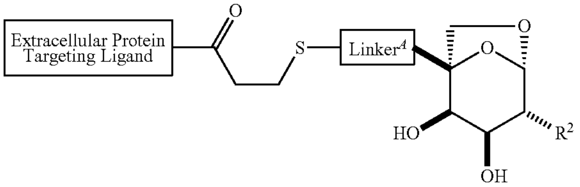
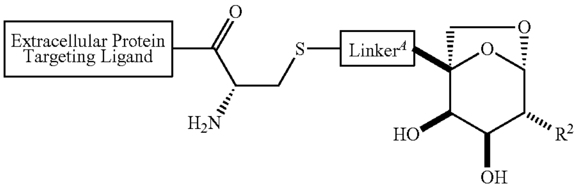
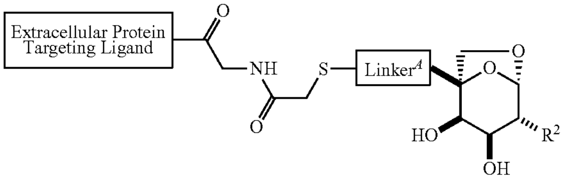
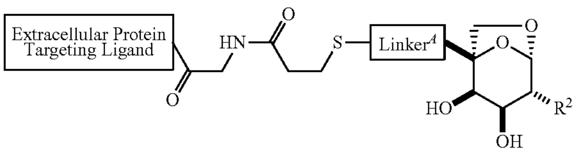

-continued
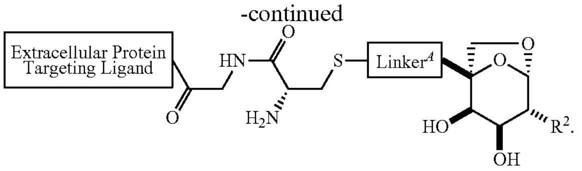
In certain embodiments the compound of the present invention is selected from:
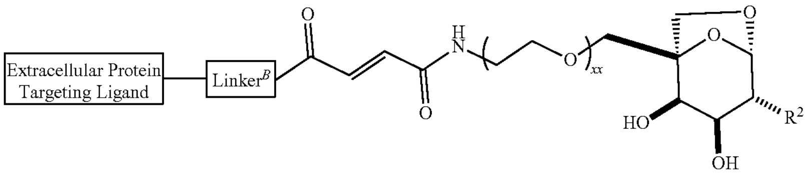
In certain embodiments the compound of the present invention is selected from:
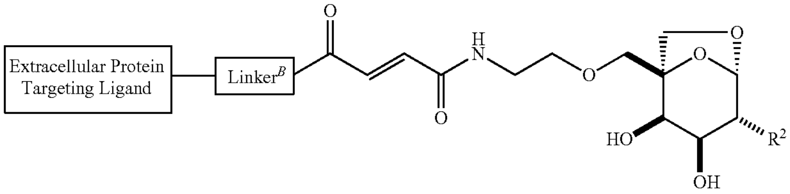
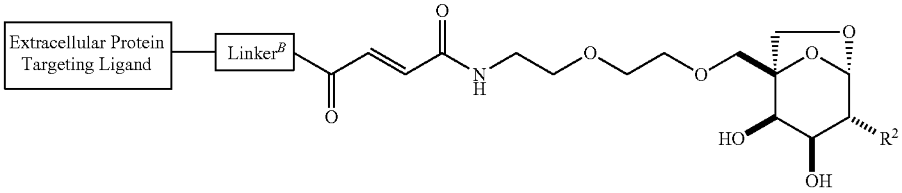
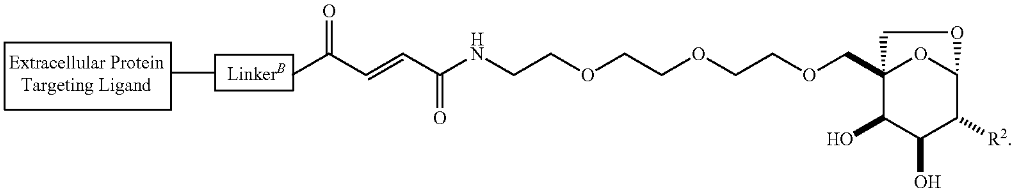
In certain embodiments the compound of the present invention is selected from:
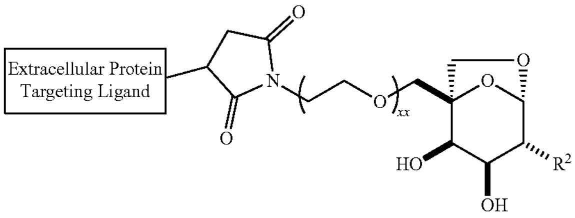
In certain embodiments the compound of the present invention is selected from:

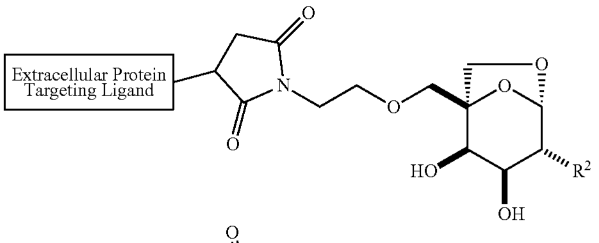
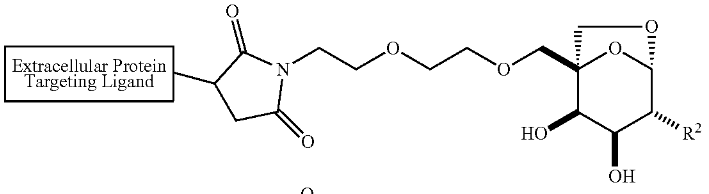
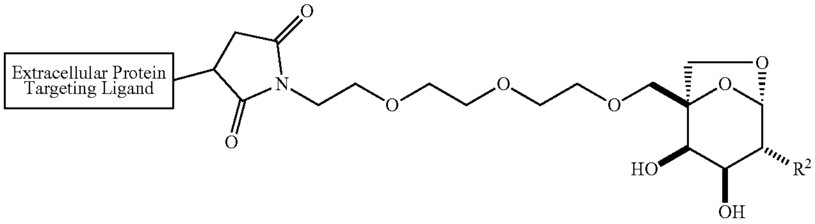
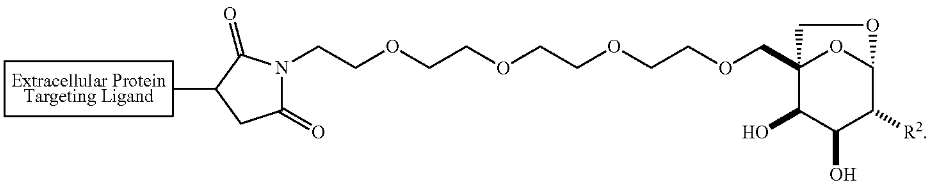
In certain embodiments the compound of the present invention is selected from:
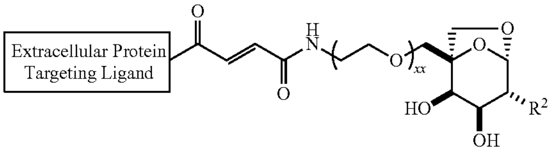
In certain embodiments the compound of the present invention is selected from:
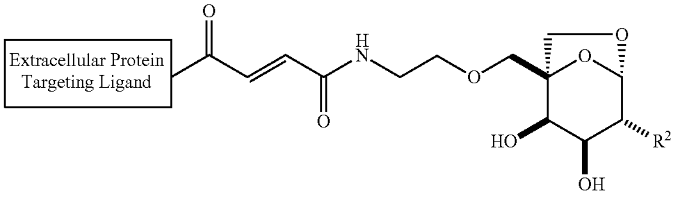
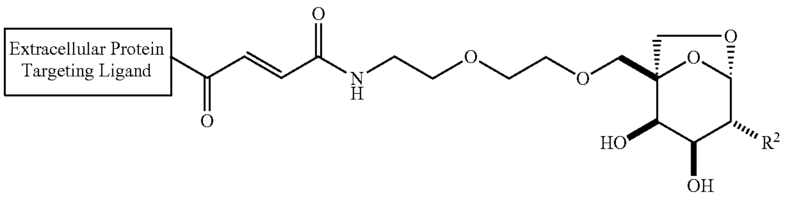

-continued
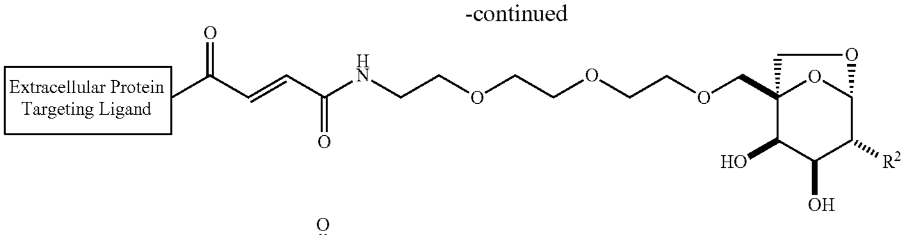
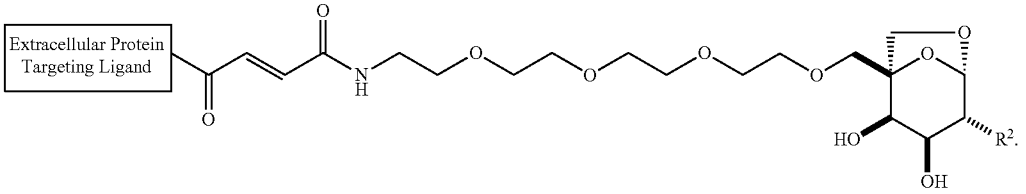
In certain embodiments the compound of the present invention is selected from:
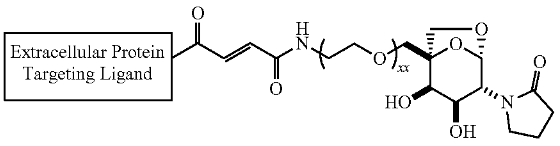
In certain embodiments the compound of the present invention is selected from:
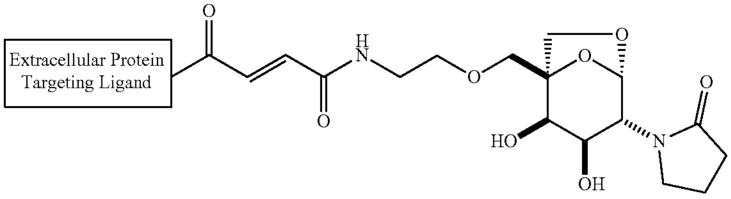
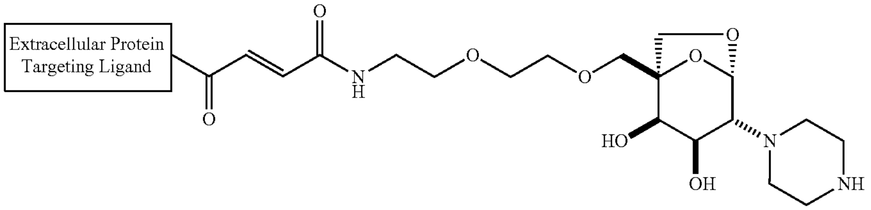
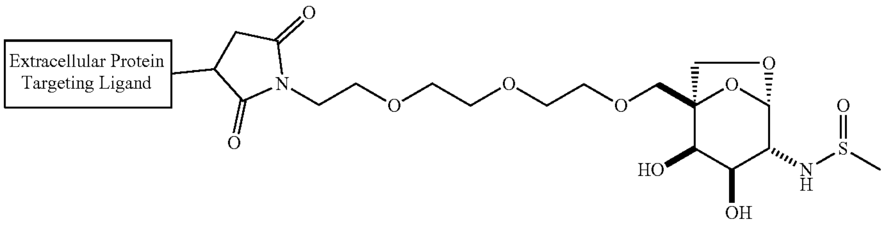
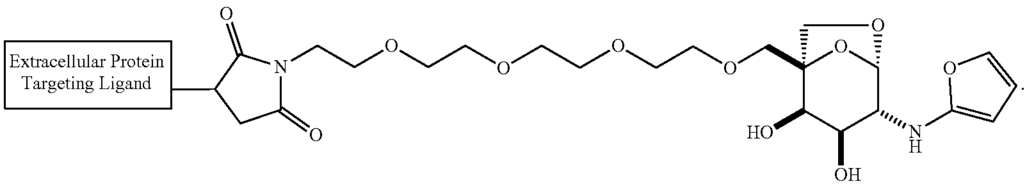

In certain embodiments the compound of the present invention is selected from:
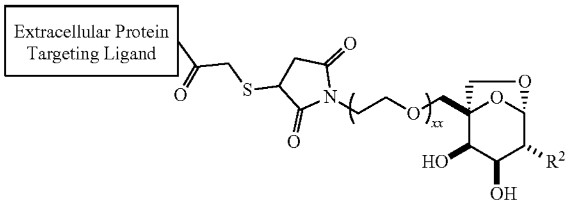
In certain embodiments the compound of the present invention is selected from:
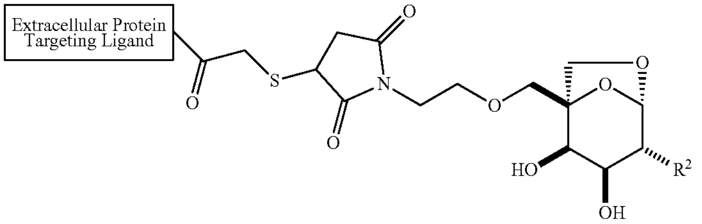
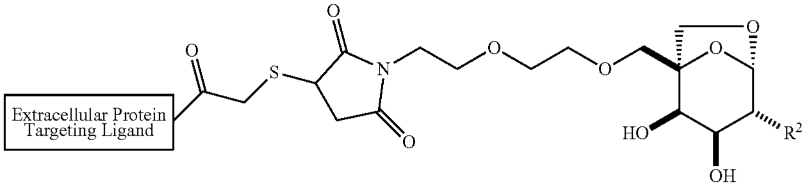
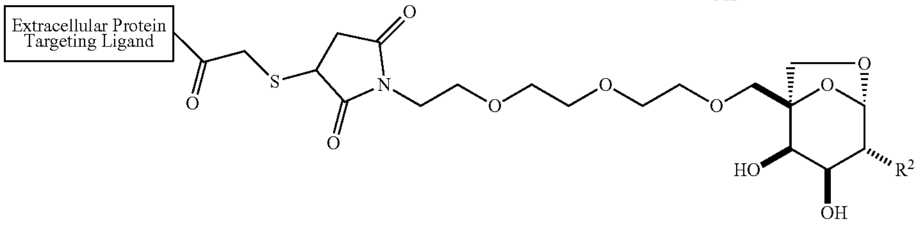
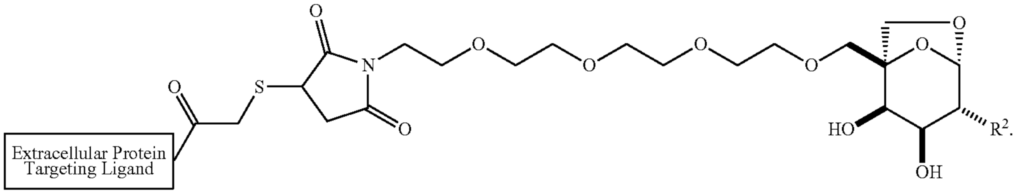
In certain embodiments the compound of the present invention is selected from:
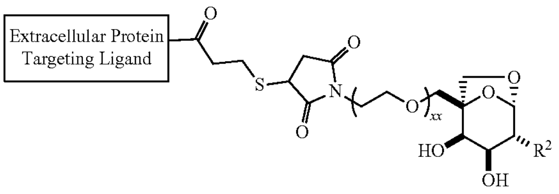
In certain embodiments the compound of the present invention is selected from:

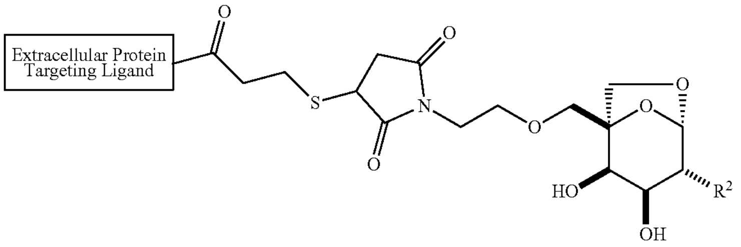
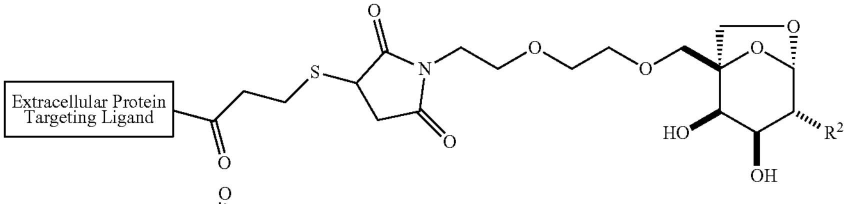
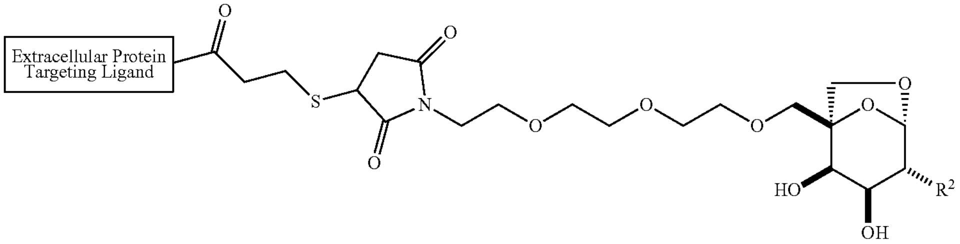
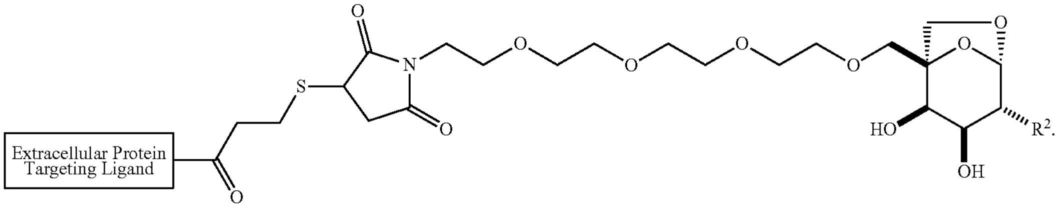
In certain embodiments the compound of the present invention is selected from:
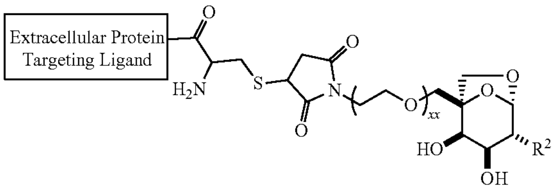
In certain embodiments the compound of the present invention is selected from:
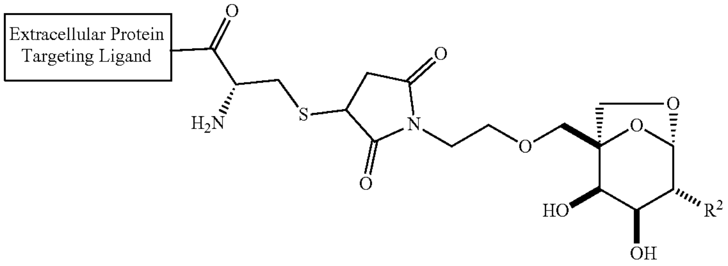

-continued
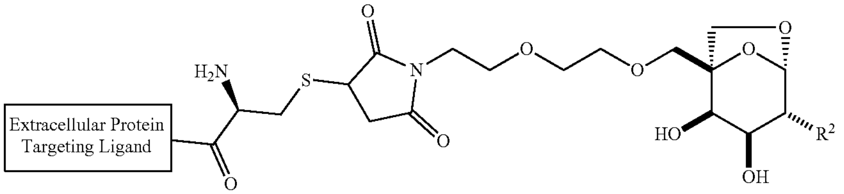
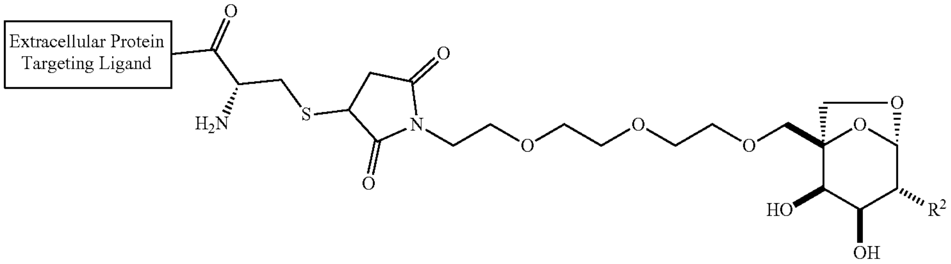
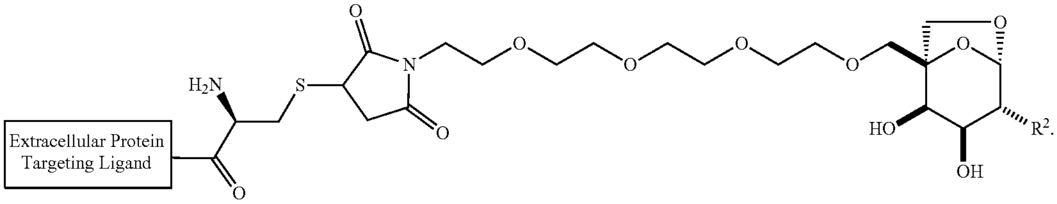
In certain embodiments the compound of the present invention is selected from:
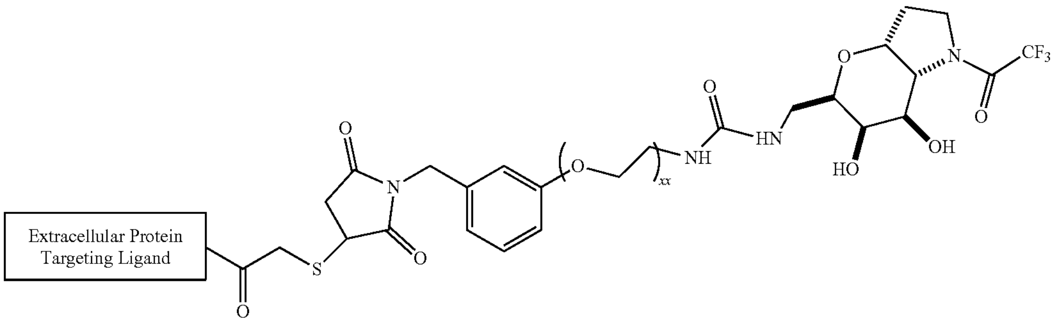
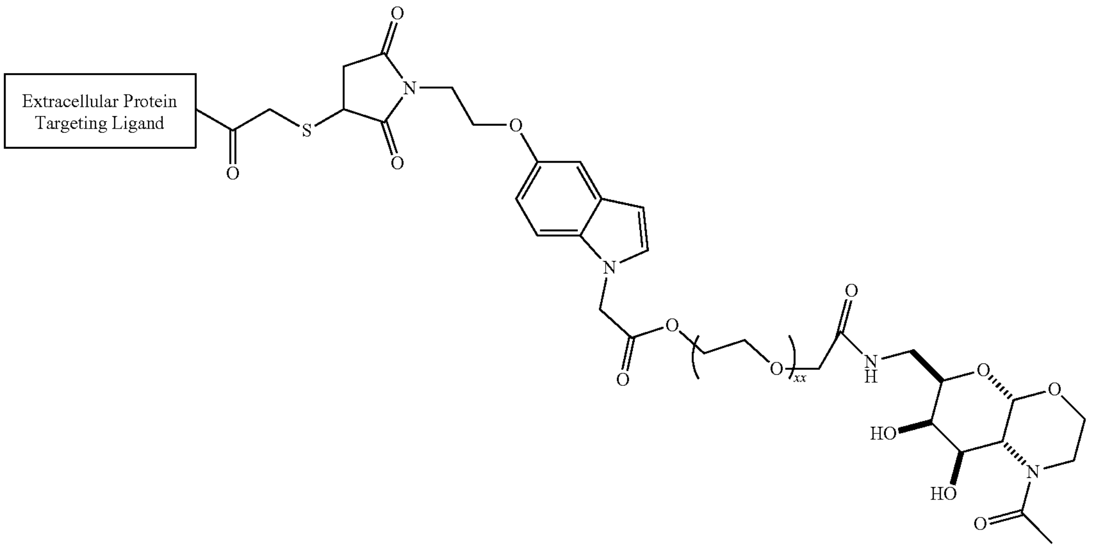

-continued
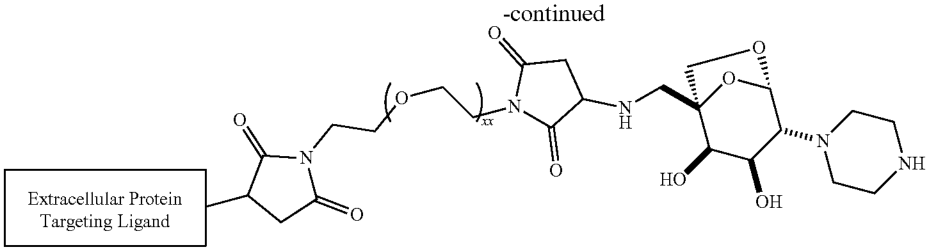
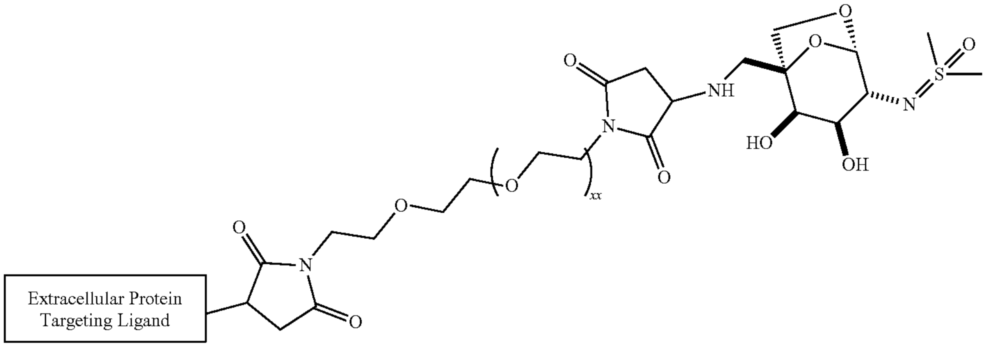
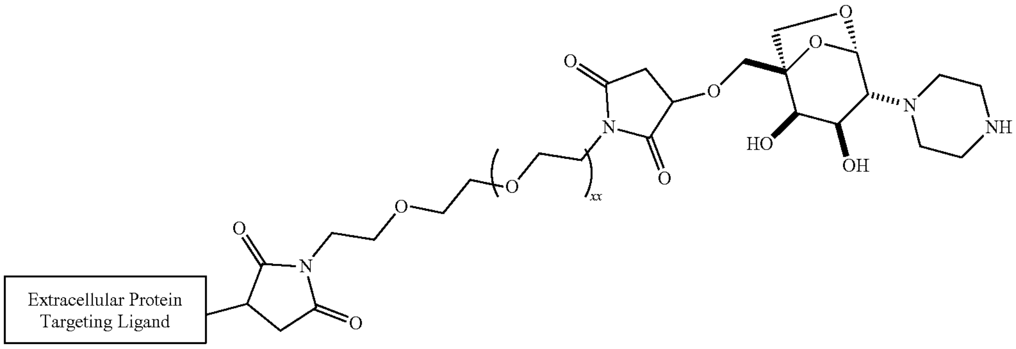
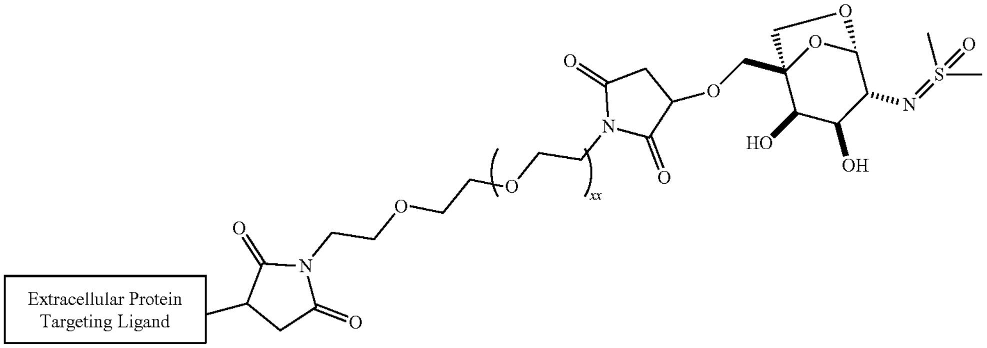

In certain embodiments the compound of the present invention is selected from:
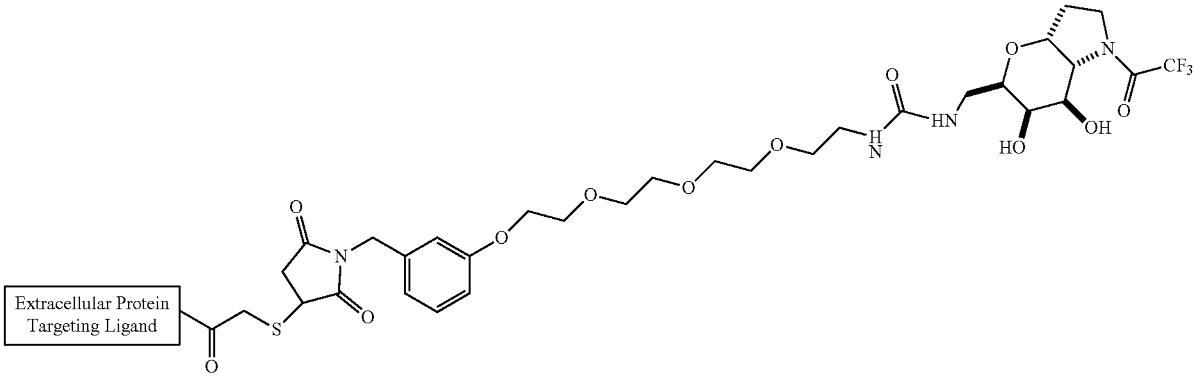
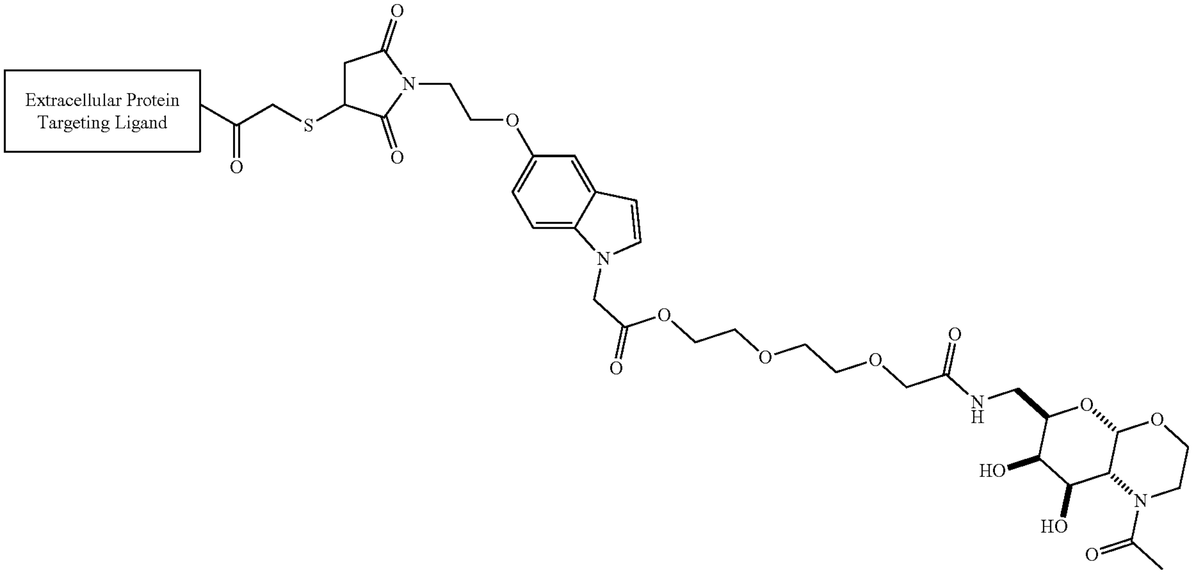
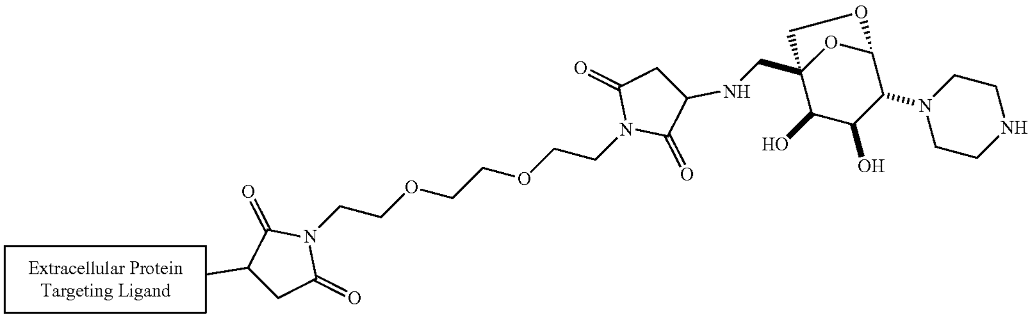
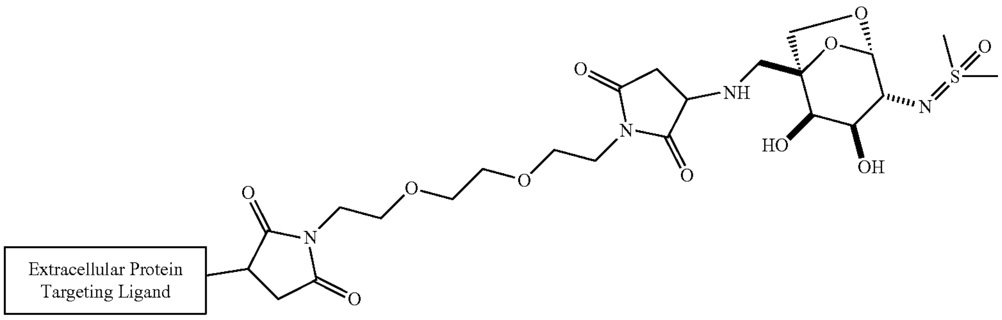

-continued
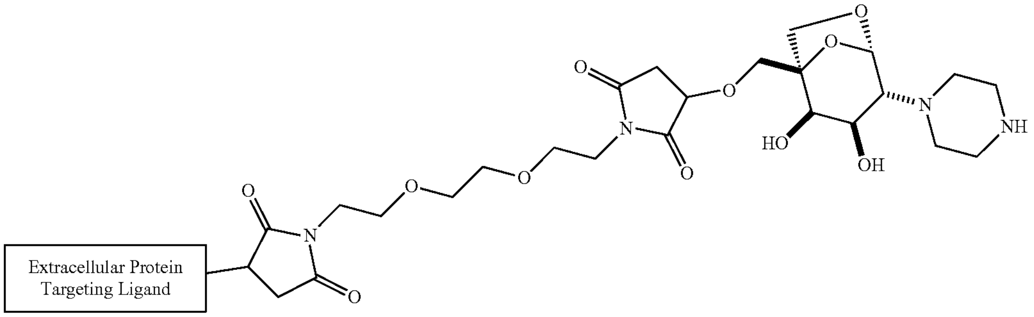
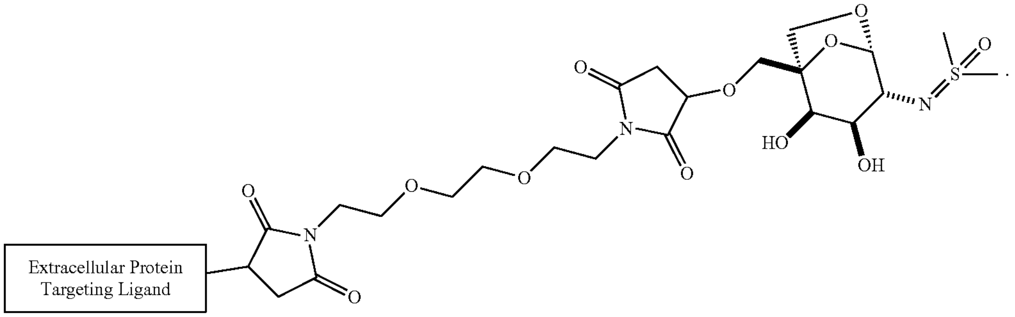
In certain embodiments the compound of the present invention is selected from:
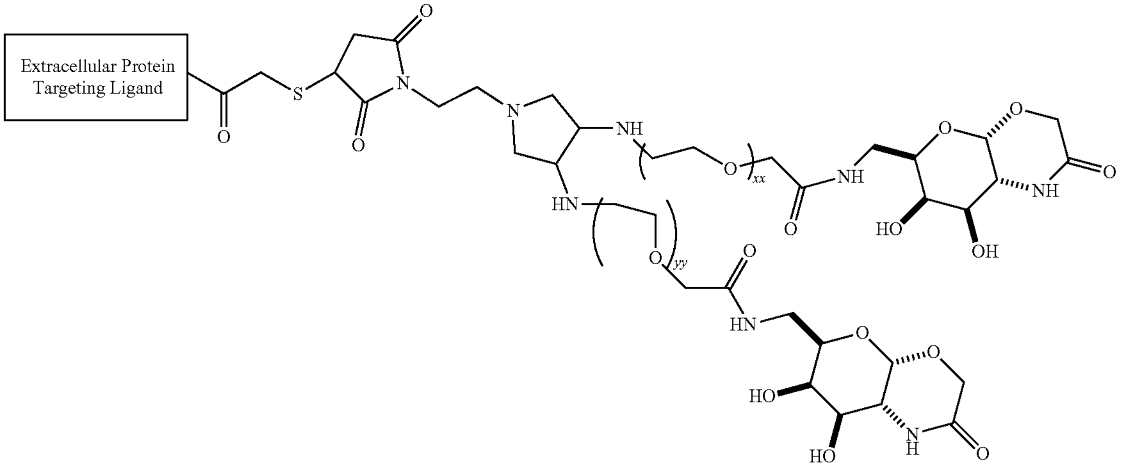
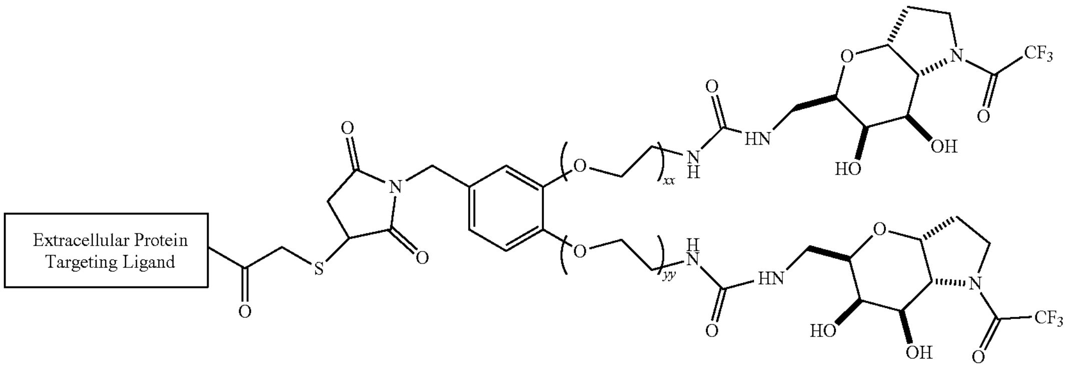

-continued
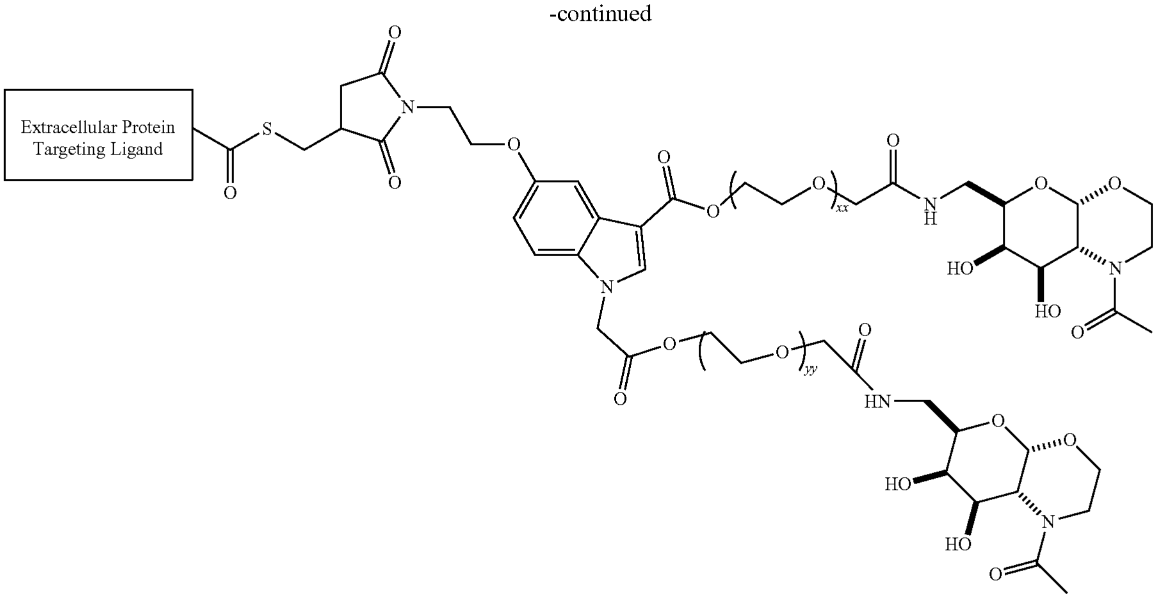
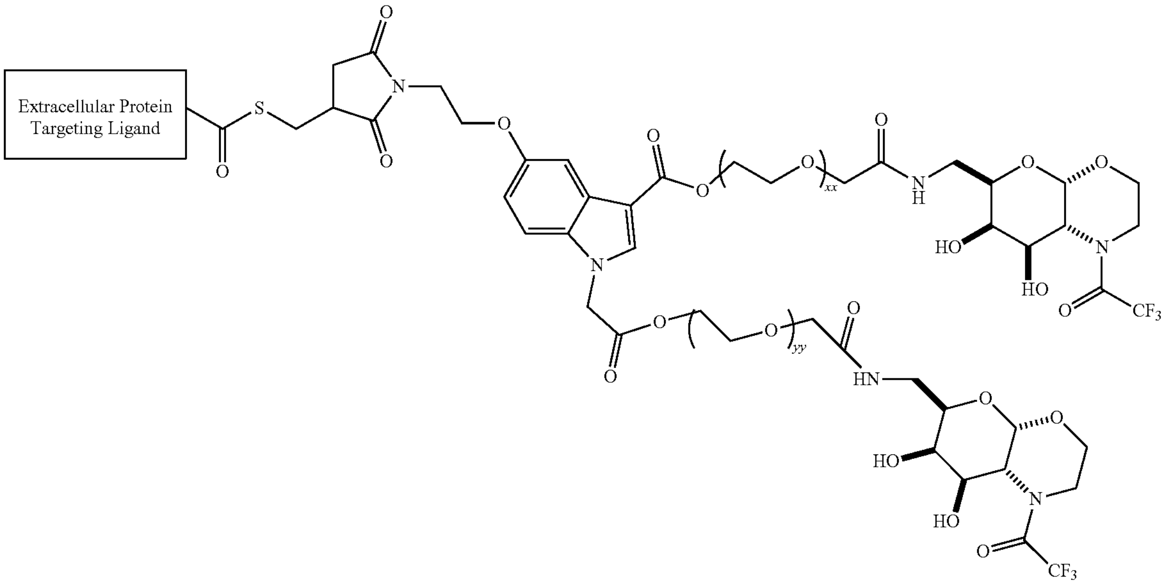
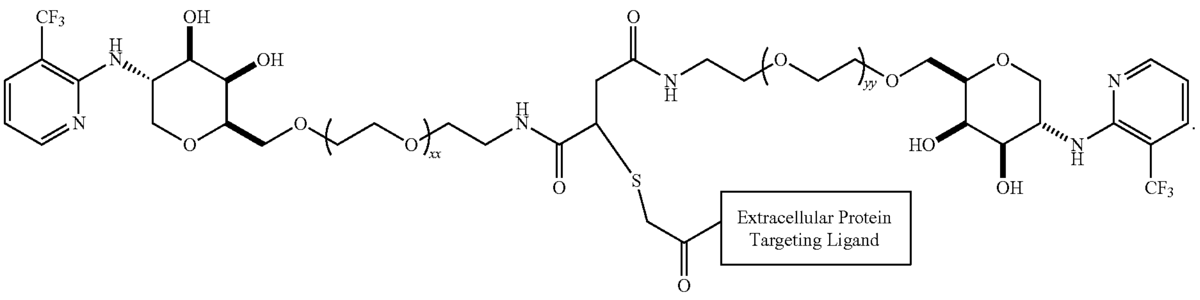

In certain embodiments the compound of the present invention is selected from:
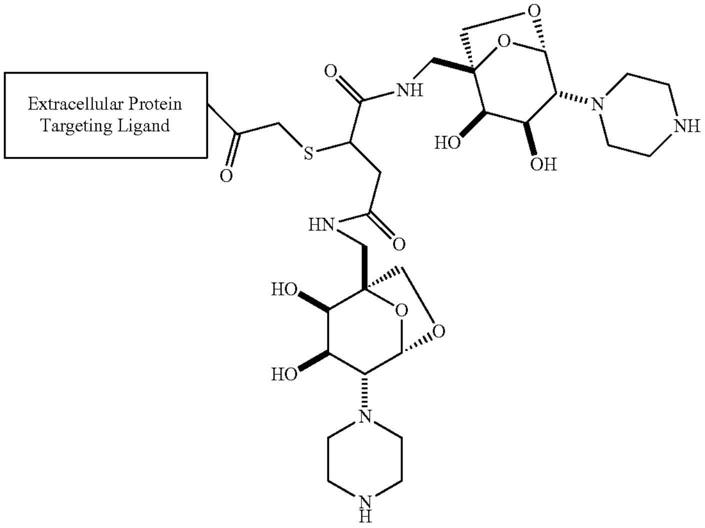
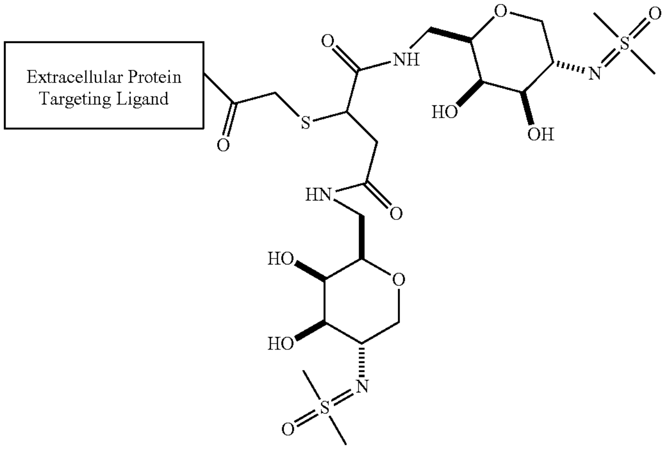
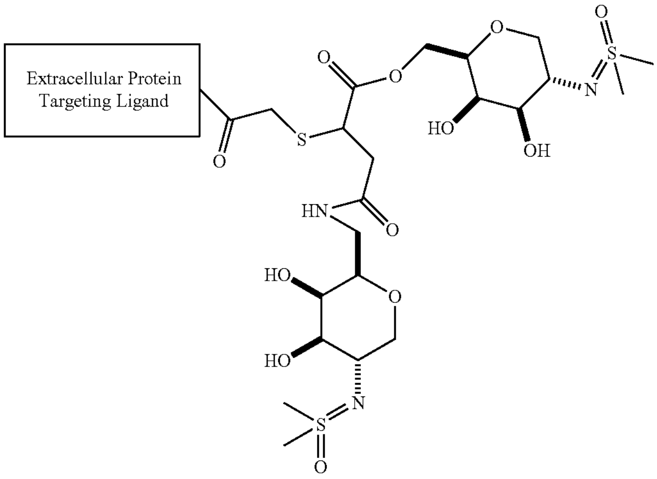

-continued
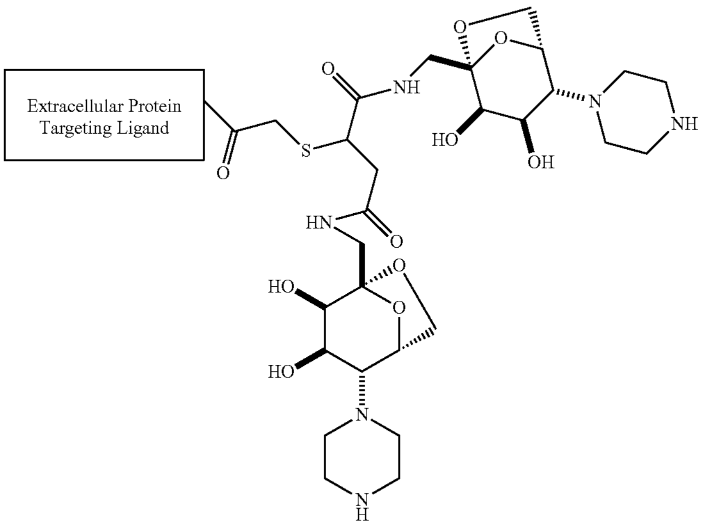
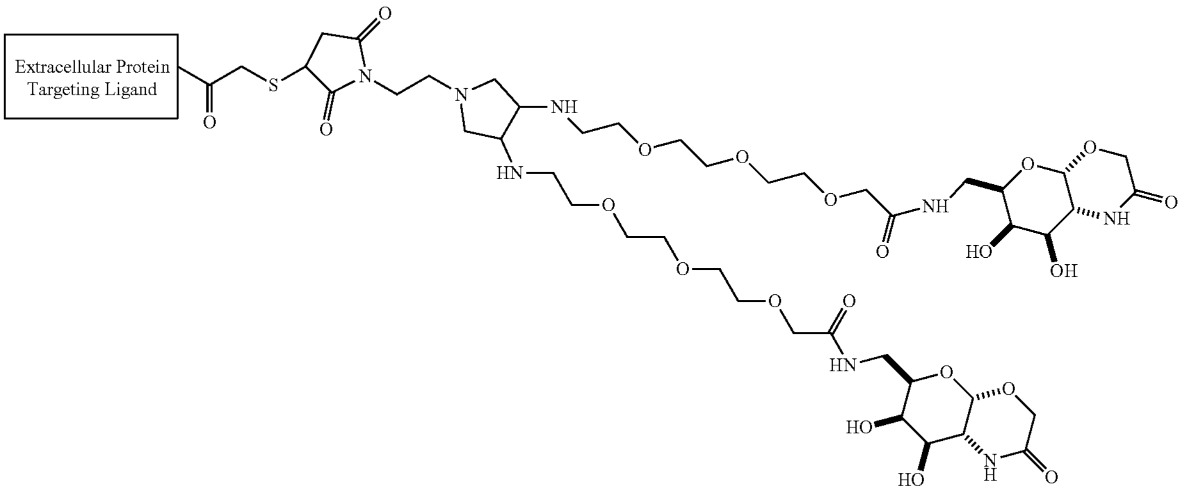
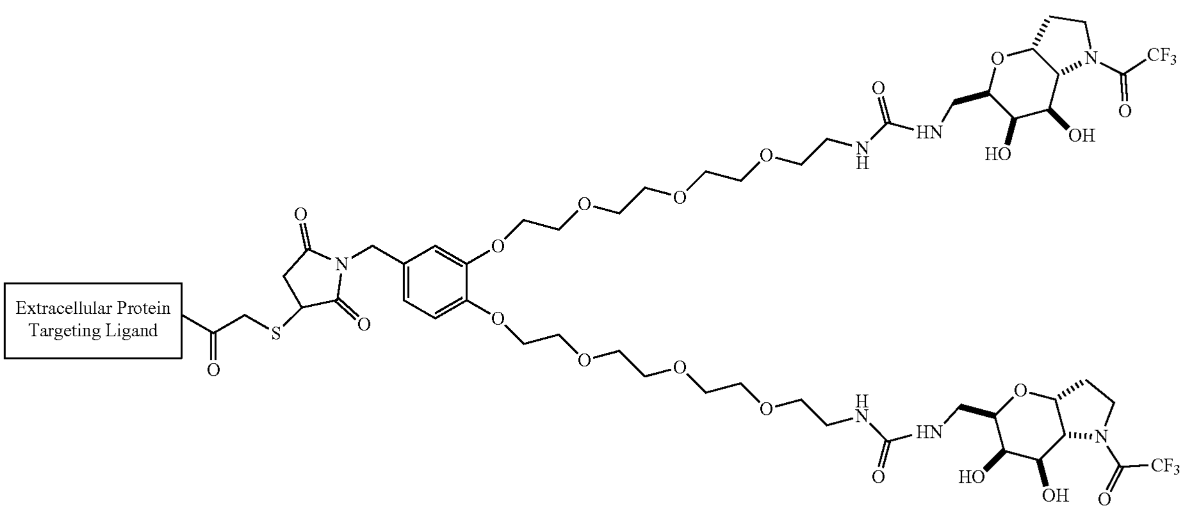

-continued
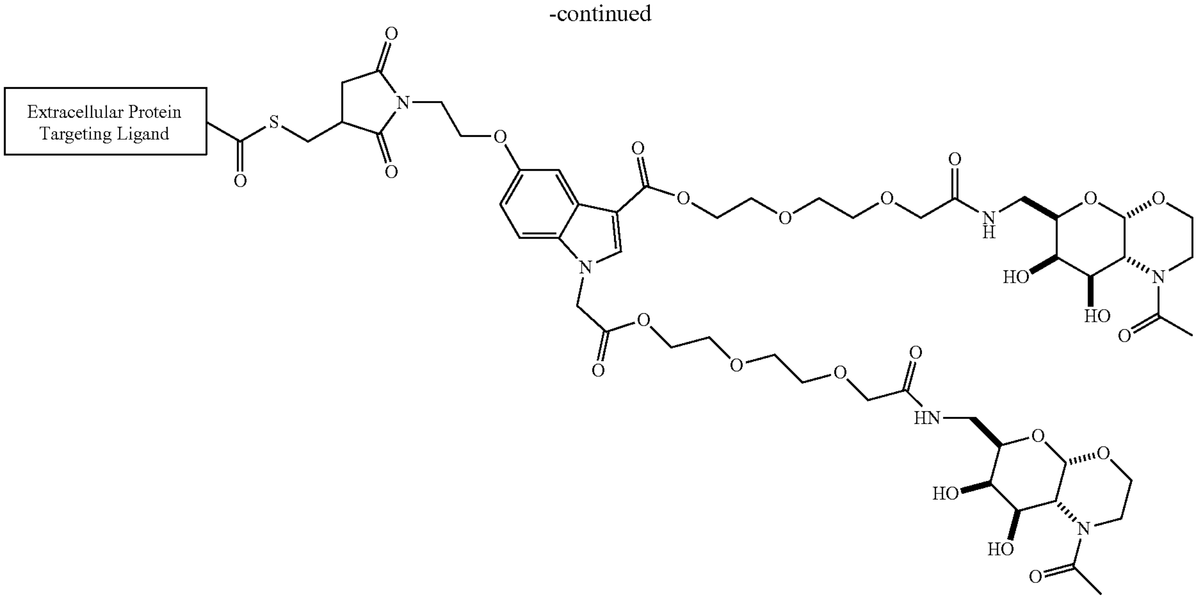
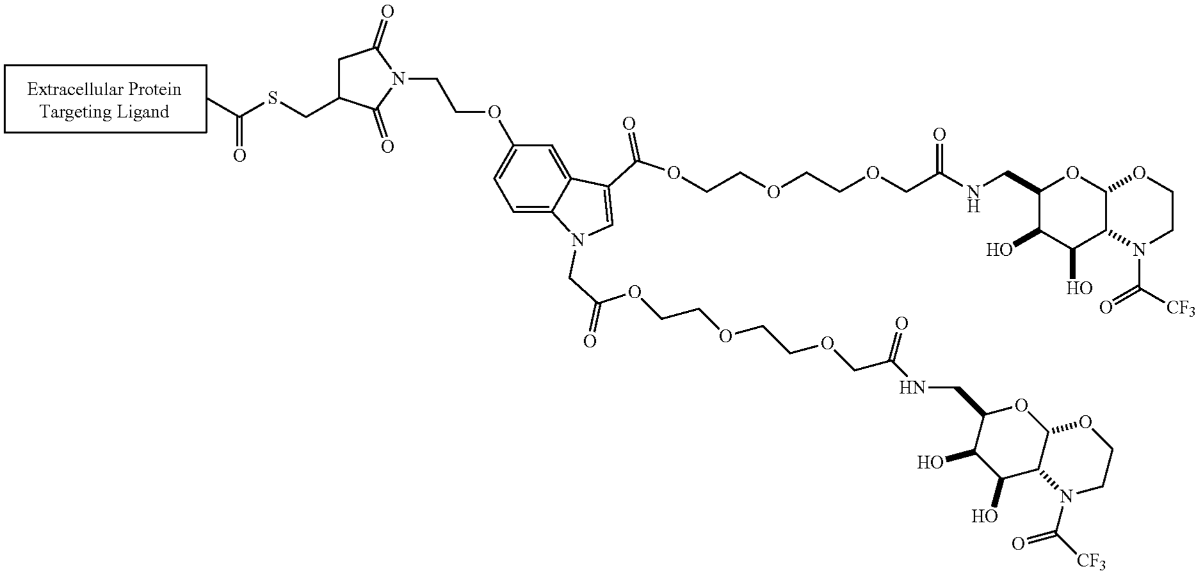
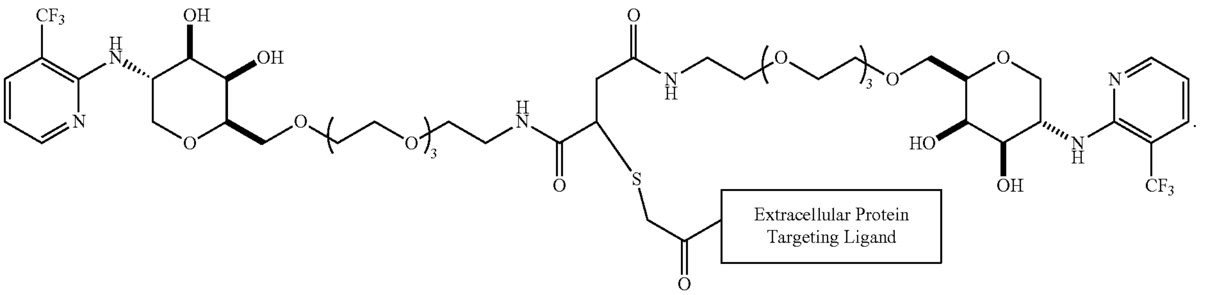

In certain embodiments the compound of the present invention is selected from:
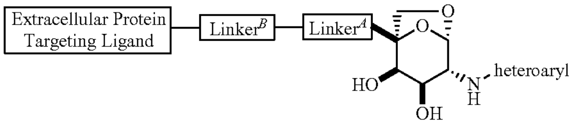
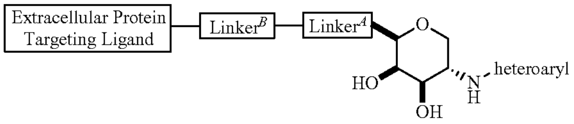
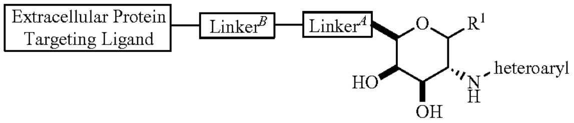
In certain embodiments the compound of the present invention is selected from:
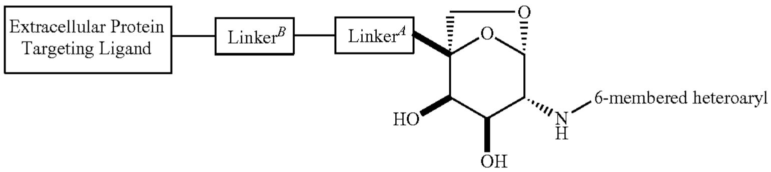
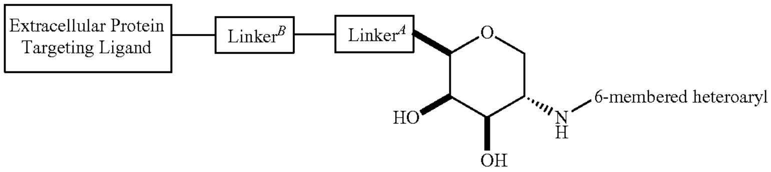
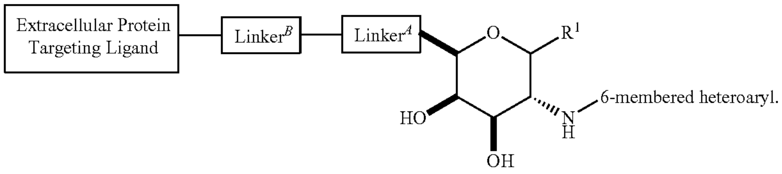
In certain embodiments the compound of the present invention is selected from:
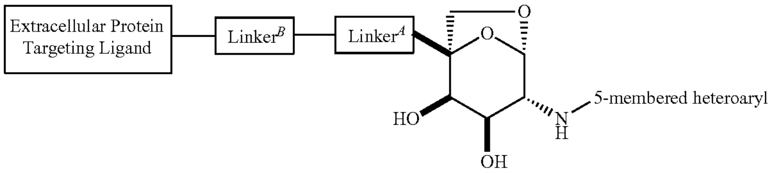
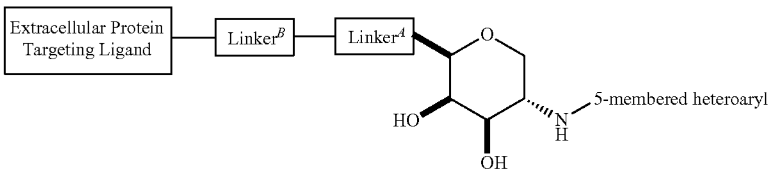

-continued
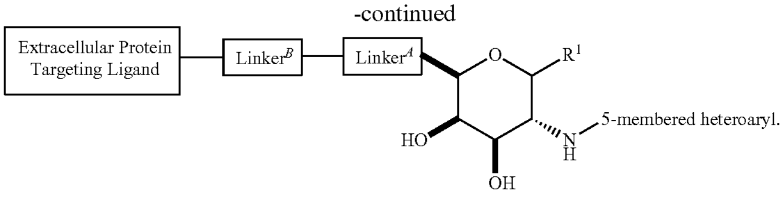
In certain embodiments the compound of the present invention is selected from:
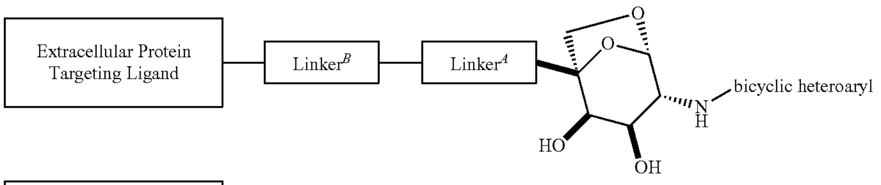
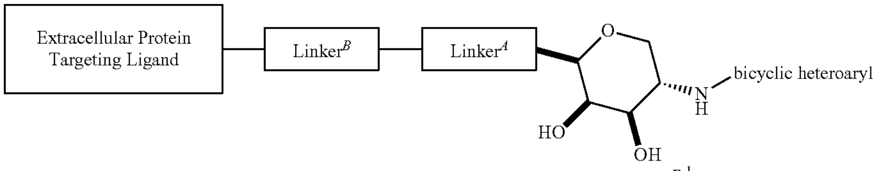
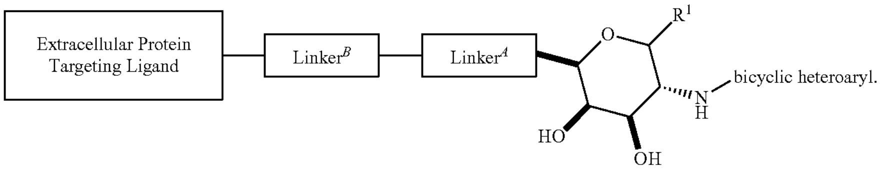
In certain embodiments the compound of the present invention is selected from:
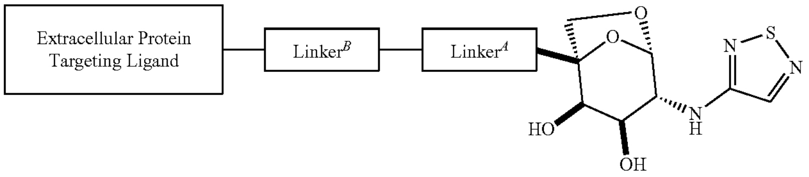
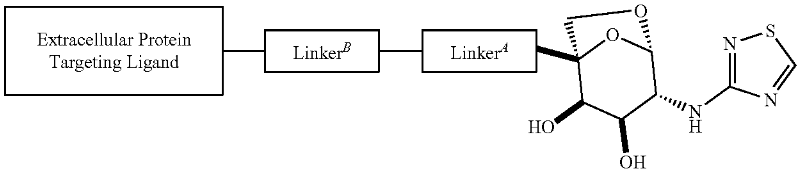
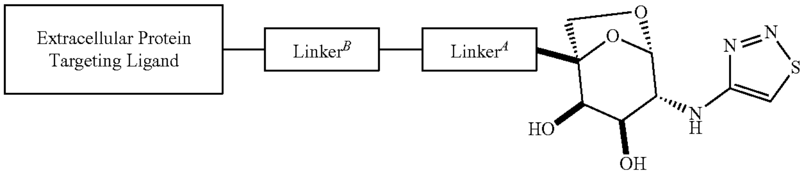
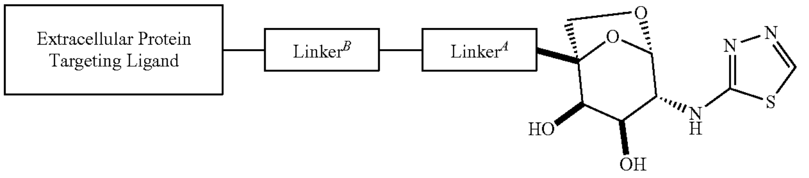

-continued
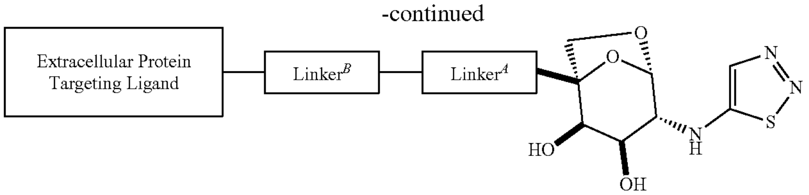
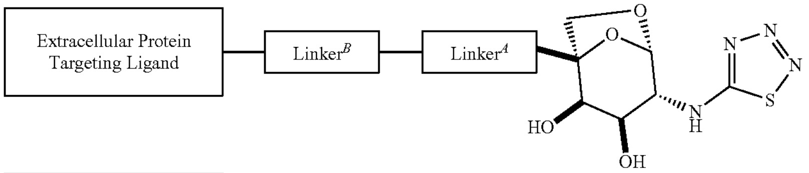
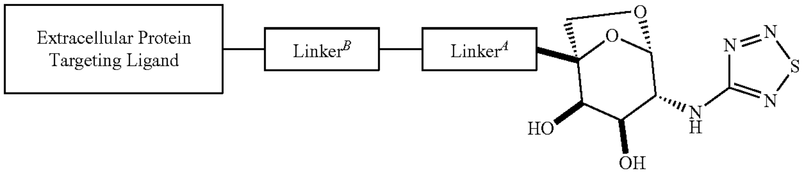
and
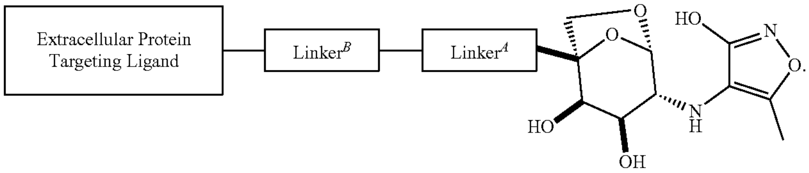
In certain embodiments the compound of the present invention is selected from:
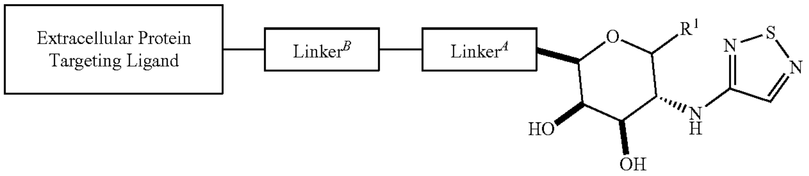
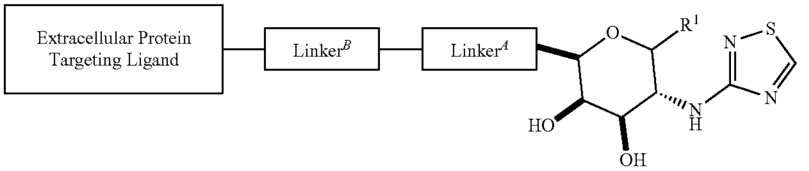
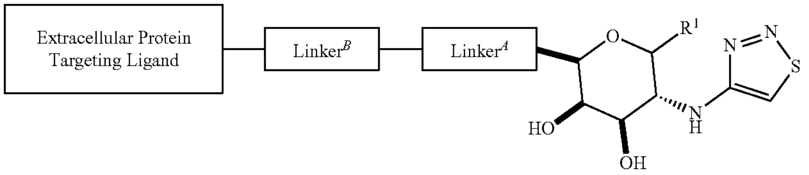
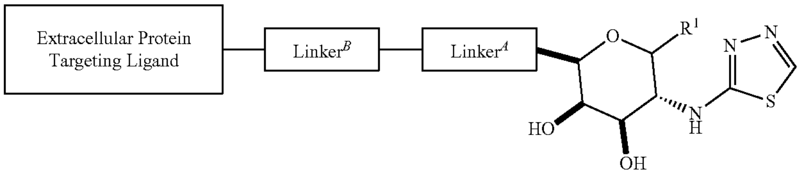
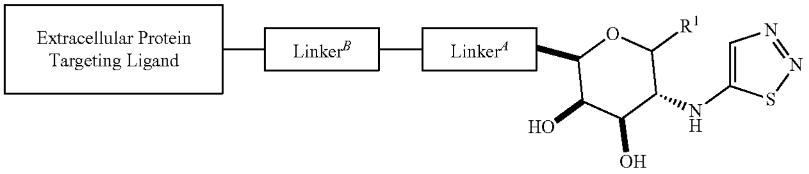

-continued
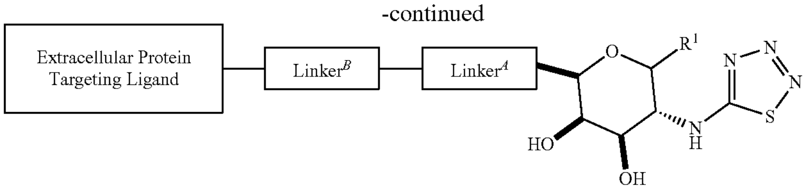
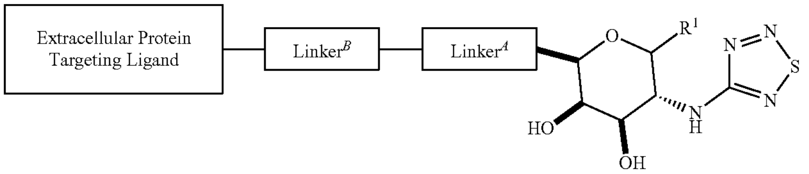
and
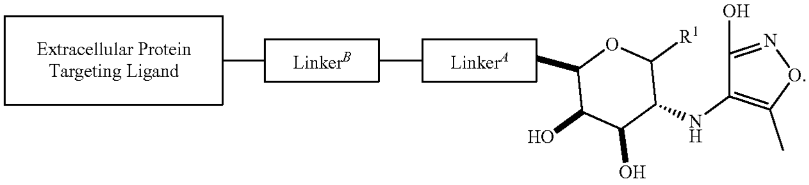
In certain embodiments the compound of the present invention is selected from:
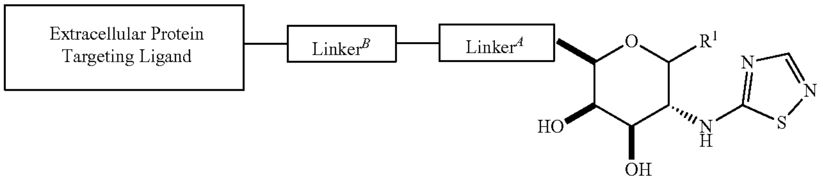
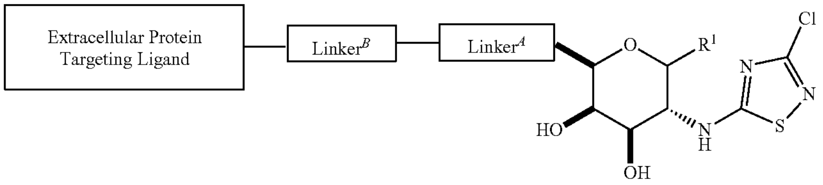
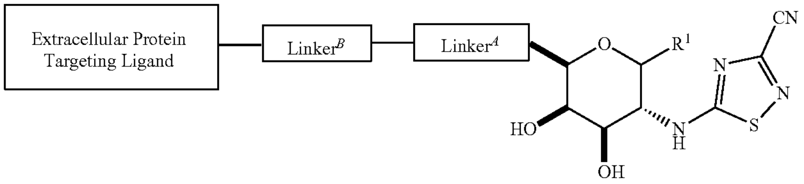
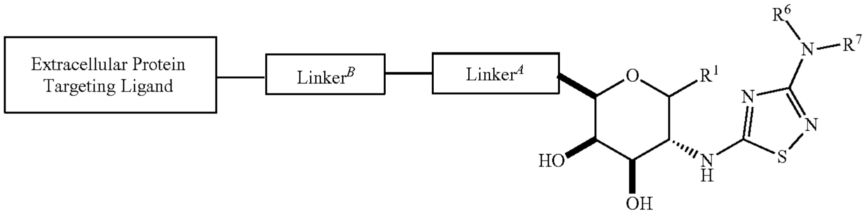
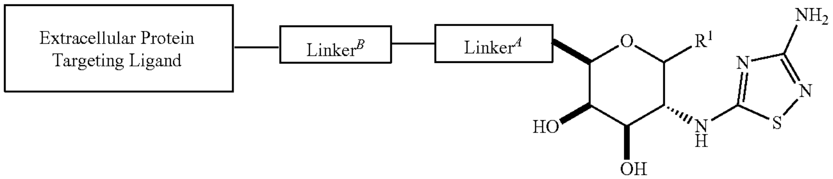

-continued
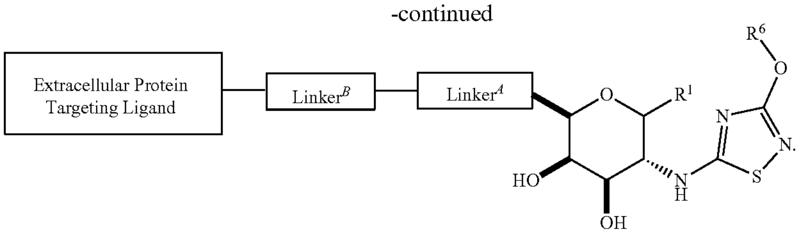
In one aspect of the present invention an Extracellular Protein degrading compound is provided wherein the ASGPR ligand is a ligand described herein
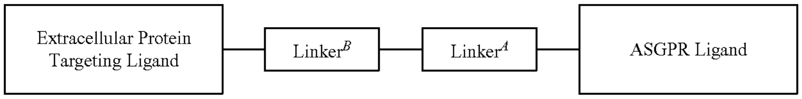
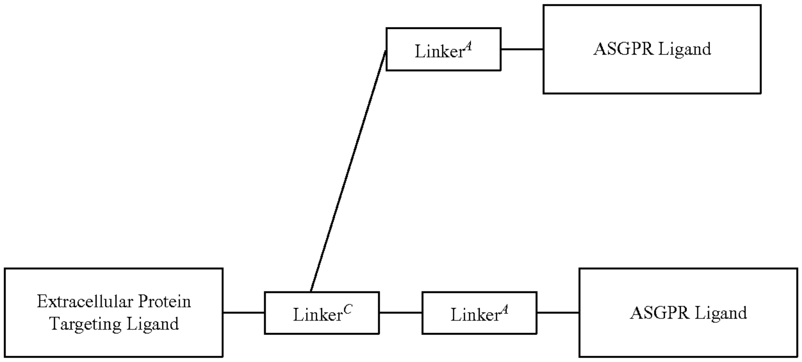
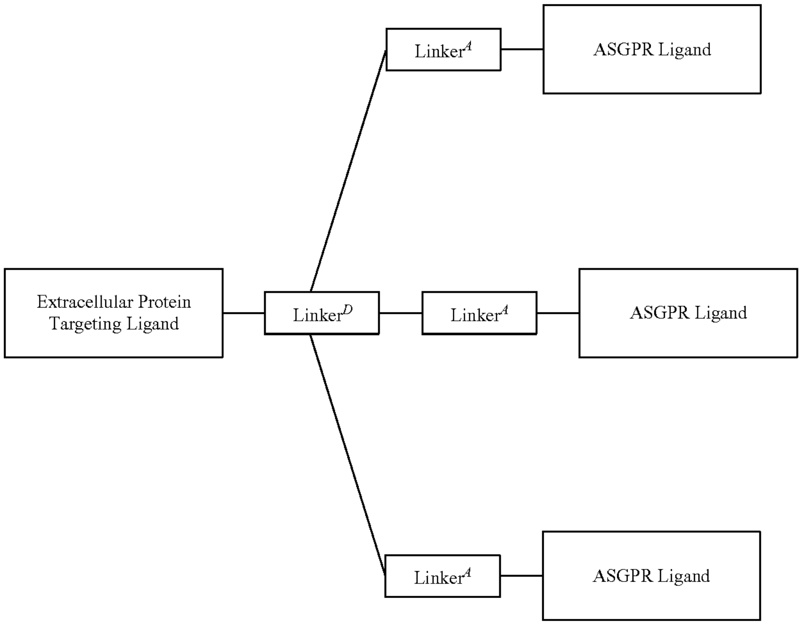
in this aspect the ASGPR ligand is linked in either the C1 or C5 ($R^1$ or $R^5$) position to form a degrading compound, for example, when the ASGPR ligand is

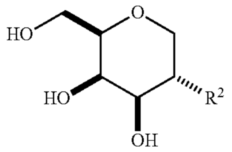

then non-limiting examples of ASGPR binding compounds contemplated by this aspect include:

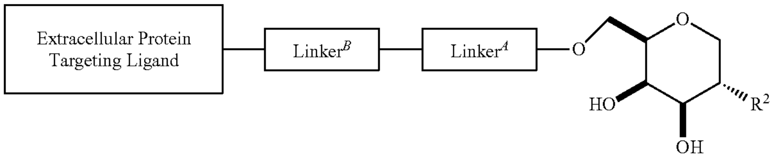

and

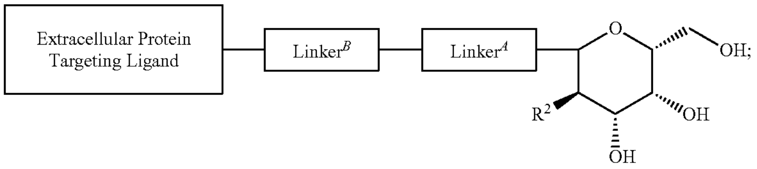

or the bi- or tri-version thereof or a pharmaceutically acceptable salt thereof.

In any of the embodiments herein where an ASGPR ligand is drawn for use in a degrader the ASGPR ligand is typically linked through to the Extracellular Protein Targeting Ligand in the $C^5$ position (e.g., which can refer to the adjacent $C^6$ carbon hydroxyl or other functional moiety that can be used for linking purposes). When the linker and Extracellular Protein Targeting Ligand is connected through the $C^1$ position, then that carbon is appropriately functionalized for linking, for example with a hydroxyl, amino, allyl, alkyne or hydroxyl-allyl group. Typically the ASGPR ligand is not linked in the $C^3$ or $C^4$ position, because these positions chelate with the calcium for ASGPR binding in the liver.

In certain embodiments, an ASGPR ligand useful for incorporation into a compound of the present invention is selected from

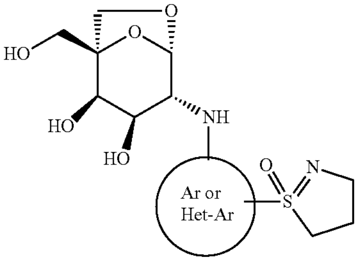

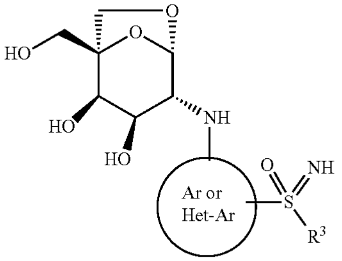

-continued

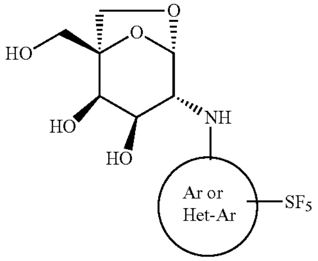

-continued

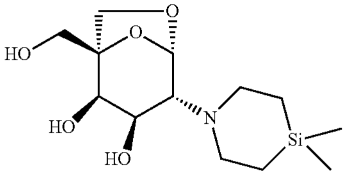

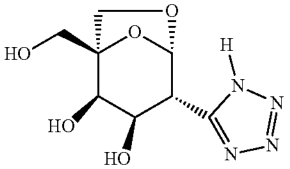

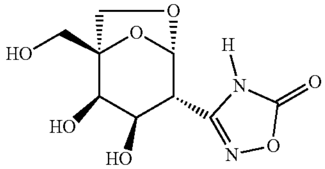

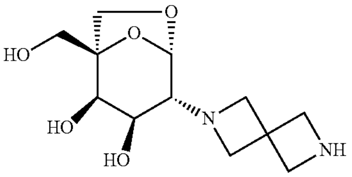

-continued
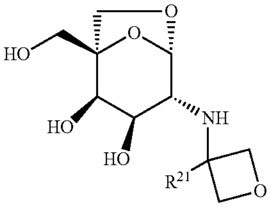
In certain embodiments, an ASGPR ligand useful for incorporation into a compound of the present invention is selected from
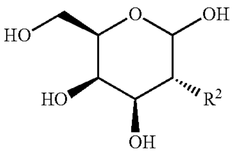
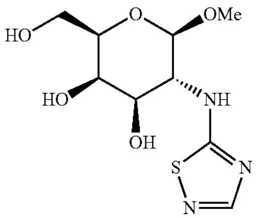
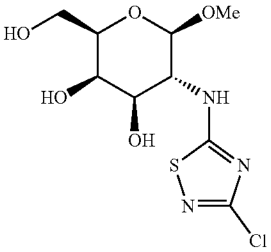
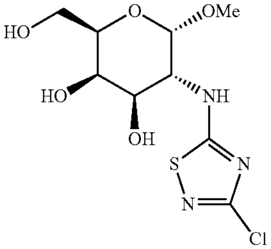 [SMILES: CO[C@H]1O[C@H](CO)[C@H](O)[C@H](O)[C@H]1Nc1nc(Br)cs1]
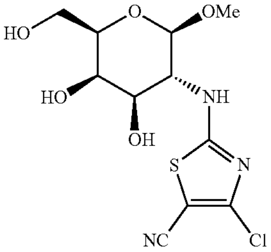
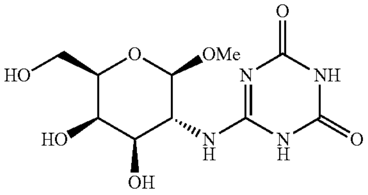
-continued
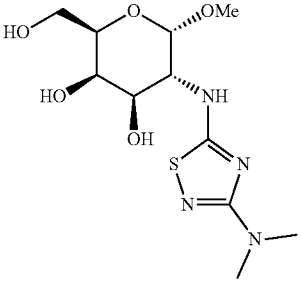
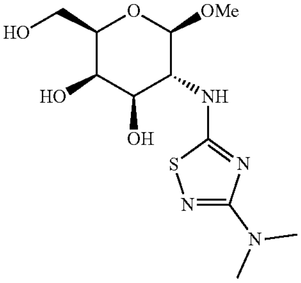
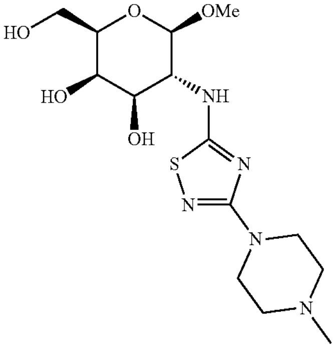
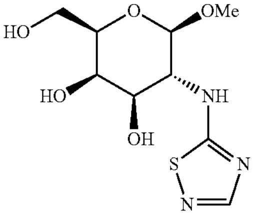
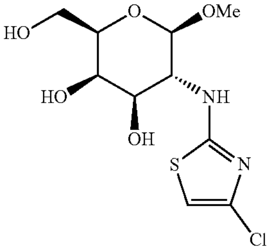
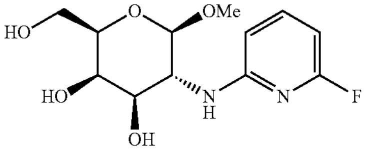

-continued
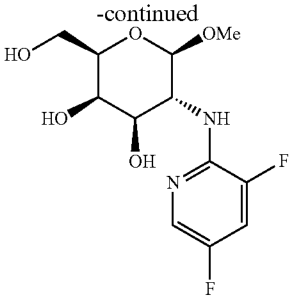
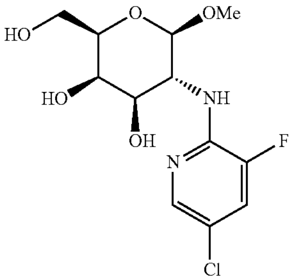
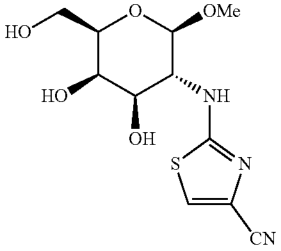
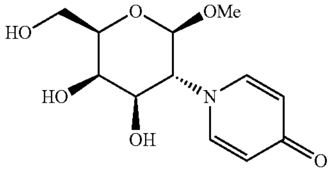
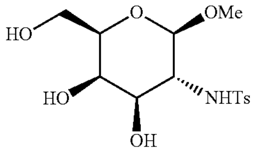
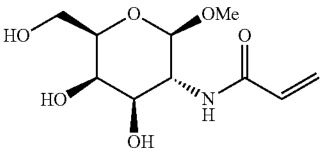
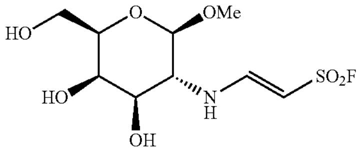
and
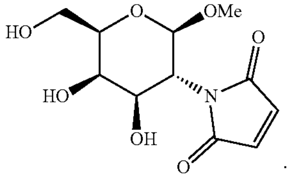
.
In certain embodiments, an ASGPR ligand useful for incorporation into a compound of the present invention is selected from
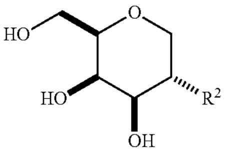
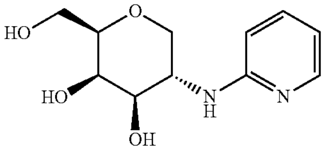
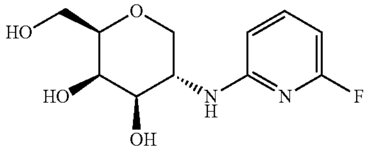
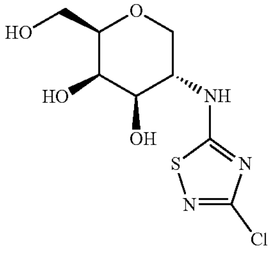
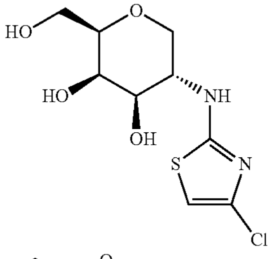
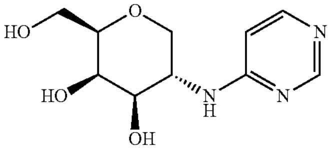
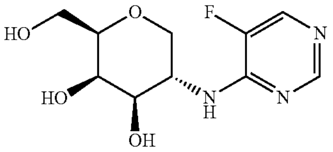
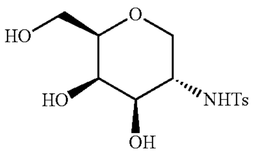
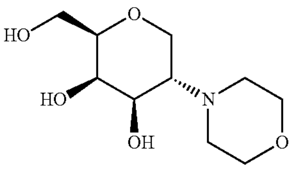
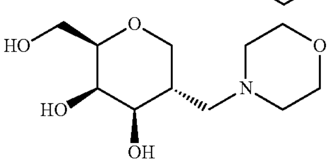
and -continued
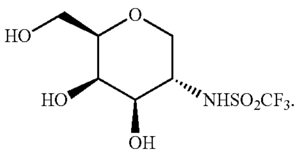
In certain embodiments, an ASGPR ligand useful for incorporation into a compound of the present invention is selected from
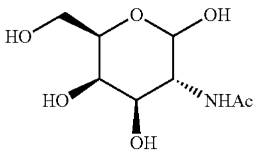
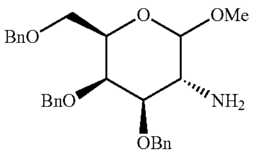
and
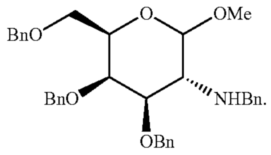
In certain embodiments, an ASGPR ligand useful for incorporation into a compound of the present invention is selected from
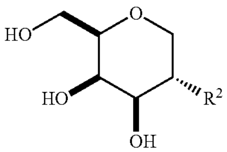
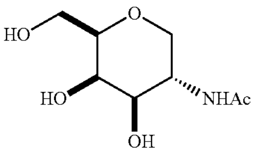
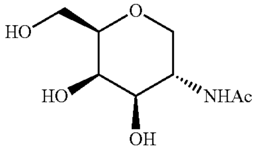
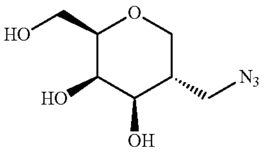
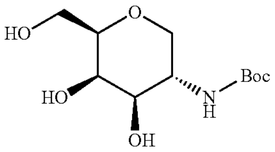
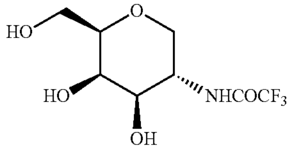
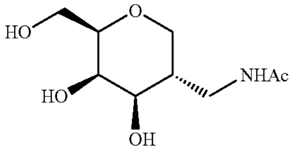
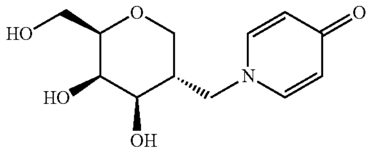
-continued
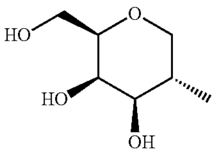
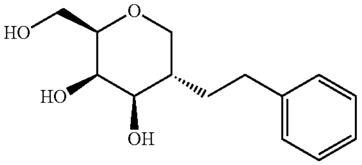
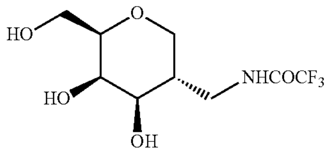
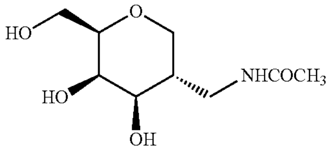
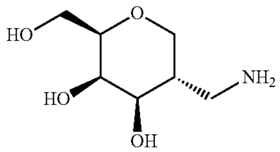
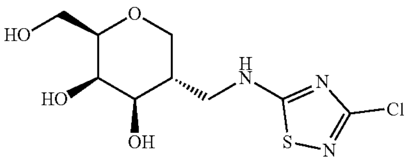
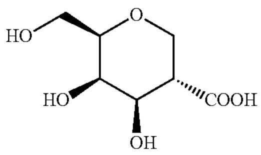
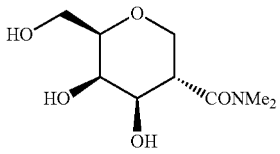
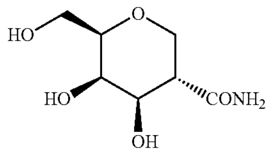
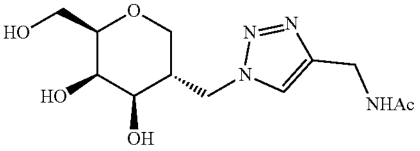
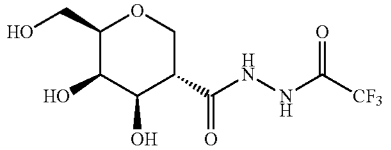

-continued
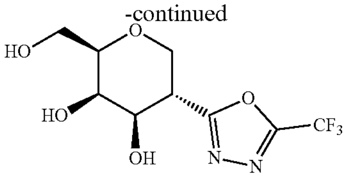
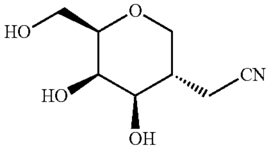
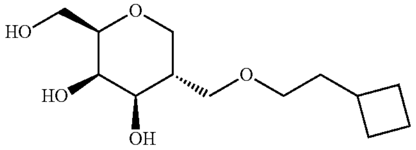
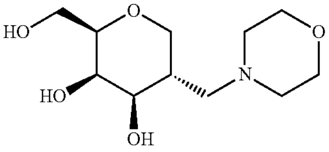
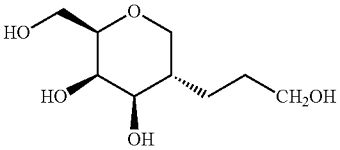
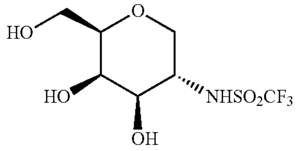
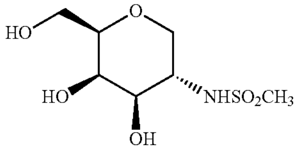
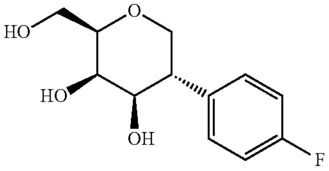
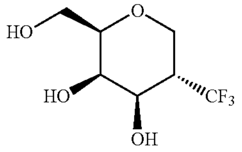
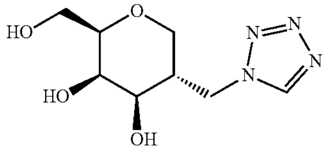
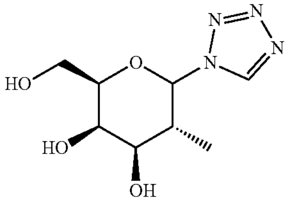
-continued
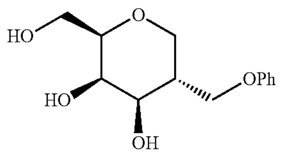
and
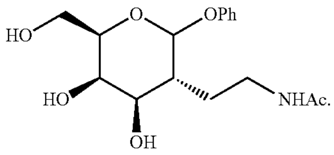
In certain embodiments, an ASGPR ligand useful for incorporation into a compound of the present invention is selected from
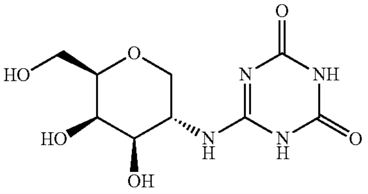
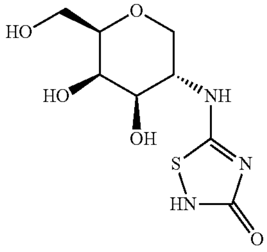
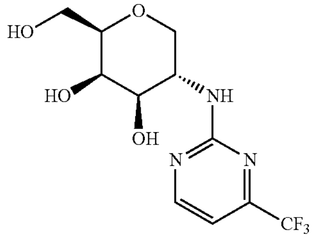
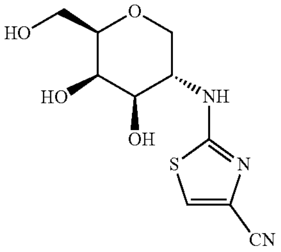
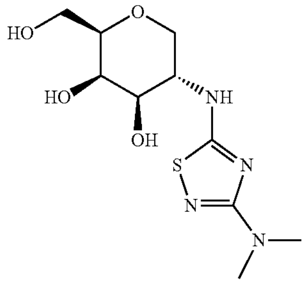

-continued
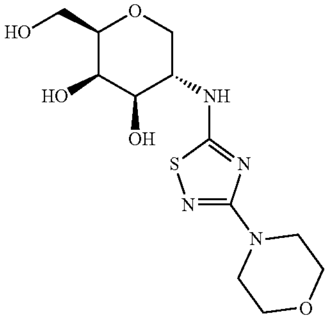
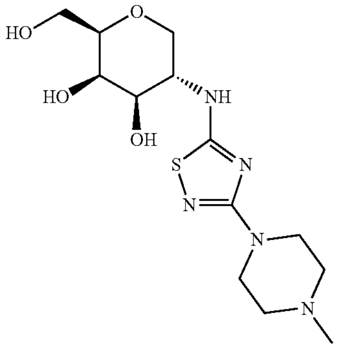
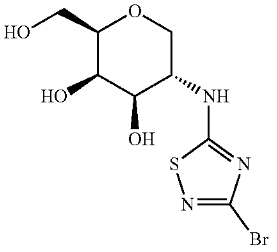
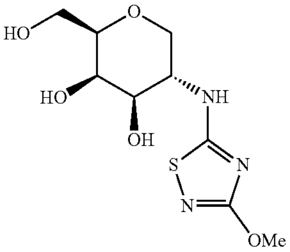
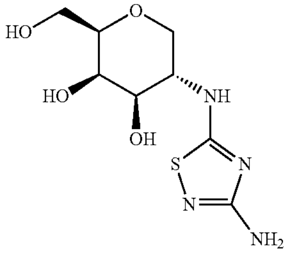
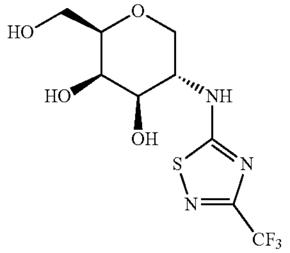
-continued
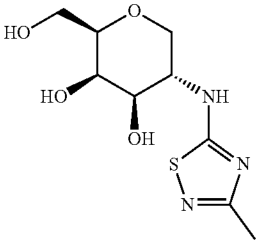
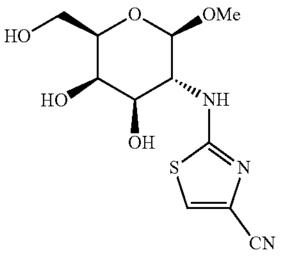
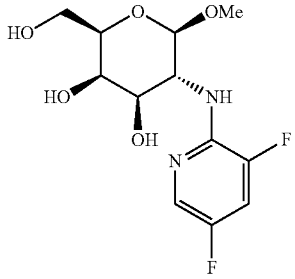
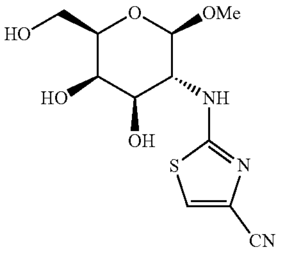
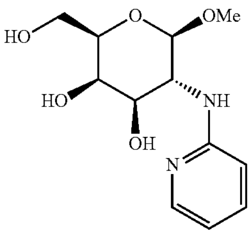
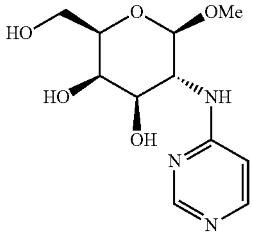
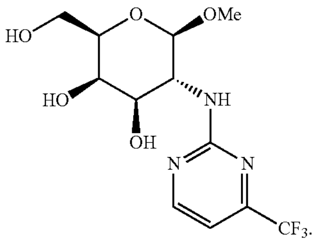
In certain embodiments, an ASGPR fig and useful for incorporation into a compound of the present invention is selected from

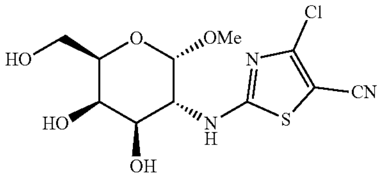
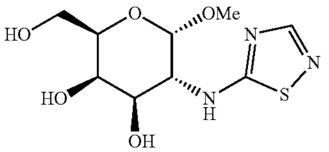
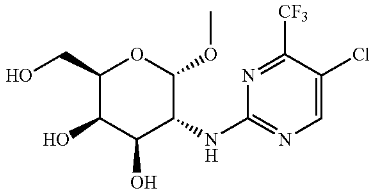
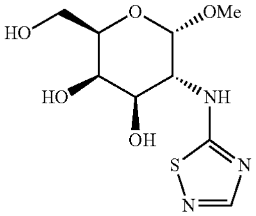
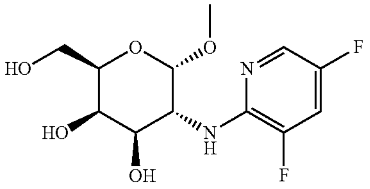
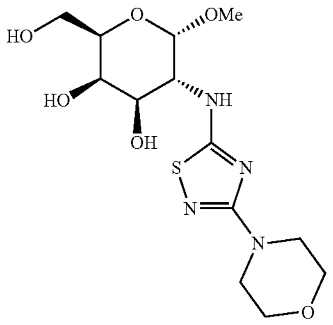
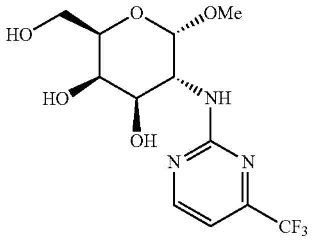
-continued
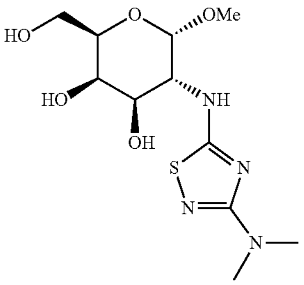
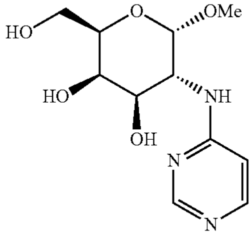
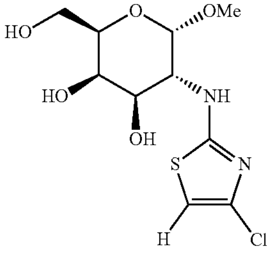
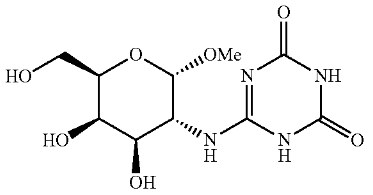
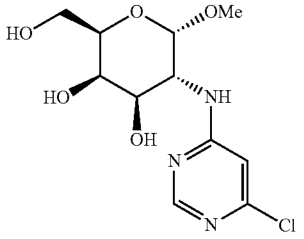
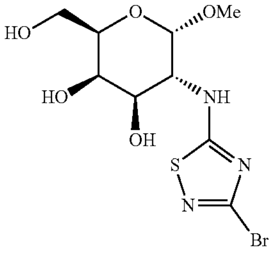
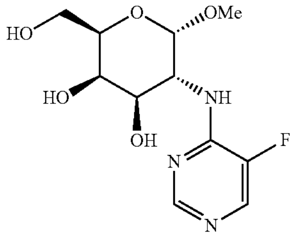
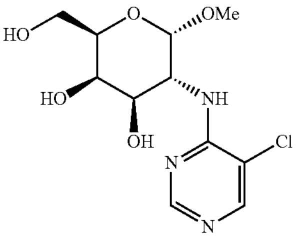

-continued
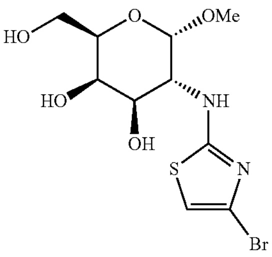
In certain embodiments, an ASGPR ligand useful for incorporation into a compound of the present invention is selected from
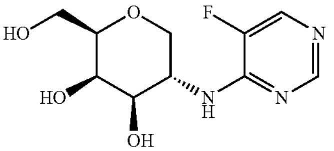
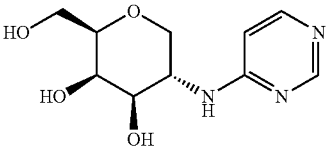
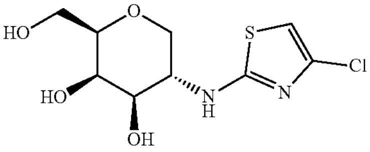
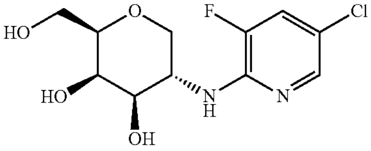
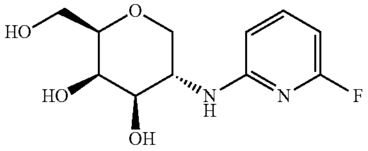
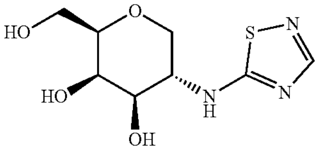
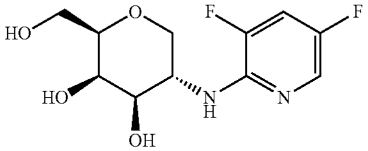
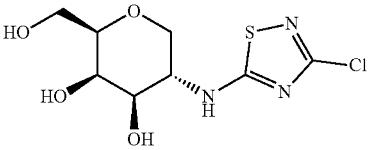
-continued
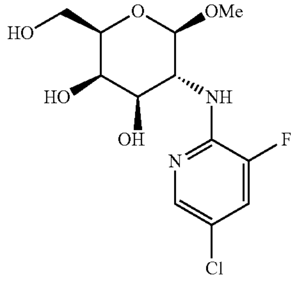
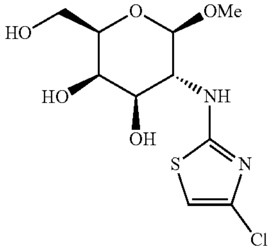
and
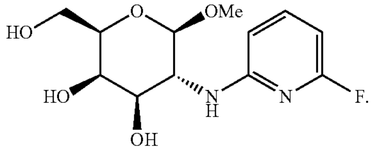
In certain embodiments, an ASGPR ligand useful for incorporation into a compound of the present invention is selected from
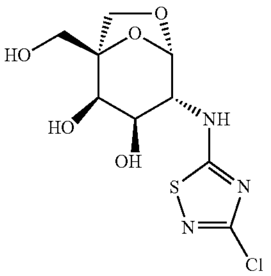
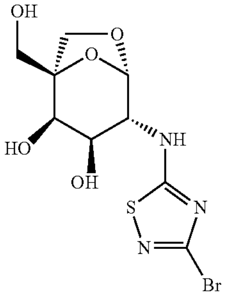
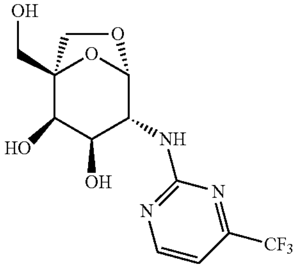
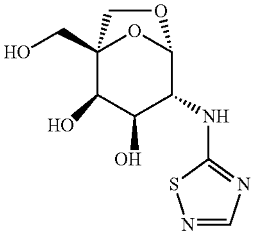
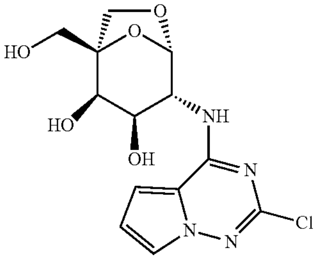

-continued

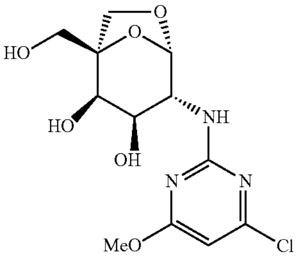

and

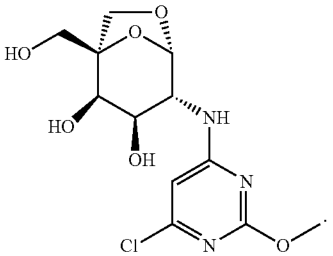

In certain embodiments, an ASGPR ligand useful for incorporation into a compound of the present invention is selected from

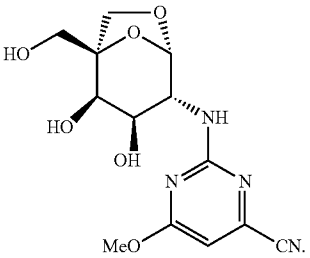 [SMILES: COc1cc(C#N)nc(N[C@H]2[C@H]3OC[C@](CO)(O3)[C@H](O)[C@@H]2O)n1]

In certain embodiments, an ASGPR ligand useful for incorporation into a compound of the present invention is selected from

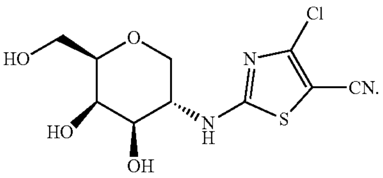 [SMILES: N#Cc1sc(N[C@H]2CO[C@H](CO)[C@H](O)[C@@H]2O)nc1Cl]

In certain embodiments, an ASGPR ligand useful for incorporation into a compound of the present invention is selected from

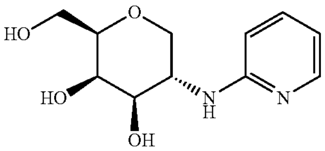

-continued

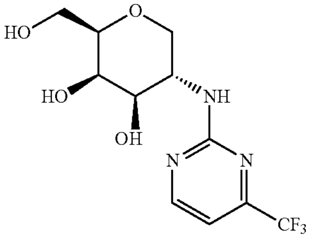

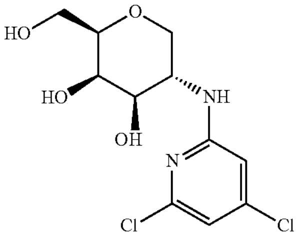

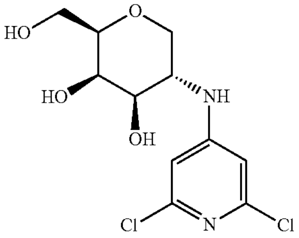

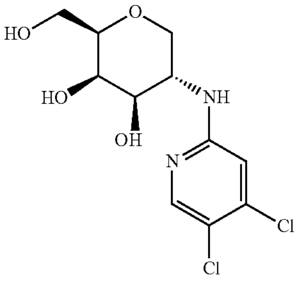

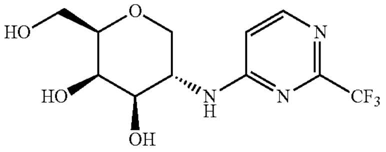

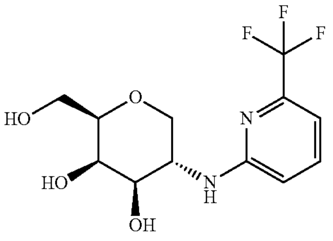

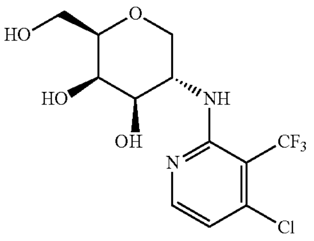

-continued
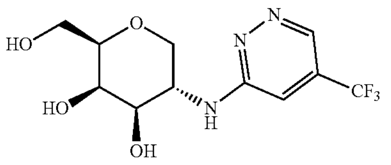
and
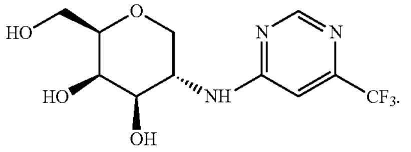
In certain embodiments, an ASGPR ligand useful for incorporation into a compound of the present invention is selected from
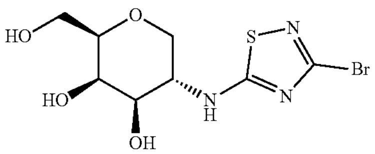
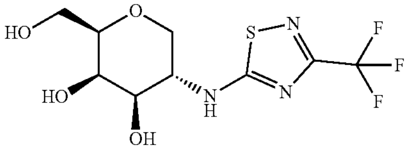
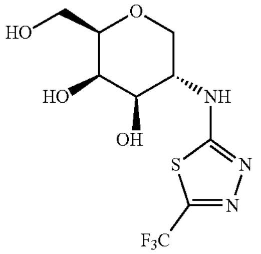
and
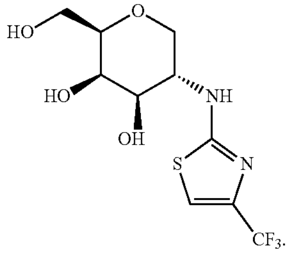
In certain embodiments, an ASGPR ligand useful for incorporation into a compound of the present invention is selected from
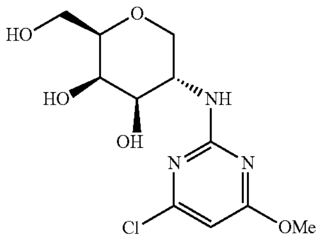
-continued
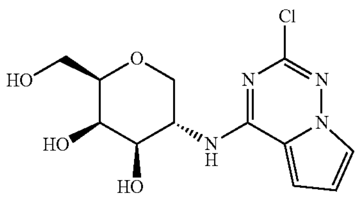
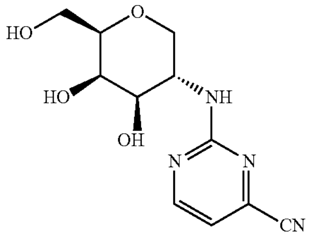
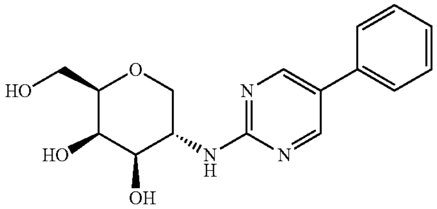
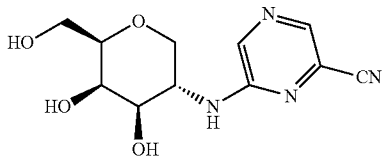
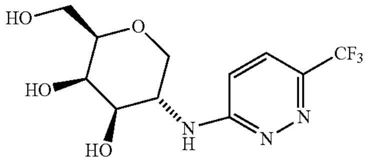
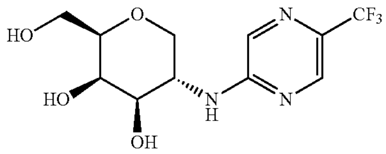
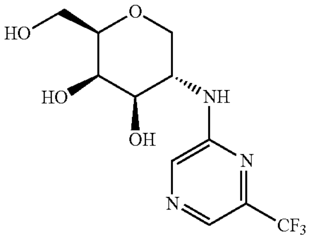
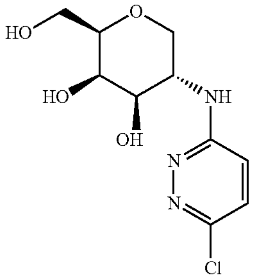

-continued
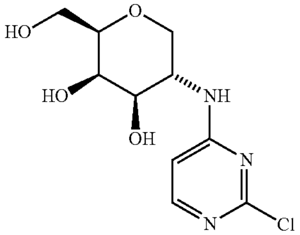
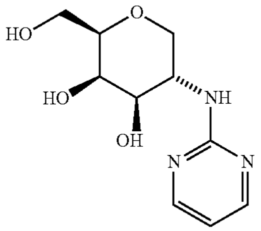
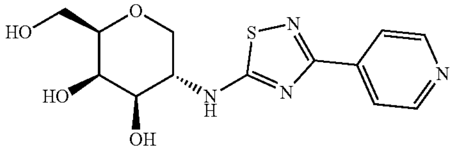
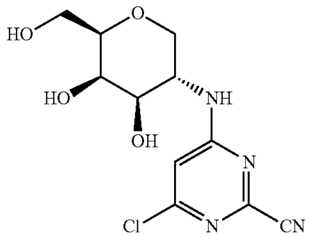
and
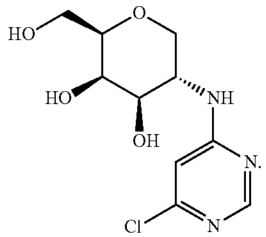
In certain embodiments, an ASGPR ligand useful for incorporation into a compound of the present invention is selected from
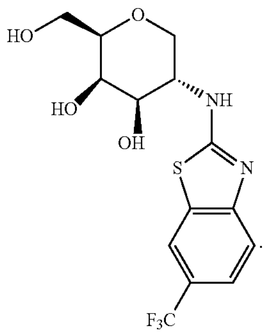 [SMILES: OC[C@H]1OC[C@H](Nc2nc3ccc(C(F)(F)F)cc3s2)[C@@H](O)[C@H]1O]
In certain embodiments, an ASGPR ligand useful for incorporation into a compound of the present invention is selected from
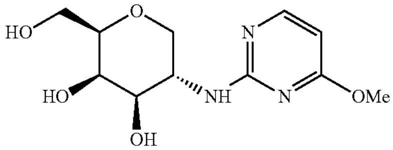
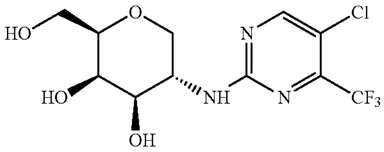
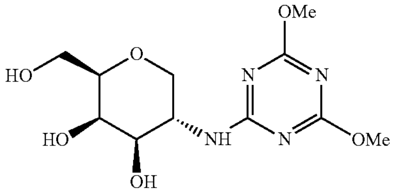
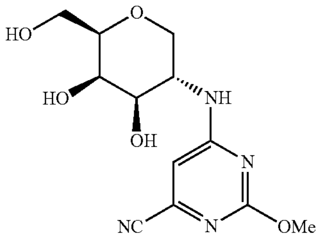
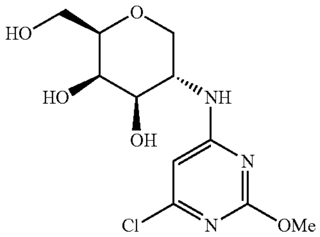
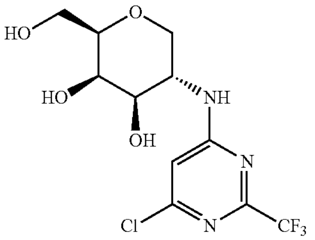
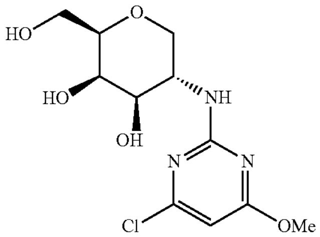
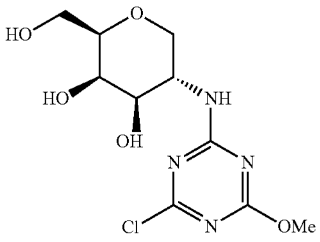

-continued
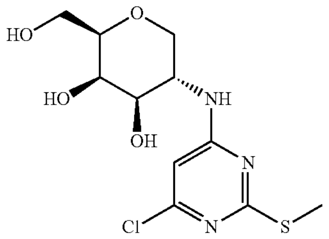
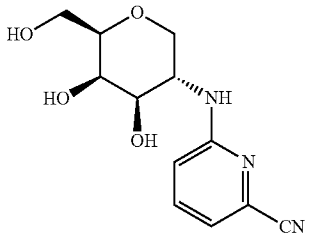
and
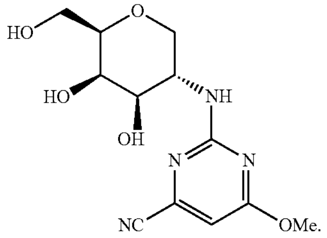
In certain embodiments, an ASGPR ligand useful for incorporation into a compound of the present invention is selected from
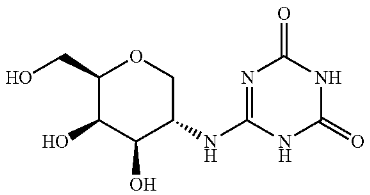
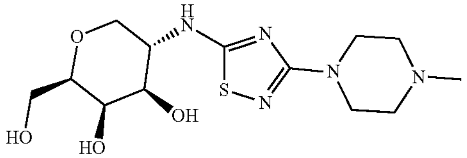
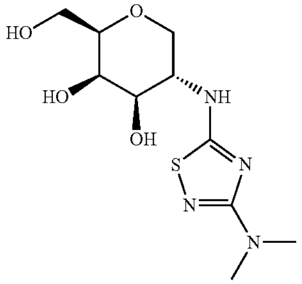
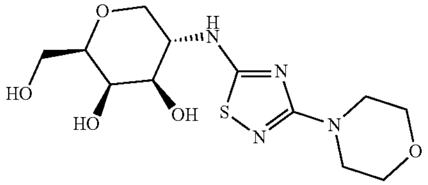
-continued
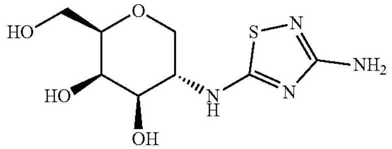
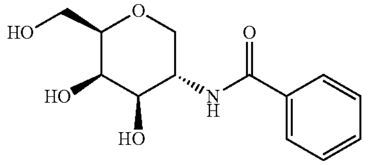
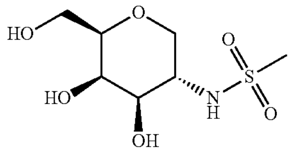
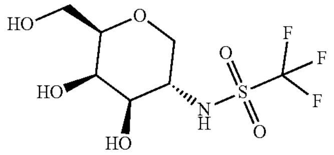
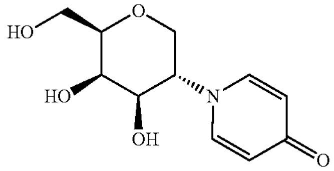
and
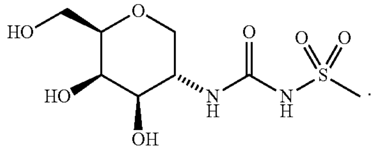
In certain embodiments, an ASGPR ligand useful for incorporation into a compound of the present invention is selected from
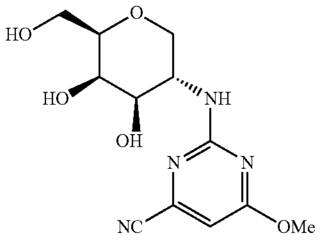
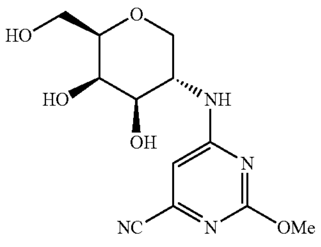

-continued
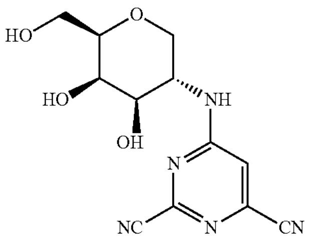
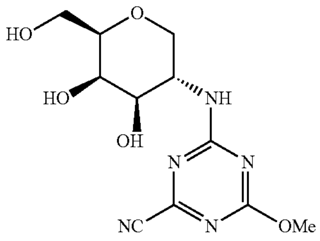
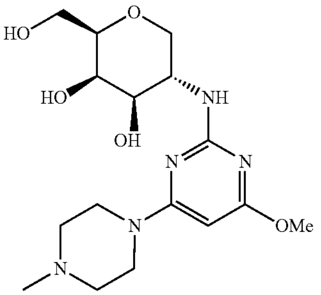
and
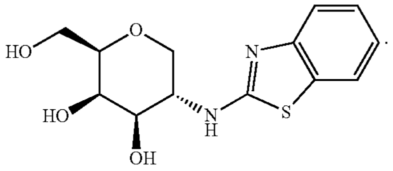
In certain embodiments, an ASGPR ligand useful for incorporation into a compound of the present invention is selected from
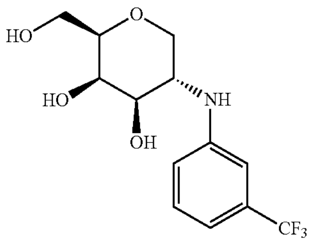
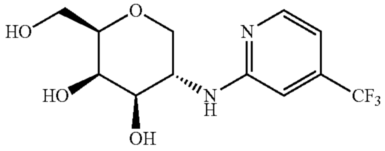
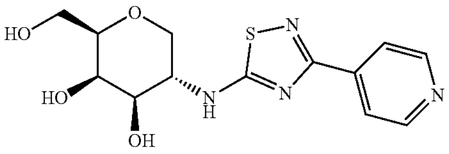
-continued
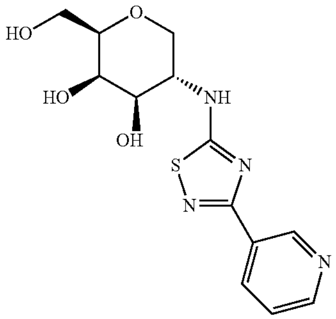
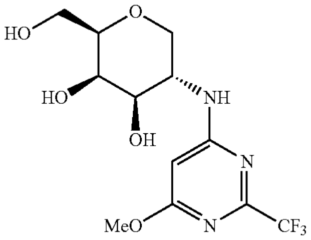
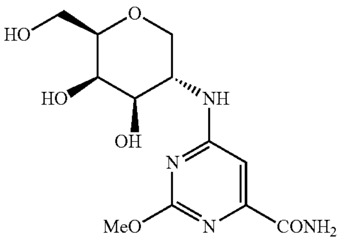
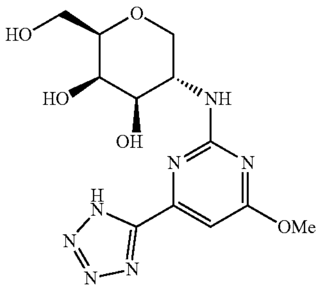
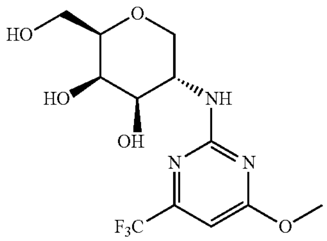
and
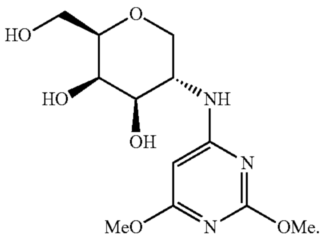
In certain embodiments, an ASGPR ligand useful for incorporation into a compound of the present invention is selected from

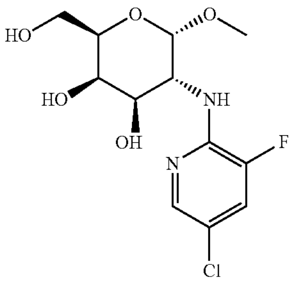
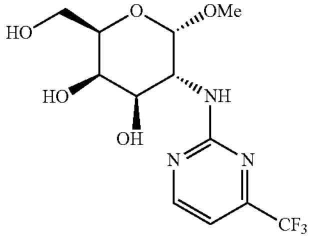
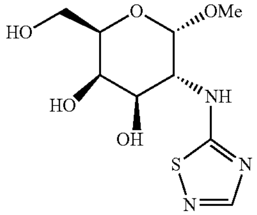
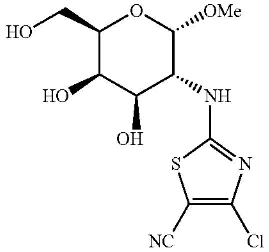
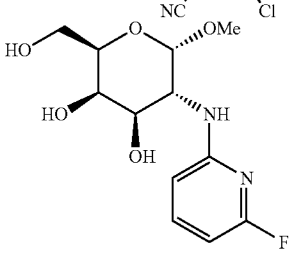
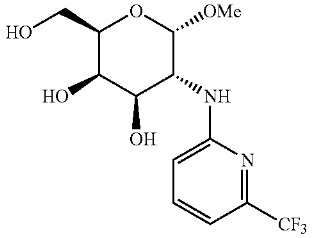
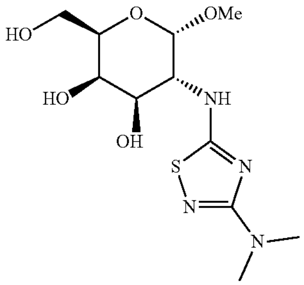
and
-continued
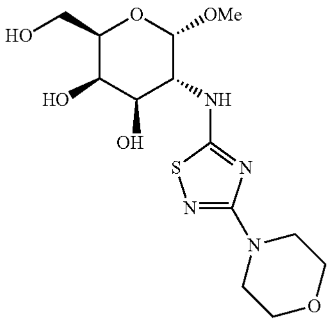
In certain embodiments, an ASGPR ligand useful for incorporation into a compound of the present invention is selected from
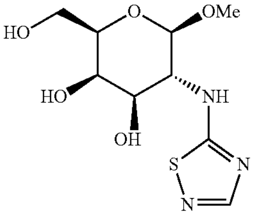
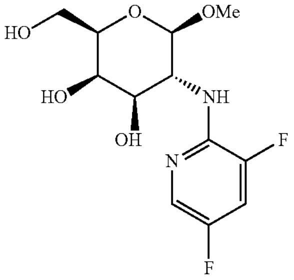
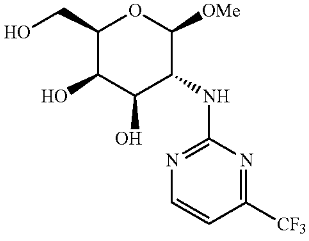
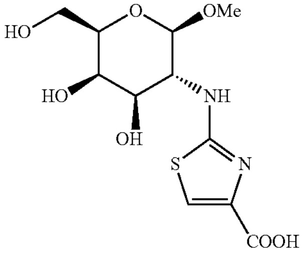
and -continued
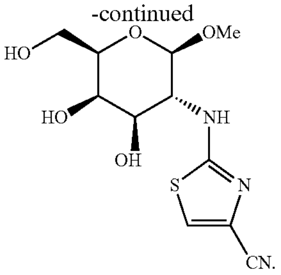
In certain embodiments, an ASGPR ligand useful for incorporation into a compound of the present invention is selected from
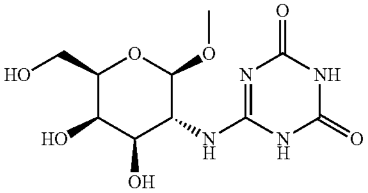
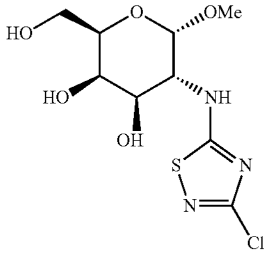
-continued
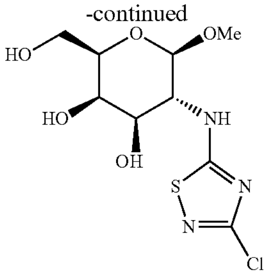
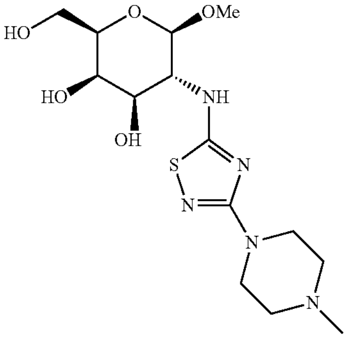
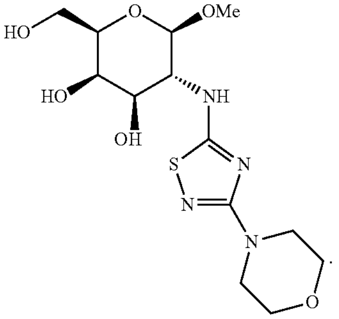
In certain embodiments, the compound of the present invention is selected from
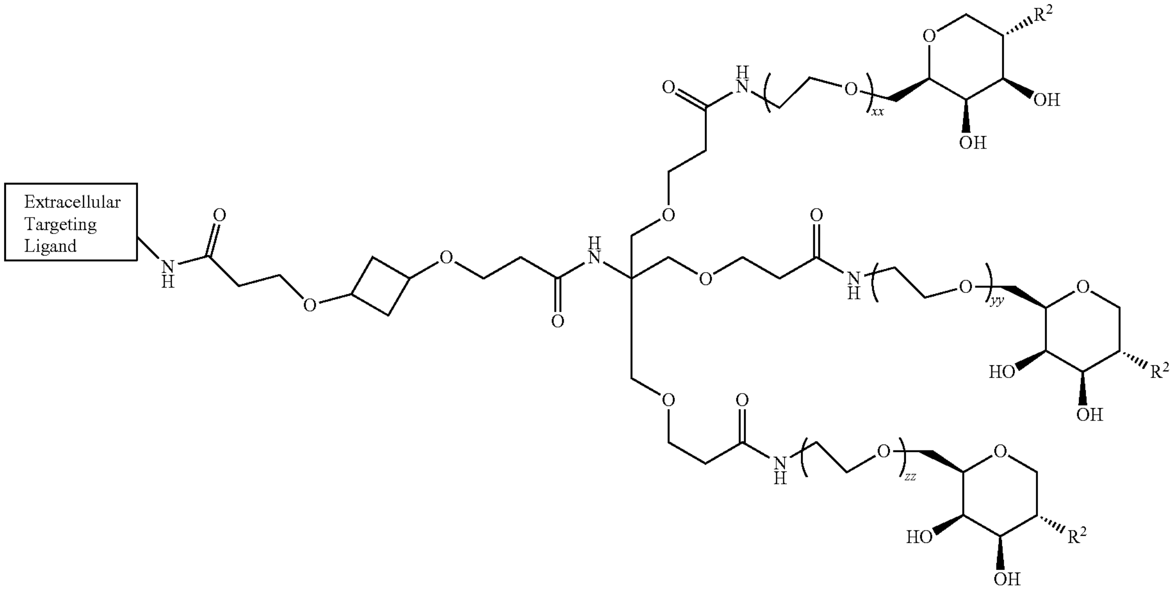

-continued
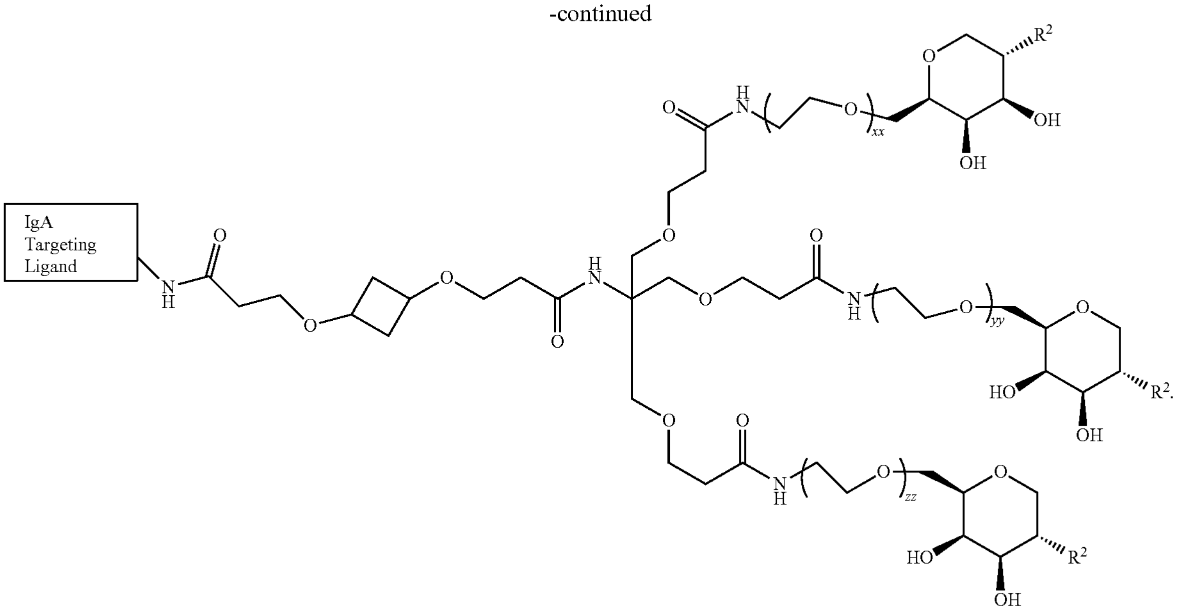
In certain embodiments, the compound of the present invention is selected from
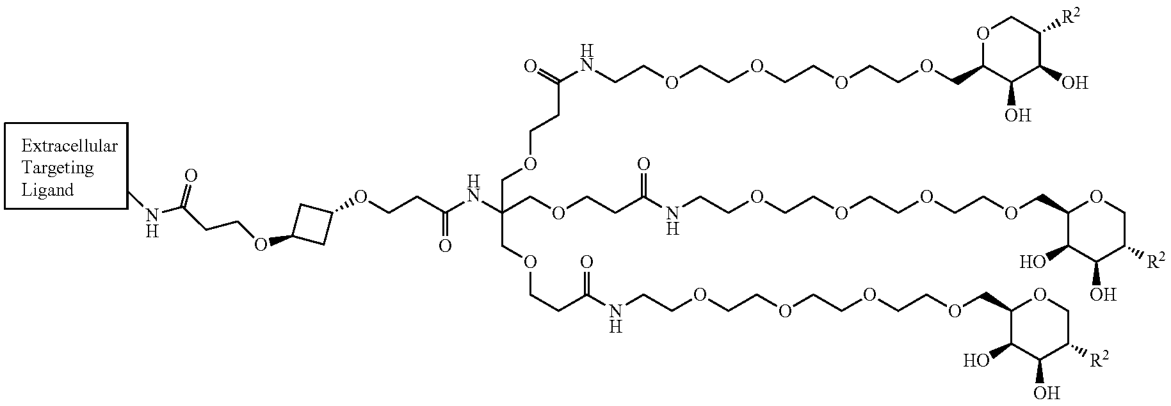
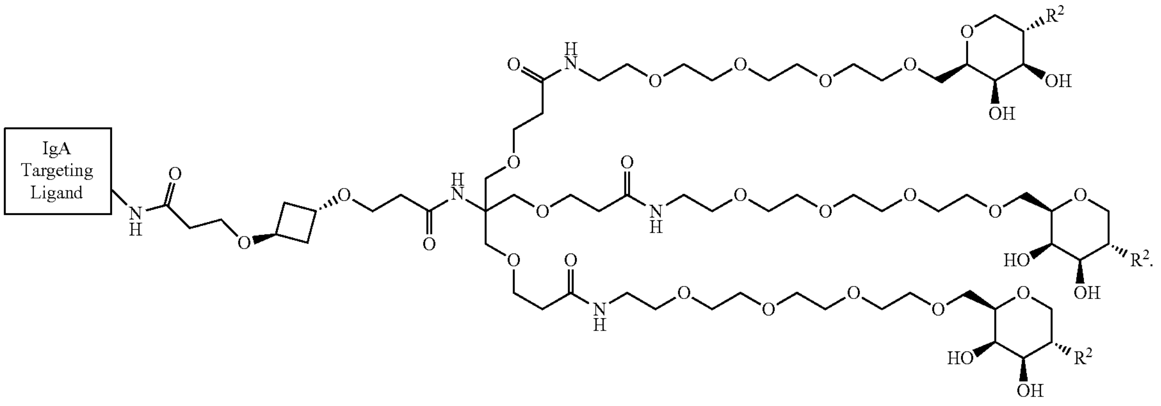

In certain embodiments, the compound of the present invention is selected from
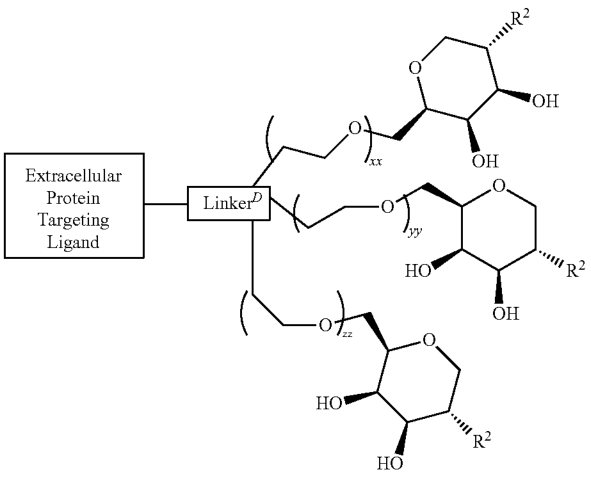
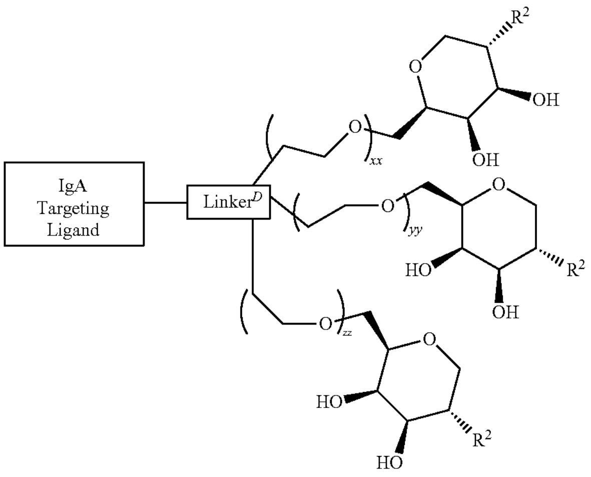
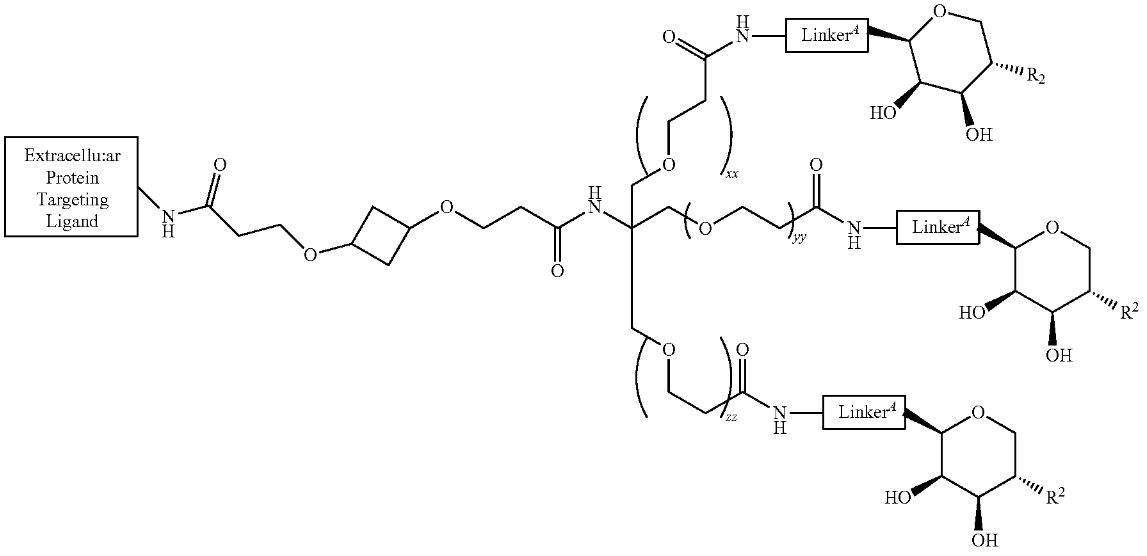
and
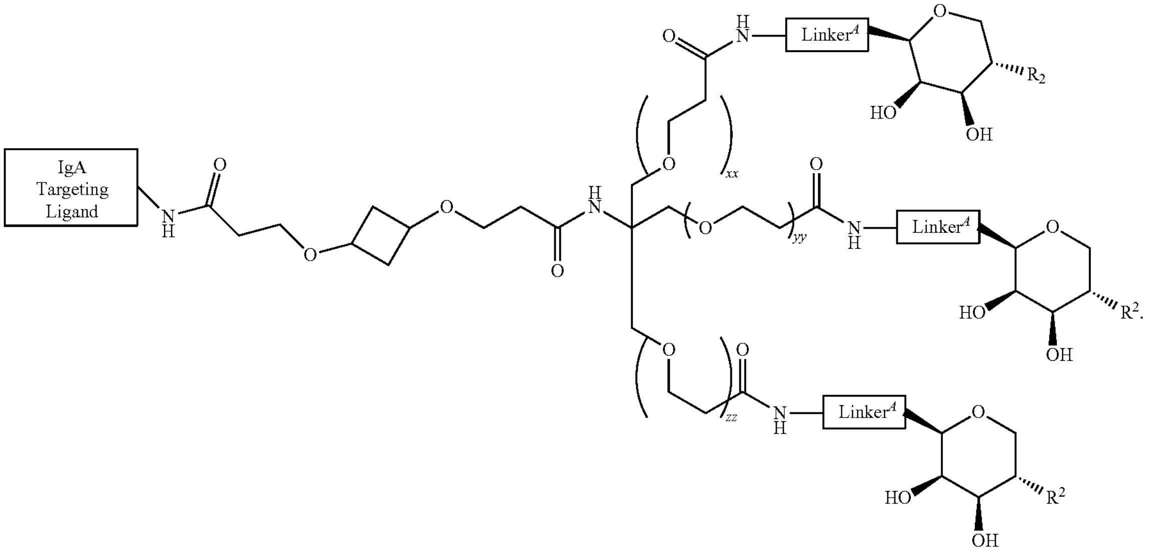

In certain embodiments, the compound of the present invention is selected from
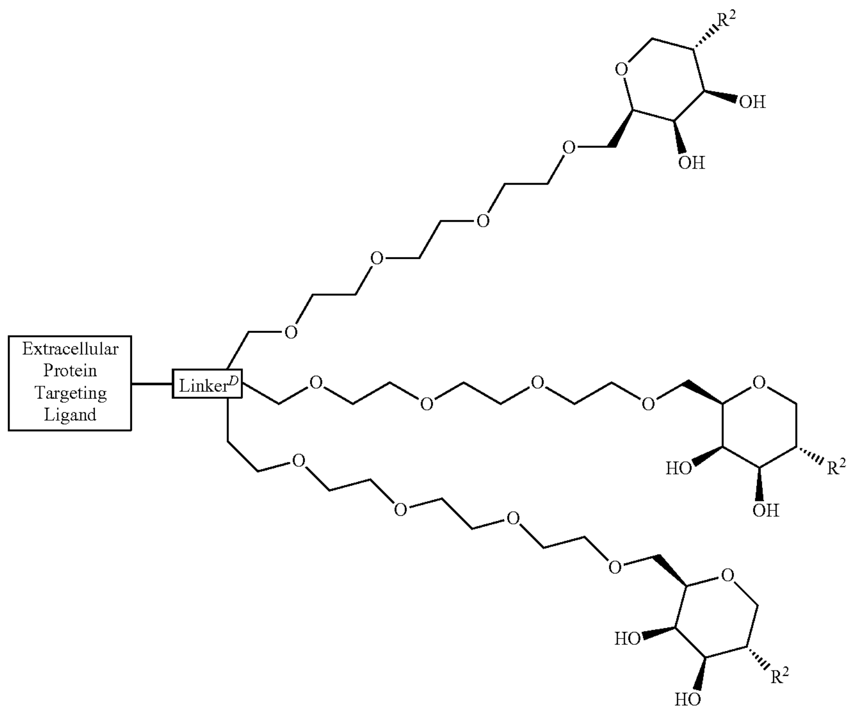
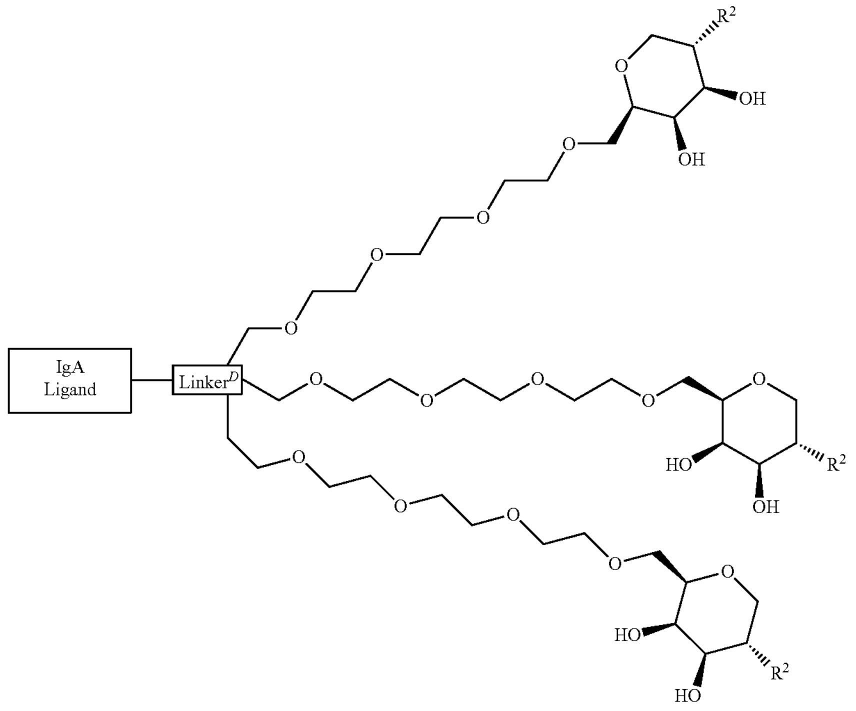

-continued
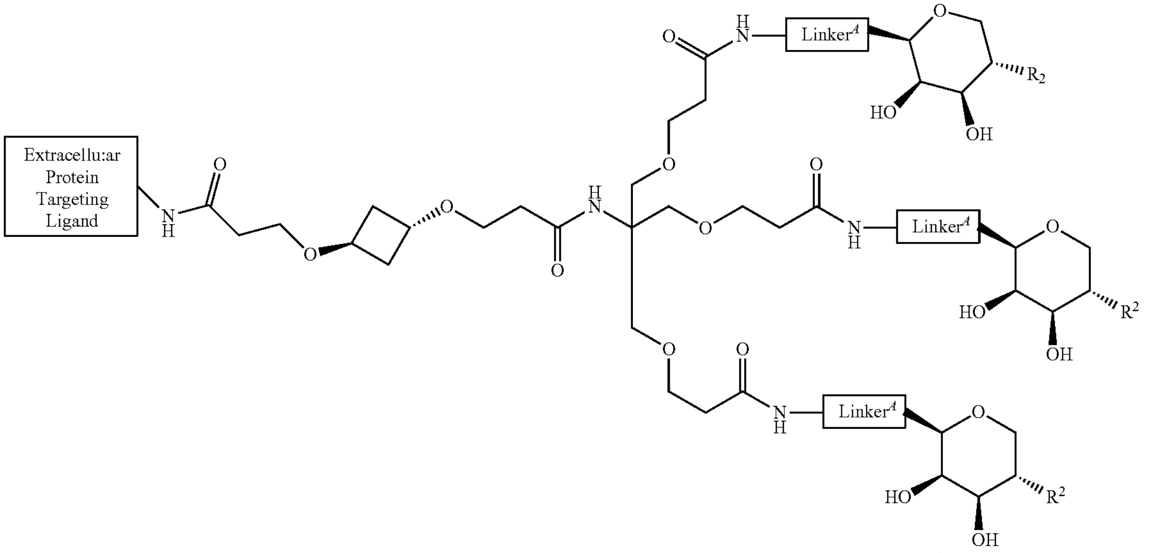
and
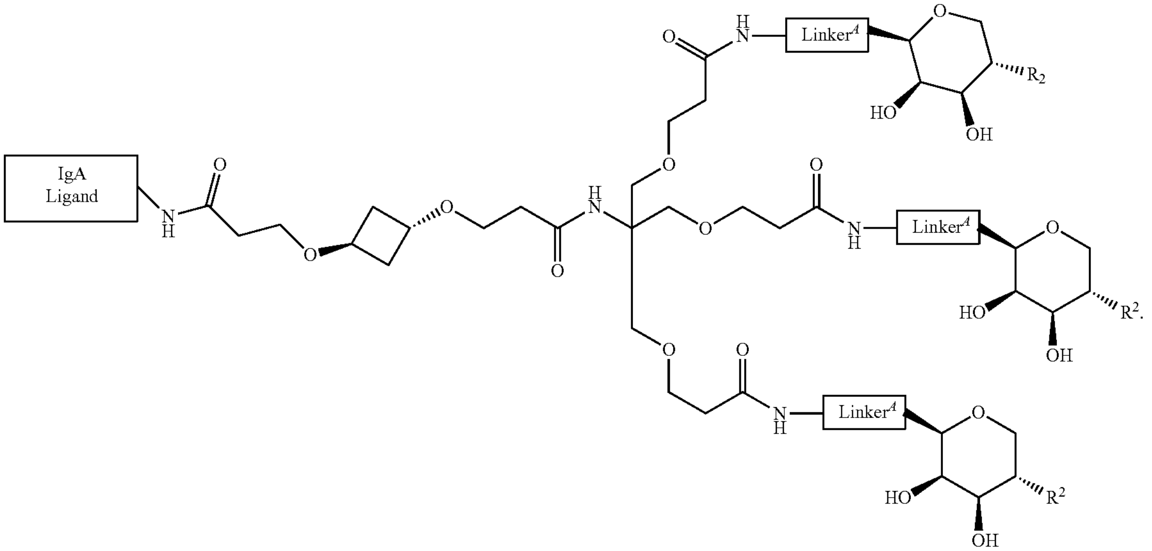
In certain embodiments, the compound of the present invention is
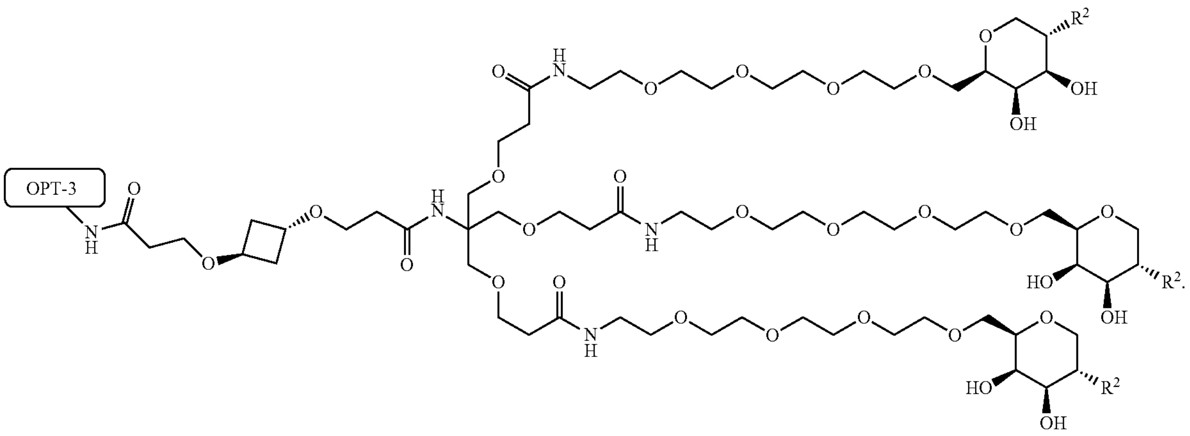

In certain embodiments, the compound of the present invention is

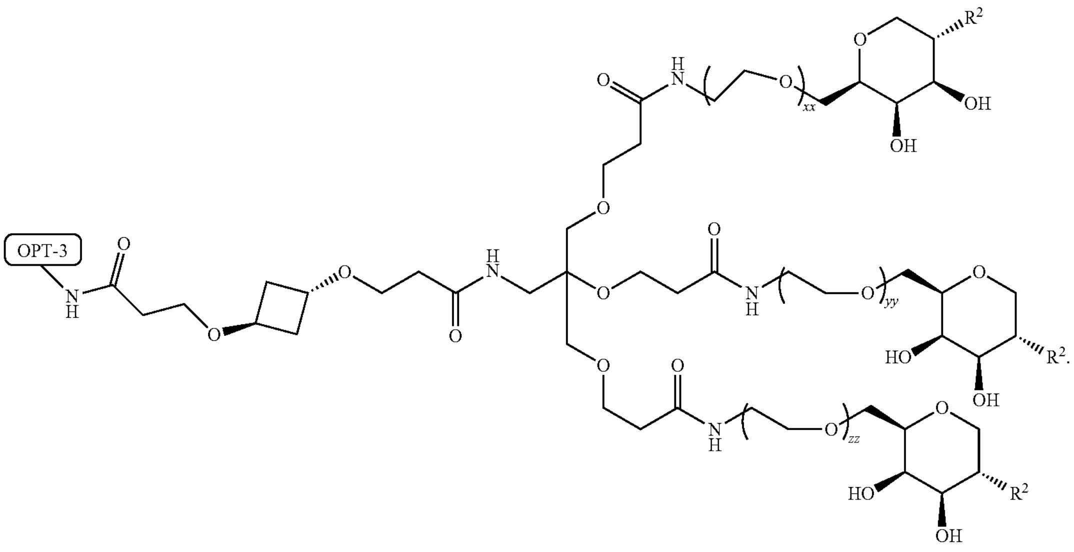

II. Talose-Based ASGPR-Binding Extracellular Protein Degraders of the Present Invention In certain embodiments the compound of the present invention is selected from:

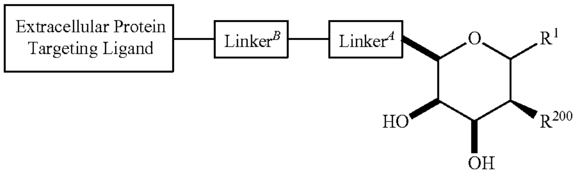

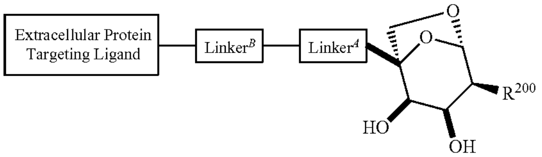

and

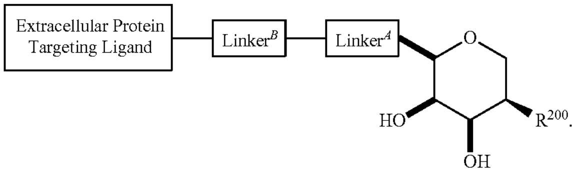

In certain embodiments the compound of the present invention is selected from:

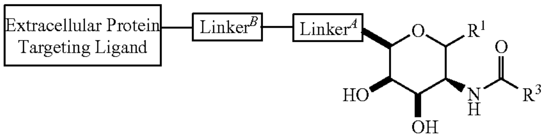

-continued

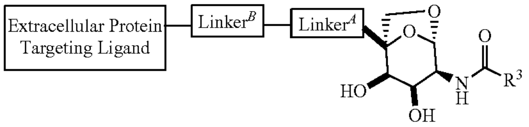

and

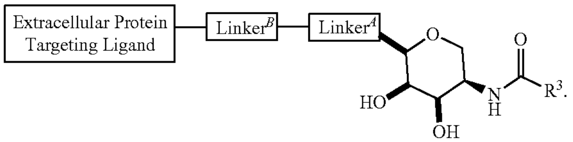

In certain embodiments the compound of the present invention is selected from:

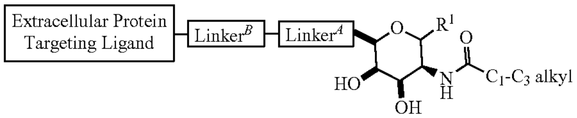

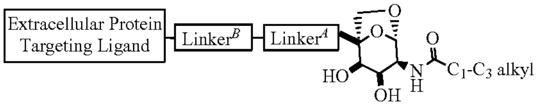

and

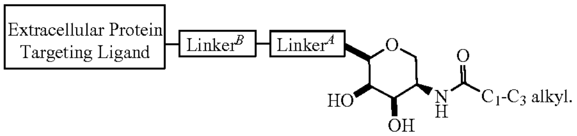

In certain embodiments the compound of the present invention is selected from:

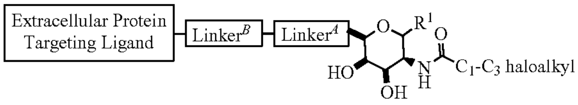

-continued
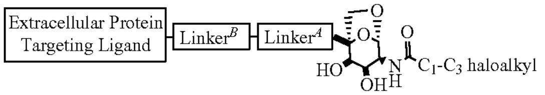
and
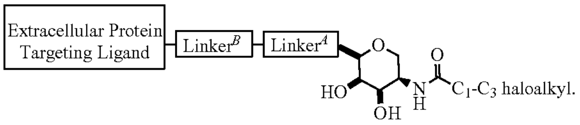
In certain embodiments the compound of the present invention is selected from:
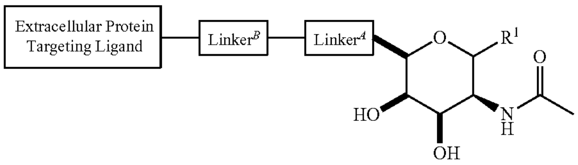
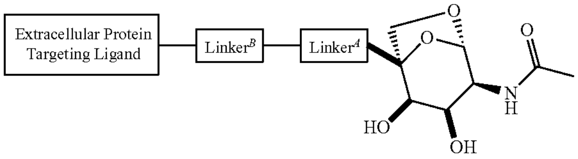
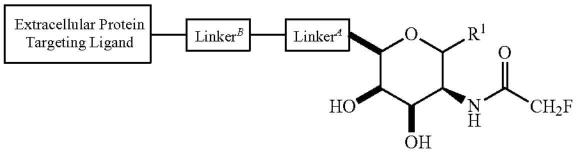
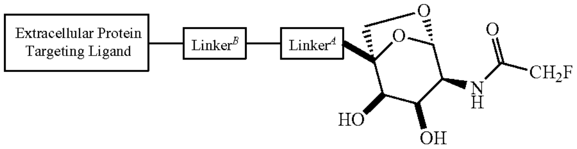
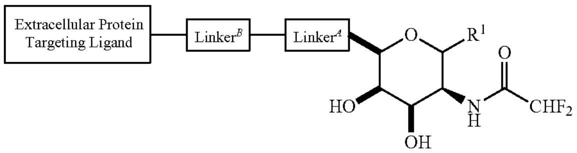
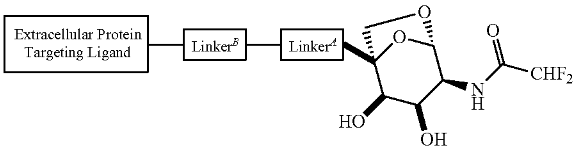
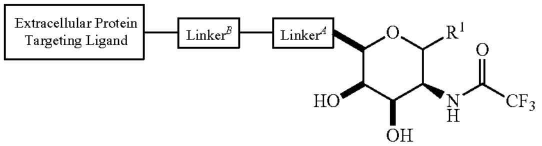
and
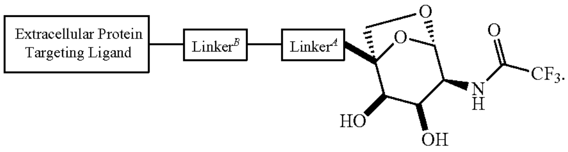
In certain embodiments the compound of the present invention is selected from:
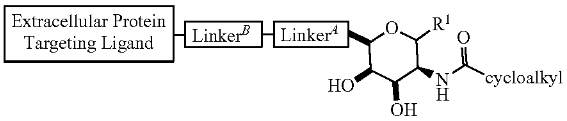
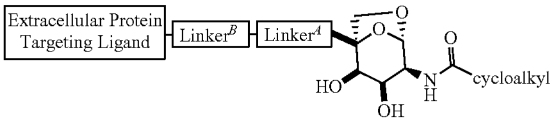
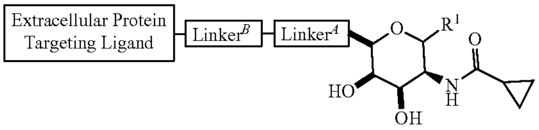
and
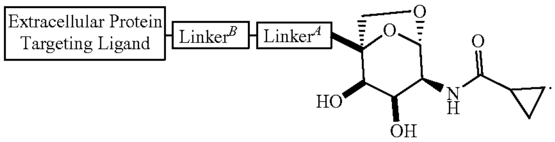
In certain embodiments the compound of the present invention is selected from:
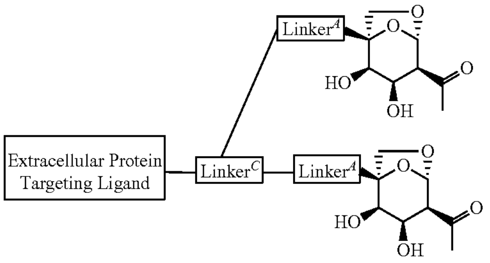
and
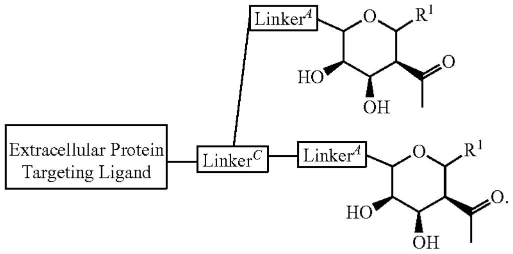
In certain embodiments the compound of the present invention is selected from:
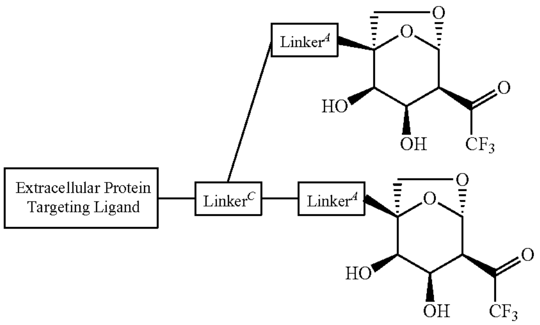
and -continued
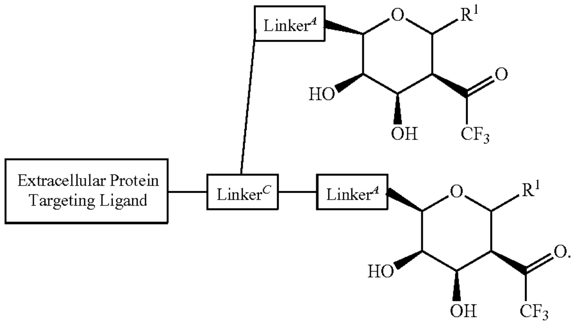
In certain embodiments the compound of the present invention is selected from:
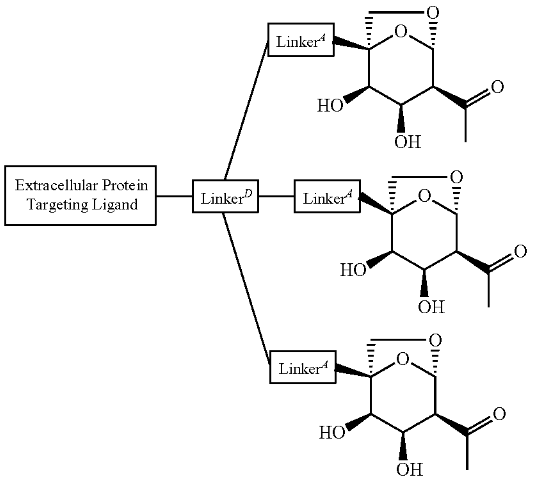
and
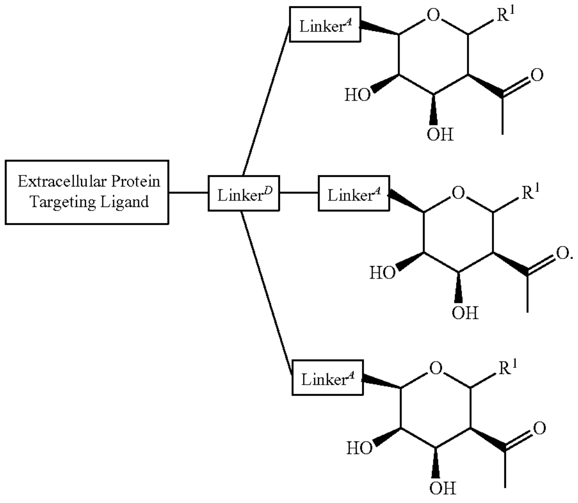
In certain embodiments the compound of the present invention is selected from:
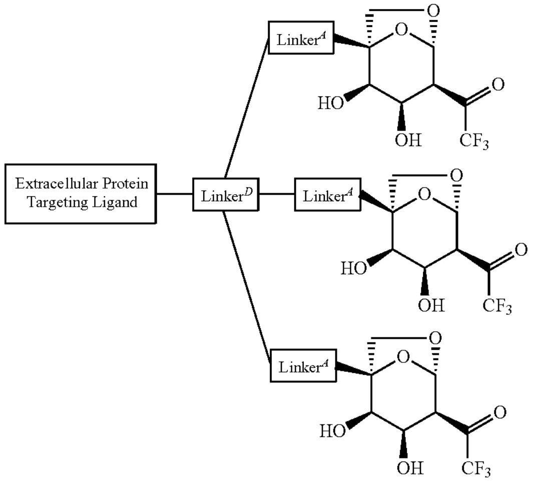
and
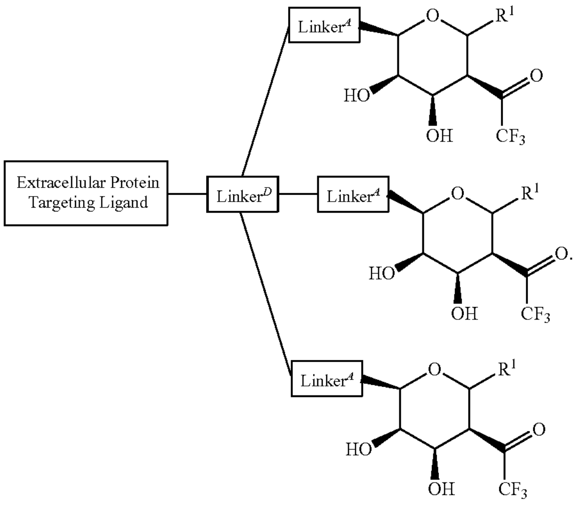
In certain embodiments the compound of the present invention is selected from:
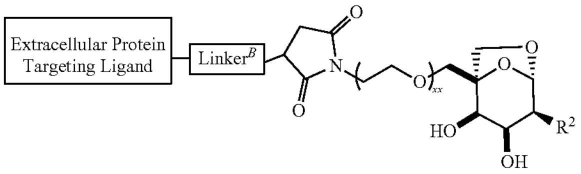
In certain embodiments the compound of the present invention is selected from:

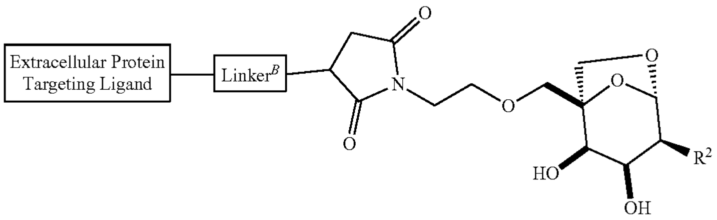
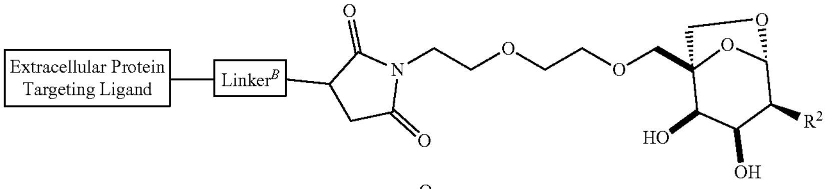
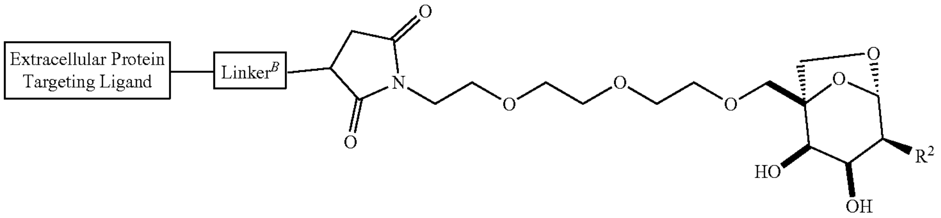
and
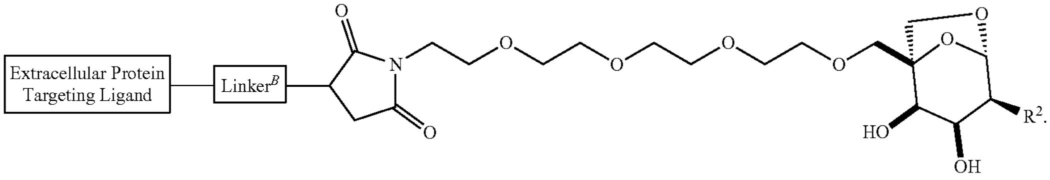
In certain embodiments the compound of the present invention is selected from:
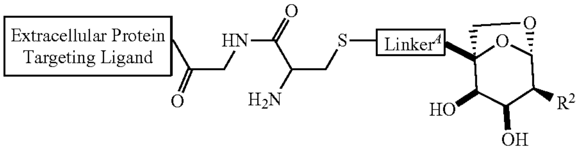
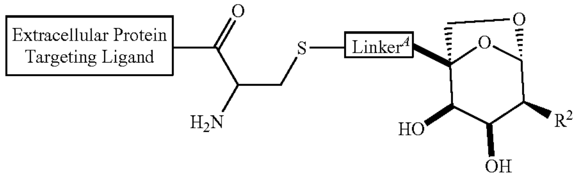
In certain embodiments the compound of the present invention is selected from:
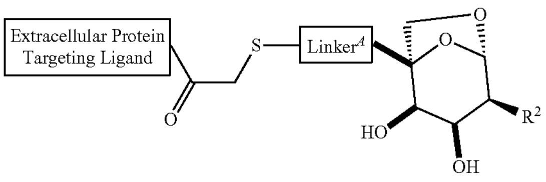
-continued
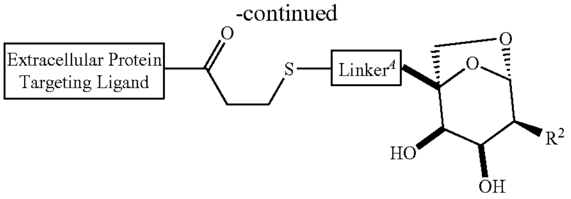
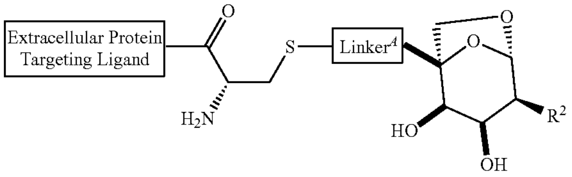
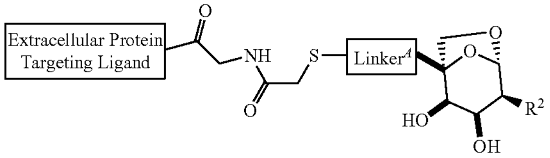
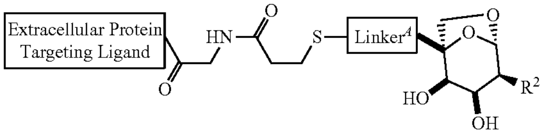
and
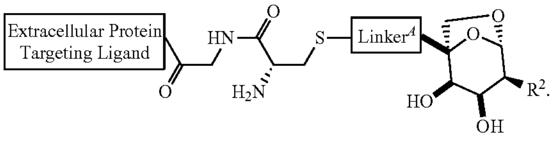
In certain embodiments the compound of the present invention is selected from:

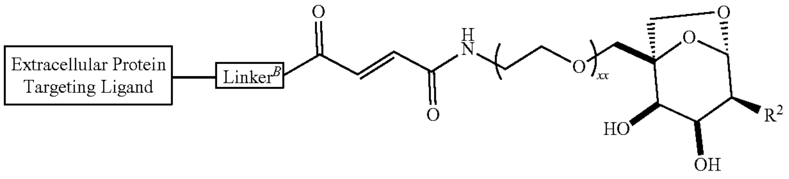
In certain embodiments the compound of the present invention is selected from:
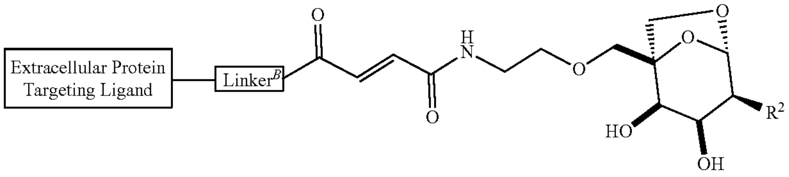
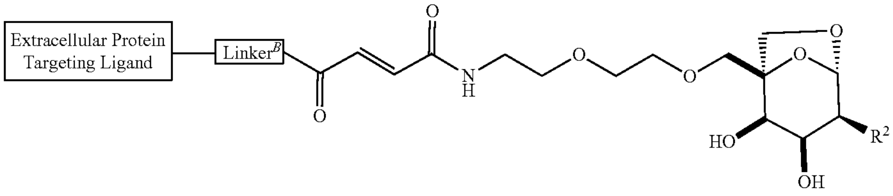
and
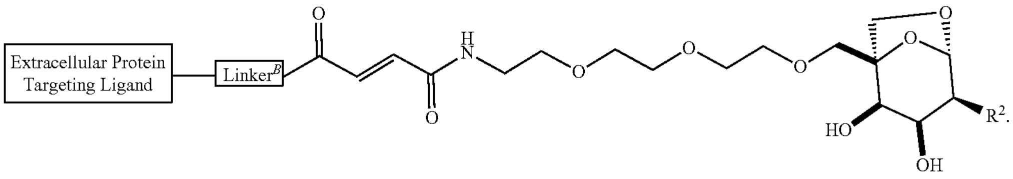
In certain embodiments the compound of the present invention is selected from:
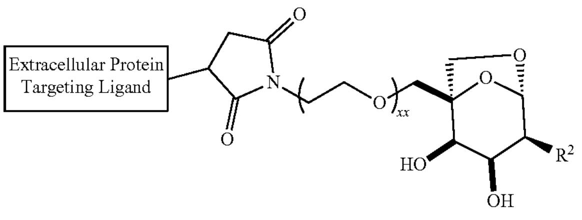
In certain embodiments the compound of the present invention is selected from:
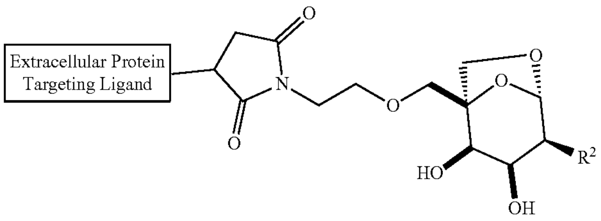

-continued
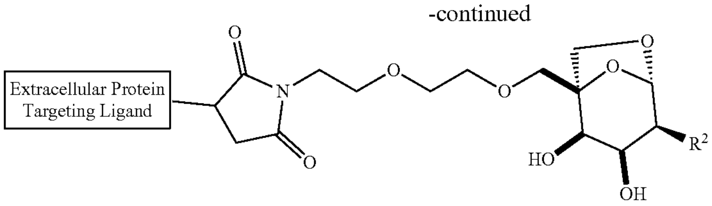
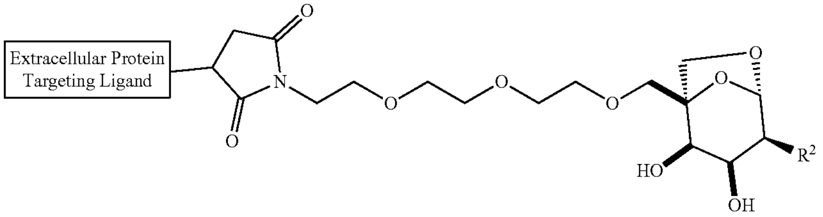
and
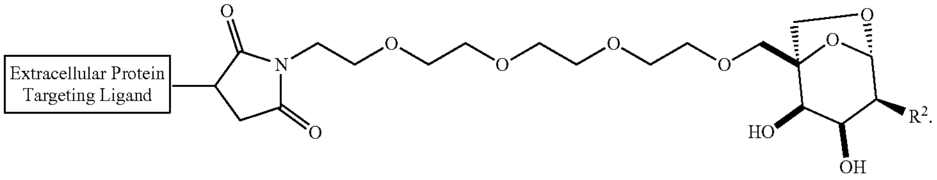
In certain embodiments the compound of the present invention is selected from:
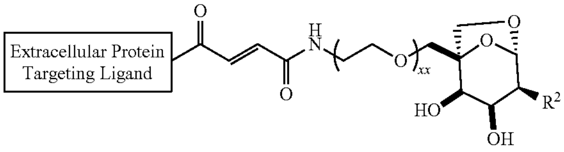
In certain embodiments the compound of the present invention is selected from:
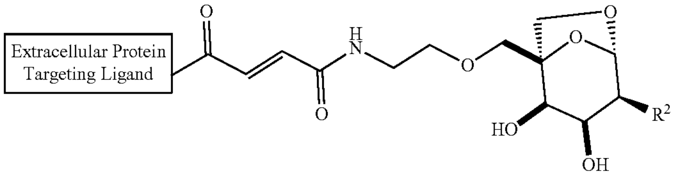
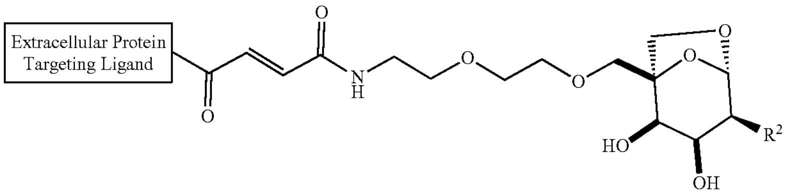
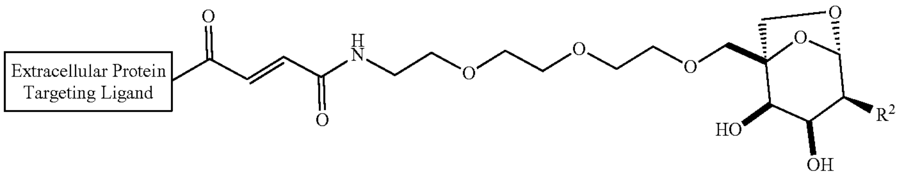
and -continued
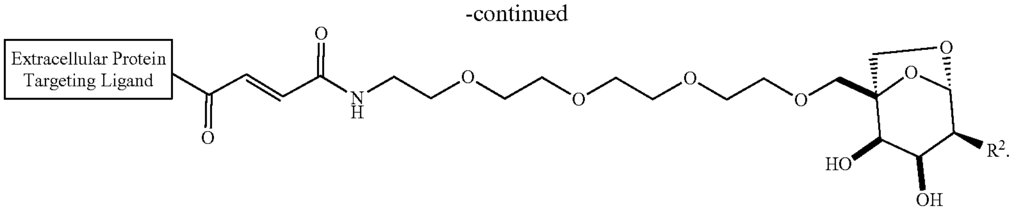
In certain embodiments the compound of the present invention is selected from:
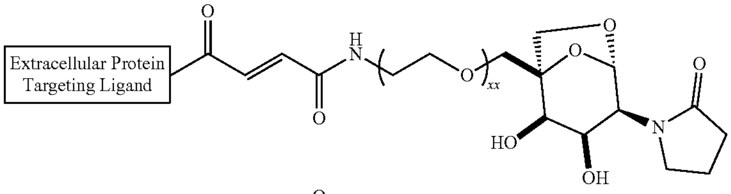
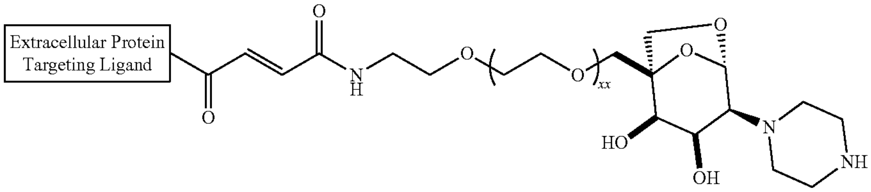
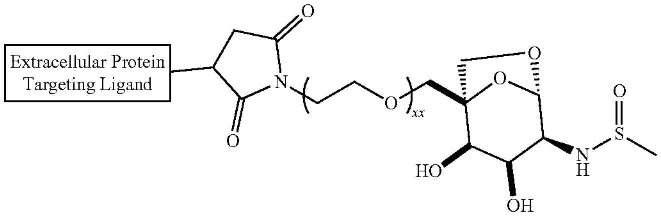
and
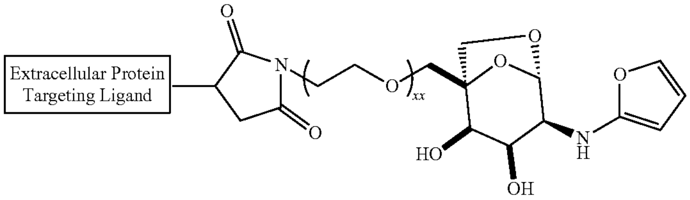
.
In certain embodiments the compound of the present invention is selected from:
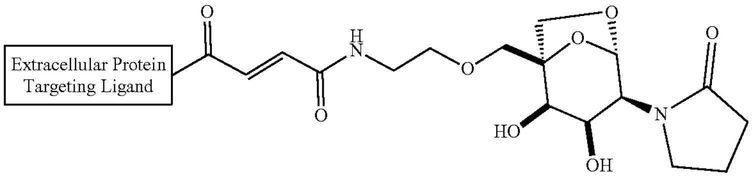
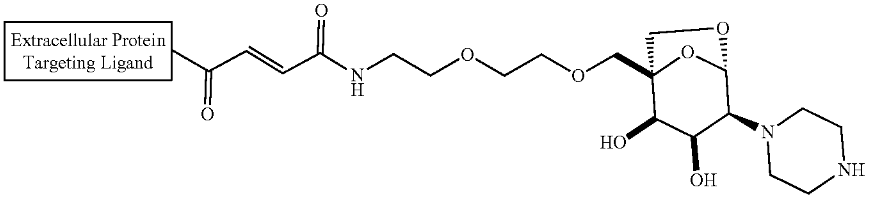

-continued
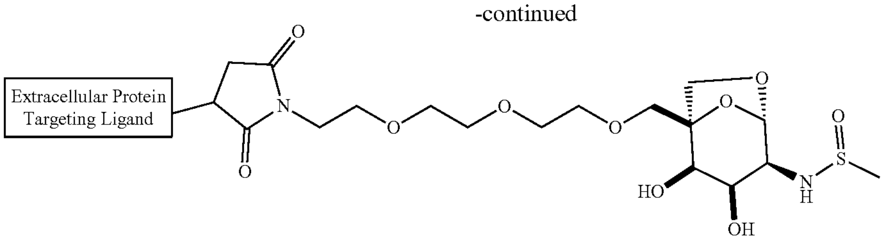
and
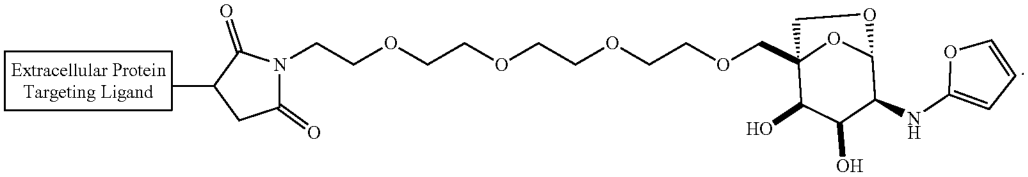
In certain embodiments the compound of the present invention is selected from:
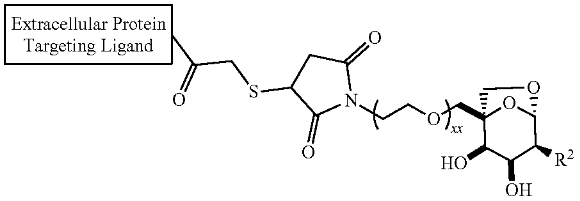
In certain embodiments the compound of the present invention is selected from:
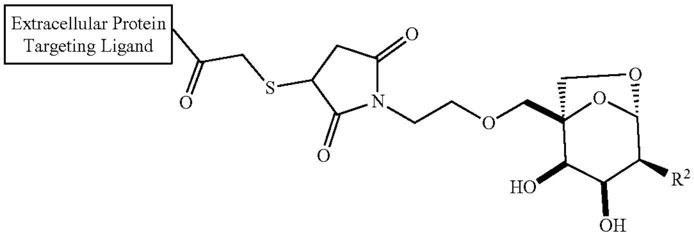
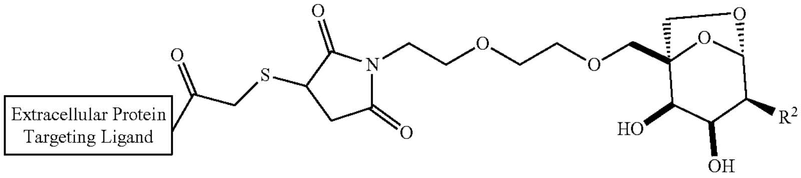
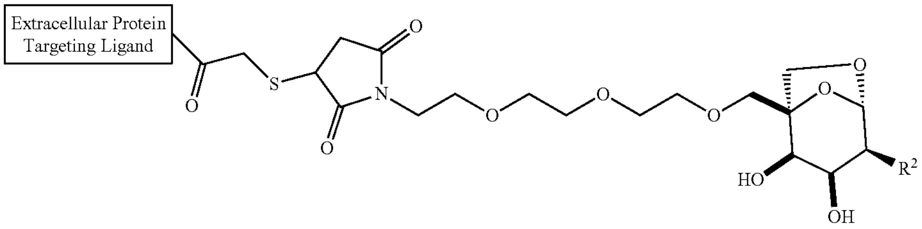
and
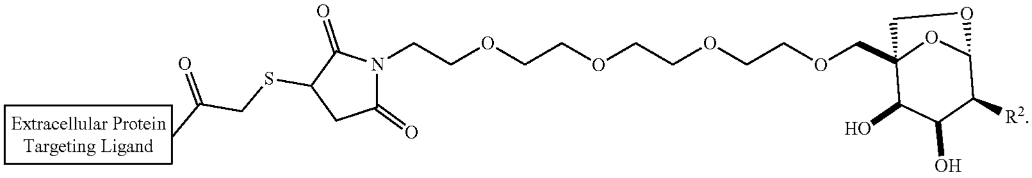

In certain embodiments the compound of the present invention is selected from:
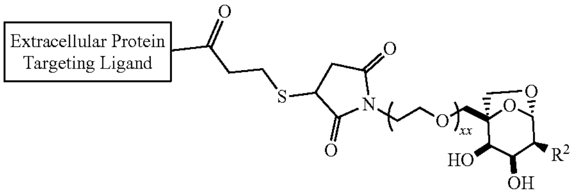
In certain embodiments the compound of the present invention is selected from:
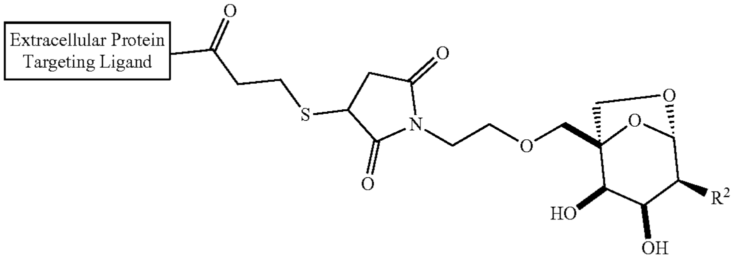
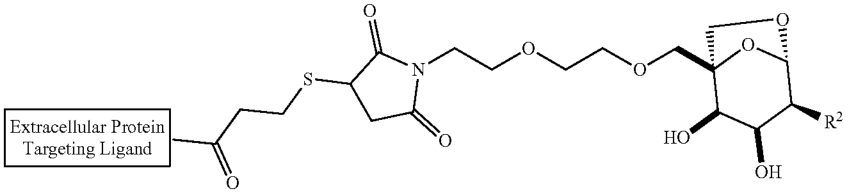
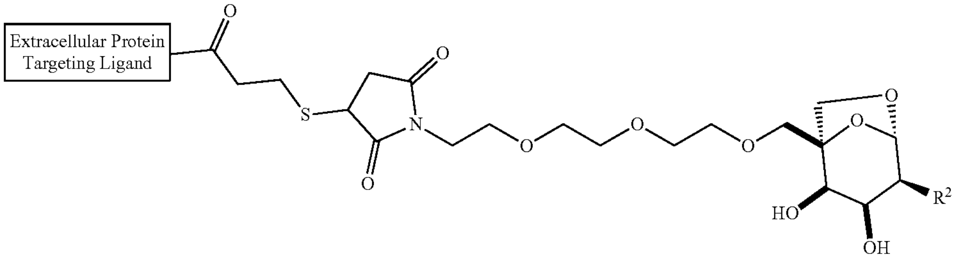
and
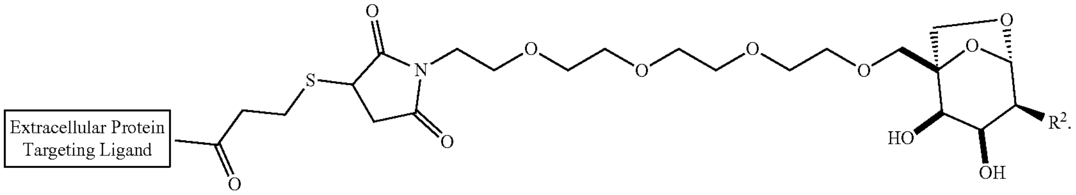
In certain embodiments the compound of the present invention is selected from:
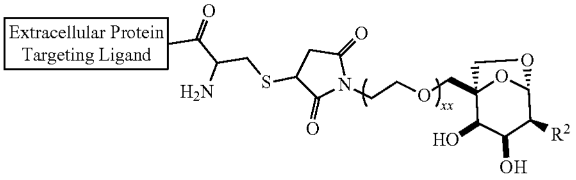
In certain embodiments the compound of the present invention is selected from:

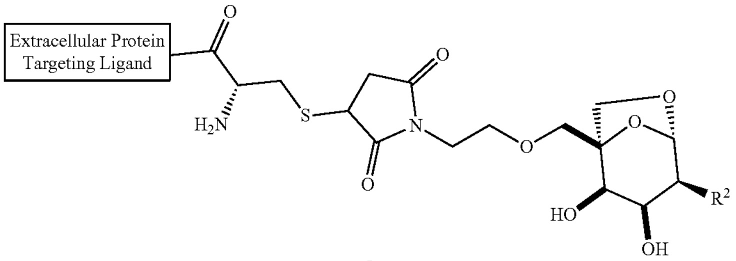
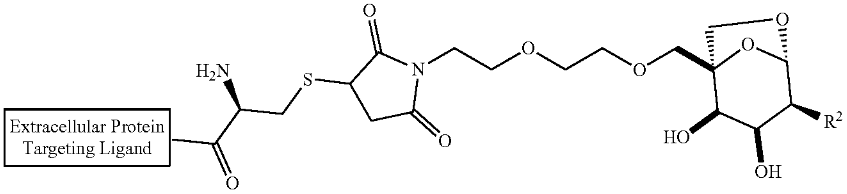
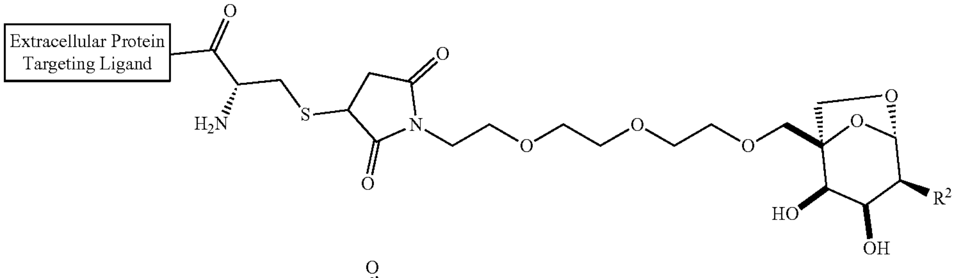
and
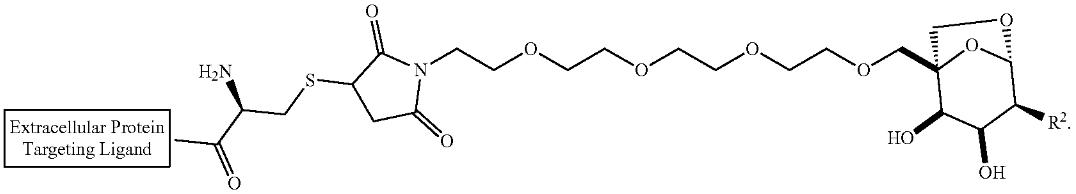
In certain embodiments the compound of the present invention is selected from:
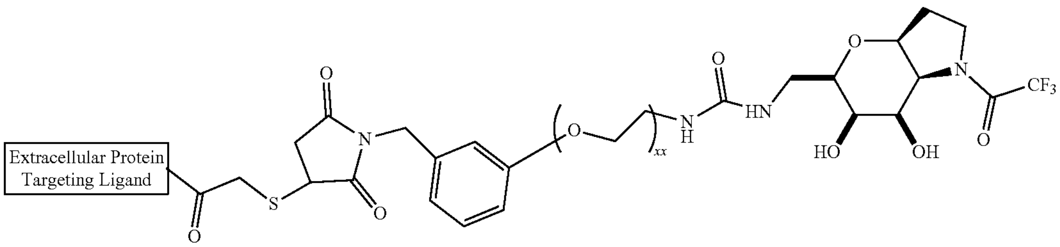
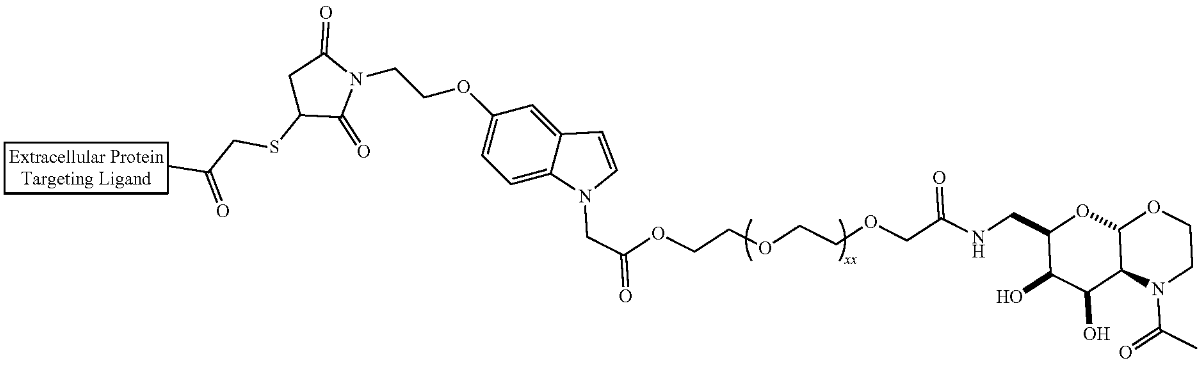

-continued
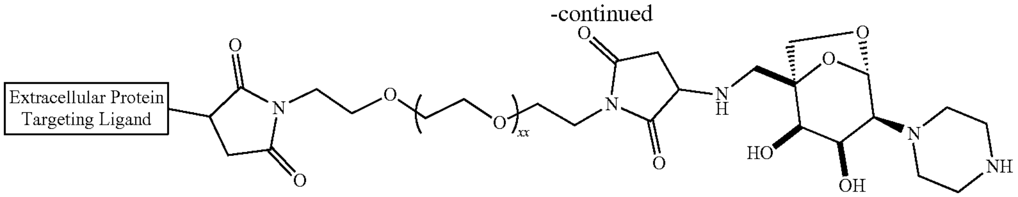
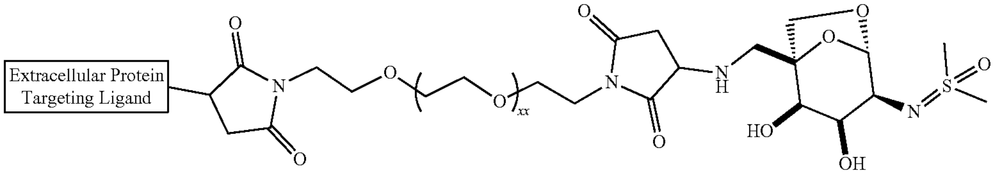
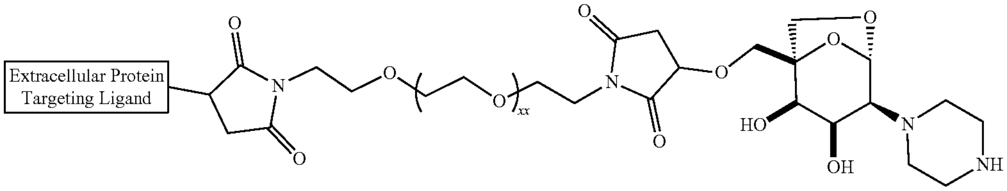
and
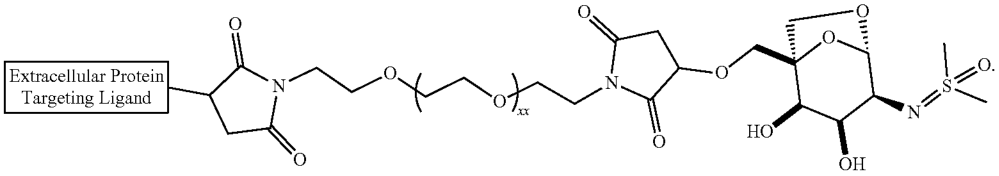
In certain embodiments the compound of the present invention is selected from:
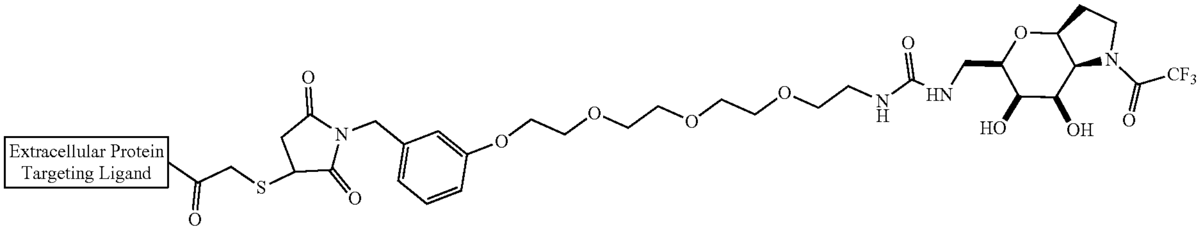
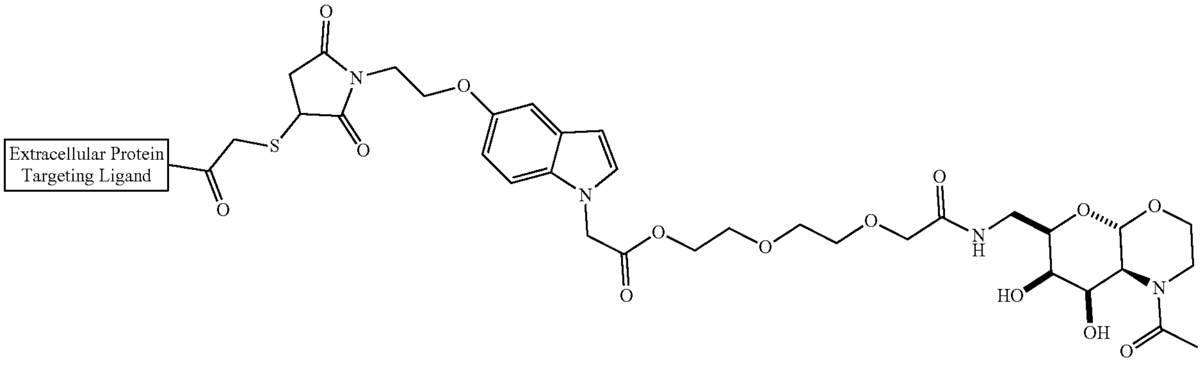
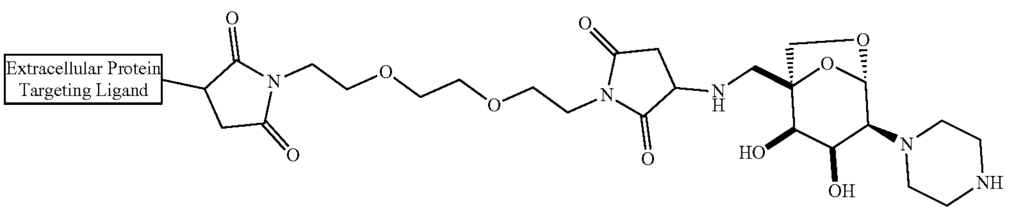

-continued
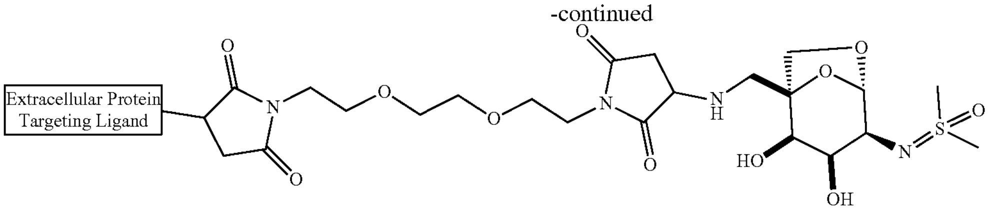
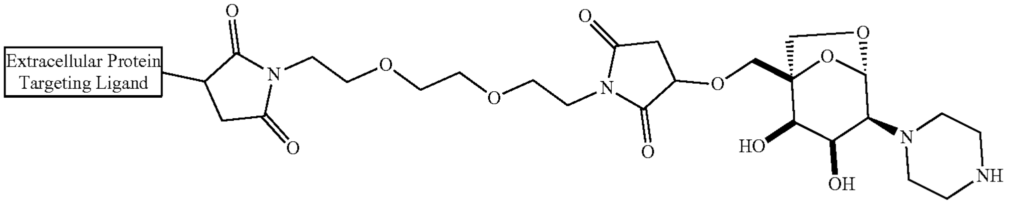
and
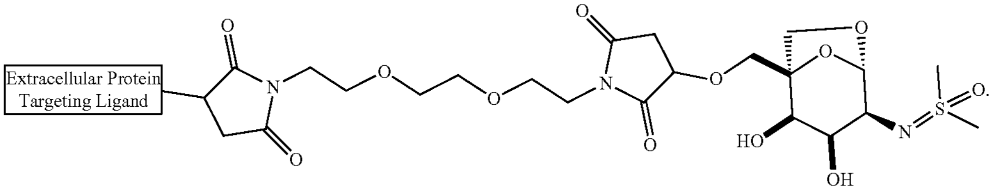
In certain embodiments the compound of the present invention is selected from:
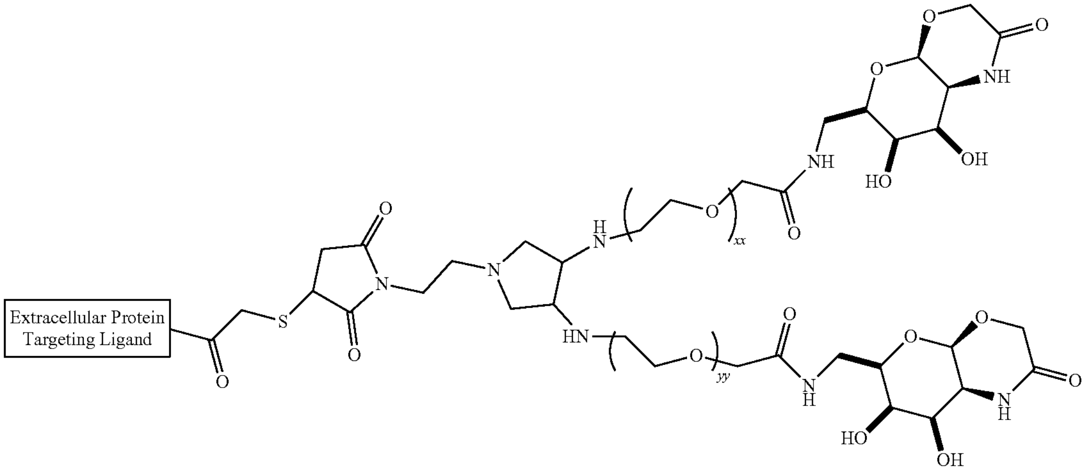
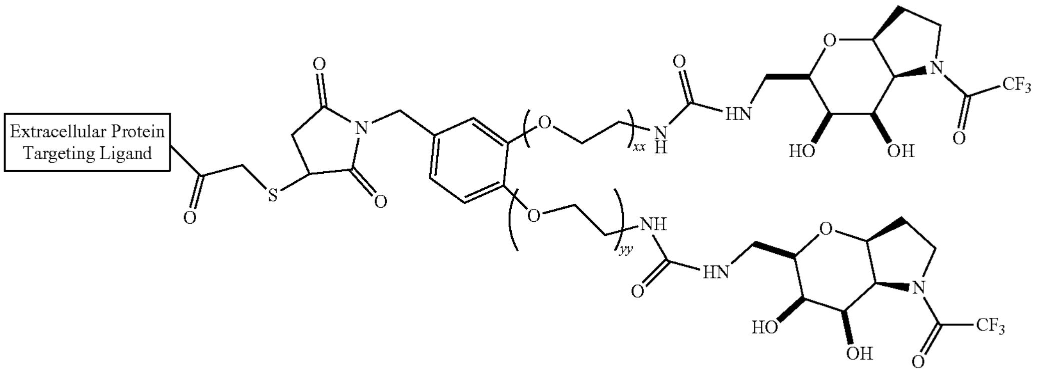

-continued
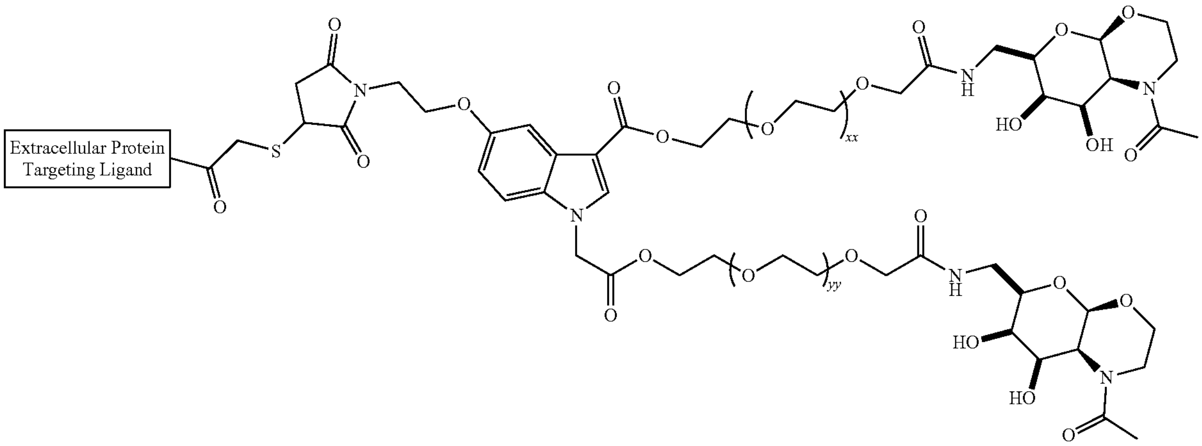
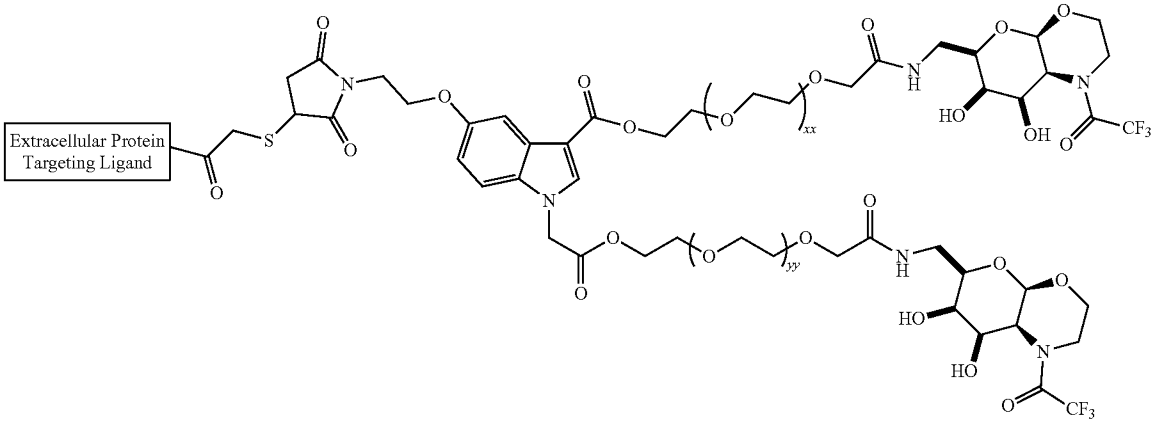
and
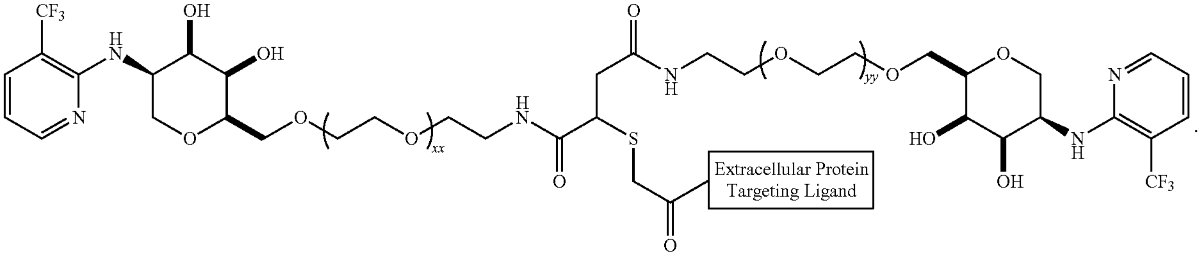
.

In certain embodiments the compound of the present invention is selected from:
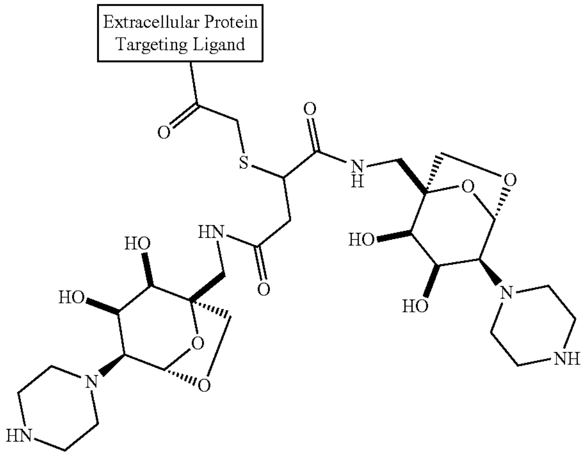
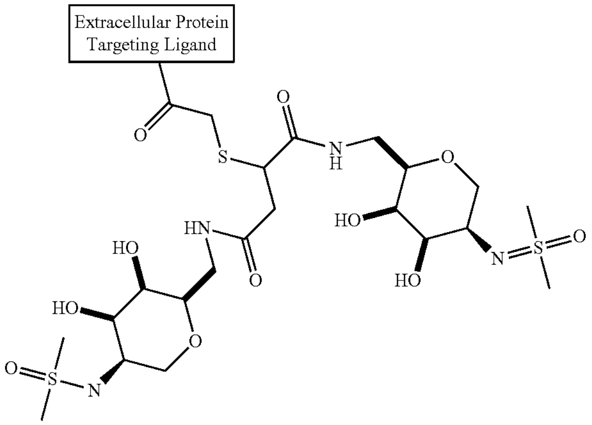
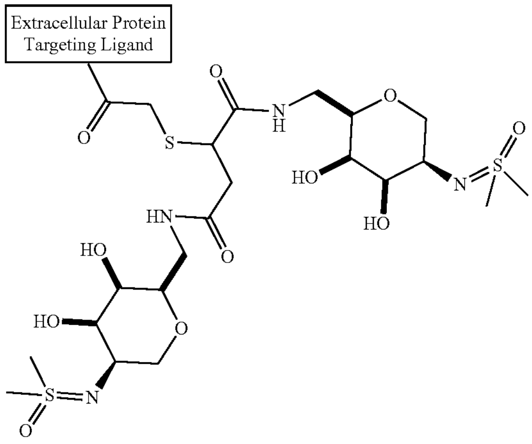
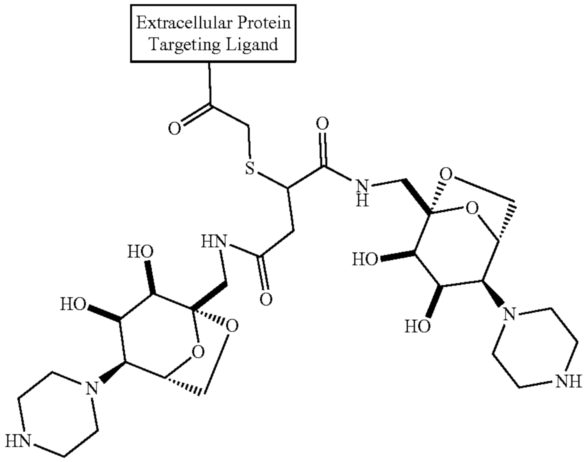
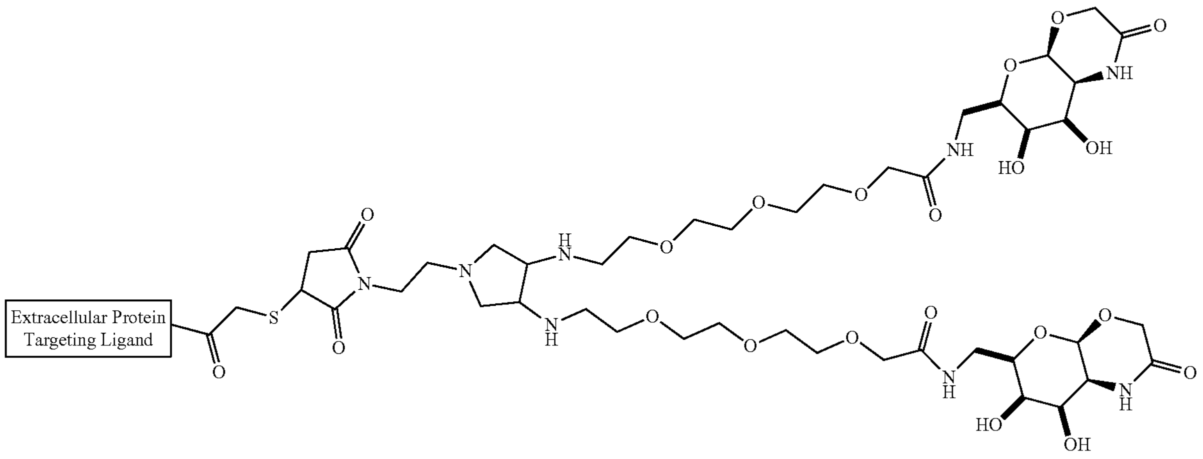

-continued
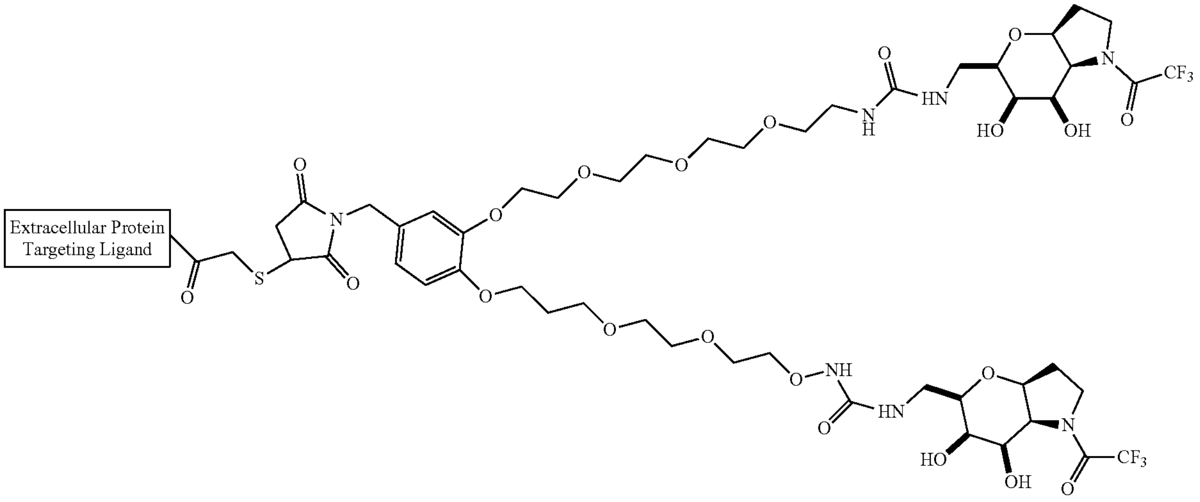
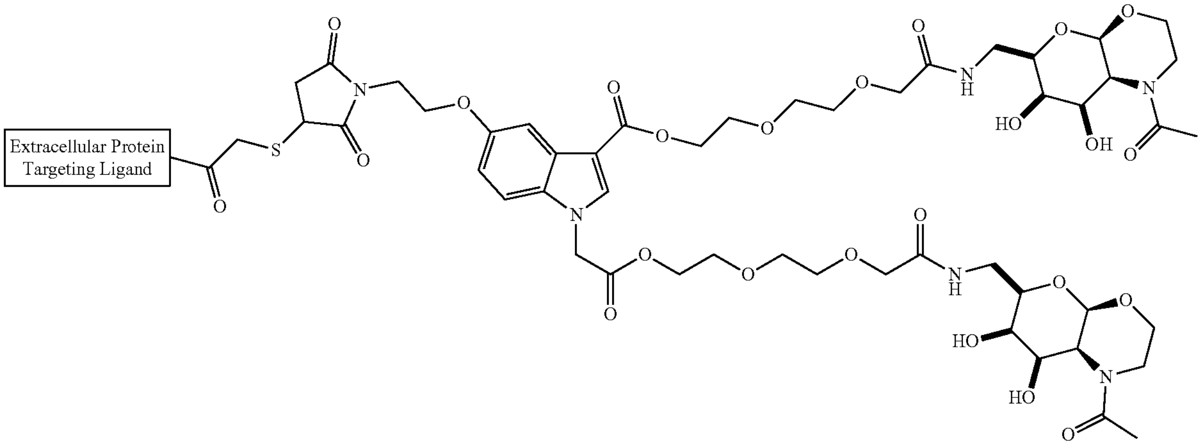
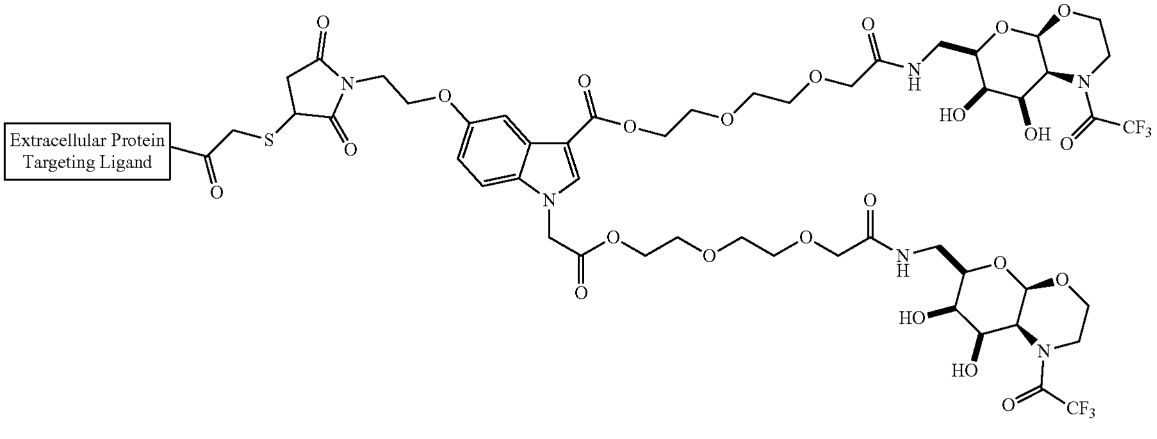
and
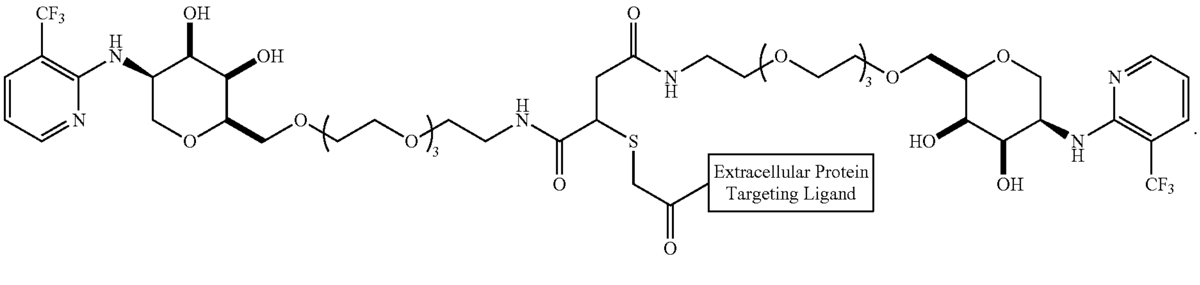
.

In certain embodiments the compound of the present invention is selected from:
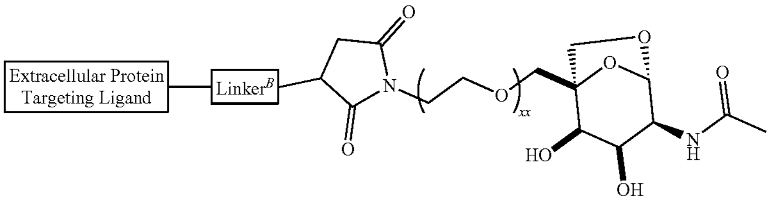
and
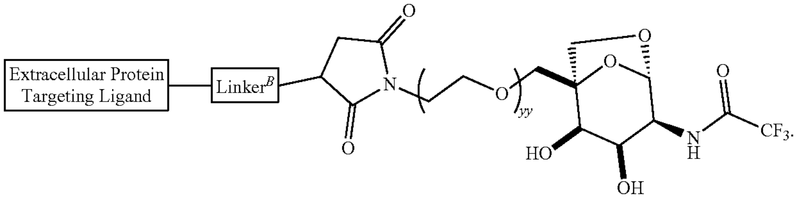
In certain embodiments the compound of the present invention is selected from:
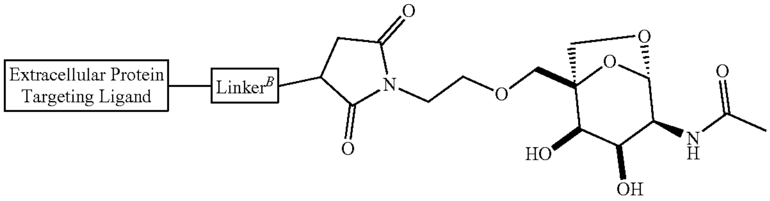
and
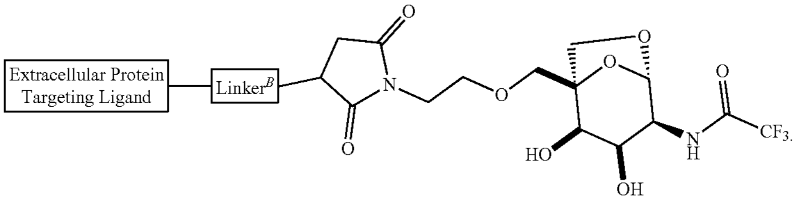
In certain embodiments the compound of the present invention is selected from:
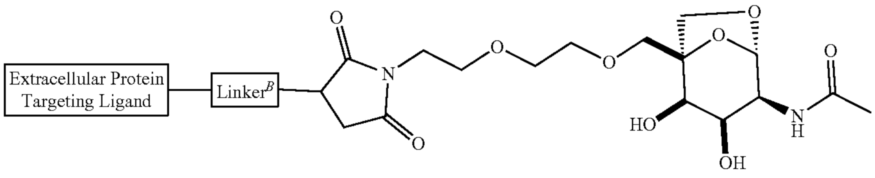
and
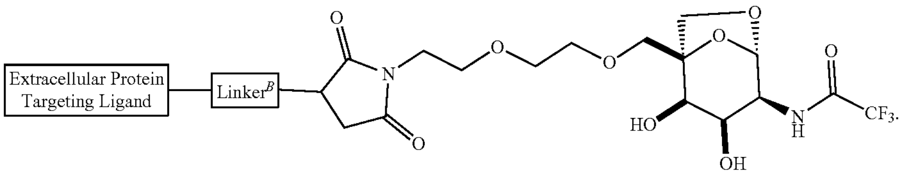

In certain embodiments the compound of the present invention is selected from:

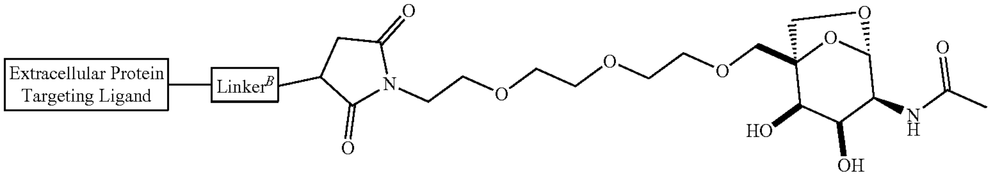

and

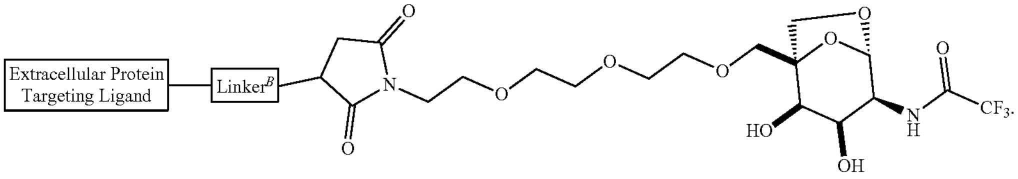

In certain embodiments the compound of the present invention is selected from:

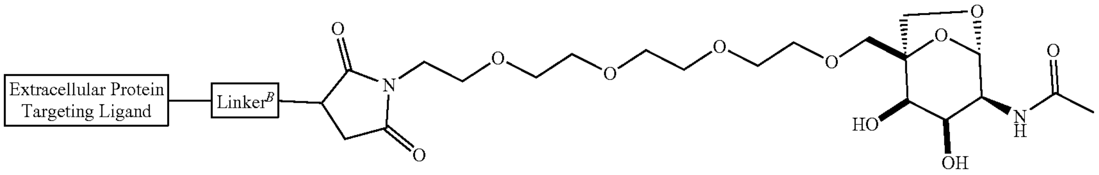

and

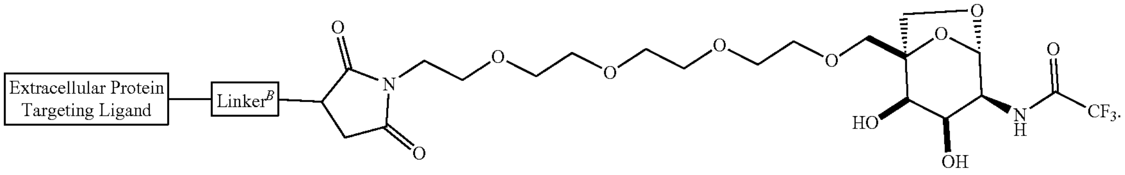

In certain embodiments the compound of the present invention is selected from:

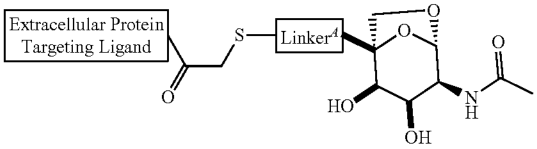

and

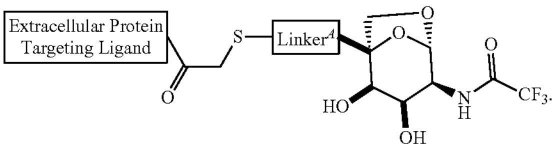

In certain embodiments the compound of the present invention is selected from:

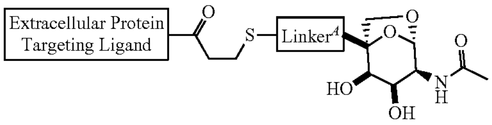

and

-continued

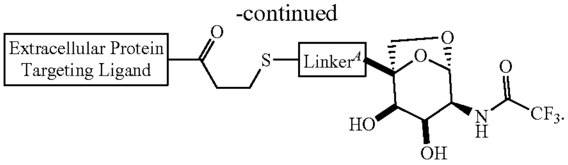

In certain embodiments the compound of the present invention is selected from:

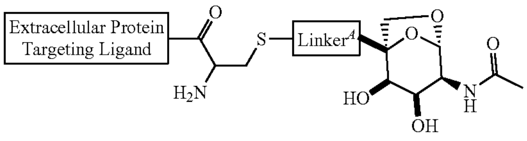

and

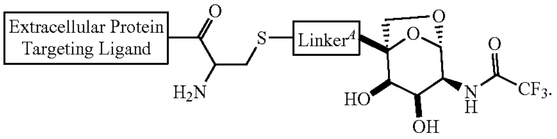

In certain embodiments the compound of the present invention is selected from:

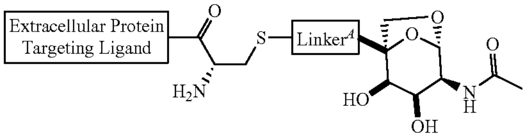

and

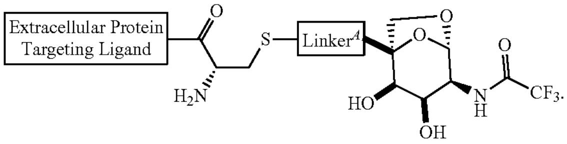

In certain embodiments the compound of the present invention is selected from:

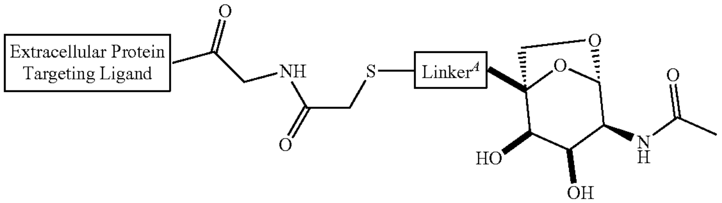

and

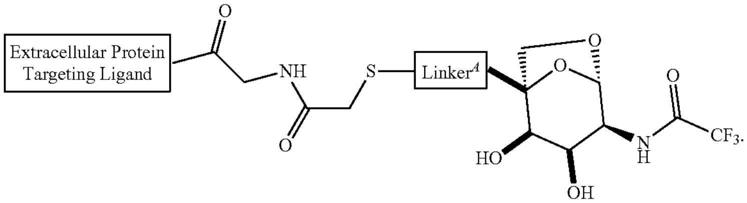

In certain embodiments the compound of the present invention is selected from:

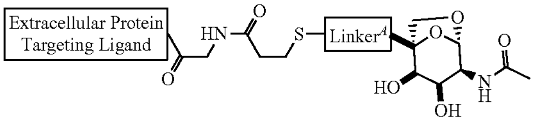

and

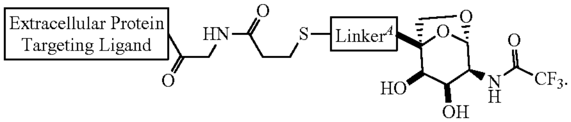

In certain embodiments the compound of the present invention is selected from:

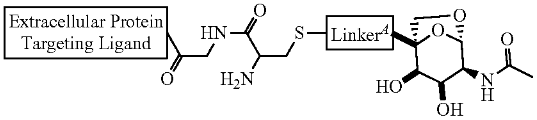

and

-continued

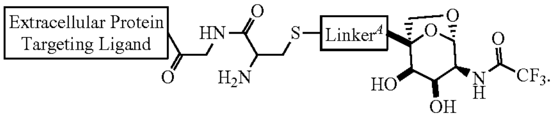

In certain embodiments the compound of the present invention is selected from:

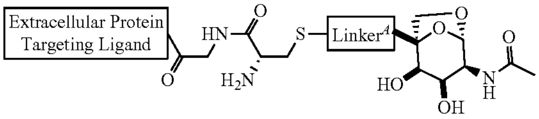

and

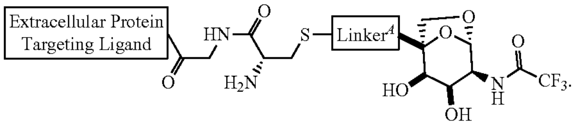

In certain embodiments the compound of the present invention is selected from:
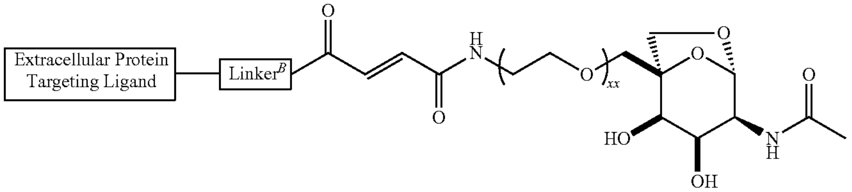
and
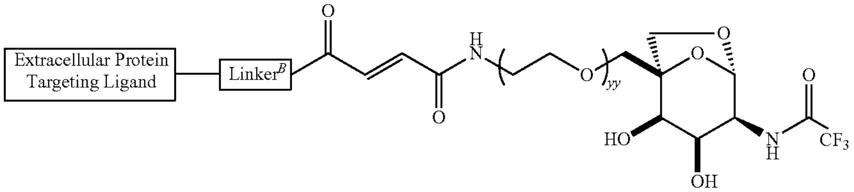
In certain embodiments the compound of the present invention is selected from:
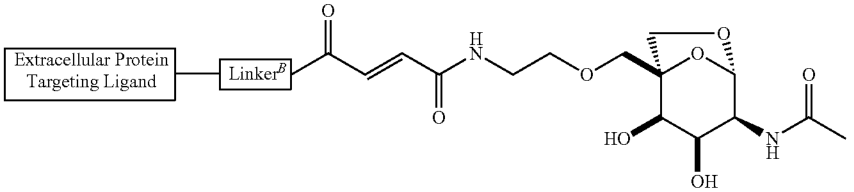
and
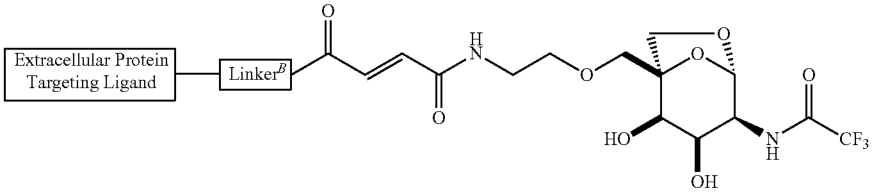
In certain embodiments the compound of the present invention is selected from:
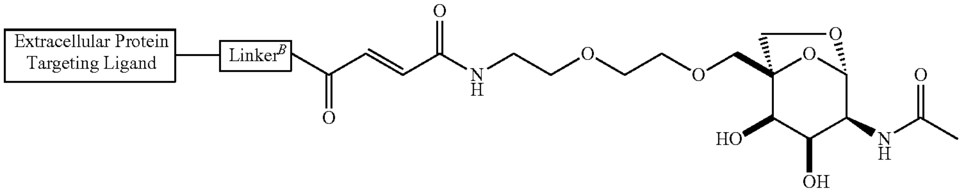
and
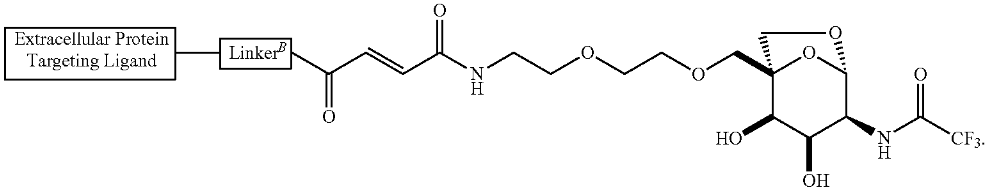

In certain embodiments the compound of the present invention is selected from:
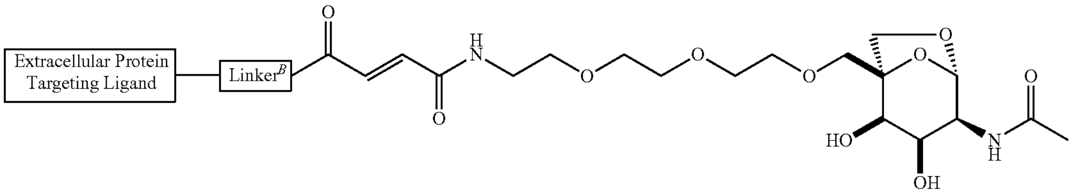
and
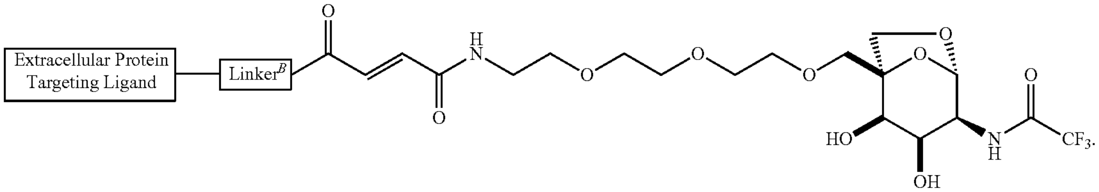
In certain embodiments the compound of the present invention is selected from:
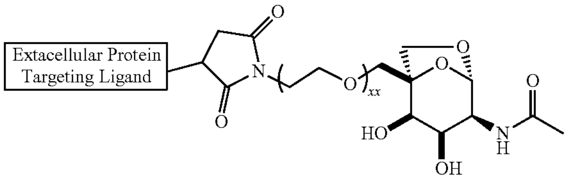
In certain embodiments the compound of the present invention is selected from:
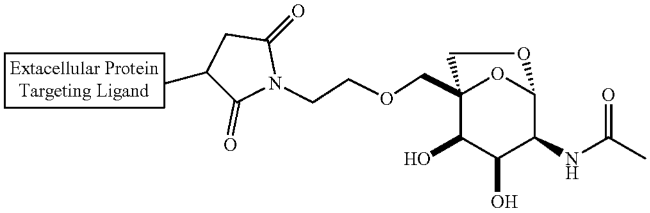
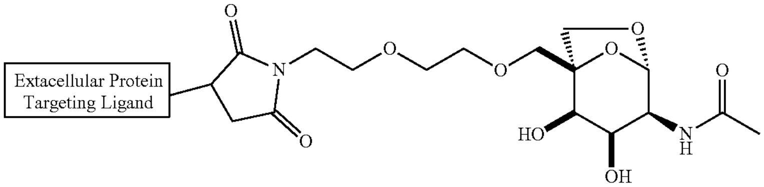
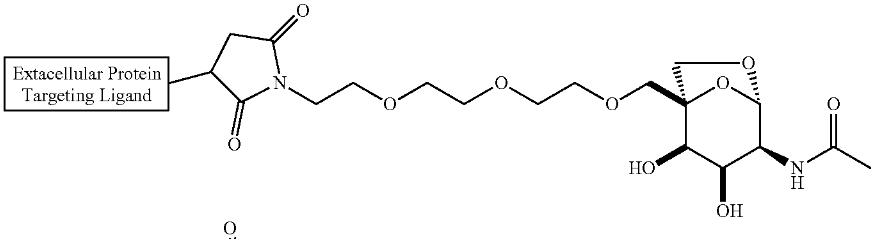
and
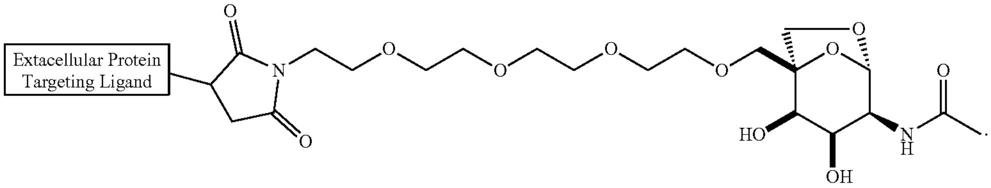

In certain embodiments the compound of the present invention is selected from:
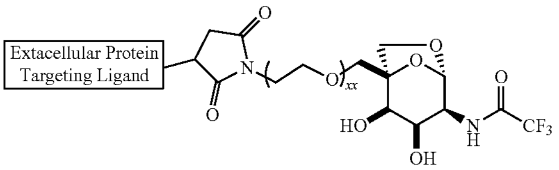
In certain embodiments the compound of the present invention is selected from:
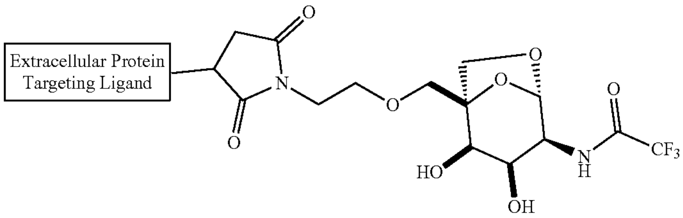
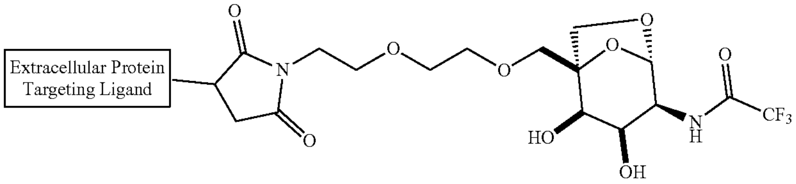
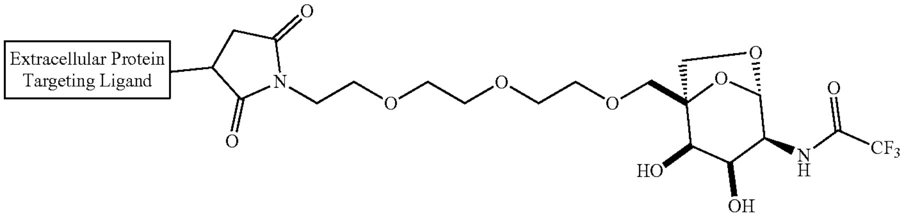
and
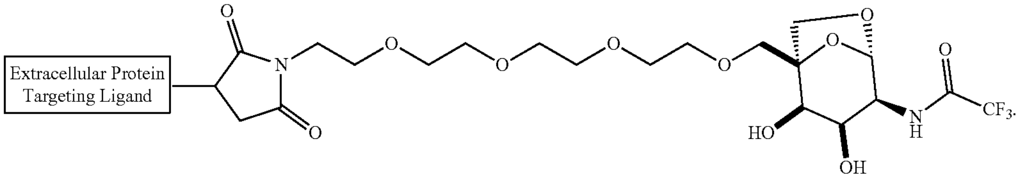
In certain embodiments the compound of the present invention is selected from:
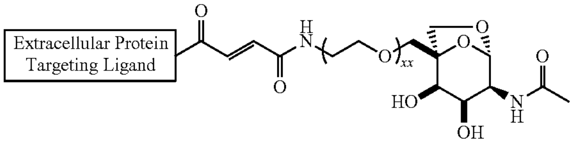

In certain embodiments the compound of the present invention is selected from:
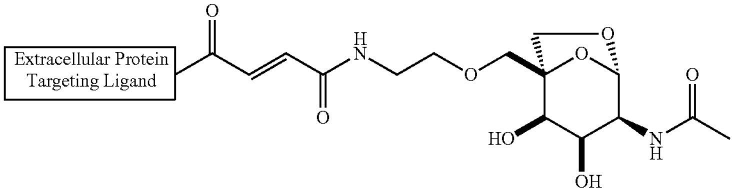
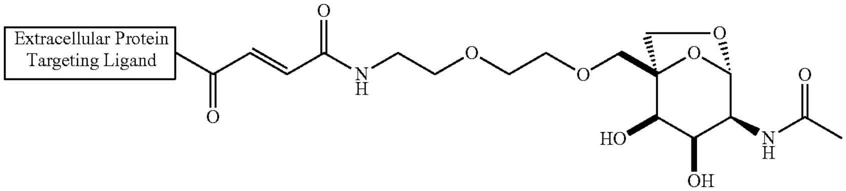
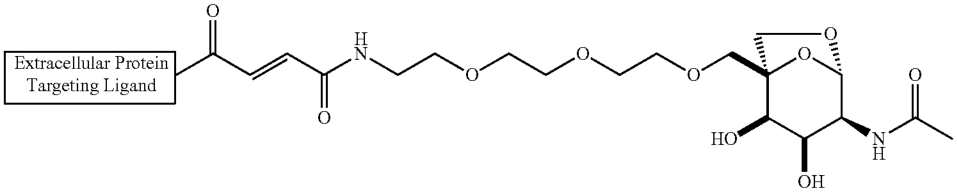
and
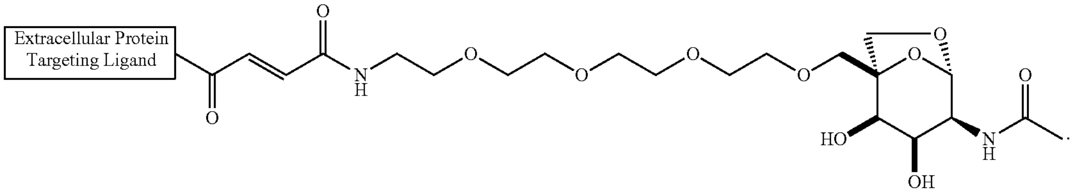
In certain embodiments the compound of the present invention is selected from:
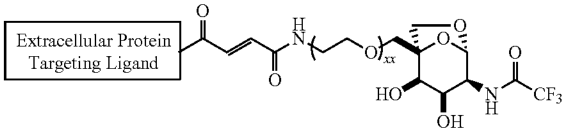
In certain embodiments the compound of the present invention is selected from:
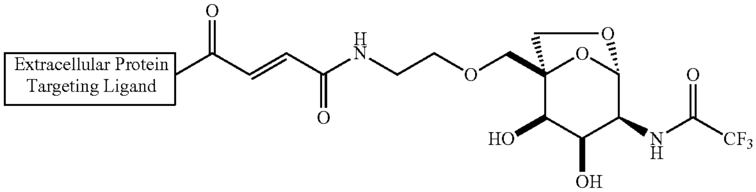
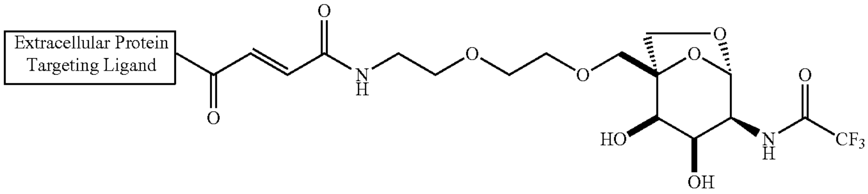

-continued
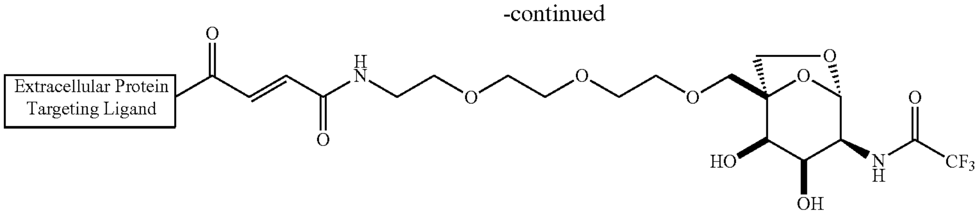
and
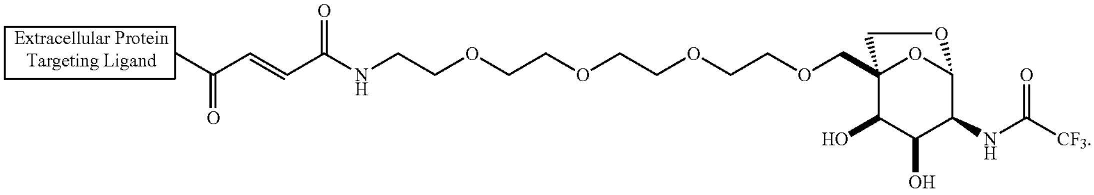
In certain embodiments the compound of the present invention is selected from:
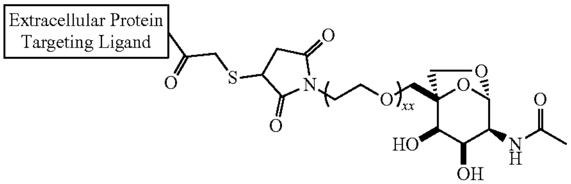
In certain embodiments the compound of the present invention is selected from:
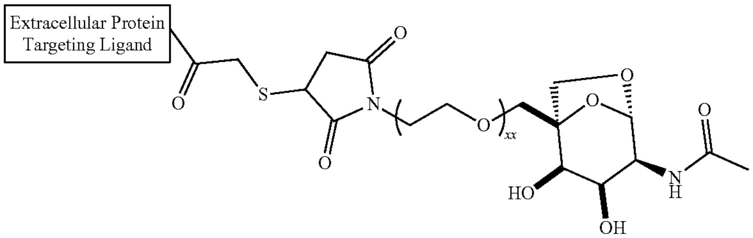
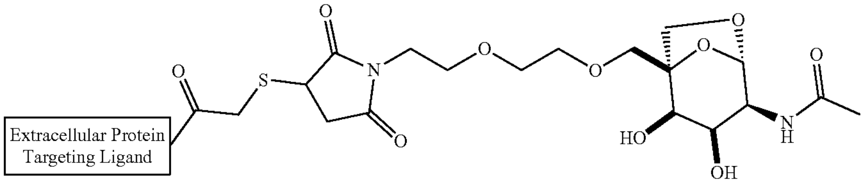
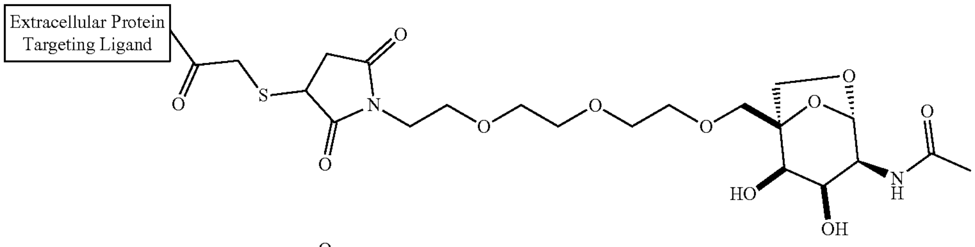
and
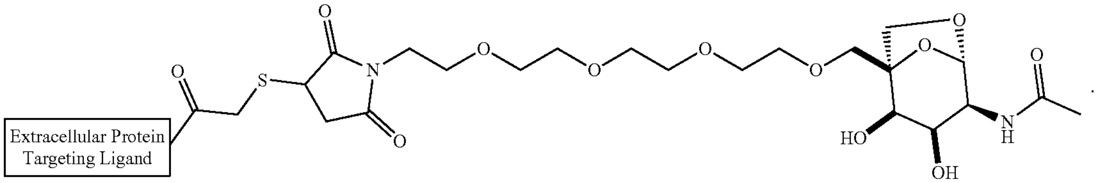

In certain embodiments the compound of the present invention is selected from:
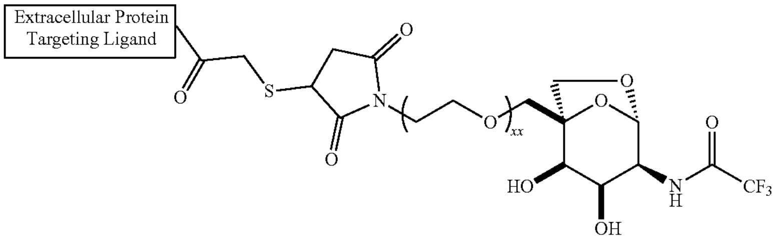
In certain embodiments the compound of the present invention is selected from:
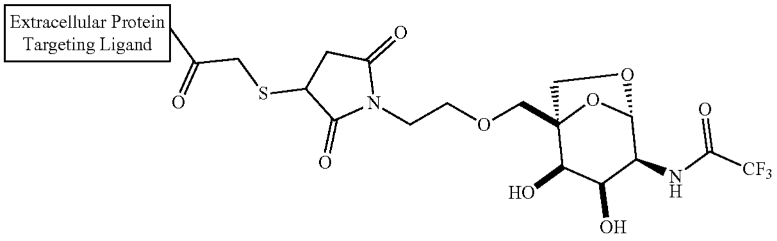
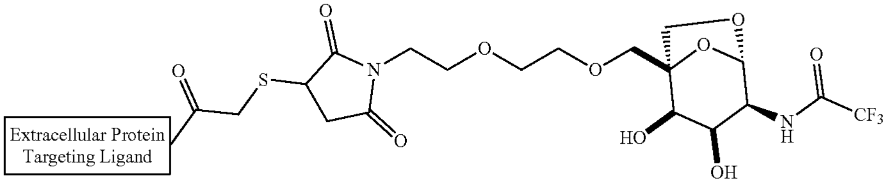
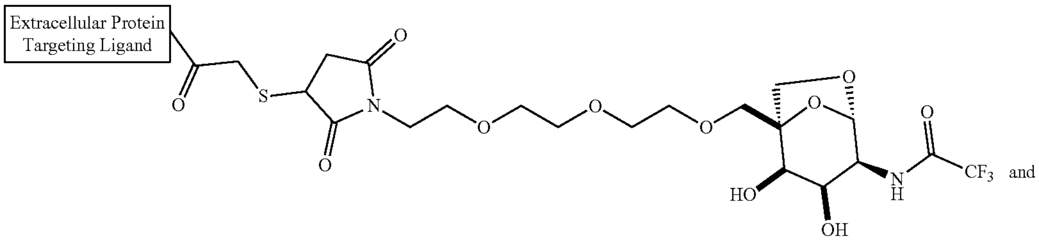
and
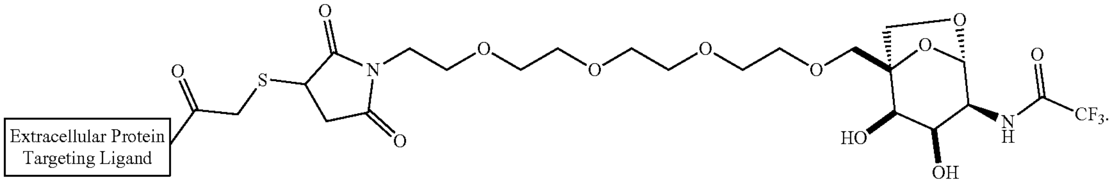

In certain embodiments the compound of the present invention is selected from:
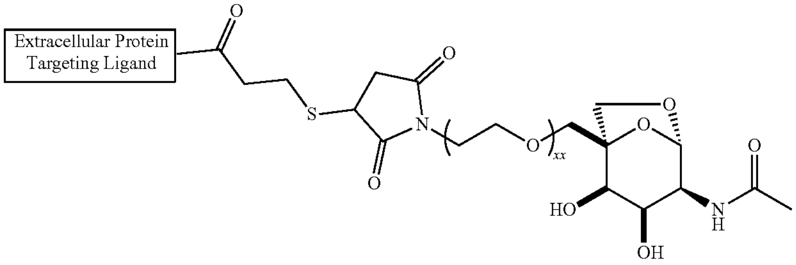
In certain embodiments the compound of the present invention is selected from:
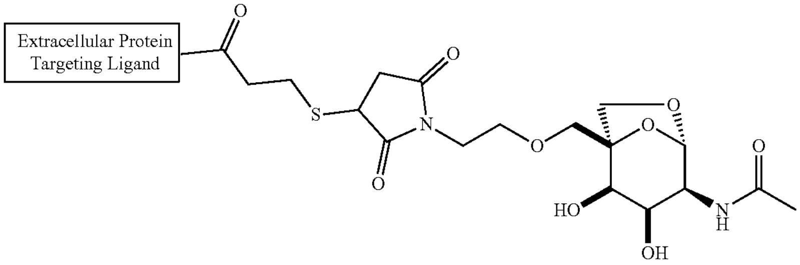
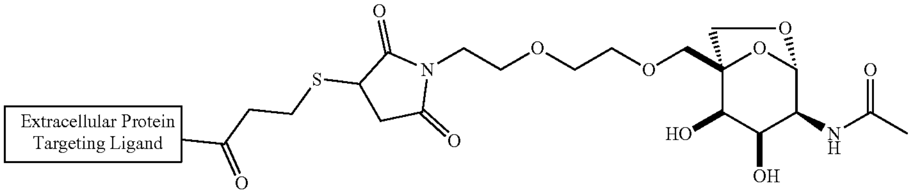
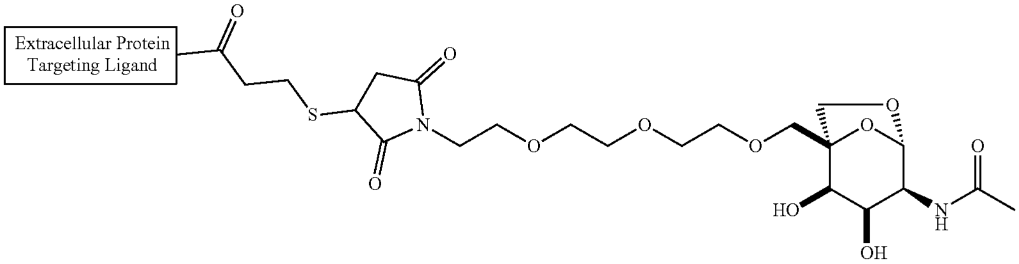
and
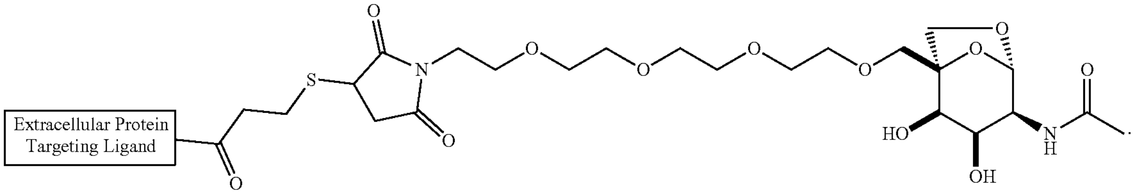
.

In certain embodiments the compound of the present invention is selected from:
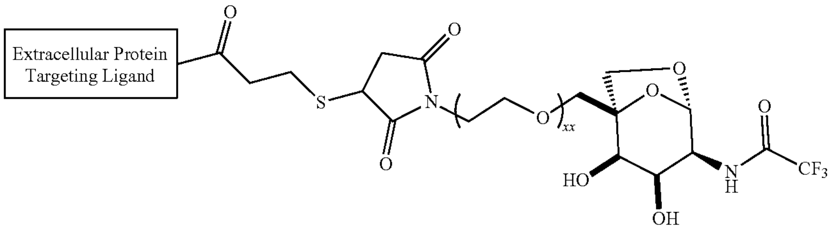
In certain embodiments the compound of the present invention is selected from:
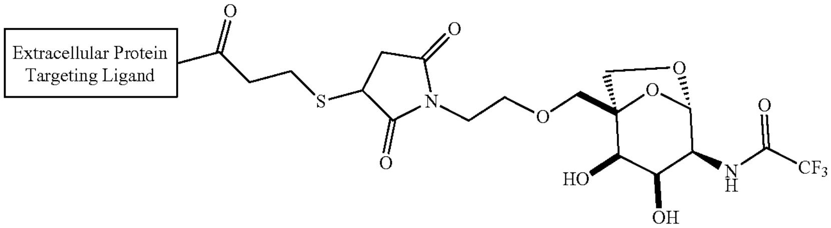
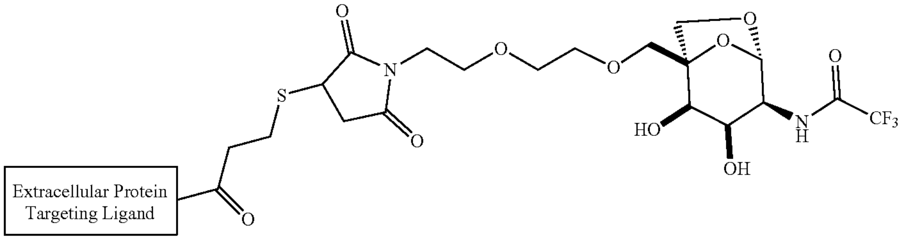
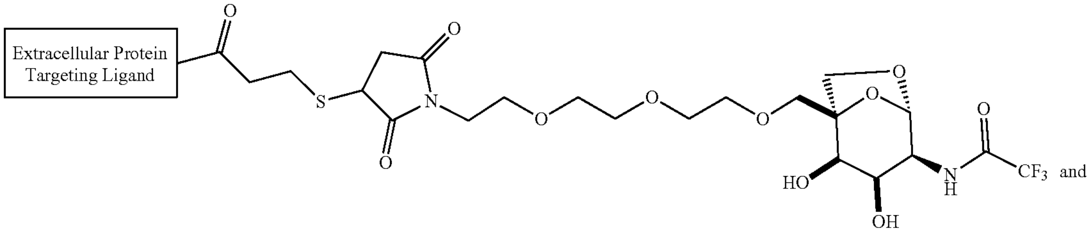
and
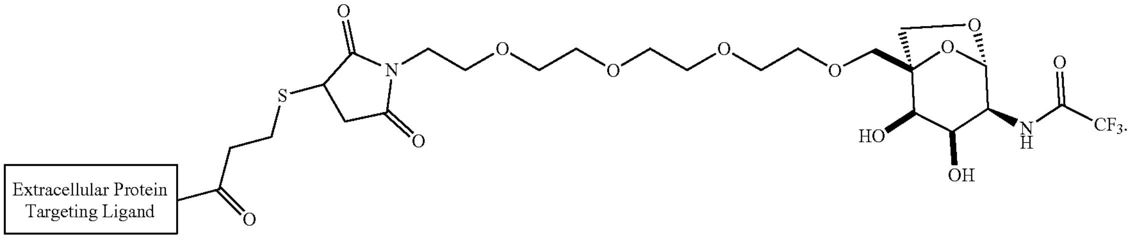

In certain embodiments the compound of the present invention is selected from:
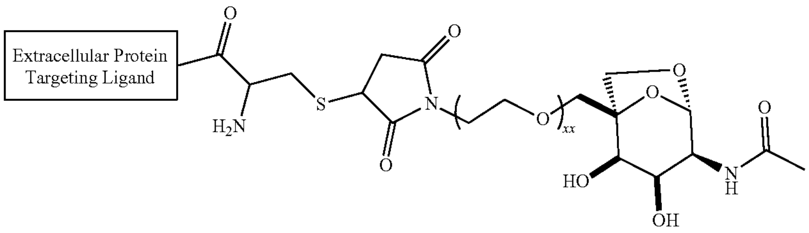
In certain embodiments the compound of the present invention is selected from:
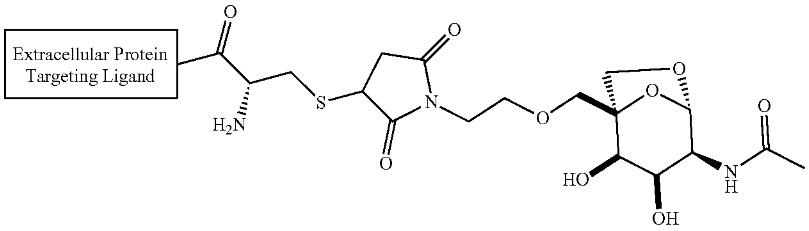
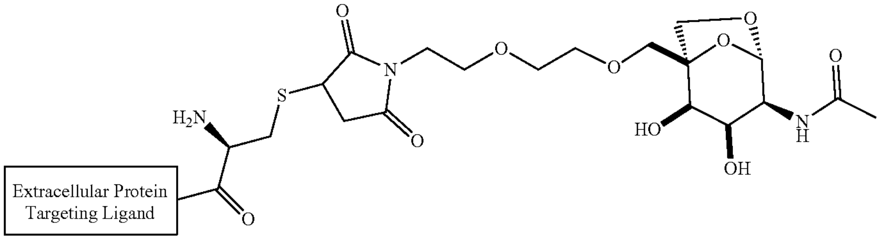
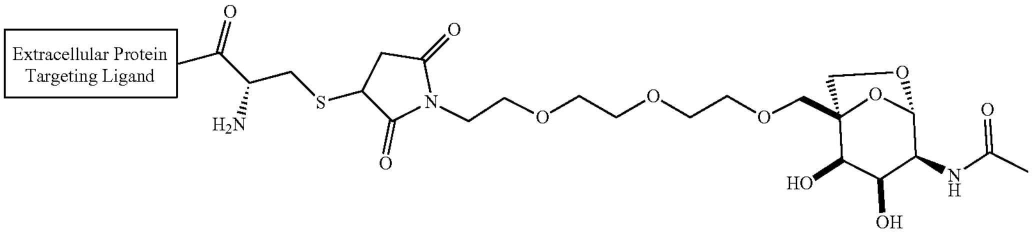
and
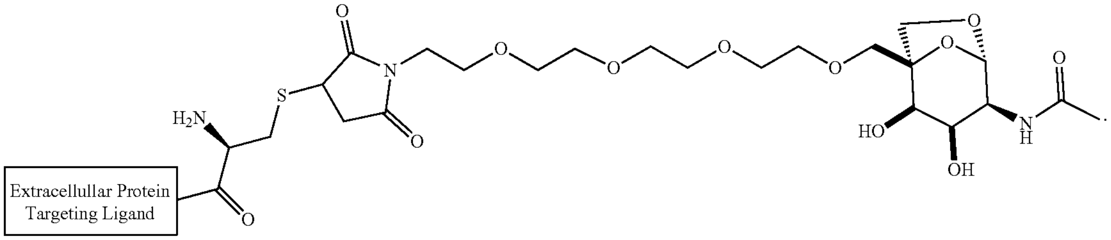

In certain embodiments the compound of the present invention is selected from:
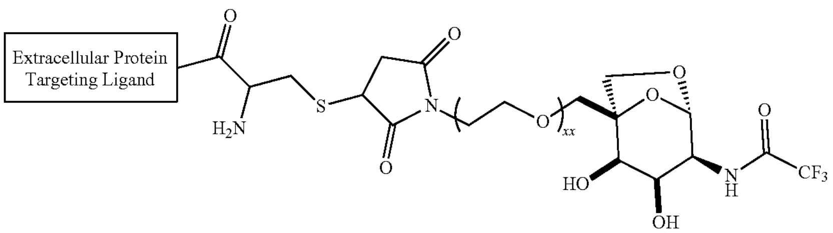
In certain embodiments the compound of the present invention is selected from:
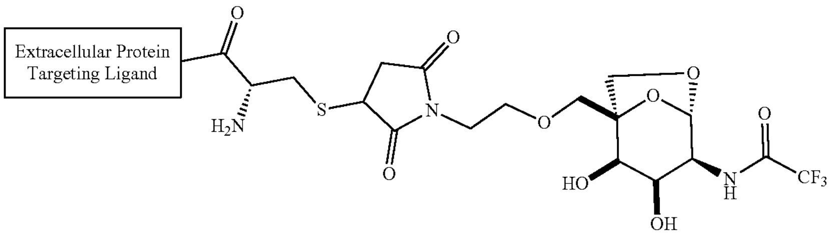
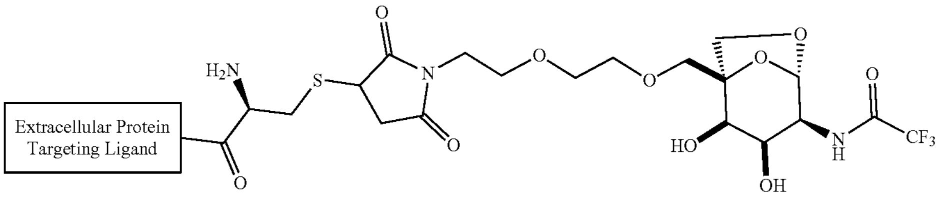
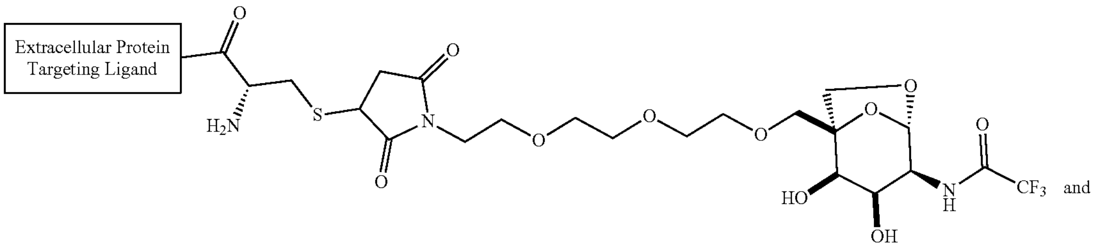
and
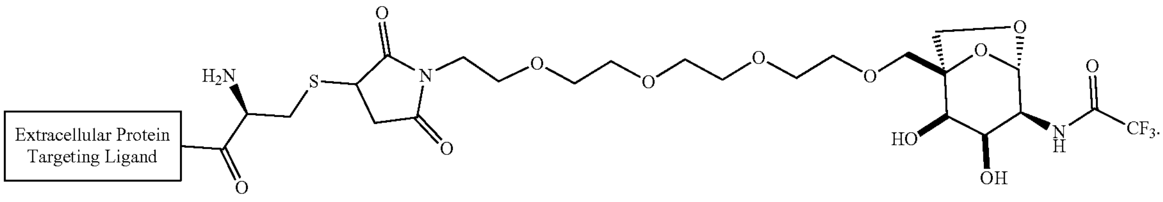

In certain embodiments the compound of the present invention is selected from:
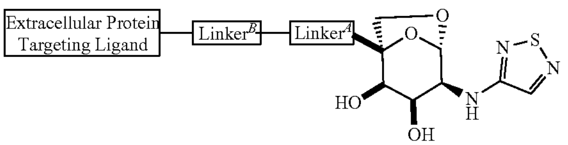
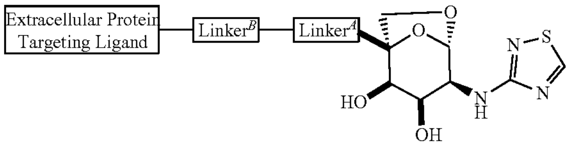
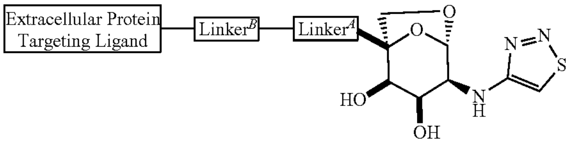
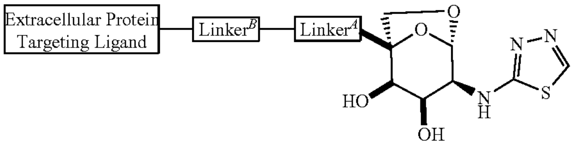
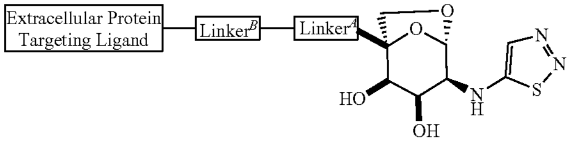
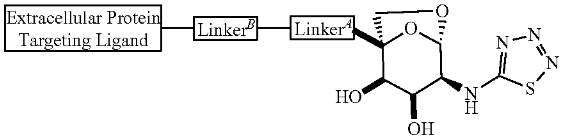
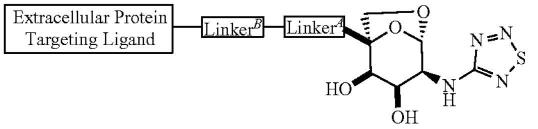
and
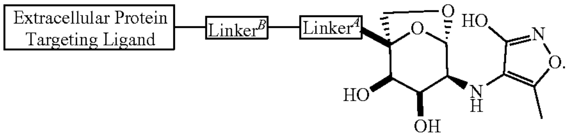
In certain embodiments the compound of the present invention is selected from:
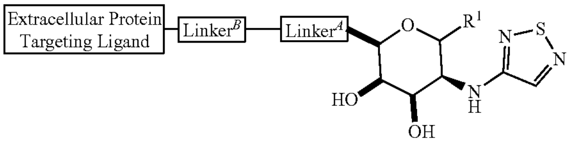
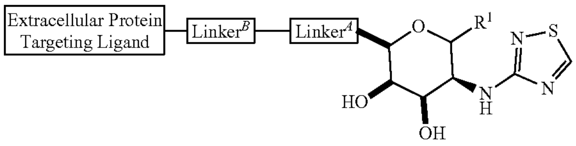
-continued
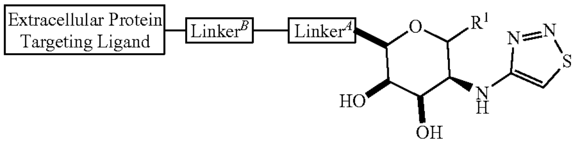
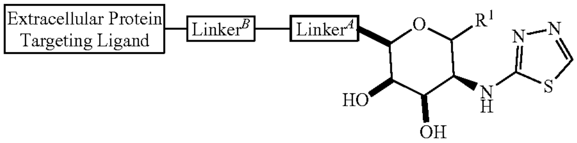
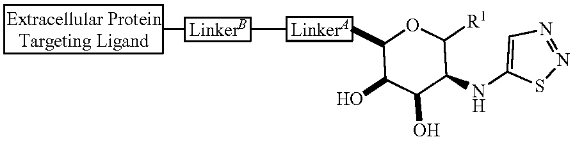
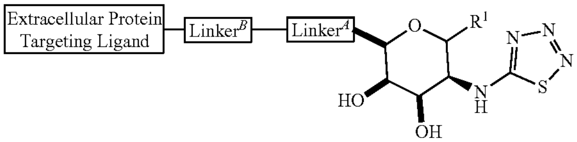
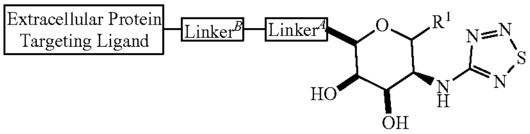
and
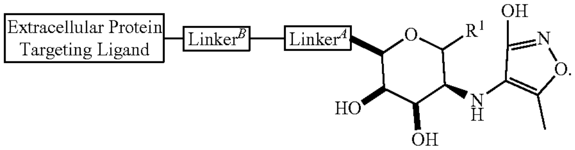
In certain embodiments the compound of the present invention is selected from:
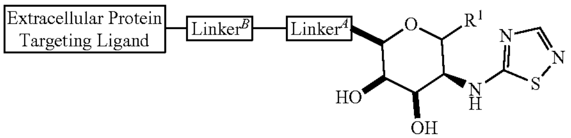
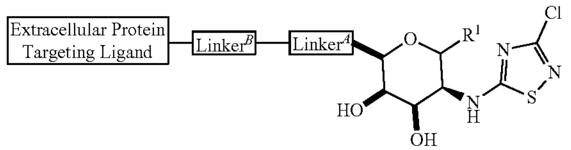
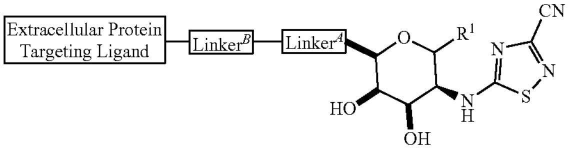
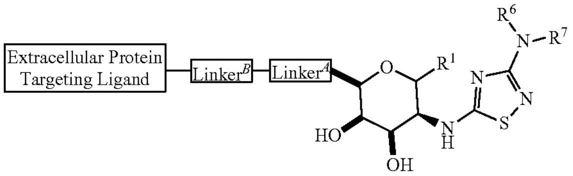

-continued
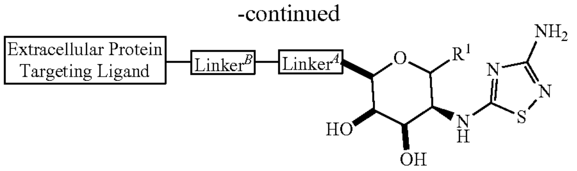
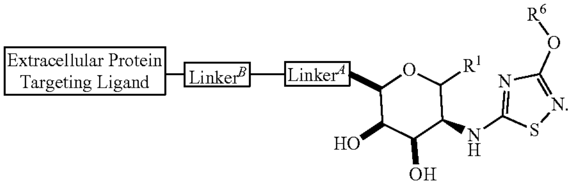
In certain embodiments the compound of the present invention is selected from:
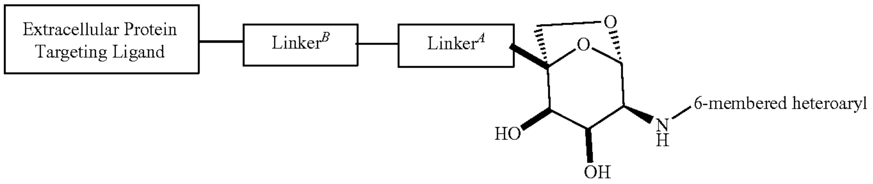
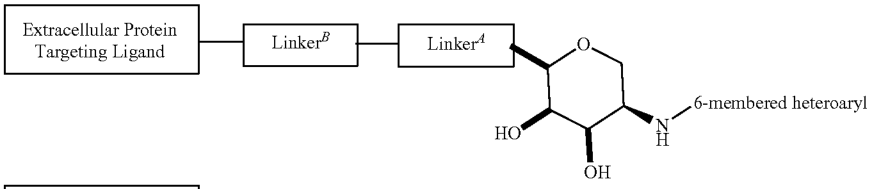
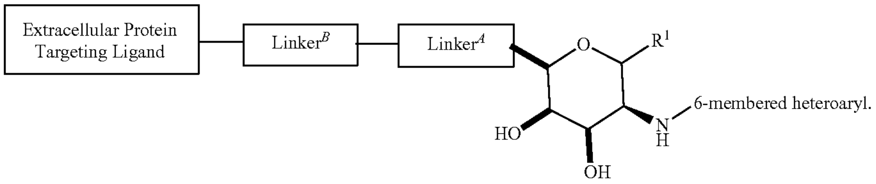
In certain embodiments the compound of the present invention is selected from:
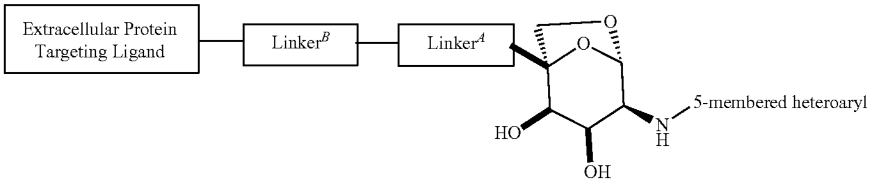
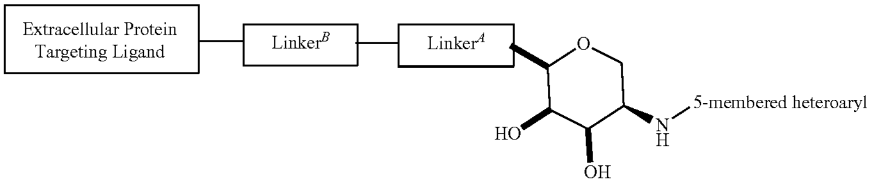
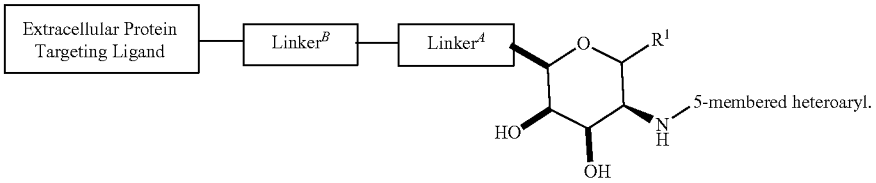

In certain embodiments the compound of the present invention is selected from:
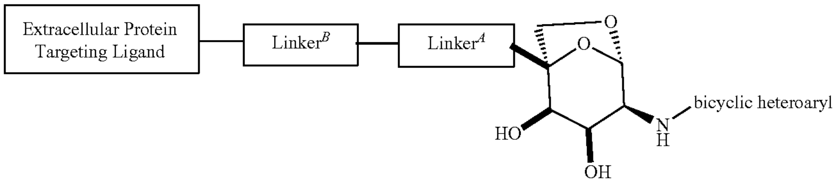
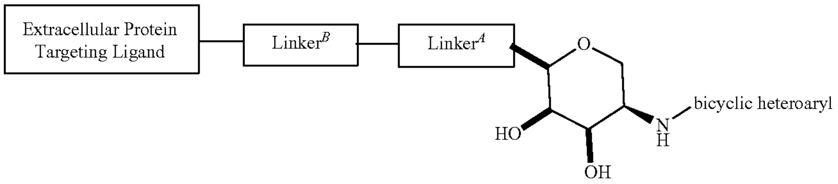
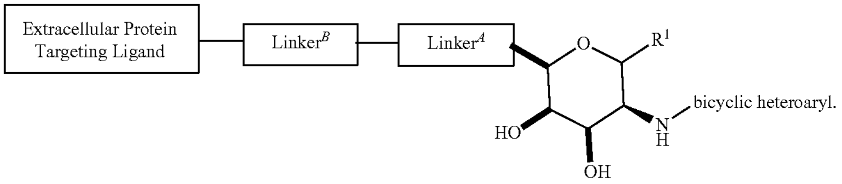
In certain embodiments the compound of the present invention is selected from:
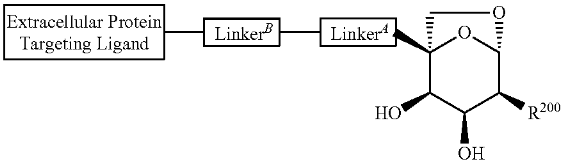
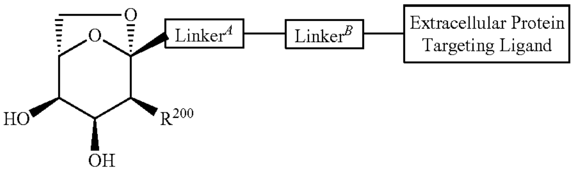
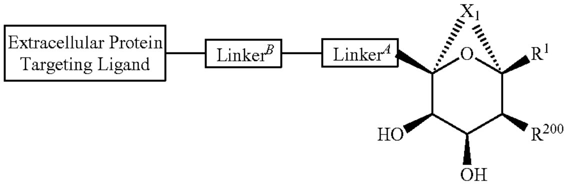
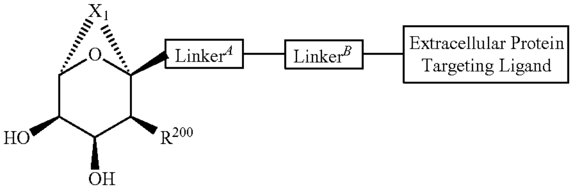
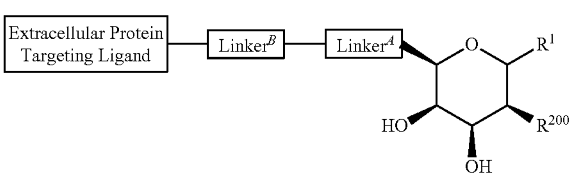
-continued
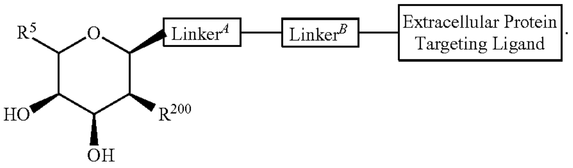
In certain embodiments the compound of the present invention is selected from:
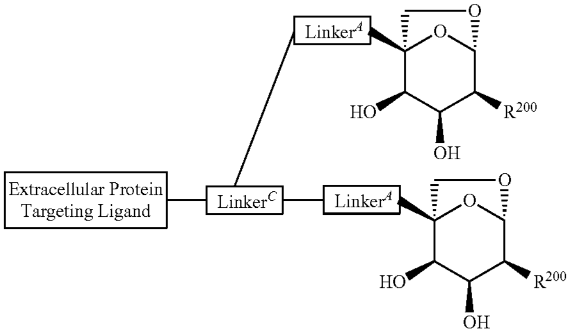
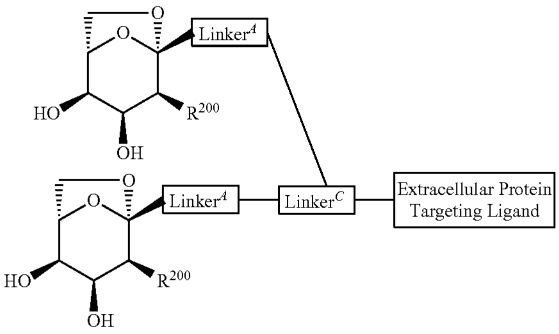

-continued
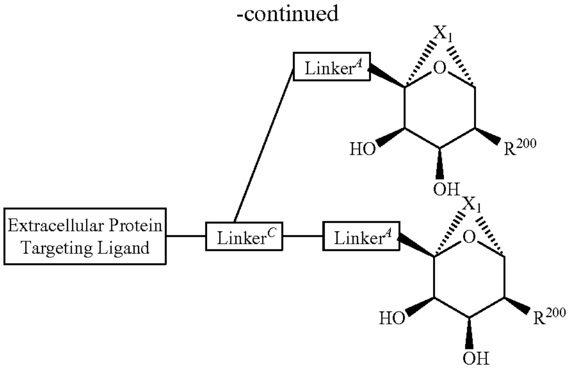
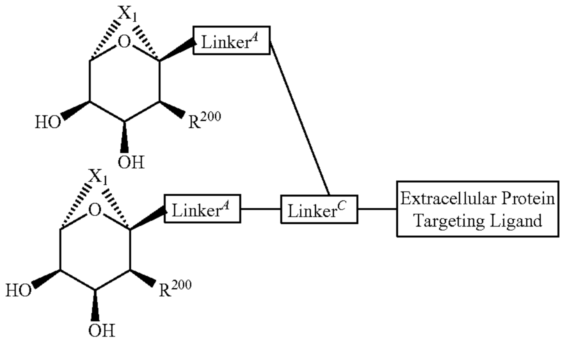
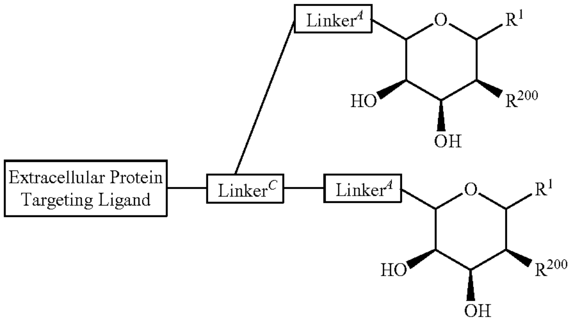
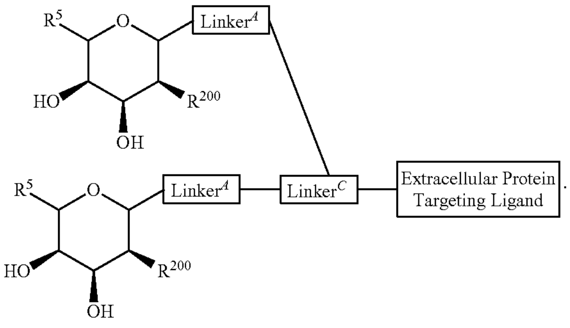
In certain embodiments the compound of the present invention is selected from:
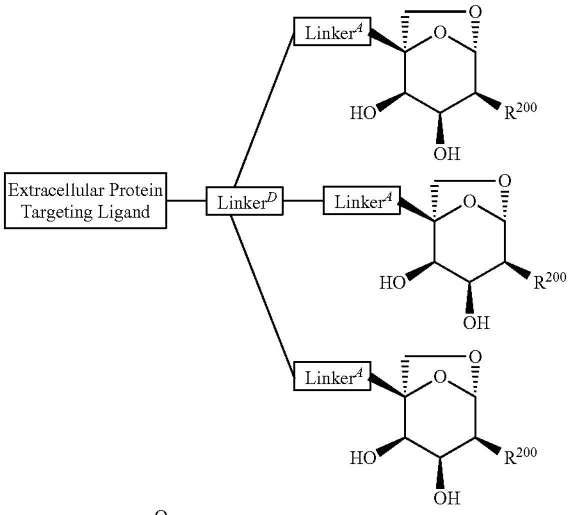
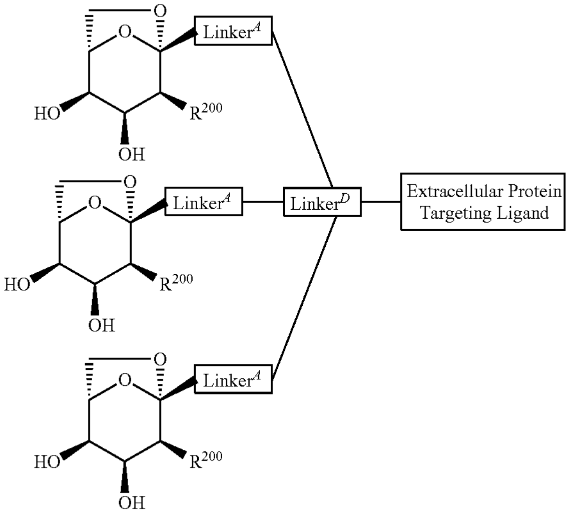
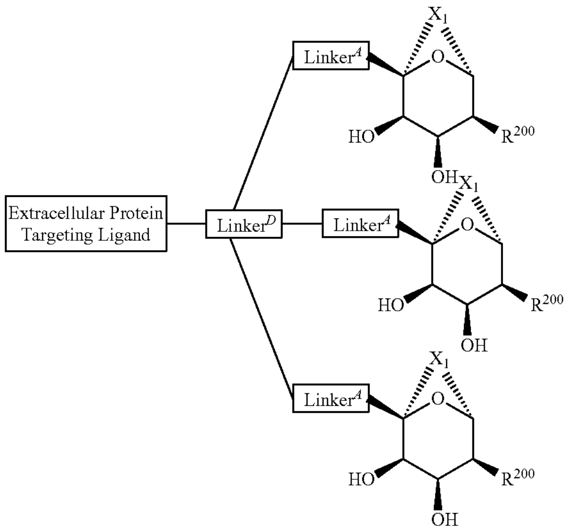

-continued
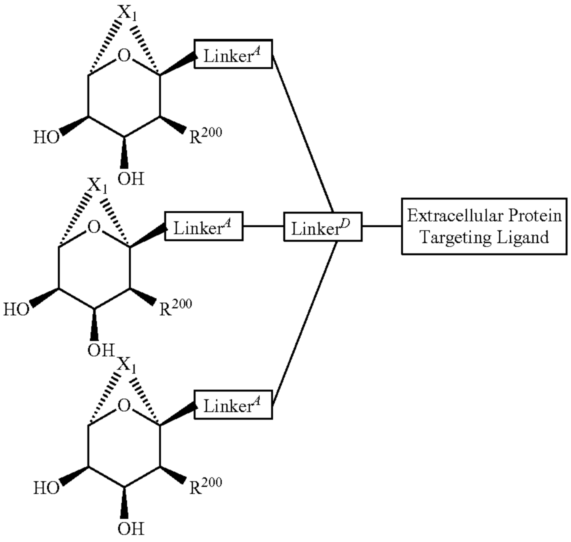
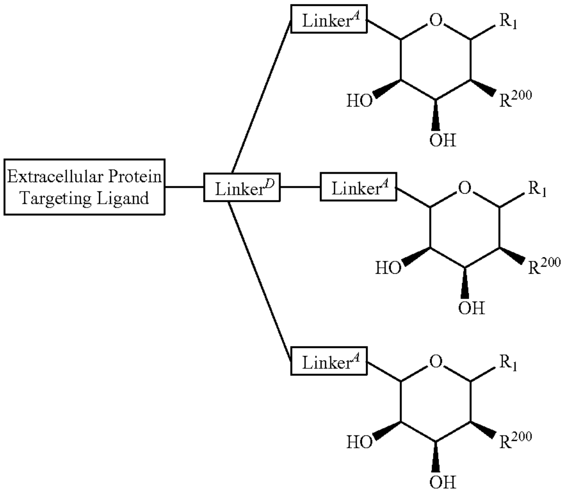
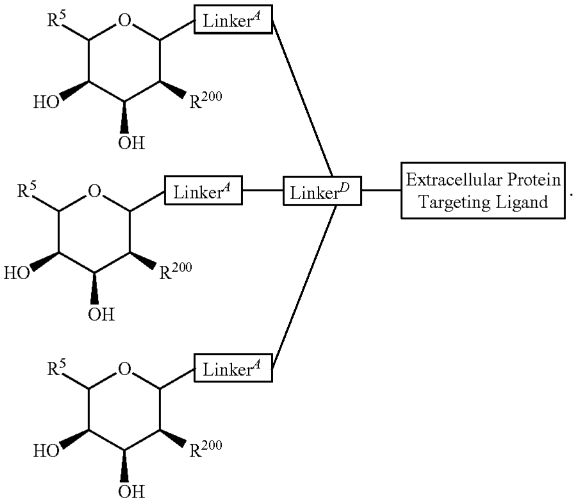
In one aspect of the present invention an Extracellular Protein degrading compound is provided wherein the ASGPR ligand is a ligand as described herein
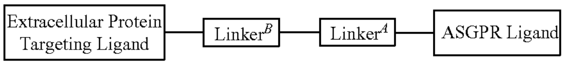
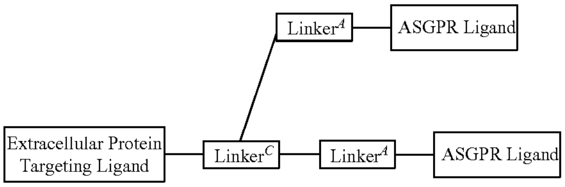
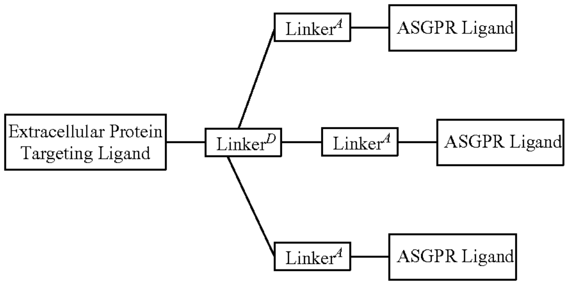
in this aspect the ASGPR ligand is linked in either the C1 or C5 ($R^1$ or $R^5$) position to form a degrading compound, for example, when the ASGPR ligand is
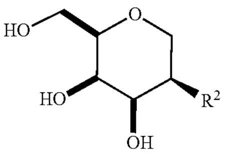

then non-limiting examples of ASGPR binding compounds contemplated by this aspect include:
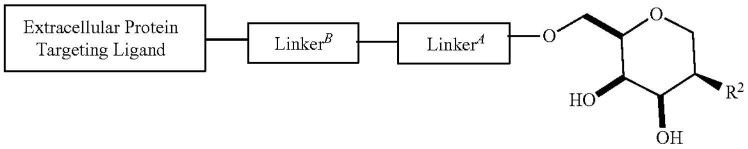
and
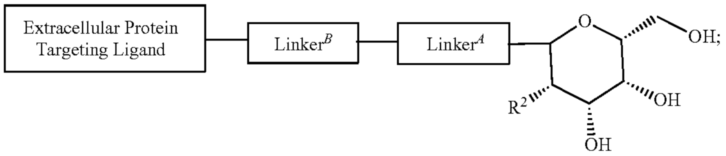
or the bi- or tri-version thereof or a pharmaceutically acceptable salt thereof.
In certain embodiments the compound of the present invention is selected from:
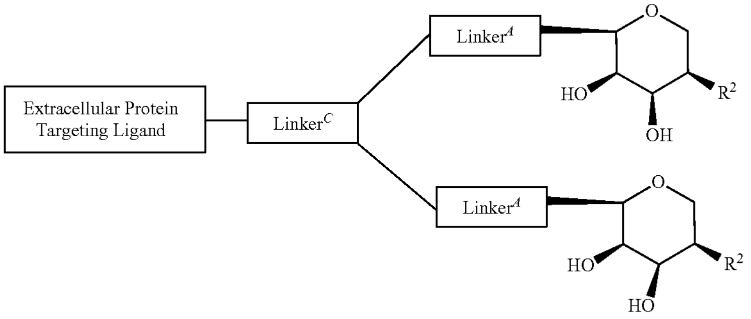
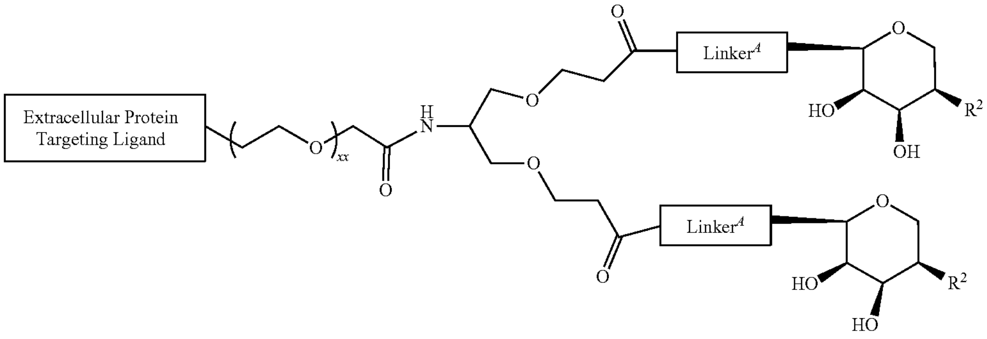
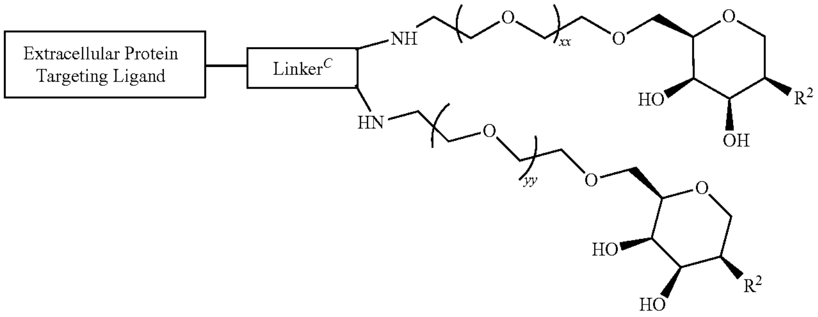
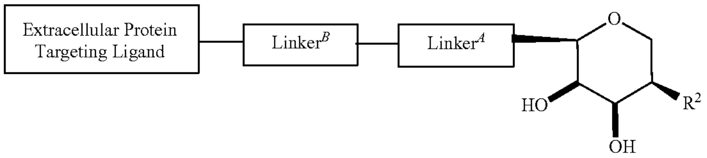

-continued

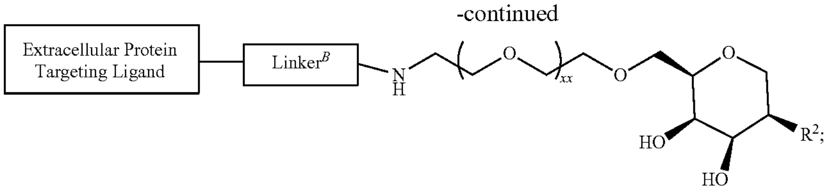

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:

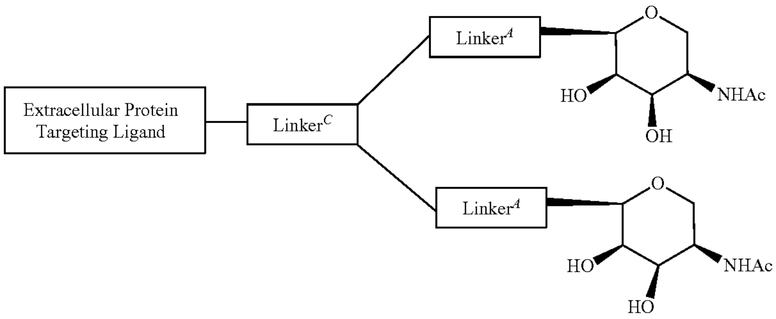

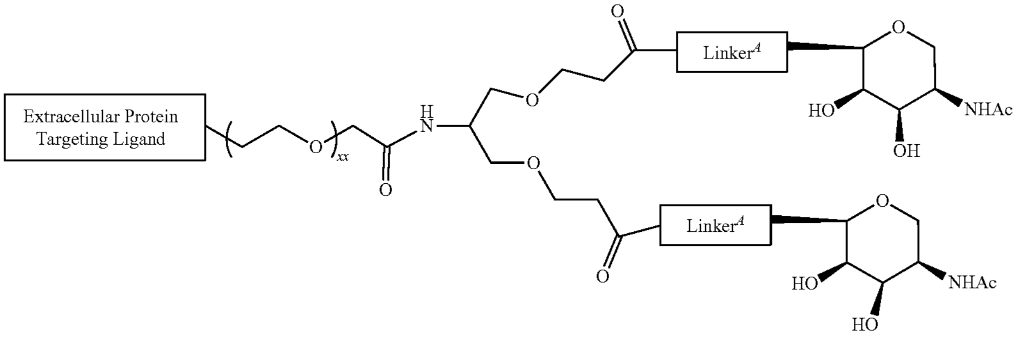

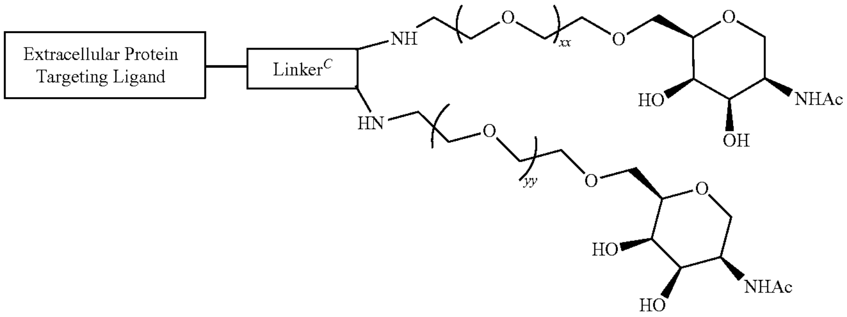

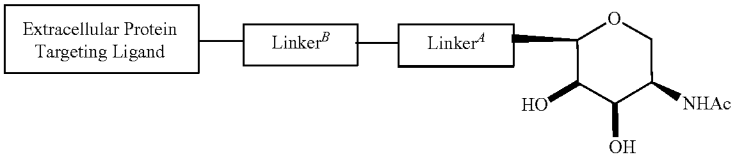

-continued
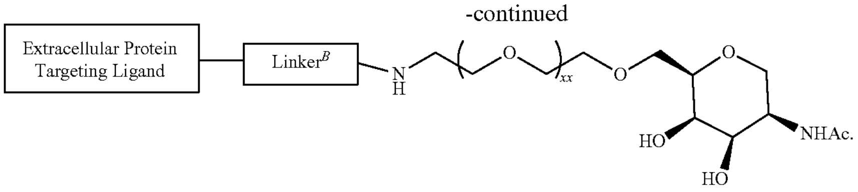
In certain embodiments the compound of the present invention is selected from:
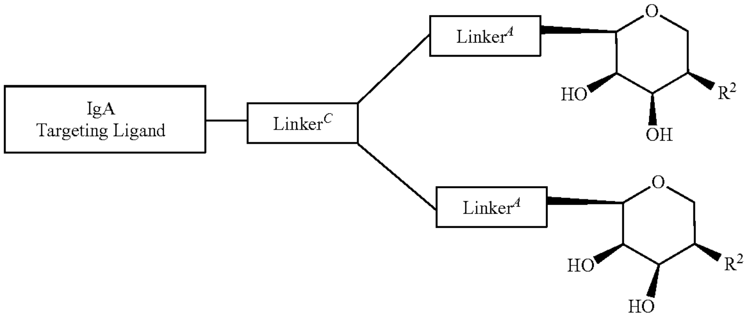
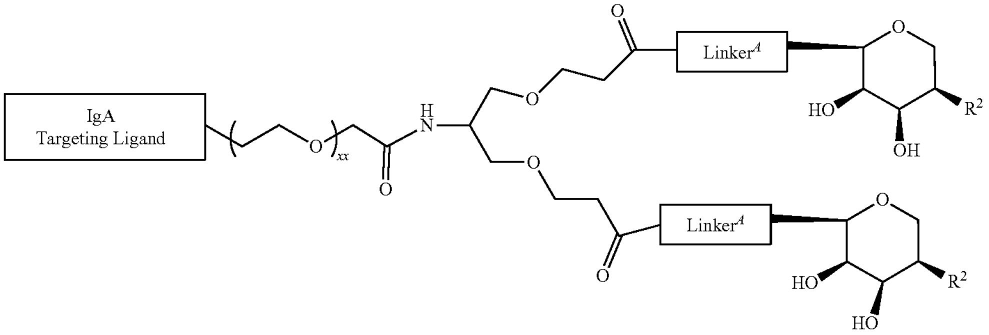
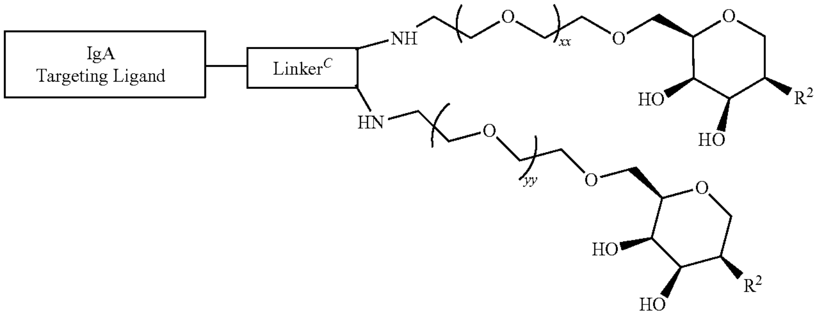
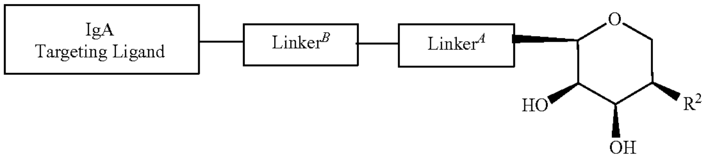
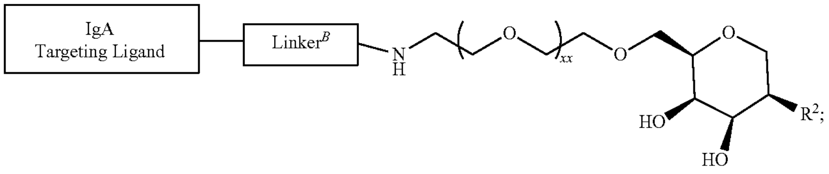

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:

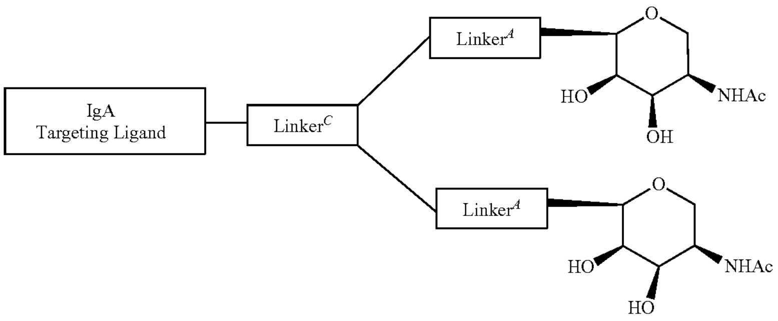

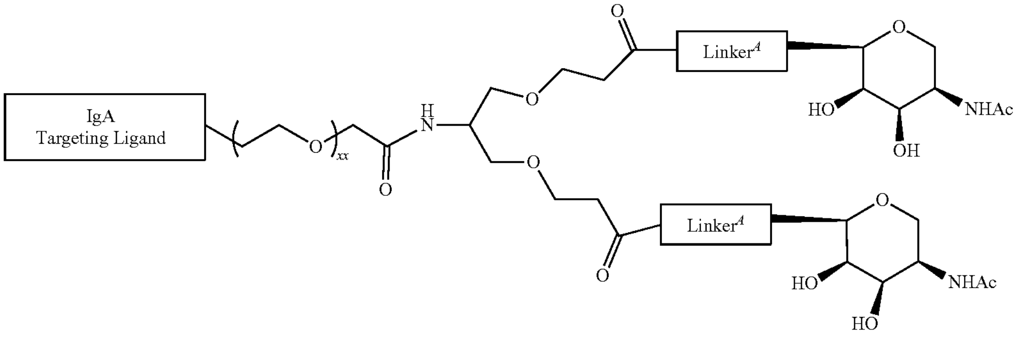

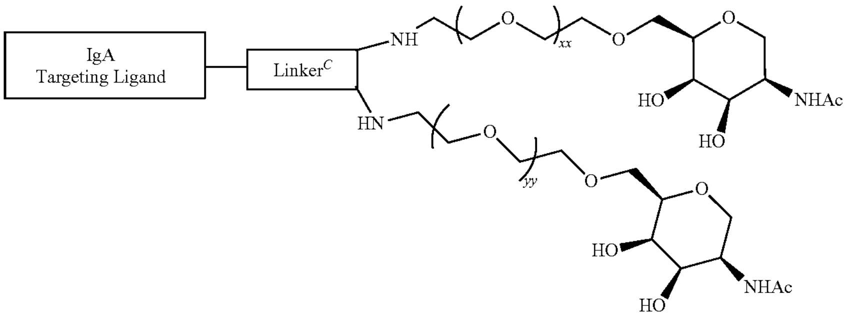

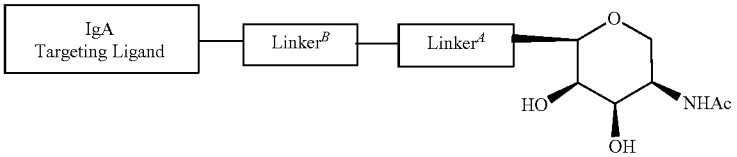

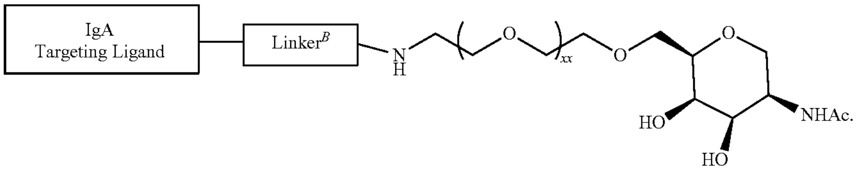

In certain embodiments the compound of the present invention is selected from:

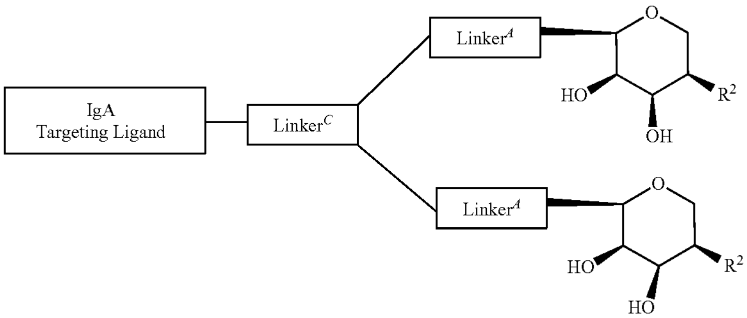

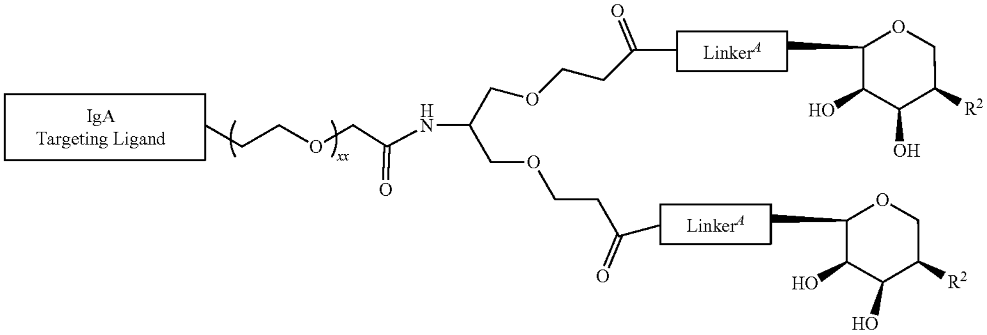

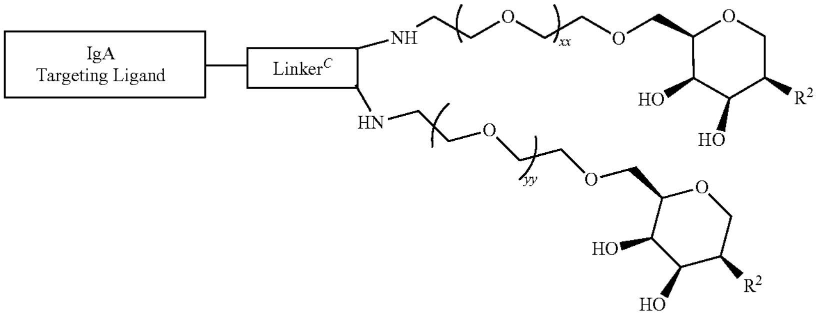

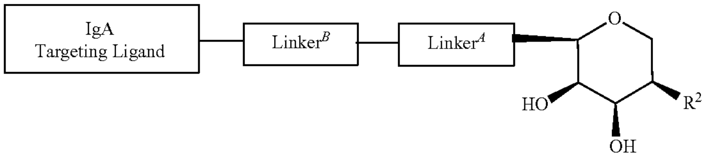

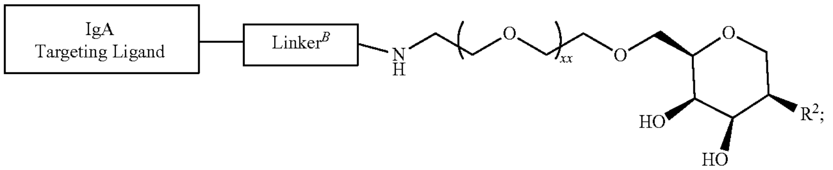

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
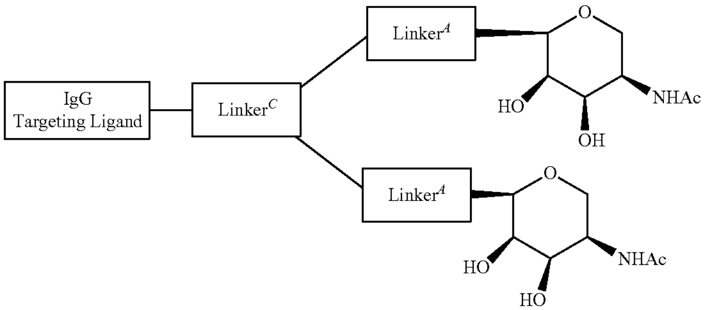
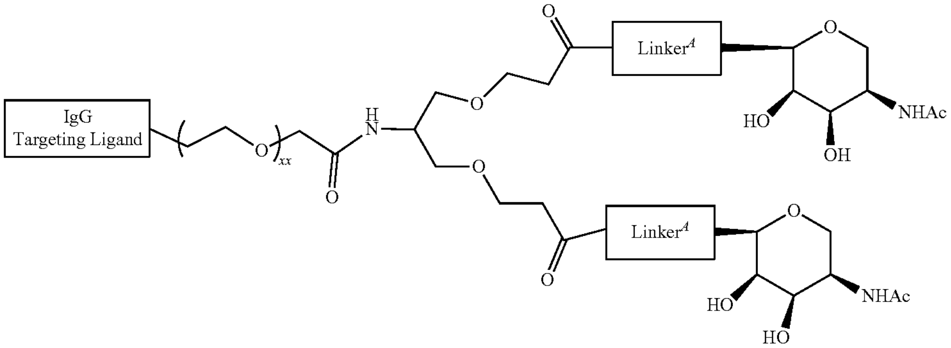
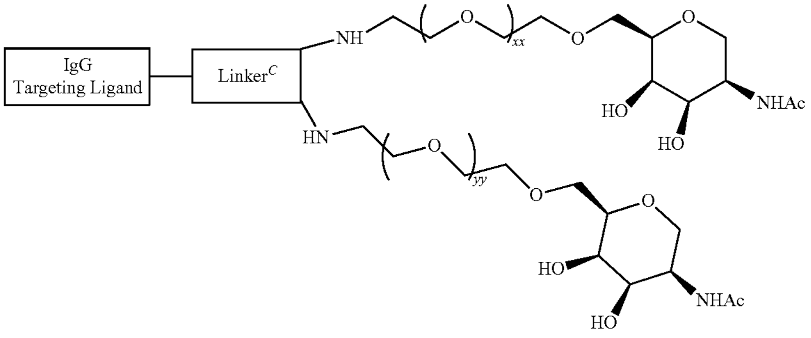
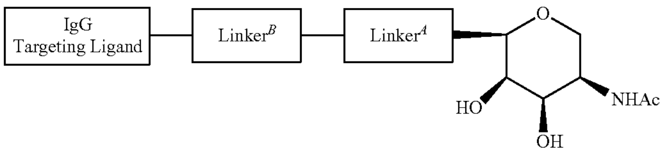
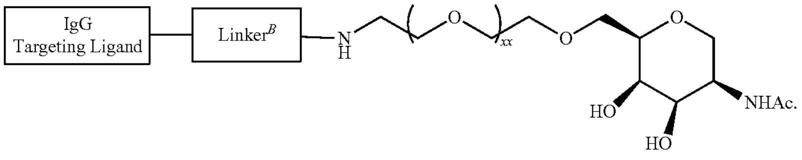

In certain embodiments the compound of the present invention is selected from:

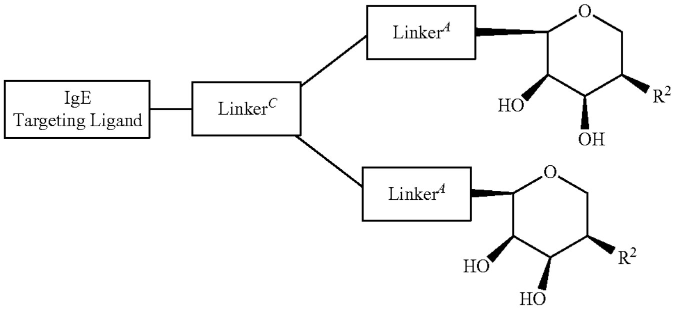

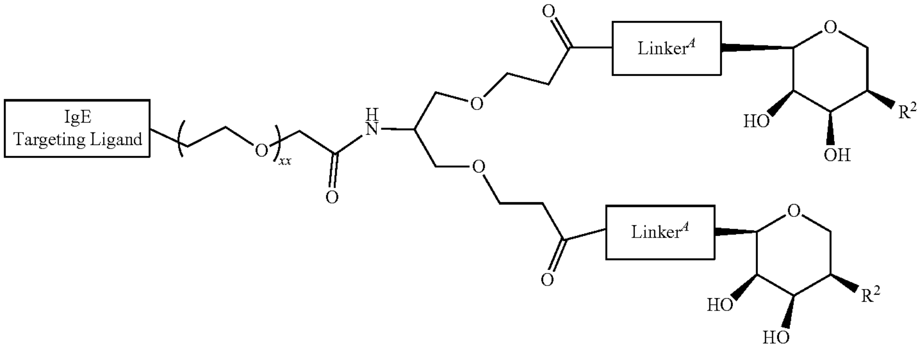

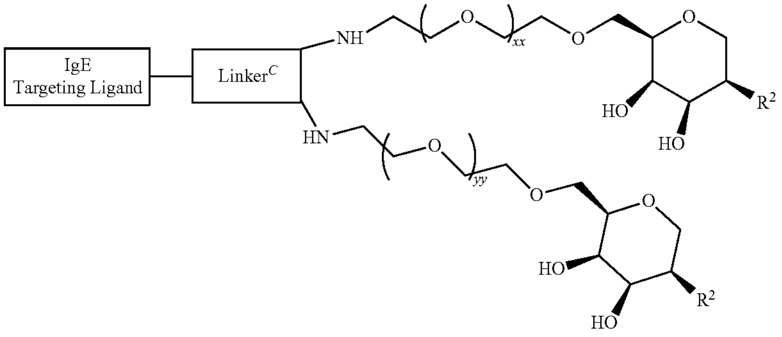

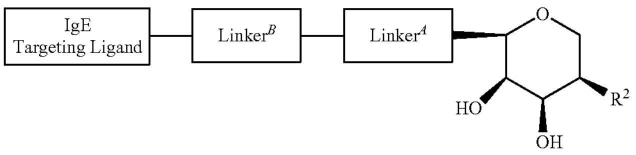

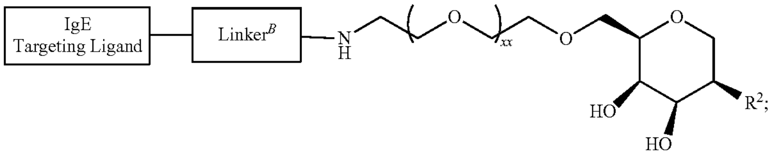

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
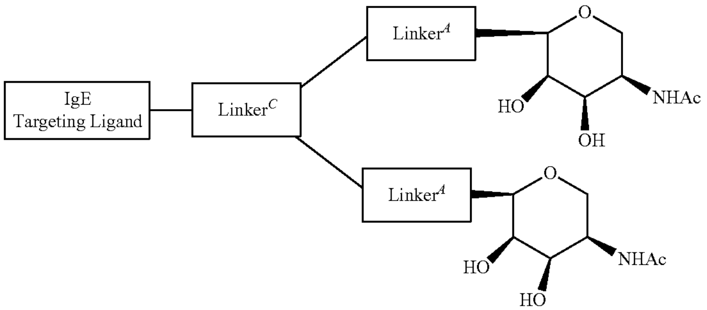
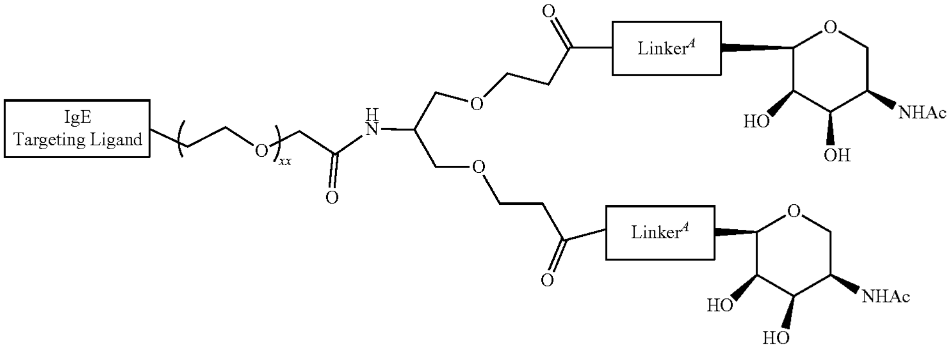
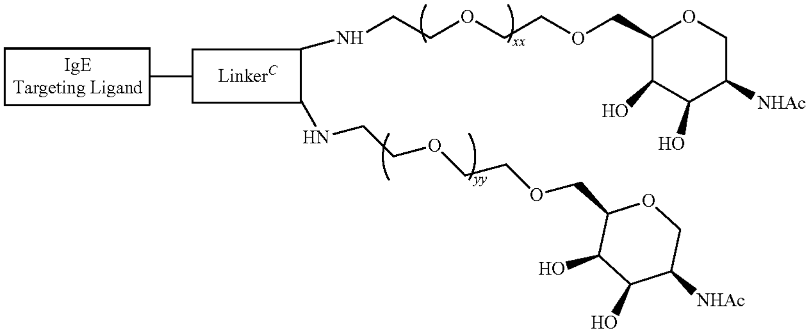
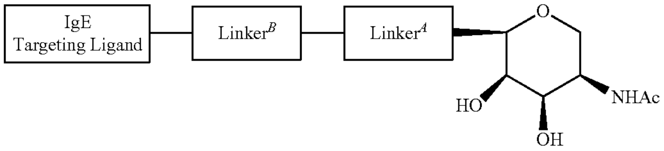
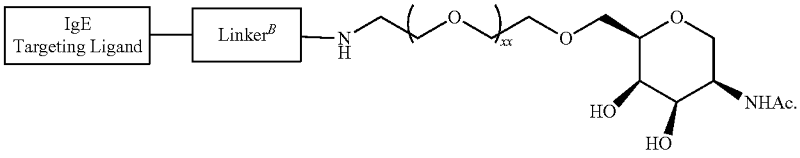

In certain embodiments the compound of the present invention is selected from:

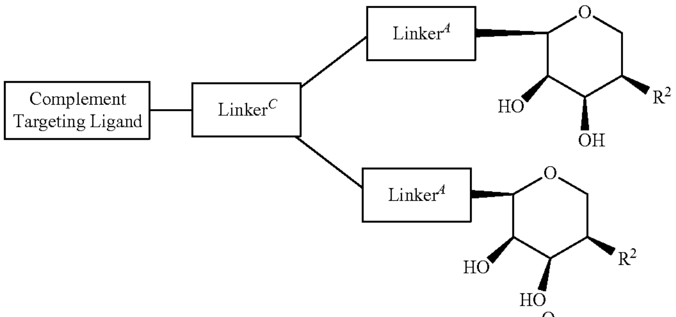

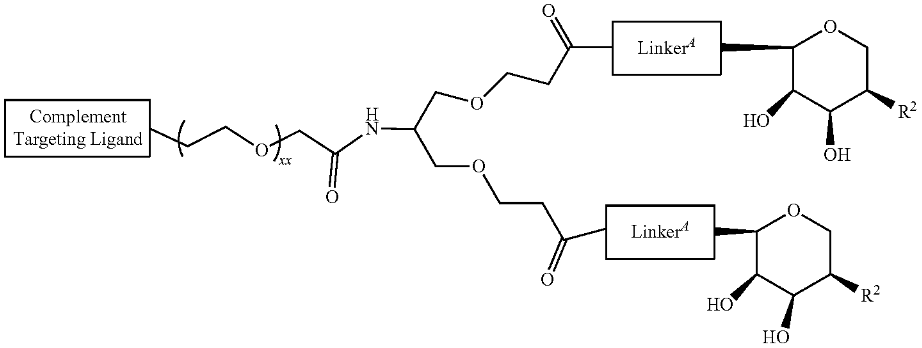

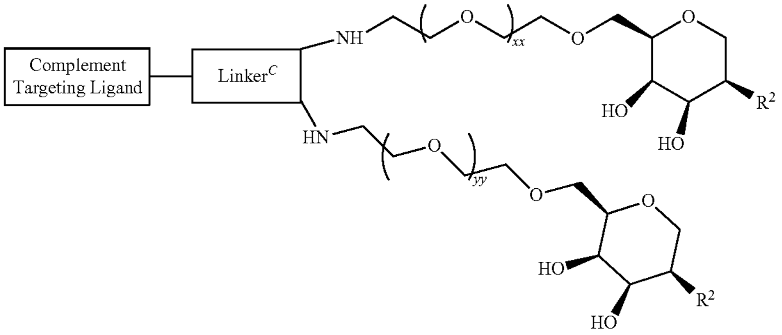

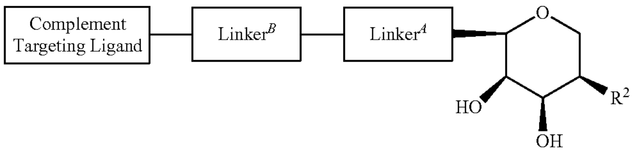

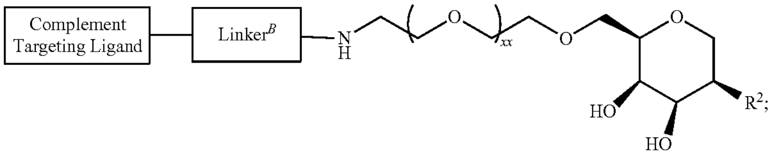

wherein in certain embodiments R is selected from —NR COW, —NR-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
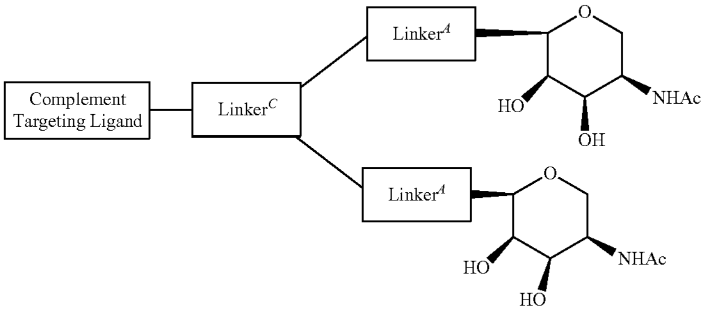
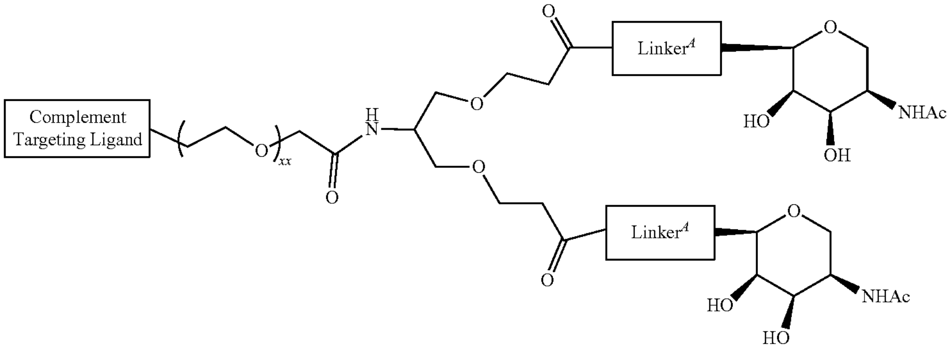
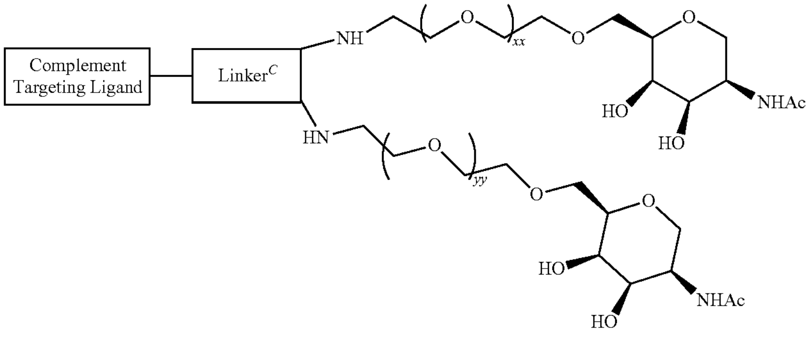
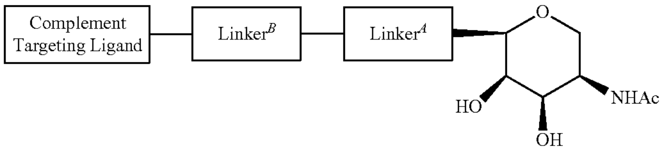
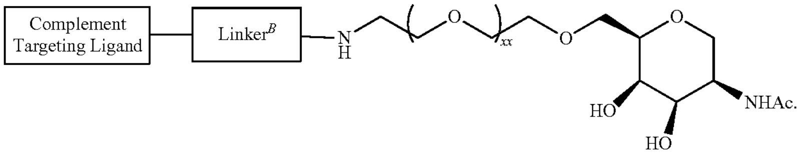

In certain embodiments the compound of the present invention is selected from:

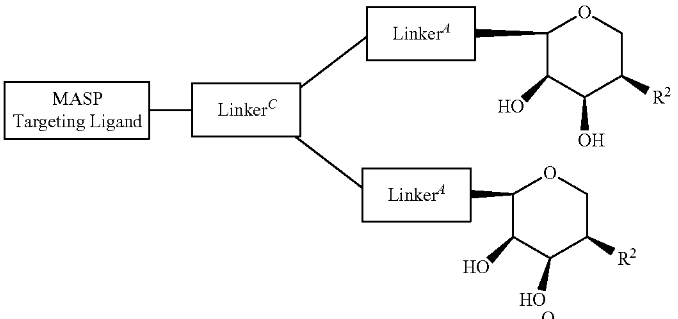

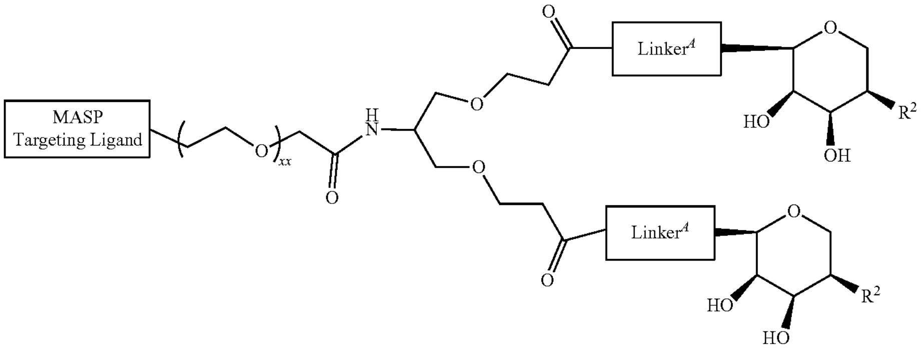

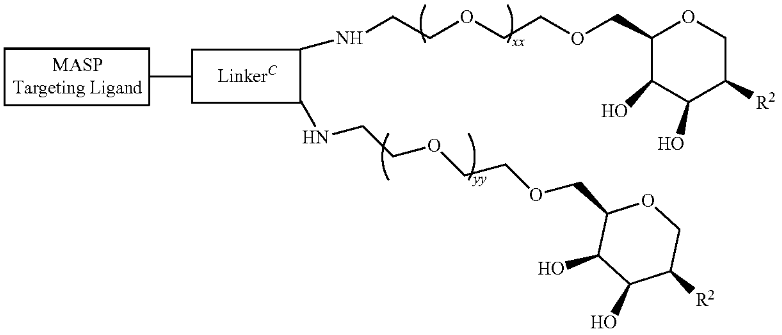

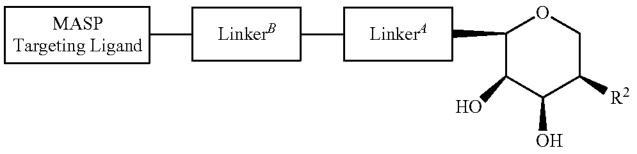

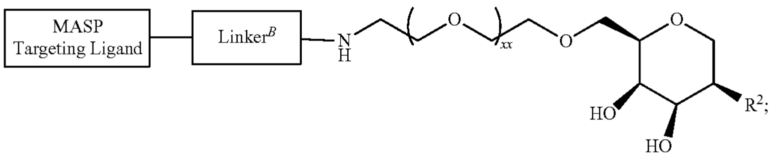

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
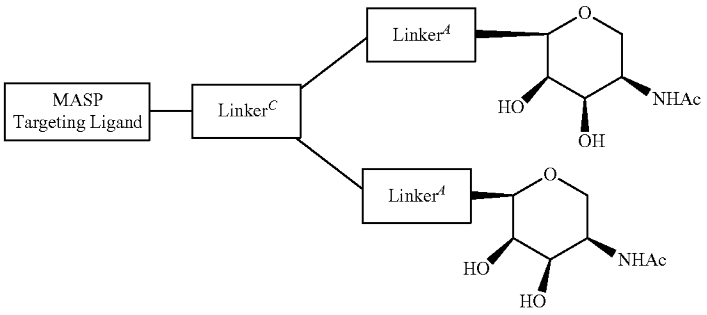
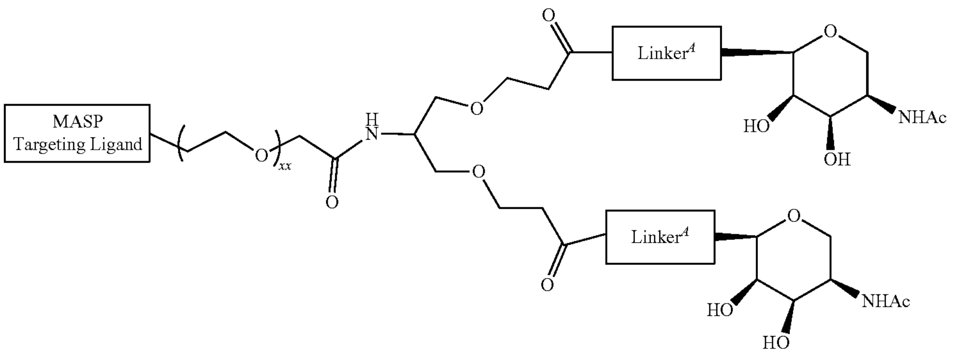
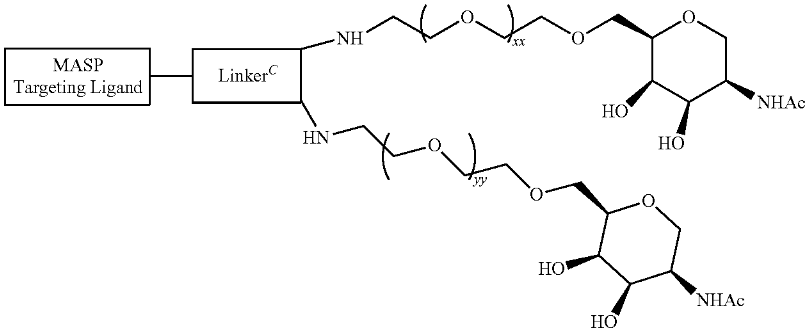
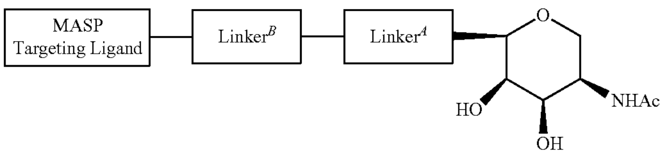

-continued
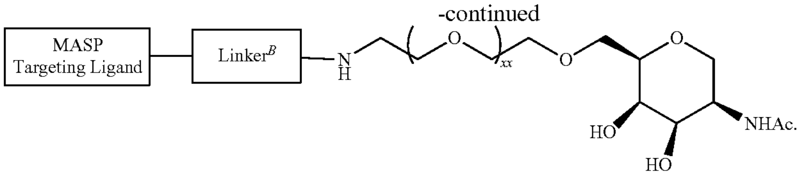
In certain embodiments the compound of the present invention is selected from:
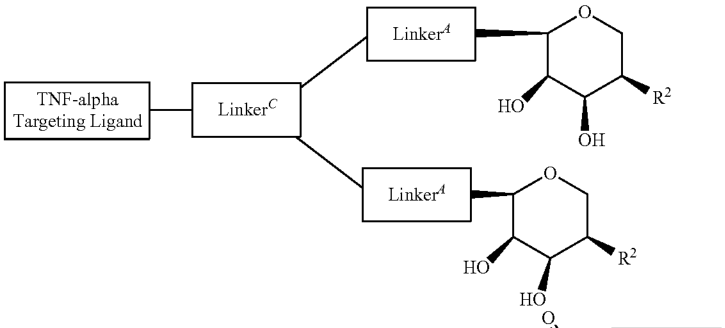
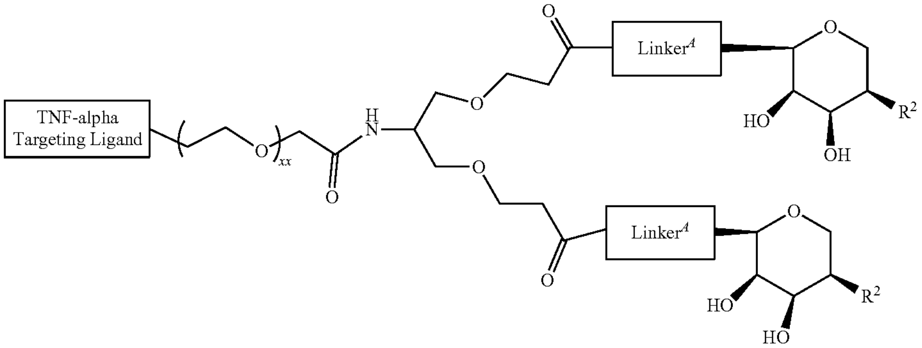
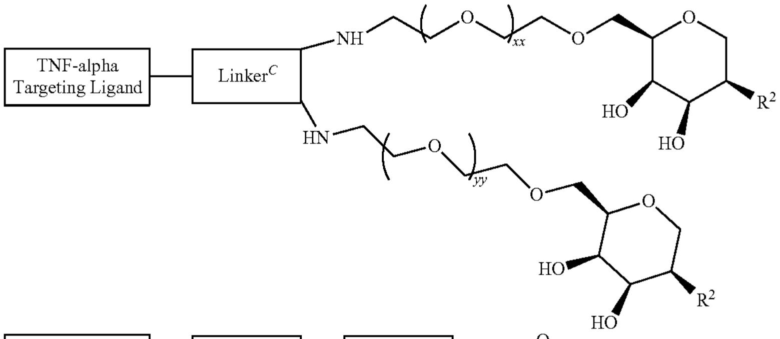
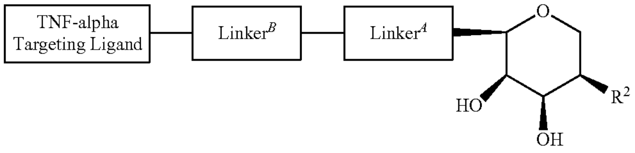
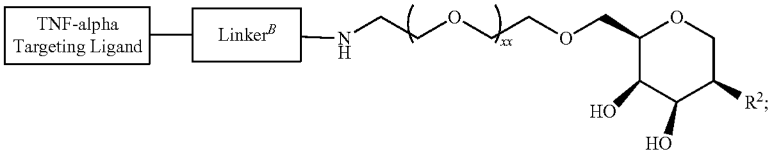

wherein in certain embodiments $R^2$ is selected from $—NR^6COR^3$, $—NR^6$-(5-membered heteroaryl), and $—NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:

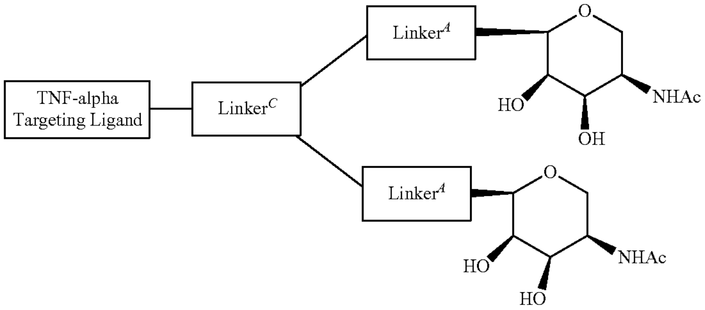

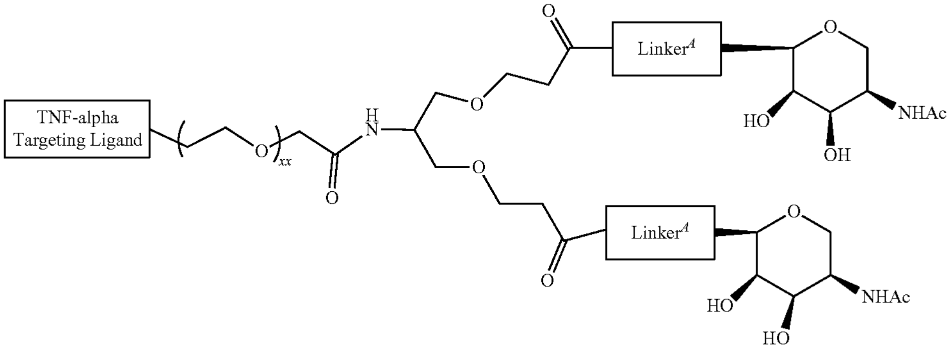

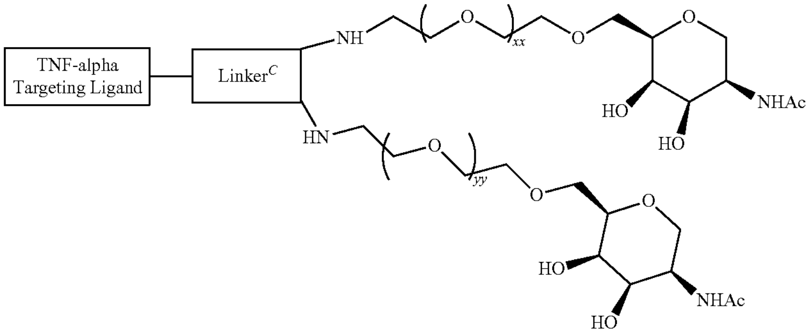

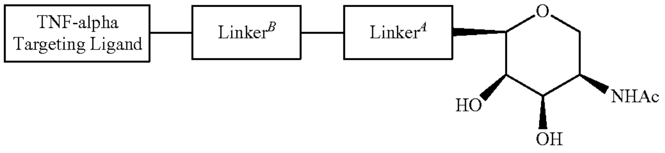

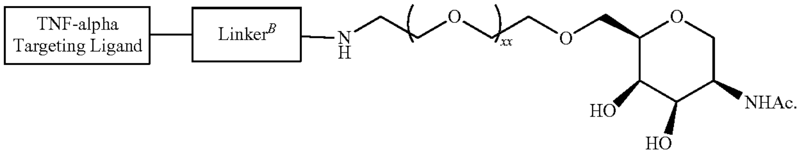

In certain embodiments the compound of the present invention is selected from:

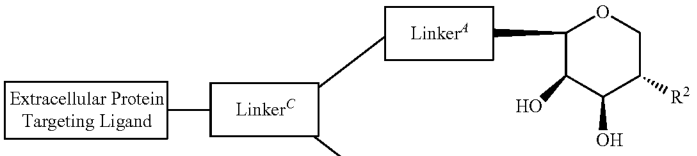

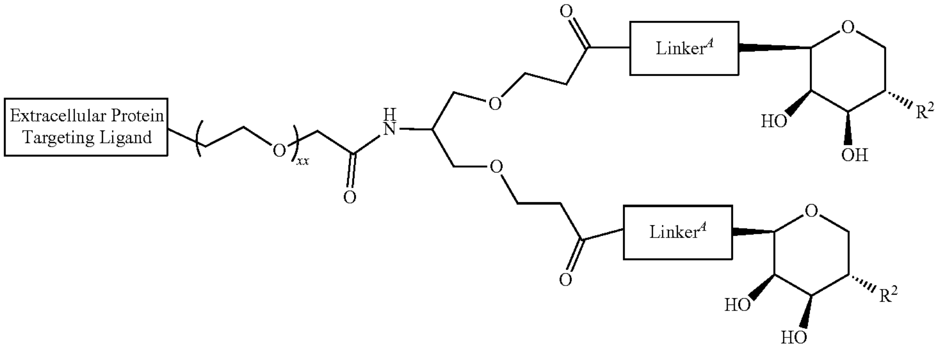

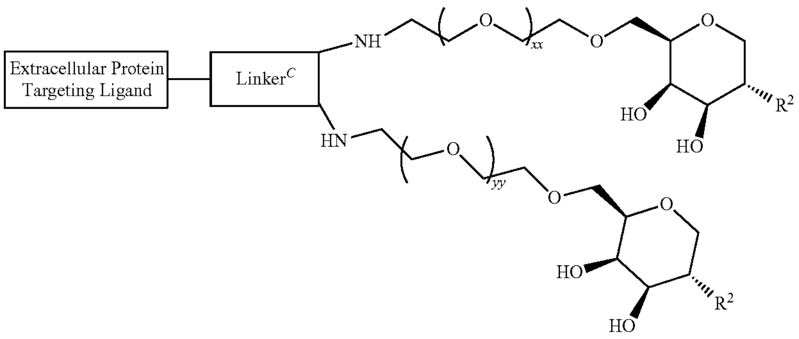

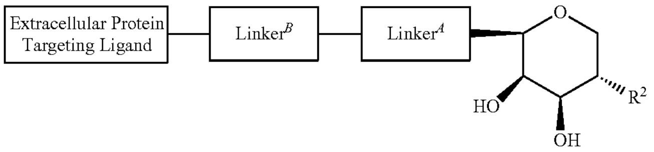

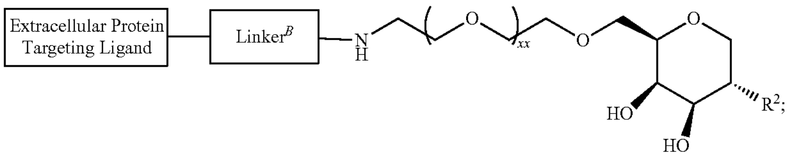

wherein in certain embodiments $R^2$ is selected from $-NR^6COR^3$, $-NR^6$-(5-membered heteroaryl), and $-NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
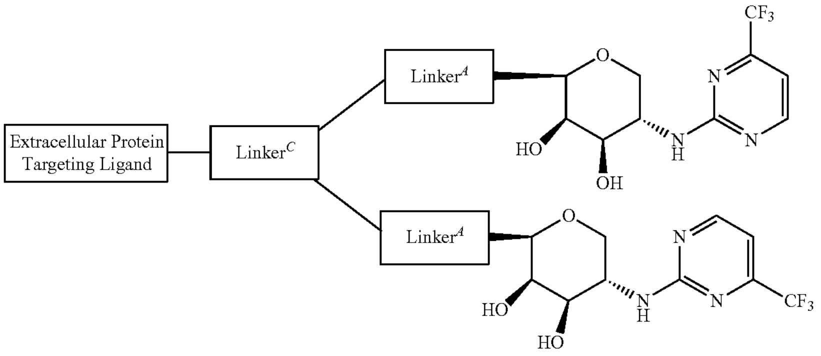
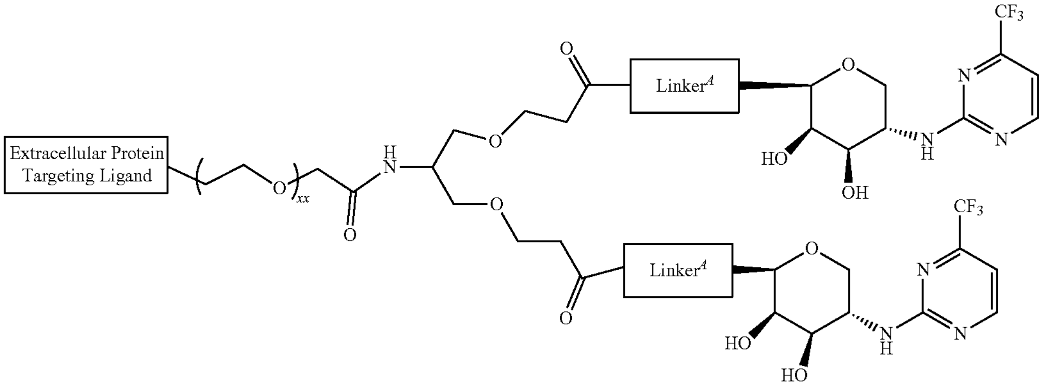
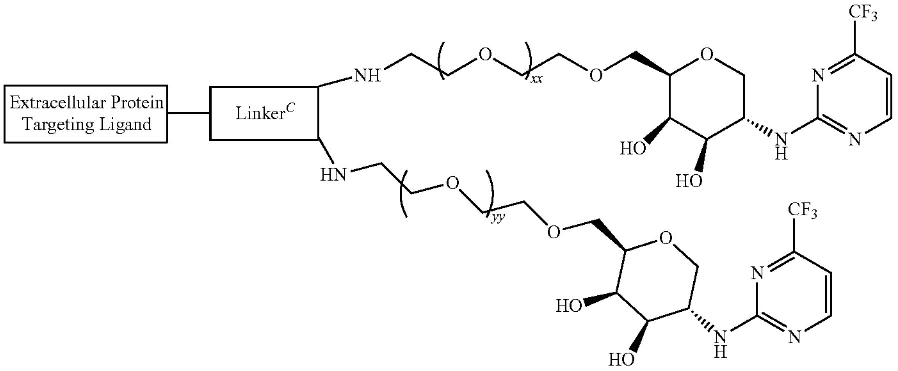
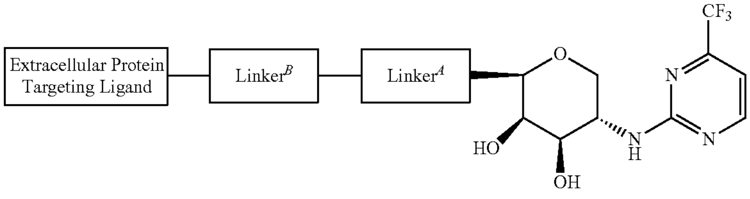
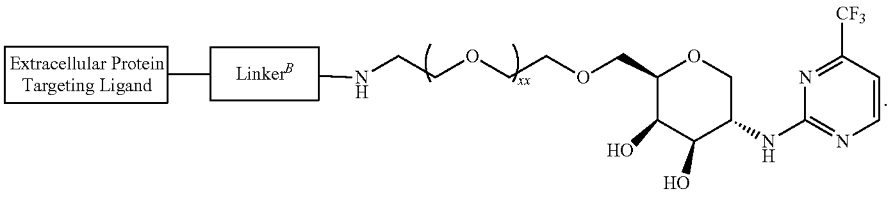

In certain embodiments the compound of the present invention is selected from:

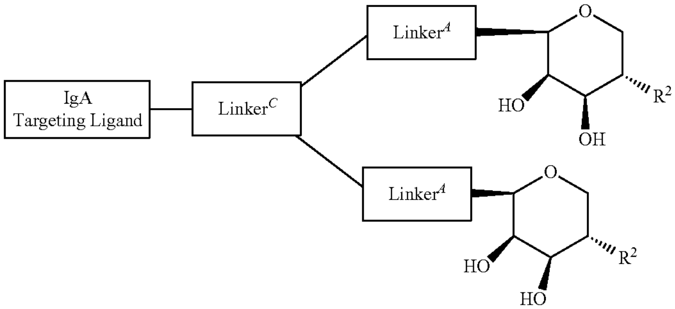

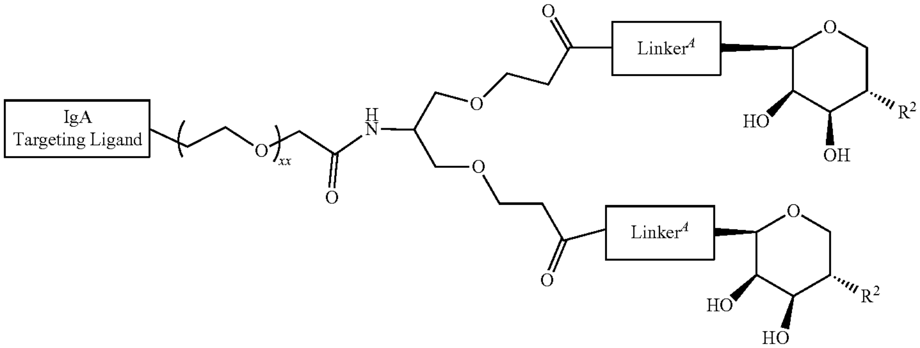

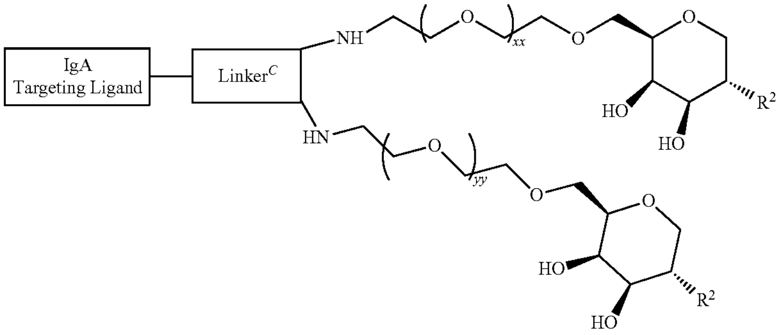

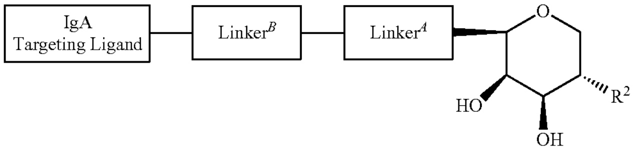

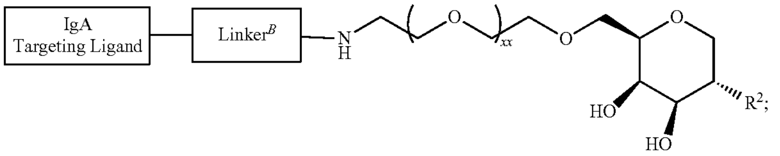

wherein in certain embodiments $R^2$ is selected from $-NR^6COR^3$, $-NR^6$-(5-membered heteroaryl), and $-NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from
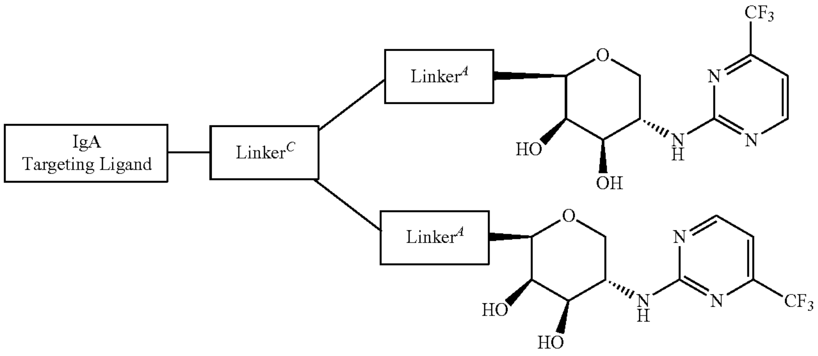
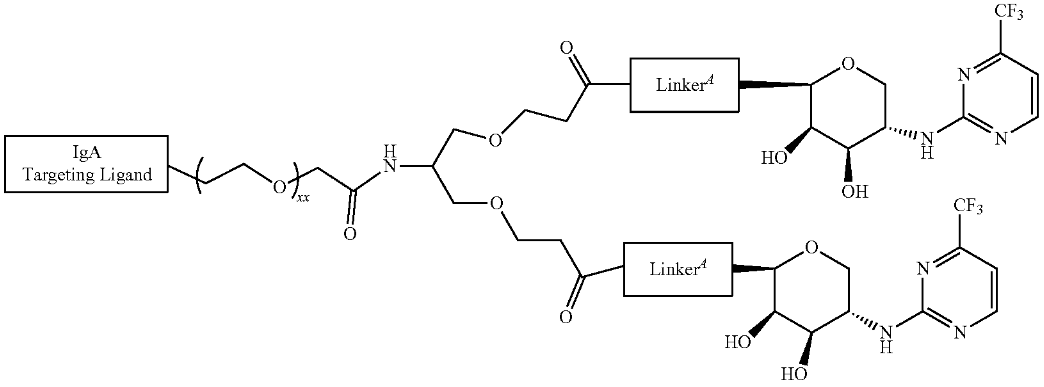
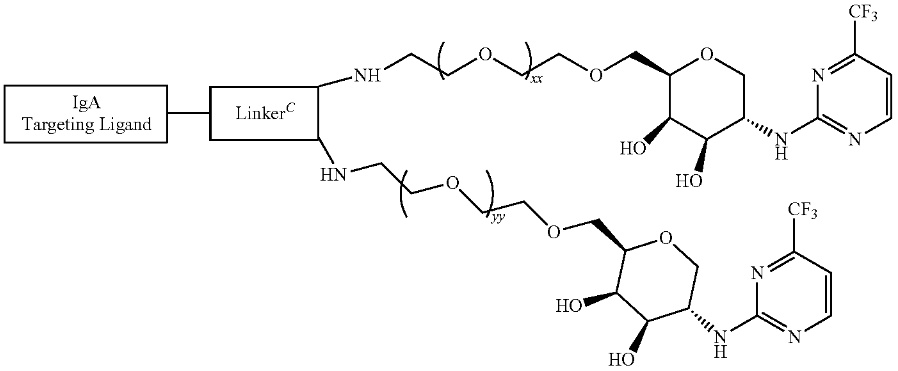
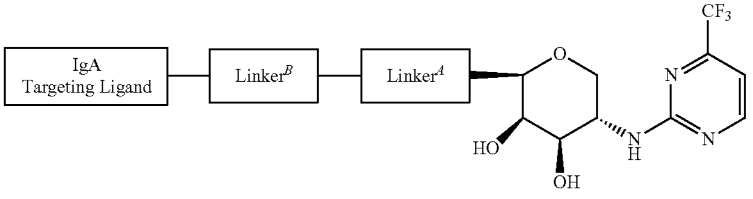
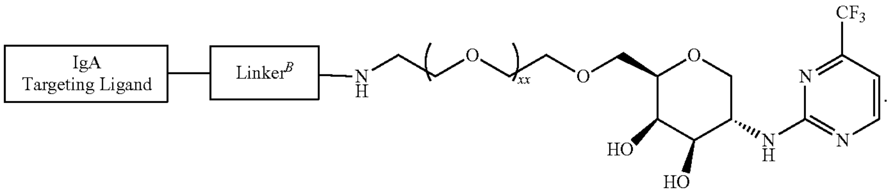

In certain embodiments the compound of the present invention is selected from:

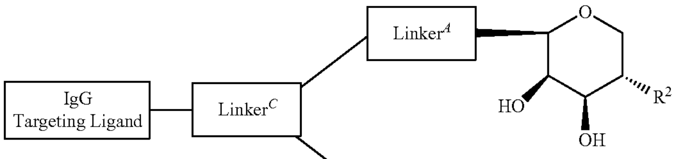

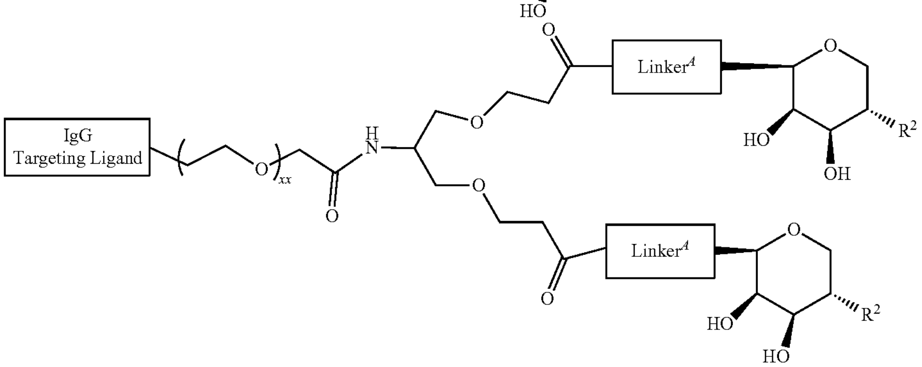

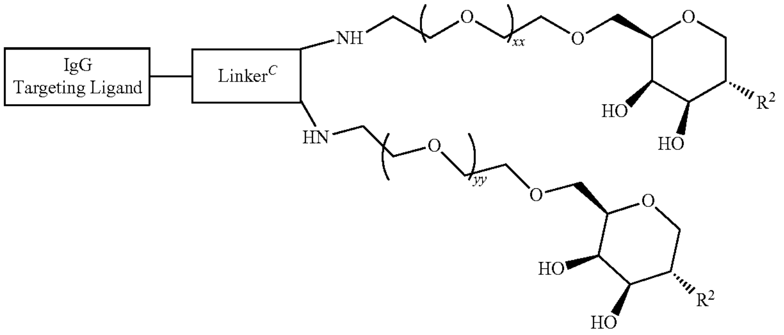

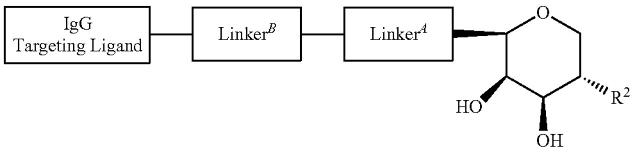

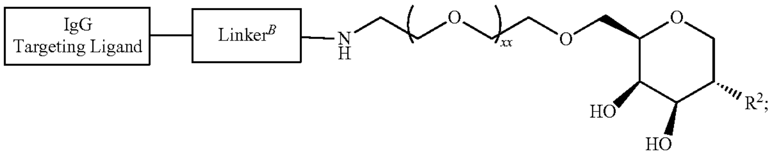

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
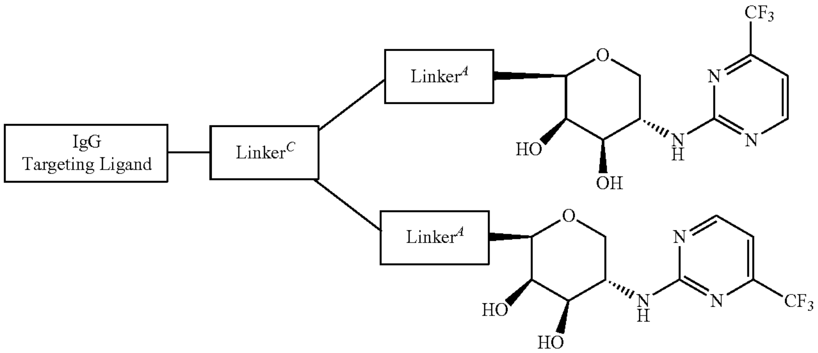
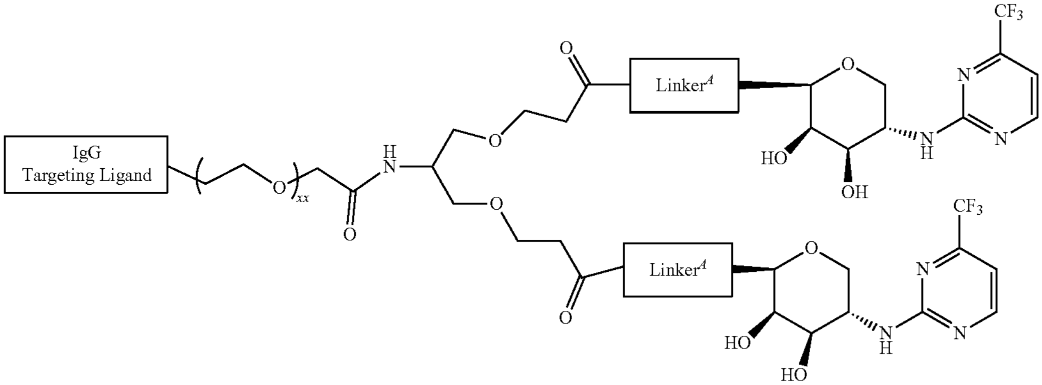
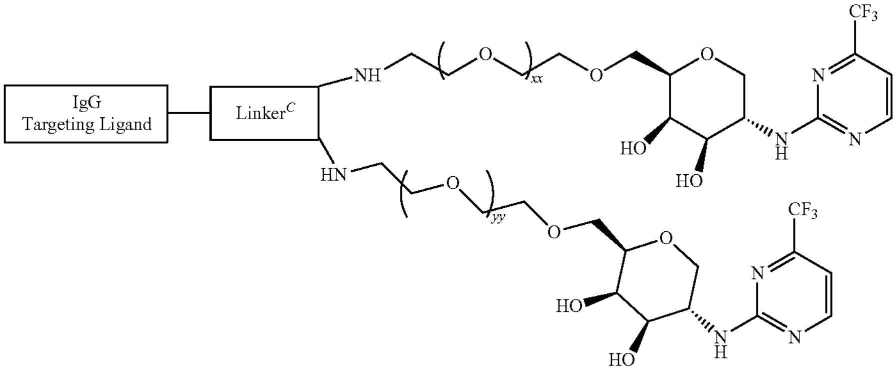
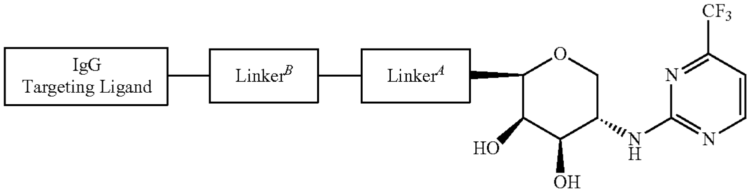
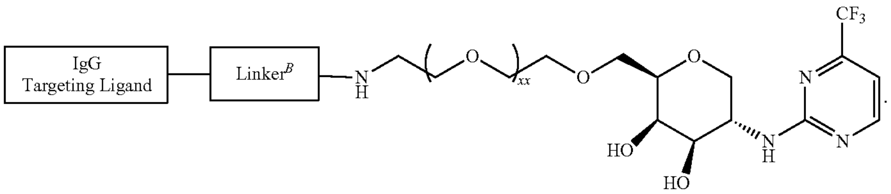

In certain embodiments the compound of the present invention is selected from:

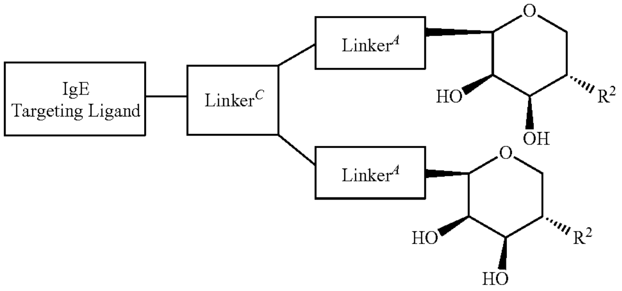

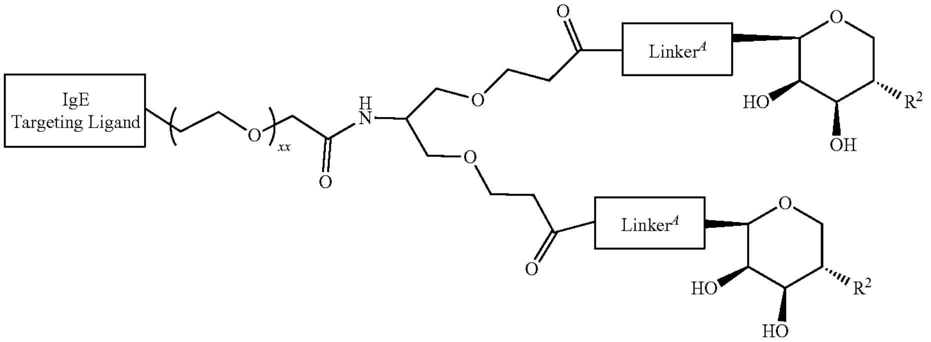

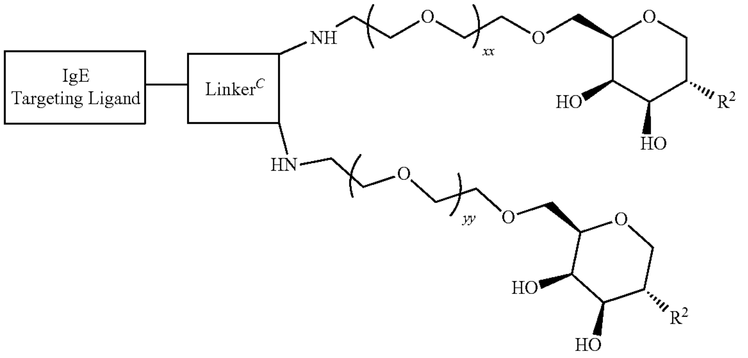

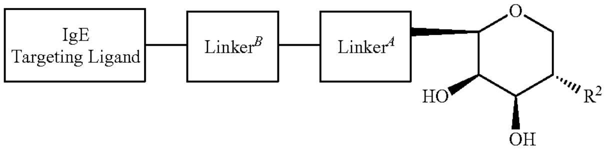

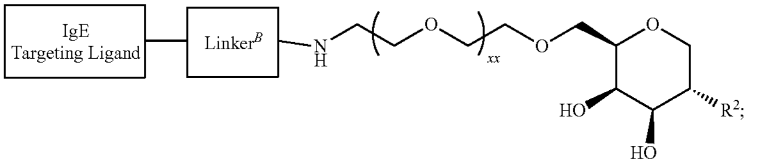

wherein in certain embodiments $R^2$ is selected from —$NR^6COR^3$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
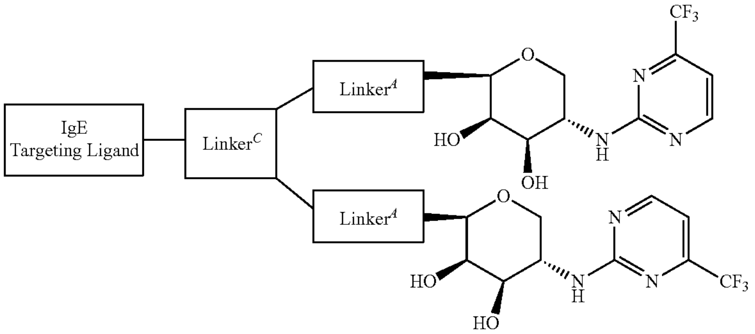
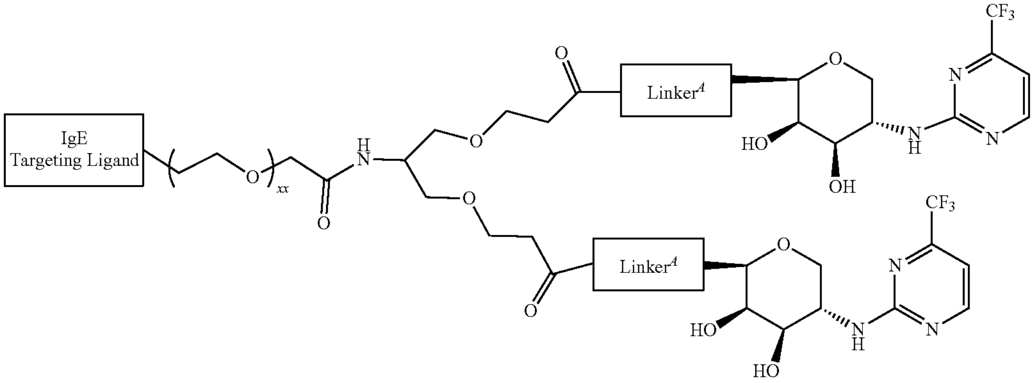
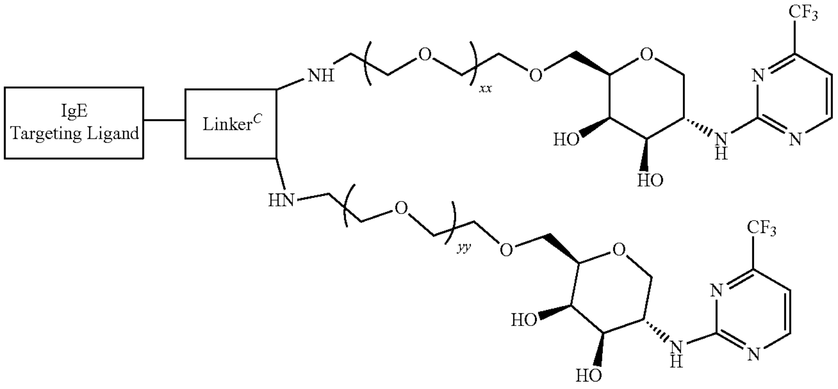
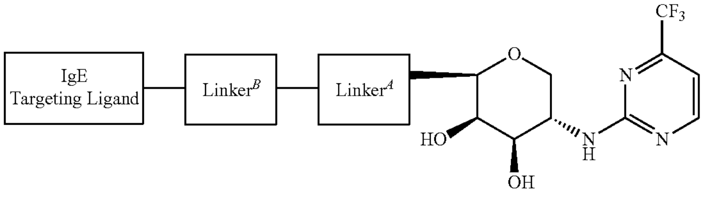
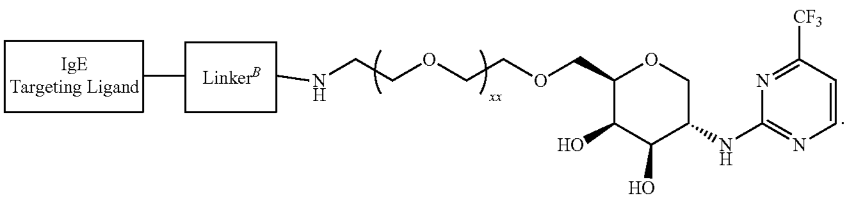

In certain embodiments the compound of the present invention is selected from:

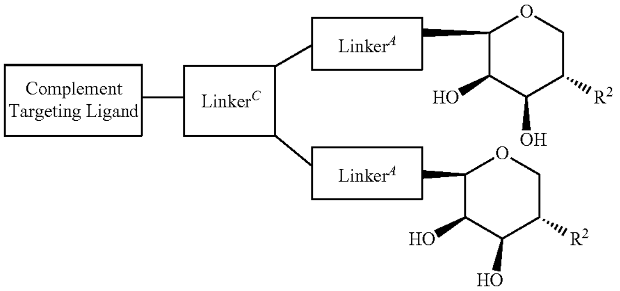

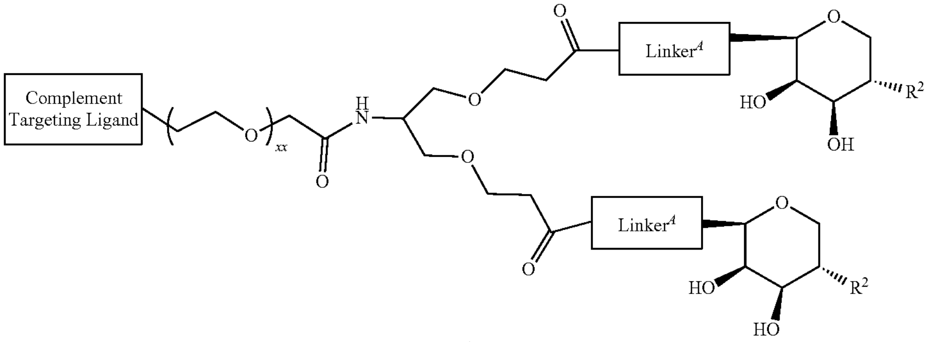

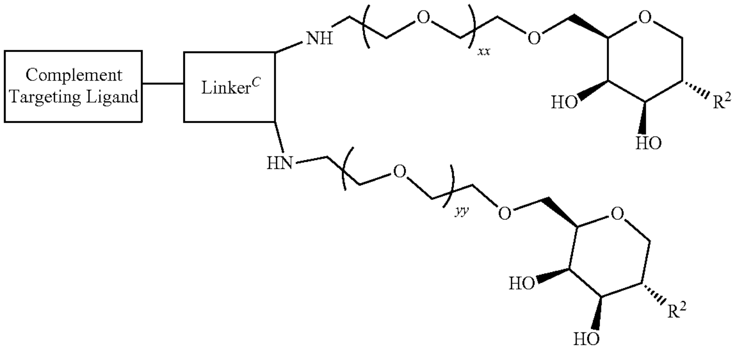

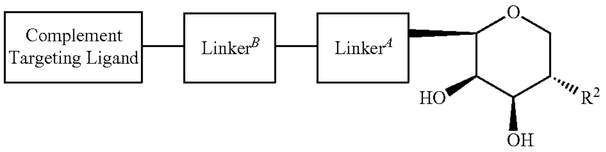

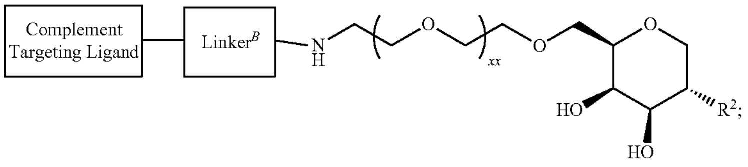

wherein in certain embodiments $R^2$ is selected from —$NR^6COR^{10}$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
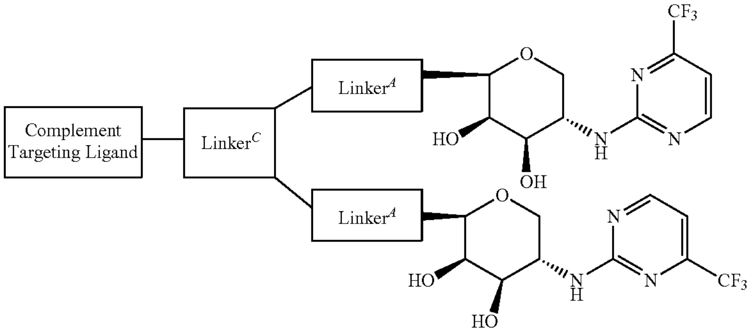
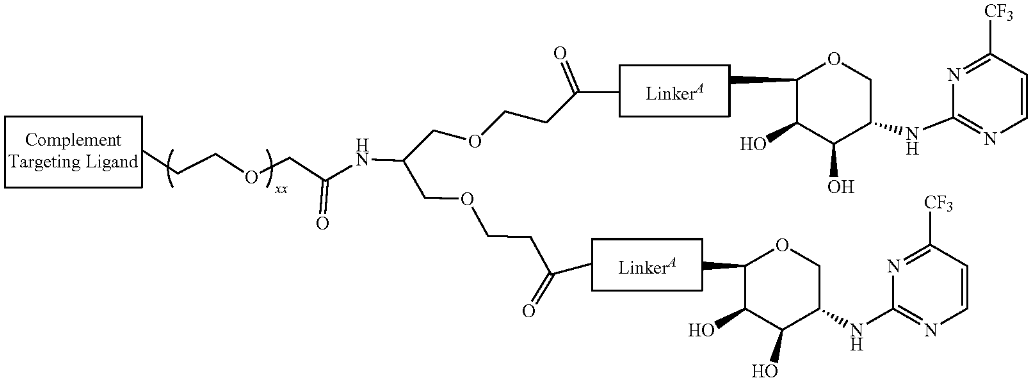
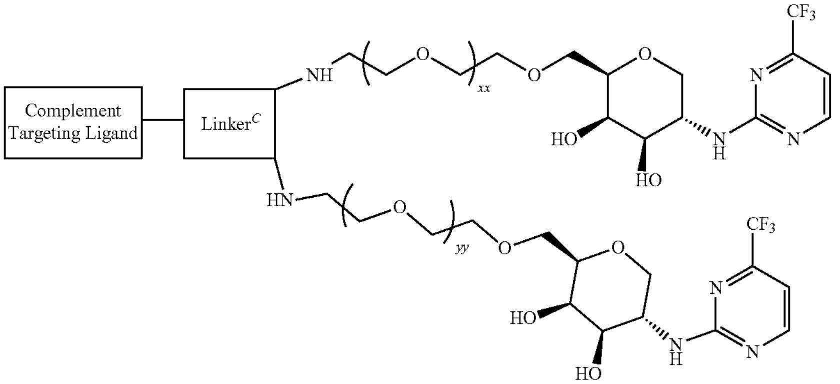
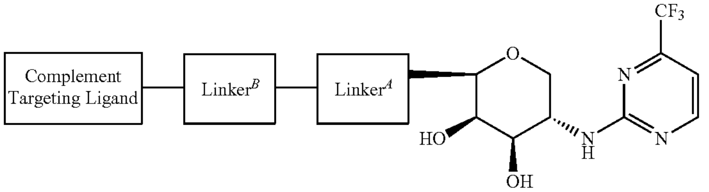
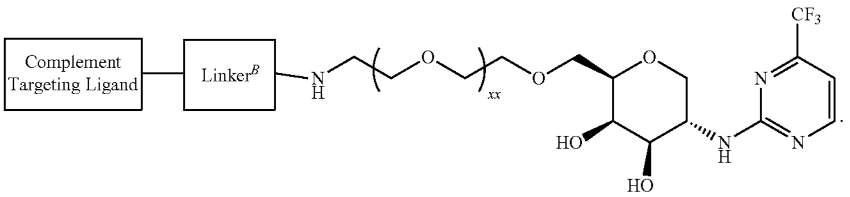

In certain embodiments the compound of the present invention is selected from:

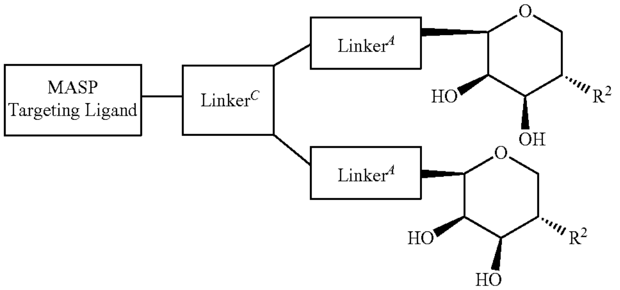

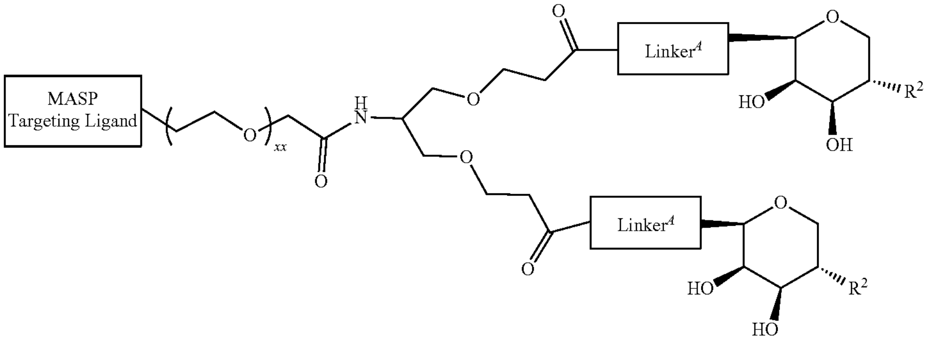

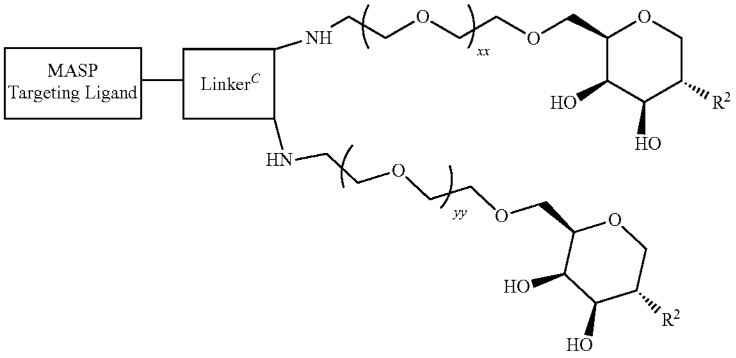

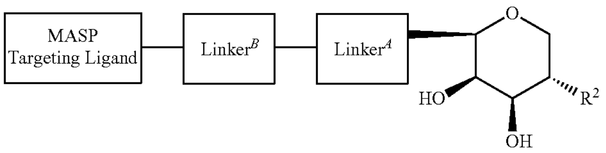

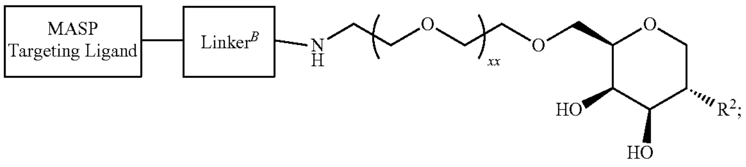

wherein in certain embodiments $R^2$ is selected from —$NR^6COR^{10}$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
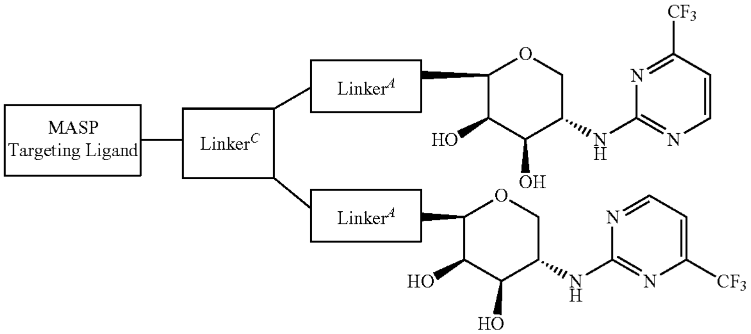
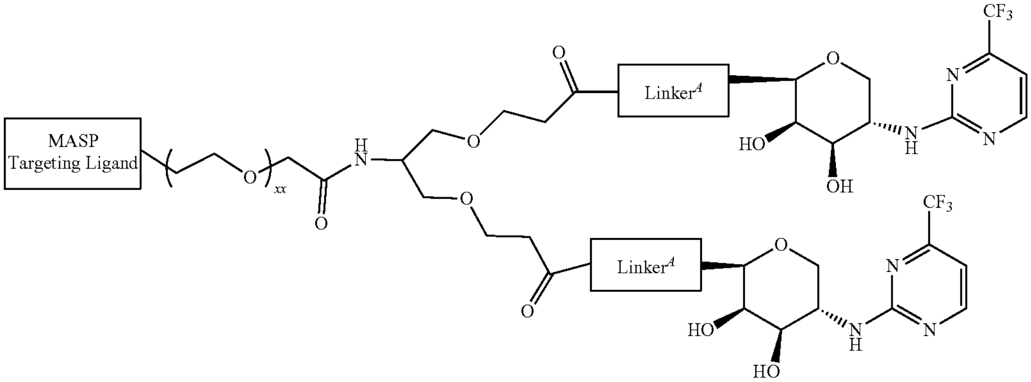
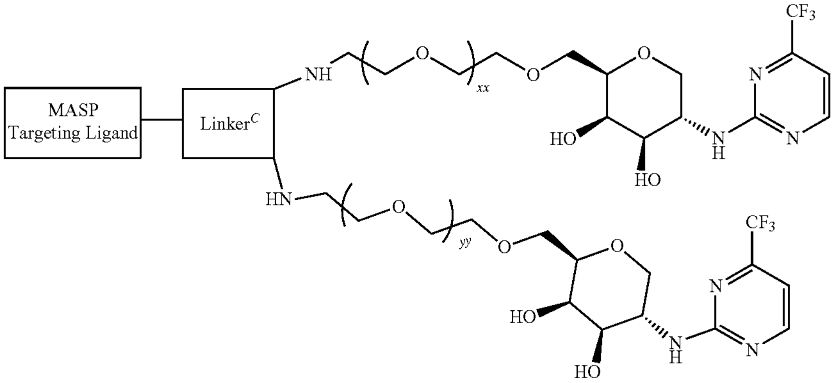
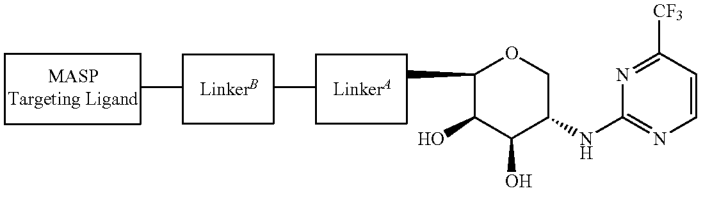
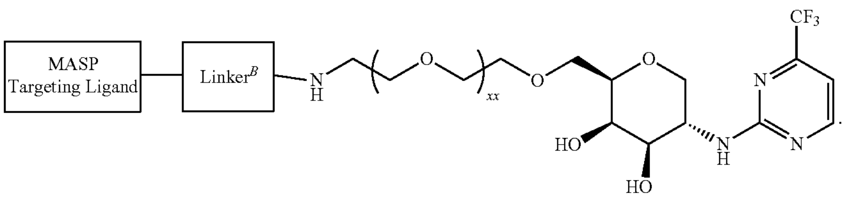

In certain embodiments the compound of the present invention is selected from:

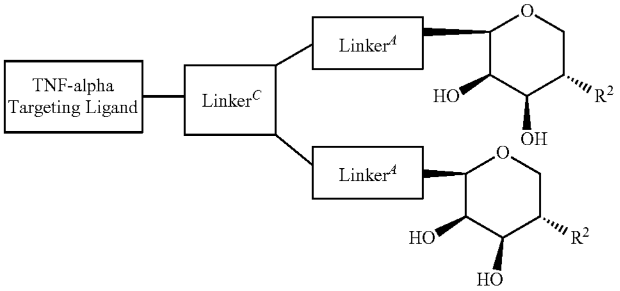

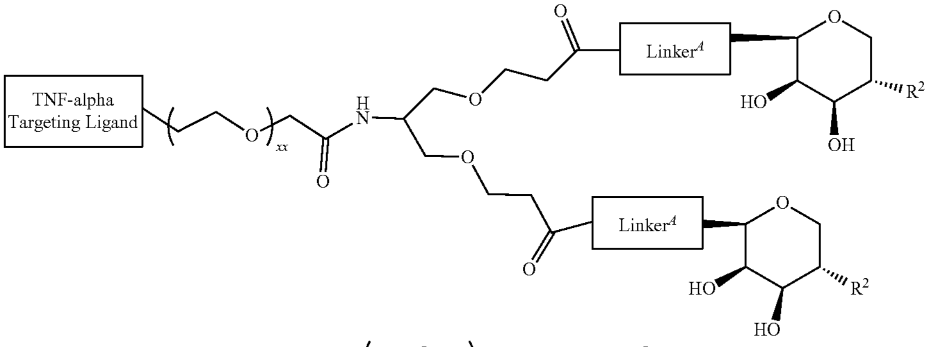

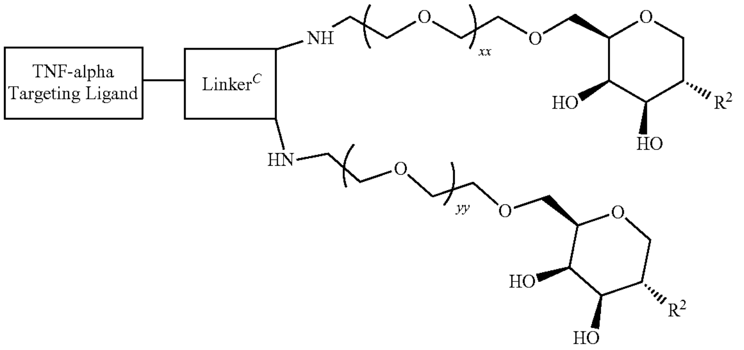

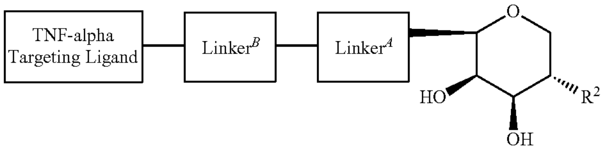

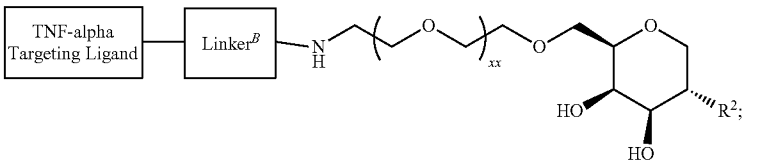

wherein in certain embodiments $R^2$ is selected from —$NR^6COR^{10}$, —$NR^6$-(5-membered heteroaryl), and —$NR^6$-(6-membered heteroaryl), each of which $R^2$ groups is optionally substituted with 1, 2, 3, or 4 independent substituents as described herein, for example 1, 2, 3, or 4 substitutents independently selected from F, Cl, Br, haloalkyl, or alkyl.

In certain embodiments the compound of the present invention is selected from:
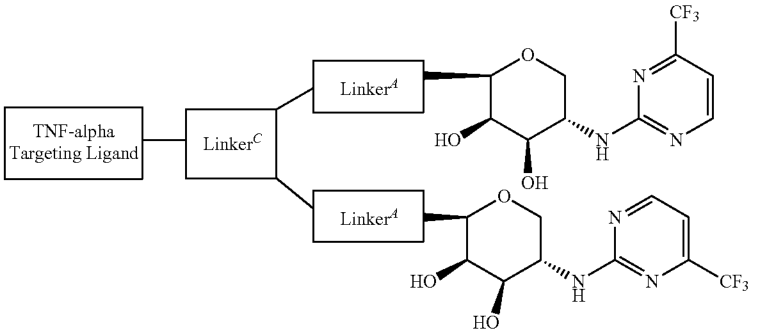
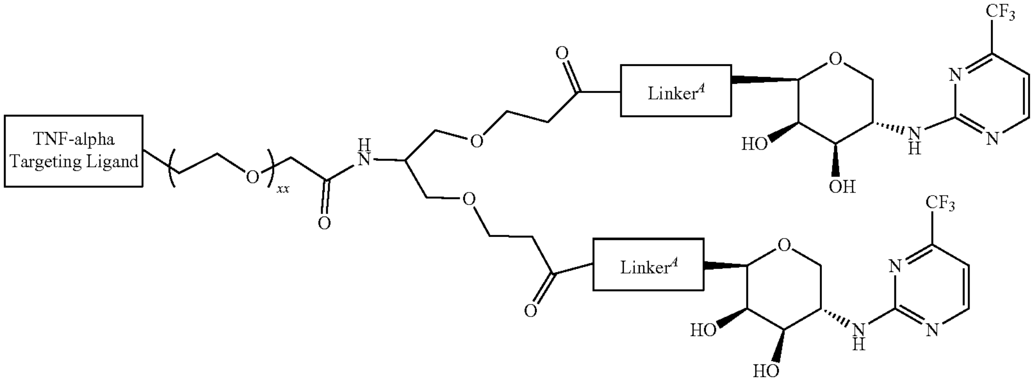
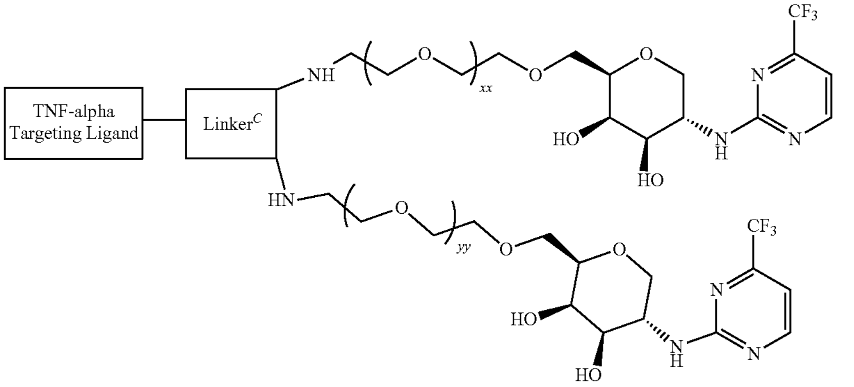
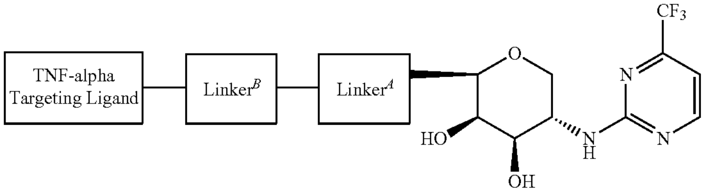
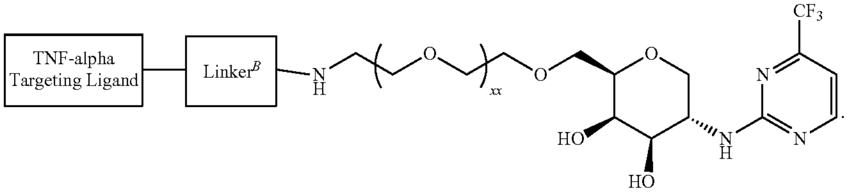

In certain embodiments the compound of the present invention is selected from:
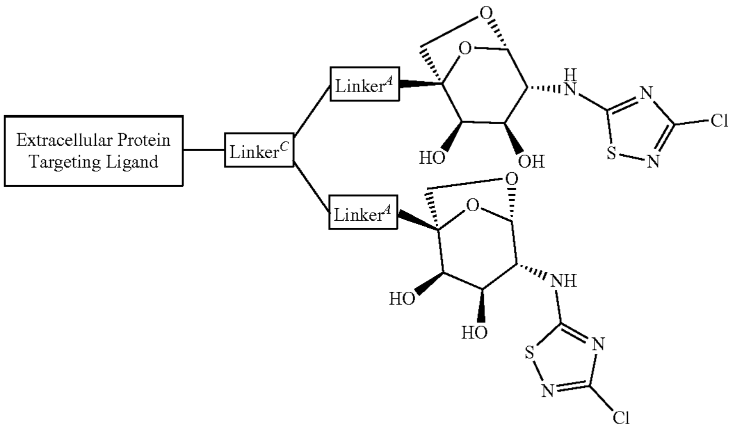
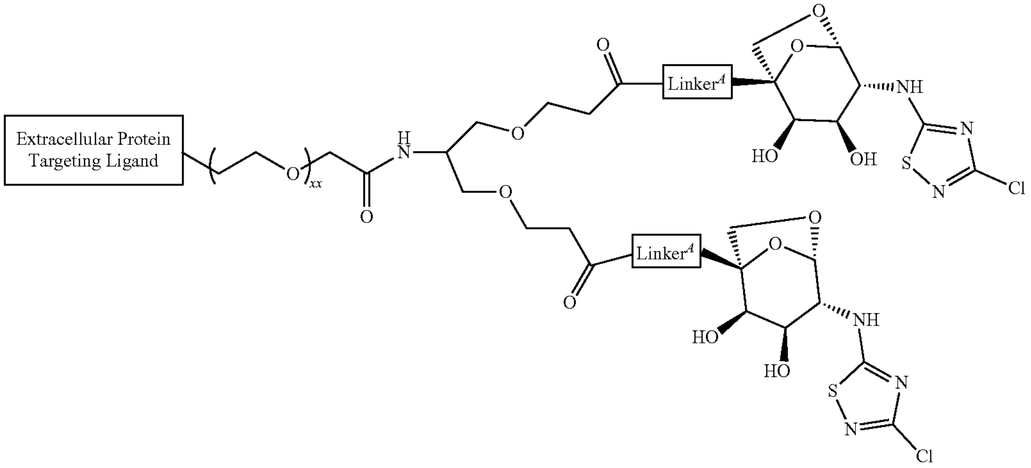
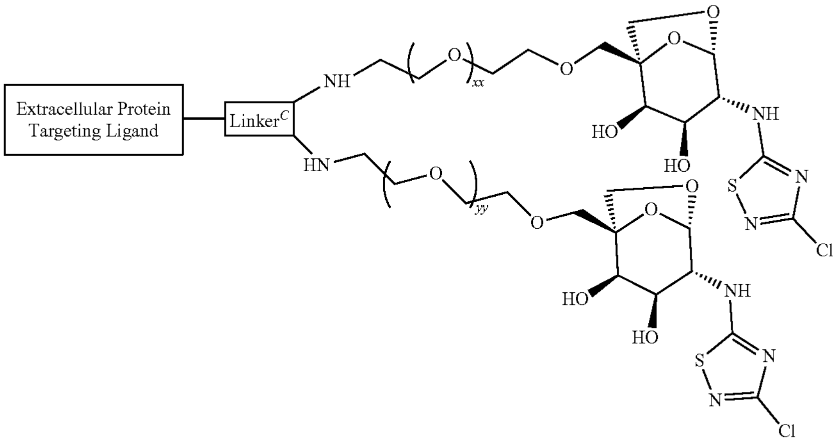
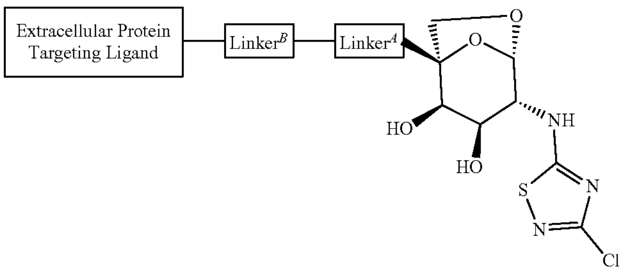

-continued
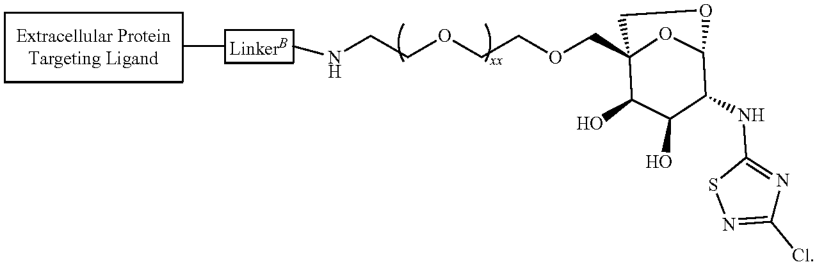
In certain embodiments the compound of the present invention is selected from:
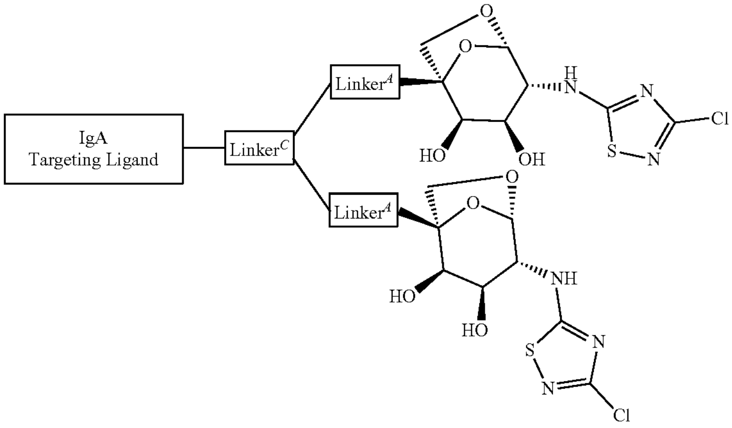
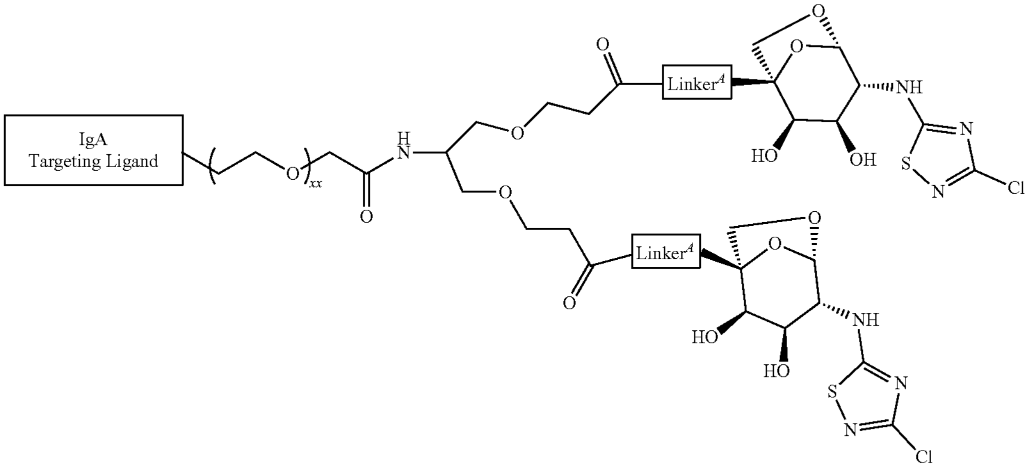

-continued
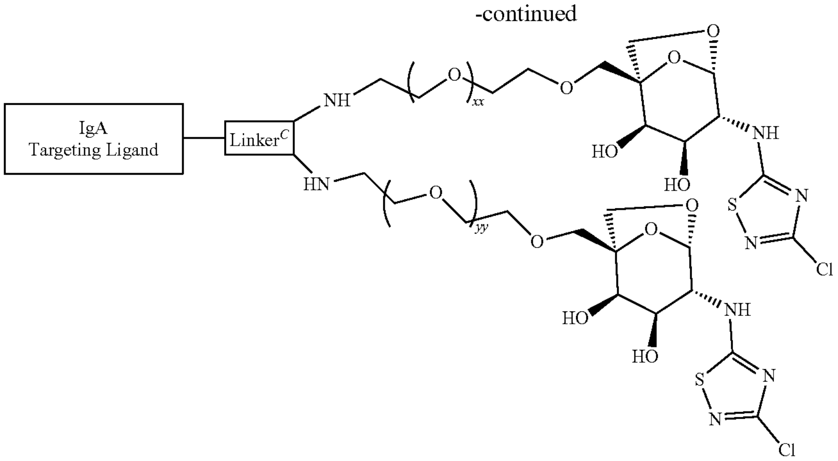
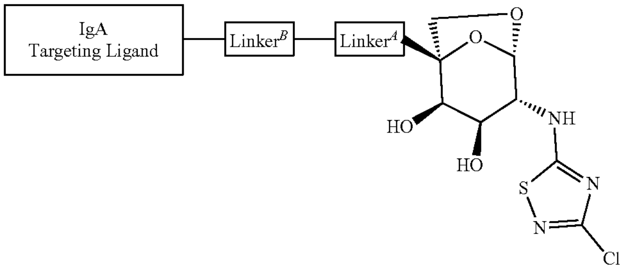
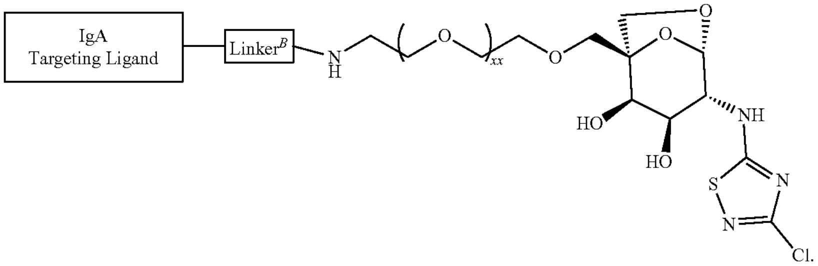
In certain embodiments the compound of the present invention is selected from:
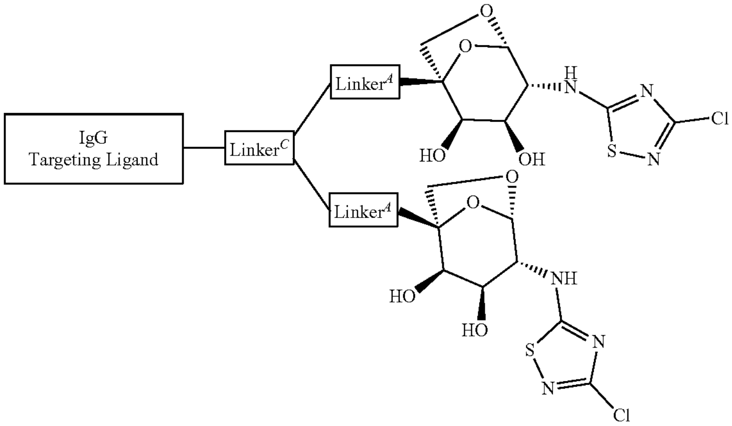

-continued
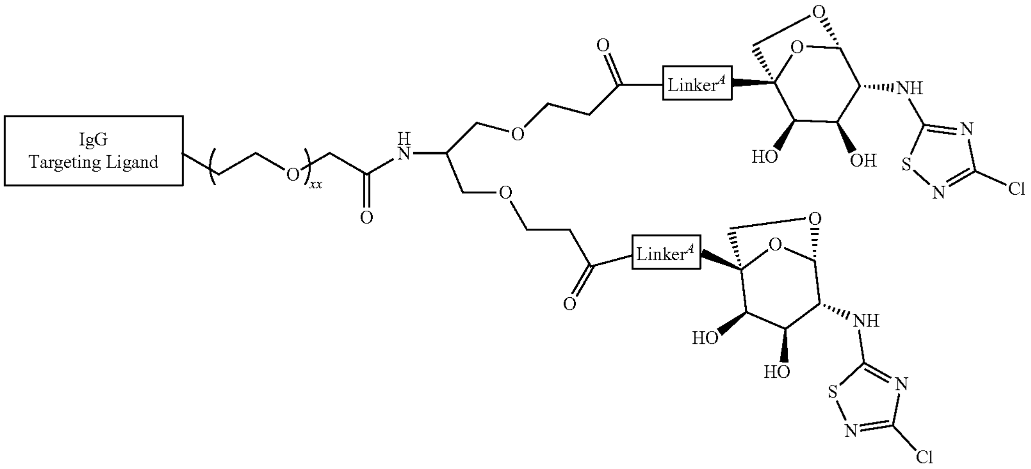
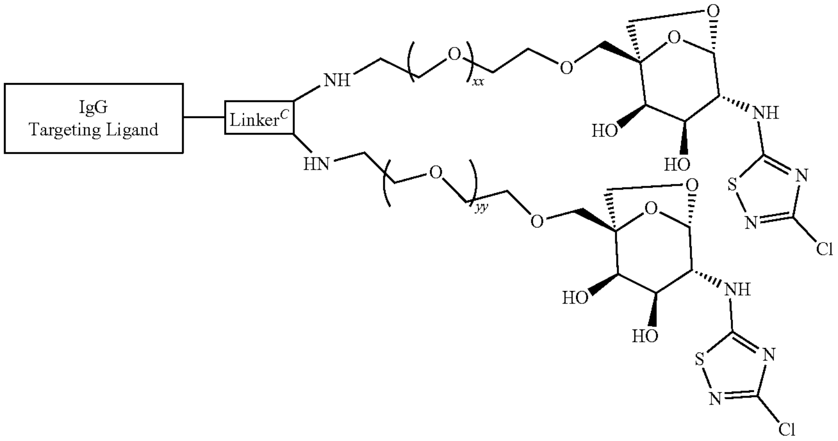
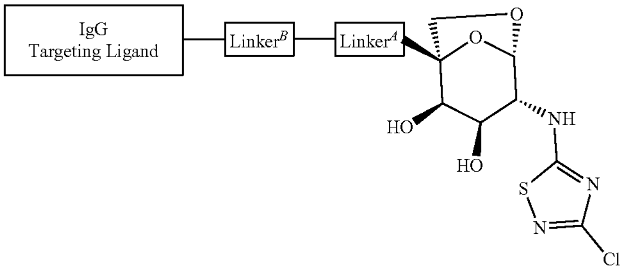
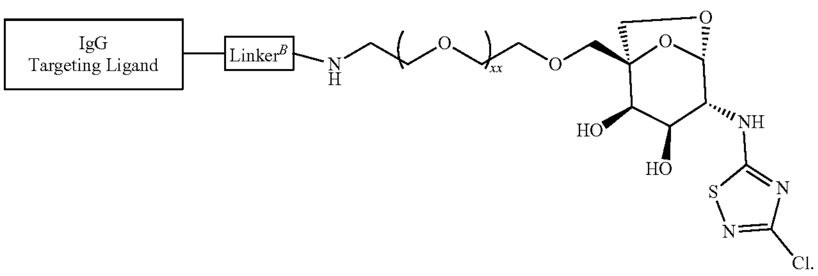

In certain embodiments the compound of the present invention is selected from:
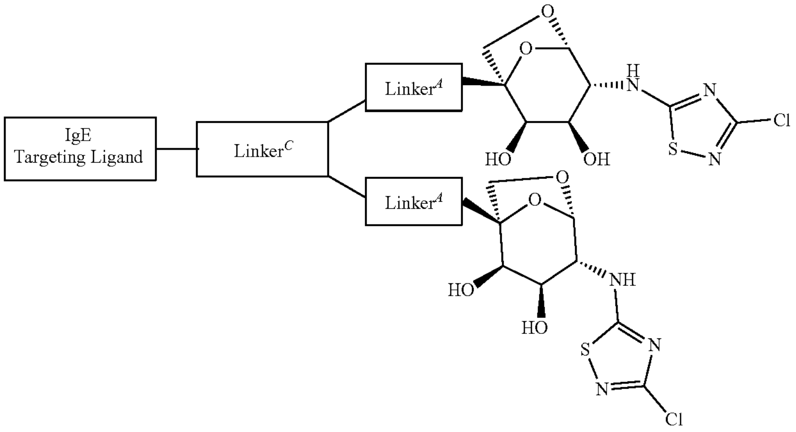
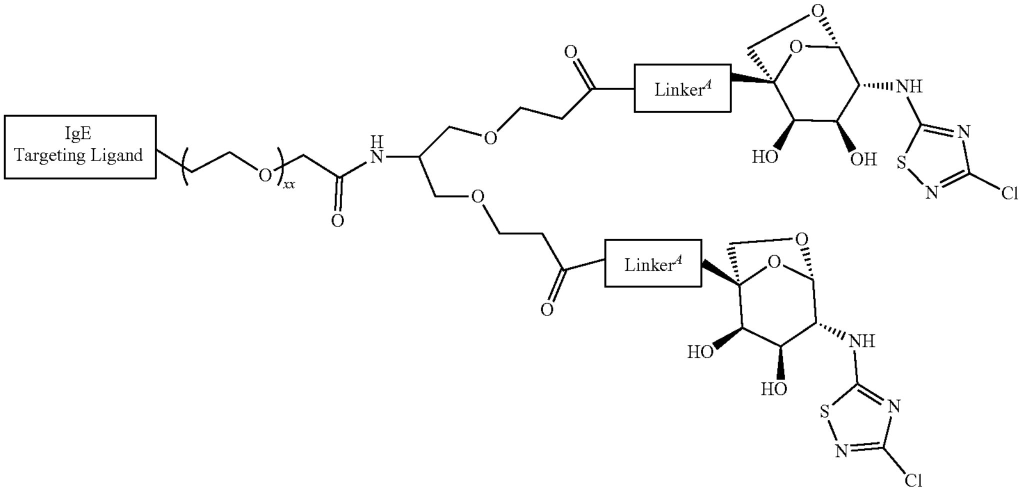
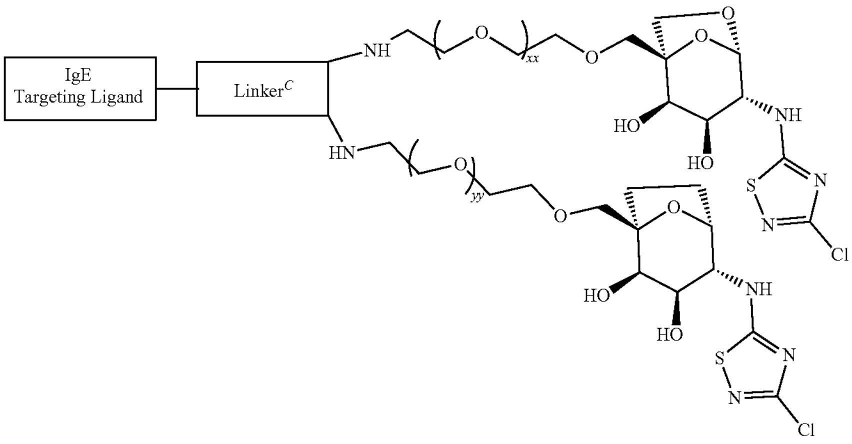
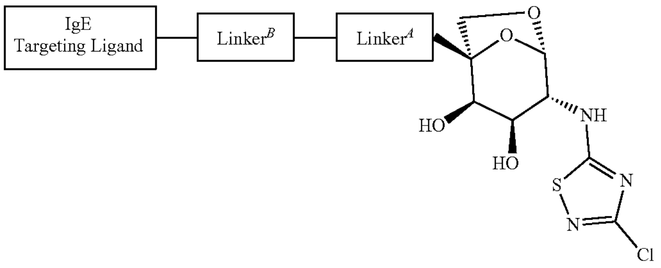

-continued
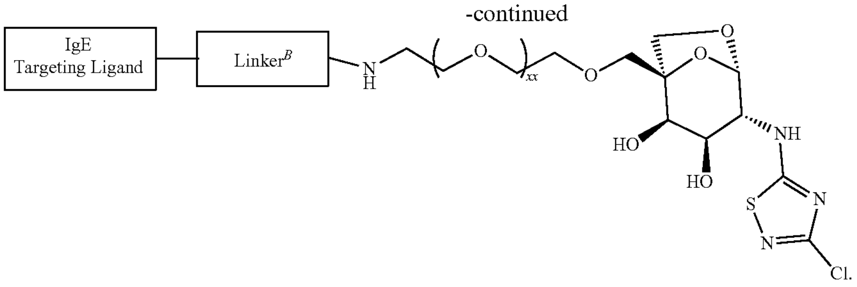
In certain embodiments the compound of the present invention is selected from:
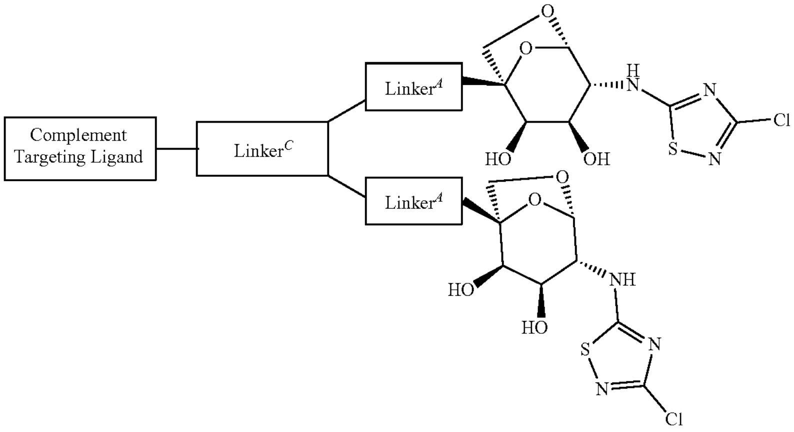
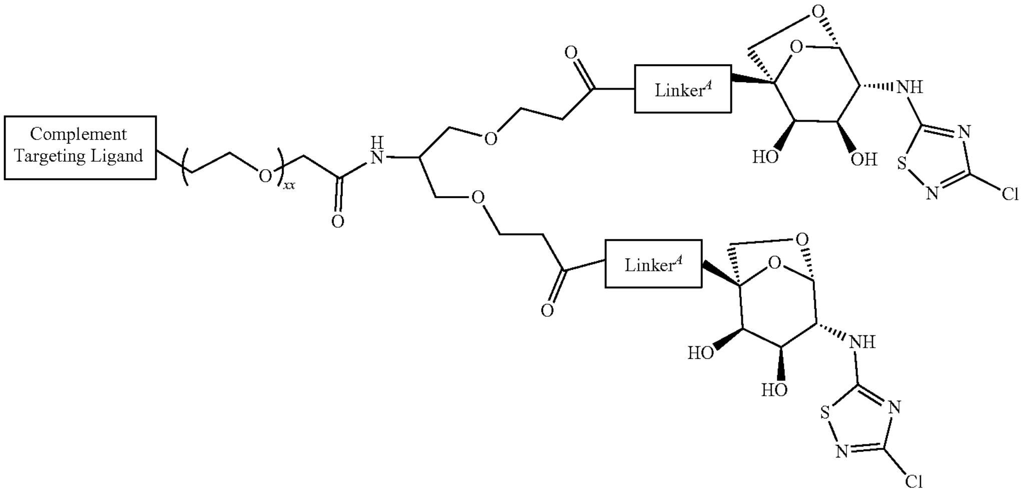

-continued
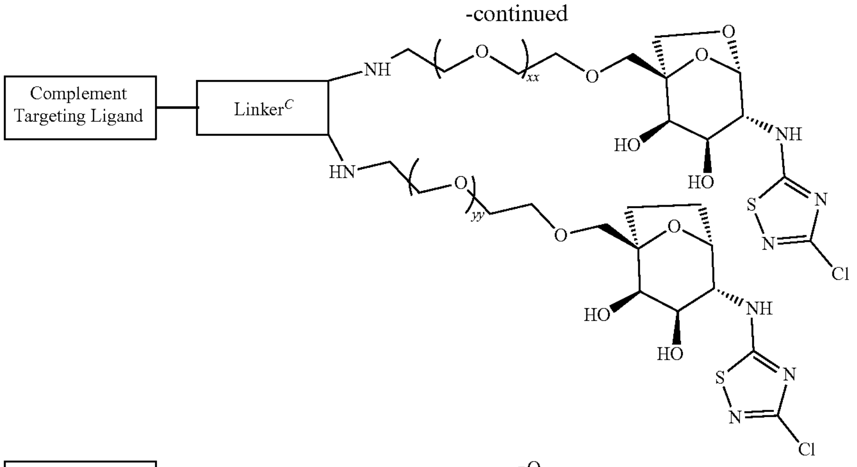
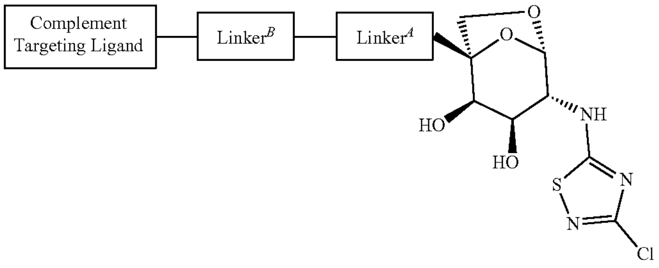
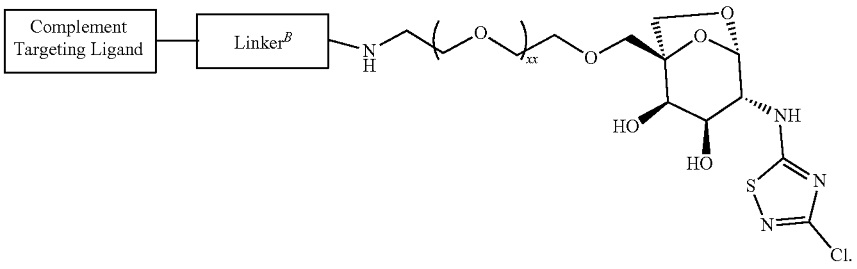
In certain embodiments the compound of the present invention is selected from:
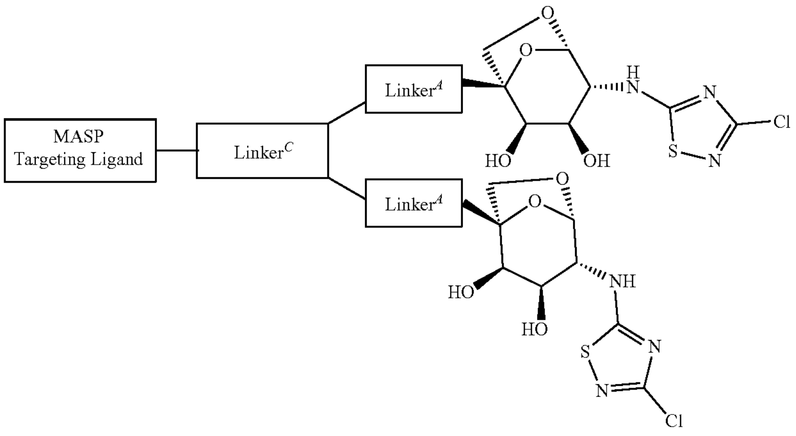

-continued
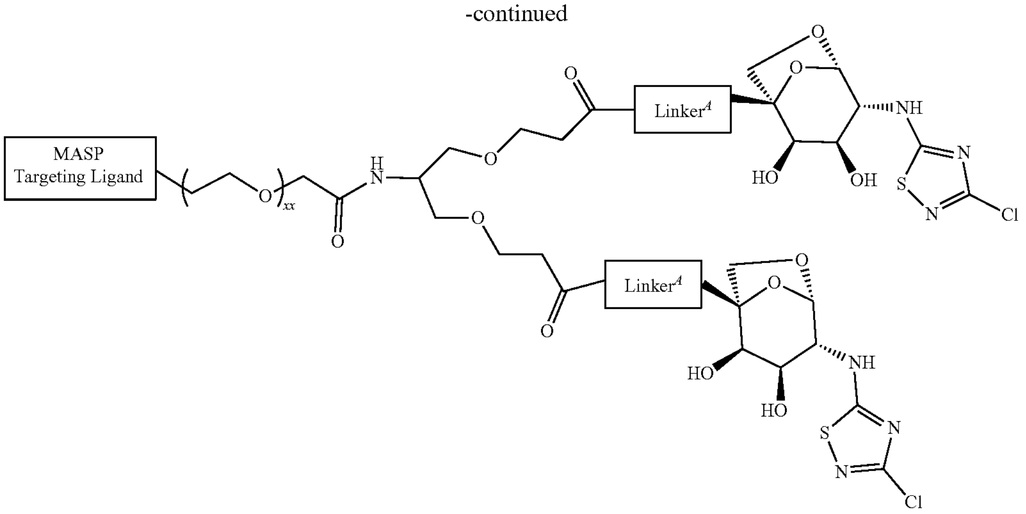
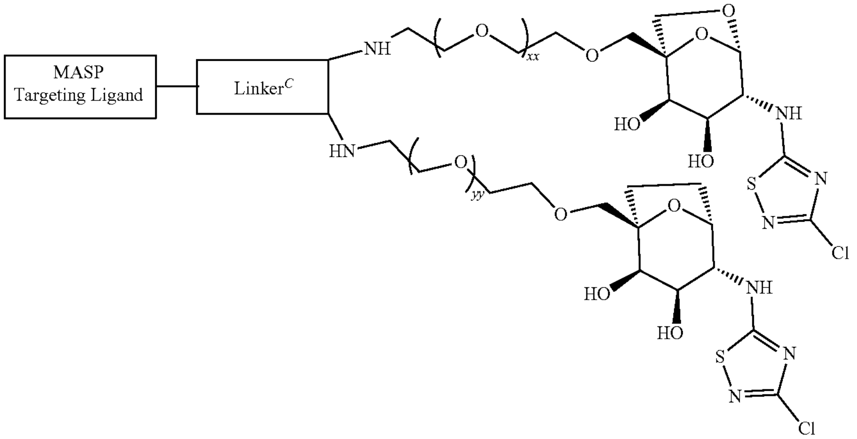
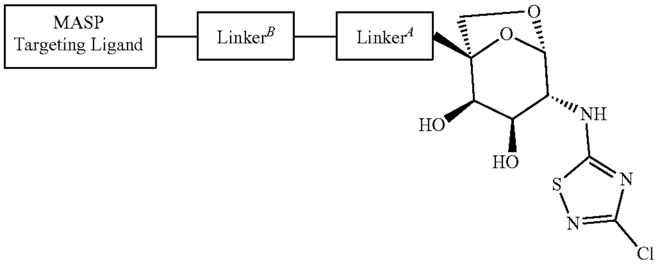
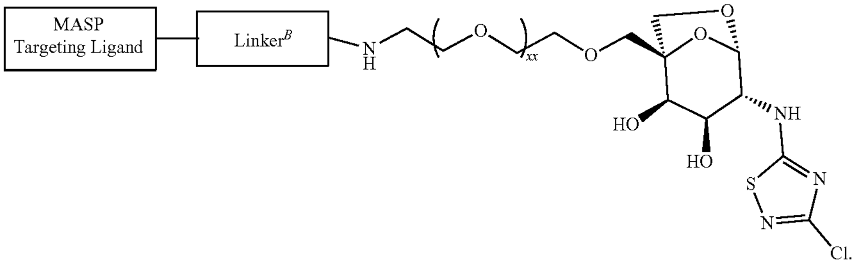

In certain embodiments the compound of the present invention is selected from:
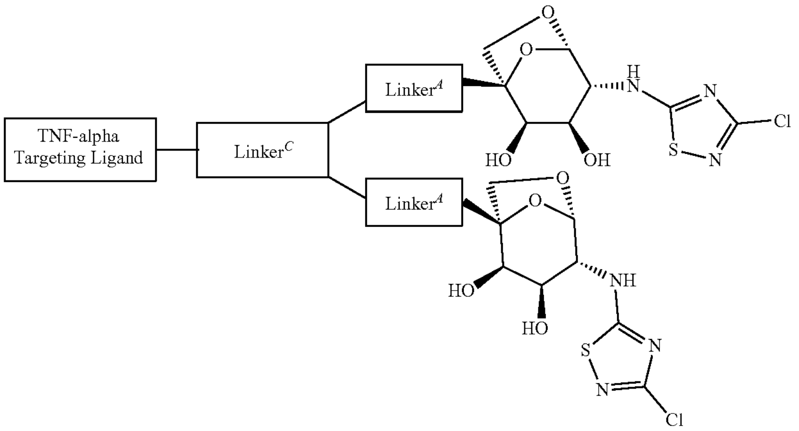
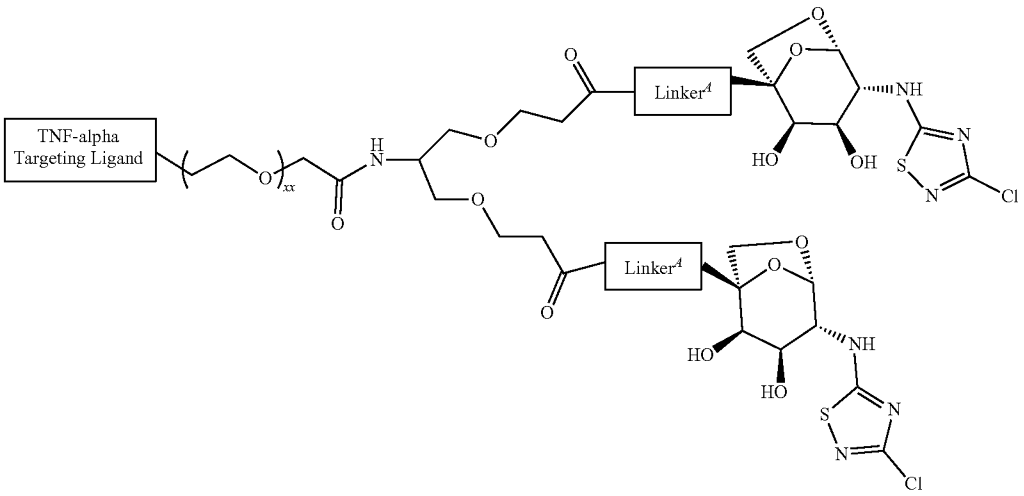
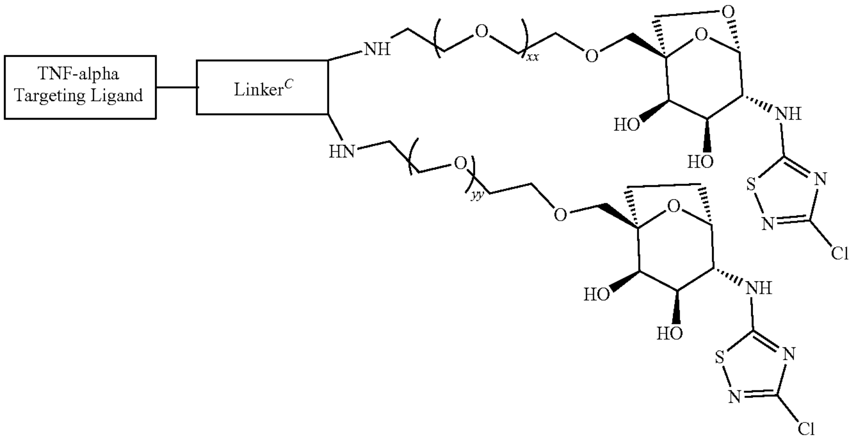
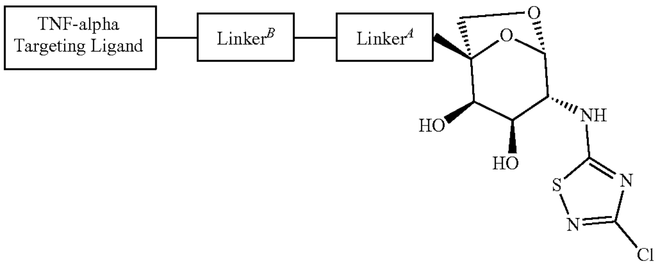

-continued
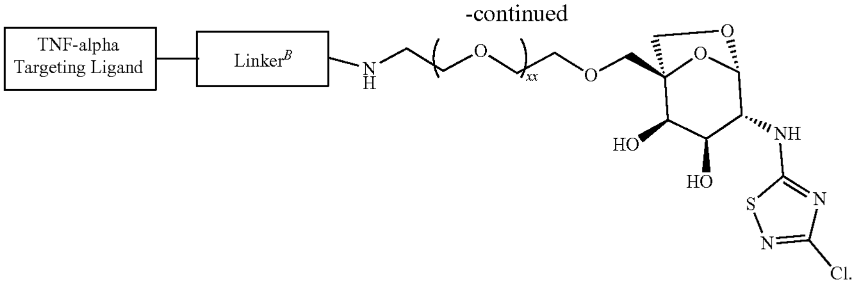
In certain embodiments the compound of the present invention is selected from:
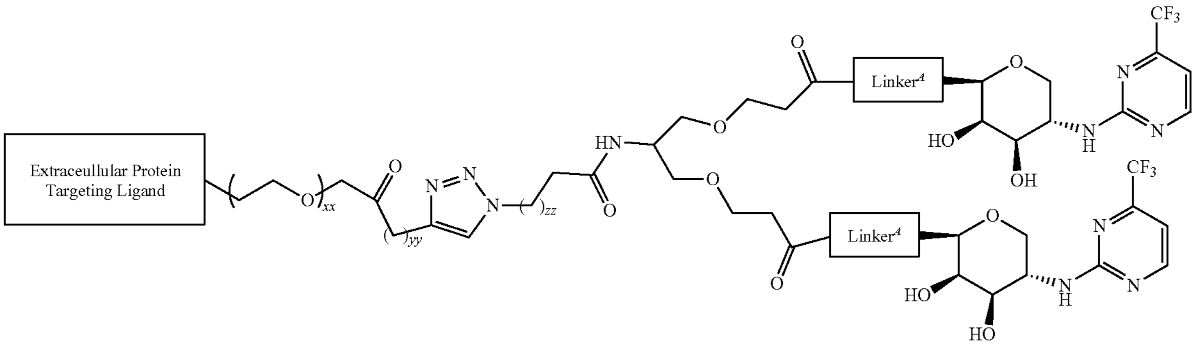
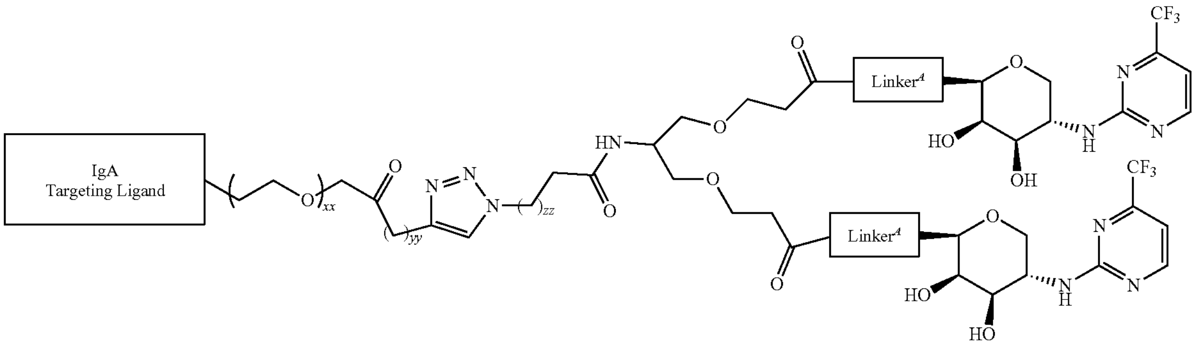
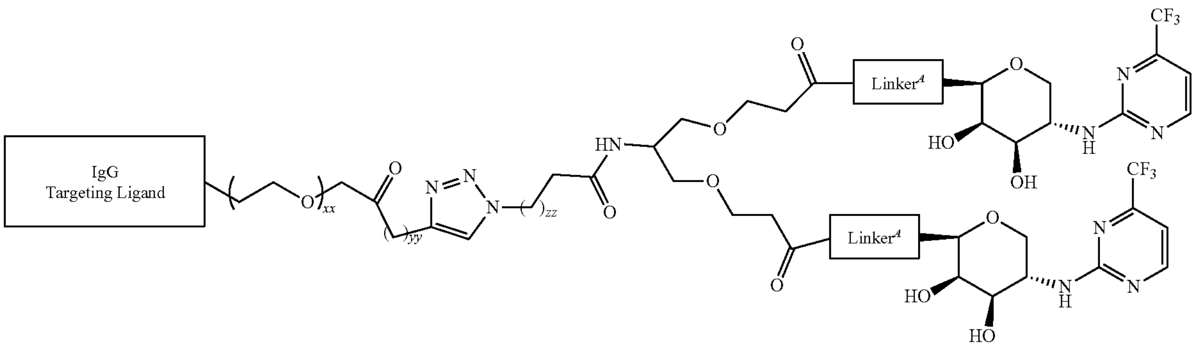

-continued
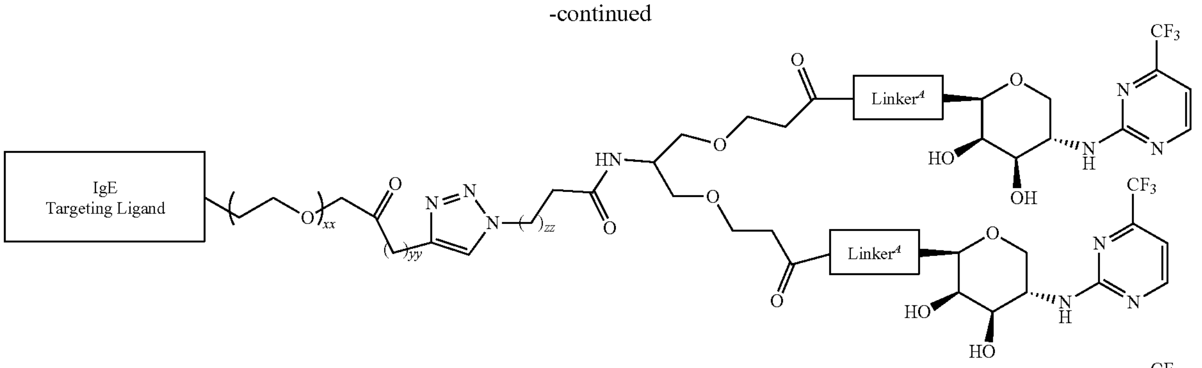
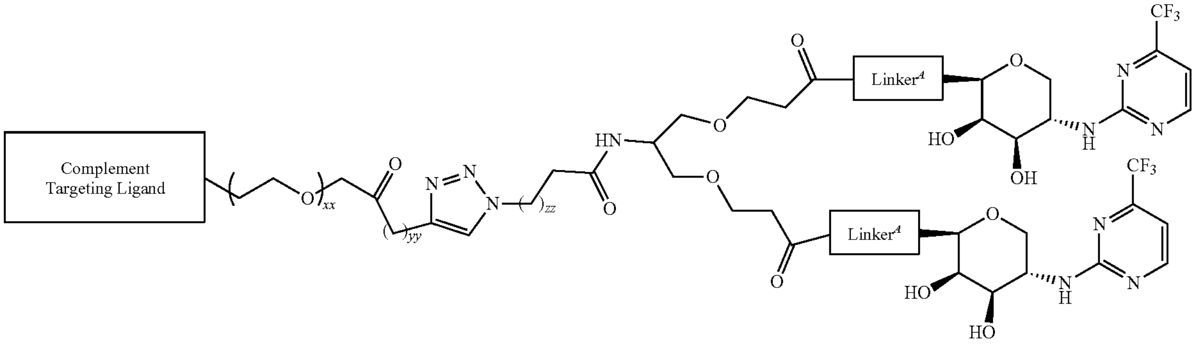
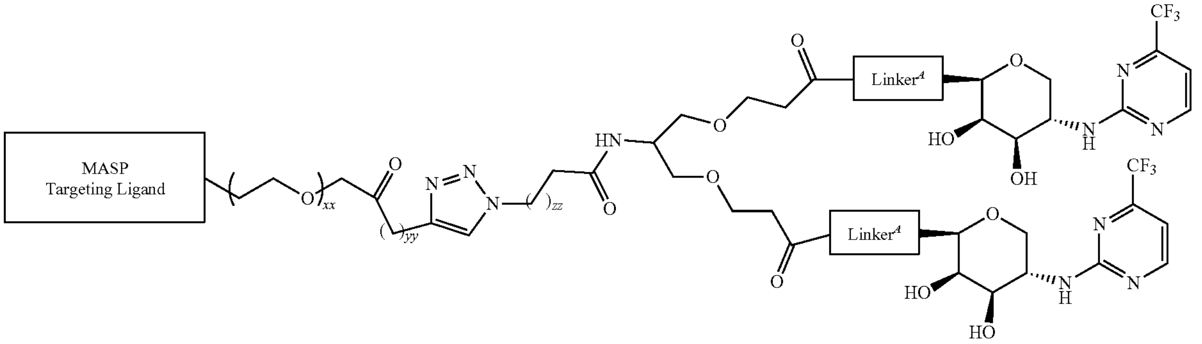
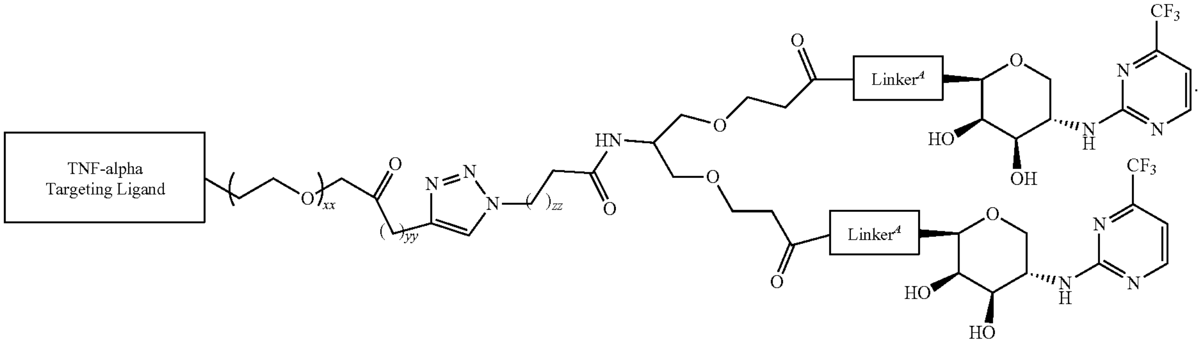
In certain embodiments, an ASGPR ligand useful for incorporation into a compound of the present invention is selected from
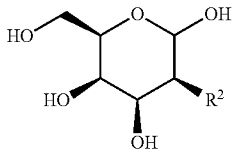
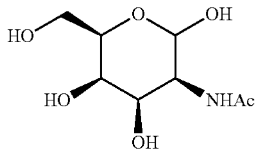
-continued
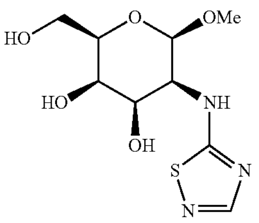
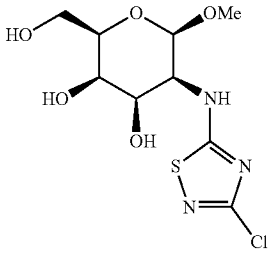

-continued
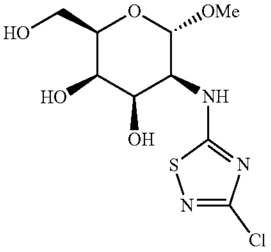
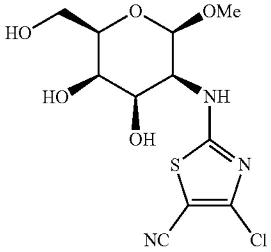
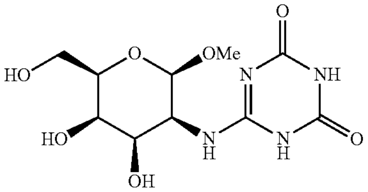
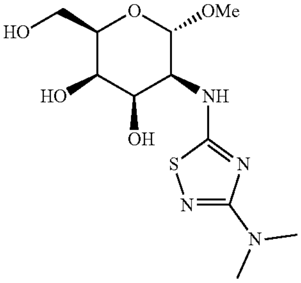
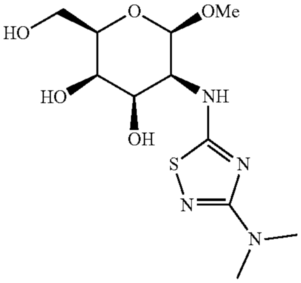
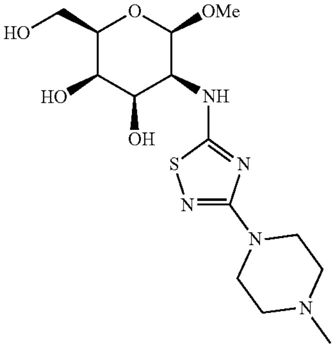
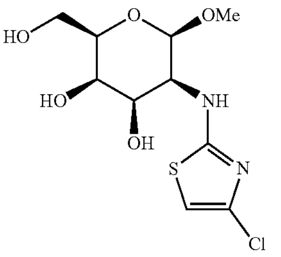
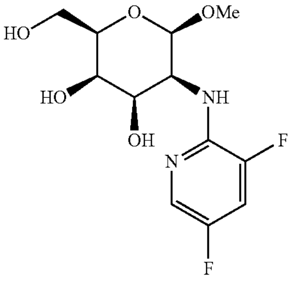
-continued
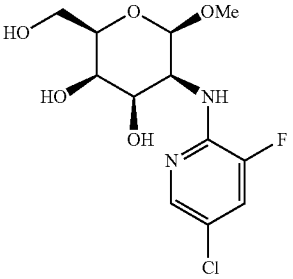
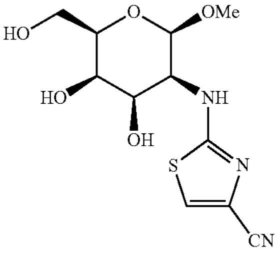
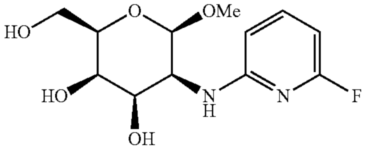
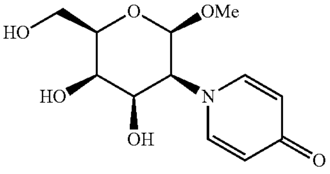
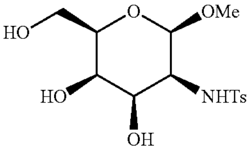
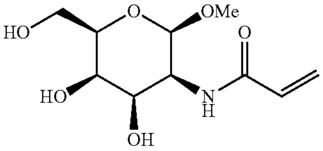
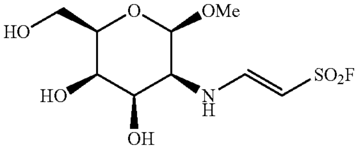
and
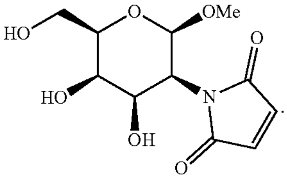
In certain embodiments, an ASGPR ligand useful for incorporation into a compound of the present invention is selected from
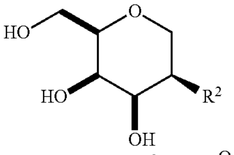
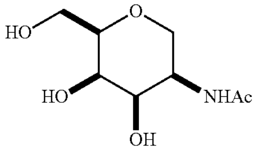
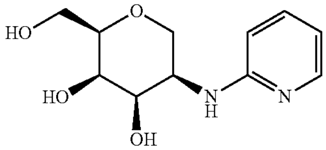

-continued
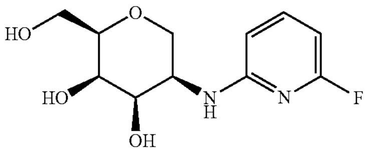
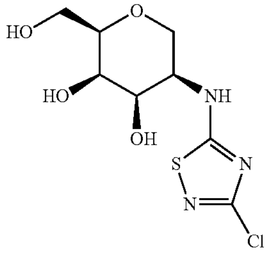
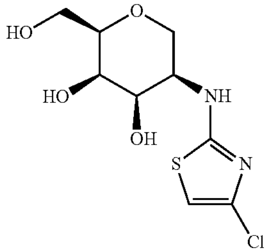
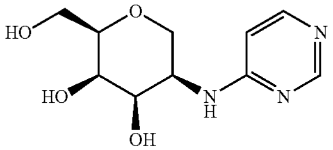
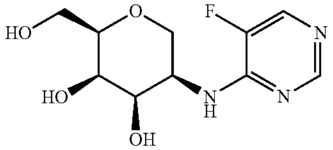
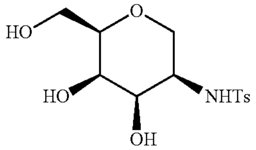
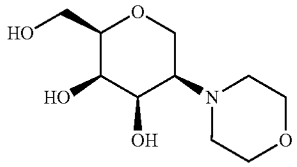
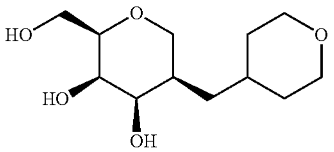
and
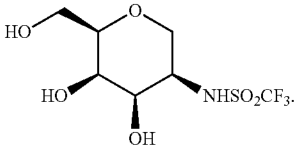
In certain embodiments, an ASGPR ligand useful for incorporation into a compound of the present invention is selected from
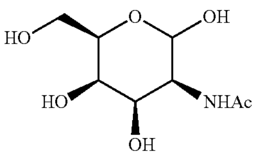
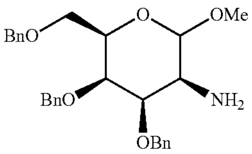
and
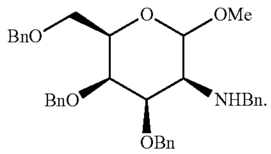
In certain embodiments, an ASGPR ligand useful for incorporation into a compound of the present invention is selected from
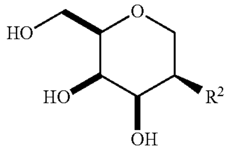
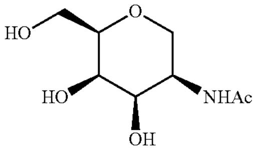
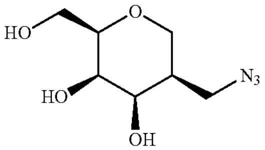
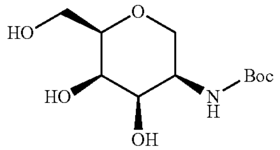
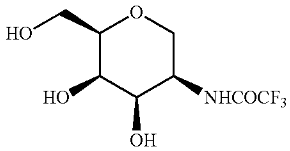
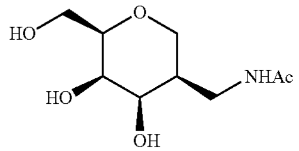
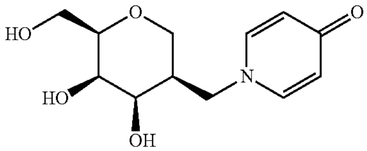
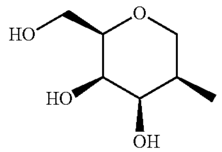
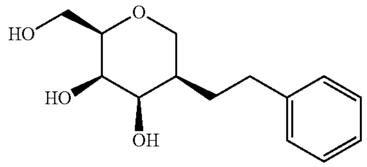
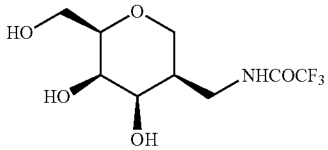

-continued
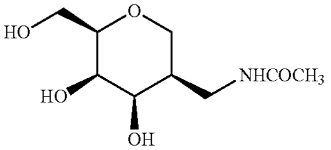
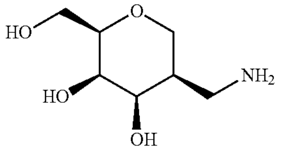
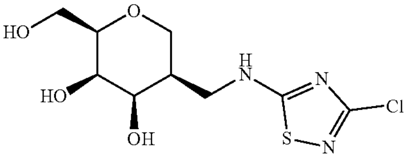
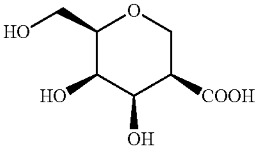
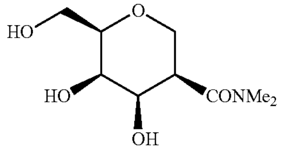
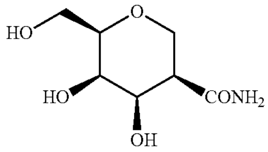
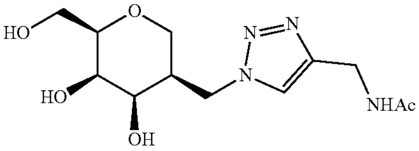
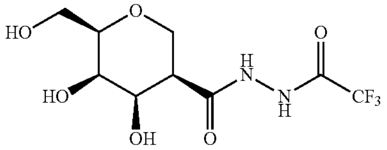
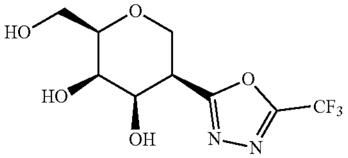
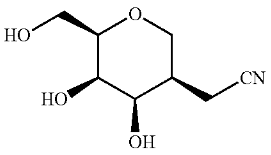
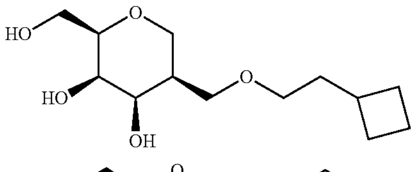
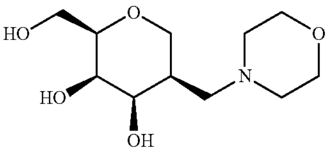
-continued
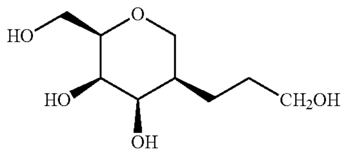
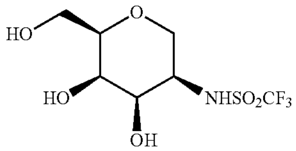
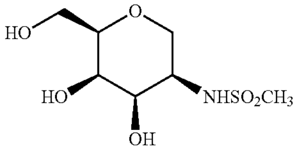
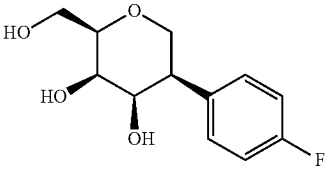
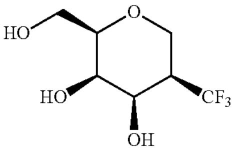
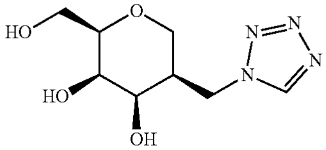
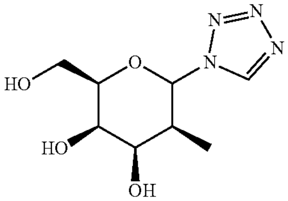
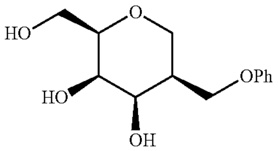
and
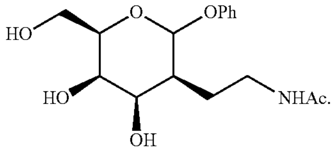
In certain embodiments, an ASGPR ligand useful for incorporation into a compound of the present invention is selected from
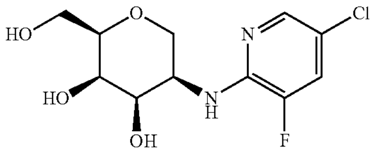

-continued

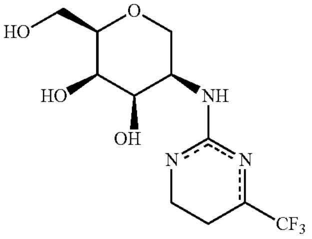

and

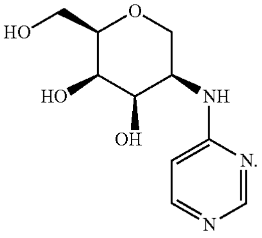

In certain embodiments, an ASGPR ligand useful for incorporation into a compound of the present invention is selected from

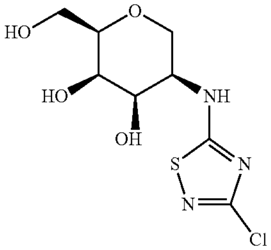

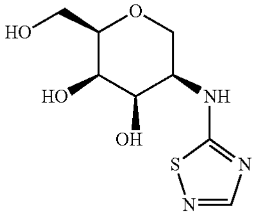

and

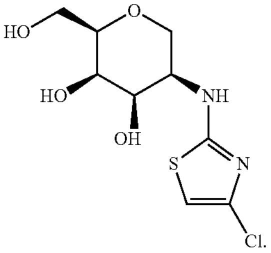

In certain embodiments, an ASGPR ligand useful for incorporation into a compound of the present invention is selected from

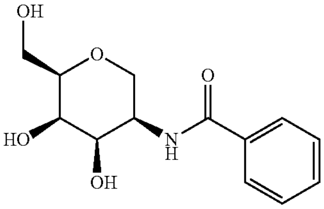

-continued

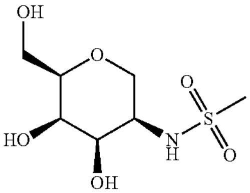

and

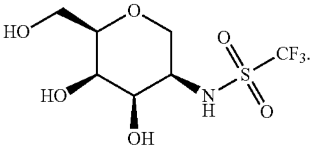

In certain embodiments, an ASGPR ligand useful for incorporation into a compound of the present invention is selected from

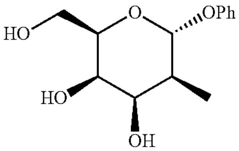

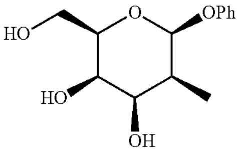

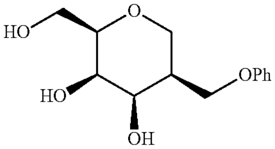

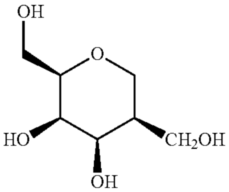

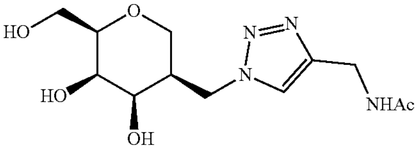

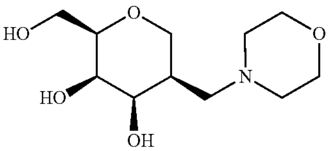

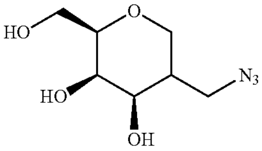

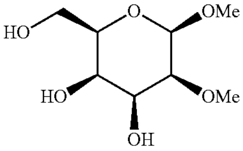

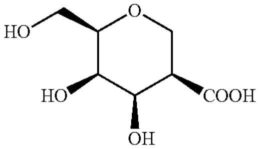

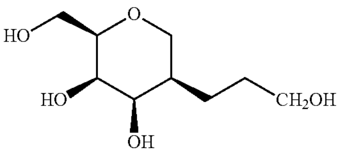

-continued

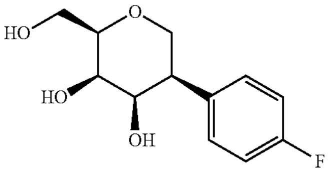

and

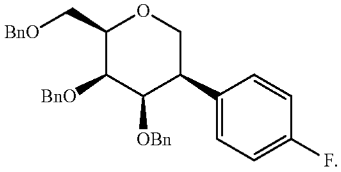

In certain embodiments, an ASGPR ligand useful for incorporation into a compound of the present invention is selected from

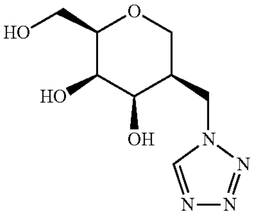

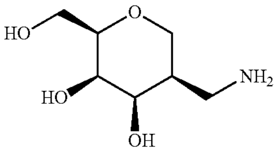

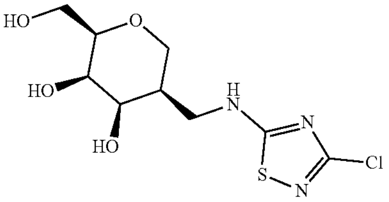

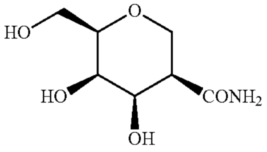

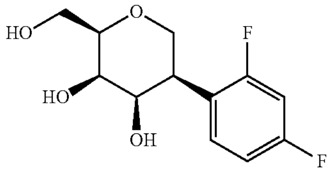

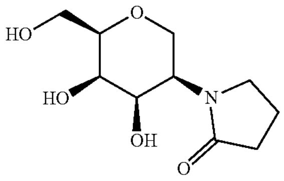

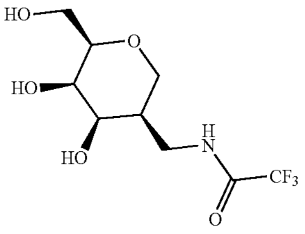

-continued

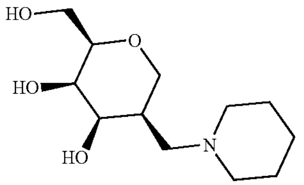

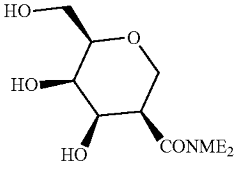

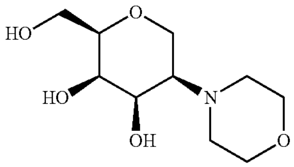

and

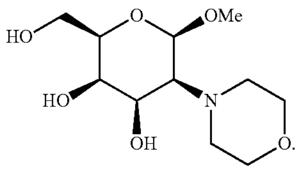

In certain embodiments, an ASGPR ligand useful for incorporation into a compound of the present invention is selected from

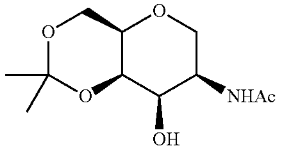

and

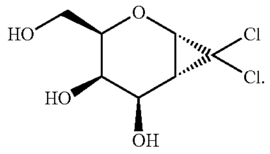

In certain embodiments, an ASGPR ligand useful for incorporation into a compound of the present invention is selected from

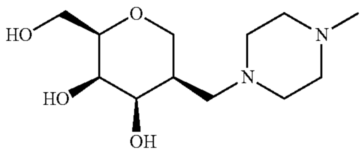

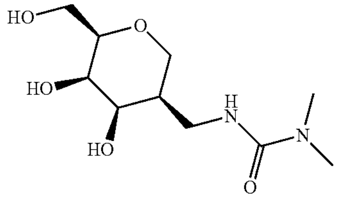

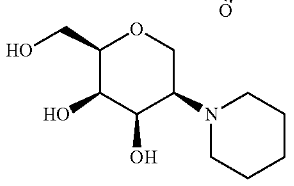

-continued
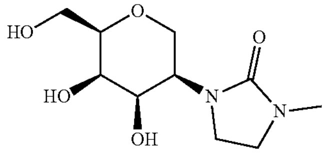
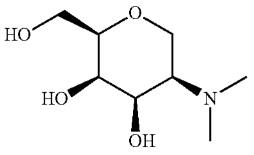
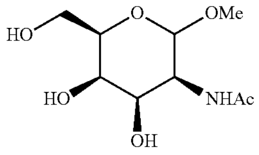
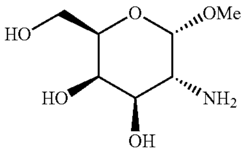
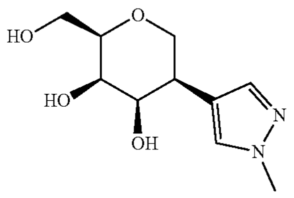
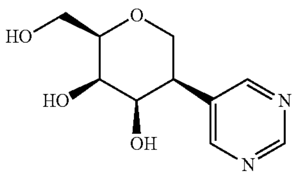
-continued
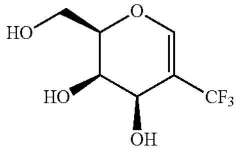
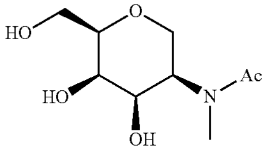
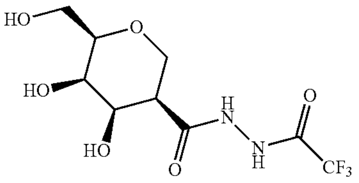
and
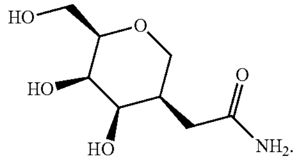 [SMILES: NC(=O)C[C@@H]1CO[C@H](CO)[C@H](O)[C@@H]1O]
In certain embodiments, an ASGPR ligand useful for incorporation into a compound of the present invention is selected from
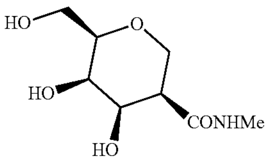
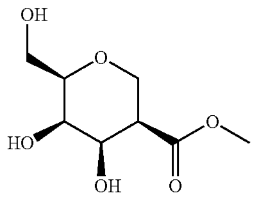
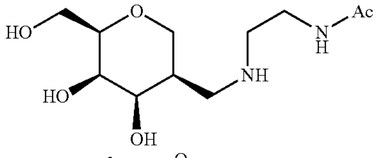
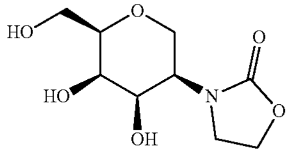
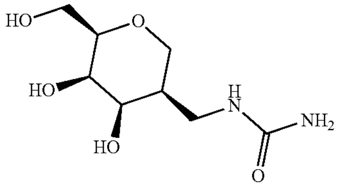
and
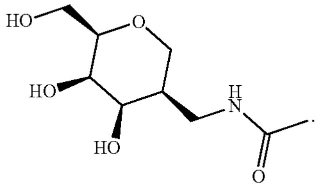

In certain embodiments, the compound of the present invention is selected from
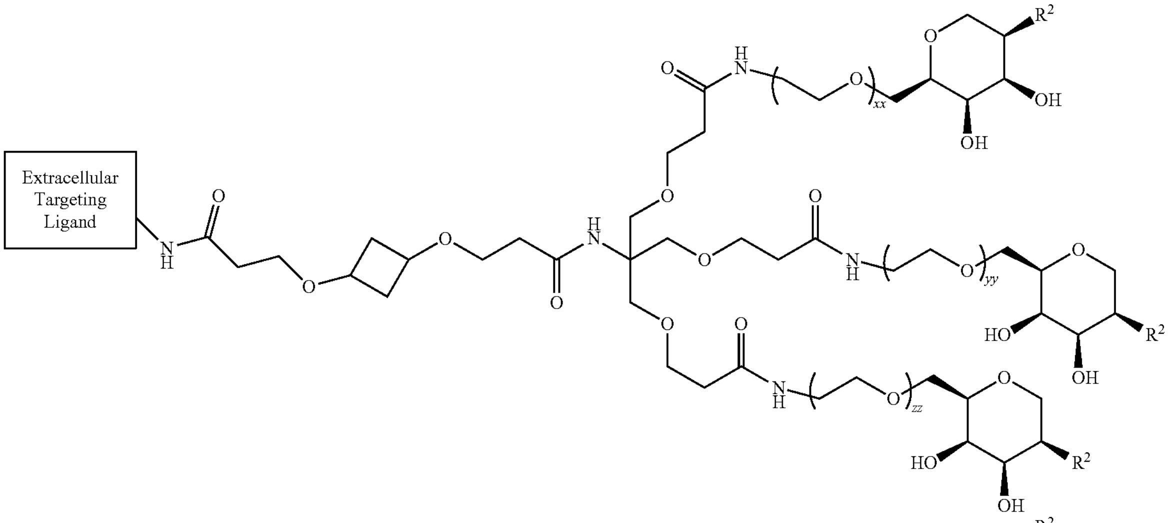
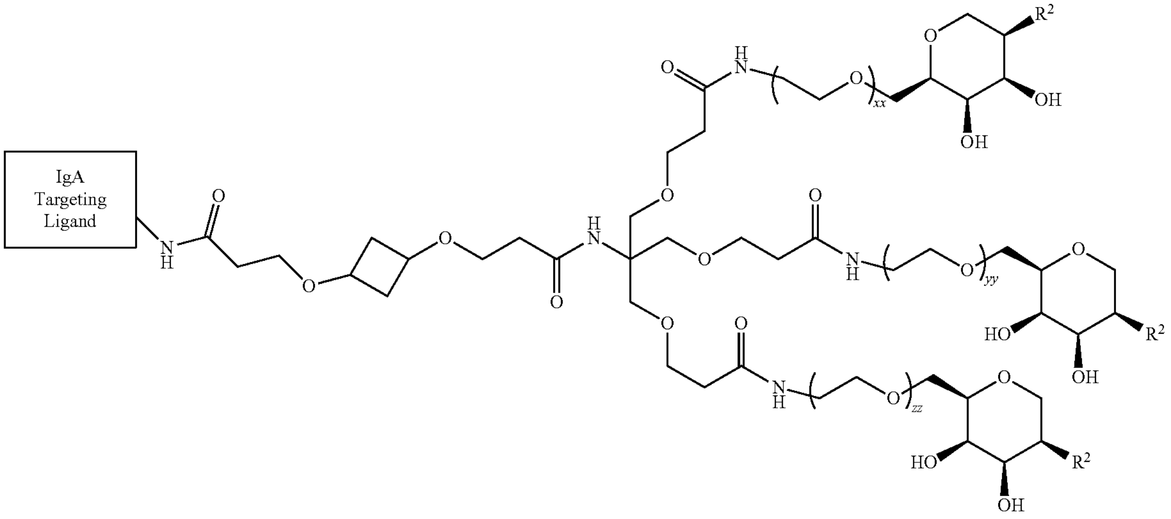
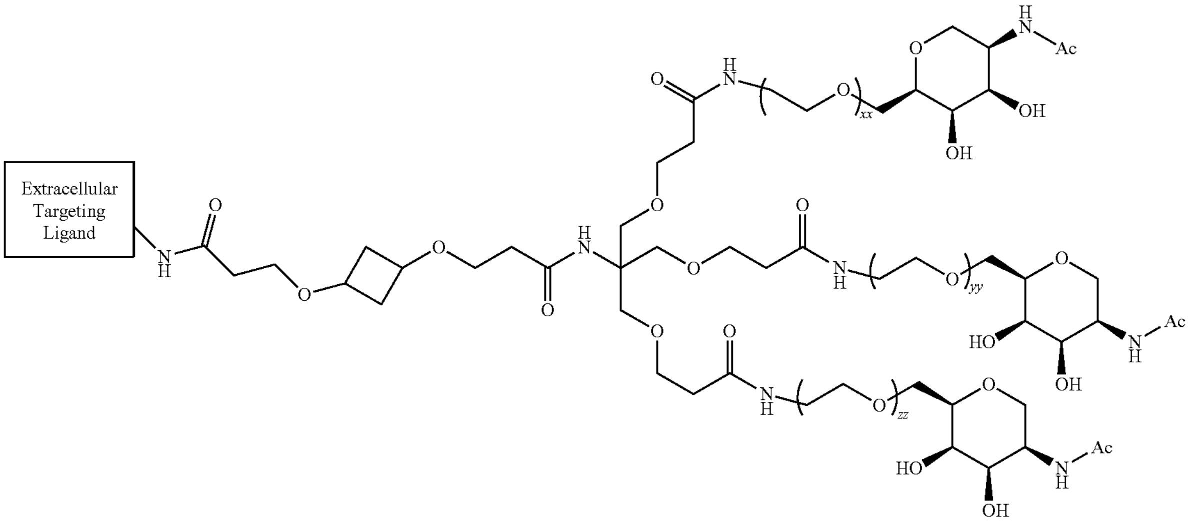

-continued
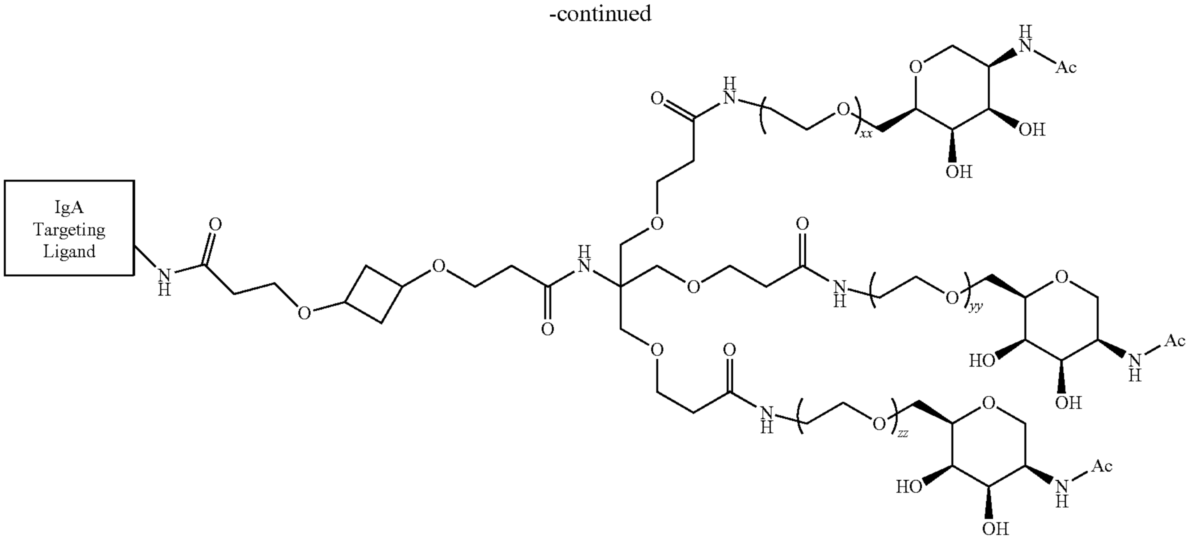
In certain embodiments, the compound of the present invention is selected from
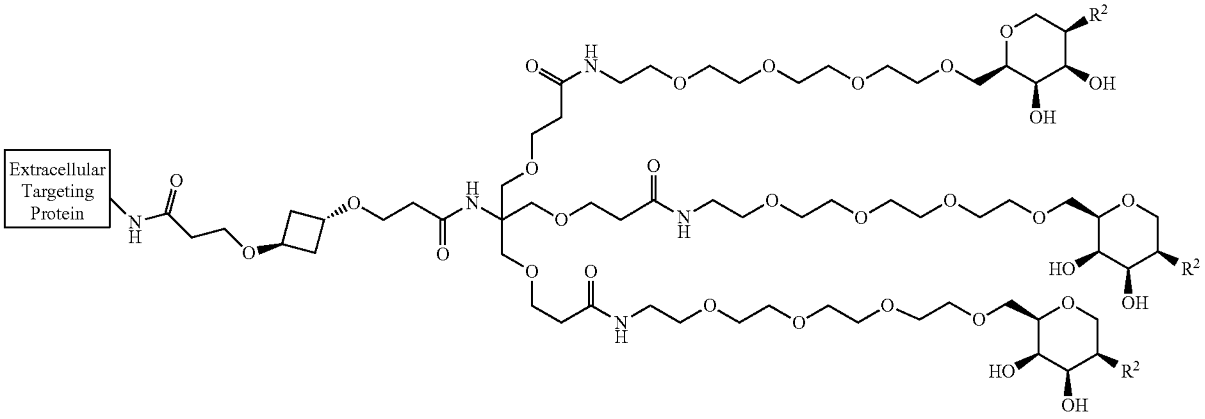
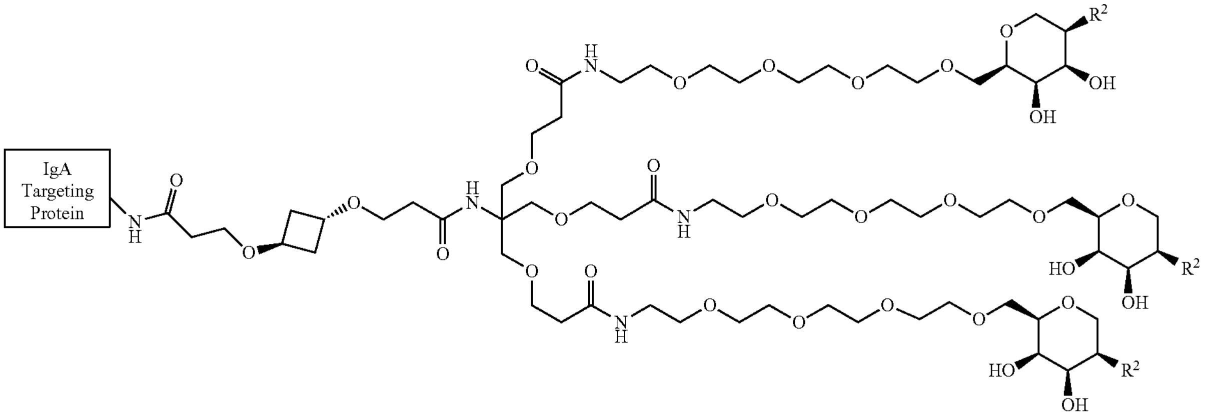

-continued
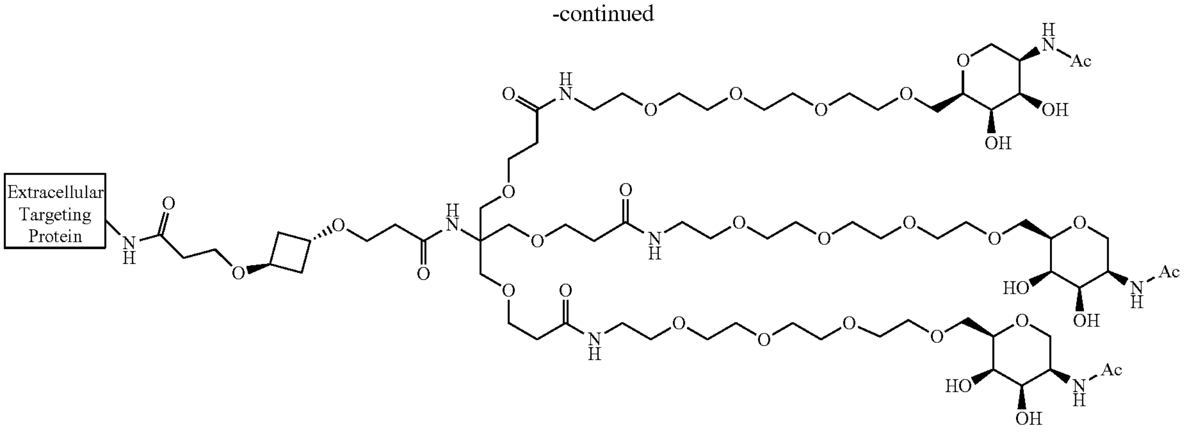
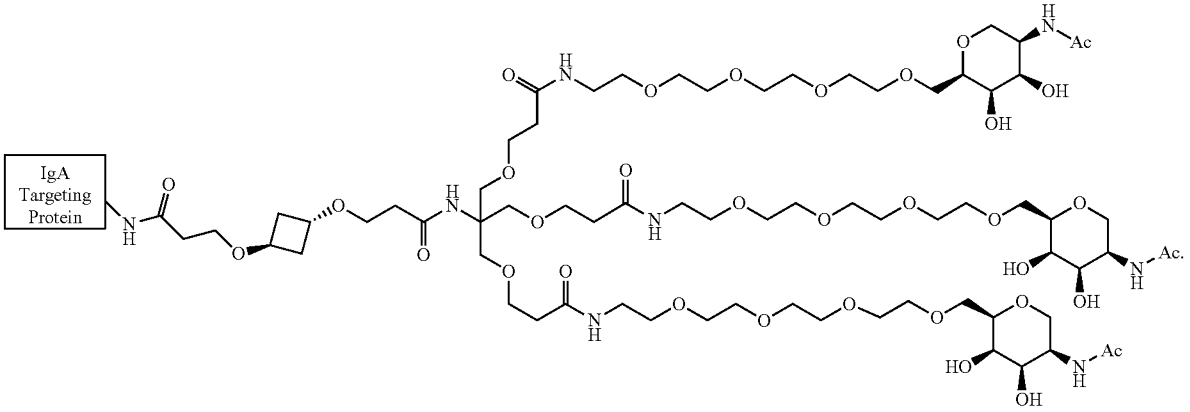
In certain embodiments, the compound of the present invention is selected from
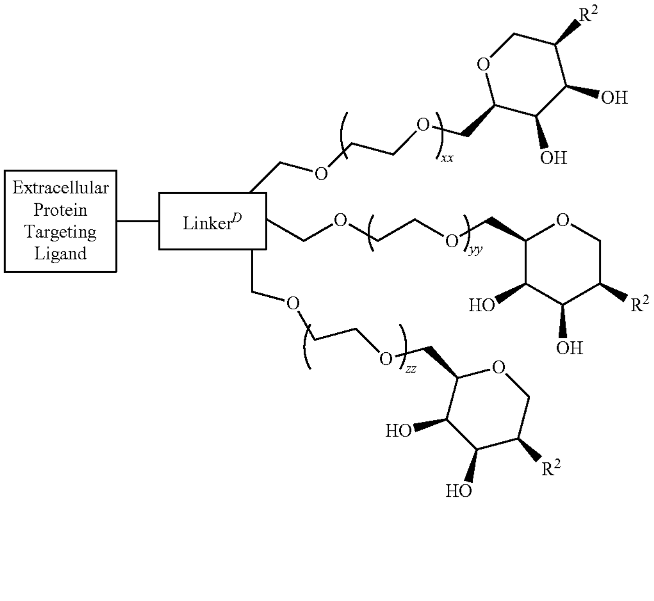

-continued
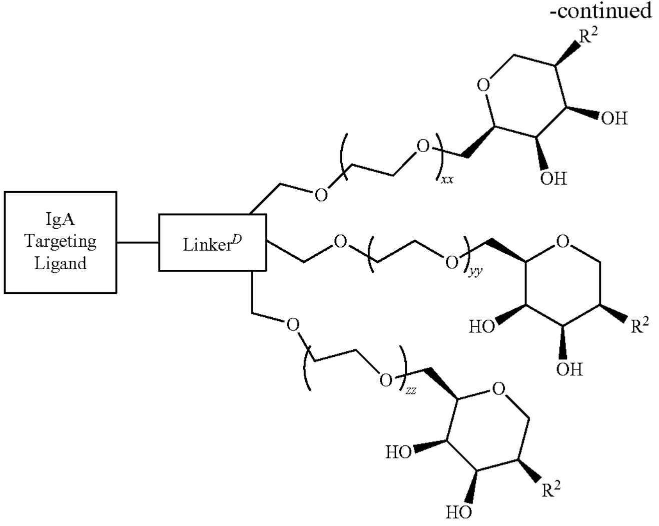
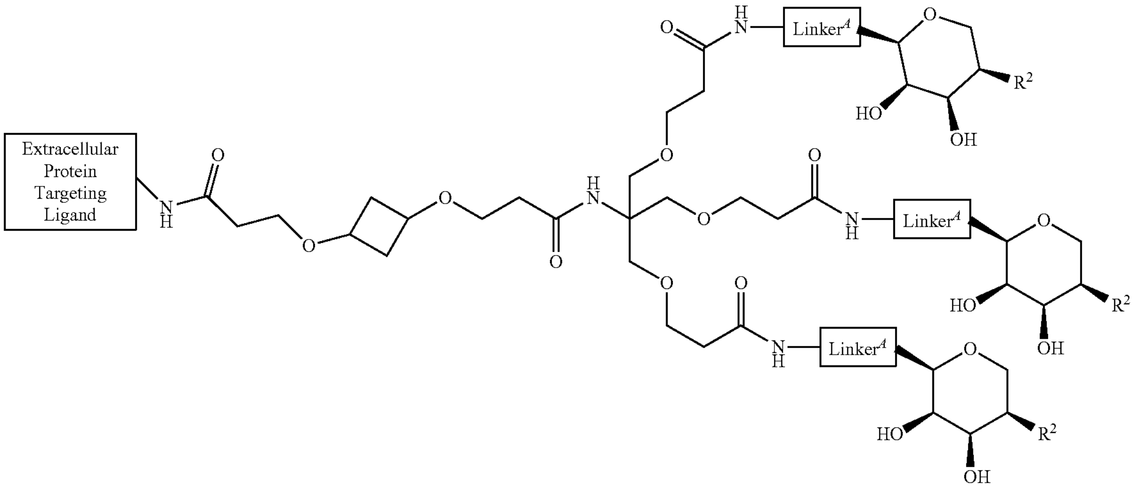
and
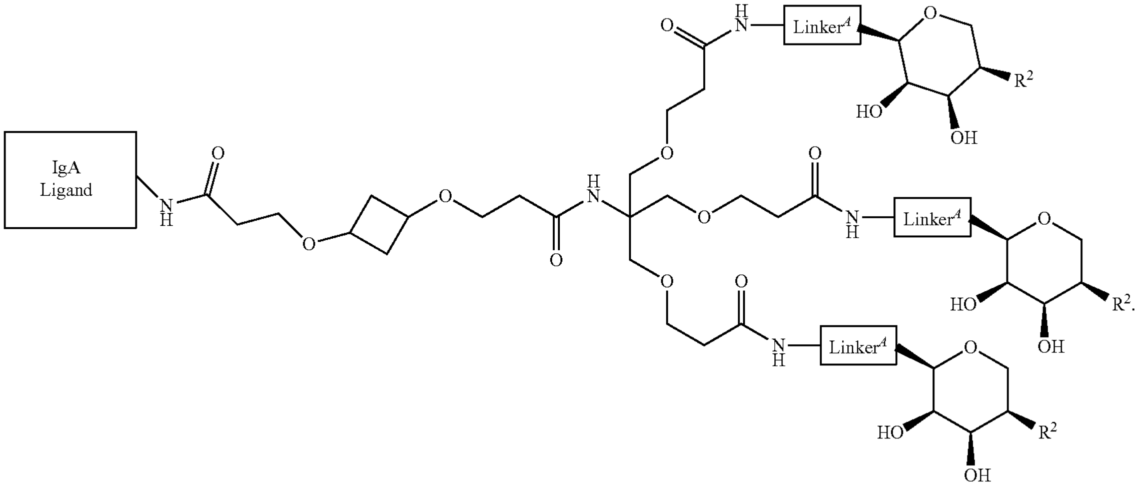
.

In certain embodiments, the compound of the present invention is selected from
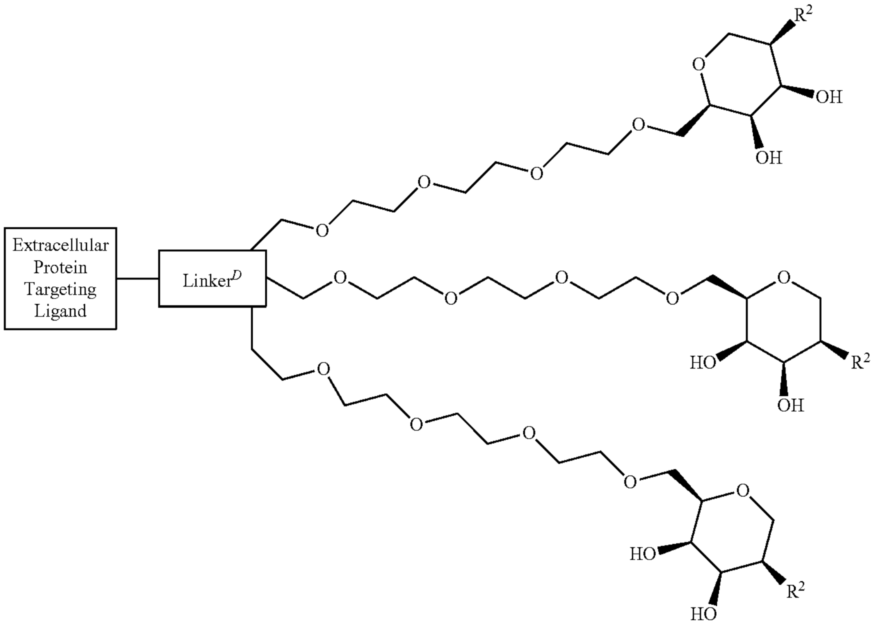
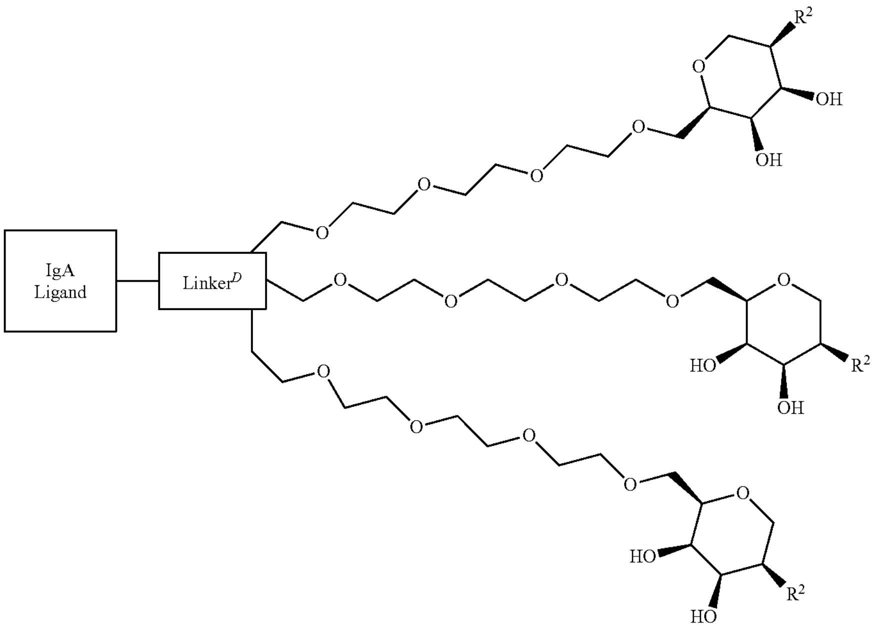

-continued
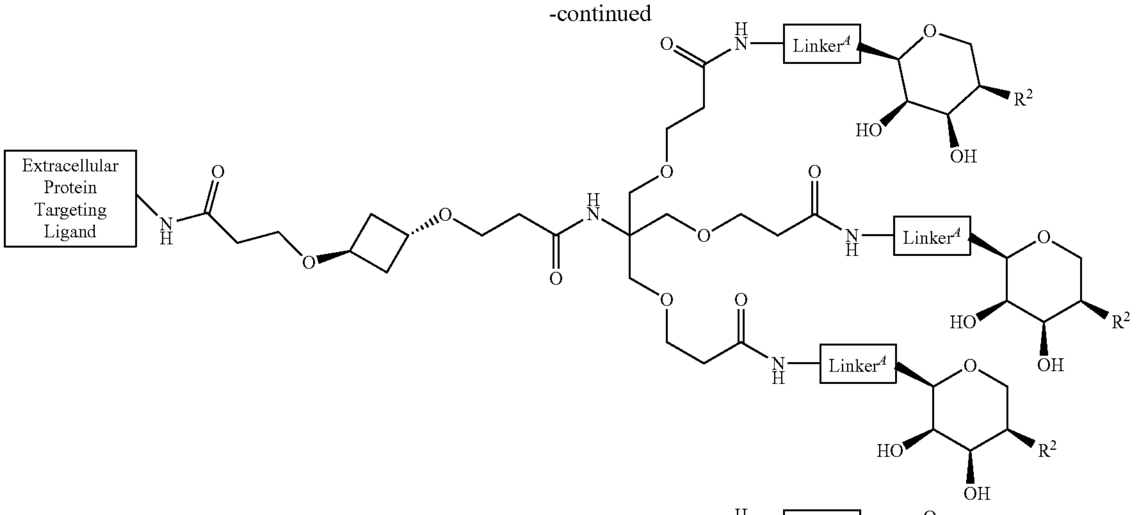
and
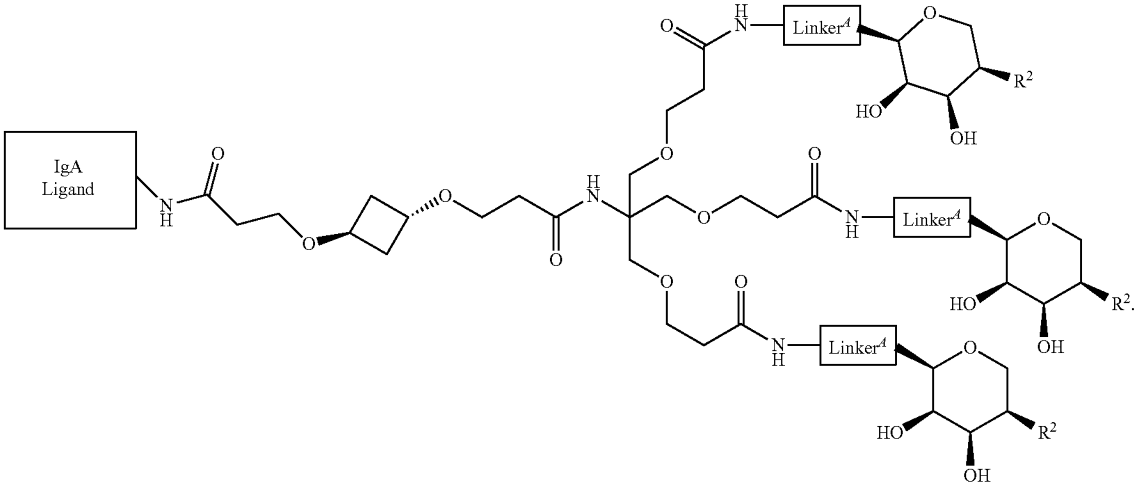
In certain embodiments, the compound of the present invention is selected from
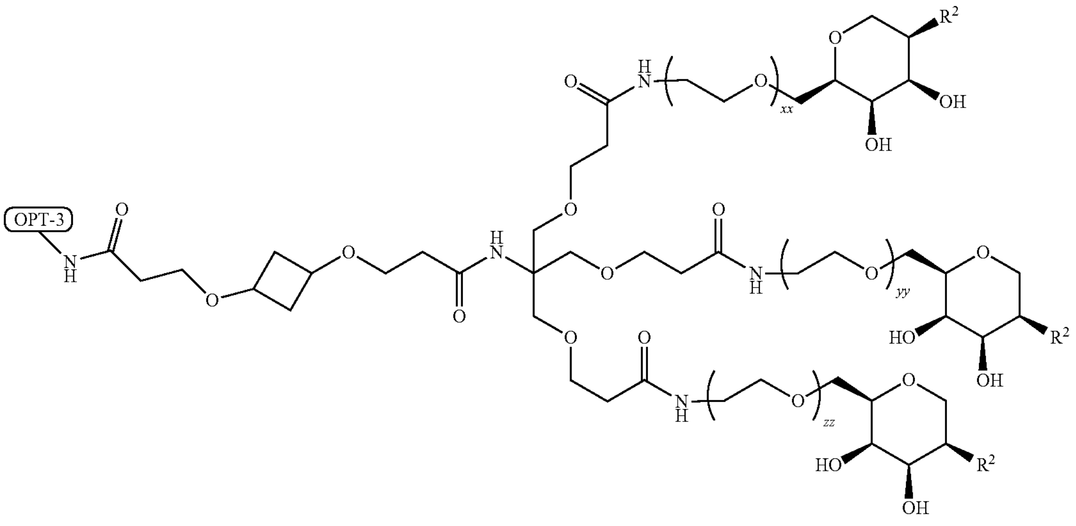
and -continued
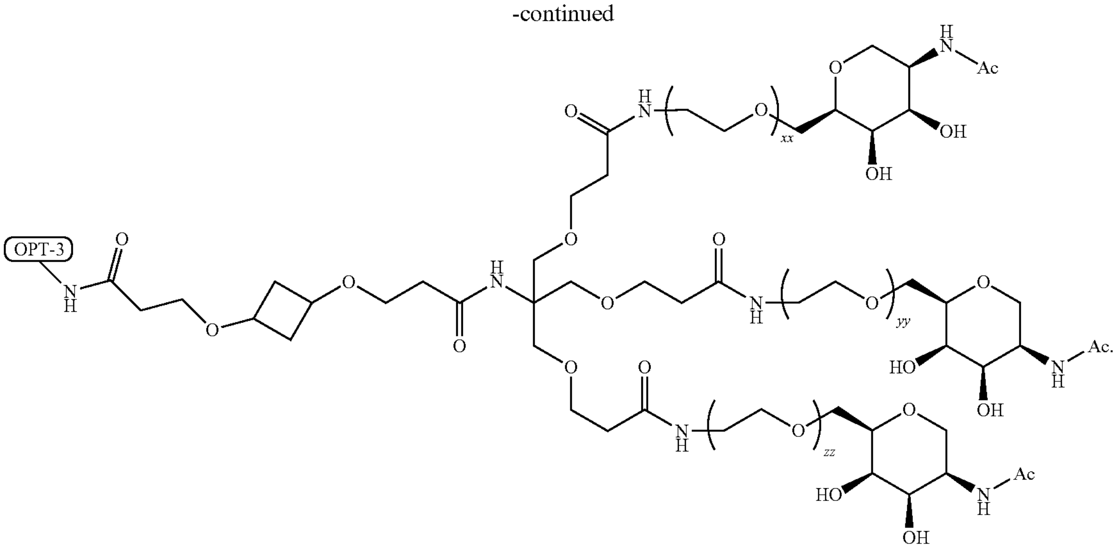
In certain embodiments, the compound of the present invention is selected from
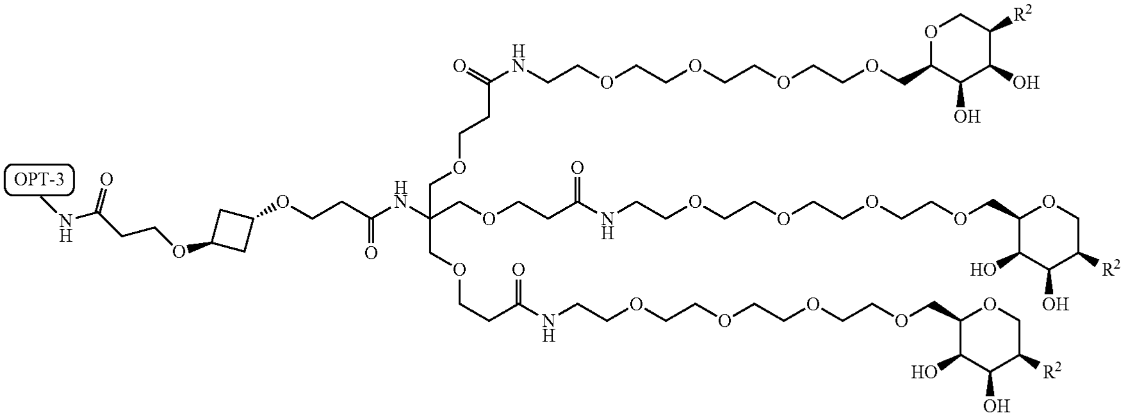
and
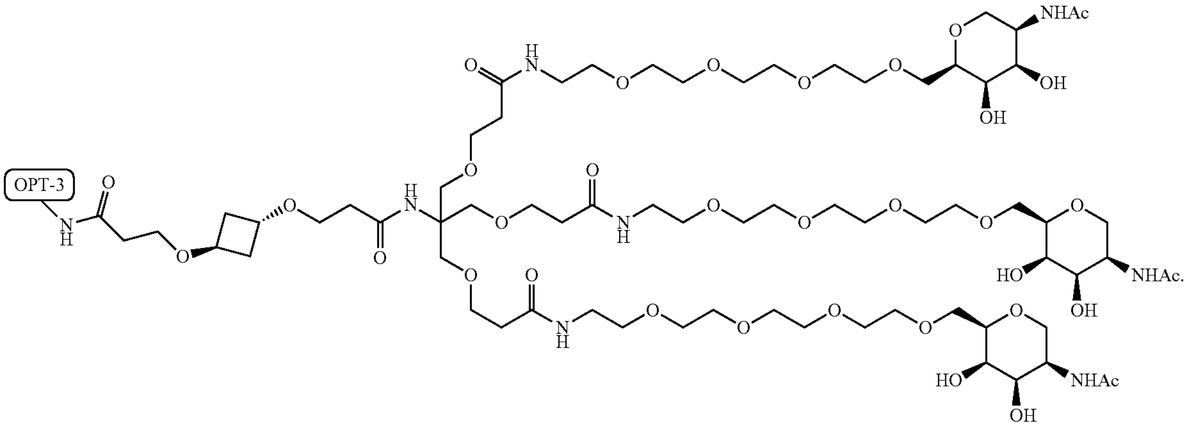

III. Embodiments of the ASGPR Ligand

Embodiments of $R^1$

In certain embodiments $R^1$ is hydrogen.

In certain embodiments $R^1$ is

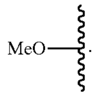

In certain embodiments $R^1$ is

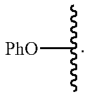

In certain embodiments $R^1$ is

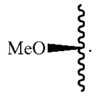

In certain embodiments $R^1$ is

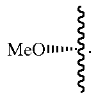

In certain embodiments $R^1$ is

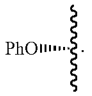

In certain embodiments $R^1$ is

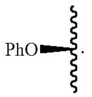

In certain embodiments $R^1$ is heteroalkyl optionally substituted with 1, 2, 3, or 4 substituents.

In certain embodiments $R^1$ is $C_0$-$C_6$ alkyl-cyano optionally substituted with 1, 2, 3, or 4 substituents.

In certain embodiments $R^1$ is alkyl optionally substituted with 1, 2, 3, or 4 substituents.

In certain embodiments $R^1$ is alkenyl optionally substituted with 1, 2, 3, or 4 substituents.

In certain embodiments $R^1$ is alkynyl optionally substituted with 1, 2, 3, or 4 substituents.

In certain embodiments $R^1$ is haloalkyl optionally substituted with 1, 2, 3, or 4 substituents.

In certain embodiments $R^1$ is F.

In certain embodiments $R^1$ is Cl.

In certain embodiments $R^1$ is Br.

In certain embodiments $R^1$ is aryl optionally substituted with 1, 2, 3, or 4 substituents.

In certain embodiments $R^1$ is arylalkyl optionally substituted with 1, 2, 3, or 4 substituents.

In certain embodiments $R^1$ is heteroaryl optionally substituted with 1, 2, 3, or 4 substituents.

In certain embodiments $R^1$ is heteroarylalkyl optionally substituted with 1, 2, 3, or 4 substituents.

In certain embodiments $R^1$ is heterocycle optionally substituted with 1, 2, 3, or 4 substituents.

In certain embodiments $R^1$ is heterocycloalkyl optionally substituted with 1, 2, 3, or 4 substituents.

In certain embodiments $R^1$ is haloalkoxy optionally substituted with 1, 2, 3, or 4 substituents.

In certain embodiments $R^1$ is —O-alkenyl, —O-alkynyl, $C_0$-$C_6$ alkyl-$OR^6$, $C_0$-$C_6$ alkyl-$SR^6$, $C_0$-$C_6$ alkyl-$NR^6R^7$, $C_0$-$C_6$ alkyl-C(O)$R^3$, $C_0$-$C_6$ alkyl-S(O)$R^3$, $C_0$-$C_6$ alkyl-C(S)$R^3$, $C_0$-$C_6$ alkyl-$S(O)_2R^3$, $C_0$-$C_6$ alkyl-N($R^8$)—C(O)$R^3$, $C_0$-$C_6$ alkyl-N($R^8$)—S(O)$R^3$, $C_0$-$C_6$ alkyl-N($R^8$)—C(S)$R^3$, $C_0$-$C_6$ alkyl-N($R^8$)—$S(O)_2R^3$, $C_0$-$C_6$ alkyl-O—C(O)$R^3$, $C_0$-$C_6$ alkyl-O—S(O)$R^3$, $C_0$-$C_6$ alkyl-O—C(S)$R^3$, —N═S(O)$(R^3)_2$, $C_0$-$C_6$ alkyl$N_3$, or $C_0$-$C_6$ alkyl-O—$S(O)_2R^3$, each of which is optionally substituted with 1, 2, 3, or 4 substituents.

Embodiments of $R^2$

In certain embodiments $R^2$ is aryl optionally substituted with 1, 2, 3, or 4 substituents.

In certain embodiments $R^2$ is heterocycle optionally substituted with 1, 2, 3, or 4 substituents.

In certain embodiments $R^2$ is heteroaryl containing 1 or 2 heteroatoms independently selected from N, O, and S optionally substituted with 1, 2, 3, or 4 substituents.

In certain embodiments $R^2$ is selected from

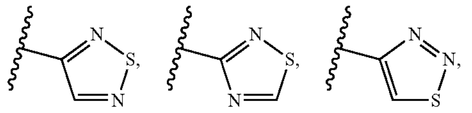

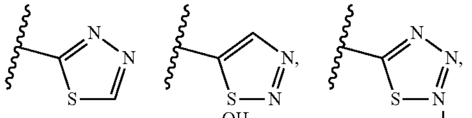

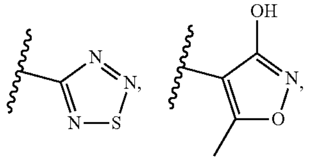

and

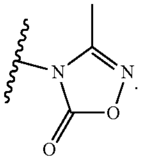

In certain embodiments $R^2$ is heterocycle optionally substituted with 1, 2, 3, or 4 substituents.

In certain embodiments $R^2$ is —$NR^8$—S(O)—$R^3$ optionally substituted with 1, 2, 3, or 4 substituents.

In certain embodiments $R^2$ is —$NR^8$—C(S)—$R^3$ optionally substituted with 1, 2, 3, or 4 substituents.

In certain embodiments $R^2$ is —$NR^8$—S(O)($NR^6$)—$R^3$ optionally substituted with 1, 2, 3, or 4 substituents.

In certain embodiments $R^2$ is —N═S(O)$(R^3)_2$ optionally substituted with 1, 2, 3, or 4 substituents.

In certain embodiments $R^2$ is —$NR^8C(O)NR^9S(O)_2R^3$ optionally substituted with 1, 2, 3, or 4 substituents.

In certain embodiments $R^2$ is $—NR^8—S(O)_2—R^{10}$ optionally substituted with 1, 2, 3, or 4 substituents.

In certain embodiments $R^2$ is $—NR^8—C(NR^6)—R^3$ optionally substituted with 1, 2, 3, or 4 substituents.

In certain embodiments $R^2$ is hydrogen.

In certain embodiments $R^2$ is $R^{10}$.

In certain embodiments $R^2$ is alkyl-C(O)—$R^3$.

In certain embodiments $R^2$ is —C(O)—$R^3$.

In certain embodiments $R^2$ is alkyl.

In certain embodiments $R^2$ is haloalkyl.

In certain embodiments $R^2$ is —OC(O)$R^3$.

In certain embodiments $R^2$ is $—NR^8—C(O)R^{10}$.

In certain embodiments $R^2$ is alkenyl optionally substituted with 1, 2, 3, or 4 substituents.

In certain embodiments $R^2$ is allyl optionally substituted with 1, 2, 3, or 4 substituents.

In certain embodiments $R^2$ is alkynyl optionally substituted with 1, 2, 3, or 4 substituents.

In certain embodiments $R^2$ is $—NR^6$-alkenyl optionally substituted with 1, 2, 3, or 4 substituents.

In certain embodiments $R^2$ is —O-alkenyl optionally substituted with 1, 2, 3, or 4 substituents.

In certain embodiments $R^2$ is $—NR^6$-alkynyl optionally substituted with 1, 2, 3, or 4 substituents.

In certain embodiments $R^2$ is $—NR^6$-heteroaryl optionally substituted with 1, 2, 3, or 4 substituents.

In certain embodiments $R^2$ is $—NR^6$-aryl optionally substituted with 1, 2, 3, or 4 substituents.

In certain embodiments $R^2$ is —O-heteroaryl optionally substituted with 1, 2, 3, or 4 substituents.

In certain embodiments $R^2$ is —O-aryl optionally substituted with 1, 2, 3, or 4 substituents.

In certain embodiments $R^2$ is —O-alkynyl optionally substituted with 1, 2, 3, or 4 substituents.

In certain embodiments $R^2$ is selected from

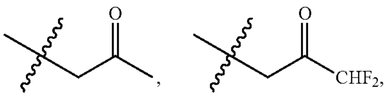

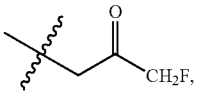

and

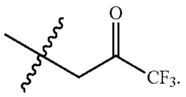

In certain embodiments $R^2$ is selected from:

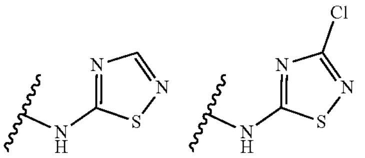

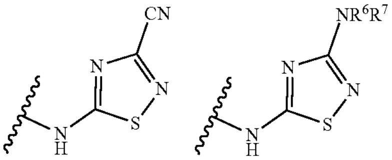

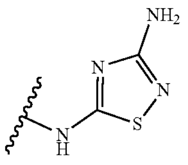

and

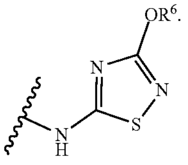

In certain embodiments $R^2$ is selected from

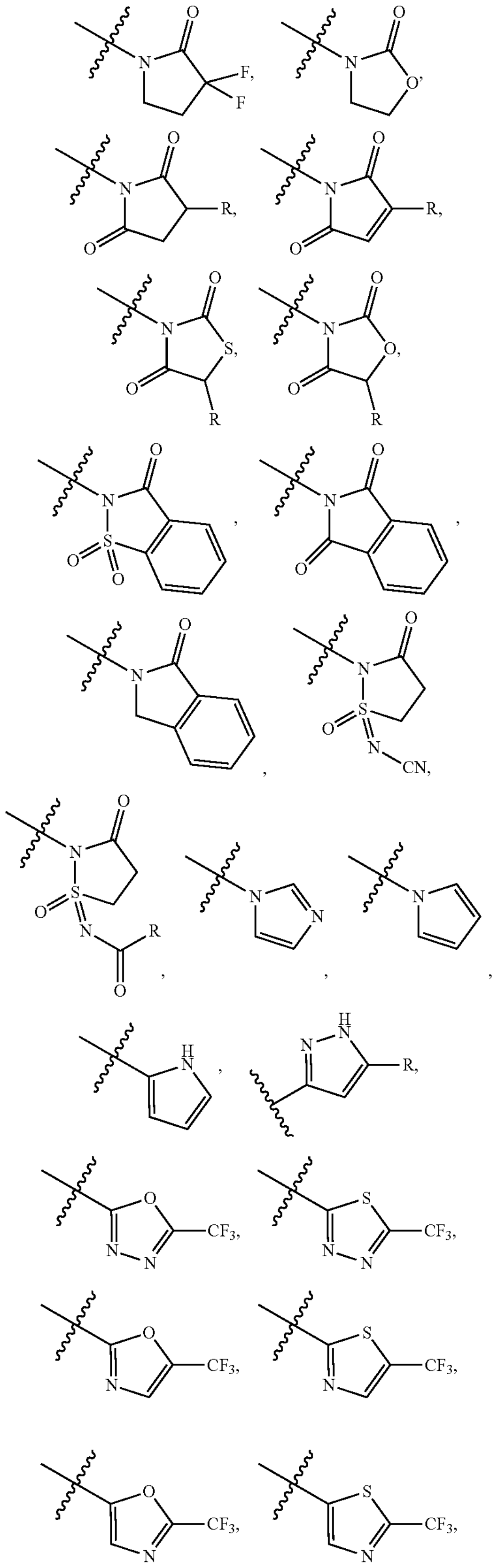

-continued
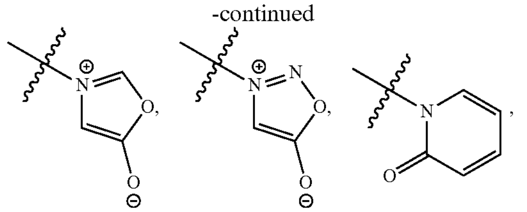
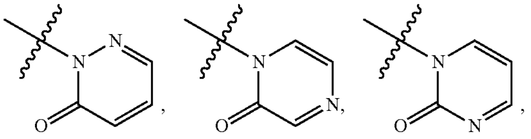
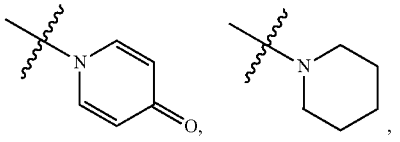
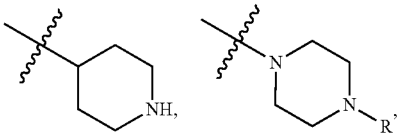
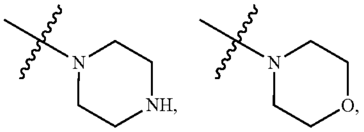
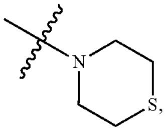
and
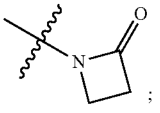
wherein R is an optional substituent as defined herein.
In certain embodiments $R^2$ is selected from
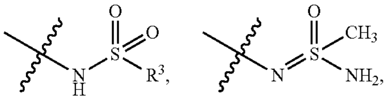
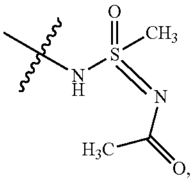
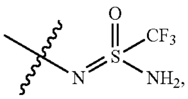
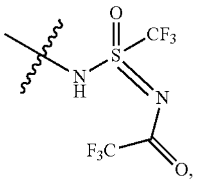
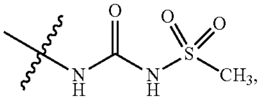
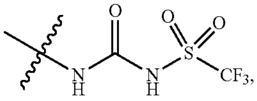
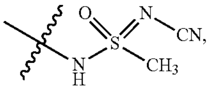
and
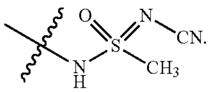
In certain embodiments $R^{2A}$ is selected from
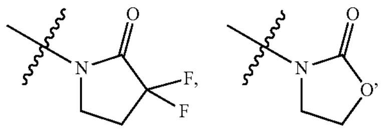
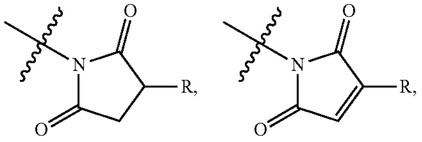
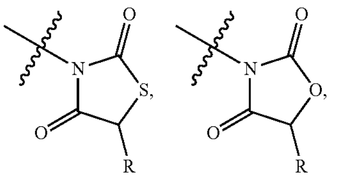
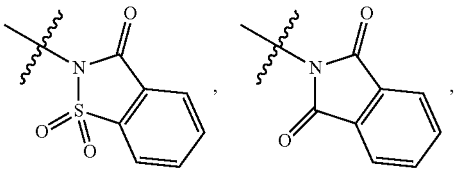
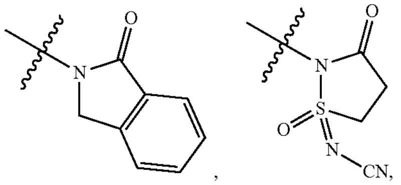
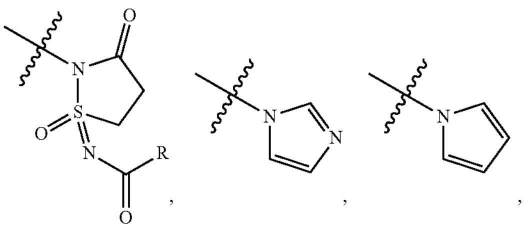
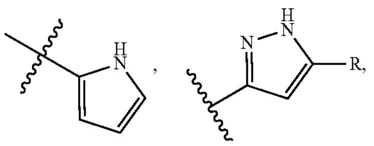
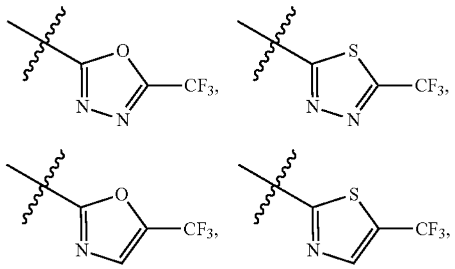
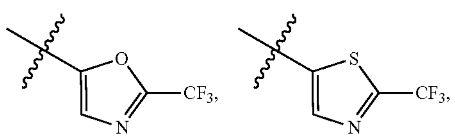

-continued
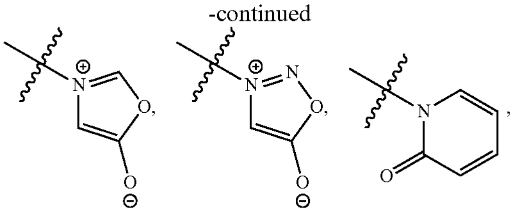
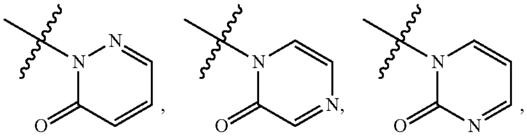
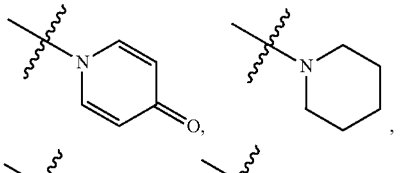
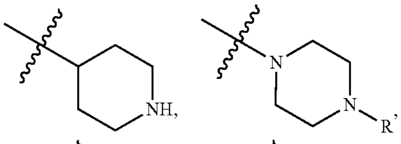
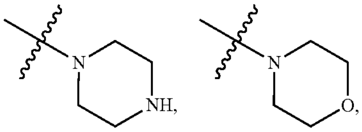
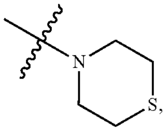
and
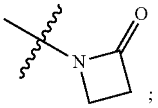
wherein R is an optional substituent as defined herein.
In certain embodiments $R^{2A}$ is selected from
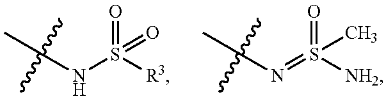
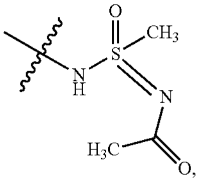
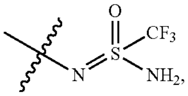
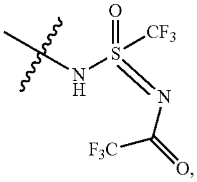
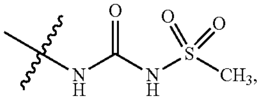
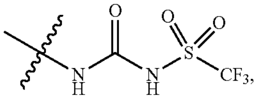
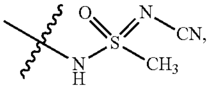
and
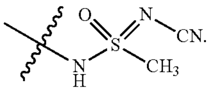
In certain embodiment, $R^2$ is selected from
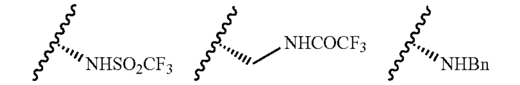
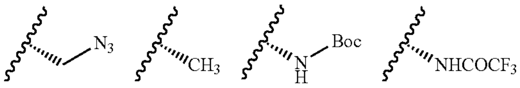
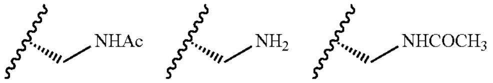
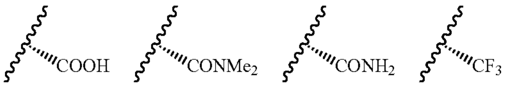
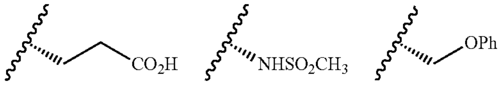
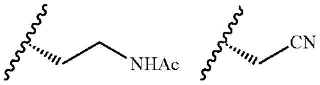
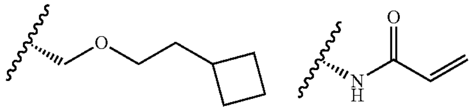
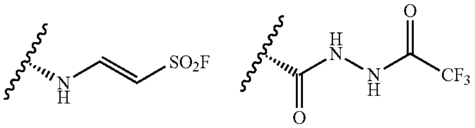
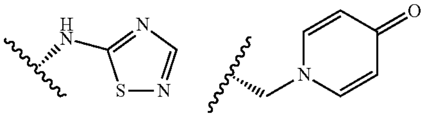
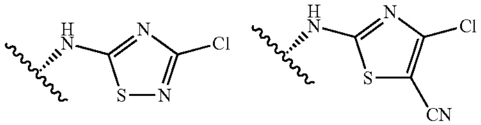
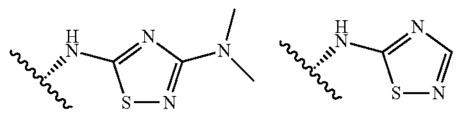
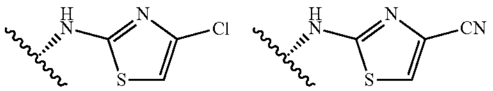
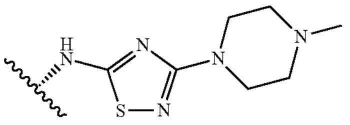
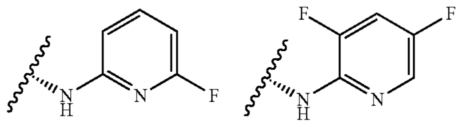
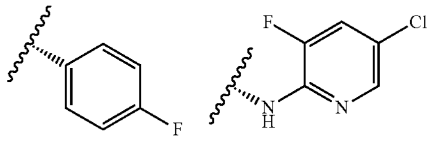

-continued
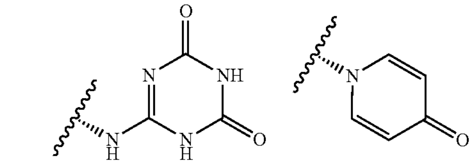
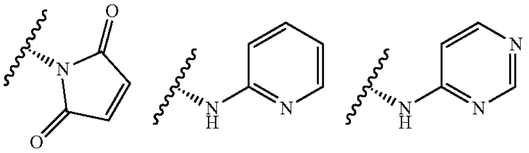
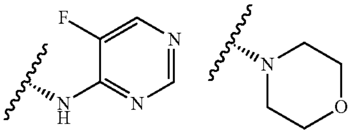
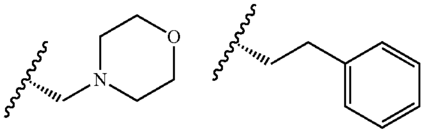
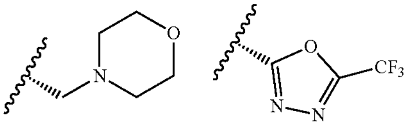
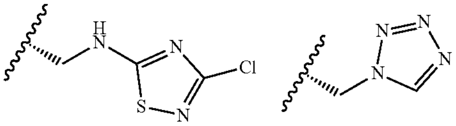
and
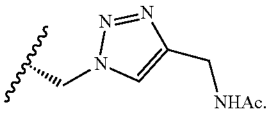
In certain embodiments, $R^2$ is selected from
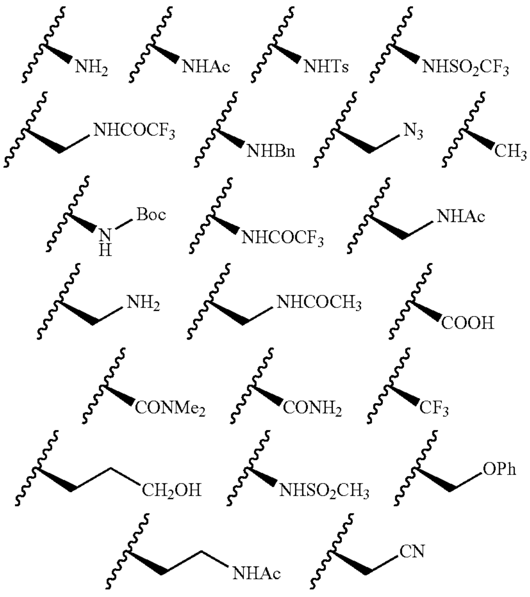
-continued
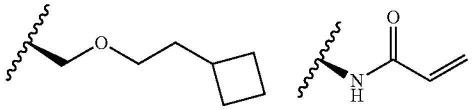
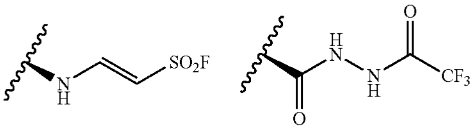
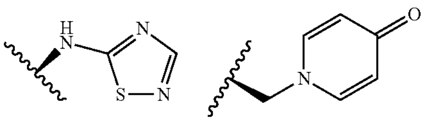
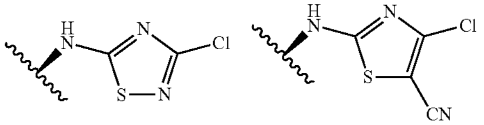
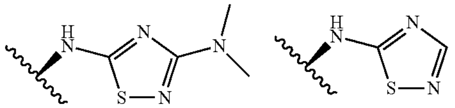
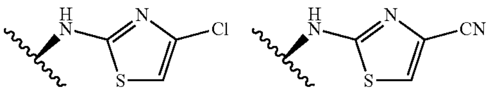
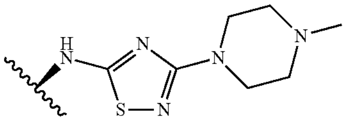
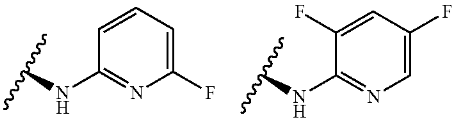
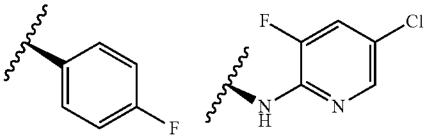
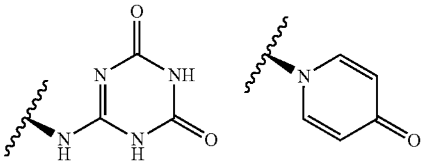
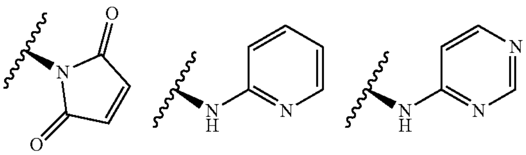
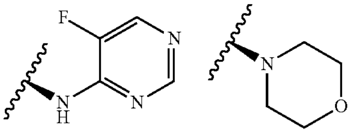
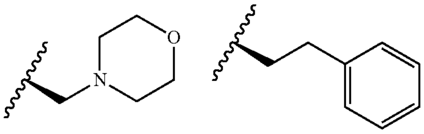

-continued
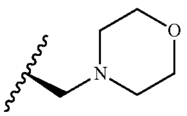 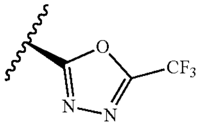
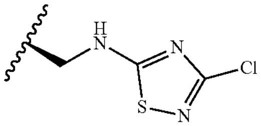 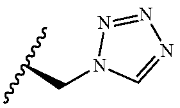 and
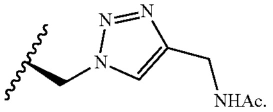
In certain embodiments $R^2$ is selected from
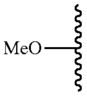 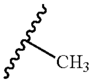 and 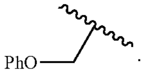
In certain embodiments $R^2$ is selected from
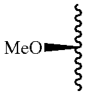 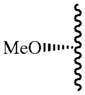 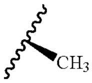 and 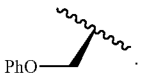
In certain embodiments $R^2$ is selected from
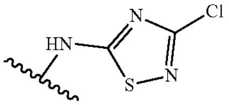 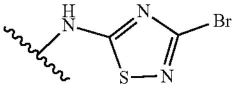
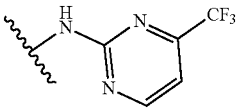 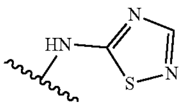
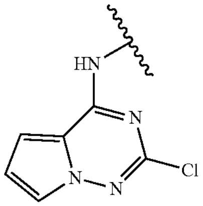 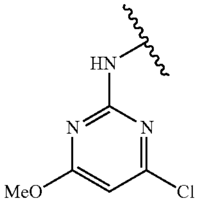 and
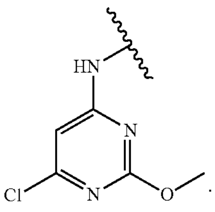
In certain embodiments $R^2$ is selected from
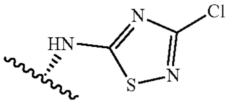 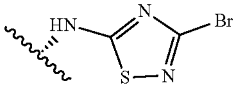
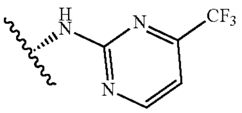 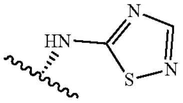
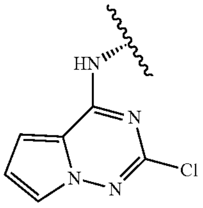 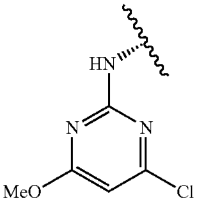 and
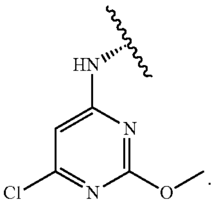
In certain embodiments $R^2$ is selected from
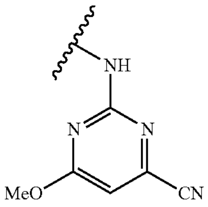 and 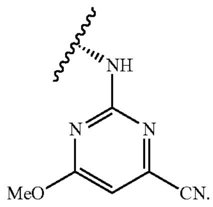
In certain embodiments $R^2$ is selected from
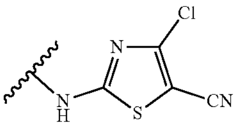 and
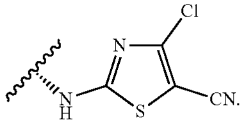
In certain embodiments $R^2$ is selected from
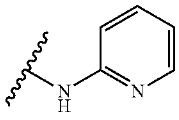 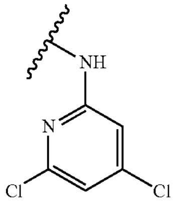

-continued
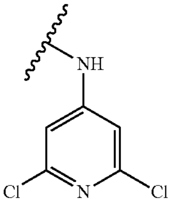
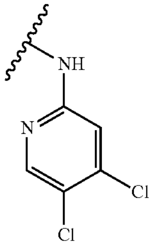
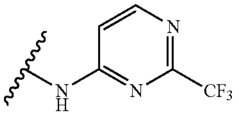
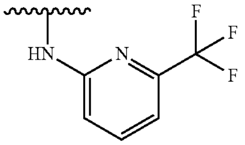
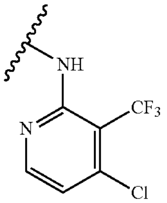
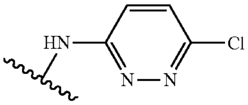
and
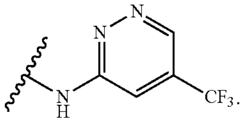
In certain embodiments $R^2$ is selected from
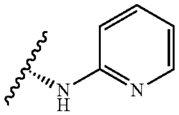
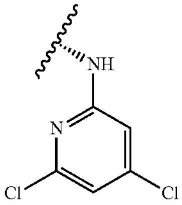
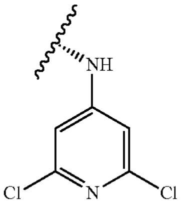
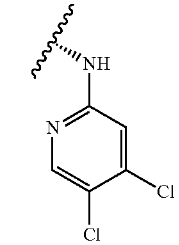
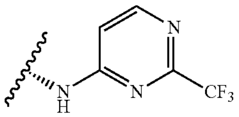
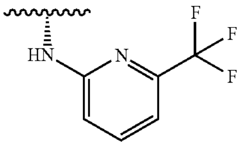
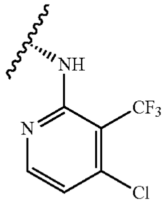
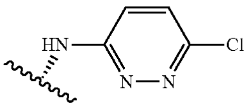
and
-continued
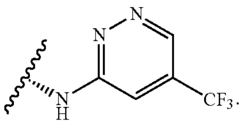
In certain embodiments $R^2$ is selected from
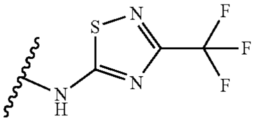
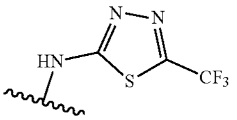
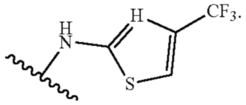
In certain embodiments $R^2$ is selected from
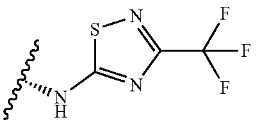
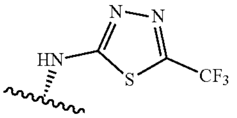
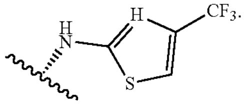
In certain embodiments $R^2$ is selected from
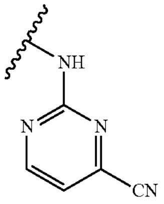
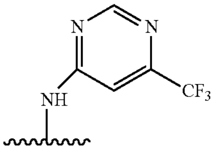
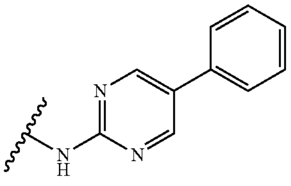
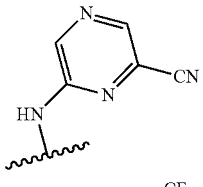
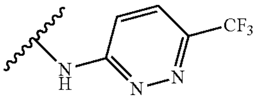
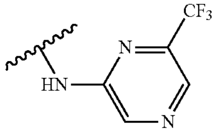
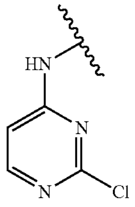
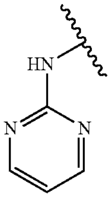

-continued
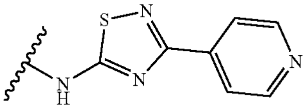
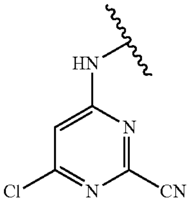
and
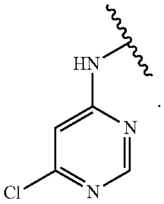
.
In certain embodiments $R^2$ is selected from
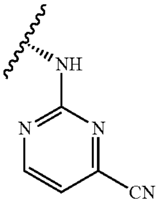
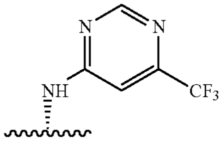
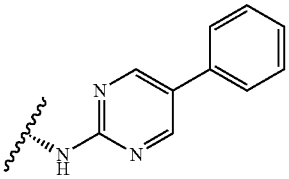
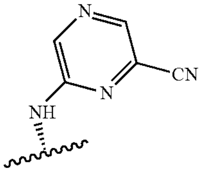
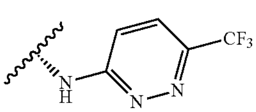
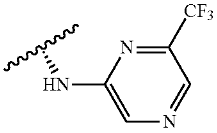
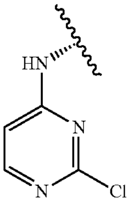
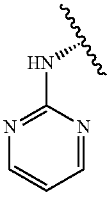
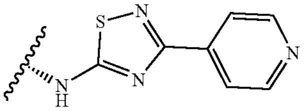
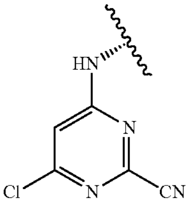
and
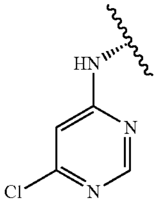
.
In certain embodiments $R^2$ is selected from
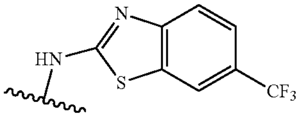
-continued
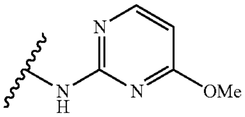
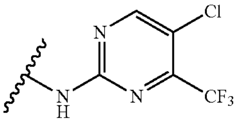
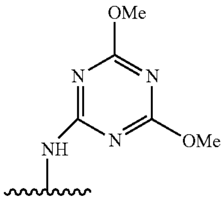
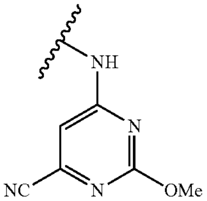
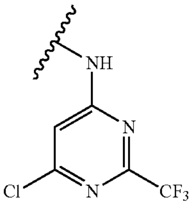
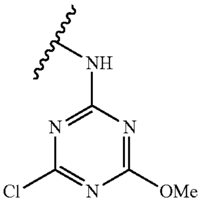
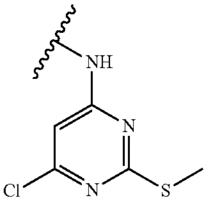
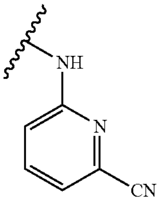
and
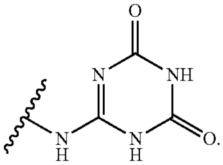
.
In certain embodiments $R^2$ is selected from
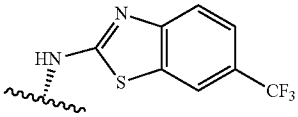
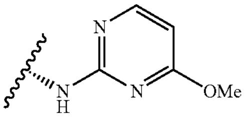
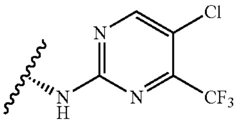
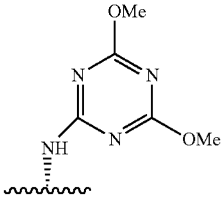
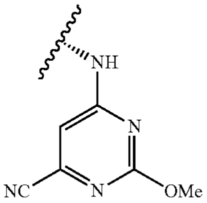
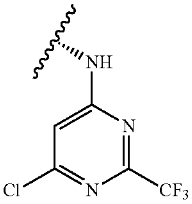
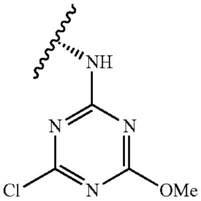

-continued
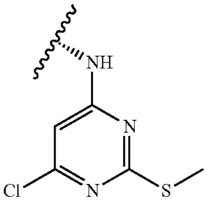
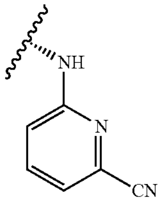
and
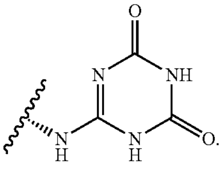
In certain embodiments $R^2$ is selected from
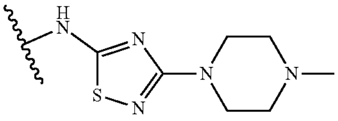
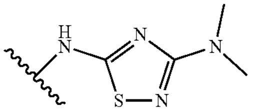
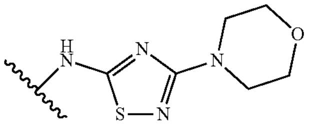
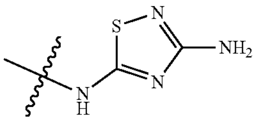
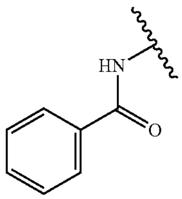
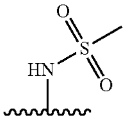
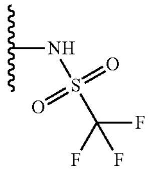
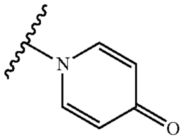
and
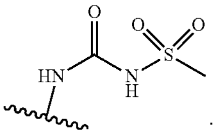
.
In certain embodiments $R^2$ is selected from
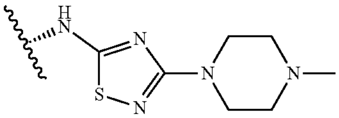
-continued
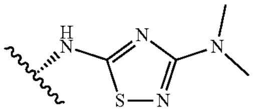
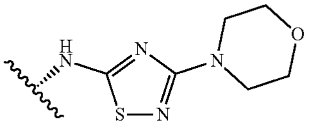
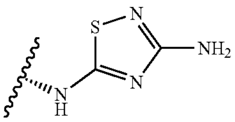
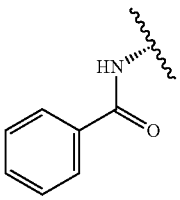
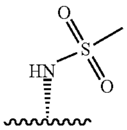
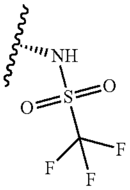
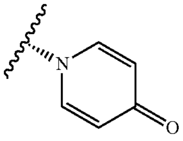
and
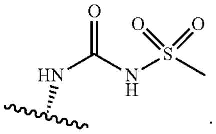
.
In certain embodiments $R^2$ is selected from
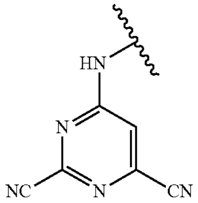
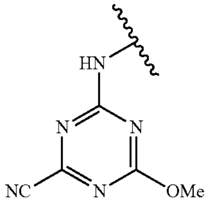
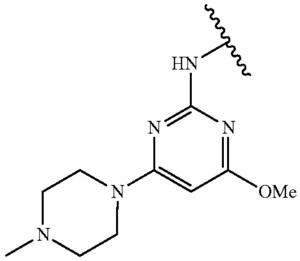
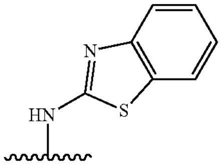
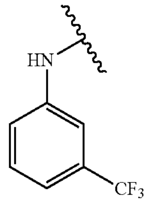

-continued
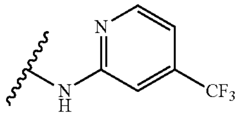
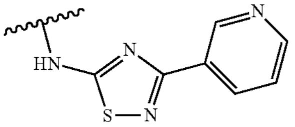
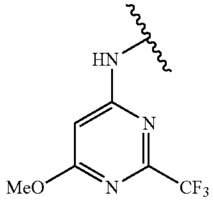
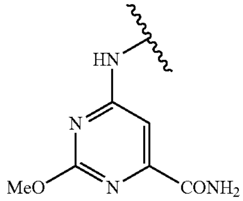
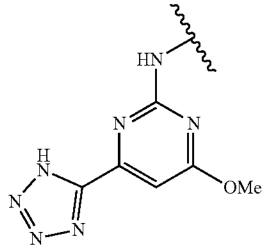
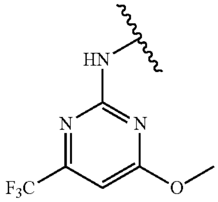
and
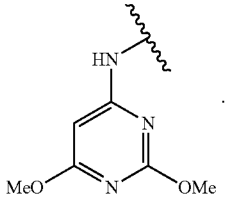
.
In certain embodiments $R^2$ is selected from
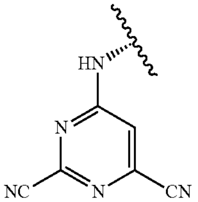
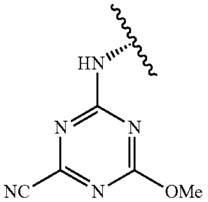
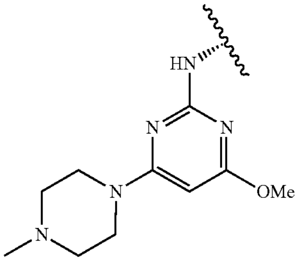
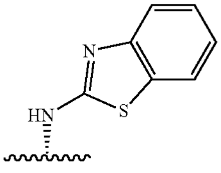
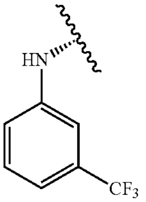
-continued
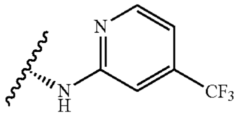
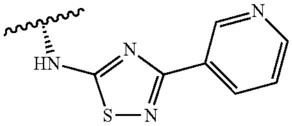
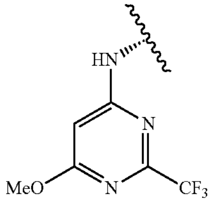
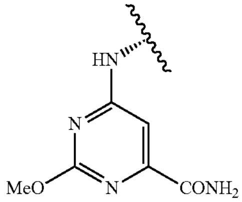
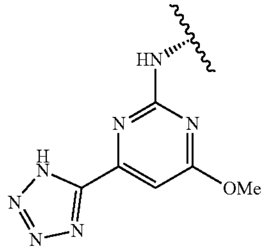
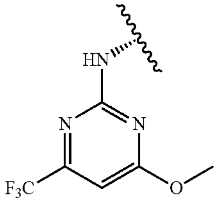
and
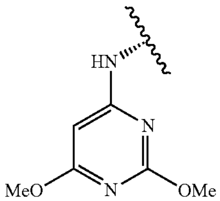
.
In certain embodiments $R^2$ is selected from
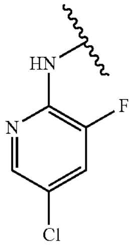
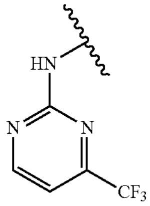
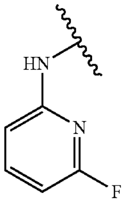
and
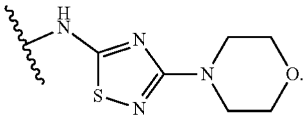

In certain embodiments $R^2$ is selected from
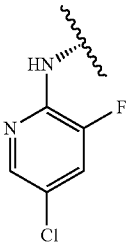
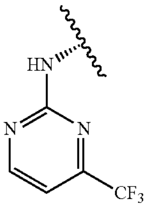
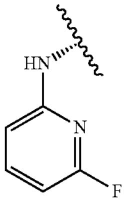
and
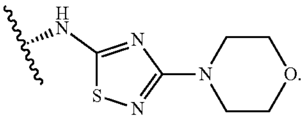
In certain embodiments $R^2$ is selected from
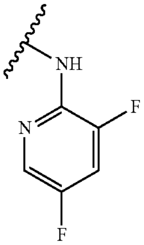
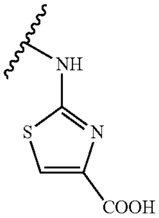
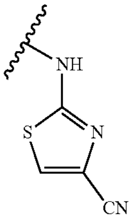
and
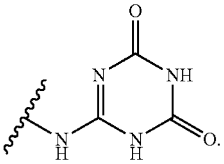
In certain embodiments $R^2$ is selected from
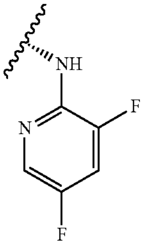
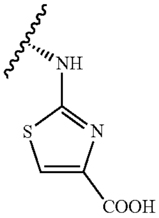
-continued
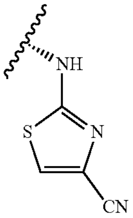
and
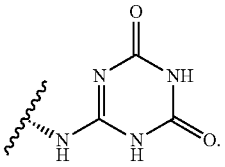
In certain embodiments $R^2$ is selected from
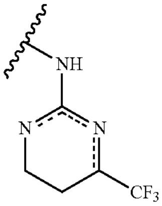
and
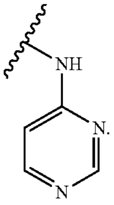
In certain embodiments $R^2$ is selected from
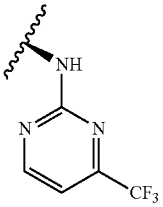
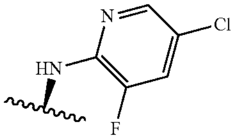
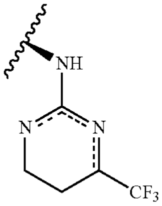
and
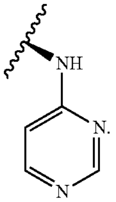
In certain embodiments $R^2$ is selected from
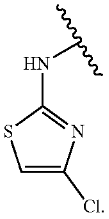
In certain embodiments $R^2$ is selected from
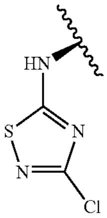
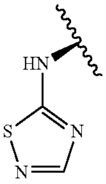
and -continued
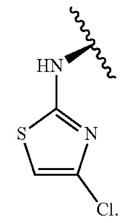
In certain embodiments $R^2$ is selected from
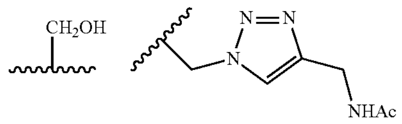
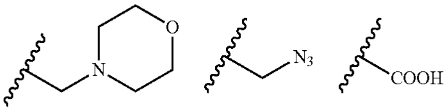
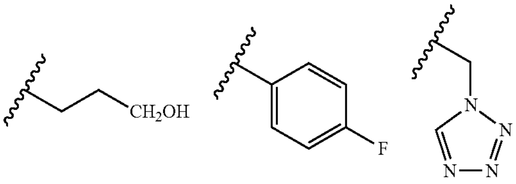
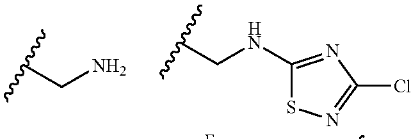
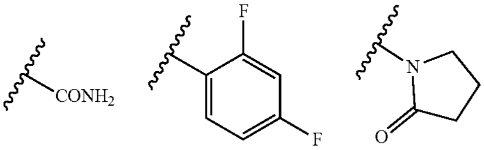
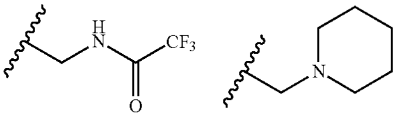
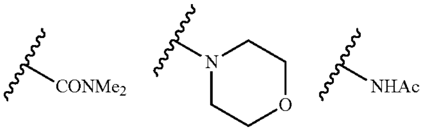
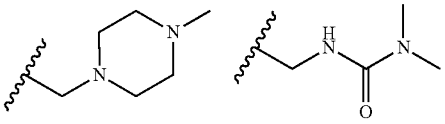
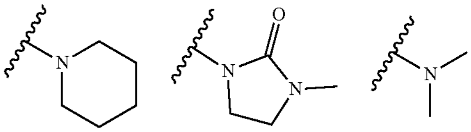
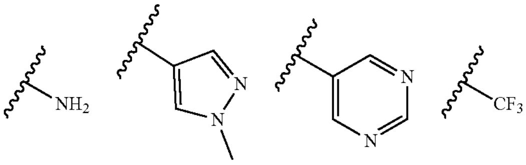
-continued
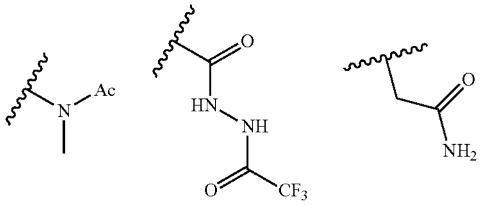
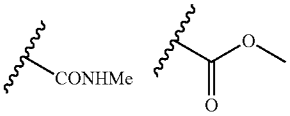
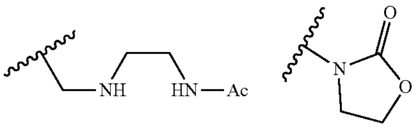
and
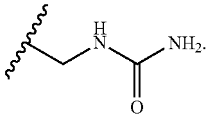
In certain embodiments $R^2$ is selected from
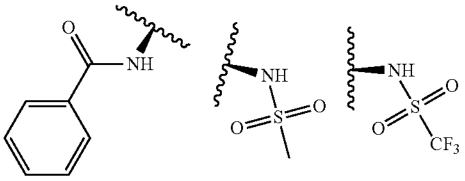
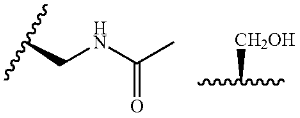
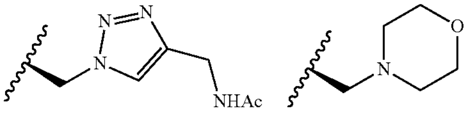
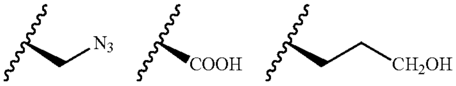
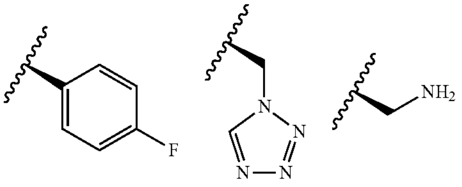
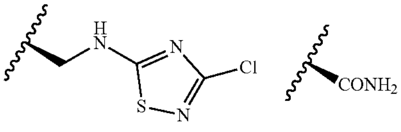
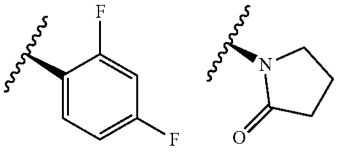

-continued
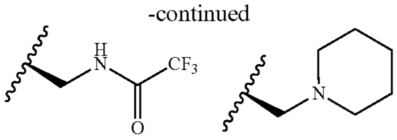
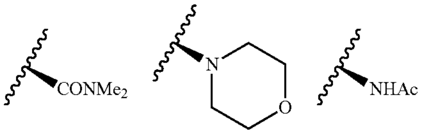
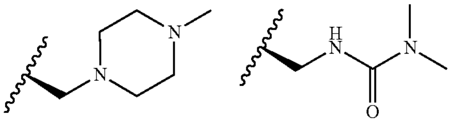
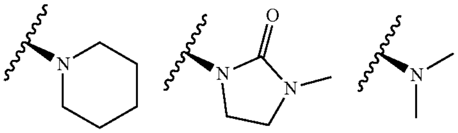
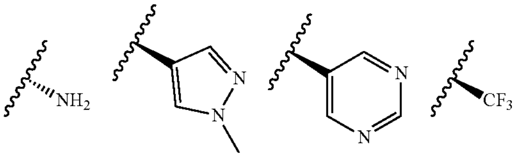
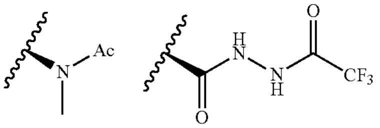
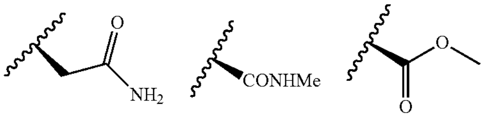
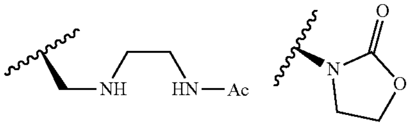
and
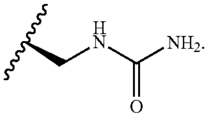
In certain embodiments $R^2$ is selected from
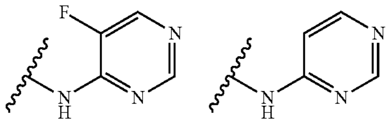
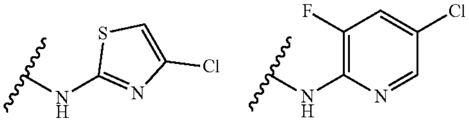
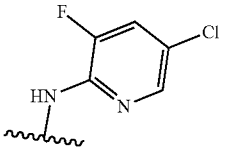
and
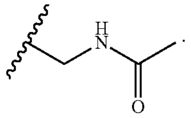
In certain embodiments $R^2$ is selected from
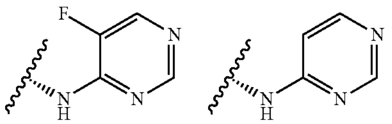
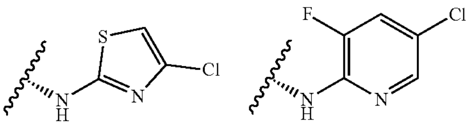
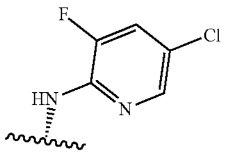
and
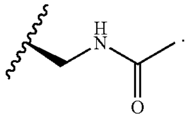
In certain embodiments $R^2$ is selected from
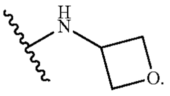 [SMILES: *NC1COC1]
In certain embodiments $R^2$ is
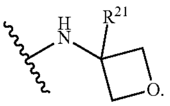
In certain embodiments $R^2$ is a spirocyclic heterocycle for example
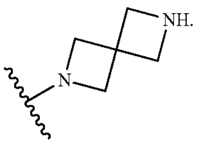 [SMILES: *N1CC2(CNC2)C1]
In certain embodiments $R^2$ is a silicon containing heterocycle for example
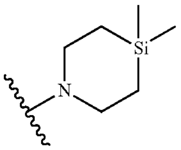 [SMILES: *N1CC[Si](C)(C)CC1]

In certain embodiments $R^2$ is substituted with $SF_5$ for example

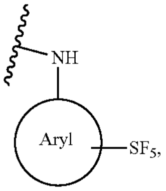
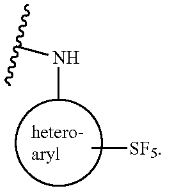

In certain embodiments $R^2$ is substituted with a sulfoxime for example

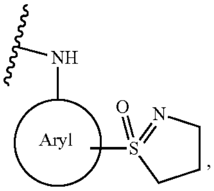
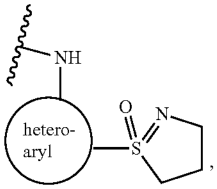
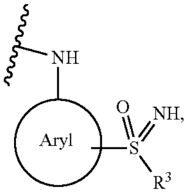
or
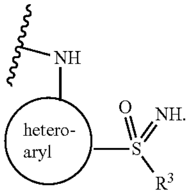

Embodiments of $R^{10}$

In certain embodiments, $R^{10}$ is selected from bicyclic heterocycle.

In certain embodiments, $R^{10}$ is selected from spirocyclic heterocycle.

In certain embodiments, $R^{10}$ is selected from —$NR^6$-heterocycle.

In certain embodiments, $R^{10}$ is selected from

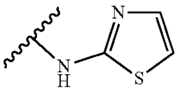
and
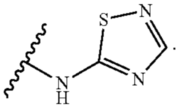

In certain embodiments, $R^{10}$ is selected from

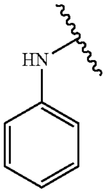
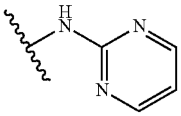
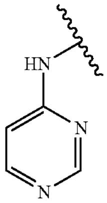

-continued

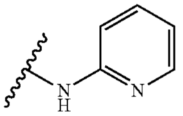
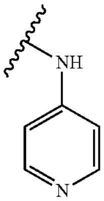
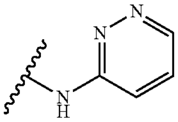
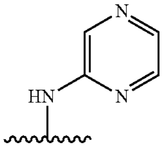
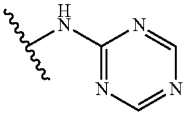
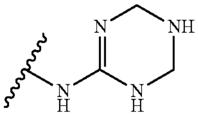
and
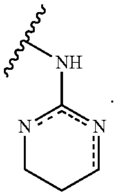

In certain embodiments, $R^{10}$ is selected from

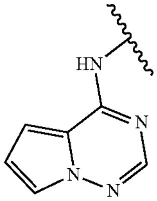
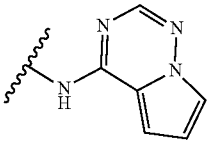
and
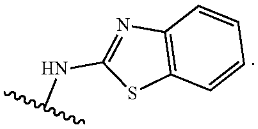

In certain embodiments, $R^{10}$ is selected from

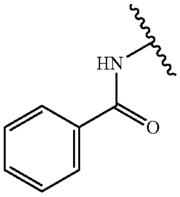
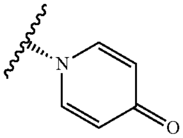
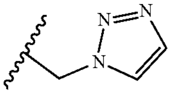
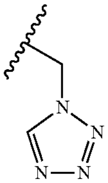
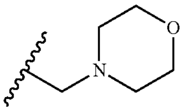
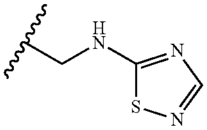
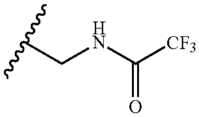

-continued
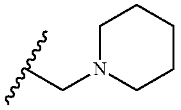
and
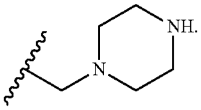
Embodiments of Cycle
In certain embodiments Cycle is selected from
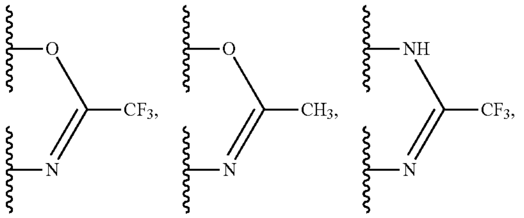
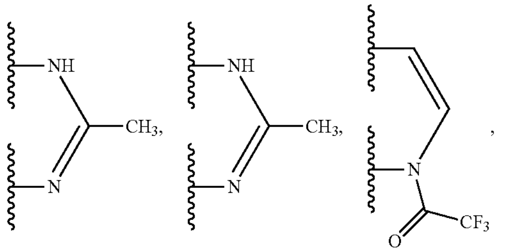
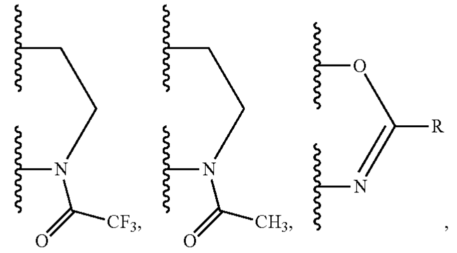
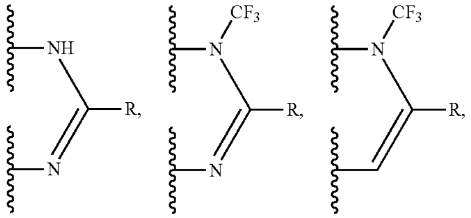
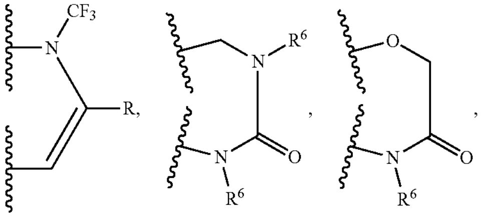
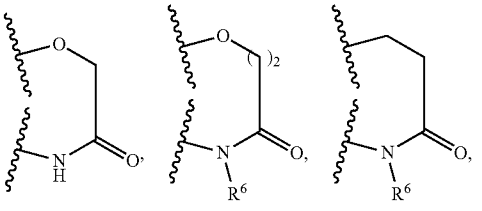
-continued
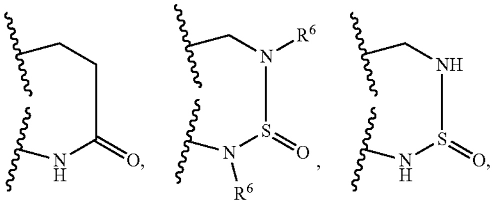
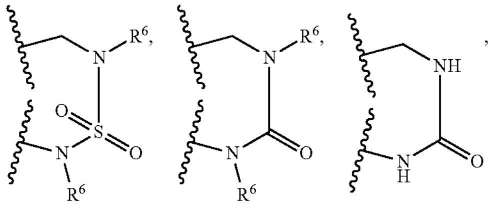
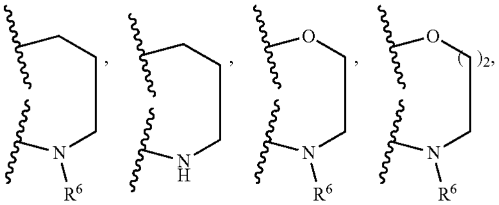
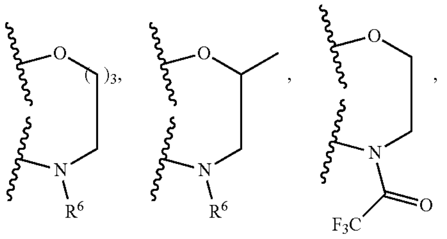
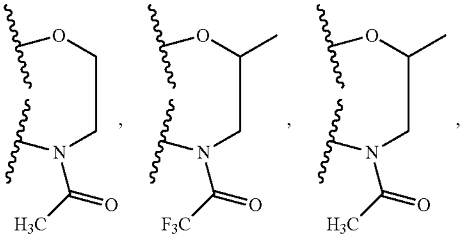
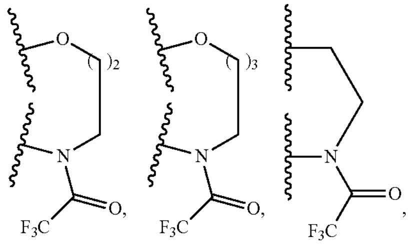
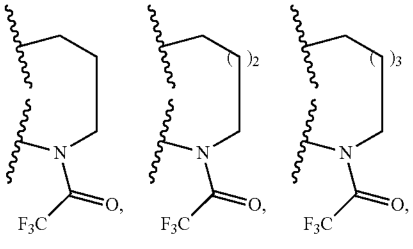

-continued
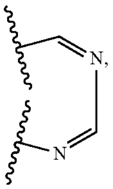 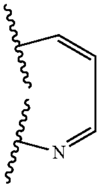 , 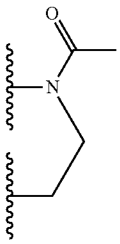 ,
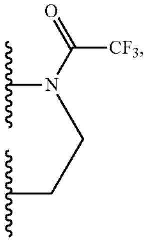 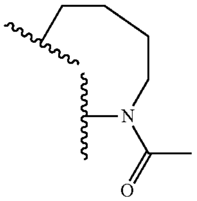 ,
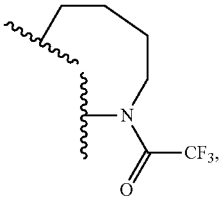 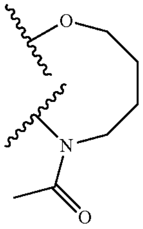 ,
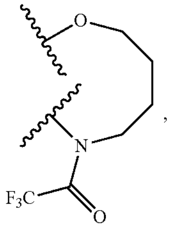 ,
Embodiments of $R^{30}$
In one embodiment $R^{30}$ is selected from:
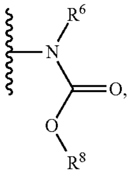 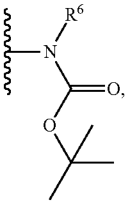 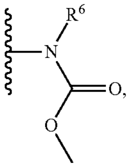
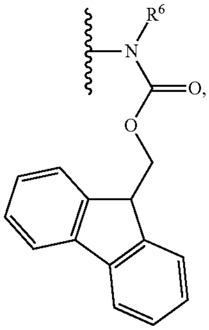 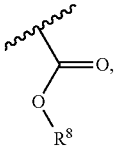 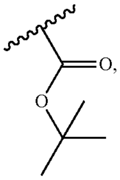
-continued
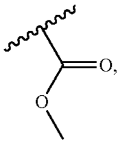 and 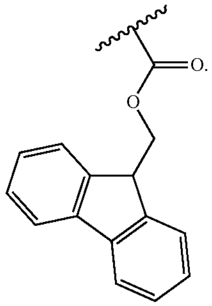
Embodiments of $R^{200}$
In certain embodiments $R^{200}$ is
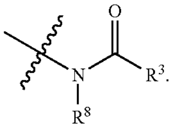
In certain embodiments $R^{200}$ is
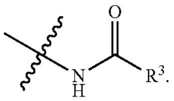
In certain embodiments $R^{200}$ is
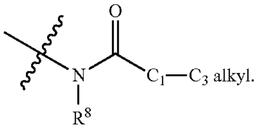
In certain embodiments $R^{200}$ is
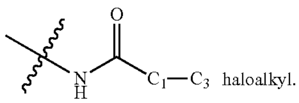
In certain embodiments $R^{200}$ is
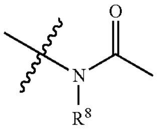 .

In certain embodiments $R^{200}$ is

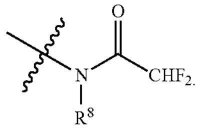

In certain embodiments $R^{200}$ is

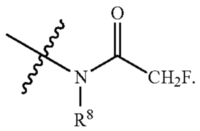

In certain embodiments $R^{200}$ is

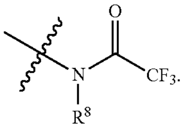

In certain embodiments $R^{200}$ is

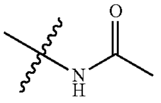

.

In certain embodiments $R^{200}$ is

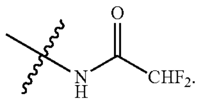 [SMILES: *NC(=O)C(F)F]

In certain embodiments $R^{200}$ is

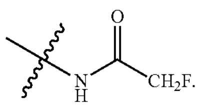

In certain embodiments $R^{200}$ is H

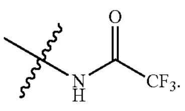 [SMILES: *NC(=O)C(F)(F)F]

IV. Embodiments of the Linker

In non-limiting embodiments, $Linker^A$ and $Linker^B$ are independently selected from:

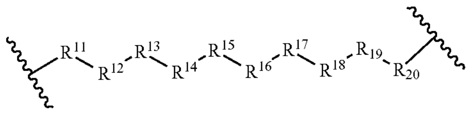

;

wherein:

$R^{11}$, $R^{12}$, $R^{13}$, $R^{14}$, $R^{15}$, $R^{16}$, $R^{17}$, $R^{18}$, $R^{19}$, and $R^{20}$ are independently at each occurrence selected from the group consisting of a bond, alkyl, —C(O)—, —C(O)O—, —OC(O)—, —$SO_2$—, —S(O)—, —C(S)—, —C(O)$NR^6$—, —$NR^6$C(O)—, —O—, —S—, —$NR^6$—, —C($R^{21}R^{21}$)—, —P(O)($R^3$)$_0$—, —P(O)($R^3$)—, a divalent residue of a natural or unnatural amino acid, alkenyl, alkynyl, haloalkyl, alkoxy, aryl, heterocycle, heteroaryl, —$CH_2CH_2$—[O—$(CH_2)_2$]$_n$—O—, —$CH_2CH_2$—[O—$(CH_2)_2$]$_n$—$NR^6$—, —$CH_2CH_2$—[O—$(CH_2)_2$]$_n$—, —[—$(CH_2)_2$—O—]$_n$—, —[O—$(CH_2)_2$]$_n$—, —[O—CH($CH_3$)C(O)]$_n$—, —[C(O)—CH($CH_3$)—O]$_n$—, —[O—$CH_2$C(O)]$_n$—, —[C(O)—$CH_2$—O]$_n$—, a divalent residue of a fatty acid, a divalent residue of an unsaturated or saturated mono- or di-carboxylic acid; each of which is optionally substituted with 1, 2, 3, or 4 substituents independently selected from $R^{21}$;

n is independently selected at each instance from 0, 1, 2, 3, 4, 5, 6, 7, 8, 9, or 10;

$R^{21}$ is independently at each occurrence selected from the group consisting of hydrogen, alkyl, alkenyl, alkynyl, F, Cl, Br, I, hydroxyl, alkoxy, azide, amino, cyano, —$NR^6R^7$, —$NR^8SO_2R^3$, —$NR^8S(O)R^3$, haloalkyl, heteroalkyl, aryl, heteroaryl, and heterocycle;

and the remaining variables are as defined herein.

In one embodiment $Linker^A$ is bond and $Linker^B$ is

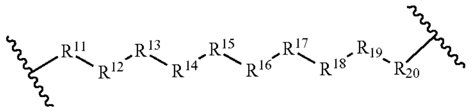

.

In one embodiment $Linker^B$ is bond and $Linker^A$ is

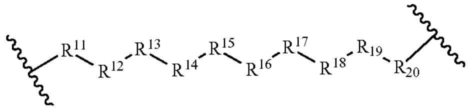

.

In one embodiment, a divalent residue of an amino acid is selected from

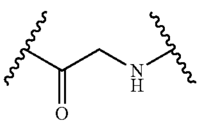

,

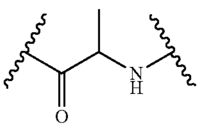

,

-continued
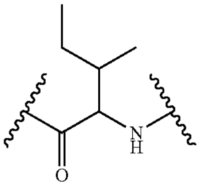 , 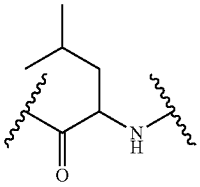 ,
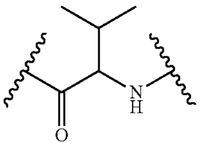 , 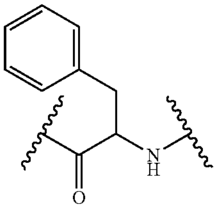 ,
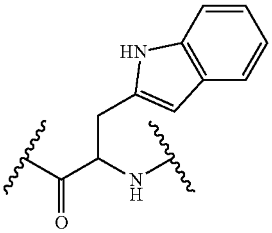 ,
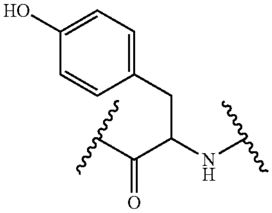 , 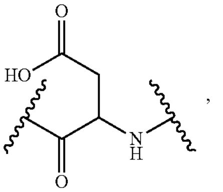 ,
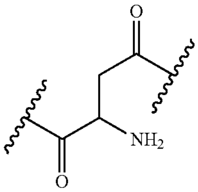 , 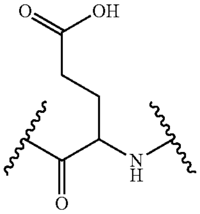 ,
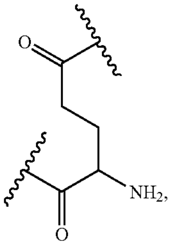 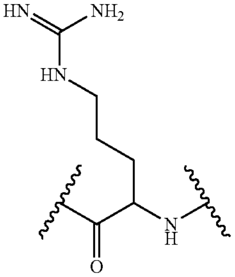 ,
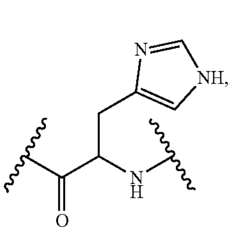 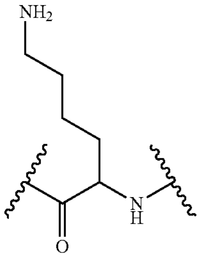 ,
-continued
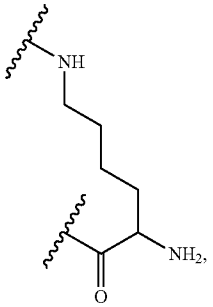 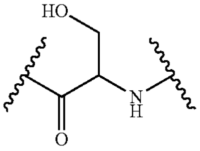 ,
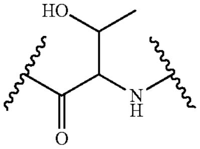 , 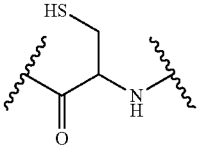 ,
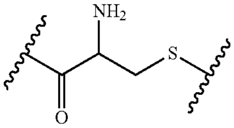 , 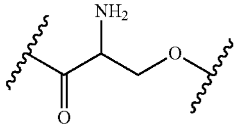 ,
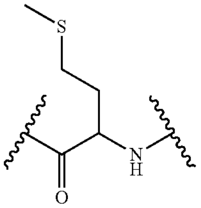 , 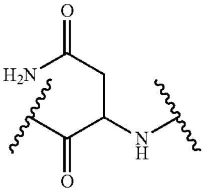 ,
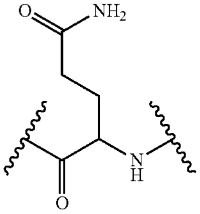 , 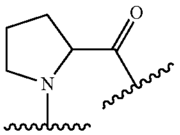
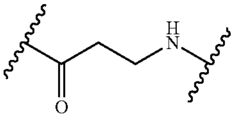 , 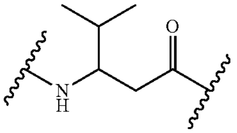 ,
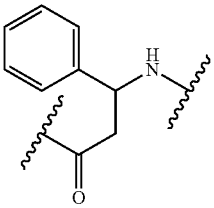 , 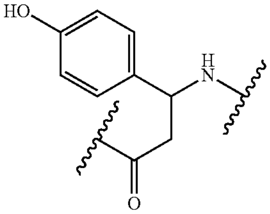 ,
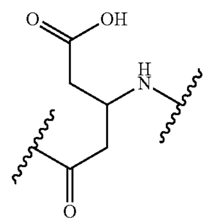 , 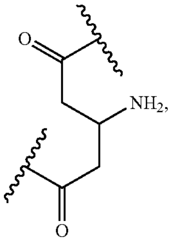

-continued

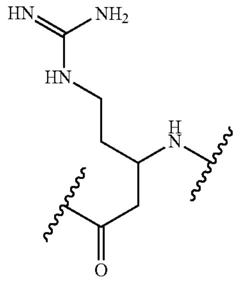
,
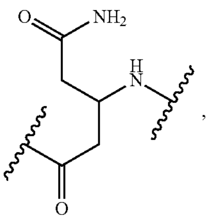
,
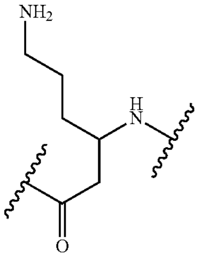
, and
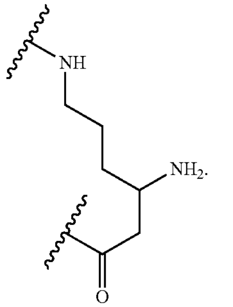

wherein the amino acid can be oriented in either direction and wherein the amino acid can be in the L- or D-form or a mixture thereof.

In one embodiment, a divalent residue of a dicarboxylic acid is generated from a nucleophilic addition reaction:

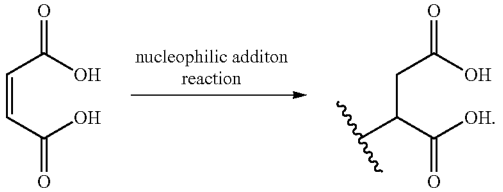 [SMILES: O=C(O)/C=C\C(=O)O ; *C(CC(=O)O)C(=O)O]

Non-limiting embodiments of a divalent residue of a dicarboxylic acid generated from a nucleophilic addition reaction include:

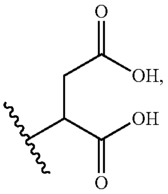
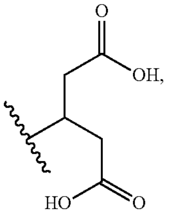
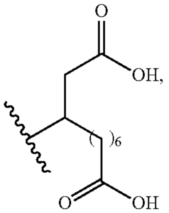
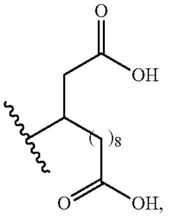
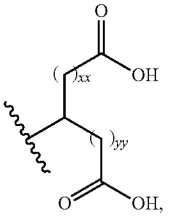
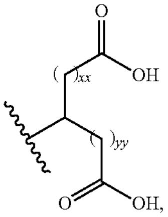

-continued

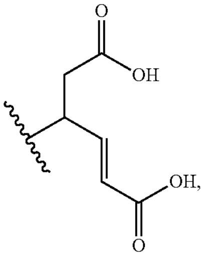
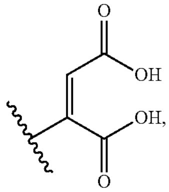
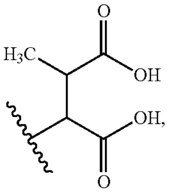
and
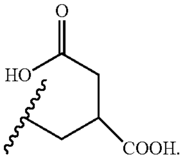

In one embodiment, a divalent residue of a dicarboxylic acid is generated from a condensation reaction:

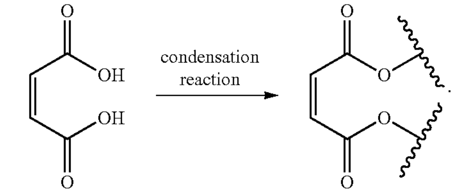 [SMILES: O=C(O)/C=C\C(=O)O ; *OC(=O)/C=C\C(=O)O*]

Non-limiting embodiments of a divalent residue of a dicarboxylic acid generated from a condensation include:

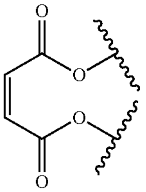
,
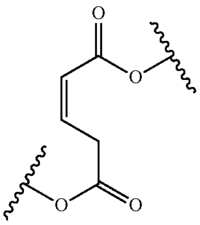
,
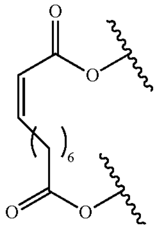
,
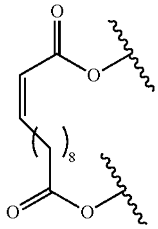
,
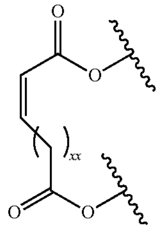
,
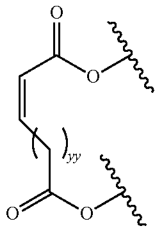
,
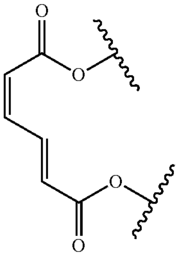
, -continued

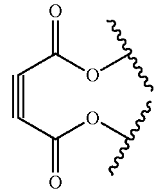
,
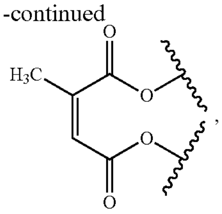
, and
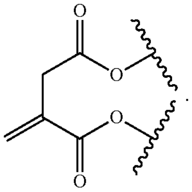
.

Non-limiting embodiments of a divalent residue of a saturated dicarboxylic acid include:

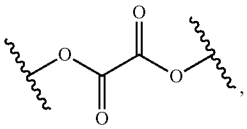
,
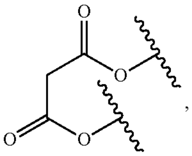
,
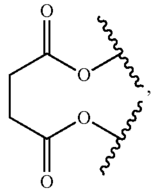
,
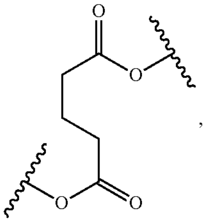
,
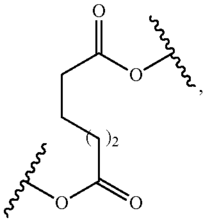
,
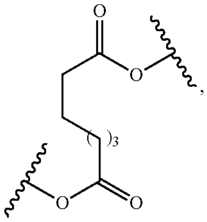
,
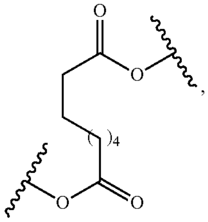
,
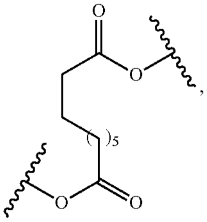
, -continued

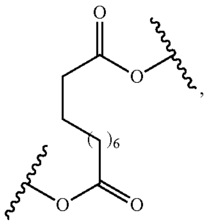
,
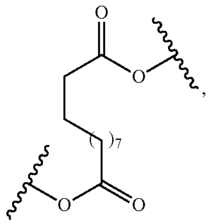
,
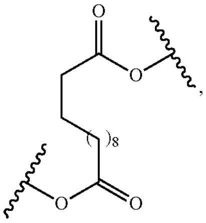
, and
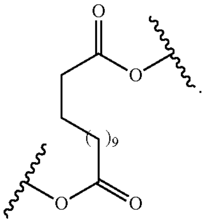
.

Non-limiting embodiments of a divalent residue of a saturated dicarboxylic acid include:

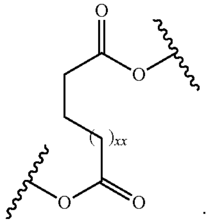
.

Non-limiting embodiments of a divalent residue of a saturated monocarboxylic acid is selected from butyric acid ($—OC(O)(CH_2)_2CH_2—$), caproic acid ($—OC(O)(CH_2)_4CH_2—$), caprylic acid ($—OC(O)(CH_2)_5CH_2—$), capric acid ($—OC(O)(CH_2)_8CH_2—$), lauric acid ($—OC(O)(CH_2)_{10}CH_2—$), myristic acid ($—OC(O)(CH_2)_{12}CH_2—$), pentadecanoic acid ($—OC(O)(CH_2)_{13}CH_2—$), palmitic acid ($—OC(O)(CH_2)_{14}CH_2—$), stearic acid ($—OC(O)(CH_2)_{16}CH_2—$), behenic acid ($—OC(O)(CH_2)_{20}CH_2—$), and lignoceric acid ($—OC(O)(CH_2)_{22}CH_2—$);

Non-limiting embodiments of a divalent residue of a fatty acid include residues selected from linoleic acid, palmitoleic acid, vaccenic acid, paullinic acid, oleic acid, elaidic acid, gondoic acid, gadoleic acid, nervonic acid, myristoleic acid, and erucic acid:

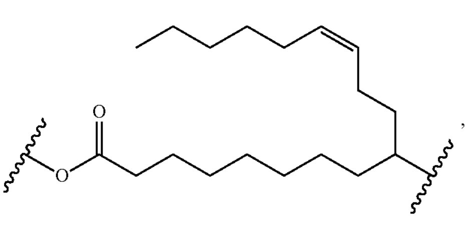
,
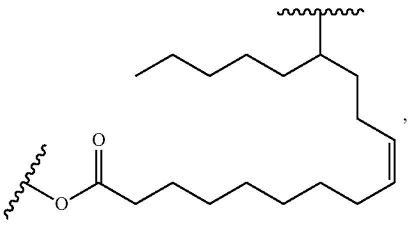
,

-continued

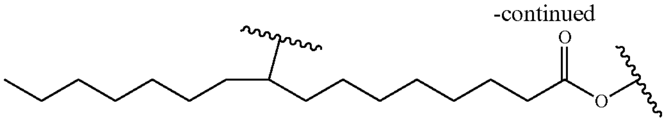,

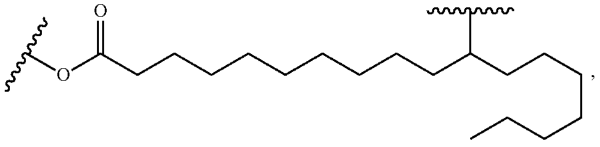,

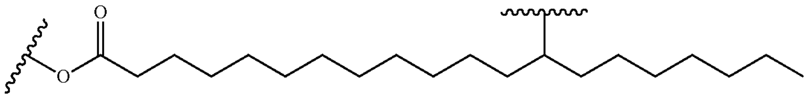,

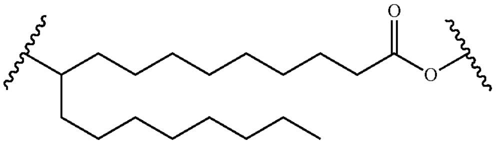, 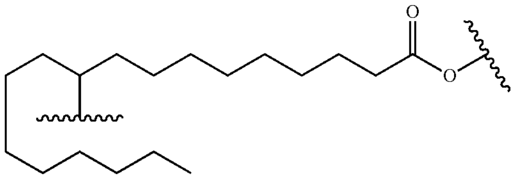,

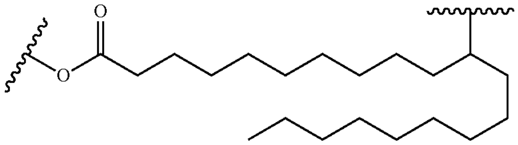, 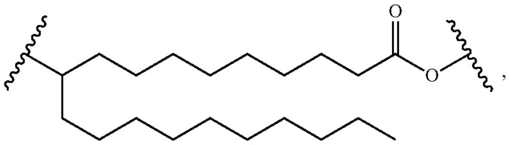,

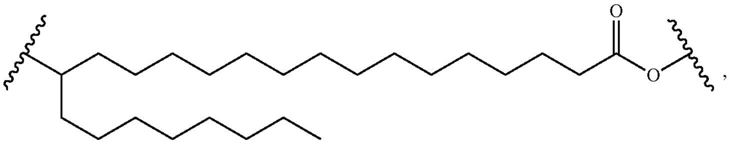,

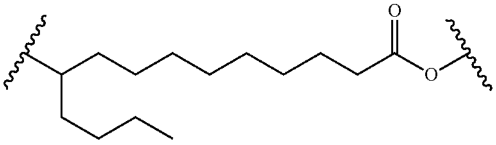, and

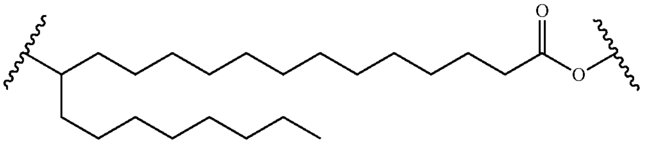;

Non-limiting embodiments of a divalent residue of a fatty acid is selected from linoleic acid ($-C(O)(CH_2)_7(CH)_2CH_2(CH)_2(CH_2)_4CH_2-$), docosahexaenoic acid ($-C(O)(CH_2)_2(CHCHCH_2)_6CH_2-$), eicosapentaenoic acid ($-C(O)(CH_2)_3(CHCHCH_2)_5CH_2-$), alpha-linolenic acid ($-C(O)(CH_2)_7(CHCHCH_2)_3CH_2-$) stearidonic acid ($-C(O)(CH_2)_4(CHCHCH_2)_4CH_2-$), y-linolenic acid ($-C(O)(CH_2)_4(CHCHCH_2)_3(CH_2)_3CH_2-$), arachidonic acid ($-C(O)(CH_2)_3(CHCHCH_2)_4(CH_2)_4CH_2-$), docosatetraenoic acid ($-C(O)(CH_2)_5(CHCHCH_2)_4(CH_2)_4CH_2-$), palmitoleic acid ($-C(O)(CH_2)_7CHCH(CH_2)_5CH_2-$), vaccenic acid ($-C(O)(CH_2)_9CHCH(CH_2)_5CH_2-$), paullinic acid ($-C(O)(CH_2)_{11}CHCH(CH_2)_5CH_2-$), oleic acid ($-C(O)(CH_2)_7CHCH(CH_2)_7CH_2-$), elaidic acid ($-C(O)(CH_2)_7CHCH(CH_2)_7CH_2-$), gondoic acid ($-C(O)(CH_2)_9CHCH(CH_2)_7CH_2-$), gadoleic acid ($-C(O)(CH_2)_7CHCH(CH_2)_9CH_2-$), nervonic acid ($-C(O)(CH_2)_{13}CHCH(CH_2)_7CH_2-$), mead acid ($-C(O)(CH_2)_3(CHCHCH_2)_3(CH_2)_6CH_2-$), myristoleic acid ($-C(O)(CH_2)_7CHCH(CH_2)_3CH_2-$), and erucic acid ($-C(O)(CH_2)_{11}CHCH(CH_2)_7CH_2-$).

In certain embodiments $Linker^C$ is selected from:

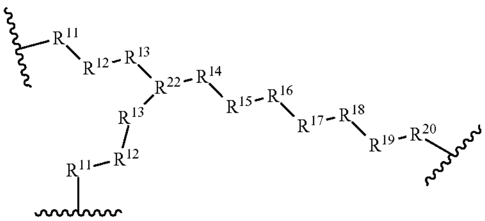.

wherein:

$R^{22}$ is independently at each occurrence selected from the group consisting of alkyl, $-C(O)N-$, $-NC(O)-$, $-N-$, $-C(R^{21})-$, $-P(O)O-$, $-P(O)-$, $-P(O)(NR^6R^7)N-$, alkenyl, haloalkyl, aryl, heterocycle, and heteroaryl, each of which is optionally substituted with 1, 2, 3, or 4 substituents independently selected from $R^{21}$;

and the remaining variables are as defined herein.

In certain embodiments Linker$^D$ is selected from:

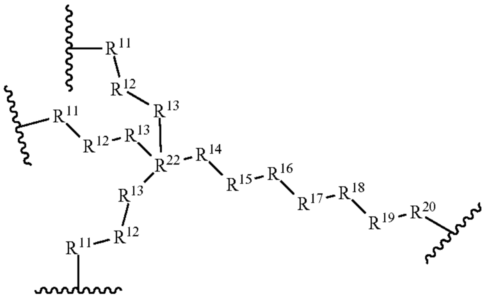

;

wherein:

$R^{32}$ is independently at each occurrence selected from the group consisting of alkyl, $N^+X^-$, —C—, alkenyl, haloalkyl, aryl, heterocycle, and heteroaryl, each of which is optionally substituted with 1, 2, 3, or 4 substituents independently selected from $R^{21}$;

$X^-$ is an anionic group, for example $Br^-$ or $Cl^-$; and all other variables are as defined herein.

In certain embodiments Linker$^A$ is selected from:

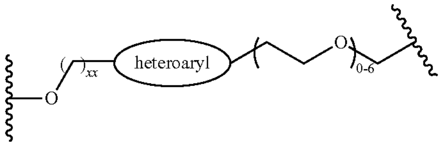

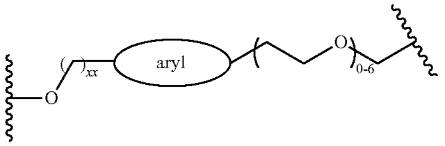

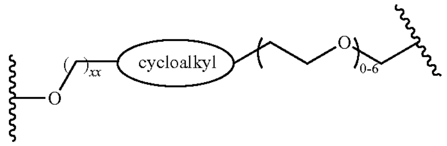

and

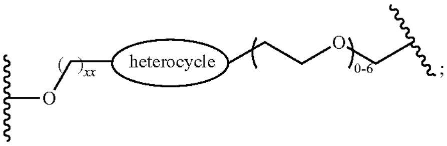

;

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^A$ is selected from:

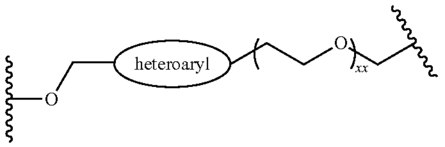

-continued

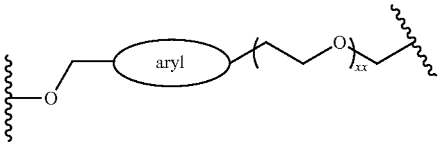

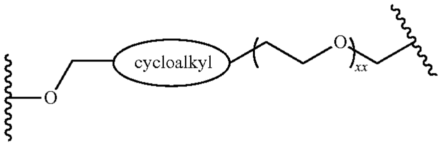

and

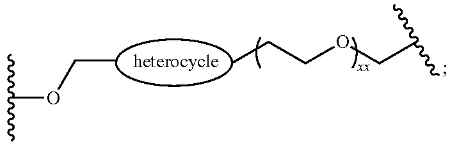

;

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^A$ is selected from:

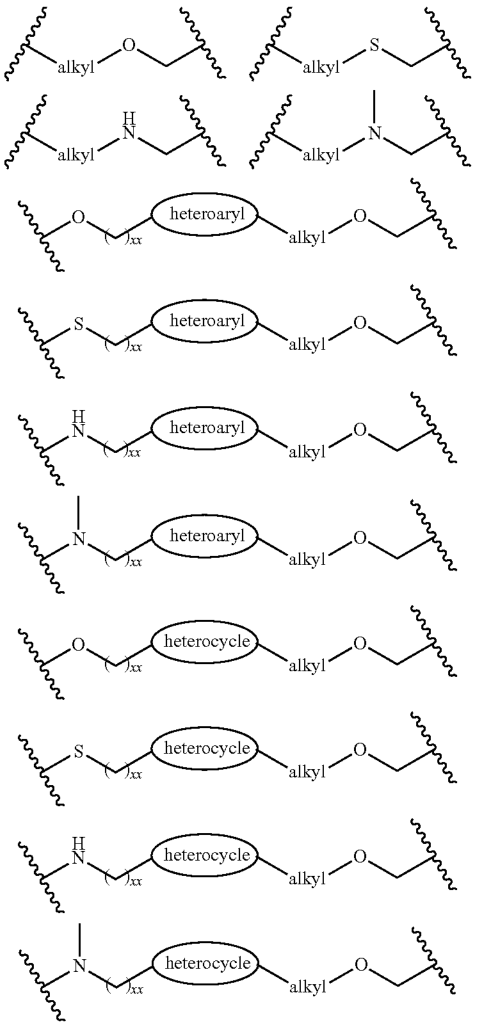

-continued

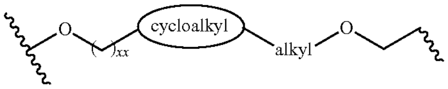

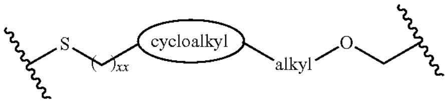

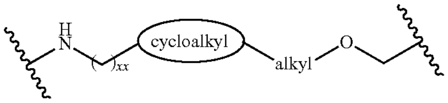

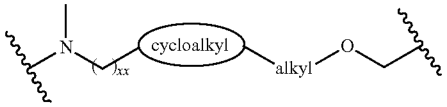

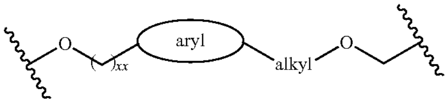

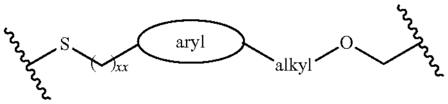

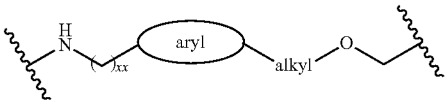

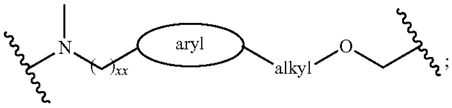
;

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence.

In certain embodiments Linker$^B$ is selected from:

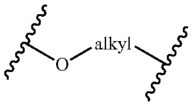
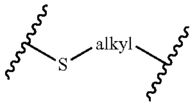

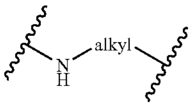
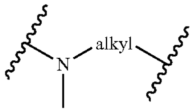

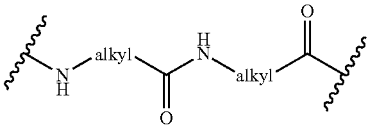

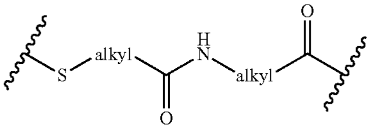

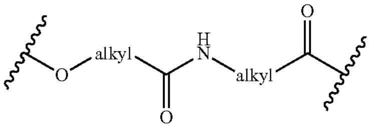

-continued

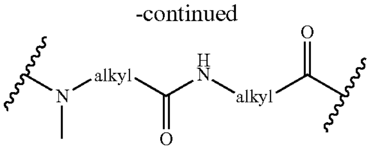

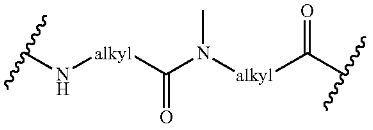

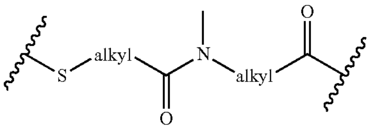

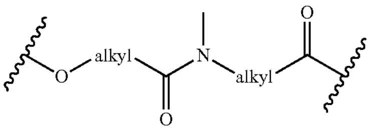
and

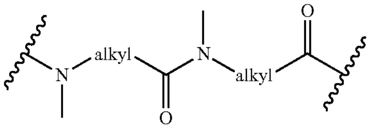
.

In certain embodiments Linker$^B$ is selected from:

Non-limiting embodiments of a divalent residue of a saturated dicarboxylic acid include:

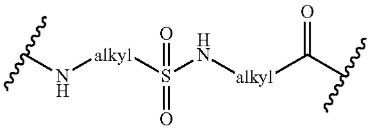

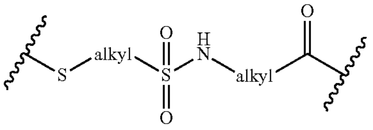

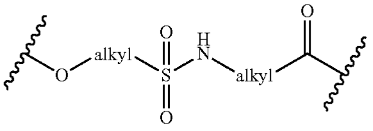

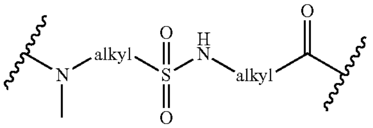

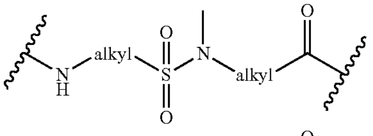

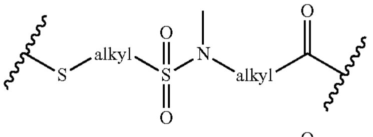

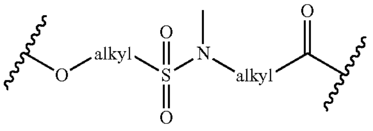

-continued
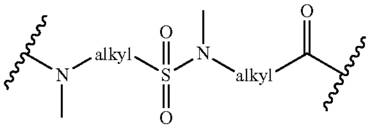
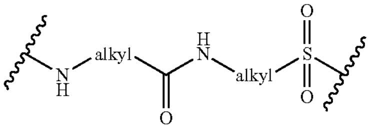
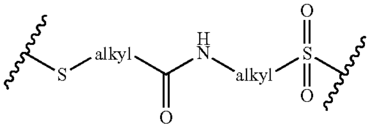
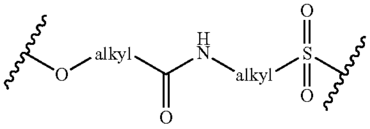
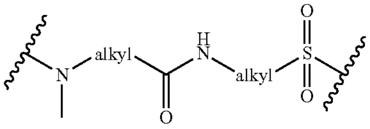
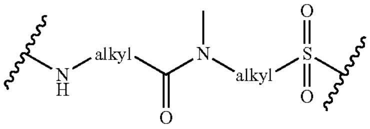
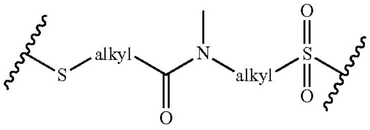
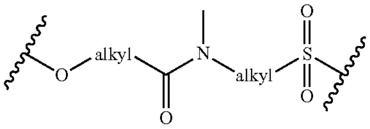
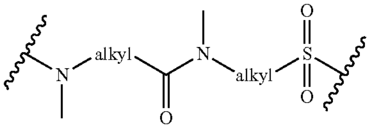
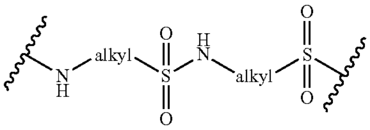
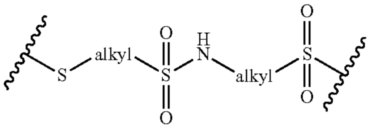
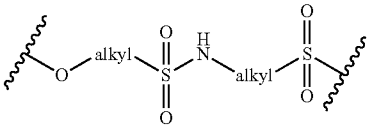
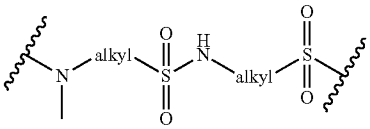
-continued
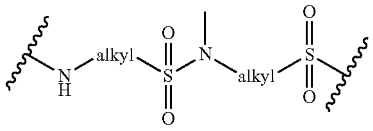
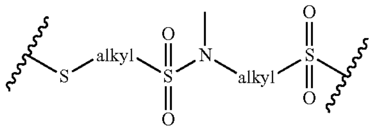
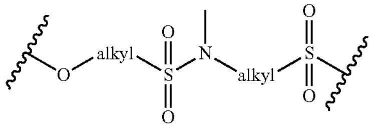
and
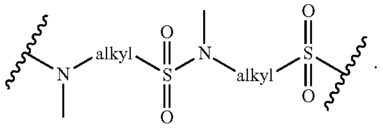
In certain embodiments Linker$^B$, Linker$^C$, or Linker$^D$ is selected from:
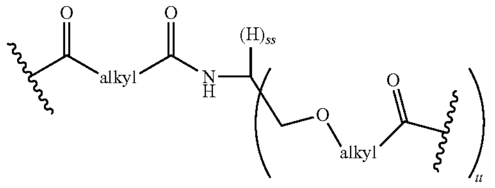
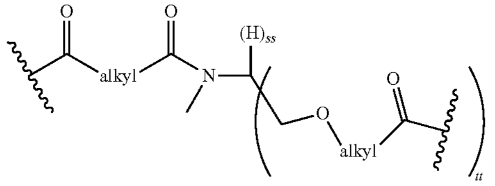
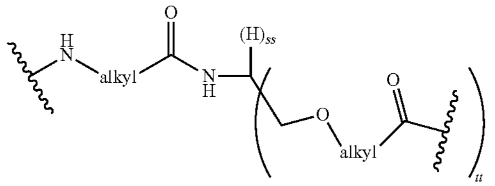
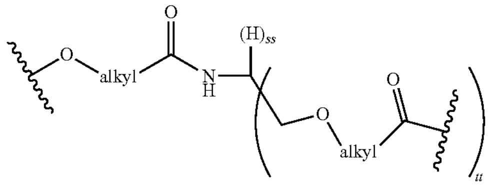
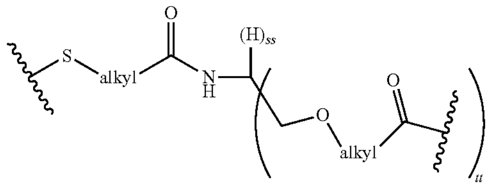

-continued
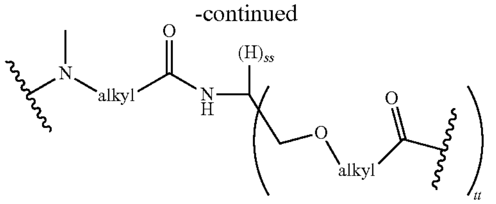
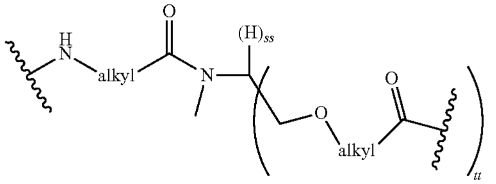
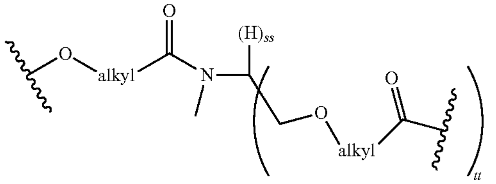
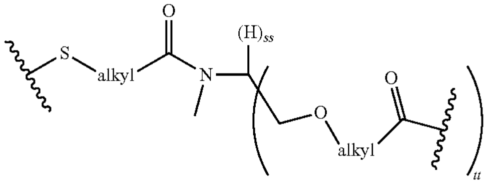
and
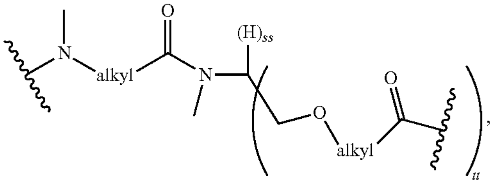
,
wherein tt is independently selected from 1, 2, or 3 and ss is 3 minus tt.
In certain embodiments Linker$^B$, Linker$^C$, or Linker$^D$ is selected from:
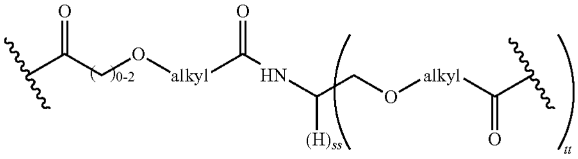
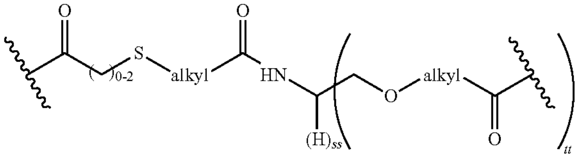
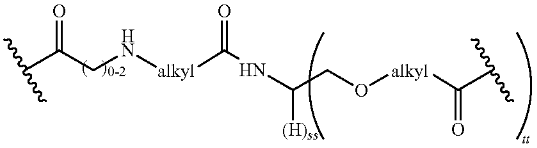
and
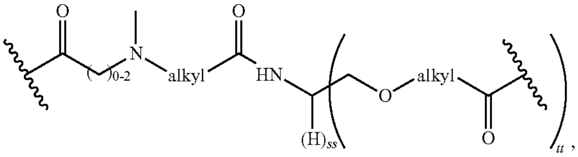
,
wherein tt and ss are as defined herein.
In certain embodiments Linker$^B$, Linker$^C$, or Linker$^D$ is selected from:
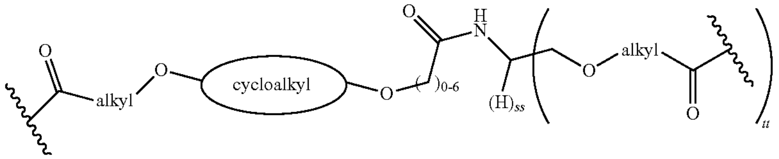
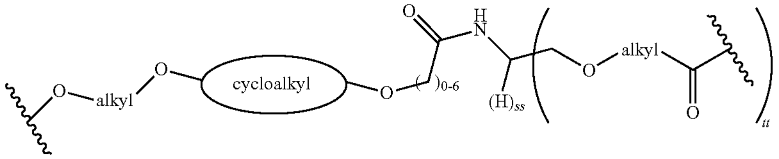
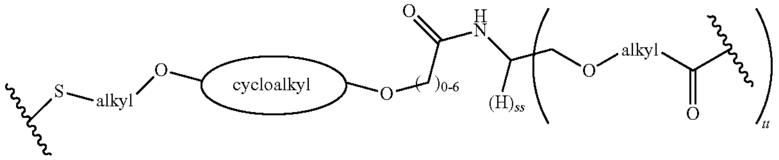
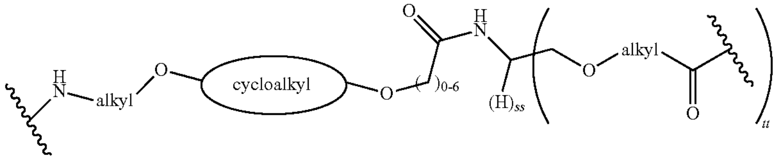

-continued
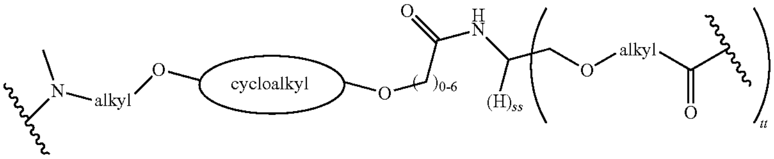
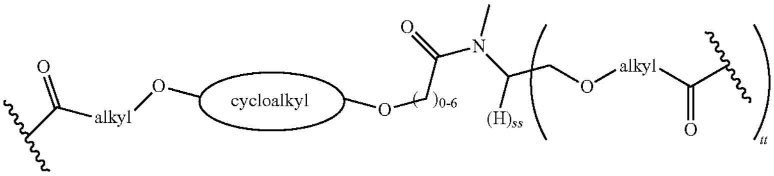
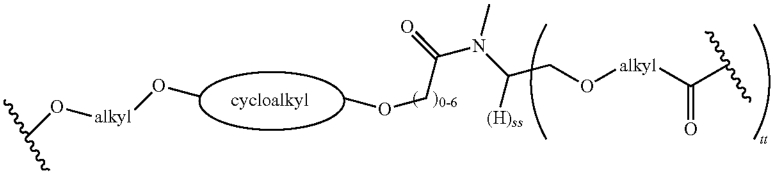
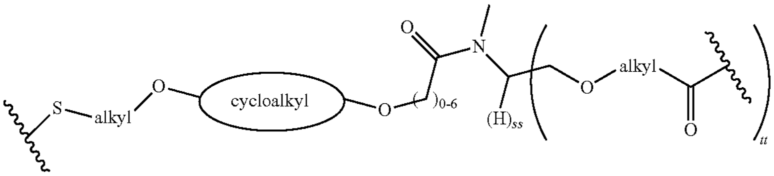
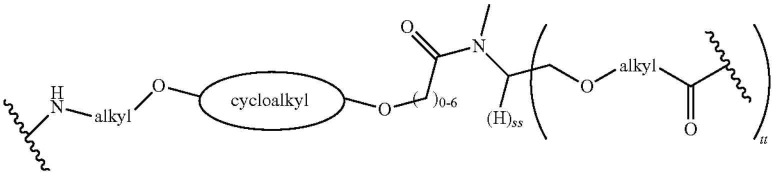
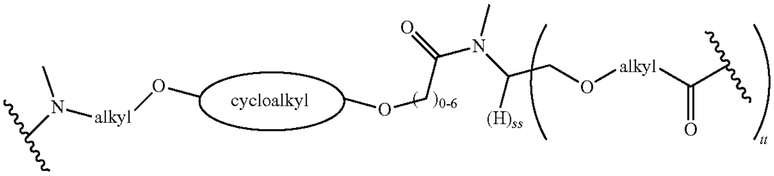
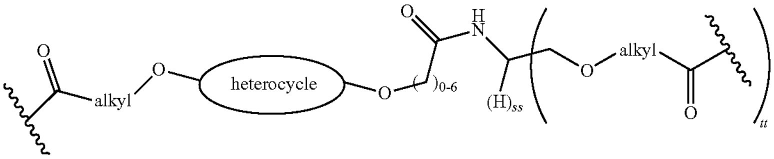
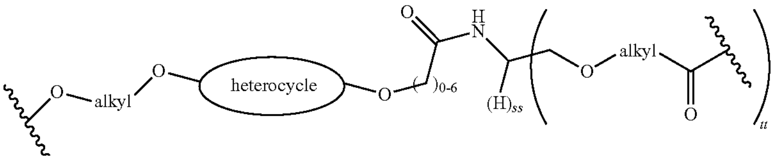
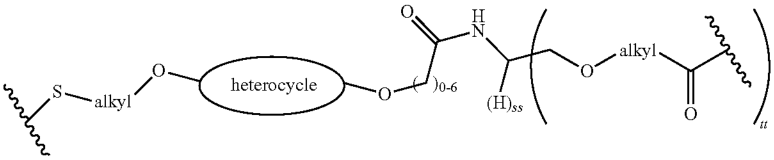
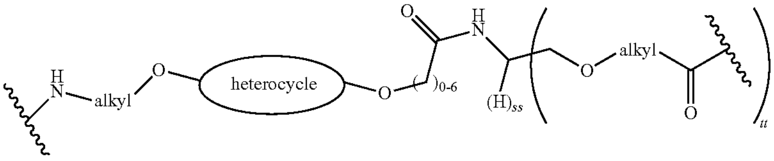

-continued
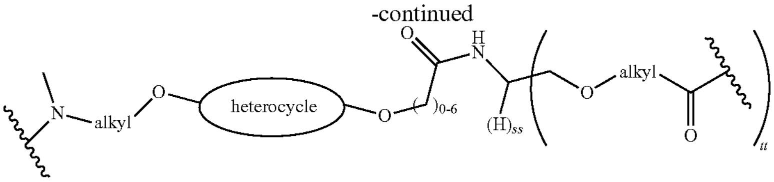
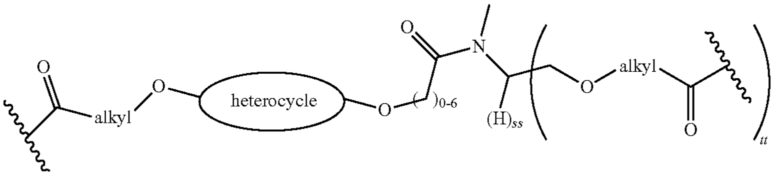
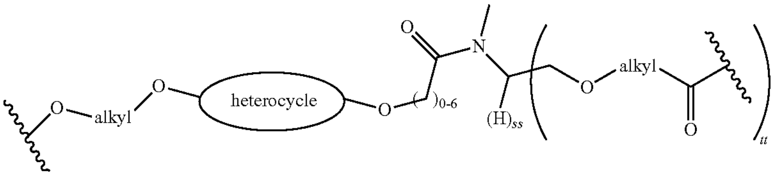
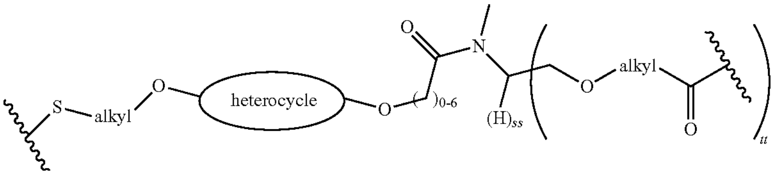
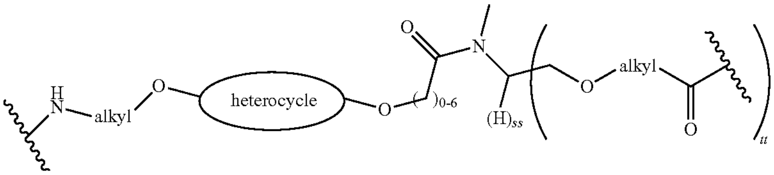
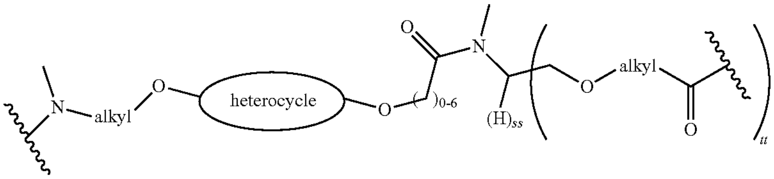
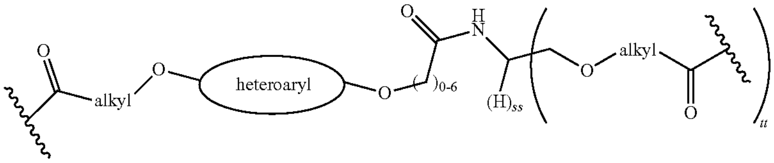
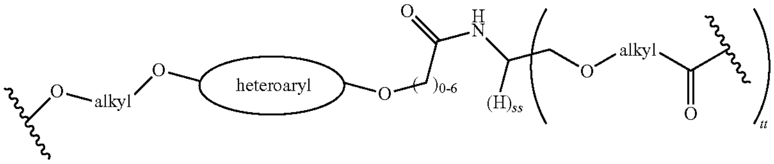
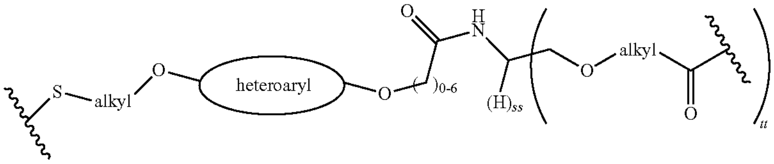
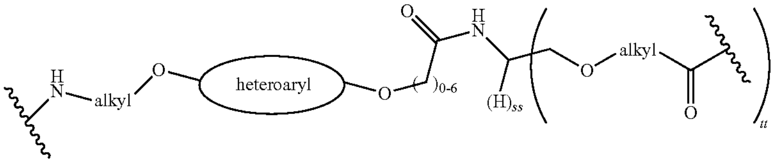

-continued
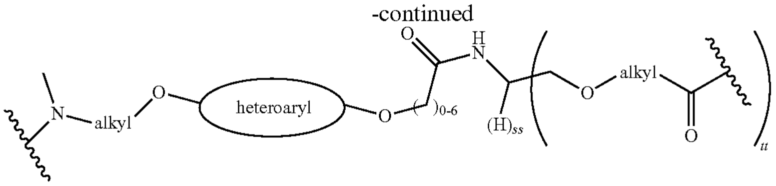
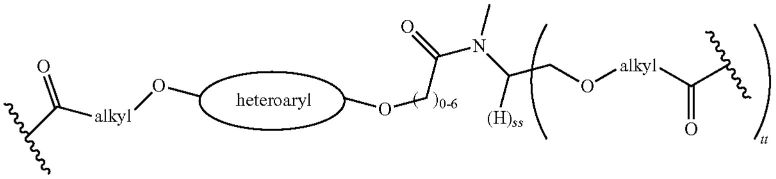
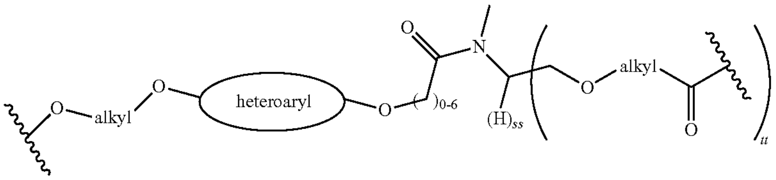
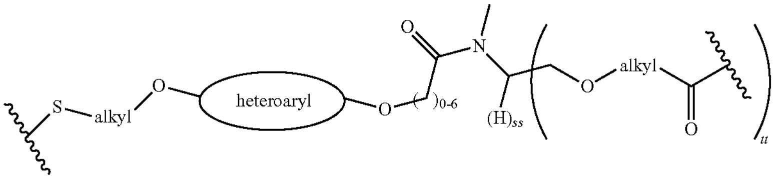
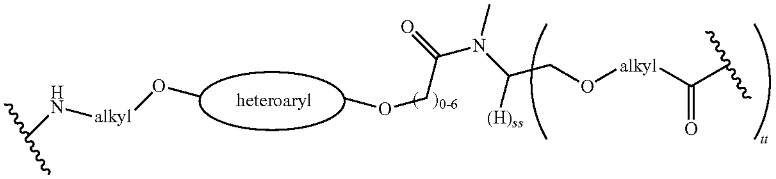
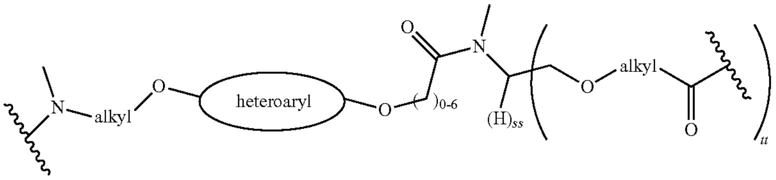
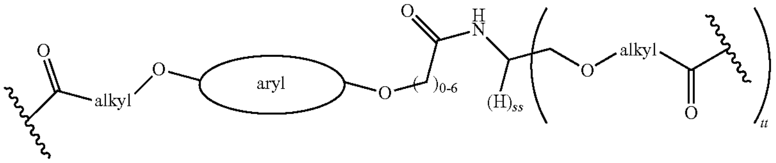
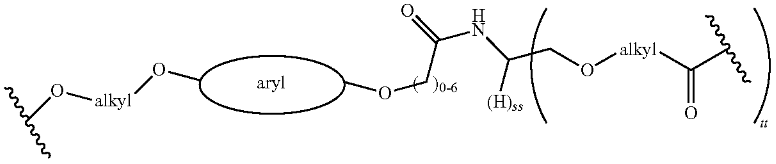
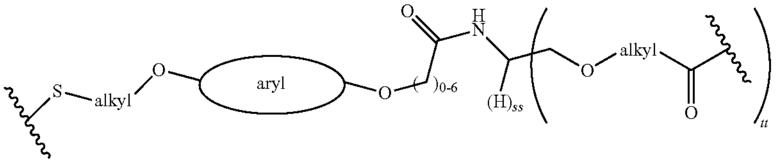
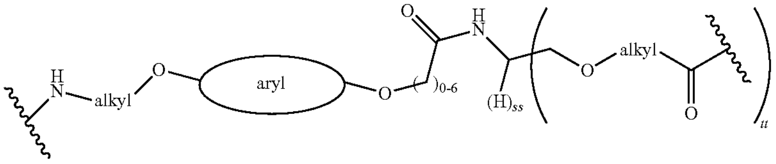

-continued

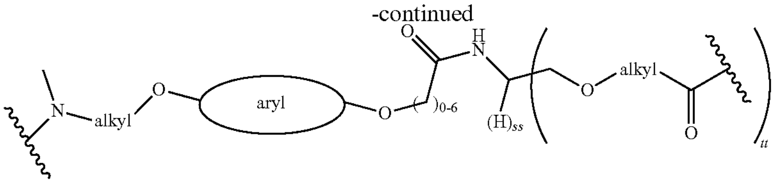

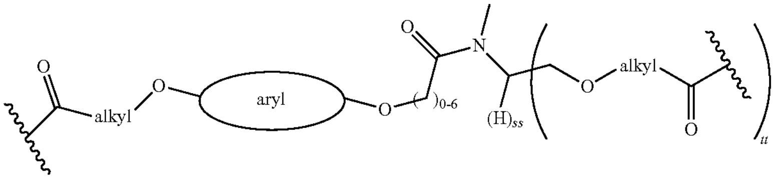

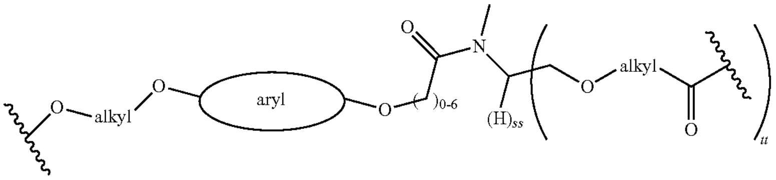

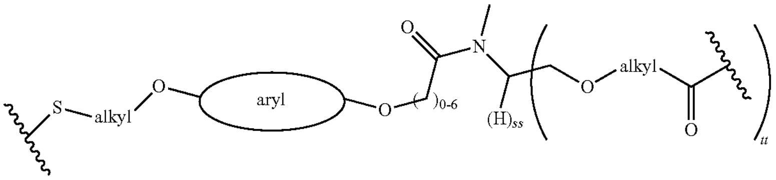

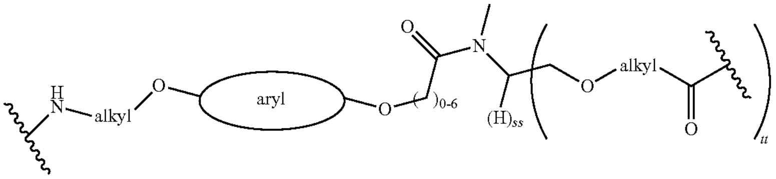

and

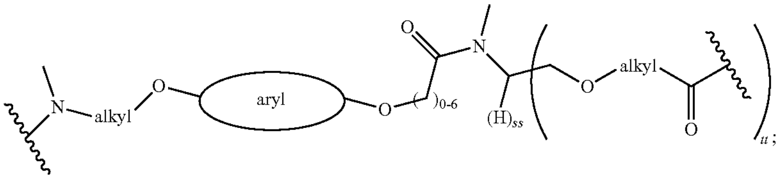

;

wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.

In certain embodiments Linker$^B$, Linker$^C$, or Linker$^D$ is selected from:

Non-limiting embodiments of a divalent residue of a saturated dicarboxylic acid include:

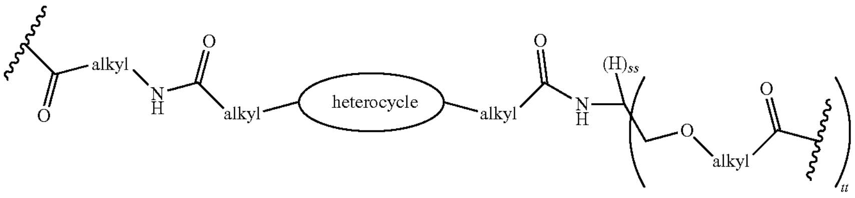

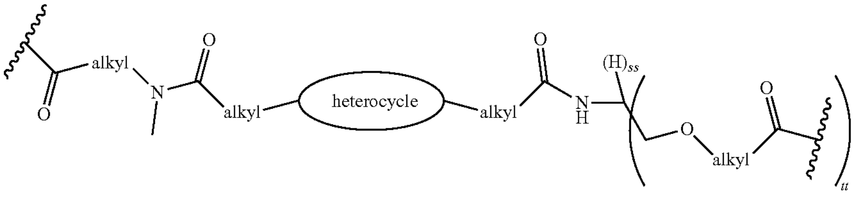

-continued
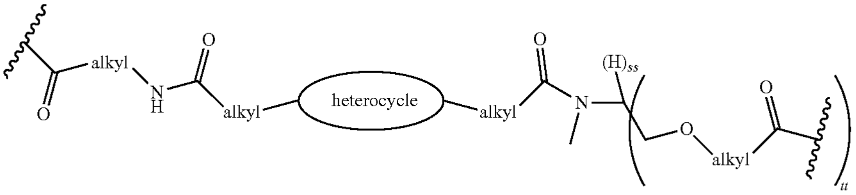
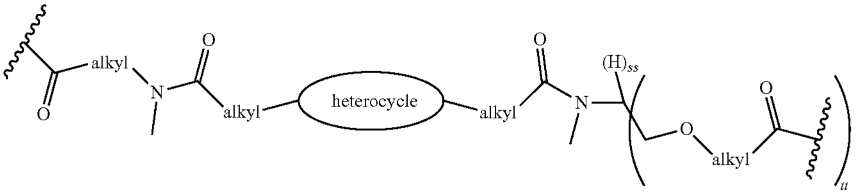
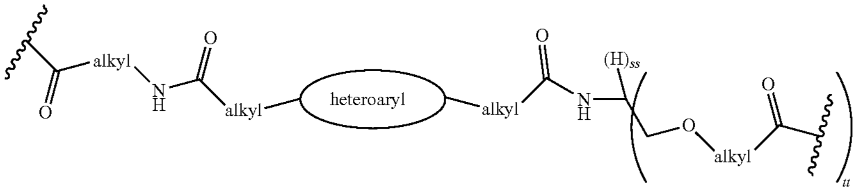
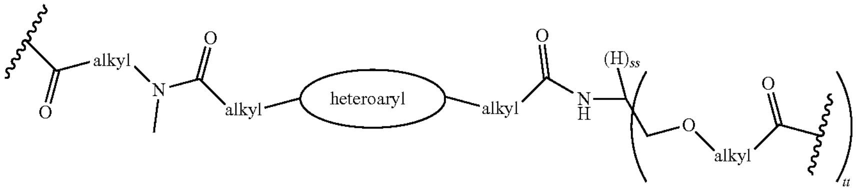
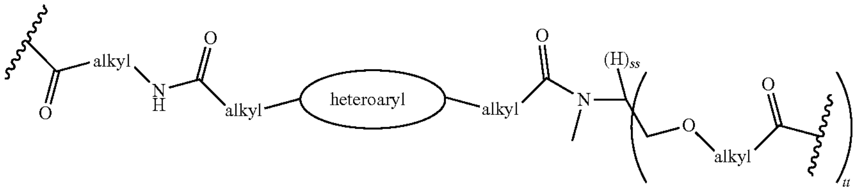
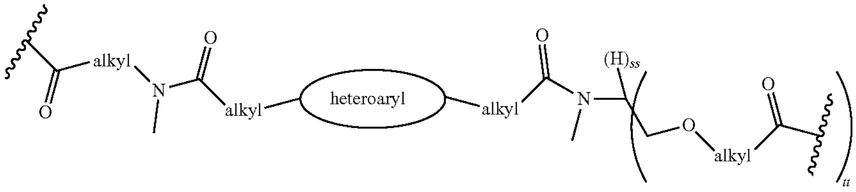
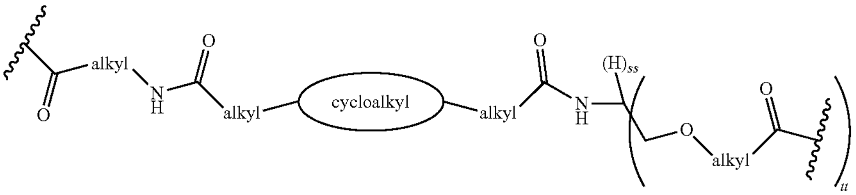
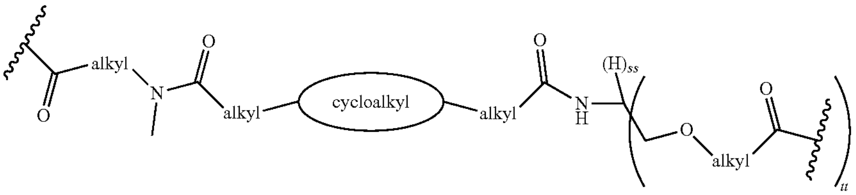

-continued
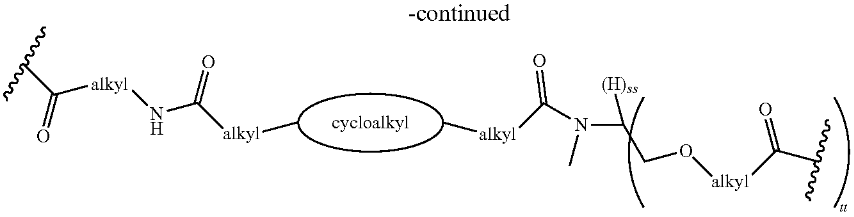
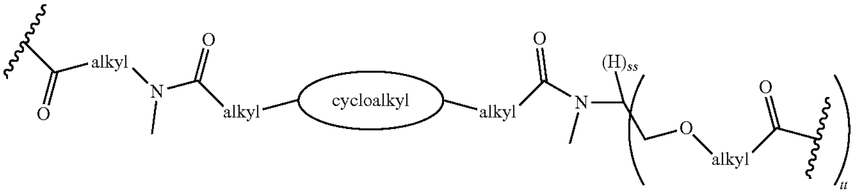
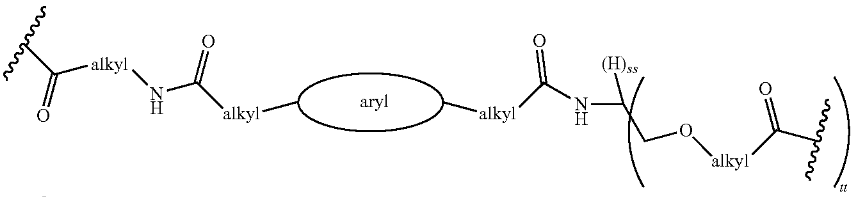
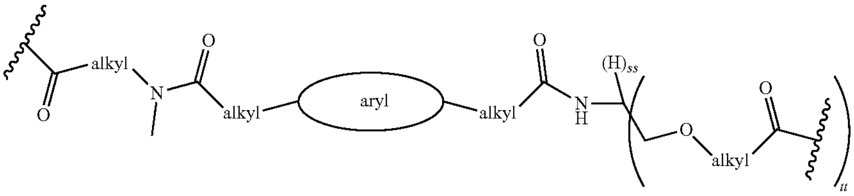
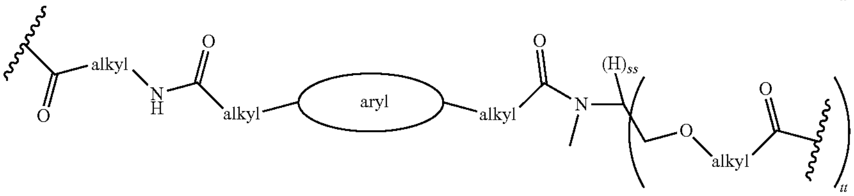
and
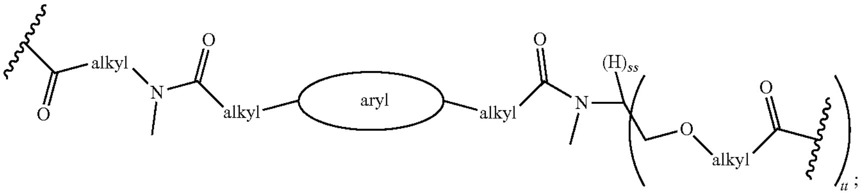
;
wherein each heteroaryl, heterocycle, cycloalkyl, and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.
In certain embodiments $Linker^B$, $Linker^C$, or $Linker^D$ is selected from:
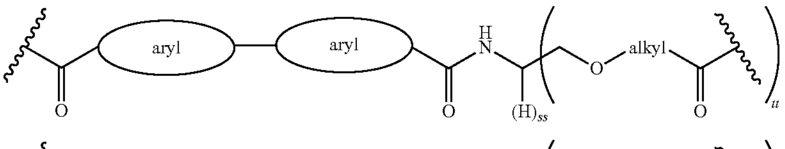
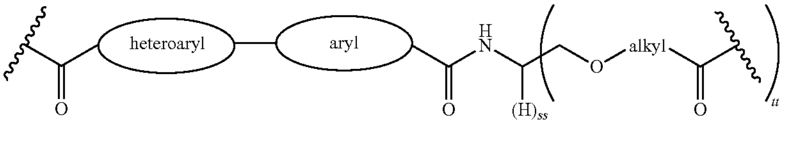

-continued
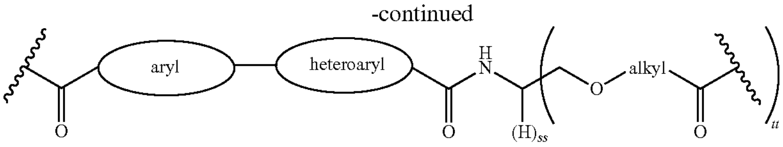
and
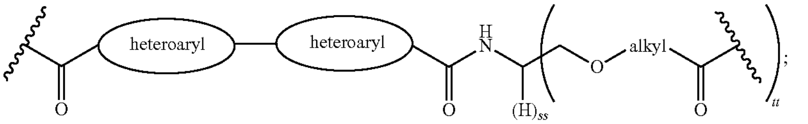
wherein each heteroaryl and aryl can optionally be substituted with 1, 2, 3, or 4 of any combination of halogen, alkyl, haloalkyl, aryl, heteroaryl, heterocycle, or cycloalkyl, as allowed by valence; and tt and ss are as defined herein.
In certain embodiments Linker$^A$ is selected from:
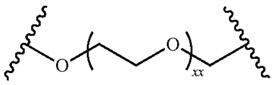
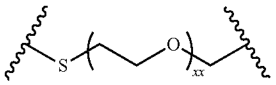
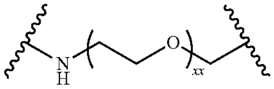
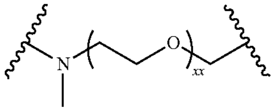
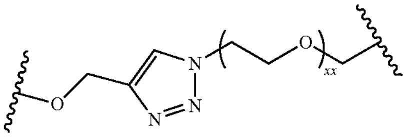
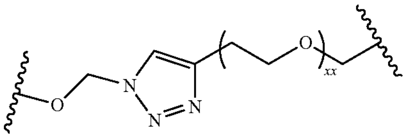
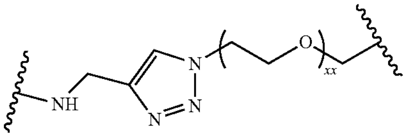
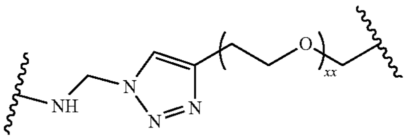
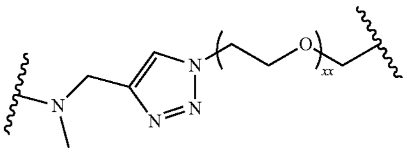
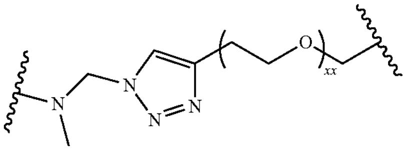
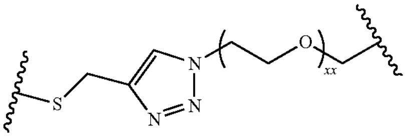
and
-continued
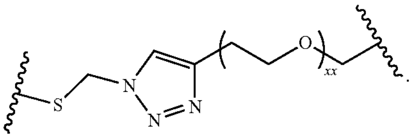
In certain embodiments Linker$^A$ is selected from:
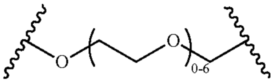
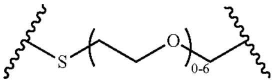
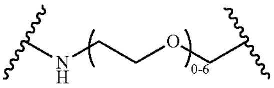
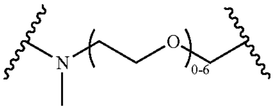
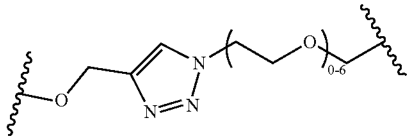
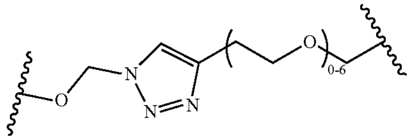
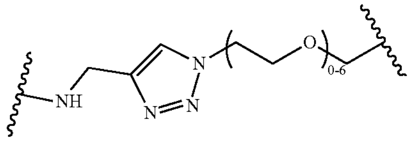
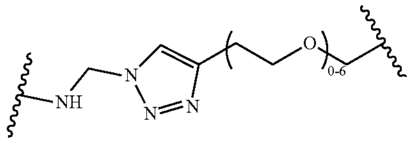
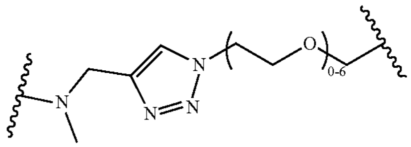

-continued
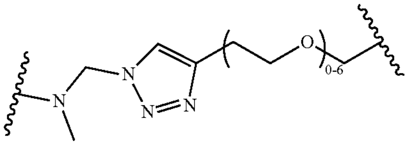
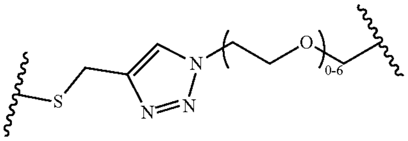
and
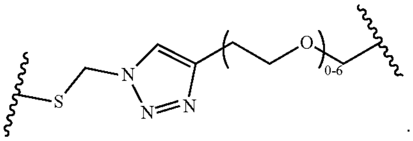
.
In certain embodiments Linker$^A$ is selected from:
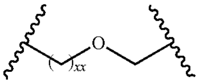
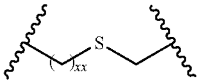
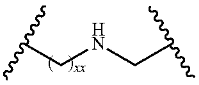
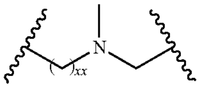
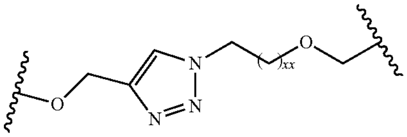
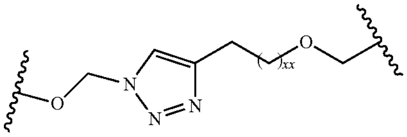
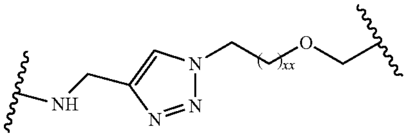
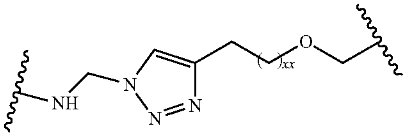
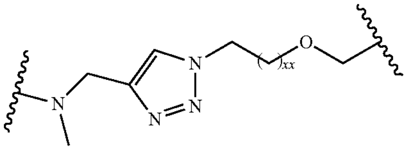
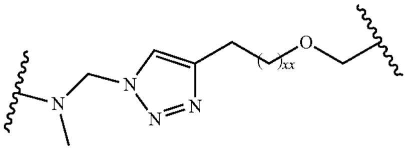
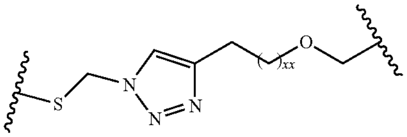
and
-continued
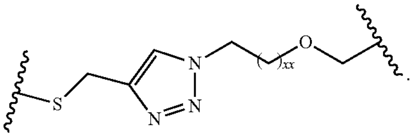
.
In certain embodiments Linker$^A$ is selected from:
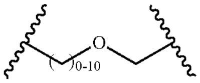
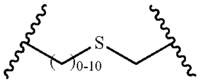
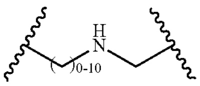
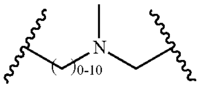
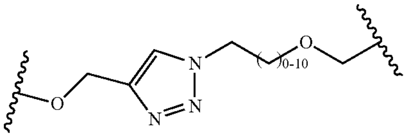
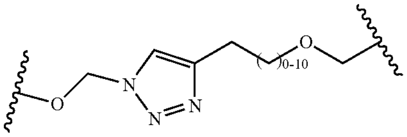
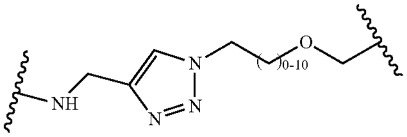
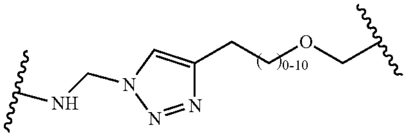
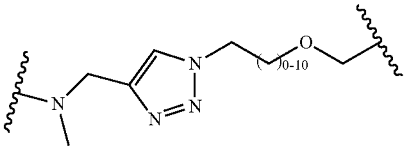
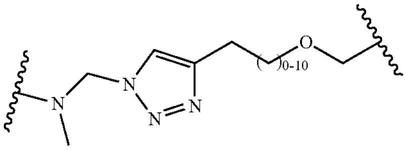
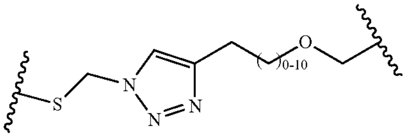
and
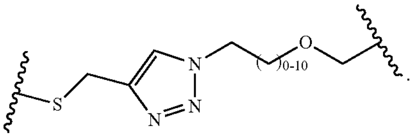
.

In certain embodiments Linker$^B$ is selected from:
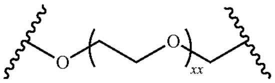
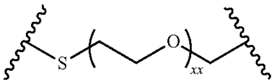
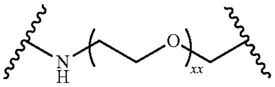
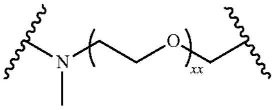
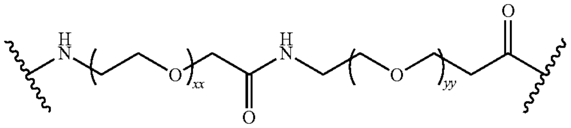
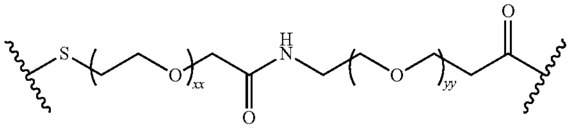
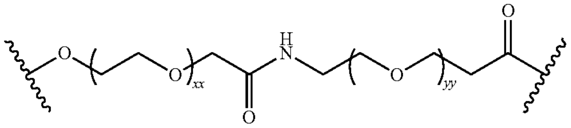
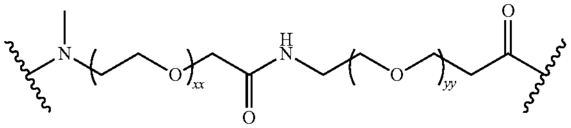
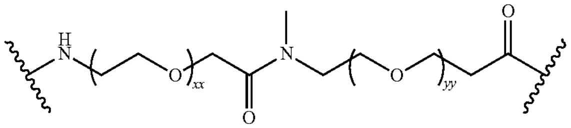
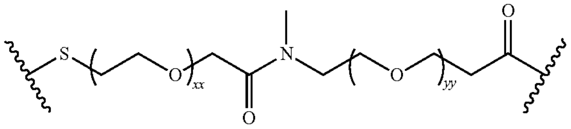
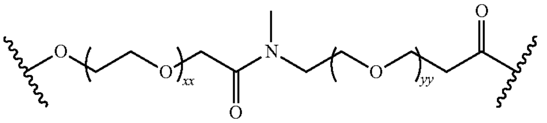
and
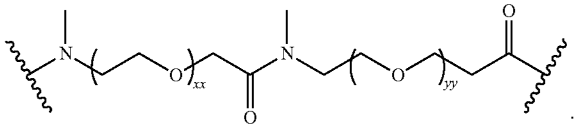
.
In certain embodiments Linker$^B$ is selected from:
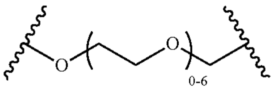
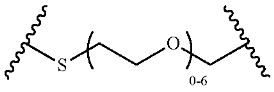
-continued
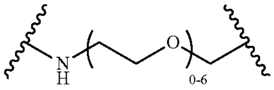
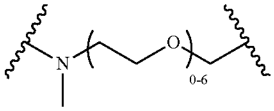
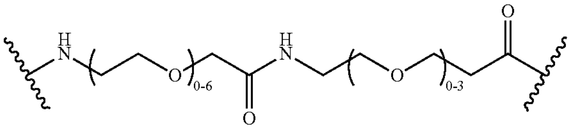
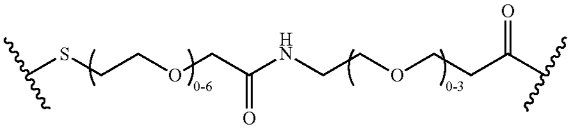
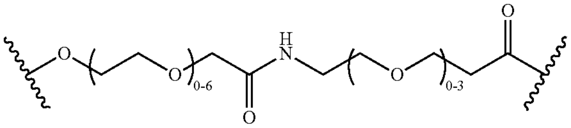
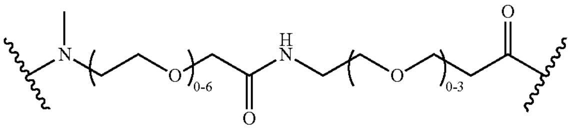
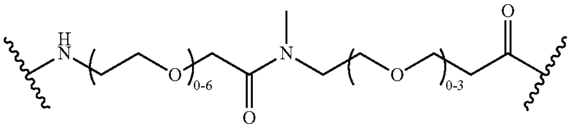
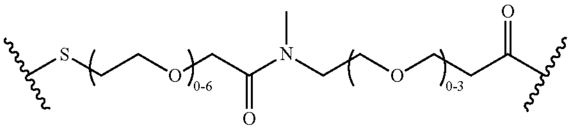
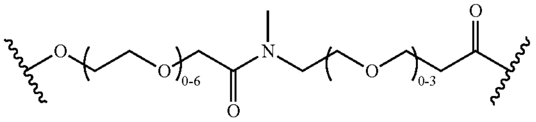
and
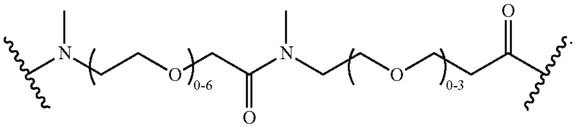
.
In certain embodiments Linker$^B$ is selected from:
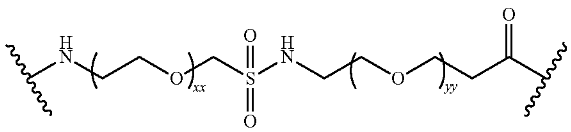
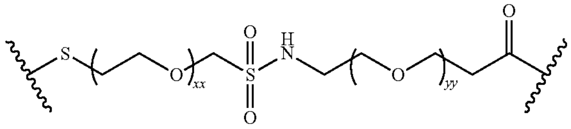
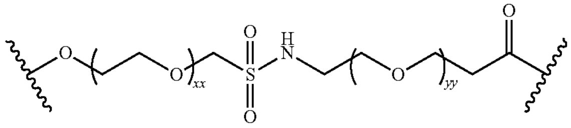

-continued
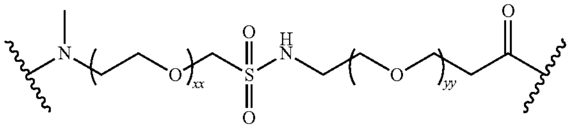
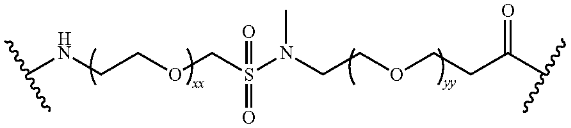
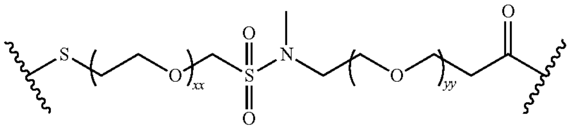
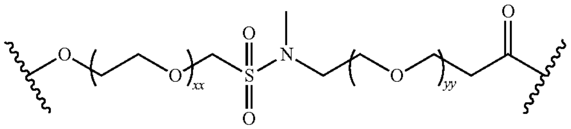
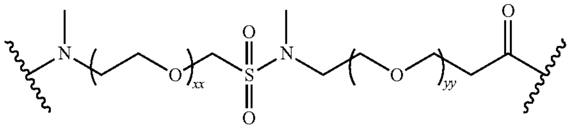
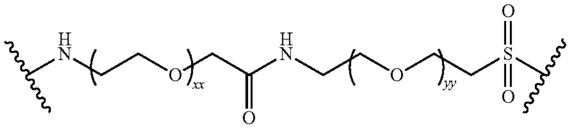
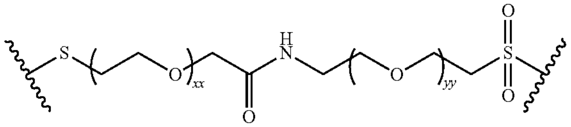
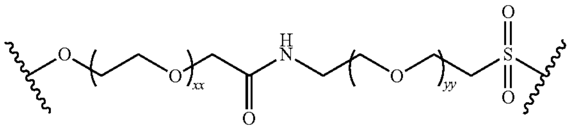
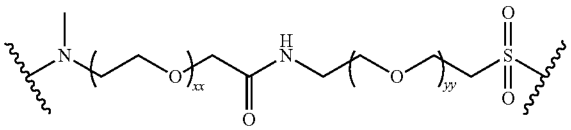
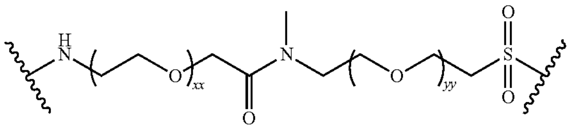
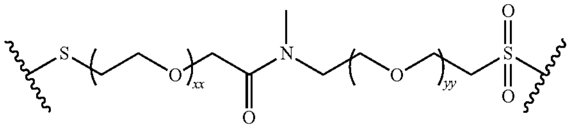
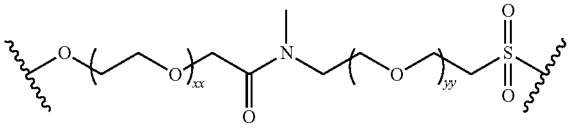
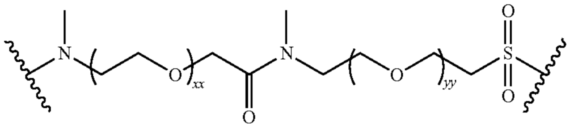
-continued
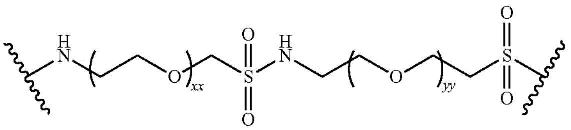
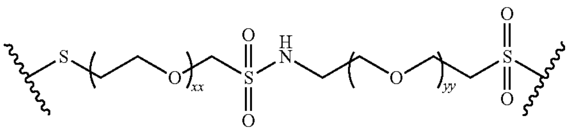
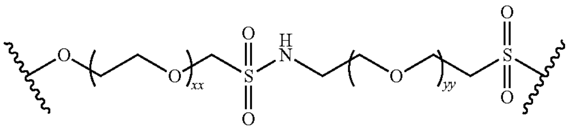
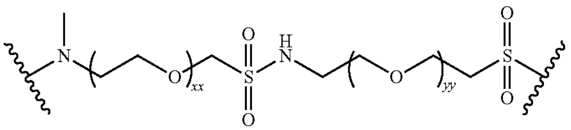
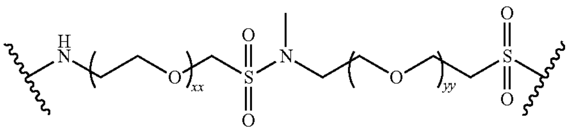
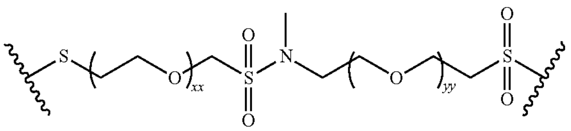
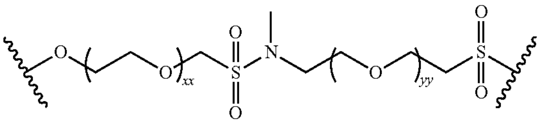
and
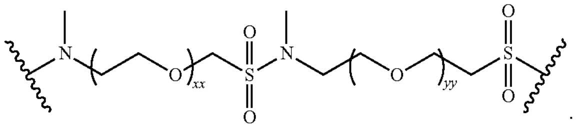
.
In certain embodiments Linker is selected from:
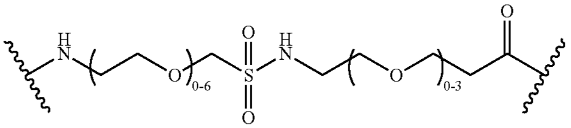
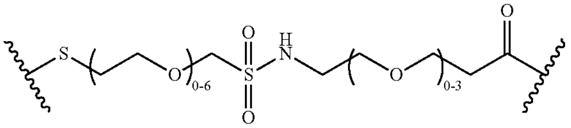
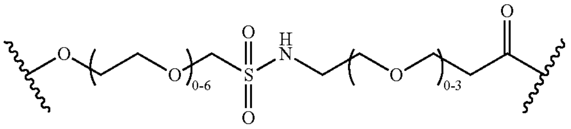
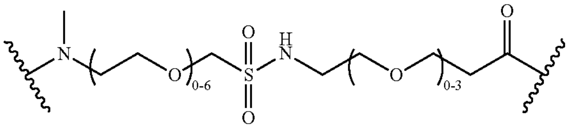

-continued
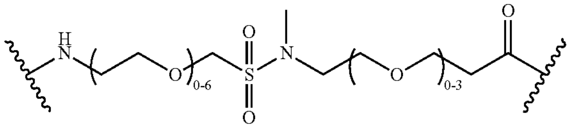
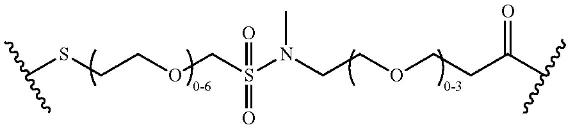
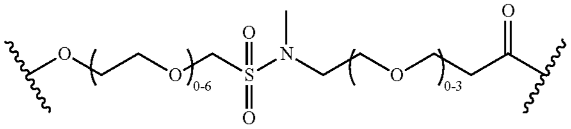
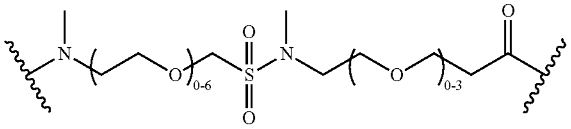
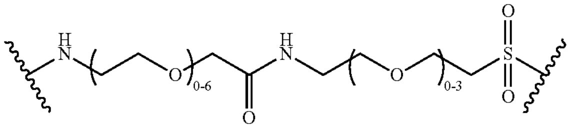
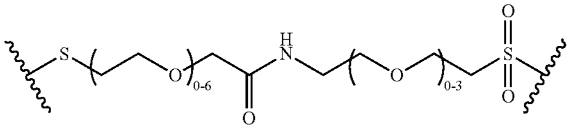
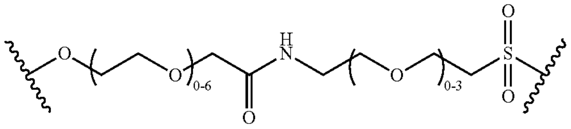
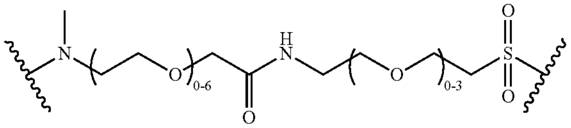
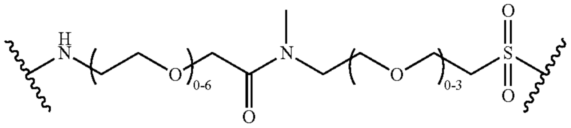
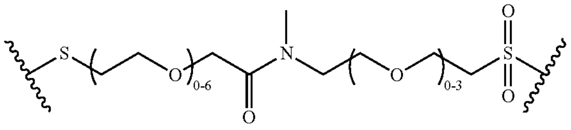
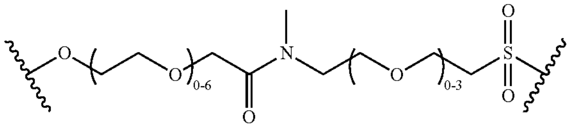
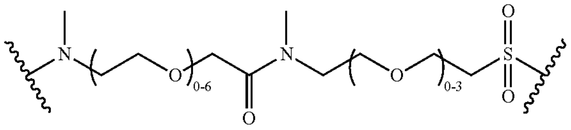
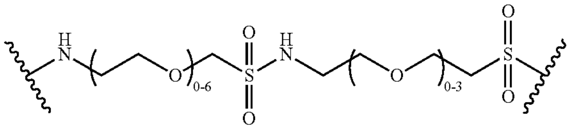
-continued
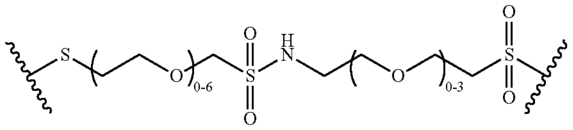
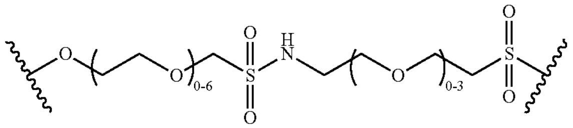
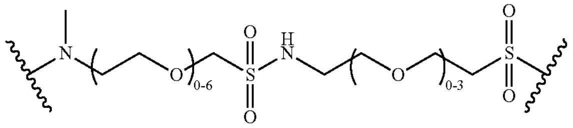
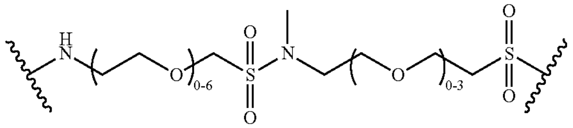
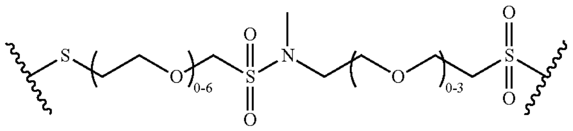
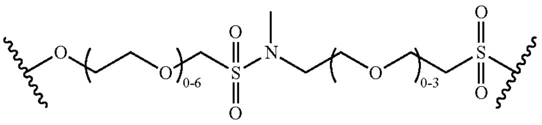
and
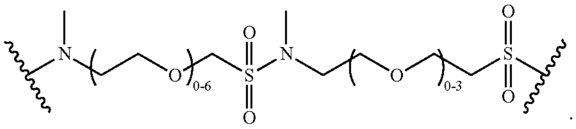
.
In certain embodiments Linker$^C$, is selected from:
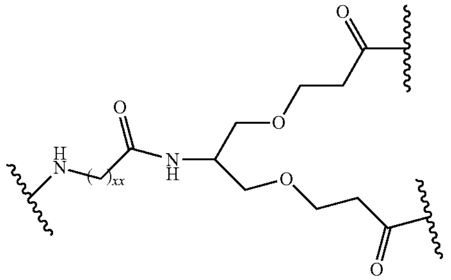
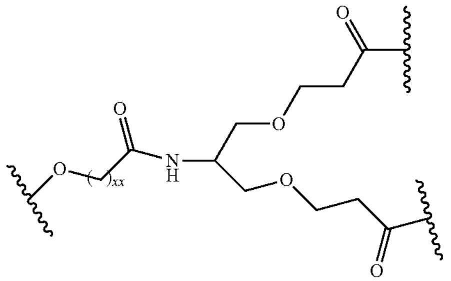

-continued
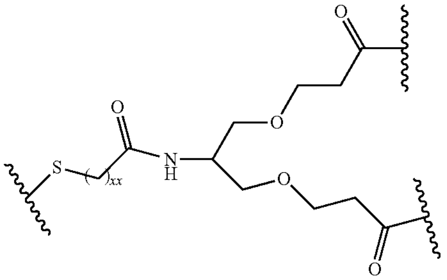
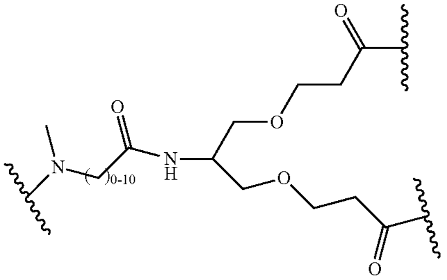
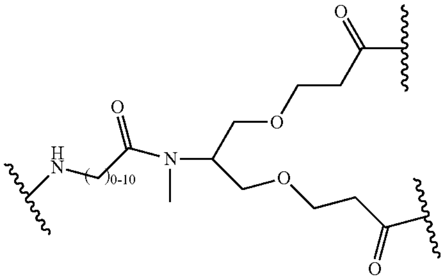
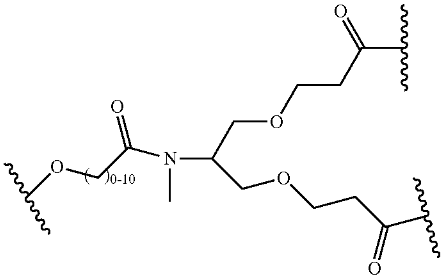
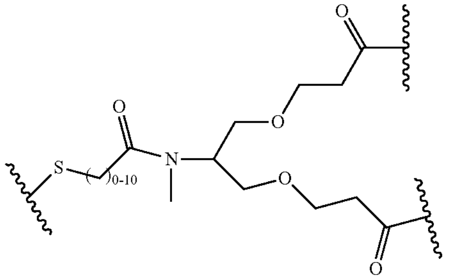
and
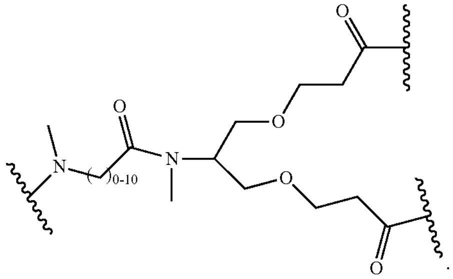
.
In certain embodiments Linker$^C$, is selected from:
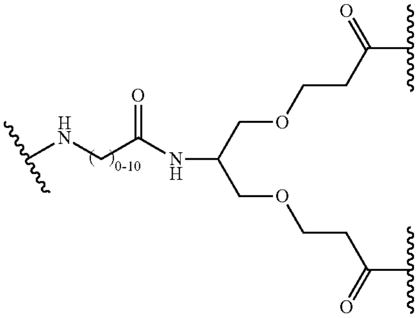
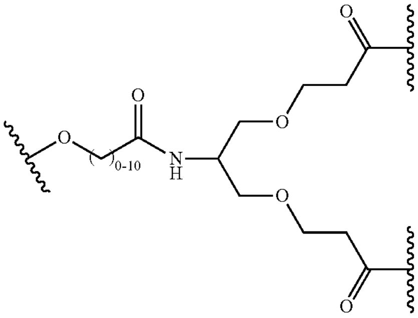
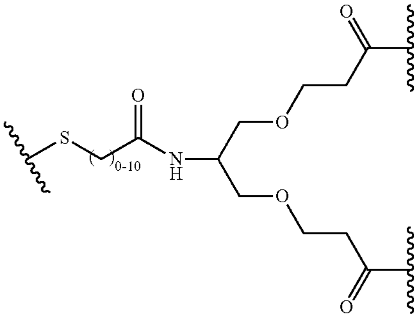
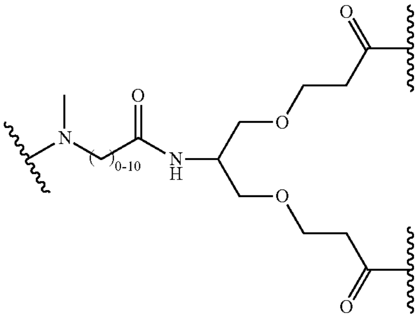
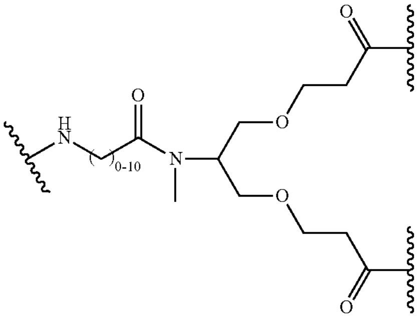

-continued
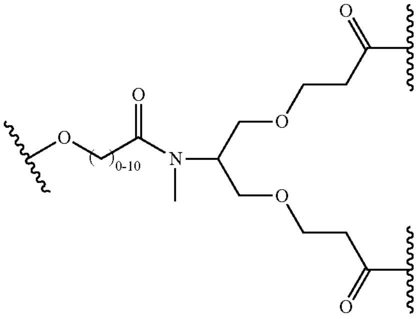
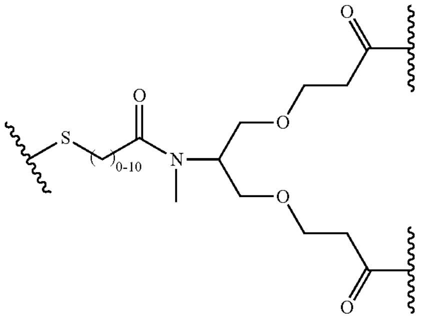
and
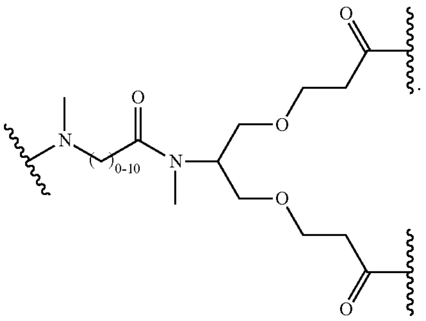
In certain embodiments Linker$^C$, is selected from:
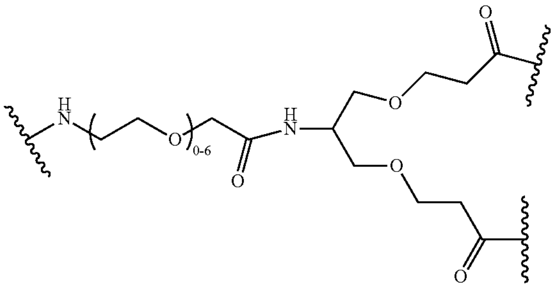
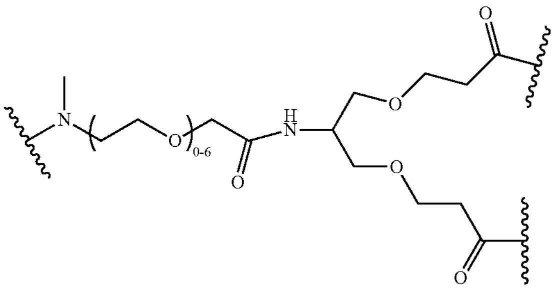
-continued
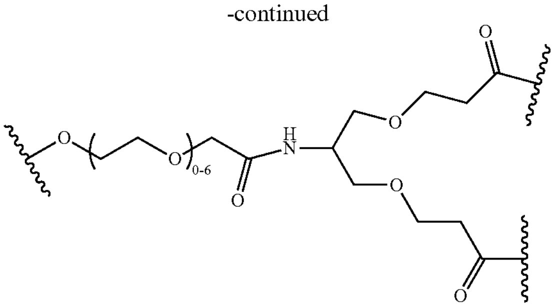
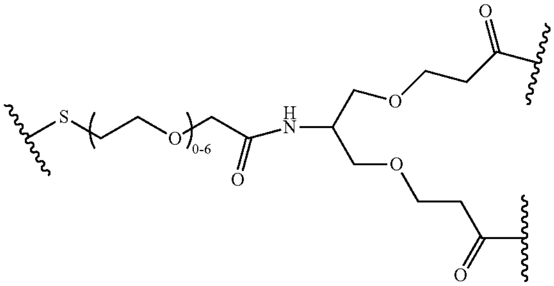
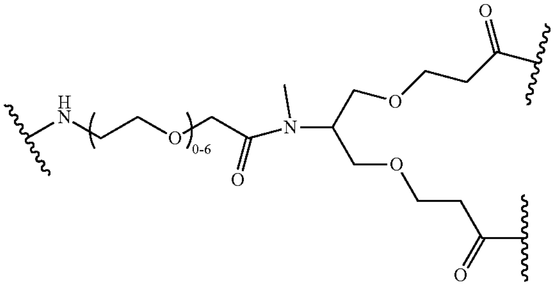
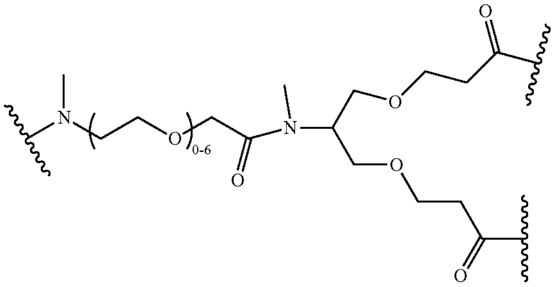
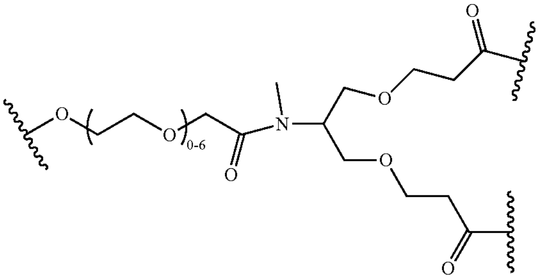
and
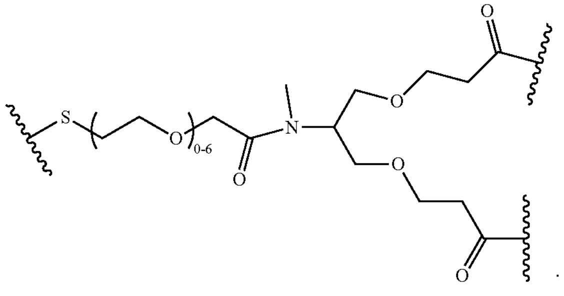

In certain embodiments $Linker^C$, is selected from:
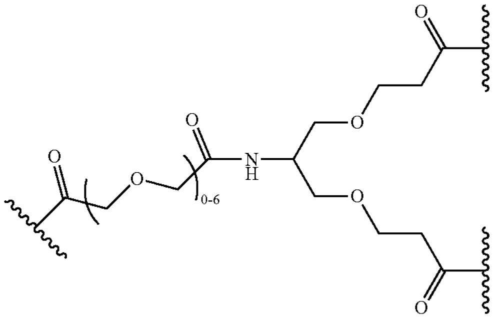
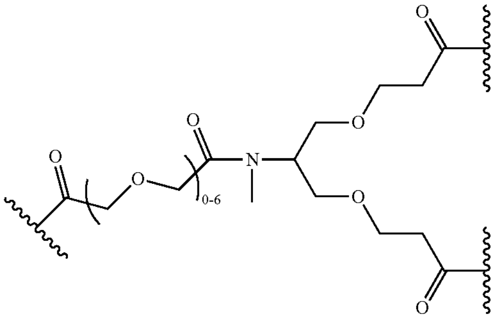
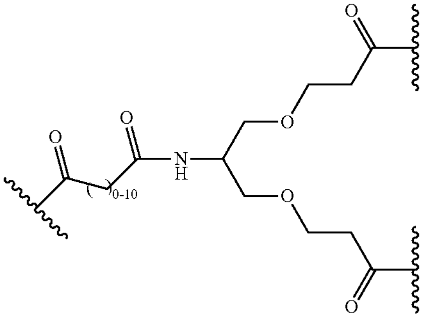
and
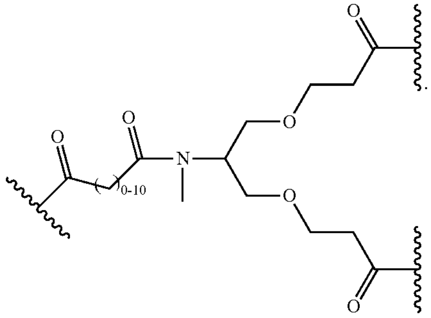
In certain embodiments $Linker^C$ is selected from:
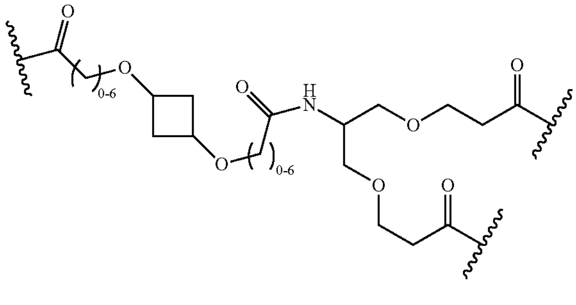
-continued
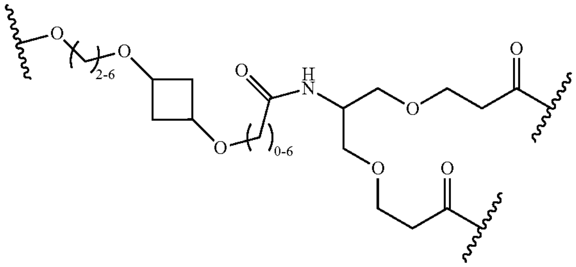
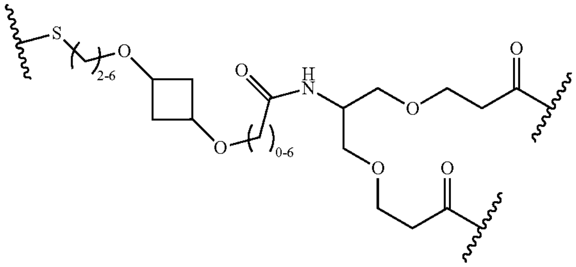
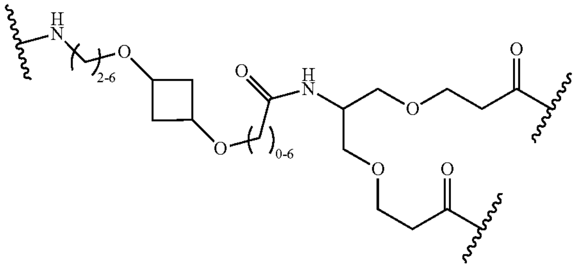
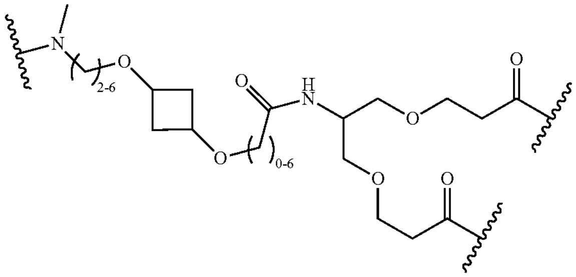
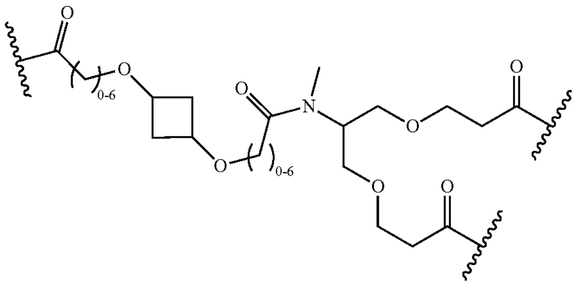
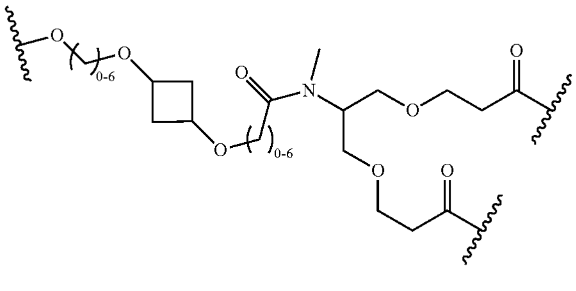

-continued
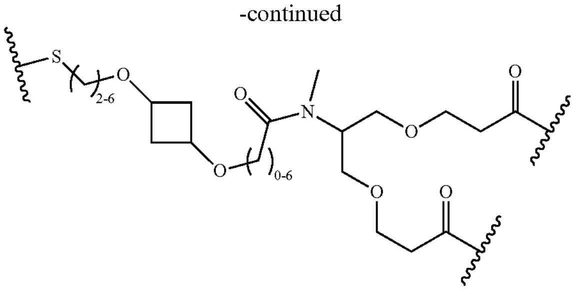
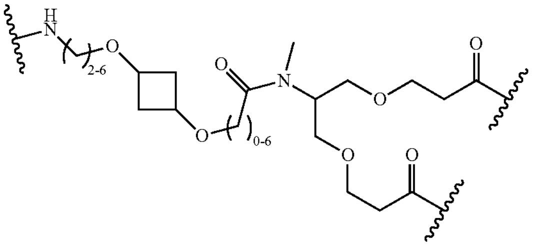
and
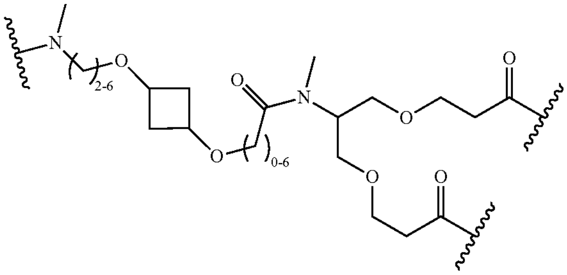
.
In certain embodiments Linker$^C$ is selected from:
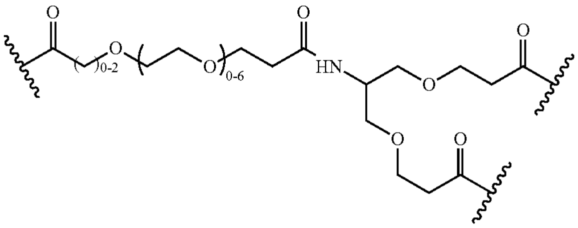
-continued
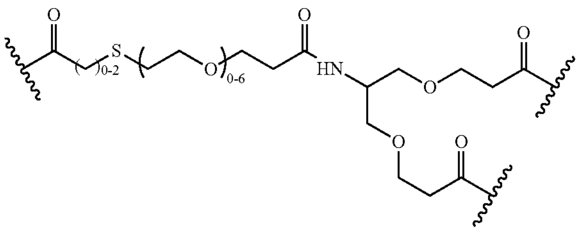
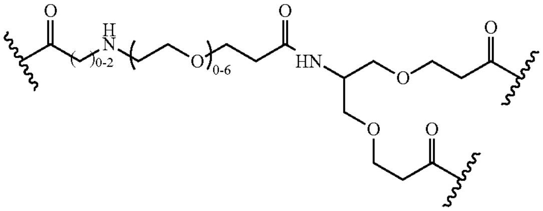
and
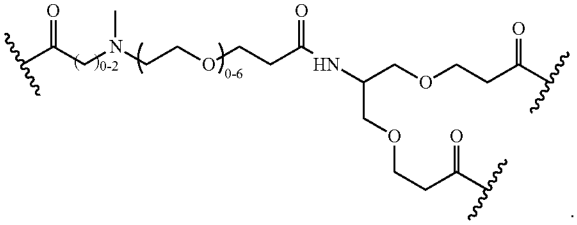
.
In certain embodiments Linker$^C$ is selected from:
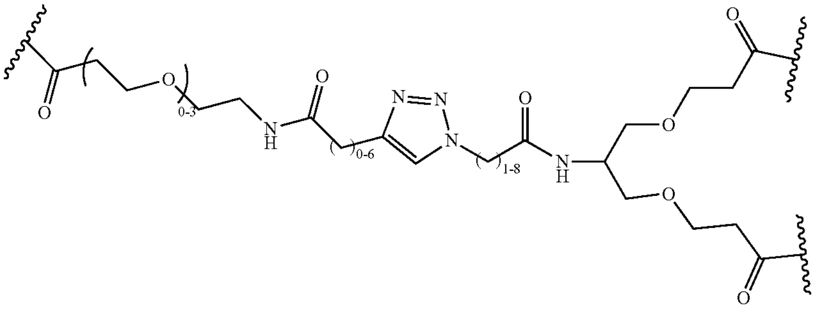

-continued
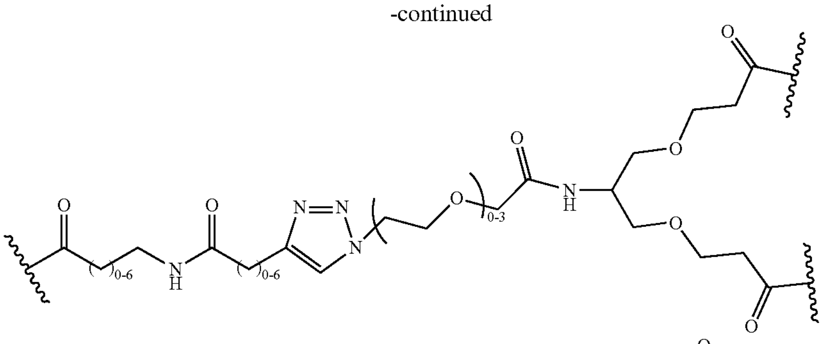
and
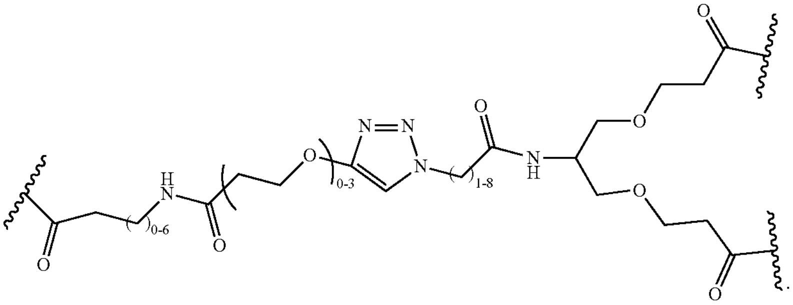
.
In certain embodiments Linker$^C$ is selected from:
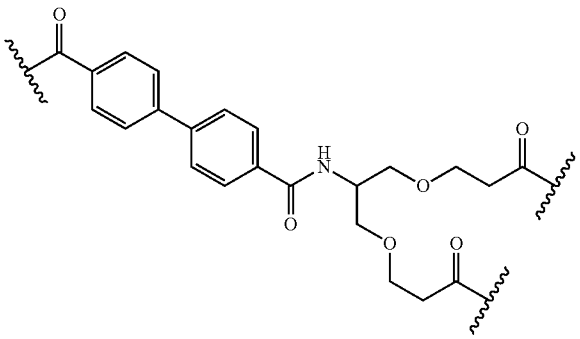
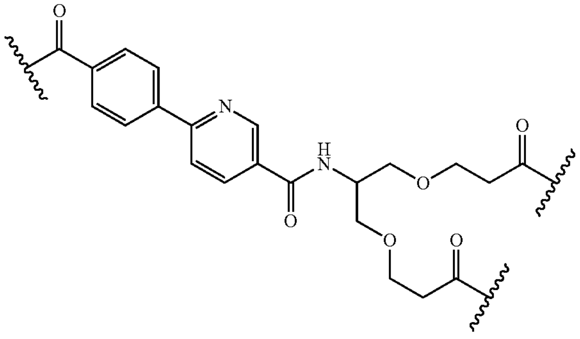
-continued
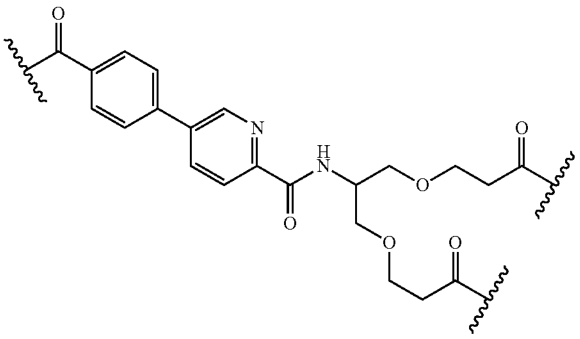
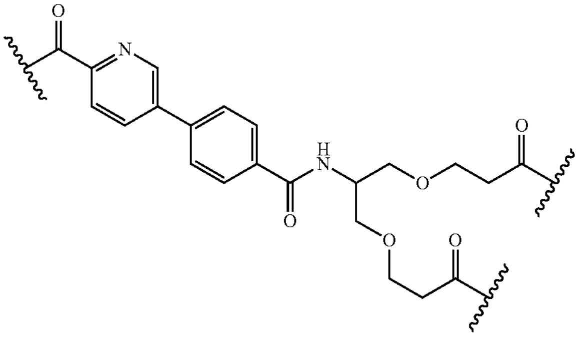
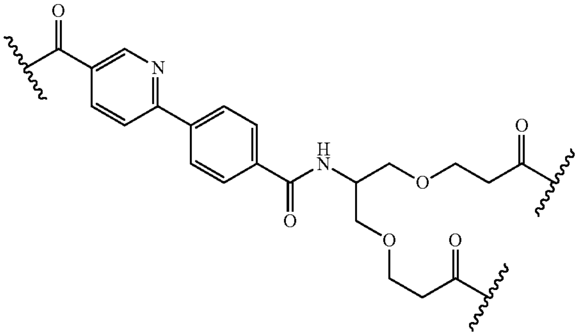

-continued
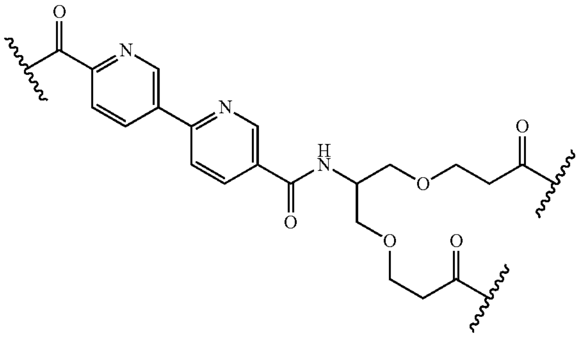
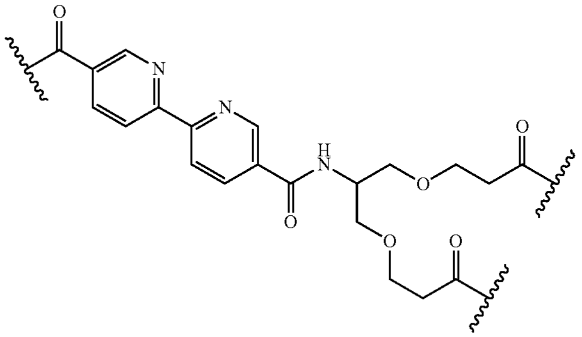
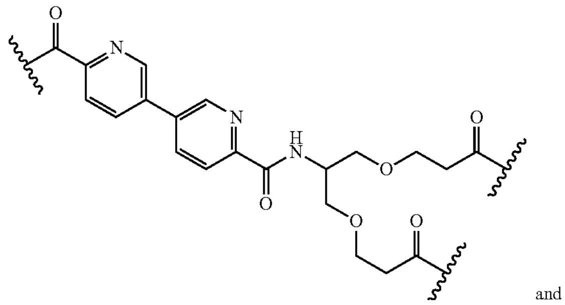
and
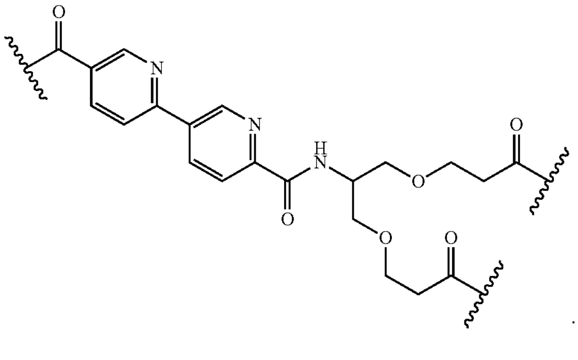
.
In certain embodiments Linker$^D$ is selected from:
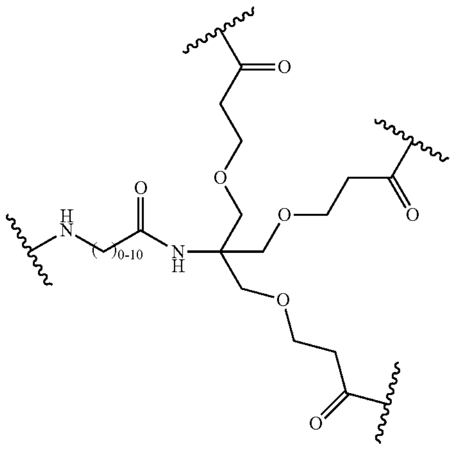
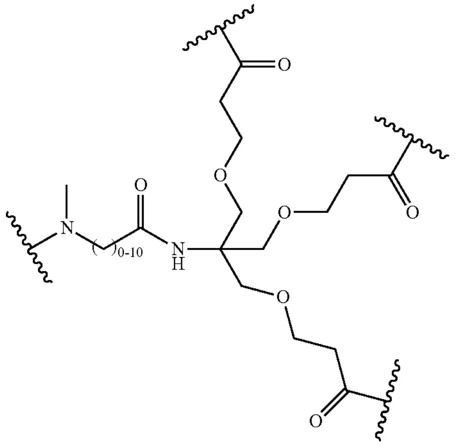
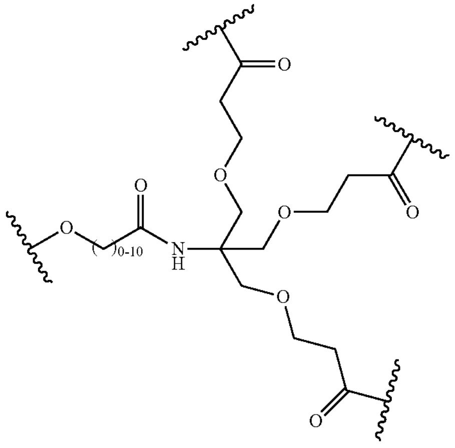

-continued
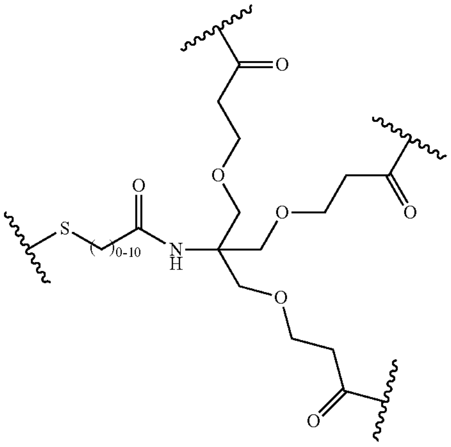
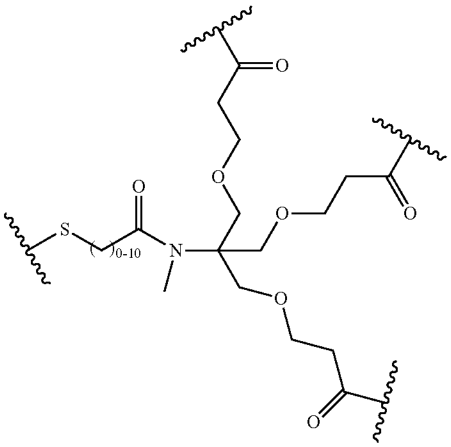
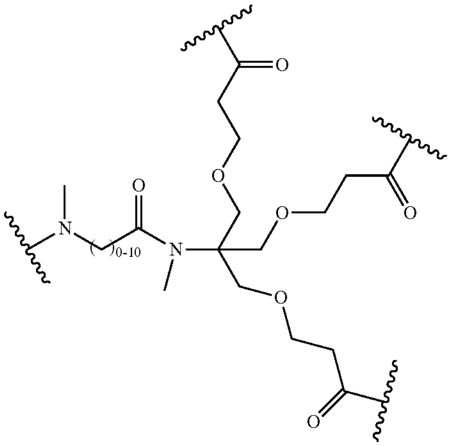
-continued
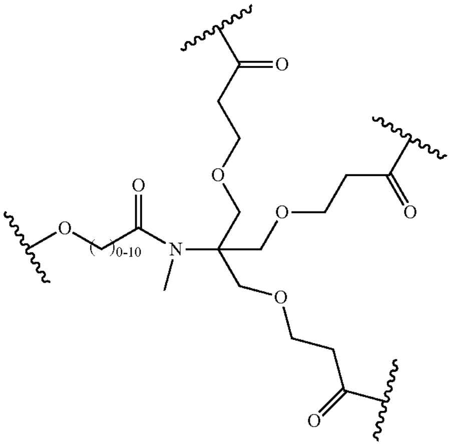
and
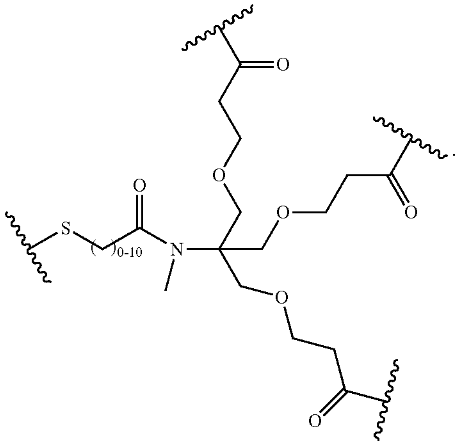
In certain embodiments Linker$^D$ is selected from:
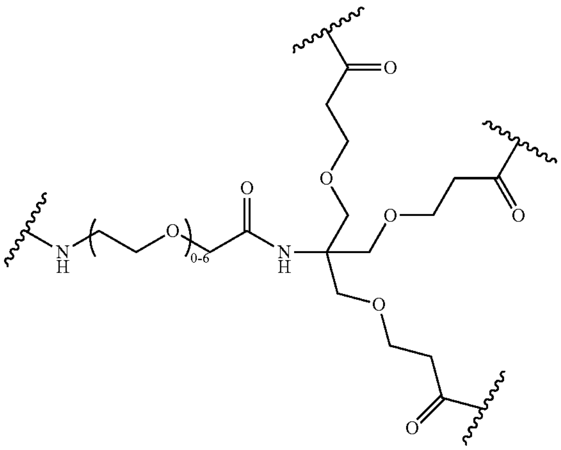

-continued
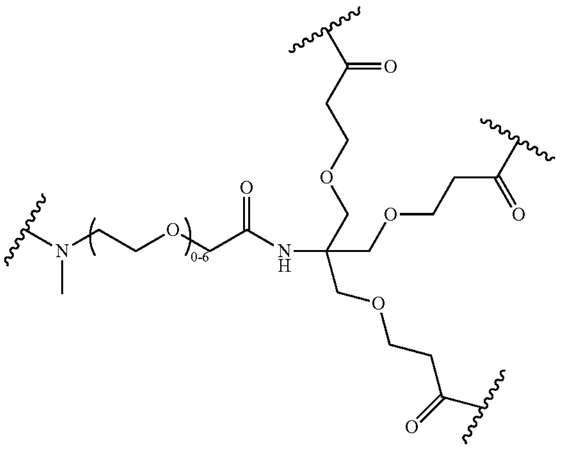
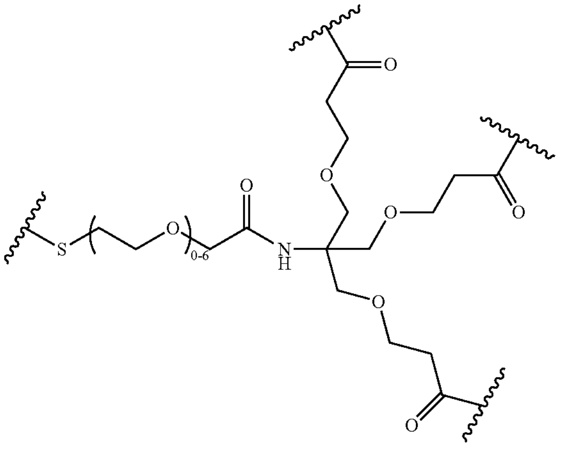
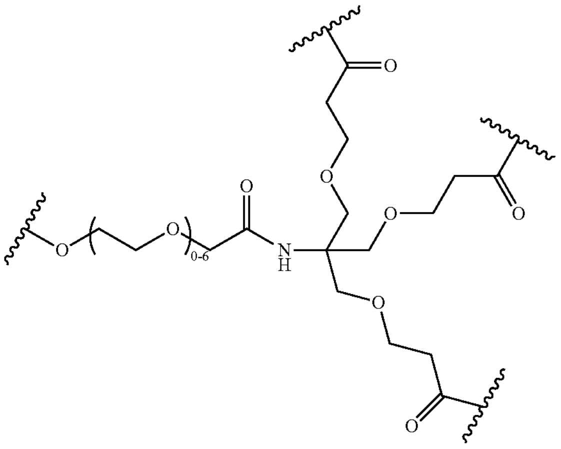
-continued
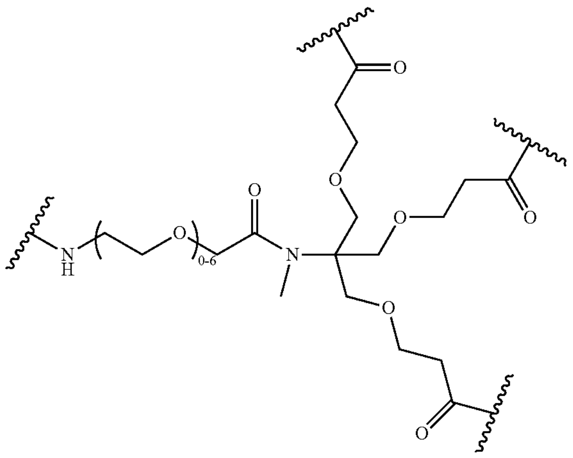
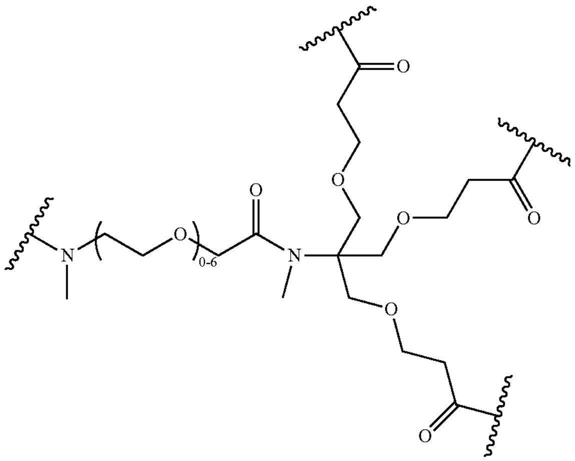
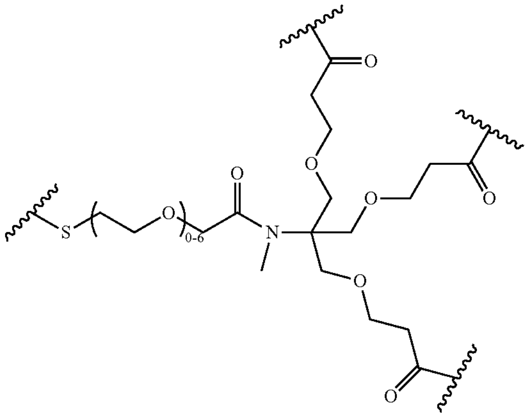
and -continued
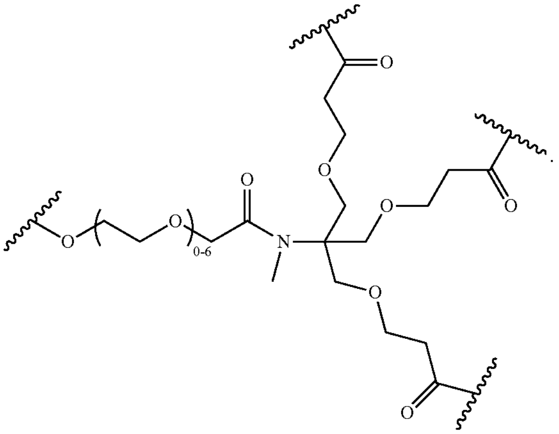
In certain embodiments $Linker^D$ is selected from:
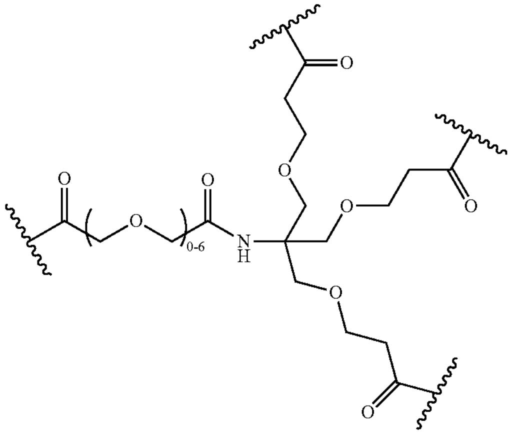
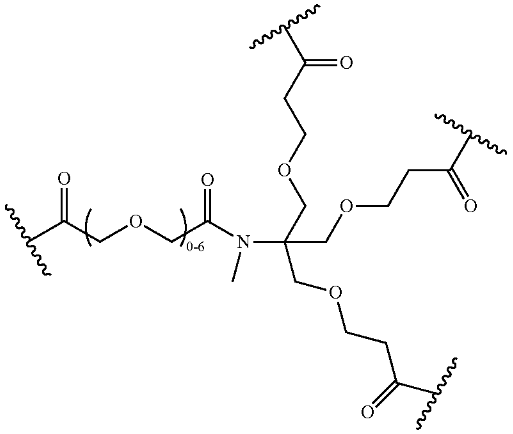
-continued
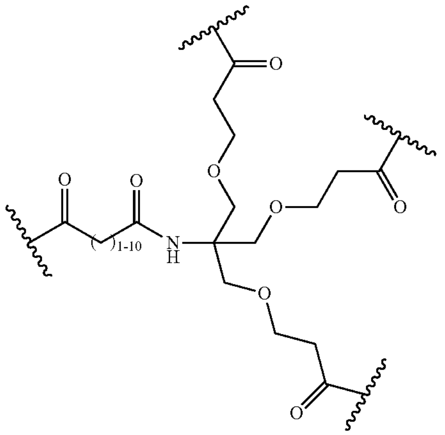
and
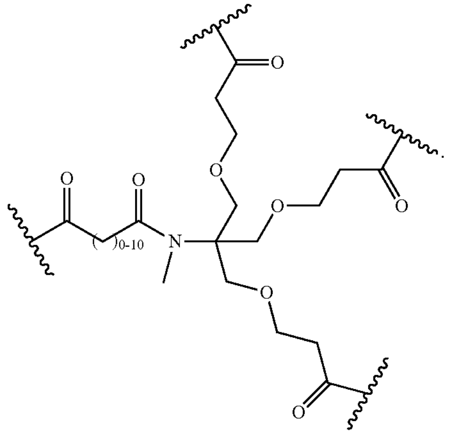
In certain embodiments $Linker^D$ is selected from:
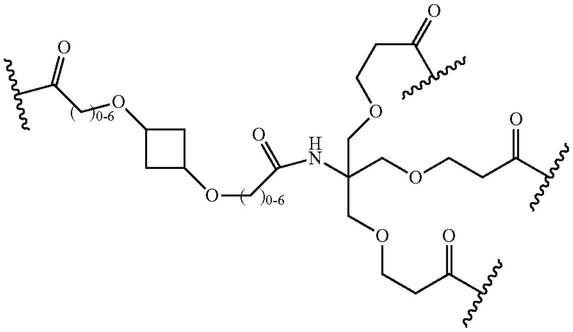
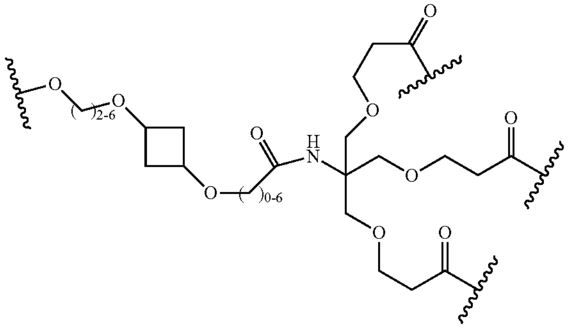

-continued
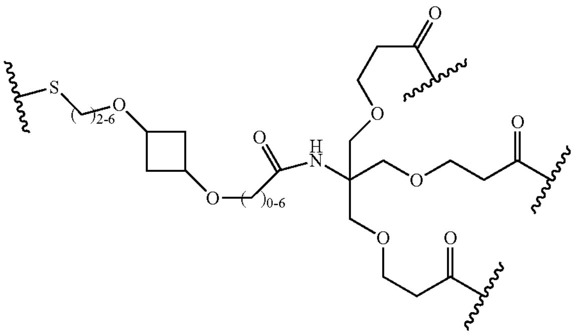
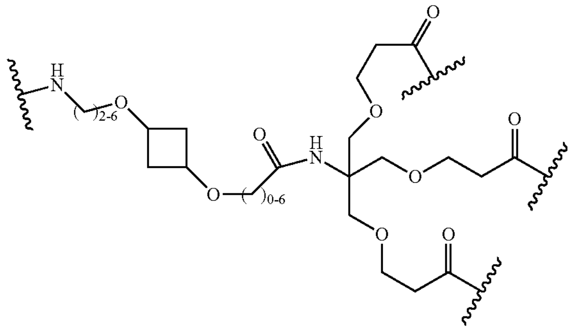
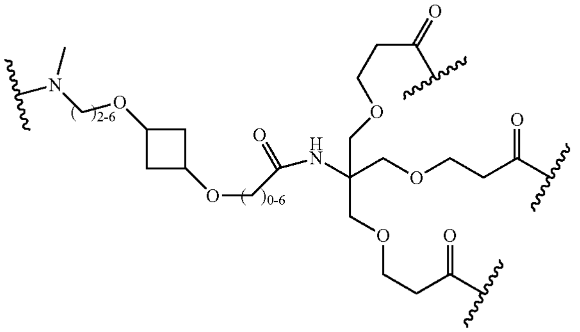
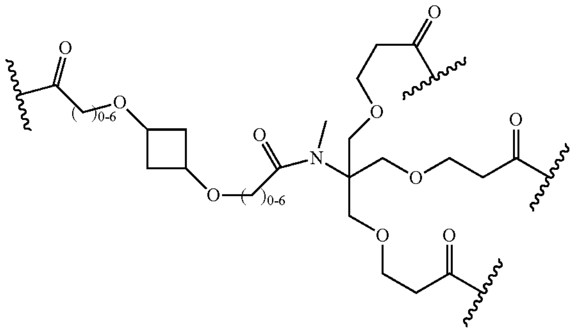
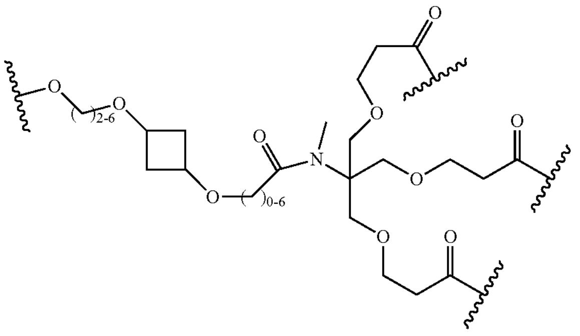
-continued
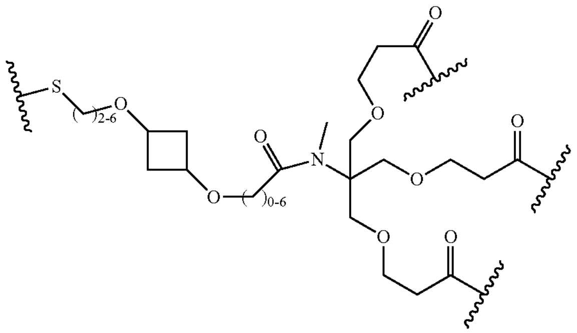
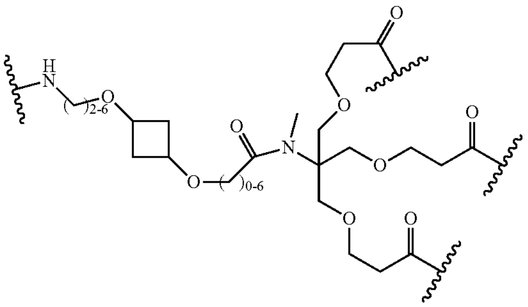
and
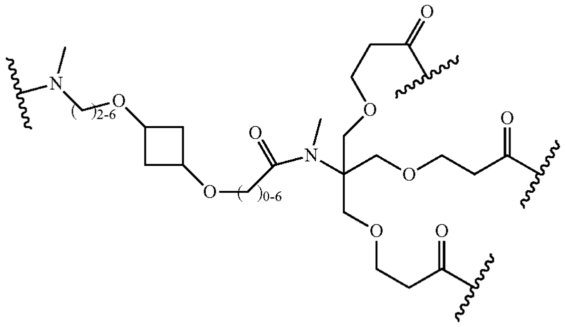
.
In certain embodiments Linker$^D$ is selected from:
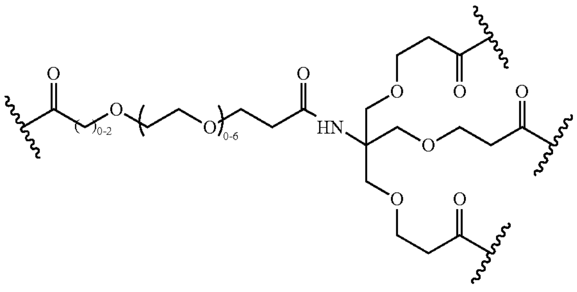
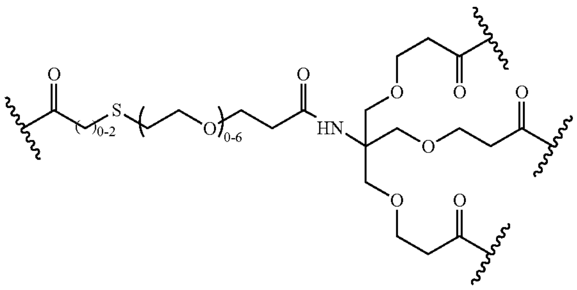

-continued
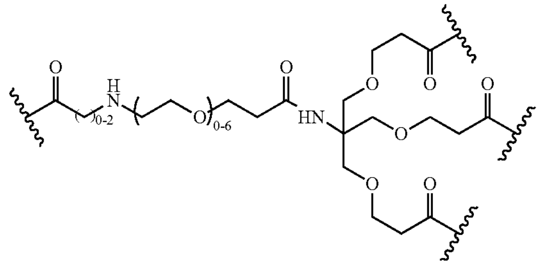
and
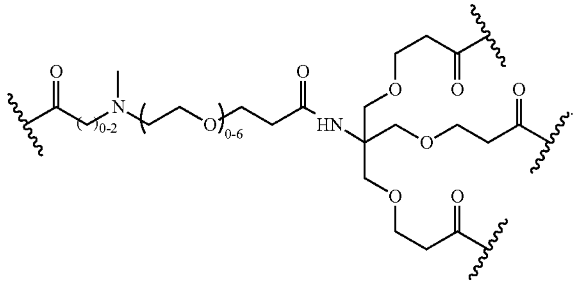
In certain embodiments Linker is selected from:
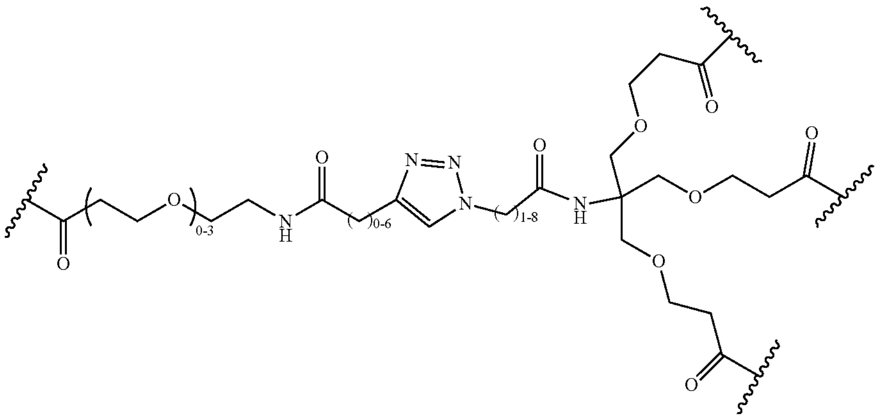
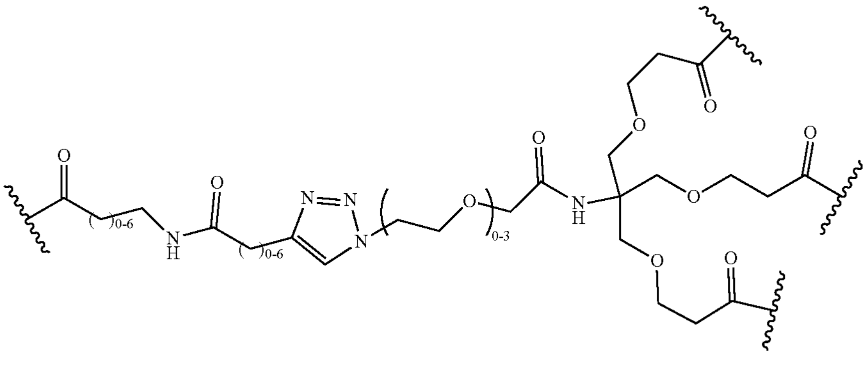
and -continued
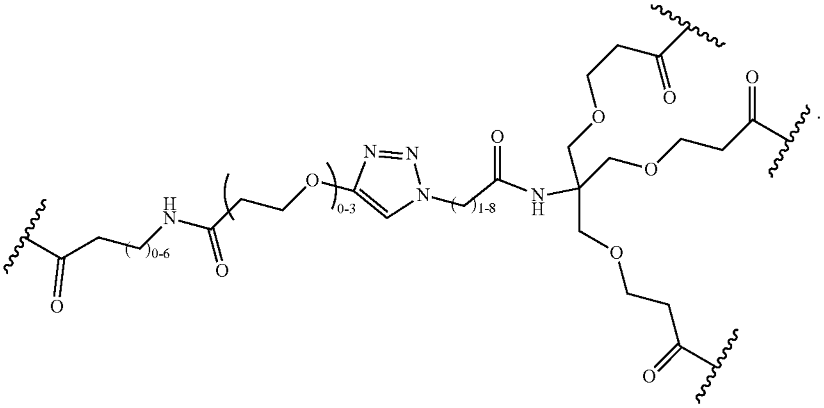
In certain embodiments Linker$^D$ is selected from:
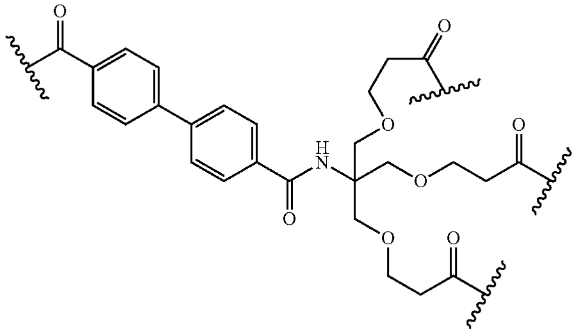
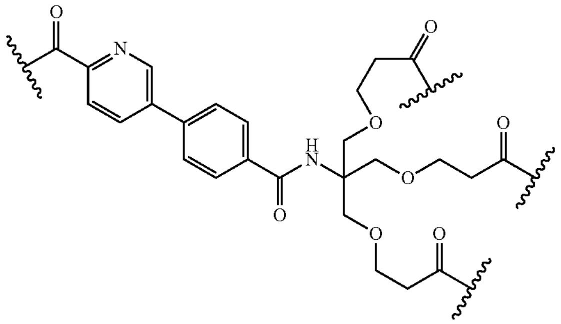
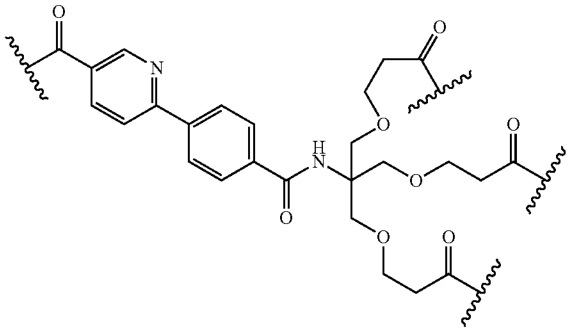
-continued
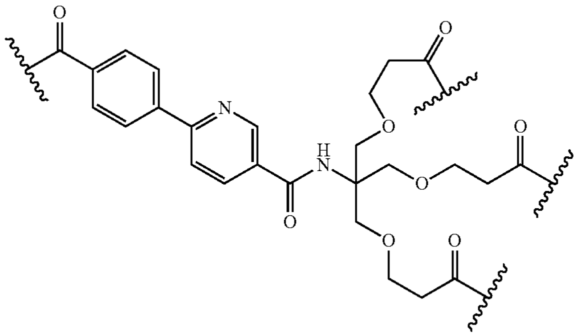
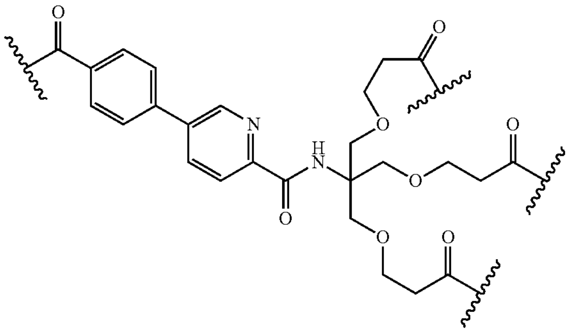
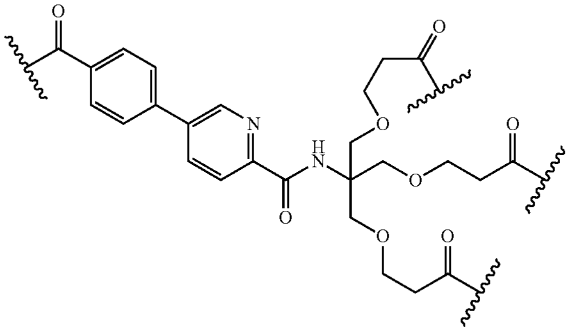

-continued
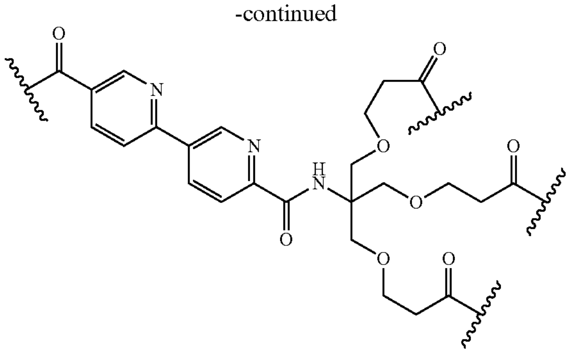
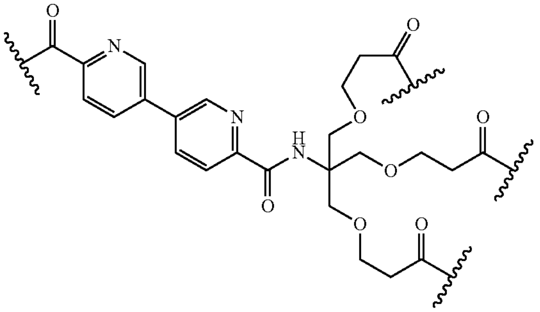
and
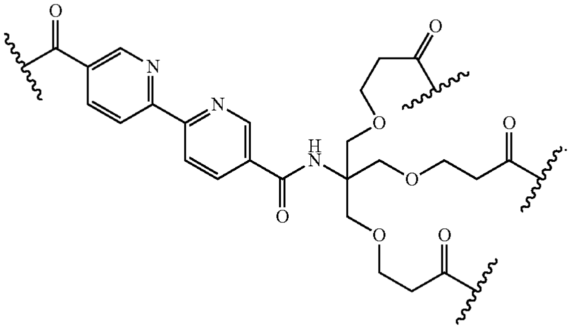 [SMILES: *C(=O)CCOCC(COCCC(*)=O)(COCCC(*)=O)NC(=O)c1ccc(-c2ccc(C(*)=O)cn2)nc1]
In certain embodiments, the Linker$^{A}$ is selected from
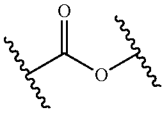
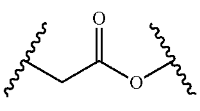
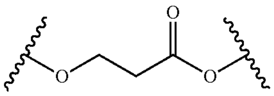
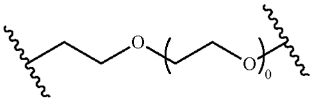
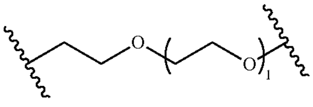
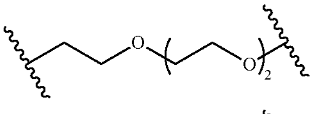
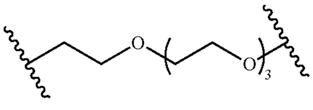
-continued
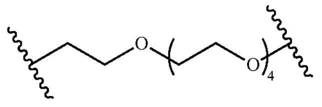
and
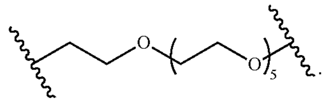
In certain embodiments, the Linker$^{A}$ is selected from
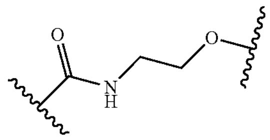
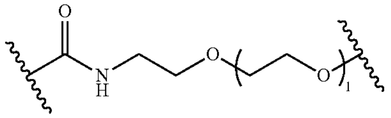
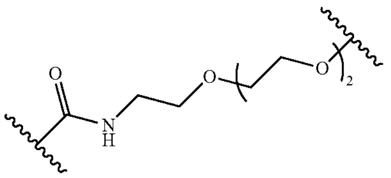
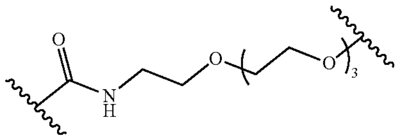
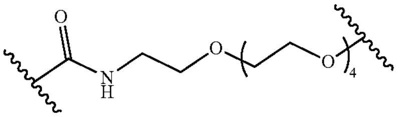
and
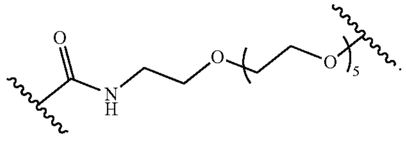
In certain embodiments, the Linker$^{A}$ is selected from
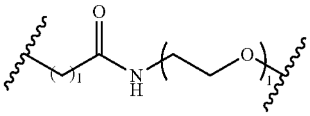
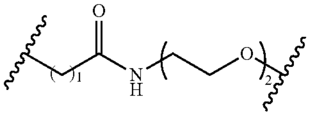
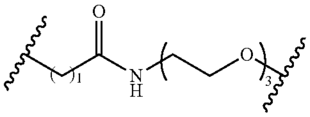

-continued
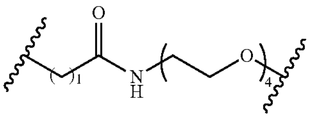
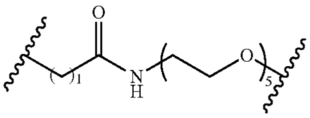
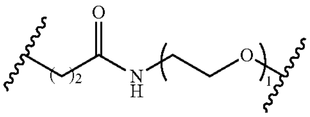
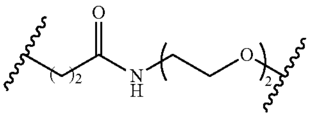
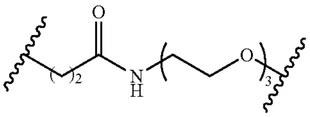
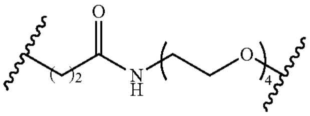
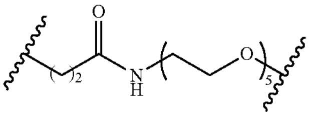
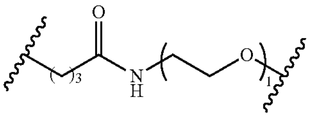
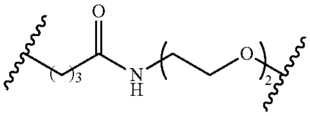
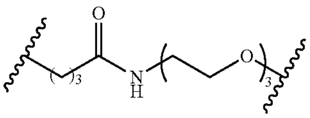
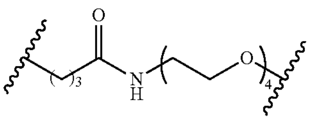
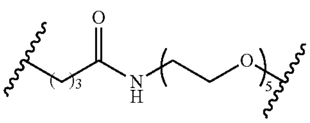
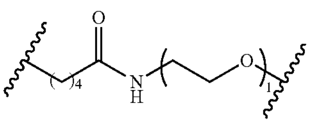
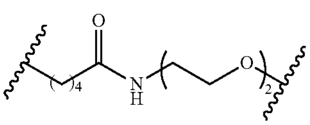
-continued
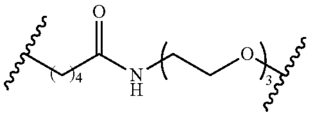
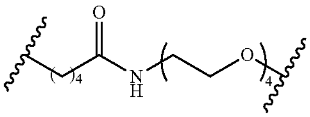
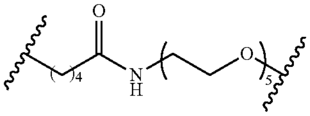
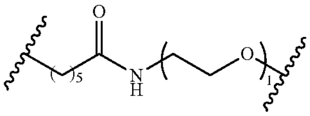
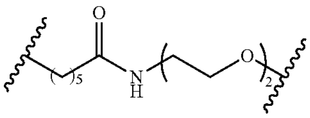
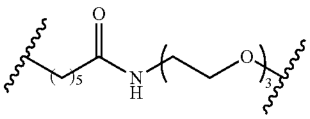
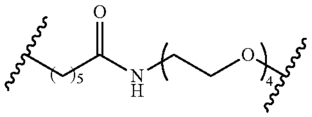
and
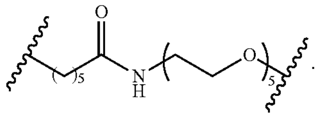
.
In certain embodiments, the Linker$^A$ is selected from
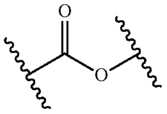
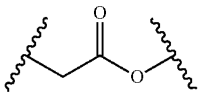
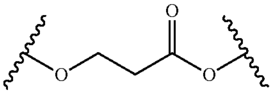
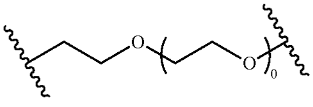
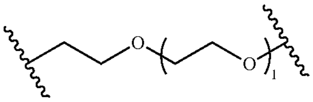
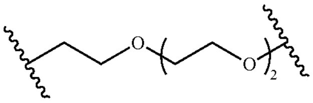
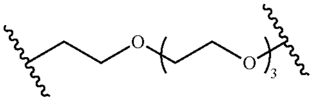

-continued
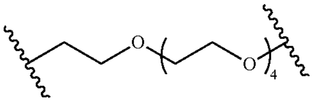
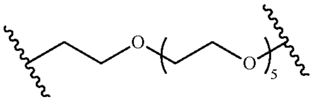
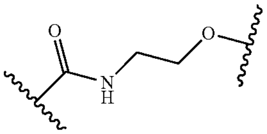
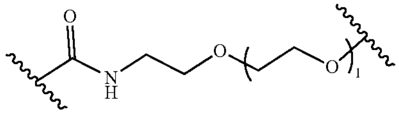
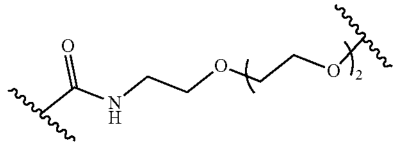
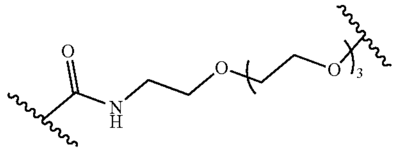
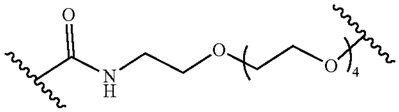
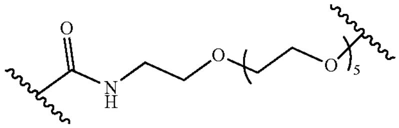
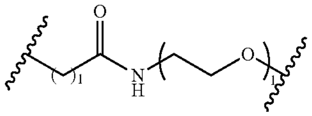
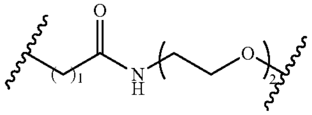
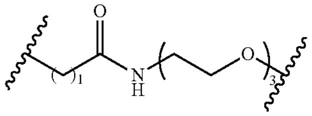
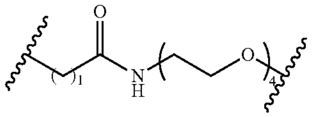
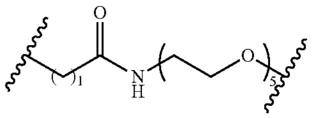
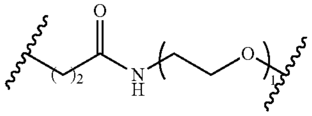
-continued
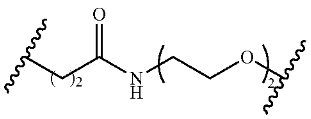
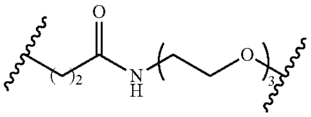
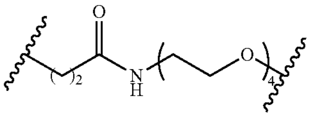
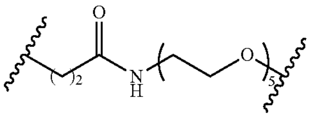
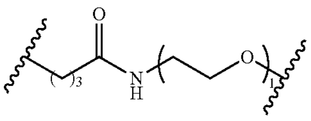
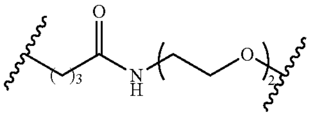
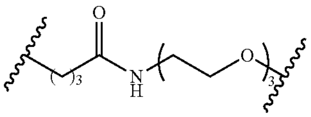
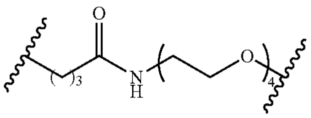
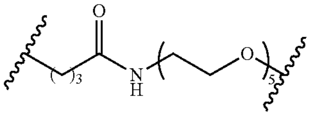
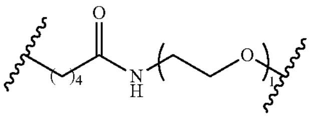
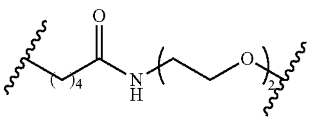
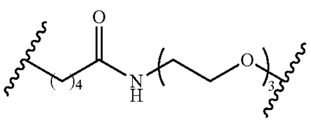
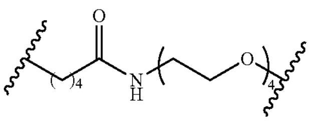
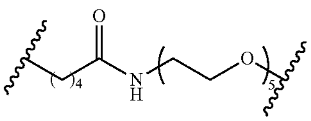

-continued
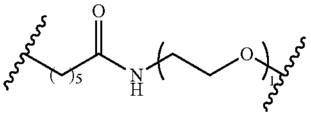
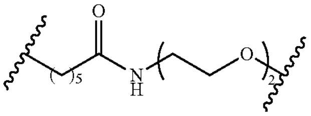
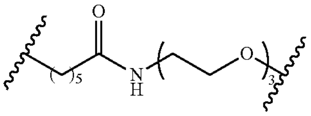
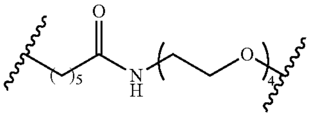
and
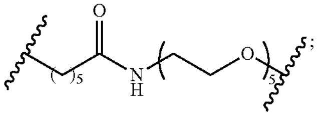
;
wherein each is optionally substituted with 1, 2, 3, or 4 substituents substituent selected from $R^{21}$.
In certain embodiments Linker$^A$ is selected from:
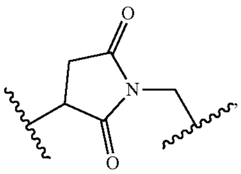
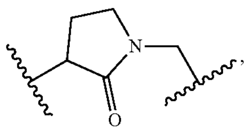
,
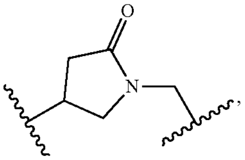
, and
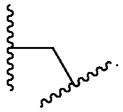
.
In certain embodiments Linker$^A$ is selected from:
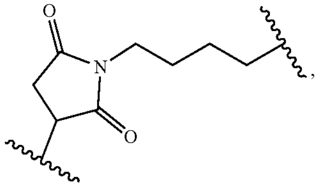
,
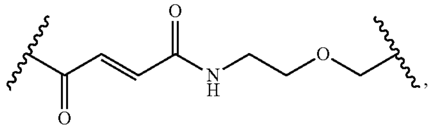
,
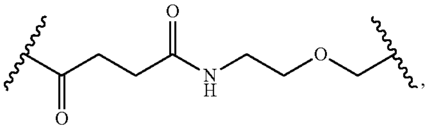
, and
-continued
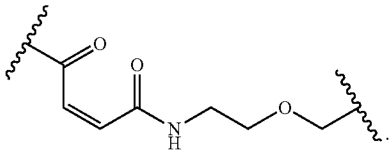
.
In certain embodiments Linker$^A$ is selected from:
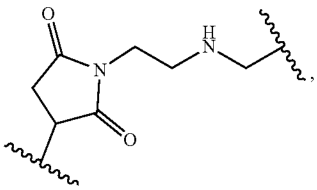
,
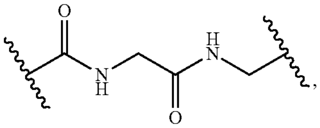
,
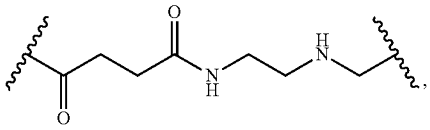
, and
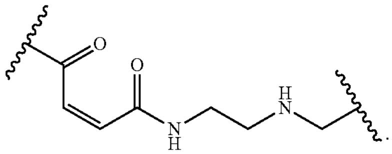
.
In certain embodiments Linker$^A$ is selected from:
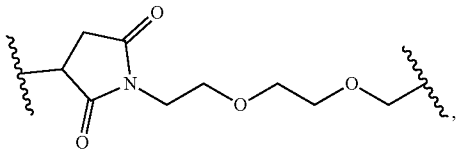
,
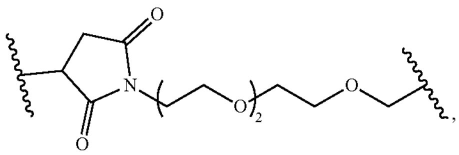
,
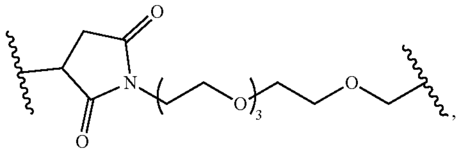
,
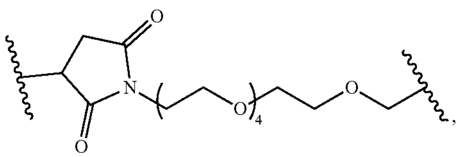
, and -continued
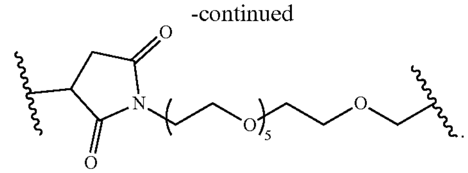
In certain embodiments $Linker^A$ is selected from:
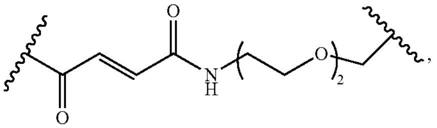
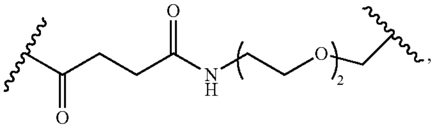
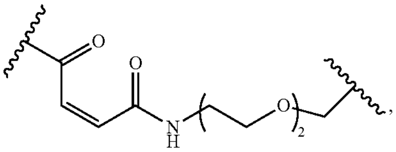
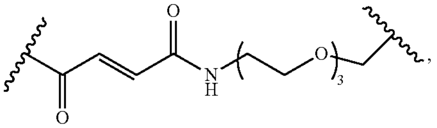
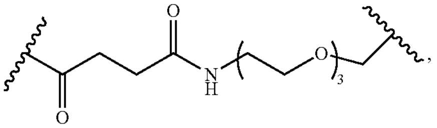
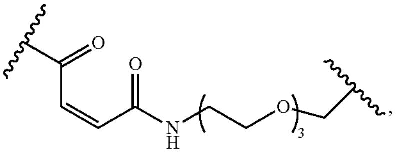
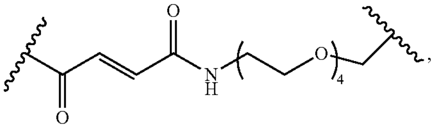
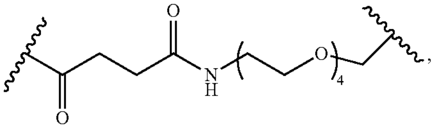
and
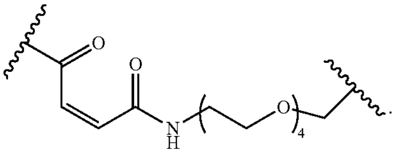
In certain embodiments $Linker^A$ is selected from:
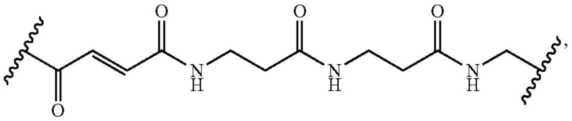
-continued
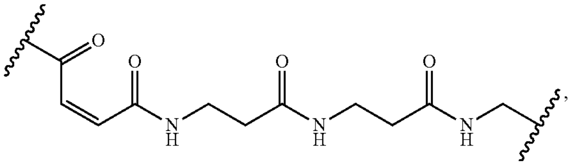
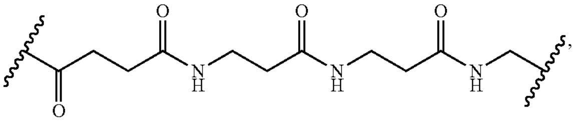
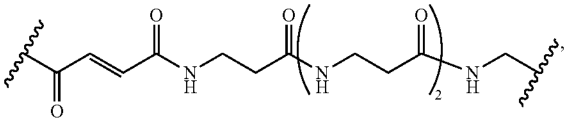
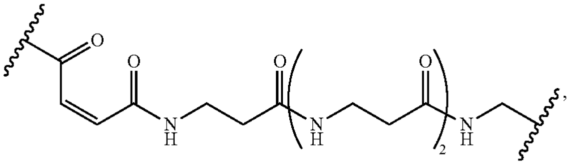
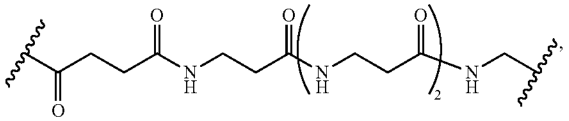
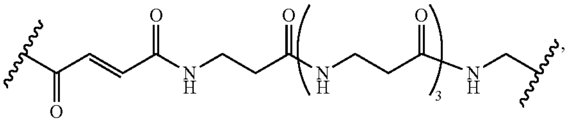
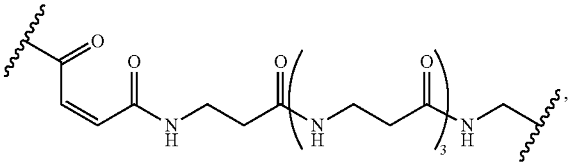
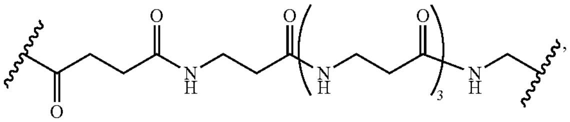
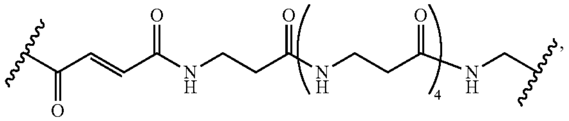
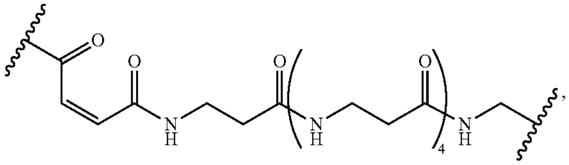
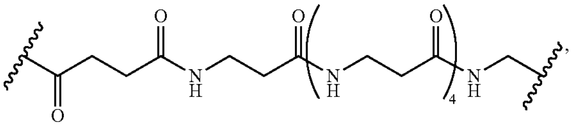
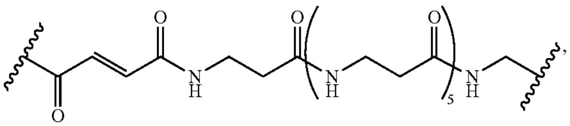

-continued
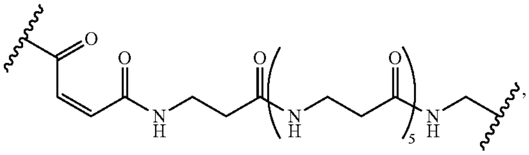
and
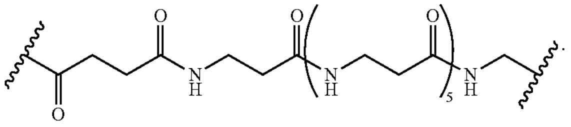
In certain embodiments Linker$^A$ is selected from:
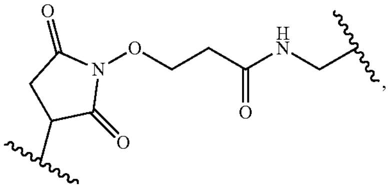
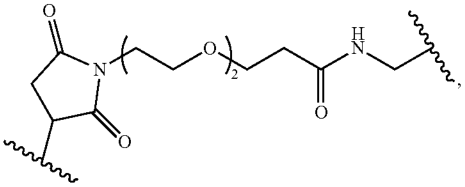
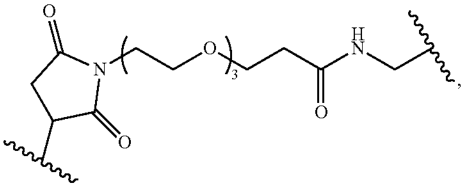
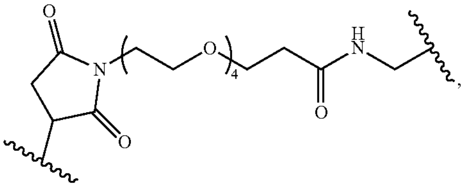
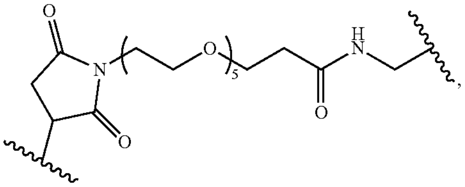
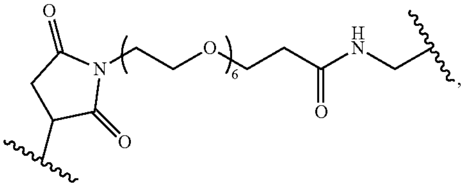
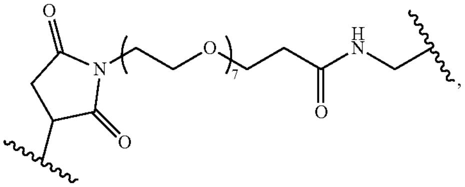
-continued
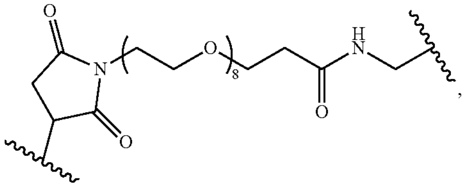
and
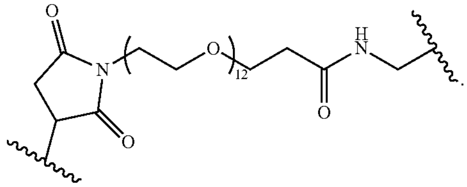
In certain embodiments Linker$^A$ is selected from:
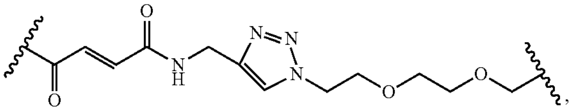
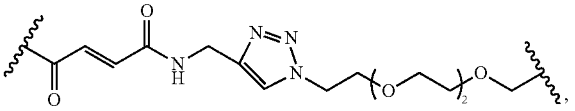
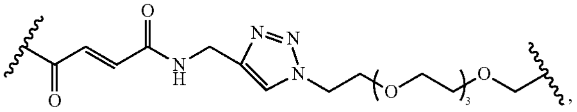
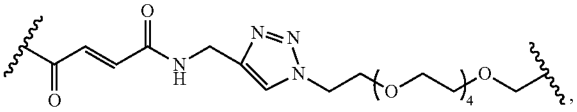
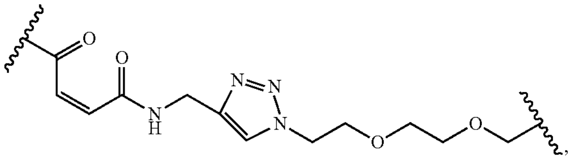
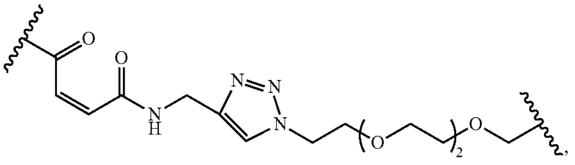
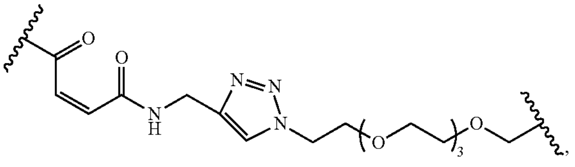
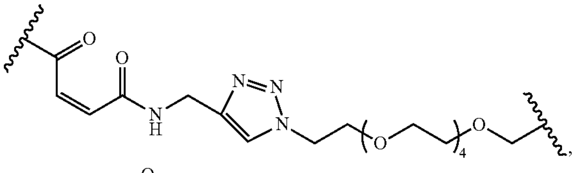
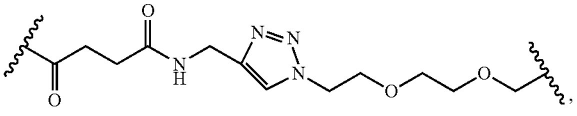

-continued
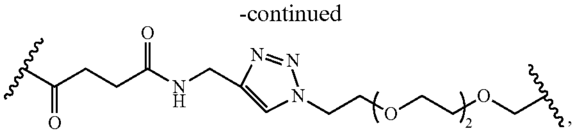,
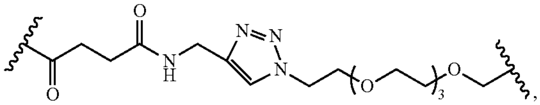, and
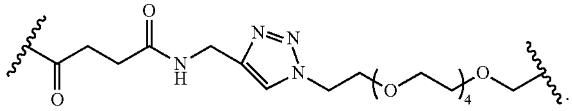.
In certain embodiments Linker$^A$ is selected from:
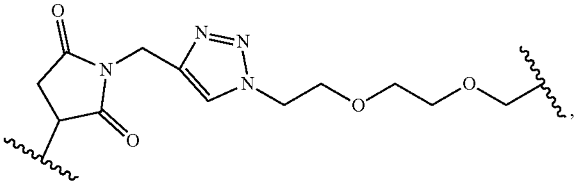,
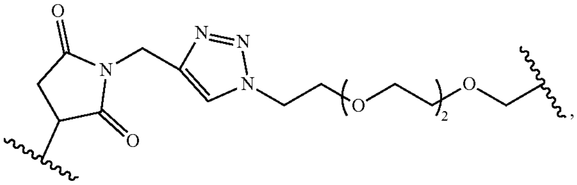,
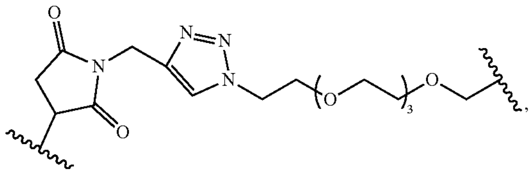, and
-continued
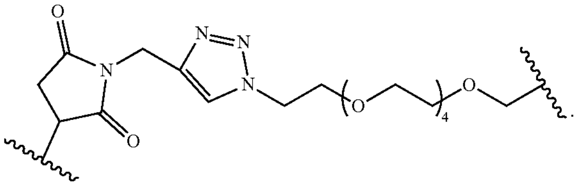.
In certain embodiments Linker$^A$ is selected from:
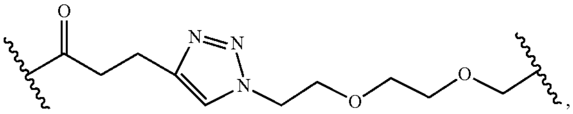,
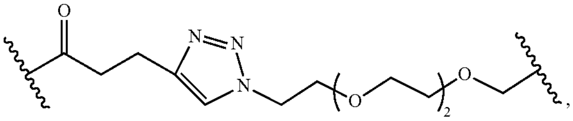,
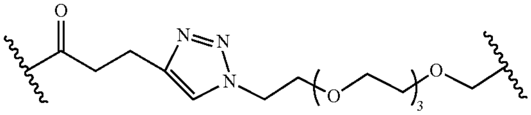 and
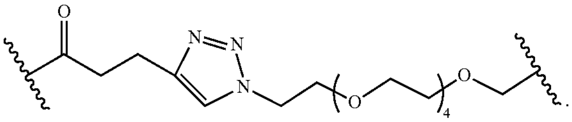.
In certain embodiments Linker$^A$ is selected from:
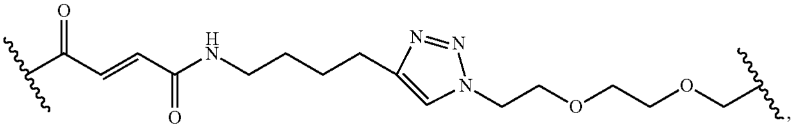,
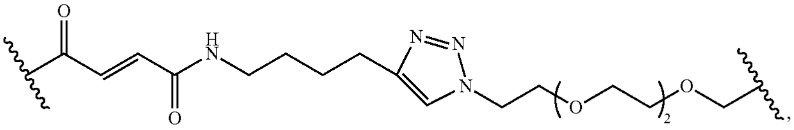,
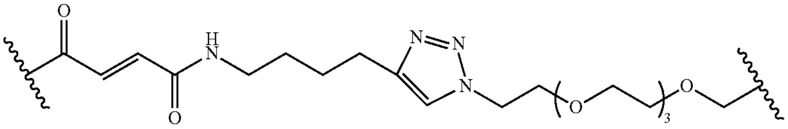 and
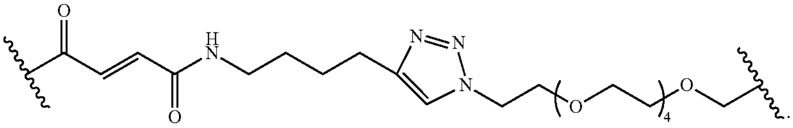.

In certain embodiments Linker$^A$ is selected from:
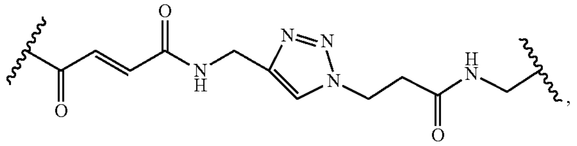
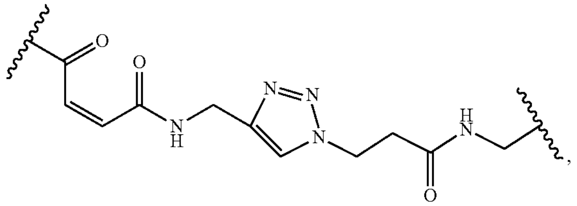
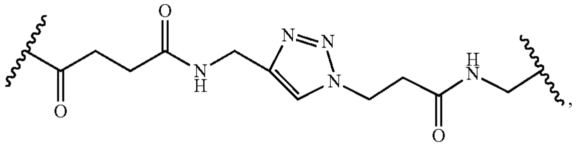
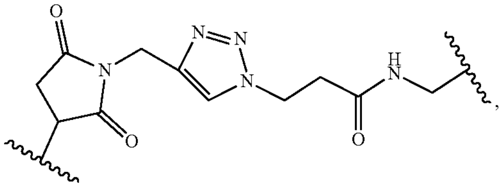
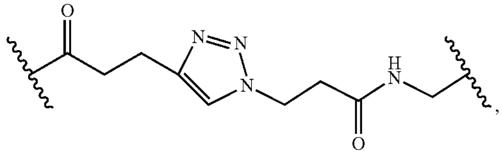
and
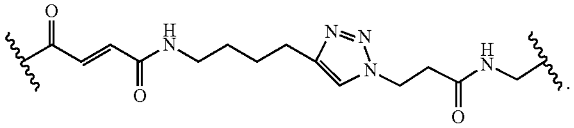
In certain embodiments Linker$^A$ is selected from:
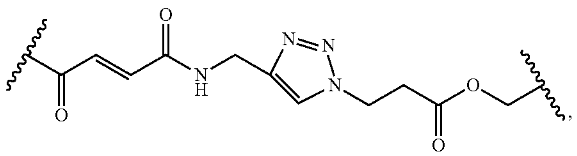
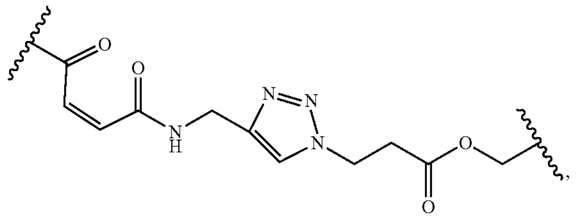
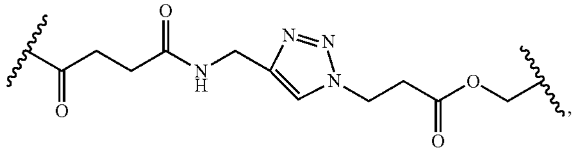
-continued
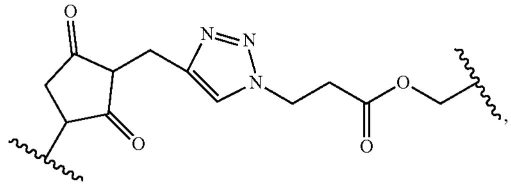
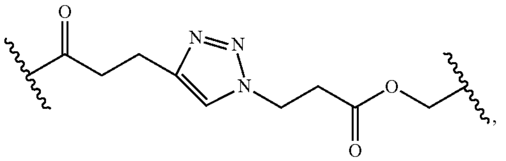
and
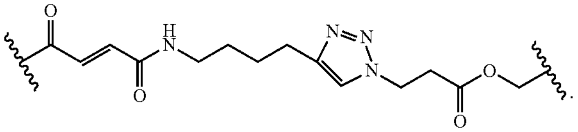
In certain embodiments, the Linker$^B$ is selected from
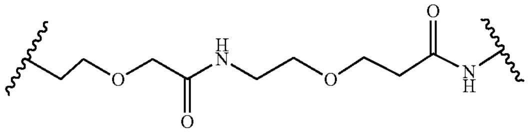
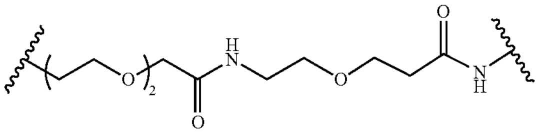
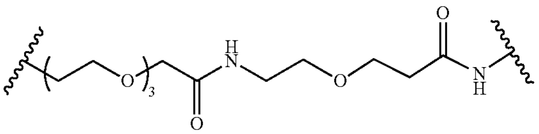
and
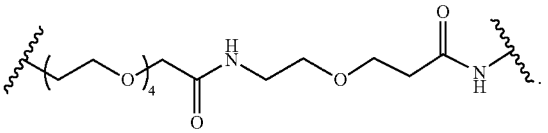
In certain embodiments, the Linker$^B$ is selected from
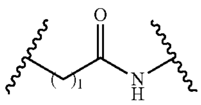
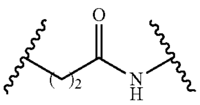
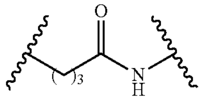
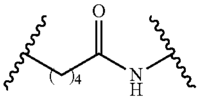
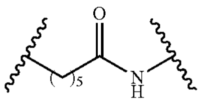
and
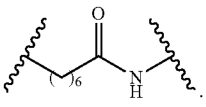

In certain embodiments, the Linker$^B$ is selected from
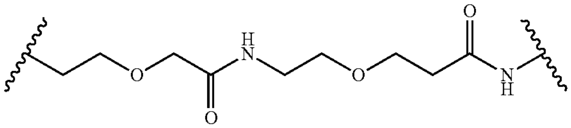
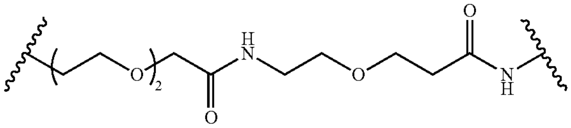
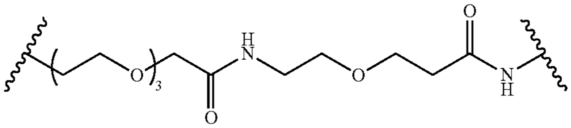
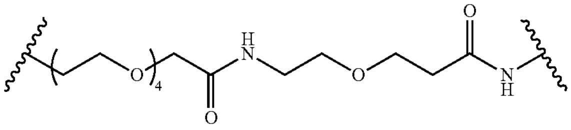
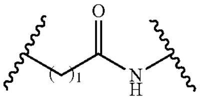 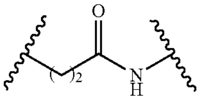
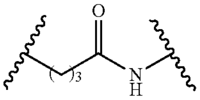 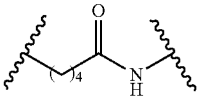
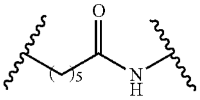 and 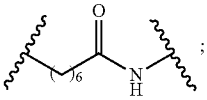 ;
wherein each is optionally substituted with 1, 2, 3, or 4 substituents substituent selected from $R^{21}$.
In certain embodiments Linker$^B$ is selected from:
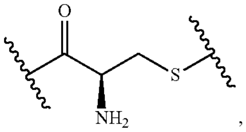 , 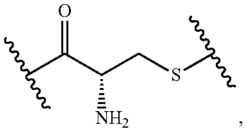 ,
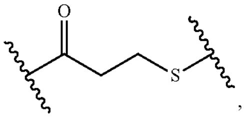 , 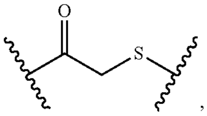 ,
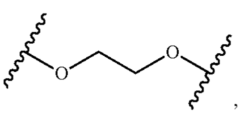 , 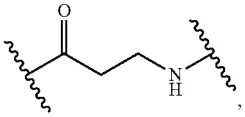 ,
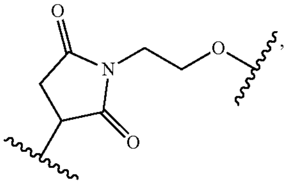 ,
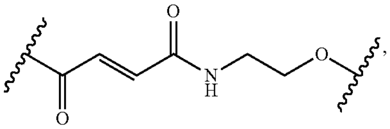 ,
-continued
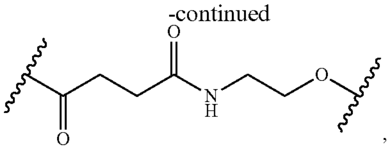 , and
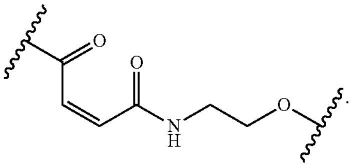 .
In certain embodiments Linker$^B$ is selected from:
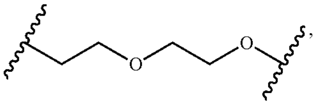 ,
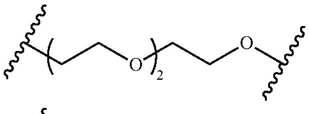 ,
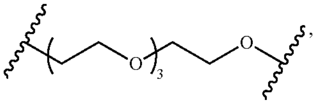 ,
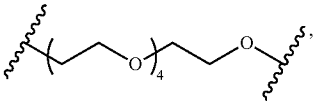 , and
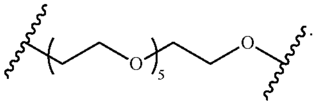 .
In certain embodiments Linker$^B$ is selected from:
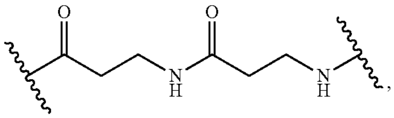 ,
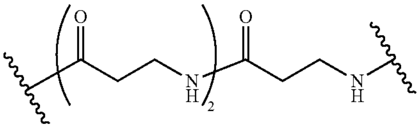 ,
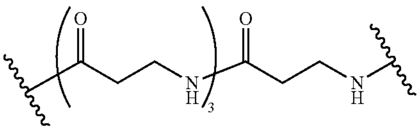 ,
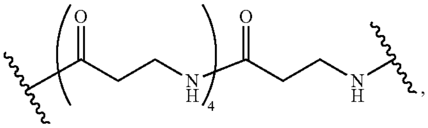 , and
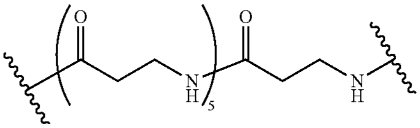 .

In certain embodiments $Linker^B$ is selected from:
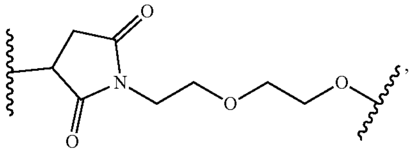
,
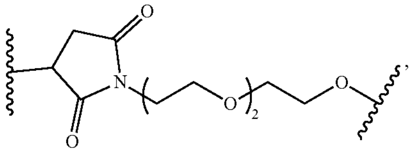
,
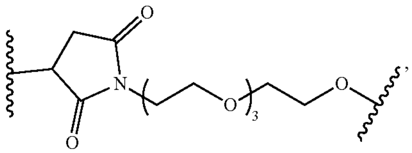
,
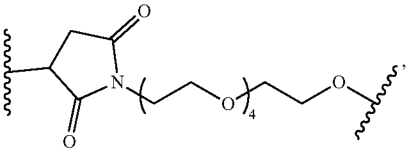
, and
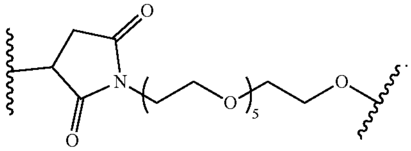
.
In certain embodiments $Linker^B$ is selected from:
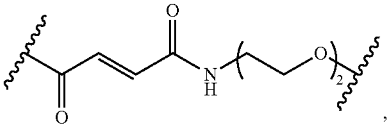
,
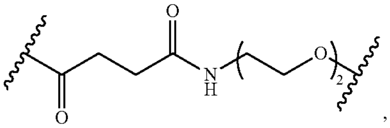
,
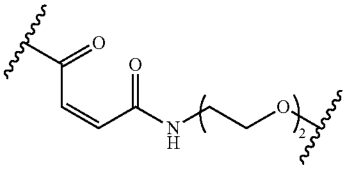
,
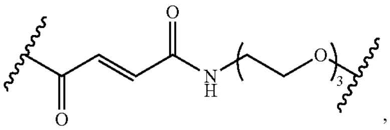
,
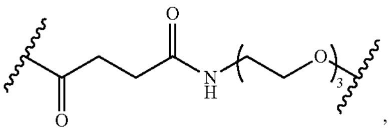
,
-continued
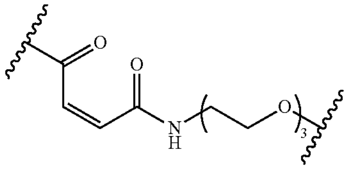
,
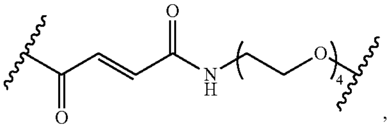
,
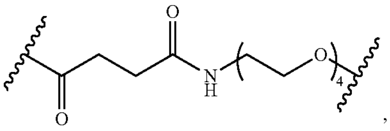
, and
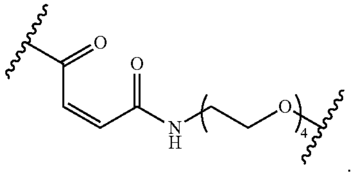
.
In certain embodiments $Linker^B$ is selected from:
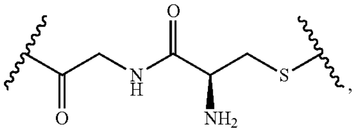
,
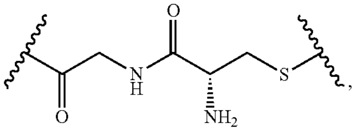
,
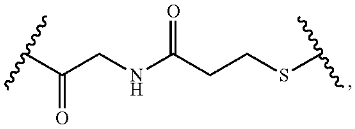
,
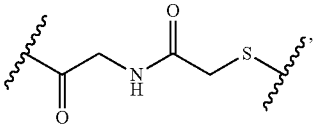
,
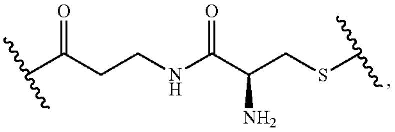
,
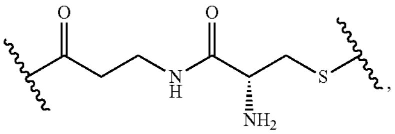
,
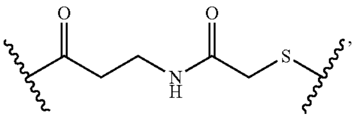
, and -continued
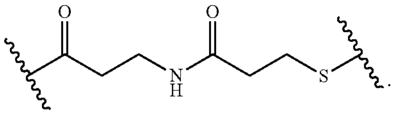
.
In certain embodiments Linker$^B$ is selected from:
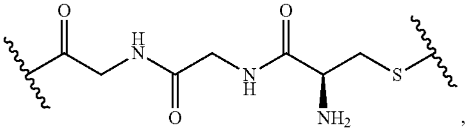
,
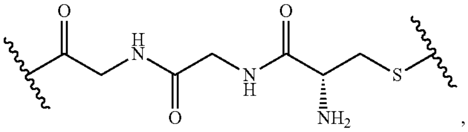
,
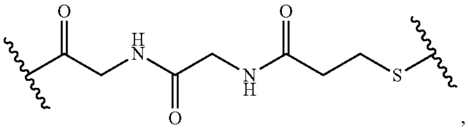
,
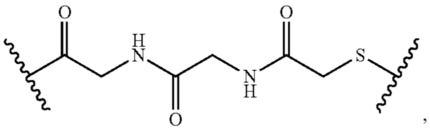
,
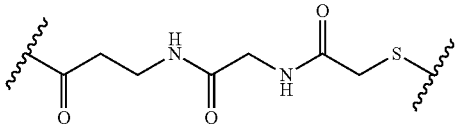
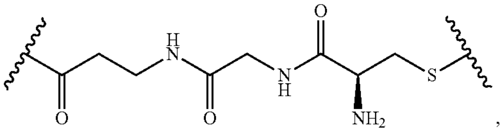
,
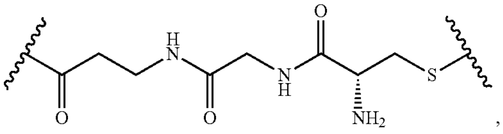
,
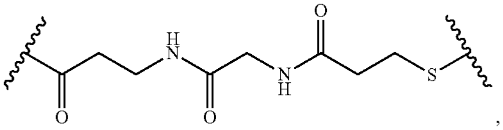
,
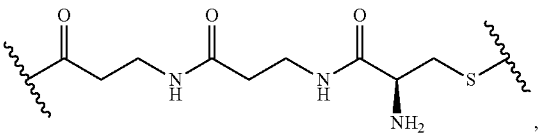
,
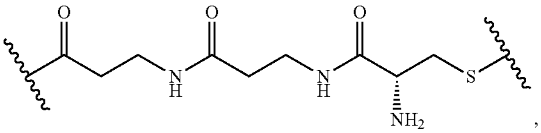
,
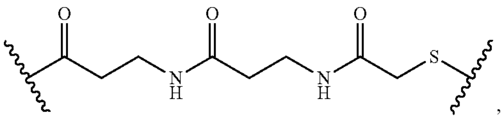
, and
-continued
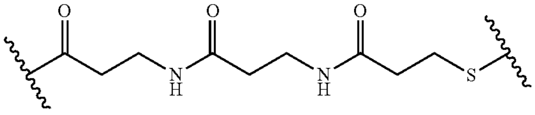
.
In certain embodiments Linker$^B$ is selected from:
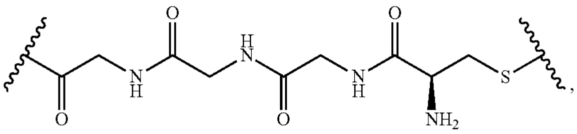
,
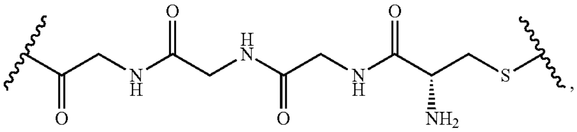
,
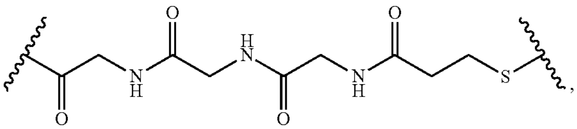
,
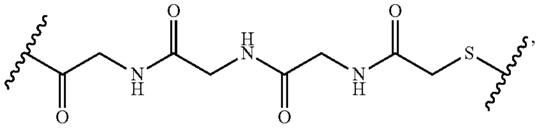
,
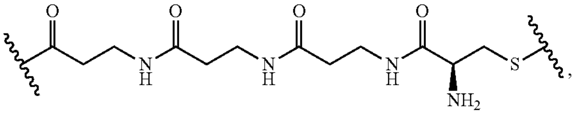
,
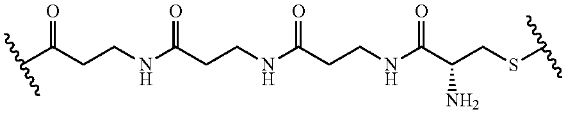
,
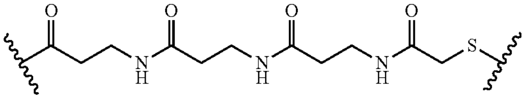
, and
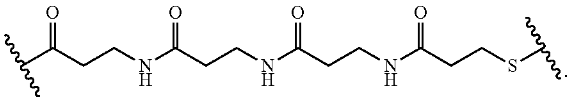
.
In certain embodiments Linker$^B$-Linker$^A$ is selected from:
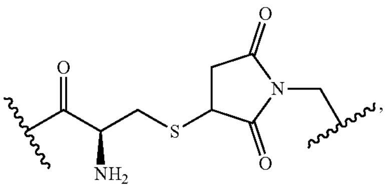
,
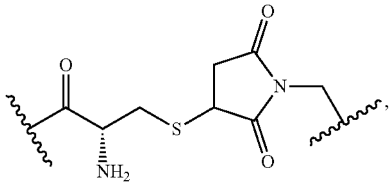
, and -continued
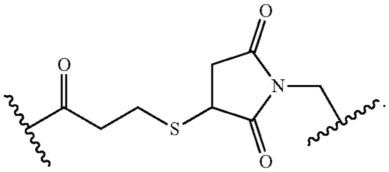
In certain embodiments Linker$^B$-Linker$^A$ is selected from:
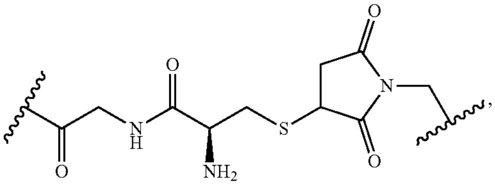
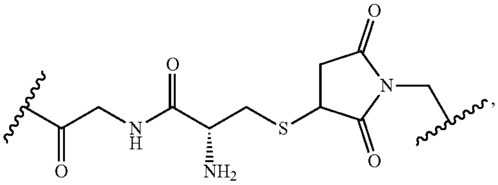
and
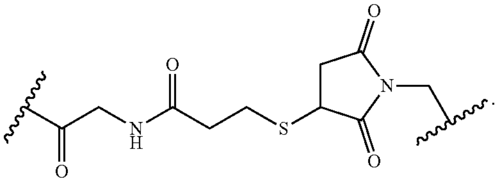
In certain embodiments, the Linker$^C$ is selected from
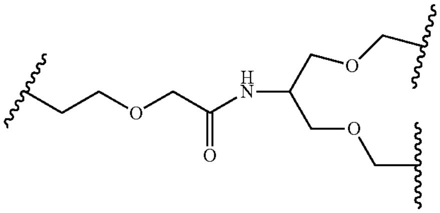
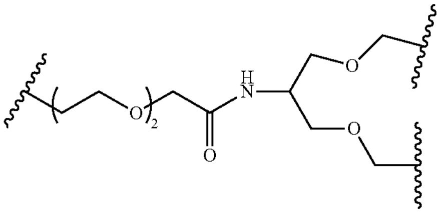
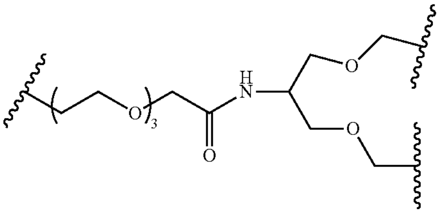
and
-continued
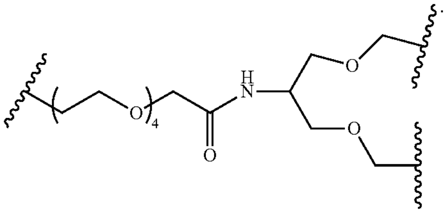
In certain embodiments, the Linker$^C$ is selected from
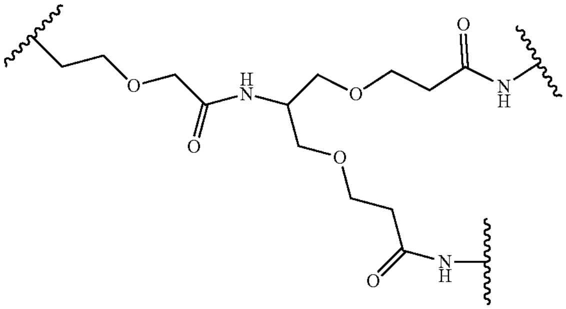
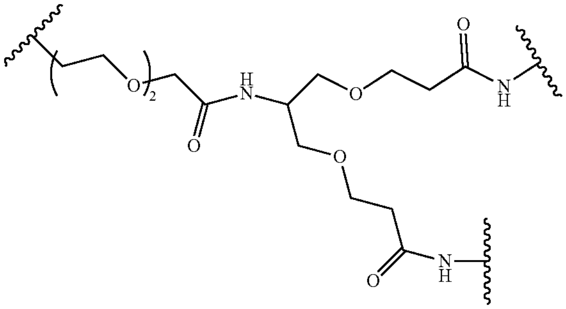
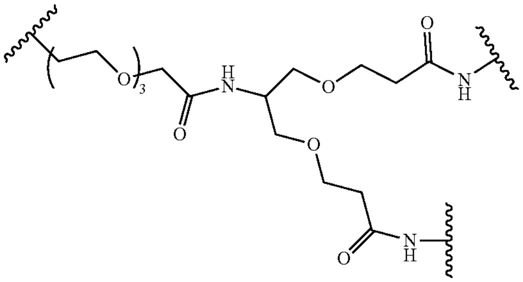
and
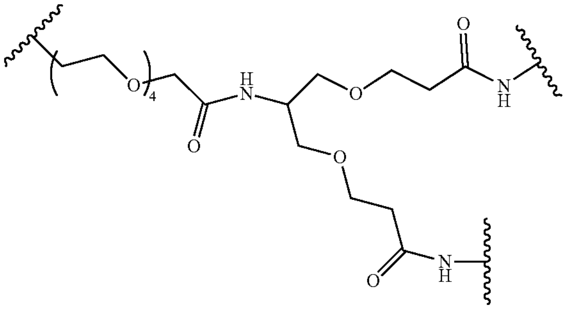

In certain embodiments, the Linker$^C$ is selected from
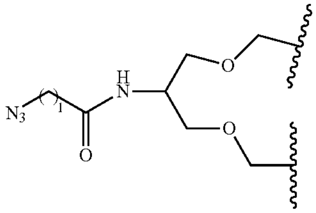
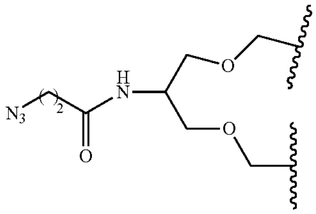
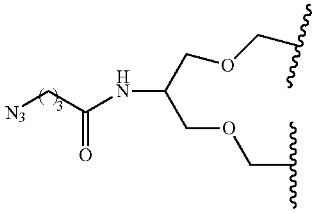
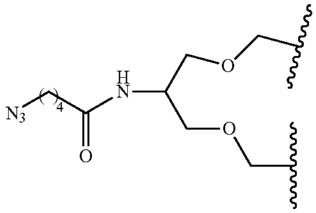
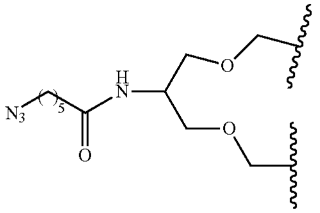
and
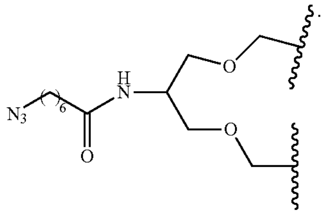
.
In certain embodiments, the Linker$^C$ is selected from
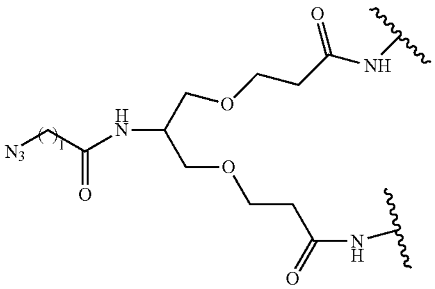
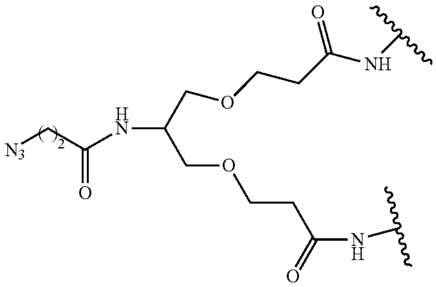
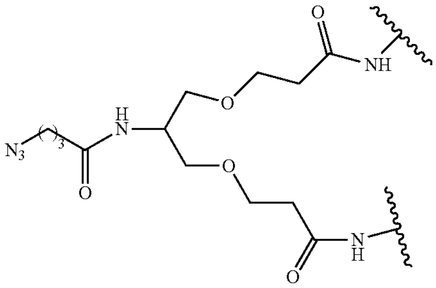
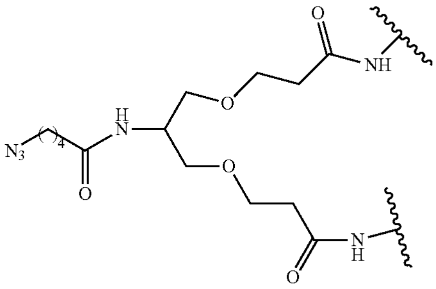
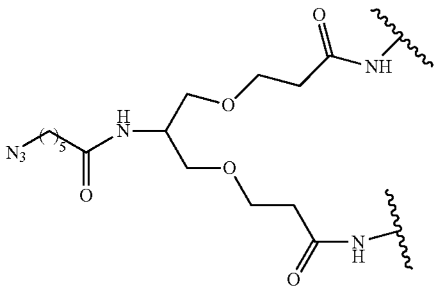
and -continued
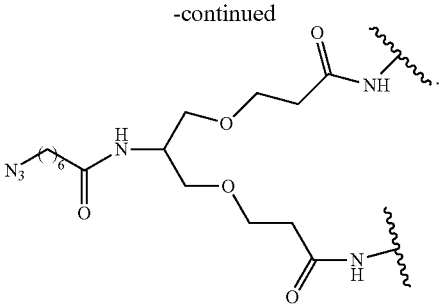
In certain embodiments, the Linker$^C$ is selected from
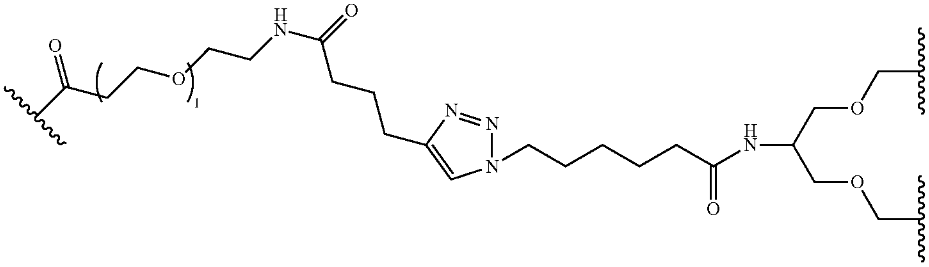
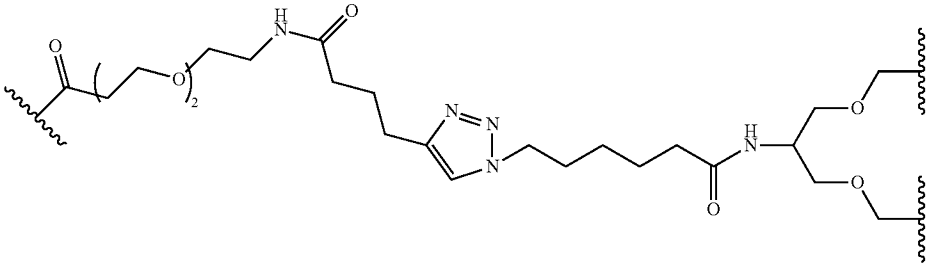
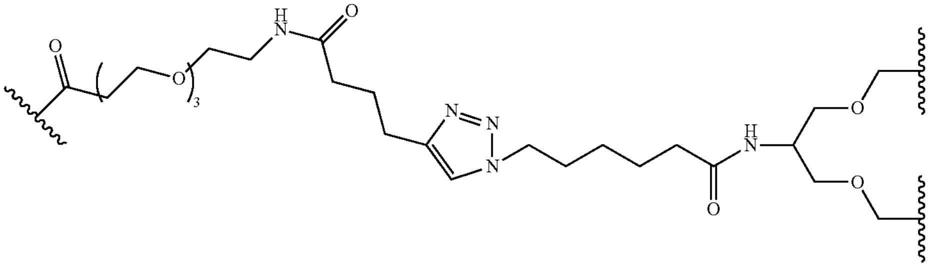
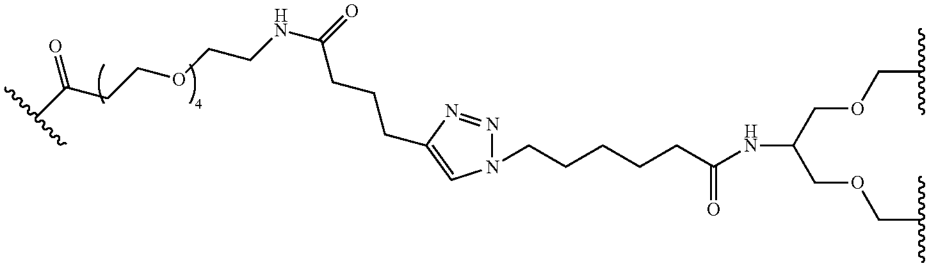
and -continued
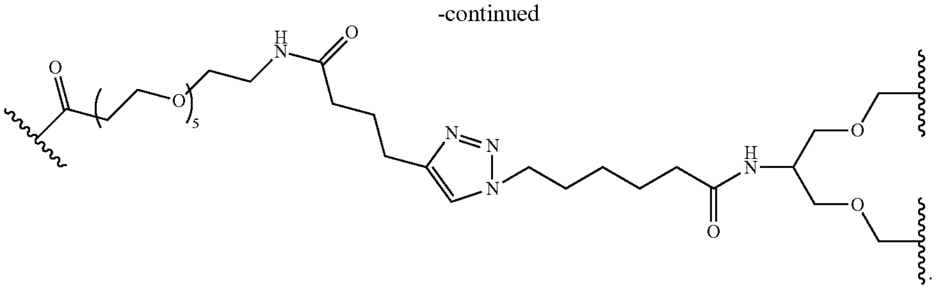
In certain embodiments, the Linker$^C$, is selected from
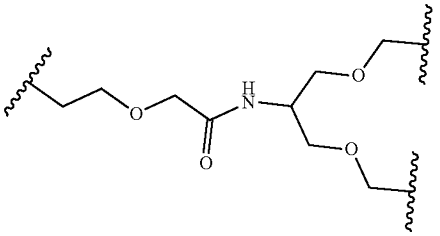
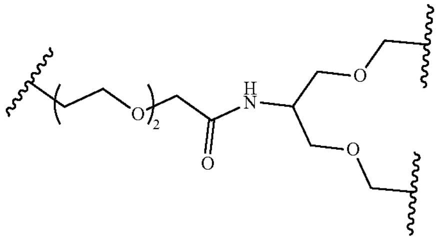
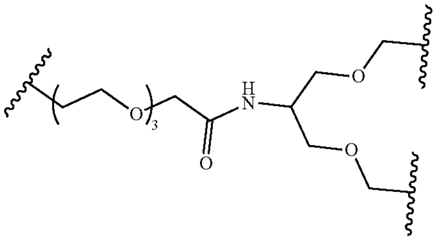
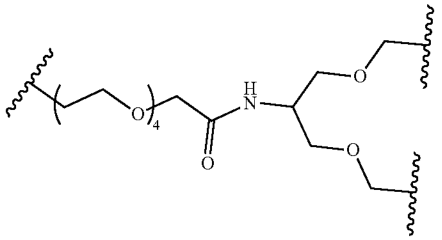
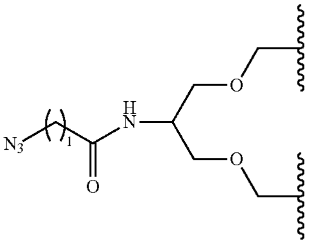
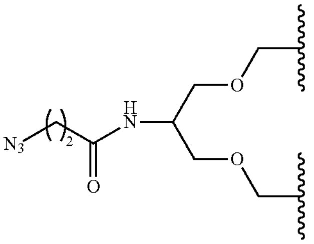
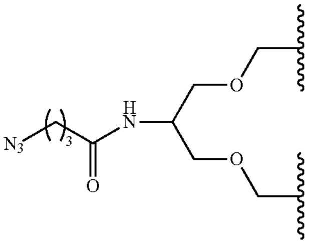
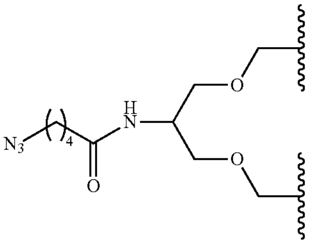
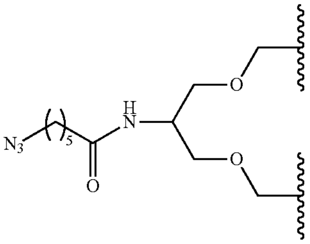
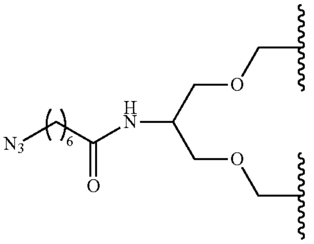

-continued
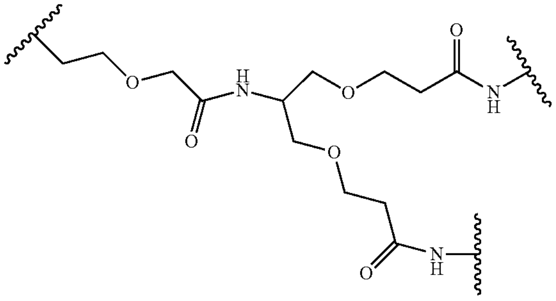
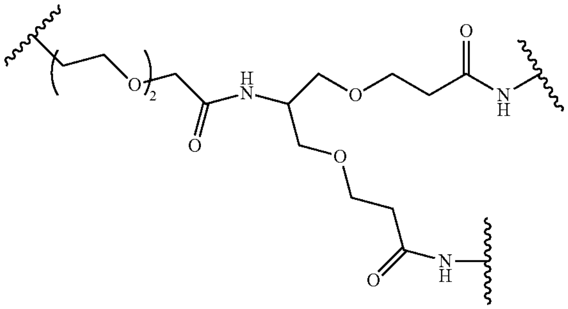
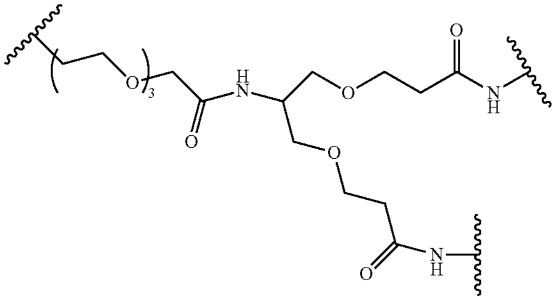
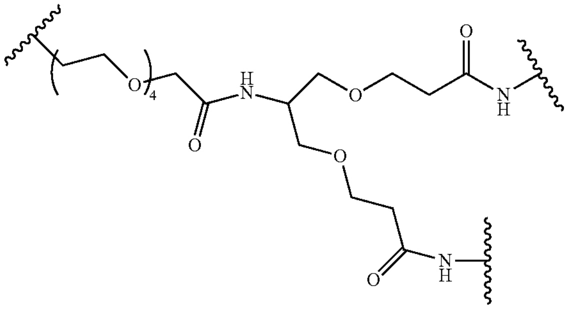
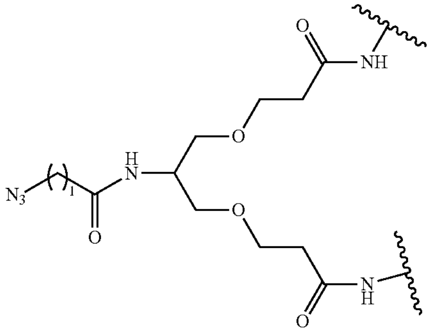
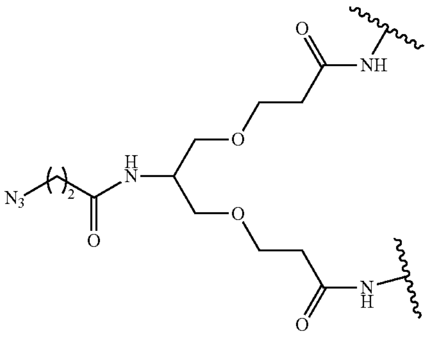
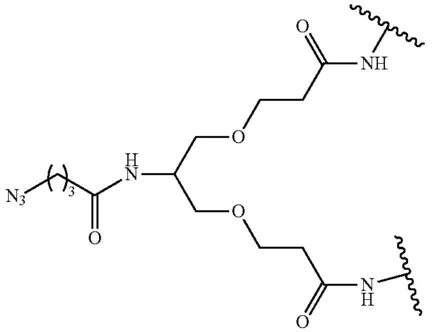
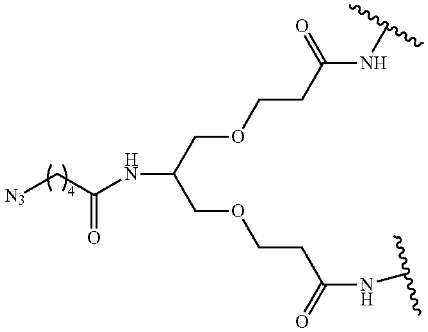
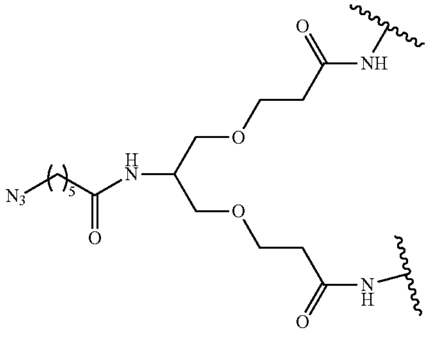
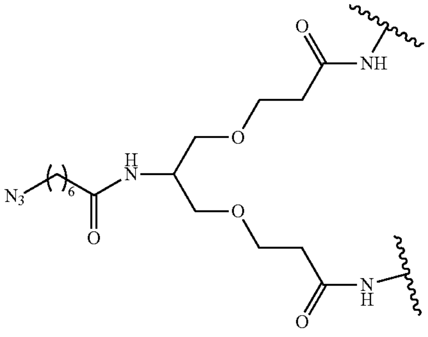

-continued
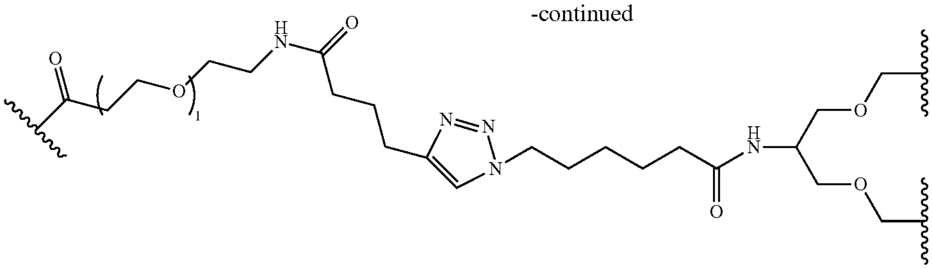
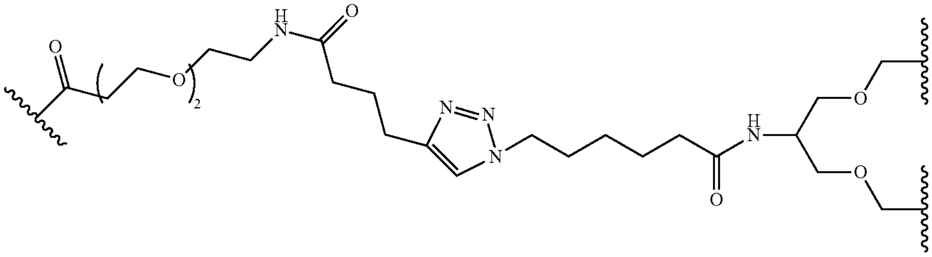
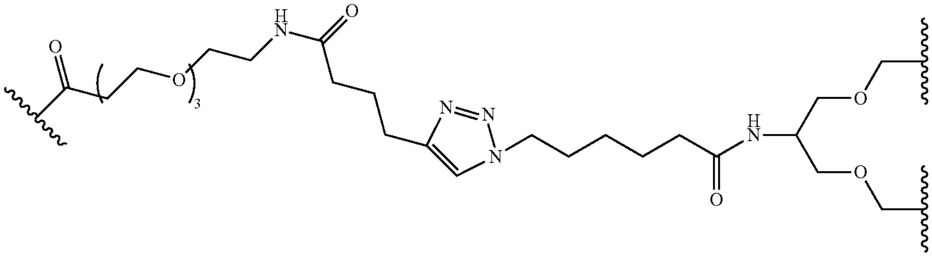
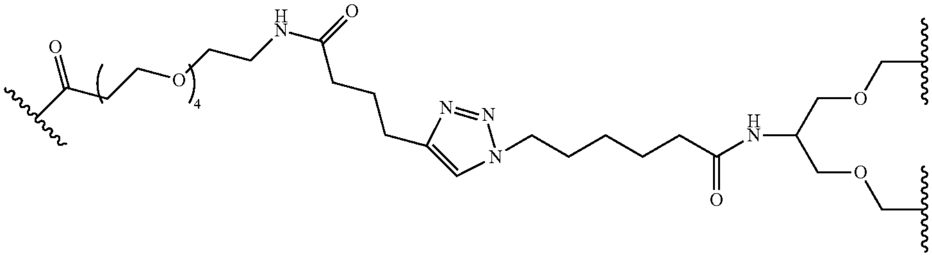
and
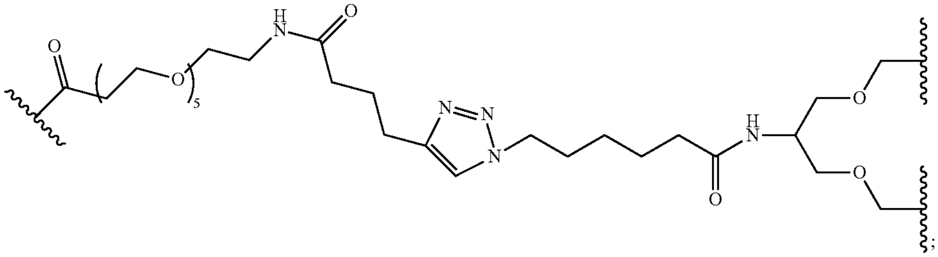
;
wherein each is optionally substituted with 1, 2, 3, or 4 substituents substituent selected from $R^{21}$.
In certain embodiments Linker$^C$, is selected from:
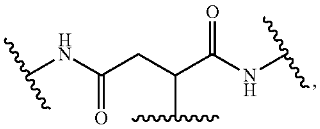
,
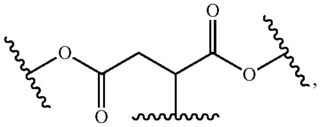
,
-continued
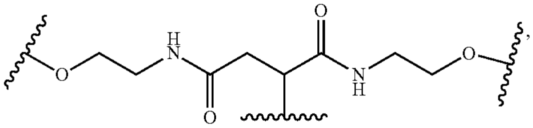
,
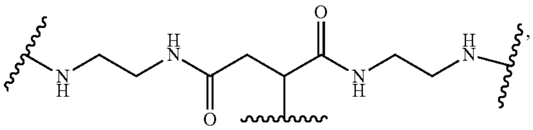
, -continued
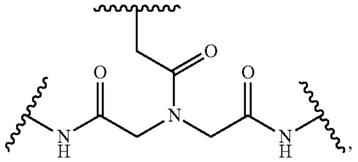
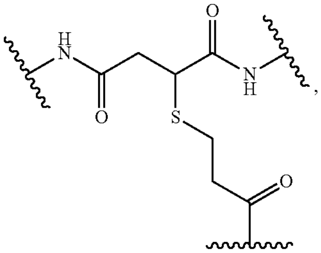
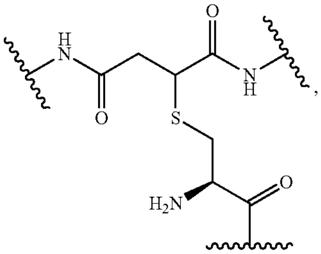
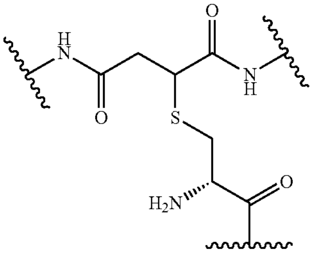
, and
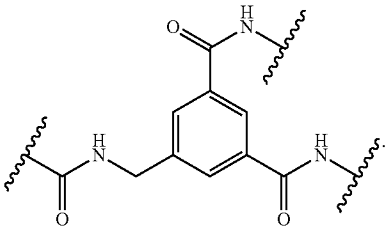
In certain embodiments Linker$^C$, is selected from:
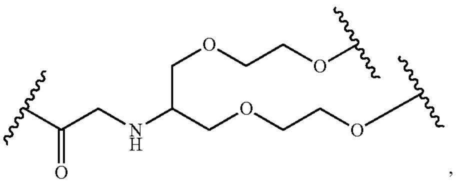
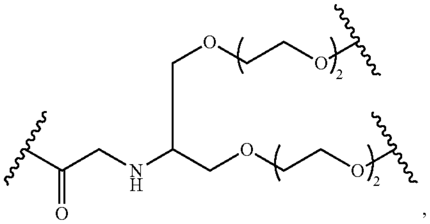
-continued
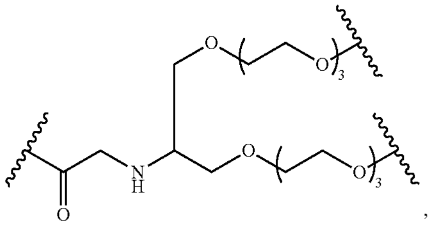
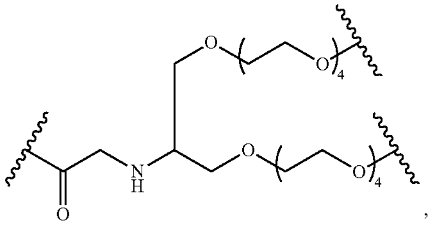
, and
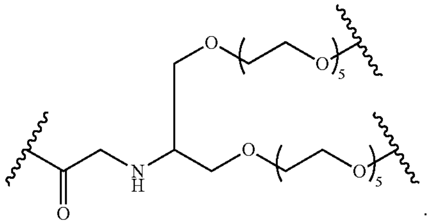
In certain embodiments Linker$^C$ is selected from:
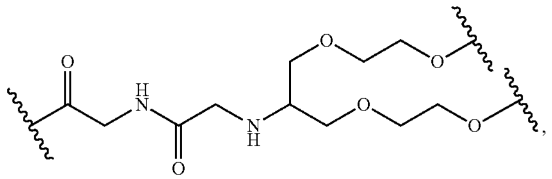
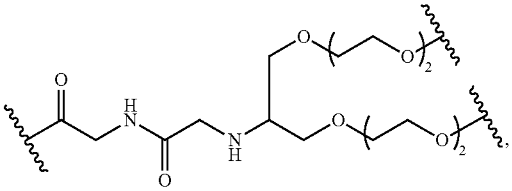
, and
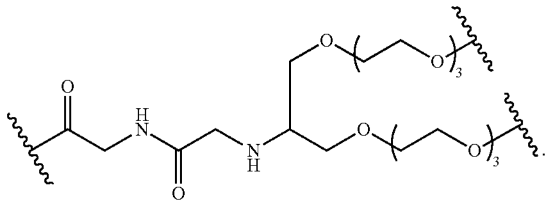
In certain embodiments Linker$^C$ is selected from:
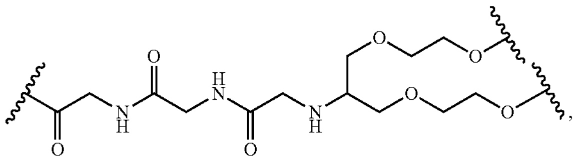

-continued
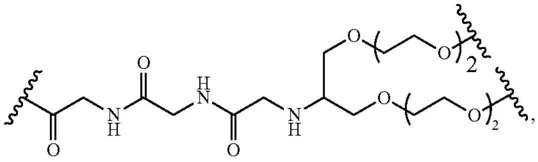
, and
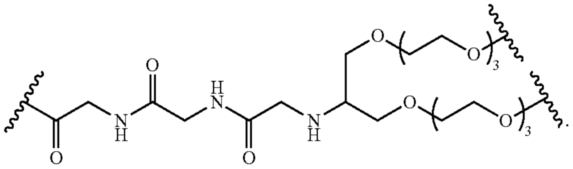
.
In certain embodiments $Linker^C$ is selected from:
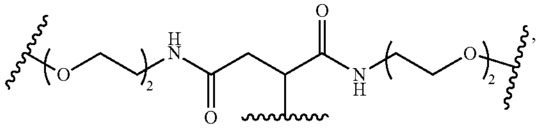
,
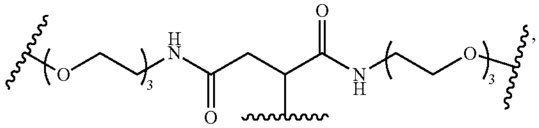
,
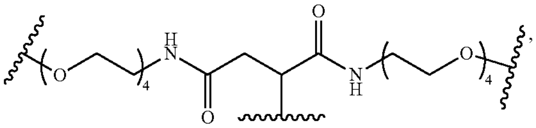
, and
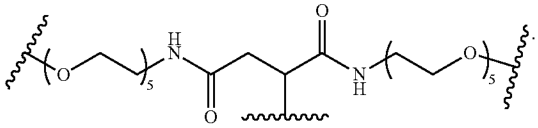
.
In certain embodiments $Linker^C$ is selected from:
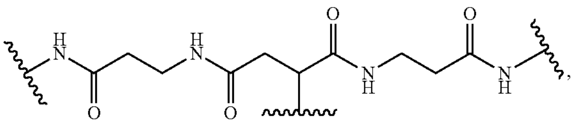
,
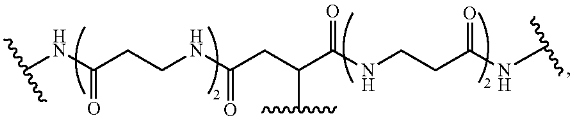
,
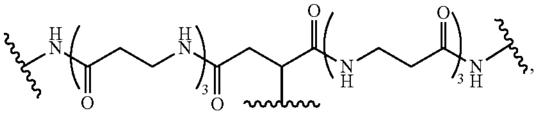
, and
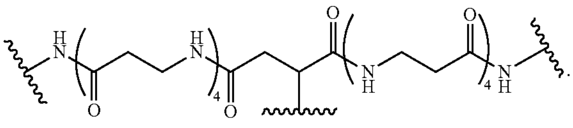
.
In certain embodiments $Linker^C$, is selected from:
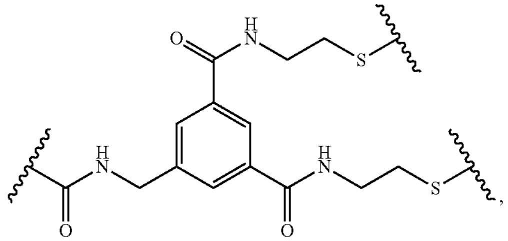
,
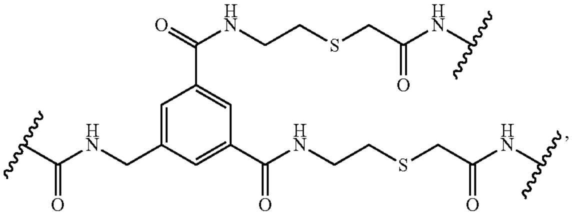
,
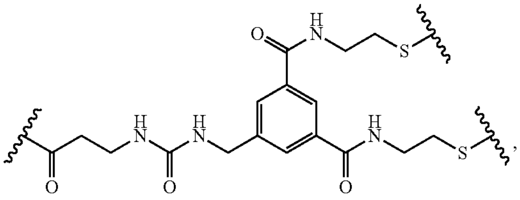
, and
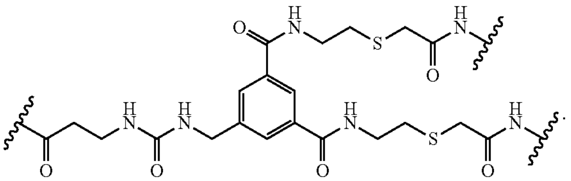
.
In certain embodiments $Linker^C$-$(Linker^A)_2$ is selected from:
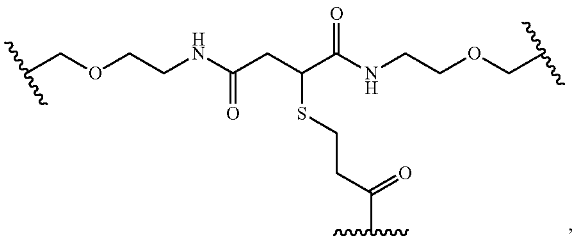
,
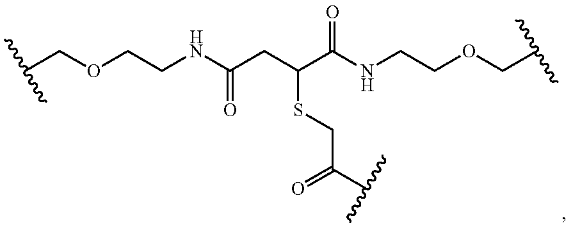
, -continued
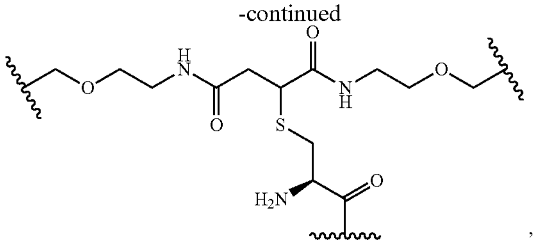
, and
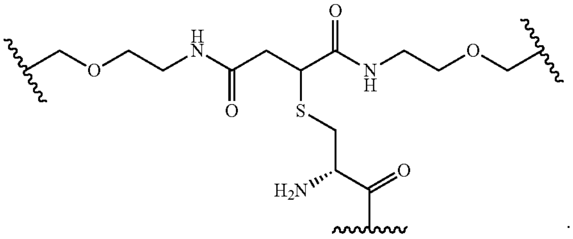
.
In certain embodiments Linker$^{C}$-(Linker$^{A}$)$_2$ is selected from:
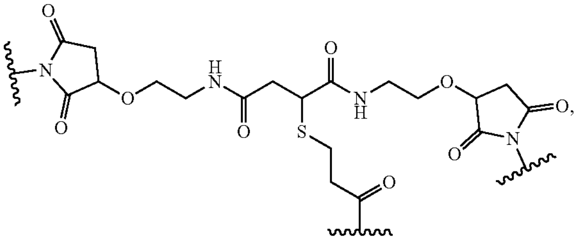
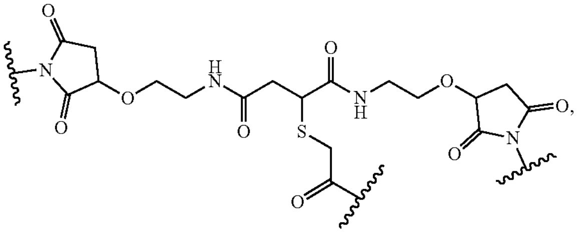
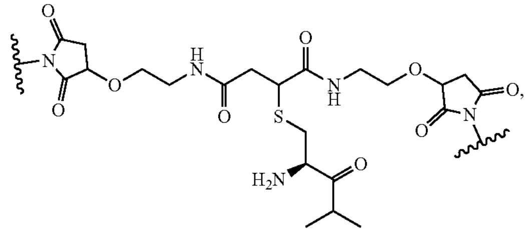
and
-continued
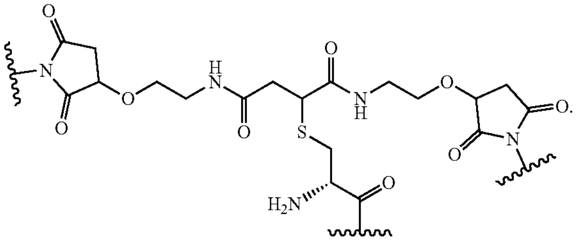
In certain embodiments Linker$^{C}$-(Linker$^{A}$)$_2$ is selected from:
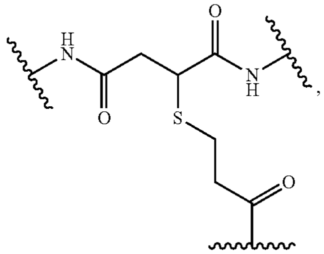
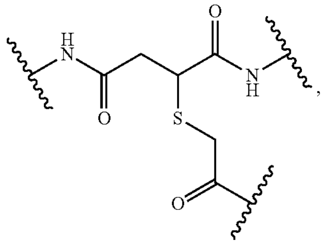
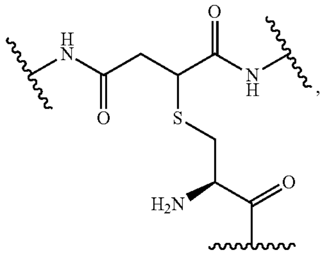
, and
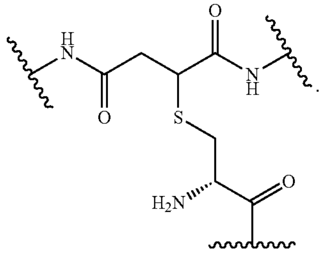

In certain embodiments $Linker^C$-$(Linker^A)_2$ is selected from:
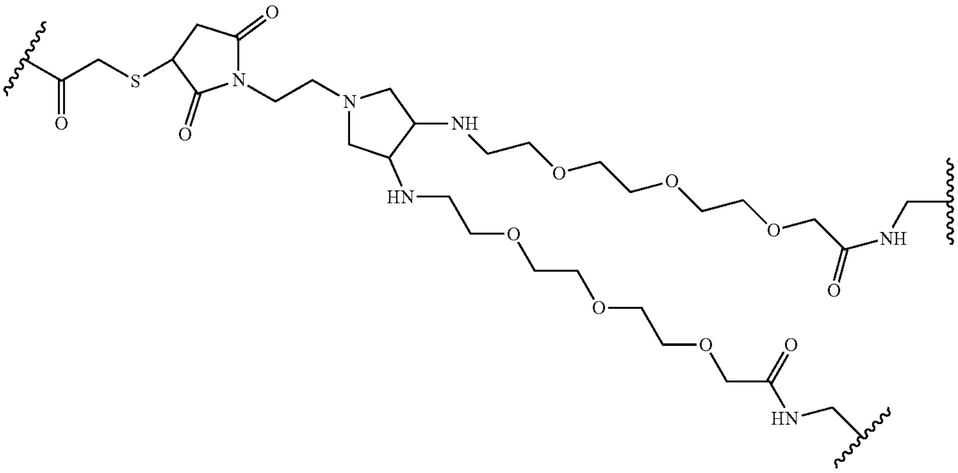
,
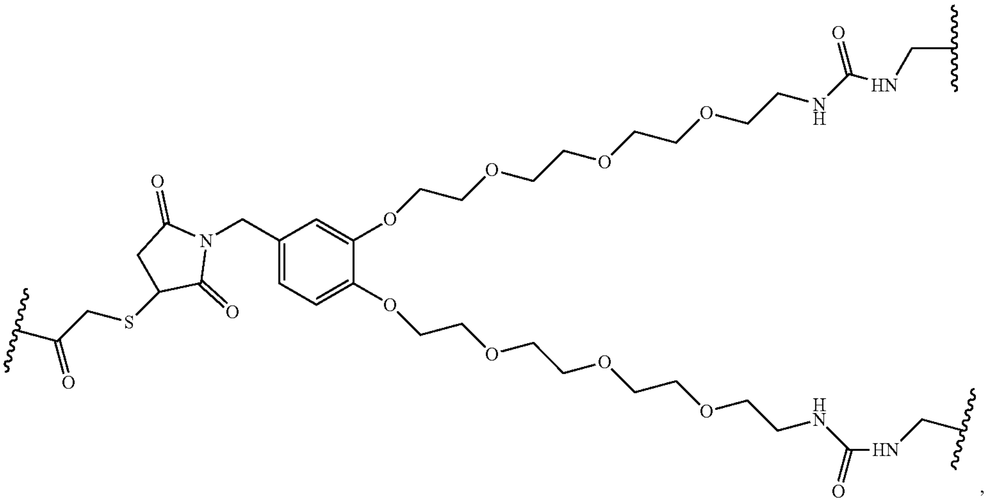
,
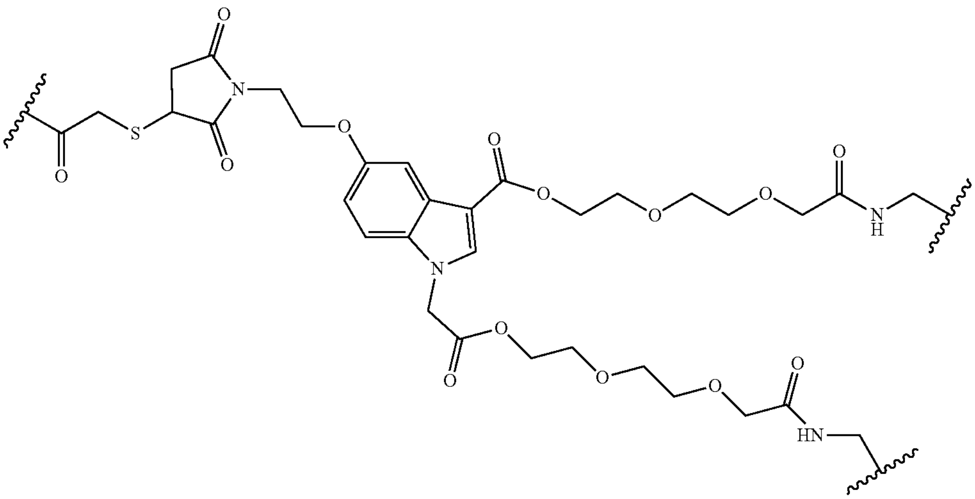
, and -continued
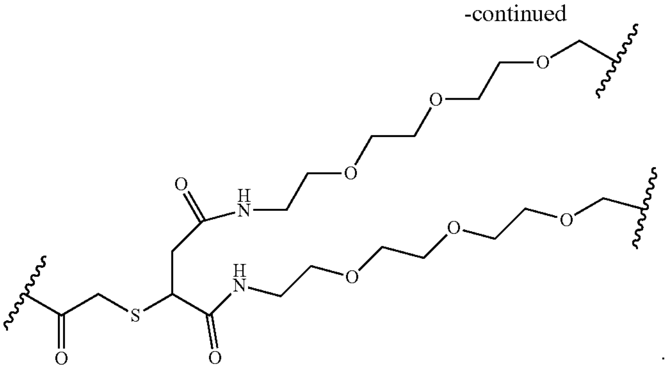
In certain embodiments, the Linker$^D$ is selected from
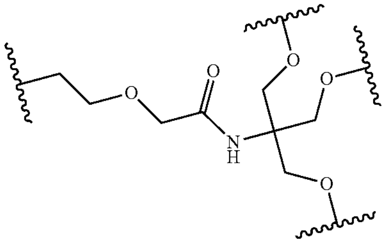
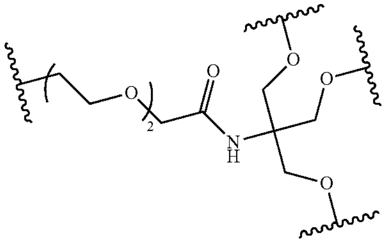
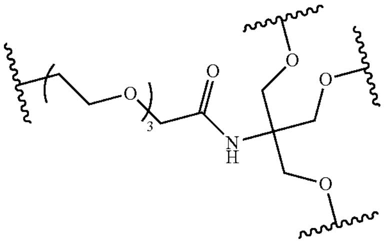
and
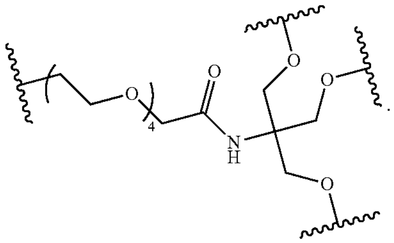
.
In certain embodiments, the Linker$^D$ is selected from
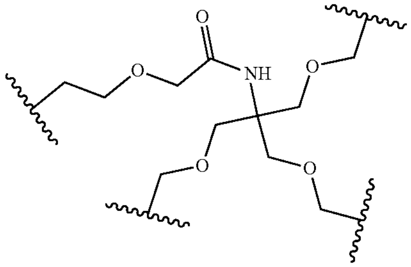
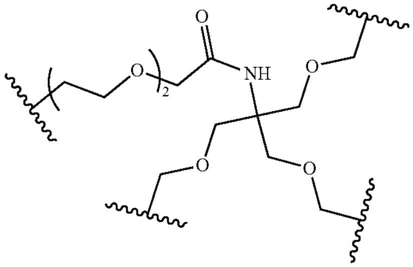
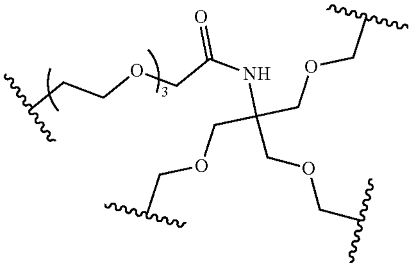
and
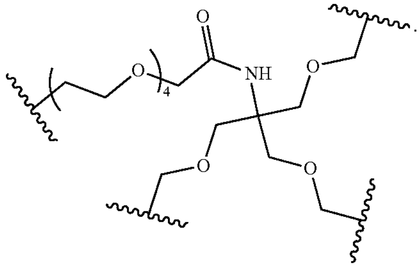
.

In certain embodiments the Linker$^D$ is selected from
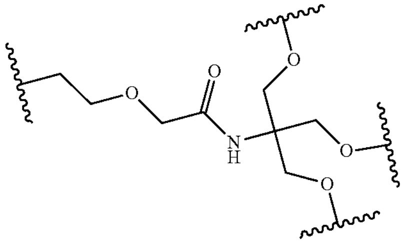
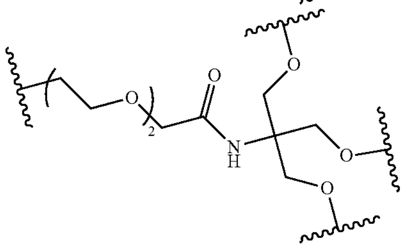
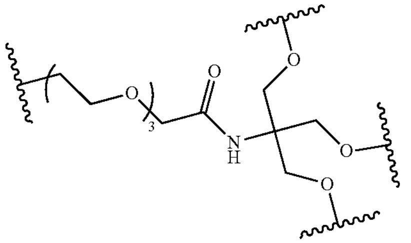
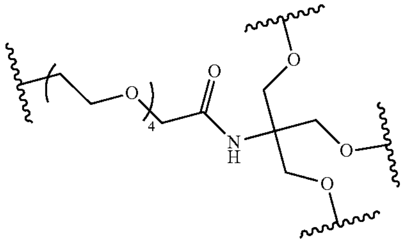
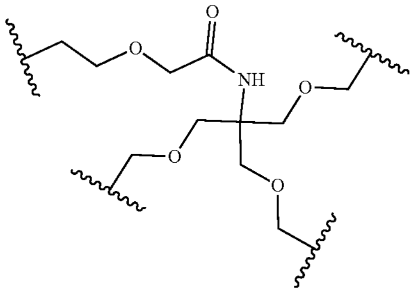
-continued
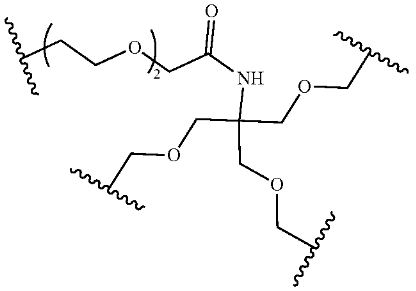
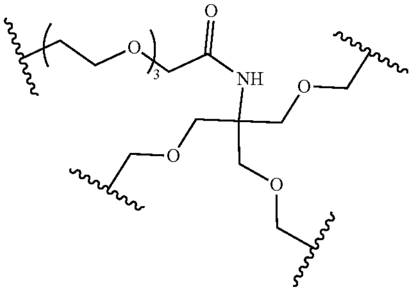
and
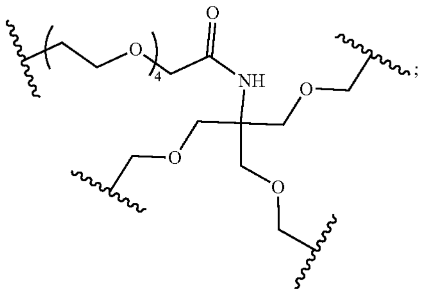
;
wherein each is optionally substituted with 1, 2, 3, or 4 substituents are selected from $R^{21}$.
In certain embodiments, Linker$^B$-(Linker$^A$) is selected from
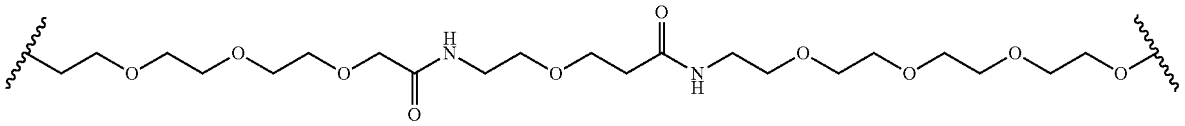
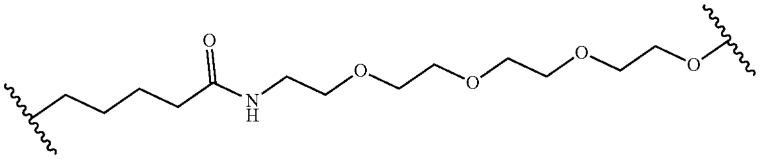

-continued
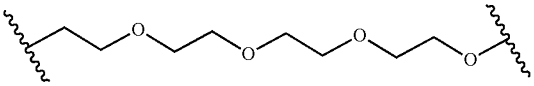
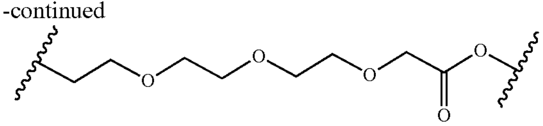
and
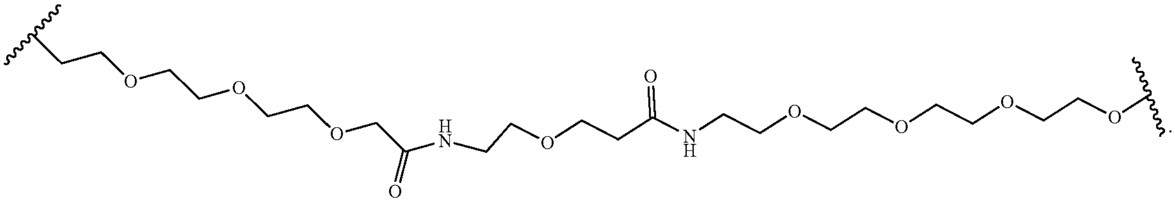
.
In certain embodiments, Linker$^C$-(Linker$^A$) is selected from
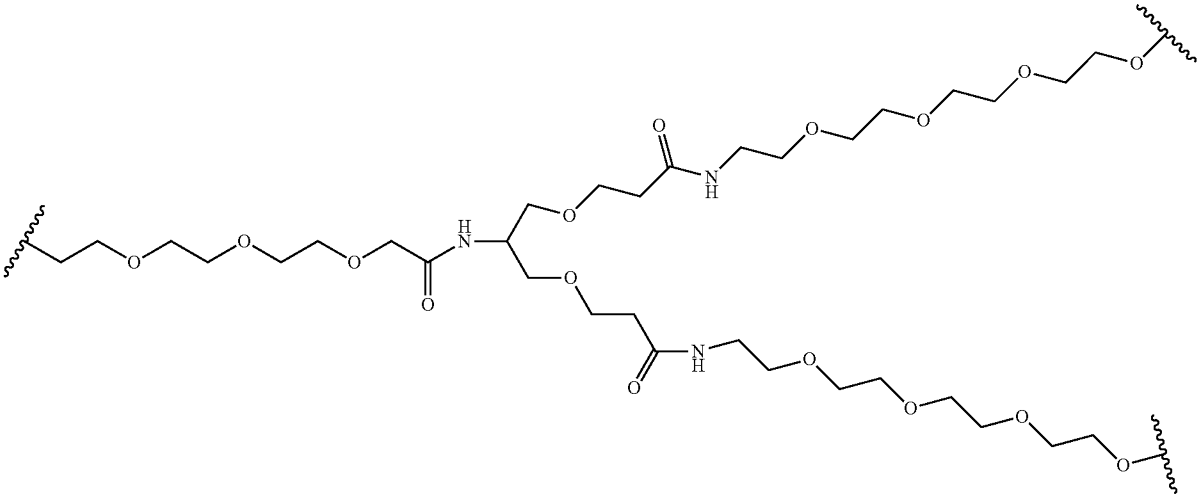
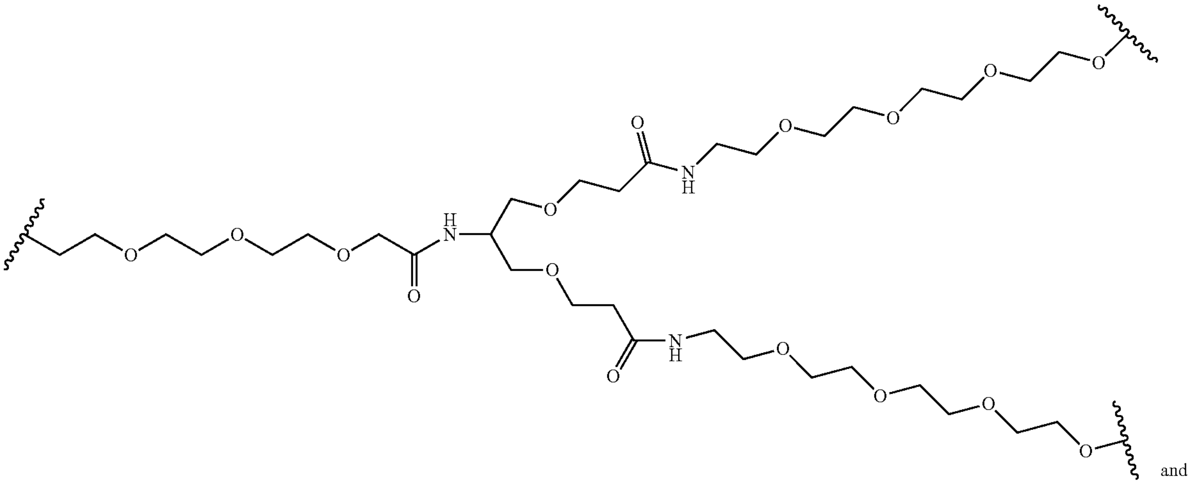
and -continued
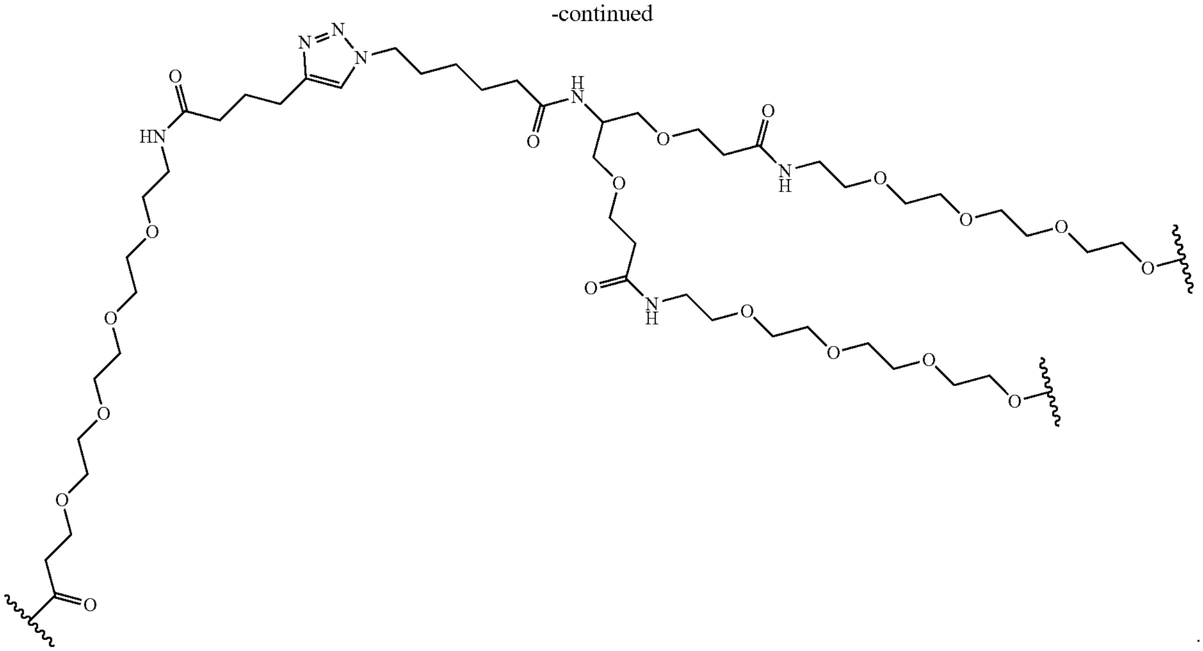
.
In certain embodiments, Linker$^D$-(Linker$^A$) is selected from
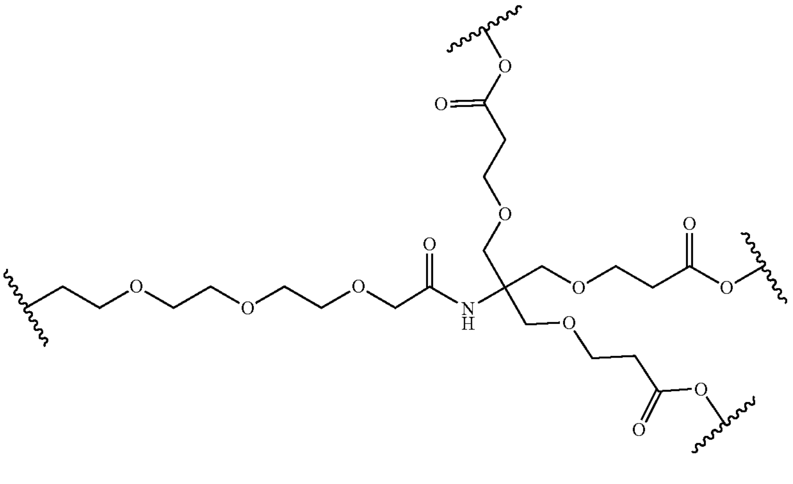
and -continued

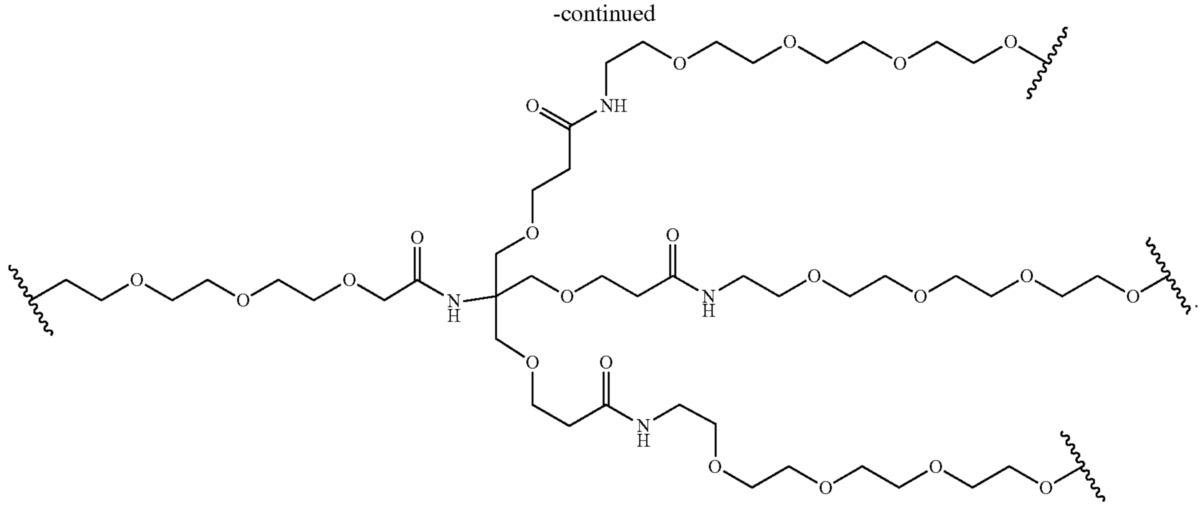

V. Compound Terminology

Compounds are described using standard nomenclature. Unless defined otherwise, all technical and scientific terms used herein have the same meaning as is commonly understood by one of skill in the art to which this invention belongs.

The compounds in any of the Formulas described herein include as separate embodiments enantiomers, diastereomers, tautomers, racemates, rotamers or mixtures thereof, as if each is specifically described, unless otherwise indicated or otherwise excluded by context.

The terms “a” and “an” do not denote a limitation of quantity, but rather denote the presence of at least one of the referenced item. The term “or” means “and/or”. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., “such as”), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

The present invention includes compounds with at least one desired isotopic substitution of an atom, at an amount above the natural abundance of the isotope, i.e., enriched.

Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{17}O$, $^{18}O$, $^{18}F$ $^{31}P$, $^{32}P$, $^{35}S$, $^{36}Cl$, and $^{125}I$ respectively. In one embodiment, isotopically labelled compounds can be used in metabolic studies (with, for example $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. For example, a $^{18}F$ labeled compound may be desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium (H) and tritium (3H) may optionally be used anywhere in described structures that achieves the desired result. Alternatively, or in addition, isotopes of carbon, e.g., $^{13}C$ and $^{14}C$, may be used. In one embodiment, the isotopic substitution is replacing hydrogen with a deuterium at one or more locations on the molecule to improve the performance of the drug, for example, the pharmacodynamics, pharmacokinetics, biodistribution, half-life, stability, AUC, Tmax, Cmax, etc. For example, the deuterium can be bound to carbon in a location of bond breakage during metabolism (an $\alpha$-deuterium kinetic isotope effect) or next to or near the site of bond breakage (a $\beta$-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95 or 99% or more enriched in an isotope at any location of interest. In certain embodiments deuterium is 80, 85, 90, 95 or 99% enriched at a desired location. Unless otherwise stated, the enrichment at any point is above natural abundance, and in an embodiment is enough to alter a detectable property of the drug in a human.

In one embodiment, the substitution of a hydrogen atom for a deuterium atom occurs within any variable group. For example, when any variable group is, or contain for example through substitution, methyl, ethyl, or methoxy, the alkyl residue may be deuterated (in nonlimiting embodiments, $CDH_2$, $CD_2H$, $CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, a variable group has a “'” or an “a” designation, which in one embodiment can be deuterated. In certain other embodiments, when two substituents of the central core ring are combined to form a cyclopropyl ring, the unsubstituted methylene carbon may be deuterated.

The compound of the present invention may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a compound of the invention and water. Pharmaceutically acceptable solvates in accordance with the invention include those wherein the solvent of crystallization may be isotopically substituted, e.g. $D_2O$, $d_6$-acetone, $d_6$-DMSO. A solvate can be in a liquid or solid form.

A dash ("-") that is not between two letters or symbols is used to indicate a point of attachment for a substituent. For example, —(C═O)$NH_2$ is attached through carbon of the keto (C═O) group.

The term "substituted", as used herein, means that any one or more hydrogens on the designated atom or group is replaced with a moiety selected from the indicated group, provided that the designated atom's normal valence is not exceeded and the resulting compound is stable. For example, when the substituent is oxo (i.e., ═O) then two hydrogens on the atom are replaced. For example a pyridyl group substituted by oxo is a pyridone. Combinations of substituents and/or variables are permissible only if such combinations result in stable compounds or useful synthetic intermediates.

"Alkyl" is a branched, straight chain, or cyclic saturated aliphatic hydrocarbon group. In one embodiment, the alkyl contains from 1 to about 12 carbon atoms, more generally from 1 to about 6 carbon atoms, from 1 to about 4 carbon atoms, or from 1 to 3 carbon atoms. In one embodiment, the alkyl contains from 1 to about 8 carbon atoms. In certain embodiments, the alkyl is $C_1$-$C_2$, $C_1$-$C_3$, $C_1$-$C_4$, $C_1$-$C_5$ or $C_1$-$C_6$. The specified ranges as used herein indicate an alkyl group which is considered to explicitly disclose as individual species each member of the range described as a unique species. For example, the term $C_1$-$C_6$ alkyl as used herein indicates a straight or branched alkyl group having from 1, 2, 3, 4, 5, or 6 carbon atoms and also a carbocyclic alkyl group of 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. When $C_0$-$C_n$ alkyl is used herein in conjunction with another group, for example, ($C_3$-$C_7$cycloalkyl)$C_0$-$C_4$ alkyl, or —$C_0$-$C_4$ alkyl ($C_3$-$C_7$cycloalkyl), the indicated group, in this case cycloalkyl, is either directly bound by a single covalent bond ($C_0$ alkyl), or attached by an alkyl chain in this case 1, 2, 3, or 4 carbon atoms. Alkyls can also be attached via other groups such as heteroatoms as in —O—$C_0$-$C_4$ alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, 2,3-dimethylbutane, and hexyl.

When a term is used that includes "alk" it should be understood that "cycloalkyl" or "carbocyclic" can be considered part of the definition, unless unambiguously excluded by the context. For example and without limitation, the terms alkyl, alkenyl, alkynyl, alkoxy, alkanoyl, alkenloxy, haloalkyl, etc. can all be considered to include the cyclic forms of alkyl, unless unambiguously excluded by context.

"Alkenyl" is a branched or straight chain aliphatic hydrocarbon group having one or more carbon-carbon double bonds that may occur at a stable point along the chain. Nonlimiting examples are $C_2$-$C_8$ alkenyl, $C_2$-$C_7$ alkenyl, $C_2$-$C_6$ alkenyl, $C_2$-$C_5$ alkenyl and $C_2$-$C_4$ alkenyl. The specified ranges as used herein indicate an alkenyl group having each member of the range described as an independent species, as described above for the alkyl moiety. Examples of alkenyl include, but are not limited to, ethenyl and propenyl.

"Alkynyl" is a branched or straight chain aliphatic hydrocarbon group having one or more carbon-carbon triple bonds that may occur at any stable point along the chain, for example, $C_2$-$C_8$ alkynyl or $C_2$-$C_6$alkynyl. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkoxy" is an alkyl group as defined above covalently bound through an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "alkylthio" or a "thioalkyl" group is an alkyl group as defined above with the indicated number of carbon atoms covalently bound through a sulfur bridge (—S—). In one embodiment, the alkoxy group is optionally substituted as described above.

"Haloalkyl" indicates both branched and straight-chain alkyl groups substituted with 1 or more halogen atoms, up to the maximum allowable number of halogen atoms. Examples of haloalkyl include, but are not limited to, trifluoromethyl, monofluoromethyl, difluoromethyl, 2-fluoroethyl, and penta-fluoroethyl.

"Aryl" indicates an aromatic group containing only carbon in the aromatic ring or rings. In one embodiment, the aryl group contains 1 to 3 separate or fused rings and is 6 to 14 or 18 ring atoms, without heteroatoms as ring members. The term "aryl" includes groups where a saturated or partially unsaturated carbocycle group is fused with an aromatic ring. The term "aryl" also includes groups where a saturated or partially unsaturated heterocycle group is fused with an aromatic ring so long as the attachment point is the aromatic ring. Such compounds may include aryl rings fused to a 4 to 7 or a 5 to 7-membered saturated or partially unsaturated cyclic group that optionally contains 1, 2 or 3 heteroatoms independently selected from N, O, B, P, Si and S, to form, for example, a 3,4-methylenedioxyphenyl group. Aryl groups include, for example, phenyl and naphthyl, including 1-naphthyl and 2-naphthyl. In one embodiment, aryl groups are pendant. An example of a pendant ring is a phenyl group substituted with a phenyl group.

The term "heterocycle" refers to saturated and partially saturated heteroatom-containing ring radicals, where the heteroatoms may be selected from N, S, and O. The term "heterocycle" includes monocyclic 3-12 membered rings, as well as bicyclic 5-16 membered ring systems (which can include fused, bridged, or spiro, bicyclic ring systems). It does not include rings containing —O—O—or —S—S— portions. Examples of saturated heterocycle groups include saturated 4- to 7-membered monocyclic groups containing 1 to 4 nitrogen atoms [e.g., pyrrolidinyl, imidazolidinyl, piperidinyl, pyrrolinyl, azetidinyl, piperazinyl, and pyrazolidinyl]; saturated 4 to 6-membered monocyclic groups containing 1 to 2 oxygen atoms and 1 to 3 nitrogen atoms [e.g., morpholinyl]; saturated 3 to 6-membered heteromonocyclic group containing 1 to 2 sulfur atoms and 1 to 3 nitrogen atoms [e.g., thiazolidinyl]. Examples of partially saturated heterocycle radicals include but are not limited to, dihydrothienyl, dihydropyranyl, dihydrofuryl, and dihydrothiazolyl. Examples of partially saturated and saturated heterocycle groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl. "Bicyclic heterocycle" includes groups wherein the heterocyclic radical is fused with an aryl radical wherein the point of attachment is the heterocycle ring. "Bicyclic heterocycle" also includes heterocyclic radicals that are fused or bridged with a carbocycle radical. For example partially unsaturated condensed heterocyclic group containing 1 to 5 nitrogen atoms, for example, indoline, isoindoline, partially unsaturated condensed heterocyclic group containing 1 to 2 oxygen atoms and 1 to 3 nitrogen atoms, partially unsaturated condensed heterocyclic group containing 1 to 2 sulfur atoms and 1 to 3 nitrogen atoms, and saturated condensed heterocyclic group containing 1 to 2 oxygen or sulfur atoms.

Non-Limiting Examples of Bicyclic Heterocycles Include:

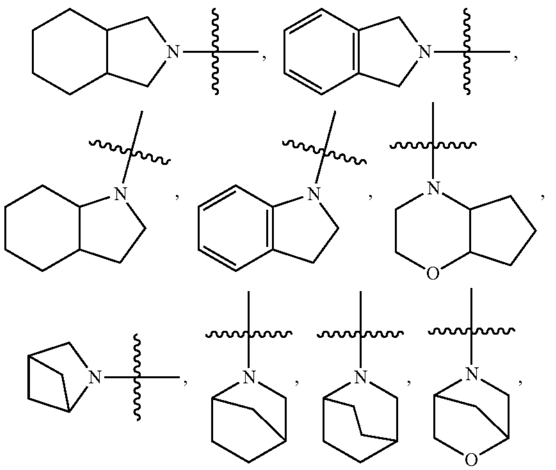

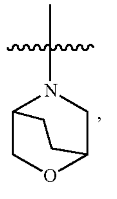

, and

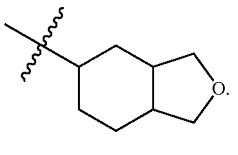

Unless otherwise drawn or clear from the context, the term "bicyclic heterocycle" includes cis and trans diastereomers. Non-limiting examples of chiral bicyclic heterocycles include:

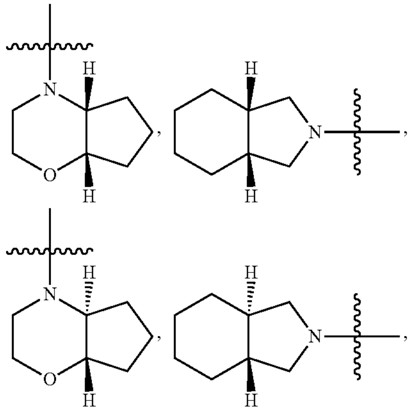

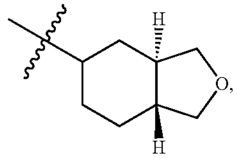

and

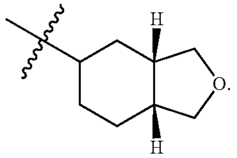

In certain alternative embodiments the term "heterocycle" refers to saturated and partially saturated heteroatom-containing ring radicals, where the heteroatoms may be selected from N, S, O, B, Si, and P.

"Heteroaryl" refers to a stable monocyclic, bicyclic, or multicyclic aromatic ring which contains from 1 to 3, or in some embodiments from 1, 2, or 3 heteroatoms selected from N, O, S, B, and P (and typically selected from N, O, and S) with remaining ring atoms being carbon, or a stable bicyclic or tricyclic system containing at least one 5, 6, or 7 membered aromatic ring which contains from 1 to 3, or in some embodiments from 1 to 2, heteroatoms selected from N, O, S, B or P with remaining ring atoms being carbon. In one embodiment, the only heteroatom is nitrogen. In one embodiment, the only heteroatom is oxygen. In one embodiment, the only heteroatom is sulfur. Monocyclic heteroaryl groups typically have from 5 or 6 ring atoms. In some embodiments bicyclic heteroaryl groups are 8- to 10-membered heteroaryl groups, that is, groups containing 8 or 10 ring atoms in which one 5, 6, or 7-member aromatic ring is fused to a second aromatic or non-aromatic ring wherein the point of attachment is the aromatic ring. When the total number of S and O atoms in the heteroaryl group exceeds 1, these heteroatoms are not adjacent to one another. In one embodiment, the total number of S and O atoms in the heteroaryl group is not more than 2. In another embodiment, the total number of S and O atoms in the aromatic heterocycle is not more than 1. Examples of heteroaryl groups include, but are not limited to, pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, tetrahydrofuranyl, and furopyridinyl. Heteroaryl groups are optionally substituted independently with one or more substituents described herein.

"Heteroaryloxy" is a heteroaryl group as described bound to the group it substituted via an oxygen, —O—, linker.

"Heteroarylalkyl" is an alkyl group as described herein substituted with a heteroaryl group as described herein.

"Arylalkyl" is an alkyl group as described herein substituted with an aryl group as described herein.

"Heterocycloalkyl" is an alkyl group as described herein substituted with a heterocyclo group as described herein.

The term "heteroalkyl" refers to an alkyl, alkenyl, alkynyl, or haloalkyl moiety as defined herein wherein a $CH_2$ group is either replaced by a heteroatom or a carbon atom is substituted with a heteroatom for example, an amine, carbonyl, carboxy, oxo, thio, phosphate, phosphonate, nitrogen, phosphorus, silicon, or boron. In one embodiment, the only heteroatom is nitrogen. In one embodiment, the only heteroatom is oxygen. In one embodiment, the only heteroatom is sulfur. In one embodiment, "heteroalkyl" is used to indicate a heteroaliphatic group (cyclic, acyclic, substituted, unsubstituted, branched or unbranched) having 1-20 carbon atoms. Nonlimiting examples of heteroalkyl moieties include polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

When a compound moiety is "optionally substituted" it may be substituted as allowed by valence with one or more groups selected from alkyl (including $C_1$-$C_4$ alkyl), alkenyl (including $C_2$-$C_4$ alkenyl), alkynyl (including $C_2$-$C_4$alkynyl), haloalkyl (including $C_1$-$C_4$ haloalkyl), —$OR^6$, F, Cl, Br, I, —$NR^6R^7$, heteroalkyl, cyano, nitro, $C(O)R^3$,

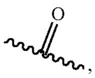, 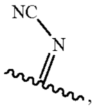, 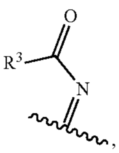, and 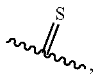, wherein the optional substituent is selected such that a stable compound results. For example

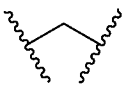 [SMILES: *C*]

could be substituted with 1 or 2 groups independently selected from alkyl, alkenyl, alkynyl, haloalkyl, —$OR^6$, F, Cl, Br, I, —$NR^6R^7$, heteroalkyl, cyano, nitro, $C(O)R^3$ so long as a stable compound results but only one group selected from

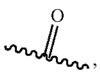, 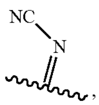, 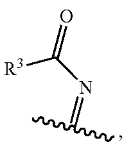, and 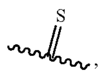, so long as a stable compound results

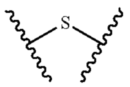

on the other hand could only be substituted with 1 or 2 groups selected from

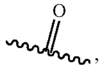, 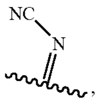, and 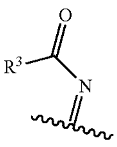.

Non-limiting examples of optionally substituted $CH_2$ groups include:

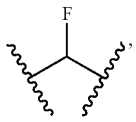, 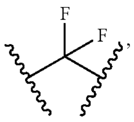, 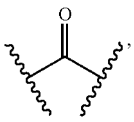, and

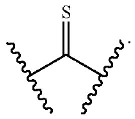.

Non-limiting examples of optionally substituted —S— groups include:

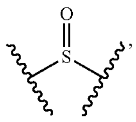, 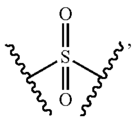, 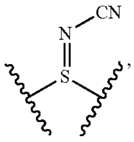, and

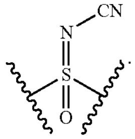.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, subcutaneous, intramuscular, parenteral, systemic, intravenous, and the like. A "dosage form" can also include an implant for controlled delivery.

"Pharmaceutical compositions" are compositions comprising at least one active agent, and at least one other substance, such as a carrier. The present invention includes pharmaceutical compositions of the described compounds.

"Pharmaceutical combinations" are combinations of at least two active agents which may be combined in a single dosage form or provided together in separate dosage forms with instructions that the active agents are to be used together to treat any disorder described herein.

A "pharmaceutically acceptable salt" is a derivative of the disclosed compound in which the parent compound is modified by making an inorganic or organic, pharmaceutically acceptable, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include salts which are acceptable for human consumption and the quaternary ammonium salts of the parent compound formed, for example, from inorganic or organic acids. Examples, of such salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_{1-4}$—COOH, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, acceptable for human consumption, and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein. Typically the host is a human. A "patient" or "host" or "subject" also refers to for example, a mammal, primate (e.g., human), cow, sheep, goat, horse, dog, cat, rabbit, rat, mice, bird and the like.

A "therapeutically effective amount" of a compound, pharmaceutical composition, or combination of this invention means an amount effective, when administered to a host, that provides a therapeutic benefit such as an amelioration of symptoms or reduction or diminution of the disease itself. In another aspect, a preventative amount can be administered that prevents or minimizes the risk of the disease mediated by the Extracellular Target Protein.

Embodiments of "Alkyl"

In one embodiment "alkyl" is a $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, or $C_1$-$C_2$ alkyl.

In one embodiment "alkyl" has one carbon.

In one embodiment "alkyl" has two carbons.

In one embodiment "alkyl" has three carbons.

In one embodiment "alkyl" has four carbons.

In one embodiment "alkyl" has five carbons.

In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In an alternative embodiment the "alkyl" group is optionally substituted.

In an alternative embodiment the "alkenyl" group is optionally substituted.

In an alternative embodiment the "alkynyl" group is optionally substituted.

Embodiments of "Haloalkyl"

In one embodiment "haloalkyl" is a $C_1$-$C_{10}$ haloalkyl, $C_1$-$C_9$ haloalkyl, $C_1$-$C_8$ haloalkyl, $C_1$-$C_7$ haloalkyl, $C_1$-$C_6$ haloalkyl, $C_1$-$C_5$ haloalkyl, $C_1$-$C_4$ haloalkyl, $C_1$-$C_3$ haloalkyl, and $C_1$-$C_2$ haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

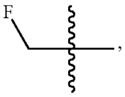,
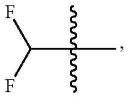, and
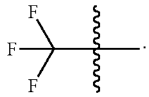.

Additional Non-Limiting Examples of "Haloalkyl" Include:

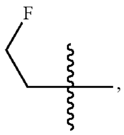,
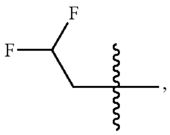,
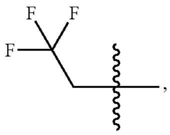,
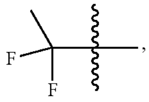,
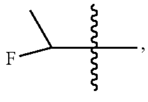,
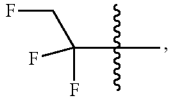,
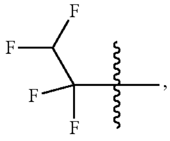,
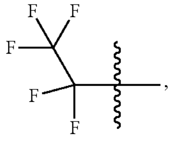,
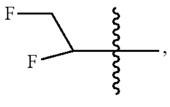, -continued

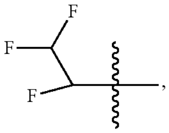, and 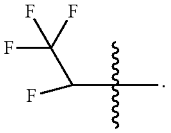.

Additional Non-Limiting Examples of "Haloalkyl" Include:

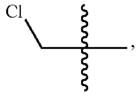, 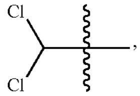, and 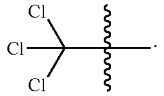.

Additional Non-Limiting Examples of "Haloalkyl" Include:

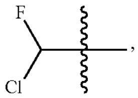, 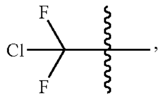, and 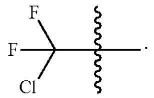.

Embodiments of "Heteroaryl"

Non-limiting examples of 5 membered "heteroaryl" groups include pyrrole, furan, thiophene, pyrazole, imidazole, triazole, isoxazole, oxazole, oxadiazole, oxatriazole, isothiazole, thiazole, thiadiazole, and thiatriazole.

Additional non-limiting examples of 5 membered "heteroaryl" groups include:

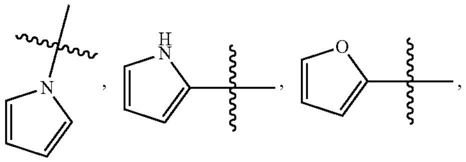,

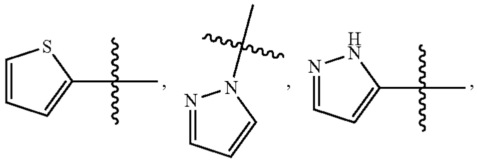,

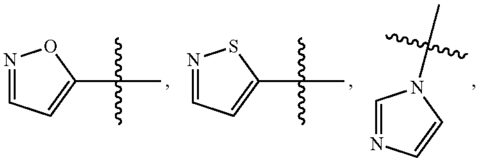,

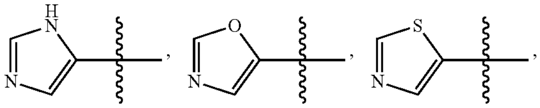,

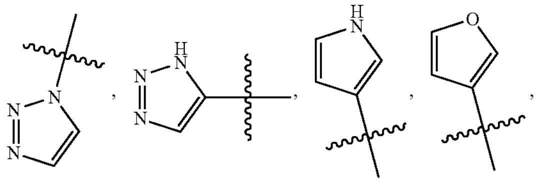,

-continued

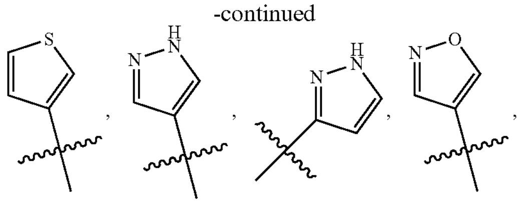,

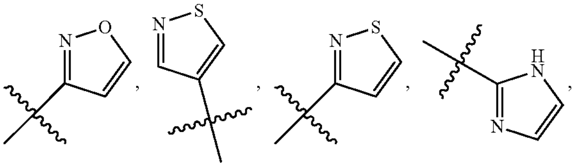,

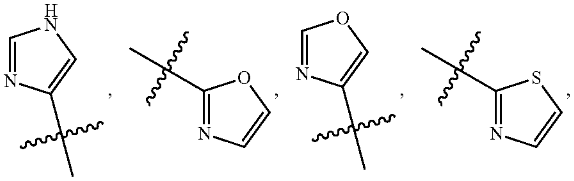,

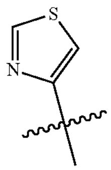, and 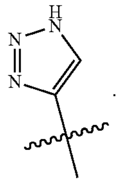.

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

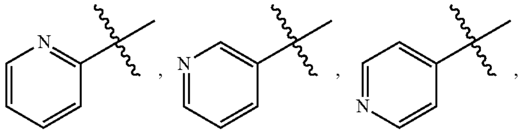,

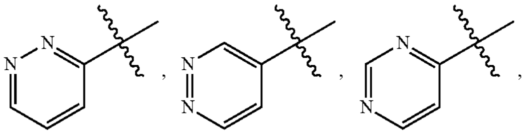,

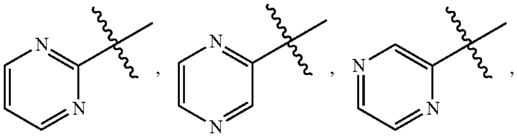, and

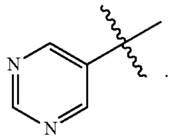.

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

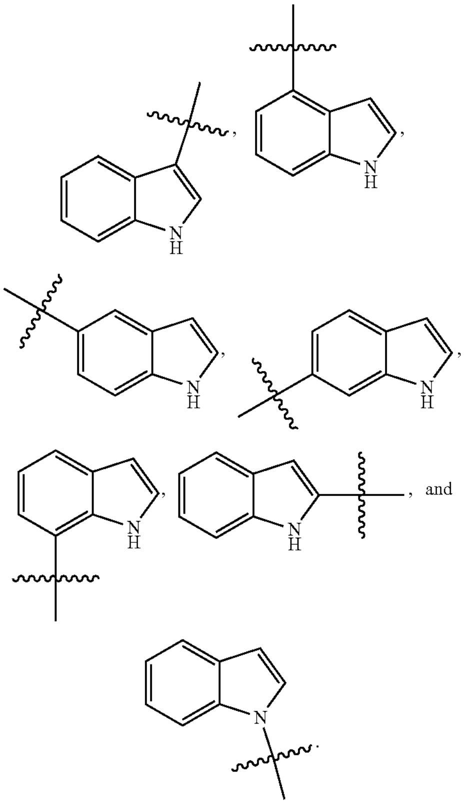

, and

Additional non-limiting examples of "heteroaryl" groups that are bicyclic include:

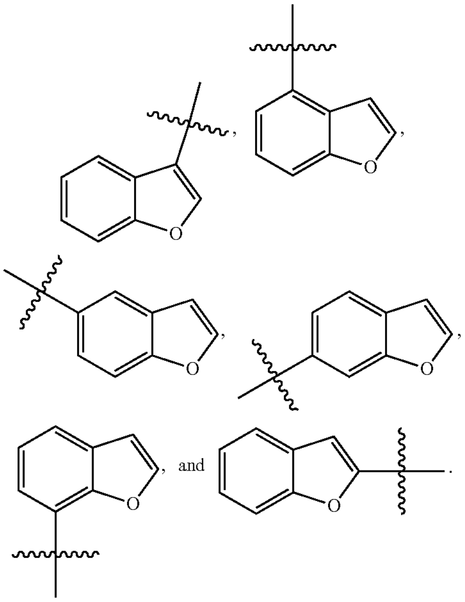

, and

Additional non-limiting examples of "heteroaryl" groups that are bicyclic include:

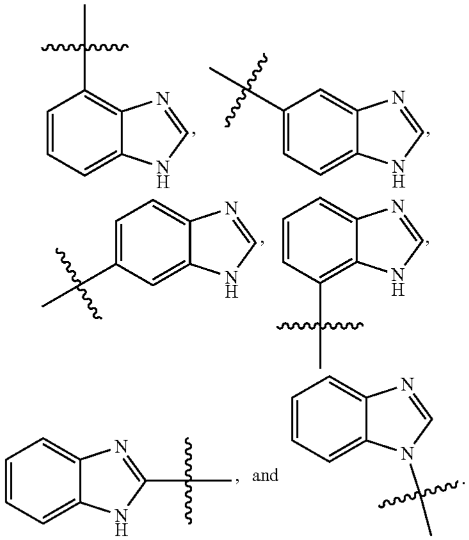

, and

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

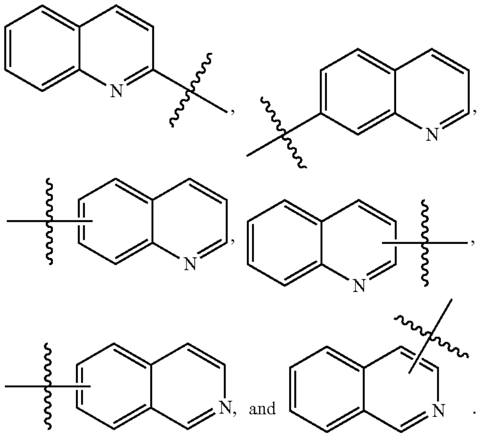

, and

Embodiments of "Heterocycle"

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

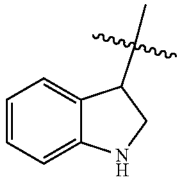 [SMILES: *C1CNc2ccccc21]

is a "heterocycle" group.

However,

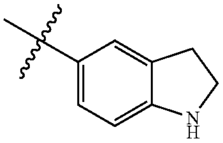 [SMILES: *c1ccc2c(c1)CCN2]

is an "aryl" group.

Non-limiting examples of "heterocycle" also include:

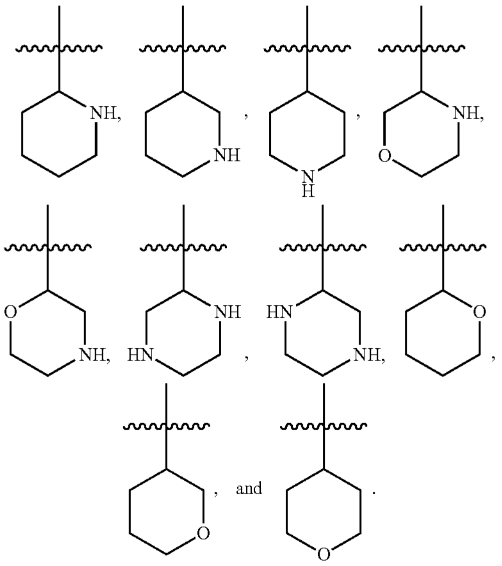

and

Additional non-limiting examples of "heterocycle" include:

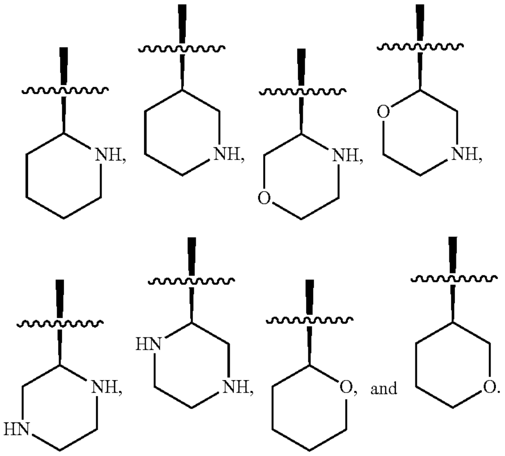

and

Additional non-limiting examples of "heterocycle" include:

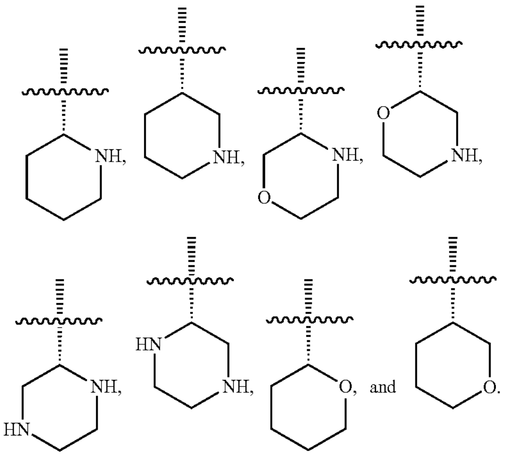

and

Non-limiting examples of "heterocycle" also include:

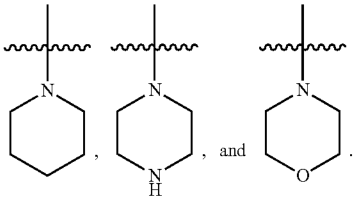

and

Non-limiting examples of "heterocycle" also include:

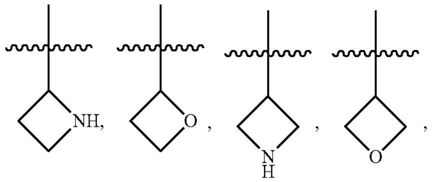

-continued

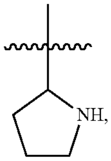, 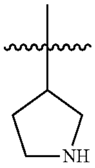, 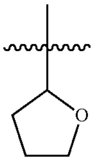, and 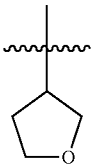.

Additional non-limiting examples of"heterocycle" include:

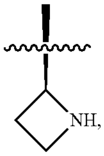, 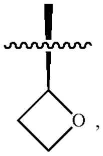, 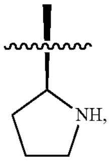, 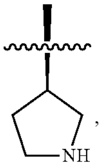, 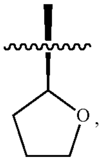, and 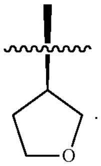.

Additional non-limiting examples of"heterocycle" include:

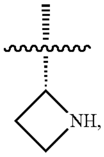, 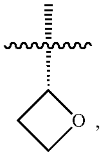, 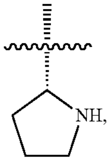, 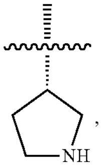, 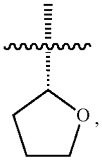, and 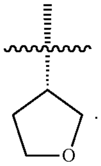.

Aryl

In one embodiment "aryl" is a 6 carbon aromatic group (phenyl).

In one embodiment "aryl" is a 10 carbon aromatic group (naphthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

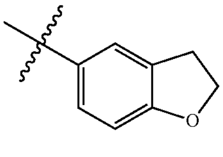 [SMILES: *c1ccc2c(c1)CCO2]

is an "aryl" group.

However,

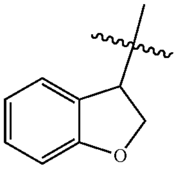 [SMILES: *C1COc2ccccc21]

is a "heterocycle" group.

Embodiments of "Arylalkyl"

Non-limiting examples of "arylalkyl" include:

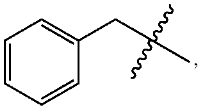, 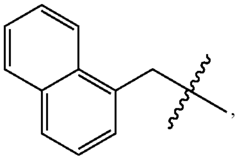, 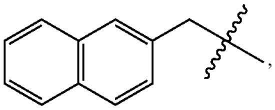, 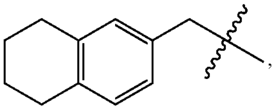, 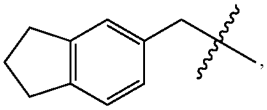, or 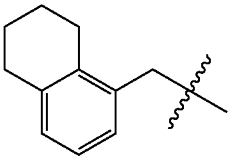

In one embodiment "arylalkyl" is

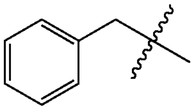.

In one embodiment the "arylalkyl" refers to a 2 carbon alkyl group substituted with an aryl group.

Non-limiting examples of "arylalkyl" include:

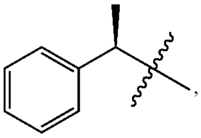, 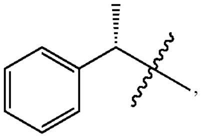,

-continued

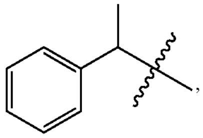, and 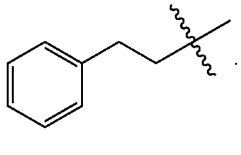.

VI. Extracellular Proteins and Targeting Ligands

A wide range of well-known and characterized extracellular proteins can cause, modulate, or amplify diseases in vivo, such as abnormal cellular proliferation such as tumors and cancer, autoimmune disorders, inflammation and aging-related diseases. For example, extracellular proteins such as growth factors, cytokines, and chemokines bind to cell surface receptors, often initiate aberrant signaling in multiple diseases such as cancer and inflammation.

The extracellular protein degrader described herein or its pharmaceutically acceptable salt and/or its pharmaceutically acceptable compositions can be used to treat a disorder which is mediated by the selected Target Protein that binds to the Targeting Ligand. The described degraders are capable of targeting specific extracellular Target Proteins that mediate pathological disorders for lysosomal degradation. The selected extracellular Target Protein may modulate a disorder in a human via a mechanism of action such as modification of a biological pathway, pathogenic signaling, or modulation of a signal cascade or cellular entry. In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense, yet for therapeutic purposes, degradation of the protein is preferred to inhibition. The extracellular Target Protein is recruited with a Targeting Ligand, which is a ligand for the extracellular Target Protein. Typically, the Targeting Ligand binds the Target Protein in a non-covalent fashion. In an alternative embodiment, the Target Protein is covalently bound to the Targeting Ligand in a manner that can be irreversible or reversible.

Accordingly, in some embodiments, a method to treat a host with a disorder mediated by an extracellular Target Protein is provided that includes administering an effective amount of a degrader targeting an extracellular protein or its pharmaceutically acceptable salt described herein to the host, typically a human, optionally in a pharmaceutically acceptable composition.

The extracellular Target Protein can be any amino acid sequence to which the degrader comprising a Targeting Ligand can be bound which through degradation thereof, results in a beneficial therapeutic effect. In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be an extracellular mutant protein, or a protein, for example, where a partial, or full, gain-of-function or loss-of-function is encoded by nucleotide polymorphisms. In some embodiments, the degrader targets the aberrant form of the protein and not the normal form of the protein.

The Targeting Ligand is a ligand which covalently or non-covalently binds to a Target Protein which has been selected for lysosomal degradation. A Targeting Ligand is a small molecule or moiety (for example a peptide, nucleotide, antibody fragment, aptamer, biomolecule, or other chemical structure) that binds to a Target Protein, and wherein the Target Protein is a mediator of disease in a host as described in detail below. Exemplary Target Ligands are provided in FIG. 1.

Anchor Bond

The Extracellular Protein Target Ligand ("EPTL") is covalently bound to Linker in the ASGPR-binding extracellular protein degrader compound through the Anchor Bond (which is the chemical bond between the EPTL and either Linker B, Linker C or Linker D). This bond can be placed at any location on the ligand that does not unacceptably disrupt the ability of the EPTL to bind to the Extracellular Protein Target. The Anchor Bond is depicted on the non-limiting examples of Extracellular Protein Target Ligands in FIG. 1 as:

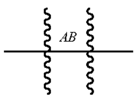 [SMILES: **]

A number of exemplary extracellular proteins targeted for medical therapy described below have characterizing structural information in the well-known Protein Data Bank ("PDB"), which is a database for the three-dimensional structural information for large biological molecules such as proteins and nucleic acids. PDB includes x-ray crystallography and other information submitted by scientists around the world, and is freely accessible. See for example www.rcsb.org; www.wwpdb.org and www.uniprot.org. Using the PDB codes for example provided in Section ** or in the Data Bank itself, and technical references provided herein or otherwise publicly available, the skilled artisan can determine appropriate locations where the EPTL can be linked through an Anchor Bond to Linker B, Linker C or Linker D to the ASGPR-binding moiety. For many of these proteins, published references describe how a range of ligands bind to the target proteins, and from this information, one can determine reasonable Anchor Bond locations.

For example, the skilled artisan can use available visualization tools, including those available on the PDB website, to determine where the Extracellular Protein Targeting Ligand docks into to the Extracellular Protein. The skilled artisan can also import the crystal structure and the selected Extracellular Protein Targeting Ligand of interest into modeling software (including for example PyMOL, Glide, Maestro, RasMol, Visual Molecular Dynamics, Jmol, and AutoDock) to determine what portion of the Extracellular Protein Targeting Ligand is bound to the Extracellular Protein. The ASGPR ligand is then bound through the Linker and the Anchor Bond at a point that does not unduly adversely affect binding to the extracellular protein.

Non-Limiting Examples of Extracellular Target Proteins

Immunoglobulin A (IgA)

In some embodiments, the Target Protein is human immunoglobulin A(IgA). IgA is an antibody that plays a crucial role in the immune function of mucous membranes. The amount of IgA produced in association with mucosal membranes is greater than all other types of antibody combined. IgA has two subclasses (IgA1 and IgA2) and can be produced as a monomeric as well as a dimeric form. The IgA dimeric form is the most prevalent. In the blood, IgA interacts with an Fc receptor called FcαRI (or CD89), which is expressed on immune effector cells, to initiate inflammatory reactions. Ligation of FcαRI by IgA containing immune complexes causes antibody-dependent cell-mediated cytotoxicity (ADCC), degranulation of eosinophils and basophils, phagocytosis by monocytes, macrophages, and neutrophils, and triggering of respiratory burst activity by polymorphonuclear leukocytes. Aberrant IgA expression has been implicated in a number of autoimmune and immune-mediated disorders, including IgA nephropathy, celiac disease, Henoch-Sconiein purpura (HSP), liner IgA bullous dermatosis, and IgA pemphigus.

The Protein Data Bank website provides the crystal structure of IgA, as well as the crystal structure of IgA bound to various compounds searchable by 5 E8 E (Baglin, T. P., et al., J. Thromb. Haemost., 2016, 14: 137-142), and 2QTJ (Bonner, A., et al., J. Immunol., 2008, 180: 1008-1018). Additionally, Hatanaka T. et al., provides great insight into the specificity and high binding affinity of IgA to OPT-1 peptides (J Biol Chem., 2012, 287(51), 43126-43136).

Representative IgA Targeting Ligands are provided in FIG. 1.

Additional representative IgA Targeting Ligands include:

```
                                       SEQ ID NO: 1
MLKKIE
(Jerlstrom et al. Infect. Immun. 1996 July; 64(7):
2787-2793;

Opt-1-
                                       SEQ ID NO: 2
HMVCLAYRGRPVCFAL
(Hatanaka et al. J. Biol. Chem. Vol. 287, No. 51,
pp. 43126-43136, Dec. 14, 2012);

Opt-2-
                                       SEQ ID NO: 3
HMVCLSYRGRPVCFSL
(Hatanaka et al. J. Biol. Chem. Vol. 287, No. 51,
pp. 43126-43136, Dec. 14, 2012);

Opt-3-
                                       SEQ ID NO: 4
HQVCLSYRGRPVCFST
(Hatanaka et al. J. Biol. Chem. Vol. 287, No. 51,
pp. 43126-43136, Dec. 14, 2012);

                                       SEQ ID NO: 5
QMRCLSYKGRRVCLWL
(U.S. Pat. No. 9,593,147);

                                       SEQ ID NO: 6
KRLCLQYKGSKVCFRL
(U.S. Pat. No. 9,593,147);

                                       SEQ ID NO: 7
RMRCLTYRGRRVCLEL
(U.S. Pat. No. 9,593,147);

                                       SEQ ID NO: 8
SMRCLQYRGSRVCLTL
(U.S. Pat. No. 9,593,147);

                                       SEQ ID NO: 9
HLRCLRYKGTRVCFSL
(U.S. Pat. No. 9,593,147);

                                      SEQ ID NO: 10
HVRCLSYKGREVCVQL
(U.S. Pat. No. 9,593,147);
```

-continued

```
                                      SEQ ID NO: 11
PRMCLFIYKGRRVCIPY
(U.S. Pat. No. 9,593,147);

                                      SEQ ID NO: 12
HMRCLHYKGRRVCFLL
(U.S. Pat. No. 9,593,147);

                                      SEQ ID NO: 13
HKRCLHYRGRMVCFLI
(U.S. Pat. No. 9,593,147);

                                      SEQ ID NO: 14
QKRCLKYKGSRVCFFL
(U.S. Pat. No. 9,593,147);

                                      SEQ ID NO: 15
HVRCLRYRGKNVCFLL
(U.S. Pat. No. 9,593,147);

                                      SEQ ID NO: 16
SDVCLRYRGRPVCFQV
(U.S. Pat. No. 9,593,147);

                                      SEQ ID NO: 17
RDVCLRYRGRPVCFQV
(U.S. Pat. No. 9,593,147);

                                      SEQ ID NO: 18
HDVCLRYRGRPVCFQV
(U.S. Pat. No. 9,593,147);

                                      SEQ ID NO: 19
SMVCLRYRGRPVCFQV
(U.S. Pat. No. 9,593,147);

                                      SEQ ID NO: 20
SAVCLRYRGRPVCFQV
(U.S. Pat. No. 9,593,147);

                                      SEQ ID NO: 21
SDVCLNYRGRPVCFQV
(U.S. Pat. No. 9,593,147);

                                      SEQ ID NO: 22
SDVCLHYRGRPVCFQV
(U.S. Pat. No. 9,593,147);

                                      SEQ ID NO: 23
SDVCLAYRGRPVCFQV
(U.S. Pat. No. 9,593,147);

                                      SEQ ID NO: 24
SDVCLRYRGRPVCFAV
(U.S. Pat. No. 9,593,147);

                                      SEQ ID NO: 25
SDVCLRYRGRPVCFQL
(U.S. Pat. No. 9,593,147);

                                      SEQ ID NO: 26
SDVCLRYRGRPVCFQA
(U.S. Pat. No. 9,593,147);

                                      SEQ ID NO: 27
HMVCLSYRGRPVCF
(U.S. Pub. No. 20150044701);

                                      SEQ ID NO: 28
HMVCLSYRGRPVCFS
(U.S. Pub. No. 20150044701);

                                      SEQ ID NO: 29
HQVCLSYRGQPVCFSL
(U.S. Pub. No. 20150044701);

                                      SEQ ID NO: 30
HQVCLSYRGRPTCFSL
(U.S. Pub. No. 20150044701);
```

-continued

SEQ ID NO: 31
HQVCLSYRGRPVCYSL
(U.S. Pub. No. 20150044701);

SEQ ID NO: 32
HQVCLSYRGQPVCFST
(U.S. Pub. No. 20150044701);

SEQ ID NO: 33
HQVCLSYRGRPTCFST
(U.S. Pub. No. 20150044701);

SEQ ID NO: 34
HQVCLSYRGQPTCFST
(U.S. Pub. No. 20150044701);

Immunoglobulin G (IgG)

In some embodiments, the Target Protein is a human immunoglobulin G (IgG). IgG represents approximately 75% of serum antibodies in humans. IgG is the most common type of antibody found in blood circulation. IgG antibodies are large globular proteins with a molecular weight of about 150 kDa made of four peptide chains.[6] It contains two identical γ (gamma) heavy chains of about 50 kDa and two identical light chains of about 25 kDa, thus a tetrameric quaternary structure. The two heavy chains are linked to each other and to a light chain each by disulfide bonds. The resulting tetramer has two identical halves, which together form the Y-like shape. Each end of the fork contains an identical antigen binding site. The various regions and domains of a typical IgG are depicted in the figure to the left. The Fc regions of IgGs bear a highly conserved N-glycosylation site at asparagine 297 in the constant region of the heavy chain. The N-glycans attached to this site are predominantly core-fucosylated biantennary structures of the complex type. In addition, small amounts of these N-glycans also bear bisecting GlcNAc and α-2,6-linked sialic acid residues. The N-glycan composition in IgG has been linked to several autoimmune, infectious and metabolic diseases. In addition, overexpression of IgG4 has been associated with IG4-related diseases, which generally include multiple organs, and disorders include type 1 autoimmune pancreatitis, interstitial nephritis, Riedel's thyroiditis, Mikulicz's disease, Küttner's tumor, inflammatory pseudotumors (in various sites of the body), mediastinal fibrosis and some cases of retroperitoneal fibrosis, aortitis, retroperitoneal fibrosis, proximal biliary strictures, tubulointerstitial nephritis, pachymeningitis, pancreatic enlargement and pericarditis.

The Protein Data Bank website provides the crystal structure of IgG searchable by 1H3X (Krapp, S., et al., J. Mol. Biol., 2003, 325: 979); and 5V43 (Lee, C. H., et al., Nat. Immunol., 2017, 18: 889-898); as well as the crystal structure of IgG bound to various compounds searchable by 5YC5 (Kiyoshi M., et al., Sci. Rep., 2018, 8: 3955-3955); 5XJE (Sakae Y., et al., Sci. Rep., 2017, 7: 13780-13780); 5GSQ (Chen, C. L., et al., ACS Chem. Biol., 2017, 12: 1335-1345); and 1HZH (Saphire E. O., et al., Science, 2001, 293: 1155-1159). Additionally, Kiyoshi, M., et al., provides insight into the structural basis for binding of human IgG1 to its high-affinity human receptor FcγRI. (Kiyosi M., et al., Nat Commun., 2015, 6, 6866).

Representative IgG Targeting Ligands are provided in FIG. 1.

Additional Representative IgG Targeting Ligands Include:

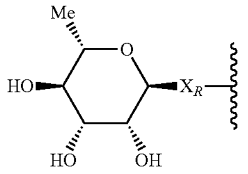

α-L-Rhamnose

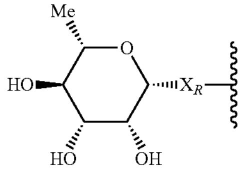

β-L-Rhamnose

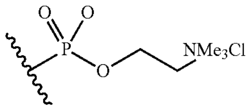

Phosphoryl Choline

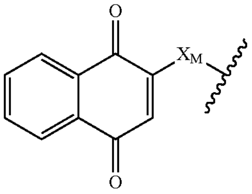

Menadione

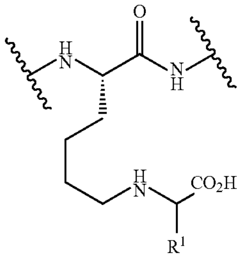

Carboxyethyl Lysine ($R^1$ = Me)

wherein $X_R$ is O, S, NH, or N—$C_1$-$C_3$ alkyl; and $X_M$ is O, S, NH, or N—$C_1$-$C_3$ alkyl.

In other embodiments the IgG Targeting Ligand is selected from:

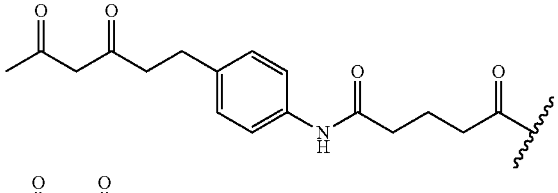

,

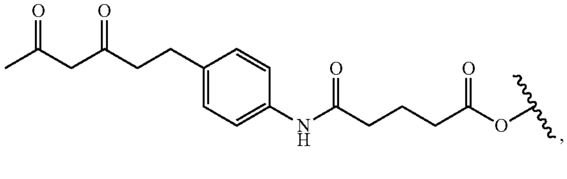

,

-continued

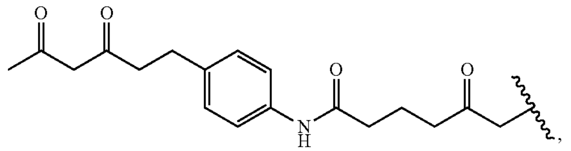
,

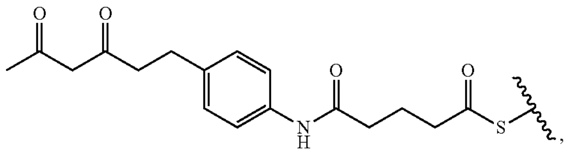
,

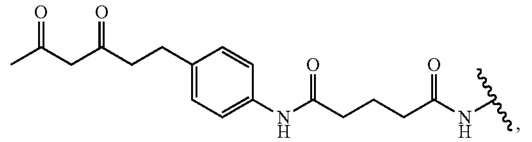
, and

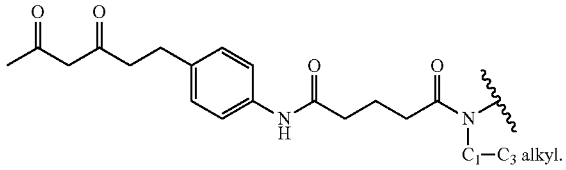

In some embodiments, the IgG Targeting Ligand is a group according to the chemical structure:

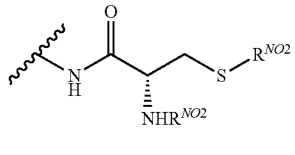

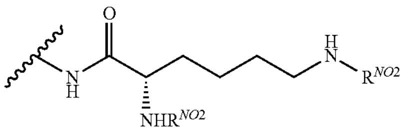

wherein $R^{NO2}$ is a dinitrophenyl group optionally linked through $CH_2$, S(O), $S(O)_2$, —$S(O)_2O$, —$OS(O)_2$, or $OS(O)_2O$.

In certain embodiments the IgG Targeting Ligand is selected from:

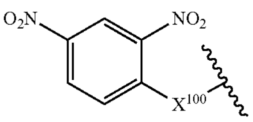

wherein $X^{100}$ is selected from O, $CH_2$, NH, N—$C_1$-$C_3$ alkyl, NC(O)$C_1$-$C_3$ alkyl, S(O), $S(O)_2$, —$S(O)_2O$, —$OS(O)_2$, or $OS(O)_2O$.

In some embodiments, the IgG Targeting Ligand is a 3-indoleacetic acid group according to the chemical structure:

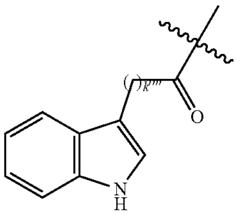

where k'''' is 1-4 (preferably 2-3, most often 3) or a

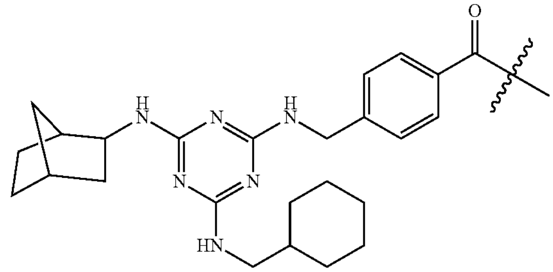
;

group.

In some embodiments, the IgG Targeting Ligand is a peptide. Nonlimiting examples of IgG Targeting Ligand peptides include:

```
                                        SEQ ID NO: 35
PAM (RTY)4K2KG
(Fassina, et al, J. Mol. Recognit. 1996, 9, 564-
569);
```

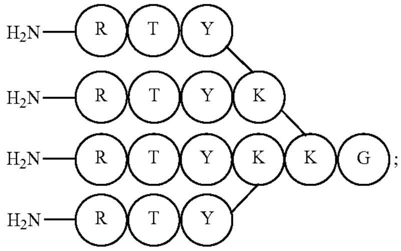

;

PAM; $K_d$ 0.3 μM

D-PAM, wherein the amino acids of the PAM sequence are all D-amino acids (Verdoliva, et al, J. Immunol. Methods, 2002, 271, 77-88) $(RTY)_4K_2KG$ SEQ ID NO: 36; D-PAM-Φ, wherein the amino acids of the PAM sequence are all D-amino acids with further modifications wherein the four N-terminal arginines are acetylated with phenyllactic acid (Dinon, et al J. Mol. Recognit. 2011, 24, 1087-1094) $(RTY)_4K_2KG$ SEQ ID NO: 37;

SEQ ID NO: 38
TWKTSRISIF
(Krook, et al,.J. Immunol. Methods 1998, 221, 151-157);

SEQ ID NO: 39
FGRLVSSIRY
(Krook, et al, J. Immunol. Methods 1998, 221, 151-157);

SEQ ID NO: 40
Fc-III (DCAWHLGELVWCT-NH2)
(DeLano et al, Science 2000, 287, 1279-1283)

Fc-III

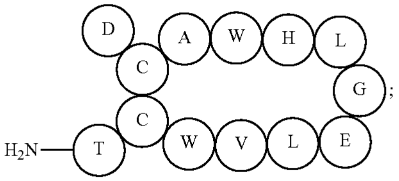

$K_d$ 16 *n*M

FCBP-Ser

SEQ ID NO: 41
DSAWHLGELWST
(see WO2014010813);

SEQ ID NO: 42
DCHKRSFWADNCT
(see WO2014010813);

SEQ ID NO: 43
DCRTQFRPNQTCT
(see WO2014010813);

SEQ ID NO: 44
DCQLCDFWRTRCT
(see WO2014010813);

SEQ ID NO: 45
DCFEDFNEQRTCT
(see WO2014010813);

SEQ ID NO: 46
DCLAKFLKGKDCT
(see WO2014010813);

SEQ ID NO: 47
DCWHRRTHKTFCT
(see WO2014010813);

SEQ ID NO: 48
DCRTIQTRSCT
(see WO2014010813);

SEQ ID NO: 49
DCIKLAQLHSVCT
(see WO2014010813);

SEQ ID NO: 50
DCWRHRNATEWCT
(see WO2014010813);

SEQ ID NO: 51
DCQNWIKDVHKCT
(see WO2014010813);

SEQ ID NO: 52
DCAWHLGELVWCT
(see WO2014010813);

-continued

SEQ ID NO: 53
DCAFHLGELVWCT
(see WO2014010813);

SEQ ID NO: 54
DCAYHLGELVWCT
(see WO2014010813)

FcBP-1

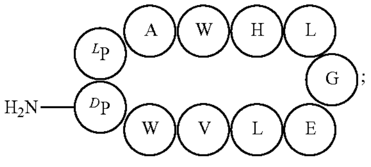

$K_i$ 14 μM

FcBP-2

SEQ ID NO: 56
PDCAWHLGELVWCTP
(Dias, et al, J . Am. Chem. Soc. 2006, 128, 2726-2732);

FcBP-2

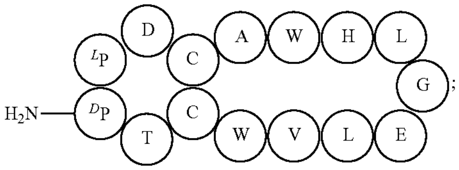

$K_d$ 1.8 *n*M

Fc-111-4c

SEQ ID NO: 57
CDCAWHLGELVWCTC
(Gong, et al, Bioconjug. Chem. 2016, 27, 1569-1573)

Fc-III-4C

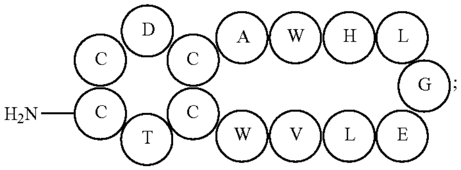

$K_d$ 2.45 *n*M

SEQ ID NO: 58
EPIHRSTLTALL;
(Ehrlich, et al, J. Biochem. Biophys. Method 2001, 49, 443-454);

SEQ ID NO: 59
APAR;
(Camperi, et al, Biotechnol. Lett. 2003, 25, 1545-1548);

-continued

SEQ ID NO: 60
FcRM $(CFHH)_2KG$
(Fc Receptor Mimetic, Verdoliva, et al., ChemBioChem 2005, 6, 1242-1253)

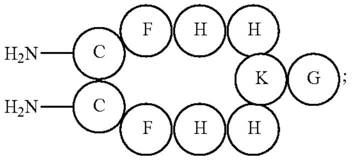

FcRM; $K_d$ 20 μM

SEQ ID NO: 61
HWRGWV
(Yang, et al., J Peptide Res. 2006, 66, 110-137);

SEQ ID NO: 62
HYFKFD
(Yang, et al, J. Chromatogr. A 2009, 1216, 910-918);

SEQ ID NO: 63
HFRRHL
(Menegatti, et al, J. Chromatogr. A 2016, 1445, 93-104);

SEQ ID NO: 64
HWCitGW;
(Menegatti, et al, J. Chromatogr. A 2016, 1445, 93-104);

SEQ ID NO: 65
HWmetCitGWmetV
(U.S. 10,266,566);

SEQ ID NO: 66
$D_2AAG$
(Small Synthetic peptide ligand, Lund, et al, J. Chromatogr. A 2012, 1225,158-167);

SEQ ID NO: 67
DAAG
(Small Synthetic peptide ligand, Lund, et al, J. Chromatogr. A 2012, 1225, 158-167);

SEQ ID NO: 68
cyclo[(Nα-Ac) S(A)-RWHYFK-Lact-E]
(Menegatti, et al, Anal. Chem. 2013, 85, 9229-9237);

SEQ ID NO: 69
cyclo[(Nα-Ac)-Dap(A)-RWHYFK-Lact-E]
(Menegatti, et al, Anal. Chem. 2013, 85,9229-9237);

SEQ ID NO: 70
cyclo[Link M-WFRHYK]
(Menegatti, et al, Biotechnol. Bioeng. 2013,110, 857-870);

SEQ ID NO: 71
NKFRGKYK
(Sugita, et al, Biochem. Eng. J. 2013, 79, 33-40);

SEQ ID NO: 72
NARKFYKG
(Sugita, et al, Biochem. Eng. J. 2013, 79, 33-40);

SEQ ID NO: 73
FYWHCLDE
(Zhao, et al, Biochem. Eng. J. 2014, 88, 1-11);

-continued

SEQ ID NO: 74
FYCHWALE
(Zhao, et al, J Chromatogr. A 2014, 1355, 107-114);

SEQ ID NO: 75
FYCHTIDE
(Zhao, et al., Z Chromatogr. A 2014, 1359, 100-111);

SEQ ID NO: 76
Dual 1/3
(FYWHCLDE-FYCHTIDE)
(Zhao, et al, J. Chromatogr. A 2014, 1369, 64-72);

SEQ ID NO: 77
RRGW
(Tsai, et al, Anal. Chem. 2014, 86, 293 1-2938);

SEQ ID NO: 78
KHRFNKD;
(Yoo and Choi, BioChip J. 2015, 10, 88-94);

SEQ. ID NO: 79
CPSTHWK
(Sun et al. Polymers 2018, 10, 778);

SEQ. ID NO: 80
NVQYFAV
(Sun et al. Polymers 2018, 10, 778);

SEQ. ID NO: 81
ASHTQKS
(Sun et al. Polymers 2018, 10, 778);

SEQ. ID NO: 82
QPQMSHM
(Sun et al. Polymers 2018, 10, 778);

SEQ. ID NO: 83
TNIESLK
(Sun et al. Polymers 2018, 10, 778);

SEQ. ID NO: 84
NCHKCWN
(Sun et al. Polymers 2018, 10, 778);

SEQ. ID NO: 85
SHLSKNF
(Sun et al. Polymers 2018, 10, 778).

Immunoglobulin E (IgE)

In some embodiments, the Target Protein is human immunoglobulin E (IgE). IgE is a type of immunoglobulin that plays an essential role in type I hypersensitivity, which can manifest into various allergic diseases, such as allergic asthma, most types of sinusitis, allergic rhinitis, food allergies, and specific types of chronic urticaria and atopic dermatitis. IgE also plays a pivotal role in responses to allergens, such as: anaphylactic drugs, bee stings, and antigen preparations used in desensitization immunotherapy.

The Protein Data Bank website provides the crystal structure of IgE searchable by 1F2Q (Garman, S. C., Kinet, J. P., Jardetzky, T. S., Cell, 1998, 95: 951-961); as well as the crystal structure of IgE bound to various compounds searchable by 1F6A (Garman, S. C., et al., Nature, 2000, 406 259-266); 1RPQ (Stamos, J., et al., Structure, 2004, 12 1289-1301); 2Y7Q (Holdom, M. D., et al., Nat. Struct. Mol. Biol., 2011, 18 571); and 4GRG (Kim, B., et al., Nature, 2012, 491: 613-617). Additionally, Wan et al., provides insight into the crystal structure of IgE Fc, revealing an asymmetrically bent conformation (Wan et al., Nat. Immunol., 2002, 3(7), 681-6); and Dhaliwal et al, provides insight into the crystal structure of IgE bound to its B-cell receptor CD23 reveals a mechanism of reciprocal allosteric inhibition with high affinity receptor FcεRI (Dhaliwal, B., et al., Proc Natl Acad Sci USA., 2012, 109(31), 12686-91).

Additional Immunoglobin Targeting Ligands

Additional, Non-Limiting Examples of Extracellular Targeting Ligands Include:

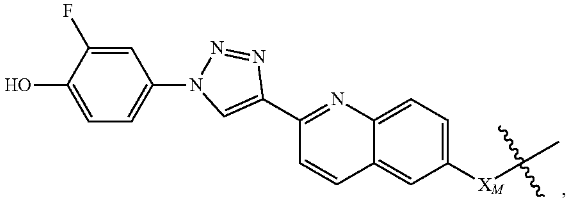

,

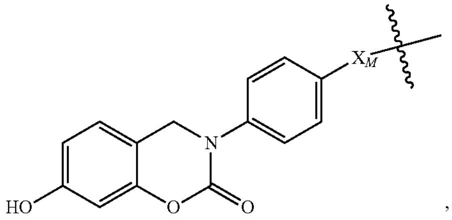

, or

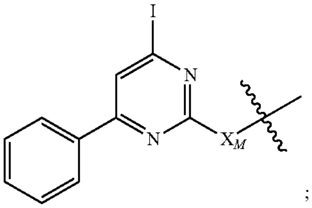

;

wherein $X_M$ is —$(CH_2)_{0-6}$, —O—$(CH_2)_{0-6}$, S—$(CH_2)_{0-6}$, $NR_M$—$(CH_2)_{0-6}$, C(O)—$(CH_2)_{0-6}$, a PEG group containing from 1 to 8, preferably 1-4 ethylene glycol residues, or a —$C(O)(CH_2)_{0-6}NR_M$ group;

$R_M$ is H or a $C_1$-$C_3$ alkyl group which is optionally substituted with one or two hydroxyl groups, where 0-6 is preferably 1, 2, 3, or 4, more preferably 1.

Additional, non-limiting examples of Extracellular Targeting Ligands include:

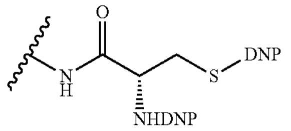

and

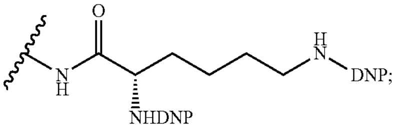

wherein DNP is a 2,4-dinitrophenyl group; or a group according to the chemical structure:

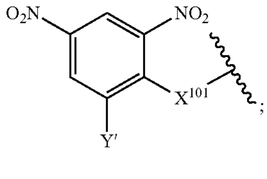

;

wherein Y' is H or $NO_2$ (preferably H);

$X^{101}$ is O, $CH_2$, S, $NR^{101}$, S(O), $S(O)_2$, —$S(O)_2O$, —OS$(O)_2$, or $OS(O)_2O$; and $R^{101}$ is H, a $C_1$-$C_3$ alkyl group, or a —C(O)($C_1$-$C_3$ alkyl) group.

Additional, non-limiting examples of Extracellular Targeting Ligands include:

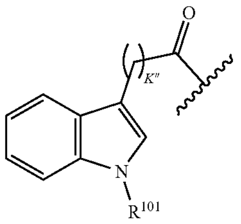

and

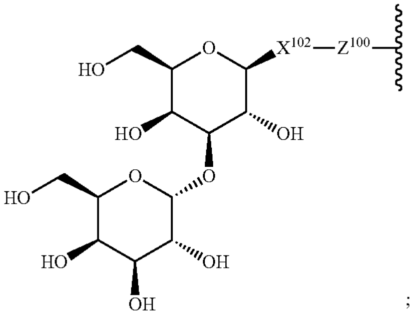

;

wherein $X^{102}$ is CH, O, N—$R^{101}$, or S, preferably O;

$R^{101}$ is H or $C_1$-$C_3$ alkyl; and

Z is a bond, a monosaccharide, disaccharide, oligosaccharide, more preferably a sugar group selected from the monosaccharides, including aldoses and ketoses, and disaccharides, including those disaccharides described herein. Monosaccharide aldoses include monosaccharides such as aldotriose (D-glyceraldehyde, among others), aldotetroses (D-erythrose and D-Threose, among others), aldopentoses, (D-ribose, D-arabinose, D-xylose, D-lyxose, among others), aldohexoses (D-allose, D-altrose, D-Glucose, D-Mannose, D-gulose, D-idose, D-galactose and D-Talose, among others), and the monosaccharide ketoses include monosaccharides such as ketotriose (dihydroxyacetone, among others), ketotetrose (D-erythrulose, among others), ketopentose (D-ribu!ose and D-xylulose, among others), ketohexoses (D-Psicone, D-Fructose, D-Sorbose, D-Tagatose, among others), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose; (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), b,b-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others.

TNF-α

In some embodiments, the Target Protein is human TNF-α (UniProtKB—P01375 (TNFA_HUMAN)). TNF-α is a pro-inflammatory cytokine active in the bodily immune response and serious inflammatory diseases. TNF-α has been implicated in a number of disorders, including but not limited to rheumatoid arthritis, inflammatory bowel disease, graft-vs-host disease, ankylosing spondylitis, psoriasis, hidradenitis suppurativa, refractory asthma, systemic lupis erythematosus, diabetes, and the induction of cachexia.

The Protein Data Bank website provides the crystal structure of TNF-α searchable by 6RMJ (Valentinis, B., et al., Int. J. Mol. Sci., 2019, 20); 5UUI (Carrington et al., Biophys J., 2017, 113 371-380); 6OOY, 6OOZ and 6OPO (O'Connell, J., et al., Nat. Commun., 2019, 10 5795-5795); and 5TSW (Cha, S. S., J Biol Chem., 1998, 273 2153-2160); as well as the crystal structure of TNF-α bound to various compounds searchable by 5YOY (Ono et al., Protein Sci., 2018, 27 1038-1046); 2AZ5 (He., M. M., et al., Science, 2005, 310: 1022-1025); 5WUX (Lee, J. U., Int J Mol Sci., 2017, 18); 5MU8 (Blevitt et al., J Med Chem., 2017, 60 3511-3517); 4Y60 (Feldman J. L., et al., Biochemistry, 2015, 54 3037-3050); 3WD5 (Hu, S., et al., J Biol Chem, 2013, 288 27059-27067); and 4G3Y (Liang, S. Y., J Biol Chem., 2013, 288 13799-13807).

Representative TNF-α Targeting Ligands are provided in FIG. 1. Additional TNF-α Targeting Ligands can be found in, for example, U.S. Pat. No. 8,541,572; J Chem Inf Model. 2017 May 22; 57(5): 1101-1111; each of which is incorporated by reference herein.

IL-1

In some embodiments, the Target Protein is human interleukin-1 (IL-1) (UniProtKB—P01584 (IL1B_HUMAN)). IL-1 is a potent proinflammatory cytokine. Initially discovered as the major endogenous pyrogen, induces prostaglandin synthesis, neutrophil influx and activation, T-cell activation and cytokine production, B-cell activation and antibody production, and fibroblast proliferation and collagen production. IL-1 promotes Th17 differentiation of T-cells, and Synergizes with IL12/interleukin-12 to induce IFNG synthesis from T-helper 1 (Th1) cells. IL-1 has been implicated in a number of auto-inflammatory and autoimmune disorders, including, but not limited to, Blau syndrome, cryopyrin-associated periodic syndromes, familial Mediterranean fever, Majeed syndrome; mevalonate kinase deficiency syndrome, pyogenic arthritis-pyoderma gangrenosum-acne syndrome, tumor necrosis factor receptor-associated periodic syndrome, Behçet's Disease, Sjogren's Syndrome, gout and chondrocalcinosis, periodic fever, aphthous stomatitis, pharyngitis, and cervical adenitis (or PFAPA) syndrome, rheumatoid arthritis, Type 2 diabetes mellitus, acute pericarditis, Chronic interstitial lung diseases (ILDs), Still's Disease, The Protein Data Bank website provides the crystal structure of IL-1 searchable by 9ILB (Yu, B., et al., Proc Natl Acad Sci USA, 1999, 96 103-108); 1I1B (Finzel, B. C., et al., J Mol Biol., 1989, 209 779-791); and 3040 (Wang et al., Nat. Immunol., 2010, 11: 905-911); as well as the crystal structure of IL-1 bound to various compounds searchable by 4G6J (Blech, M., et al., J Mol Biol., 2013, 425 94-111); 5BVP (Rondeau e al., MAbs, 2015, 7 1151-1160); and 3LTQ (Barthelmes, K., et al., J Am Chem. Soc., 2011, 133 808-819). Additionally, Guy et al., provides insight into the crystal structure of a small antagonist peptide bound to interleukin-1 receptor type 1 (Guy et al., The Journal of Biological Chemistry, 2000, 275, 36927-36933).

Potential IL-1 direct or indirect inhibitors are described in FIG. 1. Additional IL-1 Targeting Ligands can be found in, for example, U.S. Pat. No. 9,694,015, each of which is incorporated herein by reference. Additional binding ligands include rilonacept or a binding fragment thereof (J Rheumatol. 2012; 39:720-727 (2012); and Canakinumab, or a binding fragment thereof (J Rheumatol. 2004; 31:1103-1111).

IL-2

In some embodiments, the Target Protein is human interleukin-2 (IL-2) (UniProtKB—P60568 (IL2_HUMAN)). IL-2 is a potent pro-inflammatory cytokine. IL-2 has been implicated in host versus graft rejection and other autoimmune disorders.

The Protein Data Bank website provides the crystal structure of IL-2 searchable by 1M4C and 1M47 (Arkin, M. R., et al., Proc. Natl. Acad. Sci. USA, 2003, 100: 1603-1608); as well as the crystal structure of IL-2 bound to various compounds searchable by 4NEJ and 4NEM (Brenke, R., et al.); 1QVN (Thanos, C. D., et al., Proc Natl Acad Sci USA, 2006, 103 15422-15427); 1PW6 and 1PY2 (Thanos, C. D., et al., J Am Chem Soc., 2003, 125 15280-15281); 1NBP (Hyde, J., et al., Biochemistry, 2003, 42 6475-6483); and 1M48, 1M49, 1M4A, 1M4B, and 1M4C (Arkin, M. R., et al., Proc Natl Acad Sci USA, 2003, 100 1603-1608). Additionally, Stauber, D. J., et al, provides insight into the crystal structure of the IL-2 signaling complex: paradigm for a heterotrimeric cytokine receptor (Stauber, D. J., et al., PNAS, 2006, 103(8), 2788-2793).

Representative IL-2 Targeting Ligands are provided in FIG. 1. Additional IL-2 Targeting Ligands can be found in, for example, U.S. Pat. Nos. 8,802,721; 9,682,976, 9,708,268; Eur J Med Chem 83: 294-306 (2014), J Med Chem 60: 6249-6272 (2017); Nature 450: 1001-1009 (2007); each of which is incorporated by reference herein.

IL-6

In some embodiments, the Target Protein is human interleukin-6 (IL-6) (UniProtKB—P05231 (IL6_HUMAN)). IL-6 is a cytokine with a wide variety of biological functions. It is a potent inducer of the acute phase response and plays an essential role in the final differentiation of B-cells into Ig-secreting cells. It is also involved in lymphocyte and monocyte differentiation. It also acts on B-cells, T-cells, hepatocytes, hematopoietic progenitor cells and cells of the CNS, and is required for the generation of T(H)17 cells. IL-6 has been implicated in a number of inflammatory diseases and cancers, including, but not limited to, Castleman's disease, metastatic castration-associated prostate cancer, renal cell carcinoma, large-cell lung carcinoma, ovarian cancer, rheumatoid arthritis, asthma.

The Protein Data Bank website provides the crystal structure of IL-6 searchable by 1P9M (Boulanger, M. J., et al., Science, 2003, 300: 2101-2104); IALU (Somers et al., EMBO J., 1997, 16, 989-997); 1IL6 and 2IL6 (Xu, G. Y., et al., J Mol Biol., 1997, 268 468-481) and $1N_{26}$ (Varghese et al., Proc Natl Acad Sci USA., 2002, 99 15959-15964); as well as the crystal structure of IL-6 bound to various compounds searchable by 4CNI (Shaw, S., et al., Mabs, 2014, 6: 773); and 4NI7 and 4NI9 (Gelinas et al., J Biol Chem. 2014, 289(12), 8720-8734). Additionally, Gelinas et al., provides insight into the crystal structure of interleukin-6 in complex with a modified nucleic acid ligand (Gelinas, A. D., et al., J Biol Chem. 2014, 289(12), 8720-8734); and Somers et al., provides insight into the crystal structure of interleukin 6: implications for a novel mode of receptor dimerization and signaling.

Potential IL-6 direct or indirect inhibitors are provided in FIG. 1. Additional potential IL-6 direct or indirect inhibitors can be found in, for example, U.S. Pat. No. 8,901,310; U.S. patent Ser. No. 10/189,796; U.S. Pat. No. 9,694,015; each incorporated herein by reference. In another embodiment the IL-6 Extracellular Targeting Ligand is AvimarC326 or a binding fragment thereof which is described in Nat Biotechnol 23, 1556-1561 (2005).

IFN-γ

In some embodiments, the Target Protein is human interferon-γ (IFN-7) (UniProtKB—Q14609 (Q14609_HUMAN)). IFN-γ is a immunoregulatory cytokine. IFN-γ has been implicated in a number of autoimmune disorders, including, but not limited to rheumatoid arthritis, multiple sclerosis (MS), corneal transplant rejection, and various autoimmune skin diseases such as psoriasis, alopecia areata, vitiligo, acne vulgaris, and others.

The Protein Data Bank website provides the crystal structure of IFN-γ searchable by 1HIG (Ealick, S. E., et al., Science 252, 1991, 698-702); as well as the crystal structure of IFN-γ bound to various compounds searchable by 6 E3K and 6 E3L (Mendoza, J. L., et al., Nature, 2019, 567 56-60). Additionally, Randal et al., provides insight into the structure and activity of a monomeric interferon-γ: α-chain receptor signaling complex (Randal, M., et al., Structure, 2001, 9(2), 155-163).

Representative IFN-γ Targeting Ligands are described in FIG. 1. Additional IFN-γ Targeting Ligands can be found in, for example, J Med Chem 57: 4511-20 (2014); which is incorporated by reference herein.

Vascular Epithelial Growth Factor (VEGF)

In some embodiments, the Target Protein is human vascular epithelial growth factor (VEGF) (UniProtKB—P15692 (VEGFA_HUMAN)). VEGF is a growth factor active in angiogenesis, vasculogenesis, and endothelial cell growth. VEGF induces endothelial cell proliferation, promotes cell migration, inhibits apoptosis and induces permeabilization of blood vessels. VEGF has been implicated in the vascularization and angiogenesis of tumors.

The Protein Data Bank website provides the crystal structure of VEGF searchable by 3QTK (Mandal, K., et al., Angew Chem Int Ed Engl., 2011, 50 8029-8033); and 4KZN (Shen et al.); as well as the crystal structure of VEGF bound to various compounds searchable by 504 E (Lobner, E., et al., MAbs, 2017, 9 1088-1104); 4QAF (Giese, T., et al.); 5DN2 (Tsai, Y. C. I., et al., FEBS, 2017, J 283 1921-1934); 4GLS (Mandal, K., et al., Proc Natl Acad Sci USA, 2012, 109 14779-14784); and 1KMX (Stauffer, M. E. et al., J Biomol NMR, 2002, 23 57-61). Additionally, Mueller, Y. A., et al, provides insight into the Crystal structure and functional mapping of the kinase domain receptor binding site of VEGF (Mueller, Y. A., et al., Proc Natl Acad Sci USA., 1997 Jul. 8; 94(14): 7192-7197).

Representative VEGF Targeting Ligands are provided in FIG. 1. Additional VEGF Targeting Ligands include, but are not limited to, (all cited referenced incorporated herein by reference) the peptide VEPNCDIHVMWEWECFERL-$NH_2$ (Biochemistry 1998, 37, 17754-177764). Additional VEGF Targeting Ligands are provided in, for example, J Med Chem 57: 3011-29 (2014), U.S. Pat. Nos. 9,884,843, 9,446,026, J Med Chem 53: 1686-99 (2010), J Med Chem 48: 8229-36 (2005), J Nat Prod 76: 29-35 (2013), each of which is incorporated herein by reference.

Transforming Growth Factor-β1 (TGF-β1)

In some embodiments, the Target Protein is human transforming growth factor-β1 (TGF-β1) (UniProtKB—P01137 (TGFB1_HUMAN)). TGF-β1 is a multifunctional protein that regulates the growth and differentiation of various cell types and is involved in various processes, such as normal development, immune function, microglia function and responses to neurodegeneration. TGF-β1 can promote either T-helper 17 cells (Th17) or regulatory T-cells (Treg) lineage differentiation in a concentration-dependent manner. TGF-β1 expression in the tumor microenvironment has been associated with a poor prognosis, and is implicated in TGF-β1 mediated tumor suppression via T-cell exclusion. TGF-β1 expression has also been implicated in hematological malignancies and fibrosis.

The Protein Data Bank website provides the crystal structure of TGF-β1 searchable by 5 E8S, 5 E8T, and 5 E8U (Tebben, A. J., et al., Acta Crystallogr D Struct Biol., 2016, 72 658-674); 2L5S (Zuniga, J. E., et al, J Mol Biol., 2011, 412 601-618); and 2PJY (Groppe, J., et al., Mol Cell, 2008, 29 157-168); as well as the crystal structure of TGF-β1 bound to various compounds searchable by 5QIK, 5QIL and 5QIM, (Zhang, Y., et al., ACS Med Chem Lett., 2018, 9 1117-1122); 6B8Y (Harikrishnan, L. S., et al., Bioorg Med Chem., 2018, 26 1026-1034); 5 E8W, 5 E8X, 5 E8Z, and 5 E90 (Tebben, A. J., et al., Acta Crystallogr D Struct Biol., 2016, 72 658-674); 3TZM (Ogunjimi, A. A. et al., Cell Signal, 2012, 24 476-483); 2X7O (Roth, G. J., et al., J Med Chem., 2010, 53 7287); 3KCF (Guckian, K., et al., Bioorg Med Chem Lett., 2010, 20 326-329); 3FAA (Bonafoux, D., et al., Bioorg Med Chem Lett., 2009, 19 912-916); 1VJY (Gellibert, F, J., et al., J Med Chem., 2004 47 4494-4506); and 1PY5 (Sawyer, J. S., et al., Bioorg Med Chem Lett., 2004, 14 3581-3584). Additionally, Hinck et al., provides insight into the structural studies of the TGF-βs and their receptors and further insight into evolution of the TGF-β superfamily (Hinck, A., FEBS, 2012, 586(14), 1860-1870).

Representative TGF-β1 Targeting Ligands are provided in FIG. 1. In some embodiments, the TGF-β1 Targeting Ligand is the peptide KRFK peptide (J. Biol. Chem. Vol. 274 (No. 19) pp. 13586-13593 (1999)(incorporated herein by reference). Additional TGF-β1 Targeting Ligands are provided in, for example, Bioorg Med Chem Lett 21: 5642-5 (2011), which is incorporated herein by reference.

Proprotein Convertase Subtilisin/Kexin Type 9 (PCSK-9)

In some embodiments, the Target Protein is human proprotein convertase subtilisin/kexin type 9 (PCSK-9) (UniProtKB—Q8NBP7 (PCSK9_HUMAN)). PCSK-9 is a crucial player in the regulation of plasma cholesterol homeostasis. PCSK-9 binds to low-density lipid receptor family members: low density lipoprotein receptor (LDLR), very low-density lipoprotein receptor (VLDLR), apolipoprotein E receptor (LRP1/APOER) and apolipoprotein receptor 2 (LRP8/APOER2), and promotes their degradation in intracellular acidic compartments. It acts via a non-proteolytic mechanism to enhance the degradation of the hepatic LDLR through a clathrin LDLRAP1/ARH-mediated pathway, and may prevent the recycling of LDLR from endosomes to the cell surface or direct it to lysosomes for degradation. PCSK-9 has been implicated in high blood cholesterol and the development of cardiovascular disease.

The Protein Data Bank website provides the crystal structure of PCSK-9 searchable by 2P4 E (Cunningham, D., et al., Nat Struct Mol Biol., 2007, 14 413-419); as well as the crystal structure of PCSK-9 bound to various compounds searchable by 3BPS (Kwon, H. J., et al., Proc Natl Acad Sci USA, 2008, 105 1820-1825); 6U26, 6U2N, 6U2P, 6U36, 6U38, and 6U3X (Petrilli, W. L., et al., Cell Chem Biol., 2019, 27 32-40.e3); 50CA (Gustafsen, C., et al., Nat Commun., 2017, 8 503-503); 4NE9 (Schroeder, C. I., et al., Chem Biol., 2014, 21 284-294); 40V6 (Mitchell, T., et al., J Pharmacol Exp Ther., 2014, 350 412-424); and 4NMX (Zhang, Y., et al., J Biol Chem., 2014, 289 942-955). Additionally, Piper et al., provides insight into the crystal structure of PCSK9 (Piper, D. E., et al., Structure, 2007, 15(5), 545-52).

Representative PCSK-9 Targeting Ligands are provided in FIG. 1. In some embodiments, the PCSK-9 Targeting Ligand is the peptide TVFTSWEEYLDWV (J. Bio. Chem. 2014 January; 289(2):942-955, incorporated herein by reference). Additional PCSK-9 Targeting Ligands are provided in, for example, U.S. Pat. No. 9,227,956, J Biol Chem 289: 942-55 (2014), each of which is incorporated by reference herein.

IL-21

In some embodiments, the Target Protein is human interleukin-21 (IL-21) (UniProtKB—Q9HBE4 (IL21_HUMAN)). IL-21 is an immunoregulatory cytokine. IL-21 has been implicated in a number of autoimmune disorders, including Sjögren's syndrome, systemic lupus erythematosus, type 1 diabetes, multiple sclerosis, rheumatoid arthritis, and inflammatory bowel disease.

The Protein Data Bank website provides the crystal structure of IL-21 searchable by 2OQP (Bondensgaard, K., et al., J Biol Chem., 2007, 282 23326-23336); and 4NZD (Hamming et al.); as well as the crystal structure of IL-21 bound to various compounds searchable by 3TGX (Hamming, O. J., et al., J Biol Chem., 2012, 287(12), 9454-9460).

Representative IL-21 Targeting Ligands are described in FIG. 1. Additional IL-21 Targeting Ligands can be found in, for example, U.S. Pat. No. 9,701,663, which is incorporated herein by reference.

IL-22

In some embodiments, the Target Protein is human interleukin-22 (IL-22) (UniProtKB—Q9GZX6 (IL22_HUMAN)). IL-22 is a member of IL-10 family cytokines that is produced by many different types of lymphocytes including both those of the innate and adaptive immune system. IL-22 has been implicated in a number of autoimmune disorders, including, but not limited to, graft versus host disease (GVHD), psoriasis, rheumatoid arthritis, atopic dermatitis, and asthma.

The Protein Data Bank website provides the crystal structure of IL-22 searchable by 1M4R (Nagem, R. A. P., et al., Structure, 2002, 10 1051-1062); as well as the crystal structure of IL-22 bound to various compounds searchable by 3DGC (Jones, B. C. et al., Structure, 2008, 16 1333-1344).

Representative IL-22 Targeting Ligands are described in FIG. 1. Additional IL-22 Targeting Ligands can be found in, for example, U.S. Pat. No. 9,701,663, which is incorporated herein by reference.

IL-10

In some embodiments, the Target Protein is human interleukin-10 (IL-10) (UniProtKB—P22301 (IL10_HUMAN)). IL-10 is an inflammatory cytokine. IL-10 has been implicated in tumor survival and protection against cytotoxic chemotherapeutic drugs.

The Protein Data Bank website provides the crystal structure of IL-10 searchable by 2ILK (Zdanov, A et al., Protein Sci., 1996, 5 1955-1962); 1ILK (Zdanov, A. et al., Structure, 1995, 3 591-601); 2H24 (Yoon, S. I., et al., J Biol Chem., 2006, 281 35088-35096) and 3LQM (Yoon, S. I., et al., Structure, 2010, 18 638-648). Additionally, Zdanov, A., et al, provides insight into crystal structure of IL-10 (Zdanov A., Current Pharmaceutical design, 2004, 10, 3873-3884).

Representative IL-10 Targeting Ligands are provided in FIG. 1. Additional IL-10 Targeting Ligands can be found, for example, in ACS Chem Biol 11: 2105-11 (2016), which is incorporated herein by reference.

IL-5

In some embodiments, the Target Protein is human interleukin-5 (IL-5) (UniProtKB—P05113 (IL5 HUMAN)). IL-5 is a cytokine that regulates eosinophil maturation, recruitment, and survival. IL-5 has been implicated in a number of allergic disorders, including, but not limited to, asthma, nasal polyposis, atopic dermatitis, eosinophilic esophagitis, hypereosinophilic syndrome, and Churg-Strauss syndrome.

The Protein Data Bank website provides the crystal structure of IL-5 searchable by 1HUL (Milburn, M. V., Nature, 1993, 363, 172-176) and 3VA2 (Kusano et al., Protein Sci., 2012, 21(6), 850-864); as well as the crystal structure of IL-5 bound to various compounds searchable by 1OBX and 1OBZ (Kang, B. S., et al., Structure, 2003, 11, 845).

Representative IL-5 Targeting Ligands are provided in FIG. 1. Additional IL-5 Targeting Ligands can be found, for example, in Bioorg Med Chem 18: 4441-5 (2010); Bioorg Med Chem 18: 4625-9 (2011); Bioorg Med Chem 21: 2543-50 (2013); Eur J Med Chem 59: 31-8 (2013); Bioorg Med Chem 23: 2498-504 (2015); Bioorg Med Chem 20: 5757-62 (2012); each of which is incorporated by reference herein.

IL8

In some embodiments, the Target Protein is human interleukin-8 (IL-8) (UniProtKB—P10145 (IL8_HUMAN)). IL-8 is a chemotactic factor that attracts neutrophils, basophils, and T-cells, but not monocytes. It is also involved in neutrophil activation. It is released from several cell types in response to an inflammatory stimulus. IL-8 has been implicated in the promotion of tumor progression, immune escape, epithelial-mesenchymal transition, and recruitment of myeloid-derived suppressor cells. Studies have demonstrated that high serum IL-8 levels correlate with poor prognosis in many malignant tumors. Preclinical studies have shown that IL-8 blockade may reduce mesenchymal features in tumor cells, making them less resistant to treatment.

The Protein Data Bank website provides the crystal structure of IL-8 searchable by 3IL8 (Baldwin, E. T., et al., Proc Natl Acad Sci USA, 1991, 88, 502-506); and 1IL8 and 2IL8 (Clore, G. M., et al., Biochemistry, 1990, 29, 1689-1696); as well as the crystal structure of IL-8 bound to various compounds searchable by 1ILP and 1ILQ (Skelton, N, J., et al., Structure, 1999, 7, 157-168); and 1ROD (Sticht, H., et al., Eur J Biochem., 1996, 235, 26-35); 4XDX (Ostrov et al.) and 5WDZ (Beckamp, S., J Biomol NMR, 2017, 69, 111-121).

Representative IL-8 Targeting Ligands are provided in FIG. 1. Additional IL-8 Targeting Ligands can be found in, for example, Bioorg Med Chem Lett 19: 4026-30 (2009), which is incorporated by reference herein.

Cholinesterase

In some embodiments, the Target Protein is human cholinesterase (UniProtKB—P06276 (CHLE_HUMAN)). Cholinesterase contributes to the inactivation of the neurotransmitter acetylcholine. Inhibition of cholinesterase results in increased levels of acetylcholine in the synaptic cleft (the space between two nerve endings). The main use of cholinesterase inhibitors is for the treatment of dementia in patients with Alzheimer's disease. People with Alzheimer's disease have reduced levels of acetylcholine in the brain. Cholinesterase inhibitors have been shown to have an effect on dementia symptoms such as cognition.

The Protein Data Bank website provides the crystal structure of cholinesterase searchable by 1P0I and 1P0Q (Nicolet, Y., et al., J Biol Chem., 2003, 278, 41141-41147); as well as the crystal structure of cholinesterase bound to various compounds searchable by 1P0M and 1P0P (Nicolet, Y., et al., J Biol Chem., 2003, 278, 41141-41147); 2J4C (Frasco, M. F., et al., FEBS J., 2007, 274 1849); 4BDT, 4BDS (Nachon, F., et al., Biochem J, 2013, 453, 393-399); 1GQR and 1GQS (Bar-on, P., et al., Biochemistry, 2002, 41, 3555); 3DJY and 3DKK (Carletti, E., et al., J Am Chem Soc., 2008, 130, 16011-16020); 4AXB, 4B00, 4BOP, and 4BBZ (Wandhammer, M., et al., Chem Biol Interact., 2013, 203, 19); 1DX6 (Greenblatt, H. M., et al., FEBS Lett., 1999, 463 321); 1GPK and 1GPN (Dvir, H., et al., Biochemistry, 2002, 41, 10810); 6CQY (Bester, S. M., et al., Chem Res Toxicol., 2018, 31, 1405-1417); 1XLV and 1XLW (Nachon, F., et al., Biochemistry, 2005, 44, 1154-1162); 2Y1K (Carletti, E., et al., Chem Res Toxicol., 2011, 24, 797); and 2WIG, 2WIJ, 2WIK, 2WIL, and 2WSL (Carletti, E., et al., Biochem J., 2009, 421, 97-106). Additionally, Ahmad et al., provides insight into the isolation, crystal structure determination and cholinesterase inhibitory potential of isotalatizidine hydrate from delphinium denudatum (Ahmad H., et al., Journal Pharmaceutical Biology, 2016, 55(1), 680-686).

Representative cholinesterase Targeting Ligands are provided in FIG. 1. Additional Targeting Ligands can be found in, for example, ACS Med Chem Lett 4: 1178-82 (2013); J Med Chem 49: 3421-5 (2006); Eur J Med Chem 55: 23-31 (2012); J Med Chem 51: 3154-70 (2008); J Med Chem 46: 1-4 (2002); Eur J Med Chem 126: 652-668 (2017); Biochemistry 52: 7486-99 (2013); Bioorg Med Chem 23: 1321-40 (2015); which are each incorporated herein by reference.

C—C Motif Chemokine Ligand 2 (CCL2)

Grygiel et al., provides insight into the synthesis by native chemical ligation and crystal structure of human CCL2 (Grygiel, T. L., et al., Biopolymers, 2010, 94(3), 350-9).

In some embodiments, the Target Protein is human C—C motif chemokine ligand 2 (CCL2) (UniProtKB—P13500 (CCL2_HUMAN)). CCL2 acts as a ligand for C—C chemokine receptor CCR2. CCL2 signals through binding and activation of CCR2 and induces a strong chemotactic response and mobilization of intracellular calcium ions. CCL2 exhibits a chemotactic activity for monocytes and basophils but not neutrophils or eosinophils.

CCL2 has been implicated in the recruitment of monocytes into the arterial wall during the disease process of atherosclerosis.

Representative CCL2 Targeting Ligands are provided in FIG. 1. Additional CCL2 Targeting Ligands can be found in, for example, J Med Chem 56: 7706-14 (2013), which is incorporated herein by reference.

Carboxypeptidase B2

In some embodiments, the Target Protein is human carboxypeptidase B2 (UniProtKB—Q96IY4 (CBPB2_HUMAN)). Carboxypeptidase B2, also known as thrombin activatable fibrinolysis inhibitor (TAFIa), cleaves C-terminal arginine or lysine residues from biologically active peptides such as kinins or anaphylatoxins in the circulation thereby regulating their activities. It down-regulates fibrinolysis by removing C-terminal lysine residues from fibrin that has already been partially degraded by plasmin. Carboxypeptidase B2 has been implicated and targeted to inhibit thrombosis.

The Protein Data Bank website provides the crystal structure of carboxypeptidase B2 (also known as thrombin-activatable fibrinolysis inhibitor (TAFI)) searchable by 3D66 (Marx, P. F., et al., Blood, 2008, 112, 2803-2809); 3DGV (Anand, K., et al., JBC, 2008, 283, 29416-29423); and 1KWM (Barbosa Pereira, P. J., et al., J Mol Biol., 2002, 321, 537-547); as well as the crystal structure of TAFI bound to various compounds searchable by 3D67 (Marx, P. F., et al., Blood, 2008, 112, 2803-2809); 5HVF, 5HVG, 5HVH (Zhou, X., et al., J Thromb Haemost., 2016, 14, 1629-1638); and 3LMS (Sanglas, L., et al., J Thromb Haemost., 2010, 8, 1056-1065). Additionally, Schreuder et al., provides insight into the interaction of TAFI and anabaenopeptin, a highly potent inhibitor of TAFI (Schreuder, H., et al., Sci Rep., 2016, 6, 32958).

Representative carboxypeptidase B2 Targeting Ligands are provided in FIG. 1. Additional carboxypeptidase B2 Targeting Ligands can be found in, for example, Bioorg Med Chem Lett 20: 92-6 (2010), J Med Chem 50: 6095-103 (2007), Bioorg Med Chem Lett 14: 2141-5 (2004), J Med Chem 58: 4839-44 (2015), J Med Chem 55: 7696-705 (2012), J Med Chem 59: 9567-9573 (2016), Bioorg Med Chem Lett 17: 1349-54 (2007), U.S. Pat. Nos. 9,662,310, 8,609,710, 9,688,645, J Med Chem 46: 5294-7 (2003), each of which is incorporated herein by reference.

Neutrophil Elastase

In some embodiments, the Target Protein is human neutrophil elastase (UniProtKB—P08246 (ELNE_HUMAN)). Neutrophil elastase modifies the functions of natural killer cells, monocytes and granulocytes. Inhibits $C_5$a-dependent neutrophil enzyme release and chemotaxis.

Neutrophil elastase has been implicated in a number of disorders, including lung disease, chronic obstructive pulmonary disease, pneumonia, respiratory distress, and acute lung injury (ALI), and cystic fibrosis, as well as chronic kidney disease.

The Protein Data Bank website provides the crystal structure of human neutrophil elastase bound to various compounds searchable by 3Q76 and 3Q77 (Hansen, G., et al., J. Mol. Biol., 2011, 409, 681-691); 5ABW (Von Nussbaum, et al., Bioorg Med Chem Lett., 2015, 25, 4370-4381); 1B0F (Cregge, R. J., et al., J Med Chem., 1998, 41, 2461-2480); 1H1B (Macdonald, S. J. F., et al., J Med Chem., 2002, 45, 3878); 2Z7F (Koizumi, M., et al., J Synchrotron Radiat., 2008, 15 308-311); 5A09, 5A0A, 5A0B, and 5A0C (Von Nussbaum, F., et al., Chem Med Chem., 2015, 10, 1163-1173); 5A8X, 5A8Y and 5A8Z (Von Nussbaum, F., et al., ChemMedChem., 2016, 11, 199-206); 1HNE (Navia, M. A., et al., Proc Natl Acad Sci USA, 1989, 86, 7-11); 6F5M (Hochscherf, J., et al., Acta Crystallogr F Struct Biol Commun., 2018, 74, 480-489); and 4WVP (Lechtenberg, B. C., et al., ACS Chem Biol., 2015, 10, 945-951).

Representative neutrophil elastase Targeting Ligands are provided in FIG. 1. Additional neutrophil elastase Targeting Ligands can be found in, for example, J Med Chem 53: 241-53 (2010), J Med Chem 38: 739-44 (1995), J Med Chem 37: 2623-6 (1994), J Med Chem 38: 4687-92 (1995), J Med Chem 45: 3878-90 (2002), Bioorg Med Chem Lett 5: 105-109 (1995), Bioorg Med Chem Lett 11: 243-6 (2001), J Med Chem 40: 1906-18 (1997), Bioorg Med Chem Lett 25: 4370-81 (2015), U.S. Pat. Nos. 8,569,314, 9,174,997, 9,290, 457, each of which is incorporated herein by reference.

Factor Xa

In some embodiments, the Target Protein is human Factor Xa (UniProtKB—P00742 (FA10_HUMAN)). Factor Xa is a vitamin K-dependent glycoprotein that converts prothrombin to thrombin in the presence of factor Va, calcium and phospholipid during blood clotting.

Factor X has been implicated in the development of deep vein thrombosis and acute pulmonary embolism, and the risk of stroke and embolism in people with nonvalvular atrial fibrillation.

The Protein Data Bank website provides the crystal structure of Factor Xa bound to various compounds searchable by 1G2L and 1G2M (Nar, H., et al., Structure, 2001, 9, 29-38); 2PR3 (Nan huis, C. A., et al., Chem Biol Drug Des., 2007, 69, 444-450); 2UWP (Young, R. J., et al., Bioorg Med Chem Lett., 2007, 17, 2927); 2VVC, 2VVV, 2VVU, 2VWL, 2VWM, 2VWN and 2VWO (Zbinden, K. G., et al., Eur J Med Chem., 2009, 44, 2787); 4Y6D, 4Y71, 4Y7A, 4Y7B, 4zh8, 4ZHA (Convery, M. A. et al.); 4Y76, 4Y79, 2J94 and 2J95 (Chan, C., et al., J Med Chem., 2007, 50 1546-1557); 1FAX (Brandstetter, H., et al., J Biol Chem., 1996, 271, 29988-29992); 2JKH (Salonen, L. M., et al., Angew Chem Int Ed Engl., 2009, 48, 811); 2PHB (Kohrt, J. T., et al., Chem Biol Drug Des., 2007, 70, 100-112); 2W26 (Roehrig, S., et al., J Med Chem., 2005, 48, 5900); 2Y5F, 2Y5G and 2Y5H (Salonen, L. M., et al., Chemistry, 2012, 18, 213); 3Q3K (Yoshikawa, K., et al., Bioorg Med Chem Lett., 2011, 21, 2133-2140); 2BMG (Matter, K., et al., J Med Chem., 2005, 48, 3290); 2BOH, 2BQ6 2BQ7, and 2BQW (Nazare, M., et al., J Med Chem., 2005, 48, 4511); 2CJI (Watson, N. S., et al, Bioorg Med Chem Lett., 2006, 16, 3784); 2J2U, 2J34, 2J38, 2J41 (Senger, S., et al., Bioorg Med Chem Lett., 2006, 16 5731); 3IIT (Yoshikawa, K., et al., Bioorg Med Chem., 2009, 17 8221-8233); 1EZQ, 1FOR and 1FOS (Maignan, S., et al., J Med Chem., 2000, 43, 3226-3232); 1FJS (Adler, M., et al., Biochemistry, 2000, 39, 12534-12542); 1KSN (Guertin, K. R., et al., Bioorg Med Chem Lett., 2002, 12, 1671-1674); 1NFU, 1NFW, 1NFX and 1NFY (Maignan, S., et al., J Med Chem., 2003, 46, 685-690); 2XBV, 2XBW, 2XBX, 2XBY, 2XC0, 2XC4 and 2XC5 (Anselm, L., et al., Bioorg Med Chem Lett., 2010, 20, 5313); 4A7I (Nazare, M., et al., Angew Chem Int Ed Engl., 2012, 51, 905); 4BTI, 4BTT and 4BTU (Meneyrol, L., et al., J Med Chem., 2013, 56, 9441); 3FFG, 3KQB, 3KQC, 3KQD and 3KQE (Quan, M. L., et al., Bioorg Med Chem Lett., 2010, 20, 1373-1377); 2P93, 2P94 and 2P95 (Qiao, J. X., et al., Bioorg Med Chem Lett., 2007, 17, 4419-4427); 1V3X (Haginoya, N., et al., J Med Chem., 2004, 47, 5167-5182); 2P16 (Pinto, D. J. P., et al., J Med Chem., 2007, 50, 5339-5356); 2RA0 (Lee, Y. K., et al., J Med Chem., 2008, 51, 282-297); 3SW2 (Shi, Y., et al., Bioorg Med Chem Lett., 2011, 21, 7516-7521); 2VH6 (Young, R. J., et al., Bioorg Med Chem Lett., 2008, 18, 23); 2WYG and 2WYJ (Kleanthous, S., et al., Bioorg Med Chem Lett., 2010, 20, 618); 2Y7X (Watson, N. S., et al., Bioorg Med Chem Lett., 2011, 21, 1588); 2Y7Z, 2Y80, 2Y81 and 2Y82 (Young, R. J., et al., Bioorg Med Chem Lett., 2011, 21, 1582); 3KL6 (Fujimoto, T., et al., J Med Chem., 2010, 53, 3517-3531); 3LIW (Meuller, M. M., et al., Biol.Chem., 2003, 383, 1185); 5K0H (Schweinitz, A., et al., Med Chem., 2006, 2, 349-361); 1XKA and 1XKB (Kamata, K., et al., Proc Natl Acad Sci USA, 1998, 95, 6630-6635); 2EI6 and 2EI7 (Nagata, T., et al., Bioorg Med Chem Lett., 2007, 17, 4683-4688); 2P3T (Ye, B., et al., J Med Chem., 2007, 50, 2967-2980); 1MQ5 and 1MQ6 (Adler, M., et al., Biochemistry, 2002, 41, 15514-15523); 3K9X and 3HPT (Shi, Y., et al., Bioorg Med Chem Lett., 2009, 19, 6882-6889); 3CEN (Corte, J. R., et al., Bioorg Med Chem Lett., 2008, 18, 2845-2849); 2W3I and 2W3K (Van Huis, C. A., et al., Bioorg Med Chem., 2009, 17, 2501); 2H9 E (Murakami, M. T., et al., J Mol Biol., 2007, 366, 602-610); 1WU1 and 2D1J (Komoriya, S., et al., Bioorg Med Chem., 2005, 13, 3927-3954); 2G00 (Pinto, D. J. P., et al., Bioorg Med Chem Lett., 2006, 16, 5584-5589); 3M36 and 3M37 (Pruitt, J. R. et al., J Med Chem., 2003, 46, 5298-5315); 3CS7 (Qiao, J. X., et al., Bioorg Med Chem Lett., 2008, 18, 4118-4123); 1Z6 E (Quan, M. L., et al., J Med Chem., 2005, 48, 1729-1744); 2FZZ (Pinto, D. J. P., et al., Bioorg Med Chem Lett., 2006, 16, 4141-4147); and 3ENS (Shi, Y., et al., J Med Chem., 2008, 51, 7541-7551).

Representative Factor Xa Targeting Ligands are provided in FIG. 1. Additional Factor Xa Targeting Ligands can be found in, for example, Bioorg Med Chem Lett 20: 5313-9 (2010), Bioorg Med Chem Lett 13: 679-83 (2003), J Med Chem 44: 566-78 (2001), J Med Chem 50: 2967-80 (2007), J Med Chem 38: 1511-22 (1995), Bioorg Med Chem Lett 18: 2845-9 (2008), J Med Chem 53: 6243-74 (2010), Bioorg Med Chem Lett 18: 2845-9 (2008), Bioorg Med Chem 16: 1562-95 (2008), each of which is incorporated herein by reference.

Factor XI

In some embodiments, the Target Protein is human Factor XI UniProtKB—P03951 (FA11_HUMAN). Factor XI triggers the middle phase of the intrinsic pathway of blood coagulation by activating factor IX.

Factor XI has been implicated in the development of deep vein thrombosis and acute pulmonary embolism, and the risk of stroke and embolism in people with nonvalvular atrial fibrillation.

The Protein Data Bank website provides the crystal structure of Factor XI bound to various compounds searchable by 1ZSL, 1ZTJ, 1ZTK, and 1ZTL (Nagafuji, P., et al.); 1ZOM (Lin, J., et al., J Med Chem., 2006, 49, 7781-7791); 5EOK and 5EOD (Wong, S. S., et al., Blood, 2016, 127, 2915-2923); 1ZHM, 1ZHP and 1ZHR (Jin, L., et al., Acta Crystallogr D Biol Crystallogr., 2005, 61, 1418-1425); 1ZMJ, 1ZLR, 1ZML and 1ZMN (Lazarova, T. I., Bioorg Med Chem Lett., 2006, 16, 5022-5027); 1ZRK, 1ZSJ and 1ZSK (Guo, Z., et al); 4CRA, 4CRB, 4CRC, 4CRD, 4CRE, 4CRF and 4CRG (Fjellstrom, O., et al., PLoS One, 2015, 10, 13705); 3SOR and 3SOS (Fradera, X., et al., Acta Crystallogr Sect F Struct Biol Cryst Commun., 2012, 68, 404-408); 1ZPB, 1ZPC, 2FDA (Deng, H., et. al., Bioorg Med Chem Lett., 2006, 16, 3049-3054); 5WB6 (Wang, C., et al., Bioorg Med Chem Lett., 2017, 27, 4056-4060); 4NA7 and 4NA8 (Quan, M. L., et al., J Med Chem., 2014, 57, 955-969); 4WXI (Corte, J. R., et al., Bioorg Med Chem Lett., 2015, 25, 925-930); 5QTV, 5QTW, 5QTX and 5QTY (Fang, T., et al., Bioorg Med Chem Lett., 2020, 126949-126949); 6C0S (Hu, Z., et al., Bioorg Med Chem Lett., 28, 987-992); 5QQP and 5QQO (Clark, C. G., et al., Bioorg Med Chem Lett., 2019, 29, 126604-126604); 5Q0D, 5Q0E, 5Q0F, 5Q0G, and 5Q0H (Corte, J. R., et al., Bioorg Med Chem Lett., 2017, 27, 3833-3839); 5QCK, 5QCL, 5QCM, and 5QCN (Pinto, D. J. P., et al., J Med Chem., 2017, 60, 9703-9723); 5TKS and 5TKU (Corte, J. R., et al., J Med Chem., 2017, 60, 1060-1075); 1XXD and 1XX9 (Jin, L., et al., J Biol Chem., 2005, 280, 4704-4712); 5QTT and 5QTU (Corte, J. R., et al., J Med Chem., 2019, 63, 784-803); 4TY6, 4TY7 (Hangeland, J. J., et al., J Med Chem., 2014, 57, 9915-9932); 4X6M, 4X6N, 4X60, and 4X6P (Pinto, D. J. P., et al., Bioorg Med Chem Lett., 2015, 25, 1635-1642); and 5EXM (Corte, J. R., et al., Bioorg Med Chem., 2016, 24, 2257-2272). Additionally, Al-Horani et al., provides insight into a review of patent literature regarding Factor Xia inhibitors (Al-Horani et al., Expert Opin Ther Pat. 2016; 26(3), 323-345).

Representative Factor XI Targeting Ligands are provided in FIG. 1. Additional Factor XI Targeting Ligands can be found in, for example, U.S. Pat. No. 9,783,530, U.S. patent Ser. No. 10/143,681, U.S. patent Ser. No. 10/214,512, ACS Med Chem Lett 6: 590-5 (2015), J Med Chem 60: 9703-9723 (2017), J Med Chem 60: 9703-9723 (2017), U.S. Pat. No. 9,453,018 (2016), J Med Chem 60: 1060-1075 (2017), J Med Chem 57: 955-69 (2014), each of which is incorporated herein by reference.

Factor XII

In some embodiments, the Target Protein is human Factor XII (UniProtKB—P00748 (FA12_HUMAN)). Factor XII is a serum glycoprotein that participates in the initiation of blood coagulation, fibrinolysis, and the generation of bradykinin and angiotensin. Prekallikrein is cleaved by factor XII to form kallikrein, which then cleaves factor XII first to alpha-factor XIIa and then trypsin cleaves it to beta-factor XIIa. Alpha-factor XIIa activates factor XI to factor XIa.

Factor XII has been implicated in the development of deep vein thrombosis and acute pulmonary embolism, and the risk of stroke and embolism in people with nonvalvular atrial fibrillation.

The Protein Data Bank website provides the crystal structure of factor XII bound to various compounds searchable by 4XDE and 4XE4 (Pathak, M., et al., J Thromb Haemost., 2015, 13(4), 580-591); 6GT6 and 6QF7 (Pathak, M., et al., Acta Crystallogr D Struct Biol., 2019, 75, 578-591); and 6B74 and 6B77 (Dementiev, A. A., et al., Blood Adv., 2018, 2, 549-558). Additionally, Pathak et al., provides insight into the crystal structure of factor XII (Pathak, M., et al., J Thromb Haemost., 2015, 13(4), 580-591).

Representative Factor XII Targeting Ligands are provided in FIG. 1. Additional Factor XII Targeting Ligands can be found in, for example, J Med Chem 60: 1151-1158 (2017), J Med Chem 48: 2906-15 (2005), J Med Chem 50: 5727-34 (2007), J Med Chem 50: 1876-85 (2007), Chembiochem 18: 387-395 (2017), each of which is incorporated herein by reference.

Factor XIII

In some embodiments, the Target Protein is human Factor XIII UniProtKB—P00488 (F13A_HUMAN)). Factor XIII is activated by thrombin and calcium ion to a transglutaminase that catalyzes the formation of gamma-glutamyl-epsilon-lysine cross-links between fibrin chains, thus stabilizing the fibrin clot. Also cross-link alpha-2-plasmin inhibitor, or fibronectin, to the alpha chains of fibrin.

Factor XIII has been implicated in the development of deep vein thrombosis and acute pulmonary embolism, and the risk of stroke and embolism in people with nonvalvular atrial fibrillation.

The Protein Data Bank website provides the crystal structure of factor XIII searchable by 1FIE (Yee, V. C., et al., Thromb Res., 1995, 78, 389-397); and 1F13 (Weiss, M. S., et al., FEBS Lett., 1998, 423, 291-296); as well as the crystal structure of factor XIII bound to various compounds searchable by 1DE7 (Sadasivan, C., et al., J Biol Chem., 2000, 275, 36942-36948); and 5MHL, 5MHM, 5MHN, and 5MHO (Stieler, M., et al.). Additionally, Gupta et al., provides insight into the mechanism of coagulation factor XIII activation and regulation from a structure/functional perspective (Gupta, S., et al., Sci Rep., 2016; 6, 30105); and Komaromi et al., provides insight into the novel structural and functional aspect of factor XIII (Komaromi, Z., et al., J Thromb Haemost 2011, 9, 9-20).

Representative Factor XIII Targeting Ligands are provided in FIG. 1. Additional Factor XIII Targeting Ligands can be found in, for example, Eur J Med Chem 98: 49-53 (2015), J Med Chem 55: 1021-46 (2012), J Med Chem 48: 2266-9 (2005), each of which is incorporated herein by reference.

Prothrombin

In some embodiments, the Target Protein is human Prothrombin (UniProtKB—P00734 (THRB_HUMAN)). Thrombin, which cleaves bonds after Arg and Lys, converts fibrinogen to fibrin and activates factors V, VII, VIII, XIII, and, in complex with thrombomodulin, protein C.

Functions in Blood Homeostasis, Inflammation and Wound Healing.

Thrombin is involved in blood clot formation and arterial and venous thrombosis, and thromboembolism associated with atrial fibrillation.

The Protein Data Bank website provides the crystal structure of prothrombin searchable by 3NXP (Chen, Z. et al., Proc Natl Acad Sci USA, 2010, 107, 19278-19283); as well as the crystal structure of prothrombin bound to various compounds searchable by 2HPP and 2HPQ (Arni, R. K., et al., Biochemistry, 1993, 32, 4727-4737); 6BJR, 6C2W (Chinnaraj, M., et al., Sci Rep., 2018, 8, 2945-2945); 5EDK, 5EDM (Pozzi, N., et al., J Biol Chem., 2016, 291, 6071-6082); 3K65 (Adams, T. E., et al., Biochimie, 2016, 122, 235-242); and 6BJR and 6C2W (Chinnaraj, M. et al., Sci Rep., 2018, 8, 2945-2945). Additionally, Pozzi et al., provides insight into the mechanism and conformational flexibility for the crystal structure of prothrombin (Pozzi, N. et al., J Biol Chem., 2013, 288(31), 22734-22744); and Zhiwei et al., provides insight into the crystal structure of prothrombin-1 (Zhiwei, C. et al., PNAS, 2010, 107(45), 19278-19283).

Prothrombin is converted to thrombin, as such the Protein Data Bank website provides the crystal structure of thrombin bound to compounds searchable by 1XMN (Carter, W. J. et al., J.Biol.Chem., 2005, 280, 2745-2749); 4CH2 and 4CH8 (Lechtenberg, B. C. et al., J Mol Biol., 2014, 426, 881); 3PO1 (Karle, M. et al., Bioorg Med Chem Lett., 2012, 22, 4839-4843); 3DA9 (Nilsson, M. et al., J Med Chem., 2009, 52, 2708-2715); 2H9T and 3BF6 (Lima, L. M. T. R. et al., Biochim Biophys Acta., 2009, 1794, 873-881); 3BEF and 3BEI (Gandhi, P. S. et al., Proc Natl Acad Sci USA, 2008, 105, 1832-1837); 3BV9 (Nieman, M. T. et al., J Thromb Haemost., 2008, 6, 837-845); 2HWL (Pineda, A. O. et al., Biophys Chem., 2007, 125, 556-559); 2AFQ (Johnson, D. J. D. et al., Biochem J., 2005, 392, 21-28); 1SHH (Pineda, A. O. et al., J Biol Chem., 2004, 279, 31842-31853); 1JWT (Levesque, S. et al., Bioorg Med Chem Lett., 2001, 11, 3161-3164); 1G37 (Bachand, B. et al., Bioorg Med Chem Lett., 2001, 11, 287-290); 1EOJ and 1EOL (Slon-Usakiewicz, J. J. et al., Biochemistry, 2000, 39, 2384-2391); 1AWH (Weir, M. P. et al., Biochemistry, 1998, 37, 6645-6657); 1DIT (Krishnan, R. et al., Protein Sci., 1996, 5, 422-433); 1HAO and 1HAP (Padmanabhan, K. et al., Acta Crystallogr D Biol Crystallogr., 1996, 52, 272-282); and 1HBT (Rehse, P. H. et al., Biochemistry, 1995, 34, 11537-11544).

Representative prothrombin Targeting Ligands are provided in FIG. 1. Additional prothrombin Targeting Ligands can be found in, for example, J Med Chem 46: 3612-22 (2003), Bioorg Med Chem Lett 12: 1017-22 (2002), J Med Chem 40: 830-2 (1997), Bioorg Med Chem Lett 15: 2771-5 (2005), J Med Chem 42: 3109-15 (1999), J Med Chem 47: 2995-3008 (2004), Bioorg Med Chem 16: 1562-95 (2008), J Med Chem 42: 3109-15 (1999), each of which is incorporated herein by reference.

Coagulation Factor VII

In some embodiments, the Target Protein is human coagulation Factor VII (UniProtKB—P08709 (FA7_HUMAN)). Factor VII initiates the extrinsic pathway of blood coagulation. It is a serine protease that circulates in the blood in a zymogen form. Factor VII is converted to Factor VIIa by Factor Xa, Factor XIIa, Factor IXa, or thrombin by minor proteolysis. In the presence of tissue factor and calcium ions, Factor VIIa then converts Factor X to Factor Xa by limited proteolysis. Factor VIIa will also convert Factor IX to Factor IXa in the presence of tissue factor and calcium.

Factor VII is involved in blood clot formation and arterial and venous thrombosis, and thromboembolism associated with atrial fibrillation.

The Protein Data Bank website provides the crystal structure of factor VII bound to various compounds searchable by 2F9B (Rai, R., et al., Bioorg Med Chem Lett., 2006, 16, 2270-2273); 5U6J (Wurtz, N. R., et al., Bioorg Med Chem Lett., 2017, 27, 2650-2654); 5L2Y, 5L2Z, and 5L30 (Ladziata, U., et al., Bioorg Med Chem Lett., 2016, 26, 5051-5057); 5146 (Glunz, P. W., et al., J Med Chem., 2016, 59, 4007-4018); 4YLQ, 4Z6A, and 4ZMA (Sorensen, A. B., et al., J Biol Chem., 2016, 291, 4671-4683); 4YT6 and 4YT7 (Glunz, P. W., et al., Bioorg Med Chem Lett, 2015, 25, 2169-2173); 4NA9 (Quan, M. L., et al., J Med Chem., 2014, 57, 955-969); 4NG9 (hang, X., et al., ACS Med Chem Lett., 2014, 5, 188-192); 4JZD, 4JZE and 4JZF (Bolton, S. A., et al., Bioorg Med Chem Lett., 2013, 23, 5239-5243); 4JYU and 4JYV (Glunz, P. W., et al., Bioorg Med Chem Lett., 2013, 23, 5244-5248); 4ISH (Priestley, E. S., et al., Bioorg Med Chem Lett., 2013, 23, 2432-2435); 4ISI (Zhang, X., et al., Bioorg Med Chem Lett., 2013, 23, 1604-1607); 2ZZU (Shiraishi, T., et al., Chem Pharm Bull (Tokyo), 2010, 58, 38-44); 1WV7 and 1WUN (Kadono, S., et al., Biochem Biophys Res Commun., 2005, 327, 589-596); 2ZWL, 2ZP0, (Kadono, S., et al.); 2EC9 (Krishan, R., et al., Acta Crystallogr D Biol Crystallogr., 2007, 63, 689-697); 2PUQ (Larsen, K. S., et al., Biochem J., 2007, 405, 429-438); 2FLR (Riggs, J. R., et al., Bioorg Med Chem Lett., 2006, 16, 3197-3200); 2C4F (Kohrt, J. T., et al., Bioorg Med Chem Lett., 2006, 16, 1060); 2AEI (Kohrt, J. T. et al., Bioorg Med Chem Lett., 2005, 15, 4752-4756); 1WTG (Kadono, S., et al., Biochem Biophys Res Commun., 2005, 326, 859-865); 1WSS (Kadono, S., et al., Acta Crystallogr SectF Struct Biol Cryst Commun., 2005, 61, 169-173); 1W7X and 1W8B (Zbinden, K. G., et al., Bioorg Med Chem Lett., 2005, 15, 5344); 1WQV (Kadono, S., et al., Biochem Biophys Res Commun., 2004, 324, 1227-1233); 1Z6J (Schweitzer, B. A., et al., Bioorg Med Chem Lett., 2005, 15, 3006-3011); 1YGC (Olivero, A. G., et al., J Biol Chem., 2005, 280, 9160-9169); 6R2W (Sorensen, A. B., et al., J Biol Chem., 2019, 295, 517-528); 5PA8, 5PA9, 5PAA, 5PAB, 5PAC, 5PAE, 5PAF, 5PAG, 5PAI, 5PAJ, 5PAK, 5PAM, 5PAN, 5PAO, 5PAQ, 5PAR, 5PAS, 5PAT, 5PAU, 5PABV, 5PAW, 5PAX, 5PAY, 5PB0, 5PB1, 5PB2, 5PB3, 5PB4, 5PB5, and 5PB6 (Mayweg, A. V., et al.); and 5LOS (Li, Z., et al., Nat Commun., 2017, 8, 185-185). Additionally, Kemball-Cook, et al., provides insight into the crystal structure of active site-inhibited factor VIIa (Kemball-Cook, G., et al., J Struct Biol., 1999, 127(3), 213-23).

Representative Factor VII Targeting Ligands are provided in FIG. 1. Additional Factor VII Targeting Ligands can be found in, for example, U.S. Pat. No. 9,174,974, Bioorg Med Chem Lett 26: 5051-5057 (2016), Bioorg Med Chem Lett 11: 2253-6 (2001), Bioorg Med Chem Lett 15: 3006-11 (2005), Bioorg Med Chem Lett 12: 2883-6 (2002), each of which is incorporated herein by reference.

Coagulation Factor IX

In some embodiments, the Target Protein is human coagulation Factor IX (UniProtKB—P00740 (FA9_HUMAN)). Factor IX Factor IX is a vitamin K-dependent plasma protein that participates in the intrinsic pathway of blood coagulation by converting factor X to its active form in the presence of $Ca^{2+}$ ions, phospholipids, and factor VIIIa.

Factor IX is involved in blood clot formation and arterial and venous thrombosis, and thromboembolism associated with atrial fibrillation.

The Protein Data Bank website provides the crystal structure of factor IX bound to various compounds searchable by 6MV4 (Vadivel, K., et al., J Thromb Haemost., 2019, 17, 574-584); 4ZAE (Zhang, T., et al., Bioorg Med Chem Lett., 2015, 25, 4945-4949); 4YZU and 4Z0K (Parker, D. L., et al., Bioorg Med Chem Lett., 2015, 25, 2321-2325); 5TNO and 5TNT (Sakurada, I., et al., Bioorg Med Chem Lett., 2017, 27, 2622-2628); 5JB8, 5JB9, 5JBA, 5JBB and 5JBC (Kristensen, L. H., et al., Biochem J., 2016, 473, 2395-2411); 3LC3 (Wang, S., et al., J Med Chem., 2010, 53, 1465-1472); 3LC5 (Wang, S., et al., J Med Chem., 2010, 53, 1473-1482); 3KCG (Johnson, D. J. D., et al., Proc Natl Acad Sci USA, 2010, 107, 645-650); 1NL0 (Huang, M., et al., J Biol Chem., 2004, 279, 14338-14346); 1RFN (Hopfner, K. P., et al., Structure, 1999, 7, 989-996); and 6RFK (Sendall, T. J., et al.).

Representative Factor IX Targeting Ligands are provided in FIG. 1. Additional Factor IX Targeting Ligands can be found in, for example, U.S. Pat. No. 9,409,908, Bioorg Med Chem Lett 25: 5437-43 (2015), U.S. patent Ser. No. 10/189,819, each of which is incorporated herein by reference.

Fibroblast Growth Factor 1 (FGF1)

In some embodiments, the Target Protein is human fibroblast growth factor 1 (FGF1) (UniProtKB—P05230 (FGF1_HUMAN)). FGF1 plays an important role in the regulation of cell survival, cell division, angiogenesis, cell differentiation and cell migration. FGF1 acts as a ligand for FGFR1 and integrins, and binds to FGFR1 in the presence of heparin leading to FGFR1 dimerization and activation via sequential autophosphorylation on tyrosine residues which act as docking sites for interacting proteins, leading to the activation of several signaling cascades. FGF1 induces the phosphorylation and activation of FGFR1, FRS2, MAPK3/ERK1, MAPK1/ERK2 and AKT1. FGF1 can induce angiogenesis. FGF1 has been implicated in oncogenesis, cancer cell proliferation, resistance to anticancer therapies, and neoangiogenesis.

The Protein Data Bank website provides the crystal structure of FGF1 searchable by 2AFG (Blaber, M., et al., Biochemistry, 1996, 35, 2086-2094); and 1BAR (Zhu, X. et al., Science, 1991, 251, 90-93); as well as the crystal structure of FGF1 bound to various compounds searchable by 1AFC (Zhu, X., et al., Structure, 1993, 1, 27-34); 1AXM and 2AXM (DiGabriele, A. D., et al., Nature, 1998, 393, 812-817); IEVT (Plotnikov, A. N., et al., Cell, 2000, 101, 413-424); 1 E0O (Pellegrini, L., et al., Nature, 2000, 407, 1029); and 2ERM (Canales, A., et al., FEBS J, 2006, 273, 4716-4727).

Representative FGF1 Targeting Ligands are provided in FIG. 1. Additional FGF1 Targeting Ligands can be found in, for example, Bioorg Med Chem Lett 18: 344-9 (2008), Chembiochem 6: 1882-90 (2005), J Med Chem 55: 3804-13 (2012), J Med Chem 47: 1683-93 (2004), J Med Chem 53: 1686-99 (2010) each of which is incorporated herein by reference.

Fibroblast Growth Factor 2 (FGF2)

In some embodiments, the Target Protein is human fibroblast growth factor 2 (FGF2) (UniProtKB—P09038 (FGF2_HUMAN)). FGF2 acts as a ligand for FGFR1, FGFR2, FGFR3 and FGFR4. FGF2 also acts as an integrin ligand which is required for FGF2 signaling, and plays an important role in the regulation of cell survival, cell division, cell differentiation and cell migration. FGF2 also induces angiogenesis. FGF2 has been implicated in oncogenesis, cancer cell proliferation, resistance to anticancer therapies, and neoangiogenesis.

The Protein Data Bank website provides the crystal structure of FGF2 bound to various compounds searchable by 4OEE, 4OEF, and 4OEG (Li, Y. C., et al., ACS Chem Biol., 2014, 9, 1712-1717); 1EV2 (Plotnikov, A. N., et al., Cell, 2000, 101, 413-424); and 5X1O (Tsao, Y. H.).

Representative FGF2 Targeting Ligands are provided in FIG. 1. Additional FGF2 Targeting Ligands can be found in, for example, U.S. Pat. No. 8,933,099, Bioorg Med Chem Lett 12: 3287-90 (2002), Chem Biol Drug Des 86: 1323-9 (2015), Bioorg Med Chem Lett 25: 1552-5 (2015), each of which is incorporated herein by reference.

Fibronectin-1

In some embodiments, the Target Protein is human fibronectin 1 (FN1) (UniProtKB—P02751 (FINC_HUMAN)). Fibronectin (FN) polymerization is necessary for collagen matrix deposition and is a key contributor to increased abundance of cardiac myofibroblasts (MFs) after cardiac injury. Interfering with FN polymerization may attenuate MF and fibrosis and improve cardiac function after ischemia/reperfusion (I/R) injury.

The Protein Data Bank website provides the crystal structure of fibronectin-1 bound to various compounds searchable by 3M7P (Graille, M., et al., Structure, 2010, 18, 710-718); 3MQL (Erat, M. C., et al., J Biol Chem., 2010, 285, 33764-33770); and 3EJH (Erat, M. C., et al., Proc Natl Acad Sci USA, 2009, 106, 4195-4200).

Representative FN Targeting Ligands are provided in FIG. 1. Additional FN Targeting Ligands can be found in, for example, Bioorg Med Chem Lett 18: 2499-504 (2008), which is incorporated herein by reference.

Kallikrein-1 (KLK1)

In some embodiments, the Target Protein is human kallikrein-1 (UniProtKB—P06870 (KLK1_HUMAN)). Glandular kallikreins cleave Met-Lys and Arg-Ser bonds in kininogen to release Lys-bradykinin. Kallikrein has been implicated in adverse reactions in hereditary angioedema (HAE).

The Protein Data Bank website provides the crystal structure of KLK1 searchable by 1SPJ (Laxmikanthan, G., et al., Proteins, 2005, 58, 802-814); as well as the crystal structure of KLK1 bound to various compounds searchable by 5F8Z, 5F8T, 5F8X, (Xu, M., et al.); and 6A80 (Xu, M., et al., FEBS Lett., 2018, 592, 2658-2667). Additionally, Katz et al., provides insight into the crystal structure of kallikrein (Katz, B. A., et al., Protein Sci., 1998, 7(4), 875-85).

Representative kallikrein Targeting Ligands are provided in FIG. 1. Additional kallikrein Targeting Ligands can be found in, for example, U.S. Pat. No. 9,783,530, J Med Chem 38: 2521-3 (1995), U.S. Pat. No. 9,234,000, U.S. patent Ser. No. 10/221,161, U.S. Pat. Nos. 9,687,479, 9,670,157, 9,834,513, J Med Chem 38: 1511-22 (1995), U.S. patent Ser. No. 10/214,512, each of which is incorporated herein by reference.

Plasma Kallikrein

In some embodiments, the Target Protein is human plasma kallikrein (UniProtKB—P03952 (KLKB1_HUMAN)). Plasma kallikrein cleaves Lys-Arg and Arg-Ser bonds. It activates, in a reciprocal reaction, factor XII after its binding to a negatively charged surface. It also releases bradykinin from HMW kininogen and may also play a role in the renin-angiotensin system by converting prorenin into renin. Plasma kallikrein has been implicated in retinal dysfunction, the development of diabetic macular edema and hereditary angioedema (HAE).

The Protein Data Bank website provides the crystal structure of plasma kallikrein bound to various compounds searchable by 5TJX (Li, Z., et al., ACS Med Chem Lett., 2017, 8, 185-190); 6O1G and 6O1S (Patridge, J. R., et al., J Struct Biol., 2019, 206, 170-182); 4OGX and 4OGY (Kenniston, J. A., et al., J Biol Chem., 2014, 289, 23596-23608); and 5F8T, 5F8X, and 5F8Z (Xu, M., et al.).

Representative plasma kallikrein Targeting Ligands are provided in FIG. 1. Additional plasma kallikrein Targeting Ligands can be found in, for example, J Med Chem 61: 2823-2836 (2018), J Med Chem 55: 1171-80 (2012), U.S. Pat. Nos. 8,598,206, 9,738,655, Bioorg Med Chem Lett 16: 2034-6 (2006), U.S. Pat. No. 9,409,908, U.S. patent Ser. No. 10/144,746, U.S. Pat. No. 9,290,485, each of which is incorporated herein by reference.

Lipoprotein Lipase

In some embodiments, the Target Protein is human lipoprotein lipase (UniProtKB—P06858 (LIPL_HUMAN)). Lipoprotein lipase is a key enzyme in triglyceride metabolism. It catalyzes the hydrolysis of triglycerides from circulating chylomicrons and very low density lipoproteins (VLDL), and thereby plays an important role in lipid clearance from the blood stream, lipid utilization and storage. Lipoprotein lipase mediates margination of triglyceride-rich lipoprotein particles in capillaries. Lipoprotein lipase has been implicated in the development of cardiovascular disease and obesity.

The Protein Data Bank website provides the crystal structure of lipoprotein lipase bound to various compounds searchable by 6 E7K (Birrane, G., et al., Proc Natl Acad Sci USA, 2018 116 1723-1732).

Representative lipoprotein lipase Targeting Ligands are provided in FIG. 1. Additional lipoprotein lipase Targeting Ligands can be found in, for example, J Med Chem 47: 400-10 (2004), which is incorporated herein by reference.

Matrix Metallopeptidase 1 (MMP-1)

In some embodiments, the Target Protein is human matrix metallopeptidase 1 (MMP-1) (UniProtKB—P03956 (MMP1_HUMAN)). MMP-1 cleaves collagens of types I, II, and III at one site in the helical domain. It also cleaves collagens of types VII and X. MMP-1 has been implicated in cardiovascular disease.

The Protein Data Bank website provides the crystal structure of MMP-1 searchable by 3SHI (Bertini, I., et al., FEBS Lett., 2012, 586, 557-567); as well as the crystal structure of MMP-1 bound to various compounds searchable by 4AUO (Manka, S. W., et al., Proc Natl Acad Sci USA, 2012, 109, 12461); 3MA2 (Grossman, M., et al., Biochemistry, 2010, 49, 6184-6192); and 2J0T (Iyer, S., et al., J.Biol.Chem., 2007, 282, 364). Additionally, Iyer et al., provides insight into the crystal structure of an active form of MMP-1 (Iyer, S., et al., J Mol Biol., 2006, 362(1), 78-88); and Lovejoy et al., provides insight into the crystal structure of MMP1 and the selectivity of collagenase inhibitors (Lovejoy, B., et al., Nat Struct Mol Biol., 1999, 6, 217-221).

Representative MMP-1 Targeting Ligands are provided in FIG. 1. Additional MMP-1 Targeting Ligands can be found in, for example, Bioorg Med Chem Lett 5: 1415-1420 (1995), Bioorg Med Chem Lett 16: 2632-6 (2006), Bioorg Med Chem Lett 8: 837-42 (1999), Eur J Med Chem 60: 89-100 (2013), J Med Chem 54: 4350-64 (2011), Bioorg Med Chem Lett 8: 3251-6 (1999), J Med Chem 42: 4547-62 (1999), J Med Chem 61: 2166-2210 (2018), J Med Chem 41: 1209-17 (1998), which is incorporated herein by reference.

Macrophage Migration Inhibitory Factor (MIF)

In some embodiments, the Target Protein is human macrophage migration inhibitory factor (MIF) (UniProtKB—P14174 (MIF_HUMAN)). MIF is a pro-inflammatory cytokine involved in the innate immune response to bacterial pathogens. The expression of MIF at sites of inflammation suggests a role as mediator in regulating the function of macrophages in host defense. It counteracts the anti-inflammatory activity of glucocorticoids.

MIF has been implicated in tumor progression; systemic inflammation; atherosclerosis; rheumatoid arthritis; and systemic lupus erythematosus, among others.

The Protein Data Bank website provides the crystal structure of MIF searchable by 1MIF (Sun, H W. et al., Proc Natl Acad Sci USA, 1996, 93, 5191-5196); as well as the crystal structure of MIF bound to various compounds searchable by 6PEG (Cirillo, P. F. et al.); 5XEJ (Fukushima, K); 6FVE and 6FVH (Sokolov, A. V., et al., Biochemistry (Mosc), 2018, 83, 701-707); 6CB5, 6CBF, 6CBG, and 6CBH (Trivedi-Parmar, V., et al., ChemMedChem., 2018, 13, 1092-1097); 6B1C, 6B1K, 6B2C, (Dawson, T. K., et al., ACS Med Chem Lett., 2017, 8, 1287-1291); 4Z15, 4Z1T and 4Z1U (Singh, A. K., et al, J Cell Mol Med., 2017, 21, 142-153); 5HVS and 5HVT (Cisneros, J. A., et al., J Am Chem Soc., 2016, 138, 8630-8638); 4PKK (Pantouris, G., et al.); 5J7P and 5J7Q (Cisneros, J. A., et al., Bioorg Med Chem Lett., 2016, 26, 2764-2767); 5B40 (Kimura, H., et al., Chem Biol., 2010, 17, 1282-1294); 4PLU, 4TRF, 4P0H, and 4P01 (Pantouris, G., et al., Chem Biol., 2015, 22, 1197-1205); 4WR8 and 4WRB (Dziedzic, P., et al., J Am Chem Soc., 2015, 137 2996-3003); 4K9G (Ioannou, K., et al., Int J Oncol., 2014, 45, 1457-1468); 4OSF, 3WNR, 3WNS and 3WNT (Spencer, E. S., et al., Eur J Med Chem., 2015, 93, 501-510); 4OYQ (Spencer, E. S. et al.); 3SMB and 3SMC (Crichlow, G. V. et al., Biochemistry, 2012, 51, 7506-7514); 3U18 (Bai, F., et al., J Biol Chem., 2012, 287, 30653-30663); 4F2K (Tyndall, J. D. A., et al., Acta Crystallogr Sect F Struct Biol Cryst Commun., 2012, 68, 999-1002); 3IJG and 3IJJ (Cho, Y., et al., Proc Natl Acad Sci USA, 2010, 107, 11313-11318); 3L5P, 3L5R, 3L5S, 3L5T, 3L5U, and 3L5V (McLean, L. R. et al., Bioorg Med Chem Lett., 2010, 20, 1821-1824); 3JSF, 3JSG and 3JTU (McLean, L. R., et al., Bioorg Med Chem Lett., 2009, 19, 6717); 3HOF (Crawley, L., et al.); 3CE4 and 3DJI (Crichlow G. V., et al., Biochemistry, 2009, 48, 132-139); 3B9S (Winner, M. et al., Cancer Res., 2008, 68, 7253-7257); 2OOH, 2OOW and 2OOZ (Crichlow, G. V. et al., J Biol Chem., 2007, 282, 23089-23095); 1GCZ and 1GD0 (Orita, M. et al., J Med Chem., 2001, 44, 540-547); and 1CA7, 1CGQ and 1P1G (Lubetsky, J. B. et al., Biochemistry, 1999, 38, 7346-7354). Additionally, Sun et al., provides insight into the crystal structure of MIF (Proc Natl Acad Sci USA, 1996, 28; 93(11), 5191-6).

Representative MIF Targeting Ligands are provided in FIG. 1. Additional MIF Targeting Ligands can be found in, for example, ACS Med Chem Lett 8: 124-127 (2017), J Med Chem 44: 540-7 (2001), J Med Chem 52: 416-24 (2009), J Med Chem 50: 1993-7 (2007), which is incorporated herein by reference.

Transforming Growth Factor-β2 (TGF-β2)

In some embodiments, the Target Protein is human transforming growth factor-02 (TGF-β2) (UniProtKB—P61812 (TGFB2_HUMAN)). TGF-β2 is a multifunctional protein that regulates various processes such as angiogenesis and heart development. Once activated following release of LAP, TGF-beta-2 acts by binding to TGF-beta receptors (TGFBR1 and TGFBR2), which transduce signal. TGF-β2 expression in the tumor microenvironment has been associated with a poor prognosis, and is implicated in TGF-β2 mediated tumor suppression via T-cell exclusion. TGF-β2 expression has also been implicated in hematological malignancies and fibrosis.

The Protein Data Bank website provides the crystal structure of TGF-β2 searchable by 6I9J (Del Amo-Maestro L. et al., Sci Rep. 2019, 9, 8660-8660); as well as the crystal structure of TGF-β2 bound to various compounds searchable by 1M9Z (Boesen, C. C., et al. Structure, 2002, 10, 913-919); 5QIN (Zhang, Y. et al., ACS Med Chem Lett., 2018, 9, 1117-1122); 5 E8V, 5 E8Y, 5 E91 and 5 E92 (Tebben, A. J. et al., Acta Crystallogr D Struct Biol., 2016, 72, 658-674); 4P7U (Wangkanont, K. et al., Protein Expr Purif, 2015, 115, 19-25); 4XJJ (Wangkanont et al.); and 1KTZ (Hart, P. J., et al., Nat Struct Biol., 2002, 9, 203-208).

Representative TGF-β2 Targeting Ligands are provided in FIG. 1.

Thrombospondin-1 (TSP-1)

In some embodiments, the Target Protein is human thrombospondin-1 (TSP-1) (UniProtKB—P61812 (TGFB2_HUMAN)). TSP1 acts as an angiogenesis inhibitor by stimulating endothelial cell apoptosis, inhibiting endothelial cell migration and proliferation, and regulating vascular endothelial growth factor bioavailability and activity. TSP1 affects tumor immune response, tumor cell behaviors including adhesion, invasion, migration, apoptosis, and proliferation.

TSP-1 expression has been implicated in a number of diseases, including in promoting certain cancers such as breast cancer, prostate cancer, melanoma, SCLC, osteosarcoma, cutaneous squamous cell carcinoma, oral squamous cell carcinoma, papillary thyroid carcinoma, thyroid cancer, medulloblastoma, and fibrotic disorders such as diabetes, liver fibrosis, and in multiple myeloma.

The Protein Data Bank website provides the crystal structure of TSP-1 searchable by 1LSL (Tan, K. et al., J Cell Biol., 2002, 159, 373-382); 2ES3 (Tan, K., et al., J Biol Chem., 2008, 283, 3932-3941); 1Z78 and 2ERF (Tan, K., et al., Structure, 2006, 14, 33-42); and 3R6B (Klenotic, P. A., et al., Protein Expr Purif., 2011, 80, 253-259); as well as the crystal structure of TSP-1 bound to various compounds searchable by 2OUH and 2OUJ (Tan, K., et al., J Biol Chem., 2008, 283, 3932-3941); and 1ZA4 (Tan, K., et al., Structure, 2006, 14, 33-42).

Representative TSP-1 Targeting Ligands are provided in FIG. 1.

CD40 Ligand (CD40L)

In some embodiments, the Target Protein is human CD40 ligand (CD40L) (UniProtKB—P29965 (CD40L_HUMAN)). CD40L is a cytokine that acts as a ligand to CD40/TNFRSF5. It costimulates T-cell proliferation and cytokine production. Its cross-linking on T-cells generates a costimulatory signal which enhances the production of IL4 and IL10 in conjunction with the TCR/CD3 ligation and CD28 costimulation. CD40L induces the activation of NF-kappa-B, as well as kinases MAPK8 and PAK2 in T-cells. It also induces tyrosine phosphorylation of isoform 3 of CD28. CD40L mediates B-cell proliferation in the absence of co-stimulus as well as IgE production in the presence of IL4, and is involved in immunoglobulin class switching.

The Protein Data Bank website provides the crystal structure of CD40L searchable by 1ALY (Karpusas, M., et al., Structure, 1995, 3, 1031-1039); as well as the crystal structure of CD40L bound to various compounds searchable by 3QD6 (An, H. J., et al., J Biol Chem., 2011, 286, 11226-11235); and 6BRB (Karnell, J. L., et al., Sci Transl Med., 2019, 11(489), 6584).

The expression of CD40L has been implicated in HIV-associated neurocognitive disorders and cardiovascular complications. Representative CD40L Targeting Ligands are provided in FIG. 1.

Urokinase-type Plasminogen Activator (UPA)

In some embodiments, the Target Protein is human urokinase-type plasminogen activator (UPA) (UniProtKB—P00749 (UROK_HUMAN)). Urokinase-type plasminogen activator (uPA), is a serine protease present in the blood and in the extracellular matrix of many tissues. The primary physiological substrate of this enzyme is plasminogen, which is an inactive form (zymogen) of the serine protease plasmin. Activation of plasmin triggers a proteolytic cascade that, depending on the physiological environment, participates in thrombolysis or extracellular matrix degradation. This cascade had been involved in vascular diseases and cancer progression. Elevated expression levels of urokinase and several other components of the plasminogen activation system are found to be correlated with tumor malignancy.

The Protein Data Bank website provides the crystal structure of UPA bound to various compounds searchable by 5ZA7, 5ZAJ, 5ZA8, 5ZA9, 5ZAE, 5ZAF, 5ZAG, 5ZAH, and 5ZC5 (Buckley, B. J. et al., J Med Chem., 2018, 61, 8299-8320); 5LHP, 5LHQ, 5LHR, and 5LHS (Kromann-Hansen, T. et al., Sci Rep., 2017, 7, 3385-3385); 2VNT (Fish, P. V. et al. J Med Chem., 2007, 50, 2341); 1OWD, 1OWE, 1OWH, 1OWI, 1OWJ, and 1OWK (Wendt, M. D. et al., J Med Chem., 2004, 47, 303-324); 1SQA, 1SQO, and 1SQT (Wendt, M. D., et al., Bioorg Med Chem Lett., 2004, 14, 3063-3068); 1U6Q (Bruncko, M. et al., Bioorg Med Chem Lett., 2005, 15, 93-98); 3OX7, 3OY5 and 3OY6 (Jiang, L. G. et al., J Mol Biol., 2011, 412, 235-250); 4OS1, 4OS2, 4OS4, 4OS5, 4OS6 and 4OS7 (Chen, S. et al., Nat Chem., 2014, 6, 1009-1016); 3IG6 (West, C. W. et al., Bioorg Med Chem Lett., 2009, 19, 5712-5715); 4X0W and 4X1P (Jiang, L. et al., Int J Biochem Cell Biol., 2015, 62, 88-92); 4X1N, 4X1Q, 4X1R and 4X1S (Zhao, B. et al., PLoS One, 2014, 9, e115872-e115872); 5WXO and 5WXP (Jiang, L. et al., Biochim Biophys Acta., 2018, 1862, 2017-2023); 4MNV, 4MNW, 4MNX, and 4MNY (Chen, S., et al., Angew Chem Int Ed Engl., 2014, 53, 1602-1606); 4GLY (Chen, S., et al., J Am Chem Soc., 2013, 135, 6562-6569); 4JK5 and 4JK5 (Chen, S., et al., Chembiochem., 2013, 14, 1316-1322); 3QN7 (Angelini, A. et al., ACS Chem Biol., 2012, 7, 817-821); 2NWN (Zhao, G. et al., J Struct Biol., 2007, 160, 1-10); 6NMB (Wu, G. et al., Blood Adv., 2019, 3, 729-733); 1W0Z, 1W10, 1W11, 1W12, 1W13, and 1W14 (Zeslawska, E. et al., J Mol Biol., 2003, 328, 109); 4DVA (Jiang, L et al., Biochem J., 2013, 449, 161-166); 6A8G 6A8N (Wang, D. et al., J Med Chem., 2019, 62, 2172-2183); 2VIN, 2VIO, 2VIP, 2VIQ, 2VIV, and 2VIW (Frederickson, M. et al., J Med Chem., 2008, 51, 183); 1EJN (Speri, S., et al., Proc Natl Acad Sci USA, 2000, 97, 5113-5118); 3PB1 (Lin, Z. et al., J Biol Chem., 2011, 286, 7027-7032); 3U73 (Xu, X. et al., J Mol Biol., 2012, 416, 629-641); 1C5W, 1C5X, 1C5Y and IC5Z (Katz, B. A., et al., Chem Biol., 2000, 7, 299-312); 5XG4 (Xue, G. et al., Food Funct., 2017, 8, 2437-2443); 5WXF (Jiang, L. et al., Biochim Biophys Acta., 2018, 1862, 2017-2023); 5WXS, 4ZKS, 5WXQ, 5WXT, 5YC6, 5YC7, 5Z1C, (Jiang, L. et al.); 4H42 (Yu, H. Y. et al.); 6AG3 and 6AG9 (Buckley, B. et al); 3KGP, 3KHV, 3KID, 3M61, 3MHW, and 3MWI (Jiang, L. G. et al.); 4ZKN, 4ZKO and 4ZKR (Jiang, L. et al.); 208T, 208U, 208W (Zhao, G. et al.); and 4FU7, 4FU8, 4FU9, 4FUB, 4FUC, 4FUD, 4FUE, 4FUF, 4FUG, 4FUH, 4FUI, and 4FUJ (Kang, Y. N. et al.).

Representative UPA Targeting Ligands are provided in FIG. 1. Additional UPA Targeting Ligands are provided in, for example, J Med Chem 38: 1511-22 (1995), Bioorg Med Chem Lett 11: 2253-6 (2001), Bioorg Med Chem Lett 14: 3063-8 (2004), J Med Chem 52: 3159-65 (2009), CSAR 1: (2012), Bioorg Med Chem 22: 3187-203 (2014), J Med Chem 50: 2341-51 (2007), J Mol Biol 329: 93-120 (2003), Bioorg Med Chem Lett 2:1399-1404 (1992), J Med Chem 35: 4297-305 (1992), J Med Chem 35: 4150-9 (1992), J Med Chem 49: 5785-93 (2006), Bioorg Med Chem 23: 3696-704 (2015), Bioorg Med Chem Lett 10: 983-7 (2000), J Med Chem 49: 5785-93 (2006), each of which is incorporated by reference herein.

Plasminogen Activator, Tissue Type (TPA)

In some embodiments, the Target Protein is human plasminogen activator, tissue type (TPA) (UniProtKB—P00750 (TPA_HUMAN)). TPA converts the abundant, but inactive, zymogen plasminogen to plasmin by hydrolyzing a single Arg-Val bond in plasminogen. By controlling plasmin-mediated proteolysis, it plays an important role in tissue remodeling and degradation, in cell migration and many other physiopathological events. TPA plays a direct role in facilitating neuronal migration. PLA has been shown activated in various cancers including oral malignancy.

The Protein Data Bank website provides the crystal structure of TPA searchable by 1VR1 (Dekker, R. J. et al., J Mol Biol., 1999, 293, 613-627); as well as the crystal structure of TPA bound to various compounds searchable by 1RTF (Lamba, D. et al., J Mol Biol., 1996, 258, 117-135); 1A5H (Renatus, M. et al., J Biol Chem., 1997, 272, 21713-21719); and 1BDA (Renatus, M. et al., EMBO J., 1997, 16, 4797-4805).

Representative TPA Targeting Ligands are provided in FIG. 1. Additional TPA Targeting Ligands are provided in, for example, Bioorg Med Chem Lett 15: 4411-6 (2005), Bioorg Med Chem Lett 13: 2781-4 (2003), Bioorg Med Chem Lett 6: 2913-2918 (1996), J Med Chem 44: 2753-71 (2001), J Med Chem 41: 5445-56 (1999), Bioorg Med Chem Lett 12: 3183-6 (2002), U.S. patent Ser. No. 10/118,930, J Biol Chem 285: 7892-902 (2010), each of which is incorporated by reference herein.

Plasminogen (PLG)

In some embodiments, the Target Protein is human plasminogen (PLG) (UniProtKB—P00747 (PLMN_HUMAN)). PLG dissolves the fibrin of blood clots and acts as a proteolytic factor in a variety of other processes including embryonic development, tissue remodeling, tumor invasion, and inflammation. It activates the urokinase-type plasminogen activator, collagenases and several complement zymogens, such as $C_1$ and $C_5$. Its role in tissue remodeling and tumor invasion may be modulated by CSPG4.

The Protein Data Bank website provides the crystal structure of PLG searchable by 1DDJ (Wang, X. et al., J. Mol. Biol., 2000, 295, 903-914); and 4DUR and 4DUU (Law, R. H. P., et al., Cell Rep., 2012, 1, 185-190).

Representative PLG Targeting Ligands are provided in FIG. 1. Additional PLG Targeting Ligands are provided in, for example, J Med Chem 35: 4297-305 (1992), J Med Chem 38: 1511-22 (1995), J Med Chem 56: 820-31 (2013), U.S. Pat. Nos. 8,598,206, 8,921,319, J Med Chem 55: 1171-80 (2012), Bioorg Med Chem Lett 12: 3183-6 (2002), Bioorg Med Chem 23: 3696-704 (2015), Bioorg Med Chem Lett 13: 723-8 (2003), Bioorg Med Chem Lett 7: 331-336 (1997), each of which is incorporated by reference herein.

Plasminogen Activator Inhibitor-1 (PAI-1)

In some embodiments, the Target Protein is human plasminogen activator inhibitor 1 (PAI-1) (UniProtKB—P05121 (PAI1_HUMAN)). PAI-1 is a serine protease inhibitor, and a primary inhibitor of tissue-type plasminogen activator (PLAT) and urokinase-type plasminogen activator (PLAU). As PLAT inhibitor, it is required for fibrinolysis down-regulation and is responsible for the controlled degradation of blood clot. As PLAU inhibitor, it is involved in the regulation of cell adhesion and spreading, and acts as a regulator of cell migration, independently of its role as protease inhibitor. Overexpression of PAI-1 favors angiogenesis, metastasis, and poor prognosis in tumors, including, but not limited to, oral cancers and breast cancers.

The Protein Data Bank website provides the crystal structure of PAI-1 searchable by 3Q02 and 3Q03 (Jensen, J. K. et al., J Biol Chem., 2011, 286, 29709-29717); 1B3K (Sharp, A. M. et al., Structure, 1999, 7, 111-118); $1C_5G$ (Tucker, H. M. et al., Nat Struct Biol., 1995, 2, 442-445); 1DVM (Stout, T. J. et al., Biochemistry, 2000, 39, 8460-8469); and 3UT3 (Lin, Z. H. et al.); as well as the crystal structure of PAI-1 bound to various compounds searchable by 4AQH (Fjellstrom, O. et al., J Biol Chem., 2013, 288, 873); 3R4L (Jankun, J. et al., Int J Mol Med., 2012, 29 61-64); 1A7C (Xue, Y., et al., Structure, 1998, 6, 627-636); 1OC0 (Zhou, A. et al., Nat Struct Biol., 2003, 10, 541); 6I8S (Vousden, K. A. et al., Sci Rep., 2019, 9, 1605-1605); 4G80 and 4G8R (Li, S. H. et al., Proc Natl Acad Sci USA, 2013, 110, E4941-E4949); 6GWQ, 6GWN and 6GWP (Sillen, M. et al., J Thromb Haemost, 2019); and 4IC0 (Hong, Z. B. et al.).

Representative PAI-1 Targeting Ligands are provided in FIG. 1. Additional PAI-1 Targeting Ligands are provided in, for example, J Biol Chem 285: 7892-902 (2010), U.S. Pat. No. 9,120,744, Bioorg Med Chem Lett 13: 3361-5 (2003), Bioorg Med Chem Lett 12: 1063-6 (2002), Bioorg Med Chem Lett 13: 1705-8 (2003), Bioorg Med Chem Lett 11: 2589-92 (2001), U.S. Pat. No. 9,718,760, each of which is incorporated by reference herein.

Placenta Growth Factor (PlGF)

In some embodiments, the Target Protein is human placental growth factor (PGF) (UniProtKB—P49763 (PLGF_HUMAN)). PGF is growth factor active in angiogenesis and endothelial cell growth, stimulating their proliferation and migration. It binds to the receptor FLT1/VEGFR-1. Isoform PlGF-2 binds NRP1/neuropilin-1 and NRP2/neuropilin-2 in a heparin-dependent manner. PGF also promotes cell tumor growth, and has been implicated in age-related macular degeneration (AMD) and choroidal neovascularization (CNV).

The Protein Data Bank website provides the crystal structure of PlGF searchable by 1FZV (Iyer, S. et al., J Biol Chem., 2001, 276, 12153-12161); as well as the crystal structure of PlGF bound to various compounds searchable by 1RV6 (Christinger, H. W., J Biol Chem., 2004, 279, 10382-10388). Additionally, De Falco provides insight into the discovery and biological activity of placenta growth factor (De Falco, Exp Mol Med., 2012, 44, 1-9).

Representative PGF Targeting Ligands are provided in FIG. 1. Additional PGF Targeting Ligands are provided in, for example, J Med Chem 54: 1256-65 (2011), J Nat Prod 76: 29-35 (2013), each of which is incorporated by reference herein.

Phospholipase A2, Group IB (PA21B)

In some embodiments, the Target Protein is human phospholipase A2, Group IB (PA21B) (UniProtKB—P04054 (PA21B_HUMAN)). PA21B cleaves phospholipids preferentially at the sn-2 position, liberating free fatty acids and lysophospholipids. PA21B has been implicated in a number of diseases, including cardiovascular diseases, atherosclerosis, immune disorders and cancer.

The Protein Data Bank website provides the crystal structure of PA21B searchable by 3FVJ and 3FVI (Pan, Y. H. et al., Biochim.Biophys.Acta., 2010, 1804, 1443-1448).

Representative PA21B Targeting Ligands are provided in FIG. 1. Additional PA21B Targeting Ligands are provided in, for example, J Med Chem 39: 3636-58 (1996), Chembiochem 4: 181-5 (2003), J Med Chem 39: 5159-75 (1997), J Med Chem 51: 4708-14 (2008), each of which is incorporated by reference herein.

Phospholipase A2, Group IIA (PA2GA)

In some embodiments, the Target Protein is human phospholipase A2, Group IIA (PA2GA) (UniProtKB—P04054 (PA21B_HUMAN)). PA2GA catalyzes the calcium-dependent hydrolysis of the 2-acyl groups in 3-sn-phosphoglycerides. It is thought to participate in the regulation of phospholipid metabolism in biomembranes including eicosanoid biosynthesis. Independent of its catalytic activity, it also acts as a ligand for integrins. PA2GA Induces cell proliferation in an integrin-dependent manner. PA2GA has been implicated in a number of diseases, including cardiovascular diseases, atherosclerosis, immune disorders, and cancer.

The Protein Data Bank website provides the crystal structure of PA2GA bound to various compounds searchable by 2ARM and 1SV3 (Singh, N. et al., Proteins, 2006, 64, 89-100); 5G3M and 5G3N (Giordanetto, F., et al. ACS Med Chem Lett., 2016, 7, 884); 1KQU (Jansford, K. A., et al., Chembiochem., 2003, 4, 181-185); and 1ZYX (Singh, N. et al.). Additionally, Singh et al., provides insight into the crystal structure of the complexes of a group IIA phospholipase A2 with two natural anti-inflammatory agents, anisic acid, and atropine reveal a similar mode of binding (Singh, N. et al., Proteins, 2006, 64(1):89-100); and Kitadokoro et al also provides insight into the crystal structure of human secretory phospholipase A2-IIA complex with the potent indolizine inhibitor 120-1032 (Kitadokoro, K. et al., J Biochem., 1998, 123(4), 619-23).

Representative PA2GA Targeting Ligands are provided in FIG. 1. Additional PA2GA Targeting Ligands are provided in, for example, J Med Chem 48: 893-6 (2005), J Med Chem 39: 5159-75 (1997), each of which is incorporated by reference herein.

Factor B

In some embodiments, the Target Protein is human Complement factor B (UniProtKB—P00751 (CFAB_HUMAN)). Complement factor B, which is part of the alternate pathway of the complement system, is cleaved by factor D into 2 fragments: Ba and Bb. Bb, a serine protease, then combines with complement factor 3b to generate the C3 or C5 convertase. It has also been implicated in proliferation and differentiation of preactivated B-lymphocytes, rapid spreading of peripheral blood monocytes, stimulation of lymphocyte blastogenesis and lysis of erythrocytes. Ba inhibits the proliferation of preactivated B-lymphocytes.

The Protein Data Bank website provides the crystal structure of Complement Factor B searchable by $20K_5$ (Milder, F. J., et al., Nat Struct Mol Bio 2007, 14, 224-228); as well as the crystal structure of Complement factor B bound to various compounds searchable by 6QSW, 6QSX, and 6RAV (Schubart, A., et al., Proc Natl Acad Sci 2019, 116, 7926-7931); 6T8U, 6T8W, and 6T8V (Mainolfi, N., et al, J Med Chem 2020, 63, 5697-5722); and 7JTN (Xu, X., et al., J Immunol 2021, 206, doi:10.4049/jimmunol.2001260).

Figure 5:
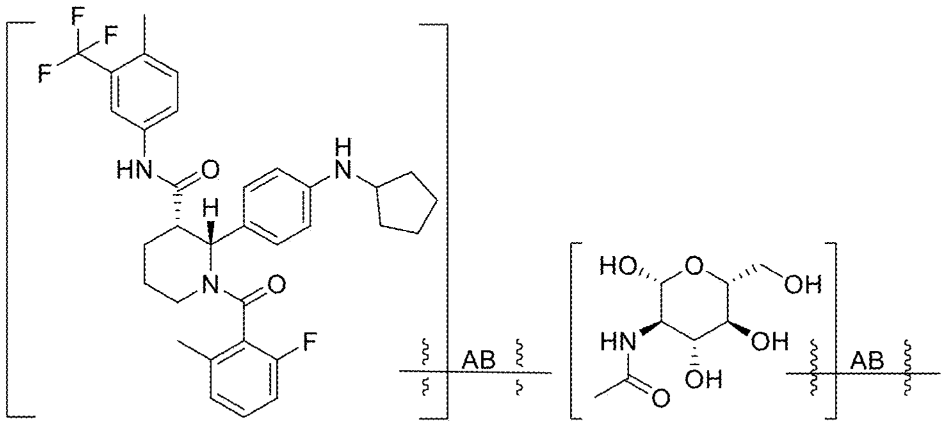
FIG. 5 provides a non-limiting list of exemplary Extracellular Protein Targeting Ligands that target complement component 5.

Representative Complement Factor B Targeting Ligands are provided in FIG. 5. Additional Complement Factor B Targeting Ligands are provided in, for example, U.S. Pat. No. 9,682,968B2, U.S. Pat. No. 9,475,806B2, U.S. Pat. No. 9,452,990B2, Proc Natl Acad Sci 116: 7926-7931 (2019), J Med Chem 52: 6042-6052 (2009), and J Med Chem 63: 5697-5722 (2020), each of which is incorporated by reference herein.

In certain embodiments the Extracellular Targeting Ligand is selected from:

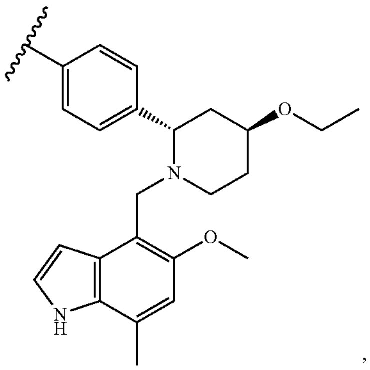

,

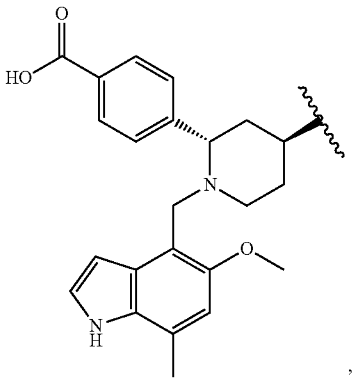

,

-continued

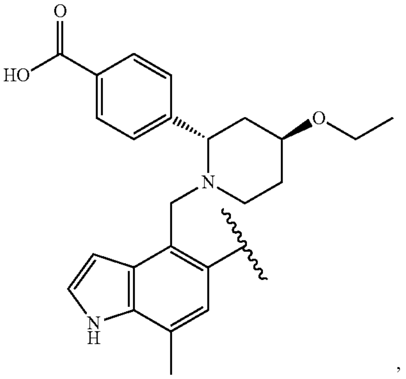

,

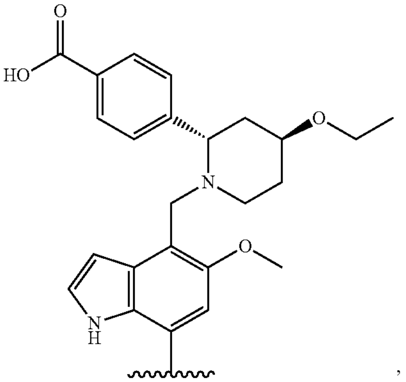

,

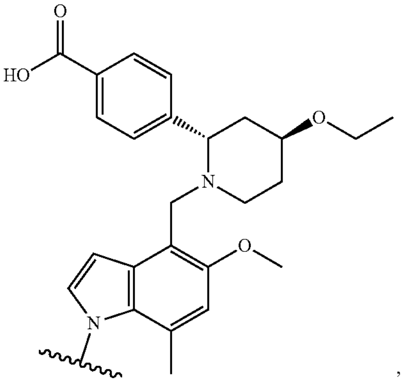

,

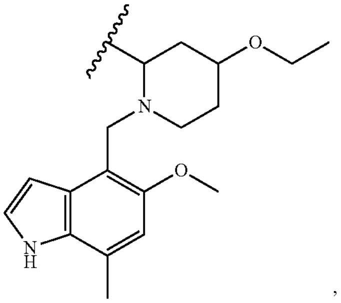

,

-continued

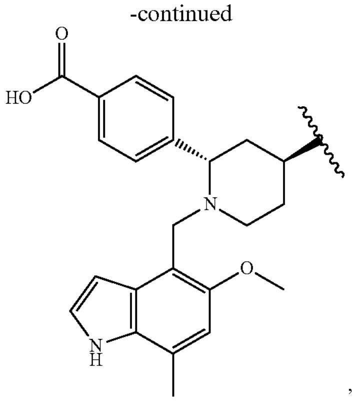

,

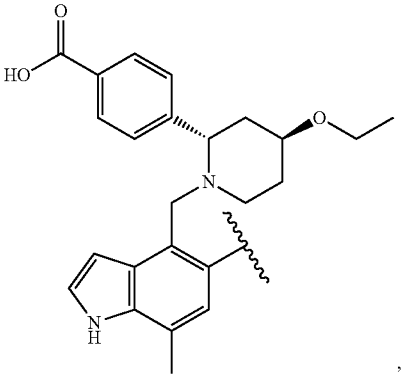

,

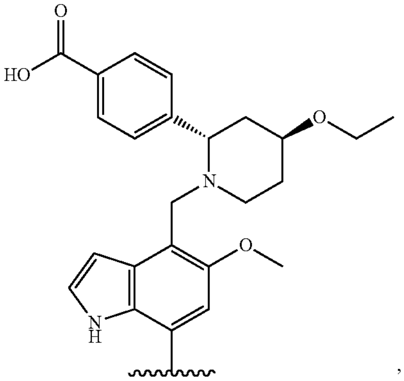

,

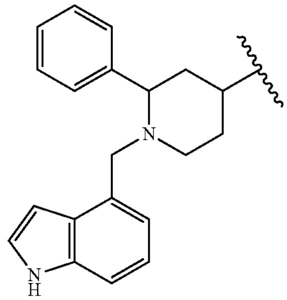

,

-continued

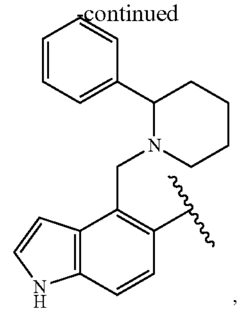

,

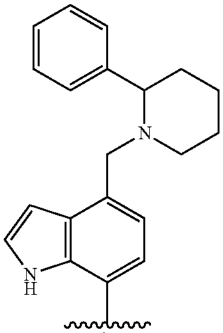

, and

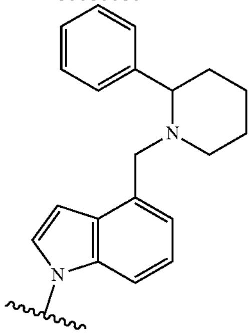

;

each of which is optionally substituted with 1, 2, 3, or 4 substituents independently selected from $R^{21}$.

In certain embodiments the Factor B Targeting Ligand is selected from a ligand described in: Mainolfi, N. et. al. Discovery of 4-((2 S,4 S)-4-Ethoxy-1-((5-Methoxy-7-Methyl-1H-Indol-4-Yl)Methyl)Piperidin-2-Yl)Benzoic Acid (LNP023), a Factor B Inhibitor Specifically Designed To Be Applicable to Treating a Diverse Array of Complement Mediated Diseases. J. Med. Chem. 2020, 63 (11), 5697-5722; WO2020/016749; WO2018/005552; WO2013/192345; or WO2015009616.

In certain embodiments the factor B Targeting Ligand-linker is selected from:

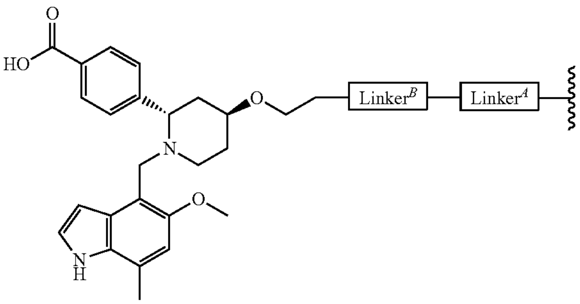

-continued
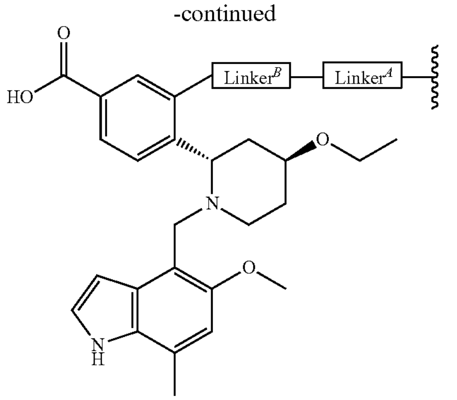
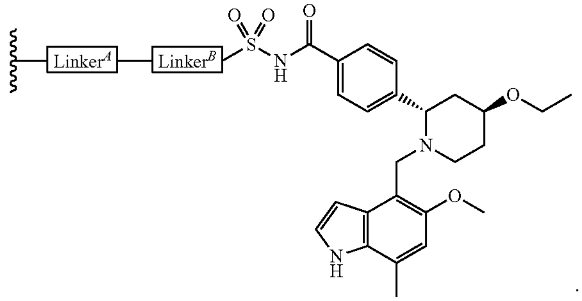
-continued
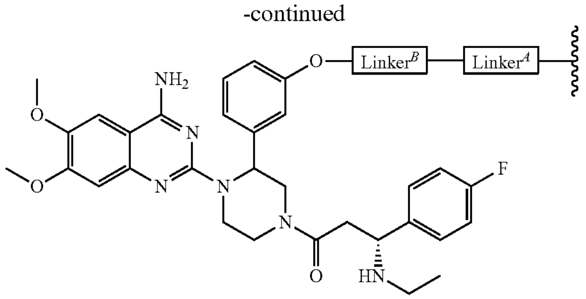
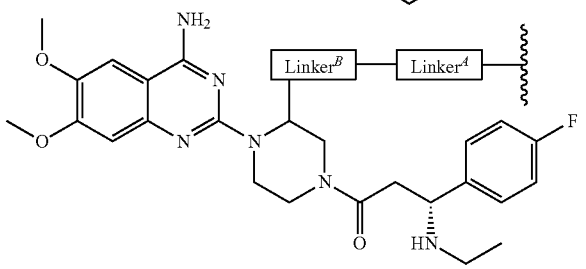
In certain embodiments the compound of the present invention is selected from the following compounds or a bi- or tri-dentate version thereof:
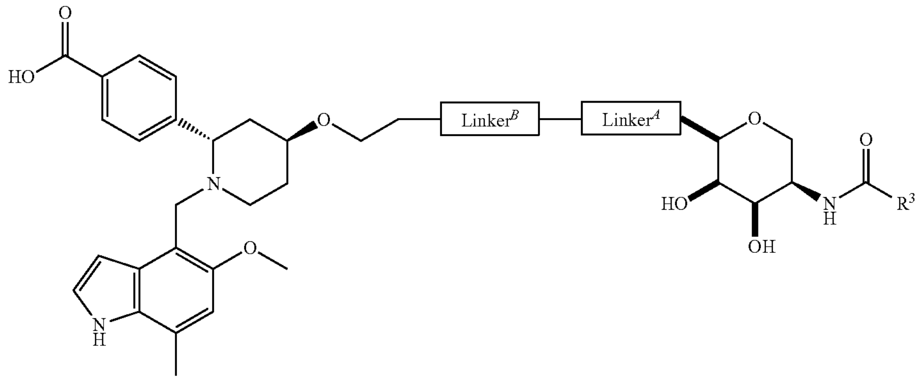
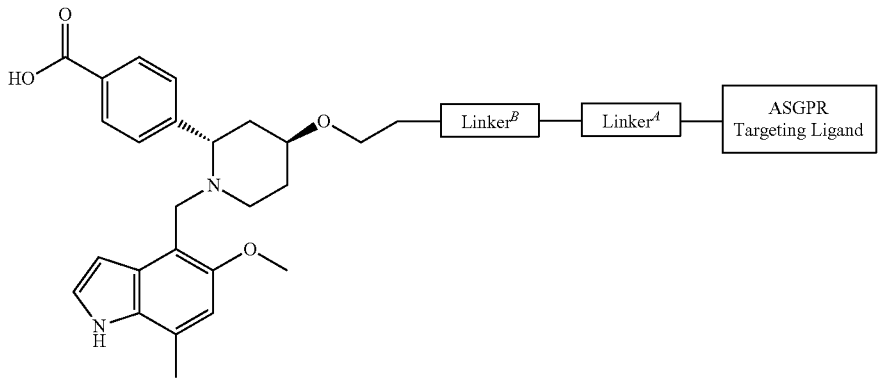

-continued
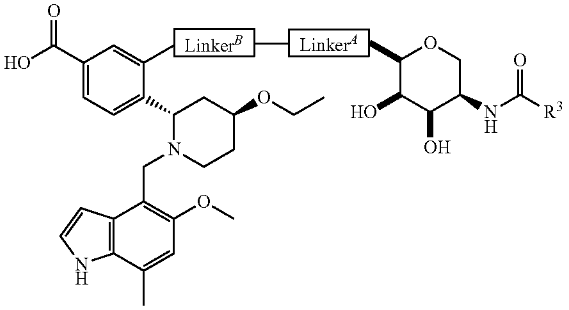
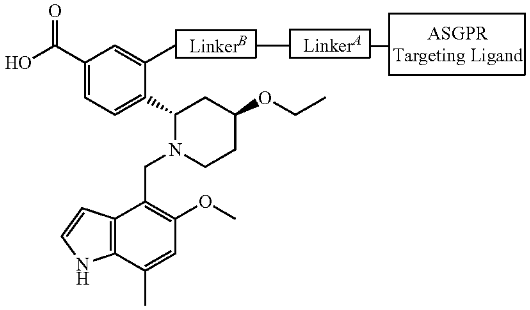
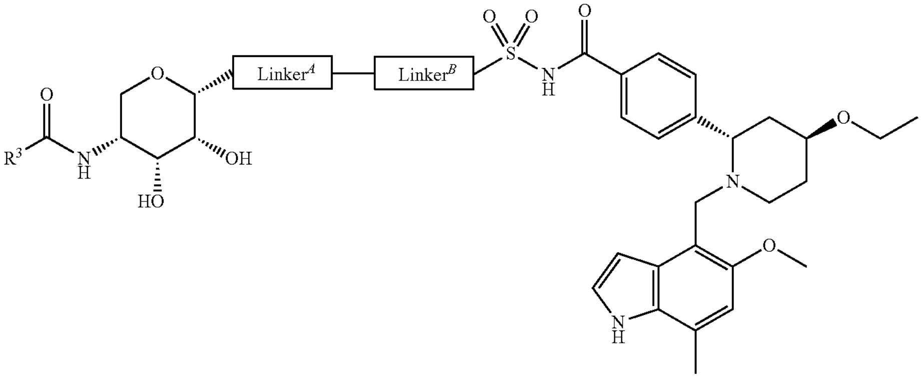
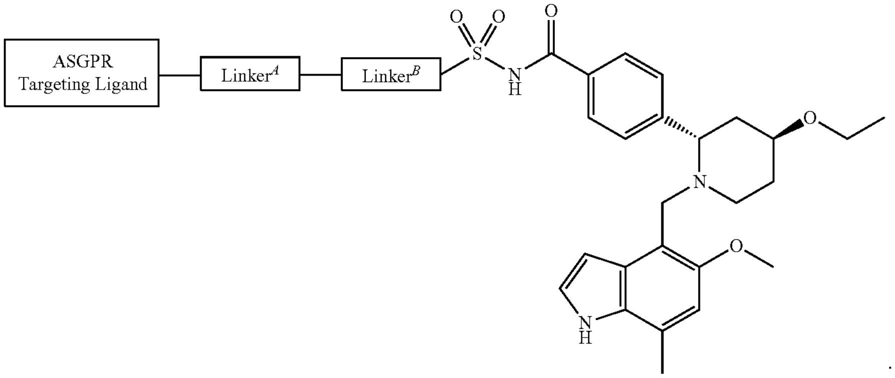
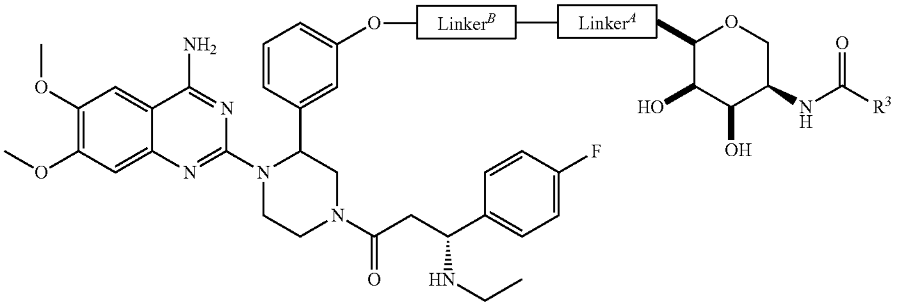
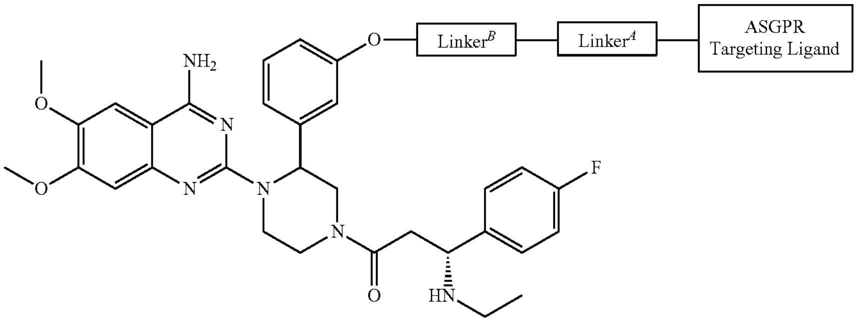

-continued

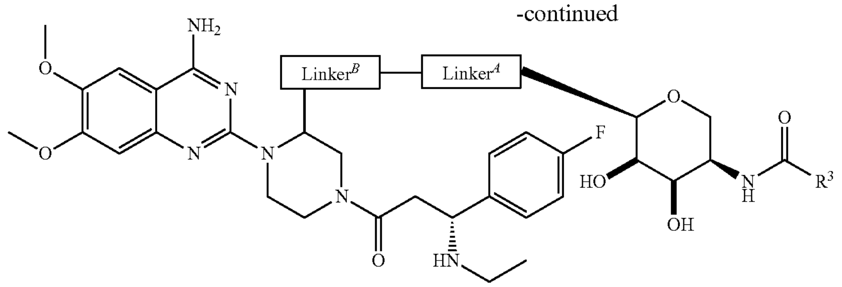

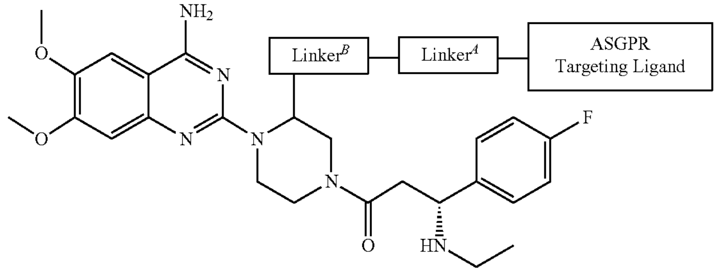

Factor D

In some embodiments, the Target Protein is human Complement factor D (UniProtKB—P00746 (CFAD_HUMAN)). Factor D cleaves factor B when the latter is complexed with factor C3b, activating the C3bbb complex, which then becomes the C3 convertase of the alternate pathway. Its function is homologous to that of C1s in the classical pathway.

The Protein Data Bank website provides the crystal structure of Complement factor D bound to various compounds searchable by 6FTZ, 6FUT, 6FUH, 6FUG, 6FUJ, and 6FUI (Vulpetti, A., et al., ACS Med Chem Lett 2018, 9, 490-495); 5TCA and 5TCC (Yang, C. Y., et al., ACS Med Chem Lett 2016, 7, 1092-1096); 5MT4 (Vulpetti, A., et al., J Med Chem 2017, 60, 1946-1958); 1DFP (Cole, L. B., et al., Acta Crystallogr D Biol Crystallogr 1997, 53, 143-150); 1DIC (Cole, L. B., et al., Acta Crystallogr D Biol Crystallogr 1998, 54, 711-717); 6QMR and 6QMT (Karki, R. G., et al., J Med Chem 2019, 62, 4656-4668).

Figure 6:
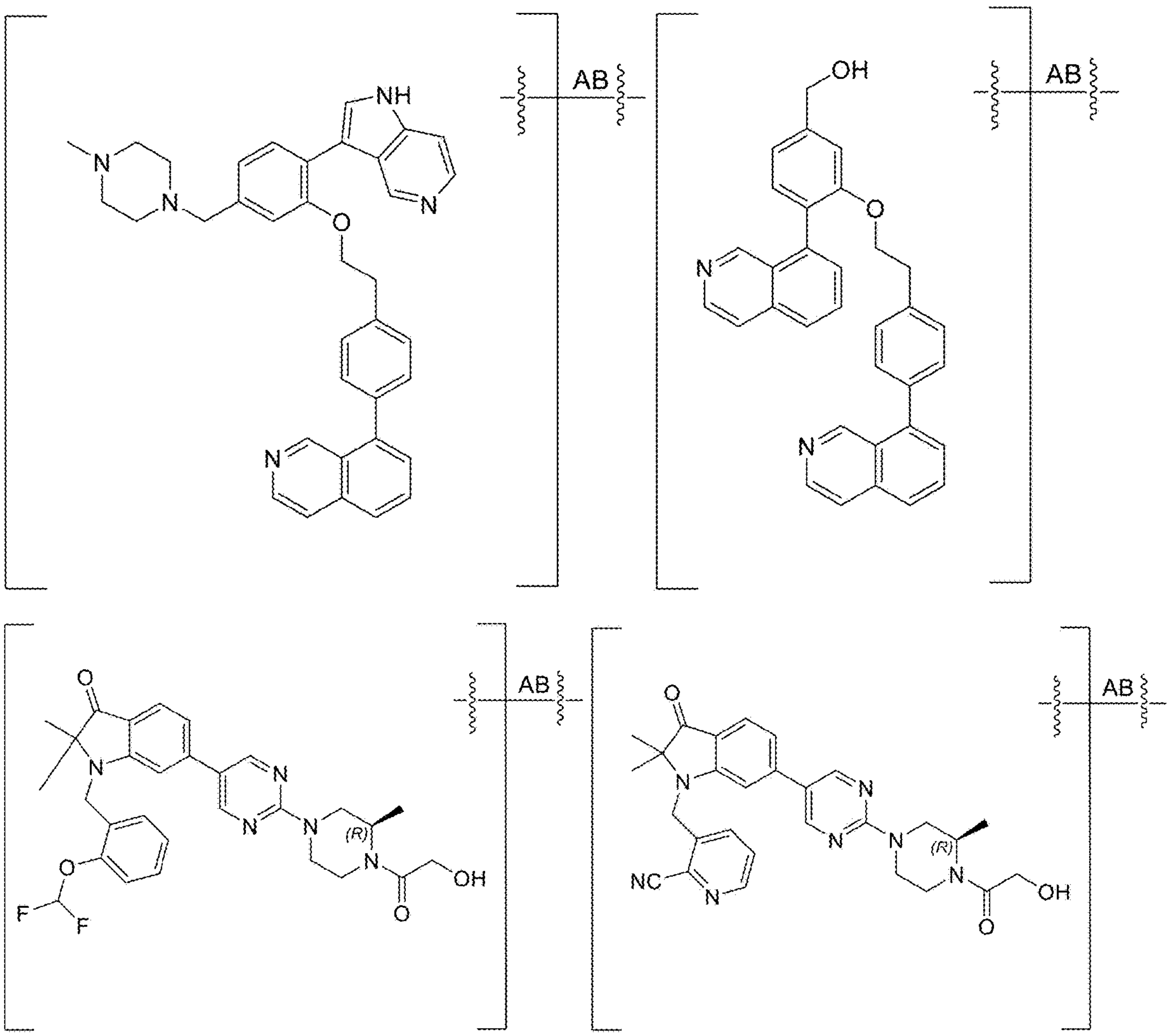
FIG. 6 provides a non-limiting list of exemplary Extracellular Protein Targeting Ligands that target TNF-alpha.

Representative Complement factor D Targeting Ligands are provided in FIG. 6. Additional Complement Factor D Targeting Ligands are provided in, for example, J Med Chem 60: 5717-5735 (2017), Nat Chem Biol 12: 1105-1110 (2016), U.S. Pat. No. 9,598,446B2, U.S. Pat. No. 9,643,986B2, US patent U.S. Pat. No. 9,663,543B2 US patent U.S. Pat. No. 9,695,205B2, U.S. Pat. No. 9,732,103B2, U.S. Pat. No. 9,732,104B2, U.S. Pat. No. 9,758,537B2, U.S. Pat. No. 9,796,741B2, U.S. Pat. No. 9,828,396B2, U.S. patent Ser. No. 10/000,516B2, U.S. patent Ser. No. 10/005,802B2, U.S. patent Ser. No. 10/011,612B2, U.S. patent Ser. No. 10/081,645B2, U.S. patent Ser. No. 10/087,203B2, U.S. patent Ser. No. 10/092,584B2, U.S. patent Ser. No. 10/100,072B2, U.S. patent Ser. No. 10/106,563B2, U.S. patent Ser. No. 10/138,225B2, U.S. patent Ser. No. 10/189,869B2, U.S. patent Ser. No. 10/253,053B2, U.S. patent Ser. No. 10/287,301B2, U.S. patent Ser. No. 10/301,336B2, U.S. patent Ser. No. 10/370,394B2, U.S. patent Ser. No. 10/385,097B2, U.S. patent Ser. No. 10/428,094B2, U.S. patent Ser. No. 10/428,095B2, U.S. patent Ser. No. 10/464,956B2, U.S. patent Ser. No. 10/550,140B2, U.S. patent Ser. No. 10/660,876B2, U.S. patent Ser. No. 10/662,175B2, U.S. patent Ser. No. 10/689,409B2, U.S. patent Ser. No. 10/807,952B2, U.S. patent Ser. No. 10/822,352B2, U.S. Pat. No. 9,464,081B2, and Haematologica 102: 466-475 (2017), each of which is incorporated by reference herein.

In certain embodiments the Extracellular Targeting Ligand is selected from:

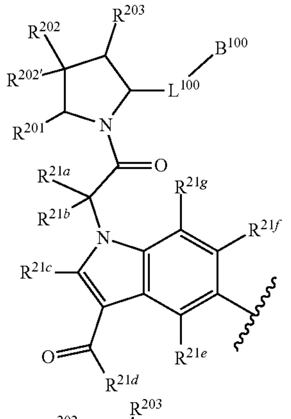

and

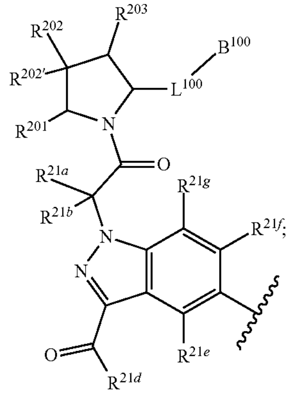

wherein:

$R^{21a}$, $R^{21b}$, $R^{21c}$, $R^{21d}$, $R^{21e}$, $R^{21f}$, and $R^{21g}$ are independently at each occurrence selected from the group consisting of hydrogen, alkyl, alkenyl, alkynyl, F, Cl, Br, I, hydroxyl, alkoxy, azide, amino, cyano, —$NR^6R^7$, —$NR^8SO_2R^3$, —$NR^8S(O)R^3$, haloalkyl, heteroalkyl, aryl, heteroaryl, heterocyclyl, —$SR^3$, —$C(O)OR^3$, —$C(O)NR^6NR^7$, —$OR^3$, and heterocycle;

$R^{201}$, $R^{202}$, $R^{202}$, and $R^{203}$ are independently selected from hydrogen, halogen, hydroxyl, nitro, cyano, amino, $C_1$-$C_6$ alkyl, $C_2$-$C_6$ alkenyl, $C_1$-$C_6$alkoxy, $C_2$-$C_6$alkynyl, $C_2$-$C_6$alkanoyl, $C_1$-$C_6$ thioalkyl, hydroxy$C_1$-$C_6$ alkyl, amino$C_1$-$C_6$ alkyl, —$C_0$-$C_4$ alkyl$NR^9R^{10}$, —$C(O)OR^9$, —$OC(O)R^9$, —$NR^9C(O)R^{10}$, —$C(O)NR^9R^{10}$, —$OC(O)NR^9R^{10}$, —O(heteroaryl), —$NR^9C(O)OR^{10}$, $C_1$-$C_2$ haloalkyl, —$C_0$-$C_4$ alkyl($C_3$-$C_7$cycloalkyl) and —O—$C_0$-$C_4$ alkyl($C_3$-$C_7$cycloalkyl), and $C_1$-$C_2$ haloalkoxy, where $R^{209}$ and $R^{210}$ are independently chosen at each occurrence from hydrogen, $C_1$-$C_6$ alkyl, and ($C_3$-$C_7$cycloalkyl)$C_0$-$C_4$ alkyl;

or $R^{202}$ and $R^{202'}$, may be taken together to form a 3- to 6-membered spiro ring optionally substituted with 1 or more substituents independently chosen from halogen, hydroxyl, cyano, —COOH, $C_1$-$C_4$ alkyl (including in particular methyl), $C_2$-$C_4$ alkenyl, $C_2$-$C_4$alkynyl, $C_1$-$C_4$alkoxy, $C_2$-$C_4$alkanoyl, hydroxy$C_1$-$C_4$ alkyl, (mono- and di-$C_1$-$C_4$ alkylamino)$C_0$-$C_4$ alkyl, —$C_0$-$C_4$ alkyl($C_3$-$C_7$cycloalkyl), —O—$C_0$-$C_4$ alkyl($C_3$-$C_7$cycloalkyl), $C_1$-$C_2$ haloalkyl, and $C_1$-$C_2$ haloalkoxy.

or $R^{201}$ and $R^{202}$ may be taken together to form a 3-membered carbocyclic ring, optionally substituted with 1, 2, or 3 substituents selected from $R^{21}$.

or $R^{201}$ and $R^{202}$ may be taken together to form a 4- to 6-membered carbocyclic ring or a 4- to 6-membered heterocyclic ring containing 1 or 2 heteroatoms independently chosen from N, O, and S, optionally substituted with 1, 2, or 3 substituents selected from $R^{21}$.

$R^{202}$ and $R^{203}$ may be taken together to form a 3- to 6-membered carbocyclic ring or a 3- to 6-membered heterocyclic ring optionally substituted with 1, 2, or 3 substituents selected from $R^{21}$.

$L^{100}$ is selected from

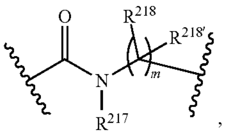
,
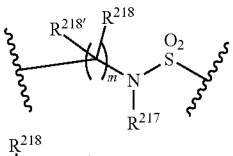
,
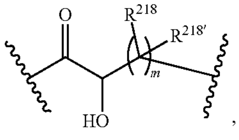
, wherein $R^{217}$ is hydrogen or $C_1$-$C_6$ alkyl and $R^{218}$ and $R^{218'}$ are independently chosen from hydrogen, halogen, hydroxymethyl, and methyl; and m is 0, 1, 2, or 3;

$B^{100}$ is a cycloalkyl, heterocycle group having 1, 2, 3, or 4 heteroatoms independently selected from N, O, and S, a $C_2$-$C_6$ alkenyl, $C_2$-$C_6$alkynyl group, —($C_0$-$C_4$ alkyl)(aryl), —($C_0$-$C_4$ alkyl)(heteroaryl), or —($C_0$-$C_4$ alkyl)(biphenyl), each of which is optionally substituted with 1, 2, 3, or 4 substituents independently selected from $R^{21}$.

In certain embodiments the Extracellular Targeting Ligand is selected from:

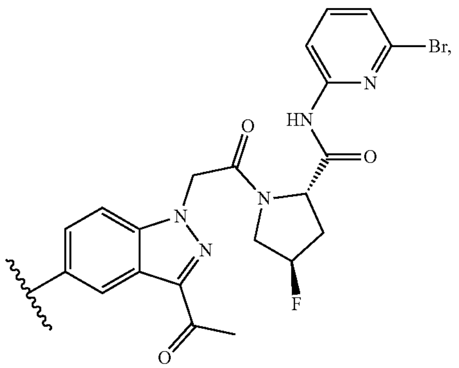

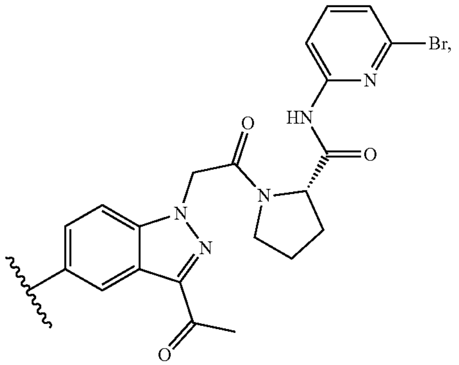

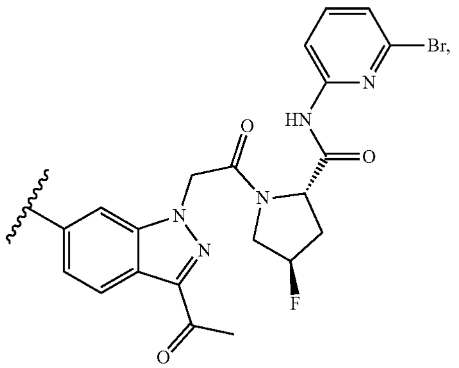

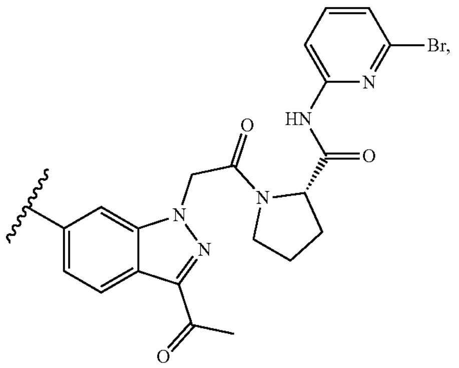

-continued

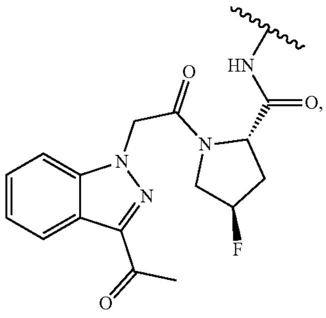

,

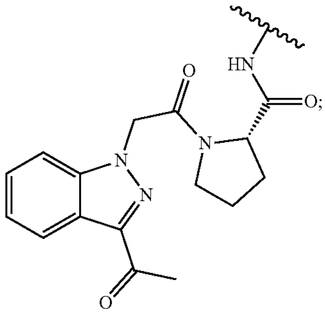

;

each of which is optionally substituted with 1, 2, 3, or 4 substituents independently selected from $R^{21}$.

In certain embodiments the Factor D Targeting Ligand is selected from a ligand described in: U.S. Pat. Nos. 9,796,741; 10,011,612; WO2018/160889; WO2019/195720; WO2019/057946; Karki, R. G. et al. Design, Synthesis, and Preclinical Characterization of Selective Factor D Inhibitors Targeting the Alternative Complement Pathway. J. Med. Chem. 2019, 62 (9), 4656-4668; or Belanger, D. B. et al.; WO2015/009977.

In certain embodiments the complement factor D targeting ligand-linker—is selected from:

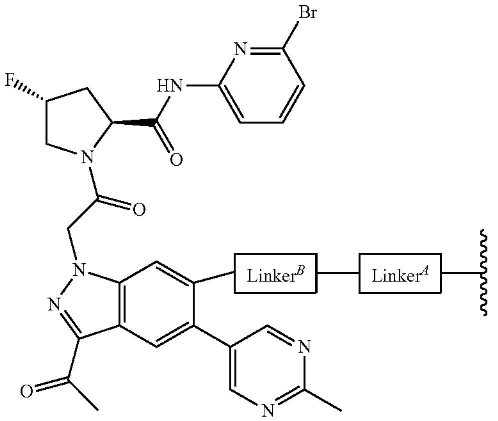

-continued

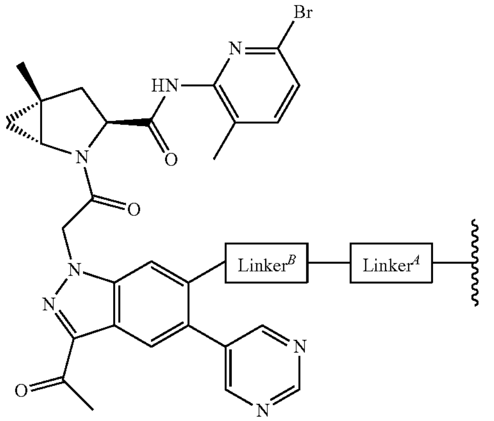

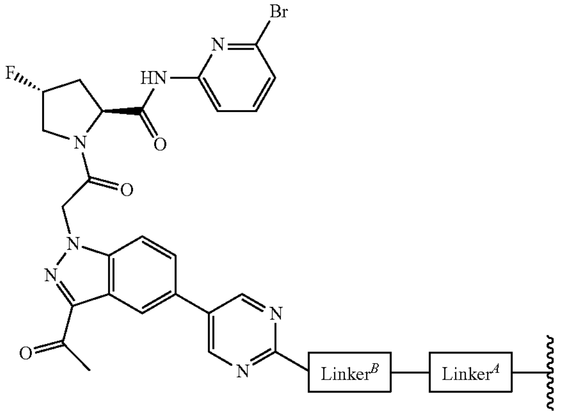

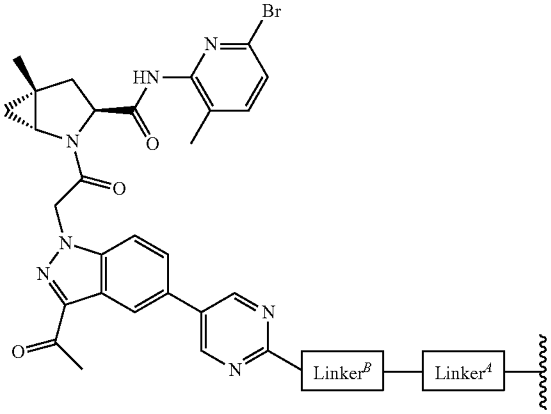

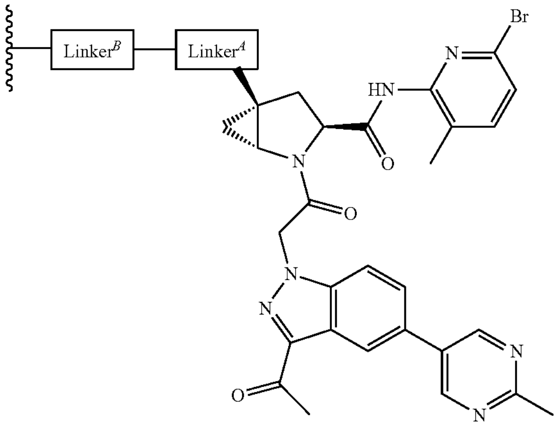

-continued
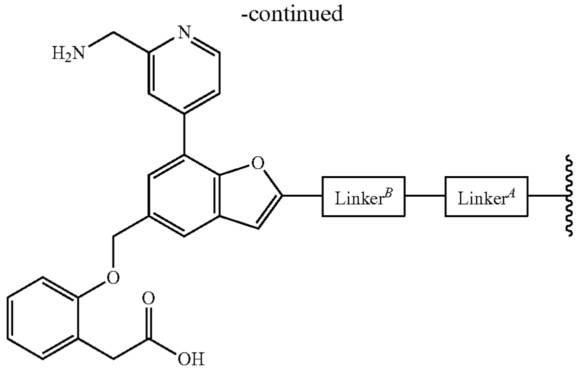
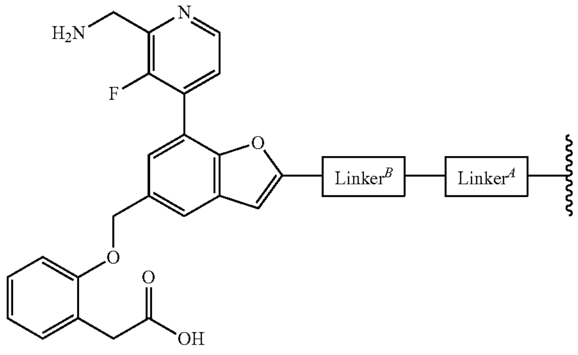
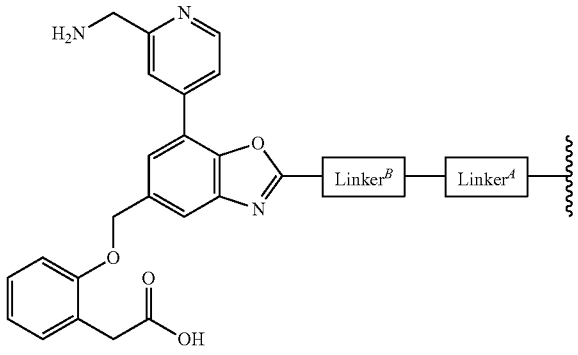
-continued
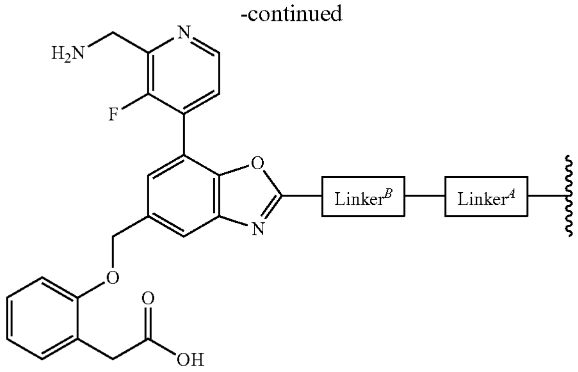
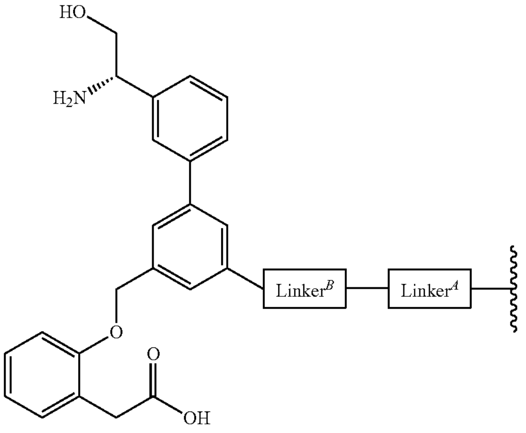
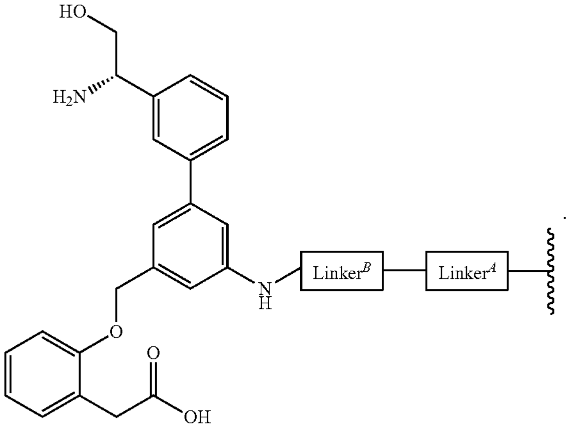
In certain embodiments the compound of the present invention is selected from the following compounds or a bi- or tri-dentate version thereof:

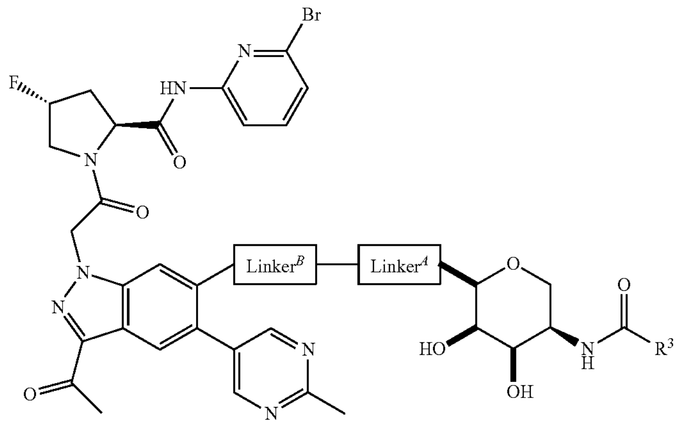
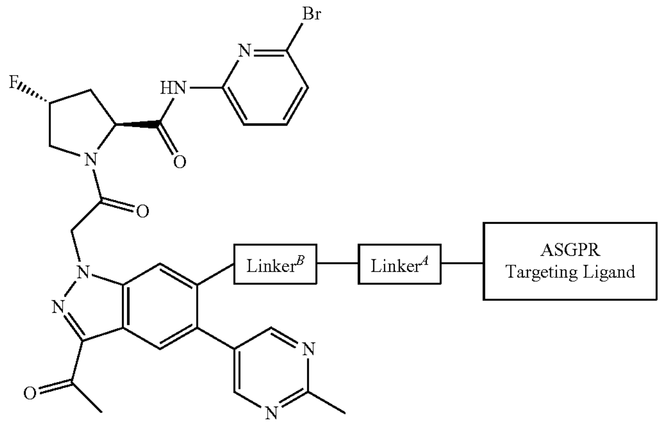
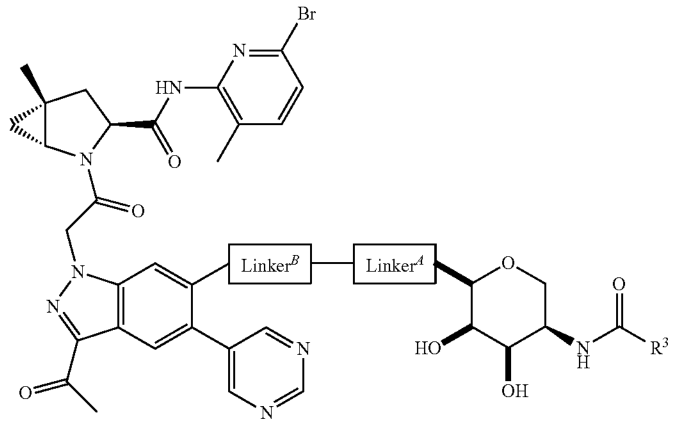
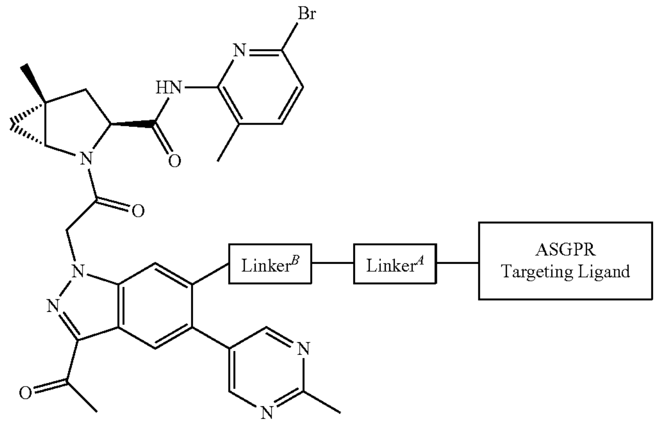

-continued
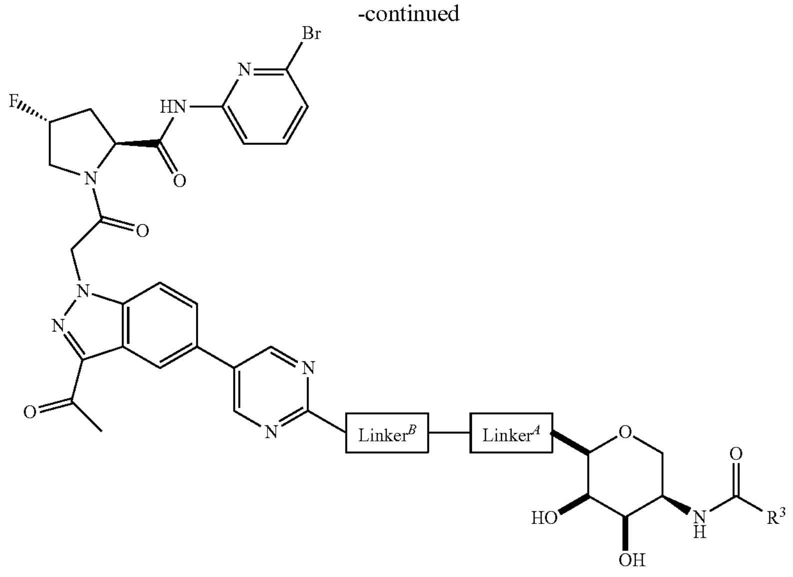
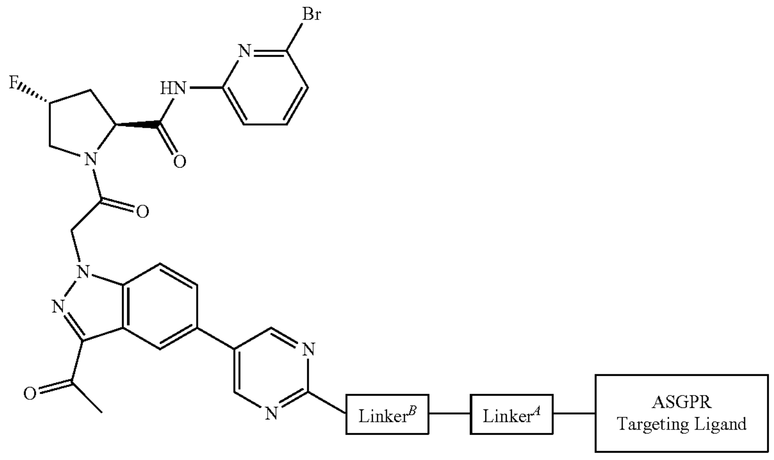
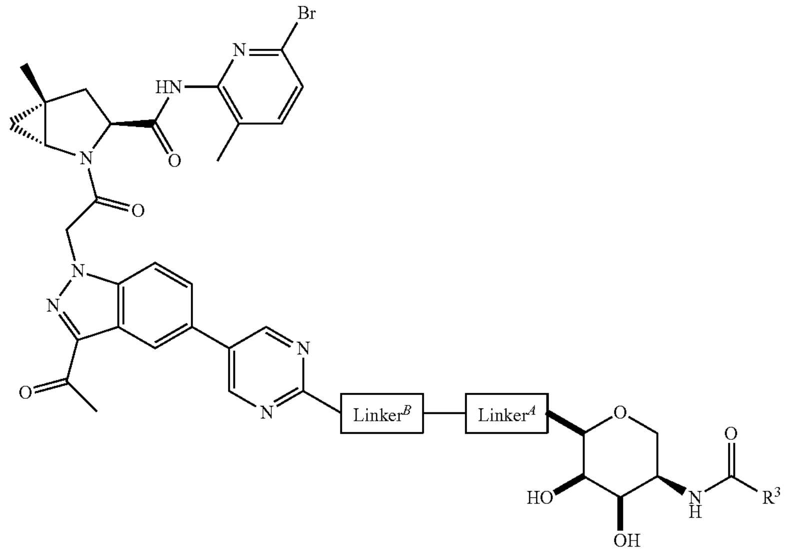

-continued
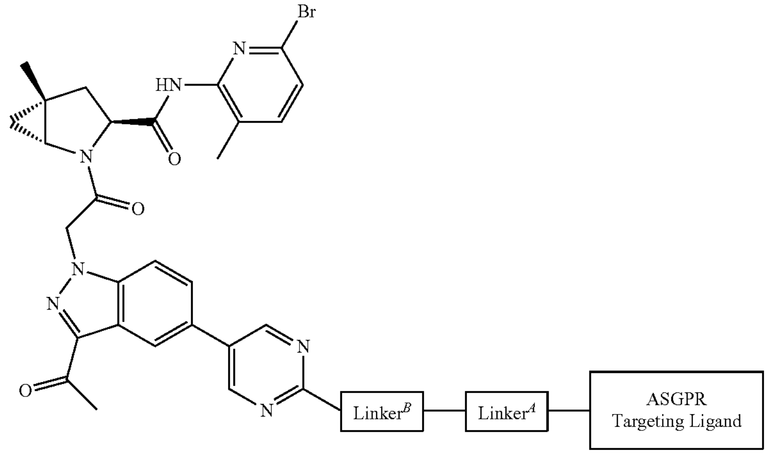
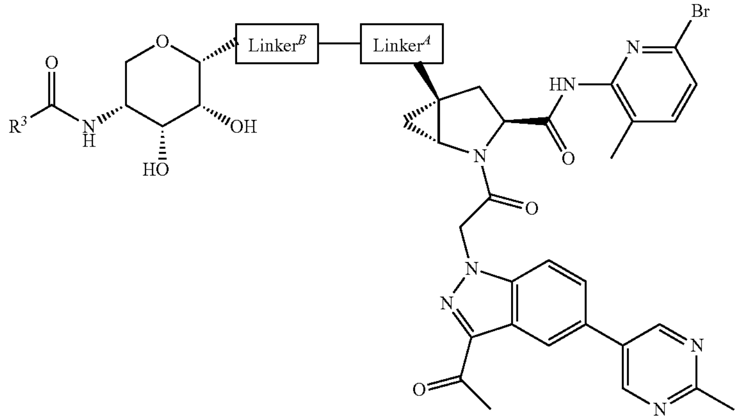
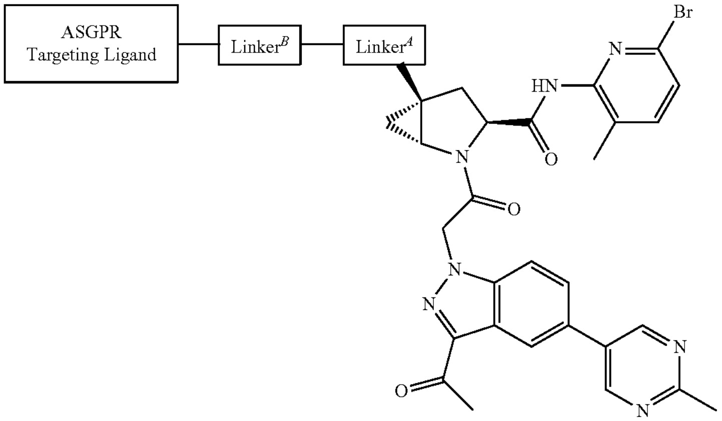
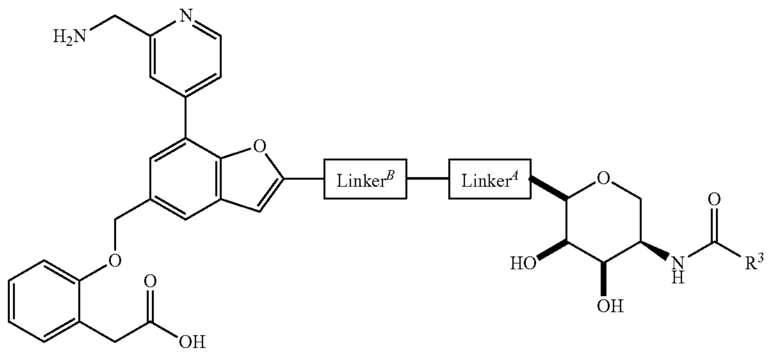

-continued
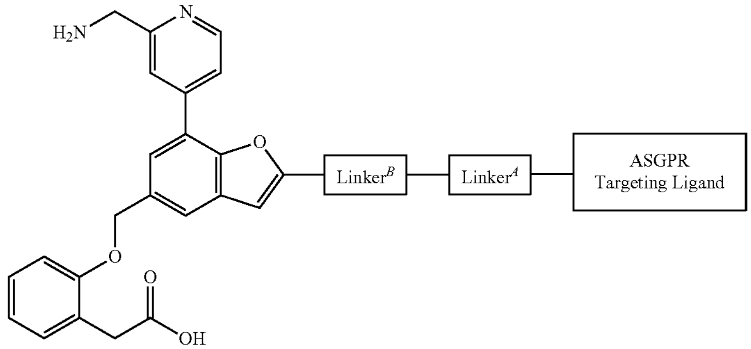
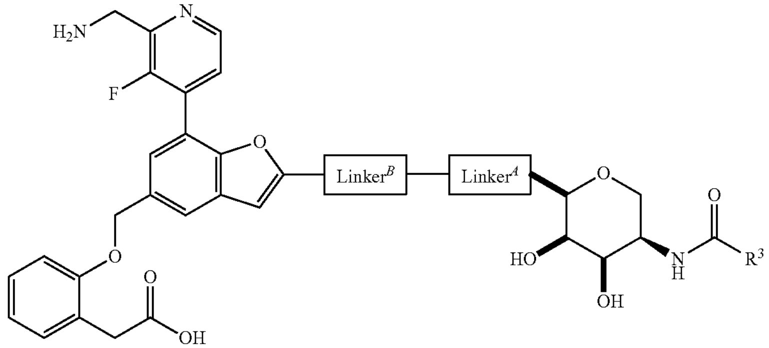
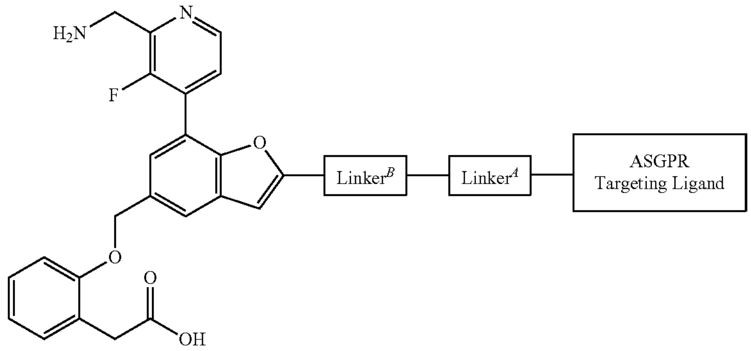
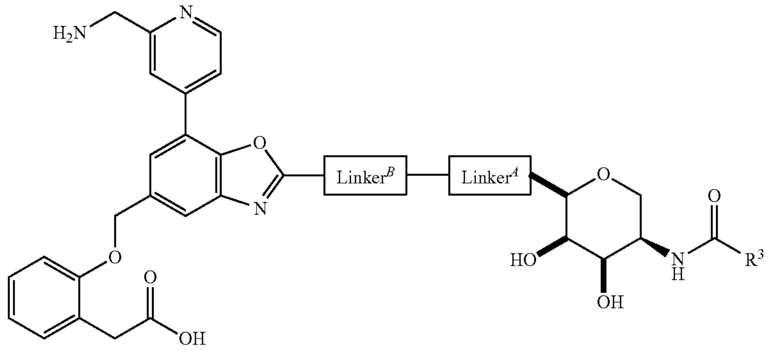

-continued
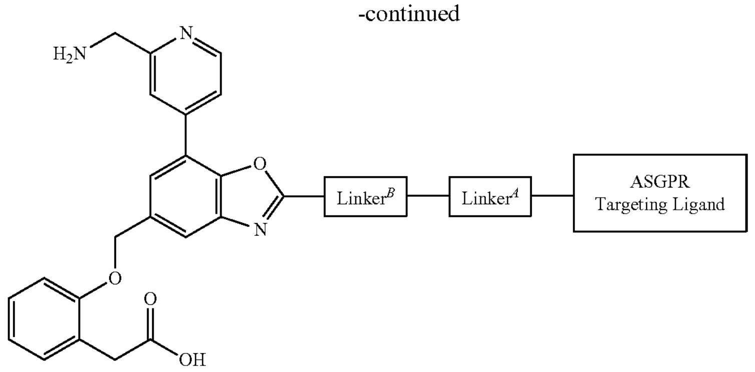
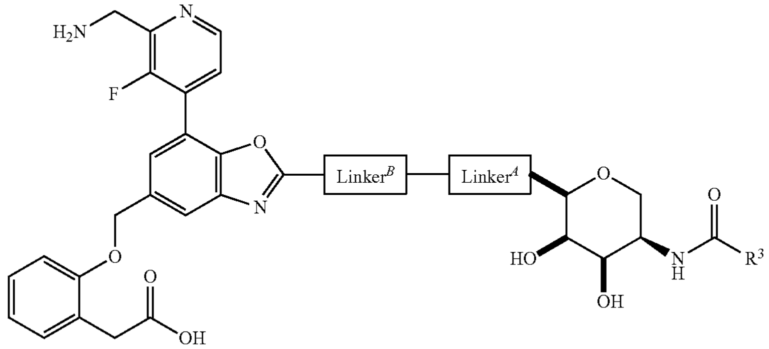
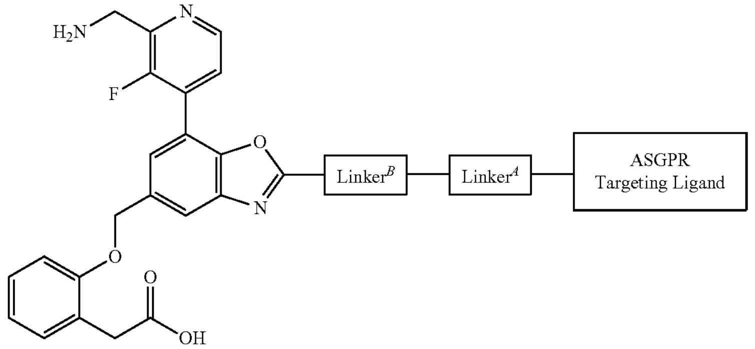
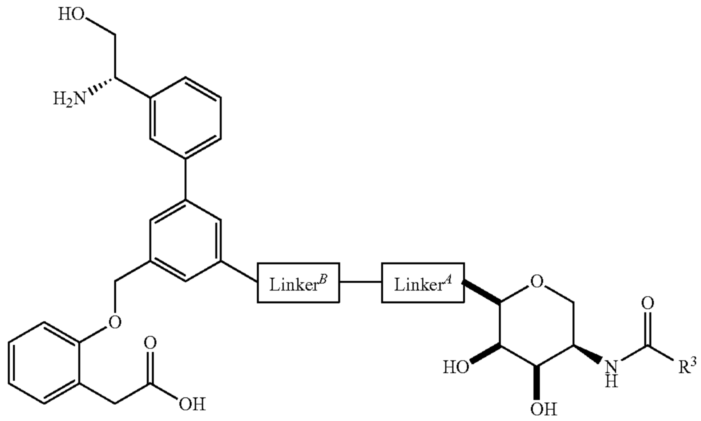

-continued
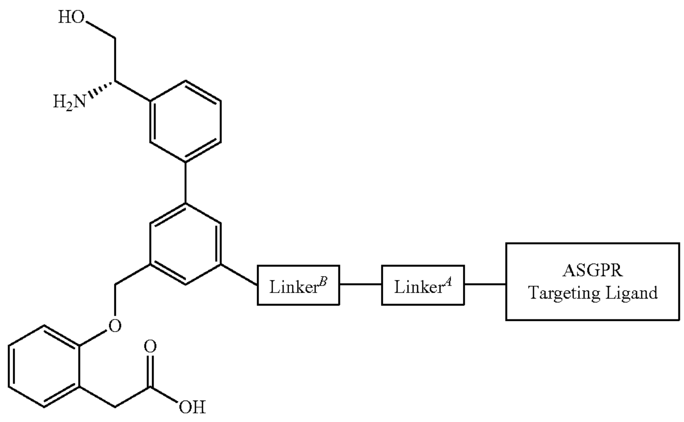
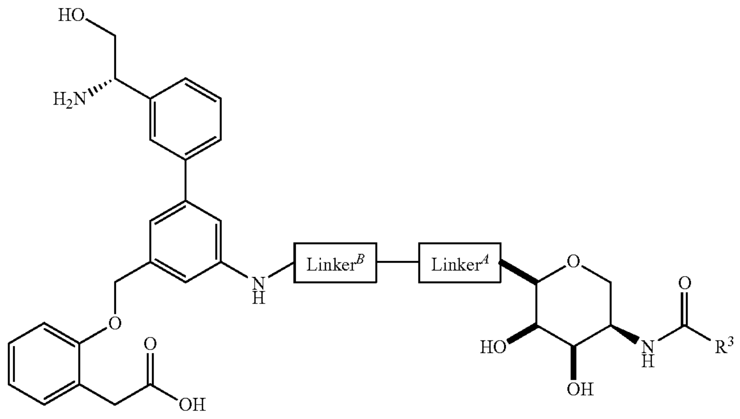
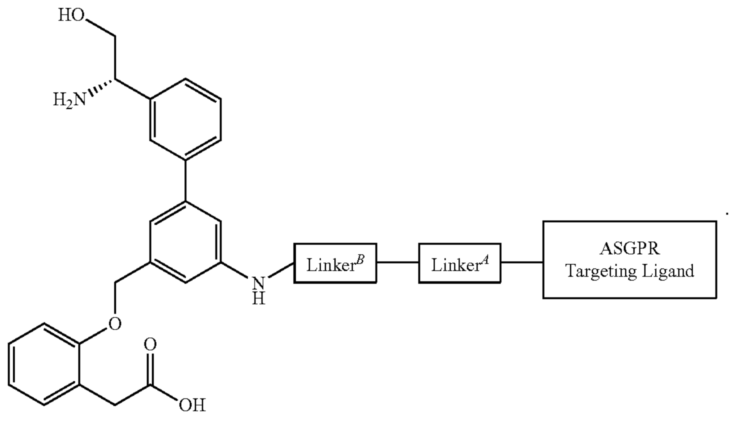
.

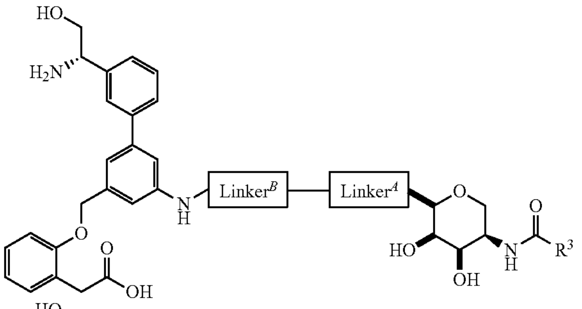

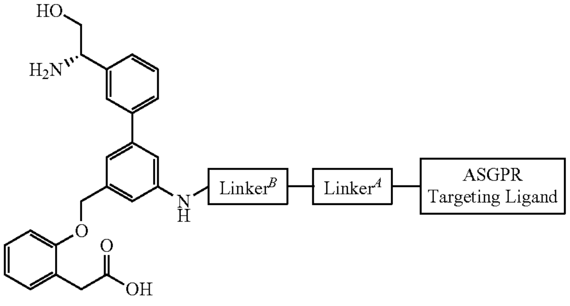

.

Factor H

In some embodiments, the Target Protein is human complement factor H (UniProtKB—P08603 (CFAH_HUMAN)). Complement factor H is a glycoprotein that plays an essential role in maintaining a well-balanced immune response by modulating complement activation. Acts as a soluble inhibitor of complement, where its binding to self-markers such as glycan structures prevents complement activation and amplification on cell surfaces. Complement factor H accelerates the decay of the complement alternative pathway (AP) C3 convertase C3bBb, thus preventing local formation of more C3b, the central player of the complement amplification loop. As a cofactor of the serine protease factor I, CFH also regulates proteolytic degradation of already-deposited C3b. In addition, it mediates several cellular responses through interaction with specific receptors. For example, CFH interacts with CR3/ITGAM receptor and thereby mediates the adhesion of human neutrophils to different pathogens. In turn, these pathogens are phagocytosed and destroyed.

The Protein Data Bank website provides the crystal structure of highly similar mutants of complement factor H searchable by 3KXV and 3KZJ (Bhattacharjee, A., et al., Mol Immunol 2010, 47, 1686-1691); as well as the crystal structure of wild type complement factor H bound to various compounds searchable by 2UWN (Prosser, B. E., et al., J Exp Med 2007, 204, 2277); 5WTB (Zhang, Y., et al., Biochem J 2017, 474, 1619-1631); 5032 and 5035 (Xue, X., et al., Nat Struct Mol Biol 2017, 24, 643-651); 4ONT (Blaum, B. S., et al., Nat Chem Biol 2015, 11, 77-82); and 4ZH1 (Blaum, B. S., et al., Glycobiology 2016, 26, 532-539).

Figure 7:
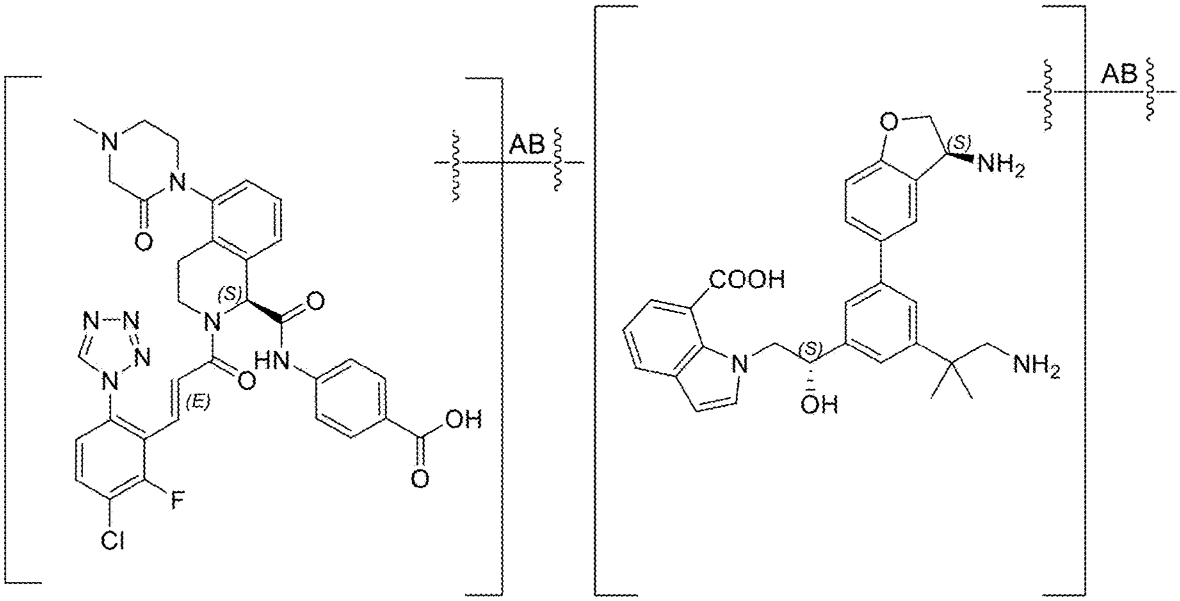
FIG. 7 provides a non-limiting list of exemplary Extracellular Protein Targeting Ligands that target factor XI.

Representative complement factor H Targeting Ligands are provided in FIG. 7. Additional complement factor H Targeting Ligands are provided in, for example, J Immunol 182: 6394-6400 (2009), PLoS Pathogens 4: e1000250 (2008), PLoS Pathogens 6: e1001027 (2010), U.S. patent Ser. No. 10/865,238B1, U.S. Pat. No. 8,962,795B2, US patent application 20160317573A1, and US patent application 20190315842A1, each of which is incorporated by reference herein.

Complement Component 5 (C5)

In some embodiments, the Target Protein is human complement component 5 ($C_5$) (UniProtKB—P01031 (CO5_HUMAN)). Activation of C5 by a C5 convertase initiates the spontaneous assembly of the late complement components, C5-C9, into the membrane attack complex. C5b has a transient binding site for C6. The C5b-C6 complex is the foundation upon which the lytic complex is assembled.

The Protein Data Bank website provides the crystal structure of Complement Component 5 searchable by 3CU7 (Fredslund, F., Nat Immunol 2008, 9, 753-760); as well as the crystal structure of Complement Component 5 bound to various compound searchable by 5I5K (Schatz-Jakobsen, J. A., et al, J Immunol 2016, 197, 337-344); 3PVM and 3PRX (Laursen, N. S., et al., EMBO J 2011, 30, 606-616); and 3KLS (Laursen, N. S., et al., Proc Natl Acad Sci 2010, 107, 3681-3686).

Figure 8:
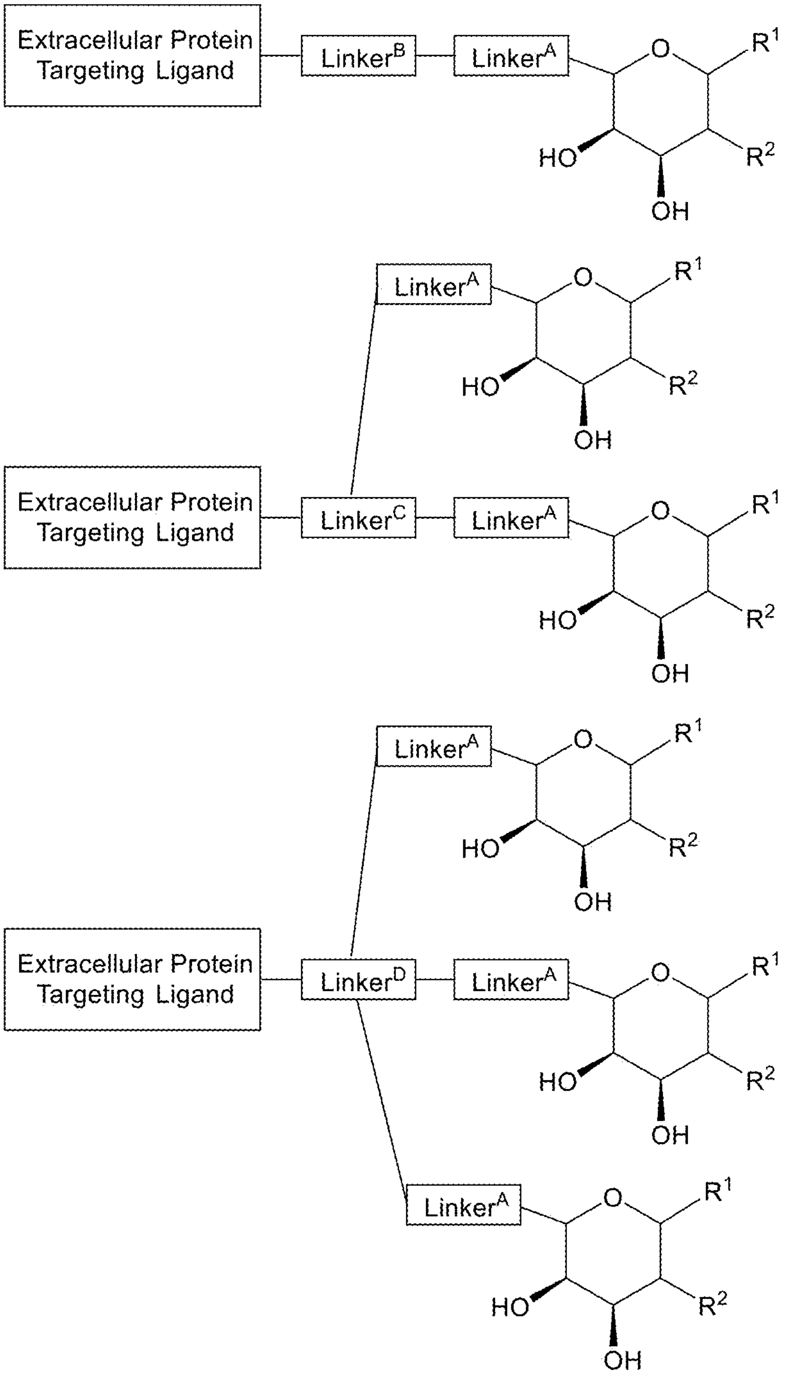
FIG. 8 provides a non-limiting list of exemplary formulas of the present invention.

Representative Complement Component 5 Targeting Ligands are provided in FIG. 8. Additional Complement Component 5 Targeting Ligands are provided in, for example, J Immunol 197: 337-344 (2016), Ther Adv Hematol 10: 1-11 (2019), BioDrugs 34: 149-158 (2020), Blood 135: 884-885 (2020), US patent application 20170342139A1, and US patent application 20200095307A1, each of which is incorporated by reference herein.

In certain embodiments the Extracellular Targeting Ligand is selected from:

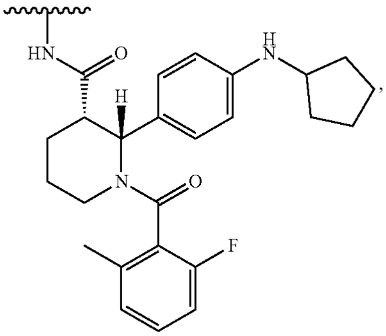

,

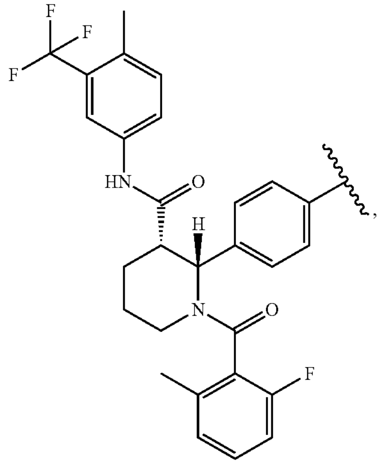

,

-continued

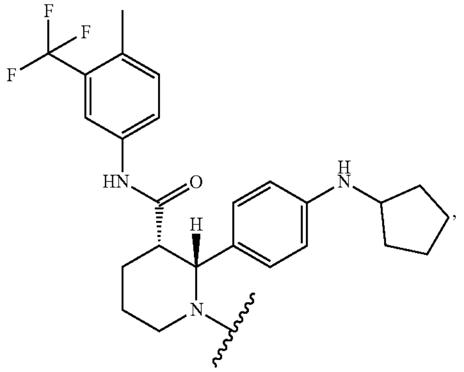

,

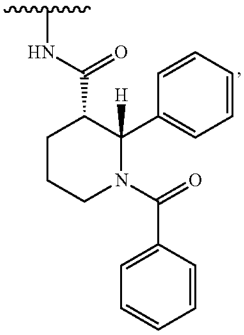

,

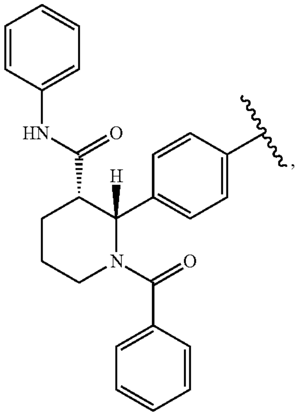

,

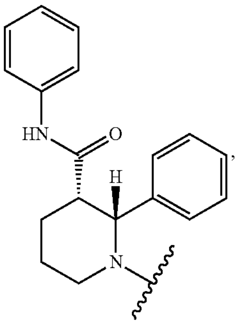

,

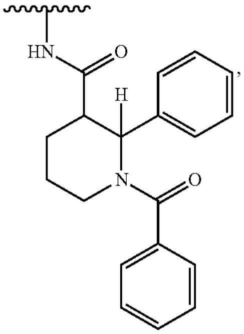

,

-continued

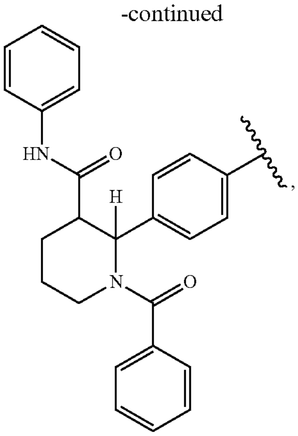

, and

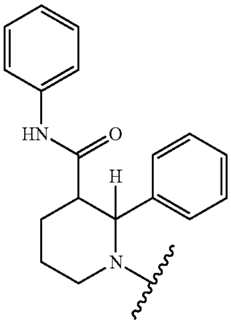

;

each of which is optionally substituted with 1, 2, 3, or 4 substituents independently selected from $R^{21}$.

In certain embodiments the complement C5 Targeting Ligand is selected from a ligand described in Jendza, K. et al. A Small-Molecule Inhibitor of C5 Complement Protein. Nat Chem Biol 2019, 15 (7), 666-668; or Zhang, M.; Yang, X. Y.; Tang, W.; Groeneveld, T. W. L.; He, P. L.; Zhu, F. H.; Li, J.; Lu, W.; Blom, A. M.; Zuo, J. P.; Nan, F. J. Discovery and Structural Modification of 1-Phenyl-3-(1-Phenylethyl) Urea Derivatives as Inhibitors of Complement. ACS Med. Chem. Lett. 2012, 3 (4), 317-321.

In certain embodiments the C5 Targeting Ligand is selected from:

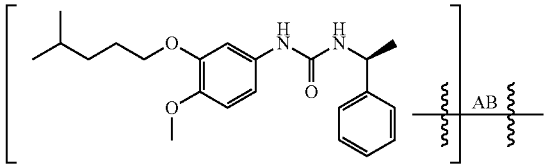

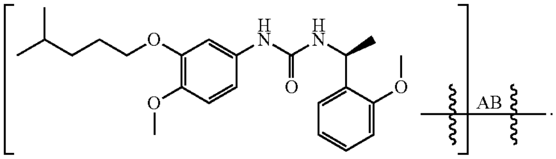

.

Complement C1s

In certain embodiments the extracellular targeting ligand is a C1s Targeting Ligand.

In certain embodiments the complement C1s Targeting Ligand is selected from a ligand described in WO2020/198062 or U.S. Pat. No. 6,683,055.

In certain embodiments the compound of the present invention is selected from the following compounds or a bi- or tri-dentate version thereof:

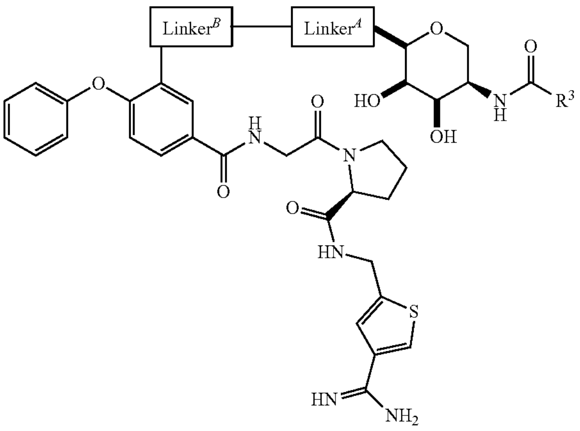

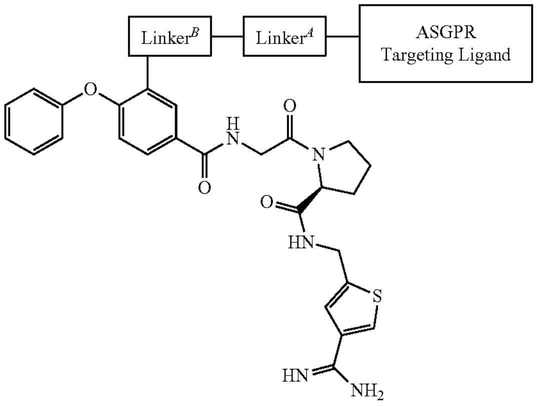

MASP

In certain embodiments the extracellular targeting ligand is a MASP Targeting Ligand.

In certain embodiments the MASP Targeting Ligand is selected from a ligand described in Héja, D. et al. Monospecific Inhibitors Show That Both Mannan-Binding Lectin-Associated Serine Protease-1 (MASP-1) and -2 Are Essential for Lectin Pathway Activation and Reveal Structural Plasticity of MASP-2. Journal of Biological Chemistry 2012, 287 (24), 20290-20300; Dobó, J.; Kocsis, A.; Gál, P. Be on Target: Strategies of Targeting Alternative and Lectin Pathway Components in Complement-Mediated Diseases. Front. Immunol. 2018, 9, 1851; or WO 2014/144542.

In certain embodiments the MSAP-1 Targeting Ligand is SGMI-1 peptide, linked through the N- or C-terminus.

In certain embodiments the MSAP-1 Targeting Ligand is SGMI-2 peptide, linked through the N- or C-terminus.

In certain embodiments the MSAP-1 Targeting Ligand is TFMI-3 peptide, linked through the N- or C-terminus.

Factor XIa

In certain embodiments the extracellular targeting ligand is a factor XIa Targeting Ligand.

In certain embodiments the factor XIa Targeting Ligand is selected from a ligand described in: Lorthiois, E. et al. Structure-Based Design and Preclinical Characterization of Selective and Orally Bioavailable Factor XIa Inhibitors: Demonstrating the Power of an Integrated Sl Protease Family Approach. J. Med. Chem. 2020, 63 (15), 8088-8113.

In certain embodiments the factor XIa Targeting Ligand is selected from a ligand described in: Quan, M. L. et al. Factor XIa Inhibitors as New Anticoagulants. J. Med. Chem. 2018, 61 (17), 7425-7447.

In certain embodiments the factor XIa Targeting Ligand is selected from a ligand described in: Yang, W. et al. Discovery of a High Affinity, Orally Bioavailable Macrocyclic FXIa Inhibitor with Antithrombotic Activity in Preclinical Species. J. Med. Chem. 2020, 63 (13), 7226-7242.

In certain embodiments the factor XIa Targeting Ligand-linker is:

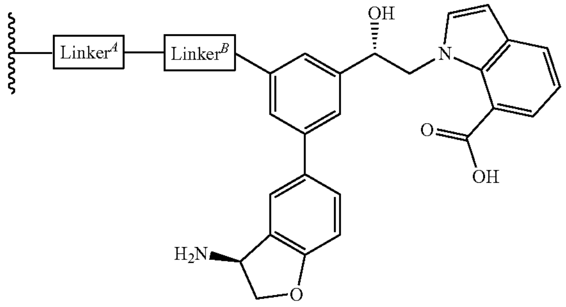

In certain embodiments the compound of the present invention is selected from the following compounds or a bi- or tri-dentate version thereof:

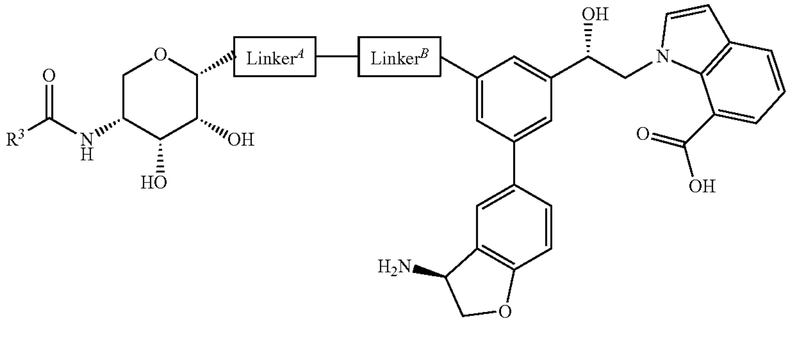

-continued

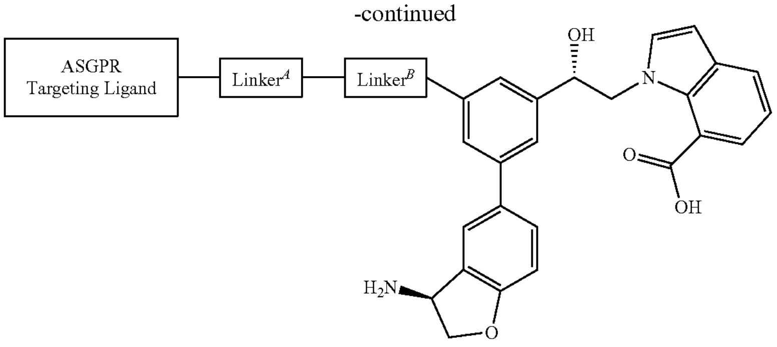

In certain embodiments the factor Xia Targeting Ligand is selected where an anchor bond is placed at any suitable location with or without functionalization.

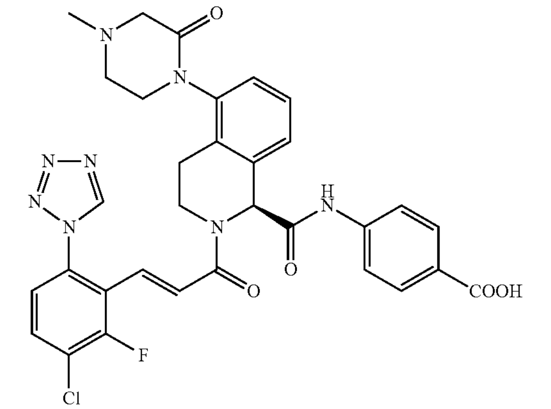

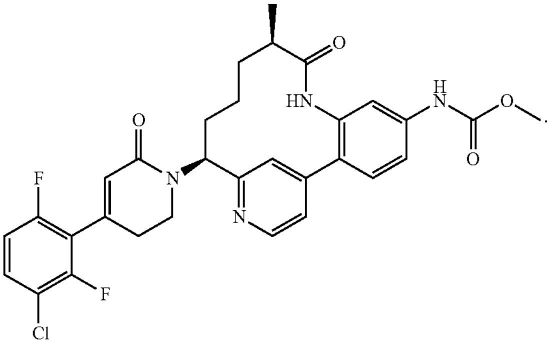

Additional Complement Extracellular Targeting Ligands

In certain embodiments the Extracellular Targeting Ligand is selected from OMS721, Amy 101, APL2, ACH-4471, LNP023, eculizumab, and avacopan. In other embodiments the extracellular targeting ligand is selected from C1-INH, rhucin, TP10, CAB-2, eculizumab, pexelizumab, ofatumumab, compstatin, PMX-53, and rhMBL. In other embodiments the extracellular targeting ligand is selected from BCX1470, TP-20, mirococept, TNX-234, TNX-558, TA106, neutrazumab, anti-properdin, HuMax-CD38, ARC1905, and JPE-1375.

TNF-alpha

In certain embodiments the Extracellular Targeting Ligand is a TNF-alpha Targeting Ligand.

In certain embodiments the TNF-alpha Targeting Ligand is selected from a ligand described in Dietrich, J. D. et al. Development of Orally Efficacious Allosteric Inhibitors of TNFα via Fragment-Based Drug Design. J. Med. Chem. 2021, 64 (1), 417-429.

In certain embodiments the TNF-alpha Targeting Ligand-linker is selected from:

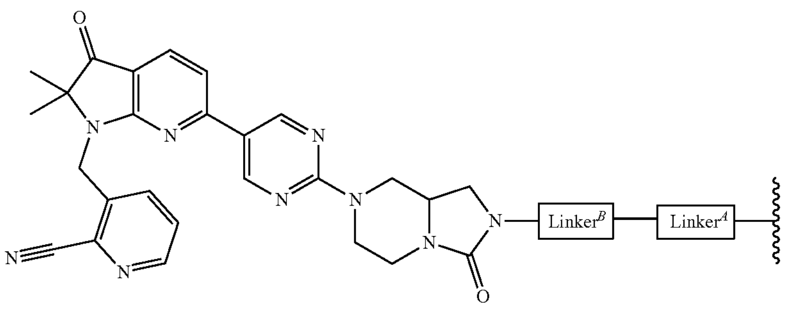

-continued
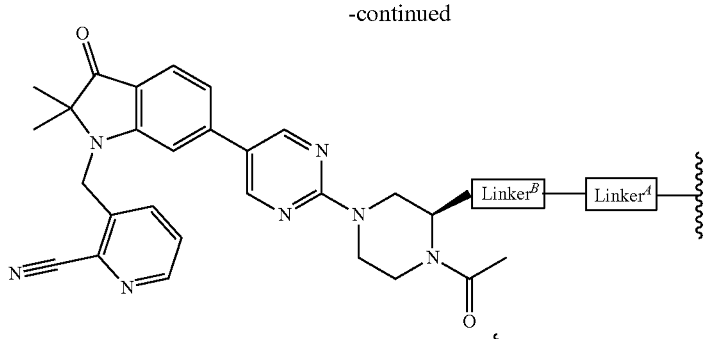
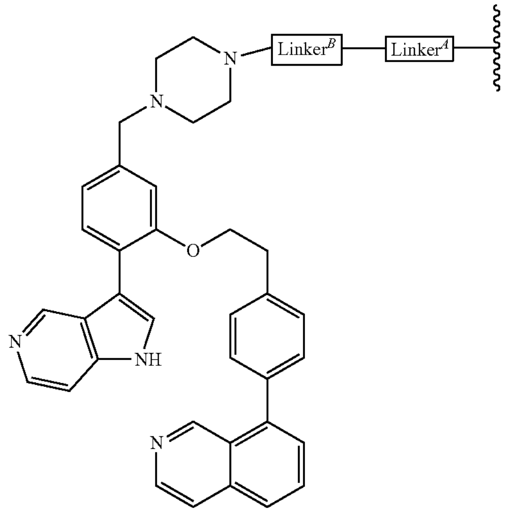
In certain embodiments the compound of the present invention is selected from the following compounds or a bi- or tri-dentate version thereof:
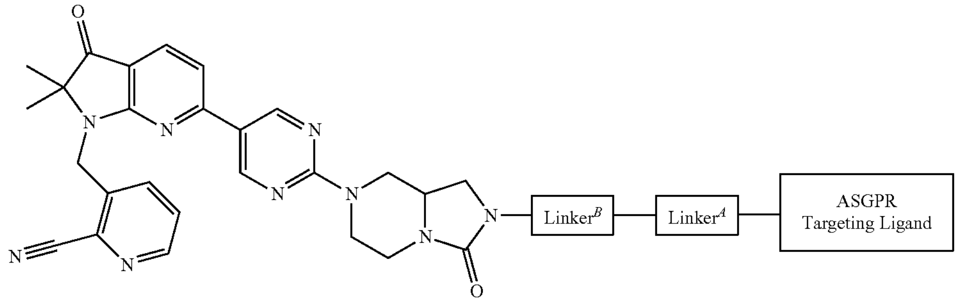
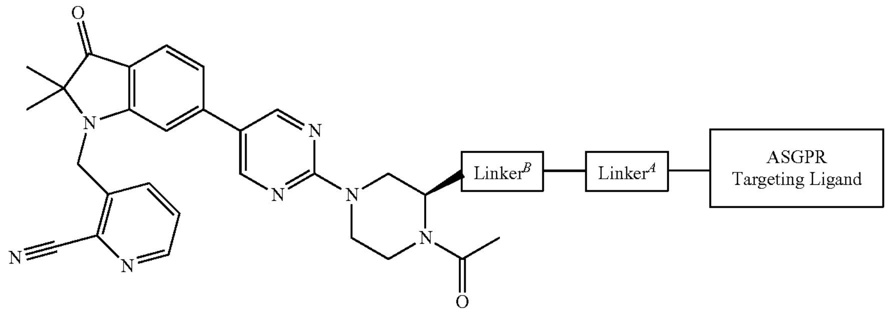

-continued
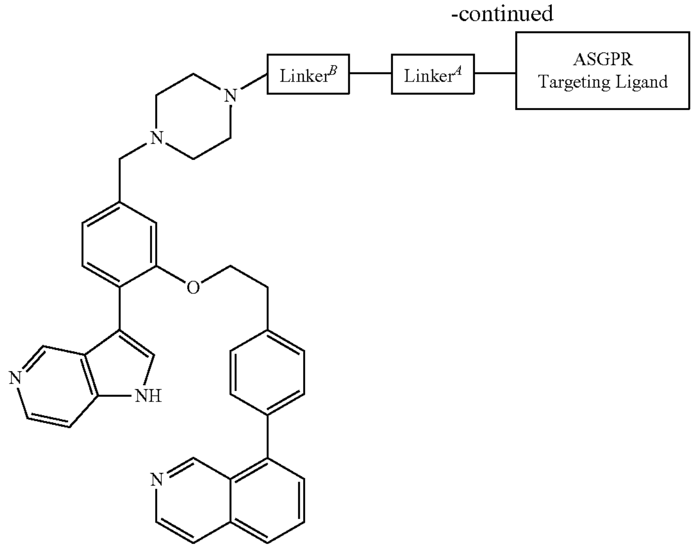
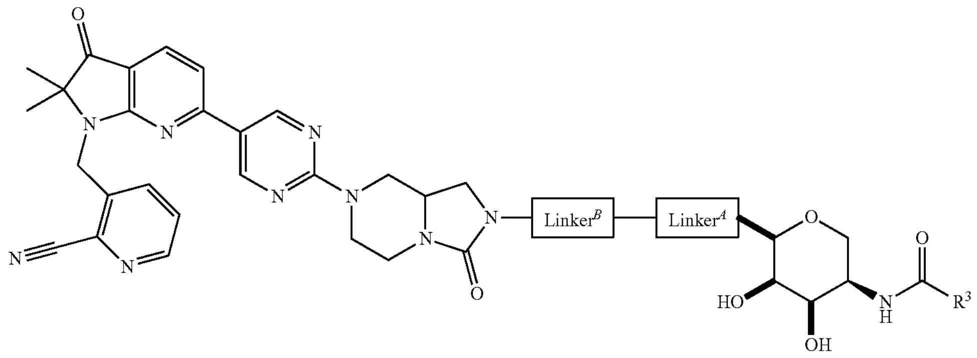
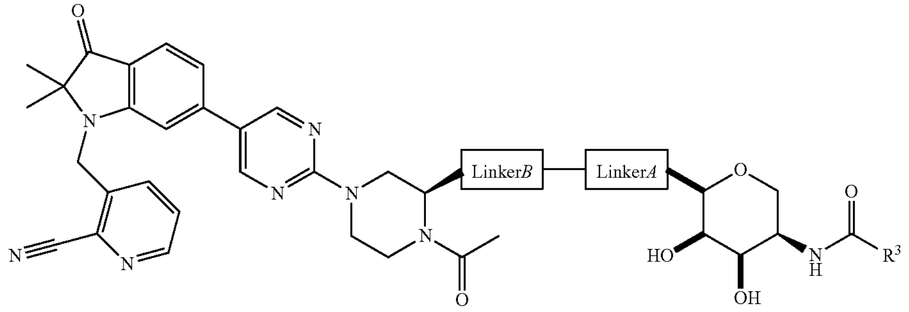
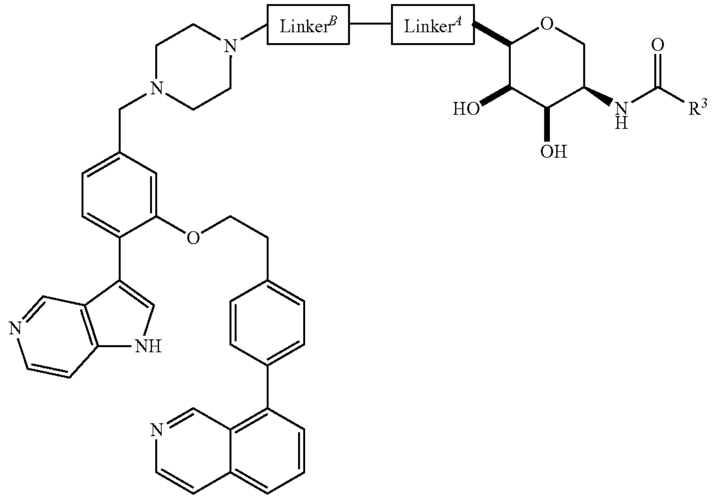

Specific Extracellular Targeting Ligands
In certain embodiments the Extracellular Protein Targeting Ligand is OPT-3. OPT-3 has the following structure. It can bound to the linker in any available location using standard linking chemistry.
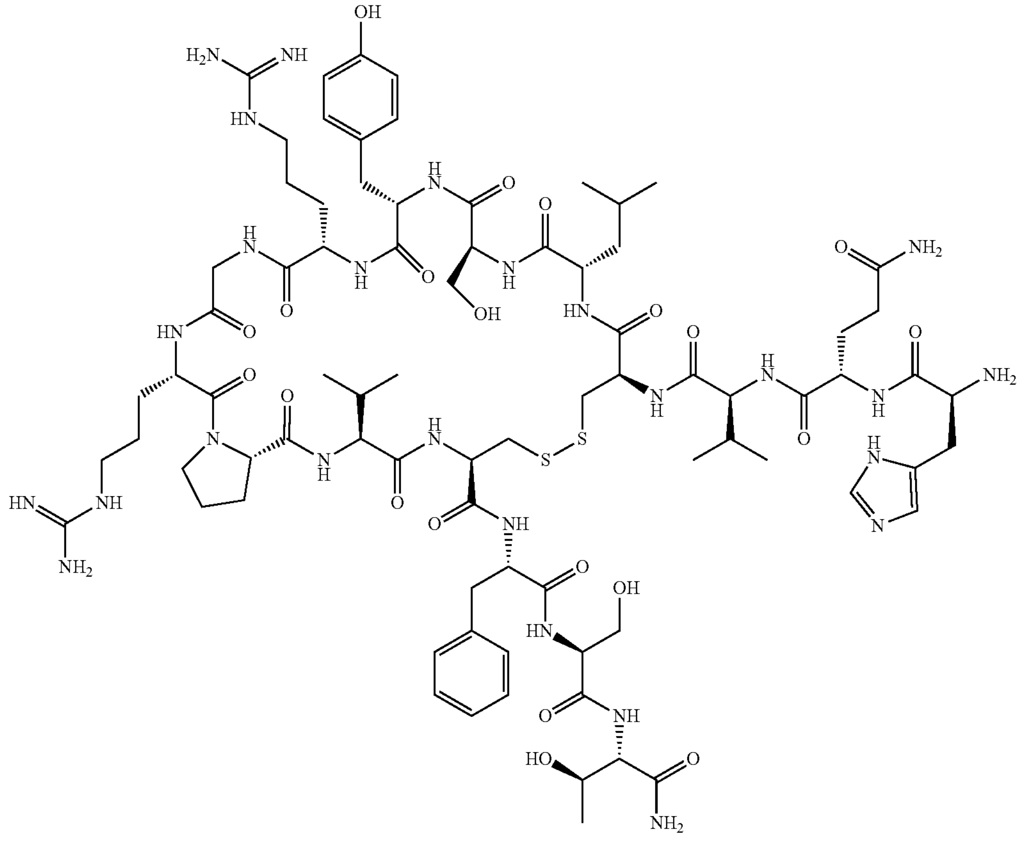 [SMILES: CC(C)C[C@@H]1NC(=O)[C@@H](NC(=O)[C@@H](NC(=O)[C@H](CCC(N)=O)NC(=O)[C@@H](N)Cc2cnc[nH]2)C(C)C)CSSC[C@@H](C(=O)N[C@@H](Cc2ccccc2)C(=O)N[C@@H](CO)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC1=O]

In certain embodiments OPT-3 is attached to the linker through the primary amine of histidine as shown below.
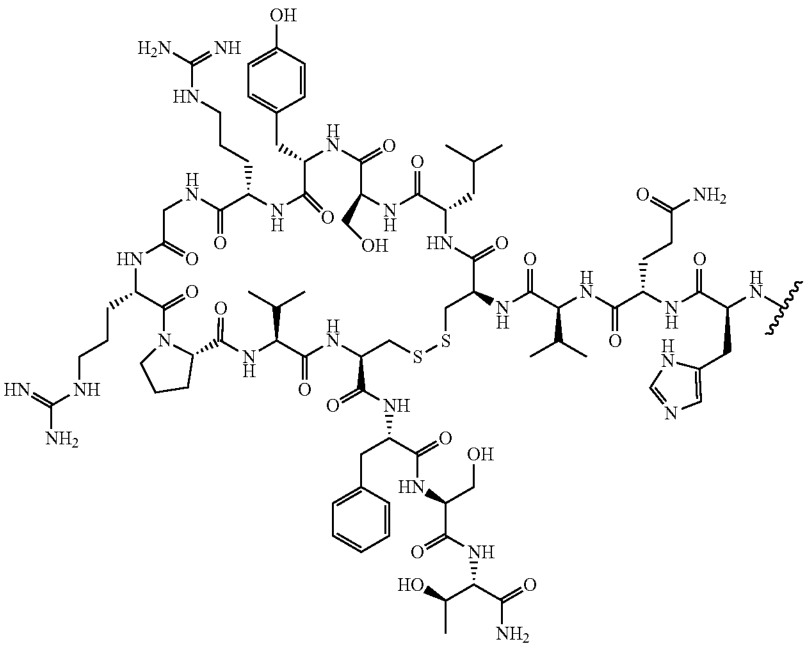 [SMILES: *N[C@@H](Cc1cnc[nH]1)C(=O)N[C@@H](CCC(N)=O)C(=O)N[C@H](C(=O)N[C@H]1CSSC[C@@H](C(=O)N[C@@H](Cc2ccccc2)C(=O)N[C@@H](CO)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC(=O)[C@H](CC(C)C)NC1=O)C(C)C]
OPT-$NH_2$ has the Structure Shown Below
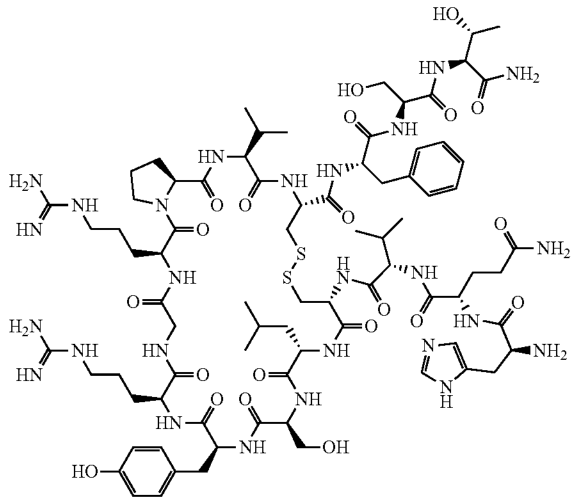 [SMILES: CC(C)C[C@@H]1NC(=O)[C@@H](NC(=O)[C@@H](NC(=O)[C@H](CCC(N)=O)NC(=O)[C@@H](N)Cc2cnc[nH]2)C(C)C)CSSC[C@@H](C(=O)N[C@@H](Cc2ccccc2)C(=O)N[C@@H](CO)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC1=O]
In certain embodiments OPT-3 is attached to the linker through an alkyne-azide click reaction. OPT-alkyne has the following structure.

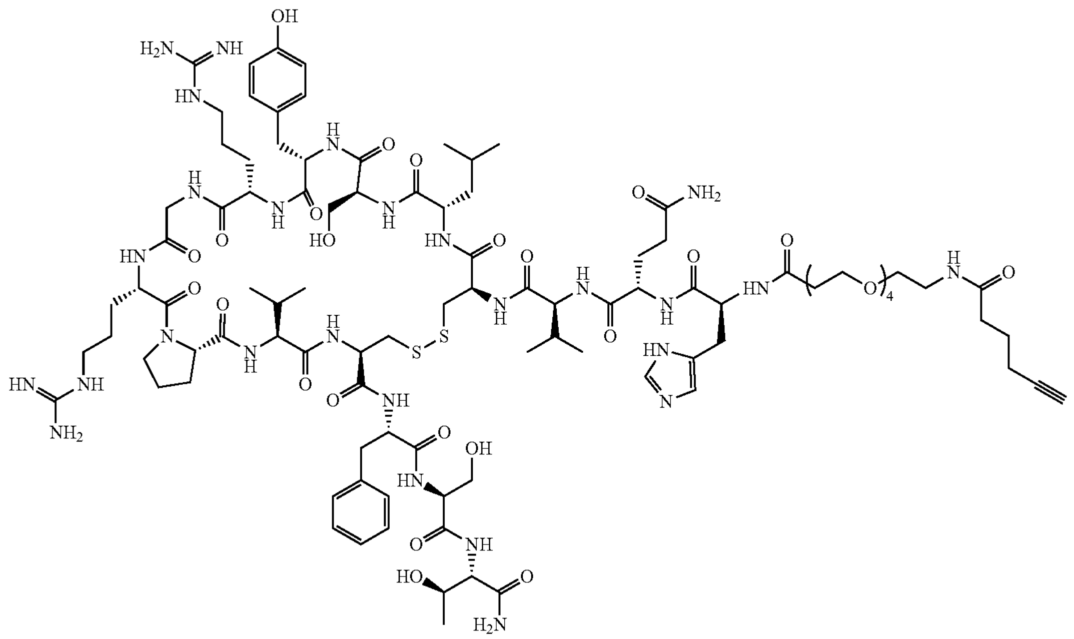
In certain embodiments the Extracellular Protein Targeting Ligand is OPT-2. OPT-2 has the following structure.
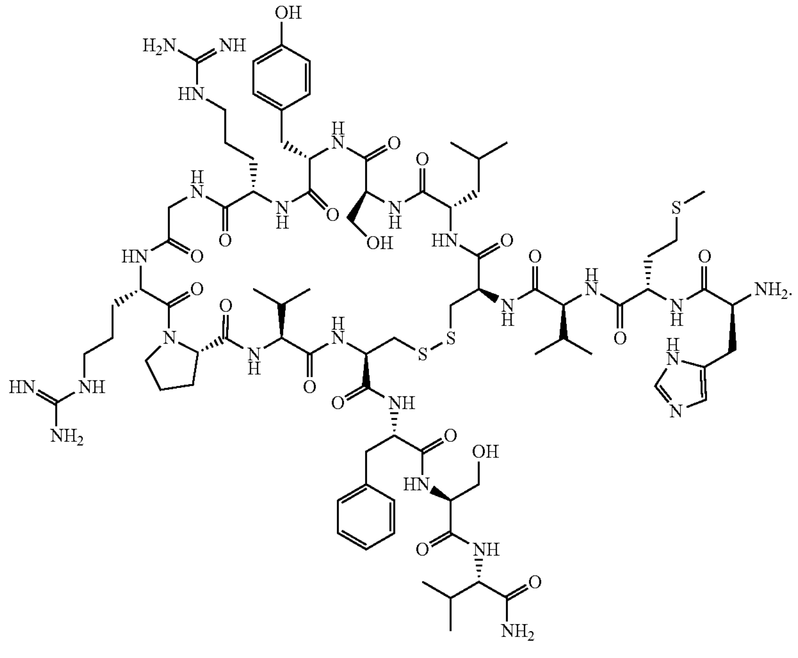 [SMILES: CSCC[C@H](NC(=O)[C@@H](N)Cc1cnc[nH]1)C(=O)N[C@H](C(=O)N[C@H]1CSSC[C@@H](C(=O)N[C@@H](Cc2ccccc2)C(=O)N[C@@H](CO)C(=O)N[C@H](C(N)=O)C(C)C)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC(=O)[C@H](CC(C)C)NC1=O)C(C)C]

In certain embodiments OPT-2 is attached to the linker through the primary amine of
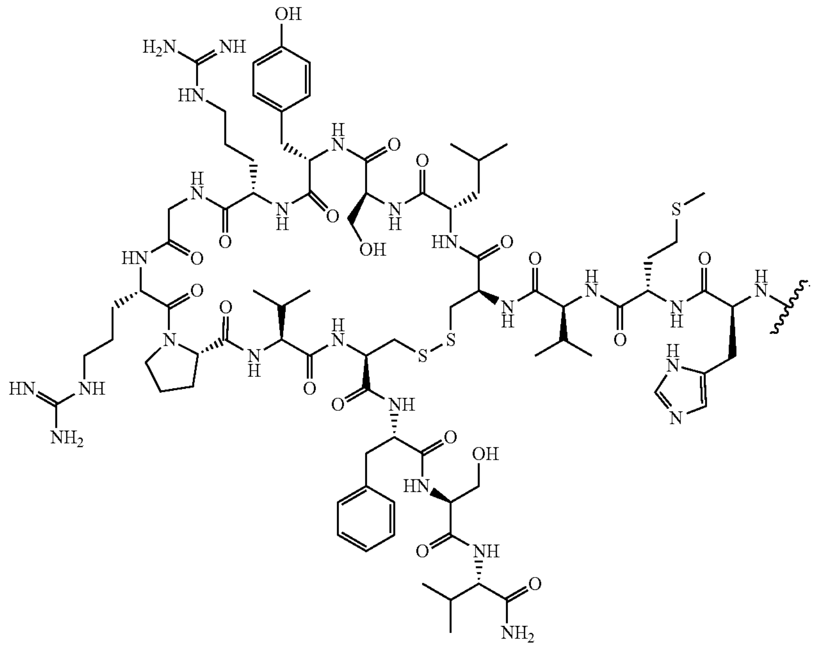 [SMILES: *N[C@@H](Cc1cnc[nH]1)C(=O)N[C@@H](CCSC)C(=O)N[C@H](C(=O)N[C@H]1CSSC[C@@H](C(=O)N[C@@H](Cc2ccccc2)C(=O)N[C@@H](CO)C(=O)N[C@H](C(N)=O)C(C)C)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](CO)NC(=O)[C@H](CC(C)C)NC1=O)C(C)C]
In certain embodiments the Extracellular Protein Targeting Ligand is OPT-1. OPT-1 has the following structure.
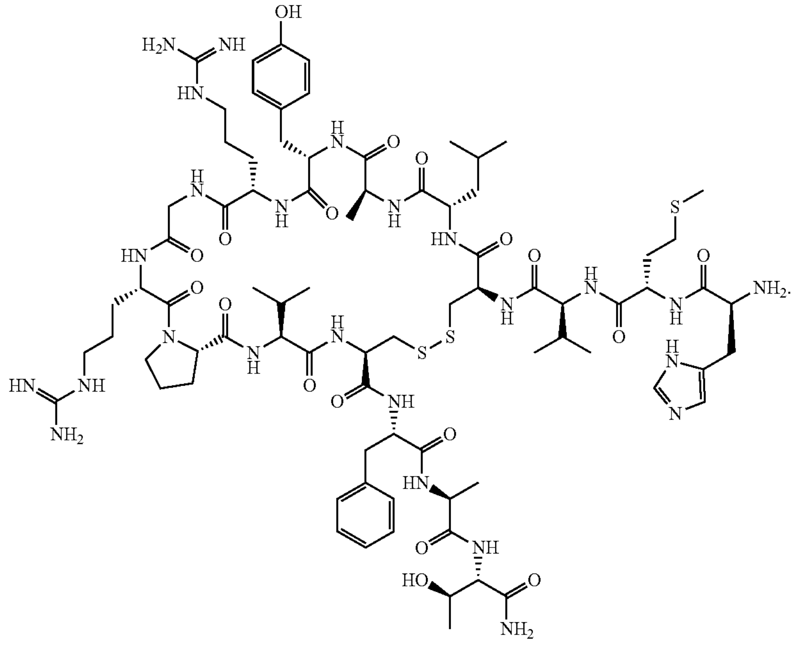 [SMILES: CSCC[C@H](NC(=O)[C@@H](N)Cc1cnc[nH]1)C(=O)N[C@H](C(=O)N[C@H]1CSSC[C@@H](C(=O)N[C@@H](Cc2ccccc2)C(=O)N[C@@H](C)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](C)NC(=O)[C@H](CC(C)C)NC1=O)C(C)C]

In certain embodiments OPT-1 is attached to the linker through the primary amine of

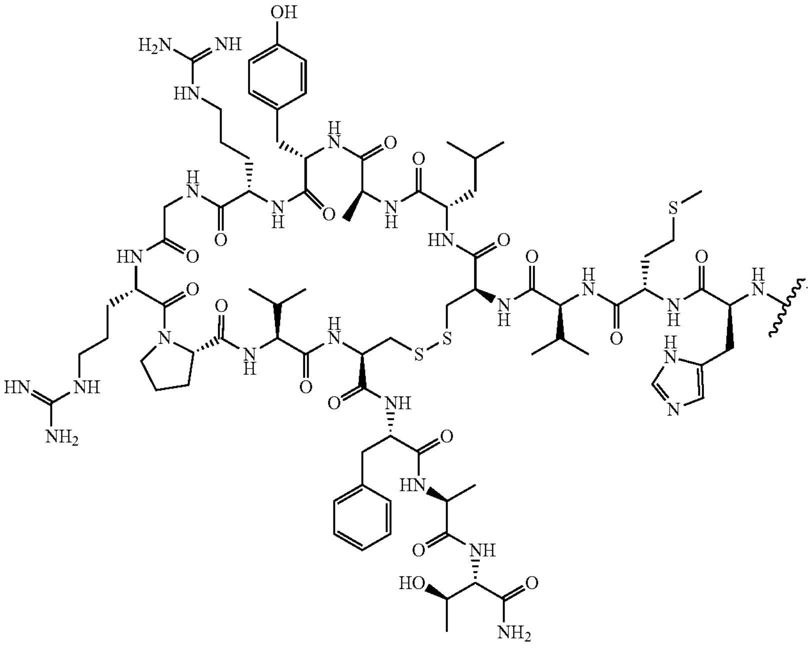 [SMILES: *N[C@@H](Cc1cnc[nH]1)C(=O)N[C@@H](CCSC)C(=O)N[C@H](C(=O)N[C@H]1CSSC[C@@H](C(=O)N[C@@H](Cc2ccccc2)C(=O)N[C@@H](C)C(=O)N[C@H](C(N)=O)[C@@H](C)O)NC(=O)[C@H](C(C)C)NC(=O)[C@@H]2CCCN2C(=O)[C@H](CCCNC(=N)N)NC(=O)CNC(=O)[C@H](CCCNC(=N)N)NC(=O)[C@H](Cc2ccc(O)cc2)NC(=O)[C@H](C)NC(=O)[C@H](CC(C)C)NC1=O)C(C)C]

IV. Pharmaceutical Compositions and Dosage Forms for the Extracellular Degrading Compounds of the Present Invention A compound of the present invention or a pharmaceutically acceptable salt, solvate or prodrug thereof as disclosed herein can be administered as a neat chemical, but is more typically administered as a pharmaceutical composition that includes an effective amount for a host, typically a human, in need of such treatment to treat a disorder mediated by the target extracellular protein, as described herein or otherwise well-known for that extracellular protein.

The ASGPR-binding Extracellular Protein degraders of the present invention can be administered in any manner that allows the degrader to bind to the Extracellular Protein, typically in the blood stream, and carry it to the ASGPR-bearing hepatocyte cells on the liver for endocytosis and degradation. As such, examples of methods to deliver the degraders of the present invention include, but are not limited to, oral, intravenous, sublingual, subcutaneous, parenteral, buccal, rectal, intra-aortal, intracranial, subdermal, transdermal, controlled drug delivery, intramuscular, or transnasal, or by other means, in dosage unit formulations containing one or more conventional pharmaceutically acceptable carriers, as appropriate. In certain embodiments, the degrader is provided in a liquid dosage form, a solid dosage form, a gel, particle, etc.

In certain embodiments the compound of the present invention is administered subcutaneously. Typically, the compound will be formulated in a liquid dosage form for subcutaneous injection, such as a buffered solution. Non-limiting examples of solutions for subcutaneous injection include phosphate buffered solution and saline buffered solution. In certain embodiments the solution is buffered with multiple salts.

In certain embodiments the compound of the present invention is administered intravenously. Typically, the compound will be formulated in a liquid dosage form for intravenous injection, such as a buffered solution. Non-limiting examples of solutions for intravaneous injection include phosphate buffered solution and saline buffered solution. In certain embodiments the solution is buffered with multiple salts.

Therefore, the disclosure provides pharmaceutical compositions comprising an effective amount of degrading compound or its pharmaceutically acceptable salt together with at least one pharmaceutically acceptable carrier for any appropriate use thereof. The pharmaceutical composition may contain a compound or salt as the only active agent, or, in an alternative embodiment, the compound and at least one additional active agent.

The term "pharmaceutically acceptable salt" as used herein refers to a salt of the described compound which is, within the scope of sound medical judgment, suitable for administration to a host such as a human without undue toxicity, irritation, allergic response, and the like, commensurate with a reasonable benefit/risk ratio, and effective for its intended use. Thus, the term "pharmaceutically acceptable salt" refers to the relatively non-toxic, inorganic and organic acid addition salts of the presently disclosed compounds. These salts can be prepared during the final isolation and purification of the compounds or by separately reacting the purified compound in its free form with a suitable organic or inorganic acid and then isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with a metal or amine, such as alkali and alkaline earth metal hydroxide, or an organic amine. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Any dosage form can be used that achieves the desired results. In certain embodiments the pharmaceutical composition is in a dosage form that contains from about 0.1 mg to about 1500 mg, from about 10 mg to about 1000 mg, from about 100 mg to about 800 mg, or from about 200 mg to about 600 mg of the active compound and optionally from about 0.1 mg to about 1500 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

In certain embodiments the dose ranges from about 0.01-100 mg/kg of patient bodyweight, for example about 0.01 mg/kg, about 0.05 mg/kg, about 0.1 mg/kg, about 0.5 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg.

In some embodiments, compounds disclosed herein or used as described are administered once a day (QD), twice a day (BID), or three times a day (TID). In some embodiments, compounds disclosed herein or used as described are administered at least once a day for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 31 days, at least 35 days, at least 45 days, at least 60 days, at least 75 days, at least 90 days, at least 120 days, at least 150 days, at least 180 days, or longer.

In certain embodiments the compound of the present invention is administered once a day, twice a day, three times a day, or four times a day.

The pharmaceutical composition may be formulated as any pharmaceutically useful form, e.g., a pill, capsule, tablet, an injection or infusion solution, a syrup, an inhalation formulation, a suppository, a buccal or sublingual formulation, a parenteral formulation, or in a medical device. Some dosage forms, such as tablets and capsules, can be subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound. If provided as in a liquid, it can be a solution or a suspension.

Representative carriers include phosphate buffered saline, water, solvent(s), diluents, pH modifying agents, preservatives, antioxidants, suspending agents, wetting agent, viscosity agents, tonicity agents, stabilizing agents, and combinations thereof. In some embodiments, the carrier is an aqueous carrier. Examples of aqueous carries include, but are not limited to, an aqueous solution or suspension, such as saline, plasma, bone marrow aspirate, buffers, such as Hank's Buffered Salt Solution (HBSS), HEPES (4-(2-hydroxyethyl)-1-piperazineethanesulfonic acid), Ringers buffer, ProVisc®, diluted ProVisc®, Provisc® diluted with PBS, Krebs buffer, Dulbecco's PBS, normal PBS, sodium hyaluronate solution (HA, 5 mg/mL in PBS), citrate buffer, simulated body fluids, plasma platelet concentrate and tissue culture medium or an aqueous solution or suspension comprising an organic solvent. Acceptable solutions include, for example, water, Ringer's solution and isotonic sodium chloride solutions. The formulation may also be a sterile solution, suspension, or emulsion in a non-toxic diluent or solvent such as 1,3-butanediol.

Viscosity agents may be added to the pharmaceutical composition to increase the viscosity of the composition as desired. Examples of useful viscosity agents include, but are not limited to, hyaluronic acid, sodium hyaluronate, carbomers, polyacrylic acid, cellulosic derivatives, polycarbophil, polyvinylpyrrolidone, gelatin, dextin, polysaccharides, polyacrylamide, polyvinyl alcohol (including partially hydrolyzed polyvinyl acetate), polyvinyl acetate, derivatives thereof and mixtures thereof.

Solutions, suspensions, or emulsions for administration may be buffered with an effective amount necessary to maintain a pH suitable for the selected administration. Suitable buffers are well known by those skilled in the art. Some examples of useful buffers are acetate, borate, carbonate, citrate, and phosphate buffers. Solutions, suspensions, or emulsions for topical, for example, ocular administration may also contain one or more tonicity agents to adjust the isotonic range of the formulation. Suitable tonicity agents are well known in the art. Some examples include glycerin, mannitol, sorbitol, sodium chloride, and other electrolytes.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound. Enteric coated oral tablets may also be used to enhance bioavailability of the compounds for an oral route of administration.

Formulations suitable for rectal administration are typically presented as unit dose suppositories. These may be prepared by admixing the active compound with one or more conventional solid carriers, for example, cocoa butter, and then shaping the resulting mixture.

VII. Treatment of Diseases with the Disclosed ASGPR-Binding Extracellular Protein Degraders The Target Proteins of the current invention may include, but are not limited to, immunoglobulins, cytokines, chemokines, growth factors, coagulation factors, extracellular matrix proteins and proteins involved in formation and/or degradation of the extracellular matrix, esterases, lipases, peptidases, convertases, among others. These proteins mediate a range of diseases that can be treated with an effective amount of the disclosed ASGPR-binding Extracellular Protein Degraders described herein.

Immunoglobulins

1) Immunoglobulin A (IgA) aberrant expression mediates a range of autoimmune and immune-mediated disorders, including IgA nephropathy (also known as Berger's disease), celiac disease, Crohn's disease, Henoch-Sconiein purpura (HSP) (also known as IgA vasculitis), liner IgA bullous dermatosis, IgA pemphigus, dermatitis herpetiformis, inflammatory bowel disease (IBD), Sjögren's syndrome, ankylosing spondylitis, alcoholic liver cirrhosis, acquired immunodeficiency syndrome, IgA multiple myeloma, α-chain disease, IgA monoclonal gammopathy, monoclonal gammopathy of undetermined significance (MGUS), and linear IgA bullous dermatosis, among others.
2) Immunoglobulin G (IgG) mediates a range of autoimmune, infectious and metabolic diseases, including systemic fibroinflammatory disease. In addition, overexpression of IgG4 is associated with IgG4-related diseases, which generally include multiple organs, and disorders include type 1 autoimmune pancreatitis, interstitial nephritis, Riedel's thyroiditis, storiform fibrosis, Mikulicz's disease, Küttner's tumor, inflammatory pseudotumors (in various sites of the body), mediastinal fibrosis, retroperitoneal fibrosis (Ormond's disease), aortitis and periaortitis, proximal biliary strictures, idiopathic hypocomplementic tubulointerstitial nephritis, multifocal fibrosclerosis, pachymeningitis, pancreatic enlargement, tumefactive lesions, pericarditis, rheumatoid arthritis (RA), inflammatory bowel disease, multiple sclerosis, myasthenic gravis, ankylosing spondylitis, primary Sjögren's syndrome, psoriatic arthritis, and systemic lupus erythematosus (SLE), sclerosing cholangitis, and IgG monoclonal gammopathy, monoclonal gammopathy of undetermined significance (MGUS), among others.
3) Immunoglobulin E (IgE)—IgE is a strong mediator of allergic disease, including but not limited to, atopic asthma, allergic rhinitis, atopic dermatitis, IgE-mediated food allergy, IgE-mediated animal allergies, allergic conjunctivitis, allergic urticaria, anaphylactic shock, nasal polyposis, keratoconjunctivitis, mastocytosis, and eosinophilic gastrointestinal disease, bullous pemphigoid, chemotherapy induced hypersensitivity reaction, seasonal allergic rhinitis, interstitial cystitis, eosinophilic esophagitis, angioedema, acute interstitial nephritis, atopic eczema, eosinophilic bronchitis, chronic obstructive pulmonary disease, gastroenteritis, hyper-IgE syndrome (Job's Syndrome), IgE monoclonal gammopathy, and monoclonal gammopathy of undetermined significance (MGUS), among others.

Cytokines/Chemokines

1) TNF-α mediates a number of disorders, including but not limited to rheumatoid arthritis, inflammatory bowel disease, graft-vs-host disease, ankylosing spondylitis, psoriasis, hidradenitis suppurativa, refractory asthma, systemic lupis erythematosus, diabetes, and the induction of cachexia.
2) IL-2 mediates host versus graft rejection in transplants and autoimmune disorders, including, but not limited to, multiple sclerosis, idiopathic arthritis, iritis, anterior uveitis, IL-2 induced hypotension, psoriasis, and other autoimmune disorders
3) IL-1 mediates a number of auto-inflammatory and autoimmune disorders, including, but not limited to, Blau syndrome, cryopyrin-associated periodic syndromes, familial Mediterranean fever, Majeed syndrome; mevalonate kinase deficiency syndrome, pyogenic arthritis-pyoderma gangrenosum-acne syndrome, tumor necrosis factor receptor-associated periodic syndrome, Behçet's Disease, Sjögren's Syndrome, gout and chondrocalcinosis, periodic fever, aphthous stomatitis, pharyngitis, and cervical adenitis (or PFAPA) syndrome, rheumatoid arthritis, Type 2 diabetes mellitus, acute pericarditis, Chronic interstitial lung diseases (ILDs), and Still's disease amongst others.
4) IFN-γ mediates a wide range of autoimmune disorders, including, but not limited to rheumatoid arthritis, multiple sclerosis (MS), corneal transplant rejection, and various autoimmune skin diseases such as psoriasis, alopecia areata, vitiligo, acne vulgaris, and others.

5) IL-21 mediates a number of autoimmune disorders, including Sjögren's syndrome, systemic lupus erythematosus, type 1 diabetes, multiple sclerosis, rheumatoid arthritis, and inflammatory bowel disease.

6) IL-22 mediates a number of autoimmune disorders, including, but not limited to, graft versus host disease (GVHD), psoriasis, rheumatoid arthritis, atopic dermatitis, and asthma.

7) IL-10 has been implicated in tumor survival and protection against cytotoxic chemotherapeutic drugs.

8) IL-5 has been implicated in a number of allergic disorders, including, but not limited to, asthma, nasal polyposis, atopic dermatitis, eosinophilic esophagitis, hypereosinophilic syndrome, and Churg-Strauss syndrome.

9) IL-6 has been implicated in a number of inflammatory diseases and cancers, including, but not limited to, Castleman's disease, metastatic castration-associated prostate cancer, renal cell carcinoma, large-cell lung carcinoma, ovarian cancer, rheumatoid arthritis, asthma.

10) IL-8 has been implicated in the promotion of tumor progression, immune escape, epithelial-mesenchymal transition, and recruitment of myeloid-derived suppressor cells. Studies have demonstrated that high serum IL-8 levels correlate with poor prognosis in many malignant tumors. Preclinical studies have shown that IL-8 blockade may reduce mesenchymal features in tumor cells, making them less resistant to treatment.

11) C—C motif chemokine ligand 2 (CCL2) has been implicated in the recruitment of monocytes into the arterial wall during the disease process of atherosclerosis.

12) Macrophage Migration Inhibitory Factor (MIF) is a mediator of tumor progression; systemic inflammation; atherosclerosis; rheumatoid arthritis; and systemic lupus erythematosus, among others.

Growth Factors

1) Fibroblast Growth Factor 1 (FGF1) can induce angiogenesis. FGF1 has been implicated in oncogenesis, cancer cell proliferation, resistance to anticancer therapies, and neoangiogenesis.

2) Fibroblast Growth Factor 2 (FGF2) has been implicated in oncogenesis, cancer cell proliferation, resistance to anticancer therapies, and neoangiogenesis.

3) Vascular Epithelial Growth Factor (VEGF-A) has been implicated in the vascularization and angiogenesis of tumors.

4) Transforming Growth Factor-β1 (TGF-β 1) expression in the tumor microenvironment has been associated with a poor prognosis, and is implicated in TGF-β1 mediated tumor suppression via T-cell exclusion. TGF-β1 expression has also been implicated in hematological malignancies and fibrosis.

5) Transforming Growth Factor-β2 (TGF-β2) expression in the tumor microenvironment has been associated with a poor prognosis, and is implicated in TGF-β2 mediated tumor suppression via T-cell exclusion. TGF-β2 expression has also been implicated in hematological malignancies and fibrosis.

6) Placental Growth Factor (PGF) promotes cell tumor growth, and has been implicated in age-related macular degeneration (AMD) and choroidal neovascularization (CNV).

Esterase

1) Cholinesterase has been implicated in cognitive disorders such as dementia and Alzheimer's disease.

Coagulation Factors

1) Carboxypeptidase B2 has been implicated and targeted to inhibit thrombosis.

2) Coagulation Factor Xa is a mediator in the development of deep vein thrombosis and acute pulmonary embolism, and the risk of stroke and embolism in people with nonvalvular atrial fibrillation.

3) Coagulation Factor XI is a mediator in the development of deep vein thrombosis and acute pulmonary embolism, and the risk of stroke and embolism in people with nonvalvular atrial fibrillation.

4) Coagulation Factor XII has been implicated in the development of deep vein thrombosis and acute pulmonary embolism, and the risk of stroke and embolism in people with nonvalvular atrial fibrillation.

5) Coagulation Factor XIII has been implicated in the development of deep vein thrombosis and acute pulmonary embolism, and the risk of stroke and embolism in people with nonvalvular atrial fibrillation.

6) Prothrombin is involved in blood clot formation and arterial and venous thrombosis, and thromboembolism associated with atrial fibrillation.

7) Coagulation Factor VII is involved in blood clot formation and arterial and venous thrombosis, and thromboembolism associated with atrial fibrillation.

8) Coagulation Factor IX is involved in blood clot formation and arterial and venous thrombosis, and thromboembolism associated with atrial fibrillation.

Extracellular Matrix Proteins

1) Neutrophil Elastase—Neutrophil elastase has been implicated in a number of disorders, including lung disease, chronic obstructive pulmonary disease, pneumonia, respiratory distress, and acute lung injury (ALI), and cystic fibrosis, as well as chronic kidney disease.

2) Fibronectin-1—Interfering with FN polymerization may attenuate myofibroblasts and fibrosis and improve cardiac function after ischemia/reperfusion (I/R) injury.

3) Thrombospondin-1—TSP-1 has been implicated in a number of diseases, including in promoting certain cancers such as breast cancer, prostate cancer, melanoma, SCLC, osteosarcoma, cutaneous squamous cell carcinoma, oral squamous cell carcinoma, papillary thyroid carcinoma, thyroid cancer, medulloblastoma, and fibrotic disorders such as diabetes, liver fibrosis, and in multiple myeloma.

4) Urokinase-type Plasminogen Activator (UPA)—UPA has been implicated in vascular diseases and cancer progression. Elevated expression levels of urokinase and several other components of the plasminogen activation system are found to be correlated with tumor malignancy.

5) Plasminogen Activator, Tissue Type (TPA)—PLA has been shown activated in various cancers including oral malignancy.

6) Plasminogen (PLG)—PLG has been implicated in tumor invasion and inflammation.

7) Plasminogen Activator Inhibitor-1 (PAI-1)-PAI-1 has been implicated in angiogenesis, metastasis, and poor prognosis in tumors, including, but not limited to, oral cancers and breast cancers.

Peptidase

1) Kallikrein-1—Kallikrein has been implicated in adverse reactions in hereditary angioedema (HAE).

2) Plasma Kallikrein—Plasma kallikrein has been implicated in retinal dysfunction, the development of diabetic macular edema and hereditary angioedema (HAE).
3) Matrix Metallopeptidase—1—MMP-1 has been implicated in cardiovascular disease, development of fibrosis, and growth of certain cancers such as bladder cancer.
4) Phospholipase A2, Group IIA (PA2GA)—PA2GA has been implicated in a number of diseases, including cardiovascular diseases, atherosclerosis, immune disorders, and cancer.

Lipase

1) Lipoprotein Lipase—Lipoprotein lipase has been implicated in the development of cardiovascular disease and obesity.
2) Phospholipase A2, Group IB (PA21B)—PA21B has been implicated in a number of diseases, including cardiovascular diseases, atherosclerosis, immune disorders and cancer.

Convertase

1) Proprotein Convertase Subtilisin/Kexin Type 9 (PCSK-9)—PCSK-9 has been implicated in high blood cholesterol and the development of cardiovascular disease.

Certain extracellular protein targets include but are not limited to: SAA (serum amyloid A), amyloid light chains, antibodies to *Klebsiella* dipeptidase protein; Ig antibodies to anionic phospholipids and beta-2-glycoprotein-I; IL-13; MIF; Transthyretin (misfolded), IgG autoantibodies to thyroid peroxidase, thyroglobulin and TSH receptors; TNF-$\alpha$; Protein arginine deiminase (PAD, PALD4); antibodies to citrullinated protein antibody (ACPA); anti-DNA antibodies; IL-17; Lysyl Oxidase 2 (LOXL2); IL-18; Blys; B cell activating factor (BAFF); CD40 (soluble); CXCL12; soluble PSMA; matrix metalloproteinase IX (MMP-9); hormone-sensitive lipase; lipoprotein-associated phospholipase A2; Factor Xa; DPP4; thrombin; PCSK9; ApoB-100; Complement component C3b; PKK (pre-kallikrein); Factor XL; PF4; Anti-vWF antibodies; anticardiolipin antibodies and lupus anticoagulant; FGF23 (fibroblast growth factor 23); Plasminogen activator inhibitor type 1 (PAI-1); Myeloperoxidase (MPO) extracellular; Myostatin; Beta2-m; suPAR (soluble urokinase plasminogen activator receptor); anti-ganglioside IgG; amyloid beta; Tau; CD-associate prion; anti-ganglioside IgG; HTT; anti-ganglioside IgG; synuclein; elastase; PABA (protective antigen of *Bacillus anthracis*); edema factor; Botulinum toxin; *C. difficile* toxin B; hemolysin; tetanus toxin; IL-2; growth hormone and ACTH.

VIII. Exemplary Methods of Treatment of Diseases Mediated by Extracellular Proteins The present invention can be used to treat any disorder that is mediated by the selected target disease-mediating extracellular protein. Nonlimiting examples of indications include autoimmune, other immune dysfunctions, complement mediated disorders, abnormal cellular proliferation, cancer, tumors, hematology-related disorders, renal disorders and liver disorders.

In certain embodiments, the degrader or its salt or composition as described herein is used in the treatment of an autoimmune disorder. In some aspects, the extracellular protein is an Ig, such as IgA or IgG. IgG degradation can treat for example, thyroid eye disease, myasthenia gravis, chronic inflammatory demyelinating polyneuropathy, and warm autoimmune hemolytic anemia.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In an embodiment, the degrader or its salt or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome. Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in MRI scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In some embodiments the degrader or its salt or composition as described herein is provided at an effective dose to treat a patient with type 1 diabetes. In one aspect the degrader or its salt or composition as described herein is provided at an effective dose to treat a patient with type 2 diabetes.

Type 1 diabetes is an autoimmune disease. An autoimmune disease results when the body's system for fighting infection (the immune system) turns against a part of the body. The pancreas then produces little or no insulin.

As examples, the degrader or its salt or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitoneal fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, *Pityriasis lichenoides* et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton myasthenic syndrome, Oshtoran syndrome, pediatric autoimmune neuropsychiatric disorder associated with *streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

In certain aspects, an effective amount of the degrader or its salt or composition as described herein is used to treat a medical disorder mediated by the Targeted Extracellular Protein. For example, when the Targeted Extracellular Protein is a complement protein, for example complement factor B, factor D, factor H, C1s, C3, or C5, then the medical disorder to be treated may be an inflammatory or immune condition, a disorder mediated by the complement cascade (including a dysfunctional cascade), or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In some aspects, the disorder treated by the degrader or its salt or composition as described herein is selected from fatty liver and conditions stemming from fatty liver, such as nonalcoholic steatohepatitis (NASH), liver inflammation, cirrhosis and liver failure.

In other embodiments, the degrader or its salt or composition as described herein is used to modulate an immune response prior to or during surgery or other medical procedure. Non-limiting examples are the use in connection with acute or chronic graft versus host disease, which is a common complication as a result of allogeneic tissue transplant, and can also occur as a result of a blood transfusion.

In certain embodiments, the present invention provides a method of treating or preventing dermatomyositis by administering to a subject in need thereof an effective amount of the degrader or its salt or composition as described herein.

In certain embodiments, the present invention provides a method of treating or preventing amyotrophic lateral sclerosis by administering to a subject in need thereof an effective amount of the degrader or its salt or composition as described herein.

In certain embodiments, the present invention provides a method of treating or preventing abdominal aortic aneurysm, hemodialysis complications, hemolytic anemia, or hemodialysis by administering to a subject in need thereof an effective amount of the degrader or its salt or composition as described herein.

In certain embodiments, a method is provided for the treatment or prevention of cytokine or inflammatory reactions in response to the administration of pharmaceutical or biotherapeutic (e.g. CAR T-cell therapy or monoclonal antibody therapy) in a host by administering an effective amount of the degrader or its salt or composition as described herein. Various types of cytokine or inflammatory reactions may occur in response to a number of factors, such as the administrations of biotherapeutics. In one aspect, the cytokine or inflammatory reaction is cytokine release syndrome. In one embodiment, the cytokine or inflammatory reaction is tumor lysis syndrome (which also leads to cytokine release). Symptoms of cytokine release syndrome range from fever, headache, and skin rashes to bronchospasm, hypotension and even cardiac arrest. Severe cytokine release syndrome is described as cytokine storm, and can be fatal.

In another embodiment, the disorder is episcleritis, idiopathic episcleritis, anterior episcleritis, or posterior episcleritis. In one embodiment, the disorder is idiopathic anterior uveitis, HLA-B27 related uveitis, herpetic keratouveitis, Posner Schlossman syndrome, Fuch's heterochromic iridocyclitis, or cytomegalovirus anterior uveitis.

In another embodiment, the present invention provides a method of treating or preventing a C3 glomurenopathy by administering to a subject in need thereof an effective amount of the degrader or its salt or composition as described herein. In one embodiment, the disorder is selected from dense deposit disease (DDD) and C3 glomerulonephritis (C3GN).

In yet another embodiment, the present invention provides a method of treating or preventing a IC-MPGN by administering to a subject in need thereof an effective amount of the degrader or its salt or composition as described herein.

In a further embodiment, the present invention provides a method of treating or preventing a paroxysmal nocturnal hemoglobinuria (PNH) by administering to a subject in need thereof an effective amount of the degrader or its salt or composition as described herein.

In another embodiment, the present invention provides a method of treating or preventing age-related macular degeneration (AMD) by administering to a subject in need thereof an effective amount of the degrader or its salt or composition as described herein.

In one embodiment, the present invention provides a method of treating or preventing rheumatoid arthritis by administering to a subject in need thereof an effective amount of the degrader or its salt or composition as described herein.

In one embodiment, the present invention provides a method of treating or preventing multiple sclerosis by administering to a subject in need thereof an effective amount of the degrader or its salt or composition as described herein.

In one embodiment, the present invention provides a method of treating or preventing myasthenia gravis by administering to a subject in need thereof an effective amount of the degrader or its salt or composition as described herein.

In one embodiment, the present invention provides a method of treating or preventing atypical hemolytic uremic syndrome (aHUS) by administering to a subject in need thereof an effective amount of the degrader or its salt or composition as described herein.

In one embodiment, the present invention provides a method of treating or preventing neuromyelitis optica (NMO) by administering to a subject in need thereof an effective amount of the degrader or its salt or composition as described herein.

In yet other embodiments, the present invention provides a method of treating or preventing a disorder as described below by administering to a subject in need thereof an effective amount of the degrader or its salt or composition as described herein, including: for example: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In additional embodiments, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In further embodiments, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), TL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In other embodiments, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In further embodiments, the disorder is selected from: hyperlipidemia, hypertension, hypoalbuminemia, hypovolemic shock, hypocomplementemic urticarial vasculitis syndrome, hypophosphatasia, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lapidarian; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thyroiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In other embodiments, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, intermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or central retinal vein occlusion (CVRO).

Disorders that may be treated or prevented by the degrader or its salt or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (I/R injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, implants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In another embodiment, a method for the treatment of sickle cell in a host is provided that includes the administration of an effective amount of the degrader or its salt or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of the degrader or its salt or composition as described herein. In one embodiment, a method for the treatment of ANCA-vasculitis in a host is provided that includes the administration of an effective amount of the degrader or its salt or composition as described herein. In one embodiment, a method for the treatment of IgA nephropathy in a host is provided that includes the administration of an effective amount of the degrader or its salt or composition as described herein. In one embodiment, a method for the treatment of rapidly progressing glomerulonephritis (RPGN), in a host is provided that includes the administration of an effective amount of the degrader or its salt or composition as described herein. In one embodiment, a method for the treatment of lupus nephritis, in a host is provided that includes the administration of an effective amount of the degrader or its salt or composition as described herein. In one embodiment, a method for the treatment of hemorraghic dengue fever, in a host is provided that includes the administration of an effective amount of the degrader or its salt or composition as described herein.

In another aspect, an effective amount of the degrader or its salt or composition as described herein is used to treat an abnormal proliferation disorder such as a tumor or cancer.

Non-limiting examples of cancers that can be treated according to the present invention include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarcinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL)—also known as acute lymphoblastic leukemia or acute lymphoid leukemia (e.g., B-cell ALL, T-cell ALL), acute myelocytic leukemia (AIL) (e.g., B-cell AIL, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendocrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic adenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In another embodiment, the disorder is myelodysplastic syndrome (MDS).

In certain embodiments, the cancer is a hematopoietic cancer. In certain embodiments, the hematopoietic cancer is a lymphoma. In certain embodiments, the hematopoietic cancer is a leukemia. In certain embodiments, the leukemia is acute myelocytic leukemia (AML).

In certain embodiments, the proliferative disorder is a myeloproliferative neoplasm. In certain embodiments, the myeloproliferative neoplasm (MPN) is primary myelofibrosis (PMF).

In certain embodiments, the cancer is a solid tumor. A solid tumor, as used herein, refers to an abnormal mass of tissue that usually does not contain cysts or liquid areas. Different types of solid tumors are named for the type of cells that form them. Examples of classes of solid tumors include, but are not limited to, sarcomas, carcinomas, and lymphomas, as described above herein. Additional examples of solid tumors include, but are not limited to, squamous cell carcinoma, colon cancer, breast cancer, prostate cancer, lung cancer, liver cancer, pancreatic cancer, and melanoma.

Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

In certain embodiments, the condition is associated with an immune response.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In other non-limiting embodiments, degraders of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Exemplary cancers which may be treated by the present disclosed compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+DLBCL of the elderly; primary mediastinal (thymic) large B-cell lymphoma, primary cutaneous DLBCL, leg type, ALK+large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

Nonlimiting general examples of disorders mediated by extracellular proteins also include, but are not limited to: AMD, macular edema, DME, diabetic retinopathy, mCNV; neurodegenerative disorders, metastatic colorectal cancer, non-squamous non-small-cell lung carcinoma, GMB, metastatic renal cell carcinoma, cervical cancer, AA amyloidosis, amyloid light chain (AL) amyloidosis, ankylosing spondylitis, antiphospholipid Ab syndrome, asthma, progression of parasite *Schistosoma mansoni* infection (IL-13), ATTR amyloidosis, Behcet syndrome, sepsis, inflammation, rheumatoid arthritis, atherosclerosis, ischemia/reperfusion injury; MGUS, Necrobiotic xanthogranuloma, JIA, psoriatic arthritis, plaque psoriasis, Crohn's disease, ulcerative colitis, Hidradenitis suppurativa uveitis; GvH disease; Castleman's disease, liver fibrosis, Still's Disease; cutaneous skin diseases including atopic dermatitis, transplant rejection, multiple myeloma, osteosclerotic multiple myeloma with peripheral neuropathy; pancreatic tumors; paraproteinemia (NR), prostate, gastric cancer; glioblastoma multiforme; acute coronary syndrome; hyperlipidemia (Rare/Broad), chronic urticaria, scleroderma, scleromyxedema, hereditary angioedema, clotting disorders, heparin-induced thrombocytopenia; Acquired Von Willebrand disease (AVWD), antiphospholipid antibody syndrome (APS or APLS); cryoglobulinemia; granulomatosis with polyangiitis (Wegener's)—sub-type of ANCA-associated vasculitis; idiopathic (Immune); thrombocytopenic purpura; IgG4-RD; Non-IgM MGUS; X-linked hypophosphatemia; Multiple System Atrophy (MSA), Parkinson's disease, Cachexia, Sarcopenia, Sporadic inclusion body myositis, muscular dystrophy, COPD; rhabdomyolysis; dialysis-related amyloidosis; focal segmental glomerulosclerosis (FSGS); IgA nephropathy (IgAN) and Henoch Schonlein Purpura (HSP); acute disseminated encephalomyelitis (ADEM); acute inflammatory demyelinating polyneuropathy (AIDP); Guillaine-Barre Syndrome; Alzheimer' disease & FTD; chronic inflammatory demyelinating polyneuropathy (CIDP); Creutzfeldt-Jakob disease (CJD); Huntington's disease; Miller Fisher Syndrome; Neuromyelitis optica spectrum disorder (NMOSD); Opsoclonus-myoclonus syndrome; PANDAS syndrome (pediatric autoimmune neuropsychiatric disorders associated with Streptococcal infections); Transverse myelitis; Emphysema, respiratory failure; Anthrax; Botulism; Sepsis; *Staph. aureus* toxic shock syndrome; Tetanus; Transplantation; Acromegaly; Cushing's disease; prion disease; secondary membranous nephropathy; and vasculitis.

IX. Processes of Manufacture

The extracellular protein degrading compounds of the present invention can be manufactured according to routes described in the Working Examples below or as otherwise known in the patent or scientific literature and if appropriate supported by the knowledge of the ordinary worker or common general knowledge.

Some of the carbons in the extracellular protein degrading compounds described herein are drawn with designated stereochemistry. Other carbons are drawn without stereochemical designation. When drawn without designated stereochemistry, that carbon can be in any desired stereochemical configuration that achieves the desired purpose. One skilled in the art will recognize that pure enantiomers, enantiomerically enriched compounds, racemates and diastereomers can be prepared by methods known in the art as guided by the information provided herein. Examples of methods to obtain optically active materials include at least the following:

i) chiral liquid chromatography—a technique whereby diastereomers are separated in a liquid mobile phase by virtue of their differing interactions with a stationary phase (including vial chiral HPLC). The stationary phase can be made of chiral material or the mobile phase can contain an additional chiral material to provoke the differing interactions;
ii) non-chiral chromatography of diastereomers-Often diastereomers can be separated using normal non-chiral column conditions;
iii) chiral gas chromatography—a technique whereby the racemate is volatilized and enantiomers are separated by virtue of their differing interactions in the gaseous mobile phase with a column containing a fixed non-racemic chiral adsorbent phase;
iv) simultaneous crystallization—a technique whereby the individual diastereomers are separately crystallized from a solution;
v) enzymatic resolutions—a technique whereby partial or complete separation of diastereomers are separated by virtue of differing rates of reaction with an enzyme;
vi) chemical asymmetric synthesis—a synthetic technique whereby the desired diastereomer is synthesized from an achiral precursor under conditions that produce asymmetry (i.e. chirality) in the product, which may be achieved by chiral catalysts or chiral auxiliaries;
vii) diastereomer separations—a technique whereby a racemic compound is reaction with an enantiomerically pure reagent (the chiral auxiliary) that converts the individual enantiomers to diastereomers. The resulting diastereomers are then separated by chromatography or crystallization by virtue of their now more distinct structural differences the chiral auxiliary later removed to obtain the desired enantiomer; and
viii) extraction with chiral solvents—a technique whereby diastereomers are separated by virtue of preferential dissolution of one over the others in a particular chiral solvent.

General Procedures Applied to the Working Examples of Synthesis

All reagents were purchased from commercial suppliers (Sigma-Aldrich, Alfa, Across etc.) and used without further purification unless otherwise stated. THE was continuously refluxed and freshly distilled from sodium and benzophenone under nitrogen, dichloromethane was continuously refluxed and freshly distilled from $CaH_2$ under nitrogen.

Reactions were monitored via TLC on silica gel 60 HSGF254 percolated plates (0.15-0.2 mm $SiO_2$) and visualized using UV light (254 nm or 365 nm) and/or staining with phosphomolybdic acid ethanol solution (10 g in 100 mL ethanol) and subsequent heating or monitored via LCMS.

LCMS were performed on SHIMADZU LCMS-2010EV (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@10% B, 2.7 min gradient (10-95% B), then 0.8 min@95% B, Flow rate: 3 mL/min, temperature: 40° C.).

Preparative HPLC were performed either on Method A: SHIMADZU LC-8A (Column: YMC Pack ODS-A (150*30 mm, 10 μm)) or Method B: LC-6AD (Column: Shim=Pack PREP-ODS-H (250*20 mm, 10 m)) with UV detection which were controlled by LC solution Chemstation software. $H_2O$ (0.1% HCOOH) and MeOH (MeCN) as mobile phase at the indicated flow rate. Analytical HPLC were performed on SHIMADZU LC-2010A (Chromolith SpeedROD, RP-18e, 50×4.6 mm, mobile phase: Solvent A: $CH_3CN/H_2O/HCOOH$=10/90/0.05, Solvent B: $CH_3CN/H_2O/HCOOH$=90/10/0.05, 0.8 min@10% B, 2.7 min gradient (10-95% B), then 0.8 min@95% B, Flow rate: 3 mL/min, temperature: 40° C.).

Chiral HPLC were performed on SHIMADZU LC-2010A (Chiral column, mobile phase: Solvent A: hexane (or contained 0.1% diethylamine), Solvent B: Ethanol or Isopropanol; Flow rate: 0.8 mL/min, temperature: 30° C.).

$^1H$ spectra were recorded on Bruker Avance II 400 MHz, Chemical shifts (δ) were reported in ppm relative to tetramethylsilane (δ=0.000 ppm) and the spectra were calibrated to the residual solvent signal of chloroform (δ=7.26), Dimethyl sulfoxide (δ=2.50), methanol (δ=3.30). Data for $^1H$ NMR spectra were reported as following: chemical shift (multiplicity, number of hydrogens). Abbreviations were described as following: s (singlet), d (doublet), t (triplet), q (quartet), quant (quintet), m (multiple), br (broad).

X. WORKING EXAMPLES

Example 1. Synthesis of Boc-Protected and Bn-Protected Intermediates

Synthesis 1-1. Preparation of tert-Butyl (((3aR,4S,8R,8aR)-8-amino-2,2-dimethyltetrahydro-4,7-epoxy[1,3]dioxolo[4,5-d]oxepin-4(5H)-yl)methyl)carbamate (Intermediate 1)

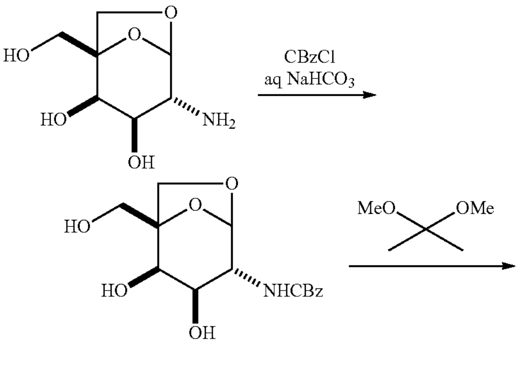

-continued

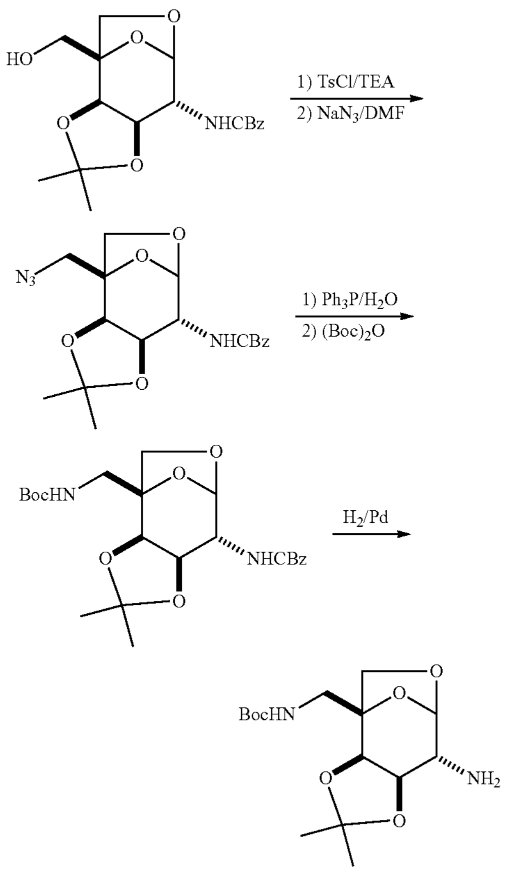

Intermediate 1

Synthesis 1-2. Preparation of tert-Butyl (((3aS,4R,7R,7aR)-7-amino-6-hydroxy-2,2-dimethyltetrahydro-4H-[1,3]dioxolo[4,5-c]pyran-4-yl)methyl) carbamate (Intermediate 2)

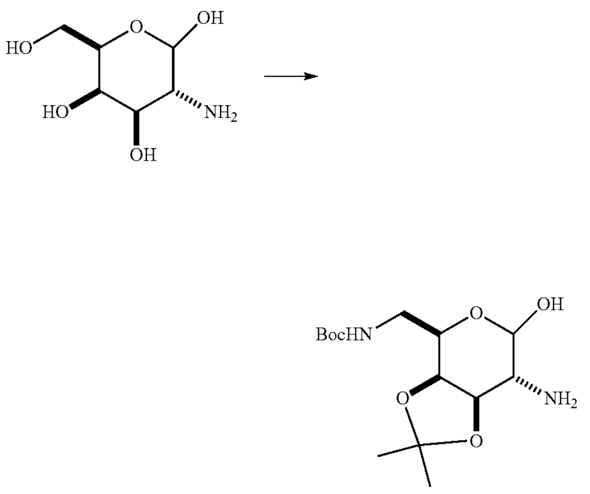

Intermediate 2

Synthesis 1-3: Preparation of (2R,3R,4R,5R,6R)-4,5-Bis(benzyloxy)-6-((benzyloxy)methyl)-2-methoxytetrahydro-2H-pyran-3-amine (Intermediate 3)

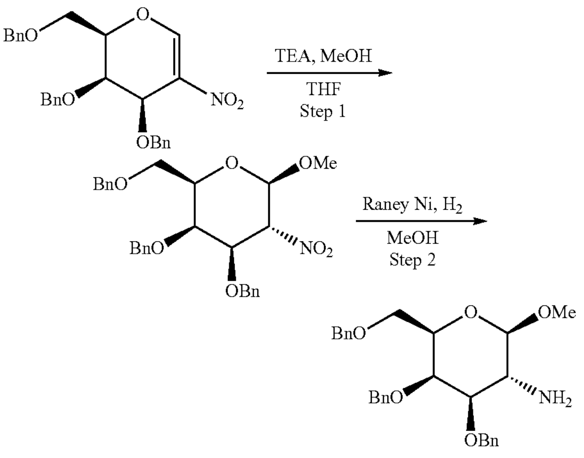

Intermediate 3

Step 1: To a stirred mixture of 1 mL methanol (24.5 mmol) and TEA (5 mL) was added a solution of (2R,3R,4R)-3,4-bis(benzyloxy)-2-((benzyloxy)methyl)-5-nitro-3,4-dihydro-2H-pyran (1.0 g, 2.17 mmol) in dry THF (5 mL) dropwise under argon. After stirring for 5 h at rt, the volatiles were removed in vacuo. The resulting crude material was purified by column to give (2R,3R,4R,5R,6R)-3,4-bis(benzyloxy)-2-((benzyloxy)methyl)-6-methoxy-5-nitrotetrahydro-2H-pyran (535 mg, 50%) and (2R,3R,4R)-3,4-bis(benzyloxy)-2-((benzyloxy)methyl)-5-nitro-3,4-dihydro-2H-pyran (65 mg, 6%). LC-MS (ESI) of both found: 494 $[M+H]^+$.

Step 2: To a solution of (2R,3R,4R,5R,6R)-3,4-bis(benzyloxy)-2-((benzyloxy)methyl)-6-methoxy-5-nitrotetrahydro-2H-pyran (535 mg, 1.09 mmol) in MeOH (10 mL) was added Raney Ni (50 mg). The mixture was charged with $H_2$ for three times and stirred at rt for 12 h under a $H_2$ balloon. The mixture was filtered and the filtrate was concentrated to give (2R,3R,4R,5R,6R)-4,5-bis(benzyloxy)-6-((benzyloxy)methyl)-2-methoxytetrahydro-2H-pyran-3-amine (300 mg, 59% yield) as white solid. LC-MS (ESI) found: 464 $[M+H]^+$.

Synthesis 1-4: Preparation of N-((3aR,4R,6R,7R,7aR)-4-(Hydroxymethyl)-6-methoxy-2,2-dimethyltetrahydro-4H-[1,3]dioxolo[4,5-c]pyran-7-yl)acetamide (Intermediate 4)

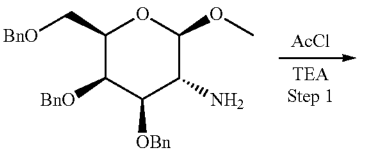

Intermediate 3

-continued

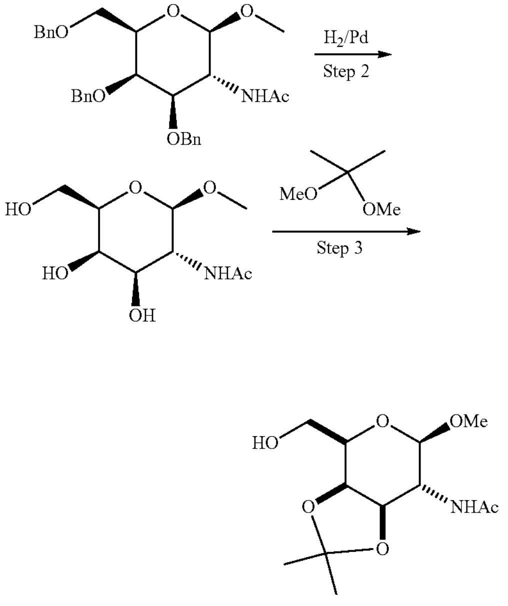

Intermediate 4

Step 1: To a solution of (2R,3R,4R,5R,6R)-4,5-bis(benzyloxy)-6-((benzyloxy)methyl)-2-methoxytetrahydro-2H-pyran-3-amine (1.5 g, 3.24 mmol) in DCM (15 mL) was added AcCl (508 mg, 6.48 mmol) and TEA (3 mL). The mixture was stirred at rt for 2 h. The mixture was concentrated and purified by silica column to give N-((2R,3R,4R,5R,6R)-4,5-bis(benzyloxy)-6-((benzyloxy)methyl)-2-methoxytetrahydro-2H-pyran-3-yl)acetamide (1.6 g, 98%) as white solid. LC-MS (ESI) found: 506 $[M+H]^+$.

Step 2: To a solution of N-((2R,3R,4R,5R,6R)-4,5-bis(benzyloxy)-6-((benzyloxy)methyl)-2-methoxytetrahydro-2H-pyran-3-yl)acetamide (1.6 g, 3.17 mmol) in MeOH (15 mL) was added Pd/C (100 mg, 10% wt, 60% wet). The mixture was stirred at rt for 12 h under a $H_2$ balloon. The mixture was filtered and concentrated to give N-((2R,3R,4R,5R,6R)-4,5-dihydroxy-6-(hydroxymethyl)-2-methoxytetrahydro-2H-pyran-3-yl)acetamide (670 mg, 90% yield). LC-MS (ESI) found: 236 $[M+H]^+$. $^1H$ NMR (400 MHz, $CD_3OD$): δ 4.68 (d, J=3.7 Hz, 1H), 4.27 (dd, J=10.9, 3.6 Hz, 1H), 3.87 (d, J=3.1 Hz, 1H), 3.79-3.69 (m, 3H), 3.37 (d, J=5.6 Hz, 3H), 2.02-1.93 (m, 3H).

Step 3: To a solution of N-((2S,3R,4R,5R,6R)-4,5-dihydroxy-6-(hydroxymethyl)-2-methoxytetrahydro-2H-pyran-3-yl)acetamide (670 mg, 2.85 mmol) in DMF (5 mL) and 2,2-dimethoxypropane (0.8 mL, 6.42 mmol) were added (+/−)-camphor-10-sulphonic acid (330 mg, 1.42 mmol). The reaction mixture was stirred at 70° C. for 24 h. Then it was cooled to room temperature and neutralized with triethylamine. The solvent was evaporated and the residue was co-evaporated 3 times with toluene. The resulting crude material was purified by column to give N-((3aR,4R,6S,7R,7aR)-4-(hydroxymethyl)-6-methoxy-2,2-dimethyltetrahydro-4H-[1,3]dioxolo[4,5-c]pyran-7-yl)acetamide (392 mg, 50%) as white solid. LC-MS (ESI) found: 276 $[M+H]^+$. $^1H$ NMR (400 MHz, $CD_3OD$): δ 4.30 (dd, J=8.6, 5.5 Hz, 1H), 4.16 (ddd, J=13.6, 6.8, 3.5 Hz, 2H), 3.88-3.71 (m, 3H), 3.48-3.41 (m, 3H), 3.34 (s, 1H), 2.01-1.90 (m, 3H), 1.53-1.44 (m, 3H), 1.32 (d, J=11.4 Hz, 3H).

Example 2. Synthesis of ASGPR Ligands

Synthesis 2-1. General Synthesis of Sulfonamide-Containing Ligands

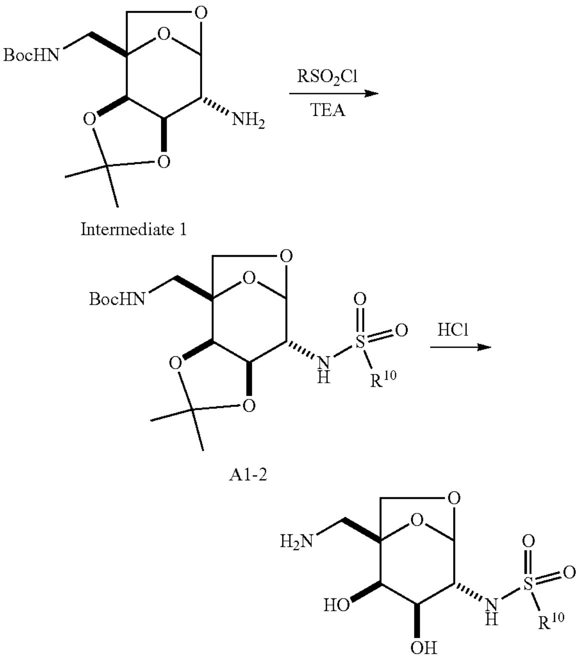

Intermediate 1

A1-2

Compound A1

Synthesis 2-2. General Synthesis of Sulfonimidamide-Containing Ligands

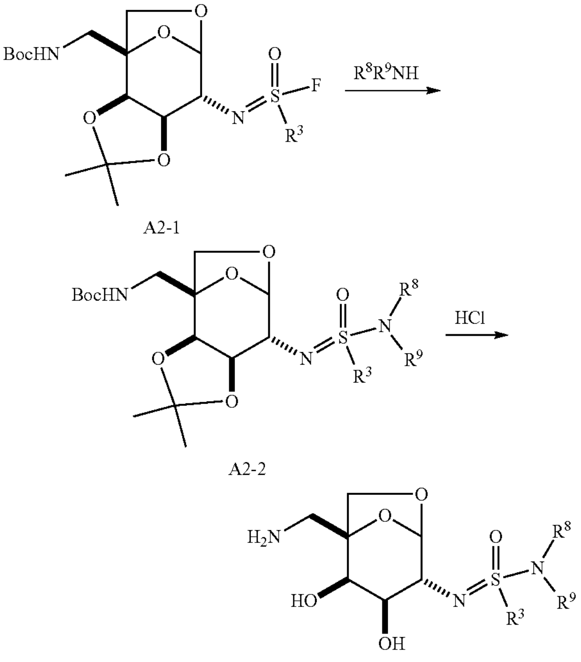

A2-1

A2-2

Compound A2

Synthesis 2-3. General Synthesis of Sulfonyl Urea-Containing Compounds

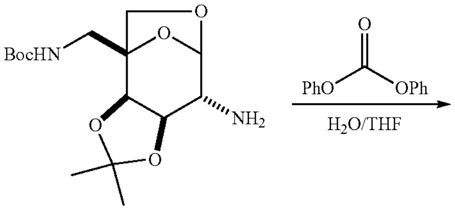

Intermediate 1

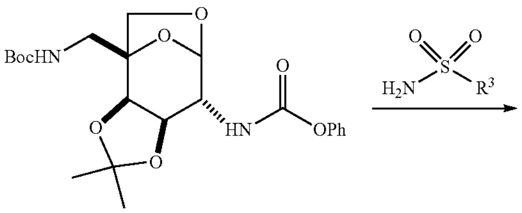

A3-2

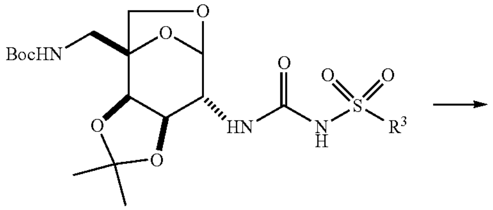

A3-3
Org. Biomol. Chem., 2017, 15, 4992-4999

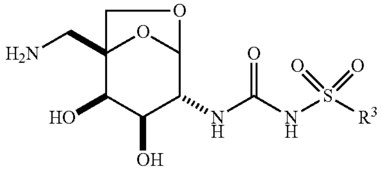

Compound A3-a

Synthesis 2-4: Alternative General Synthesis of Sulfonyl Urea-Containing Compounds

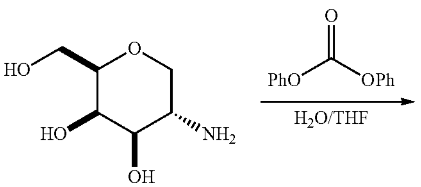

A3-5

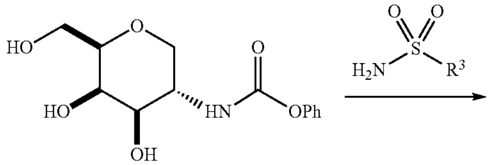

A3-6
Org. Biomol. Chem., 2017, 15, 4992-4999

-continued

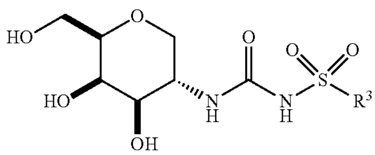

A3-b

Synthesis 2-5. General Synthesis of Sulfonimidamide-Containing Ligands

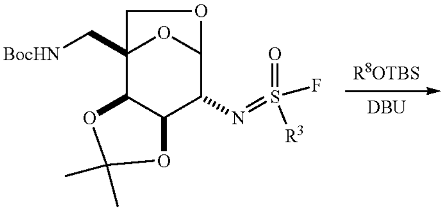

A4-1

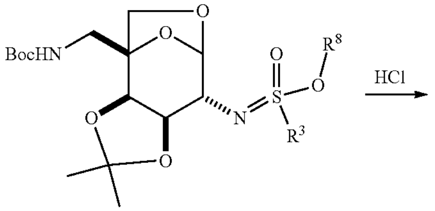

A4-2

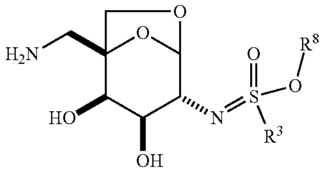

Compound A4

Synthesis 2-6. General Synthesis of ASGPR Ligands

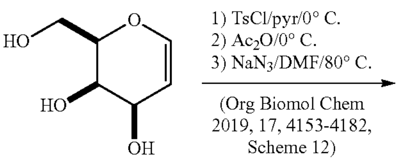

A5-1

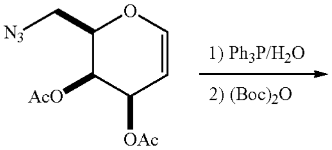

A5-2

-continued
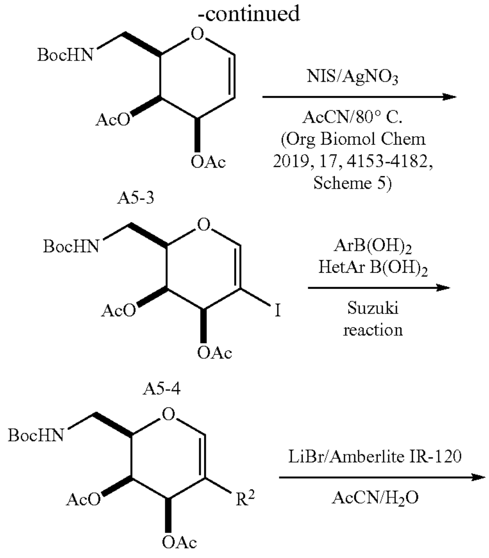
A5-3
A5-4
A5-5
-continued
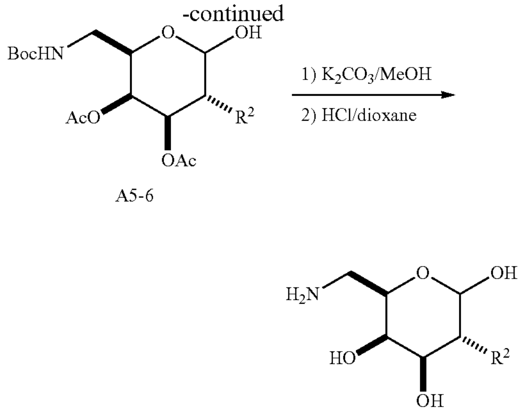
A5-6
Compound A5
Synthesis 2-7. General Synthesis of ASGPR Ligands
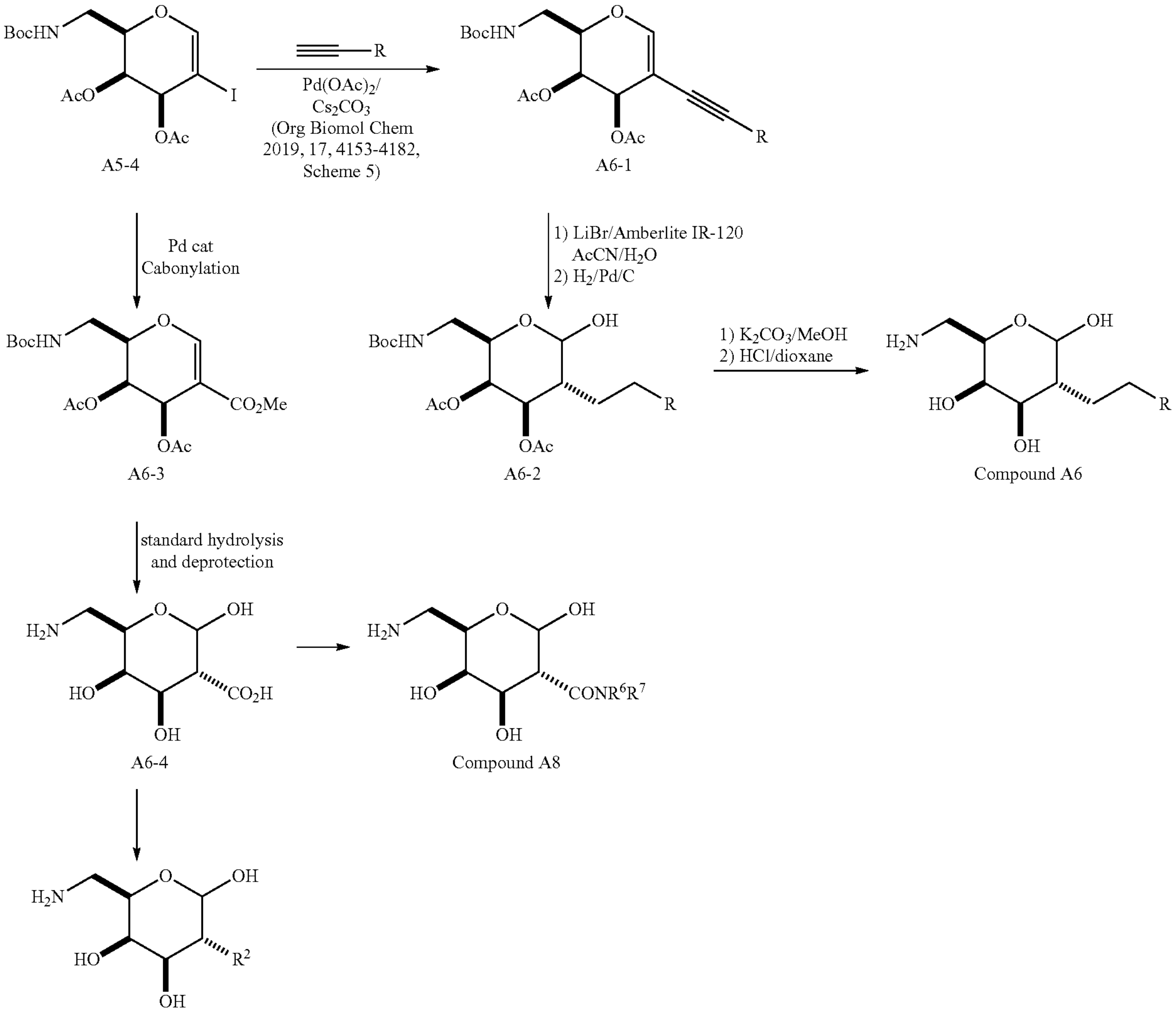
A5-4
A6-1
A6-3
A6-2
Compound A6
A6-4
Compound A8
Compound A7

Synthesis 2-6 and Synthesis 2-7 can be Used to Synthesize Ligands with the Following $R^2$ Groups

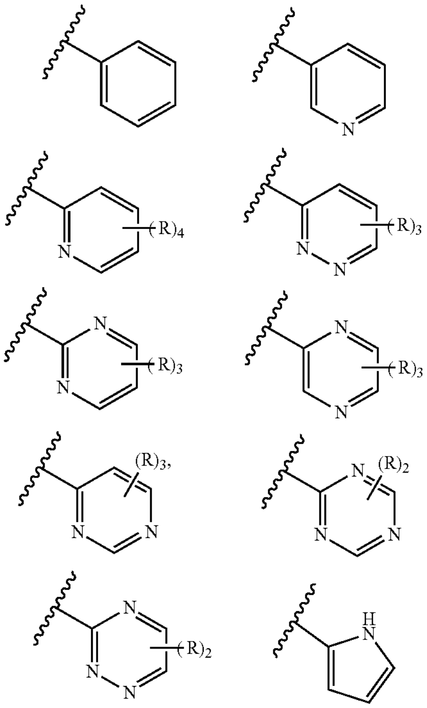

-continued

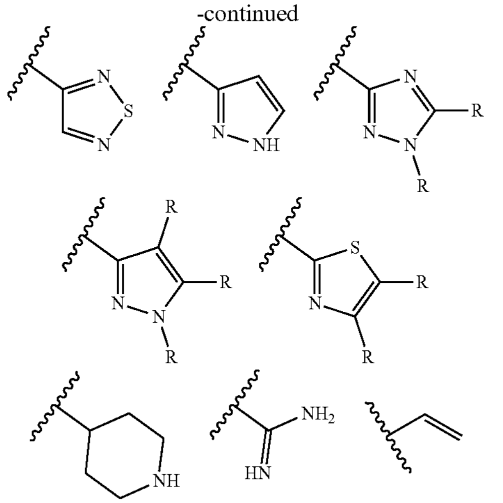

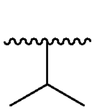

and

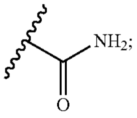

wherein R is an optimal substituent has defined herein.

Synthesis 2-8. Preparation of N-(((3R,4R,5R,6R)-2,4,5-Trihydroxy-6-(hydroxymethyl)tetrahydro-2H-pyran-3-yl)methyl)acetamide (Compound A9) and N-(((3R,4R,5R,6R)-6-(aminomethyl)-2,4,5-trihydroxytetrahydro-2H-pyran-3-yl)methyl)acetamide (Compound A10)

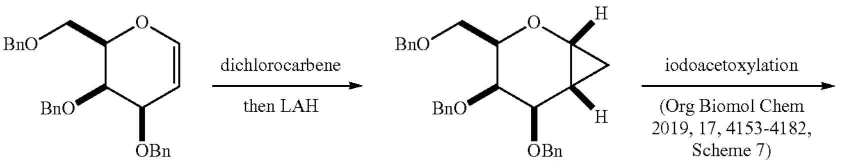

A10-1 A10-2

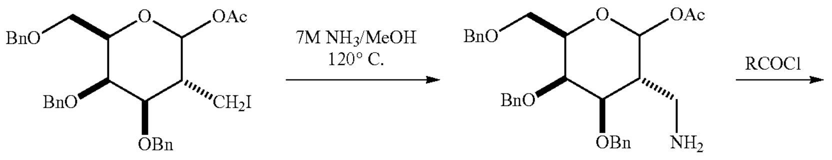

A10-3 A10-4

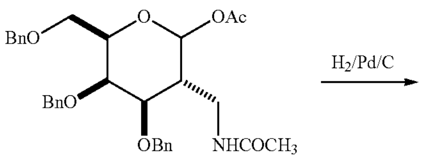

A10-5

-continued
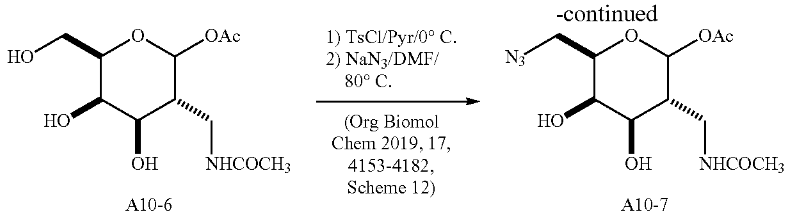
A10-6 A10-7
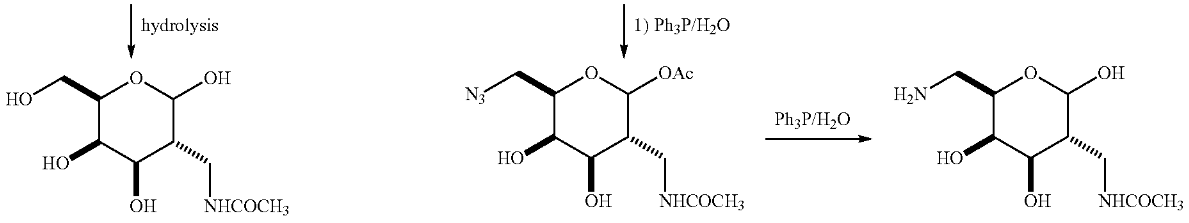
Compound A9 A10-8 Compound A10
Synthesis 2-9. General Synthesis of Amide-Containing Ligands
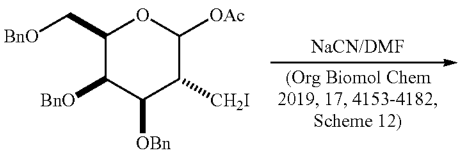
A10-3
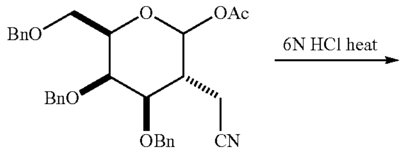
A14-1
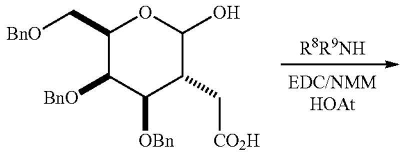
A14-2
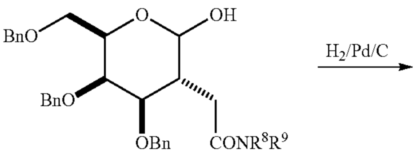
A14-3
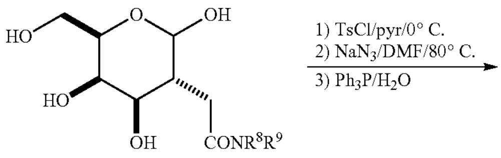
Compound A13
-continued
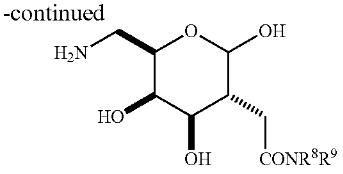
Compound A14
Synthesis 2-10. Preparation of 1-((1S,2R,3R,4R)-1-(Aminomethyl)-2,3-dihydroxy-6,8-dioxabicyclo[3.2.1]octan-4-yl)pyrrolidin-2-one (Compound A15)
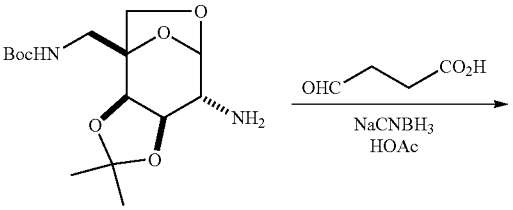
Intermediate 1
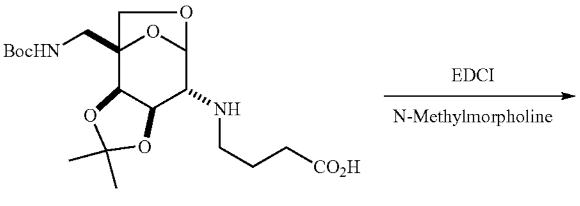
A15-1
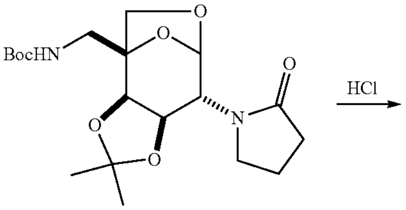
A15-2

-continued

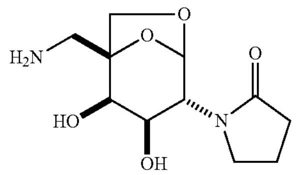

Compound A15

EDCI = 1-Ethyl-3-(3-dimethylaminopropyl)carbodiimide

Synthesis 2-11. Preparation of 3-((1S,2R,3R,4R)-1-(Aminomethyl)-2,3-dihydroxy-6,8-dioxabicyclo[3.2.1]octan-4-yl)oxazolidin-2-one (Compound A16)

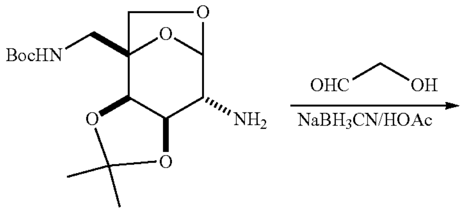

Intermediate 1

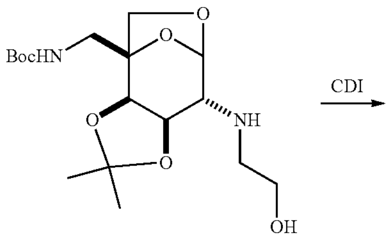

A16-1

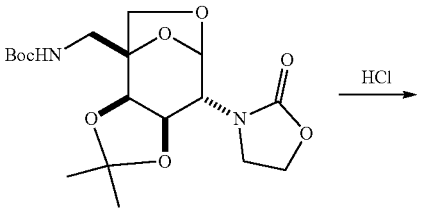

A16-2

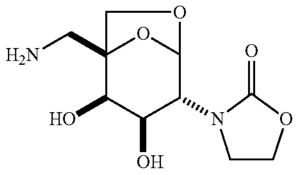

Compound A16

CDI = Carbonyldiimidazole

Synthesis 2-12. Preparation of 1-((1S,2R,3R,4R)-1-(Aminomethyl)-2,3-dihydroxy-6,8-dioxabicyclo[3.2.1]octan-4-yl)imidazolidin-2-one (Compound A17)

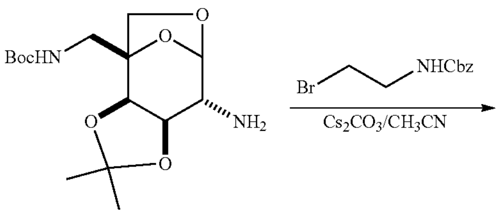

Intermediate 1

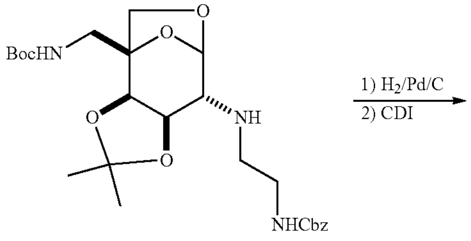

A17-1

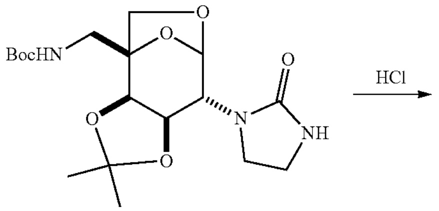

A17-2

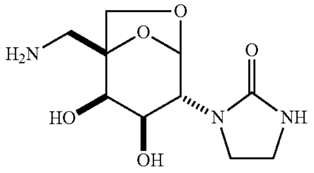

Compound A17

Synthesis 2-13. Preparation of 1-((1S,2R,3R,4R)-1-(Aminomethyl)-2,3-dihydroxy-6,8-dioxabicyclo[3.2.1]octan-4-yl)imidazolidine-2-thione (Compound A18)

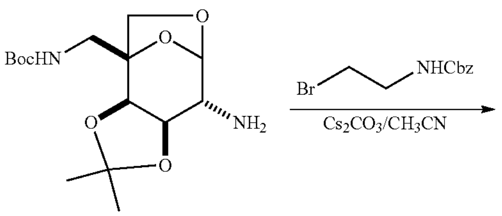

Intermediate 1

-continued

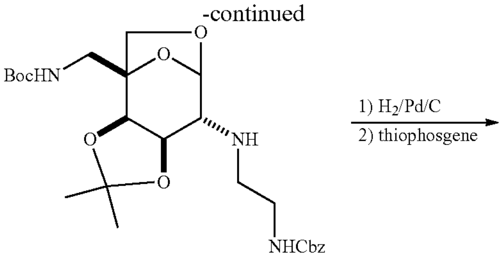

A18-1

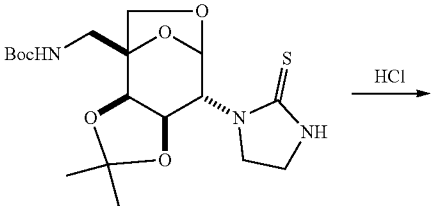

A18-2

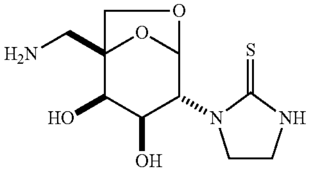

Compound A18

Synthesis 2-14. Preparation of 1-((1S,2R,3R,4R)-1-(Aminomethyl)-2,3-dihydroxy-6,8-dioxabicyclo[3.2.1]octan-4-yl)pyrrolidine-2,5-dione (Compound A19)

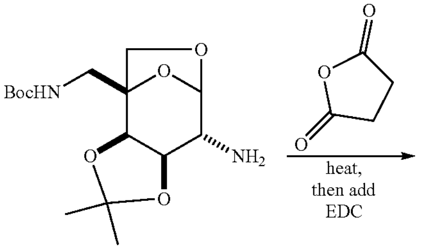

Intermediate 1

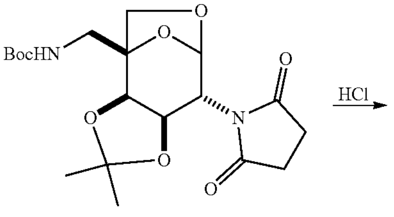

A19-1

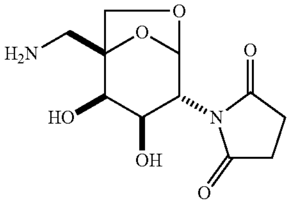

Compound A19

Synthesis 2-15. Preparation of 1-((1S,2R,3R,4R)-1-(Aminomethyl)-2,3-dihydroxy-6,8-dioxabicyclo[3.2.1]octan-4-yl)-1H-pyrrole-2,5-dione (Compound A20)

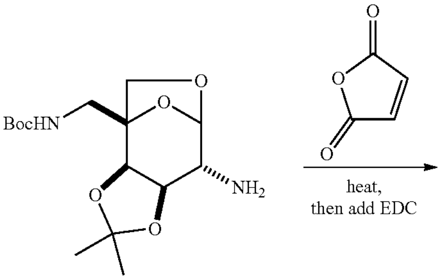

Intermediate 1

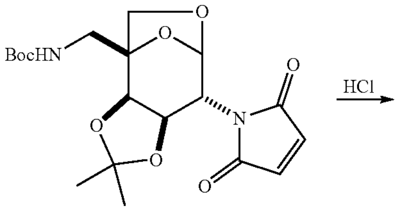

A-20

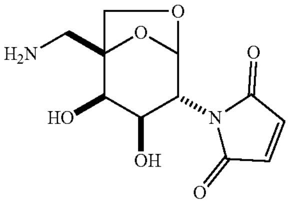

Compound A20

Synthesis 2-16. Preparation of 3-((1S,2R,3R,4R)-1-(Aminomethyl)-2,3-dihydroxy-6,8-dioxabicyclo[3.2.1]octan-4-yl)thiazolidine-2,4-dione (Compound A21)

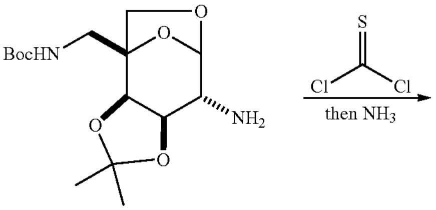

Intermediate 1

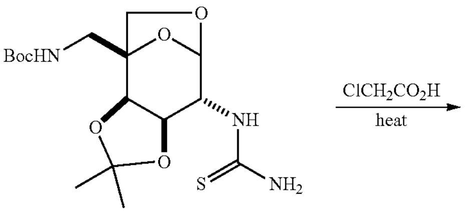

A21-1

-continued

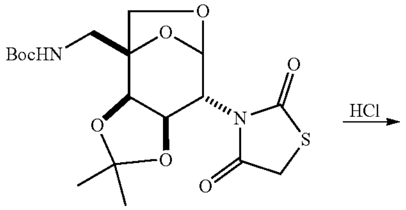

A21-2

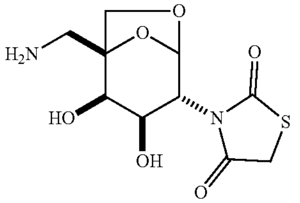

Compound A21

Synthesis 2-17. Preparation of 3-((1S,2R,3R,4R)-1-(Aminomethyl)-2,3-dihydroxy-6,8-dioxabicyclo[3.2.1]octan-4-yl)oxazolidine-2,4-dione (Compound A22)

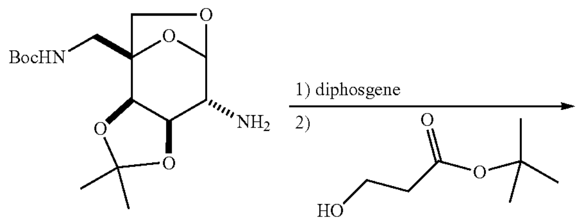

Intermediate 1

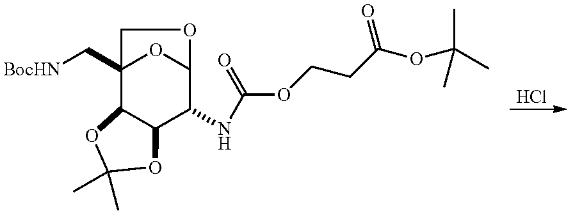

A22-1

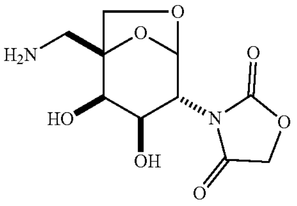

Compound A22

Synthesis 2-18. Preparation of 2-((1S,2R,3R,4R)-1-(Aminomethyl)-2,3-dihydroxy-6,8-dioxabicyclo[3.2.1]octan-4-yl)isoindoline-1,3-dione (Compound A23)

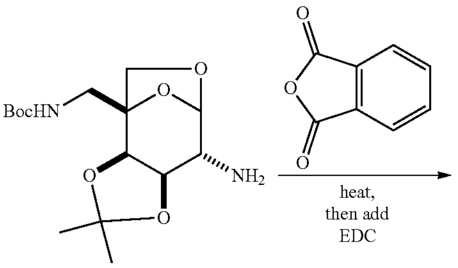

Intermediate 1

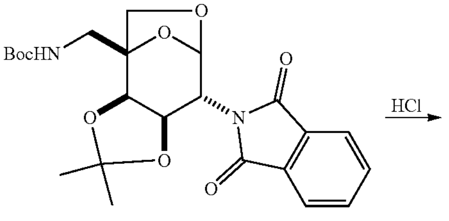

A23-1

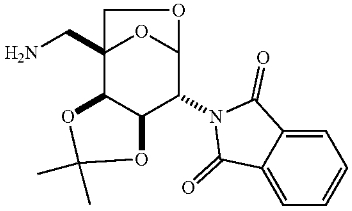

Compound A-23

Synthesis 2-19. Preparation of 2-((1S,2R,3R,4R)-1-(Aminomethyl)-2,3-dihydroxy-6,8-dioxabicyclo[3.2.1]octan-4-yl)isoindolin-1-one (Compound A24)

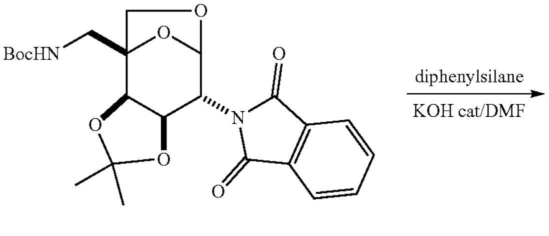

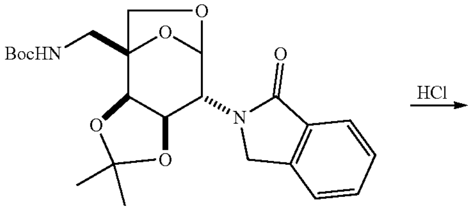

A23-1

-continued

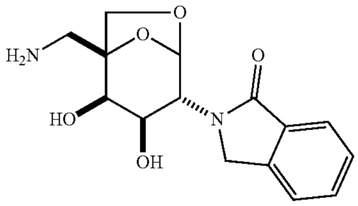

Compound A24

Synthesis 2-20. Preparation of (1S,2R,3R,4R)-1-(Aminomethyl)-4-(1H-imidazol-1-yl)-6,8-dioxabicyclo[3.2.1]octane-2,3-diol (Compound A25)

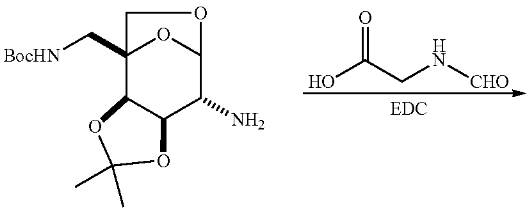

Intermediate 1

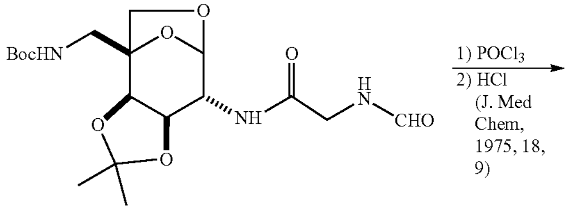

A25-1

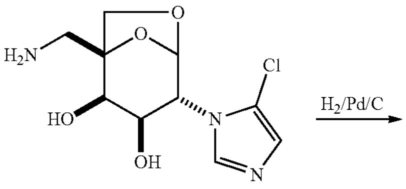

A25-2

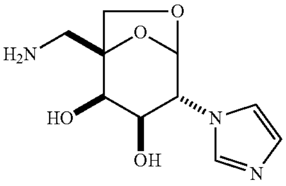

Compound A25

Synthesis 2-21. Preparation of (1S,2R,3R,4R)-1-(Aminomethyl)-4-(1H-pyrrol-1-yl)-6,8-dioxabicyclo[3.2.1]octane-2,3-diol (Compound A26)

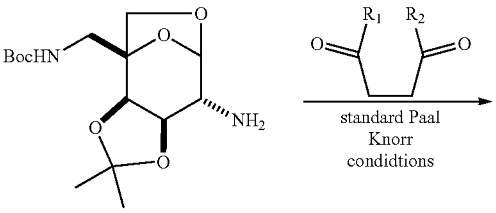

Intermediate 1

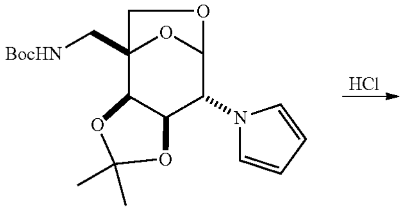

A26-1

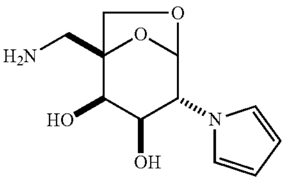

Compound A26

Synthesis 2-22. Preparation of 1-((1S,2R,3R,4R)-1-(Aminomethyl)-2,3-dihydroxy-6,8-dioxabicyclo[3.2.1]octan-4-yl)pyridin-2(1H)-one (Compound A27)

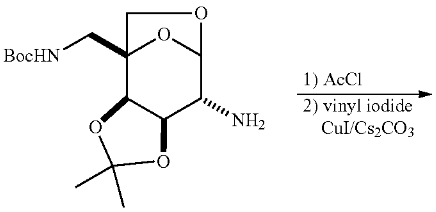

Intermediate 1

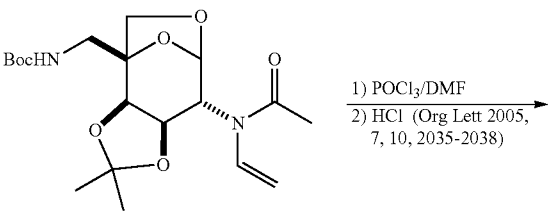

A27-1

-continued

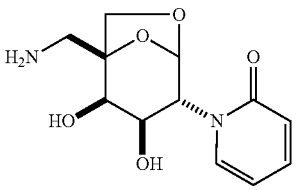

Compound A27

Synthesis 2-23. Preparation of 1-((1S,2R,3R,4R)-1-(Aminomethyl)-2,3-dihydroxy-6,8-dioxabicyclo[3.2.1]octan-4-yl)pyrimidin-2(1H)-one (Compound A28)

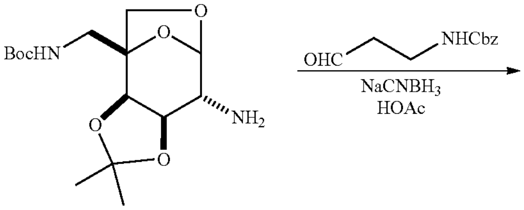

Intermediate 1

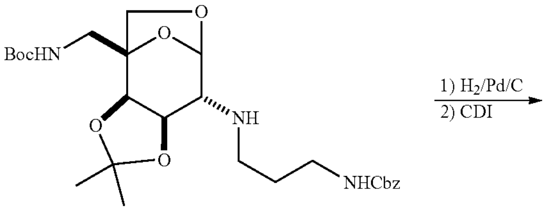

A28-1

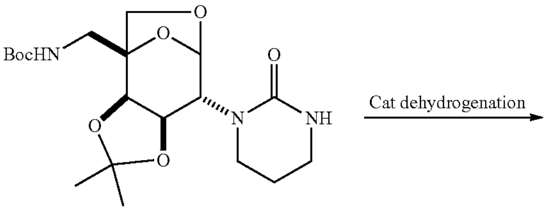

A28-2

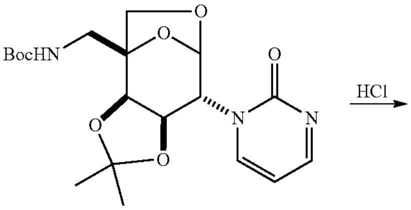

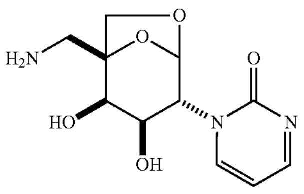

Compound A28

Synthesis 2-24. Preparation of 1-((1S,2R,3R,4R)-1-(Aminomethyl)-2,3-dihydroxy-6,8-dioxabicyclo[3.2.1]octan-4-yl)pyridin-4(1H)-one (Compound A29)

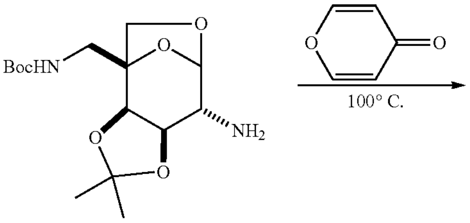

Intermediate 1

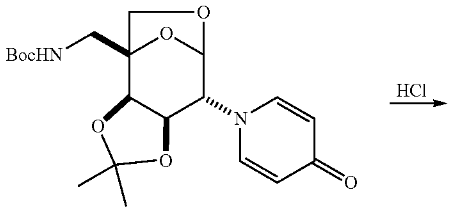

A29-1

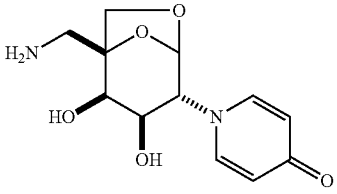

Compound A29

Synthesis 2-25. Preparation of (3R,4R,5R,6R)-6-(Aminomethyl)-3-(piperidin-1-yl)tetrahydro-2H-pyran-2,4,5-triol (Compound A30)

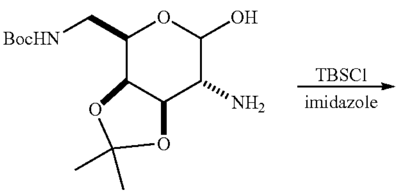

Intermediate 2

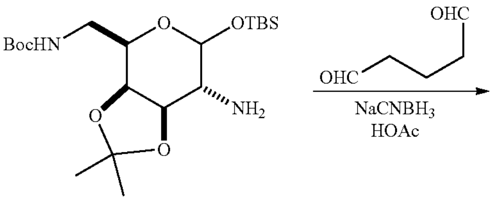

A30-1

-continued

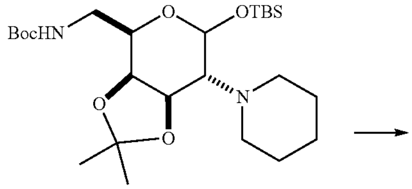

A30-2

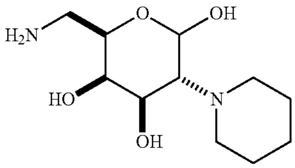

Compound A30

Synthesis 2-26. Preparation of (3R,4R,5R,6R)-6-(Aminomethyl)-3-morpholinotetrahydro-2H-pyran-2,4,5-triol (Compound A31)

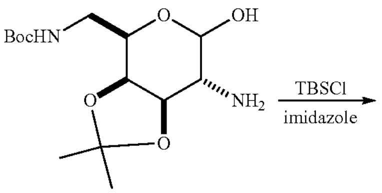

Intermediate 2

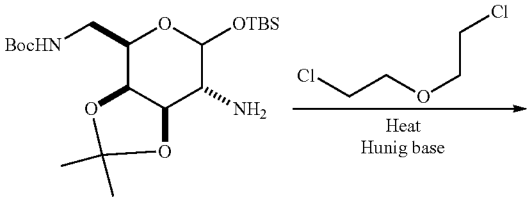

A31-1

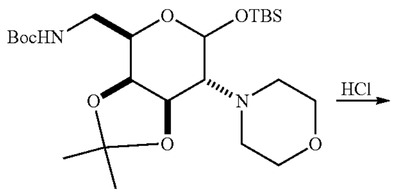

A31-2

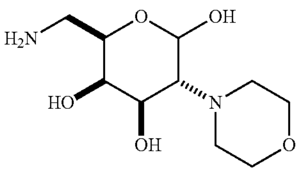

Compound A31

Synthesis 2-27. Preparation of (3R,4R,5R,6R)-6-(Aminomethyl)-3-thiomorpholinotetrahydro-2H-pyran-2,4,5-triol (Compound A32)

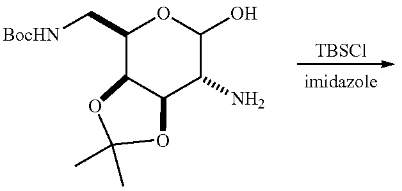

Intermediate 2

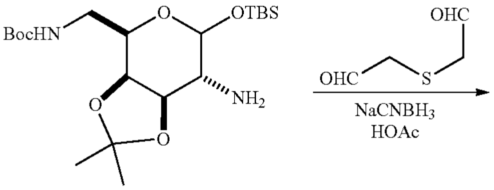

A32-1

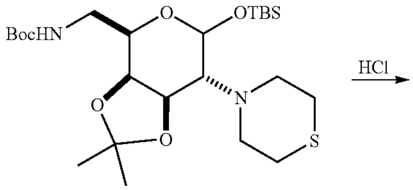

A32-2

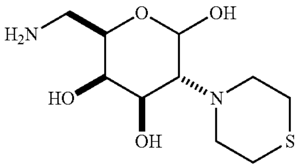

Compound A32

Synthesis 2-28. Preparation of 1-((1S2R,3R,4R)-1-Aminomethyl)-2,3-dihydroxy-6,8-dioxabicyclo[3.2.1]octan-4-yl)azetidin-2-one (Compound A33)

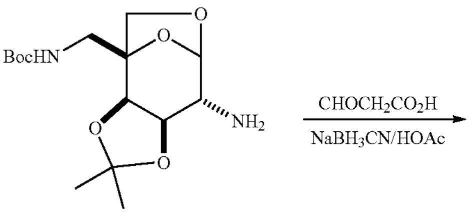

Intermediate 1

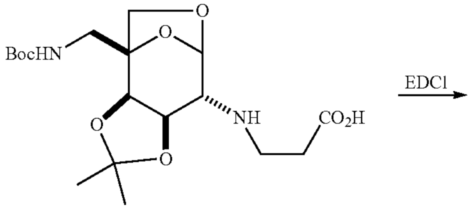

A33-1

-continued
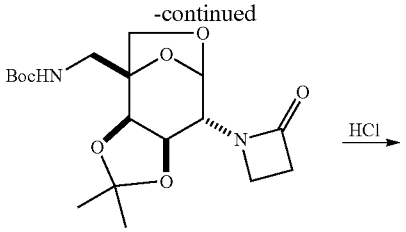
A33-2
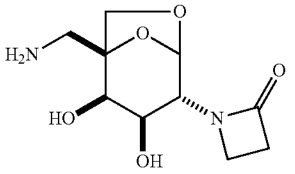
Compound A33
Synthesis 2-29. Preparation of (4R,5R,6R)-6-(Aminomethyl)tetrahydro-2H-pyran-2,4,5-triol (Compound A34) and (4R,5R,6R)-6-(hydroxymethyl) tetrahydro-2H-pyran-2,4,5-triol (Compound A35)
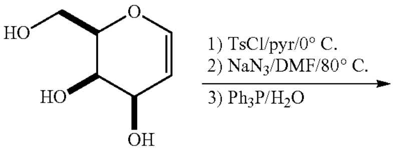
A35-1
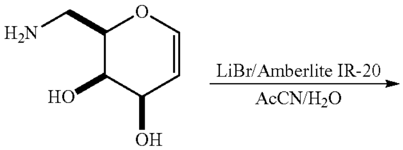
A35-2
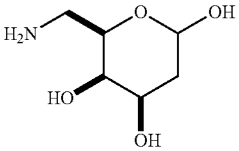
Compound A34
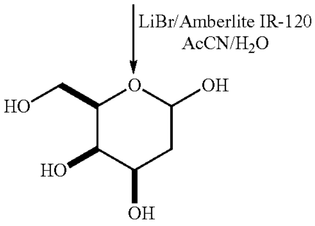
Compound A35
Synthesis 2-30. Preparation of 1-((3R,4R,5R,6R)-6-(Aminomethyl)-2,4,5-trihydroxytetrahydro-2H-pyran-3-yl)tetrahydropyrimidin-2(1H)-one (Compound A36)
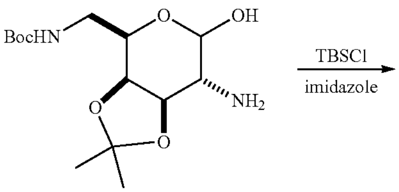
Intermediate 2
-continued
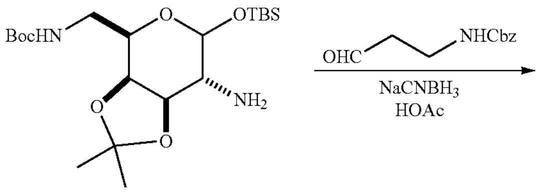
A36-1
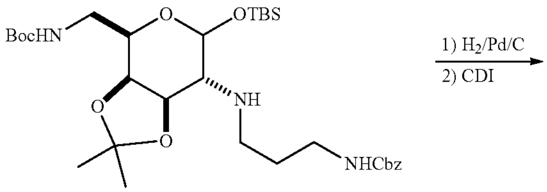
A36-2
-continued
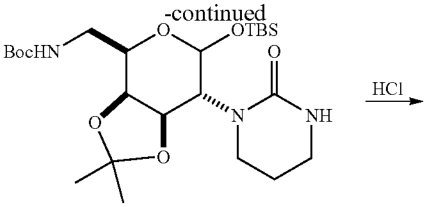
A28-2
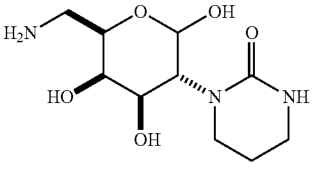
Compound A36

Synthesis 2-31. Preparation of N-((1S,2R,3R,4R)-1-(Aminomethyl)-2,3-dihydroxy-6,8-dioxabicyclo[3.2.1]octan-4-yl)methanesulfinamide (Compound A37) and N-((1S,2R,3R,4R)-1-(aminomethyl)-2,3-dihydroxy-6,8-dioxabicyclo[3.2.1]octan-4-yl)-1,1,1-trifluoromethanesulfonamide (Compound A38)

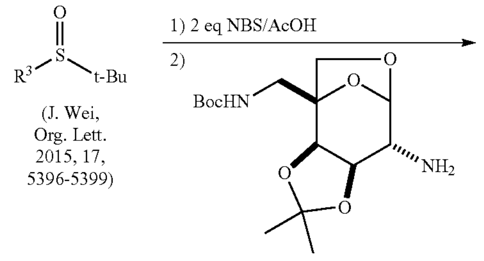

(J. Wei, Org. Lett. 2015, 17, 5396-5399)

Intermediate 1

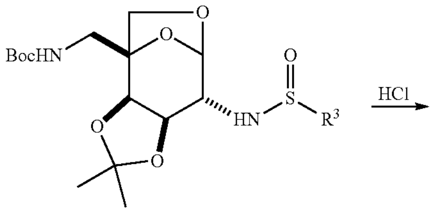

A37-1

-continued

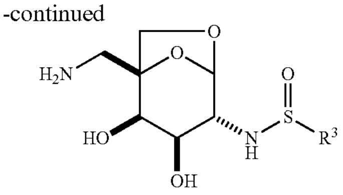

Compound A37 ($R^3 = CH_3$)
Compound A38 ($R^3 = CF_3$)

Synthesis 2-32. Preparation of (4aR,6R,7R,8R,8aR)-6-(Aminomethyl)-7,8-dihydroxyhexahydro-1H,3H-pyrano[3,2-c][1,2,6]thiadiazine 2,2-dioxide (Compound A39), (4aR,6R,7R,8R,8aR)-6-(aminomethyl)-7,8-dihydroxyhexahydro-1H-pyrano[3,2-d]pyrimidin-2(3H)-one (Compound A40), and (4aS,6R,7R,8R,8aR)-6-(aminomethyl)-7,8-dihydroxyhexahydropyrano[3,2-d][1,3]oxazin-2(1H)-one (Compound A41)

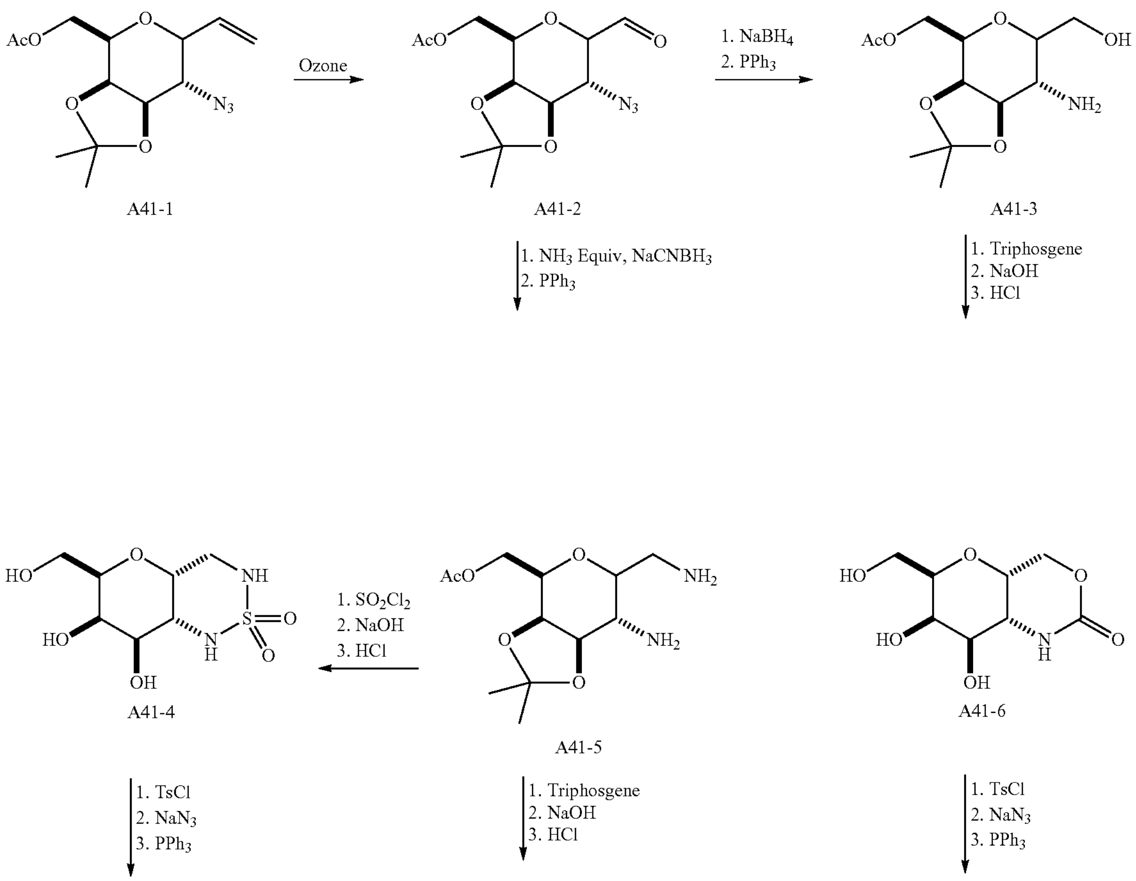

A41-1 A41-2 A41-3 A41-4 A41-5 A41-6

-continued

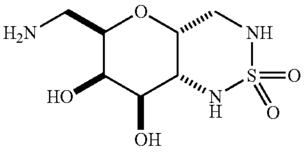

Compound A39

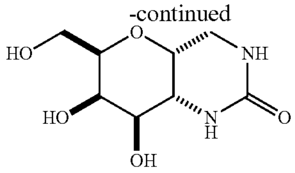

A41-7

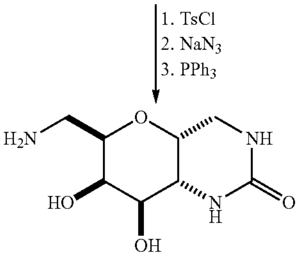

Compound A40

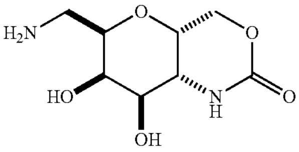

Compound A41

Synthesis 2-33. Alternative Preparation of (4aS,6R,7R,8R,8aR)-6-(Aminomethyl)-7,8-dihydroxytetrahydro-1H,6H-pyrano[2,3-b][1,4]oxazin-2(3H)-one (Compound A41)

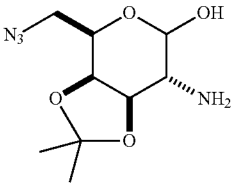

A41-7

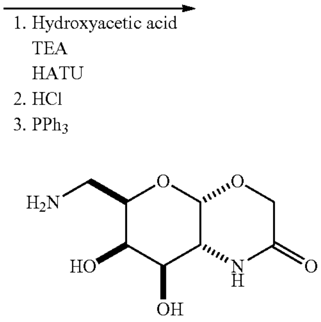

Compound A41

Synthesis 2-34. Preparation of (3aR,5R,6R,7R,7aR)-7-Amino-5-(hydroxymethyl)-2-methyl-3a,6,7,7a-tetrahydro-5H-pyrano[3,2-d]oxazol-6-ol (Compound A43) and (3aR,5R,6R,7R,7aR)-7-amino-5-(hydroxymethyl)-2-(trifluoromethyl)-3a,6,7,7a-tetrahydro-5H-pyrano[3,2-d]oxazol-6-ol (Compound A44)

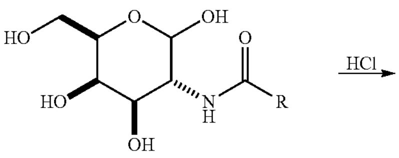

A44-1

-continued

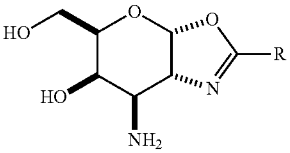

Compound A43 (R = $CH_3$)
Compound A44 (R = $CF_3$)

Synthesis 2-35. Preparation of (5R,6R,7R)-5-(Hydroxymethyl)-2-methyl-6,7-dihydro-5H-pyrano[3,2-d]oxazole-6,7-diol (Compound A45) and (5R,6R,7R)-5-(hydroxymethyl)-2-(trifluoromethyl)-6,7-dihydro-5H-pyrano[3,2-d]oxazole-6,7-diol (Compound A46)

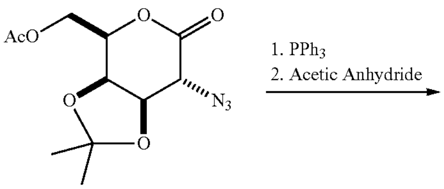

A46-1

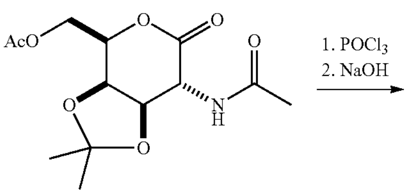

A46-2

-continued

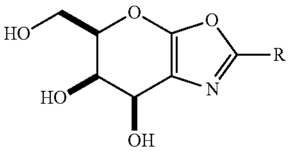

Compound A45 ($R = CH_3$)
Compound A46 ($R = CF_3$)

Synthesis 2-36. Preparation of (3aS,5R,6R,7R,7aR)-7-Amino-5-(hydroxymethyl)-2-methyl-3,3a,5,6,7,7a-hexahydropyrano[2,3-d]imidazol-6-ol (Compound A47) and (3aS,5R,6R,7R,7aR)-7-amino-5-(hydroxymethyl)-2-(trifluoromethyl)-3,3a,5,6,7,7a-hexahydropyrano[2,3-d]imidazol-6-ol (Compound A48)

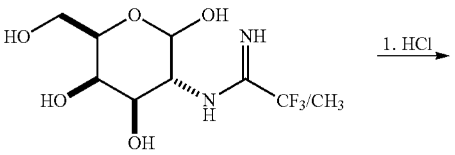

A48-1

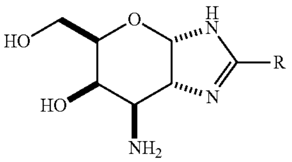

Compound A47 ($R = CH_3$)
Compound A48 ($R = CF_3$)

Synthesis 2-37. Preparation of (5R,6R,7R)-5-(Hydroxymethyl)-2-methyl-3,5,6,7-tetrahydropyrano[2,3-d]imidazole-6,7-diol (Compound A49) and (5R,6R,7R)-5-(hydroxymethyl)-2-(trifluoromethyl)-3,5,6,7-tetrahydropyrano[2,3-d]imidazole-6,7-diol (Compound A50)

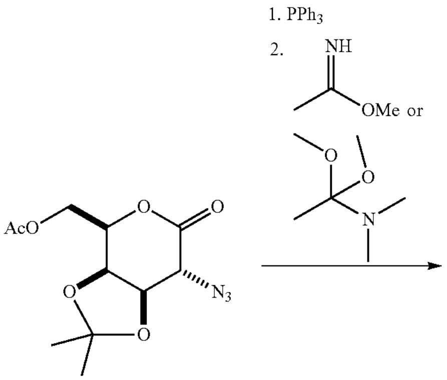

A50-1

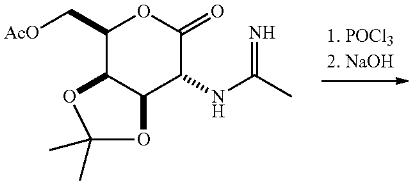

A50-2

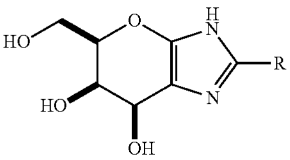

Compound A49 ($R = CH_3$)
Compound A50 ($R = CF_3$)

Synthesis 2-38. Preparation of 1-((3aR,5R,6R,7R,7aR)-5-(Aminomethyl)-6,7-dihydroxyhexahydropyrano[3,2-b]pyrrol-1(2H)-yl)-2,2,2-trifluoroethan-1-one (Compound A51) and 1-((5R,6R,7R)-5-(aminomethyl)-6,7-dihydroxy-6,7-dihydropyrano[3,2-b]pyrrol-1(5H)-yl)-2,2,2-trifluoroethan-1-one (Compound A52)

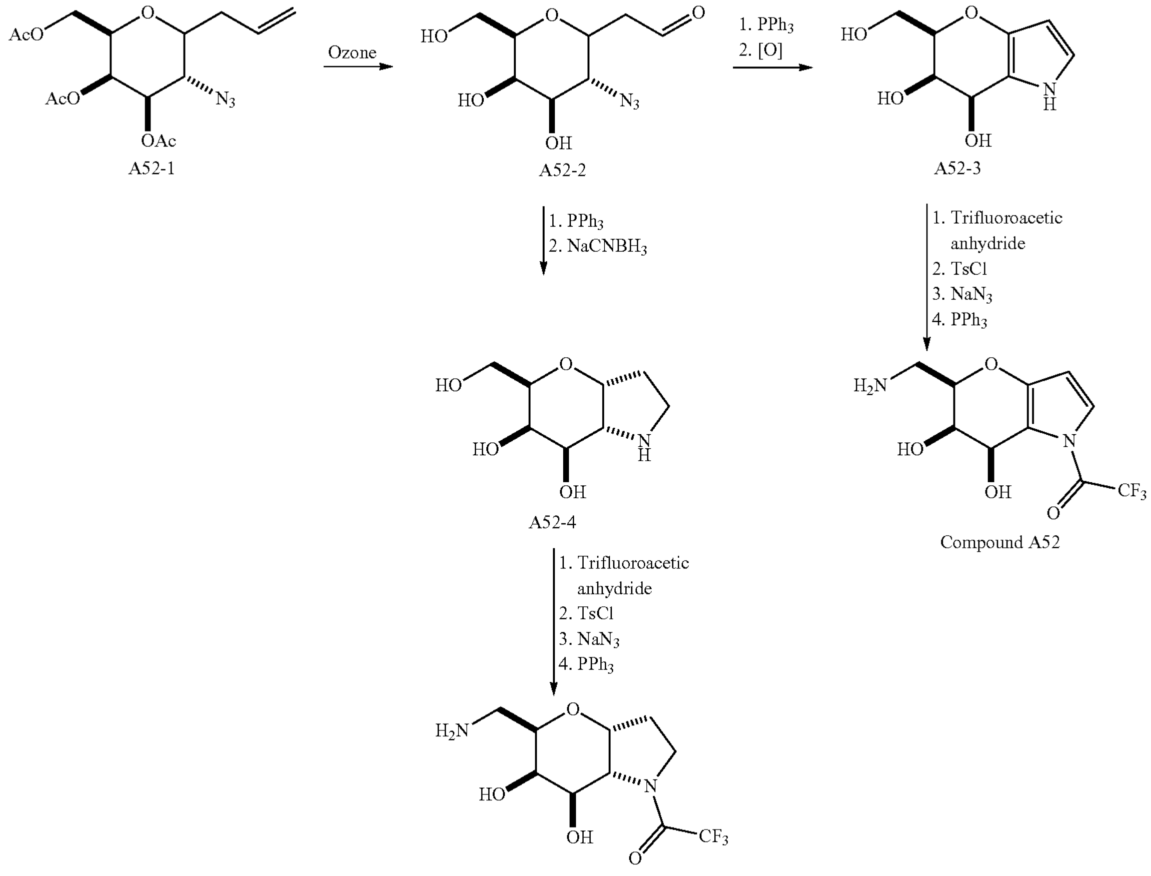

A52-1

A52-2

A52-3

A52-4

Compound A52

Compound A51

Synthesis 2-39. Preparation of 1-((4aS,6R,7R,8R,8aR)-6-(Aminomethyl)-7,8-dihydroxyhexahydro-1H,6H-pyrano[2,3-b][1,4]oxazin-1-yl)ethan-1-one (Compound A53) and 1-((4aS,6R,7R,8R,8aR)-6-(aminomethyl)-7,8-dihydroxyhexahydro-1H,6H-pyrano[2,3-b][1,4]oxazin-1-yl)-2,2,2-trifluoroethan-1-one (Compound A54)

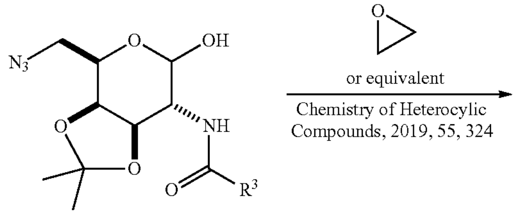

A54-1

-continued

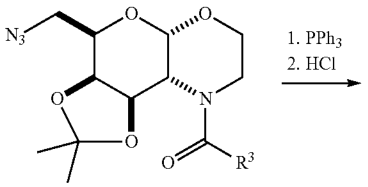

A54-2

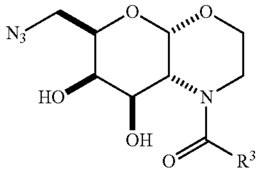

Compound A53 ($R^3$ = $CH_3$)
Compound A54 ($R^3$ = $CF_3$)

Synthesis 2-40. Preparation of 1-((3aS,4R,5aS,9aR,9bR)-4-(Aminomethyl)-2,2,7-trimethylhexahydro-4H,9H-[1,3]dioxolo[4',5':4,5]pyrano[2,3-b][1,4]oxazin-9-yl)ethan-1-one (Compound A55) and 1-((3aS,4R,5aS,9aR,9bR)-4-(Aminomethyl)-2,2,7-trimethylhexahydro-4H,9H-[1,3]dioxolo[4',5':4,5]pyrano[2,3-b][1,4]oxazin-9-yl)-2,2,2-trifluoroethan-1-one (Compound A56)

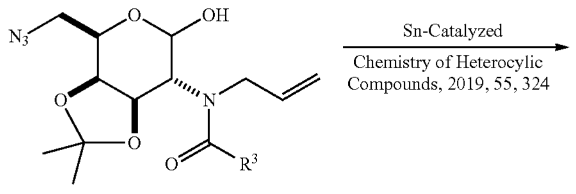

A56-1

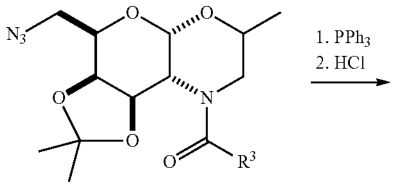

A56-2

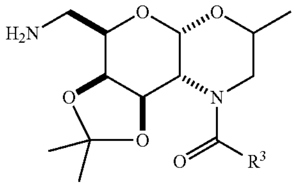

Compound A55 ($R^3 = CH_3$)
Compound A56 ($R^3 = CF_3$)

Synthesis 2-41. Preparation of 1-((3aS,4R,5aS,11aR,11bR)-4-(Aminomethyl)-2,2-dimethyloctahydro-4H,11H-[1,3]dioxolo[4',5':4,5]pyrano[2,3-b][1,4]oxazocin-11-yl)ethan-1-one (Compound A57) and 1-((3aS,4R,5aS,11aR,11bR)-4-(Aminomethyl)-2,2-dimethyloctahydro-4H,11H-[1,3]dioxolo[4',5':4,5]pyrano[2,3-b][1,4]oxazocin-11-yl)-2,2,2-trifluoro-ethan-1-one (Compound A58)

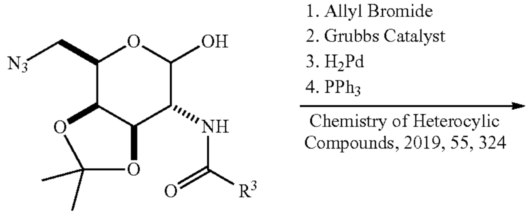

A58-1

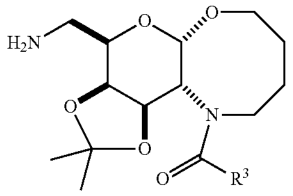

Compound A57 ($R^3 = CH_3$)
Compound A58 ($R^3 = CF_3$)

Synthesis 2-42. Preparation of 1-((3aR,5R,6R,7R,7aR)-6,7-Dihydroxy-5-(hydroxymethyl)hexahydro-pyrano[3,2-b]pyrrol-1(2H)-yl)ethan-1-one (Compound A59) and (2R,3R,4R,4aR,8aR)-2-(Hydroxymethyl)octahydro-2H-pyrano[3,2-b]pyridine-3,4-diol (Compound A60)

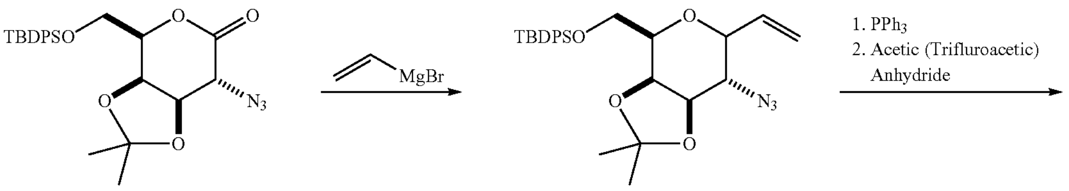

A60-1 A60-2

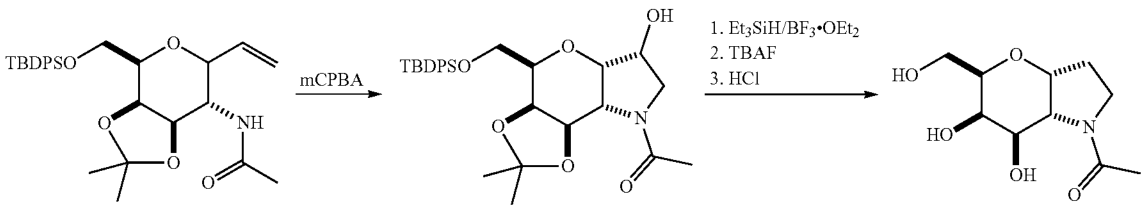

A60-3 A60-4 Compound A59

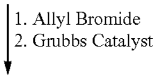

-continued
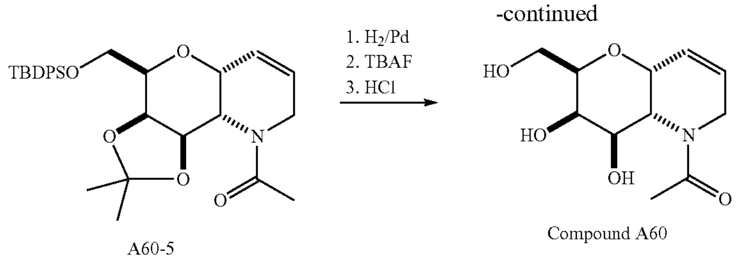
A60-5
Compound A60
Synthesis 2-43. Preparation of 1-((2R,3R,4R,4aR,9aR)-3,4-Dihydroxy-2-(hydroxymethyl)octahydropyrano[3,2-b]azepin-5(2H)-yl)ethan-1-one (Compound A61)
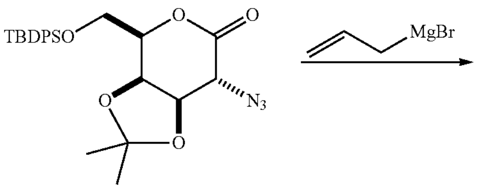
A61-1
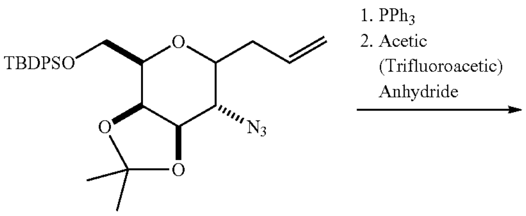
A61-2
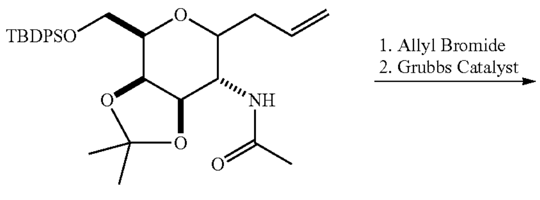
A61-3
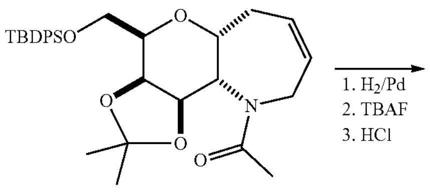
A61-4
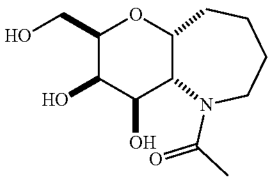
Compound A61
Synthesis 2-44. Preparation of ((3aR,4R,5aR,9aS,9bR)-2,2-Dimethyl-8-oxooctahydro-4H-[1,3]dioxolo[4',5':4,5]pyrano[3,2-b]pyridin-4-yl)methyl acetate (Compound A62)
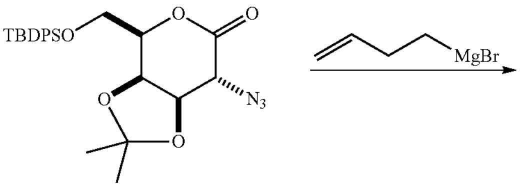
A62-1
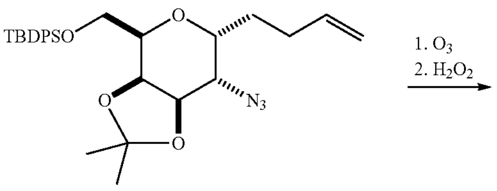
A62-2
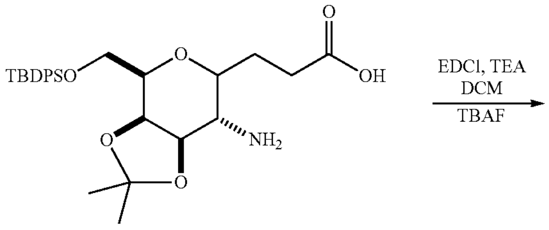
A62-3
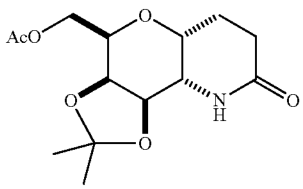
Compound A62

Synthesis 2-45. Preparation of (2R,3R,4R)-2-(Hydroxymethyl)-3,4-dihydro-2H-pyrano[3,2-b]pyridine-3,4-diol (Compound A63) and ((3aR,4R,9bR)-2,2-dimethyl-8-oxooctahydro-4H-[1,3]dioxolo[4',5':4,5]pyrano[3,2-b]pyridin-4-yl)methyl acetate (Compound A64)
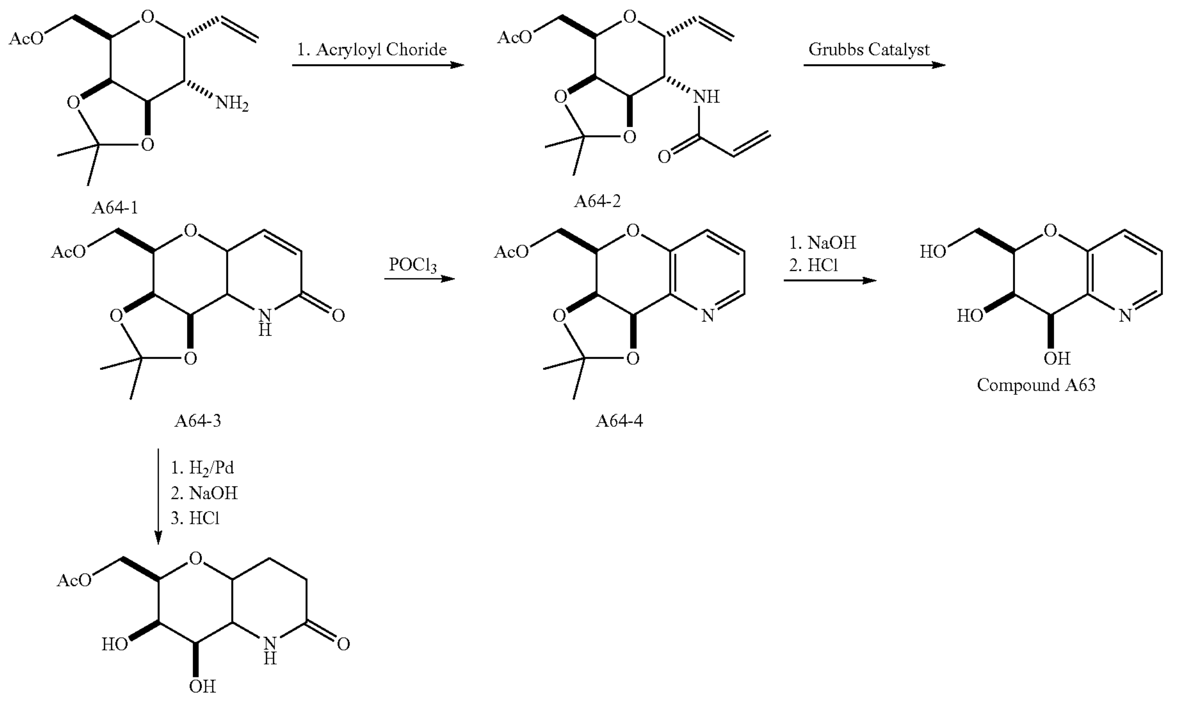
A64-1
A64-2
A64-3
A64-4
Compound A63
Compound A64
Synthesis 2-46. Preparation of N-((3aR,8R,8aR)-4-(Hydroxymethyl)-2,2-dimethylhexahydro-4H-4,7-epoxy[1,3]dioxolo[4,5-d]azepin-8-yl)acetamide (Compound A65)
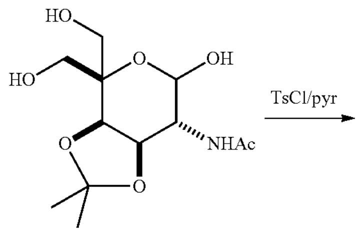
A65-1
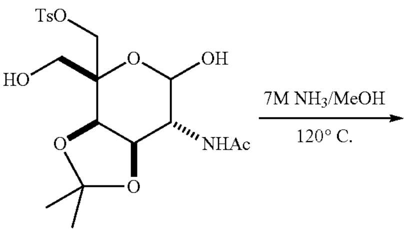
A65-2
-continued
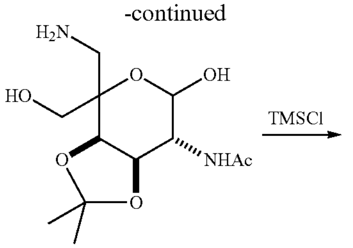
A65-3
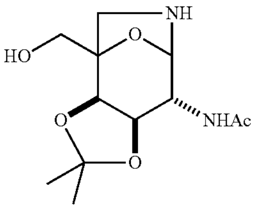
Compound A65

Synthesis 2-47. Preparation of N-((3aR,4R,9R,9aR)-9-(Hydroxymethyl)-2,2-dimethyloctahydro-5,9-epoxy[1,3]dioxolo[4,5-d]azocin-4-yl)acetamide (Compound A66)

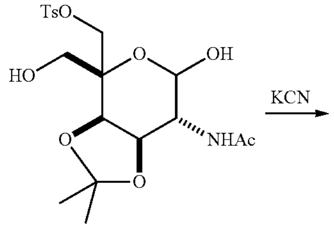

A65-2

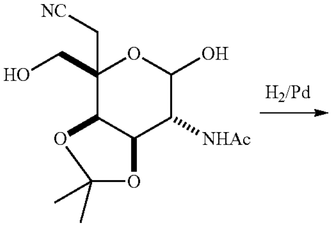

A66-1

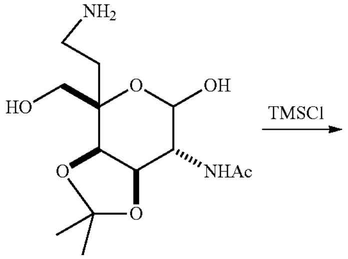

A66-2

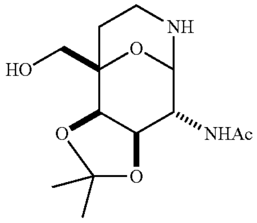

Compound A66

Synthesis 2-48. Preparation of N-((3aR,4R,9R,9aR)-9-(Hydroxymethyl)-2,2-dimethylhexahydro-5H-5,9-epoxy[1,3]dioxolo[4,5-d]oxocin-4-yl)acetamide (Compound A67)

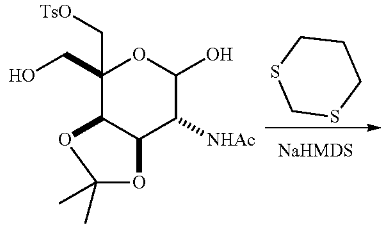

A65-2

-continued

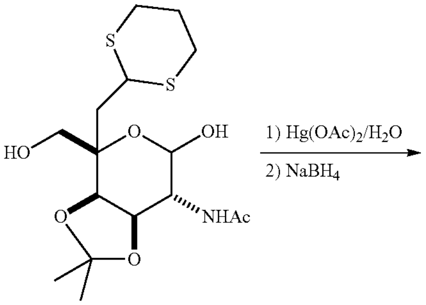

A67-1

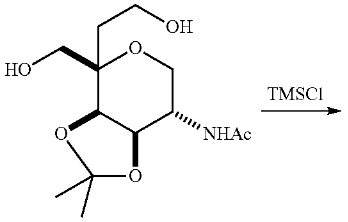

A67-2

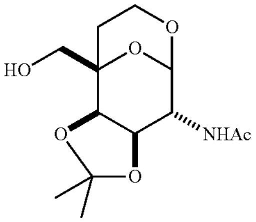

Compound A67

Compound A68, Compound A69, and Compound A70 can also be synthesized using Synthesis 2-46, 2-47, and 2-48.

Compound A68

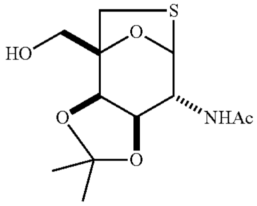

Compound A69

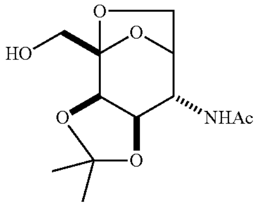

Compound A70

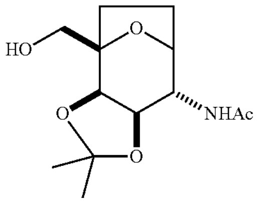

Synthesis 2-49. Preparation of (3R,4R,5R,6R)-6-(Aminomethyl)-3-(trifluoromethyl)tetrahydro-2H-pyran-2,4,5-triol (Compound A71)

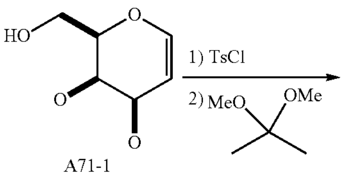

A71-1

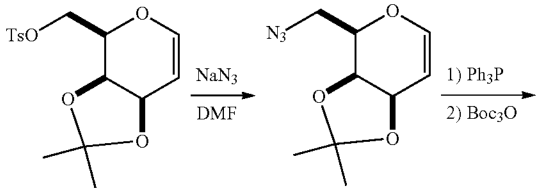

A71-2 A71-3

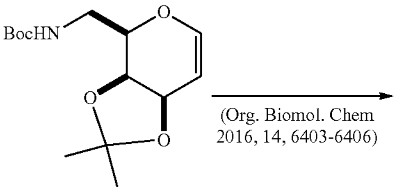

A71-4

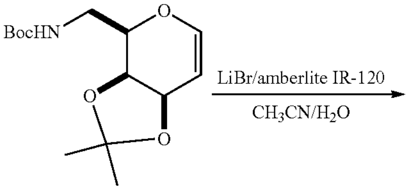

A71-5

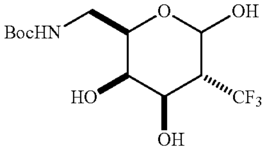

Compound A71

Synthesis 2-50. Preparation of General Synthesis to Install $R^2$

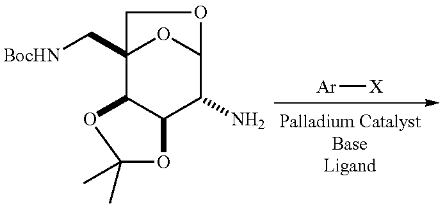

A72-1

-continued

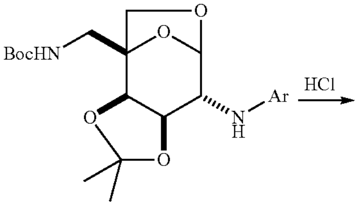

A72-2

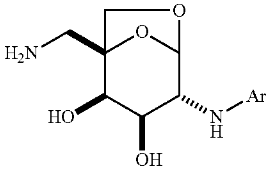

Compound A72

Synthesis 2-51. Alternative General Synthesis to Install $R^2$

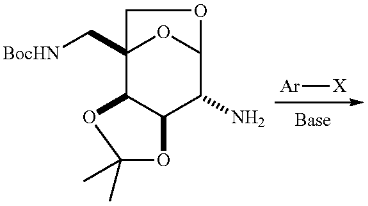

A72-1

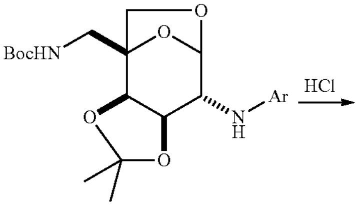

A72-2

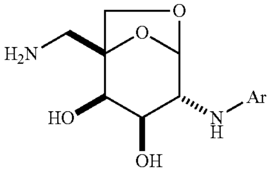

Compound A72

Synthesis 2-52. Preparation of (1S,2R,3R,4R)-1-(Aminomethyl)-4-(isoxazol-5-ylamino)-6,8-dioxabicyclo[3.2.1]octane-2,3-diol (Compound A73)

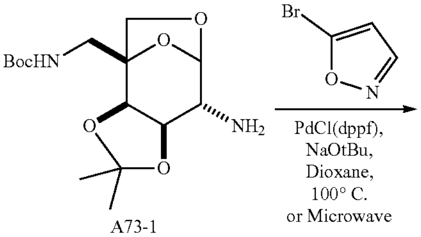

A73-1

-continued

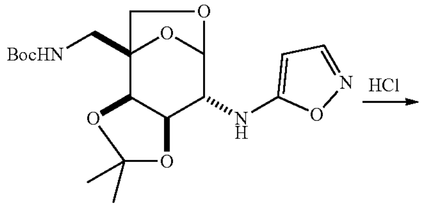

A73-2

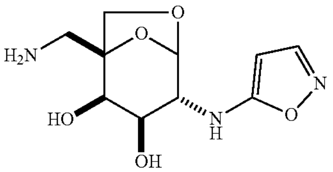

Compound A73

Synthesis 2-53. Preparation of (1S,2R,3R,4R)-1-(Aminomethyl)-4-((4,6-dichloro-1,3,5-triazin-2-yl)amino)-6,8-dioxabicyclo[3.2.1]octane-2,3-diol (Compound A74)

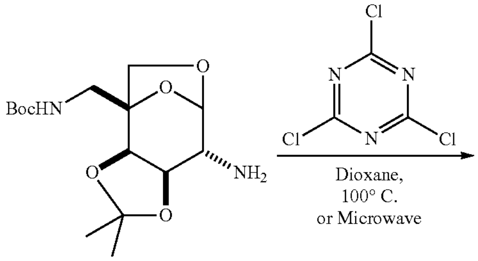

A74-1

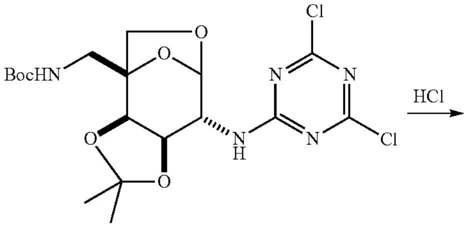

A74-2

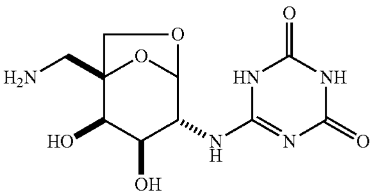

Compound A74

Synthesis 2-54. Preparation of (3R,4R,5R,6R)-6-(Aminomethyl)-3-(thiazol-2-ylamino)tetrahydro-2H-pyran-2,4,5-triol (Compound A75)

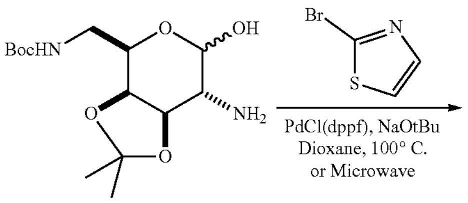

A75-1

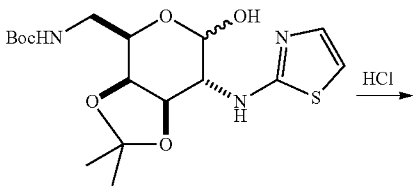

A75-2

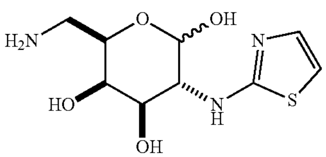

Compound A75

Synthesis 2-55. Preparation of (2R,3R,4R,5S)-2-(Hydroxymethyl)-5-((3-(trifluoromethyl)pyridin-2-yl)amino)tetrahydro-2H-pyran-3,4-diol (Compound A76)

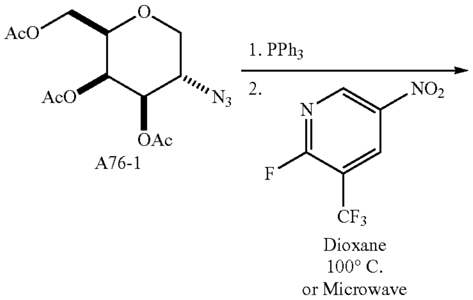

A76-1

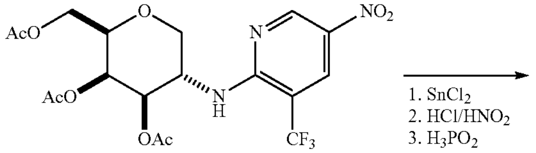

A76-2

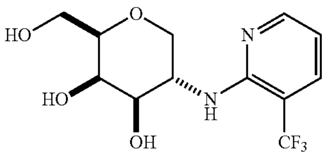

Compound A76

Synthesis 2-56. Preparation of (3aR,4R,8S,8aR)-8-Azido-4-(azidomethyl)-2,2-dimethylhexahydro-4H-4,7-epoxycyclohepta[d][1,3]dioxole (Compound A78)
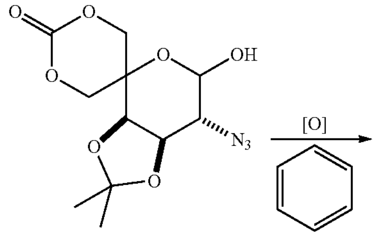
A78-1
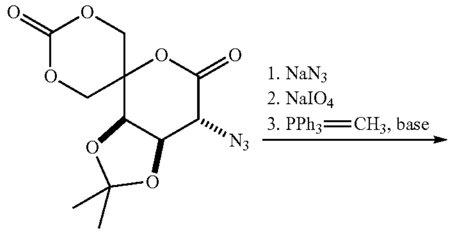
A78-2
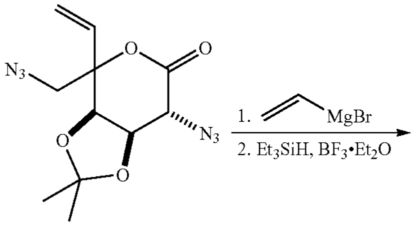
A78-3
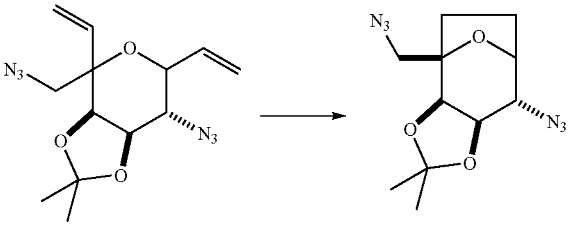
A78-4
Compound A78
Synthesis 2-57. Preparation of (3R,4S,5R,6R)-6-(aminomethyl)-3-(oxazol-2-yloxy)tetrahydro-2H-pyran-2,4,5-triol (Compound A79)
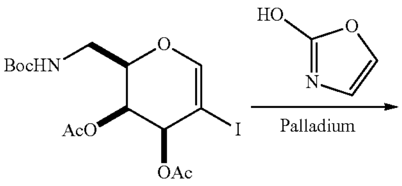
A79-1
-continued
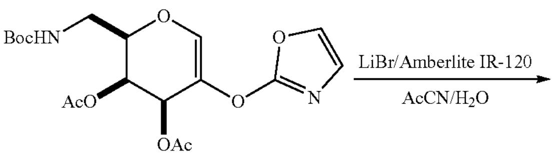
A79-2
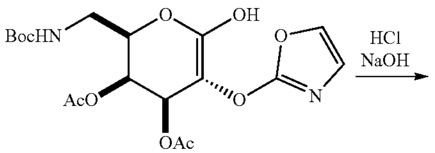
A79-3
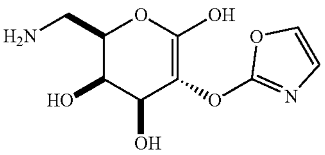
Compound A79
Synthesis 2-58. Preparation of (3R,4S,5R,6R)-6-(aminomethyl)-2,4,5-trihydroxytetrahydro-2H-pyran-3-yl acetate (Compound A80)
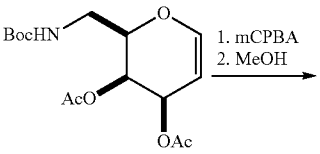
A80-1
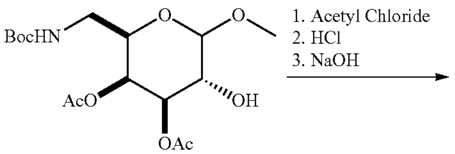
A80-2
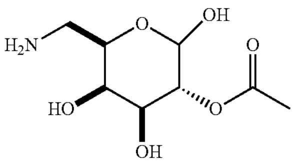
Compound A80

Synthesis 2-59. Preparation of 1-((3R,4R,5R,6R)-6-(aminomethyl)-2,4,5-trihydroxytetrahydro-2H-pyran-3-yl)guanidine (Compound A81) and (Compound A82)
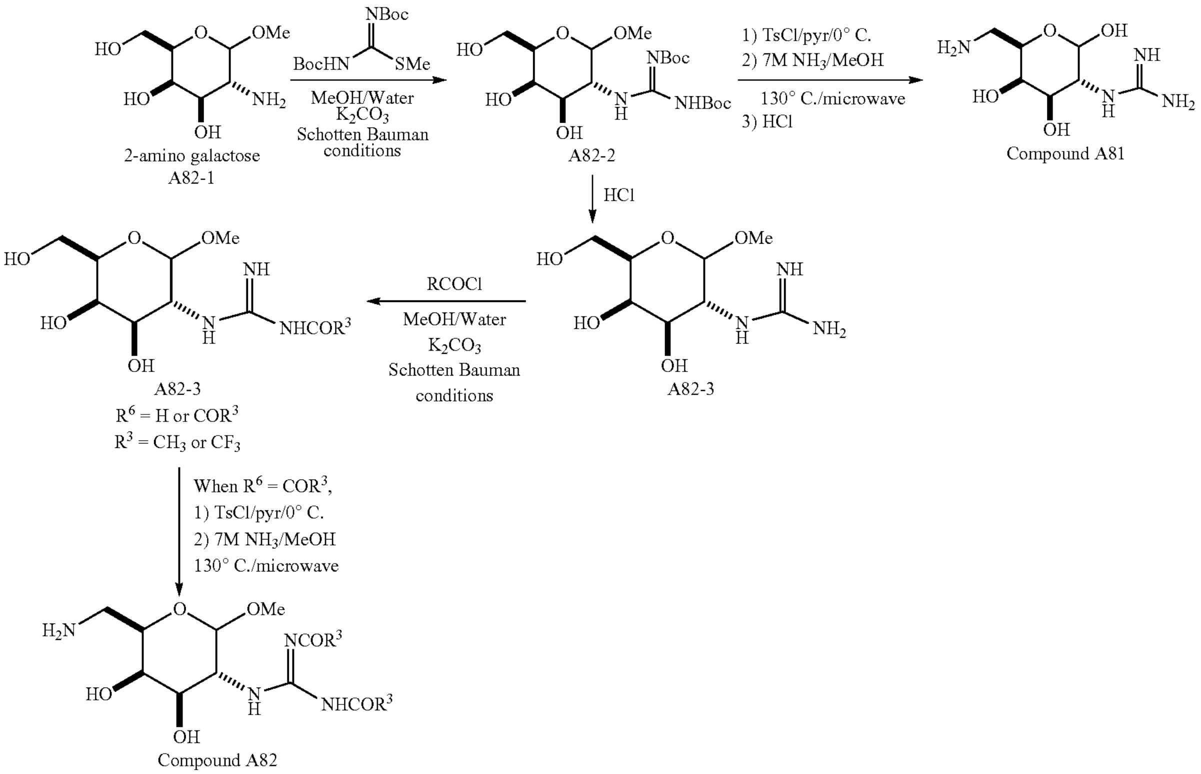
2-amino galactose A82-1
A82-2
Compound A81
A82-3
A82-3
$R^6$ = H or $COR^3$
$R^3$ = $CH_3$ or $CF_3$
Compound A82
Synthesis 2-60. Preparation of Compound A83 and Compound A84
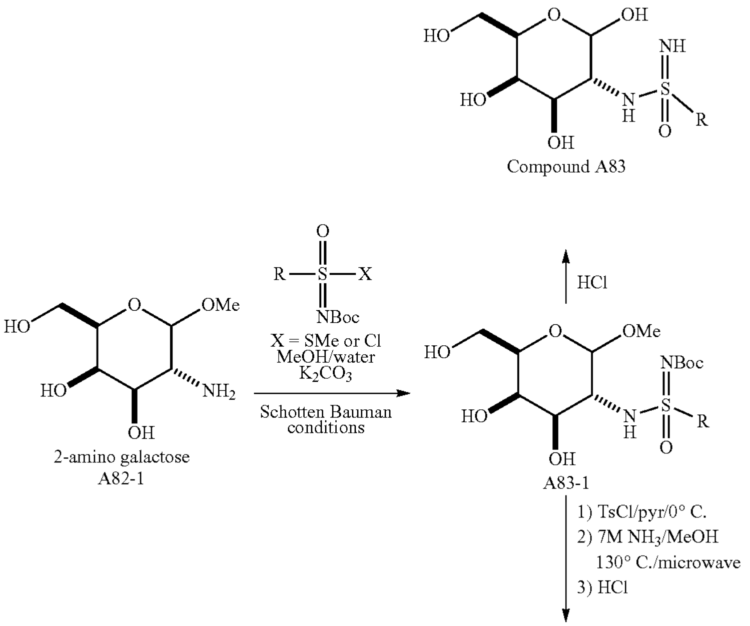
Compound A83
2-amino galactose A82-1
A83-1

-continued

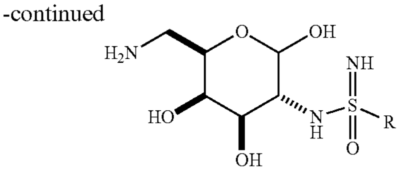

Compound A84

Alternatively, Compound A85 can be synthesized if

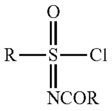

is used instead of

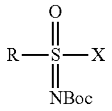

in the Schotten Bauman reaction step.

Compound A85

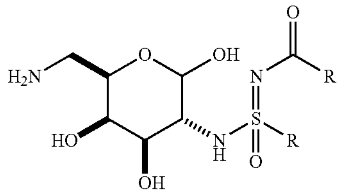

Synthesis 2-61. Preparation of Compound A88

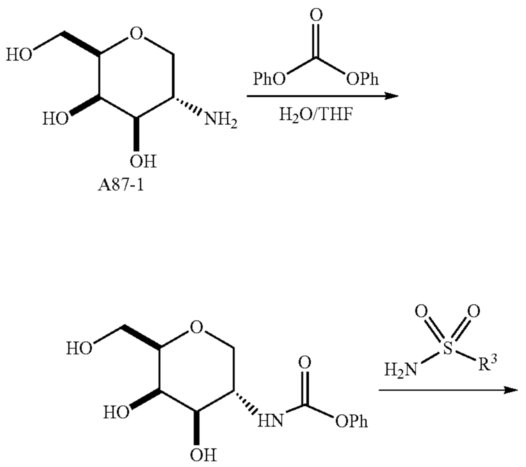

A87-1

A88-2

-continued

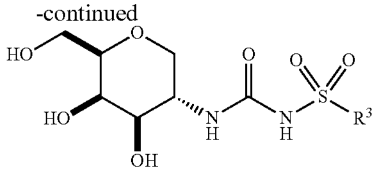

Compound A88

Org. Biomol. Chem., 2017, 15, 4992-4999

Synthesis 2-62: Preparation of (2R,3R,4R,5R,6R)-5-azido-2-(hydroxymethyl)-6-methoxytetrahydro-2H-pyran-3,4-diol (Compound A89) and (2R,3R,4R,5R,6R)-5-amino-2-(hydroxymethyl)-6-methoxytetrahydro-2H-pyran-3,4-diol (Compound A90)

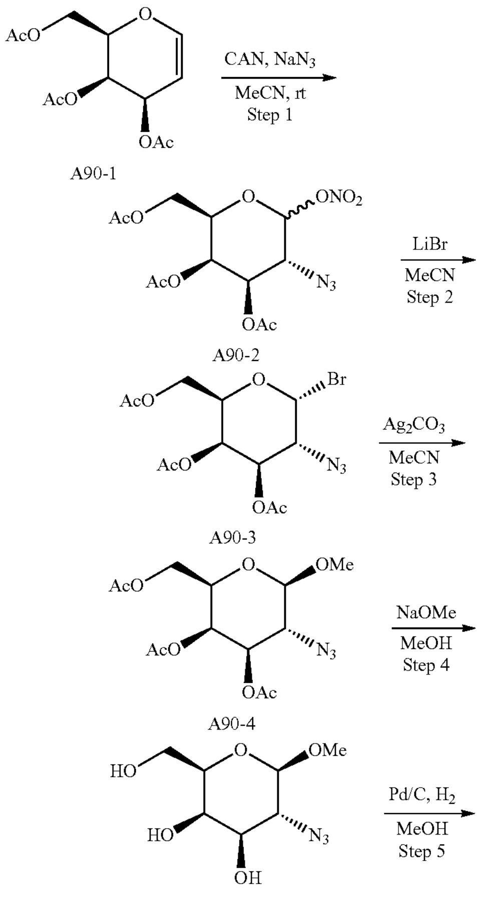

A90-1

A90-2

A90-3

A90-4

A89

-continued

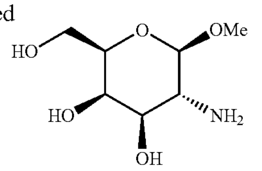

A90

Step 1: $NaN_3$ (4.3 g, 66 mmol) and CAN (87 g, 158 mmol) were added to a nitrogen-flushed flask, and the mixture were stirred vigorously at −10° C. Then a solution of (2R,3R,4R)-2-(acetoxymethyl)-3,4-dihydro-2H-pyran-3,4-diyl diacetate (A90-1, 12 g, 44 mmol) in MeCN (250 mL) were added dropwise to the above mixture. The mixture was stirred at rt for 12 h. Then the reaction mixture was diluted with 500 mL EA. The organic phase was washed with $H_2O$ (400 mL×3) and brine, filtered and concentrated to give a yellow oil, which was purified by column chromatography to give (2R,3R,4R,5R)-2-(acetoxymethyl)-5-azido-6-(nitrooxy)tetrahydro-2H-pyran-3,4-diyl diacetate (A90-2, 7.5 g, 45% yield) as white solid. LC-MS (ESI) found: 377 $[M+H]^+$.

Step 2: To a solution of (2R,3R,4R,5R)-2-(acetoxymethyl)-5-azido-6-(nitrooxy)tetrahydro-2H-pyran-3,4-diyl diacetate (A90-2, 15.0 g, 40.0 mmol) in anhydrous MeCN (120 mL) was added LiBr (34.6 g, 400 mmol) at room temperature under an argon atmosphere. The reaction was stirred at room temperature for 3 h. TLC indicated the starting material was consumed. EA (350 mL) was added to the reaction mixture. The organic phase was washed with water (50 mL×2), saturated $NaHCO_3$ (60 mL×2), water (50 mL×2), brine (50 mL), dried ($Na_2SO_4$), filtered. The filtrate was concentrated to give a crude (2R,3R,4R,5R,6R)-2-(acetoxymethyl)-5-azido-6-bromotetrahydro-2H-pyran-3,4-diyl diacetate (A90-3, 15.0 g, 96%) as white foam. LC-MS (ESI) found: 394 $[M+H]^+$.

Step 3: To a solution of (2R,3R,4R,5R,6R)-2-(acetoxymethyl)-5-azido-6-bromotetrahydro-2H-pyran-3,4-diyl diacetate (A90-3, 15.0 g, 38.1 mmol) in MeOH (100 mL) was added $Ag_2CO_3$ (15.7 g, 57.1 mmol) in portions at rt. The mixture was stirred at 60° C. under $N_2$ in the dark for 12 h. EA (350 mL) was added to the reaction mixture. The organic phase was washed with water (50 mL×2), saturated $NaHCO_3$ (60 mL×2), water (50 mL×2), brine (50 mL), dried ($Na_2SO_4$), filtered. The filtrate was concentrated to give a crude product, which was purified by column chromatography to give (2R,3R,4R,5R,6R)-2-(acetoxymethyl)-5-azido-6-methoxytetrahydro-2H-pyran-3,4-diyl diacetate (A90-4, 10.0 g, 76%) as colorless oil. LC-MS (ESI) found: 346 $[M+H]^+$. $^1H$ NMR (400 MHz, $CD_3OD$): δ 5.33-5.29 (m, 1H), 4.91-4.86 (m, 1H), 4.43 (d, J=8.0 Hz, 1H), 4.16-4.10 (m, 2H), 4.07-4.00 (m, 1H), 3.63-3.59 (m, 1H), 3.57 (d, J=3.7 Hz, 3H), 2.15-2.13 (m, 3H), 2.03-1.97 (m, 6H).

Step 4: To a solution of (2R,3R,4R,5R,6R)-2-(acetoxymethyl)-5-azido-6-methoxytetrahydro-2H-pyran-3,4-diyl diacetate (A90-4, 10.0 g, 29.0 mmol) in MeOH (150 mL) was added NaOMe (23.2 mL, 5 M in MeOH) in portions at rt. The mixture was stirred at rt for 2 h. The reaction was neutralized by the addition of acidic Amberlite IR 120 ($H^+$) ion exchange resin. The solution was filtered through a glass fritted vacuum filter funnel equipped with a pad of Celite to remove the acidic resin. The filtrate was concentrated and purified by column to give (2R,3R,4R,5R,6R)-5-azido-2-(hydroxymethyl)-6-methoxytetrahydro-2H-pyran-3,4-diol (A89, 5.5 g, 78%) as white solid. LC-MS (ESI) found: 220 $[M+H]^+$. $^1H$ NMR (400 MHz, CD3OD): δ 4.21-4.15 (m, 1H), 3.79 (t, J=3.5 Hz, 1H), 3.76-3.70 (m, 2H), 3.54 (s, 3H), 3.49-3.42 (m, 1H), 3.41 (dd, J=4.0, 2.6 Hz, 2H).

Step 5: To a solution of (2R,3R,4R,5R,6R)-5-azido-2-(hydroxymethyl)-6-methoxytetrahydro-2H-pyran-3,4-diol (A-89, 1.0 g, 4.57 mmol) in MeOH (20 mL) was added Pd/C (100 mg, 10% wt, 60% wet) under $H_2$ atmosphere. The mixture was stirred at rt for 12 h under a $H_2$ balloon. The mixture was filtered and concentrated to give (2R,3R,4R,5R,6R)-5-amino-2-(hydroxymethyl)-6-methoxytetrahydro-2H-pyran-3,4-diol (A90, 749 mg, 85% yield) as white solid. LC-MS (ESI) found: 194 $[M+H]^+$.

Synthesis 2-63: Preparation of (2R,3R,4R,5R,6S)-5-amino-2-(hydroxymethyl)-6-methoxytetrahydro-2H-pyran-3,4-diol (Compound A91)

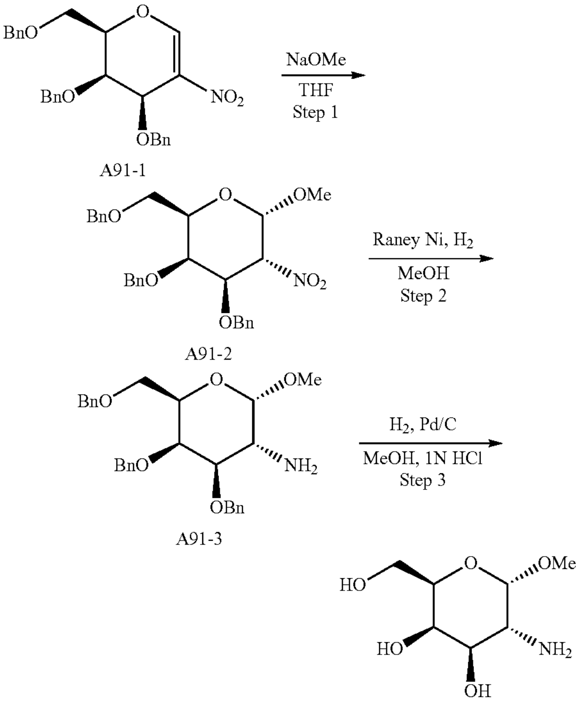

A91-1, A91-2, A91-3, A91

Step 1: To a stirred solution of (2R,3R,4R)-3,4-bis(benzyloxy)-2-((benzyloxy)methyl)-5-nitro-3,4-dihydro-2H-pyran (A91-1, 1.0 g, 2.17 mmol) in dry THF (10 ml) was added NaOMe (0.65 mL, 5 M in MeOH). After stirring at rt for 1 h, the reaction mixture was neutralized with Amberlite IR-120 resin ($H^+$). The reaction mixture was filtered, the filtrate was concentrated to give a crude product, which was purified by column to get ((2R,3R,4R,5R,6S)-3,4-bis(benzyloxy)-2-((benzyloxy)methyl)-6-methoxy-5-nitrotetrahydro-2H-pyran (A91-2, 425 mg, 39% yield) and (2R,3R,4R,5R,6R)-3,4-bis(benzyloxy)-2-((benzyloxy)methyl)-6-methoxy-5-nitrotetrahydro-2H-pyran (52 mg, 5%). LC-MS (ESI) of both found: 494 $[M+H]^+$.

Step 2: To a solution of (2R,3R,4R,5R,6S)-3,4-bis(benzyloxy)-2-((benzyloxy)methyl)-6-methoxy-5-nitrotetrahydro-2H-pyran (A91-2, 425 mg, 0.86 mmol) in MeOH (10 mL) was added Raney Ni (50 mg). The mixture was stirred at rt for 12 h under a $H_2$ balloon. The mixture was filtered and concentrated to give (2S,3R,4R,5R,6R)-4,5-bis(benzyloxy)-6-((benzyloxy)methyl)-2-methoxytetrahydro-2H-pyran-3-amine (A91-3, 473 mg, 72% yield). LC-MS (ESI) found: 464 $[M+H]^+$.

Step 3: To a solution of (2S,3R,4R,5R,6R)-4,5-bis(benzyloxy)-6-((benzyloxy)methyl)-2-methoxytetrahydro-2H-pyran-3-amine (A91-3, 200 mg, 0.431 mmol) in MeOH (10 mL) was added Pd/C (20 mg, 10% wt, 60% wet) and several drops of 1N HCl. The mixture was stirred at rt for 12 h under a $H_2$ balloon. The mixture was filtered and concentrated to give (2R,3R,4R,5R,6S)-5-amino-2-(hydroxymethyl)-6-methoxytetrahydro-2H-pyran-3,4-diol (A91, 452 mg, 62% yield) as colorless oil. LC-MS (ESI) found: 194 $[M+H]^+$.

Alternatively, (2R,3R,4R,5R,6S)-5-amino-2-(hydroxymethyl)-6-methoxytetrahydro-2H-pyran-3,4-diol (Compound A91) can be Synthesized in the Following Manner

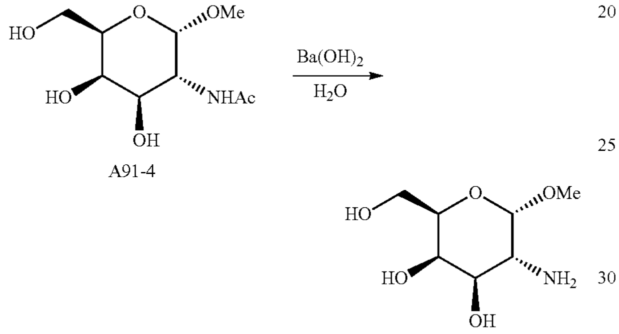

A91-4

A91

To a solution of N-[(2S,3R,5R,6R)-4,5-dihydroxy-6-(hydroxymethyl)-2-methoxyoxan-3-yl]acetamide (A91-4, 2 g, 8.5 mmol) in $H_2O$ (11 mL) was added $Ba(OH)_2$ (9.5 g, 55.3 mmol). The mixture was heated for reflux at 120° C. overnight. Later the solution of $(NH_4)_2SO_4$ (7.0 g, 55.3 mmol) in $H_2O$ (55 mL) was slowly added into the mixture. The mixture was heated to reflux at 120° C. for fully reaction. After cooling down to room temperature, the mixture was filtered and the filtrate was concentrated. The residual was then adjusted to pH=7 by adding MeONa through the environment of MeOH. The solution was concentrated and recrystallized in i-PrOH to give (2R,3R,4R,5R,6S)-5-amino-2-(hydroxymethyl)-6-methoxytetrahydro-2H-pyran-3,4-diol (A91, 1.6 g, 97% yield) as a white solid. LC-MS (ESI) found: 194 $[M+H]^+$. $^1H$ NMR (400 MHz, $CD_3OD$): δ 4.71 (d, J=3.7 Hz, 1H), 3.83 (d, J=3.2 Hz, 1H), 3.78-3.66 (m, 3H), 3.54 (dd, J=10.4, 3.2 Hz, 1H), 3.40 (s, 3H), 2.96 (dd, J=10.4, 3.7 Hz, 1H).

Synthesis 2-64: Preparation of (2R,3R,4R,5S)-5-amino-2-(hydroxymethyl)tetrahydro-2H-pyran-3,4-diol (Compound A92)

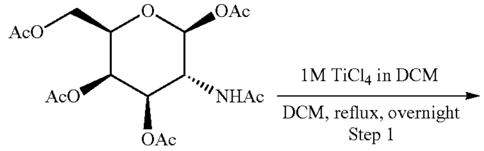

A92-1

-continued

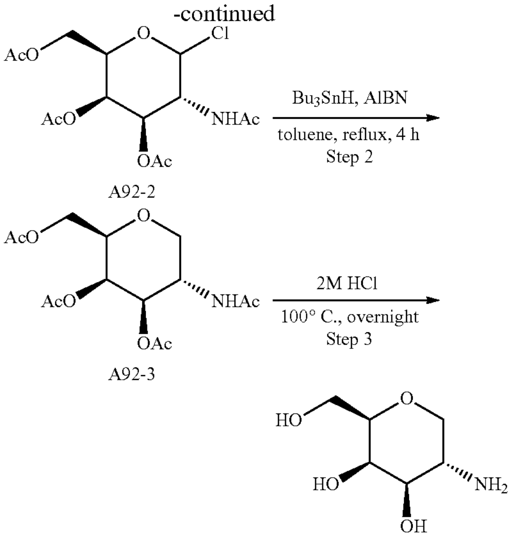

A92-2

A92-3

A92

Step 1: To a mixture of (2S,3R,4R,5R,6R)-3-acetamido-6-(acetoxymethyl)tetrahydro-2H-pyran-2,4,5-triyl triacetate (A92-1, 20.0 g, 51.4 mmol) in DCM (200 mL) was added $TiCl_4$ (61.6 mL, 1 M in DCM) at 0° C. under $N_2$. After refluxing at 50° C. overnight, the mixture was concentrated and purified by chromatography (0-80% ethyl acetate in petroleum) to give (2R,3R,4R,5R)-5-acetamido-2-(acetoxymethyl)-6-chlorotetrahydro-2H-pyran-3,4-diyl diacetate (A92-2, 8.5 g, 45% yield) as white solid. LC-MS (ESI) found: 366 $[M+1]^+$.

Step 2: To a mixture of (2R,3R,4R,5R)-5-acetamido-2-(acetoxymethyl)-6-chlorotetrahydro-2H-pyran-3,4-diyl diacetate (A92-2, 8.5 g, 23.2 mmol) in toluene (85 mL) was added $Bu_3SnH$ (8.1 g, 27.9 mmol) and AIBN (0.08 g, 0.46 mmol) at rt under $N_2$. After refluxing at 110° C. for 1.5 h, the mixture was concentrated and purified by chromatography on silica gel (70-100% ethyl acetate in petroleum) to give (2R,3R,4R,5S)-5-acetamido-2-(acetoxymethyl)tetrahydro-2H-pyran-3,4-diyl diacetate (A92-3, 6.6 g, 86%) as white solid. LC-MS (ESI) found: 332 $[M+1]^+$.

Step 3: To a mixture of (2R,3R,4R,5S)-5-acetamido-2-(acetoxymethyl)tetrahydro-2H-pyran-3,4-diyl diacetate (A92-3, 6.6 g, 19.9 mmol) in $H_2O$ (48 mL) was added HCl (12 mL, 2.5 M in $H_2O$) at rt under $N_2$. After refluxing at 100° C. for 2 h, the mixture was concentrated. EtOH (10 mL) and $Et_2O$ (10 mL) were added. The solid formed was filtered to give (2R,3R,4R,5S)-5-amino-2-(hydroxymethyl)tetrahydro-2H-pyran-3,4-diol hydrochloride (A-92, 2.7 g, 68%) as white solid. LC-MS (ESI) found: 164 $[M+H]^+$.

Synthesis 2-65: Preparation of (3S,4R,5R,6R)-4,5-bis(benzyloxy)-6-((benzyloxy)methyl)tetrahydro-2H-pyran-3-amine (Compound A9)

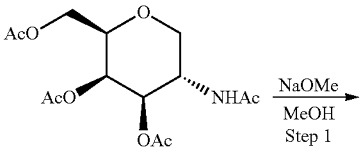

A92-3

-continued

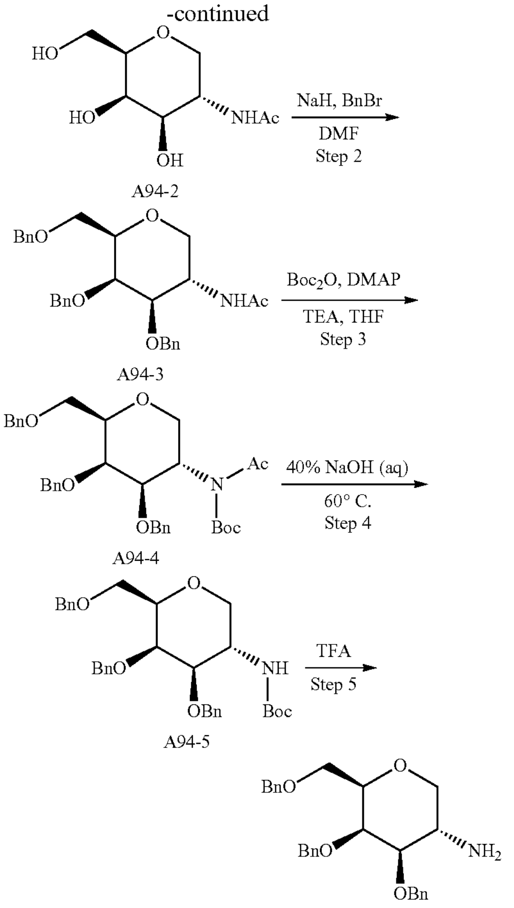

A94-2

A94-3

A94-4

A94-5

A-94

Step 1: To a mixture of (2R,3R,4R,5S)-5-acetamido-2-(acetoxymethyl)tetrahydro-2H-pyran-3,4-diyl diacetate (A94-1, 1.5 g, 4.5 mmol) in MeOH (20 mL) was added NaOMe (2.7 mL, 5 M in MeOH) at 0° C. under $N_2$. After stirring at rt for 2 h, the mixture was neutralized with HCl (2 M) and concentrated. Then the mixture was purified by chromatography on silica gel (0-20% methanol in DCM) to give N-((3S,4R,5R,6R)-4,5-dihydroxy-6-(hydroxymethyl) tetrahydro-2H-pyran-3-yl)acetamide (A94-2, 560 mg, 60%) as white solid. LC-MS (ESI) found: 206 $[M+H]^+$.

Step 2: To a mixture of N-((3S,4R,5R,6R)-4,5-dihydroxy-6-(hydroxymethyl)tetrahydro-2H-pyran-3-yl)acetamide (A-94-2, 130 mg, 0.63 mmol) in DMF (5.0 mL) was added NaH (101 mg, 4.2 mmol) at 0° C. under $N_2$. After stirring at 0° C. for 30 min, BnBr (0.07 mL, 0.63 mmol) was added slowly and the reaction was stirred for another 1 hour. The mixture was quenched with $H_2O$ and extracted with EA. The combined organic layers were washed with brine, dried over anhydrous $Na_2SO_4$. The residue was concentrated and purified by chromatography on silica gel (0-20% methanol in DCM) to give N-((3S,4R,5R,6R)-4,5-bis(benzyloxy)-6-((benzyloxy)methyl)tetrahydro-2H-pyran-3-yl)acetamide (A94-3, 130 mg, 43%) as white solid. LC-MS (ESI) found: 476 $[M+H]^+$.

Step 3: To a mixture of N-((3S,4R,5R,6R)-4,5-bis(benzyloxy)-6-((benzyloxy)methyl)tetrahydro-2H-pyran-3-yl)acetamide (A94-3, 1.2 g, 2.5 mmol) in THF (15 mL) was added $Et_3N$ (1.1 mL, 7.6 mmol), DMAP (30 mg, 0.25 mmol) and $Boc_2O$ (7.0 mL, 30.2 mmol) at 0° C. under $N_2$. After stirring at rt overnight, the mixture was concentrated and purified by chromatography on silica gel (0-10% methanol in DCM) to give tert-butyl acetyl((3S,4R,5R,6R)-4,5-bis(benzyloxy)-6-((benzyloxy)methyl)tetrahydro-2H-pyran-3-yl)carbamate (A94-4, 860 mg, 60%) as colorless oil. LC-MS (ESI) found: 576 $[M+1]^+$.

Step 4: To a mixture of tert-butyl acetyl((3S,4R,5R,6R)-4,5-bis(benzyloxy)-6-((benzyloxy)methyl)tetrahydro-2H-pyran-3-yl)carbamate (A94-4, 860 mg, 1.5 mmol) in THF (10 mL) was added 2 mL NaOH (40% aq) under $N_2$. After refluxing at 60° C. overnight, the mixture was diluted with $H_2O$ and extracted with EA. The combined organic layer was washed with brine, dried over $Na_2SO_4$, filtered. The filtrate was concentrated and purified by chromatography on silica gel (0-70% ethyl acetate in petroleum) to give tert-butyl ((3S,4R,5R,6R)-4,5-bis(benzyloxy)-6-((benzyloxy)methyl)tetrahydro-2H-pyran-3-yl)carbamate (A94-5, 450 mg, 56%) as a white solid. LC-MS (ESI) found: 534 $[M+1]^+$.

Step 5: To a solution of tert-butyl ((3S,4R,5R,6R)-4,5-bis(benzyloxy)-6-((benzyloxy)methyl)tetrahydro-2H-pyran-3-yl)carbamate (A94-5, 450 mg, 0.84 mmol) in DCM (9.0 mL) was added TFA (3.0 mL) at rt under $N_2$. After stirring for 2 h, the mixture was quenched with $NaHCO_3$(aq) and extracted with EA. The combined organic layer was washed with brine, dried over anhydrous $Na_2SO_4$. The residue was concentrated and purified by chromatography on silica gel (0-50% ethyl acetate in petroleum) to give (3S,4R,5R,6R)-4,5-bis(benzyloxy)-6-((benzyloxy)methyl)tetrahydro-2H-pyran-3-amine (A94, 280 mg, 77%) as colorless oil. LC-MS (ESI) found: 434 $[M+1]^+$.

Synthesis 2-66: Preparation of 4-chloro-2-(((3S,4R,5R,6R)-4,5-dihydroxy-6-(hydroxymethyl)tetrahydro-2H-pyran-3-yl)amino)thiazole-5-carbonitrile (Compound A95)

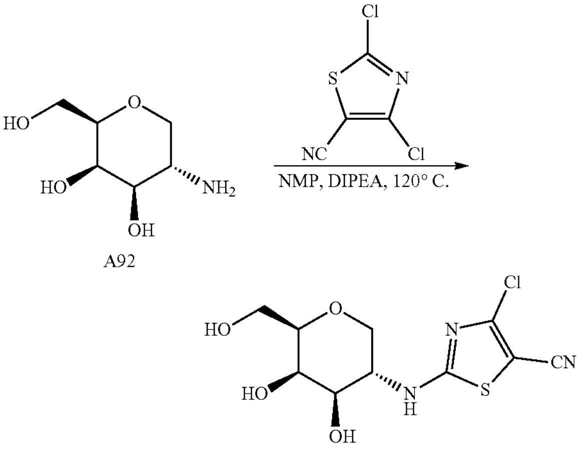

A92

A95

To a mixture of (2R,3R,4R,5S)-5-amino-2-(hydroxymethyl)tetrahydro-2H-pyran-3,4-diol hydrochloride (A92, 50 mg, 0.25 mmol) in NMP (2.0 mL) was added 2,4-dichlorothiazole-5-carbonitrile (135 mg, 0.75 mmol) and DIPEA (0.17 mL, 1.0 mmol) at rt under $N_2$. After stirring at 120° C. overnight, the mixture was concentrated and purified by prep-TLC to give 4-chloro-2-(((3S,4R,5R,6R)-4,5-dihydroxy-6-(hydroxymethyl)tetrahydro-2H-pyran-3-yl)amino) thiazole-5-carbonitrile (A95, 6.3 mg, 8% yield) as brown solid. LC-MS (ESI) found: 306 $[M+H]^+$. $^1H$ NMR (400

MHz, $CD_3OD$): δ 4.12-4.00 (m, 2H), 3.90 (d, J=2.5 Hz, 1H), 3.77-3.65 (m, 2H), 3.58 (dd, J=10.1, 3.2 Hz, 1H), 3.46-3.41 (m, 1H), 3.16 (t, J=10.5 Hz, 1H).

Synthesis 2-67: Preparation of (2R,3R,4R,5S)-2-(hydroxymethyl)-5-(pyridin-2-ylamino)tetrahydro-2H-pyran-3,4-diol (Compound A96)

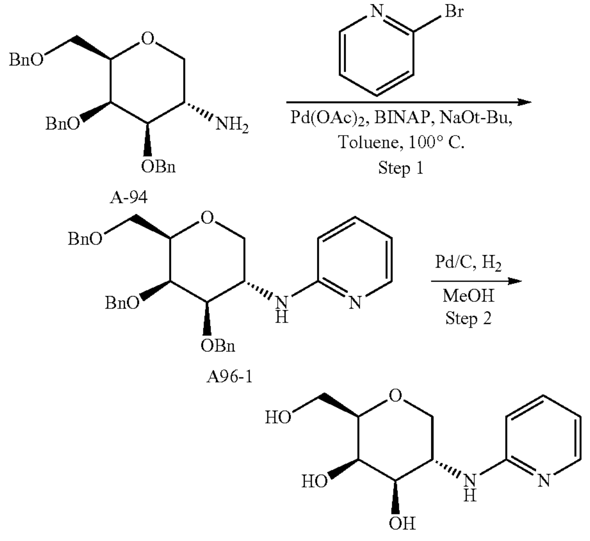

A-94

A96-1

A-96

Step 1: To a solution of (3S,4R,5R,6R)-4,5-bis(benzyloxy)-6-((benzyloxy)methyl)tetrahydro-2H-pyran-3-amine (A-94, 40.0 mg, 0.092 mmol) in toluene (4 mL) was added 2-bromopyridine (21.9 mg, 0.139 mmol), $Pd(OAc)_2$ (2.07 mg, 0.009 mmol), BINAP (5.75 mg, 0.009 mmol), and NaOt-Bu (26.6 mg, 0.277 mmol). The mixture was stirred under $N_2$ at 100° C. for 24 h. The reaction mixture was concentrated and purified by prep-HPLC (Method A) to give N-((3S,4R,5R,6R)-4,5-bis(benzyloxy)-6-((benzyloxy)methyl)tetrahydro-2H-pyran-3-yl)pyridin-2-amine (A96-1, 15 mg, 32%) as white solid. LC-MS (ESI) found: 511 $[M+H]^+$.

Step 2: To a solution of N-((3S,4R,5R,6R)-4,5-bis(benzyloxy)-6-((benzyloxy)methyl)tetrahydro-2H-pyran-3-yl)pyridin-2-amine (A96-1, 15 mg, 0.03 mmol) in MeOH (5 mL) was added Pd/C (2 mg, 10% wt, 60% wet). The mixture was stirred at rt for 12 h under a $H_2$ balloon. The mixture was filtered and the filtrate was concentrated to give (2R,3R,4R,5S)-2-(hydroxymethyl)-5-(pyridin-2-ylamino)tetrahydro-2H-pyran-3,4-diol (A96, 0.6 mg, 9% yield) as white solid. LC-MS (ESI) found: 241 $[M+H]^+$. $^1H$ NMR (400 MHz, Methanol-$d_4$): δ 8.03-7.81 (m, 1H), 7.42 (ddd, J=8.8, 7.0, 2.0 Hz, 1H), 6.67-6.38 (m, 2H), 4.67-4.37 (m, 1H), 4.16-3.96 (m, 1H), 3.89 (d, J=3.1 Hz, 1H), 3.79-3.58 (m, 2H), 3.54 (dd, J=9.9, 3.0 Hz, 1H), 3.44 (t, J=6.0 Hz, 1H), 3.21-2.99 (m, 1H).

The following compounds below were made using the method described in Synthesis 2-66 or Synthesis 2-67:

| | |
|---|---|
| 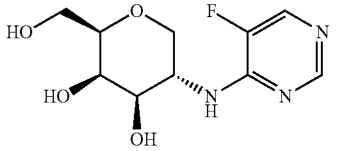 [SMILES: OC[C@H]1OC[C@H](Nc2ncncc2F)[C@@H](O)[C@H]1O] | A97 |
| 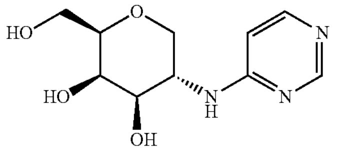 [SMILES: OC[C@H]1OC[C@H](Nc2ccncn2)[C@@H](O)[C@H]1O] | A98 |
| 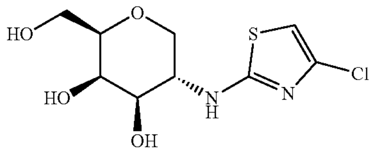 [SMILES: OC[C@H]1OC[C@H](Nc2nc(Cl)cs2)[C@@H](O)[C@H]1O] | A99 |
| 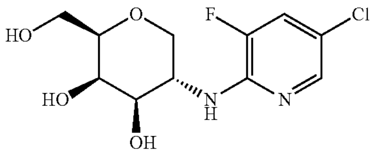 [SMILES: OC[C@H]1OC[C@H](Nc2ncc(Cl)cc2F)[C@@H](O)[C@H]1O] | A100 |
| 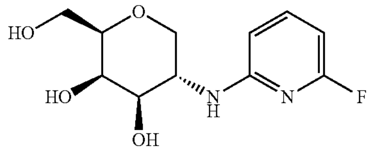 [SMILES: OC[C@H]1OC[C@H](Nc2cccc(F)n2)[C@@H](O)[C@H]1O] | A101 |

-continued

| | |
|---|---|
| 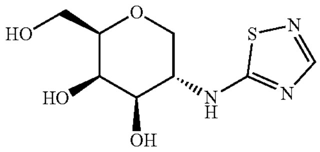 [SMILES: OC[C@H]1OC[C@H](Nc2ncns2)[C@@H](O)[C@H]1O] | A102 |
| 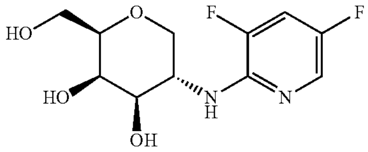 [SMILES: OC[C@H]1OC[C@H](Nc2ncc(F)cc2F)[C@@H](O)[C@H]1O] | A103 |
| 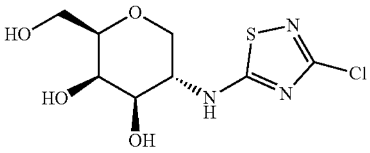 [SMILES: OC[C@H]1OC[C@H](Nc2nc(Cl)ns2)[C@@H](O)[C@H]1O] | A104 |

| ID | Characterization data |
|---|---|
| A97 | LC-MS (ESI) found: 260 $[M + H]^+$ . $^1H$ NMR (400 MHz, Methanol-$d_4$): δ 8.25 (d, J = 2.2 Hz, 1H), 8.10-7.91 (m, 1H), 4.59 (td, J = 10.7, 5.3 Hz, 1H), 4.05 (dd, J = 11.0, 5.3 Hz, 1H), 3.92 (dd, J = 3.3, 1.0 Hz, 1H), 3.81-3.65 (m, 3H), 3.46 (ddd, J = 6.6, 5.0, 1.1 Hz, 1H), 3.21 (t, J = 10.9 Hz, 1H). |
| A98 | Yield: 3.0 mg, 12%, white solid. LC-MS (ESI) found: 242 $[M + H]^+$ . $^1H$ NMR (400 MHz, Methanol-$d_4$): δ 8.37 (s, 1H), 7.99 (d, J = 5.9 Hz, 1H), 6.54 (d, J = 5.4 Hz, 1H), 4.66-4.49 (m, 1H), 4.07 (dd, J = 9.8, 5.0 Hz, 1H), 3.90 (d, J = 1.8 Hz, 1H), 3.80-3.73 (m, 1H), 3.68 (dd, J = 11.4, 5.0 Hz, 1H), 3.59 (dd, J = 10.4, 3.1 Hz, 1H), 3.44 (ddd, J = 6.9, 5.1, 1.2 Hz, 1H), 3.12 (t, J = 10.9 Hz, 1H). |
| A99 | Yield: 2.2 mg, 3.1%, yellow solid. LC-MS (ESI) found: 281 $[M + H]^+$ . $^1H$ NMR (400 MHz, $CD_3OD$): δ 6.33 (s, 1H), 4.11 (dd, J = 11.1, 5.2 Hz, 1H), 3.93 (dt, J = 10.5, 5.2 Hz, 1H), 3.88 (d, J = 3.0 Hz, 1H), 3.77-3.65 (m, 2H), 3.54 (dd, J = 10.3, 3.2 Hz, 1H), 3.44-3.41 (m, 1H), 3.13 (t, J = 10.9 Hz, 1H). |
| A100 | Yield: 32 mg, 20%, white solid. LC-MS (ESI) found: 293 $[M + H]^+$ . $^1H$ NMR (400 MHz, $CD_3OD$): δ 7.79 (d, J = 2.1 Hz, 1H), 7.34 (dd, J = 10.7, 2.1 Hz, 1H), 4.41 (td, J = 10.6, 5.2 Hz, 1H), 4.10 (dd, J = 11.0, 5.2 Hz, 1H), 3.90 (d, J = 2.8 Hz, 1H), 3.76 (dd, J = 11.3, 7.0 Hz, 1H), 3.71-3.65 (m, 2H), 3.47-3.43 (m, 1H), 3.15 (t, J = 10.8 Hz, 1H). |
| A101 | Yield: 2.8 mg, 9%, white solid. LC-MS (ESI) found: 259 $[M + H]^+$ . $^1H$ NMR (400 MHz, $CD_3OD$): δ 7.46 (dd, J = 16.3, 8.1 Hz, 1H), 6.37 (dd, J = 8.1, 2.2 Hz, 1H), 6.07 (dd, J = 7.7, 2.0 Hz, 1H), 4.21-4.08 (m, 2H), 3.90 (d, J = 2.7 Hz, 1H), 3.76 (dd, J = 11.4, 7.1 Hz, 1H), 3.69 (dd, J = 11.4, 5.0 Hz, 1H), 3.56 (dd, J = 10.3, 3.2 Hz, 1H), 3.46-3.41 (m, J = 6.9, 5.0, 0.9 Hz, 1H), 3.08 (t, J = 10.7 Hz, 1H). $^{19}F$ NMR (377 MHz, $CD_3OD$): δ-73.05 (s). |
| A102 | Yield: 11 mg, 17%, yellow solid. LC-MS (ESI) found: 248 $[M + H]^+$ . $^1H$ NMR (400 MHz, $CD_3OD$): δ 7.85 (s, 1H), 4.13 (dd, J = 11.1, 5.2 Hz, 1H), 3.92 (dd, J = 21.5, 3.7 Hz, 2H), 3.78-3.66 (m, 2H), 3.61 (dd, J = 10.3, 3.2 Hz, 1H), 3.45 (ddd, J = 6.9, 5.0, 1.0 Hz, 1H), 3.19 (t, J = 10.9 Hz, 1H). |
| A103 | Yield: 3.6 mg, 4%, white solid. LC-MS (ESI) found: 277 $[M + H]^+$ . $^1H$ NMR (400 MHz, $CD_3OD$): δ 7.16-7.05 (m, 2H), 3.98 (dd, J = 11.3, 5.1 Hz, 1H), 3.91 (d, J = 2.5 Hz, 1H), 3.80-3.72 (m, 2H), 3.69 (dd, J = 11.4, 5.0 Hz, 1H), 3.61 (dd, J = 10.0, 3.2 Hz, 1H), 3.45 (ddd, J = 6.9, 5.0, 0.9 Hz, 1H), 3.18 (t, J = 11.0 Hz, 1H). |
| A104 | Yield: 7 mg, 10%, white solid. LC-MS (ESI) found: 282 $[M + H]^+$ . $^1H$ NMR (400 MHz, $CD_3OD$): δ 4.12 (dd, J = 11.1, 5.1 Hz, 1H), 3.90 (d, J = 2.6 Hz, 2H), 3.71 (dt, J = 11.4, 5.4 Hz, 2H), 3.60 (dd, J = 10.3, 3.2 Hz, 1H), 3.46-3.43 (m, 1H), 3.19 (t, J = 10.9 Hz, 1H). |

Synthesis 2-68: Preparation of (2R,3R,4R,5R,6S)-5-((3-chloro-1,2,4-thiadiazol-5-yl)amino)-2-(hydroxymethyl)-6-methoxytetrahydro-211-pyran-3,4-diol (Compound A105) and (2R,3R,4R,5R,6R)-5-((3-chloro-1,2,4-thiadiazol-5-yl)amino)-2-(hydroxymethyl)-6-methoxytetrahydro-2H1-pyran-3,4-diol (Compound A106)

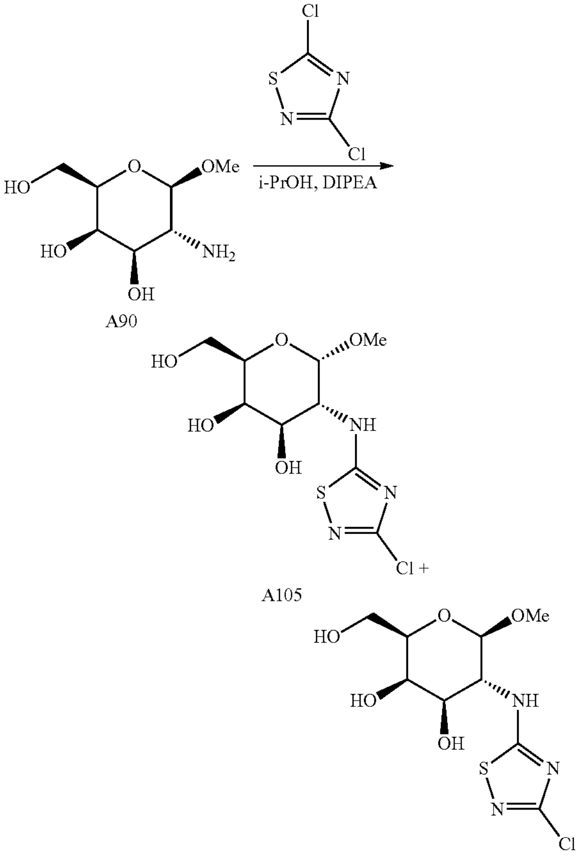

A90 A105 A106

A solution of (2R,3R,4R,5R,6R)-5-amino-2-(hydroxymethyl)-6-methoxytetrahydro-2H-pyran-3,4-diol (A90, 224.0 mg, 1.2 mmol), 3,5-dichloro-1,2,4-thiadiazole (372.0 mg, 2.4 mmol) and DIEA (464.4 mg, 3.6 mmol) in i-PrOH (10 mL) was stirred at rt overnight. The mixture was concentrated in vacuo. The crude product was purified by flash chromatography (silica gel, 0-10% MeOH in DCM) and pre-HPLC (Method B) to give (2R,3R,4R,5R,6S)-5-((3-chloro-1,2,4-thiadiazol-5-yl)amino)-2-(hydroxymethyl)-6-methoxytetrahydro-2H-pyran-3,4-diol (0.8 mg, 0.2% yield) as a white solid and (2R,3R,4R,5R,6R)-5-((3-chloro-1,2,4-thiadiazol-5-yl)amino)-2-(hydroxymethyl)-6-methoxytetrahydro-2H-pyran-3,4-diol (3.7 mg, 1% yield) as white solid. Compound A105: LC-MS (ESI) found: 312 $[M+H]^+$. $^1$H NMR (400 MHz, Methanol-$d_4$): δ 4.85-4.80 (m, 1H), 4.23-4.11 (m, 1H), 3.91 (d, J=3.1 Hz, 1H), 3.85-3.77 (m, 2H), 3.76-3.69 (m, 2H), 3.40 (s, 3H). Compound A106: LC-MS (ESI) found: 312 $[M+H]^+$. $^1$H NMR (400 MHz, Methanol-$d_4$): δ 4.33 (d, J=8.1 Hz, 1H), 3.87 (d, J=3.2 Hz, 1H), 3.84-3.70 (m, 2H), 3.68 (dd, J=10.4, 3.3 Hz, 1H), 3.53 (ddd, J=6.7, 5.4, 1.1 Hz, 1H), 3.48 (s, 3H), 3.46-3.40 (m, 1H).

Synthesis 2-69: Preparation of (2R,3R,4R,5R,6R)-5-((6-fluoropyridin-2-yl)amino)-2-(hydroxymethyl)-6-methoxytetrahydro-2H-pyran-3,4-diol (Compound A107)

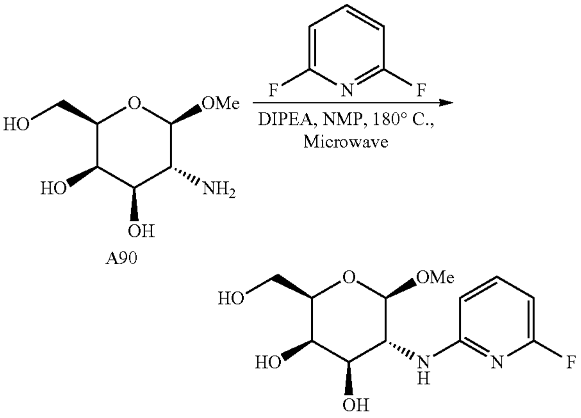

A90 A107

To a solution of (2R,3R,4R,5R,6R)-5-amino-2-(hydroxymethyl)-6-methoxytetrahydro-2H-pyran-3,4-diol (A90, 50.0 mg, 0.259 mmol) in NMP (2 mL) was added 2,6-difluoropyridine (89.0 mg, 0.777 mmol) and DIPEA (101 mg, 0.777 mmol). The mixture was stirred at 180° C. for 1 h under microwave. The reaction mixture was lyophilized and purified by prep-HPLC (Method A) to give (2R,3R,4R,5R,6R)-5-((6-fluoropyridin-2-yl)amino)-2-(hydroxymethyl)-6-methoxytetrahydro-2H-pyran-3,4-diol (A107, 1.4 mg, 2% yield) as white solid. LC-MS (ESI) found: 289 $[M+H]^+$. $^1$H NMR (400 MHz, Methanol-$d_4$): δ 7.47 (q, J=8.2 Hz, 1H), 6.43 (dd, J=8.2, 2.3 Hz, 1H), 6.07 (dd, J=7.7, 2.0 Hz, 1H), 4.31 (d, J=8.2 Hz, 1H), 3.95-3.84 (m, 2H), 3.77 (h, J=4.9 Hz, 2H), 3.62 (dd, J=10.4, 3.3 Hz, 1H), 3.53 (ddd, J=6.7, 5.4, 1.1 Hz, 1H), 3.45 (s, 3H).

The following compounds below were made using the method described in Synthesis 2-68 or Synthesis 2-69:

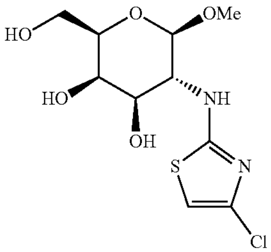 [SMILES: CO[C@@H]1O[C@H](CO)[C@H](O)[C@H](O)[C@H]1Nc1nc(Cl)cs1]

A108

-continued

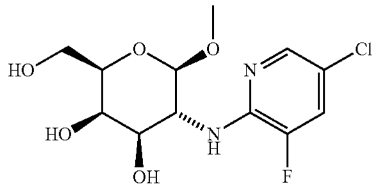 [SMILES: CO[C@@H]1O[C@H](CO)[C@H](O)[C@H](O)[C@H]1Nc1ncc(Cl)cc1F]

A109

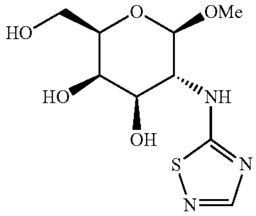 [SMILES: CO[C@@H]1O[C@H](CO)[C@H](O)[C@H](O)[C@H]1Nc1ncns1]

A110

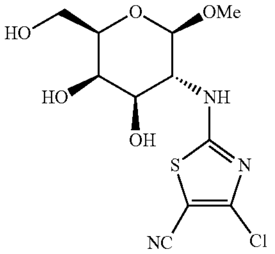 [SMILES: CO[C@@H]1O[C@H](CO)[C@H](O)[C@H](O)[C@H]1Nc1nc(Cl)c(C#N)s1]

A111

| ID | Characterization data | Starting Material |
|---|---|---|
| A111 | LC-MS (ESI) found: 336 [M + H]+ . $^1$H NMR (400 MHz, $CD_3OD$): δ 4.30 (d, J = 7.8 Hz, 1H), 3.86 (d, J = 2.1 Hz, 1H), 3.81-3.71 (m, 2H), 3.64 (dt, J = 14.5, 7.3 Hz, 2H), 3.54-3.50 (m, 1H), 3.48 (s, 3H). | 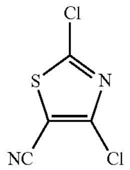 |
| A110 | LC-MS (ESI) found: 277 [M + H]+ . $^1$H NMR (400 MHz, $CD_3OD$): δ 7.82 (s, 1H), 4.34 (d, J = 8.1 Hz, 1H), 3.87 (d, J = 3.1 Hz, 1H), 3.83-3.68 (m, 4H), 3.55-3.51 (m, 1H), 3.47 (s, 3H). | 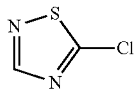 |
| A109 | Yield: 2 mg, 6%, white solid. LC-MS (ESI) found: 323 $[M + H]^+$ . $^1$H NMR (400 MHz, $CD_3OD$): δ 7.76 (d, J = 2.1 Hz, 1H), 7.34 (dd, J = 10.8, 2.0 Hz, 1H), 4.44 (d, J = 8.4 Hz, 1H), 4.32-4.26 (m, 1H), 3.88 (d, J = 3.1 Hz, 1H), 3.84-3.76 (m, 2H), 3.73 (dd, J = 10.6, 3.3 Hz, 1H), 3.54 (t, J = 6.2 Hz, 1H), 3.45 (s, 3H). $^{19}$F NMR (377 MHz, CD+hd 3+l OD): δ −139.12 (s). | 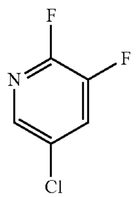 |
| A108 | Yield: 0.5 mg, 2%, white solid. LC-MS (ESI) found: 311 $[M + H]^+$ . $^1$H NMR (400 MHz, Methanol-d4): δ 6.31 (s, 1H), 4.29 (d, J = 8.0 Hz, 1H), 3.86 (d, J = 3.2 Hz, 1H), 3.77 (t, J = 6.1 Hz, 2H), 3.63 (dd, J = 10.3, 3.2 Hz, 1H), 3.56 (d, J = 8.0 Hz, 1H), 3.52 (d, J = 6.1 Hz, 1H), 3.47 (s, 3H). | 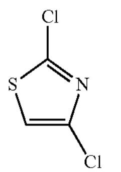 |

Preparation of (2R,3R,4R,5R,6R)-5-((1,2,4-thiadiazol-5-yl)amino)-2-(hydroxymethyl)-6-methoxytetrahydro-2H-pyran-3,4-diol (Compound A110)

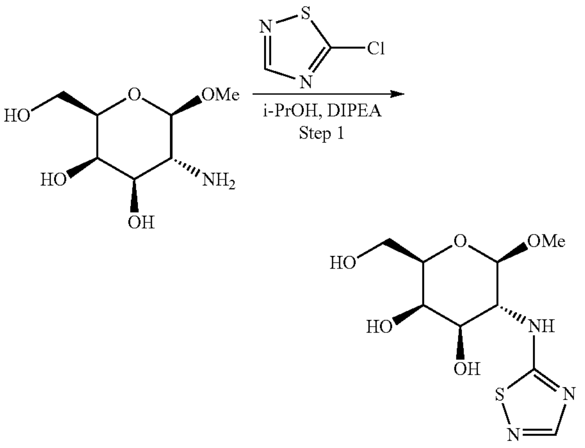

Step 1: A solution of (2R,3R,4R,5R,6R)-5-amino-2-(hydroxymethyl)-6-methoxytetrahydro-2H-pyran-3,4-diol (30 mg, 0.16 mmol), DIPEA (40 mg, 0.31 mmol) and 5-chloro-1,2,4-thiadiazole (22.4 mg, 0.19 mmol) in i-PrOH (1 mL) was stirred at 120° C. overnight. The mixture was concentrated and the residue was purified by prep-HPLC (Method A) to give (2R,3R,4R,5R,6R)-5-((1,2,4-thiadiazol-5-yl)amino)-2-(hydroxymethyl)-6-methoxytetrahydro-2H-pyran-3,4-diol (6.8 mg, 16% yield) as a white solid.

Synthesis 2-70: Preparation of 6-(((2R,3R,4R,5R,6R)-4,5-dihydroxy-6-(hydroxymethyl)-2-methoxytetrahydro-2H-pyran-3-yl)amino)-1,3,5-triazine-2,4(1H,3H)-dione (Compound A112)

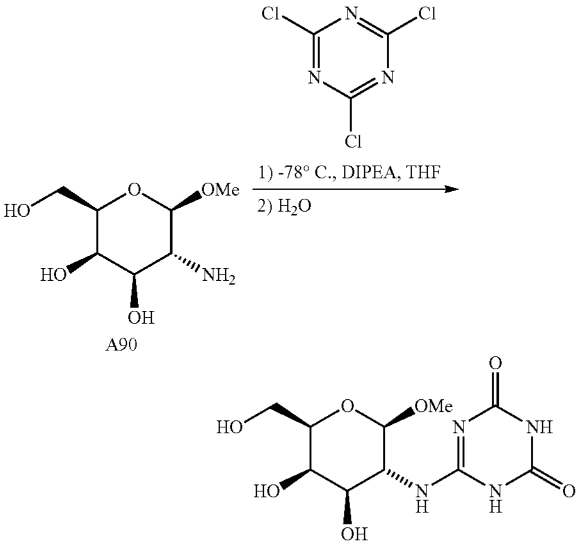

A90

A112

To a solution of 2,4,6-trichloro-1,3,5-triazine (187 mg 1.03 mmol) in THF (5 mL) was added DIPEA (200 mg, 1.55 mmol) at −78° C. (2R,3R,4R,5R,6R)-5-amino-2-(hydroxymethyl)-6-methoxytetrahydro-2H-pyran-3,4-diol (A90, 100 mg, 0.51 mmol) was then added at −78° C. The mixture was further stirred for 2 h at −78° C. Then it was quenched by adding $H_2O$ (5 mL). The mixture was warmed to rt and stirred for another 2 h. The solvent was evaporated and the residual was purified by prep-HPLC (Method A) to give 6-(((2R,3R,4R,5R,6R)-4,5-dihydroxy-6-(hydroxymethyl)-2-methoxytetrahydro-2H-pyran-3-yl)amino)-1,3,5-triazine-2,4(1H,3H)-dione (A112, 6.1 mg, 4% yield) as white solid. LC-MS (ESI) found: 305 $[M+H]^+$. $^1H$ NMR (400 MHz, $D_2O$): δ 4.39 (d, J=8.4 Hz, 1H), 4.02 (dd, J=10.7, 8.5 Hz, 1H), 3.88 (d, J=3.2 Hz, 1H), 3.81-3.67 (m, 3H), 3.63 (dd, J=7.8, 4.3 Hz, 1H).

The following compound below was made using the method described in Synthesis 2-70 with (2R,3R,4R,5R,6S)-5-amino-2-(hydroxymethyl)-6-methoxytetrahydro-2H-pyran-3,4-diol instead of A90:

A113

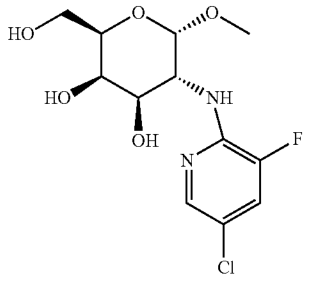 [SMILES: CO[C@H]1O[C@H](CO)[C@H](O)[C@H](O)[C@H]1Nc1ncc(Cl)cc1F]

| ID | Characterization data |
|---|---|
| A113 | LC-MS (ESI) found: 323 $[M + H]^+$. $^1H$ NMR (400 MHz, $CD_3OD$): δ 8.51 (s, 1H), 7.79 (d, J = 2.1 Hz, 1H), 7.37 (dd, J = 10.7, 2.1 Hz, 1H), 4.83 (s, 1H), 4.56 (d, J = 3.7 Hz, 1H), 3.93 (d, J = 3.1 Hz, 1H), 3.86 (dd, J = 10.8, 3.2 Hz, 1H), 3.82-3.79 (m, 1H), 3.77-3.71 (m, 2H), 3.37 (s, 3H). |

Synthesis 2-71: Preparation of (2R,3R,4R,5R,6S)-5-((3-(dimethylamino)-1,2,4-thiadiazol-5-yl)amino)-2-(hydroxymethyl)-6-methoxytetrahydro-2H-pyran-3,4-diol (Compound A114)

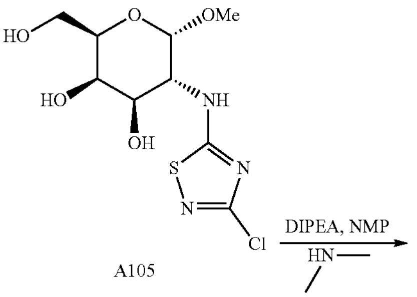

A105

-continued

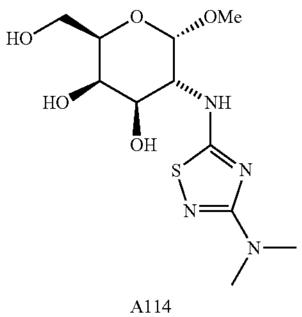

A114

A solution of (2R,3R,4R,5R,6S)-5-((3-chloro-1,2,4-thiadiazol-5-yl)amino)-2-(hydroxymethyl)-6-methoxytetrahydro-2H-pyran-3,4-diol (A105, 10.0 mg, 0.03 mmol), dimethylamine (0.1 mL, 0.1 mmol, 1 M in THF) and DIEA (11.6 mg, 0.09 mmol) in NMP (4 mL) was stirred at 120° C. overnight. The mixture was concentrated in vacuo. The crude product was purified by pre-HPLC (Method B) to give (2R,3R,4R,5R,6S)-5-((3-(dimethylamino)-1,2,4-thiadiazol-5-yl)amino)-2-(hydroxymethyl)-6-methoxytetrahydro-2H-pyran-3,4-diol (A114, 0.8 mg, 8.3% yield) as white solid. LC-MS (ESI) found: 321 $[M+H]^+$. $^1H$ NMR (400 MHz, Methanol-$d_4$): δ 4.85-4.81 (m, 1H), 4.12 (d, J=13.7 Hz, 1H), 3.90 (d, J=3.2 Hz, 1H), 3.81 (ddd, J=11.4, 7.8, 3.3 Hz, 2H), 3.77-3.67 (m, 2H), 3.39 (s, 3H), 3.04 (s, 6H).

The following compounds below were made using the method described in Synthesis 2-71 with the appropriate amine and, A106 instead of A105:

A115

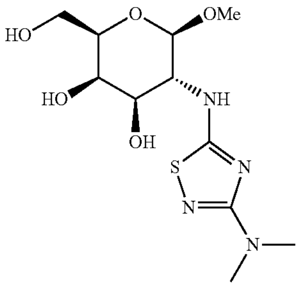

A116

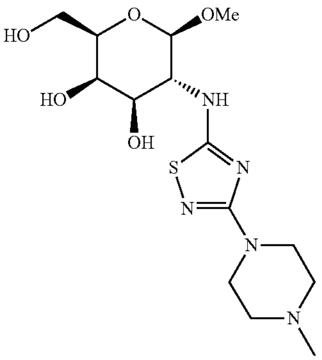

-continued

A117

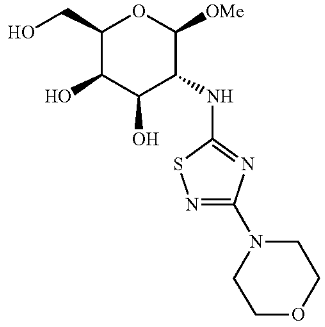

Preparation of (2R,3R,4R,5R,6R)-2-(hydroxymethyl)-6-methoxy-5-((3-(4-methylpiperazin-1-yl)-1,2,4-thiadiazol-5-yl)amino)tetrahydro-2H-pyran-3,4-diol (Compound A116)

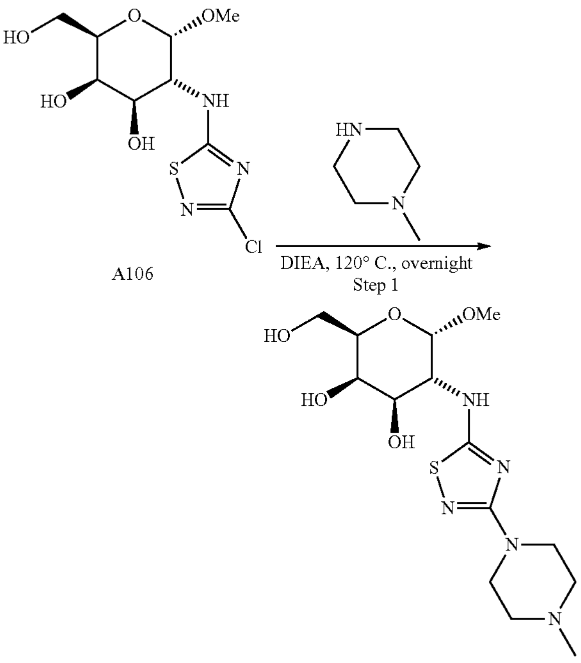

A106

A116

Step 1: A solution of (2R,3R,4R,5R,6R)-5-((3-chloro-1,2,4-thiadiazol-5-yl)amino)-2-(hydroxymethyl)-6-methoxytetrahydro-2H-pyran-3,4-diol (10 mg, 0.03 mmol), 1-methylpiperazine (5.0 mg, 0.05 mmol) and DIEA (11.6 mg, 0.09 mmol) in i-PrOH (4 mL) was stirred at 120° C. overnight. The mixture was concentrated in vacuo. The crude product was purified by prep-HPLC (Method A) to give product (1.4 mg, 7% yield) as white solid. LC-MS (ESI) found: 376 $[M+H]^+$. $^1H$ NMR (400 MHz, Methanol-$d_4$): δ 4.35 (d, J=8.2 Hz, 1H), 3.86 (d, J=3.2 Hz, 1H), 3.81-3.74 (m, 2H), 3.70 (dd, J=10.5, 3.4 Hz, 1H), 3.57 (t, J=5.1 Hz, 4H), 3.54-3.50 (m, 2H), 3.48 (s, 3H), 2.48 (t, J=5.1 Hz, 4H), 2.31 (s, 3H).

Preparation of (2R,3R,4R,5R,6R)-2-(hydroxymethyl)-6-methoxy-5-((3-morpholino-1,2,4-thiadiazol-5-yl)amino)tetrahydro-2H-pyran-3,4-diol (Compound A117)

A117

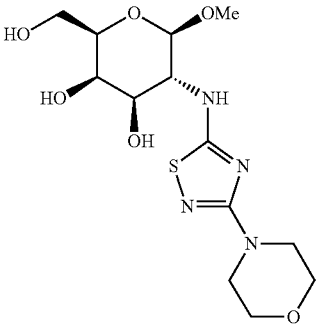

It was prepared according to the procedure same as that for A116. Yield: 1.0 mg, 9%, white solid. LC-MS (ESI) found: 363 $[M+H]^+$. $^1H$ NMR (400 MHz, Methanol-$d_4$): δ 4.35 (d, J=8.2 Hz, 1H), 3.86 (d, J=3.2 Hz, 1H), 3.77 (t, J=6.2 Hz, 2H), 3.73-3.69 (m, 6H), 3.54-3.45 (m, 8H).

| ID | Characterization data |
|---|---|
| A115 | LC-MS (ESI) found: 321 $[M + H]^+$. $^1H$ NMR (400 MHz, $CD_3OD$): δ 4.36 (d, J = 8.2 Hz, 1H), 3.86 (d, J = 3.1 Hz, 1H), 3.81-3.69 (m, 3H), 3.55-3.50 (m, 1H), 3.48 (s, 3H), 3.46-3.40 (m, 1H), 3.03 (s, 6H). |
| A116 | LC-MS (ESI) found: 376 $[M + H]^+$. $^1H$ NMR (400 MHz, $CD_3OD$) δ: 4.35 (d, J = 8.2 Hz, 1H), 3.86 (d, J = 3.2 Hz, 1H), 3.81-3.74 (m, 2H), 3.70 (dd, J = 10.5, 3.4 Hz, 1H), 3.57 (t, J = 5.1 Hz, 4H), 3.54-3.50 (m, 2H), 3.48 (s, 3H), 2.48 (t, J = 5.1 Hz, 4H), 2.31 (s, 3H). |
| A117 | LC-MS (ESI) found: 363 $[M + H]^+$. $^1H$ NMR (400 MHz, Methanol-$d_4$): δ 4.35 (d, J = 8.2 Hz, 1H), 3.86 (d, J = 3.2 Hz, 1H), 3.77 (t, J = 6.2 Hz, 2H), 3.73-3.69 (m, 6H), 3.54-3.45 (m, 8H). |

Synthesis 2-72: Preparation of N-((2R,3R,4R,5R,6R)-4,5-dihydroxy-6-(hydroxymethyl)-2-methoxytetrahydro-2H-pyran-3-yl)acrylamide (Compound A118)

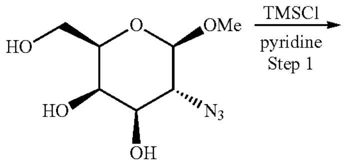

A89

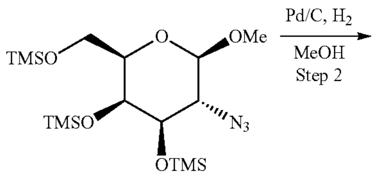

A118-1

-continued

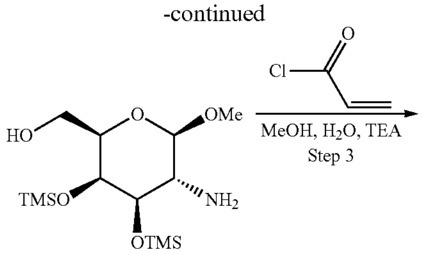

A118-2

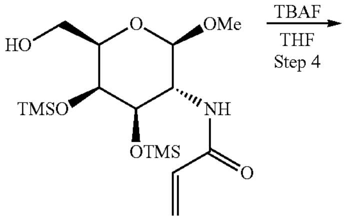

A118-3

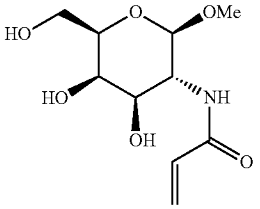

A118

Step 1: A solution of compound (2R,3R,4R,5R,6R)-5-azido-2-(hydroxymethyl)-6-methoxytetrahydro-2H-pyran-3,4-diol (A89, 1 g, 4.6 mmol) in anhydrous pyridine (20 mL) was treated with trimethylsilyl chloride (3.5 mL, 27.8 mmol) and the mixture was stirred for 12 h at room temperature. The solvent was evaporated and the residue was diluted in ethyl acetate/water. The organic layer was separated and further washed by water, brine, dried over anhydrous $MgSO_4$, filtered, and concentrated to afford desired product as a yellow oil (1.6 g, 81% yield). LC-MS (ESI) found: 436 $[M+H]^+$.

Step 2: To a solution of (((2R,3S,4R,5R,6R)-5-azido-6-methoxy-2-(((trimethylsilyl)oxy)methyl)tetrahydro-2H-pyran-3,4-diyl)bis(oxy))bis(trimethylsilane)(A118-1, 1.0 g, 2.29 mmol) in MeOH (20 mL) was added Pd/C (100 mg, 10% wt, 60% wet). The mixture was stirred at rt for 12 h under a $H_2$ balloon. The mixture was filtered and concentrated to give ((2R,3S,4R,5R,6R)-5-amino-6-methoxy-3,4-bis((trimethylsilyl)oxy)tetrahydro-2H-pyran-2-yl)methanol (A118-2, 401 mg, 52% yield). LC-MS (ESI) found: 338 $[M+H]^+$.

Step 3: To a solution of ((2R,3S,4R,5R,6R)-5-amino-6-methoxy-3,4-bis((trimethylsilyl)oxy)tetrahydro-2H-pyran-2-yl)methanol (A118-2, 150 mg, 0.444 mmol) in MeOH (1 mL) $H_2O$ (1 mL) was added prop-2-enoyl chloride (0.04 mL, 0.533 mmol) and TEA (0.02 mL, 0.148 mmol). The mixture was stirred at 0° C. for 4 h. The solvent was evaporated and the residue was diluted in DCM/water. The organic layer was separated and further washed by water, brine, dried over anhydrous $MgSO_4$, filtered, and concentrated to afford a crude product, which was purified by silica gel column to give N-((2R,3R,4R,5S,6R)-6-(hydroxymethyl)-2-methoxy-4,5-bis((trimethylsilyl)oxy)tetrahydro-2H-pyran-3-yl)acrylamide (A118-3, 70 mg, 40%). LC-MS (ESI) found: 392 $[M+H]^+$.

Step 4: To a solution of N-((2R,3R,4R,5S,6R)-6-(hydroxymethyl)-2-methoxy-4,5-bis((trimethylsilyl)oxy)tetrahydro-2H-pyran-3-yl)acrylamide (A118-3, 70 mg, 0.179 mmol) in THF (1 mL) was added TBAF (0.2 mL, 1 M in THF). The mixture was stirred at 0° C. for 30 min. The solvent was evaporated and the residual was purified by prep-HPLC (Method A) to give N-((2R,3R,4R,5R,6R)-4,5-dihydroxy-6-(hydroxymethyl)-2-methoxytetrahydro-2H-pyran-3-yl)acrylamide (A118, 17 mg, 38%) as white solid. LC-MS (ESI) found: 248 $[M+H]^+$. $^1H$ NMR (400 MHz, Methanol-$d_4$): δ 6.04-6.17 (m, 2H), 5.63-5.66 (m, 1H), 4.29 (d, J=8.4 Hz, 1H), 3.79-3.83 (m, 2H), 3.55-3.65 (m, 4H), 3.35 (s, 3H).

Synthesis 2-73: Preparation of 1-((2R,3R,4R,5R,6R)-4,5-dihydroxy-6-(hydroxymethyl)-2-methoxytetrahydro-2H-pyran-3-yl)pyridin-4(1H)-one (Compound A119)

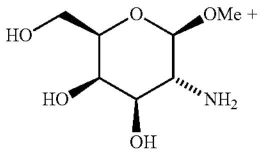

A90

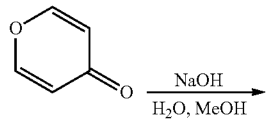

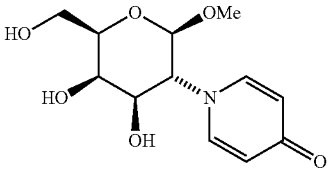

A119

To a solution of 4H-pyran-4-one (9.6 mg, 0.100 mmol) in MeOH (3 mL) was added NaOH (8 mg, 0.2 mmol) in $H_2O$ (2 mL) to adjust pH to 11, then (2R,3R,4R,5R,6R)-5-amino-2-(hydroxymethyl)-6-methoxytetrahydro-2H-pyran-3,4-diol (A90, 20 mg, 0.1 mmol) was added to the mixture. The mixture was stirred at 60° C. for 3 h. Then the solvent was evaporated and the residual was purified by prep-HPLC (Method A) to give 1-((2R,3R,4R,5R,6R)-4,5-dihydroxy-6-(hydroxymethyl)-2-methoxytetrahydro-2H-pyran-3-yl)pyridin-4(1H)-one (A119, 2.1 mg, 7.7%) as white solid. LC-MS (ESI) found: 272 $[M+H]^+$. $^1H$ NMR (400 MHz, Methanol-$d_4$): δ 8.49 (s, 1H), 7.86 (d, J=7.6 Hz, 2H), 6.46 (d, J=7.6 Hz, 2H), 4.65 (d, J=8.3 Hz, 1H), 4.08 (dd, J=10.9, 3.3 Hz, 1H), 3.98-3.89 (m, 2H), 3.85-3.75 (m, 2H), 3.68 (t, J=6.1 Hz, 1H), 3.42 (s, 3H).

Synthesis 2-74: Preparation of N-((2R,3R,4R,5R,6R)-4,5-dihydroxy-6-(hydroxymethyl)-2-methoxytetrahydro-2H-pyran-3-yl)-4-methylbenzenesulfonamide (Compound A120)

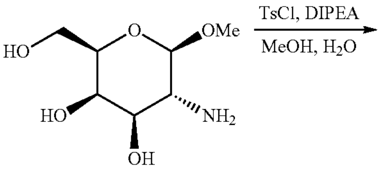

A90

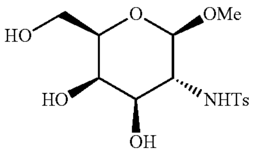

A120

A solution of (2R,3R,4R,5R,6R)-5-amino-2-(hydroxymethyl)-6-methoxytetrahydro-2H-pyran-3,4-diol (A90, 50 mg, 0.26 mmol) in MeOH (0.5 mL) and $H_2O$(0.5 mL) was added DIPEA (0.92 mL, 5.2 mmol) and 4-methylbenzene-1-sulfonyl chloride (0.25 mL, 1.3 mmol). After stirring under $N_2$ at rt overnight, the mixture was concentrated to give crude product which was further purified by prep-HPLC (Method B) to afford N-((2R,3R,4R,5R,6R)-4,5-dihydroxy-6-(hydroxymethyl)-2-methoxytetrahydro-2H-pyran-3-yl)-4-methylbenzenesulfonamide (A120, 7.0 mg, 15%) as white solid. LC-MS (ESI) found: 348 $[M+1]^+$. $^1H$ NMR (400 MHz, DMSO-$d_6$): δ 7.64 (d, J=8.3 Hz, 2H), 7.48 (s, 1H), 7.31 (d, J=8.0 Hz, 2H), 4.55 (dd, J=7.7, 3.6 Hz, 2H), 4.50 (d, J=6.6 Hz, 1H), 3.88 (d, J=8.1 Hz, 1H), 3.63 (t, J=3.6 Hz, 1H), 3.53-3.40 (m, 2H), 3.30 (dd, J=6.7, 3.2 Hz, 1H), 3.22 (dd, J=8.0, 4.2 Hz, 2H), 2.85 (s, 3H), 2.36 (s, 3H).

Synthesis 2-75: Preparation of N-((3S,4R,5R,6R)-4,5-dihydroxy-6-(hydroxymethyl)tetrahydro-2H-pyran-3-yl)-4-methylbenzenesulfonamide (Compound A121)

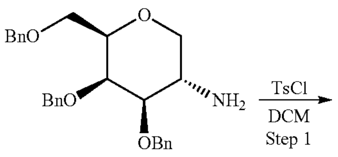

A94

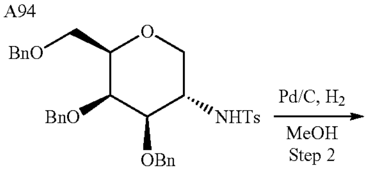

A121-1

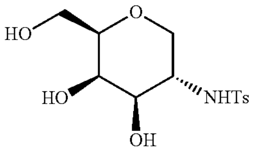

A121

Step 1: To a mixture of (3S,4R,5R,6R)-4,5-bis(benzyloxy)-6-((benzyloxy)methyl)tetrahydro-2H-pyran-3-amine (A94, 50 mg, 0.12 mmol) in MeOH (1.0 mL) and $H_2O$ (1.0 mL) was added TsCl (219 mg, 1.2 mmol) and TEA (175 mg, 1.7 mmol) at 0° C. under $N_2$. After string for 2 h, the mixture was concentrated and purified by prep-HPLC (Method A) to give N-((3S,4R,5R,6R)-4,5-bis(benzyloxy)-6-((benzyloxy)methyl)tetrahydro-2H-pyran-3-yl)-4-methylbenzenesulfonamide (A121-1, 30 mg, 44%) as a white solid. LC-MS (ESI) found: 588 $[M+1]^+$.

Step 2: To a mixture of N-((3S,4R,5R,6R)-4,5-bis(benzyloxy)-6-((benzyloxy)methyl)tetrahydro-2H-pyran-3-yl)-4-methylbenzenesulfonamide (A121-1, 30 mg, 0.051 mmol) in MeOH (3.0 mL) was added Pd/C (10 mg, 10% wt, 60% wet) at rt. The mixture was stirred at rt for 12 h under a $H_2$ balloon. The mixture was filtered and concentrated to afford N-((3S,4R,5R,6R)-4,5-dihydroxy-6-(hydroxymethyl)tetrahydro-2H-pyran-3-yl)-4-methylbenzenesulfonamide (A121, 10 mg, 62%) as white solid. LC-MS (ESI) found: 318 $[M+1]^+$. $^1H$ NMR (400 MHz, $CD_3OD$): δ 7.78 (d, J=8.3 Hz, 2H), 7.36 (d, J=8.0 Hz, 2H), 3.80 (dd, J=2.9, 0.8 Hz, 1H), 3.75 (dd, J=11.2, 4.8 Hz, 1H), 3.62 (ddd, J=16.4, 11.4, 6.0 Hz, 2H), 3.45-3.31 (m, 3H), 3.08-3.00 (m, 1H), 2.42 (s, 3H).

Synthesis 2-7: Preparation of (3R,4R,5R,6R)-3-(4-fluorophenyl)-6-(hydroxymethyl)tetrahydro-2H-pyran-2,4,5-triol (Compound A122)

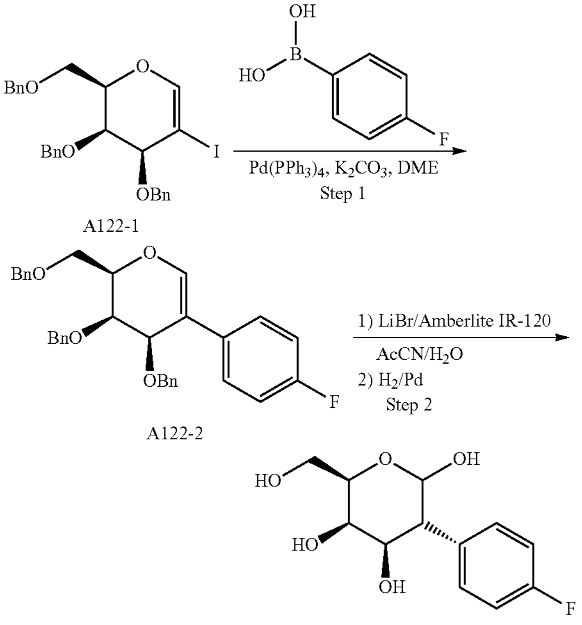

A122-1
A122-2
A122

Step 1: To a solution of (2R,3S,4S)-3,4-bis(benzyloxy)-2-((benzyloxy)methyl)-5-iodo-3,4-dihydro-2H-pyran (A122-1, 100 mg, 0.184 mmol) in DME (10 mL) was added $Pd(PPh_3)_4$ (21 mg, 0.018 mmol), $K_2CO_3$ (76 mg, 0.552 mmol) and (4-fluorophenyl)boronic acid (34 mg, 0.239 mmol). The mixture was charged with $N_2$ for three times and stirred at 90° C. under $N_2$ for 16 h. The mixture was filtered, the filtrate was concentrated under reduced pressure to give a crude product, which was purified by flash chromatography (silica gel, 5-10% EtOAc in PE) to give (2R,3R,4R)-4-(benzyloxy)-2-((benzyloxy)methyl)-5-(4-fluorophenyl)-3,4-dihydro-2H-pyran-3-ol (A122-2, 25 mg, 31% yield) as colorless oil. LC-MS (ESI) found: 533 $[M+23]^+$.

(2R,3R,4R,5R)-5-(2,4-difluorophenyl)-2-(hydroxymethyl)tetrahydro-2H-pyran-3,4-diol (Compound A122a), (2R,3R,4R,5R)-2-(hydroxymethyl)-5-(1H-pyrazol-3-yl)tetrahydro-2H-pyran-3,4-diol (Compound A122b) and (2R,3R,4R,5R)-2-(hydroxymethyl)-5-(1H-pyrazol-4-yl)tetrahydro-2H-pyran-3,4-diol (Compound A122c) were Prepared Using the Procedure Shown in Synthesis 2-7

A122a

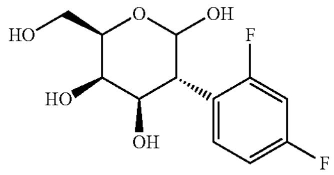

A122b

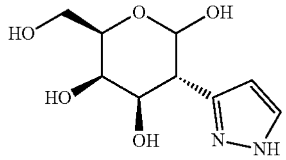

A122c

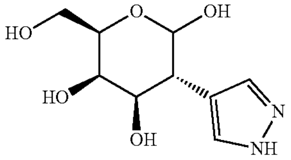

Alternatively, (2R,3R,4R,5R)-5-(2,4-difluorophenyl)-2-(hydroxymethyl)tetrahydro-2H-pyran-3,4-diol (Compound A122a) can be synthesized in the following manner:

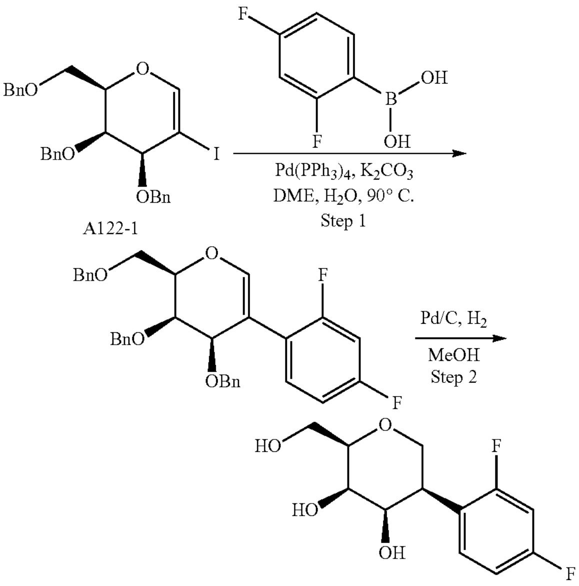

A122-1
A122a

Step 1: To a solution of (2R,3S,4S)-3,4-bis(benzyloxy)-2-((benzyloxy)methyl)-5-iodo-3,4-dihydro-2H-pyran (433 mg, 0.80 mmol) in DME (30 mL) and water (10 mL) were added (2,4-difluorophenyl)boronic acid (164 mg, 1.0 mmol) and $K_2CO_3$(331 mg, 2.4 mmol). The mixture was stirred at 90° C. under $N_2$ for 16 h. The mixture was concentrated under reduced pressure to give a crude product, which was purified by silica gel column to give (2R,3R,4R)-3,4-bis(benzyloxy)-2-((benzyloxy)methyl)-5-(2,4-difluorophenyl)-3,4-dihydro-2H-pyran (200 mg, 47% yield). LC-MS (ESI) found: 529 $[M+H]^+$.

Step 2: To a solution of (2R,3R,4R)-3,4-bis(benzyloxy)-2-((benzyloxy)methyl)-5-(2,4-difluorophenyl)-3,4-dihydro-2H-pyran (30 mg, 0.057 mmol) in MeOH (10 mL) was added Pd/C (5 mg, 10% wt, 60% wet), the mixture was stirred at rt overnight under a $H_2$ balloon. The mixture was filtered, the filtrate was concentrated to give (2R,3R,4R,5R)-5-(2,4-difluorophenyl)-2-(hydroxymethyl)tetrahydro-2H-pyran-3,4-diol (9.7 mg, 65% yield). LC-MS (ESI) found: 261 $[M+H]^+$. $^1H$ NMR (400 MHz, MeOD): δ 7.79 (m, 1H), 6.84 (m, 2H), 4.20 (dd, J=11.7, 6.9 Hz, 1H), 4.09 (dd, J=13.0, 8.9 Hz, 1H), 4.04-3.95 (m, 1H), 3.92-3.86 (m, 1H), 3.76 (m, 2H), 3.66 (dd, J=11.7, 4.1 Hz, 1H), 3.33 (dd, J=7.3, 3.9 Hz, 1H).

Example 3. Synthesis of Degraders

Synthesis 3-1. Preparation of Bidentate Fumaramide OPT-3 (Compound 1)

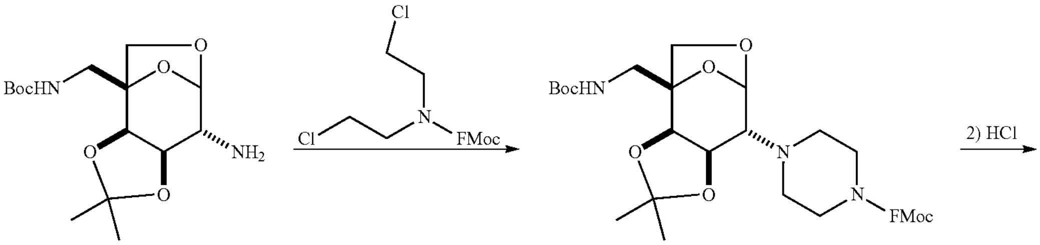

Intermediate 1

1-2

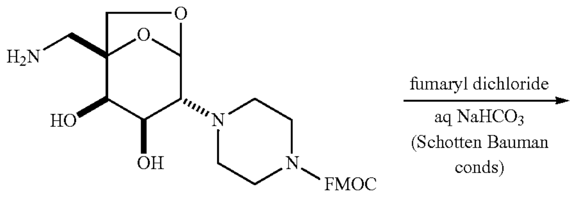

1-3

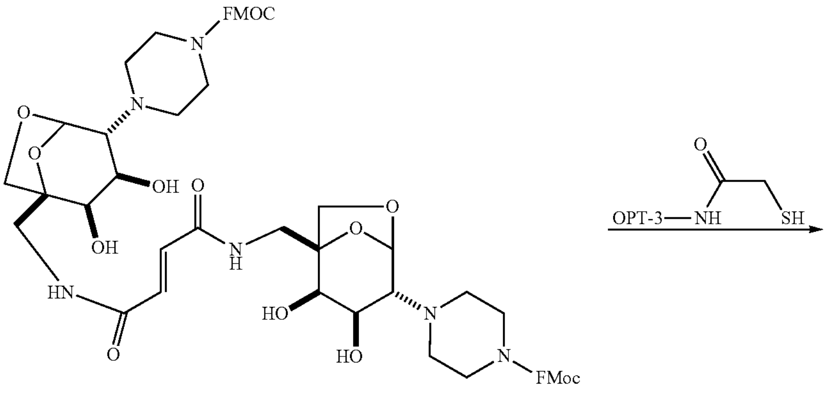

1-4

-continued
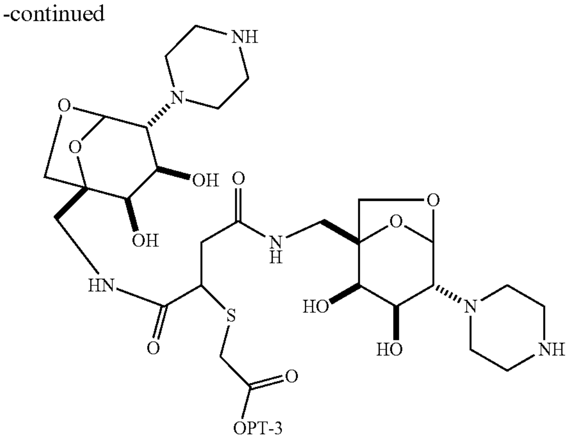
Compound 1
The —NH(OPT-3)C(O)$CH_2SH$ is generated in situ from $NH_2OH$ treatment of SATA-(N-succinimidyl S-acetylthioacetate)-OPT-3.
Synthesis 3-2. General Synthesis of Bidentate Fumaramide OPT-3 Conjugate-Sulfoximine Compounds
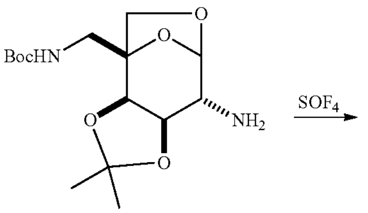
Intermediate 1
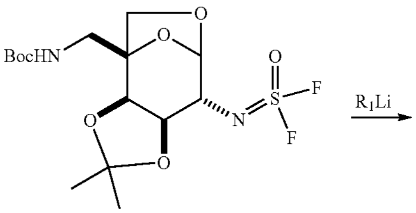
2-1
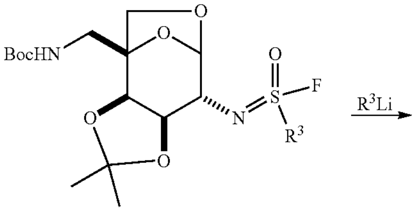
A4-1
-continued
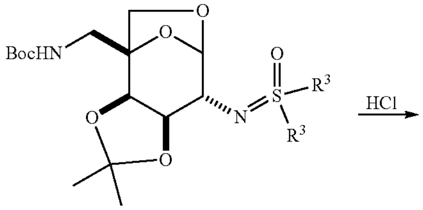
2-2
(Angew Chem I.E.E. 2018 57(7), 1939-1943)
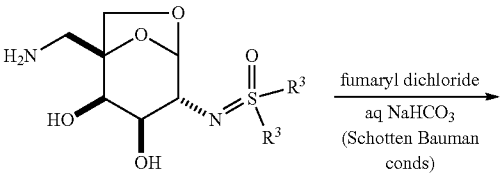
2-3
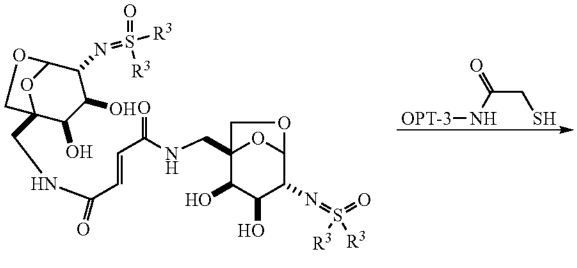
2-4

-continued
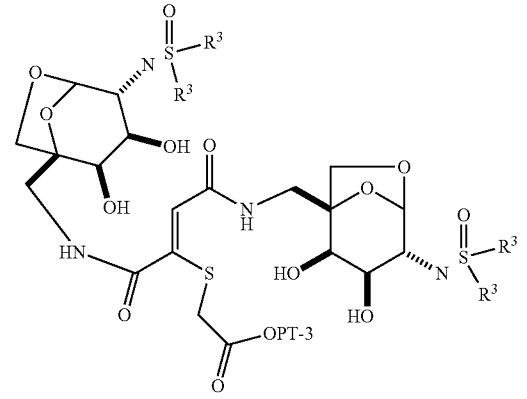
Compound 2
Compound 3
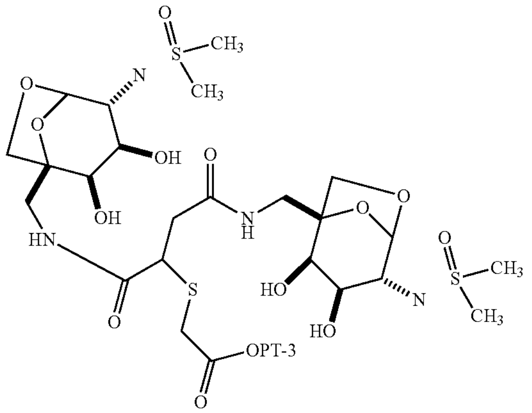
The —NH(OPT-3)C(O)$CH_2$SH is generated in situ from $NH_2OH$ treatment of SATA-(N-succinimidyl S-acetylthioacetate)-OPT-3. Compound 3 can be synthesized using the procedure of Scheme 2-59 with MeLi.
Synthesis 3-3. Preparation of Compound 4
Compound 4-1 is synthesized from ASGPR Ligand A41 from Synthesis 2-33
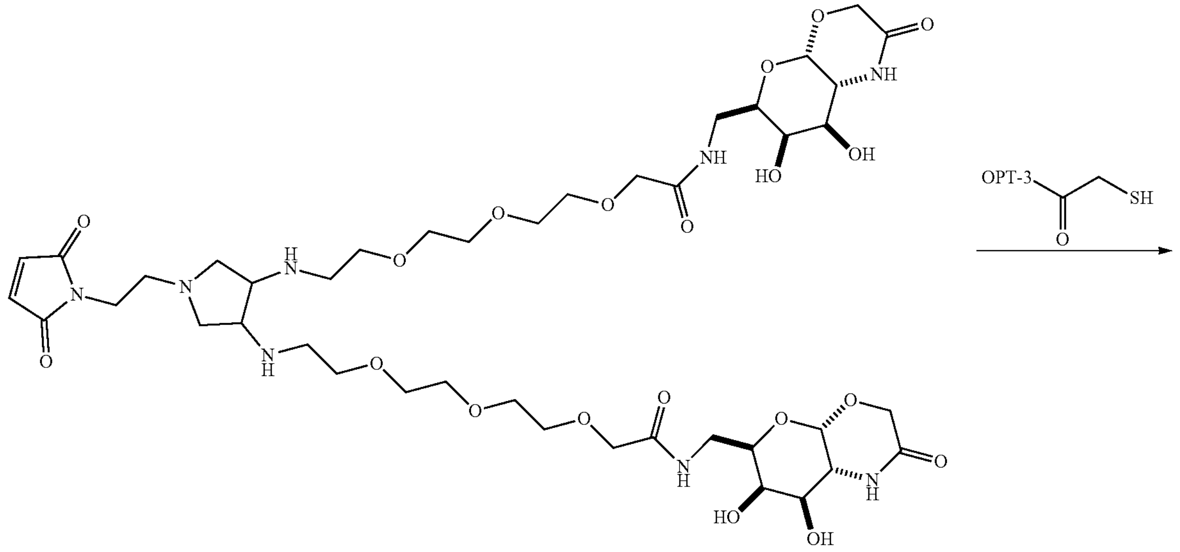
4-1

-continued
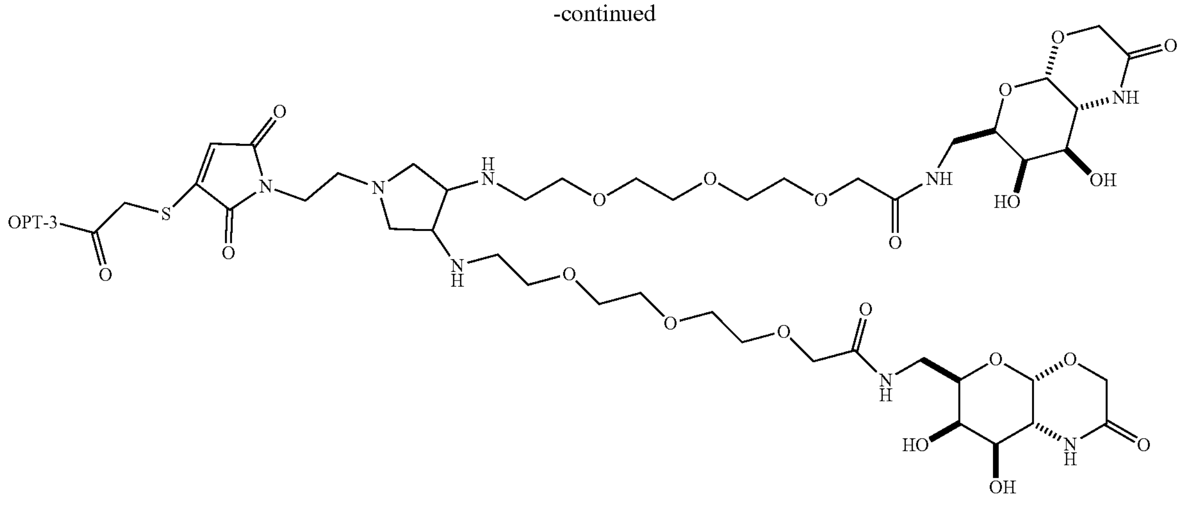
Compound 4
Synthesis 3-4. Preparation of Compound 5
Compound 5-1 is synthesized from ASGPR Ligand A51 from Synthesis 2-39
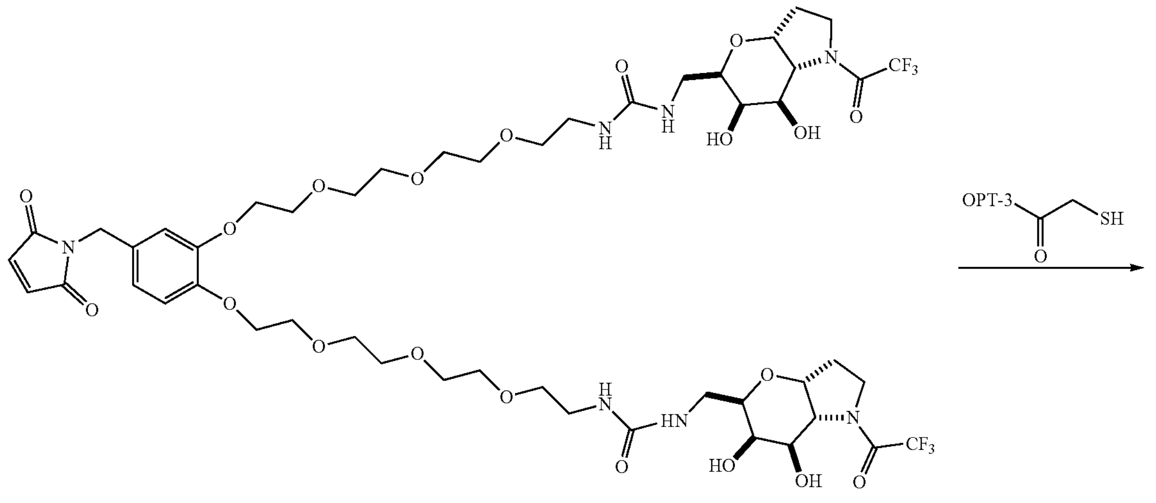
5-1

-continued
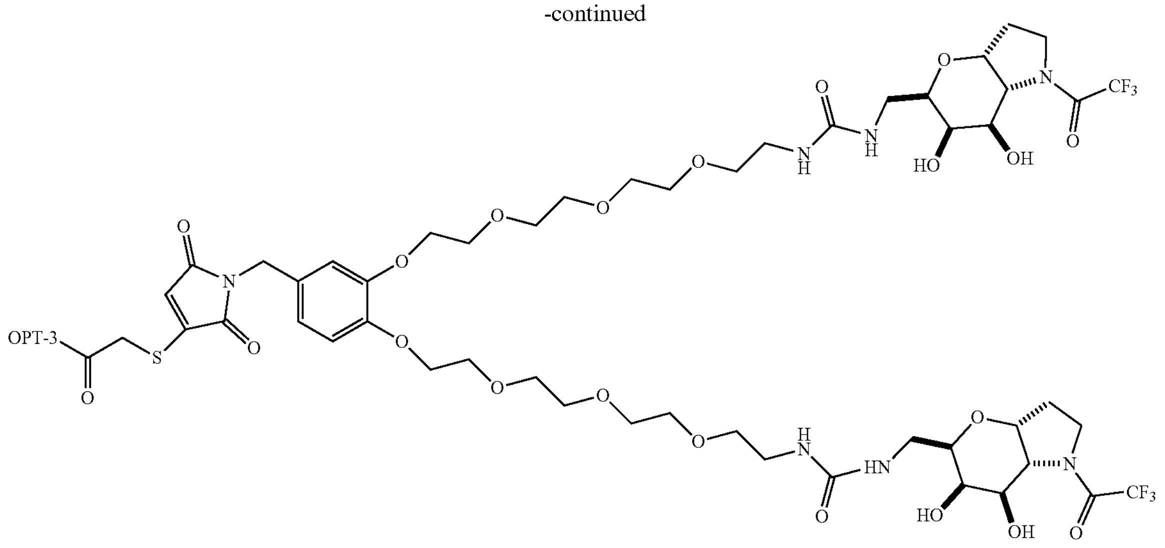
Compound 5
Synthesis 3-5. Preparation of Compound 6 and Compound 7
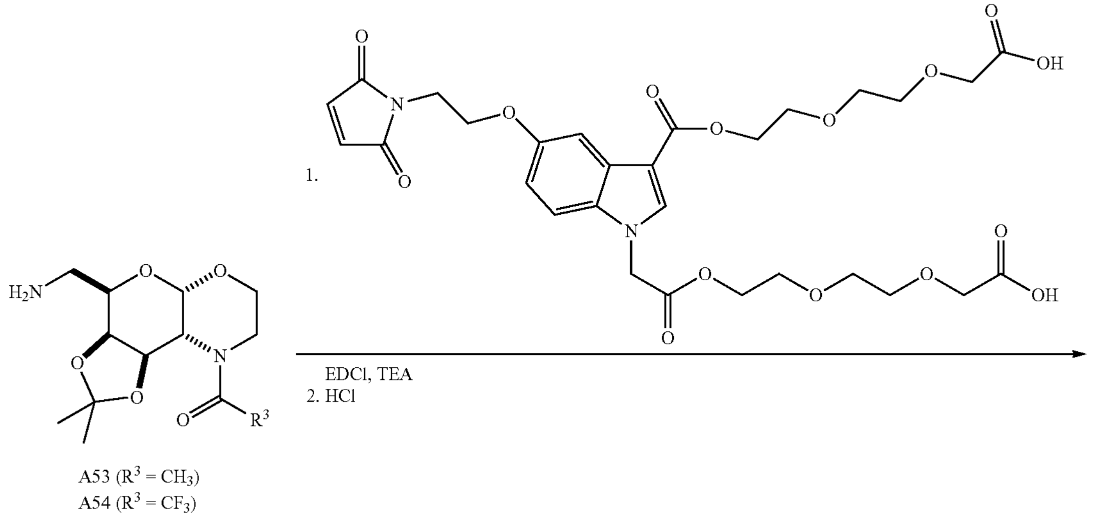

-continued
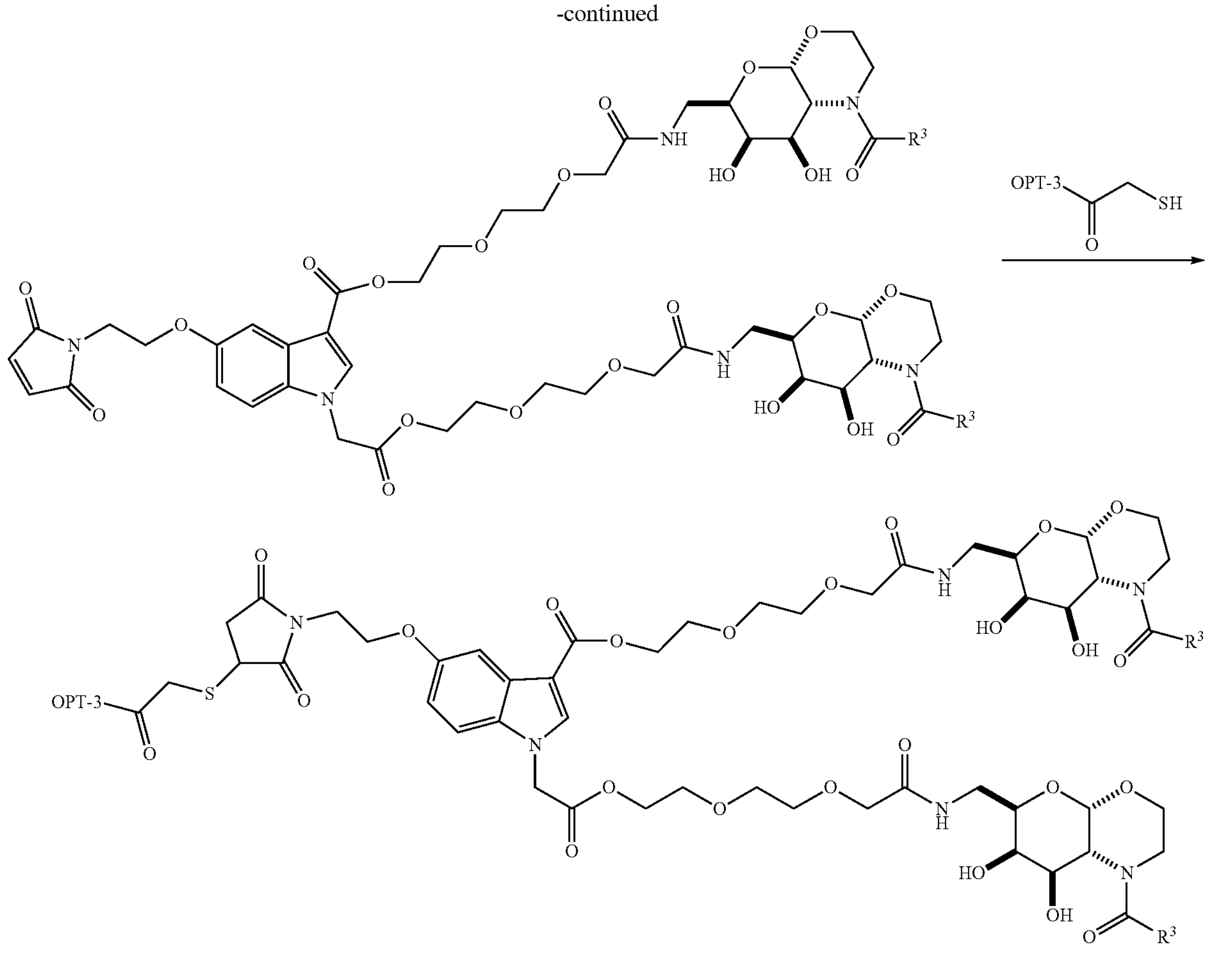
Compound 6 ($R^3 = CH_3$)
Compound 7 ($R^3 = CF_3$)
Synthesis 3-6. Preparation of Compound 8
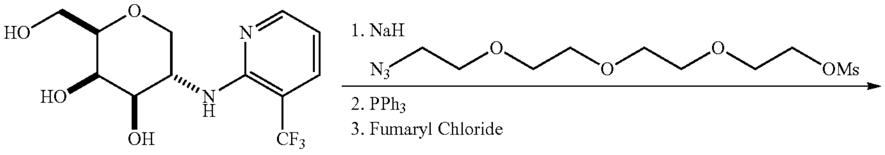
A76
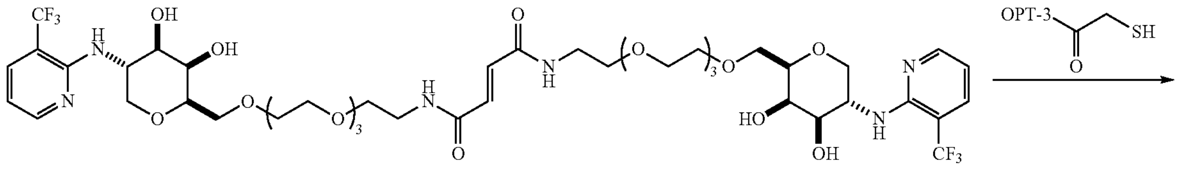

-continued
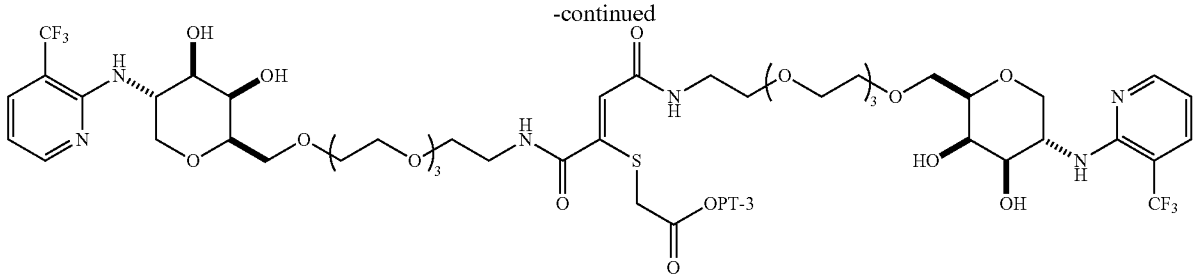
Compound 8
Synthesis 3-7. Preparation of Compound 9
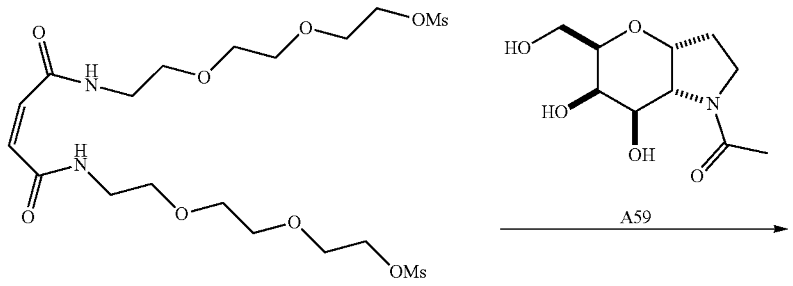
9-1
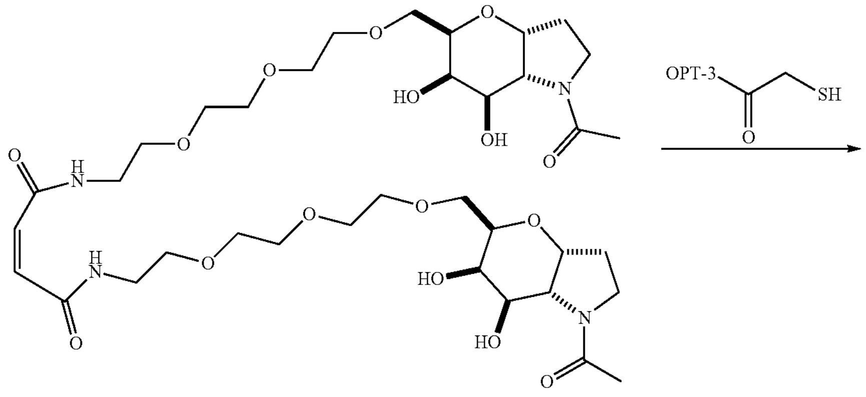
9-2
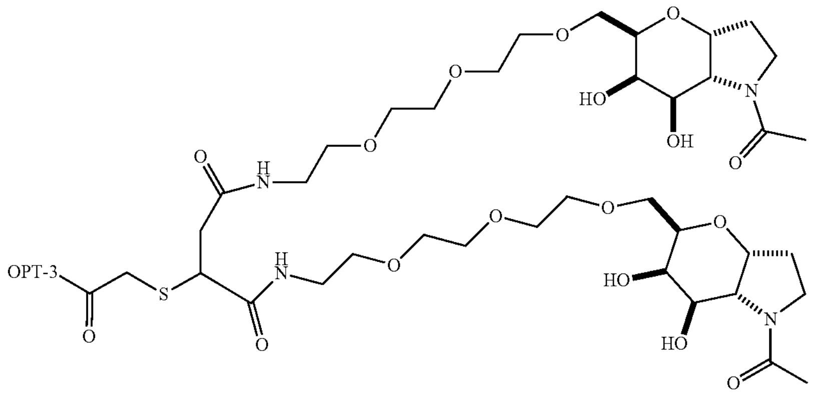
Compound 9

Example 4. Synthesis of Talose-Based ASGPR Ligands
Synthesis 4-1. Preparation of Bicyclic Talose amine Compound A123, Compound A124, and Compound A12
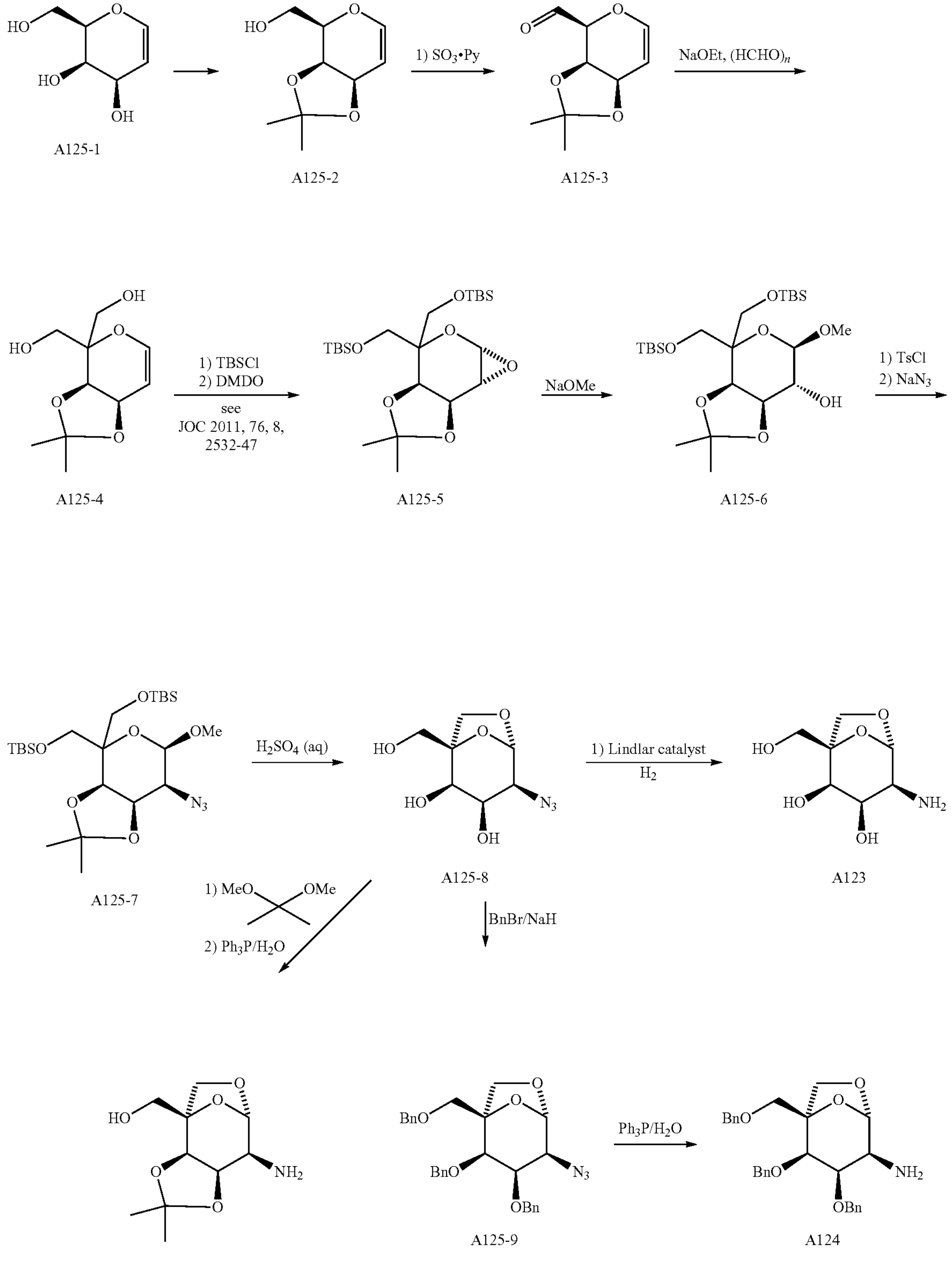
A125-1
A125-2
A125-3
A125-4
A125-5
A125-6
A125-7
A125-8
A123
A125
A125-9
A124

Synthesis 4-2. Preparation of tert-Butyl (((3aR,4S,8S,8aR)-8-amino-2,2-dimethyltetrahydro-4,7-epoxy[1,3]dioxolo[4,5-d]oxepin-4(5H)-yl)methyl)carbamate (Intermediate 1b)

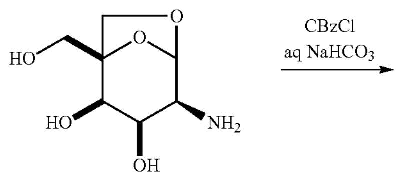

A-123

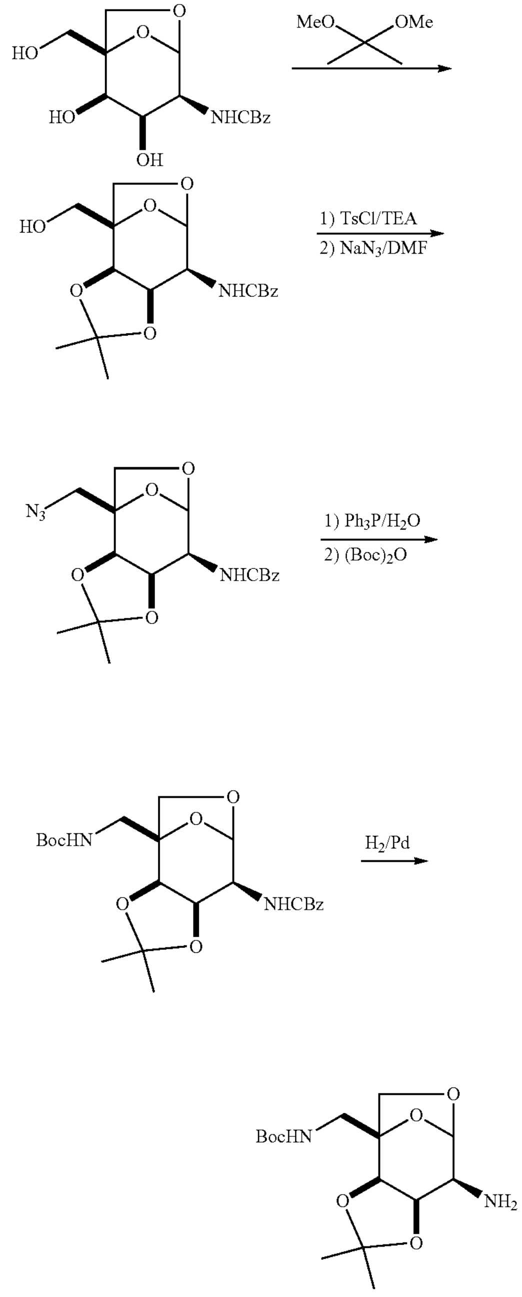

Intermediate 1b

Synthesis 4-3. Preparation of (2R,3R,4R)-3,4-bis(benzyloxy)-2-((benzyloxy)methyl)-3,4-dihydro-2H-pyran (Compound A126)

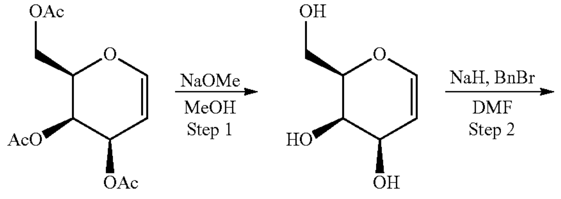

A126-1 A126-2

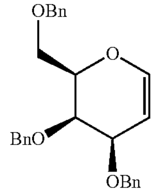

A126

Step 1: To a solution of (2R,3R,4R)-2-(acetoxymethyl)-3,4-dihydro-2H-pyran-3,4-diyl diacetate (A126-1, 30.0 g, 55.1 mmol) in MeOH (300 mL) was added NaOMe (31.0 mL, 165.3 mmol, 5.4 M in MeOH) at room temperature. The mixture was stirred at room temperature for 2 hours. The reaction was neutralized by the addition of Amberlite IR 120 ($H^+$) ion exchange resin. The solution was filtered through a glass fritted funnel with a pad of Celite to remove the resin. The filtrate was concentrated to dryness to give a crude triol. The crude material was passed through a plug of silica (70:30 to 85:15 EtOAc/hexanes) to give D-galactal triol (A126-2, 15.0 g 93%) as white solid. LC-MS (ESI) found: 147 $[M+H]^+$.

Step 2: To a solution of (2R,3R,4R)-2-(hydroxymethyl)-3,4-dihydro-2H-pyran-3,4-diol (A126-2, 15.0 g, 51.3 mmol) in DMF (200 mL) was added NaH (8.2 g, 205.3 mmol, 60% in mineral oil) at 0° C. in portions. The mixture was stirred at 0° C. for 0.5 hours. Benzyl bromide (49.0 mL, 205.3 mmol) was added at 0° C. in portions. The mixture was stirred at room temperature for 2 hours. The mixture was quenched with $H_2O$, extracted with ethyl acetate, washed with $H_2O$, and concentrated and purified by column to give (2R,3R,4R)-3,4-bis(benzyloxy)-2-((benzyloxy)methyl)-3,4-dihydro-2H-pyran (A126, 29.0 g, 68%) as white oil. LC-MS (ESI) found: 417 $[M+H]^+$.

Synthesis 4-4. Preparation of N-((3R,4R,5R,6R)-4,5-dihydroxy-6-(hydroxymethyl)tetrahydro-2H-pyran-3-yl)acetamide (Compound A127)

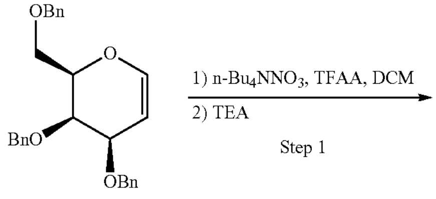

A126

-continued

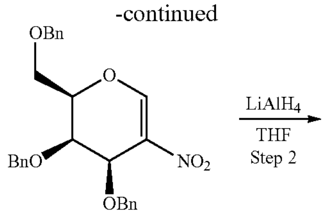

A91-1

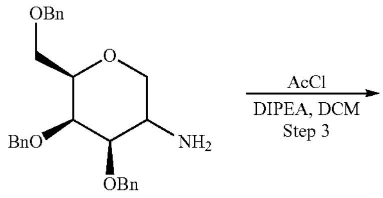

A91-1

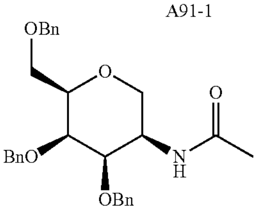

+

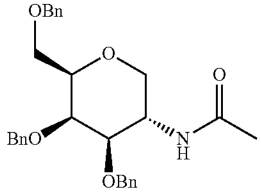

A127-3 A127-4

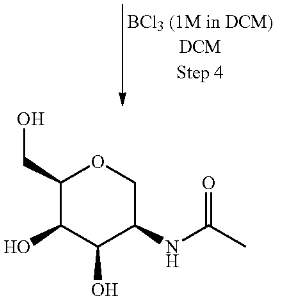

A127

Step 1: To a solution of (2R,3R,4R)-3,4-bis(benzyloxy)-2-((benzyloxy)methyl)-3,4-dihydro-2H-pyran from Synthesis 4-3 (A126, 6.6 g, 15.8 mmol) and n-$Bu_4NNO_3$ (5.3 g, 17.4 mmol) in dry DCM (70 mL) was added dropwise TFAA (3.7 g, 17.430 mmol) at 0° C. under $N_2$ atmosphere. After the addition was complete, the reaction was stirred at room temperature for 1 hour. Once the starting material was consumed (TLC monitoring), the reaction vessel was again cooled to 0° C., TEA (2.4 mL, 17.4 mmol) was slowly added and the reaction mixture was stirred for another 15 minutes. The reaction mixture was quenched with 10 mL ice water. Extraction was done with DCM (50 mL×3), and the combined organic extracts were washed with water (50 mL×3) and brine (150 mL), dried over $Na_2SO_4$. The mixture was concentrated in vacuo. The crude product was purified by flash chromatography (silica gel, 0-20% EtOAc in PE) to give (2R,3R,4R)-3,4-bis(benzyloxy)-2-((benzyloxy)methyl)-5-nitro-3,4-dihydro-2H-pyran (A126-1, 4 g, 8.7 mmol, 54.7% yield) as a yellow oil. $^1$H NMR (400 MHz, $CDCl_3$): δ 8.09 (s, 1H), 7.36-7.29 (m, 15H), 4.90 (dd, J=3.7, 1.3 Hz, 1H), 4.86 (d, J=10.8 Hz, 1H), 4.79 (d, J=10.8 Hz, 1H), 4.70 (dd, J=13.4, 8.5 Hz, 2H), 4.62 (d, J=11.9 Hz, 1H), 4.56 (d, J=11.9 Hz, 1H), 4.47 (d, J=11.9 Hz, 1H), 3.96-3.90 (m, 3H).

Step 2: To a solution of $LiAlH_4$ (0.66 g, 17.3 mmol) in dry THF (40 mL) was added (2R,3R,4R)-3,4-bis(benzyloxy)-2-((benzyloxy)methyl)-5-nitro-3,4-dihydro-2H-pyran (A126-1, 4 g, 8.7 mmol) in THF (10 mL) dropwise at 0° C. under $N_2$ atmosphere. The reaction mixture was stirred at rt for 1 h. The reaction was cooled to 0° C. and quenched with water (0.66 g), NaOH (0.66 g, 15% (w/w) in water), water (1.98 g). The mixture was filtered and concentrated in vacuo. The crude product was purified by flash chromatography (silica gel, 0-90% EtOAc in PE) to give (4R,5R,6R)-4,5-bis(benzyloxy)-6-((benzyloxy)methyl)tetrahydro-2H-pyran-3-amine (A126-2, 1 g, 2.307 mmol, 26.6% yield) as a colorless oil, as approximate 4:1 mixture of 3R/3S epimers. $^1$H NMR (400 MHz, $CDCl_3$): δ 7.39-7.27 (m, 15H), 4.90 (dd, J=22.9, 11.5 Hz, 1H), 4.74-4.68 (m, 1H), 4.67-4.60 (m, 1H), 4.58-4.50 (m, 2H), 4.44 (d, J=11.9 Hz, 1H), 4.05 (dd, J=12.0, 2.0 Hz, 1H), 3.92-3.85 (m, 1H), 3.73-3.66 (m, 1H), 3.59-3.51 (m, 3H), 3.48 (dd, J=8.4, 5.0 Hz, 1H), 3.15-3.07 (m, 1H).

Step 3: To a solution of (4R,5R,6R)-4,5-bis(benzyloxy)-6-((benzyloxy)methyl)tetrahydro-2H-pyran-3-amine (A126-2. 7.4 g, 17.1 mmol) and DIPEA (8.5 mL, 51.2 mmol) in DCM (80 mL) was added acetyl chloride (2.4 mL, 34.1 mmol) dropwise at 0° C. The reaction mixture was stirred at rt for 1.5 h. The resulting mixture was diluted with DCM (100 mL), washed with $H_2O$ (80 mL×2) and brine (80 mL), dried over $Na_2SO_4$, filtered. The organic layer was separated and concentrated in vacuo to give a crude product, which was purified by flash chromatography (silica gel, 0~80% EA in PE) to give N-((3R,4R,5R,6R)-4,5-bis(benzyloxy)-6-((benzyloxy)methyl)tetrahydro-2H-pyran-3-yl)acetamide (A127-3, 4.0 g, 8.4 mmol, 49.3%) as a colorless oil and N-((3S,4R,5R,6R)-4,5-bis(benzyloxy)-6-((benzyloxy)methyl)tetrahydro-2H-pyran-3-yl)acetamide (A127-4, 1.0 g, 2.1 mmol, 12.3% yield) as white solid. N-((3R,4R,5R,6R)-4,5-bis(benzyloxy)-6-((benzyloxy)methyl)tetrahydro-2H-pyran-3-yl)acetamide (A127-3): LC-MS (ESI) found: 476 $[M+H]^+$. $^1$H NMR (400 MHz, $CDCl_3$): δ 7.38-7.28 (m, 15H), 7.20 (d, J=8.5 Hz, 1H), 4.88 (d, J=10.3 Hz, 1H), 4.74 (d, J=11.8 Hz, 1H), 4.58 (d, J=11.8 Hz, 1H), 4.55-4.50 (m, 2H), 4.48 (d, J=10.9 Hz, 2H), 4.01 (dd, J=12.2, 1.8 Hz, 1H), 3.95-3.92 (m, 1H), 3.63 (d, J=6.4 Hz, 2H), 3.59 (dd, J=4.4, 2.9 Hz, 1H), 3.55-3.50 (m, 1H), 3.46 (dd, J=12.2, 1.7 Hz, 1H), 1.77 (s, 3H). N-((3S,4R,5R,6R)-4,5-bis(benzyloxy)-6-((benzyloxy)methyl)tetrahydro-2H-pyran-3-yl)acetamide (127-4): LC-MS (ESI) found: 476 $[M+H]^+$. $^1$H NMR (400 MHz, $CDCl_3$): δ 7.39-7.28 (m, 15H), 5.05 (s, 1H), 4.88 (d, J=11.5 Hz, 1H), 4.73 (d, J=12.2 Hz, 1H), 4.60 (d, J=11.6 Hz, 1H), 4.51 (d, J=11.9 Hz, 1H), 4.42 (dd, J=14.7, 12.0 Hz, 2H), 4.24-4.16 (m, 2H), 4.00 (d, J=1.8 Hz, 1H), 3.66-3.60 (m, 1H), 3.58-3.49 (m, 3H), 3.15 (t, J=11.9 Hz, 1H), 1.85 (s, 3H).

Step 4: To a solution of N-((3R,4R,5R,6R)-4,5-bis(benzyloxy)-6-((benzyloxy)methyl)tetrahydro-2H-pyran-3-yl)acetamide (A127-3, 100 mg, 0.2 mmol) in dry DCM (5 mL) was added $BCl_3$ (2.1 mL, 2.1 mmol, 1 M in DCM) dropwise at −10° C. under $N_2$ atmosphere. The reaction mixture was stirred at rt for 0.5 h. Then the reaction was cooled to 0° C. and quenched with saturated sodium bicarbonate solution. The mixture was filtered and concentrated in vacuo. The crude product was purified by flash chromatography (silica gel, 0-40% MeOH in DCM) to give N-((3R,4R,5R,6R)-4,5-dihydroxy-6-(hydroxymethyl)tetrahydro-2H-pyran-3-yl)acetamide (A127, 20 mg, 0.1 mmol, 46.4% yield) as a colorless oil. LC-MS (ESI) found: 206$[M+H]^+$. H NMR (400 MHz, $CD_3OD$): δ 4.08 (d, J=3.3 Hz, 1H), 3.93-3.86 (m, 2H), 3.79-3.73 (m, 2H), 3.67 (dd, J=11.5, 4.8 Hz, 1H), 3.53 (dd, J=12.0, 1.7 Hz, 1H), 3.44-3.37 (m, 1H).

Synthesis 4-5. Preparation of N-((3aR,4R,7R,7aR)-4-(hydroxymethyl)-2,2-dimethyltetrahydro-4H-[1,3]dioxolo[4,5-c]pyran-7-yl)acetamide (Intermediate 5) and N-((4aR,7R,8R,8aR)-8-hydroxy-2,2-dimethyl-hexahydropyrano[3,2-d][1,3]dioxin-7-yl)acetamide (A127-2c)

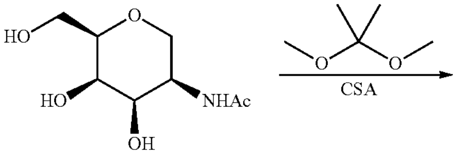

A-127

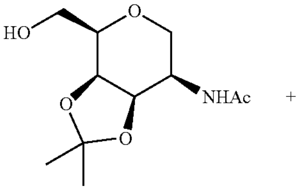

Intermediate 5

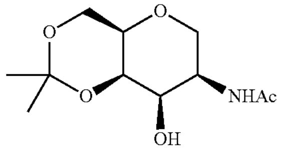

To a solution of N-((3R,4R,5R,6R)-4,5-dihydroxy-6-(hydroxymethyl)tetrahydro-2H-pyran-3-yl)acetamide from Synthesis 4-4 (A127, 100 mg, 0.49 mmol) in 2,2-dimethoxy-propane (2 mL) was added CSA (16.7 mg, 0.1 mmol) at room temperature under $N_2$. The reaction was stirred at room temperature overnight. The crude product was purified by prep-HPLC (Method A) to give N-((3aR,4R,7R,7aR)-4-(hydroxymethyl)-2,2-dimethyltetrahydro-4H-[1,3]dioxolo[4,5-c]pyran-7-yl)acetamide (Intermediate 5, 19 mg, 16% yield) and N-((4aR,7R,8R,8aR)-8-hydroxy-2,2-dimethyl-hexahydropyrano[3,2-d][1,3]dioxin-7-yl)acetamide (A127-2c, 27 mg, 23% yield) as a colorless oil. LC-MS (ESI) of both products found: 246[M+H]$^+$.

Synthesis 4-6. Preparation of (2R,3R,4R,5R)-5-amino-2-(hydroxymethyl)tetrahydro-2H-pyran-3,4-diol (Compound A128)

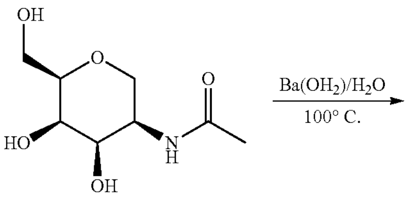

A127

-continued

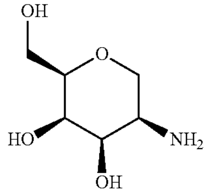

A128

To a solution of N-((3R,4R,5R,6R)-4,5-dihydroxy-6-(hydroxymethyl)tetrahydro-2H-pyran-3-yl)acetamide from Synthesis 4-4 (A127, 20.0 mg, 0.09 mmol) in $H_2O$ (2 mL) was added $Ba(OH)_2$ (166.0 mg, 0.97 mmol) at rt under $N_2$. The reaction mixture was stirred at 100° C. overnight. The resulting mixture was filtered and concentrated in vacuo. The crude product was purified by SCX cartridges to give (2R,3R,4R,5R)-5-amino-2-(hydroxymethyl)tetrahydro-2H-pyran-3,4-diol (A128, 4.5 mg, 28%) as colorless oil. LC-MS (ESI) found: 164 [M+H]$^+$. $^1$H NMR (400 MHz, $CD_3OD$): δ 3.96 (dd, J=12.1, 1.9 Hz, 1H), 3.82-3.80 (m, 1H), 3.76 (dd, J=11.4, 7.2 Hz, 1H), 3.68-3.64 (m, 1H), 3.62-3.58 (m, 2H), 3.38-3.35 (m, 1H), 2.97 (dd, J=3.8, 1.8 Hz, 1H).

Synthesis 4-7. Preparation of (3R,4R,5R,6R)-4,5-bis(benzyloxy)-6-((benzyloxy)methyl)tetrahydro-2H-pyran-3-amine (Compound A127-2a) and (3S,4R,5R,6R)-4,5-bis(benzyloxy)-6-((benzyloxy)methyl)tetrahydro-2H-pyran-3-amine (Compound A127-2b)

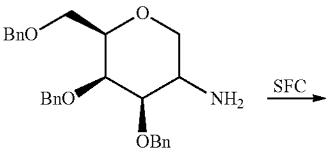

A127-2

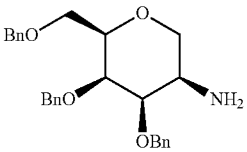

+

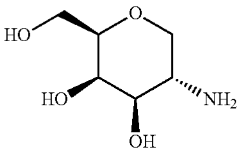

A127-2a A127-2b 75 mg of (3R,4R,5R,6R)-4,5-bis(benzyloxy)-6-((benzyloxy)methyl)tetrahydro-2H-pyran-3-amine (A127-2a) and 20 mg of (3S,4R,5R,6R)-4,5-bis(benzyloxy)-6-((benzyloxy)methyl)tetrahydro-2H-pyran-3-amine (A127-2b) were obtained by SFC separation from 100 mg of (3R,4R,5R,6R)-4,5-bis(benzyloxy)-6-((benzyloxy)methyl)tetrahydro-2H-pyran-3-amine (A127-2 from Synthesis 4-4). The SFC was performed on Waters Thar 80 preparative SFC (ChiralPak IC, 250×21.2 mm I.D., 5 μm; mobile phase: A for C02 and B for MeOH+0.1% $NH_3H_2O$, gradient (40% B); Flow rate: 50 mL/min, temperature: 35° C.).

Synthesis 4-8. Preparation of tert-butyl ((3R,4R,5R,6R)-4,5-dihydroxy-6-(hydroxymethyl)tetrahydro-2H-pyran-3-yl)carbamate (Compound A129)

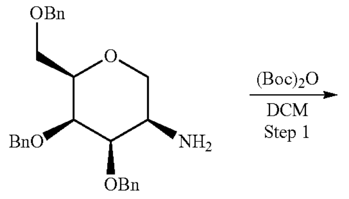

A127-2a

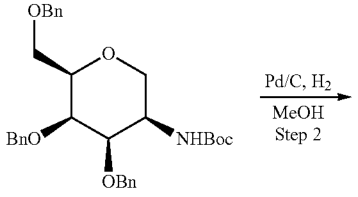

A129-1

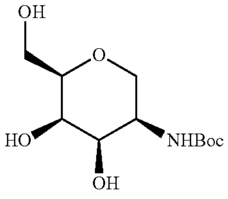

A129

Step 1: To a solution of (3R,4R,5R,6R)-4,5-bis(benzyloxy)-6-((benzyloxy)methyl)tetrahydro-2H-pyran-3-amine (A127-2a, 60 mg, 0.14 mmol) from Synthesis 4-7 in DCM (3 mL) was added $(Boc)_2O$ (60 mg, 0.28 mmol) at rt. After stirring at rt for 2 h, the mixture was concentrated. Then the residue was purified by flash chromatography (silica gel, 0-20% EtOAc in PE) to give tert-butyl ((3R,4R,5R,6R)-4,5-bis(benzyloxy)-6-((benzyloxy)methyl)tetrahydro-2H-pyran-3-yl)carbamate (A129-1, 65 mg, 0.12 mmol, 88%) as a colorless oil. LC-MS (ESI) found: 556 $[M+Na]^+$. $^1H$ NMR (400 MHz, $CDCl_3$): δ 7.41-7.27 (m, 15H), 6.25 (d, J=9.1 Hz, 1H), 4.97 (d, J=10.7 Hz, 1H), 4.79 (d, J=11.8 Hz, 1H), 4.50-4.46 (m, 4H), 4.20 (dd, J=9.0, 2.8 Hz, 1H), 4.04 (dd, J=12.1, 1.8 Hz, 1H), 3.87 (t, J=7.0 Hz, 1H), 3.60-3.56 (m, 3H), 3.47 (dd, J=12.1, 1.8 Hz, 1H), 1.57 (s, 9H).

Step 2: To a solution of tert-butyl ((3R,4R,5R,6R)-4,5-bis(benzyloxy)-6-((benzyloxy)methyl)tetrahydro-2H-pyran-3-yl)carbamate (A129-1, 60 mg, 0.11 mmol) in MeOH (2 mL) was added Pd/C (5 mg, 10% wt, 60% wet). The reaction was charged with $H_2$ for three time and stirred at rt for 16 h. The mixture was filtered through a Celite pad, and the filtrate was concentrated. The residue was purified by prep-HPLC (Column YMC Triart C18 250*20 mm, ID: 5 um. A: $H_2O$ (0.1% FA), B: ACN, A % from 95 to 55) to give tert-butyl ((3R,4R,5R,6R)-4,5-dihydroxy-6-(hydroxymethyl)tetrahydro-2H-pyran-3-yl)carbamate (A129, 20 mg, 0.076 mmol, 67.5%) as a colorless oil. LC-MS (ESI) found: 264 $[M+H]^+$. $^1H$ NMR (400 MHz, $CD_3OD$): δ 3.89 (dd, J=11.9, 1.4 Hz, 1H), 3.85-3.82 (m, 1H), 3.75 (dd, J=11.4, 7.1 Hz, 2H), 3.72-3.69 (m, 1H), 3.64 (dd, J=11.5, 4.8 Hz, 1H), 3.48 (dt, J=8.4, 4.2 Hz, 1H), 3.39-3.34 (m, 1H), 1.44 (s, 9H).

Synthesis 4-9. Alternative Preparation of (2R,3R,4R,5R)-5-amino-2-(hydroxymethyl)tetrahydro-2H-pyran-3,4-diol (Compound A128)

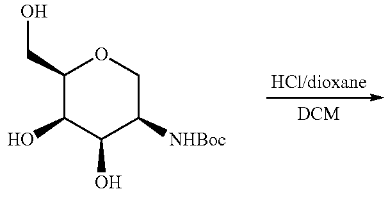

A129

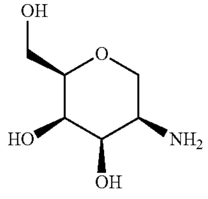

A128

A solution of tert-butyl ((3R,4R,5R,6R)-4,5-dihydroxy-6-(hydroxymethyl)tetrahydro-2H-pyran-3-yl)carbamate from Synthesis 4-8 (A129, 10 mg, 0.04 mmol) in DCM(1 mL) was treated with HCl/dioxane (1 mL). The reaction mixture was stirred at rt for 3 h and then evaporated to give (2R,3R,4R,5R)-5-amino-2-(hydroxymethyl)tetrahydro-2H-pyran-3,4-diol (A130, 3.5 mg, 0.021 mmol, 56.5%) as a colorless oil. LC-MS (ESI) found: 164 $[M+H]^+$.

Synthesis 4-10. Preparation of N-((3R,4R,5R,6R)-4,5-bis(benzyloxy)-6-((benzyloxy)methyl)tetrahydro-2H-pyran-3-yl)methanesulfonamide (Compound A130)

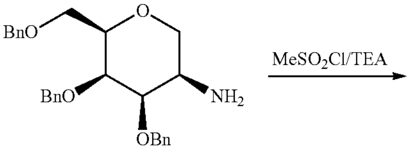

A127-2a

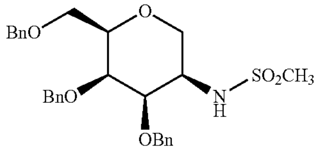

A130

To a solution of (3R,4R,5R,6R)-4,5-bis(benzyloxy)-6-(benzyloxymethyl)tetrahydro-2H-pyran-3-amine (100 mg, 0.23 mmol) and TEA (0.1 mL, 0.69 mmol) in dry DCM (5 mL) at 0° C. under $N_2$ atmosphere was added dropwise MsCl (0.04 mL, 0.46 mmol). The reaction mixture was stirred for 2 h. The resulting mixture was diluted with DCM (50 mL), washed with $H_2O$ (20 mL×2) and brine (30 mL), dried over $Na_2SO_4$. The organic layer was separated and concentrated in vacuo. The crude product was purified by flash chromatography (silica gel, 0~80% EA in PE) to give N-((3R,4R,5R,6R)-4,5-bis(benzyloxy)-6-((benzyloxy)methyl)tetrahydro-2H-pyran-3-yl)methanesulfonamide (100 mg, 85% yield) as a colorless oil. LC-MS (ESI) found: 534 [M+Na]$^+$. $^1$H NMR (400 MHz, $CDCl_3$): δ 7.40-7.27 (m, 15H), 6.09 (d, J=8.9 Hz, 1H), 4.88 (d, J=11.0 Hz, 1H), 4.77 (d, J=11.7 Hz, 1H), 4.57 (dd, J=21.4, 11.7 Hz, 3H), 4.45 (d, J=11.8 Hz, 1H), 4.06 (dd, J=12.2, 1.8 Hz, 1H), 3.95 (dd, J=7.4, 2.3 Hz, 2H), 3.62 (dd, J=9.0, 6.0 Hz, 1H), 3.58-3.48 (m, 4H), 2.89 (s, 3H).

Synthesis 4-11. Preparation of N-((3R,4R,5R,6R)-4,5-dihydroxy-6-(hydroxymethyl)tetrahydro-2H-pyran-3-yl)methanesulfonamide (Compound A131)

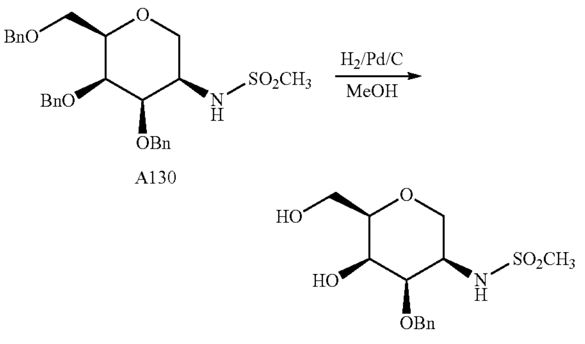

A130

A131

To a solution of N-((3R,4R,5R,6R)-4,5-bis(benzyloxy)-6-((benzyloxy)methyl)tetrahydro-2H-pyran-3-yl)methanesulfonamide (50 mg, 0.1 mmol) in MeOH (3 mL) was added Pd/C (5 mg, 10% wt, 60% wet) and HCl (1 mL, 1 M in $H_2O$) at rt under a $H_2$ balloon. The reaction was stirred at rt for 3 h. The resulting mixture was filtered and concentrated in vacuo. The crude product was purified by prep-HPLC (Method A) to give N-((3R,4R,5R,6R)-4,5-dihydroxy-6-(hydroxymethyl)tetrahydro-2H-pyran-3-yl) methanesulfonamide (1.9 mg, 8% yield) as a colorless oil. LC-MS (ESI) found: 242 [M+H]$^+$. $^1$H NMR (400 MHz, MeOD): δ 3.99 (dd, J=12.1, 2.1 Hz, 1H), 3.87-3.84 (m, 1H), 3.79-3.71 (m, 2H), 3.65 (dd, J=11.5, 4.8 Hz, 1H), 3.60-3.54 (m, J=13.6, 2.1 Hz, 2H), 3.40-3.35 (m, J=6.9, 4.8, 1.3 Hz, 1H), 3.04 (s, 3H).

Synthesis 4-12. Preparation of N-((3R,4R,5R,6R)-4,5-bis(benzyloxy)-6-((benzyloxy)methyl)tetrahydro-2H-pyran-3-yl)-1,1,1-trifluoromethanesulfonamide (Compound A132)

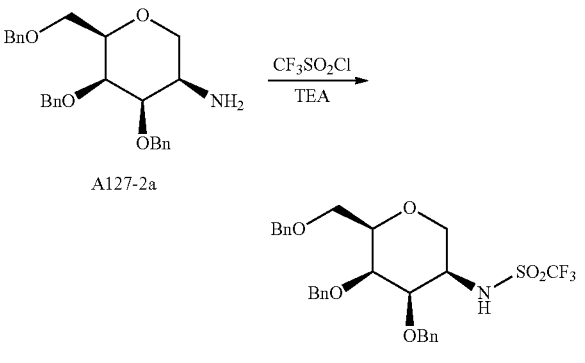

A127-2a

A132

Alternatively, Preparation of N-((3R,4R,5R,6R)-4,5-bis(benzyloxy)-6-((benzyloxy)methyl)tetrahydro-2H-pyran-3-yl)-1,1,1-trifluoromethanesulfonamide (Compound A132) can be Synthesized in the Following Manner

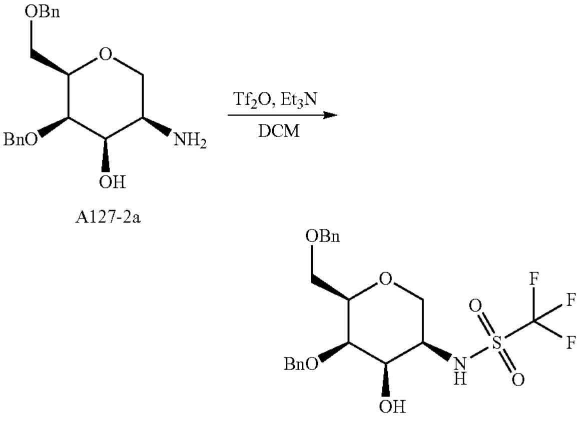

A127-2a

A132

To a solution of (3R,4R,5R,6R)-4,5-bis(benzyloxy)-6-((benzyloxy)methyl)tetrahydro-2H-pyran-3-amine (50 mg, 0.12 mmol) and TEA (0.05 mL, 0.35 mmol) in DCM (2 mL) was added $Tf_2O$ (0.04 mL, 0.23 mmol) at 0° C. The reaction was stirred at rt for 1.5 h. The resulting mixture was diluted with DCM (10 mL), washed with $H_2O$ (5 mL×2) and brine (5 mL), dried over $Na_2SO_4$. The organic layer was separated and concentrated in vacuo. The crude product was purified by flash chromatography (silica gel, 0~80% EA in PE) to give N-((3R,4R,5R,6R)-4,5-bis(benzyloxy)-6-((benzyloxy)methyl)tetrahydro-2H-pyran-3-yl)-1,1,1-trifluoromethanesulfonamide (35 mg, 54% yield) as a colorless oil. LC-MS (ESI) found: 588 [M+Na]$^+$. $^1$H NMR (400 MHz, $CDCl_3$): δ 7.40-7.26 (m, 15H), 7.00 (d, J=8.7 Hz, 1H), 4.92 (d, J=10.7 Hz, 1H), 4.83 (d, J=11.9 Hz, 1H), 4.57-4.50 (m, 3H), 4.44 (d, J=11.8 Hz, 1H), 4.06 (dd, J=12.5, 1.9 Hz, 1H), 4.00 (d, J=6.1 Hz, 1H), 3.95-3.92 (m, 1H), 3.59 (dd, J=8.8, 5.8 Hz, 1H), 3.55-3.46 (m, 4H).

Synthesis 4-13. Preparation of N-((3R,4R,5R,6R)-4,5-dihydroxy-6-(hydroxymethyl)tetrahydro-2H-pyran-3-yl)-1,1,1-trifluoromethanesulfonamide (Compound A133)

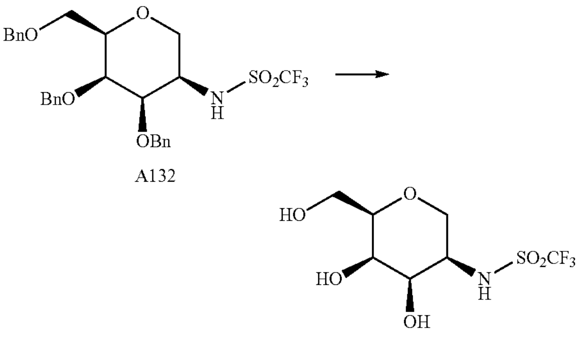

A132

A133

Alternatively, Preparation of N-((3R,4R,5R,6R)-4,5-dihydroxy-6-(hydroxymethyl)tetrahydro-2H-pyran-3-yl)-1,1,1-trifluoromethanesulfonamide (Compound A133) can be Synthesized in the Following Manner

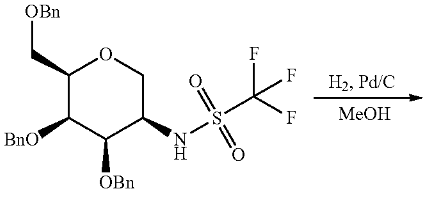

A132

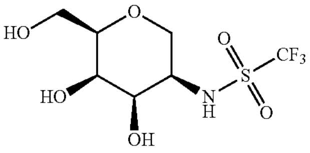

A133

To a solution of N-((3R,4R,5R,6R)-4,5-bis(benzyloxy)-6-((benzyloxy)methyl)tetrahydro-2H-pyran-3-yl)-1,1,1-trifluoromethanesulfonamide (35 mg, 0.06 mmol) in MeOH (3 mL) was added Pd/C (4 mg, 10% wt, 60% wet) and HCl (1 mL, 1 M in $H_2O$) at rt under a $H_2$ balloon. The resulting mixture was filtered and concentrated in vacuo. The crude product was purified by prep-HPLC (Method B) to give N-((3R,4R,5R,6R)-4,5-dihydroxy-6-(hydroxymethyl)tetrahydro-2H-pyran-3-yl)-1,1,1-trifluoromethanesulfonamide (10 mg, 55% yield) as a colorless oil. LC-MS (ESI) found: 294 $[M-H]^-$. $^1H$ NMR (400 MHz, MeOD): δ 3.96 (dd, J=12.3, 2.1 Hz, 1H), 3.90-3.86 (m, 1H), 3.80-3.73 (m, 2H), 3.72-3.63 (m, 2H), 3.60 (dd, J=12.3, 1.5 Hz, 1H), 3.44-3.39 (m, 1H). $^{19}F$ NMR (377 MHz, MeOD): δ−79.56 (s).

Synthesis 4-14. Preparation of N-((3R,4R,5R,6R)-4,5-dihydroxy-6-(hydroxymethyl)tetrahydro-2H-pyran-3-yl)-2,2,2-trifluoroacetamide (Compound A134) and N-((3S,4R,5R,6R)-4,5-dihydroxy-6-(hydroxymethyl)tetrahydro-2H-pyran-3-yl)-2,2,2-trifluoroacetamide (Compound A135)

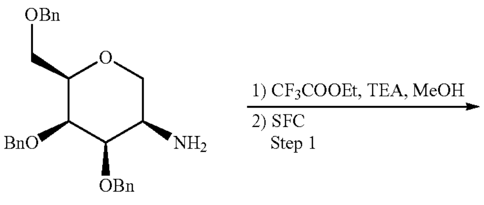

A127-2

-continued

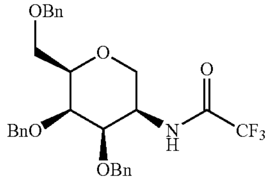

+

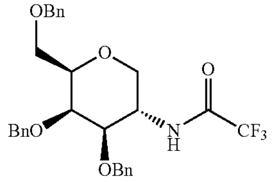

A134-1

A135-1

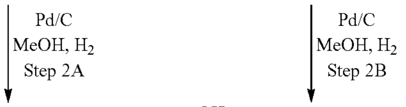

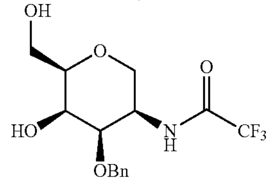

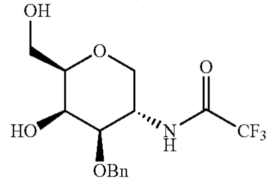

A134

A135

Step 1: To a solution of (4R,5R,6R)-4,5-bis(benzyloxy)-6-((benzyloxy)methyl)tetrahydro-2H-pyran-3-amine from Synthesis 4-7 (A127-2, 1.0 g, 2.3 mmol) and TEA (0.8 mL, 5.8 mmol) in MeOH (5 mL) was added dropwise $CF_3COOEt$ (0.41 mL, 3.46 mmol) at 0° C. and the reaction was stirred at rt for 1.5 h. The resulting mixture was diluted with DCM (50 mL), washed with $H_2O$ (15 mL×2) and brine (20 mL), dried over $Na_2SO_4$, filtered. The organic layer was concentrated in vacuo to get a crude product, which was purified by flash chromatography (silica gel, 0~80% EA in PE) to give the mixture (1.0 g) as a colorless oil. The mixture (100 mg) was then separated by SFC(OJ-H 4.6*250 mm, MeOH+0.05% DEA, 40%, 8 min) to give N-((3R,4R,5R,6R)-4,5-bis(benzyloxy)-6-((benzyloxy)methyl)tetrahydro-2H-pyran-3-yl)-2,2,2-trifluoroacetamide (A134-1, 50.0 mg) and N-((3S,4R,5R,6R)-4,5-bis(benzyloxy)-6-((benzyloxy)methyl)tetrahydro-2H-pyran-3-yl)-2,2,2-trifluoroacetamide (A135-1, 15.0 mg). N-((3R,4R,5R,6R)-4,5-bis(benzyloxy)-6-((benzyloxy)methyl)tetrahydro-2H-pyran-3-yl)-2,2,2-trifluoroacetamide (A134-1): LC-MS (ESI) found: 530 $[M+H]^+$. $^1H$ NMR (400 MHz, $CDCl_3$): δ 7.40-7.29 (m, 15H), 6.09 (d, J=5.9 Hz, 1H), 4.90 (d, J=11.5 Hz, 1H), 4.71 (d, J=12.1 Hz, 1H), 4.62 (d, J=11.5 Hz, 1H), 4.54-4.44 (m, 2H), 4.39 (d, J=12.1 Hz, 1H), 4.36-4.27 (m, 1H), 4.25-4.18 (m, 1H), 4.06 (d, J=2.2 Hz, 1H), 3.64-3.48 (m, 4H), 3.21 (t, J=10.8 Hz, 1H). N-((3S,4R,5R,6R)-4,5-bis(benzyloxy)-6-((benzyloxy)methyl)tetrahydro-2H-pyran-3-yl)-2,2,2-trifluoroacetamide (A-135-1): LC-MS (ESI) found: 530 $[M+H]^+$. $^1H$ NMR (400 MHz, $CDCl_3$): δ 8.26 (d, J=8.3 Hz, 1H), 7.41-7.24 (m, 15H), 4.86 (d, J=10.6 Hz, 1H), 4.72 (d, J=11.8 Hz, 1H), 4.57-4.44 (m, 5H), 4.04 (dd, J=12.5, 1.6 Hz, 1H), 3.96 (s, 1H), 3.65-3.49 (m, 5H).

Step 2A: To a solution of N-((3R,4R,5R,6R)-4,5-bis(benzyloxy)-6-((benzyloxy)methyl)tetrahydro-2H-pyran-3-yl)-2,2,2-trifluoroacetamide (A134-1, 35 mg, 0.07 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated in vacuo. The crude product was purified by prep-HPLC (Method A) to give N-((3R,4R,5R,6R)-4,5-dihydroxy-6-(hydroxymethyl)tetrahydro-2H-pyran-3-yl)-2,2,2-trifluoroacetamide (A134, 6.6 mg, 39%) as a white solid. LC-MS (ESI) found: 258 $[M-H]^-$. H NMR (400 MHz, $CD_3OD$): δ 4.28-4.15 (m, 1H), 3.95-3.86 (m, 2H), 3.76-3.61 (m, 3H), 3.44-3.39 (m, 1H), 3.20 (t, J=11.0 Hz, 1H). $^{19}F$ NMR (377 MHz, CD3OD): δ−77.23 (s).

Step 2B: To a solution of N-((3S,4R,5R,6R)-4,5-bis(benzyloxy)-6-((benzyloxy)methyl)tetrahydro-2H-pyran-3-yl)-2,2,2-trifluoroacetamide (A135-1, 15 mg, 0.03 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated in vacuo. The crude product was purified by (Method B) to give N-((3S,4R,5R,6R)-4,5-dihydroxy-6-(hydroxymethyl)tetrahydro-2H-pyran-3-yl)-2,2,2-trifluoroacetamide (A135, 4.9 mg, 66%) as a colorless oil. LC-MS (ESI) found: 258 $[M-H]^-$. $^1H$ NMR (400 MHz, MeOD): δ 4.12 (d, J=2.3 Hz, 1H), 3.97-3.89 (m, 2H), 3.83-3.74 (m, 2H), 3.70-3.57 (m, 2H), 3.45-3.39 (m, 1H). $^{19}F$ NMR (377 MHz, MeOD): δ−78.03 (s).

Synthesis 4-15. Preparation of N-((3R,4R,5R,6R)-4,5-dihydroxy-6-(hydroxymethyl)tetrahydro-2H-pyran-3-yl)benzamide (Compound A136) and N-((3S,4R,5R,6R)-4,5-dihydroxy-6-(hydroxymethyl)tetrahydro-2H-pyran-3-yl)benzamide (Compound A137)

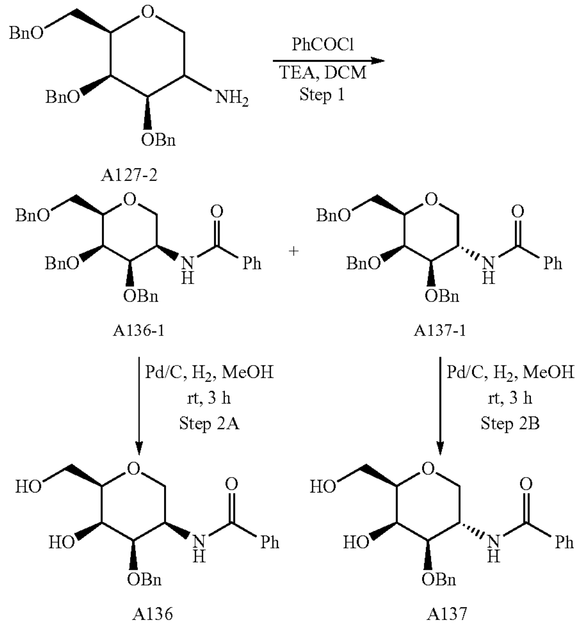

A127-2
A136-1 + A137-1
A136 A137

Step 1: To a solution of (4R,5R,6R)-4,5-bis(benzyloxy)-6-((benzyloxy)methyl)tetrahydro-2H-pyran-3-amine from Synthesis 4-7 (A127-2, 0.74 g, 1.7 mmol) and DIPEA (0.85 mL, 5.1 mmol) in DCM (8.0 mL) was added benzoyl chloride (0.48 g, 3.4 mmol) dropwise at 0° C. The reaction mixture was stirred at rt for 1.5 h. The resulting mixture was diluted with DCM (10 mL), washed with $H_2O$ (10 mL×2) and brine (10 mL), dried over $Na_2SO_4$, filtered. The organic layer was concentrated in vacuo to give a crude product, which was purified by flash chromatography (silica gel, 0~80% EA in PE) to give N-((3R,4R,5R,6R)-4,5-bis(benzyloxy)-6-((benzyloxy)methyl)tetrahydro-2H-pyran-3-yl)benzamide (A136-1) and N-((3S,4R,5R,6R)-4,5-bis(benzyloxy)-6-((benzyloxy)methyl)tetrahydro-2H-pyran-3-yl)benzamide (A137-1). LC-MS (ESI) of both found: 538 $[M+H]^+$.

Step 2A: To a solution of N-((3R,4R,5R,6R)-4,5-bis(benzyloxy)-6-((benzyloxy)methyl)tetrahydro-2H-pyran-3-yl)benzamide (A136-1, 35 mg, 0.065 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated in vacuo. The crude product was purified by prep-HPLC (Method A) to give N-((3R,4R,5R,6R)-4,5-dihydroxy-6-(hydroxymethyl)tetrahydro-2H-pyran-3-yl)benzamide (A136). LC-MS (ESI) of found: 268 $[M+H]^+$.

Step 2B: To a solution of N-((3S,4R,5R,6R)-4,5-bis(benzyloxy)-6-((benzyloxy)methyl)tetrahydro-2H-pyran-3-yl)benzamide (A137-1, 35 mg, 0.065 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated in vacuo. The crude product was purified by prep-HPLC (Method A) to give N-((3S,4R,5R,6R)-4,5-dihydroxy-6-(hydroxymethyl)tetrahydro-2H-pyran-3-yl)benzamide (A136). LC-MS (ESI) of found: 268 $[M+H]^+$.

Synthesis 4-16. Alternative Preparation of (2R,3R,4R,5R)-5-amino-2-(hydroxymethyl)tetrahydro-2H-pyran-3,4-diol (Compound A128) and (2R,3R,4R,5S)-5-amino-2-(hydroxymethyl)tetrahydro-2H-pyran-3,4-diol (Compound A92)

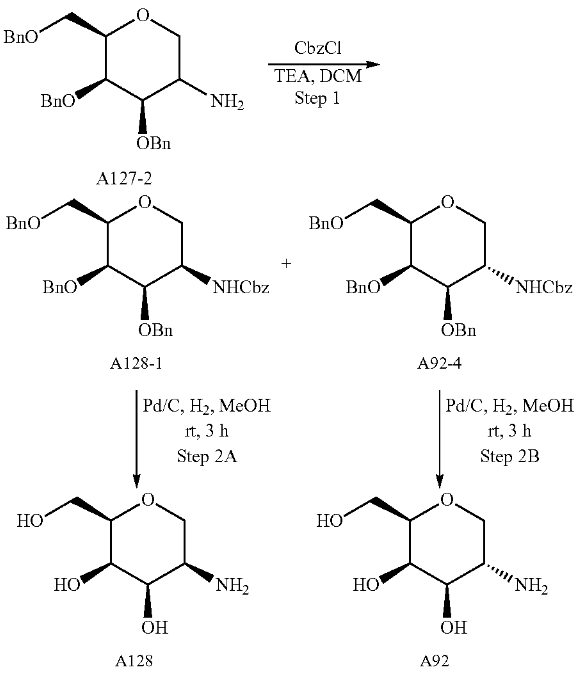

A127-2
A128-1 + A92-4
A128 A92

Step 1: To a solution of (4R,5R,6R)-4,5-bis(benzyloxy)-6-((benzyloxy)methyl)tetrahydro-2H-pyran-3-amine from Synthesis 4-7 (A127-2, 0.74 g, 1.7 mmol) and DIPEA (0.85 mL, 5.1 mmol) in DCM (8.0 mL) was added CbzCl (0.58 g, 3.4 mmol) dropwise at 0° C. The reaction mixture was stirred at rt for 1.5 h. The resulting mixture was diluted with DCM (10 mL), washed with $H_2O$ (10 mL×2) and brine (10 mL), dried over $Na_2SO_4$, filtered. The organic layer was concentrated in vacuo to give a crude product, which was purified by flash chromatography (silica gel, 0~80% EA in PE) to give benzyl ((3R,4R,5R,6R)-4,5-bis(benzyloxy)-6-

((benzyloxy)methyl)tetrahydro-2H-pyran-3-yl)carbamate (A128-1) and benzyl ((3S,4R,5R,6R)-4,5-bis(benzyloxy)-6-((benzyloxy)methyl)tetrahydro-2H-pyran-3-yl)carbamate (A92-4). LC-MS (ESI) of both found: 568 $[M+H]^+$.

Step 2A: To a solution of benzyl ((3R,4R,5R,6R)-4,5-bis(benzyloxy)-6-((benzyloxy)methyl)tetrahydro-2H-pyran-3-yl)carbamate (A128-1, 35 mg, 0.06 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated to give (2R,3R,4R,5R)-5-amino-2-(hydroxymethyl)tetrahydro-2H-pyran-3,4-diol (A128). LC-MS (ESI) of both found: 164 $[M+H]^+$.

Step 2B: To a solution of benzyl ((3S,4R,5R,6R)-4,5-bis(benzyloxy)-6-((benzyloxy)methyl)tetrahydro-2H-pyran-3-yl)carbamate (A92-4, 35 mg, 0.06 mmol) in MeOH (3 mL) was added Pd/C (5 mg, 10% wt, 60% wet) at rt under $H_2$. The reaction was stirred at rt under $H_2$ atmosphere for 3 h. The resulting mixture was filtered and concentrated to give (2R,3R,4R,5S)-5-amino-2-(hydroxymethyl)tetrahydro-2H-pyran-3,4-diol (A92). LC-MS (ESI) of both found: 164 $[M+H]^+$.

Synthesis 4-17. Preparation of (2R,3R,4R,5R)-5-((5-chloro-3-fluoropyridin-2-yl)amino)-2-(hydroxymethyl)tetrahydro-2H-pyran-3,4-diol (Compound A138)

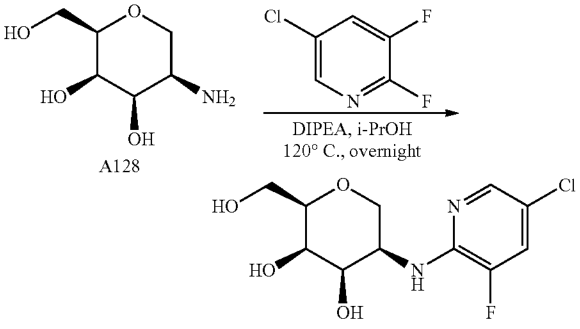

A128

A138

A solution of (2R,3R,4R,5R)-5-amino-2-(hydroxymethyl)tetrahydro-2H-pyran-3,4-diol (A128, 3.5 mg, 0.02 mmol), 5-chloro-2,3-difluoropyridine (8.9 mg, 0.06 mmol) and DIPEA (11.6 mg, 0.09 mmol) in i-PrOH (4 mL) was stirred at 120° C. overnight. The mixture was concentrated in vacuo. The crude product was purified by pre-HPLC (Method A) to give (2R,3R,4R,5R)-5-((5-chloro-3-fluoropyridin-2-yl)amino)-2-(hydroxymethyl)tetrahydro-2H-pyran-3,4-diol (A138) as a white solid (1.0 mg, 16%). LC-MS (ESI) found: 293 $[M+H]^+$.

The following compounds are prepared by the SNAr reaction in a method similar to that of Synthesis 4-17 using either heating in isopropanol or NMP with Hunig's base and the corresponding commercially available chloro or fluoro heterocycle.

A139

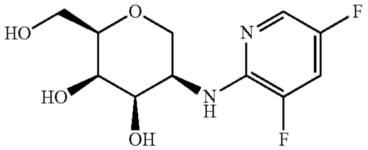

-continued

A140

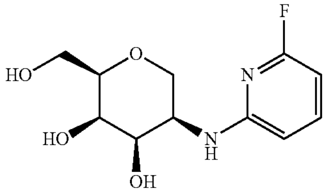

A141

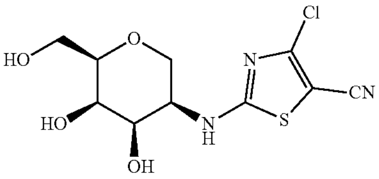

A142

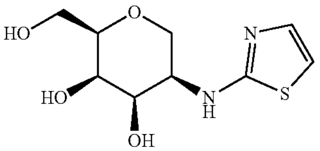

A143

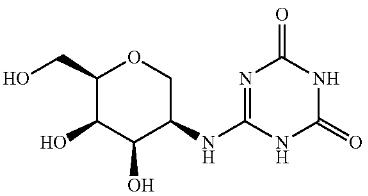

A144

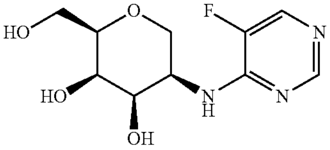

A145

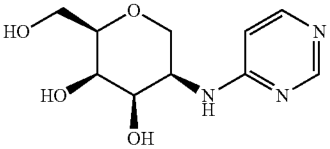

A146

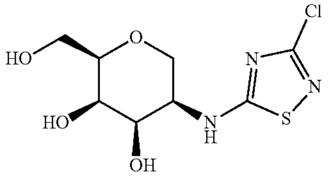

A147

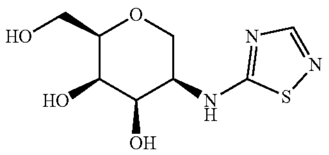

-continued

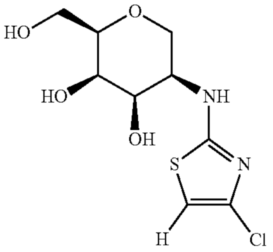

A148

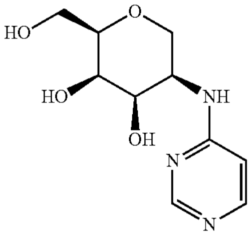

A149

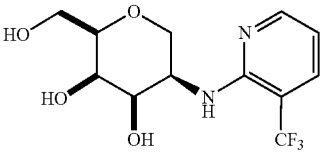

A150

Preparation of (2R,3R,4R,5R)-5-((3-chloro-1,2,4-thiadiazol-5-yl)amino)-2-(hydroxy methyl)tetrahydro-2H-pyran-3,4-diol (Compound A146)

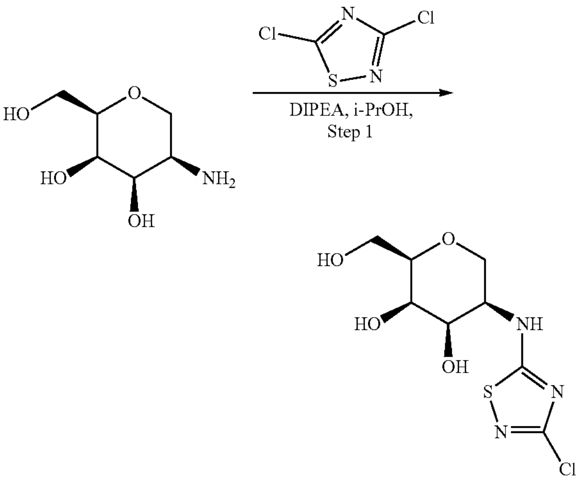

A146

Step 1: To a solution of (2R,3R,4R,5R)-5-amino-2-(hydroxymethyl)tetrahydro-2H-pyran-3,4-diol (50 mg, 0.3 mmol) and 3,5-dichloro-1,2,4-thiadiazole (142.5 mg, 0.92 mmol) in iPrOH (2 mL) was added DIPEA (0.25 mL, 1.53 mmol). The mixture was stirred at 80° C. under $N_2$ overnight. The resulting mixture was filtered. The crude product was purified by flash chromatography (silica gel, 0~~10%0 MeOH in DCM) to give (2R,3R,4R,5R)-5-((3-chloro-1,2,4-thiadiazol-5-yl)amino)-2-(hydroxymethyl)tetrahydro-2H-pyran-3,4-diol. (15 mg, 1700 yield) as a colorless oil. LC-MS (ESI) found: 282 $[M+H]^+$. $^1H$ NMR (400 MHz, MeOD): δ 4.08 (dd, J=12.2, 1.9 Hz, 1H), 4.01 (s, 1H), 3.92-3.88 (m, 1H), 3.85-3.76 (m, 2H), 3.68 (dd, J=11.5, 4.7 Hz, 1H), 3.60 (dd, J=12.2, 1.6 Hz, 1H), 3.46-3.42 (in, 1H).

| ID | Characterization data | |
|---|---|---|
| 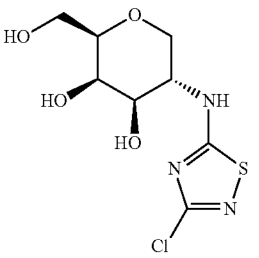 A146 | Yield: 15 mg, 17%, colorless oil. LC-MS (ESI) found: 282 $[M + H]^+$ . $^1H$ NMR (400 MHz, MeOD): δ 4.08 (dd, J = 12.2, 1.9 Hz, 1H), 4.01 (s, 1H), 3.92-3.88 (m, 1H), 3.85-3.76 (m, 2H), 3.68 (dd, J = 11.5, 4.7 Hz, 1H), 3.60 (dd, J = 12.2, 1.6 Hz, 1H), 3.46-3.42 (m, 1H). | 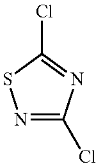 |
| 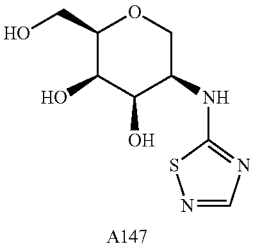 A147 | Yield: 9.1 mg, 12.1%, colorless oil. LC-MS (ESI) found: 248 $[M + H]^+$ . $^1H$ NMR (400 MHz, MeOD): δ 7.86 (s, 1H), 4.09 (dd, J = 12.2, 2.0 Hz, 1H), 3.96 (s, 1H), 3.92-3.89 (m, 1H), 3.82 (ddd, J = 18.6, 8.0, 5.2 Hz, 2H), 3.68 (dd, J = 11.5, 4.7 Hz, 1H), 3.59 (dd, J = 12.2, 1.6 Hz, 1H), 3.45 (ddd, J = 6.9, 4.7, 1.2 Hz, 1H). | 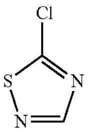 |

-continued

| ID | Characterization data | |
| --- | --- | --- |
| 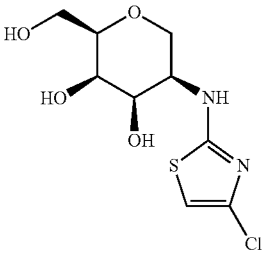 A148 | Yield: 5.1 mg, 5.9%, white solid. LC-MS (ESI) found: 281 $[M + H]^+$. $^1H$ NMR (400 MHz, MeOD): δ 6.35 (s, 1H), 4.08 (dd, J = 12.1, 2.0 Hz, 1H), 3.92-3.89 (m, 2H), 3.81-3.76 (m, 2H), 3.67 (dd, J = 11.5, 4.7 Hz, 1H), 3.54 (dd, J = 12.1, 1.6 Hz, 1H), 3.42 (ddd, J = 7.0, 4.7, 1.2 Hz, 1H). | 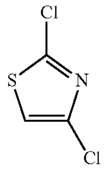 |
| 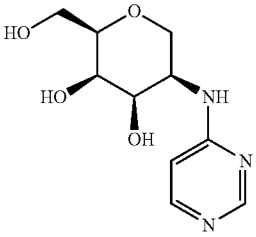 A149 | Yield: 10 mg, 71%, colorless oil. LC-MS (ESI) found: 242 $[M + H]^+$. $^1H$ NMR (400 MHz, MeOD): δ 8.60 (s, 1H), 8.05 (s, 1H), 6.86 (d, J = 6.6 Hz, 1H), 4.03 (d, J = 10.9 Hz, 1H), 3.94 (s, 1H), 3.91-3.88 (m, 1H), 3.82-3.65 (m, 4H), 3.50-3.45 (m, 1H). | 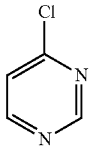 |

Synthesis 4-18. Preparation of (2R,3R,4R,5R)-5-((3-(dimethylamino)-1,2,4-thiadiazol-5-yl)amino)-2-(hydroxymethyl)tetrahydro-2H-pyran-3,4-diol (Compound A151)

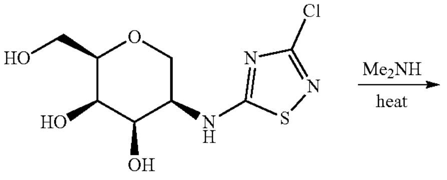

A146

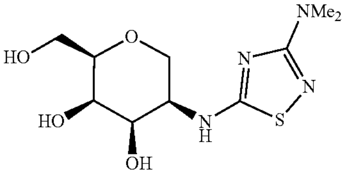

A151

Synthesis 4-19. General Synthesis of Amine-Containing Compounds

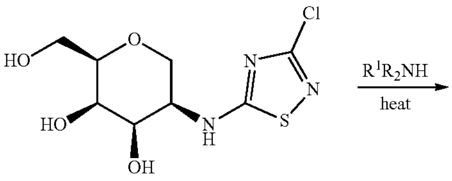

A146

-continued

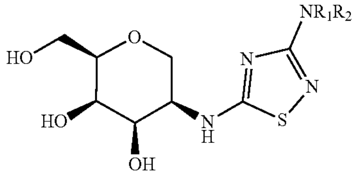

A152

Synthesis 4-20. Preparation of N-((3S,4R,5R,6R)-6-(aminomethyl)-4,5-dihydroxy-2-methoxytetrahydro-2H-pyran-3-yl)acetamide (Compound A53) and N-((3S,4R,5R,6R)-6-(aminomethyl)-4,5-dihydroxy-2-methoxytetrahydro-2H-pyran-3-yl)-2,2,2-trifluoroacetamide (Compound A154)

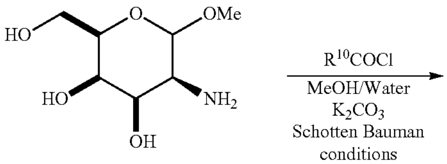

A154-1

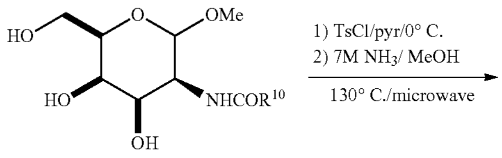

A154-2

-continued

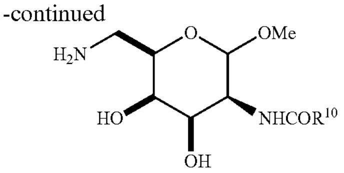

Compound A153 ($R^{10}$ = $CH_3$)

Compound A154 ($R^{10}$ = $CF_3$)

Alternatively, N-((3S,4R,5R,6R)-4,5-dihydroxy-6-(hydroxymethyl)-2-methoxytetrahydro-2H-pyran-3-yl)acetamide (Compound A153) can be Synthesized in the Following Manner

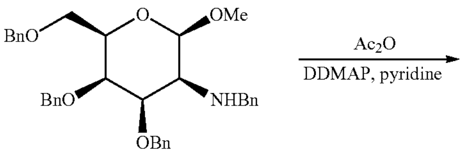

A214-4

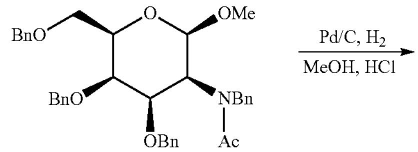

A153-1

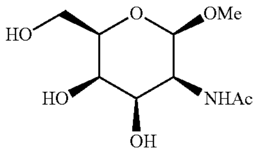

A153

Step 1: To a solution of (2R,3S,4R,5R,6R)—N-benzyl-4,5-bis(benzyloxy)-6-((benzyloxy)methyl)-2-methoxytetrahydro-2H-pyran-3-amine (280 mg, 0.506 mmol) DMAP (12.36 mg, 0.101 mmol) and pyridine(0.818 mL, 10.120 mmol) in DCM (5 mL) was added acetic anhydride (0.475 mL, 5.060 mmol) at ice-bath. The mixture was allowed to warm to rt and stirred for 3 h. Then the solvent was removed. The residue was purified by prep-HPLC (Method A) to give N-benzyl-N-((2R,3S,4R,5R,6R)-4,5-bis(benzyloxy)-6-((benzyloxy)methyl)-2-methoxytetrahydro-2H-pyran-3-yl) acetamide (160 mg, 53% yield). LC-MS (ESI) found: 596 $[M+H]^+$.

Step 2: The solution of N-benzyl-N-((2R,3S,4R,5R,6R)-4,5-bis(benzyloxy)-6-((benzyloxy)methyl)-2-methoxytetrahydro-2H-pyran-3-yl)acetamide (100 mg, 0.198 mmol) in MeOH (5 mL) was added Pd/C (10 mg, 10% wt, 60% wet) and HCl (1 mL, 1 M in $H_2O$) at rt under a $H_2$ balloon. The mixture was stirred overnight. The solvent was removed under vacuum. The residue was purified by prep-HPLC (Method A) to give product (A153, 5 mg, 10% yield) as colorless oil. LC-MS (ESI) found: 236 $[M+H]^+$.

Example 5. Synthesis of ASGPR Ligands

Synthesis 5-1. General Synthesis of Sulfonamide-Containing Ligands

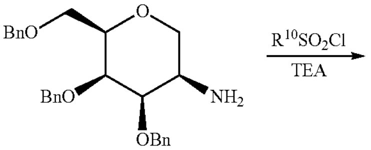

A127-2a

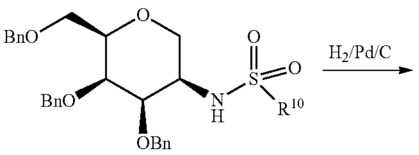

A155-1

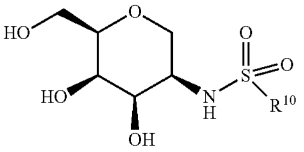

A155

Synthesis 5-2. General Synthesis of Sulfonyl Urea-Containing Compounds

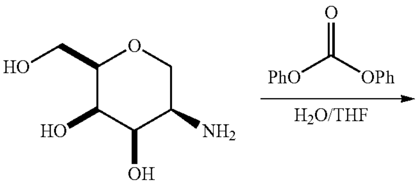

A127-2a

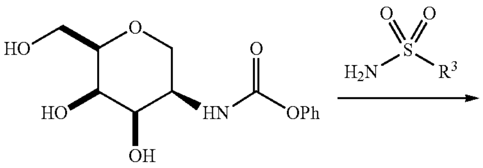

A156-1

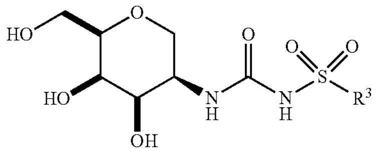

A156

Org. Biomol. Chem., 2017, 15, 4992-4999

Synthesis 5-3. Preparation of N-(((3S,4R,5R,6R)-4,5-dihydroxy-6-(hydroxymethyl)tetrahydro-2H-pyran-3-yl)carbamoyl)methanesulfonamide (Compound A157)

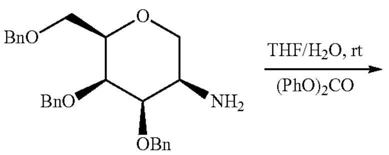

A127-2b

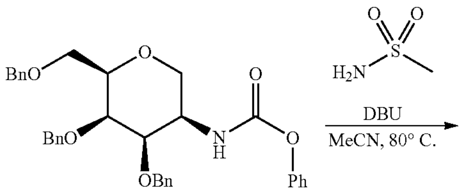

A157-1

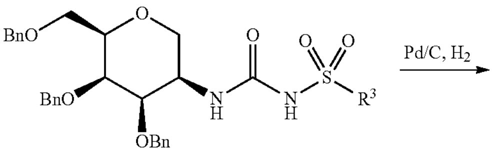

A157-2

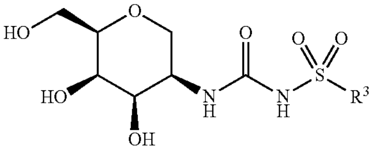

A157

Step 1: To the solution of (3R,4R,5R,6R)-3-amino-6-(hydroxymethyl)tetrahydro-2H-pyran-2,4,5-triol hydrochloride (200 mg, 0.461 mmol) in THF (1 ml) and $H_2O$ (9 ml) was dropwise added diphenyl carbonate (119 mg, 0.554 mmol). The mixture was stirred at rt overnight. The mixture was extracted with EA, washed with NaOH solution, dried over $Na_2SO_4$, concentrated and purified by silica (silica gel, 0-100% EA in PE) to give phenyl N-[2,4,5-trihydroxy-6-(hydroxymethyl)oxan-3-yl]carbamate (100 mg, 39% yield) as solid. LC-MS (ESI) found: 554 $[M+H]^+$.

Step 2: A solution of phenyl N-[4,5-bis(benzyloxy)-6-[(benzyloxy)methyl]oxan-3-yl]carbamate (20 mg, 0.036 mmol), methanesulfonamide (7 mg, 0.072 mmol) and DBU (17 mg, 0.108 mmol) in $CH_3CN$ (5 mL) was stirred at 80° C. overnight. The mixture was concentrated and purified by column (silica gel, 0-10% MeOH in DCM) to give 1-[4,5-bis(benzyloxy)-6-[(benzyloxy)methyl]oxan-3-yl]-3-methanesulfonylurea (10 mg, 50% yield) as white solid. LC-MS (ESI) found: 555 $[M+H]^+$.

Step 3: To the solution of 1-[4,5-bis(benzyloxy)-6-[(benzyloxy)methyl]oxan-3-yl]-3-methanesulfonylurea (10 mg, 0.018 mmol) in MeOH (2 mL) was added Pd/C (4 mg, 10% wt, 60% wet), the mixture was stirred at rt overnight under a $H_2$ balloon. The mixture was filtered and purified by prep-HPLC (Method A) to give N-(((3S,4R,5R,6R)-4,5-dihydroxy-6-(hydroxymethyl)tetrahydro-2H-pyran-3-yl)carbamoyl)methanesulfonamide (9 mg, 46%) as white solid. LC-MS (ESI) found: 285 $[M+H]^+$. $^1$H NMR (400 MHz, MeOD): δ 4.03 (dd, J=10.6, 5.2 Hz, 1H), 3.95 (dd, J=10.5, 5.0 Hz, 1H), 3.86 (d, J=2.7 Hz, 1H), 3.72 (dd, J=10.7, 7.7 Hz, 1H), 3.65 (dd, J=11.3, 4.9 Hz, 1H), 3.50 (dd, J=10.3, 3.1 Hz, 1H), 3.44-3.38 (m, 1H), 3.22 (s, 1H), 3.12 (t, J=10.5 Hz, 1H).

Synthesis 5-4. General Synthesis of Sulfonimidamide-Containing Ligands

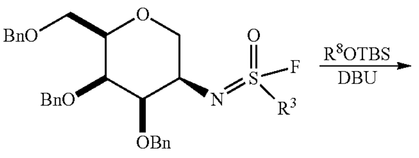

A158-1

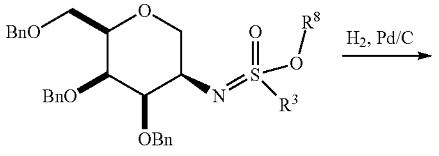

A158-2

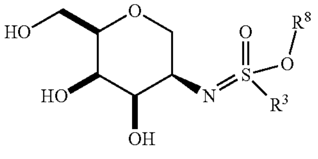

A158

Synthesis 5-5. Alternative General Synthesis of Sulfonimidamide-Containing Ligands

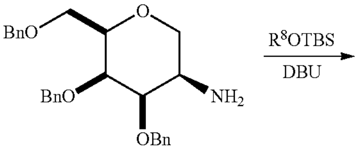

A127-2a

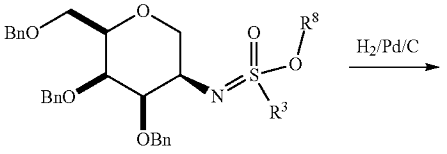

A158-2

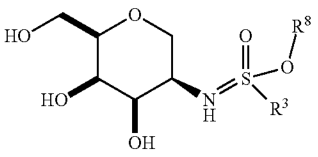

A158

Synthesis 5-6. General Synthesis of ASGPR Ligands

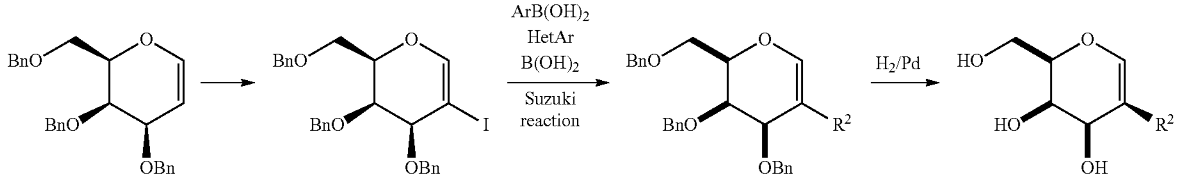

A126 A122-1 A159-1 A159-2

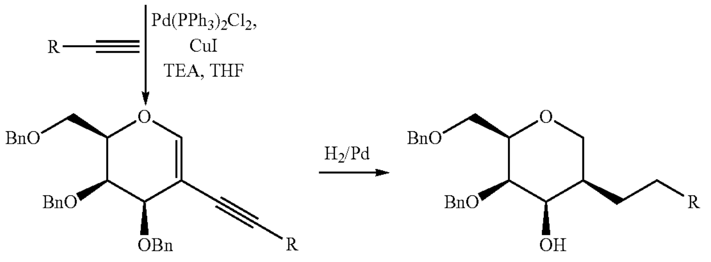

A159-3 A159

Synthesis 5-7. Preparation of (2R,3R,4R,5R)-2-(hydroxymethyl)-5-phenethyltetrahydro-2H-pyran-3,4-diol (Compound A161)

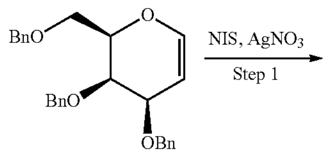

A126

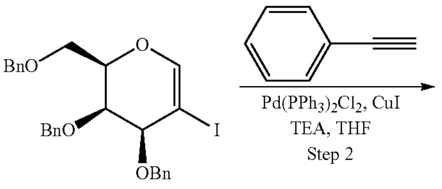

A122-1

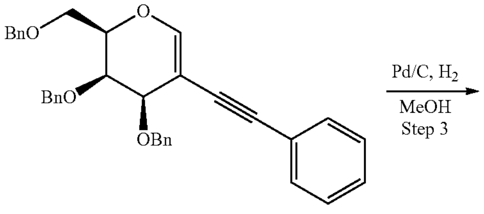

A160-1

-continued

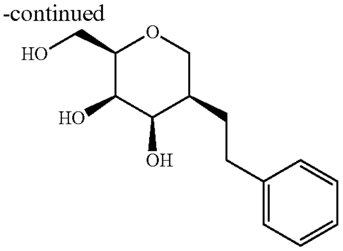

A160

Step 1: A solution of (2R,3R)-3,4-bis(benzyloxy)-2-[(benzyloxy)methyl]-3,4-dihydro-2H-pyran (A126, 6.0 g, 14.4 mmol), NIS (3.8 g, 17.3 mmol) and $AgNO_3$ (0.5 g, 2.9 mmol) in $CH_3CN$ (100 mL) was stirred at 80° C. for 30 min. The mixture was filtered and concentrated to give a yellow solid, which was purified by column chromatography on silica gel to give (2R,3S,4S)-3,4-bis(benzyloxy)-2-((benzyloxy)methyl)-5-iodo-3,4-dihydro-2H-pyran (A122-1, 3.4 g, 44%) as a white solid. LC-MS (ESI) found: 543 $[M+H]^+$. H NMR (400 MHz, $CD_3OD$): δ 7.45-7.22 (m, 15H), 6.63 (d, J=1.2 Hz, 1H), 4.81-4.67 (m, 3H), 4.60-4.38 (m, 3H), 4.34 (t, J=7.0 Hz, 1H), 4.20 (t, J=5.5 Hz, 1H), 4.13 (dt, J=12.2, 6.1 Hz, 1H), 3.76-3.60 (m, 2H).

Step 2: To a solution of (2R,3S,4S)-3,4-bis(benzyloxy)-2-((benzyloxy)methyl)-5-iodo-3,4-dihydro-2H-pyran (A122-1, 400 mg, 0.74 mmol) in THF (3 mL) was added CuI (14 mg, 0.074 mmol), TEA (223.45 mg, 2.212 mmol), $Pd(PPh_3)_2Cl_2$ (85 mg, 0.074 mmol) and ethynylbenzene (0.12 mL, 1.106 mmol). The mixture was charged with $N_2$ for three times and stirred at 60° C. under $N_2$ atmosphere overnight. The mixture was concentrated and purified by flash eluting with PE/EA (from 95/5 to 50/50) to give desired product (A160-1, 360 mg, 95%) as off-white solid. LC-MS (ESI) found: 517 $[M+H]^+$.

Step 3: To a solution of (2R,3R,4R)-3,4-bis(benzyloxy)-2-((benzyloxy)methyl)-5-(phenylethynyl)-3,4-dihydro-2H-pyran (160-1, 25 mg, 0.048 mmol) in MeOH (3 mL) was added Pd/C (5 mg, 10% wt, 60% wet). The mixture was stirred at rt under $H_2$ atmosphere for 12 h. The mixture was filtered and concentrated to give 4.1 mg of (2R,3R,4R,5R)-2-(hydroxymethyl)-5-phenethyltetrahydro-2H-pyran-3,4-diol (A160). LC-MS (ESI) found: 253 $[M+H]^+$. $^1H$ NMR (400 MHz, $CD_3OD$): δ 7.55-6.74 (m, 5H), 3.95-3.84 (m, 2H), 3.83-3.77 (m, 1H), 3.74 (t, J=3.1 Hz, 1H), 3.66 (dd, J=11.8, 4.0 Hz, 1H), 3.51 (dt, J=7.3, 3.6 Hz, 1H), 3.43 (dd, J=11.7, 3.0 Hz, 1H), 2.70 (ddd, J=13.6, 10.3, 5.8 Hz, 1H), 2.54 (ddd, J=13.6, 9.8, 6.4 Hz, 1H), 2.05-1.76 (m, 2H), 1.70 (dt, J=9.2, 4.5 Hz, 1H). nOe experiment was consistent with the indicated stereochemistry of the product.

Using the Procedure Shown in Synthesis 5-7, (2R,3R,4R,5R)-2-(hydroxymethyl)-5-(3-hydroxypropyl)tetrahydro-2H-pyran-3,4-diol (Compound A162) and N-(3-((3R,4R,5R,6R)-4,5-dihydroxy-6-(hydroxymethyl)tetrahydro-2H-pyran-3-yl)propyl)acetamide (Compound A163) were Prepared

A162

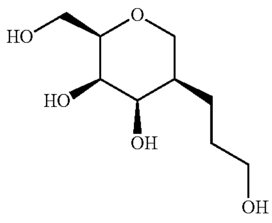

A163

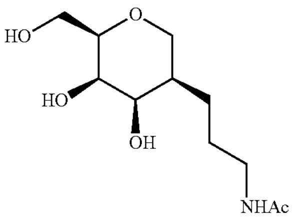

Synthesis 5-8. Preparation of (2R,3R,4R,5R)-5-(4-fluorophenyl)-2-(hydroxymethyl)tetrahydro-2H-pyran-3,4-diol (Compound A164)

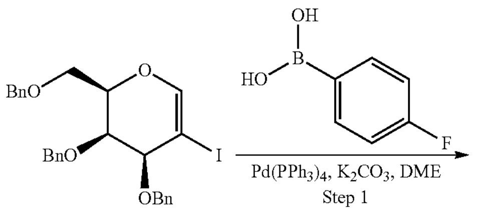

A122-1

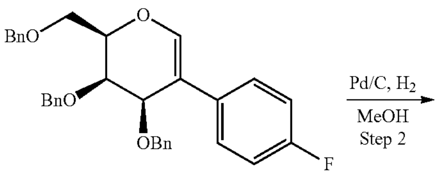

A164-1

-continued

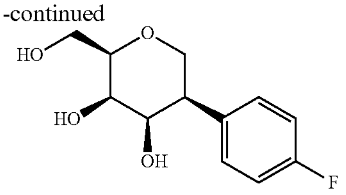

A164

Step 1: To a solution of (2R,3S,4S)-3,4-bis(benzyloxy)-2-((benzyloxy)methyl)-5-iodo-3,4-dihydro-2H-pyran from Synthesis 5-7 (A122-1, 100 mg, 0.184 mmol) in DME (10 mL) was added $Pd(PPh_3)_4$ (21 mg, 0.018 mmol), $K_2CO_3$ (76 mg, 0.552 mmol) and (4-fluorophenyl)boronic acid (34 mg, 0.239 mmol). The mixture was charged with $N_2$ for three times and stirred at 90° C. under $N_2$ for 16 h. The mixture was filtered, the filtrate was concentrated under reduced pressure to give a crude product, which was purified by flash chromatography (silica gel, 5-10% EtOAc in PE) to give (2R,3R,4R)-3,4-bis(benzyloxy)-2-((benzyloxy)methyl)-5-(4-fluorophenyl)-3,4-dihydro-2H-pyran (A164-1, 25 mg, 31% yield) as colorless oil. LC-MS (ESI) found: 533 $[M+23]^+$.

Step 2: To a solution of (2R,3R,4R)-3,4-bis(benzyloxy)-2-((benzyloxy)methyl)-5-(4-fluorophenyl)-3,4-dihydro-2H-pyran (A164-1, 20 mg, 0.039 mmol) in MeOH (5 mL) was added Pd/C (5 mg, 10% wt, 60% wet). The mixture was stirred at rt for 12 h under $H_2$ atmosphere. The mixture was filtered and concentrated to give (2R,3R,4R,5R)-5-(4-fluorophenyl)-2-(hydroxymethyl)tetrahydro-2H-pyran-3,4-diol (A164, 5.0 mg, 53% yield). LC-MS (ESI) found: 243 $[M+H]^+$. $^1H$ NMR (400 MHz, $CD_3OD$): δ 7.56-7.42 (m, 2H), 7.04-6.88 (m, 2H), 4.23 (dd, J=11.7, 7.1 Hz, 1H), 4.09 (td, J=9.0, 2.8 Hz, 1H), 4.01-3.95 (m, 1H), 3.92-3.85 (m, 1H), 3.76 (ddd, J=13.7, 7.4, 3.6 Hz, 2H), 3.71-3.62 (m, 1H), 3.02-2.91 (m, 1H).

Using the Procedures Shown in Synthesis 5-8, (2R,3R,4R,5R)-5-(2,4-difluorophenyl)-2-(hydroxymethyl)tetrahydro-2H-pyran-3,4-diol (Compound A165), (2R,3R,4R,5R)-2-(hydroxymethyl)-5-(1H-pyrazol-3-yl)tetrahydro-2H-pyran-3,4-diol (Compound A166) and (2R,3R,4R,5R)-2-(hydroxymethyl)-5-(1H-pyrazol-4-yl)tetrahydro-2H-pyran-3,4-diol (Compound A167) were Prepared

A165

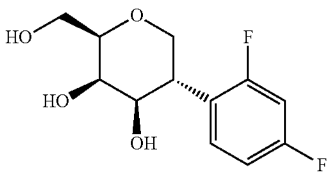

A166

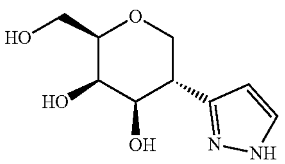

-continued

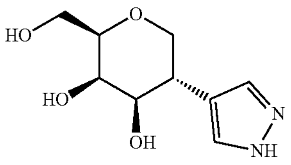

A167

Synthesis 5-9. Alternative General Synthesis of ASGPR Ligands

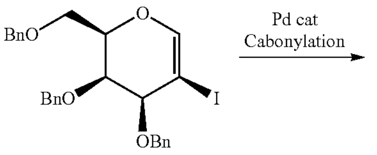

A122-1

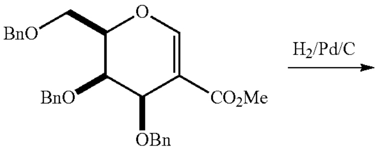

A168-1

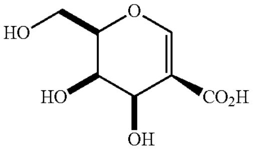

A168-2

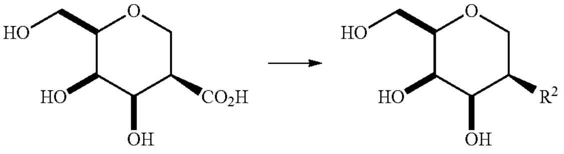

A168-3

$R^2$ = amides, C-linked heterocycles

A168

Synthesis 5-6 and Synthesis 5-9 can be Used to Synthesize Ligands with the Following $R^2$ Groups

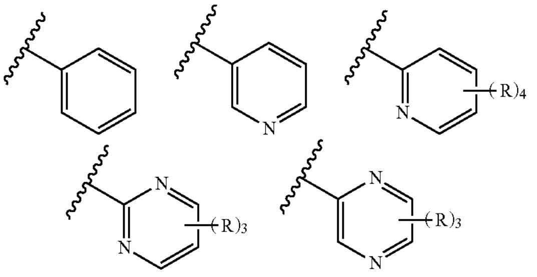

-continued

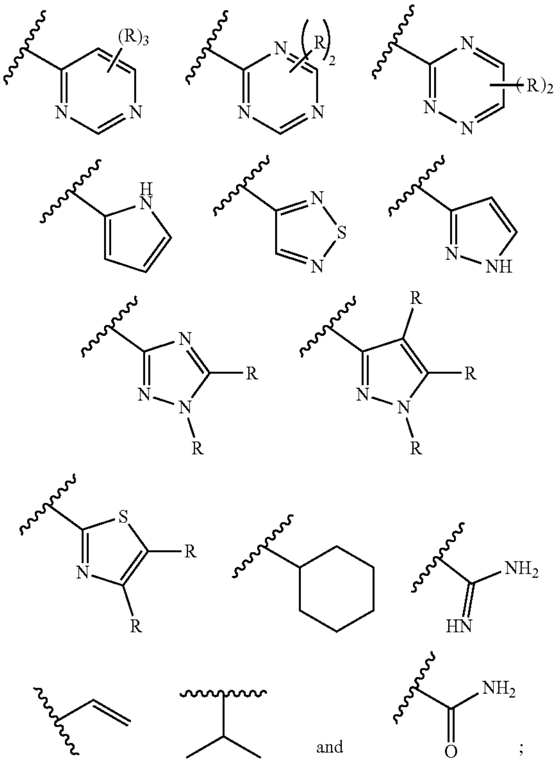

and ;

wherein R is an optimal substituent has defined herein.

Synthesis 5-10: Preparation of (3R,4R,5R,6R)-4,5-dihydroxy-6-(hydroxymethyl)-N,N-dimethyltetrahydro-2H-pyran-3-carboxamide (Compound A170) and (3R,4R,5R,6R)-4,5-dihydroxy-6-(hydroxymethyl)tetrahydro-2H-pyran-3-carboxylic acid (Compound A169)

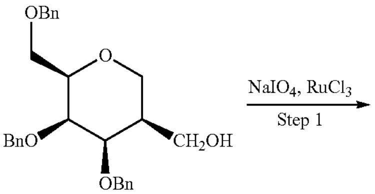

A170-1

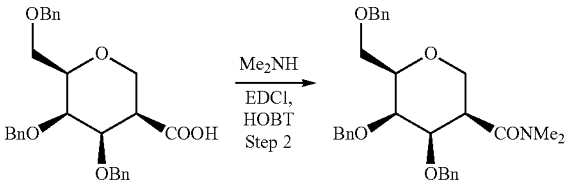

A169-1 A170-2

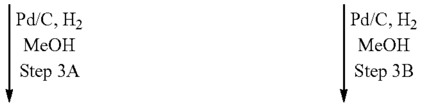

-continued

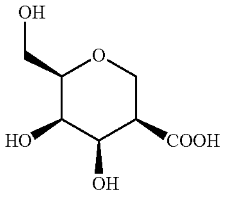

A169

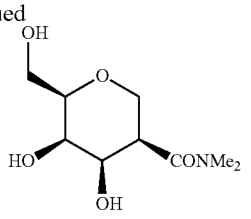

A170

Step 1: A solution of ((3R,4R,5R,6R)-4,5-bis(benzyloxy)-6-((benzyloxy)methyl)tetrahydro-2H-pyran-3-yl)methanol (A170-1, 500 mg, 1.115 mmol), $NaIO_4$ (978 mg, 4.570 mmol) and $RuCl_3$ (0.002 mL, 0.028 mmol) in $CCl_4$ (10 mL), $H_2O$ (15 mL), and MeCN (10 mL) was stirred at rt for 2 h. The mixture was extracted with DCM (10 mL×3). The combined organic phase was washed with brine, dried over $Na_2SO_4$, filtered and concentrated in vacuo to give a crude product, which was purified by column to give (3R,4R,5R,6R)-4,5-bis(benzyloxy)-6-((benzyloxy)methyl)tetrahydro-2H-pyran-3-carboxylic acid (A169-1, 400 mg, 78%) as white solid. LC-MS (ESI) found: 463 $[M+H]^+$. $^1H$ NMR (400 MHz, MeOD): δ 7.35-7.19 (m, 15H), 4.75-4.62 (m, 3H), 4.59-4.39 (m, 3H), 4.28-4.22 (m, 1H), 4.05 (dd, J=12.0, 7.8 Hz, 1H), 3.93 (ddd, J=22.1, 13.1, 5.9 Hz, 2H), 3.81 (dd, J=4.0, 2.6 Hz, 1H), 3.66-3.57 (m, 2H), 2.84 (dt, J=8.0, 4.2 Hz, 1H).

Step 2: To a solution of (3R,4R,5R,6R)-4,5-bis(benzyloxy)-6-((benzyloxy)methyl)tetrahydro-2H-pyran-3-carboxylic acid (A169-1, 60 mg, 0.13 mmol) in THF (5 mL) was added EDCI (30 mg, 0.16 mmol), HOBT (26 mg, 0.19 mmol), and dimethylamine (0.13 mmol, 1 M in THF). The mixture was stirred at rt for 12 h. The mixture was extracted by DCM (10 mL×3). The combined organic phase was washed with brine, dried over $Na_2SO_4$, filtered and concentrated in vacuo to give a crude product, which was purified by silica gel column to give desired product (A170-2). LC-MS (ESI) found: 490 $[M+H]^+$.

Step 3A: To a solution of (3R,4R,5R,6R)-4,5-bis(benzyloxy)-6-((benzyloxy)methyl)tetrahydro-2H-pyran-3-carboxylic acid (A169-1, 30 mg, 0.065 mmol) in MeOH (3 mL) was added Pd/C (5 mg, 10% wt, 60% wet). The mixture was stirred at rt for 12 h under $H_2$ atmosphere. The mixture was filtered and concentrated to give (3R,4R,5R,6R)-4,5-dihydroxy-6-(hydroxymethyl)tetrahydro-2H-pyran-3-carboxylic acid (A169), 3.0 mg. LC-MS (ESI) found: 193 $[M+H]^+$.

Alternatively, Step 3A can be performed in the following manner: To a solution of (3R,4R,5R,6R)-4,5-bis(benzyloxy)-6-((benzyloxy)methyl)tetrahydro-2H-pyran-3-carboxylic acid (15 mg, 0.032 mmol) in MeOH (1 mL) was added Pd/C (10 mg, 10% wt, 60% wet). The mixture was stirred at rt for 12 h under a $H_2$ balloon. The mixture was filtered and concentrated to give (3R,4R,5R,6R)-4,5-dihydroxy-6-(hydroxymethyl)tetrahydro-2H-pyran-3-carboxylic acid (6 mg, 96%) as a yellow solid. LC-MS (ESI) found: 193 $[M+H]^+$. $^1H$ NMR (400 MHz, MeOD): δ 4.27 (d, J=10.8 Hz, 1H), 3.96 (dd, J=5.7, 3.5 Hz, 1H), 3.84-3.72 (m, 2H), 3.72-3.59 (m, 2H), 3.46-3.36 (m, 1H), 2.86 (d, J=20.2 Hz, 1H).

Step 3B: To a solution of (3R,4R,5R,6R)-4,5-bis(benzyloxy)-6-((benzyloxy)methyl)-N,N-dimethyltetrahydro-2H-pyran-3-carboxamide (A170-2, 30 mg, 0.061 mmol) in MeOH (3 mL) was added Pd/C (5 mg, 10% wt, 60% wet). The mixture was stirred at rt for 12 h under $H_2$ atmosphere. The mixture was filtered and concentrated to give 2 mg of (3R,4R,5R,6R)-4,5-dihydroxy-6-(hydroxymethyl)-N,N-dimethyltetrahydro-2H-pyran-3-carboxamide (A170). LC-MS (ESI) found: 220 $[M+H]^+$. $^1H$ NMR (400 MHz, MeOD): δ 4.04 (dd, J=12.3, 0.8 Hz, 1H), 3.97 (dt, J=15.6, 7.8 Hz, 1H), 3.76 (dt, J=13.4, 6.7 Hz, 1H), 3.69 (ddd, J=12.4, 6.4, 4.2 Hz, 3H), 3.47 (dd, J=5.9, 3.6 Hz, 1H), 3.39-3.32 (m, 1H), 3.14 (s, 3H), 2.99 (s, 3H).

Using the Procedure Shown in Synthesis 5-10, 1-(4-((3R,4R,5R,6R)-4,5-dihydroxy-6-(hydroxymethyl)tetrahydro-2H-pyran-3-carbonyl)piperazin-1-yl)ethan-1-one (Compound A171), ((3R,4R,5R,6R)-4,5-dihydroxy-6-(hydroxymethyl)tetrahydro-2H-pyran-3-yl)(4-methylpiperazin-1-yl)methanone (Compound A172), ((3R,4R,5R,6R)-4,5-dihydroxy-6-(hydroxymethyl)tetrahydro-2H-pyran-3-yl)(piperidin-1-yl)methanone (Compound A173), and (3R,4R,5R,6R)-4,5-dihydroxy-6-(hydroxymethyl) tetrahydro-2H-pyran-3-carboxamide (Compound A174 were Prepared

A171

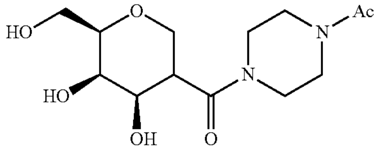

A172

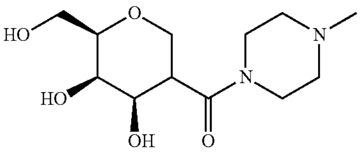

A173

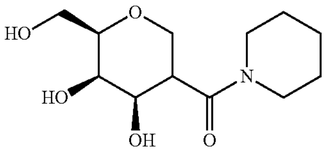

A174

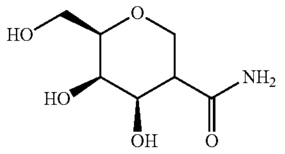

Alternatively, (3R,4R,5R,6R)-4,5-dihydroxy-6-(hydroxymethyl)tetrahydro-2H-pyran-3-carboxamide (Compound A174) can be Synthesized in the Following Manner

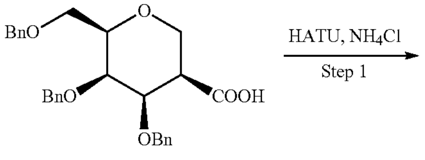

A169-1

-continued

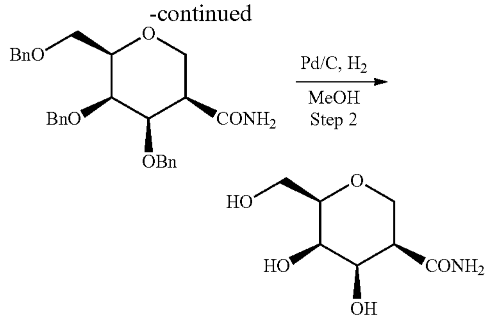

A174

Step 1: To a solution of (3R,4R,5R,6R)-4,5-bis(benzyloxy)-6-((benzyloxy)methyl)tetrahydro-2H-pyran-3-carboxylic acid (A169-1, 100 mg, 0.22 mmol) in DMF (10 mL) was added HATU (107 mg, 0.28 mmol). After stirring at rt for 1 h, $NH_4Cl$ (23 mg, 0.43 mmol) and TEA (65 mg, 0.65 mmol) were added. The mixture was stirred at rt for 1 h, then diluted with ethyl acetate and washed with water. The organic layer was dried over sodium sulfate, filtered, concentrated under reduced pressure to give a crude product, which was purified by silica gel column to give (3R,4R,5R,6R)-4,5-bis(benzyloxy)-6-((benzyloxy)methyl)tetrahydro-2H-pyran-3-carboxamide (20 mg, 20% yield). LC-MS (ESI) found: 462 $[M+H]^+$.

Step 2: To a solution of (3R,4R,5R,6R)-4,5-bis(benzyloxy)-6-((benzyloxy)methyl)tetrahydro-2H-pyran-3-carboxamide (20 mg, 0.043 mmol) in MeOH (10 mL) was added Pd/C (20 mg, 10% wt, 60% wet). The mixture was stirred at rt overnight under a $H_2$ balloon. The mixture was filtered, the filtrate was concentrated to give (3R,4R,5R,6R)-4,5-dihydroxy-6-(hydroxymethyl)tetrahydro-2H-pyran-3-carboxamide(3.5 mg, 42% yield). LC-MS (ESI) found: 192 $[M+H]^+$. $^1$H NMR (400 MHz, MeOD): δ 3.92 (dd, J=11.4, 4.8 Hz, 1H), 3.77-3.67 (m, 2H), 3.59 (ddd, J=16.4, 11.4, 6.0 Hz, 2H), 3.39-3.26 (m, 2H), 2.72 (m, 1H).

Synthesis 5-11. Preparation of (3R,4R,5R,6R)-4,5-bis(benzyloxy)-6-((benzyloxy)methyl)-N'-(2,2,2-trifluoroacetyl)tetrahydro-2H-pyran-3-carbohydrazide (Compound A175)

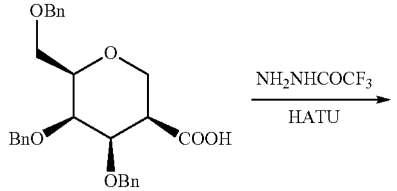

A169-1

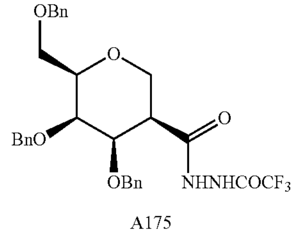

A175

Alternatively, (3R,4R,5R,6R)-4,5-bis(benzyloxy)-6-((benzyloxy)methyl)-N'-(2,2,2-trifluoroacetyl)tetrahydro-2H-pyran-3-carbohydrazide (Compound A175) can be Synthesized in the Following Manner

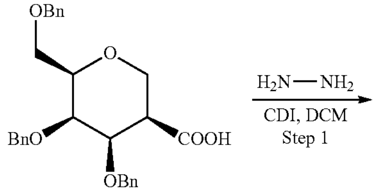

A169-1

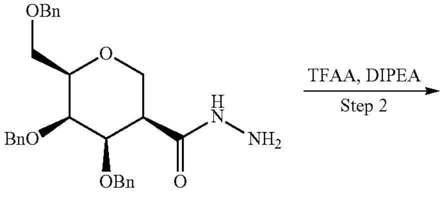

A175-1

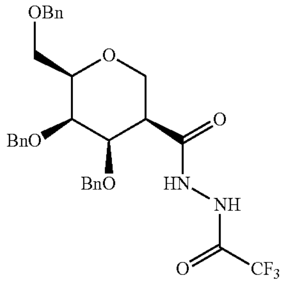

A175

Step 1: To a solution of (4R,5R,6R)-4,5-bis(benzyloxy)-6-[(benzyloxy)methyl]oxane-3-carboxylic acid(400 mg, 0.865 mmol) and CDI (0.12 mL, 0.951 mmol) in DCM (20 mL) was added hydrazine hydrate (4.2 mL, 86.5 mmol) at 0° C. The mixture was stirred at rt for 12 h. the mixture was concentrated and purified by column to give (3R,4R,5R,6R)-4,5-bis(benzyloxy)-6-((benzyloxy)methyl)tetrahydro-2H-pyran-3-carbohydrazide (140 mg, 34% yield) as yellow solid. LC-MS (ESI) found: 477 $[M+H]^+$.

Step 2: To a solution of (4R,5R,6R)-4,5-bis(benzyloxy)-6-[(benzyloxy)methyl]oxane-3-carbohydrazide (140 mg, 0.30 mmol) and TFAA (0.08 mL, 0.60 mmol) in MeCN (10 mL) was added DIPEA (46 mg, 0.353 mmol) at 0° C. The mixture was stirred at rt for 2 h. The mixture was concentrated and purified by column to give (3R,4R,5R,6R)-4,5-bis(benzyloxy)-6-((benzyloxy)methyl)-N'-(2,2,2-trifluoroacetyl)tetrahydro-2H-pyran-3-carbohydrazide (135 mg, 80% yield) as yellow oil. LC-MS (ESI) found: 573 $[M+H]^+$.

Synthesis 5-12. Preparation of 2-((3R,4R,5R,6R)-4,5-bis(benzyloxy)-6-((benzyloxy)methyl)tetrahydro-2H-pyran-3-yl)-5-(trifluoromethyl)-1,3,4-oxadiazole (Compound A176)

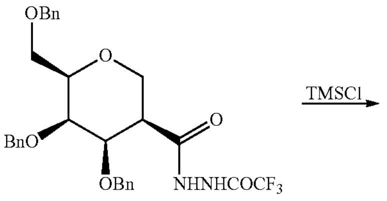

A175

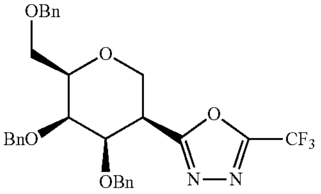

A176

Synthesis 5-13. Preparation of (2R,3R,4R,5R)-2-(hydroxymethyl)-5-(5-(trifluoromethyl)-1,3,4-oxadiazol-2-yl)tetrahydro-2H-pyran-3,4-diol (Compound A177)

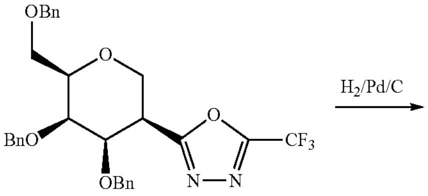

A176

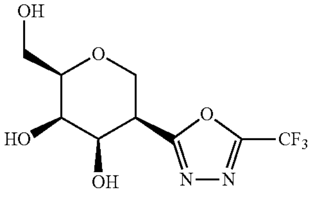

A177

Synthesis 5-14. Preparation of (3R,4R,5R,6R)-4,5-dihydroxy-6-(hydroxymethyl)-N-(methylsulfonyl)tetrahydro-2H-pyran-3-carboxamide (Compound A178)

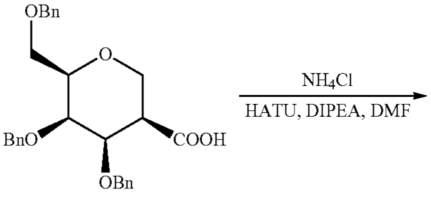

A169-1

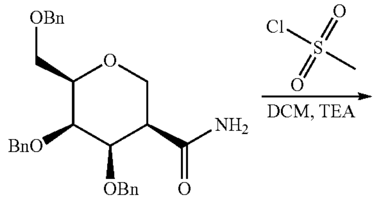

A178-1

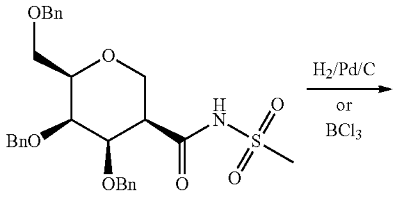

A178-2

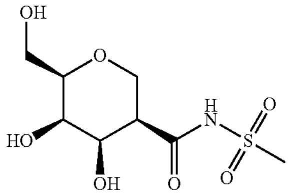

A178

Synthesis 5-15. General Synthesis of Amide-Containing Ligands

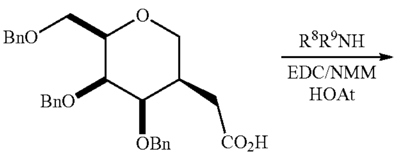

A179-1

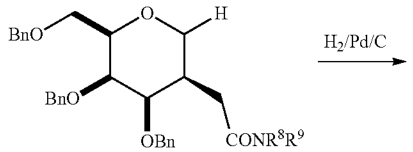

A179-2

-continued

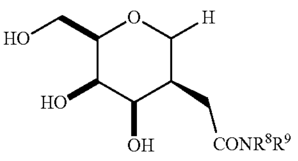

A179

Synthesis 5-16: Preparation of 1-((3R,4R,5R,6R)-4,5-dihydroxy-6-(hydroxymethyl)tetrahydro-2H-pyran-3-yl)pyrrolidin-2-one (Compound A180)

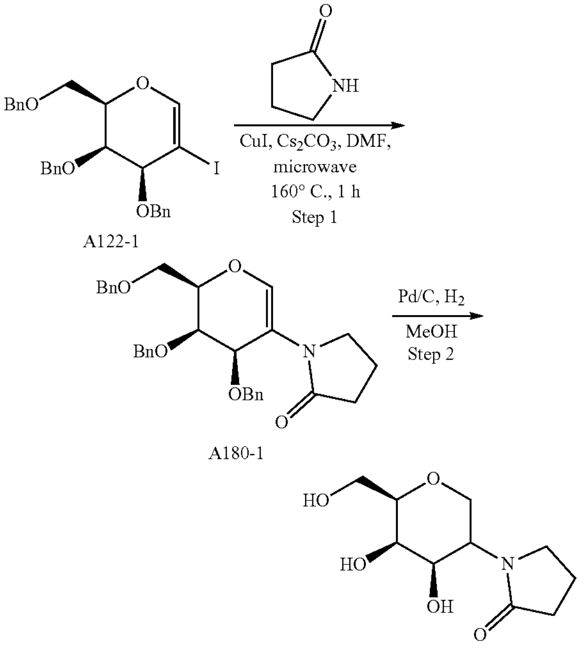

A122-1

A180-1

A180

Step 1: To a solution of (2R,3S,4S)-3,4-bis(benzyloxy)-2-((benzyloxy)methyl)-5-iodo-3,4-dihydro-2H-pyran (A122-1, 100 mg, 0.184 mmol) in DMF (3 mL) was added CuI (3.4 mg, 0.018 mmol), $Cs_2CO_3$ (120 mg, 0.368 mmol), pyrrolidin-2-one (43 mg, 0.552 mmol). The mixture was stirred at 160° C. under microwave for 1 h. The mixture was filtered, the filtrate was concentrated under reduced pressure to give a crude product, which was purified by flash chromatography to give 1-((2R,3R,4R)-3,4-bis(benzyloxy)-2-((benzyloxy)methyl)-3,4-dihydro-2H-pyran-5-yl)pyrrolidin-2-one (A180-1, 27 mg, 30% yield) as colorless oil. LC-MS (ESI) found: 500 $[M+1]^+$.

Step 2: To a solution of 1-((2R,3R,4R)-3,4-bis(benzyloxy)-2-((benzyloxy)methyl)-3,4-dihydro-2H-pyran-5-yl) pyrrolidin-2-one (A180-1, 20 mg, 0.04 mmol) in MeOH (5 mL) was added Pd/C (5 mg, 10% wt, 60% wet). The mixture was stirred at rt for 12 h under $H_2$ atmosphere. The mixture was filtered and concentrated to give 3 mg of 1-((3R,4R,5R,6R)-4,5-dihydroxy-6-(hydroxymethyl)tetrahydro-2H-pyran-3-yl)pyrrolidin-2-one (A180). LC-MS (ESI) found: 232 $[M+H]^+$.

Alternatively, 1-((3R,4R,5R,6R)-4,5-dihydroxy-6-(hydroxymethyl)tetrahydro-2H-pyran-3-yl)pyrrolidin-2-one (Compound A180) can be Synthesized in the Following Manner

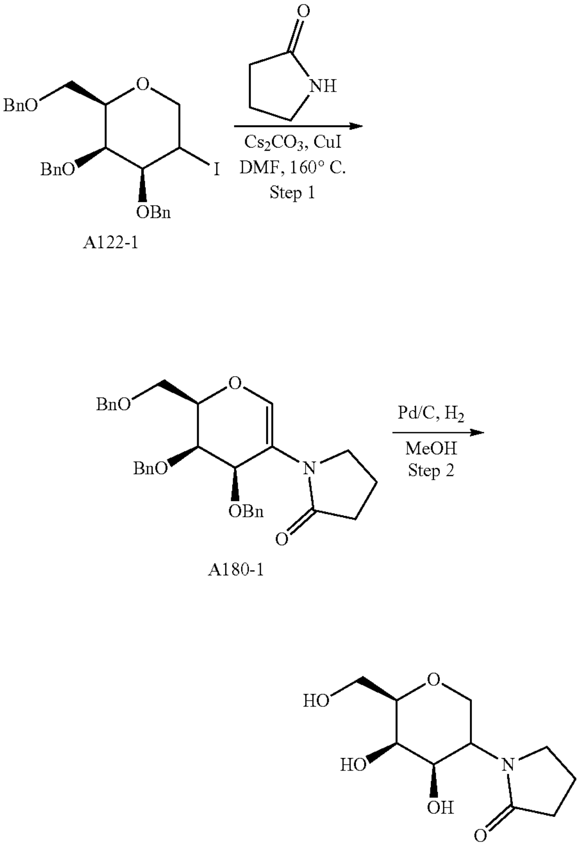

A122-1

A180-1

A180

Step 1: To a solution of (2R,3S,4S)-3,4-bis(benzyloxy)-2-((benzyloxy)methyl)-5-iodo-3,4-dihydro-2H-pyran (100 mg, 0.18 mmol) in DMF (30 mL) was added pyrrolidin-2-one (78 mg, 0.92 mmol), $Cs_2CO_3$ (180 mg, 0.55 mmol), CuI (4 mg, 0.021 mmol), the mixture was stirred at 160° C. under microwave for 1 h. The mixture was diluted with ethyl acetate and washed with water. The organic layer was dried over sodium sulfate, filtered, concentrated under reduced pressure to give a crude product, which was purified by silica gel column to give 1-((2R,3R,4R)-3,4-bis(benzyloxy)-2-((benzyloxy)methyl)-3,4-dihydro-2H-pyran-5-yl)pyrrolidin-2-one (20 mg, 21% yield). LC-MS (ESI) found: 500 $[M+H]^+$.

Step 2: To a solution of 1-((2R,3R,4R)-3,4-bis(benzyloxy)-2-((benzyloxy)methyl)-3,4-dihydro-2H-pyran-5-yl) pyrrolidin-2-one (20 mg, 0.04 mmol) in MeOH (10 mL) was added Pd/C (20 mg, 10% wt, 60% wet), the mixture was stirred at rt under a $H_2$ balloon overnight. The mixture was filtered, the filtrate was concentrated to give 1-((3R,4R,5R,6R)-4,5-dihydroxy-6-(hydroxymethyl)tetrahydro-2H-pyran-3-yl)pyrrolidin-2-one (2.3 mg, 25% yield). LC-MS (ESI) found: 232 $[M+H]^+$. $^1H$ NMR (400 MHz, MeOD): δ 4.18-4.06 (m, 2H), 3.97 (dd, J=12.7, 3.0 Hz, 1H), 3.77 (m, 2H), 3.70-3.66 (m, 1H), 3.59 (m, 2H), 3.46-3.35 (m, 2H), 2.32-2.23 (m, 2H), 1.90 (m, 2H).

Synthesis 5-17: Preparation of (2R,3R,4R,5R)-2-(hydroxymethyl)-5-methyltetrahydro-2H-pyran-3,4-diol (Compound A181) and (2R,3R,4R,5R)-2,5-bis(hydroxymethyl)tetrahydro-2H-pyran-3,4-diol (Compound A182)

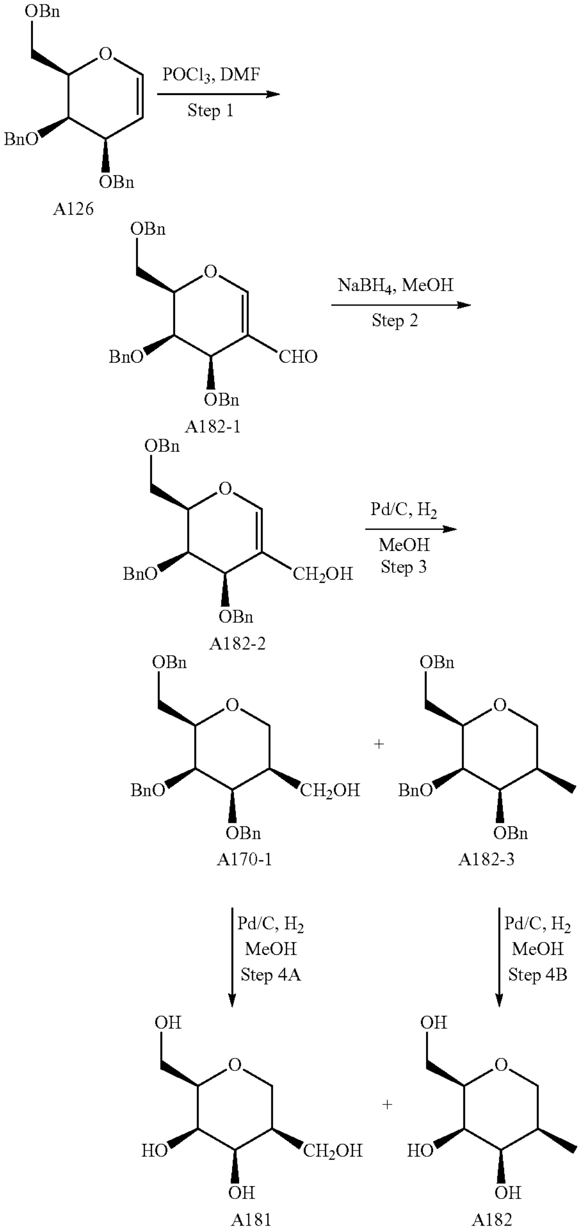

A126

A182-1

A182-2

A170-1 + A182-3

A181 + A182

Step 1: To a solution of DMF (50 mL) was added $POCl_3$ (6.2 mL, 66.3 mmol) at 0° C. in portions. The mixture was stirred at 0° C. for 0.5 h. (2R,3R,4R)-3,4-bis(benzyloxy)-2-((benzyloxy)methyl)-3,4-dihydro-2H-pyran from Synthesis 4-3 (A126, 9.2 g, 22.1 mmol) in DMF (20 mL) was added at 0° C. in portions. The mixture was stirred at rt for 5 h. The mixture was quenched with $H_2O$, extracted with EA, washed with $H_2O$ and brine, and concentrated and purified by silica gel column to give (2R,3R,4R)-3,4-bis(benzyloxy)-2-((benzyloxy)methyl)-3,4-dihydro-2H-pyran-5-carbaldehyde (A182-1, 6.0 g, 61%) as yellow oil. LC-MS (ESI) found: 445 $[M+H]^+$. $^1H$ NMR (400 MHz, $CD_3OD$): δ 9.29 (s, 1H), 7.40-7.14 (m, 15H), 4.76-4.64 (m, 4H), 4.62-4.54 (m, 2H), 4.48 (q, J=12.0 Hz, 2H), 4.00-3.80 (m, 3H).

Step 2: To a solution of (2R,3R,4R)-3,4-bis(benzyloxy)-2-((benzyloxy)methyl)-3,4-dihydro-2H-pyran-5-carbaldehyde (A182-1, 10.0 g, 22.4 mmol) in MeOH (50 mL) was added $NaBH_4$ (17.0 g, 45.0 mmol) at 0° C. in portions. The mixture was stirred at rt for 12 h. The mixture was quenched with $H_2O$, extracted with EA, and concentrated to give crude ((2R,3R,4R)-3,4-bis(benzyloxy)-2-((benzyloxy)methyl)-3,4-dihydro-2H-pyran-5-yl)methanol (A182-2, 9.5 g, 95% yield) as yellow oil. LC-MS (ESI) found: 469 $[M+Na]^+$. $^1H$ NMR (400 MHz, CD3OD); δ 7.38-7.21 (m, 15H), 6.37 (s, 1H), 4.78 (t, J=10.9 Hz, 2H), 4.63 (dd, J=20.6, 11.4 Hz, 2H), 4.54-4.37 (m, 3H), 4.28-4.14 (m, 2H), 4.08-4.02 (m, 1H), 3.89 (d, J=11.9 Hz, 1H), 3.75-3.65 (m, 2H).

Step 3: To a solution of ((2R,3R,4R)-3,4-bis(benzyloxy)-2-((benzyloxy)methyl)-3,4-dihydro-2H-pyran-5-yl)methanol (A182-2, 6.0 g, 13.4 mmol) in MeOH (2 mL) was added Pd/C (1.2 g, 10% wt, 60% wet) in portions. The mixture was stirred at rt under $H_2$ for 2 h. The mixture was filtered, concentrated, and purified by silica column to give ((3R,4R,5R,6R)-4,5-bis(benzyloxy)-6-((benzyloxy)methyl)tetrahydro-2H-pyran-3-yl)methanol (A170-1, 0.49 g, 8% yield), LC-MS (ESI) found: 449 [M+H]+, and (2R,3R,4R,5R)-3,4-bis(benzyloxy)-2-((benzyloxy)methyl)-5-methyltetrahydro-2H-pyran (A182-3, 1.1 g, 19% yield) as colorless oil, LC-MS (ESI) found: 433 $[M+H]^+$.

Step 4A: To a solution of ((3R,4R,5R,6R)-4,5-bis(benzyloxy)-6-((benzyloxy)methyl)tetrahydro-2H-pyran-3-yl)methanol (A170-1, 60.0 mg, 0.134 mmol) in MeOH(2 mL) was added Pd/C (30 mg, 10% wt, 60% wet). The mixture was stirred at rt under $H_2$ for 12 h. The mixture was filtered and concentrated to give (2R,3R,4R,5R)-2,5-bis(hydroxymethyl)tetrahydro-2H-pyran-3,4-diol (A181, 6.3 mg, 26%) as brown oil. LC-MS (ESI) found: 179 $[M+H]^+$. $^1H$ NMR (400 MHz, $CD_3OD$): δ 4.08 (dd, J=11.8, 2.0 Hz, 1H), 3.89 (ddd, J=9.1, 8.4, 5.5 Hz, 2H), 3.81 (dd, J=11.0, 4.0 Hz, 1H), 3.75 (dt, J=11.3, 5.6 Hz, 2H), 3.64 (dd, J=11.5, 4.6 Hz, 1H), 3.50 (dd, J=11.8, 2.7 Hz, 1H), 3.37 (ddd, J=13.0, 7.4, 5.1 Hz, 1H), 1.88 (d, J=2.9 Hz, 1H).

Step 4B: To a solution of (2R,3R,4R,5R)-3,4-bis(benzyloxy)-2-((benzyloxy)methyl)-5-methyltetrahydro-2H-pyran (A182-3, 50 mg, 0.11 mmol) in MeOH (2 mL) was added Pd/C (10 mg, 10% wt, 60% wet). The mixture was stirred at rt under $H_2$ for 2 h. Then the reaction mixture was filtered and concentrated to give (2R,3R,4R)-2,5-bis(hydroxymethyl)oxane-3,4-diol (A182, 8 mg, 40%) as a white solid. LC-MS (ESI) found: 185 $[M+Na]^+$. $^1H$ NMR (400 MHz, CD3OD): δ 3.85 (dd, J=11.7, 7.6 Hz, 1H), 3.79-3.62 (m, 4H), 3.55-3.42 (m, 2H), 1.93-1.79 (m, 1H), 1.11 (d, J=7.2 Hz, 3H).

Synthesis 5-18. Preparation of ((3S,4R,5R,6R)-4,5-bis(benzyloxy)-6-((benzyloxy)methyl)tetrahydro-2H-pyran-3-yl)methyl 4-methylbenzenesulfonate (Compound A183)

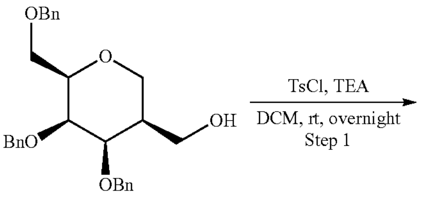

A170-1

-continued

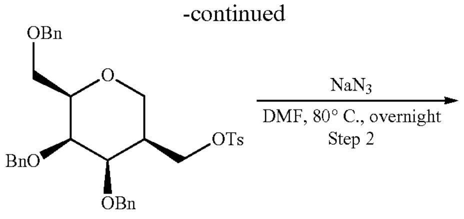

A183-1

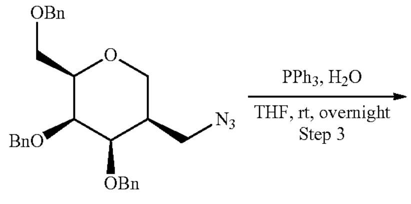

A183-2

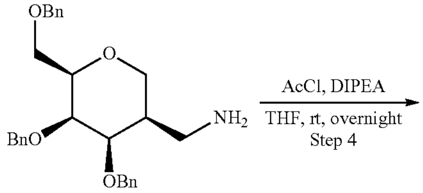

A183-3

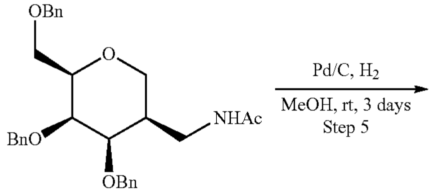

A183-4

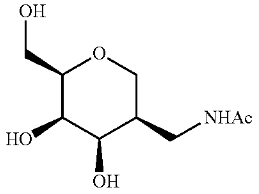

A183

Step 1: To a solution of ((4R,5R,6R)-4,5-bis(benzyloxy)-6-((benzyloxy)methyl)tetrahydro-2H-pyran-3-yl)methanol from Synthesis 5-17 (A170-1, 350 mg, 0.78 mmol) and TEA (394 mg, 3.90 mmol) in DCM (10 mL) was added TsCl (446 mg, 2.34 mmol) slowly at 0° C. The reaction mixture was stirred at rt overnight. The resulting mixture was extracted with EA (50 mL), washed with $H_2O$ (40 mL×2) and brine (40 mL), dried over $Na_2SO_4$, filtered. The organic layer was separated and concentrated in vacuo. The crude product was purified by flash chromatography (silica gel, 0~50% EA in PE) to give ((4R,5R,6R)-4,5-bis(benzyloxy)-6-((benzyloxy)methyl)tetrahydro-2H-pyran-3-yl)methyl 4-methylbenzenesulfonate (A183-1, 180 mg, 38%) as a yellow oil. LC-MS (ESI) found: 603 $[M+H]^+$.

Step 2: To a solution of (2R,3R,4R)-5-(azidomethyl)-3,4-bis(benzyloxy)-2-((benzyloxy)methyl)tetrahydro-2H-pyran (A183-1, 185 mg, 0.31 mmol) in dry DMF (10 mL) was added $NaN_3$ (180 mg, 3.10 mmol). The reaction mixture was stirred at 80° C. overnight. The mixture was extracted with EA (20 mL), washed with $H_2O$ (20 mL×2) and brine (20 mL), dried over $Na_2SO_4$, filtered. The organic layer was separated and concentrated in vacuo. The crude product was purified by flash chromatography (silica gel, 0~50% EA in PE) to give (2R,3R,4R)-5-(azidomethyl)-3,4-bis(benzyloxy)-2-((benzyloxy)methyl)tetrahydro-2H-pyran (A183-2, 65 mg, 45% yield) as a colorless oil. LC-MS (ESI) found: 496$[M+Na]^+$.

Step 3: To a solution of ((3R,4R,5R,6R)-4,5-bis(benzyloxy)-6-((benzyloxy)methyl)tetrahydro-2H-pyran-3-yl)methanamine (A183-3, 65 mg, 0.14 mmol) in THF (5 mL) was added $PPh_3$ (72 mg, 0.27 mmol) and water (5 mL). The reaction mixture was stirred at rt overnight. The mixture was concentrated in vacuo. The crude product was purified by flash chromatography (silica gel, 0-10% MeOH in DCM) to give ((3R,4R,5R,6R)-4,5-bis(benzyloxy)-6-((benzyloxy)methyl)tetrahydro-2H-pyran-3-yl)methanamine (A183-3, 60 mg, 98% yield) as a colorless oil. LC-MS (ESI) found: 448$[M+H]^+$.

Step 4: To a solution of N-(((3R,4R,5R,6R)-4,5-bis(benzyloxy)-6-((benzyloxy)methyl)tetrahydro-2H-pyran-3-yl)methyl)acetamide (A183-3, 30 mg, 0.067 mmol) in dry DCM (5 mL) was added DIPEA (30 mg, 0.07 mmol) and acetyl chloride (11 mg, 0.14 mmol) dropwise at 0° C. under $N_2$ atmosphere. The reaction mixture was stirred at rt for 8 h. The reaction was cooled to 0° C. and quenched with saturated sodium bicarbonate solution. The mixture was extracted with EA (10 mL), washed with $H_2O$ (10 mL×2) and brine (10 mL), dried over $Na_2SO_4$, filtered. The organic layer was separated and concentrated in vacuo. The crude product was purified by flash chromatography (silica gel, 0~50% EA in PE) to give N-(((3R,4R,5R,6R)-4,5-bis(benzyloxy)-6-((benzyloxy)methyl)tetrahydro-2H-pyran-3-yl)methyl)acetamide (A183-4, 14 mg, 44% yield) as a colorless oil. LC-MS (ESI) found: 490$[M+H]^+$.

Step 5: To a solution of N-(((3R,4R,5R,6R)-4,5-bis(benzyloxy)-6-((benzyloxy)methyl)tetrahydro-2H-pyran-3-yl)methyl)acetamide (A183-4, 14 mg, 0.03 mmol) in dry MeOH (5 mL) was added Pd/C (10 mg, 10% wt, 60% wet). The reaction mixture was charged with $H_2$ and stirred at rt for 3 days under $H_2$ atmosphere. The mixture was filtered and concentrated in vacuo to give N-(((3R,4R,5R,6R)-4,5-dihydroxy-6-(hydroxymethyl)tetrahydro-2H-pyran-3-yl)methyl)acetamide (A183, 1 mg, 16% yield) as a colorless oil. LC-MS (ESI) found: 220$[M+H]^+$. $^1H$ NMR (400 MHz, $CD_3OD$): δ 3.91 (dd, J=11.9, 2.8 Hz, 1H), 3.85-3.72 (m, 3H), 3.66 (dd, J=11.7, 4.3 Hz, 1H), 3.58 (dd, J=13.9, 4.3 Hz, 1H), 3.48-3.40 (m, 3H), 1.93 (s, 3H), 1.92-1.84 (m, 1H).

Synthesis 5-19. Preparation of (2R,3R,4R)-5-(azidomethyl)-2-(hydroxymethyl)tetrahydro-2H-pyran-3,4-diol (Compound A184)

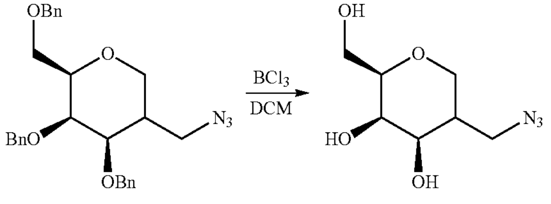

A183-2 A184

To a solution of (2R,3R,4R)-5-(azidomethyl)-3,4-bis(benzyloxy)-2-((benzyloxy)methyl)tetrahydro-2H-pyran from Synthesis 5-18 (A183-2, 20 mg, 0.04 mmol) in dry DCM (5 mL) at −78° C. under $N_2$ atmosphere was added $BCl_3$ (0.4 mL, 0.04 mmol, 1 M in DCM) slowly. After the addition was complete, the reaction was stirred at 0° C. for 45 min. On consumption of starting material (TLC monitoring), the reaction mixture was quenched with 1 mL MeOH. The mixture was concentrated in vacuo. The crude product was purified by pre-HPLC (Method A) to give (2R,3R,4R)-5-(azidomethyl)-2-(hydroxymethyl)tetrahydro-2H-pyran-3,4-diol (A184, 0.7 mg, 8% yield) as a colorless oil. LC-MS (ESI) found: 226 $[M+Na]^+$. $^1H$ NMR (400 MHz, CD3OD): δ 3.99 (dd, J=11.9, 2.0 Hz, 1H), 3.82 (dd, J=5.4, 3.3 Hz, 1H), 3.79-3.74 (m, 2H), 3.73-3.67 (m, 2H), 3.64 (dd, J=11.5, 4.5 Hz, 1H), 3.48-3.44 (m, 1H), 3.40-3.36 (m, 1H), 1.97-1.84 (m, 1H).

Synthesis 5-20. Preparation of (2R,3R,4R,5R)-5-(aminomethyl)-2-(hydroxymethyl)tetrahydro-2H-pyran-3,4-diol (Compound A185)

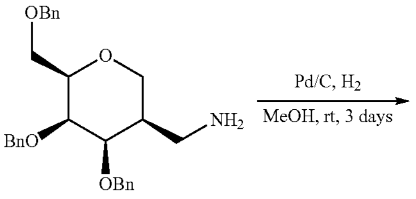

A183-3

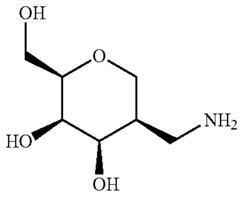

A185

To a solution of ((3R,4R,5R,6R)-4,5-bis(benzyloxy)-6-((benzyloxy)methyl)tetrahydro-2H-pyran-3-yl)methanamine from Synthesis 5-18 (A183-3, 20 mg, 0.044 mmol) in dry MeOH (5 mL) was added Pd/C (5 mg, 10% wt, 60% wet). The reaction mixture was charged with $H_2$ and stirred at rt for 3 days under $H_2$ atmosphere. Then the mixture was filtered and concentrated in vacuo to give (2R,3R,4R,5R)-5-(aminomethyl)-2-(hydroxymethyl)tetrahydro-2H-pyran-3,4-diol (A185) as a colorless oil. LC-MS (ESI) found: 178 $[M+H]^+$.

Alternatively, (2R,3R,4R,5R)-5-(aminomethyl)-2-(hydroxymethyl)tetrahydro-2H-pyran-3,4-diol (Compound A185) can be Synthesized in the Following Manner

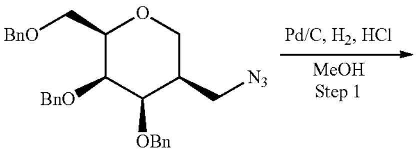

A183-2

-continued

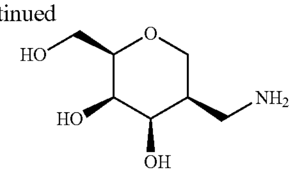

A185

Step 1: To a solution of (2R,3R,4R,5R)-5-(azidomethyl)-3,4-bis(benzyloxy)-2-((benzyloxy)methyl)tetrahydro-2H-pyran (A183-2, 50 mg, 0.11 mmol) in MeOH (5 mL) were added Pd/C (5 mg, 10% wt, 60% wet) and HCl (0.1 mL, 1N in $H_2O$). The reaction mixture was stirred at rt overnight under a balloon of $H_2$. The mixture was filtered and concentrated in vacuo to give (2R,3R,4R,5R)-5-(aminomethyl)-2-(hydroxymethyl)tetrahydro-2H-pyran-3,4-diol (A185, 16 mg, 86% yield) as yellow oil. LC-MS (ESI) found: 178 $[M+H]^+$. $^1H$ NMR (400 MHz, MeOD): δ 4.09-4.02 (m, 1H), 3.96 (dd, J=5.7, 3.3 Hz, 1H), 3.85 (d, J=2.7 Hz, 1H), 3.76-3.70 (m, 1H), 3.69-3.61 (m, 2H), 3.43-3.33 (m, 2H), 3.26 (dd, J=13.0, 3.7 Hz, 1H), 2.22-2.05 (m, 1H).

Synthesis 5-21. Preparation of N-(((3R,4R,5R,6R)-4,5-bis(benzyloxy)-6-((benzyloxy)methyl)tetrahydro-2H-pyran-3-yl)methyl)-2,2,2-trifluoroacetamide (Compound A186)

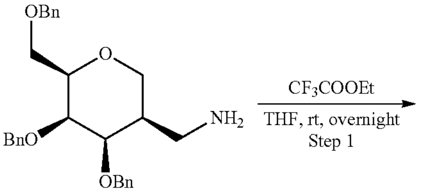

A183-3

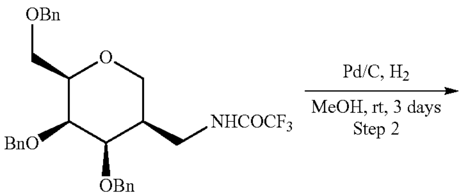

A186-1

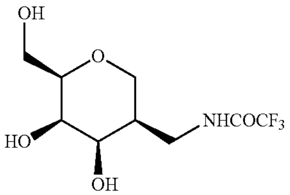

A186

Step 1: To a solution of ((3R,4R,5R,6R)-4,5-bis(benzyloxy)-6-((benzyloxy)methyl)tetrahydro-2H-pyran-3-yl) methanamine from Synthesis 5-18 (A183-3, 30 mg, 0.067 mmol) in dry MeOH (5 mL) was added ethyl 2,2,2-trifluoroacetate (19 mg, 0.134 mmol) and triethylamine (26 mg, 0.201 mmol) at rt. The reaction mixture was stirred at rt overnight. The resulting mixture was diluted with EA (10 mL), washed with $H_2O$ (10 mL×2) and brine (10 mL), dried over $Na_2SO_4$, filtered. The organic layer was concentrated in vacuo to get a crude product, which was purified by flash chromatography (silica gel, 0~50% EA in PE) to give N-(((3R,4R,5R,6R)-4,5-bis(benzyloxy)-6-((benzyloxy)methyl)tetrahydro-2H-pyran-3-yl)methyl)-2,2,2-trifluoroacetamide (A186-1, 16 mg, 44%) as a yellow oil. LC-MS (ESI) found: 566 [M+Na]$^+$.

Step 2: To a solution of N-(((3R,4R,5R,6R)-4,5-bis(benzyloxy)-6-((benzyloxy)methyl)tetrahydro-2H-pyran-3-yl)methyl)-2,2,2-trifluoroacetamide (A186-1, 16 mg, 0.029 mmol) in dry MeOH (5 mL) was added Pd/C (3 mg, 10% wt, 60% wet). The reaction mixture was charged with $H_2$ for three times and stirred at rt for 3 days under $H_2$ atmosphere. The mixture was filtered and concentrated in vacuo to give 3 mg of N-(((3R,4R,5R,6R)-4,5-dihydroxy-6-(hydroxymethyl)tetrahydro-2H-pyran-3-yl)methyl)-2,2,2-trifluoroacetamide (A186) as colorless oil. LC-MS (ESI) found: 274/296 [M+H]$^+$/[M+Na]$^+$.

Alternatively, Step 2 can be performed in the following manner: To a solution of N-(((3R,4R,5R,6R)-4,5-bis(benzyloxy)-6-((benzyloxy)methyl)tetrahydro-2H-pyran-3-yl)methyl)-2,2,2-trifluoroacetamide (16 mg, 0.029 mmol) in MeOH (5 mL), Pd/C (5 mg, 10% wt, 60% wet) and HCl (0.1 mL, 1N in $H_2O$) was added. The reaction mixture was stirred at rt overnight under a $H_2$ balloon. The mixture was filtered, the filtrate was concentrated to give N-(((3R,4R,5R,6R)-4,5-dihydroxy-6-(hydroxymethyl)tetrahydro-2H-pyran-3-yl)methyl)-2,2,2-trifluoroacetamide (A186, 7.9 mg, 99%) as yellow oil. LC-MS (ESI) found: 274 [M+H]$^+$. $^1$H NMR (400 MHz, MeOD): δ 3.91 (dd, J=12.1, 1.9 Hz, 1H), 3.86 (dd, J=5.6, 3.3 Hz, 1H), 3.81-3.79 (m, 1H), 3.78-3.74 (m, 1H), 3.73-3.68 (m, 1H), 3.67-3.61 (m, 2H), 3.51 (dd, J=12.1, 2.8 Hz, 1H), 3.39 (ddd, J=7.1, 4.5, 1.7 Hz, 1H), 2.03-1.96 (m, 1H).

Synthesis 5-22. Preparation of N-((1-(((3R,4R,5R,6R)-4,5-bis(benzyloxy)-6-((benzyloxy)methyl)tetrahydro-2H-pyran-3-yl)methyl)-1H-1,2,3-triazol-4-yl)methyl)acetamide (Compound A187)

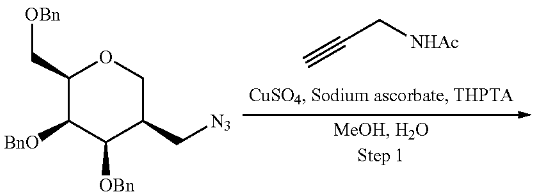

A183-2

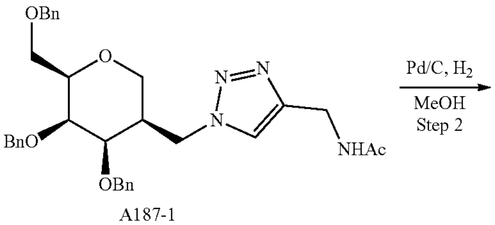

A187-1

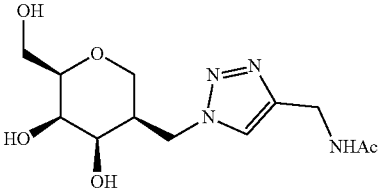

A187

Step 1: A solution of THPTA (0.32 mg, 0.001 mmol) and $CuSO_4$ (2.4 mg, 0.02 mmol) in $H_2O$ (0.5 mL) was added to a solution of (2R,3R,4R)-5-(azidomethyl)-3,4-bis(benzyloxy)-2-((benzyloxy)methyl)tetrahydro-2H-pyran from Synthesis 5-18 (A183-2, 32.0 mg, 0.07 mmol) and N-(prop-2-yn-1-yl)acetamide (8.6 mg, 0.09 mmol) in MeOH (2 mL). A freshly-prepared solution of sodium ascorbate (5.9 mg, 0.03 mmol) in $H_2O$ (0.5 mL) was added and the reaction mixture was stirred at room temperature for 24 h. Then the mixture was concentrated and the residual was purified by flash chromatography (0-5% methanol in dichloromethane) to give N-((1-(((3R,4R,5R,6R)-4,5-bis(benzyloxy)-6-((benzyloxy)methyl)tetrahydro-2H-pyran-3-yl)methyl)-1H-1,2,3-triazol-4-yl)methyl)acetamide (A187-1, 33 mg, 78%) as oil. LC-MS (ESI) found: 571 [M+H]$^+$.

Step 2: To a solution of N-((1-(((3R,4R,5R,6R)-4,5-bis(benzyloxy)-6-((benzyloxy)methyl)tetrahydro-2H-pyran-3-yl)methyl)-1H-1,2,3-triazol-4-yl)methyl)acetamide (A187-1, 16 mg, 0.03 mmol) in MeOH (3 mL) was added Pd/C (2 mg, 10% wt, 60% wet), the mixture was charged with $H_2$ for three times and stirred at the room temperature under $H_2$ atmosphere overnight. The mixture was filtered, the filtrate was concentrated under reduced pressure to give a crude product, which was purified by flash chromatography (0-50% ethyl acetate in petroleum ether) to give N-((1-(((3R,4R,5R,6R)-4,5-bis(benzyloxy)-6-((benzyloxy)methyl)tetrahydro-2H-pyran-3-yl)methyl)-1H-1,2,3-triazol-4-yl)methyl)acetamide (A187, 2 mg, 24%). LC-MS (ESI) found: 301 [M+H]$^+$. $^1$H NMR (400 MHz, $CD_3OD$): δ 7.85 (s, 1H), 4.83 (s, 1H), 4.68 (dd, J=14.1, 1.9 Hz, 1H), 4.42 (s, 2H), 3.91 (dd, J=5.3, 3.2 Hz, 1H), 3.82 (dd, J=11.5, 7.1 Hz, 2H), 3.75-3.68 (m, 2H), 3.49-3.40 (m, 2H), 2.33-2.23 (m, 1H), 1.98 (s, 3H).

Synthesis 5-23. Preparation of (2R,3R,4R,5R)-5-(((3-chloro-1,2,4-thiadiazol-5-yl)amino)methyl)-2-(hydroxymethyl)tetrahydro-2H-pyran-3,4-diol (Compound A188)

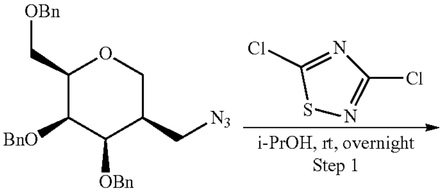

A183-3

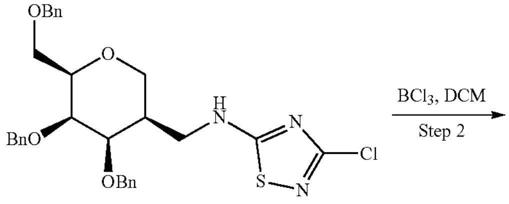

A188-1

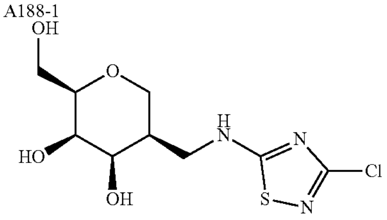

A188

Step 1: A solution of ((3R,4R,5R,6R)-4,5-bis(benzyloxy)-6-((benzyloxy)methyl)tetrahydro-2H-pyran-3-yl)methanamine from Synthesis 5-18 (A183-3, 50 mg, 0.112 mmol), 3,5-dichloro-1,2,4-thiadiazole (51 mg, 0.336 mmol) and DIPEA (44 mg, 0.336 mmol) in i-PrOH (5 mL) was stirred at rt overnight. The mixture was concentrated in vacuo. The crude product was purified by pre-HPLC (Method A) to give N-(((3R,4R,5R,6R)-4,5-bis(benzyloxy)-6-((benzyloxy)methyl)tetrahydro-2H-pyran-3-yl)methyl)-3-chloro-1,2,4-thiadiazol-5-amine (A188-1, 25 mg, 40%). LC-MS (ESI) found: 566 $[M+H]^+$ Step 2: To a solution of N-(((3R,4R,5R,6R)-4,5-bis(benzyloxy)-6-((benzyloxy)methyl)tetrahydro-2H-pyran-3-yl)methyl)-3-chloro-1,2,4-thiadiazol-5-amine (A188-1, 25 mg, 0.044 mmol) in dry DCM (5 mL) was added $BCl_3$ (0.44 mL, 1 M in DCM) dropwise at −10° C. under $N_2$ atmosphere. The reaction mixture was stirred at rt for 0.5 h. Then the reaction was cooled to 0° C. and quenched with saturated sodium bicarbonate solution. The mixture was filtered and concentrated in vacuo. The crude product was purified by prep-HPLC (Method A) to give 7 mg of (2R,3R,4R,5R)-5-(((3-chloro-1,2,4-thiadiazol-5-yl)amino)methyl)-2-(hydroxymethyl)tetrahydro-2H-pyran-3,4-diol (A188). LC-MS (ESI) found: 296 $[M+H]^+$.

Alternatively, (2R,3R,4R,5R)-5-(((3-chloro-1,2,4-thiadiazol-5-yl)amino)methyl)-2-(hydroxymethyl)tetrahydro-2H-pyran-3,4-diol (Compound A188) can be Synthesized in the Following Manner

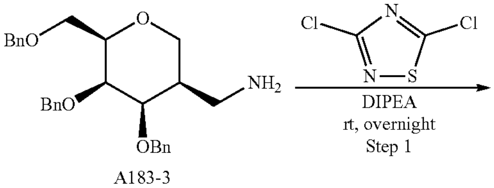

A183-3

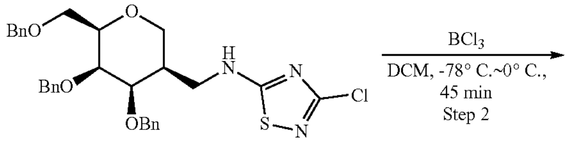

A188-1

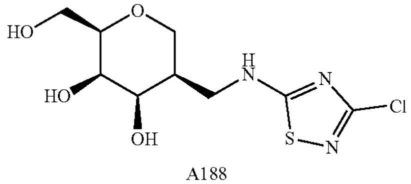

A188

Step 1: To a solution of ((3R,4R,5R,6R)-4,5-bis(benzyloxy)-6-((benzyloxy)methyl)tetrahydro-2H-pyran-3-yl)methanamine (30 mg, 0.067 mmol) in i-PrOH (5 mL) were added 3,5-dichloro-1,2,4-thiadiazole (33 mg, 0.21 mmol) and DIPEA (43 mg, 0.34 mmol). The reaction mixture was stirred at rt overnight. The resulting mixture was extracted with EA (10 mL), washed with $H_2O$ and brine, dried over $Na_2SO_4$. The organic layer was separated and concentrated in vacuo. The crude product was purified by flash chromatography to give N-(((3R,4R,5R,6R)-4,5-bis(benzyloxy)-6-((benzyloxy)methyl)tetrahydro-2H-pyran-3-yl)methyl)-3-chloro-1,2,4-thiadiazol-5-amine (10 mg, 27%) as yellow oil. LC-MS (ESI) found: 566 $[M+H]^+$.

Step 2: To a solution of N-(((3R,4R,5R,6R)-4,5-bis(benzyloxy)-6-((benzyloxy)methyl)tetrahydro-2H-pyran-3-yl)methyl)-3-chloro-1,2,4-thiadiazol-5-amine (10 mg, 0.018 mmol) in dry DCM (5 mL), $BCl_3$ (0.2 mL, 1N in DCM) was added under the −78° C. The reaction mixture was stirred at 0° C. for 45 min. The resulting mixture was extracted with DCM (10 mL), washed with $H_2O$ and brine, dried over $Na_2SO_4$. The crude product was purified by Pre-TLC to give (2R,3R,4R,5R)-5-(((3-chloro-1,2,4-thiadiazol-5-yl)amino)methyl)-2-(hydroxymethyl)tetrahydro-2H-pyran-3,4-diol (5 mg, 67%) as yellow oil. LC-MS (ESI) found: 296 $[M+H]^+$. $^1H$ NMR (400 MHz, MeOD): δ 3.97 (dd, J=12.1, 2.0 Hz, 1H), 3.87 (dd, J=5.4, 3.3 Hz, 1H), 3.83-3.77 (m, 2H), 3.76-3.55 (m, 3H), 3.50 (dd, J=12.1, 1.9 Hz, 1H), 3.44-3.39 (m, 1H), 2.09-2.02 (m, 1H).

Synthesis 5-24. Preparation of (E)-2-((((3R,4R,5R,6R)-4,5-dihydroxy-6-(hydroxymethyl)tetrahydro-2H-pyran-3-yl)methyl)amino)ethene-1-sulfonyl Fluoride (Compound A189)

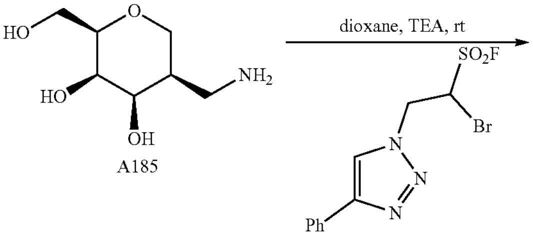

A185

Organic Letters 2022 22 (11), 4316-4321

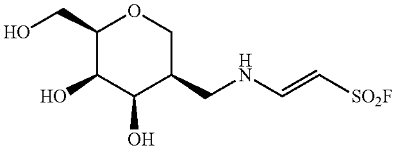

A189

Synthesis 5-25. Preparation of 2-((3R,4R,5R,6R)-4,5-dihydroxy-6-(hydroxymethyl)tetrahydro-2H-pyran-3-yl)acetonitrile (Compound A190)

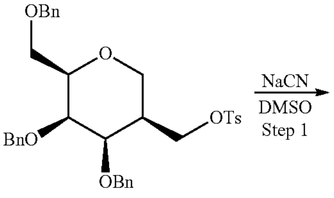

A183-1

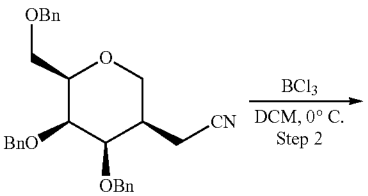

A190-1

-continued

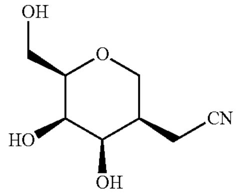

A190

Step 1: To a solution of ((3S,4R,5R,6R)-4,5-bis(benzyloxy)-6-((benzyloxy)methyl)tetrahydro-2H-pyran-3-yl) methyl 4-methylbenzenesulfonate from Synthesis 5-18 (A183-1, 200 mg, 0.46 mmol) in DMSO (5 mL) was added NaCN (68 mg, 1.39 mmol) at room temperature. The mixture was stirred at rt overnight. Then the mixture was extracted by DCM (10 mL*3) and the organic phase was concentrated. The residual was then purified by silica gel column (0-22% ethyl acetate in petroleum ether) to give 2-((3R,4R,5R,6R)-4,5-bis(benzyloxy)-6-((benzyloxy) methyl)tetrahydro-2H-pyran-3-yl)acetonitrile (A190-1, 80 mg, 38%) as an oil. LC-MS (ESI) found: 458 $[M+H]^+$.

Step 2: To a solution of 2-((3R,4R,5R,6R)-4,5-bis(benzyloxy)-6-((benzyloxy)methyl)tetrahydro-2H-pyran-3-yl)acetonitrile (A190-1.15 mg, 0.03 mmol) in dry DCM (3 mL) was added $BCl_3$ (0.33 mL, 0.33 mmol, 1 M in DCM) dropwise at −10° C. under $N_2$ atmosphere. The reaction mixture was stirred at rt for 0.5 h. Then the reaction was cooled to 0° C. and quenched with saturated sodium bicarbonate solution. The mixture was filtered and concentrated in vacuo. The crude product was purified by flash chromatography (silica gel, 0-40% MeOH in DCM) to give 2-((3R,4R,5R,6R)-4,5-dihydroxy-6-(hydroxymethyl)tetrahydro-2H-pyran-3-yl)acetonitrile (A190, 2 mg, 33%) as a colorless oil. LC-MS (ESI) found: 188 $[M+H]^+$. $^1$H NMR (400 MHz, MeOD): δ 4.05 (dd, J=12.3, 1.8 Hz, 1H), 3.80 (ddd, J=16.3, 8.4, 4.5 Hz, 3H), 3.68 (d, J=4.3 Hz, 1H), 3.66-3.58 (m, 2H), 3.42 (ddd, J=7.2, 4.5, 1.6 Hz, 1H), 2.98 (dd, J=17.4, 11.3 Hz, 1H), 2.85 (ddd, J=17.4, 3.8, 1.3 Hz, 1H).

Synthesis 5-26. Preparation of (2R,3R,4R,5S,6S)-2-(hydroxymethyl)-5-methyl-6-phenoxytetrahydro-2H-pyran-3,4-diol (Compound A191), (2R,3R,4R,5S,6R)-2-(hydroxymethyl)-5-methyl-6-phenoxytetrahydro-2H-pyran-3,4-diol (Compound A192), and (2R 3R,4R,5S)-2-(hydroxymethyl)-5-(phenoxymethyl)tetrahydro-2H-pyran-3,4-diol

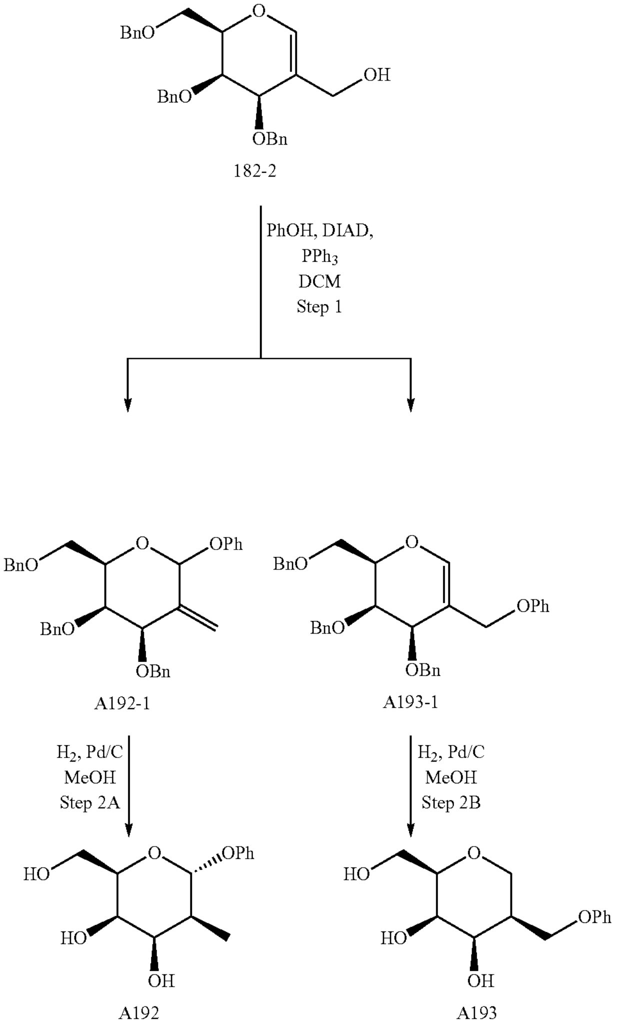

Step 1: To a solution of ((2R,3R,4R)-3,4-bis(benzyloxy)-2-((benzyloxy)methyl)-3,4-dihydro-2H-pyran-5-yl)methanol from Synthesis 5-17 (A182-2, 100 mg, 0.224 mmol, 1.0 eq), $PPh_3$ (88 mg, 0.336 mmol, 1.5 eq) and nucleophiles (1.0 eq) in dry DCM (1.1 mL) was added DIAD (0.053 mL, 0.269 mmol, 1.2 eq) dropwise at ice-bath under $N_2$ atmosphere. Then the reaction was allowed to warm to rt. The resulting reaction mixture was stirred at the same temperature for another 40 min, at which time TLC showed the disappearance of all starting material. The mixture was evaporated. The crude product was further purified by silica gel column chromatography to give desired products. Yield (A192-1): 30 mg, 26%. LC-MS (ESI) found: 545 $[M+Na]^+$. Yield (A193-1): 70 mg, 60%. LC-MS (ESI) found: 545 $[M+Na]^+$.

Step 2A: A suspension of (2R,3R,4R)-3,4-bis(benzyloxy)-2-((benzyloxy)methyl)-5-methylene-6-phenoxytetrahydro-2H-pyran (A192-1, 100 mg, 1.0 eq) and Pd/C (0.2 eq, 10% wt, 60% wet) in MeOH was charged with $H_2$ and stirred under $H_2$ atmosphere. The reaction was stirred at rt and monitored by TLC. When TLC showed the disappearance of all starting material, the mixture was filtered and evaporated. The crude product was further purified by silica gel column chromatography to give desired products. Yield (A192): 0.5 mg, 2%. Yield (A191): 7 mg, 14%. LC-MS (ESI) found: 277 $[M+Na]^+$. $^1H$ NMR (400 MHz, CD3OD) δ 7.30-7.22 (m, 2H), 7.13-7.06 (m, 2H), 6.96 (tt, J=7.4, 1.1 Hz, 1H), 5.44 (d, J=1.8 Hz, 1H), 4.11 (dd, J=5.5, 3.5 Hz, 1H), 3.89 (d, J=2.2 Hz, 2H), 3.75-3.68 (m, 2H), 2.20 (ddd, J=7.4, 5.3, 1.8 Hz, 1H), 1.23 (d, J=7.4 Hz, 3H).

Step 2B: (2R,3R,4R,5S)-2-(hydroxymethyl)-5-(phenoxymethyl)tetrahydro-2H-pyran-3,4-diol)(A193) was synthesized according to the hydrogenation procedure described for Step 2A above. Yield: 9.8 mg, 20%. LC-MS (ESI) found: 277 $[M+Na]^+$. $^1H$ NMR (400 MHz, Methanol-$d_4$): δ 7.30-7.19 (m, 2H), 6.95-6.84 (m, 3H), 4.37 (t, J=10.0 Hz, 1H), 4.24 (ddd, J=9.7, 3.0, 1.4 Hz, 1H), 4.14 (dd, J=11.7, 1.9 Hz, 1H), 3.91 (dd, J=5.6, 3.2 Hz, 1H), 3.81-3.74 (m, 2H), 3.66 (dd, J=11.5, 4.6 Hz, 1H), 3.51 (ddd, J=11.7, 2.6, 1.4 Hz, 1H), 3.41 (ddd, J=7.2, 4.6, 1.7 Hz, 1H), 2.22 (ddd, J=10.2, 5.4, 2.7 Hz, 1H).

Synthesis 5-27. Preparation of (2R,3R,4R,5S,6S)-2-(hydroxymethyl)-5-methyl-6-(1H-tetrazol-1-yl)tetrahydro-2H-pyran-3,4-diol (Compound A194), (2R,3R,4R,5S,6R)-2-(hydroxymethyl)-5-methyl-6-(1H-tetrazol-1-yl)tetrahydro-2H-pyran-3,4-diol (Compound A195), and (2R,3R,4R,5R)-5-((1H-tetrazol-1-yl)methyl)-2-(hydroxymethyl)tetrahydro-2H-pyran-3,4-diol (Compound A196)

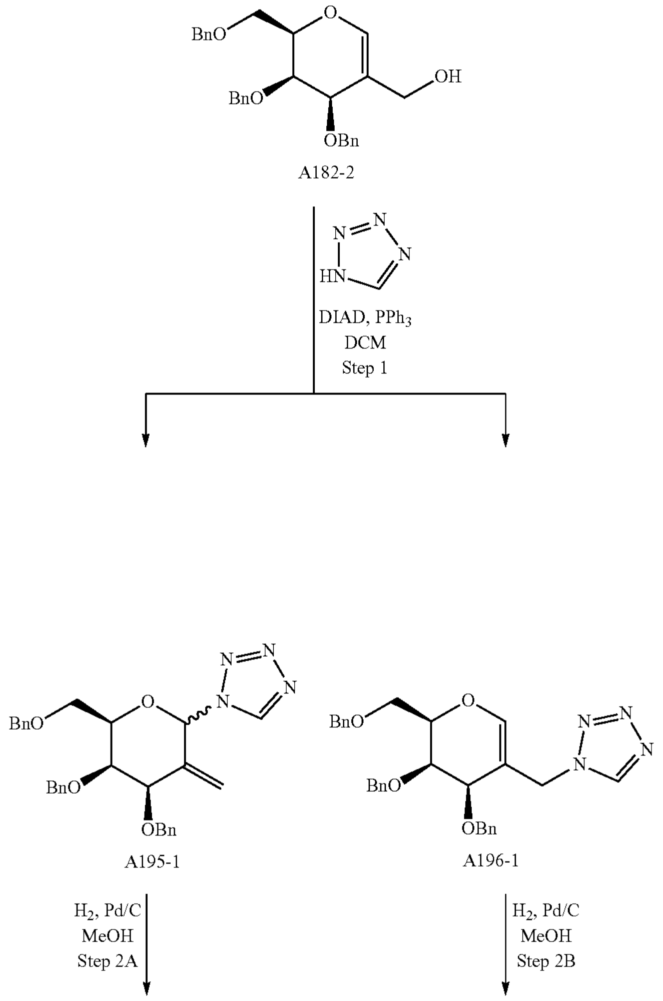

-continued

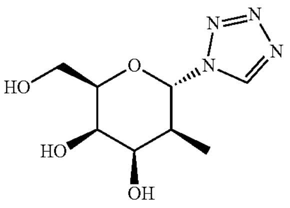

+

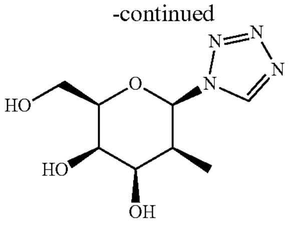

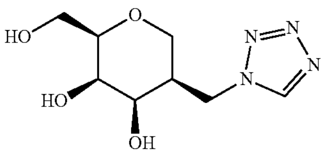

A194 A195 A196

Step 1: 1-((4R,5R,6R)-4,5-bis(benzyloxy)-6-((benzyloxy)methyl)-3-methylenetetrahydro-2H-pyran-2-yl)-1H-tetrazole (A195-1) and 1-(((2R,3R,4R)-3,4-bis(benzyloxy)-2-((benzyloxy)methyl)-3,4-dihydro-2H-pyran-5-yl)methyl)-1H-tetrazole (A196-1) were synthesized according to the Mitsunobu procedure described in Synthesis 5-26 using 500 mg of ((2R,3R,4R)-3,4-bis(benzyloxy)-2-((benzyloxy)methyl)-3,4-dihydro-2H-pyran-5-yl)methanol (A182-2) from Synthesis 5-17. 1-((4R,5R,6R)-4,5-bis(benzyloxy)-6-((benzyloxy)methyl)-3-methylenetetrahydro-2H-pyran-2-yl)-1H-tetrazole (A195-1) Yield: 50 mg, 9%. LC-MS (ESI) found: 521 $[M+Na]^+$. 1-(((2R,3R,4R)-3,4-bis(benzyloxy)-2-((benzyloxy)methyl)-3,4-dihydro-2H-pyran-5-yl)methyl)-1H-tetrazole (A196-1) Yield: 15 mg, 5%. LC-MS (ESI) found: 521 $[M+Na]^+$.

Step 2A: (2R,3R,4R,5S,6R)-2-(hydroxymethyl)-5-methyl-6-(1H-tetrazol-1-yl)tetrahydro-2H-pyran-3,4-diol (A195) and (2R,3R,4R,5S,6S)-2-(hydroxymethyl)-5-methyl-6-(1H-tetrazol-1-yl)tetrahydro-2H-pyran-3,4-diol (A194) were synthesized according to the hydrogenation procedure described in Synthesis 5-26 using 65 mg of 1-((4R,5R,6R)-4,5-bis(benzyloxy)-6-((benzyloxy)methyl)-3-methylenetetrahydro-2H-pyran-2-yl)-1H-tetrazole (A195-1): Yield ((2R,3R,4R,5S,6R)-2-(hydroxymethyl)-5-methyl-6-(1H-tetrazol-1-yl)tetrahydro-2H-pyran-3,4-diol)(A195): 3 mg, 10%. LC-MS (ESI) found: 253 $[M+Na]^+$. Yield ((2R,3R,4R,5S,6S)-2-(hydroxymethyl)-5-methyl-6-(1H-tetrazol-1-yl)tetrahydro-2H-pyran-3,4-diol)(A194): 1 mg, 3%. LC-MS (ESI) found: 253 $[M+Na]^+$.

Step 2B: (2R,3R,4R,5R)-5-((1H-tetrazol-1-yl)methyl)-2-(hydroxymethyl)tetrahydro-2H-pyran-3,4-diol (A196) was synthesized according to the hydrogenation procedure described in Synthesis 5-26 using 14.4 mg of 1-(((2R,3R,4R)-3,4-bis(benzyloxy)-2-((benzyloxy)methyl)-3,4-dihydro-2H-pyran-5-yl)methyl)-1H-tetrazole (A196-1). Yield ((2R,3R,4R,5R)-5-((1H-tetrazol-1-yl)methyl)-2-(hydroxymethyl)tetrahydro-2H-pyran-3,4-diol)(A196): 2 mg, 30%. LC-MS (ESI) found: 231 $[M+H]^+$. $^1H$ NMR (400 MHz, MeOD): δ 8.68 (s, 1H), 5.20 (dd, J=14.0, 11.0 Hz, 1H), 5.05-4.93 (m, 1H), 3.93 (dd, J=5.5, 3.2 Hz, 1H), 3.87-3.76 (m, 3H), 3.70 (dd, J=11.5, 4.6 Hz, 1H), 3.50-3.38 (m, 2H), 2.54-2.22 (m, 1H).

Synthesis 5-28. (2R,3R,4R,5R)-2-(hydroxymethyl)-5-((4-(trifluoromethyl)-1H-pyrazol-1-yl)methyl)tetrahydro-2H-pyran-3,4-diol (Compound A197), 1-(((3R,4R,5R,6R)-4,5-dihydroxy-6-(hydroxymethyl)tetrahydro-2H-pyran-3-yl)methyl)-1H-pyrazole-4-carbonitrile (Compound A198), (2R,3R,4R,5R)-5-((4-chloro-1H-pyrazol-1-yl)methyl)-2-(hydroxymethyl)tetrahydro-2H-pyran-3,4-diol (Compound A199), and (2R,3R,4R,5R)-5-((1H-pyrazolo[3,4-b]pyridin-1-yl)methyl)-2-(hydroxymethyl)tetrahydro-2H-pyran-3,4-diol (Compound A200) were Prepared Using the Procedure Shown in Synthesis 5-26

A197

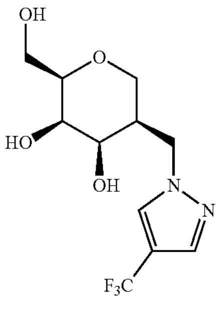

A198

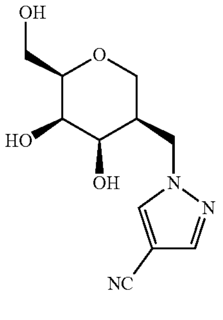

A199

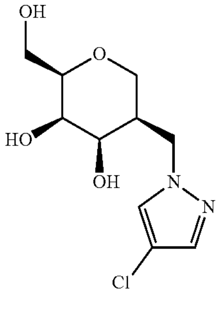

-continued

A200

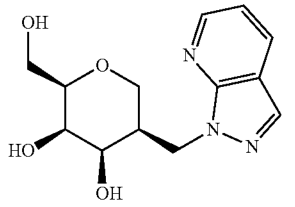

Synthesis 5-29. Preparation of (2R,3R,4R,5S,6S)-5-(2-hydroxyethyl)-2-(hydroxymethyl)-6-phenoxytetrahydro-2H-pyran-3,4-diol (Compound A200) and (2R,3R,4R,5S,6R)-5-(2-hydroxyethyl)-2-(hydroxymethyl)-6-phenoxytetrahydro-2H-pyran-3,4-diol (Compound A201)

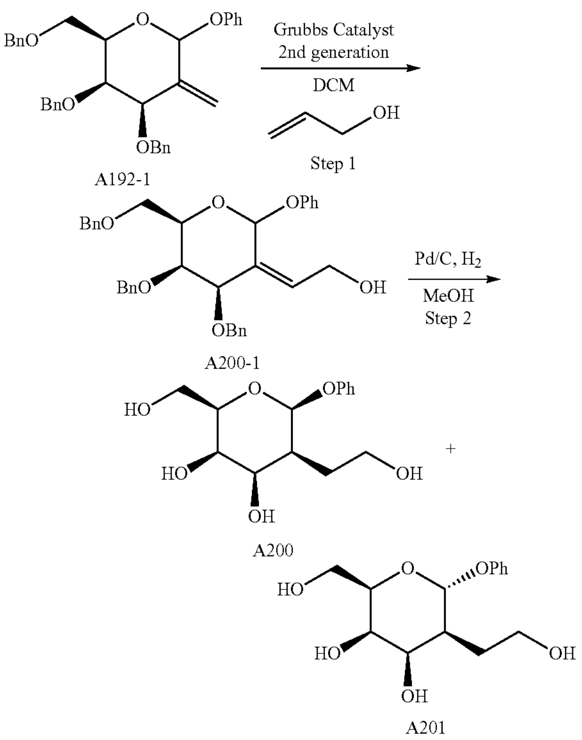

Step 1: To a solution of (2R,3R,4R)-3,4-bis(benzyloxy)-2-((benzyloxy)methyl)-5-methylene-6-phenoxytetrahydro-2H-pyran from Synthesis 5-26 (A192-1, 100 mg, 0.19 mmol) in DCM (10 mL) was added prop-2-en-1-ol (110 mg, 1.9 mmol) and Grubbs catalyst $2^{nd}$ generation (16 mg, 0.019 mmol). The reaction was charged with $N_2$ for three time and stirred at 40° C. for 16 h. LCMS showed the desired product was detected. The solvent was concentrated in vacuo to get a crude product, which was purified by column to afford (Z)-2-((4R,5R,6R)-4,5-bis(benzyloxy)-6-((benzyloxy)methyl)-2-phenoxydihydro-2H-pyran-3(4H)-ylidene)ethan-1-ol (A200-1) as yellow oil. LC-MS (ESI) found: 553 $[M+H]^+$. Reference: Journal of the American Chemical Society, 123(42), 10417-10418; 2001.

Step 2: A solution of (Z)-2-((4R,5R,6R)-4,5-bis(benzyloxy)-6-((benzyloxy)methyl)-2-phenoxydihydro-2H-pyran-3(4H)-ylidene)ethan-1-ol (A200-1, 50 mg, 0.09 mmol) and Pd/C (5 mg, 10% wt, 60% wet) in MeOH was stirred under $H_2$ atmosphere. The reaction was stirred at r.t overnight Then the mixture was filtered and evaporated. The crude product was further purified by silica gel column chromatography to give (2R,3R,4R,5S,6S)-5-(2-hydroxyethyl)-2-(hydroxymethyl)-6-phenoxytetrahydro-2H-pyran-3,4-diol (A200) and (2R,3R,4R,5S,6R)-5-(2-hydroxyethyl)-2-(hydroxymethyl)-6-phenoxytetrahydro-2H-pyran-3,4-diol (A201). LC-MS (ESI): 285 $[M+H]^+$.

Synthesis 5-30. Preparation of (2R,3R,4R,5S,6S)-5-(2-hydroxyethyl)-2-(hydroxymethyl)-6-phenoxytetrahydro-2H-pyran-3,4-diol (Compound A202) and (2R,3R,4R,5S,6R)-5-(2-hydroxyethyl)-2-(hydroxymethyl)-6-phenoxytetrahydro-2H-pyran-3,4-diol (Compound A203)

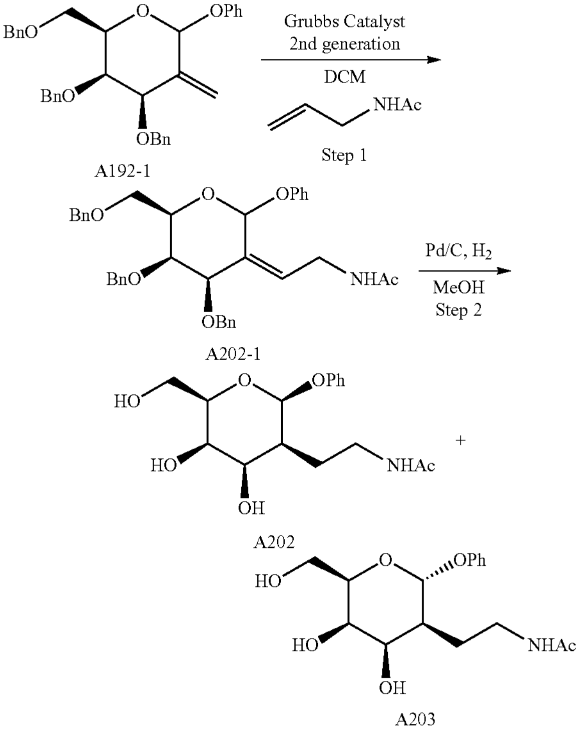

Step 1: To a solution of (2R,3R,4R)-3,4-bis(benzyloxy)-2-((benzyloxy)methyl)-5-methylene-6-phenoxytetrahydro-2H-pyran from Synthesis 5-26 (A192-1, 100 mg, 0.19 mmol) in DCM (10 mL was added N-allylacetamide (188 mg, 1.9 mmol) and Grubbs catalyst $2^{nd}$ generation (16 mg, 0.019 mmol). The reaction was charged with $N_2$ for three time and stirred at 40° C. for 16 h. LCMS showed the desired product was detected. The solvent was concentrated in vacuo to get a crude product, which was purified by column to afford N—((Z)-2-((4R,5R,6R)-4,5-bis(benzyloxy)-6-((benzyloxy)methyl)-2-phenoxydihydro-2H-pyran-3(4H)-ylidene)ethyl)acetamide (A202-1). LC-MS (ESI) found: 594 $[M+H]^+$. Reference: Journal of the American Chemical Society, 123(42), 10417-10418; 2001.

Step 2: A solution of (Z)-2-((4R,5R,6R)-4,5-bis(benzyloxy)-6-((benzyloxy)methyl)-2-phenoxydihydro-2H-pyran-3(4H)-ylidene)ethan-1-ol (A202-1, 50 mg, 0.08 mmol) and Pd/C (5 mg, 10% wt, 60% wet) in MeOH was stirred under $H_2$ atmosphere. The reaction was stirred at r.t overnight Then the mixture was filtered and evaporated. The crude product was further purified by silica gel column chromatography to give (2R,3R,4R,5S,6S)-5-(2-hydroxyethyl)-2-(hydroxymethyl)-6-phenoxytetrahydro-2H-pyran-3,4-diol (Compound A202) and (2R,3R,4R,5S,6R)-5-(2-hydroxyethyl)-2-(hydroxymethyl)-6-phenoxytetrahydro-2H-pyran-3,4-diol (Compound A203). LC-MS (ESI): 326 $[M+H]^+$.

Synthesis 5-31. Preparation of di-tert-butyl 2-(((3R,4R,5R,6R)-4,5-bis(benzyloxy)-6-((benzyloxy)methyl)tetrahydro-2H-pyran-3-yl)methyl)malonate (Compound A204)

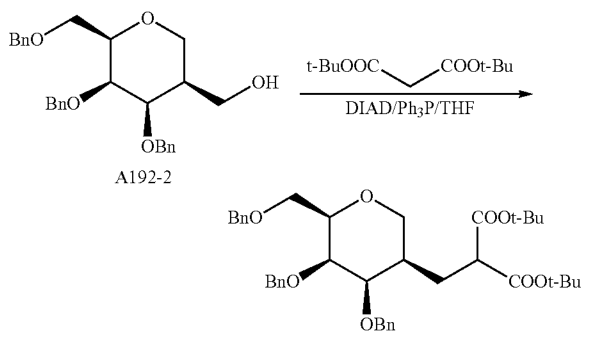

A192-2

A204

Synthesis 5-32. Preparation of 3-((3R,4R,5R,6R)-4,5-bis(benzyloxy)-6-((benzyloxy)methyl)tetrahydro-2H-pyran-3-yl)propanoic Acid (Compound A205)

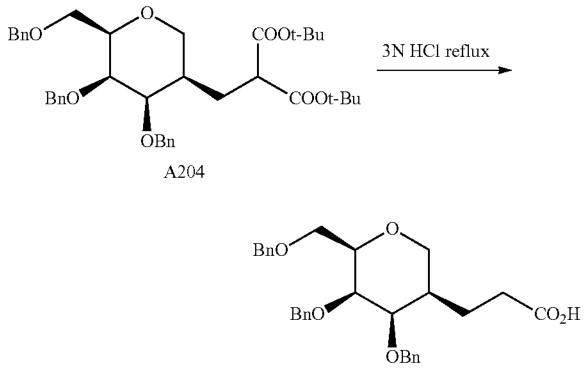

A204

A205

Synthesis 5.33. Preparation of N-(2-((3R,4R,5R,6R)-4,5-dihydroxy-6-(hydroxymethyl)tetrahydro-2H-pyran-3-yl)ethyl)acetamide (Compound A206) and N-(2-((3R,4R,5R,6R)-4,5-dihydroxy-6-(hydroxymethyl)tetrahydro-2H-pyran-3-yl)ethyl)-2,2,2-trifluoroacetamide (Compound A207)

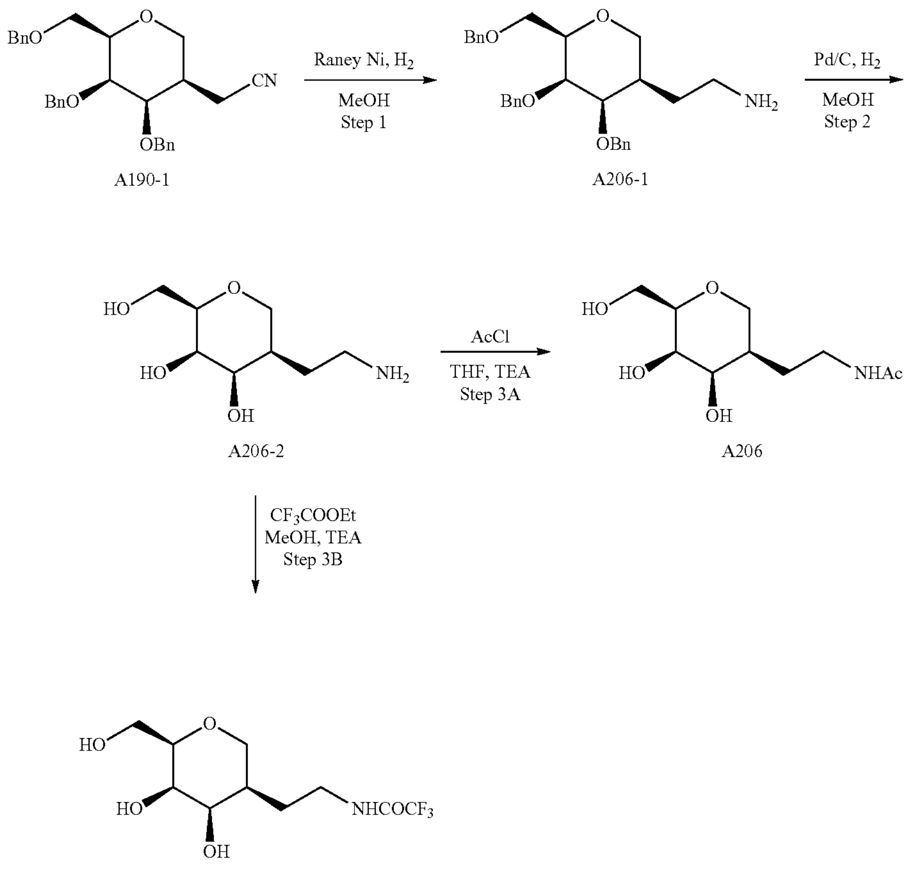

A190-1

A206-1

A206-2

A206

A207

Step 1: A solution of 2-((3R,4R,5R,6R)-4,5-bis(benzyloxy)-6-((benzyloxy)methyl)tetrahydro-2H-pyran-3-yl)acetonitrile (A190-1, 100 mg, 0.22 mmol) and Raney Ni (15 mg) in MeOH was charged with $H_2$ for three times and stirred under $H_2$ atmosphere overnight Then the mixture was filtered and evaporated. The crude product was further purified by silica gel column chromatography to give 2-((3R,4R,5R,6R)-4,5-bis(benzyloxy)-6-((benzyloxy)methyl)tetrahydro-2H-pyran-3-yl)ethan-1-amine (A206-1). LC-MS (ESI): 462 $[M+H]^+$.

Step 2: To a solution of 2-((3R,4R,5R,6R)-4,5-bis(benzyloxy)-6-((benzyloxy)methyl)tetrahydro-2H-pyran-3-yl)ethan-1-amine (A206-1, 80 mg, 0.17 mmol) in MeOH (5 mL) was added Pd/C (10 mg, 10% wt, 60% wet). The reaction was charged with $H_2$ for three time and stirred under $H_2$ atmosphere overnight. The crude product was obtained by filtration and concentration. LC-MS (ESI) found for both targets: 192 $[M+H]^+$.

Step 3A: To a solution of (2R,3R,4R,5R)-5-(2-aminoethyl)-2-(hydroxymethyl)tetrahydro-2H-pyran-3,4-diol (A206-2, 15 mg, 0.078 mmol) in THF (2 mL) was added AcCl (9.1 mg, 0.118 mmol) and TEA (23.6 mg, 0.234 mmol) at rt. The mixture was stirred at rt for 2 h. The mixture was concentrated and the crude material was purified by silica gel column to give N-(2-((3R,4R,5R,6R)-4,5-dihydroxy-6-(hydroxymethyl)tetrahydro-2H-pyran-3-yl)ethyl)acetamide (A206). LC-MS (ESI) found: 234 $[M+H]^+$.

Step 3B: To a solution of (2R,3R,4R,5R)-5-(2-aminoethyl)-2-(hydroxymethyl)tetrahydro-2H-pyran-3,4-diol (A206-2, 15 mg, 0.078 mmol) in MeOH (2 mL) was added $CF_3COOEt$ (16.7 mg, 0.118 mmol) and TEA (23.6 mg, 0.234 mmol) at rt. The mixture was stirred at rt for 2 h. The mixture was concentrated and the crude material was purified by silica gel column to give N-(2-((3R,4R,5R,6R)-4,5-dihydroxy-6-(hydroxymethyl)tetrahydro-2H-pyran-3-yl)ethyl)-2,2,2-trifluoroacetamide (A207). LC-MS (ESI) found: 288 $[M+H]^+$.

Synthesis 5-34. Preparation of 3-(((3R,4R,5R,6R)-4,5-dihydroxy-6-(hydroxymethyl)tetrahydro-2H-pyran-3-yl)methyl)-1,1-dimethylurea (Compound A208)

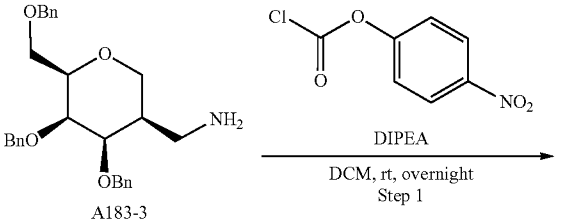

A183-3

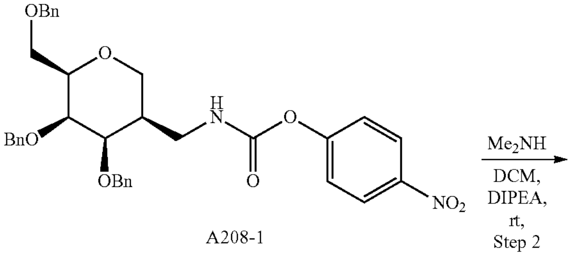

A208-1

-continued

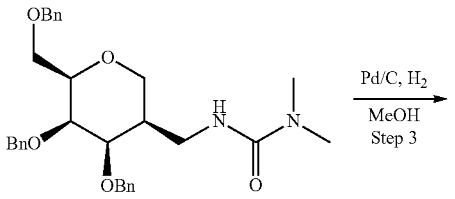

A208-2

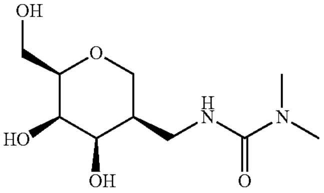

A208

Step 1: To a solution of ((3R,4R,5R,6R)-4,5-bis(benzyloxy)-6-((benzyloxy)methyl)tetrahydro-2H-pyran-3-yl)methanamine from Synthesis 5-18 (A183-3, 100 mg, 0.224 mmol) in DCM (5 mL) was added 4-nitrophenyl carbonochloridate (67.4 mg, 0.336 mmol) and DIPEA (87.0 mg, 0.672 mmol) at rt. The mixture was stirred at rt overnight. The mixture was concentrated and used directly for next step. LC-MS (ESI) found: 613 $[M+H]^+$.

Step 2: To a solution of 4-nitrophenyl (((3R,4R,5R,6R)-4,5-bis(benzyloxy)-6-((benzyloxy)methyl)tetrahydro-2H-pyran-3-yl)methyl)carbamate (A208-1, 137 mg, 0.224 mmol) in DCM (5 mL) was added dimethylamine (0.448 mmol, 1 M in THF) and DIPEA (87.0 mg, 0.672 mmol) at rt. The mixture was stirred at rt overnight. The mixture was concentrated and purified by silica gel column to give 30 mg of the desired product (A208-2). LC-MS (ESI) found: 519 $[M+H]^+$.

Step 3: To a solution of 3-(((3R,4R,5R,6R)-4,5-bis(benzyloxy)-6-((benzyloxy)methyl)tetrahydro-2H-pyran-3-yl)methyl)-1,1-dimethylurea (A208-2, 30 mg, 0.058 mmol) in MeOH (3 mL) was added Pd/C (6 mg, 10% wt, 60% wet). The reaction was charged with $H_2$ for three times and stirred under $H_2$ atmosphere overnight. The crude product was obtained by filtration and concentration. LC-MS (ESI): 249 $[M+H]^+$.

Alternatively, 3-(((3R,4R,5R,6R)-4,5-dihydroxy-6-(hydroxymethyl)tetrahydro-2H-pyran-3-yl)methyl)-1,1-dimethylurea (Compound A208) can be Synthesized in the Following Manner

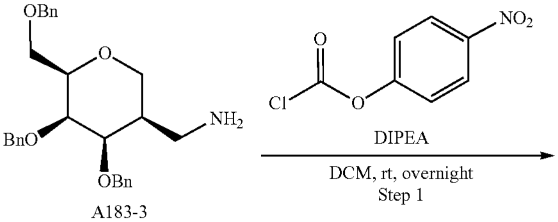

A183-3

-continued

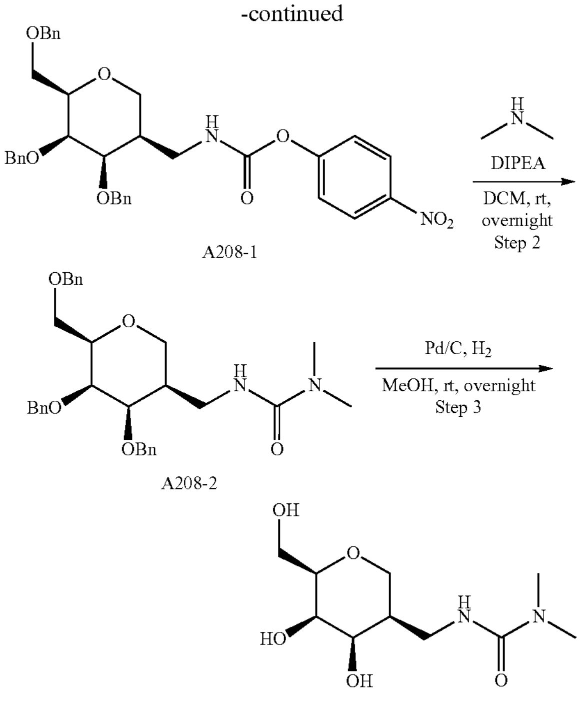

A208-1

A208-2

A208

Step 1: To a solution of ((3R,4R,5R,6R)-4,5-bis(benzyloxy)-6-((benzyloxy)methyl)tetrahydro-2H-pyran-3-yl) methanamine (45 mg, 0.110 mmol) in dry DCM (10 mL), 4-nitrophenyl carbonochloridate (34 mg, 0.170 mmol) and DIPEA (28 mg, 0.220 mmol) was added. The reaction mixture was stirred at rt overnight. The resulting mixture was extracted with EA (10 mL), washed with $H_2O$ (10 mL×2) and brine (10 mL), dried over $Na_2SO_4$ to give crude 4-nitrophenyl (((3R,4R,5R,6R)-4,5-bis(benzyloxy)-6-((benzyloxy)methyl)tetrahydro-2H-pyran-3-yl)methyl)carbamate (67 mg) as a yellow oil. LC-MS (ESI) found: 613 $[M+H]^+$.

Step 2: To a solution of 4-nitrophenyl (((3R,4R,5R,6R)-4,5-bis(benzyloxy)-6-((benzyloxy)methyl)tetrahydro-2H-pyran-3-yl)methyl)carbamate (67 mg, 0.110 mmol) in dry DCM (5 mL), dimethylamine (30 mg, 0.667 mmol) and DIPEA (60 mg, 0.467 mmol) was added. The reaction mixture was stirred at rt overnight. The resulting mixture was extracted with EA (10 mL), washed with $H_2O$ (10 mL×2) and brine (10 mL), dried over $Na_2SO_4$. The organic layer was separated and concentrated in vacuo. The crude product was purified by flash chromatography (silica gel, 0~50% EA in PE) to give 3-(((3R,4R,5R,6R)-4,5-bis(benzyloxy)-6-((benzyloxy)methyl)tetrahydro-2H-pyran-3-yl) methyl)-1,1-dimethylurea (25 mg, 44% yield) as a yellow oil. LC-MS (ESI) found: 519 $[M+H]^+$.

Step 3: To a solution of 3-(((3R,4R,5R,6R)-4,5-bis(benzyloxy)-6-((benzyloxy)methyl)tetrahydro-2H-pyran-3-yl) methyl)-1,1-dimethylurea (25 mg, 0.048 mmol) in dry MeOH (5 mL), Pd/C (5 mg, 10% wt, 60% wet) and HCl (0.1 mL, 1 M in $H_2O$) was added. The reaction mixture was stirred at rt overnight under a $H_2$ balloon. The organic mixture was filtration and concentrated in vacuo to give 3-(((3R,4R,5R,6R)-4,5-dihydroxy-6-(hydroxymethyl)tetrahydro-2H-pyran-3-yl)methyl)-1,1-dimethylurea (9 mg, 76% yield) as a yellow oil. LC-MS (ESI) found: 249 $[M+H]^+$. $^1H$ NMR (400 MHz, MeOD): δ 3.93 (dd, J=12.0, 2.1 Hz, 1H), 3.91-3.86 (m, 1H), 3.85-3.76 (m, 2H), 3.70-3.61 (m, 2H), 3.55-3.40 (m, 3H), 2.95 (s, 6H), 2.01-1.92 (m, 1H).

Synthesis 5-35. Preparation of (2R,3R,4R,5R)-2-(hydroxymethyl)-5-(morpholinomethyl)tetrahydro-2H-pyran-3,4-diol (Compound A209)

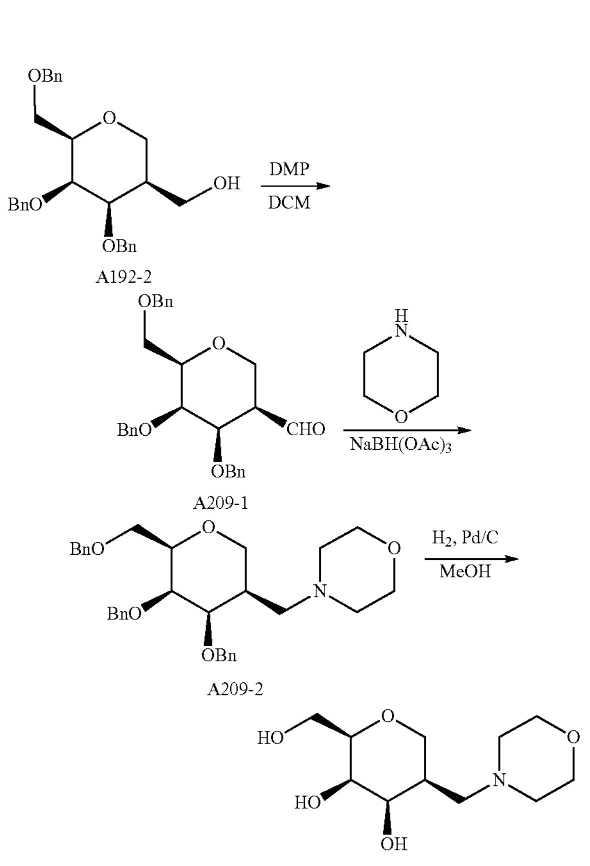

A192-2

A209-1

A209-2

A209

Step 1: To a solution of ((3R,4R,5R,6R)-4,5-bis(benzyloxy)-6-((benzyloxy)methyl)tetrahydro-2H-pyran-3-yl) methanol from Synthesis 5-17 (A192-2, 500.0 mg, 1.11 mmol) in DCM (5 mL) was added DMP (945.5 mg, 2.22 mmol) at 0° C. in portions. The mixture was stirred at rt for 5 h. The mixture was quenched with aqueous $NaHCO_3$. The two phases were separated and the organic phase was dried over $Na_2SO_4$, filtered and concentrated to give a crude product, which was purified by column to give (3R,4R,5R,6R)-4,5-bis(benzyloxy)-6-((benzyloxy)methyl)tetrahydro-2H-pyran-3-carbaldehyde (A209-1, 350.2 mg, 70%) as yellow oil. LC-MS (ESI) found: 447 $[M+H]^+$. $^1H$ NMR (400 MHz, $CD_3OD$): δ 9.93 (s, 1H), 7.47-7.14 (m, 15H), 4.81-4.37 (m, 8H), 4.17-3.95 (m, 2H), 3.79-3.62 (m, 1H), 3.59-3.41 (m, 2H), 2.70 (s, 1H).

Step 2: To a solution of (4R,5R,6R)-4,5-bis(benzyloxy)-6-[(benzyloxy)methyl]oxane-3-carbaldehyde (A209-2, 60.0 mg, 0.134 mmol) and morpholine (0.024 mL, 0.269 mmol) in DCM (2 mL) was added $NaBH(OAc)_3$ (170 mg, 0.269 mmol) at 0° C. in portions. The mixture was stirred at rt for 2 h. The mixture was quenched with $H_2O$ and concentrated in vacuo to give a crude product, which was purified by prep-HPLC to give 4-(((3R,4R,5R,6R)-4,5-bis(benzyloxy)-6-((benzyloxy)methyl)tetrahydro-2H-pyran-3-yl)methyl) morpholine (A209-2, 62 mg, 89%) as colorless oil. LC-MS (ESI) found: 518 $[M+H]^+$.

Step 3: To a solution of 4-(((3R,4R,5R,6R)-4,5-bis(benzyloxy)-6-((benzyloxy)methyl)tetrahydro-2H-pyran-3-yl)

methyl)morpholine (A290-2, 60.0 mg, 0.116 mmol) in MeOH (2 mL) was added Pd/C (30 mg, 10% wt, 60% wet). The mixture was stirred at rt for 12 h under $H_2$ atmosphere. The mixture was filtered and concentrated to give (2R,3R,4R,5R)-2-(hydroxymethyl)-5-(morpholinomethyl)tetrahydro-2H-pyran-3,4-diol (A209, 4.2 mg, 15%) as yellow oil. LC-MS (ESI) found: 248 $[M+H]^+$. $^1H$ NMR (400 MHz, MeOD); δ 3.87-3.81 (m, 2H), 3.76 (dd, J=6.8, 4.7 Hz, 2H), 3.68 (ddd, J=13.9, 9.3, 4.4 Hz, 6H), 3.56 (dd, J=12.1, 3.2 Hz, 1H), 3.37 (ddd, J=7.2, 4.5, 1.5 Hz, 1H), 3.23 (dd, J=12.8, 9.4 Hz, 1H), 2.68-2.52 (m, 4H), 2.14 (d, J=4.5 Hz, 1H).

Synthesis 5-36. Preparation of 1-((3R,4R,5R,6R)-4,5-bis(benzyloxy)-6-((benzyloxy)methyl)tetrahydro-2H-pyran-3-yl)-N,N-dimethylmethanamine (Compound A2010)

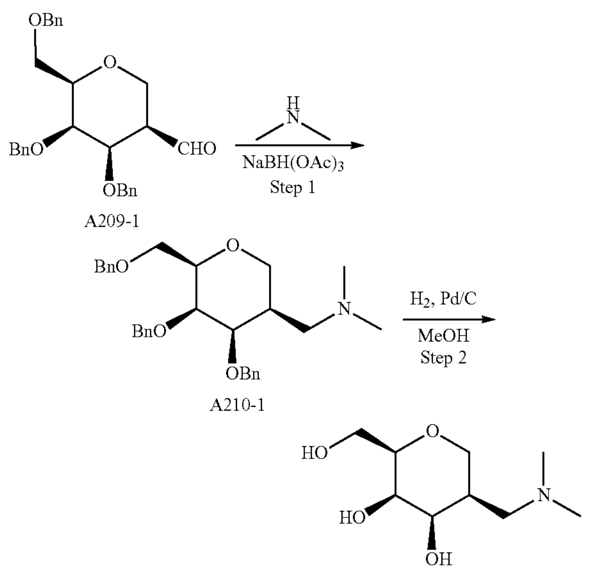

A209-1

A210-1

A210-2

Step 1: To a solution of (4R,5R,6R)-4,5-bis(benzyloxy)-6-[(benzyloxy)methyl]oxane-3-carbaldehyde from Synthesis 5-35 (A209-1, 60 mg, 0.134 mmol) and dimethylamine hydrochloride (33 mg, 0.403 mmol) in DCM (2 mL) was added $NaBH(OAc)_3$ (170 mg, 0.134 mmol) at 0° C. in portions. The mixture was stirred at rt for 2 h. The mixture was quenched with $H_2O$ and concentrated to give a crude product, which was purified by prep-HPLC (Method A) to give 1-((3R,4R,5R,6R)-4,5-bis(benzyloxy)-6-((benzyloxy)methyl)tetrahydro-2H-pyran-3-yl)-N,N-dimethylmethanamine (A210-1, 60 mg, 94%) as colorless oil. LC-MS (ESI) found: 476 $[M+H]^+$. $^1H$ NMR (400 MHz, $CD_3OD$): δ 7.42-7.20 (m, 15H), 4.79 (d, J=11.2 Hz, 1H), 4.66 (d, J=12.4 Hz, 2H), 4.56-4.41 (m, 3H), 3.94 (dd, J=11.9, 2.7 Hz, 1H), 3.89-3.80 (m, 2H), 3.70-3.61 (m, 2H), 3.52 (ddd, J=13.9, 12.7, 6.0 Hz, 2H), 2.98-2.86 (m, 1H), 2.76 (s, 1H), 2.29 (s, 6H), 2.16 (d, J=7.2 Hz, 1H).

Step 2: To a solution of 1-((3R,4R,5R,6R)-4,5-bis(benzyloxy)-6-((benzyloxy)methyl)tetrahydro-2H-pyran-3-yl)-N,N-dimethylmethanamine (A210-1, 60 mg, 0.126 mmol) in MeOH (3 mL) was added Pd/C (10 mg, 10% wt, 60% wet). The mixture was stirred at rt for 12 h under $H_2$ atmosphere. The mixture was filtered and concentrated to give (2R,3R,4R,5R)-5-((dimethylamino)methyl)-2-(hydroxymethyl)tetrahydro-2H-pyran-3,4-diol (A210) as yellow oil. LC-MS (ESI) found: 206 $[M+H]^+$.

Synthesis 5-37. 1-(4-(((3R,4R,5R,6R)-4,5-dihydroxy-6-(hydroxymethyl)tetrahydro-2H-pyran-3-yl)methyl)piperazin-1-yl)ethan-1-one (Compound A211), (2R,3R,4R,5R)-2-(hydroxymethyl)-5-((4-methylpiperazin-1-yl)methyl)tetrahydro-2H-pyran-3,4-diol (Compound A212), and (2R,3R,4R,5R)-2-(hydroxymethyl)-5-(piperidin-1-ylmethyl)tetrahydro-2H-pyran-3,4-diol (Compound A213) were Prepared Using the Procedure of Synthesis 5-36

A211

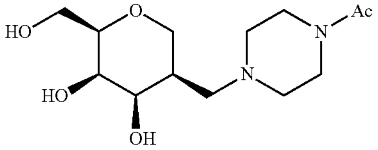 [SMILES: CC(=O)N1CCN(C[C@@H]2CO[C@H](CO)[C@H](O)[C@@H]2O)CC1]

A212

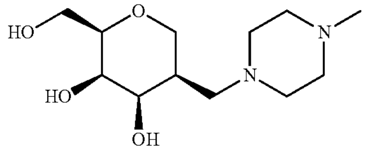 [SMILES: CN1CCN(C[C@@H]2CO[C@H](CO)[C@H](O)[C@@H]2O)CC1]

A213

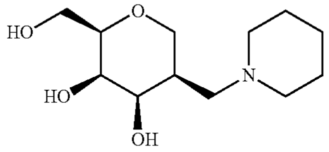 [SMILES: OC[C@H]1OC[C@@H](CN2CCCCC2)[C@@H](O)[C@H]1O]

| ID | Characterization data |
|---|---|
| A212 | LC-MS (ESI) found: 261 $[M + H]^+$. $^1H$ NMR (400 MHz, MeOD): δ 4.06-3.54 (m, 16H), 3.46-3.41 (m, 1H), 3.03 (s, 3H), 2.51-2.42 (m, 1H). |
| A213 | LC-MS (ESI) found: 246 $[M + H]^+$. $^1H$ NMR (400 MHz, MeOD): δ 3.99 (dd, J = 11.4, 4.6 Hz, 1H), 3.80 (d, J = 2.6 Hz, 1H), 3.73-3.65 (m, 3H), 3.60 (dd, J = 10.6, 3.1 Hz, 2H), 3.42-3.37 (m, 1H), 3.23-3.18 (m, 1H), 3.18-3.14 (m, 1H), 3.05-2.93 (m, 3H), 2.50-2.42 (m, 1H), 1.99-1.93 (m, 2H), 1.86-1.75 (m, 3H), 1.59-1.52 (m, 1H). |

Synthesis 5-38. Preparation of (2R,3R,4R,5S,6R)-5-amino-2-(hydroxymethyl)-6-methoxytetrahydro-2H-pyran-3,4-diol (Compound A214)

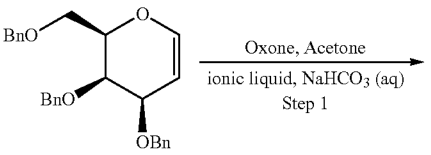

A126

-continued

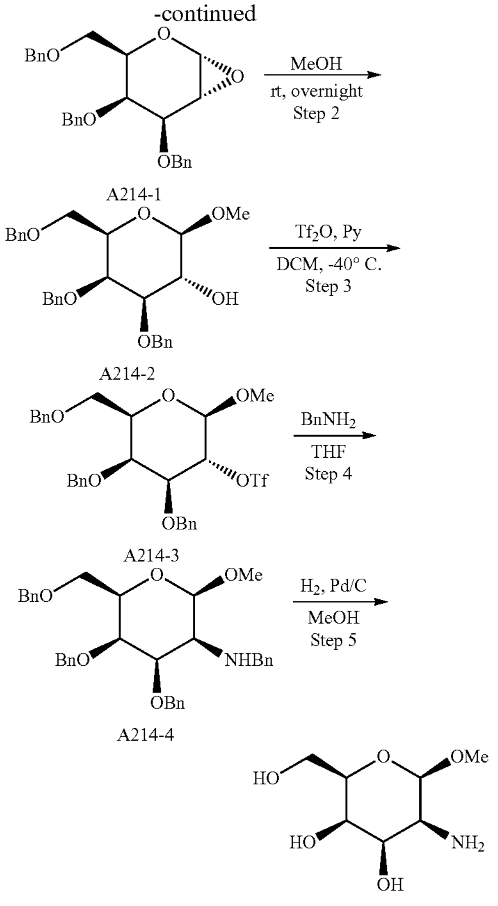

A214-1

A214-2

A214-3

A214-4

A214

Step 1: To a mixture of (2R,3R,4R)-3,4-bis(benzyloxy)-2-((benzyloxy)methyl)-3,4-dihydro-2H-pyran from Synthesis 4-3 (A126, 6.5 g, 15.6 mmol) and 1-dodecyl-3-methylimidazolium tetrafluoroborate (1.06 g, 3.1 mmol) in DCM (65 mL) was added acetone (26 mL) and $NaHCO_3$ (49 mL). Then oxone (19.5 g, mmol) in $H_2O$ (81 mL) was added dropwise to the stirring reaction at 0° C. After 2 hours, the mixture was quenched with $H_2O$ and extracted with EA. The combined organic layer was washed with brine, dried over anhydrous $Na_2SO_4$, filtered. The filtrate was concentrated to give (1S,3R,4S,5S,6R)-4,5-bis(benzyloxy)-3-((benzyloxy)methyl)-2,7-dioxabicyclo[4.1.0]heptane (A214-1, 6.0 g, 89%) as a colorless oil. LC-MS (ESI) found: 433 $[M+H]^+$.

Step 2: A solution of (1S,3R,4S,5S,6R)-4,5-bis(benzyloxy)-3-((benzyloxy)methyl)-2,7-dioxabicyclo[4.1.0]heptane (A214-1, 6.0 g, 13.9 mmol) in MeOH (0.6 mL, 13.9 mmol) was stirred at rt overnight. The mixture was concentrated and purified by chromatography on (silical gel, 0-50% ethyl acetate in petroleum ether) to give (2R,3R,4R,5S,6R)-4,5-bis(benzyloxy)-6-((benzyloxy)methyl)-2-methoxytetrahydro-2H-pyran-3-ol (A214-2, 4.5 g, 70%) as a white solid. LC-MS (ESI) found: 465 $[M+H]^+$.

Step 3: To a mixture of (2R,3R,4R,5S,6R)-4,5-bis(benzyloxy)-6-((benzyloxy)methyl)-2-methoxytetrahydro-2H-pyran-3-ol (A214-2, 200 mg, 0.43 mmol) in dry DCM (5.0 mL) was added dry pyridine (0.53 mL) and $Tf_2O$ (705 mg, 0.43 mmol) at 0° C. under $N_2$. After stirring for 2 h, the mixture was concentrated and purified by chromatography on (0-30% ethyl acetate in petroleum) to give (2R,3R,4S,5S,6R)-4,5-bis(benzyloxy)-6-((benzyloxy)methyl)-2-methoxytetrahydro-2H-pyran-3-yl trifluoromethanesulfonate (A214-3, 137 mg, 53.3%) as a yellow oil. LC-MS (ESI) found: 597 $[M+H]^+$. $^1H$ NMR (400 MHz, $CDCl_3$) δ 7.37-7.25 (m, 15H), 5.23 (dd, J=9.8, 3.7 Hz, 1H), 4.96 (d, J=3.7 Hz, 1H), 4.89 (d, J=11.2 Hz, 1H), 4.74-4.62 (m, 2H), 4.51-4.39 (m, 3H), 4.05-3.98 (m, 2H), 3.92 (t, J=6.5 Hz, 1H), 3.53 (t, J=5.2 Hz, 2H), 3.43 (d, J=10.1 Hz, 3H).

Step 4: A solution of (2R,3R,4S,5S,6R)-4,5-bis(benzyloxy)-6-((benzyloxy)methyl)-2-methoxytetrahydro-2H-pyran-3-yl trifluoromethanesulfonate (A214-3, 200 mg, 0.336 mmol) and benzyl amine (360 mg, 3.36 mmol) in dry THF (2 mL) was heated to 80° C. in seal tube. The resulting reaction mixture was monitored by TLC. When TLC showed the disappearance of all starting material, the mixture was evaporated. The crude product was further purified by silica gel column chromatography (PE/EA=1:1) to give desired product (A214-4, 250 mg, 67% yield) as yellow oil. LC-MS (ESI) found: 554$[M+H]^+$.

Step 5: To a solution of (2R,3S,4R,5R,6R)—N-benzyl-4,5-bis(benzyloxy)-6-((benzyloxy)methyl)-2-methoxytetrahydro-2H-pyran-3-amine (A214-4, 35 mg, 0.063 mmol) in MeOH (3 mL) was added Pd/C (10 mg, 10% wt, 60% wet) at rt under $H_2$. The reaction was stirred at rt under $H_2$ atmosphere for 3 h. The resulting mixture was filtered and concentrated in vacuo to give (2R,3R,4R,5S,6R)-5-amino-2-(hydroxymethyl)-6-methoxytetrahydro-2H-pyran-3,4-diol (A214) as a white solid. LC-MS (ESI) found: 194$[M+H]^+$.

Synthesis 5-39. Preparation of N-((2R,3S,4R,5R,6R)-4,5-dihydroxy-6-(hydroxymethyl)-2-methoxytetrahydro-2H-pyran-3-yl)acetamide (Compound A215)

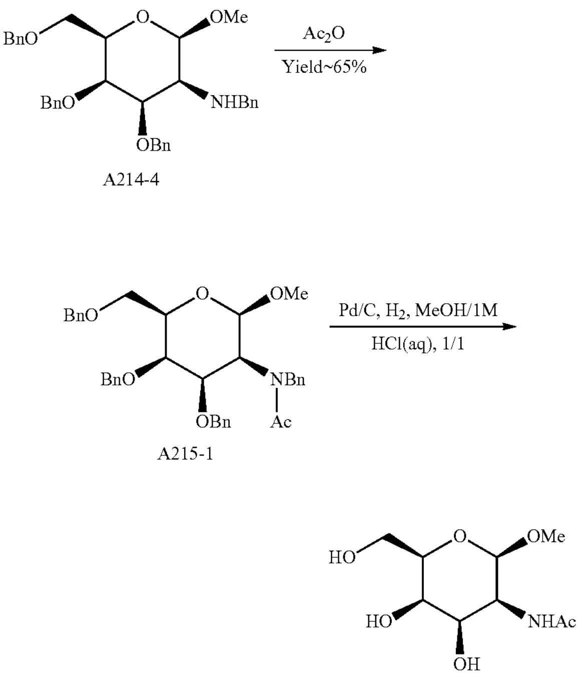

A214-4

A215-1

A215

Synthesis 5-40. Alternative Preparation of (2R,3R,4R,5S,6R)-5-amino-2-(hydroxymethyl)-6-methoxytetrahydro-2H-pyran-3,4-diol (Compound A214)

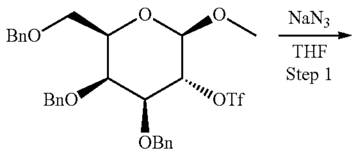

A214-3

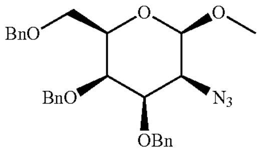

A215-2

Step 1: (2R,3S,4R,5R,6R)-3-azido-4,5-bis(benzyloxy)-6-((benzyloxy)methyl)-2-methoxytetrahydro-2H-pyran (A215-2) was prepared following a similar procedure for (2R,3S,4R,5R,6R)—N-benzyl-4,5-bis(benzyloxy)-6-((benzyloxy)methyl)-2-methoxytetrahydro-2H-pyran-3-amine (A214-4) in Synthesis 5-38. Yield: 300 mg, 73%. LC-MS (ESI) found: 512 $[M+Na]^+$.

Synthesis 5-41: Preparation of (2R,3R,4R,5S,6R)-2-(hydroxymethyl)-6-methoxy-5-(methylamino)tetrahydro-2H-pyran-3,4-diol (Compound A216)

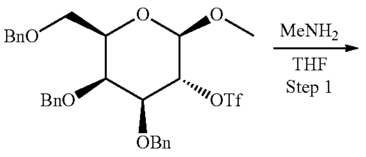

A214-3

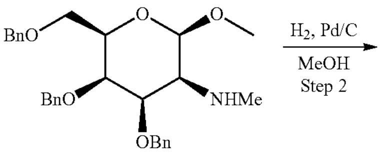

A216-1

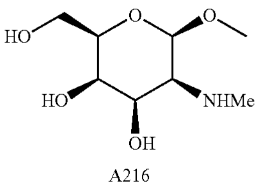

A216

Step 1: (2R,3S,4R,5R,6R)-4,5-bis(benzyloxy)-6-((benzyloxy)methyl)-2-methoxy-N-methyltetrahydro-2H-pyran-3-amine (A216-1) was prepared following a similar procedure for (2R,3S,4R,5R,6R)—N-benzyl-4,5-bis(benzyloxy)-6-((benzyloxy)methyl)-2-methoxytetrahydro-2H-pyran-3-amine (A214-4) in Synthesis 5-38. LC-MS (ESI) found: 478 $[M+H]^+$.

Step 2: (2R,3R,4R,5S,6R)-2-(hydroxymethyl)-6-methoxy-5-(methylamino)tetrahydro-2H-pyran-3,4-diol (A216) was prepared following a similar procedure for (2R,3R,4R,5S,6R)-5-amino-2-(hydroxymethyl)-6-methoxytetrahydro-2H-pyran-3,4-diol (A214) in Synthesis 5-38. LC-MS (ESI) found: 208 $[M+H]^+$.

Synthesis 5-42. Preparation of (2R,3R,4S,5S,6R)-2-(hydroxymethyl)-5,6-diethoxytetrahydro-2H-pyran-3,4-diol (Compound A217)

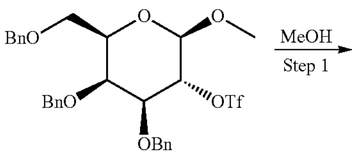

A214-3

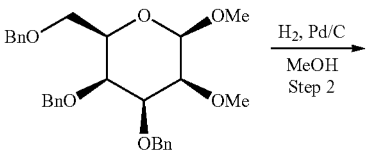

A217-1

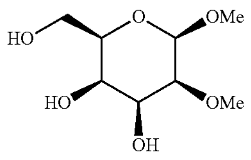

A217

Step 1: (2R,3S,4S,5S,6R)-3,4-bis(benzyloxy)-2-((benzyloxy)methyl)-5,6-dimethoxytetrahydro-2H-pyran (A217-1) was prepared following a similar procedure for (2R,3S,4R,5R,6R)—N-benzyl-4,5-bis(benzyloxy)-6-((benzyloxy)methyl)-2-methoxytetrahydro-2H-pyran-3-amine (A214-4) in Synthesis 5-38. Yield: 170 mg, 83%. LC-MS (ESI) found: 501 $[M+Na]^+$.

Step 2: (2R,3R,4S,5S,6R)-2-(hydroxymethyl)-5,6-dimethoxytetrahydro-2H-pyran-3,4-diol (A217) was prepared following a similar procedure for (2R,3R,4R,5S,6R)-5-amino-2-(hydroxymethyl)-6-methoxytetrahydro-2H-pyran-3,4-diol (A214) in Synthesis 5-38. Yield: 15 mg, 55%. LC-MS (ESI) found: 231 $[M+Na]^+$. $^1$H NMR (400 MHz, Methanol-$d_4$) δ 4.33 (d, J=4.6 Hz, 1H), 4.17 (p, J=5.0 Hz, 2H), 4.03-3.97 (m, 1H), 3.89 (t, J=4.9 Hz, 1H), 3.79-3.68 (m, 2H), 3.44 (s, 3H), 3.43 (s, 3H).

Alternatively, (2R,3R,4S,5S,6R)-2-(hydroxymethyl)-5,6-dimethoxytetrahydro-2H-pyran-3,4-diol (Compound A217) Can Be Synthesized in The Following Manner

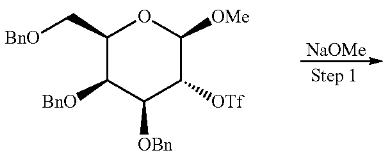

A214-3

-continued

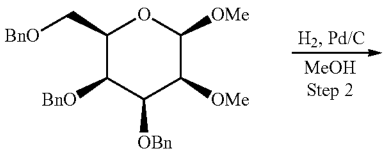

A217-1

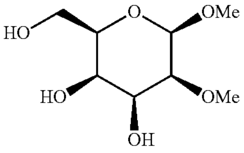

A217

Step 1: A solution of (2R,3R,4S,5S,6R)-4,5-bis(benzyloxy)-6-((benzyloxy)methyl)-2-methoxytetrahydro-2H-pyran-3-yl trifluoromethanesulfonate (200 mg, 0.336 mmol) in MeOH (1 mL) is added NaOMe (0.1 mL, 5.0 M in MeOH). The mixture was stirred at rt for 1 h. The resulting reaction mixture was monitored by TLC. When TLC showed the disappearance of all starting material, the mixture was evaporated. The crude product was further purified by silica gel column chromatography to give desired product (170 mg, 83% yield) as yellow oil. LC-MS (ESI) found: 501 $[M+Na]^+$.

Step 2: To a solution of (2R,3S,4S,5S,6R)-3,4-bis(benzyloxy)-2-((benzyloxy)methyl)-5,6-dimethoxytetrahydro-2H-pyran (35 mg, 0.063 mmol) in MeOH (3 mL) was added Pd/C (10 mg, 10% wt, 60% wet) at rt under $H_2$. The reaction was stirred at rt under a $H_2$ balloon for 3 h. The resulting mixture was filtered and concentrated in vacuo to give 2R,3R,4S,5S,6R)-2-(hydroxymethyl)-5,6-dimethoxytetrahydro-2H-pyran-3,4-diol (15 mg, 55% yield). $^1$H NMR (400 MHz, Methanol-$d_4$) δ 4.33 (d, J=4.6 Hz, 1H), 4.17 (p, J=5.0 Hz, 2H), 4.03-3.97 (m, 1H), 3.89 (t, J=4.9 Hz, 1H), 3.79-3.68 (m, 2H), 3.44 (s, 3H), 3.43 (s, 3H). LC-MS (ESI) found: 231 $[M+Na]^+$ Synthesis 5-43. Preparation of (2R,3R,4R,5S,6R)-2-(hydroxymethyl)-6-methoxy-5-morpholinotetrahydro-2H-pyran-3,4-diol (Compound A218)

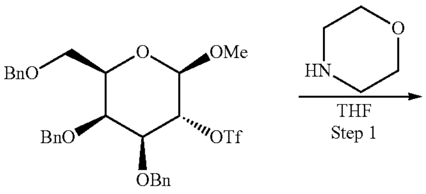

A214-3

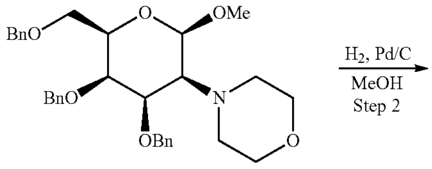

A218-1

-continued

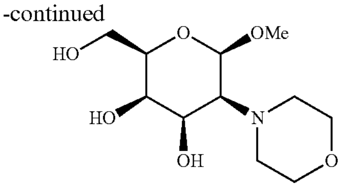

A218

Step 1: 4-((2R,3S,4R,5R,6R)-4,5-bis(benzyloxy)-6-((benzyloxy)methyl)-2-methoxytetrahydro-2H-pyran-3-yl)morpholine (A218-1) was prepared following a similar procedure for (2R,3S,4R,5R,6R)—N-benzyl-4,5-bis(benzyloxy)-6-((benzyloxy)methyl)-2-methoxytetrahydro-2H-pyran-3-amine (A214-4) in Synthesis 5-38. Yield: 550 mg, 62%. LC-MS (ESI) found: 534 $[M+H]^+$.

Step 2: (2R,3R,4R,5S,6R)-2-(hydroxymethyl)-6-methoxy-5-morpholinotetrahydro-2H-pyran-3,4-diol (A218) was prepared following a similar procedure for (2R,3R,4R,5S,6R)-5-amino-2-(hydroxymethyl)-6-methoxytetrahydro-2H-pyran-3,4-diol (A214) in Synthesis 5-38. Yield: 6 mg, 30%. LC-MS (ESI) found: 264 $[M+H]^+$. $^1$H NMR (400 MHz, $CD_3OD$): δ 4.49 (d, J=1.9 Hz, 1H), 3.85-3.79 (m, 2H), 3.78-3.74 (m, 1H), 3.74-3.66 (m, 4H), 3.60 (ddd, J=11.8, 6.0, 3.2 Hz, 2H), 3.50 (s, 3H), 3.15 (t, J=20.8 Hz, 2H), 3.03-2.93 (m, 2H), 2.88 (s, 1H).

Synthesis 5-44: Preparation of N-((2R,3S,4R,5R,6R)-4,5-dihydroxy-6-(hydroxymethyl)-2-methoxytetrahydro-2H-pyran-3-yl)-N-methylacetamide (Compound A219)

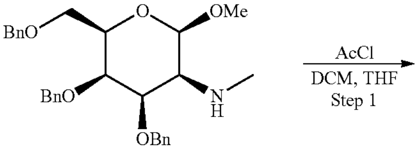

A216-1

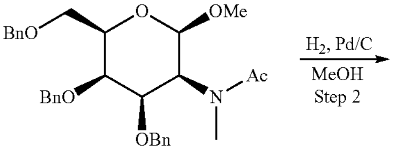

A219-1

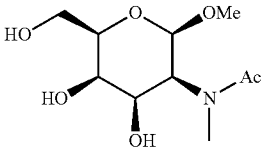

A219

Step 1: To a solution of (2R,3S,4R,5R,6R)-4,5-bis(benzyloxy)-6-((benzyloxy)methyl)-2-methoxy-N-methyltetrahydro-2H-pyran-3-amine from Synthesis 5-41 (A216-1, 100 mg, 0.210 mmol) and TEA (64 mg, 0.630 mmol) in DCM (5 mL) was added AcCl (25 mg, 0.315 mmol) dropwise at 0° C. The reaction mixture was stirred at rt for 1.5 h. The resulting mixture was diluted with DCM (10 mL), washed with $H_2O$ (10 mL×2) and brine (10 mL), dried over $Na_2SO_4$, filtered. The organic layer was concentrated in vacuo to give a crude product, which was purified by flash chromatography (silica gel, 0~80% EA in PE) to give N-((2R,3S,4R,5R,6R)-4,5-bis(benzyloxy)-6-((benzyloxy)methyl)-2-methoxytetrahydro-2H-pyran-3-yl)-N-methylacetamide (A219-1). LC-MS (ESI) of both found: 520 $[M+H]^+$.

Step 2: N-((2R,3S,4R,5R,6R)-4,5-dihydroxy-6-(hydroxymethyl)-2-methoxytetrahydro-2H-pyran-3-yl)-N-methylacetamide (A219) was prepared following a similar procedure for (2R,3R,4R,5S,6R)-5-amino-2-(hydroxymethyl)-6-methoxytetrahydro-2H-pyran-3,4-diol (A214) in Synthesis 5-38. Yield: 7 mg, 32%. LC-MS (ESI) found: 250 $[M+H]^+$.

Synthesis 5-46. Preparation of (2R,3R,4R,5R)-2-(hydroxymethyl)-5-(trifluoromethyl)tetrahydro-2H-pyran-3,4-diol (Compound A221)

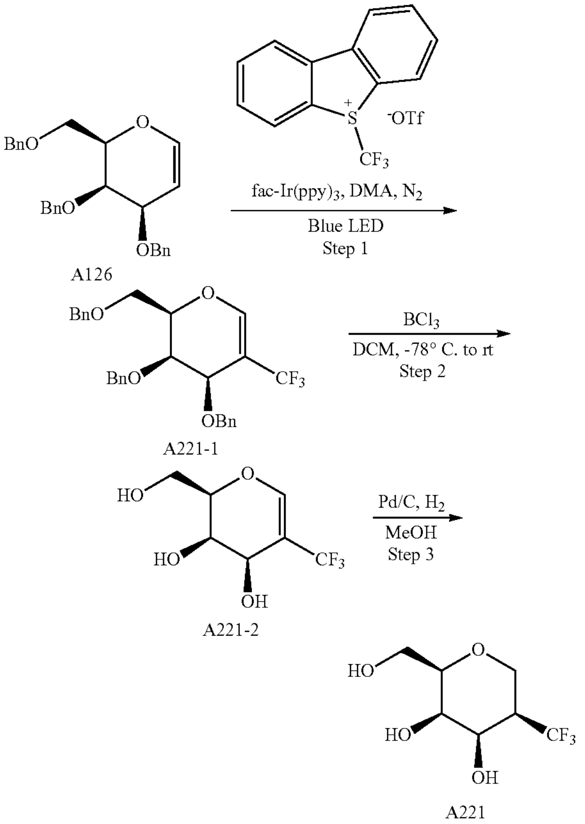

Step 1: A 10 mL flame-dried round bottom flask was charged with 5-(trifluoromethyl)-5H-dibenzo[b,d]thiophen-5-ium trifluoromethanesulfonate (A126, 1.0 g, 2.49 mmol) and fac-Ir(ppy)$_3$ (8 mg, 1.5 mol %). Then the flask was degassed and filled with argon for three times. (2R,3R,4R)-3,4-bis(benzyloxy)-2-((benzyloxy)methyl)-3,4-dihydro-2H-pyran (345 mg, 0.83 mmol) in DMA (10 mL) was added and the flask was sealed. The reaction mixture was stirred upon irradiation with blue bulbs (12 W*2; $\lambda_{max}$=465 nm) at room temperature. After 12 h, the reaction mixture was poured into water (15 mL), and then extracted with ethyl acetate (10*3 mL). The combined organic phase was washed with brine, dried over $Na_2SO_4$, filtered and concentrated to give a crude product, which was purified by column chromatography (silica gel, 0-20% MeOH in DCM) to afford the product (A221-1, 100 mg, 25% yield). LC-MS (ESI) found: 507 $[M+Na]^+$.

Step 2: To a solution of (2R,3R,4R)-3,4-bis(benzyloxy)-2-((benzyloxy)methyl)-5-(trifluoromethyl)-3,4-dihydro-2H-pyran (A221-1, 50 mg, 0.10 mmol) in dry DCM (5 mL) at −78° C. under $N_2$ atmosphere was added $BCl_3$ (1 mL, 1 M in DCM) slowly. After the addition, the reaction was stirred at room temperature for overnight. On consumption of starting material monitored by TLC, the reaction mixture was quenched with 1 mL MeOH. The mixture was concentrated in vacuo to give (2R,3R,4R)-2-(hydroxymethyl)-5-(trifluoromethyl)-3,4-dihydro-2H-pyran-3,4-diol (A221-2). LC-MS (ESI) found: 213 $[M-1]^-$.

Step 3: To a solution of (2R,3R,4R)-2-(hydroxymethyl)-5-(trifluoromethyl)-3,4-dihydro-2H-pyran-3,4-diol (A221-2, 20 mg, 0.10 mmol) in MeOH (5 mL) was added Pd/C (3 mg, 10% wt, 60% wet). The reaction mixture was charged with $H_2$ for three times and stirred at rt for 16 h under $H_2$ atmosphere. The mixture was filtered and concentrated in vacuo to give product (A221). LC-MS (ESI) found: 239 $[M+Na]^+$.

Alternatively, (2R,3R,4R)-2-(hydroxymethyl)-5-(trifluoromethyl)-3,4-dihydro-2H-pyran-3,4-diol (A221-2) can be Synthesized in the Following Manner

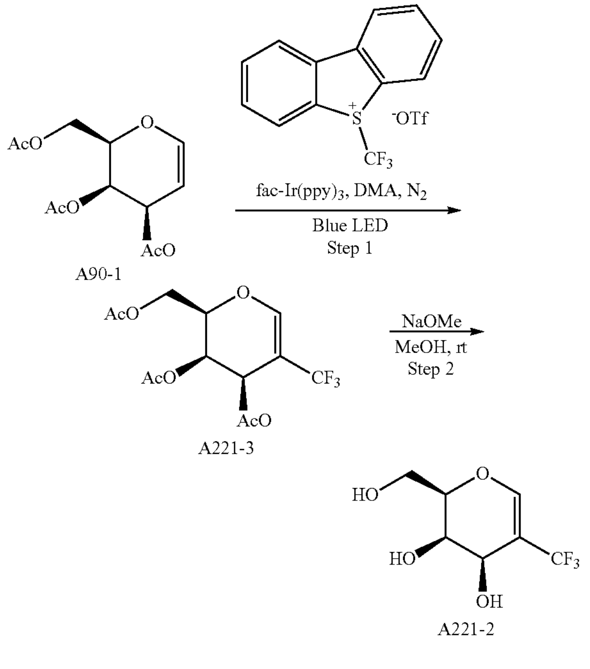

Step 1: A 10 mL flame-dried round bottom flask was charged with 5-(trifluoromethyl)-5H-dibenzo[b,d]thiophen-5-ium trifluoromethanesulfonate (996 mg, 2.48 mmol) and fac-Ir(ppy)$_3$ (8 mg, 1.5 mol %). Then the flask was degassed and filled with argon for three times. (2R,3R,4R)-2-(acetoxymethyl)-3,4-dihydro-2H-pyran-3,4-diyl diacetate (225 mg, 0.82 mmol) in DMA (10 mL) was added and the flask was sealed. The reaction mixture was stirred upon irradiation with blue bulbs (12 W*2; $\lambda_{max}$=465 nm) at room temperature. After 12 h, the reaction mixture was poured into water (15 mL), and then extracted with ethyl acetate (10*3 mL). The combined organic phase was washed with brine, dried ($Na_2SO_4$), concentrated and purified through column chromatography (silica gel, 0-20% MeOH in DCM) to afford the crude product (110 mg, purity: 80%). LC-MS (ESI) found: 341 $[M+H]^+$.

Step 2: A solution of (2R,3R,4R)-2-(acetoxymethyl)-5-(trifluoromethyl)-3,4-dihydro-2H-pyran-3,4-diyl diacetate (30 mg, 0.08 mmol) in MeOH (0.6 mL, 13.9 mmol) was added NaOMe (4.76 mg, 0.088 mmol), the mixture was stirred at rt for 2 h. The mixture was acidification with AMBERLITE IR-120. The reaction was filtered and concentrated to give (2R,3R)-2-(hydroxymethyl)-5-(trifluoromethyl)-3,4-dihydro-2H-pyran-3,4-diol (A221-2, 18 mg, 95% yield). LC-MS (ESI) found: 237 $[M+Na]^+$. $^1H$ NMR (400 MHz, MeOD): δ 7.02 (s, 1H), 4.45 (d, J=3.7 Hz, 1H), 4.11-4.04 (m, 1H), 3.98 (dd, J=4.4, 2.5 Hz, 1H), 3.89 (dd, J=11.9, 6.8 Hz, 1H), 3.79 (dd, J=11.9, 4.7 Hz, 1H).

Synthesis 5-47. Preparation of (2R,3R,4R,5R)-2-(hydroxymethyl)-5-morpholinotetrahydro-2H-pyran-3,4-diol (Compound A222)

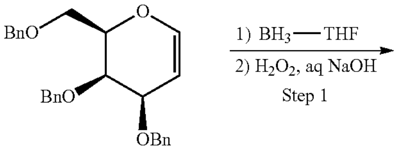

A126

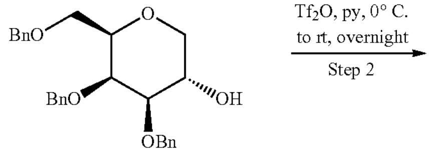

A222-1

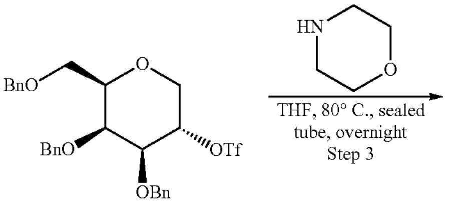

A222-2

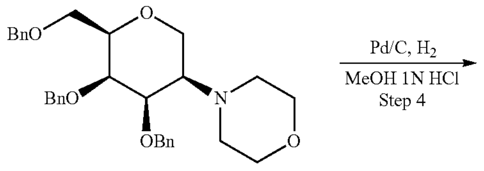

A222-3

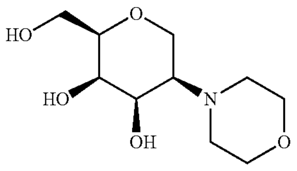

A222

Step 2: To a solution of (3S,4R,5S,6R)-4,5-bis(benzyloxy)-6-((benzyloxy)methyl)tetrahydro-2H-pyran-3-ol (100 mg, 0.23 mmol) in pyridine(2 mL) was added $Tf_2O$ (324 mg, 1.15 mmol) at 0° C. After stirring at rt overnight, the mixture was concentrated and the residue was purified by flash chromatography (silica gel, 0-30% EtOAc in PE) to give (3S,4S,5S,6R)-4,5-bis(benzyloxy)-6-((benzyloxy)methyl)tetrahydro-2H-pyran-3-yl trifluoromethanesulfonate (60 mg, 46% yield) as a colorless oil. LC-MS (ESI) found: 567 $[M+H]^+$.

Step 3: A solution of (3S,4S,5S,6R)-4,5-bis(benzyloxy)-6-((benzyloxy)methyl)tetrahydro-2H-pyran-3-yl trifluoromethanesulfonate (60 mg, 0.11 mmol) and morpholine (0.5 mL) in THF (1 mL) was stirred at 80° C. overnight. The mixture was purified by prep-HPLC (Method A) to give 4-((3R,4R,5R,6R)-4,5-bis(benzyloxy)-6-((benzyloxy)methyl)tetrahydro-2H-pyran-3-yl)morpholine (20 mg, 38% yield) as a colorless oil. LC-MS (ESI) found: 504 $[M+H]^+$. $^1H$ NMR (400 MHz, $CDCl_3$): δ 7.38-7.26 (m, 15H), 4.84 (d, J=11.4 Hz, 1H), 4.65 (d, J=11.4 Hz, 1H), 4.61 (t, J=6.0 Hz, 3H), 4.51 (d, J=12.1 Hz, 1H), 4.20 (d, J=5.5 Hz, 1H), 4.11 (t, J=9.9 Hz, 2H), 3.93 (t, J=10.6 Hz, 1H), 3.76-3.57 (m, 7H), 2.66 (d, J=47.9 Hz, 5H).

Step 4: A solution of 4-((3R,4R,5R,6R)-4,5-bis(benzyloxy)-6-((benzyloxy)methyl)tetrahydro-2H-pyran-3-yl)morpholine (20 mg, 0.04 mmol) in MeOH (2 mL) were added Pd/C (5 mg, 10% wt, 60% wet) and HCl (0.1 mL, 1 M in $H_2O$). The mixture was stirred at rt overnight under a $H_2$ balloon. The mixture was filtered through a Celite pad, and the filtrate was concentrated to give (2R,3R,4R,5R)-2-(hydroxymethyl)-5-morpholinotetrahydro-2H-pyran-3,4-diol hydrochloride (A222, 6.5 mg, 70%) as a colorless oil. LC-MS (ESI) found: 234$[M+H]^+$. $^1H$ NMR (400 MHz, $CD_3OD$): δ 4.44 (dd, J=14.3, 1.8 Hz, 1H), 4.16 (dd, J=17.3, 6.6 Hz, 2H), 4.09 (dd, J=6.0, 2.8 Hz, 1H), 4.09-4.01 (m, 2H), 3.80 (dd, J=10.0, 2.4 Hz, 2H), 3.77-3.72 (m, 2H), 3.71-3.62 (m, 2H), 3.61-3.52 (m, 2H), 3.39 (dd, J=16.4, 7.1 Hz, 2H).

Synthesis 5-48. Preparation of 3-((3R,4R,5R,6R)-4,5-dihydroxy-6-(hydroxymethyl)tetrahydro-2H-pyran-3-yl)oxazolidin-2-one (Compound A223)

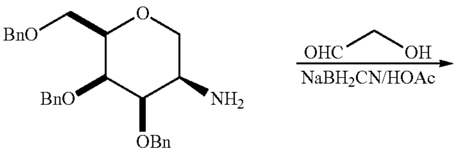

A127-2

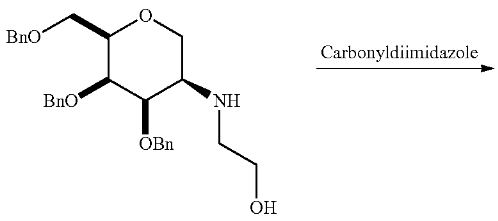

A223-1

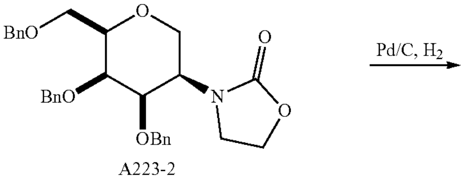

A223-2

-continued

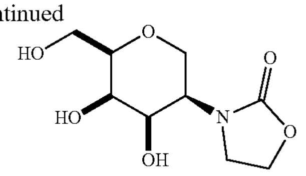

Compound A223

Alternatively, 3-((3R,4R,5R,6R)-4,5-dihydroxy-6-(hydroxymethyl)tetrahydro-2H-pyran-3-yl)oxazolidin-2-one (Compound A223) can be Prepared in the Same Manner as Compound A180

LC-MS (ESI) found: 234 $[M+H]^+$. $^1H$ NMR (400 MHz, MeOD): δ 4.41 (m, 1H), 4.31 (m, 2H), 4.10 (dd, J=12.8, 2.3 Hz, 1H), 4.03 (m, 1H), 3.89-3.76 (m, 3H), 3.75-3.63 (m, 3H), 3.45 (m, 1H).

Synthesis 5-49. Preparation of 1-((3R,4R,5R,6R)-4,5-dihydroxy-6-(hydroxymethyl)tetrahydro-2H-pyran-3-yl)imidazolidin-2-one (Compound A224)

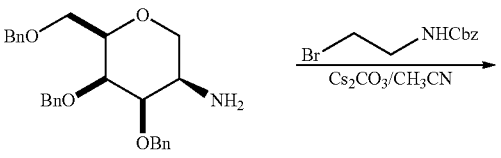

A127-2

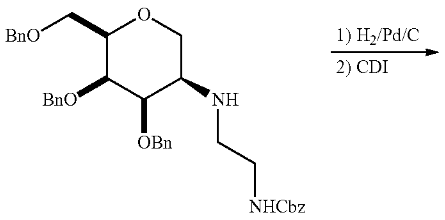

A224-1

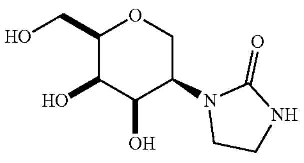

A224

Synthesis 5-50. Preparation of 1-((1S,2R,3R,4S)-1-(aminomethyl)-2,3-dihydroxy-6,8-dioxabicyclo[3.2.1]octan-4-yl)imidazolidine-2-thione (Compound A225)

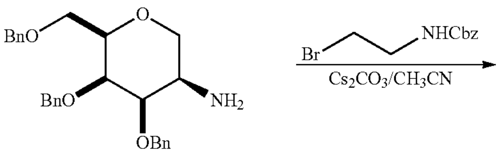

A127-2

-continued

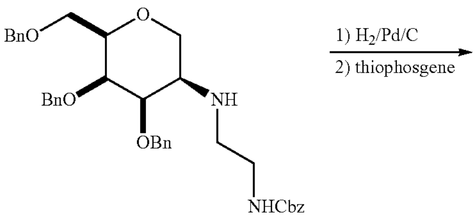

A225-1

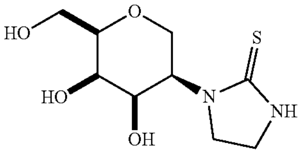

Compound A225

Synthesis 5-51. Preparation of 1-((3R,4R,5R,6R)-4,5-dihydroxy-6-(hydroxymethyl)tetrahydro-2H-pyran-3-yl)pyrrolidine-2,5-dione (Compound A226)

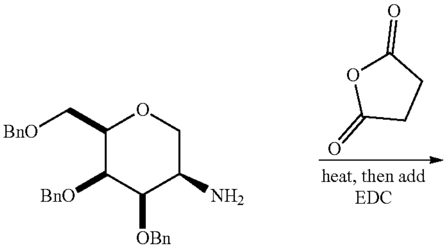

A127-2

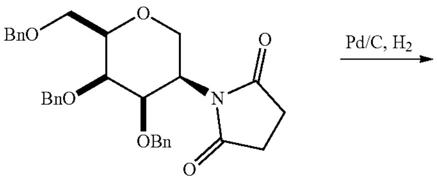

A226-1

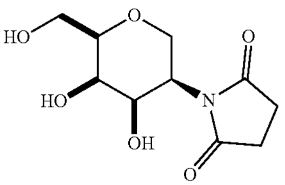

Compound A226

Synthesis 5-52. Preparation of 1-((3R,4R,5R,6R)-4,5-dihydroxy-6-(hydroxymethyl)tetrahydro-2H-pyran-3-yl)-1H-pyrrole-2,5-dione (Compound A227)

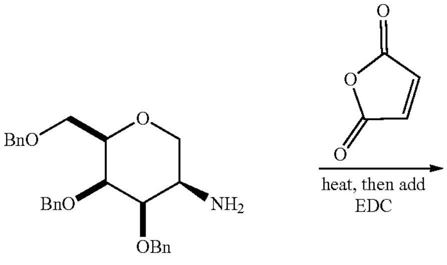

A127-2

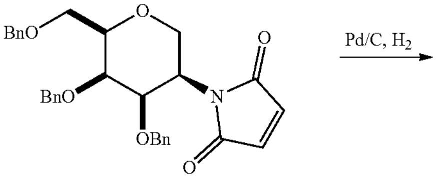

A227-1

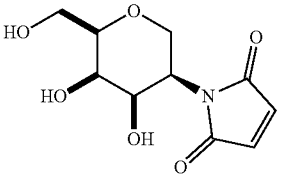

Compound A227

Synthesis 5-53. Preparation of 3-((3R,4R,5R,6R)-4,5-dihydroxy-6-(hydroxymethyl)tetrahydro-2H-pyran-3-yl)thiazolidine-2,4-dione (Compound A228)

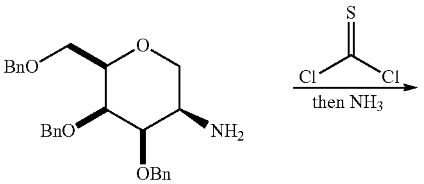

A127-2

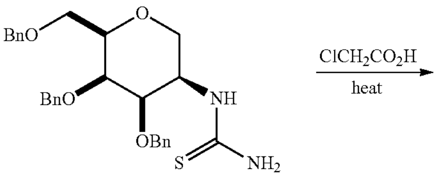

A228-1

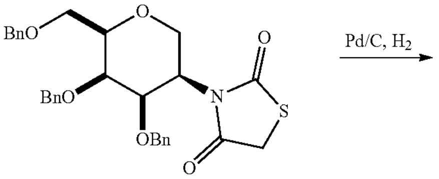

A228-2

-continued

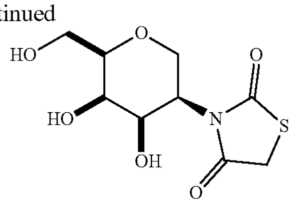

Compound A228

Synthesis 5-54. Preparation of 3-((3R,4R,5R,6R)-4,5-dihydroxy-6-(hydroxymethyl)tetrahydro-2H-pyran-3-yl)oxazolidine-2,4-dione (Compound A229)

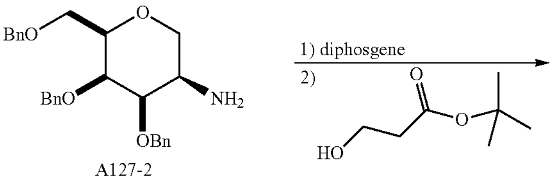

A127-2

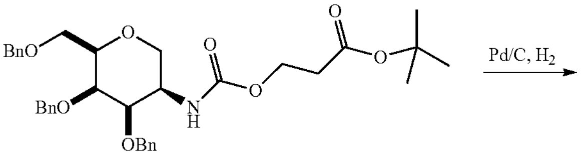

A229-1

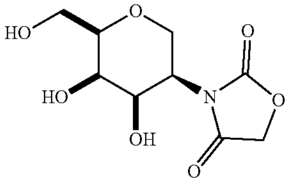

Compound A229

Synthesis 5-55. Preparation of 2-((3R,4R,5R,6R)-4,5-dihydroxy-6-(hydroxymethyl)tetrahydro-2H-pyran-3-yl)isoindoline-1,3-dione (Compound A230)

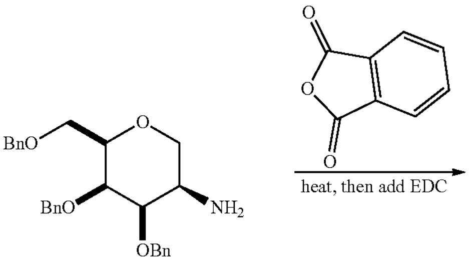

A127-2

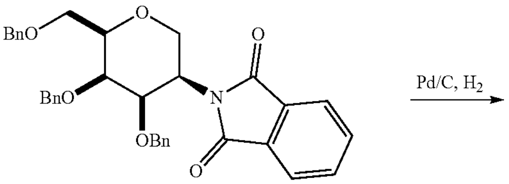

A-230-1

-continued

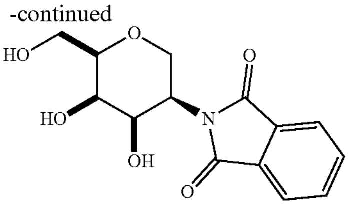

Compound A230

Synthesis 5-56. Preparation of 2-((3R,4R,5R,6R)-4,5-dihydroxy-6-(hydroxymethyl)tetrahydro-2H-pyran-3-yl)isoindolin-1-one (Compound A231)

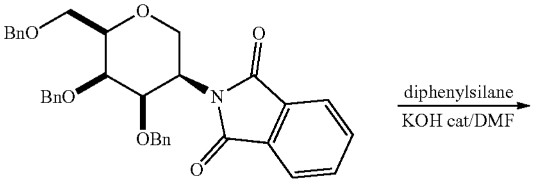

A-230-1

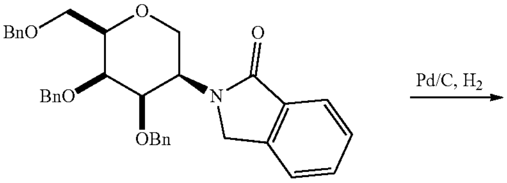

A-231-1

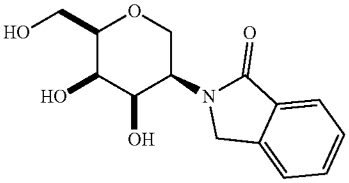

Compound A231

Synthesis 5-57. Preparation of (2R,3R,4R,5R)-2-(hydroxymethyl)-5-(1H-imidazol-1-yl)tetrahydro-2H-pyran-3,4-diol (Compound A232)

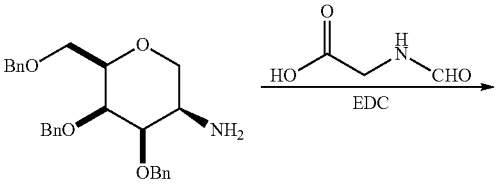

A127-2

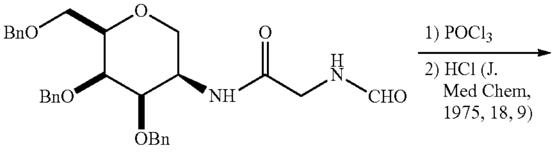

A232-1

-continued

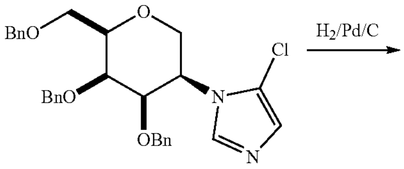

A232-2

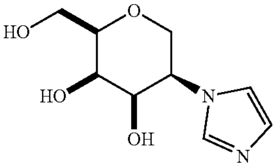

Compound A232

Synthesis 5-58. Preparation of (2R,3R,4R,5R)-2-(hydroxymethyl)-5-(1H-pyrrol-1-yl)tetrahydro-2H-pyran-3,4-diol (Compound A234)

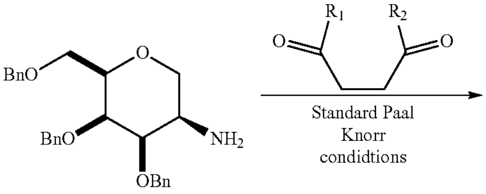

A127-2

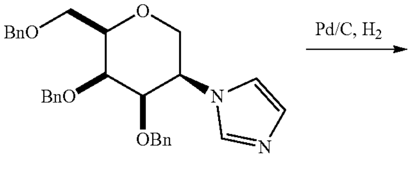

A234-1

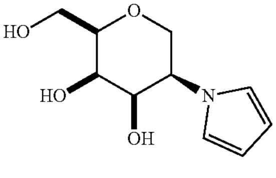

Compound A234

Synthesis 5-59. Preparation of 1-((3R,4R,5R,6R)-4,5-dihydroxy-6-(hydroxymethyl)tetrahydro-2H-pyran-3-yl)pyridin-2(1H)-one (Compound A235)

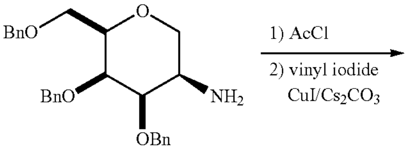

A127-2

-continued
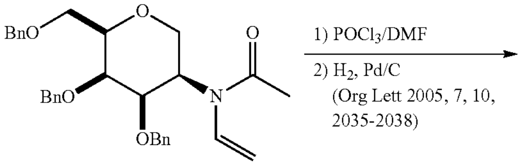
A235-1
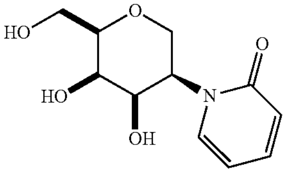
Compound A235
Synthesis 5-60. Preparation of 1-((3R,4R,5R,6R)-4,5-dihydroxy-6-(hydroxymethyl)tetrahydro-2H-pyran-3-yl)pyrimidin-2(1H)-one (Compound A236)
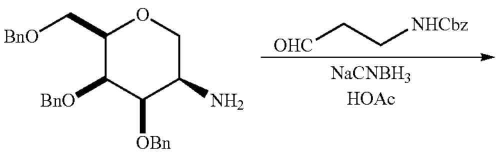
A127-2
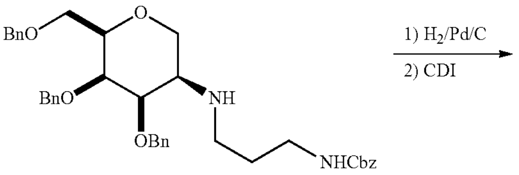
A236-1
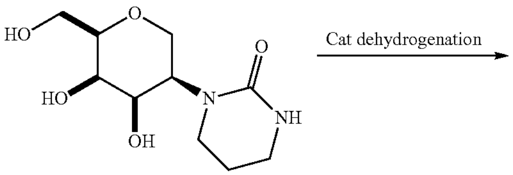
A236-2
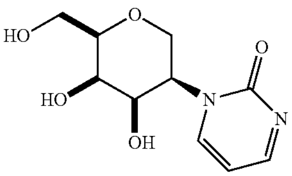
A236
Synthesis 5-61. Preparation of 1-((3R,4R,5R,6R)-4,5-dihydroxy-6-(hydroxymethyl)tetrahydro-2H-pyran-3-yl)pyridin-4(1H)-one (Compound A237)
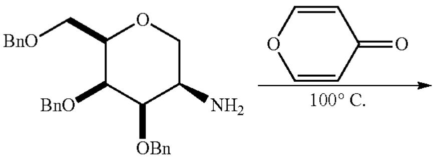
A127-2
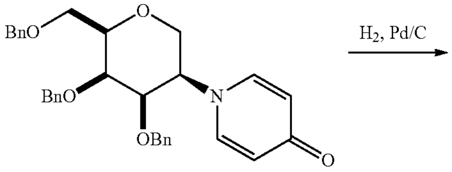
A237-1
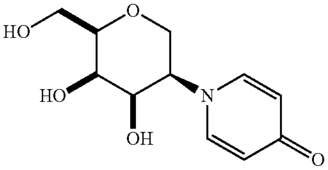
Compound A237
Synthesis 5-62. Preparation of (3S,4R,5R,6R)-6-(aminomethyl)-3-(piperidin-1-yl)tetrahydro-2H-pyran-2,4,5-triol (Compound A238)
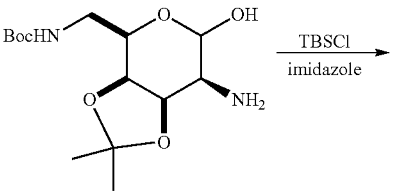
A238-1
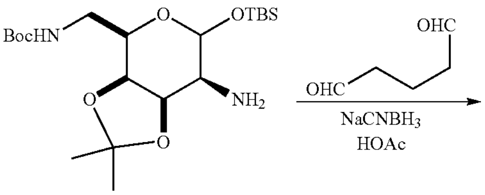
A238-2
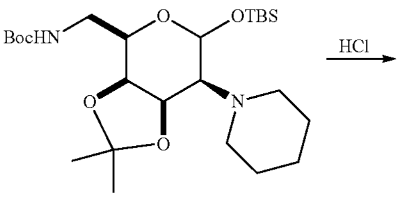
A238-3

-continued
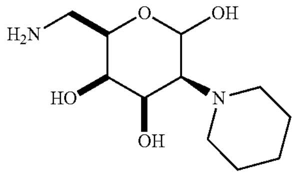
A238
Synthesis 5-63. Preparation of (3S,4R,5R,6R)-6-(aminomethyl)-3-morpholinotetrahydro-2H-pyran-2,4,5-triol (Compound A239)
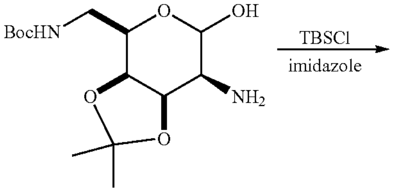
A238-1
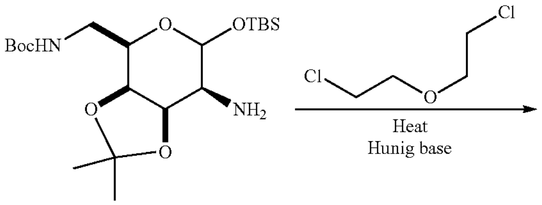
A238-2
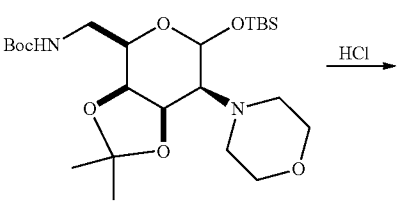
A239-1
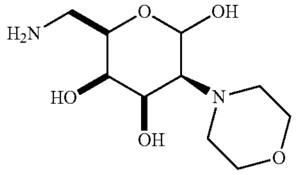
A239
Synthesis 5-64. Preparation of (3S,4R,5R,6R)-6-(aminomethyl)-3-thiomorpholinotetrahydro-2H-pyran-2,4,5-triol (Compound A240)
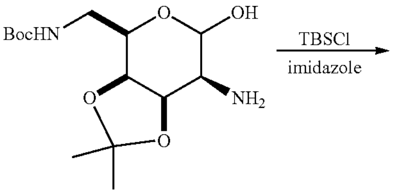
A238-1
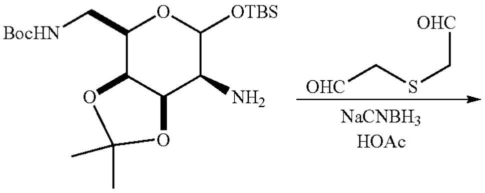
A238-2
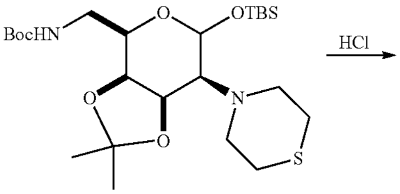
A240-1
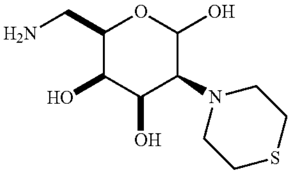
A240
Synthesis 5-65. Preparation of 1-((3R,4R,5R,6R)-4,5-dihydroxy-6-(hydroxymethyl)tetrahydro-2H-pyran-3-yl)azetidin-2-one (Compound A241)
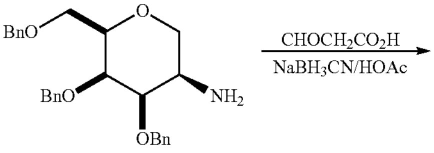
A127-2
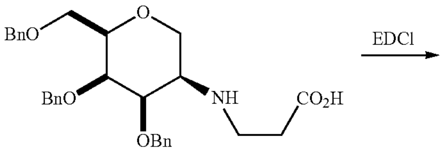
A241-1

-continued

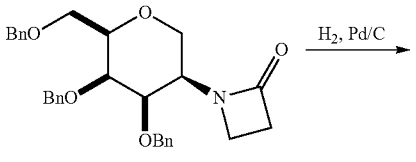

A241-2

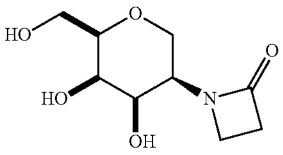

A241

Synthesis 5-66. Preparation of 1-((3S,4R,5R,6R)-6-(aminomethyl)-2,4,5-trihydroxytetrahydro-2H-pyran-3-yl)tetrahydropyrimidin-2(1H)-one (Compound A242)

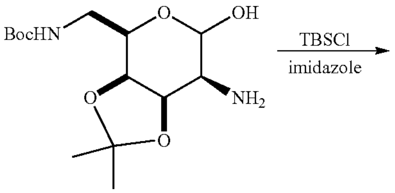

A238-1

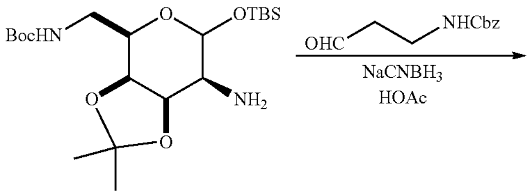

A238-2

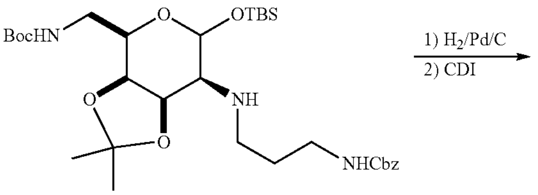

A242-1

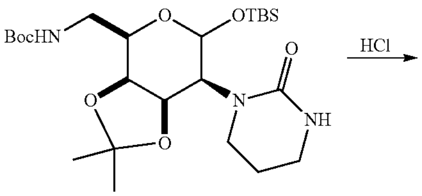

A242-2

-continued

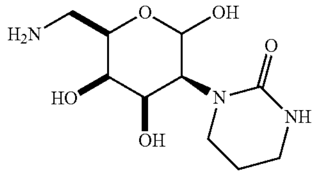

A242

Synthesis 5-67. Preparation of N-((3R,4R,5R,6R)-4,5-dihydroxy-6-(hydroxymethyl)tetrahydro-2H-pyran-3-yl)methanesulfinamide (Compound A243) and N-((3R,4R,5R,6R)-4,5-dihydroxy-6-(hydroxymethyl)tetrahydro-2H-pyran-3-yl)-1,1,1-trifluoromethanesulfonamide (Compound A244)

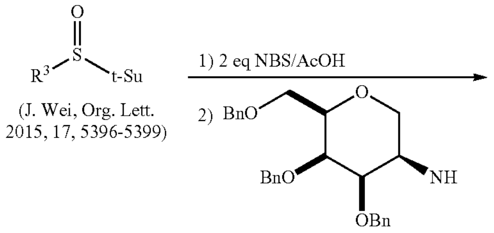

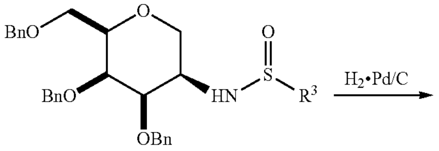

A244-1

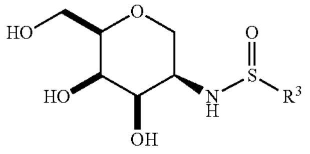

Compound A243 ($R^3 = CH_3$)
Compound A244 ($R^3 = CF_3$)

Synthesis 5-68. Alternative Preparation of (4aR,6R,7R,8R,8aS)-6-(aminomethyl)-7,8-dihydroxytetrahydro-1H,6H-pyrano[2,3-b][1,4]oxazin-2(3H)-one (Compound A245)

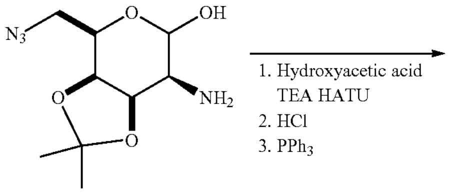

A245-1

-continued
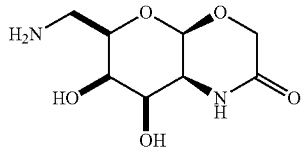
A245
Synthesis 5-69. Preparation of (4aS,6R,7R,8R,8aS)-6-(aminomethyl)-7,8-dihydroxyhexahydro-1H,3H-pyrano[3,2-c][1,2,6]thiadiazine 2,2-dioxide (Compound A246), (4aS,6R,7R,8R,8aS)-6-(aminomethyl)-7,8-dihydroxyhexahydro-1H-pyrano[3,2-d]pyrimidin-2(3H)-one (Compound A247), and (4aR,6R,7R,8R,8aS)-6-(aminomethyl)-7,8-dihydroxyhexahydropyrano[3,2-d][1,3]oxazin-2(1H)-one (Compound A248)
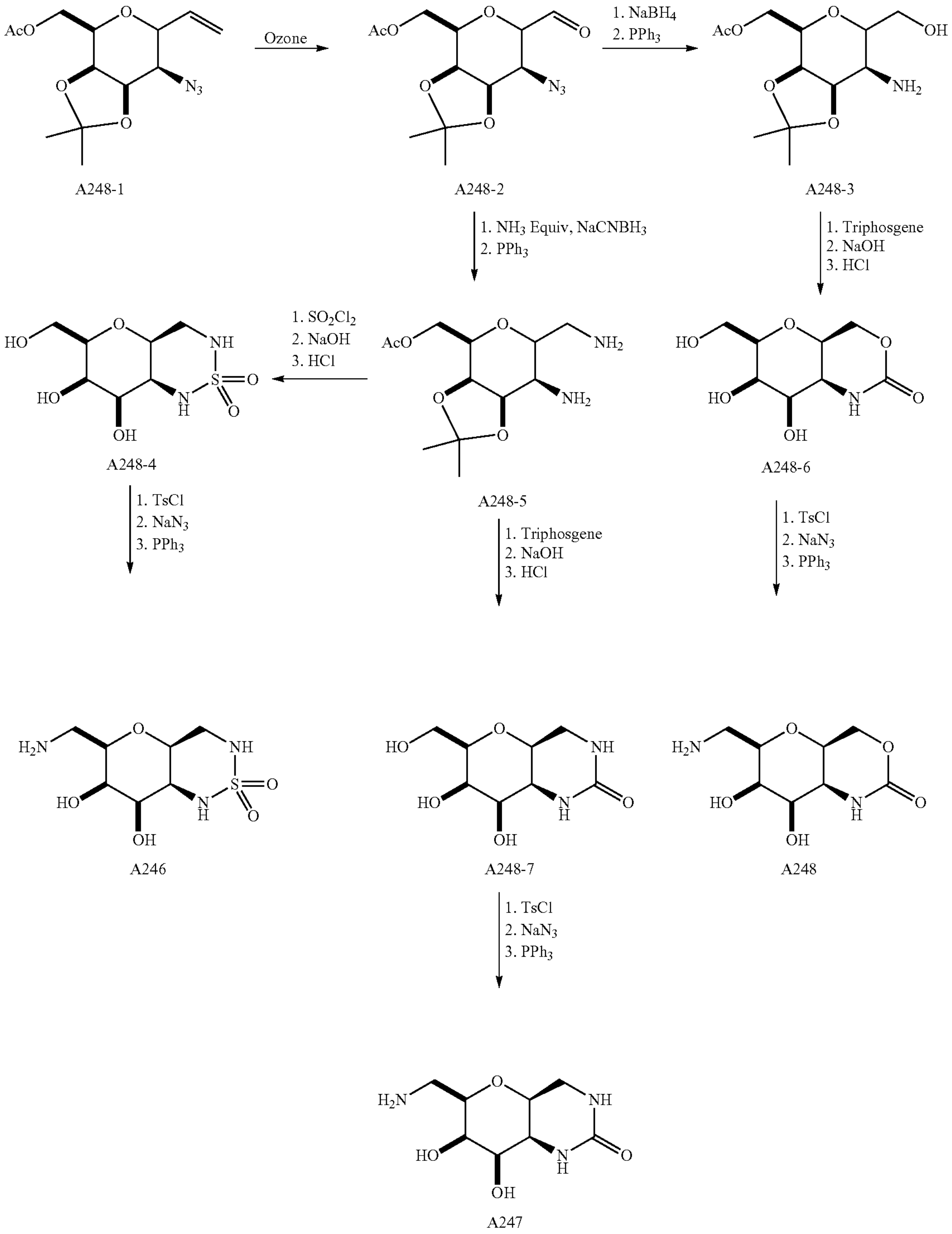

Synthesis 5-70. Preparation of ((3aS,5R,6R,7R,7aS)-7-amino-5-(hydroxymethyl)-2-methyl-3a,6,7,7a-tetrahydro-5H-pyrano[3,2-d]oxazol-6-ol (Compound A249) and (3aS,5R,6R,7R,7aS)-7-amino-5-(hydroxymethyl)-2-(trifluoromethyl)-3a,6,7,7a-tetrahydro-5H-pyrano[3,2-d]oxazol-6-ol (Compound A250)

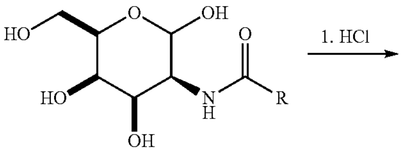

A250-1

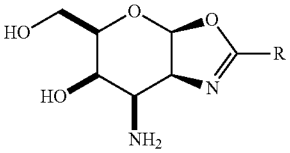

Compound A249 (R = $CH_3$)
Compound A250 (R = $CF_3$)

Synthesis 5-71. Preparation of (3aR,5R,6R,7R,7aS)-7-amino-5-(hydroxymethyl)-2-methyl-3,3a,5,6,7,7a-hexahydropyrano[2,3-d]imidazol-6-ol (Compound A251) and (3aR,5R,6R,7R,7aS)-7-amino-5-(hydroxymethyl)-2-(trifluoromethyl)-3,3a,5,6,7,7a-hexahydropyrano[2,3-d]imidazol-6-ol (Compound A252)

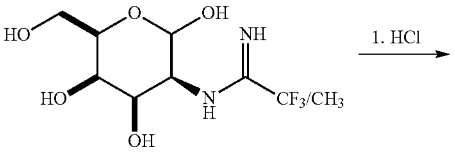

A252-1

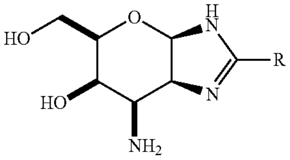

Compound A251 (R = $CH_3$)
Compound A252 (R = $CF_3$)

Synthesis 5-72. Preparation of 1-((3aS,5R,6R,7R,7aS)-5-(aminomethyl)-6,7-dihydroxyhexahydropyrano[3,2-b]pyrrol-1(2H)-yl)-2,2,2-trifluoroethan-1-one (Compound A253)

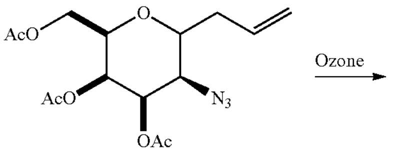

A253-1

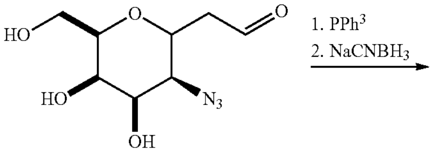

A253-2

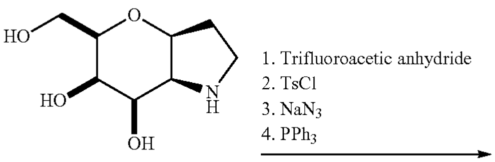

A253-4

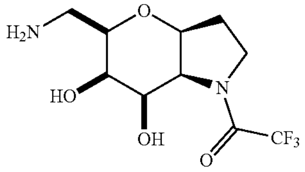

Compound A253

Synthesis 5-73. Preparation of 1-((4aR,6R,7R,8R,8aS)-6-(aminomethyl)-7,8-dihydroxyhexahydro-1H,6H-pyrano[2,3-b][1,4]oxazin-1-yl)ethan-1-one (Compound A254) and 1-((4aR,6R,7R,8R,8aS)-6-(aminomethyl)-7,8-dihydroxyhexahydro-1H,6H-pyrano[2,3-b][1,4]oxazin-1-yl)-2,2,2-trifluoroethan-1-one (Compound A255)

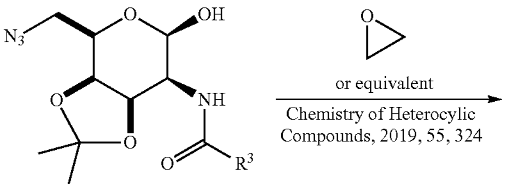

A255-1

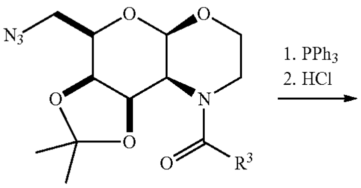

A255-2

-continued

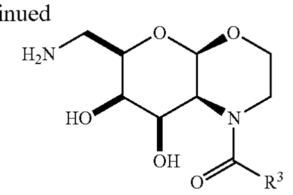

Compound A254 ($R^3 = CH_3$)
Compound A255 ($R^3 = CF_3$)

Synthesis 5-74. Preparation of 1-((3aS,4R,5aR,9aS,9bR)-4-(aminomethyl)-2,2,7-trimethylhexahydro-4H,9H-[1,3]dioxolo[4',5':4,5]pyrano[2,3-b][1,4]oxazin-9-yl)ethan-1-one (Compound A256) and 1-((3aS,4R,5aR,9aS,9bR)-4-(aminomethyl)-2,2,7-trimethylhexahydro-4H,9H-[1,3]dioxolo[4',5':4,5]pyrano[2,3-b][1,4]oxazin-9-yl)-2,2,2-trifluoroethan-1-one (Compound A257)

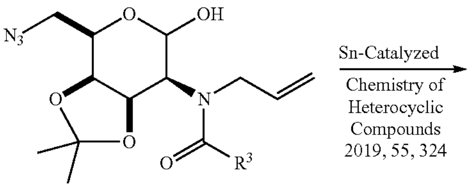

A257-1

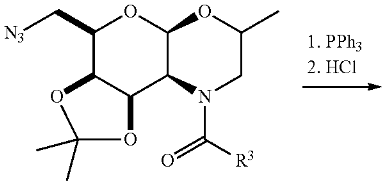

A257-2

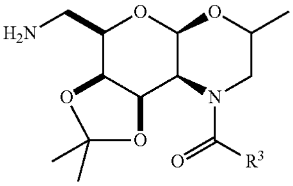

Compound A256 ($R^3 = CH_3$)
Compound A257 ($R^3 = CF_3$)

Synthesis 5-75. Preparation of 1-((3aS,4R,5aR,11aR,11bR)-4-(aminomethyl)-2,2-dimethyloctahydro-4H,11H-[1,3]dioxolo[4',5':4,5]pyrano[2,3-b][1,4]oxazocin-11-yl)ethan-1-one (Compound A258) and 1-((3aS,4R,5aR,11aR,11bR)-4-(aminomethyl)-2,2-dimethyloctahydro-4H,11H-[1,3]dioxolo[4',5':4,5]pyrano[2,3-b][1,4]oxazocin-11-yl)-2,2,2-trifluoroethan-1-one (Compound A259)

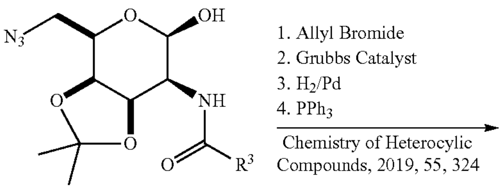

A259-1

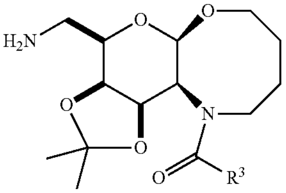

Compound A258 ($R^3 = CH_3$)
Compound A259 ($R^3 = CF_3$)

Synthesis 5-76. Preparation of 1-((3aS,5R,6R,7R,7aR)-6,7-dihydroxy-5-(hydroxymethyl)hexahydropyrano[3,2-b]pyrrol-1(2H)-yl)ethan-1-one (Compound A260) and 1-((2R,3R,4R,4aR,8aS)-3,4-dihydroxy-2-(hydroxymethyl)octahydro-5H-pyrano[3,2-b]pyridin-5-yl)ethan-1-one (Compound A261)

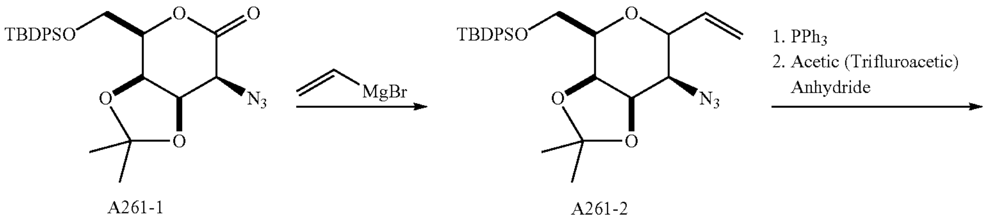

A261-1 A261-2

-continued
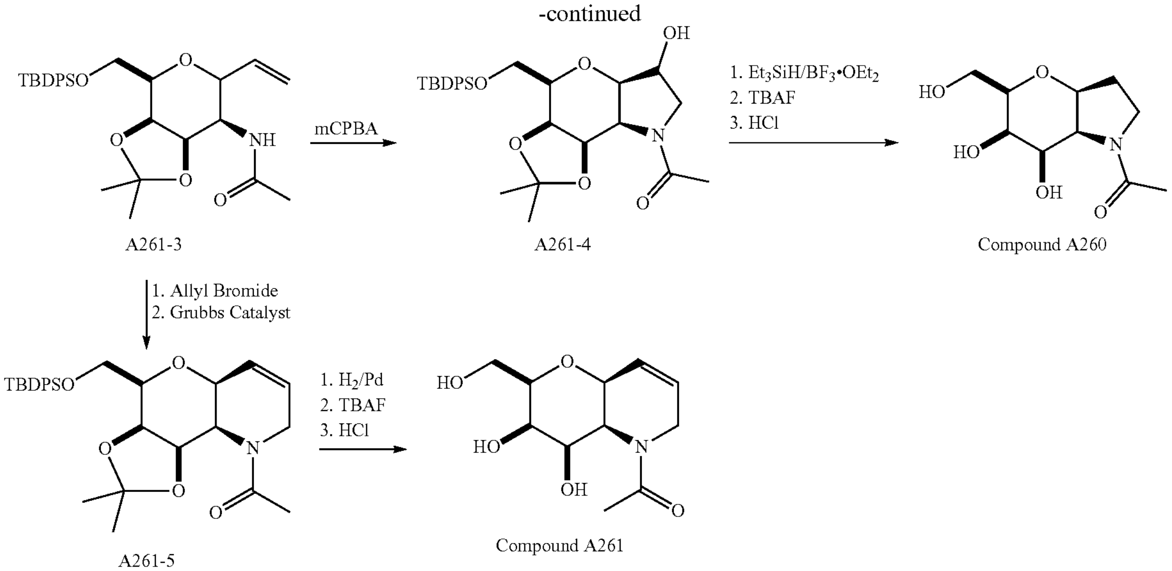
A261-3, A261-4, Compound A260, A261-5, Compound A261
Synthesis 5-77. Preparation of 1-((2R,3R,4R,4aR,9aS)-3,4-dihydroxy-2-(hydroxymethyl)octahydropyrano[3,2-b]azepin-5(2H)-yl)ethan-1-one (Compound A262)
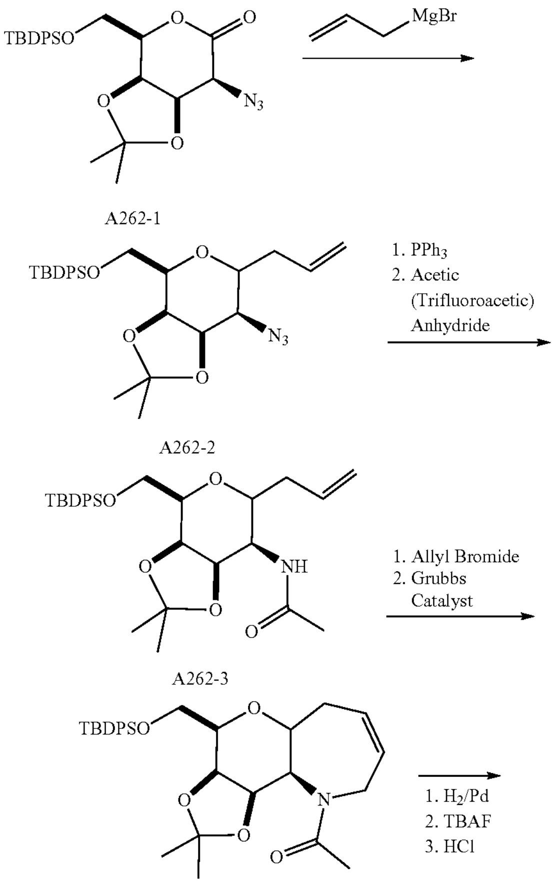
A262-1, A262-2, A262-3, A262-4
-continued
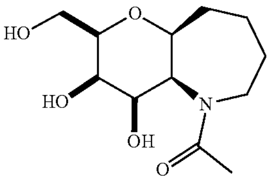
Compound A262
Synthesis 5-78. Preparation of ((3aR,4R,5aS,9aR,9bR)-2,2-dimethyl-8-oxooctahydro-4H-[1,3]dioxolo[4',5':4,5]pyrano[3,2-b]pyridin-4-yl)methyl acetate (Compound A263)
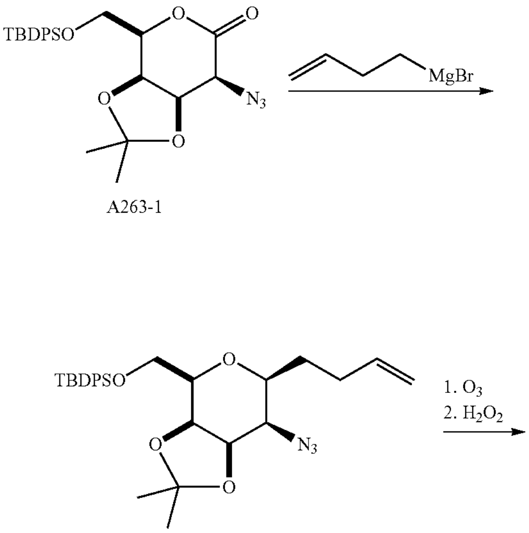
A263-1, A263-2

-continued
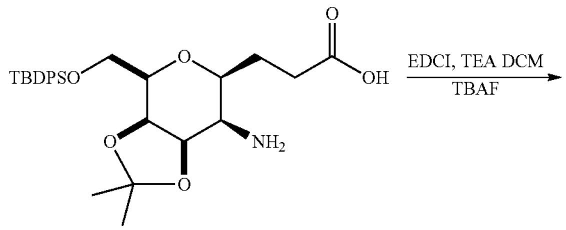
A262-3
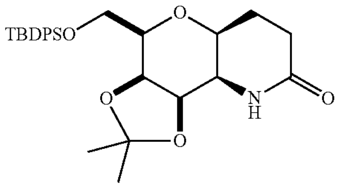
A263
Synthesis 5-79. Preparation of N-((3aR,8S,8aR)-4-(hydroxymethyl)-2,2-dimethylhexahydro-4H-4,7-epoxy[1,3]dioxolo[4,5-d]azepin-8-yl)acetamide (Compound A264)
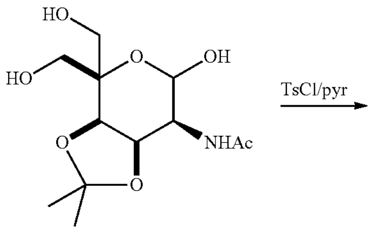
A263-1
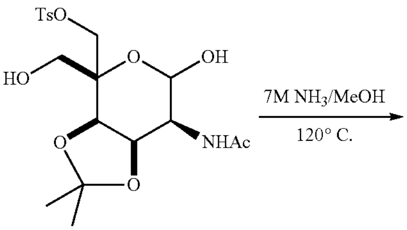
A65-2
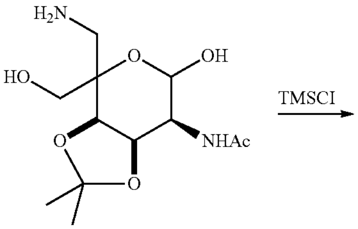
A264-2
-continued
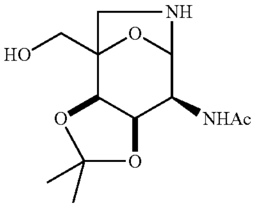
Compound A264
Synthesis 5-80. Preparation of N-((3aR,4S,9R,9aR)-9-(hydroxymethyl)-2,2-dimethyloctahydro-5,9-epoxy[1,3]dioxolo[4,5-d]azocin-4-yl)acetamide (Compound A265)
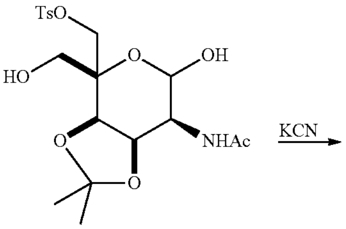
A265-1
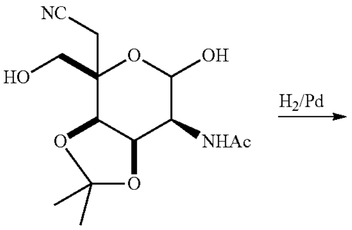
A265-2
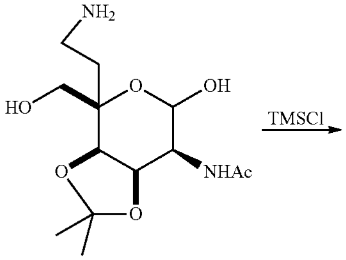
A266-3
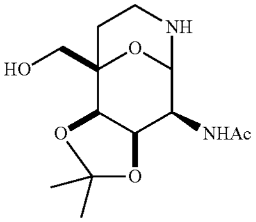
Compound A265

Synthesis 5-81. Preparation of N-((3aR,4S,9R,9aR)-9-(hydroxymethyl)-2,2-dimethylhexahydro-5H-5,9-epoxy[1,3]dioxolo[4,5-d]oxocin-4-yl)acetamide (Compound A266)

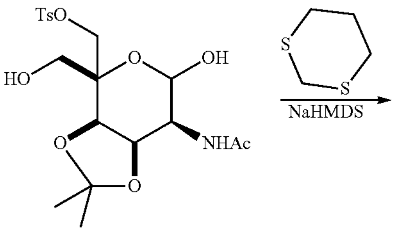

A266-1

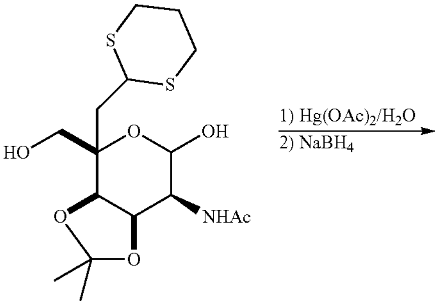

A266-2

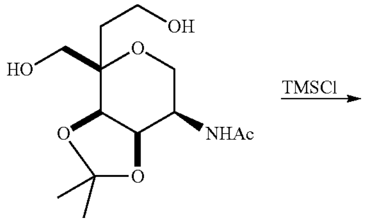

A266-3

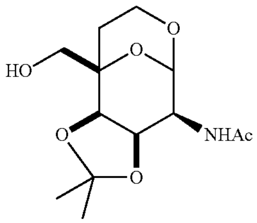

Compound A266

Synthesis 5-82. Compound A267, Compound A268, and Compound A269 can Also be Synthesized Using Synthesis 5-79-5-81

Compound A267

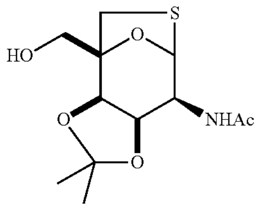

-continued

Compound A268

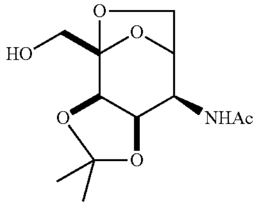

Compound A269

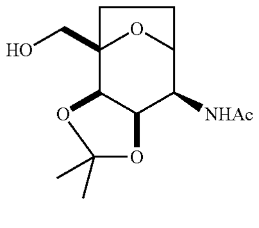

Synthesis 5-82. General Synthesis to Install $R^2$

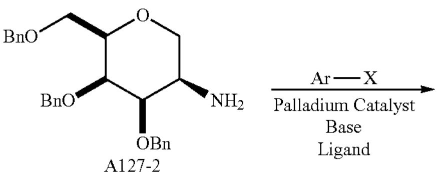

A127-2

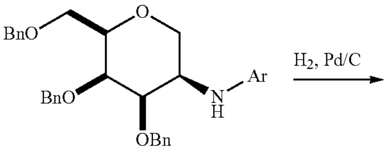

A270-2

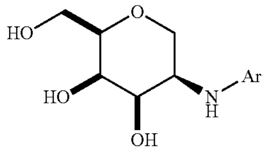

Compound A270

Synthesis 5-83. Alternative General Synthesis to Install $R^2$

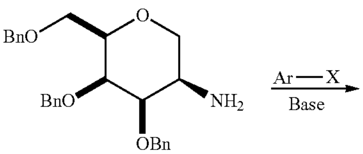

A127-2

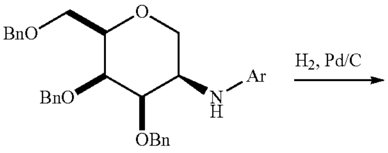

A271-2

-continued

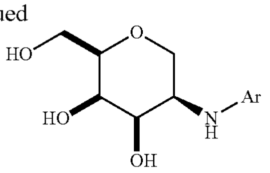

Compound A271

Synthesis 5-84. Preparation of (2R,3R,4R,5R)-2-(hydroxymethyl)-5-(isoxazol-5-ylamino)tetrahydro-2H-pyran-3,4-diol (Compound A272)

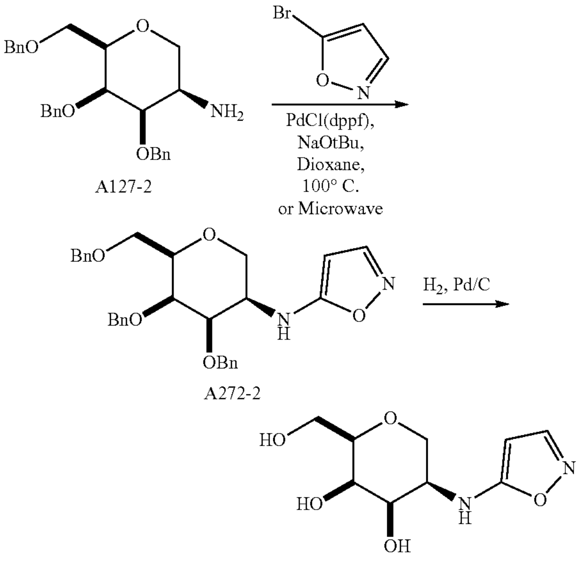

A127-2

A272-2

Compound A272

Synthesis 5-85. Preparation of (2R,3R,4R,5R)-5-((4,6-dichloro-1,3,5-triazin-2-yl)amino)-2-(hydroxymethyl)tetrahydro-2H-pyran-3,4-diol (Compound A273)

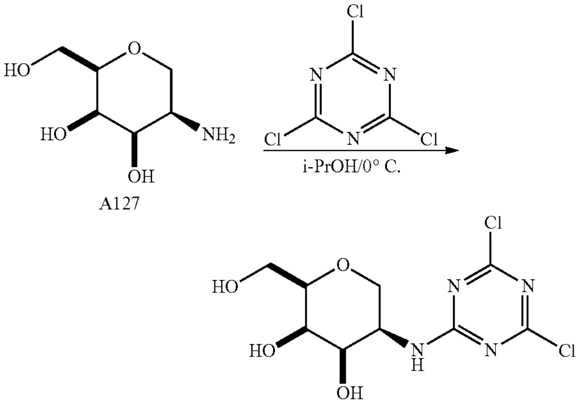

A127

Compound A273

Synthesis 5-86. Preparation of (2R,3R,4R,5R)-2-(hydroxymethyl)-5-(thiazol-2-ylamino)tetrahydro-2H-pyran-3,4-diol (Compound A274)

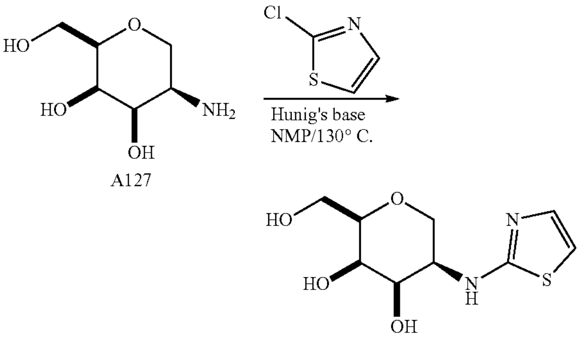

A127

Compound A274

Synthesis 5-87. Preparation of (2R,3R,4R,5R)-2-(hydroxymethyl)-5-((3-(trifluoromethyl)pyridin-2-yl)amino)tetrahydro-2H-pyran-3,4-diol. (Compound A275)

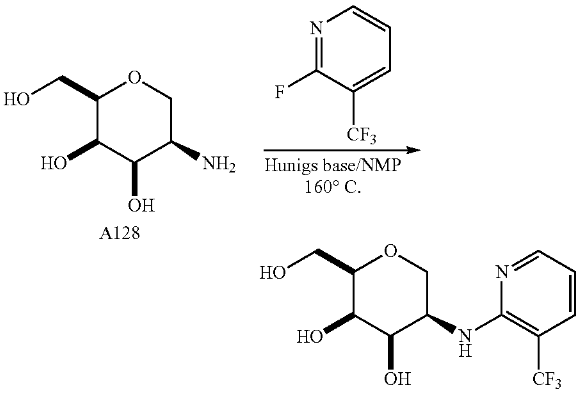

A128

Compound A275

Synthesis 5-88. Preparation of (3aR,4R,8R,8aR)-8-azido-4-(azidomethyl)-2,2-dimethylhexahydro-4H-4,7-epoxycyclohepta[d][1,3]dioxole (Compound A276)

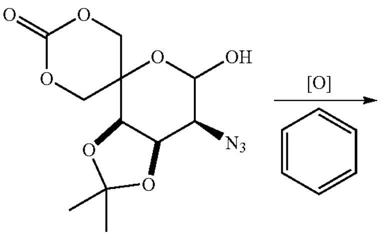

A276-1

-continued
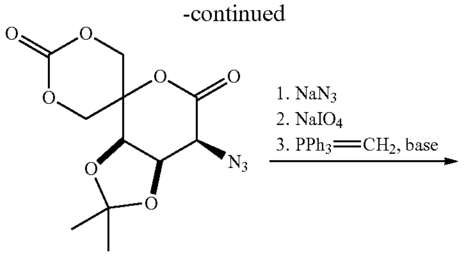
A276-2
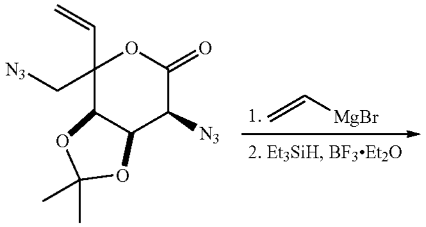
A276-3
-continued
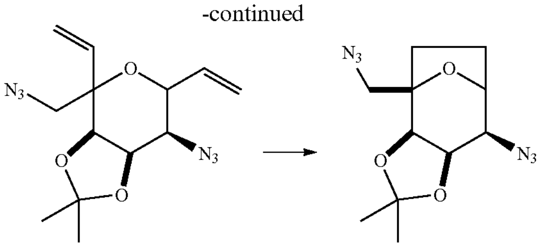
A276-4
Compound A276
Synthesis 5-89. Preparation of Compound A277 and Compound A278
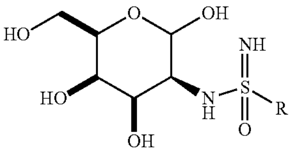
Compound A277
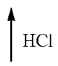
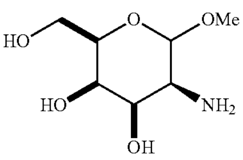
2-amino galactose
A278-1
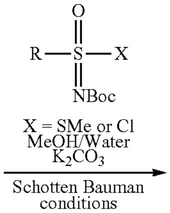
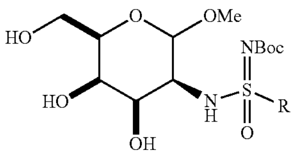
A278-1
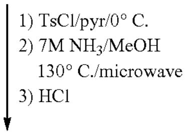
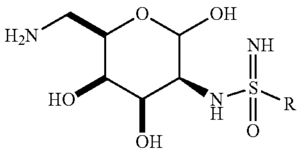
Compound A278

Alternatively, Compound A279 can be synthesized if
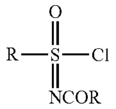
is used instead of
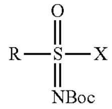
in the Schotten Bauman reaction step.
Compound A279
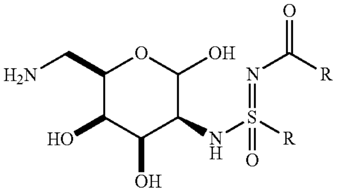
Synthesis 5-90. Preparation of 1-((3S,4R,5R,6R)-6-(aminomethyl)-2,4,5-trihydroxytetrahydro-2H-pyran-3-yl)guanidine (Compound A280) And (Compound A281)
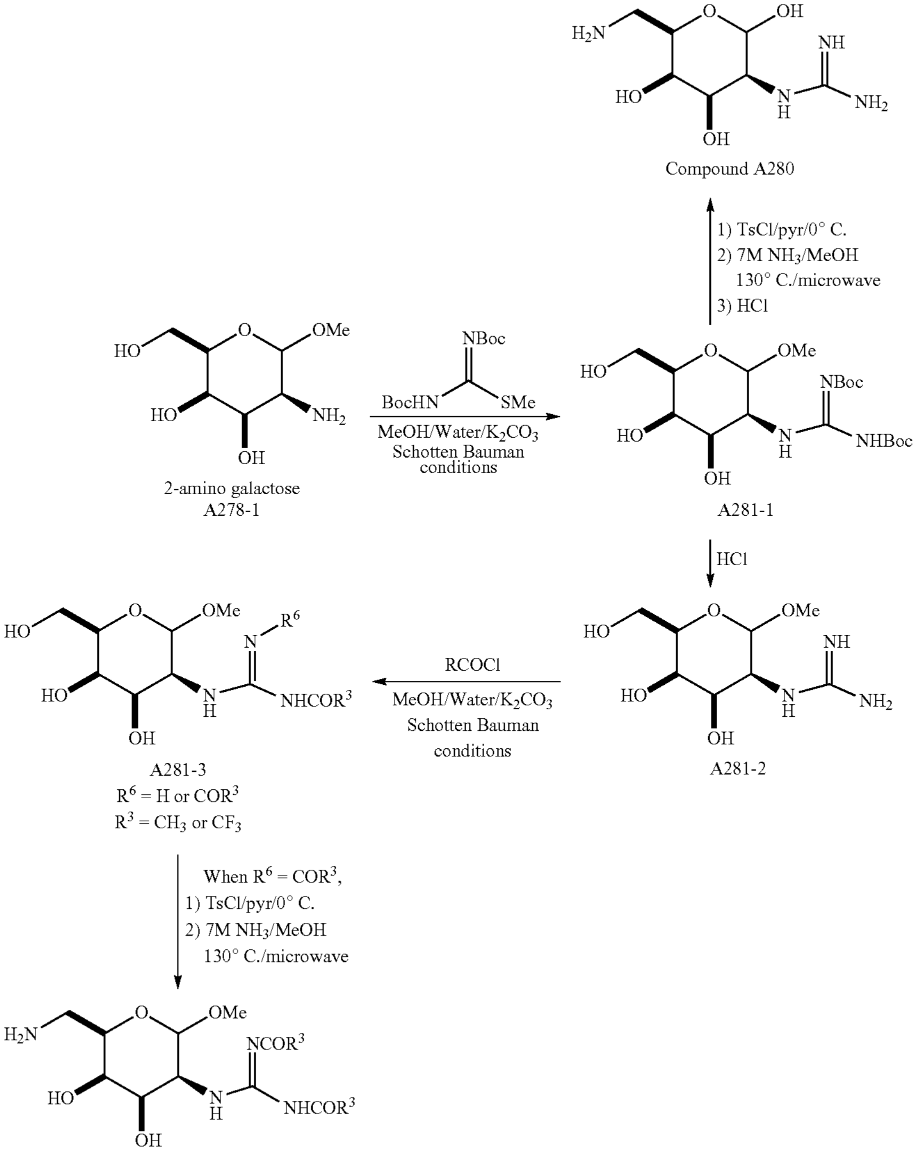
Compound A280
2-amino galactose
A278-1
A281-1
A281-2
A281-3
$R^6$ = H or $COR^3$
$R^3$ = $CH_3$ or $CF_3$
Compound A281

Synthesis 5-91. Preparation of Compound A282
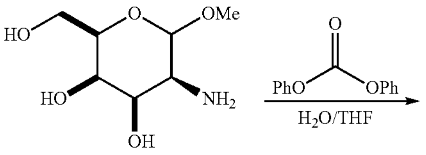
A278-1
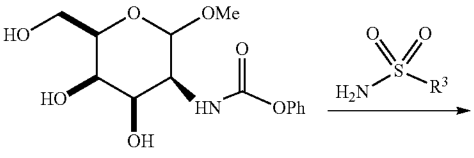
A282-1
-continued
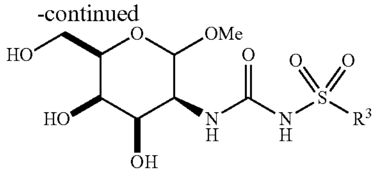
Compound A282
Org. Biomol. Chem., 2017, 15, 4992-4999
Example 6. Synthesis of Degraders
Synthesis 6-1. Preparation of Bidentate Fumaramide OPT-3 (Compound 10)
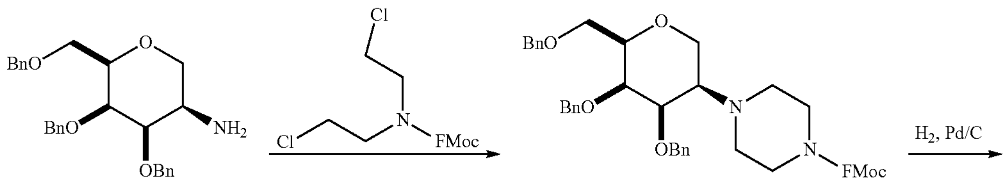
A127-2a
10-2
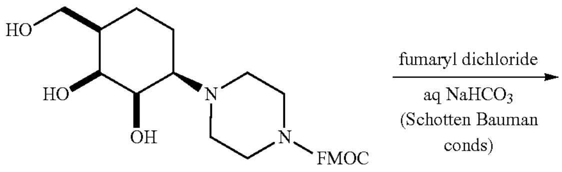
10-3
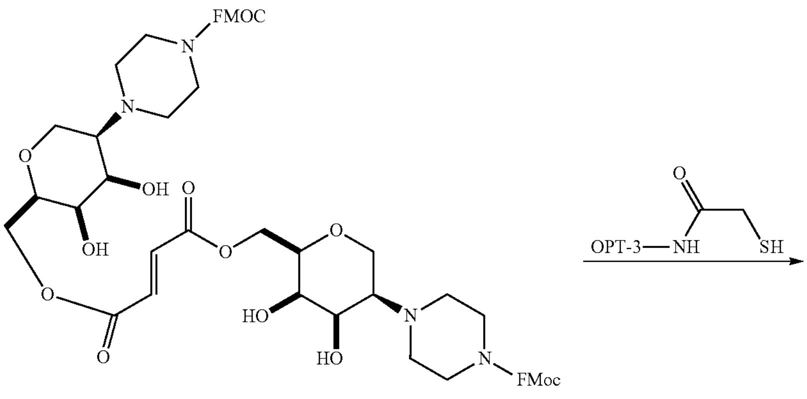
10-4

-continued

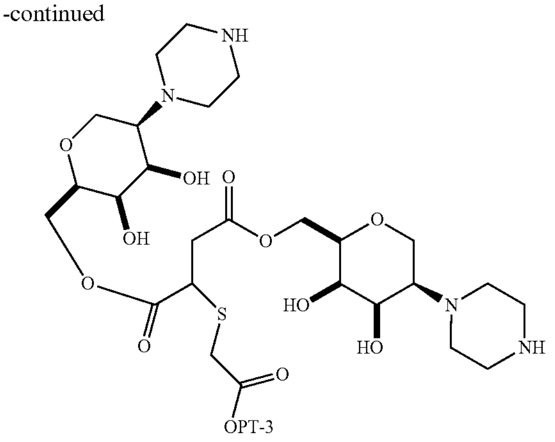

Compound 10

The —NH(OPT-3)C(O)$CH_2$SH is generated in situ from $NH_2$OH treatment of SATA-(N-succinimidyl S-acetylthioacetate)-OPT-3.

Synthesis 6-2. General Synthesis of Bidentate Fumaramide OPT-3 Conjugate-Sulfoximine Compounds

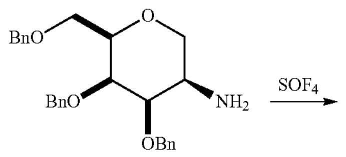

A127-2a

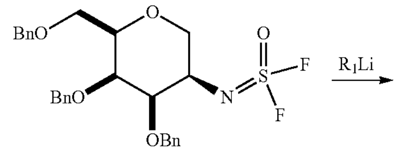

11-1

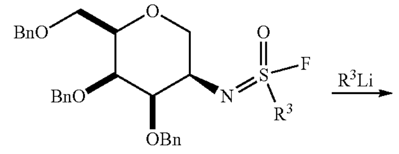

A92-1

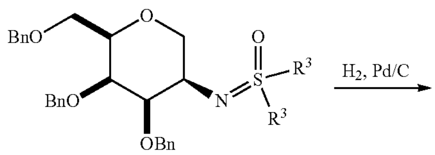

11-2
(Angew Chem I.E.E. 2018 57(7), 1939-1943)

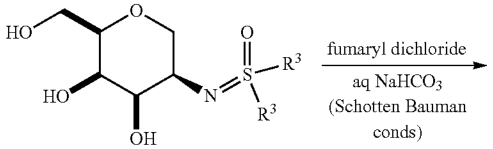

11-3

-continued

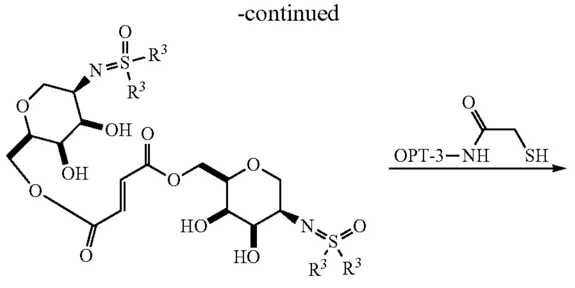

11-4

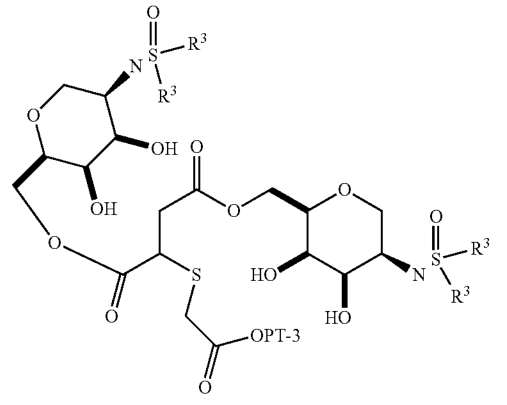

Compound 11

The —NH(OPT-3)C(O)$CH_2$SH is generated in situ from $NH_2$OH treatment of SATA-(N-succinimidyl S-acetylthioacetate)-OPT-3. Compound 12 can be synthesized using the procedure of Synthesis 2-58 with MeLi.

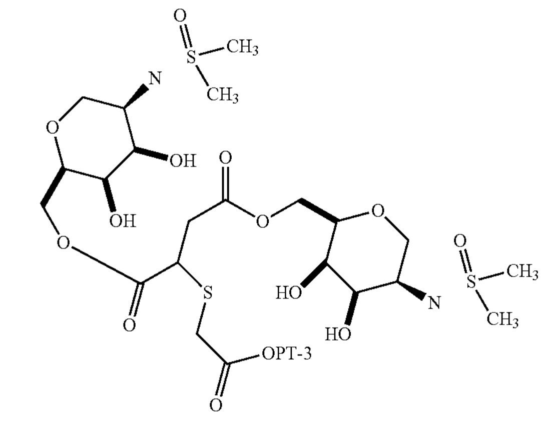
Compound 12
Synthesis 6-3. Preparation of Compound 13
Compound 13-1 is synthesized from ASGPR Ligand A245 from Synthesis 5-68
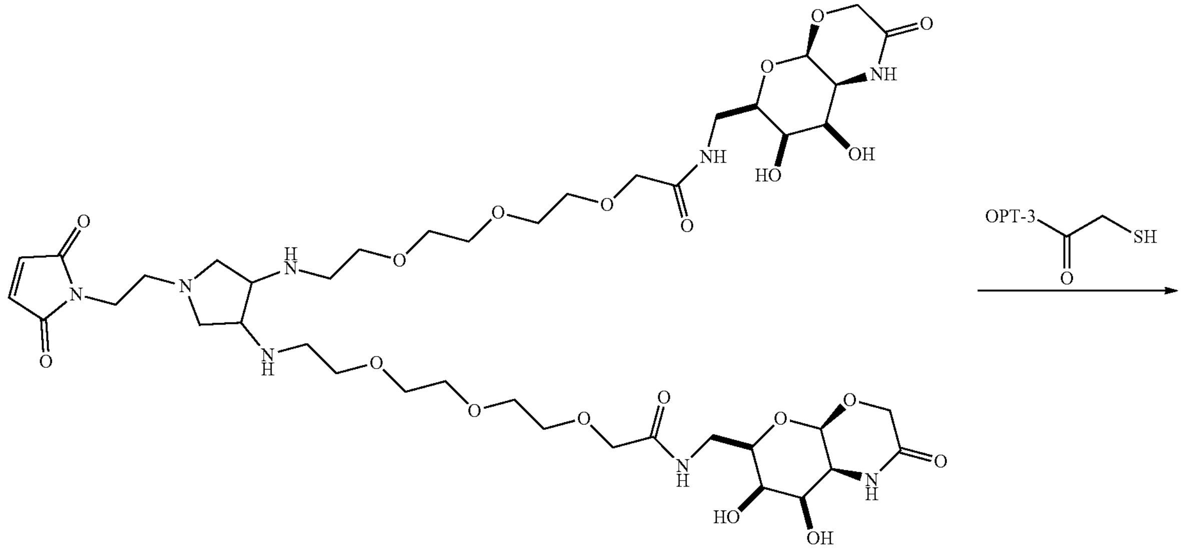
13-1
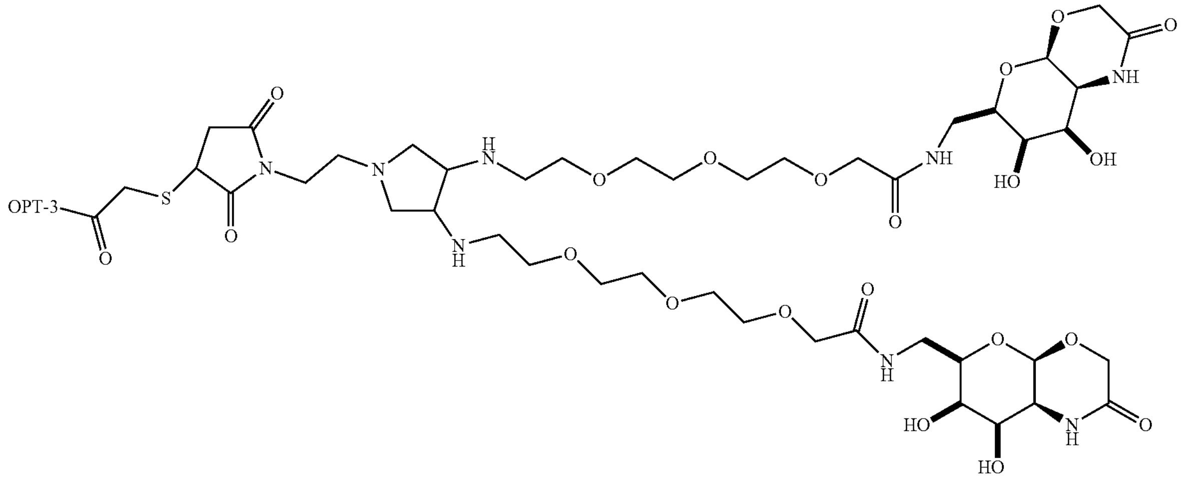
Compound 13

Synthesis 6-4. Preparation of Compound 14
Compound 14-1 is synthesized from ASGPR Ligand A253 from Synthesis 5-72
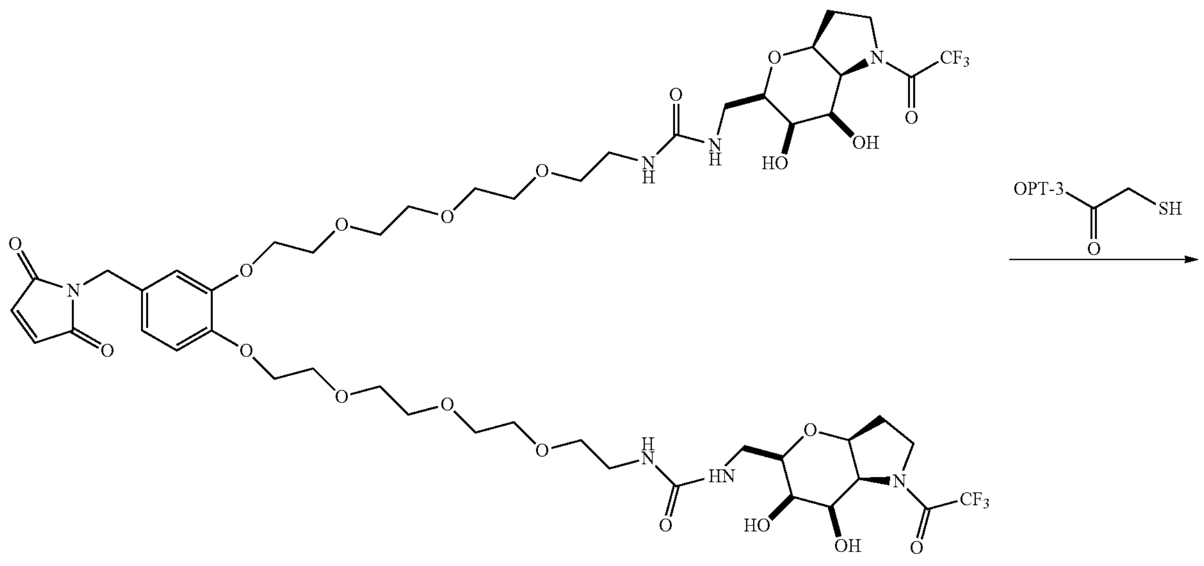
14-1
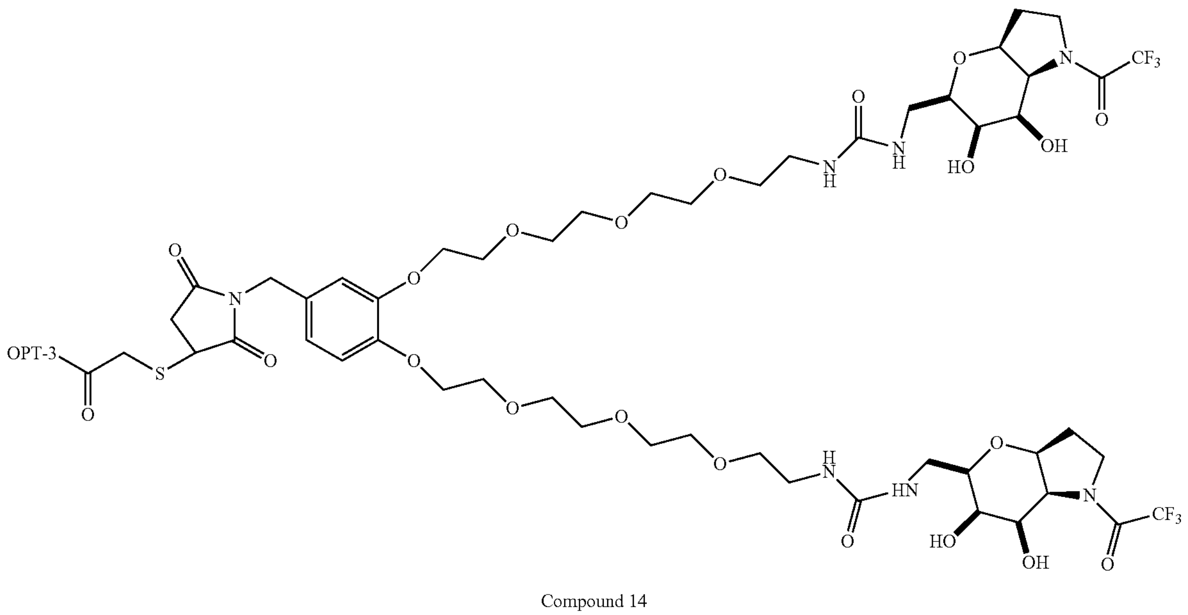
Compound 14

Synthesis 6-5. Preparation of Compound 15 and Compound 16
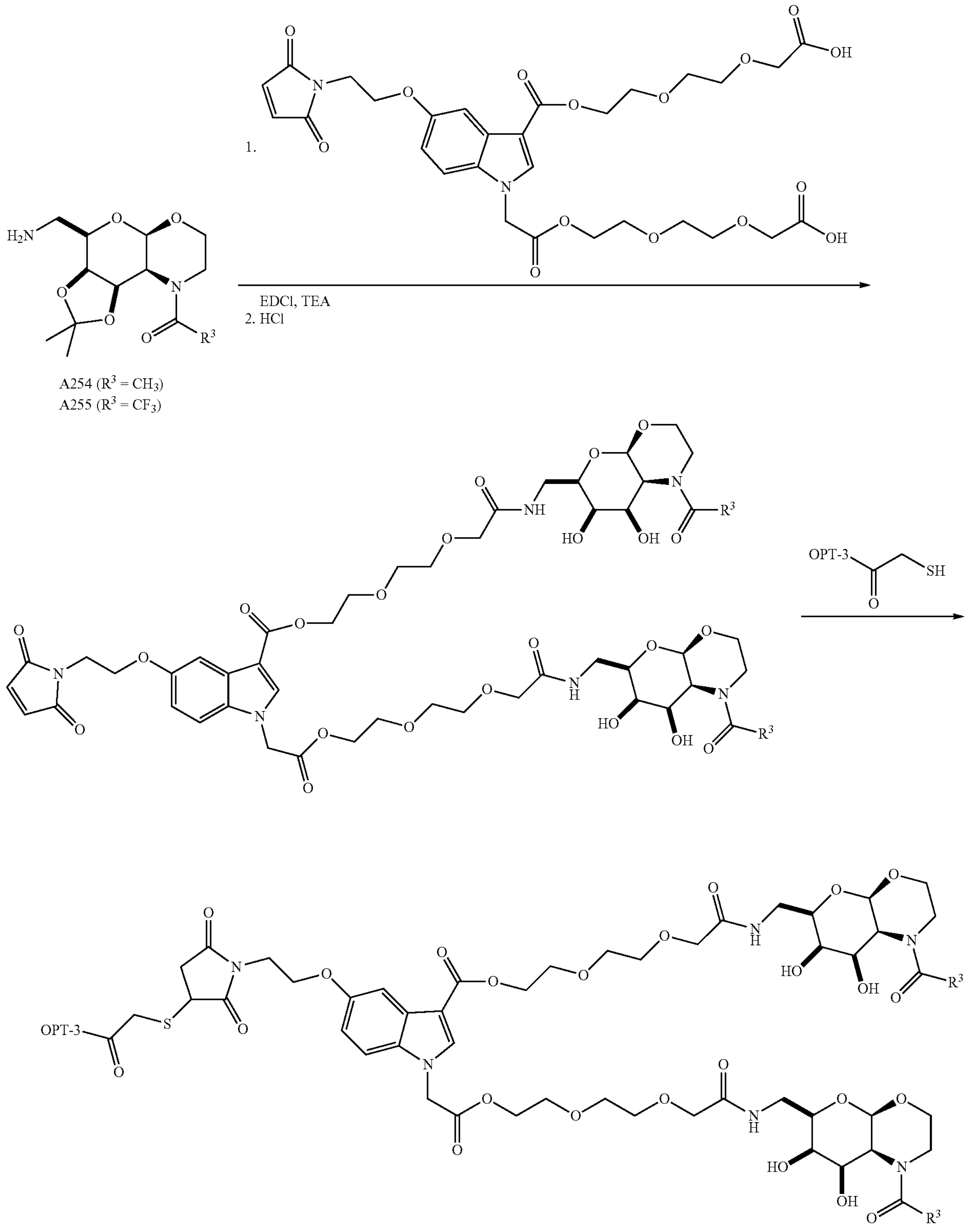
A254 ($R^3$ = $CH_3$)
A255 ($R^3$ = $CF_3$)
Compound 15 ($R^3$ = $CH_3$)
Compound 16 ($R^3$ = $CF_3$)

Synthesis 6-6. Preparation of Compound 17
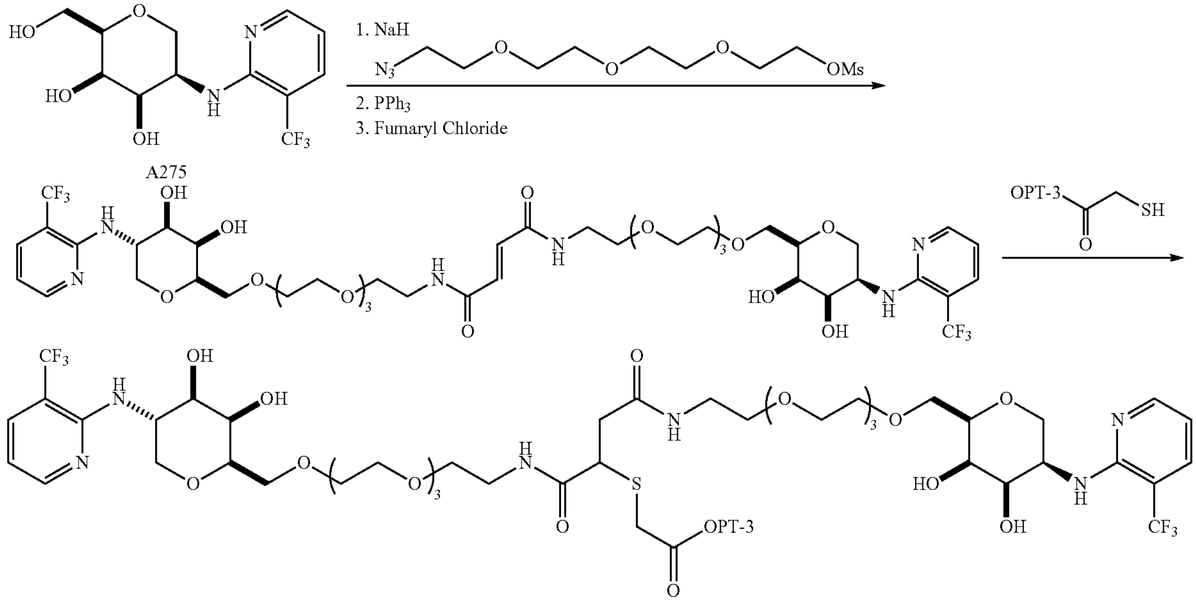
A275
Compound 17
Synthesis 6-7. Preparation of Compound 18
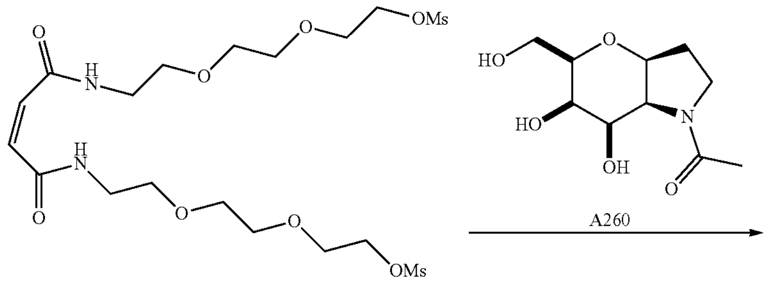
A260
18-1
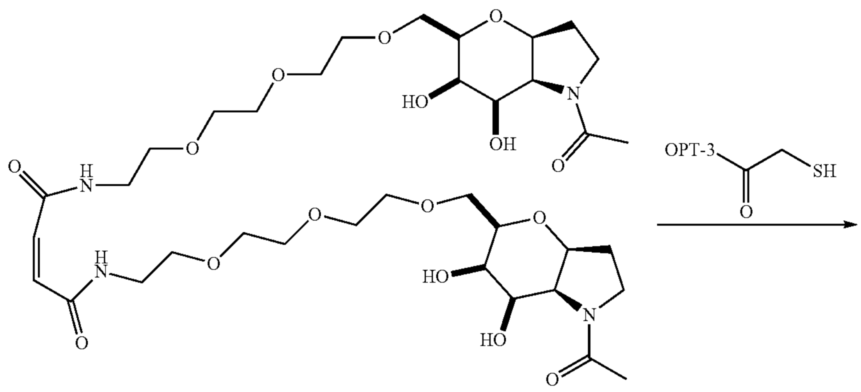
18-2

-continued
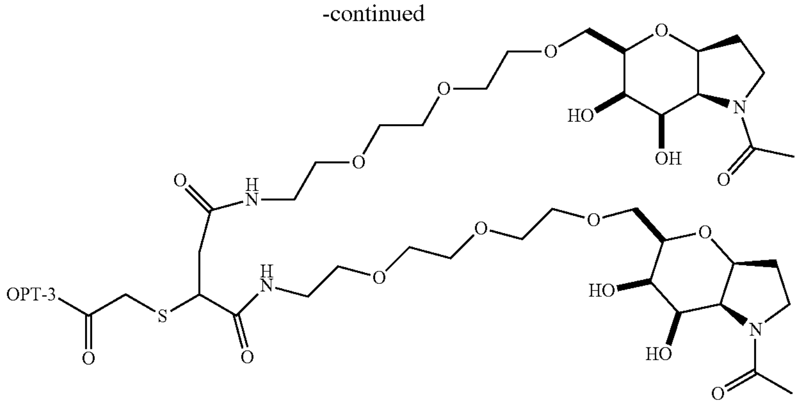
Compound 18
Synthesis 6-8. Preparation of Compound 19
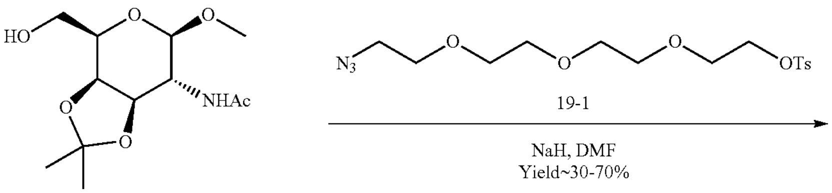
Intermediate 4
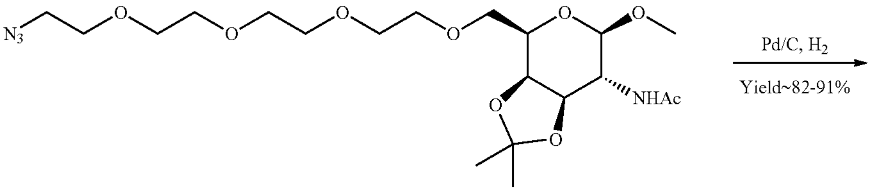
19-2
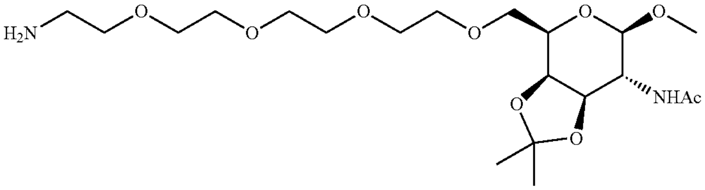
19-3
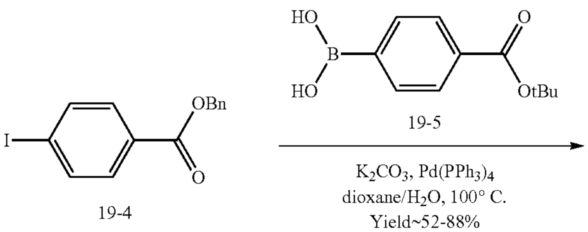
19-4
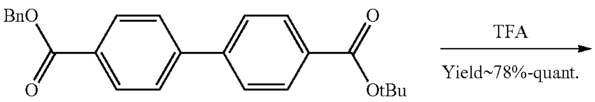
19-6

-continued
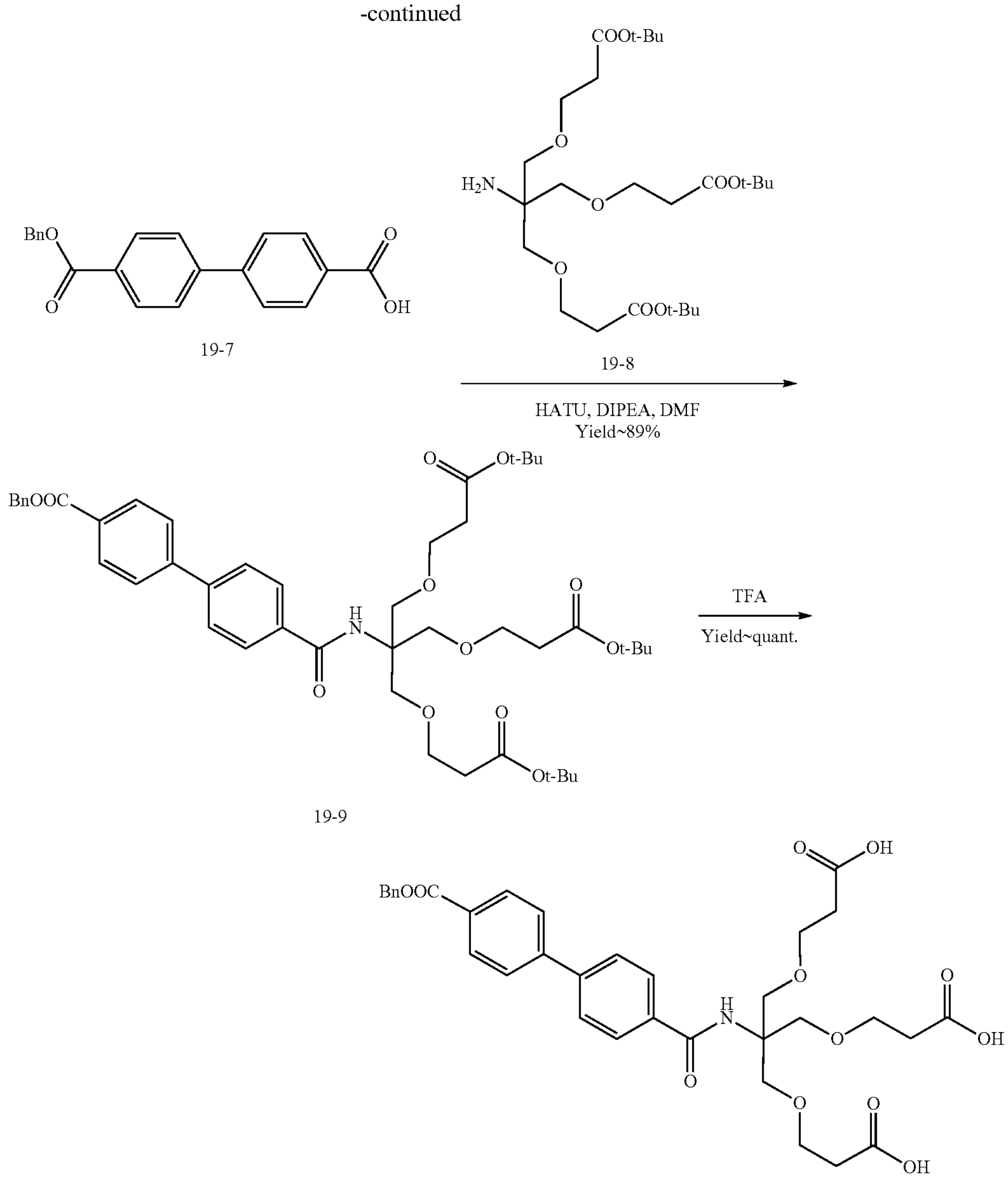
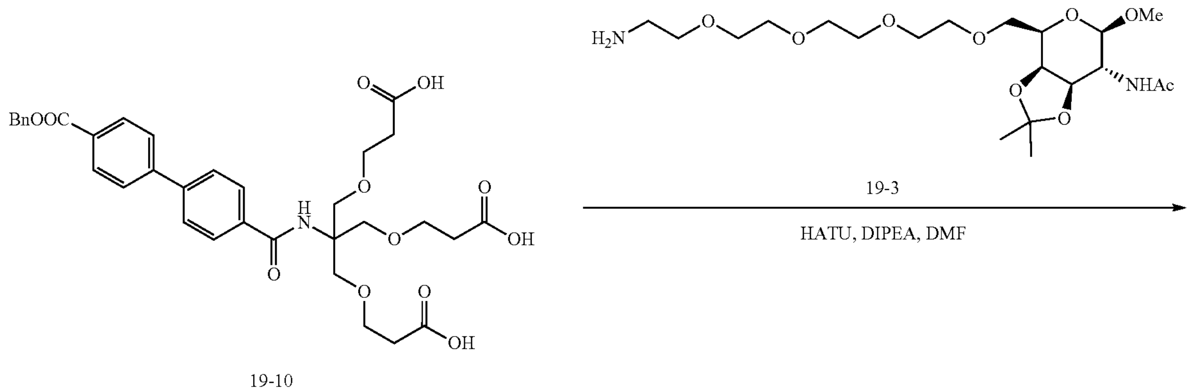

-continued
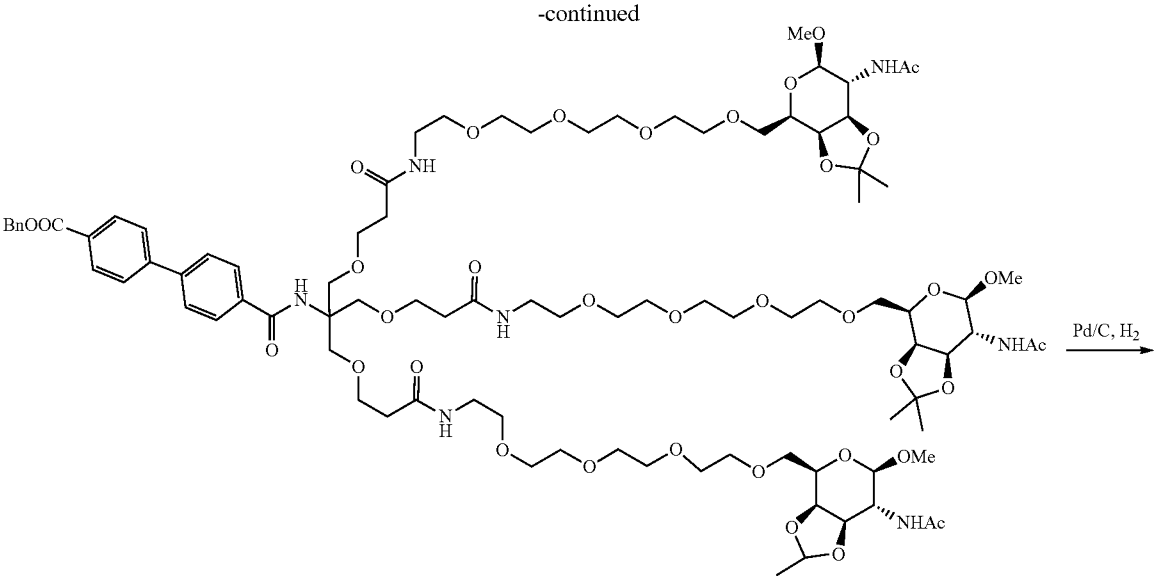
19-11
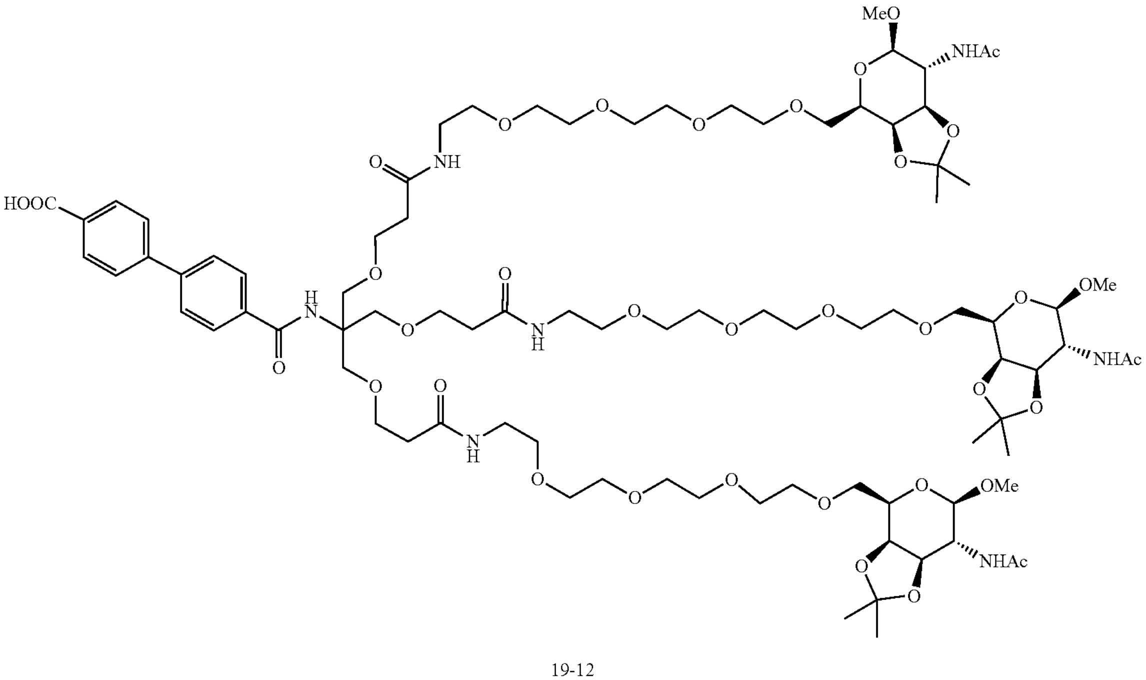
19-12

-continued
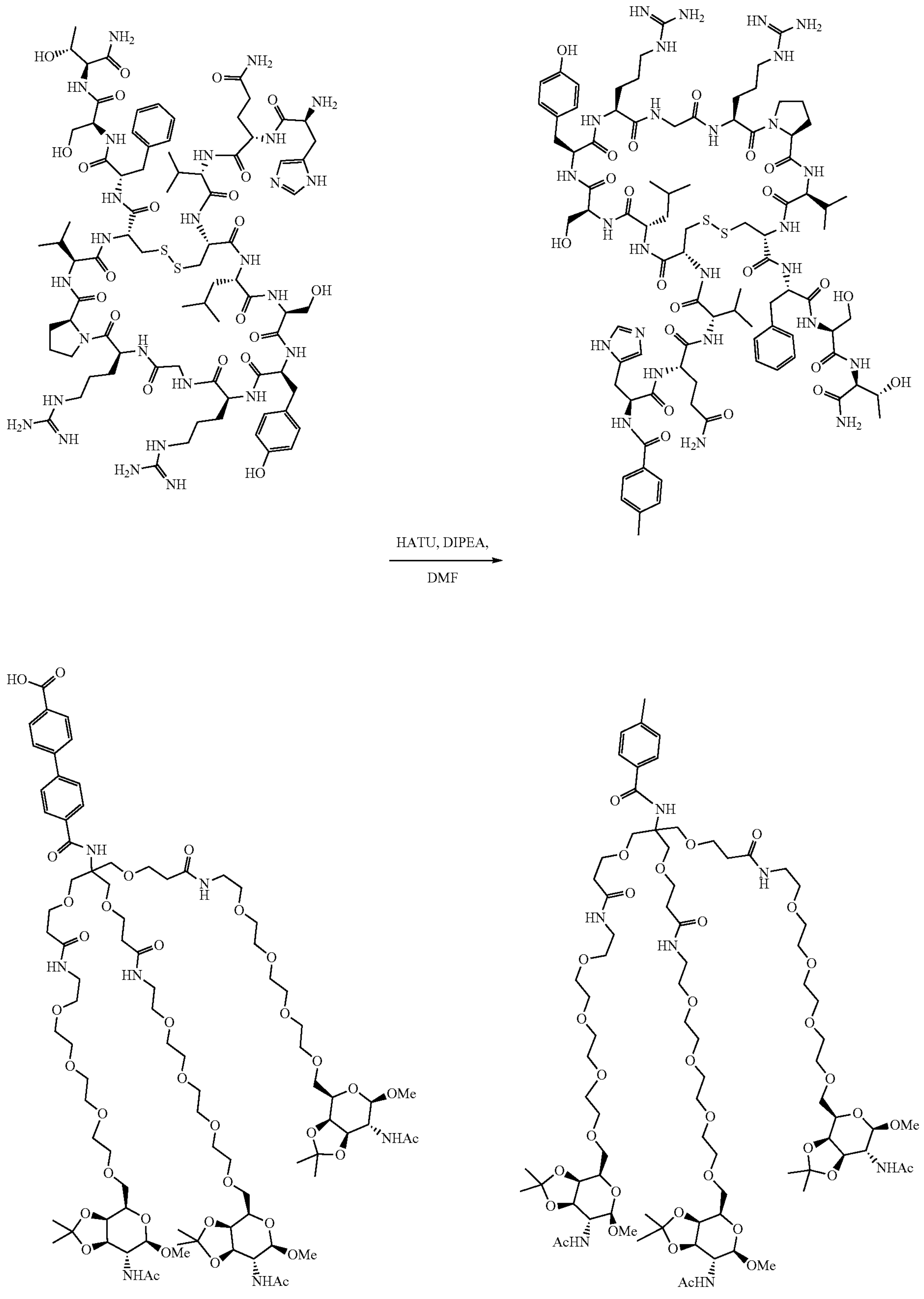
19-13
19-14

-continued
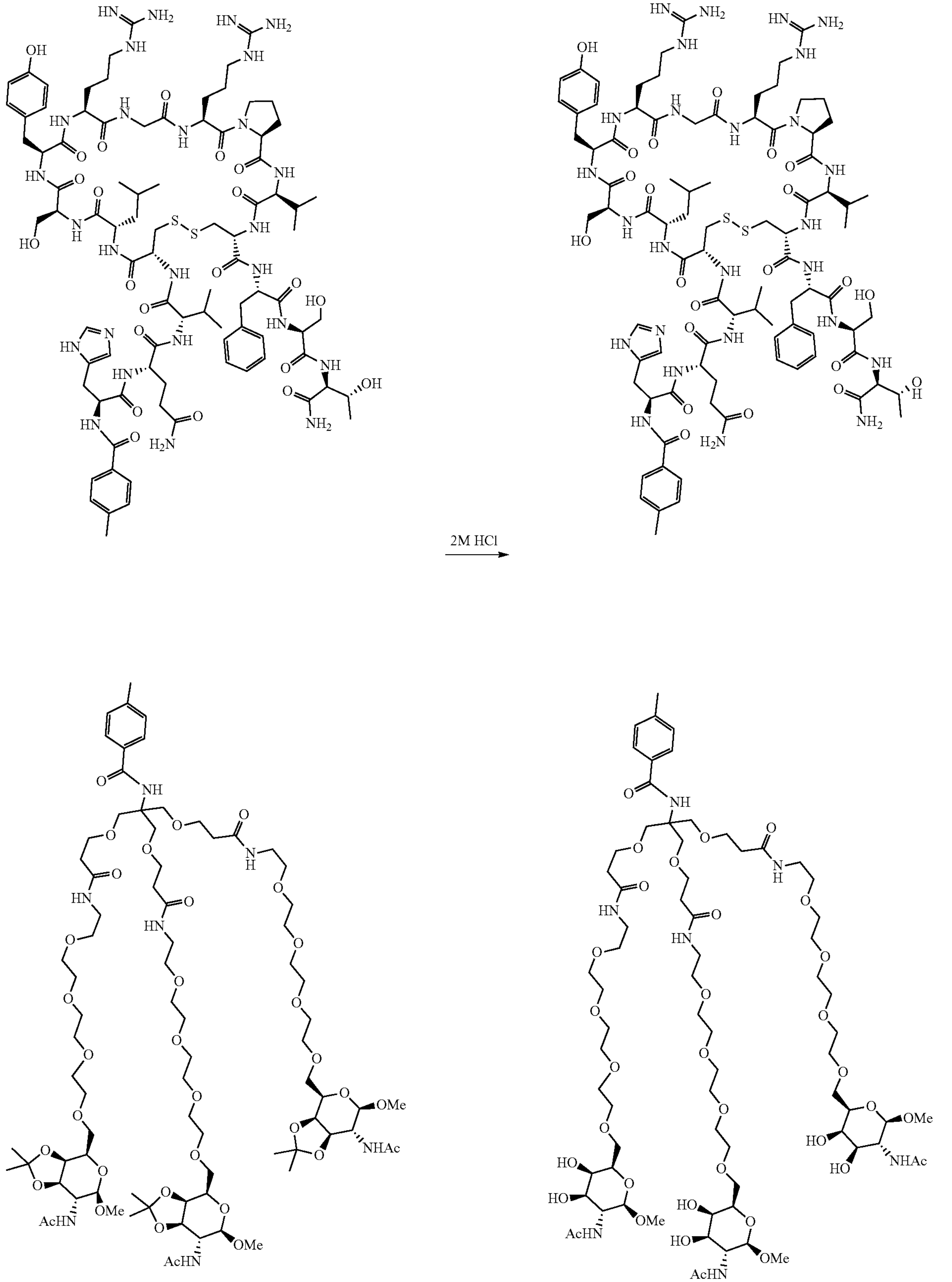
19-15
19-16

-continued
Compound 20
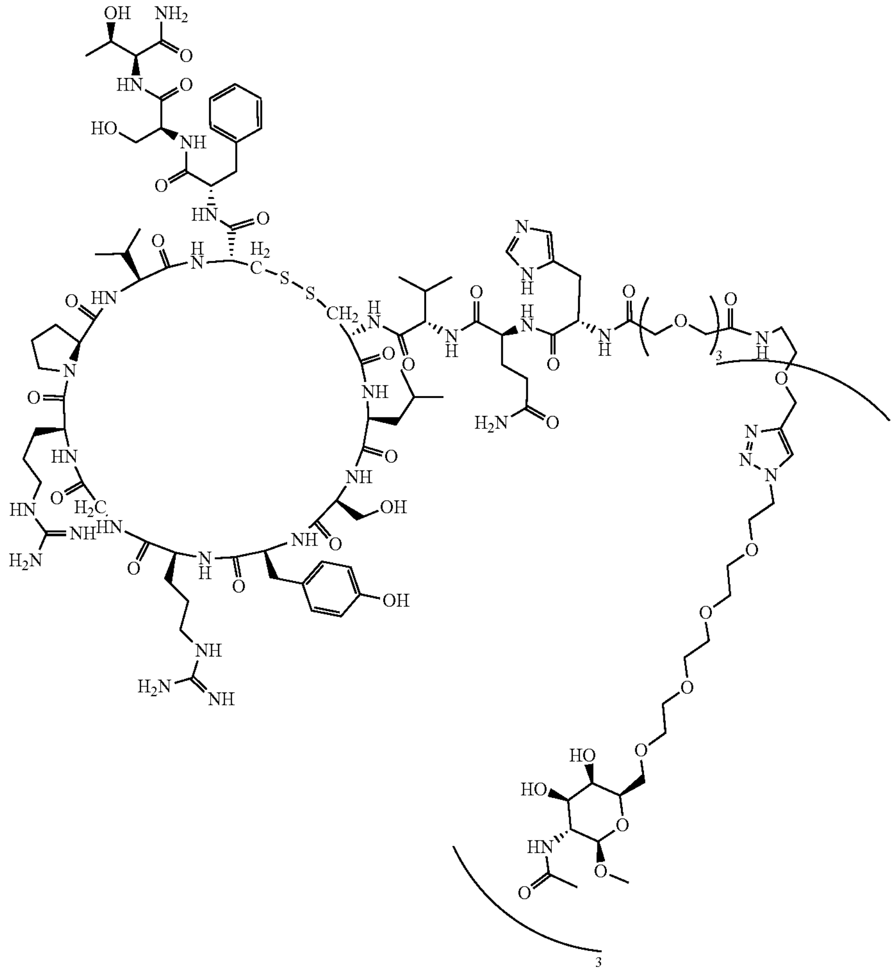

Compound 21
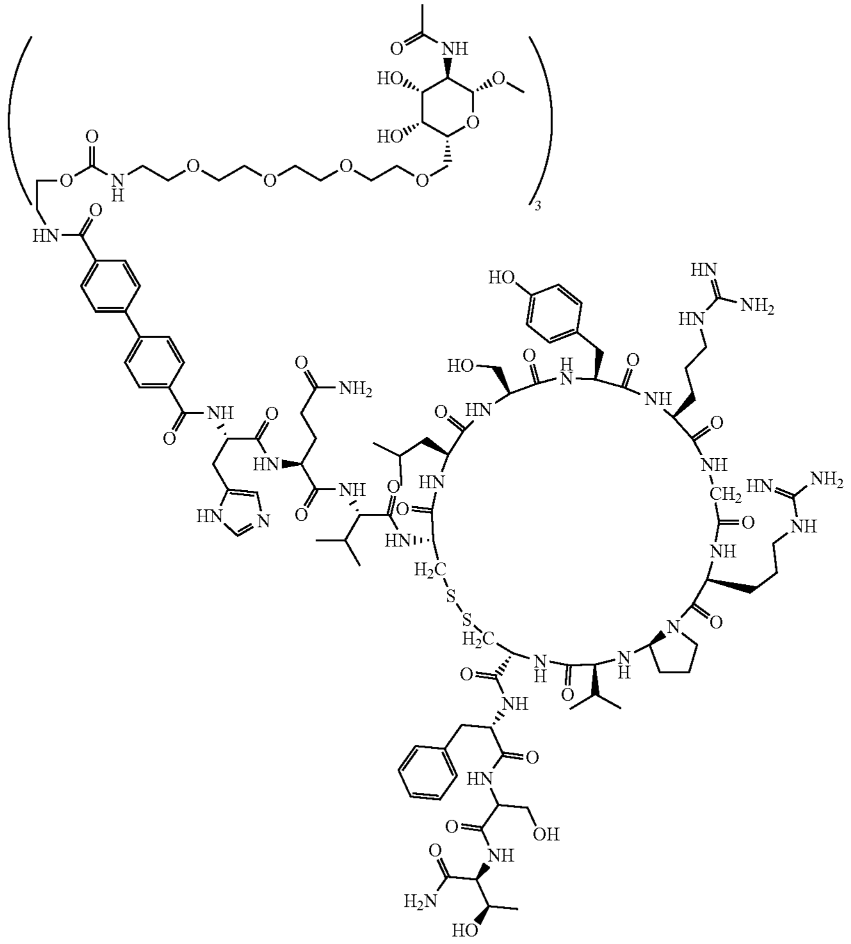

-continued
Compound 22
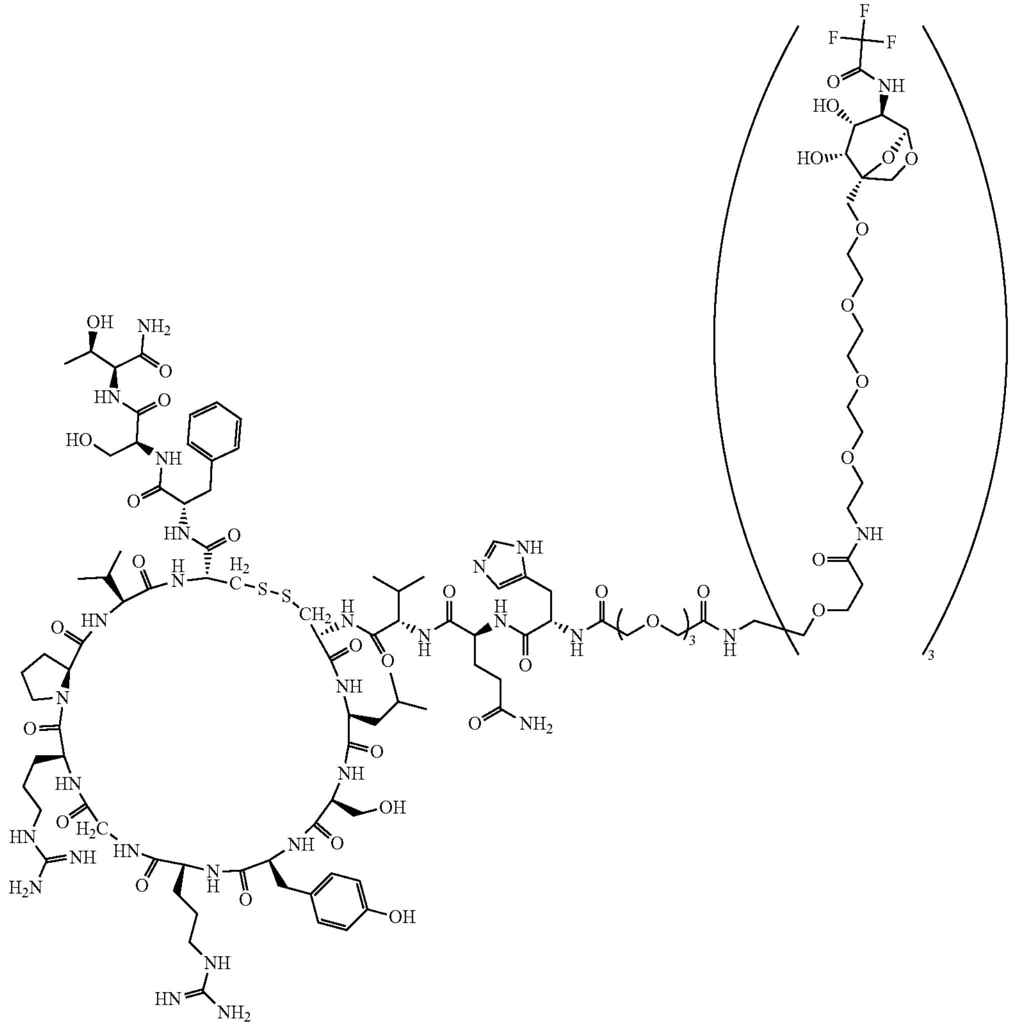

-continued
Compound 23
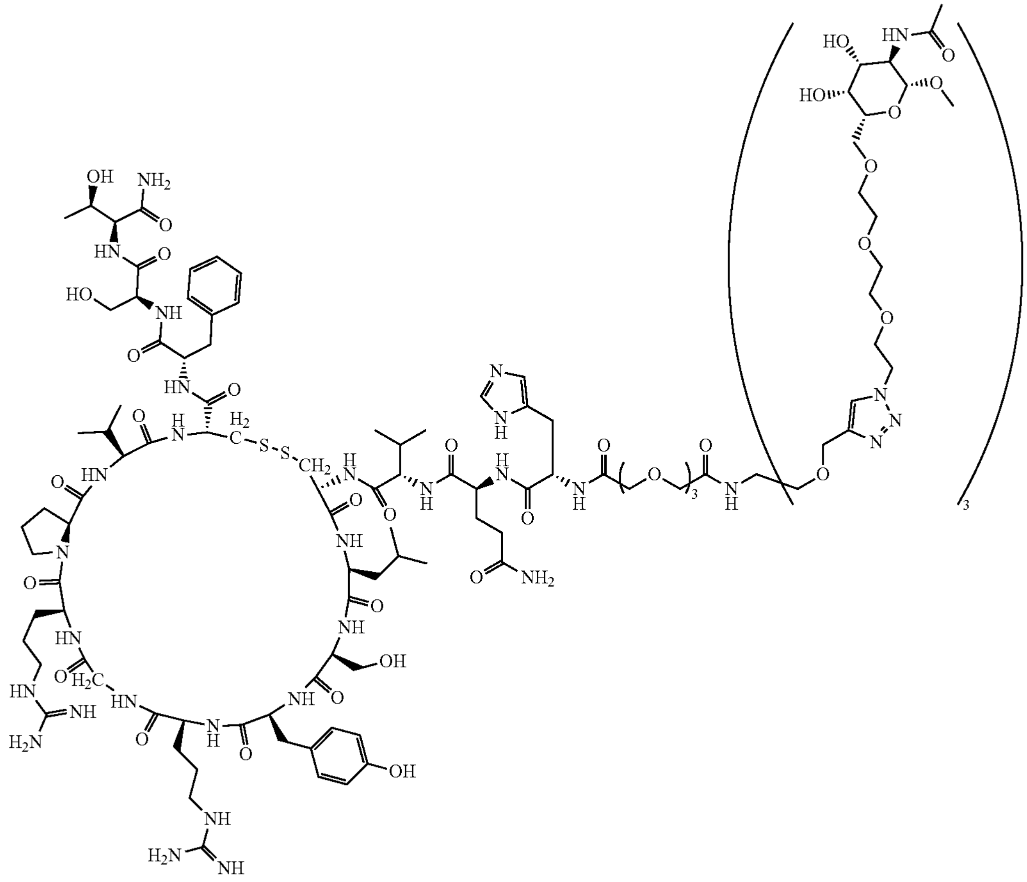

-continued
Compound 24
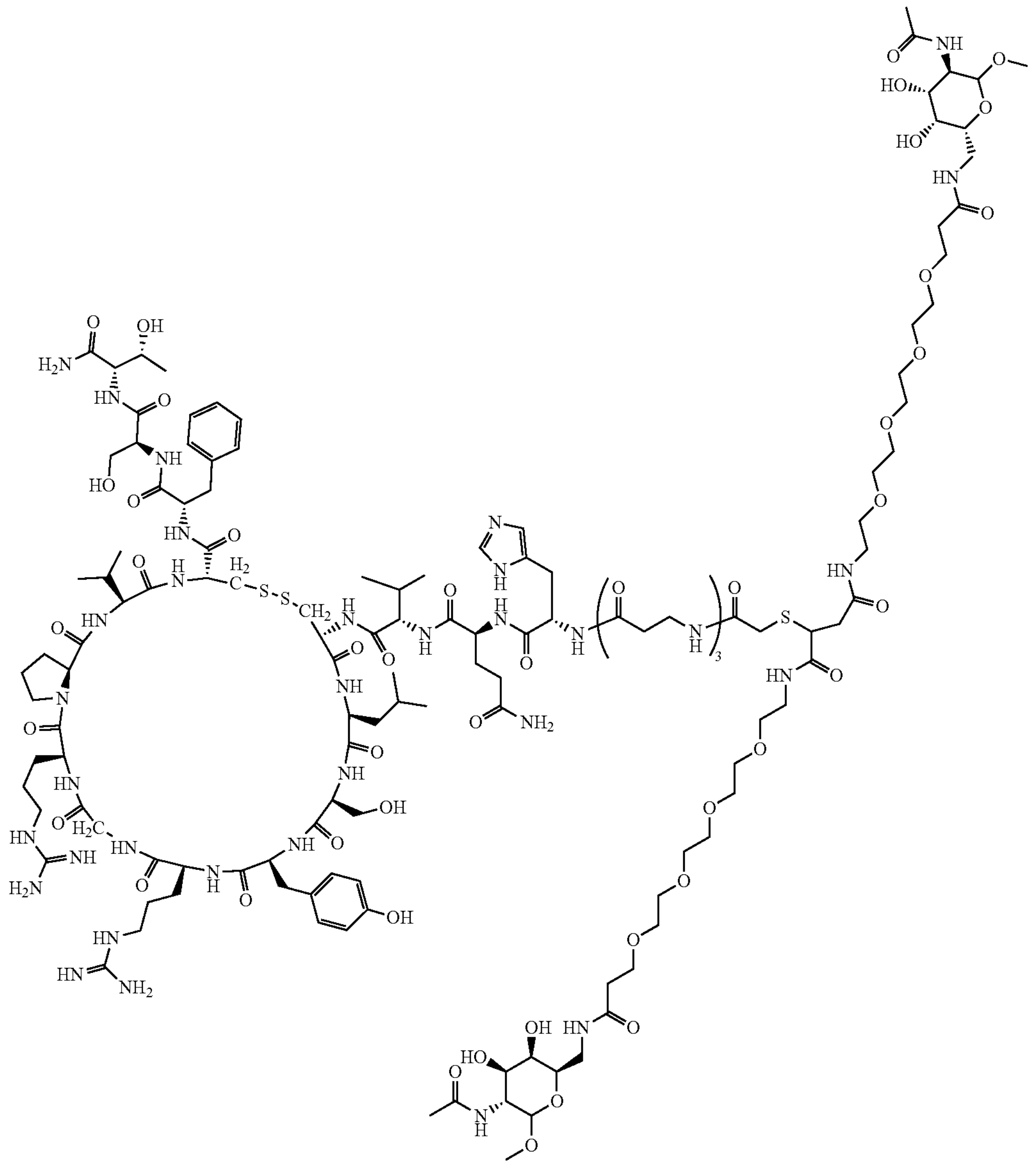

-continued
Compound 25
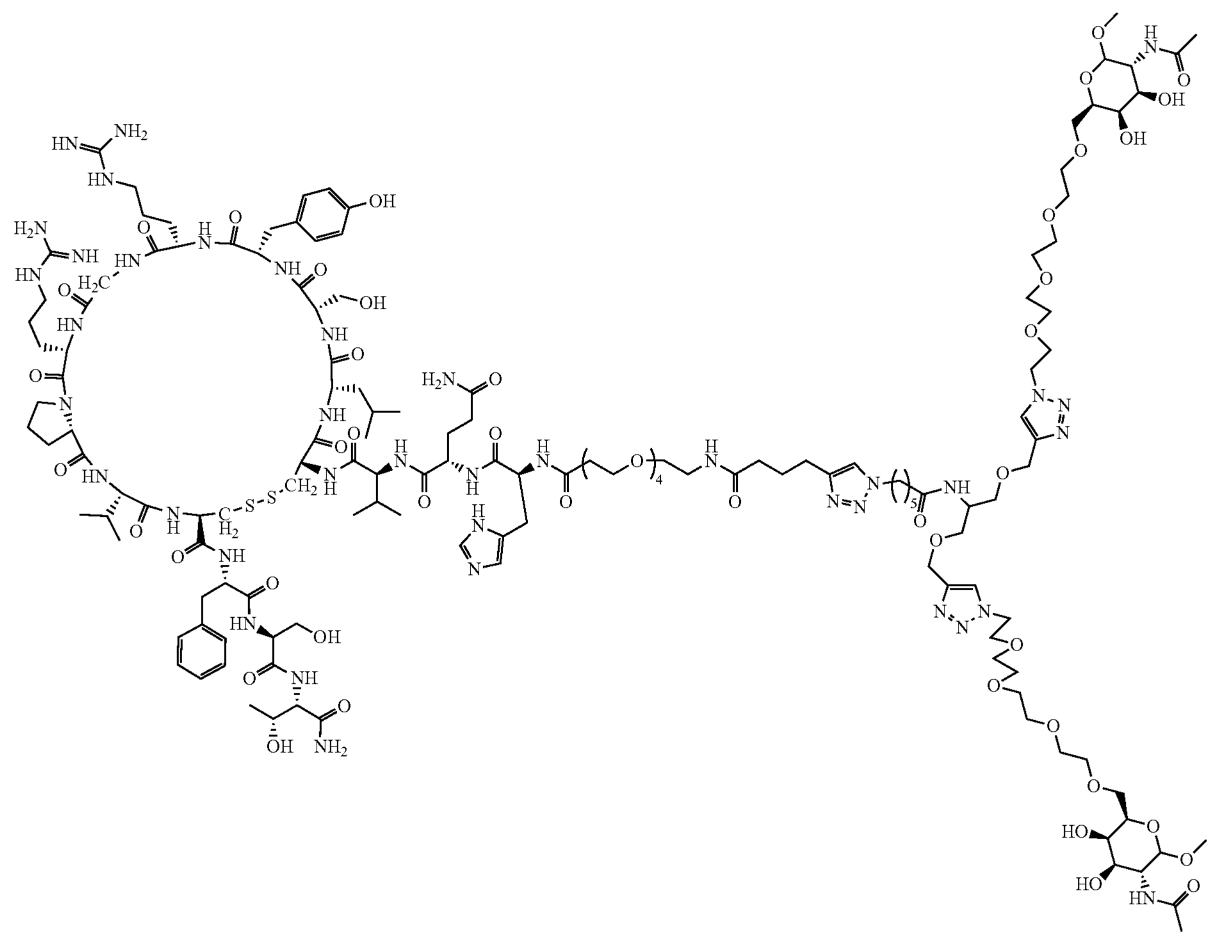
Compound 26
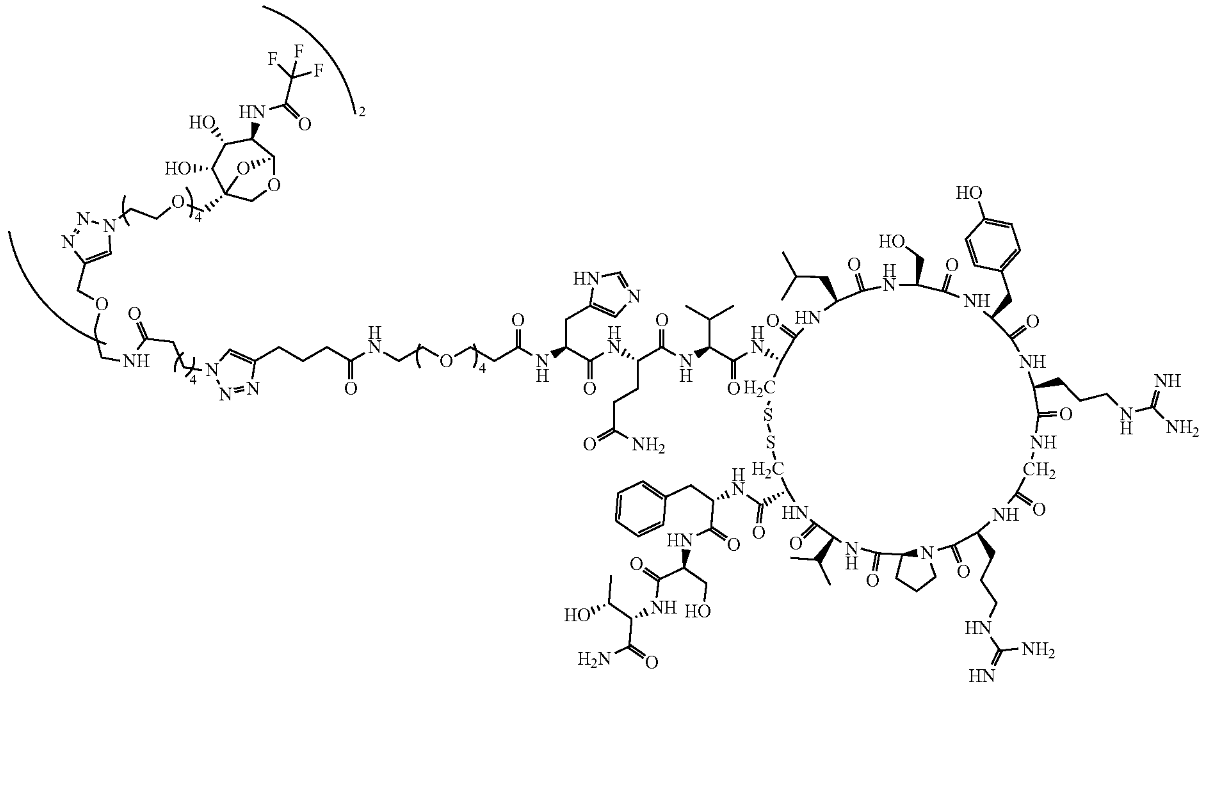

-continued

Compound 27

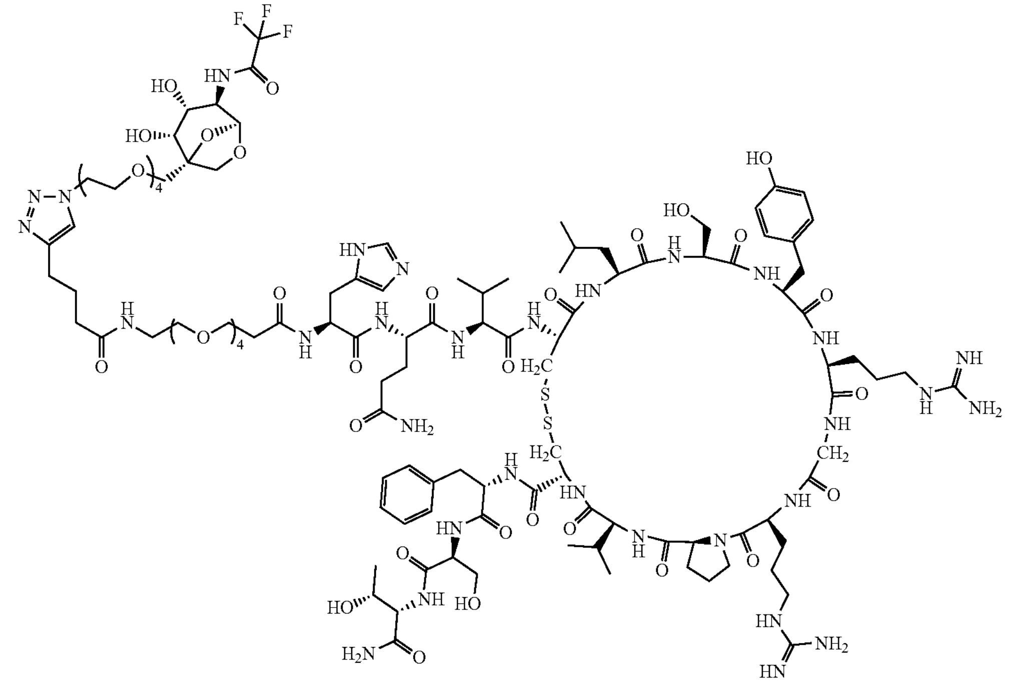

Example 7. Synthesis and Installation of Linkers

Linker$^B$ can be synthesized from any chemical moiety containing at least two reactive sites for bond formation. For example, a compound of the present invention containing Linker$^B$ can be synthesized from:

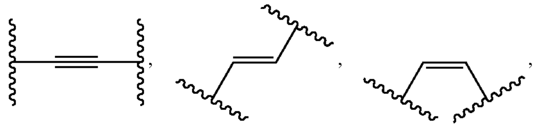

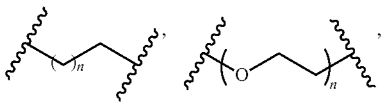

, or

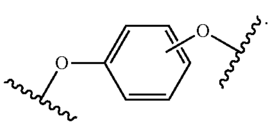

-continued

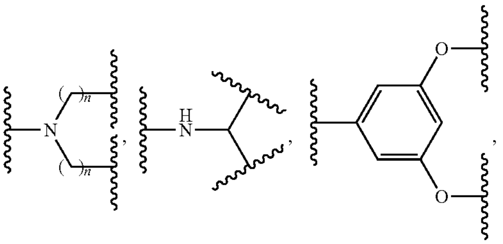

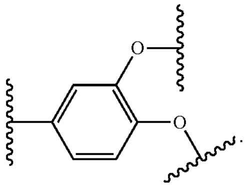

Linker$^C$ can be synthesized from any chemical moiety containing at least three reactive sites for bond formation. For example, a compound of the present invention containing Linker$^C$ can be synthesized from:

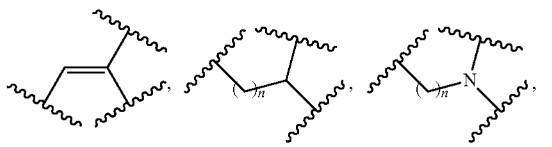

Linker$^D$ can be synthesized from any chemical moiety containing at least three reactive sites for bond formation. For example, a compound of the present invention containing Linker$^D$ can be synthesized from:

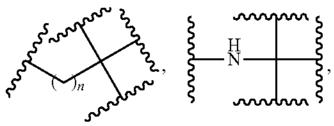

, or

-continued
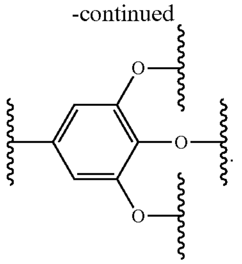
Synthesis 7-1. Attachment of Triazole-Containing Alkyl and Polyethylene Glycol Linkers for Linear Alkyl
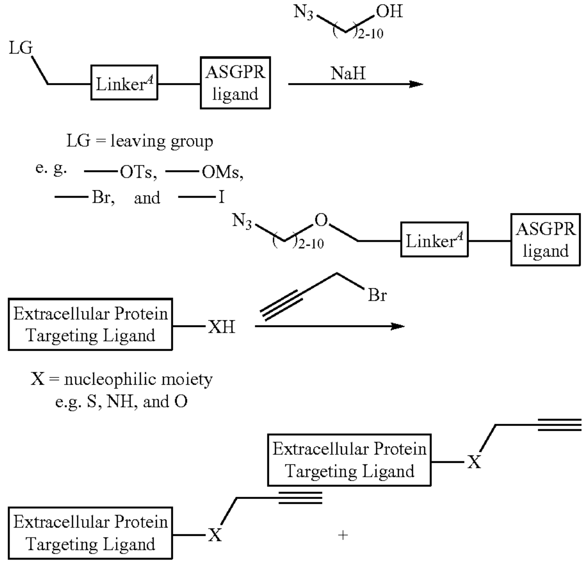
-continued
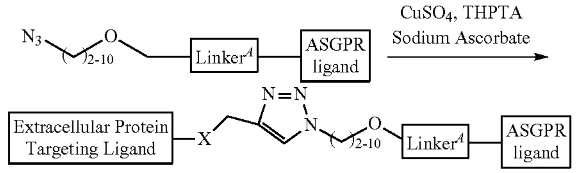
For Polyethylene Glycol:
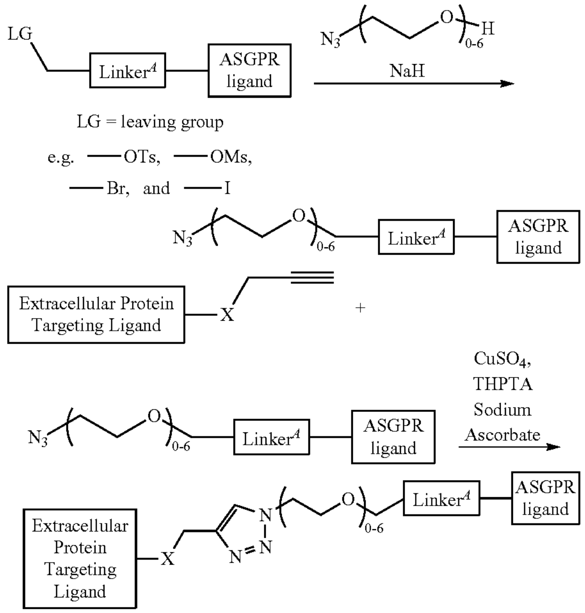
Synthesis 7-2. Attachment of 1-(3,4-dihydroxybenzyl)-1H-pyrrole-2,5-dione Linker
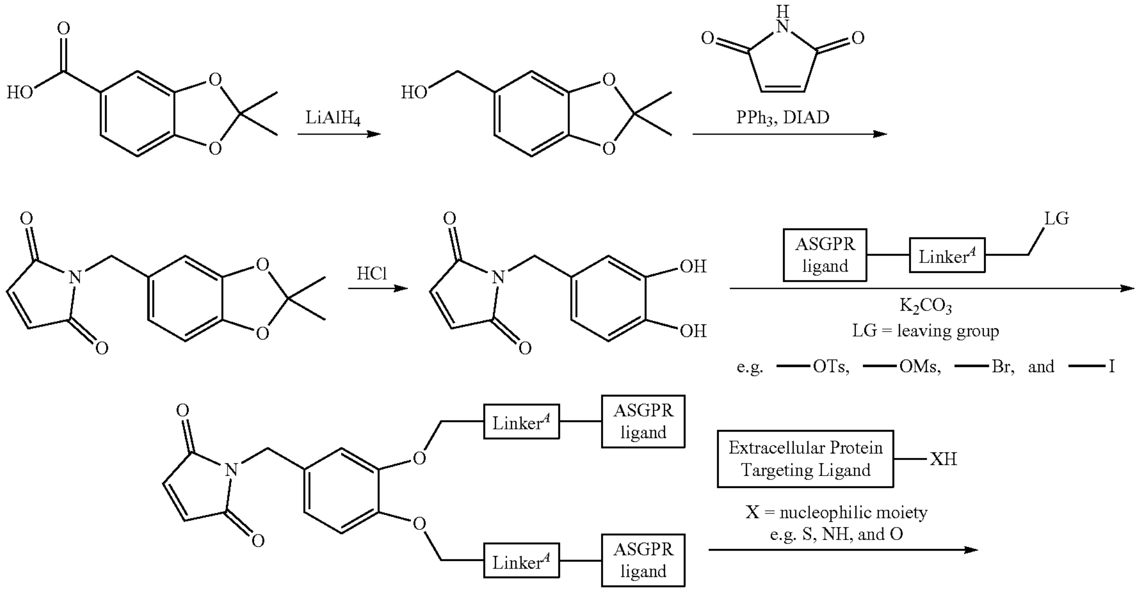

-continued
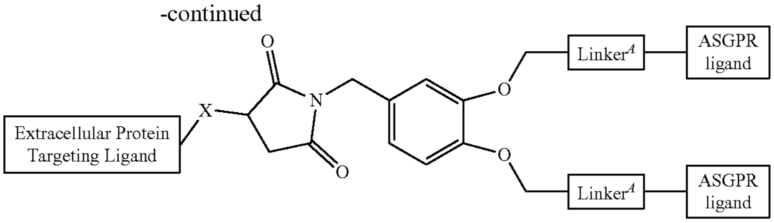
Synthesis 7-3. Attachment of 1-(carboxymethyl)-5-hydroxy-1H-indole-3-carboxylic Acid Linker
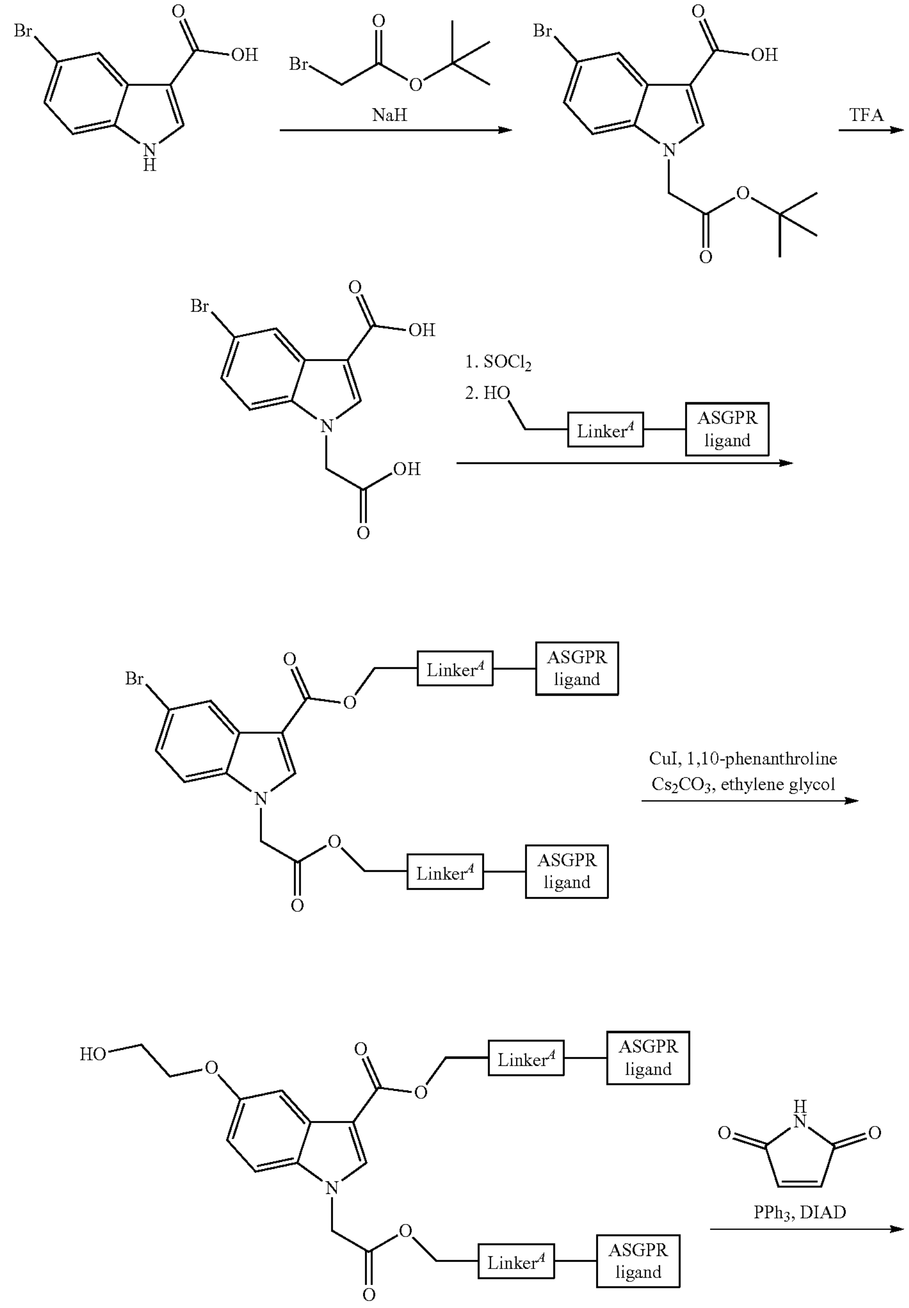

-continued
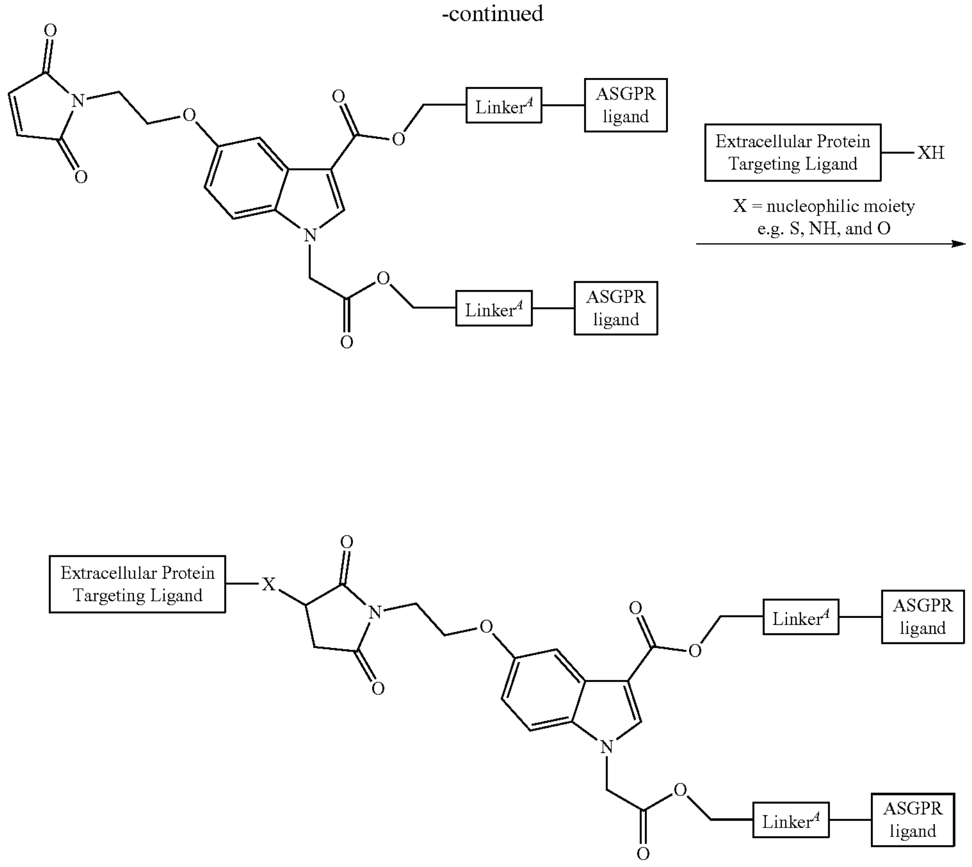
Synthesis 7-4. Attachment of pyrrolidine-3,4-diamine Linker
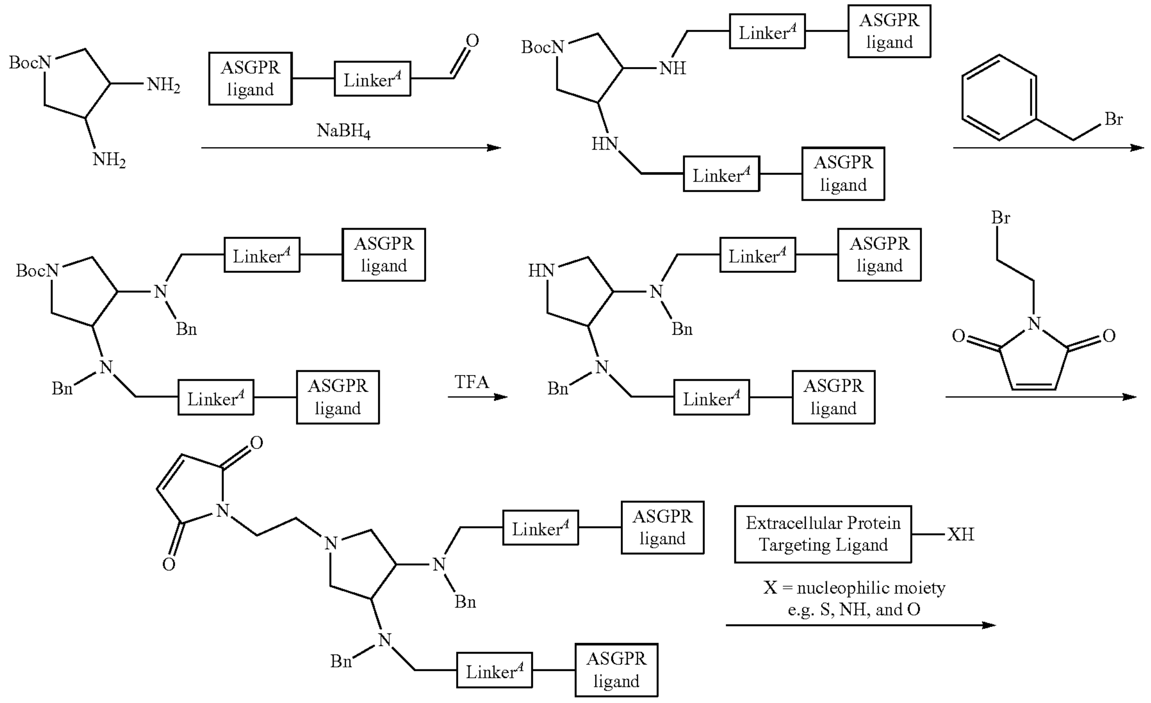

-continued
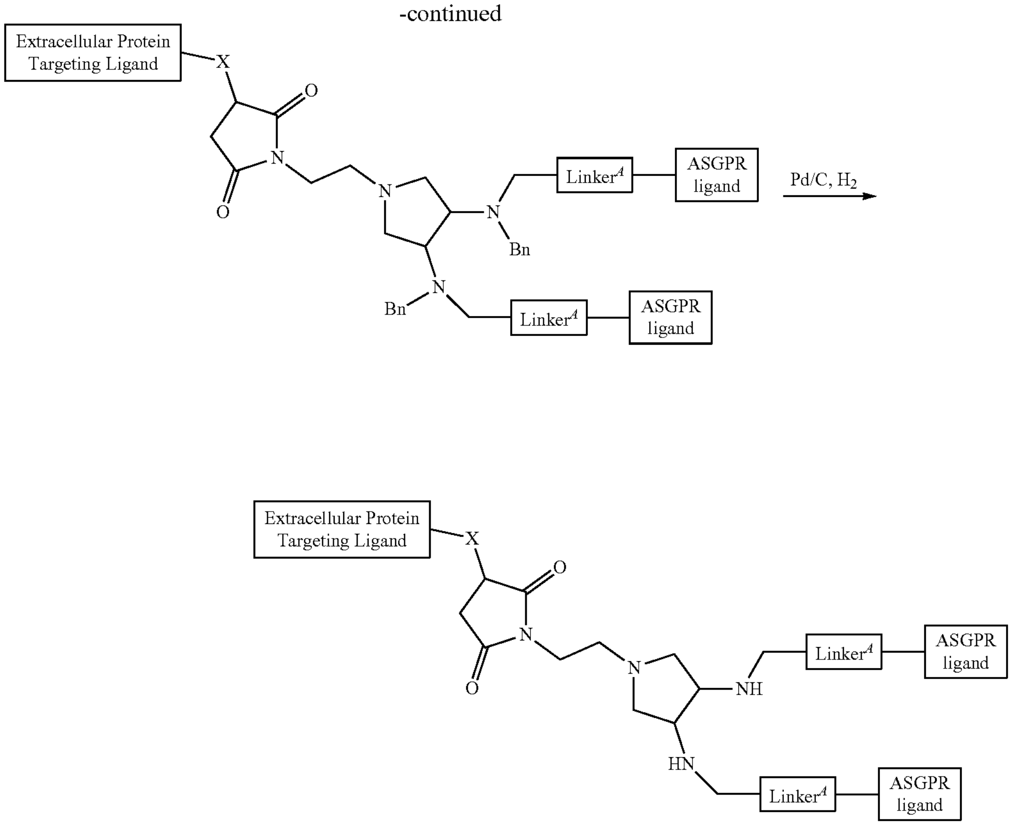
Synthesis 7-5. Attachment of cyclobutane-1,3-diol-containing Alkyl and Polyethylene Glycol Linkers
For Linear Alkyl:
$Linker^C$:
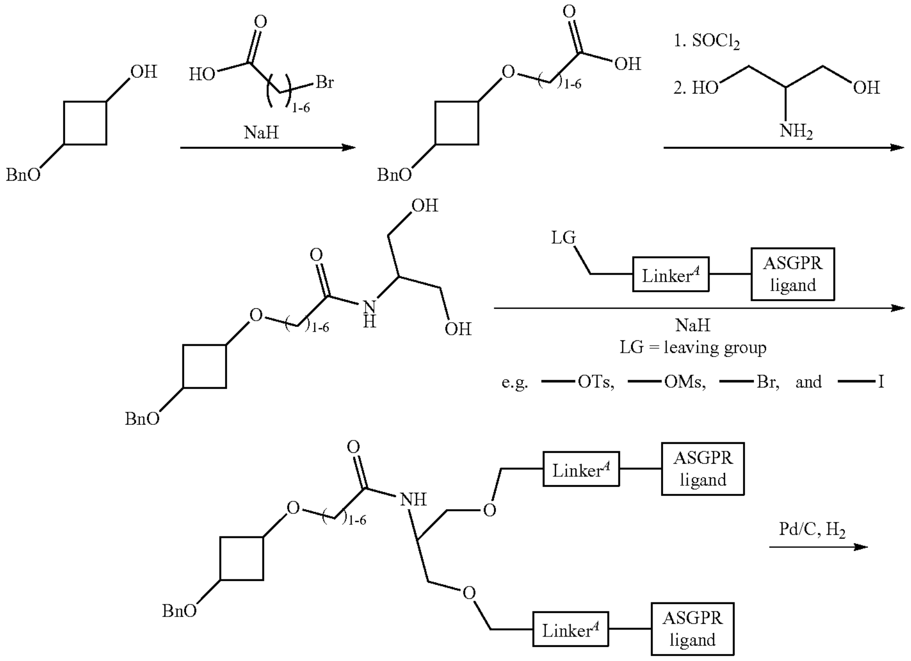

-continued
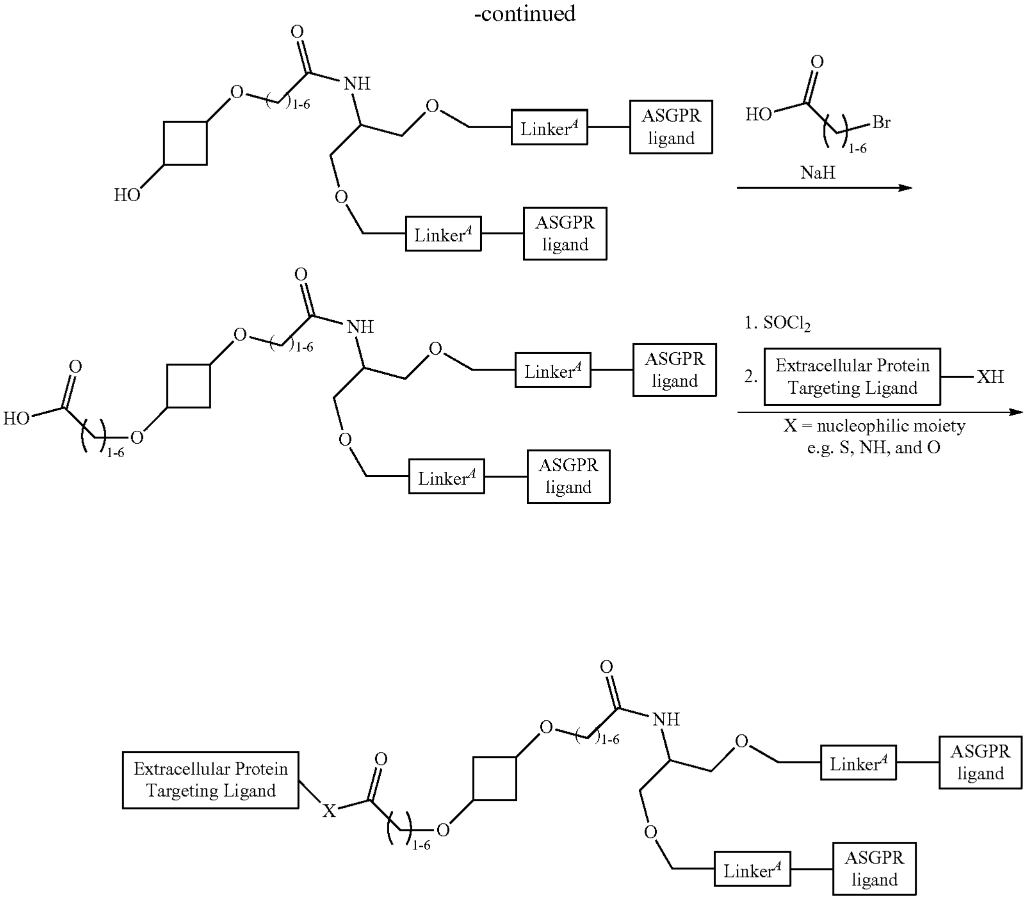
Linker$^D$:
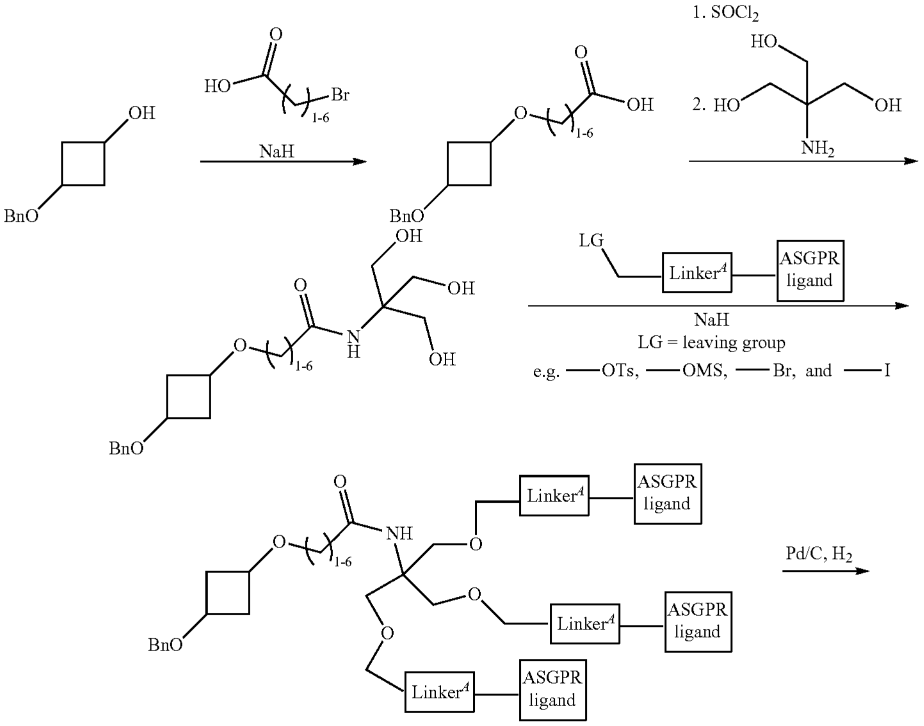

-continued
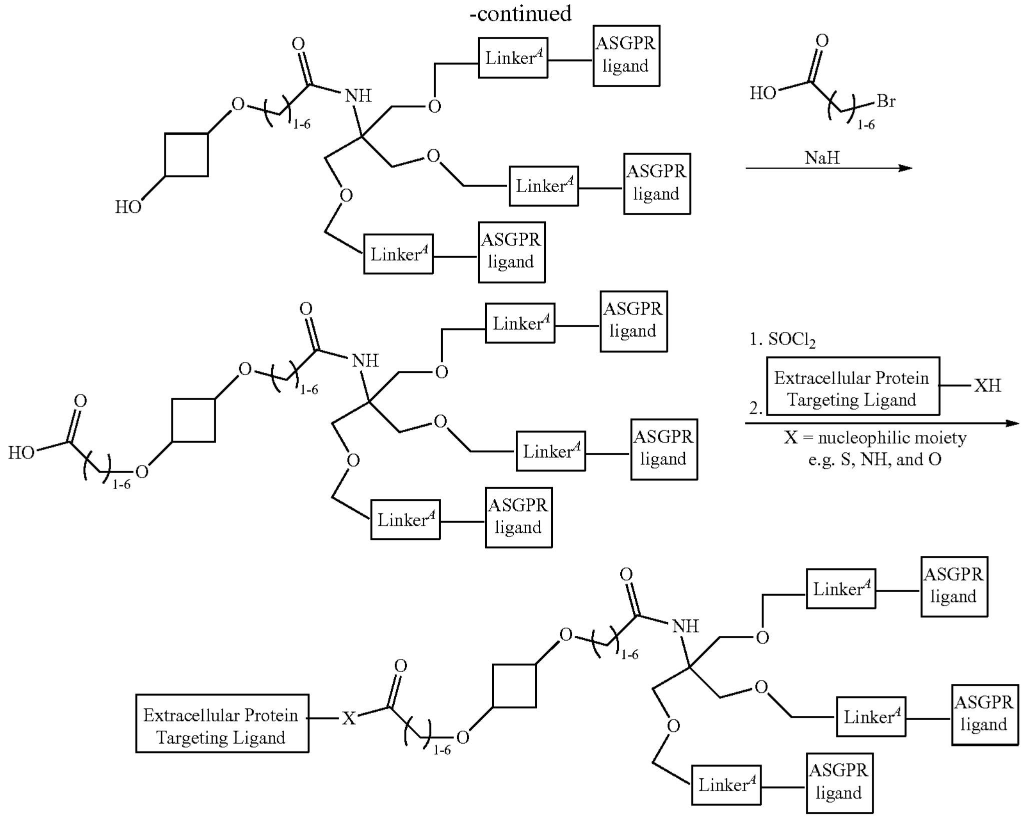
For Polyethylene Glycol:
Linker$^C$:
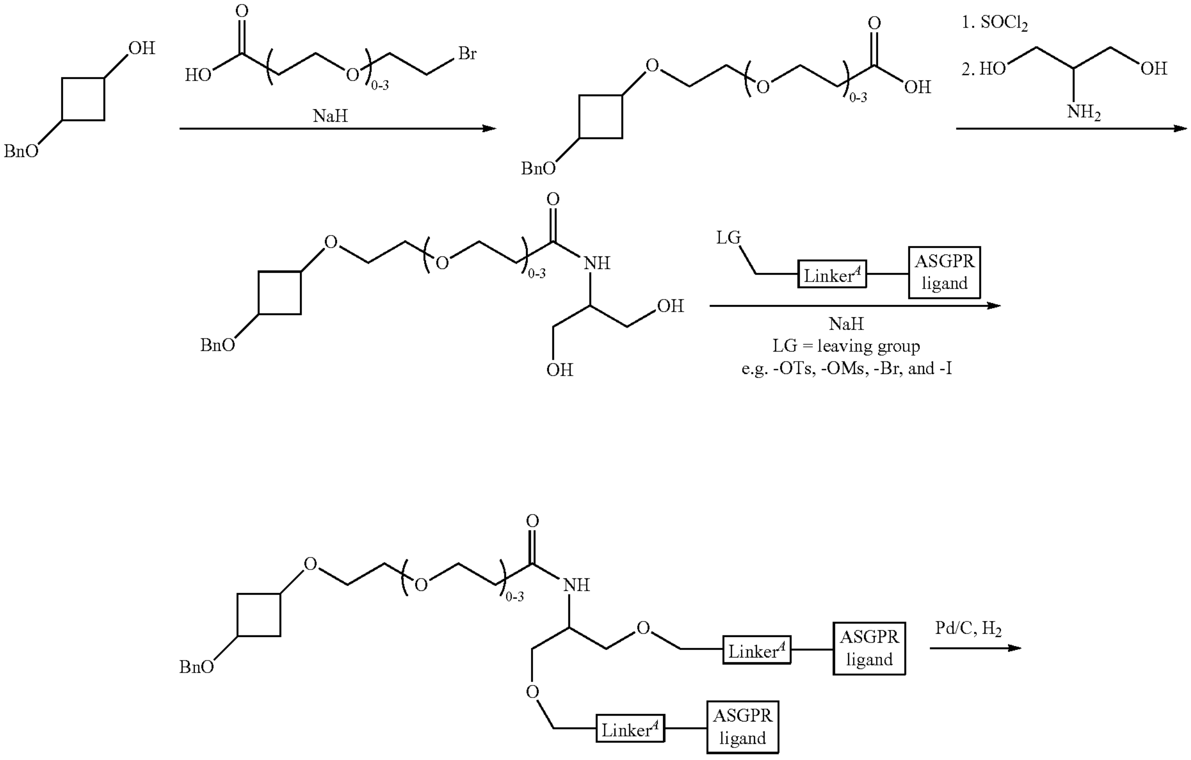

-continued
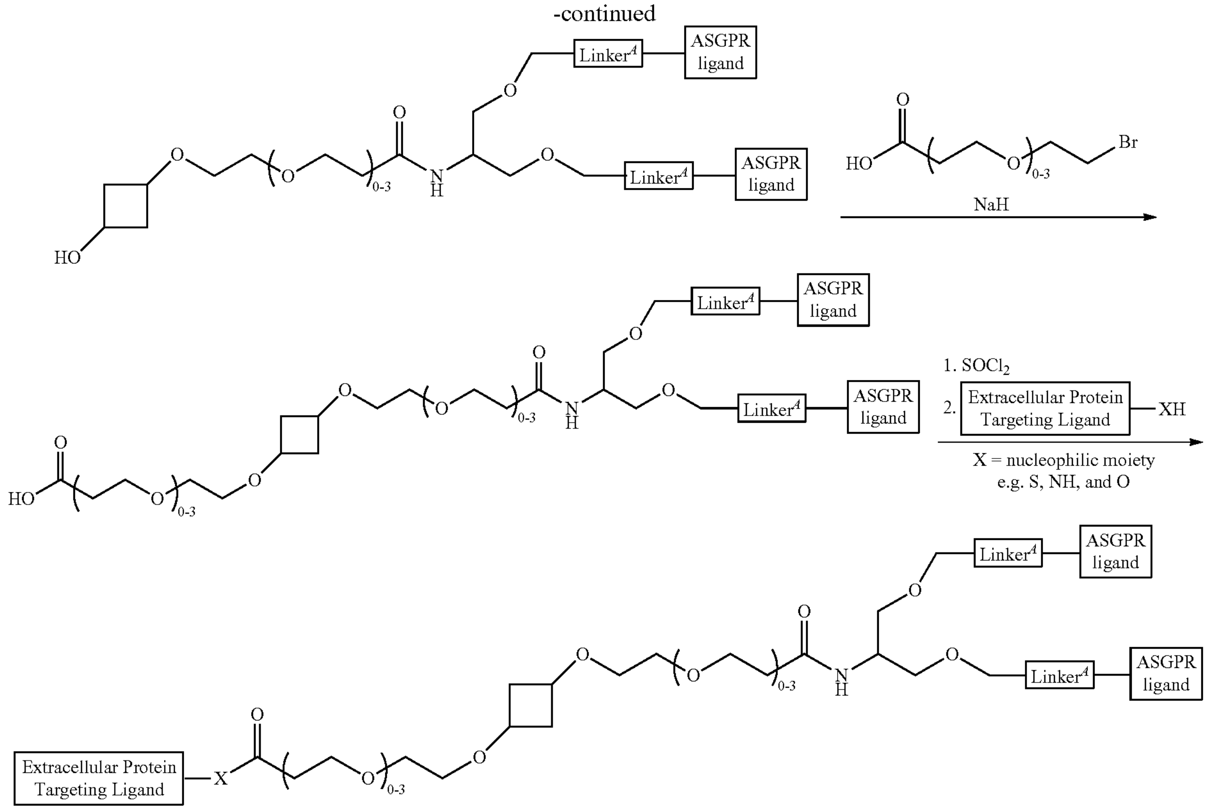
Linker$^D$
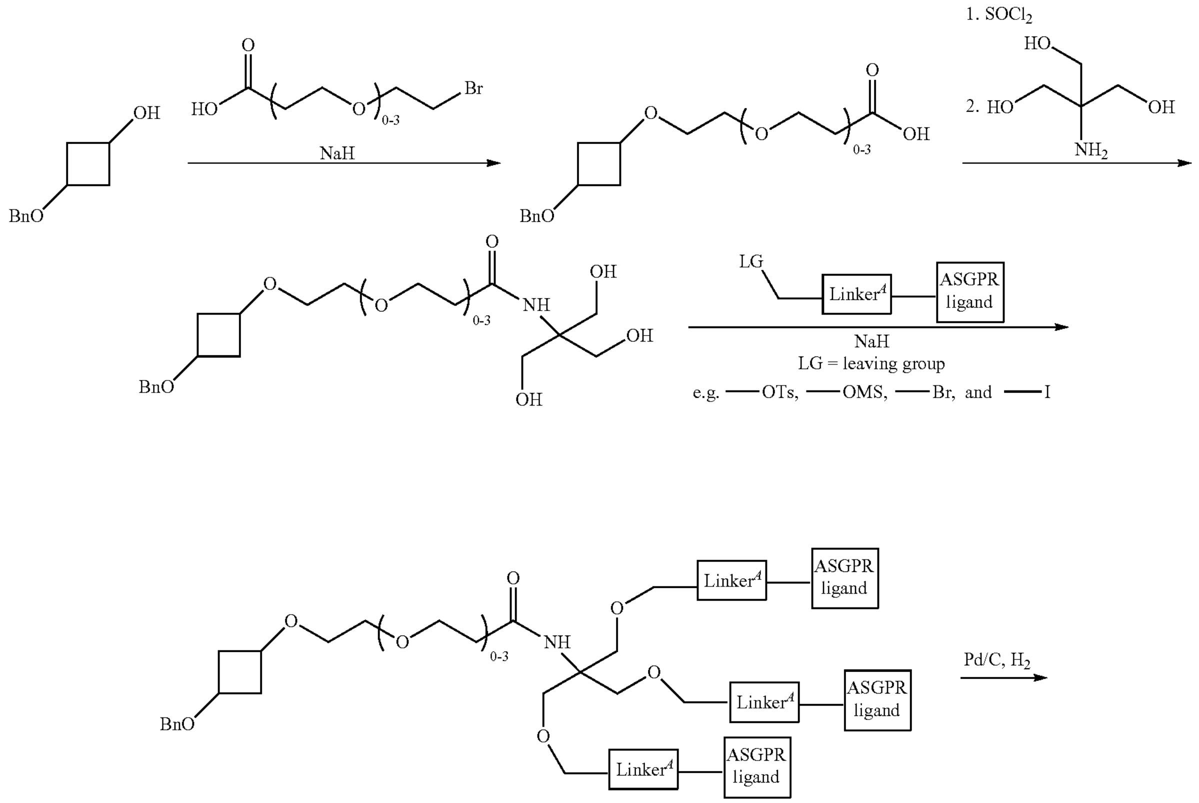

-continued
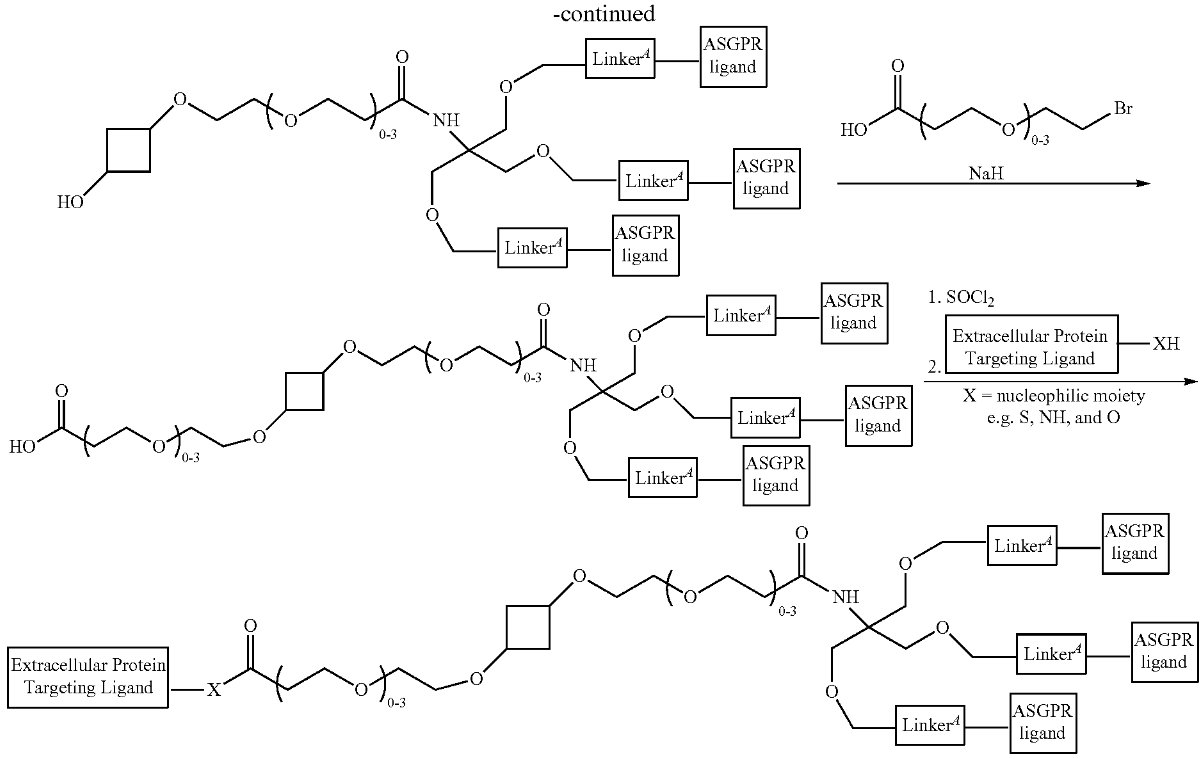
Alternatively, for Linear Alkyl:
Linker$^C$:
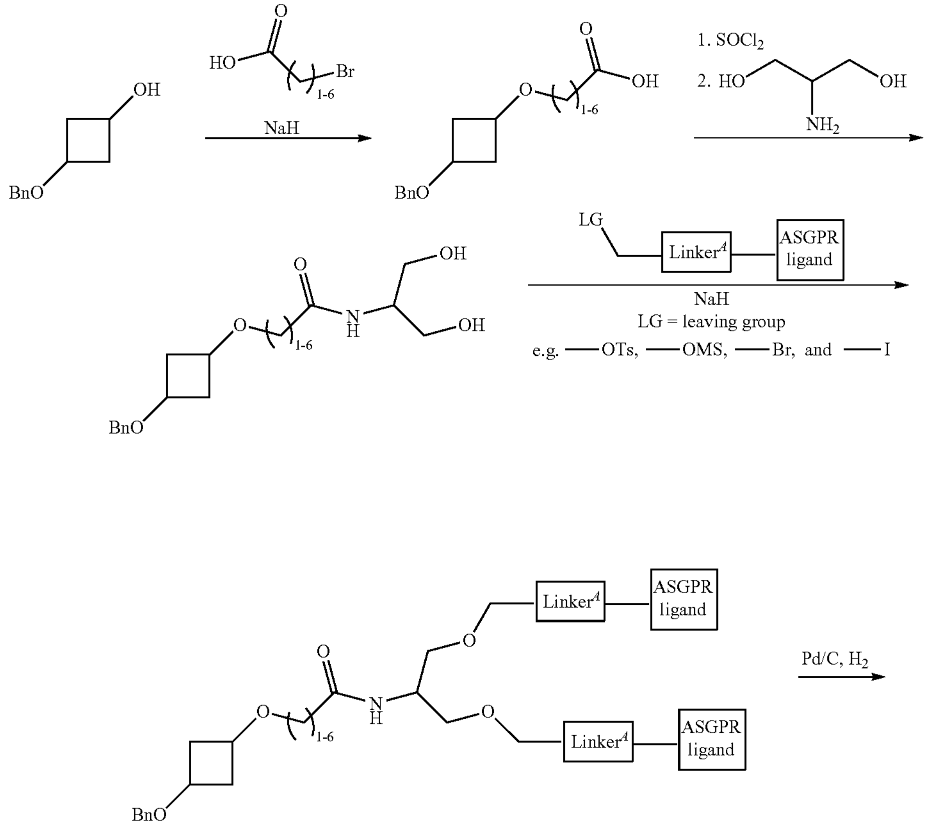

-continued
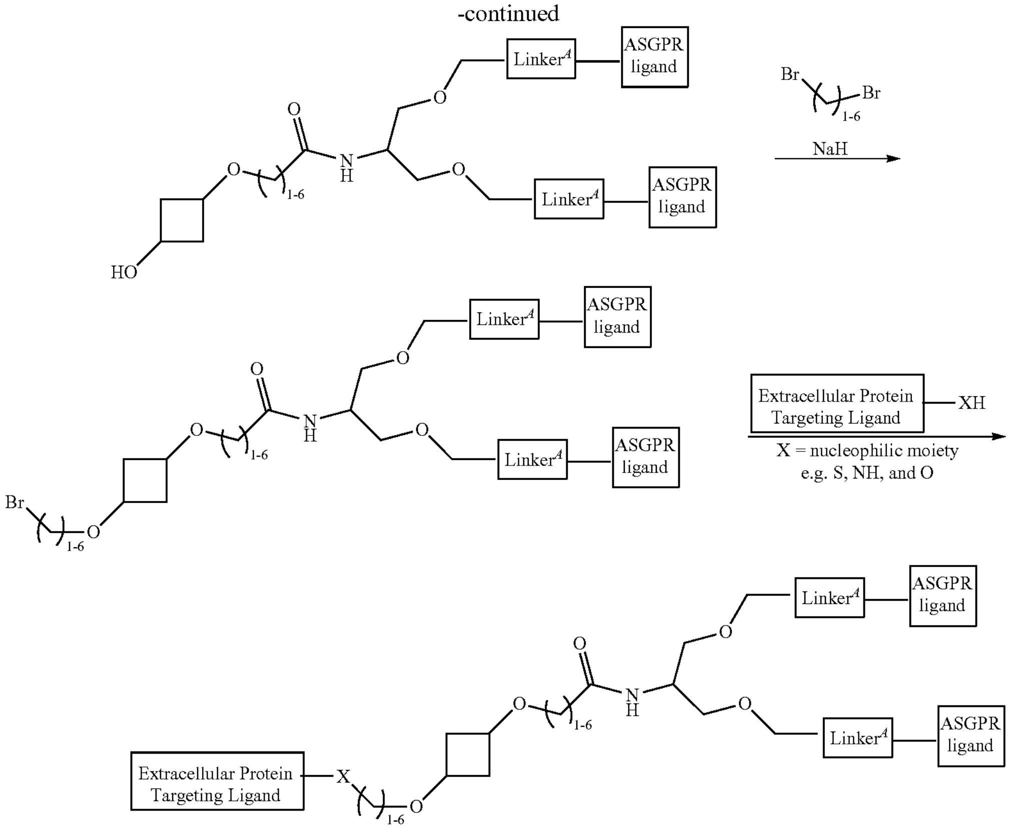
Linker$^D$
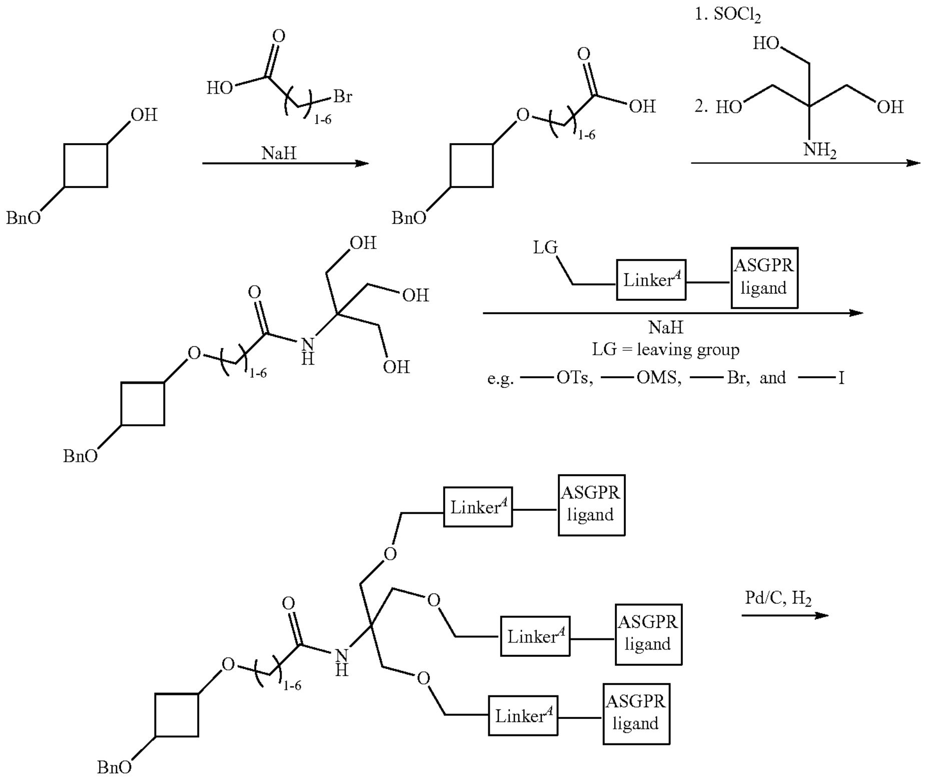

-continued
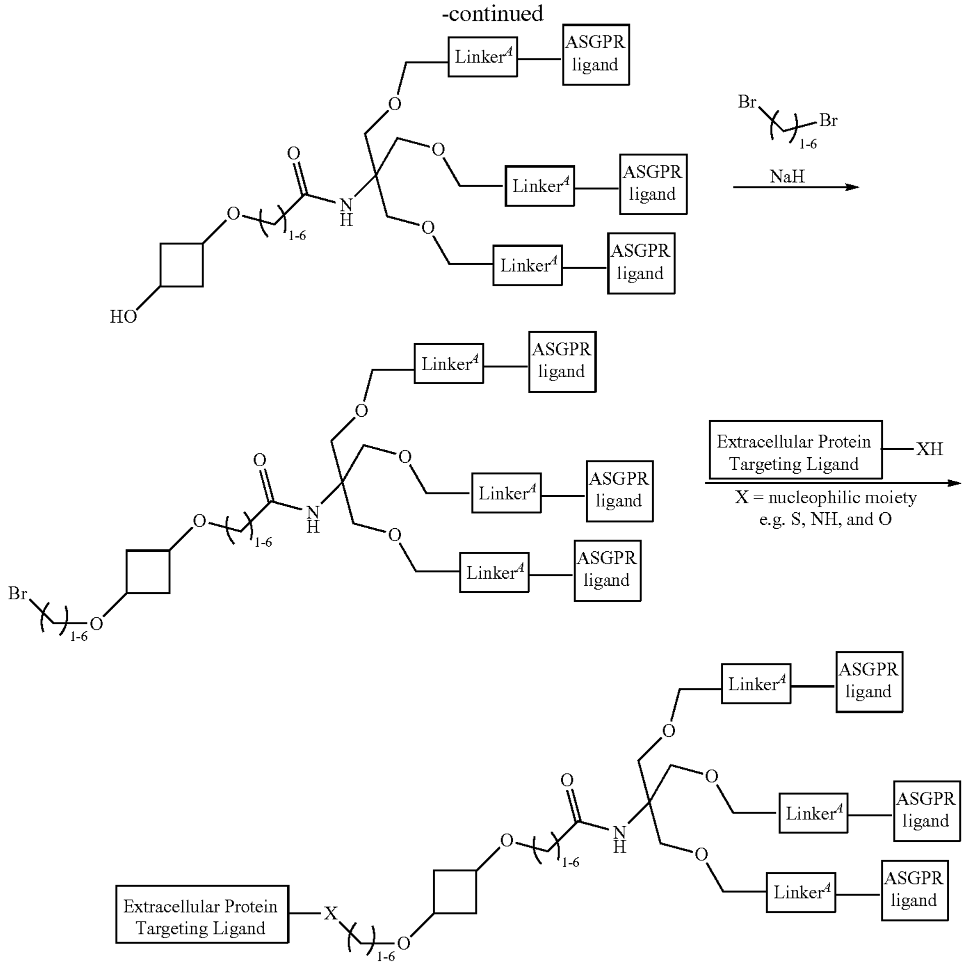
Alternatively, for Polyethylene Glycol:
Linker$^C$:
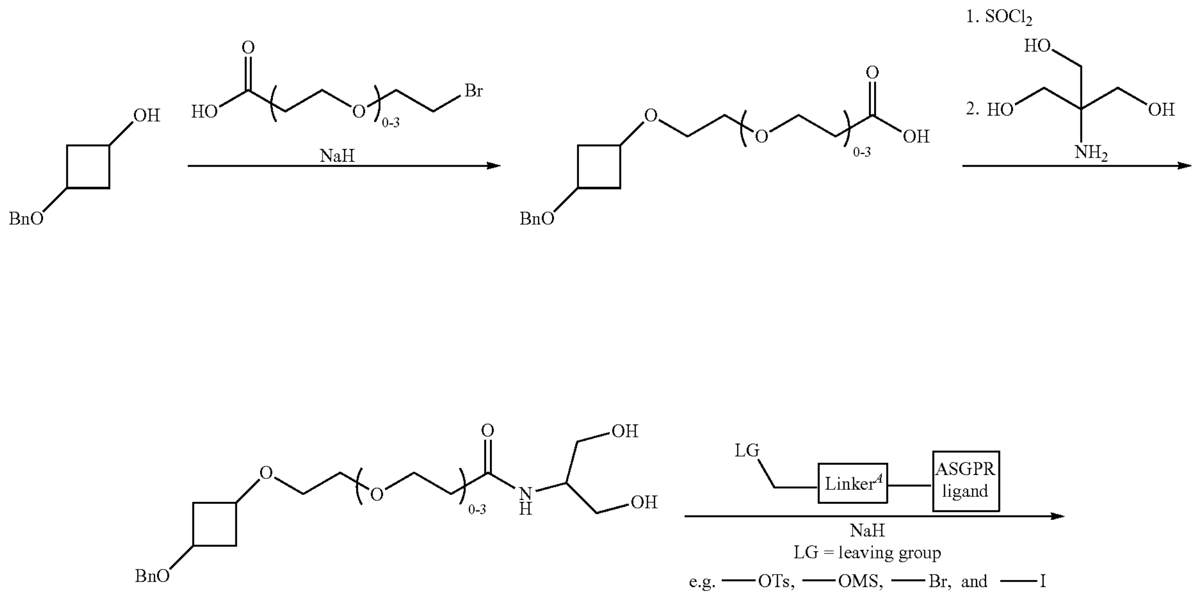

-continued
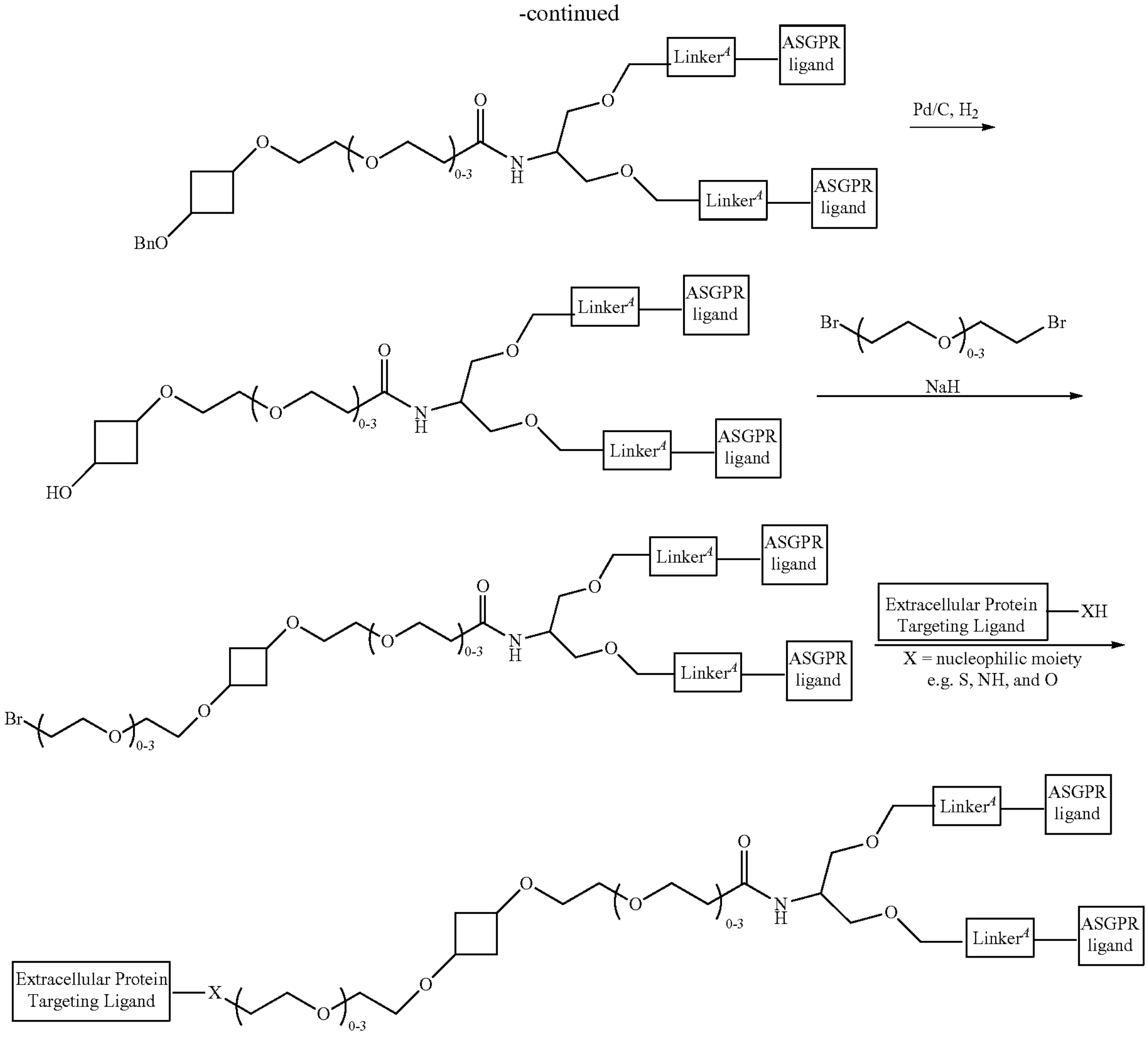
Linker$^D$:
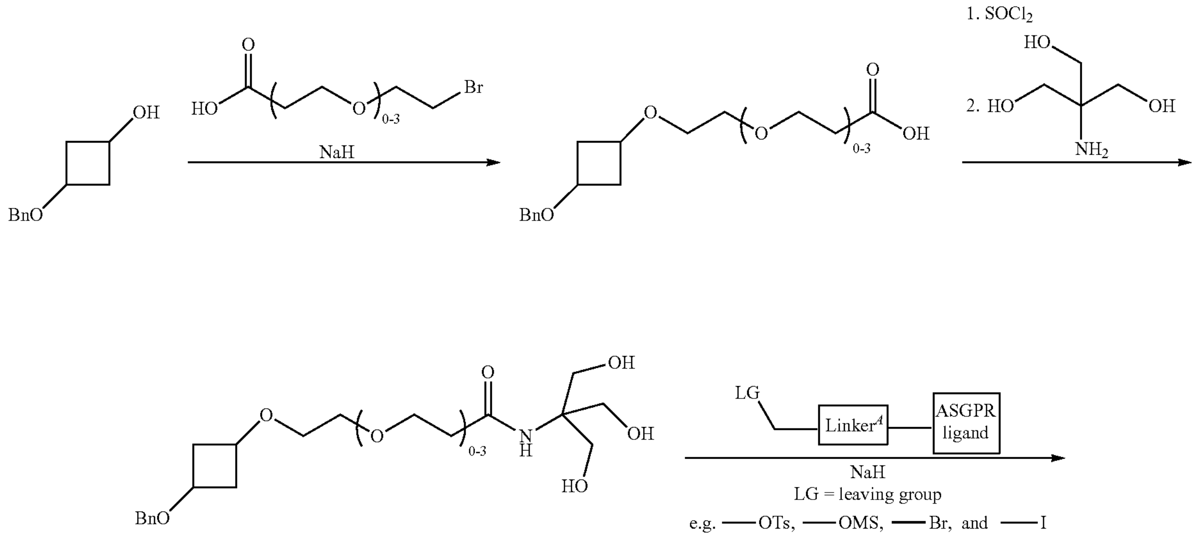

-continued

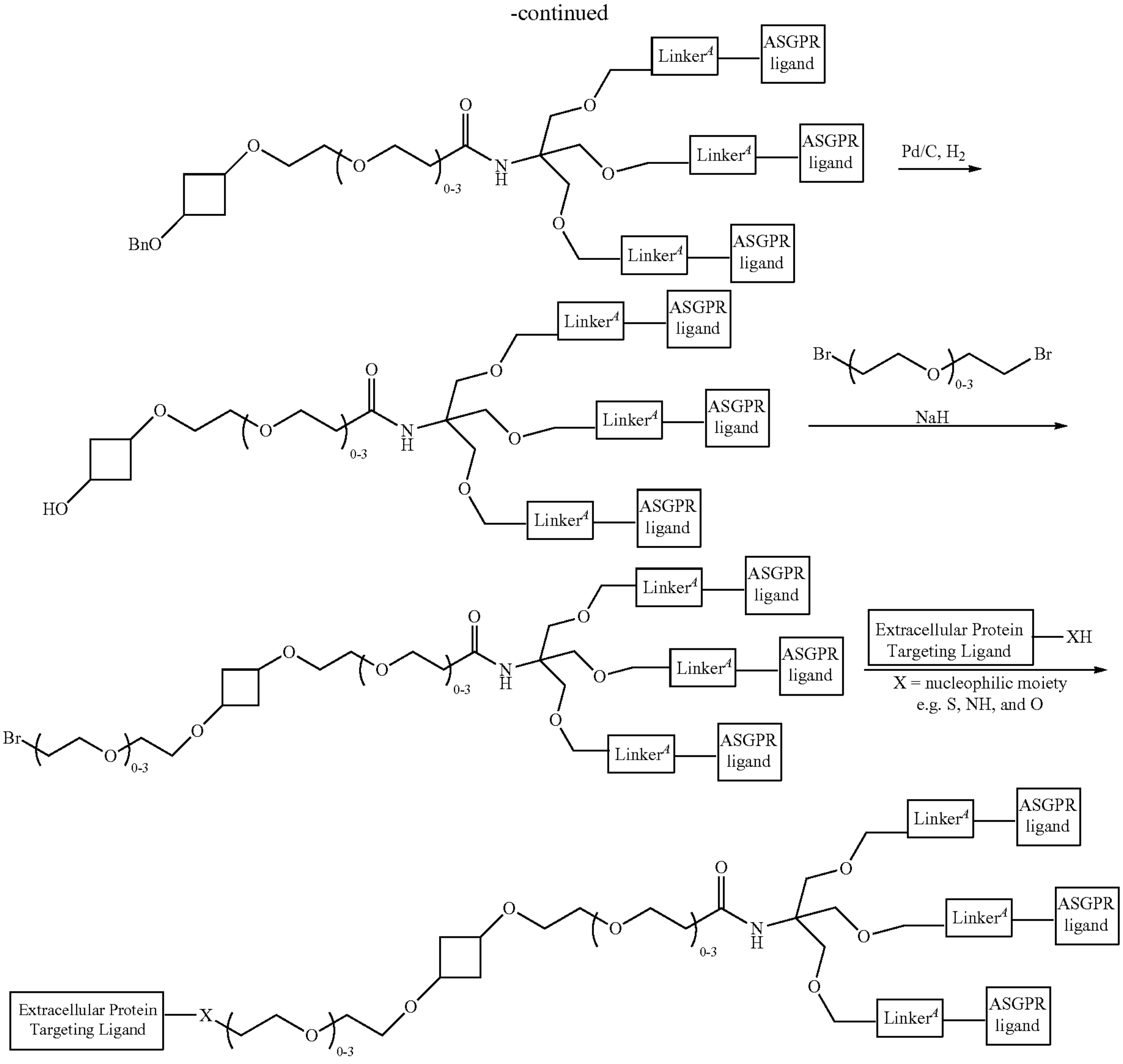

Example 8. Additional Synthetic Procedures

Preparation of (1S,2R,3R,4R,5S)-4-((3-chloro-1,2,4-thiadiazol-5-yl)amino)-1-(hydroxymethyl)-6,8-dioxabicyclo[3.2.1]octane-2,3-diol (Compound A287)

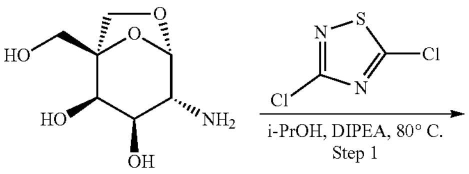

-continued

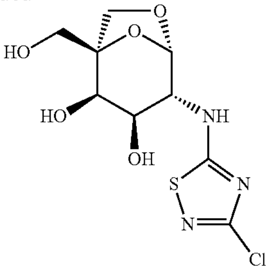

Step 1: A solution of (1S,2R,3R,4R,5S)-4-amino-1-(hydroxymethyl)-6,8-dioxabicyclo[3.2.1]octane-2,3-diol (50 mg, 0.26 mmol), 3,5-dichloro-1,2,4-thiadiazole (121 mg, 0.78 mmol) and DIPEA (169 mg, 1.3 mmol) in i-PrOH (1 mL) was stirred at 80° C. overnight. The mixture was concentrated and the residue was purified by prep to give (1S,2R,3R,4R,5S)-4-((3-chloro-1,2,4-thiadiazol-5-yl)amino)-1-(hydroxymethyl)-6,8-dioxabicyclo[3.2.1]octane-2,3-diol (A287, 60 mg, 74% yield) as a yellow solid. LC-MS (ESI) found: 310 $[M+H]^+$. $^1H$ NMR (400 MHz, MeOD): δ

5.38 (d, J=0.9 Hz, 1H), 3.97-3.86 (m, 3H), 3.83 (d, J=11.4 Hz, 1H), 3.80-3.75 (m, 2H), 3.71 (d, J=8.0 Hz, 1H).

The following compounds below were prepared according to the same procedure as A287:

| ID | Characterization data | Starting Material |
| --- | --- | --- |
| 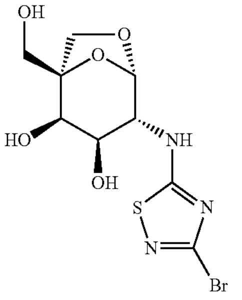 A288 | Yield: 3.5 mg, 3.2%, white solid. LC-MS (ESI) found: 354 $[M + H]^+$. $^1H$ NMR (400 MHz, MeOD): δ 5.38 (s, 1H), 3.91 (dd, J = 12.5, 7.7 Hz, 3H), 3.83 (d, J = 11.4 Hz, 1H), 3.80-3.75 (m, 2H), 3.71 (d, J = 8.0 Hz, 1H). | 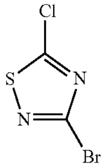 |
| 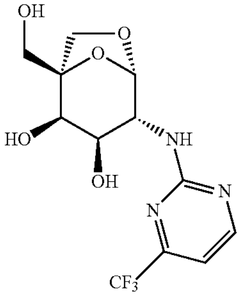 A289 | Yield: 21 mg, 48%, white solid. LC-MS (ESI) found: 338 $[M + H]^+$. $^1H$ NMR (400 MHz, MeOD): δ 8.52 (d, J = 4.9 Hz, 1H), 6.90 (dd, J = 14.0, 5.8 Hz, 1H), 5.39 (t, J = 14.0 Hz, 1H), 4.20 (d, J = 9.7 Hz, 1H), 3.96-3.78 (m, 5H), 3.71 (d, J = 7.9 Hz, 1H). | 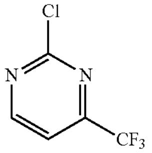 |
| 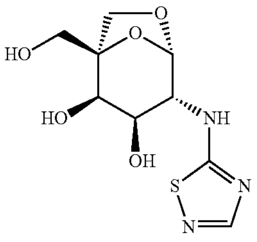 A290 | Yield: 6 mg, 20%, white solid. LC-MS (ESI) found: 276 $[M + H]^+$, $^1H$ NMR (400 MHz, MeOD): δ 7.85 (s, 1H), 5.40 (d, J = 1.0 Hz, 1H), 3.92 (dd, J = 11.8, 7.8 Hz, 3H), 3.83-3.77 (m, 3H), 3.71 (d, J = 8.0 Hz, 1H). | 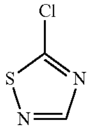 |
| 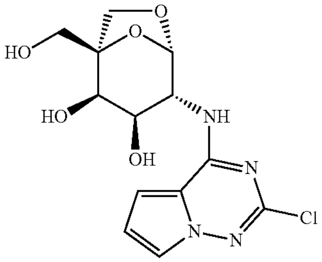 A291 | Yield: 20 mg, 22%, white solid. LC-MS (ESI) found: 343 $[M + H]^+$. $^1H$ NMR (400 MHz, MeOD): δ 7.48 (dd, J = 2.5, 1.5 Hz, 1H), 7.01 (dd, J = 4.5, 1.5 Hz, 1H), 6.62 (dd, J = 4.5, 2.6 Hz, 1H), 5.42 (d, J = 1.4 Hz, 1H), 4.50 (dd, J = 9.9, 1.1 Hz, 1H), 4.03 (dd, J = 9.9, 4.3 Hz, 1H), 3.96 (d, J = 7.5 Hz, 1H), 3.94 (s, 1H), 3.84 (dd, J = 9.6, 6.1 Hz, 2H), 3.74 (d, J = 7.9 Hz, 1H). | 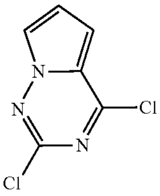 [SMILES: Clc1nc(Cl)c2cccn2n1] |
| 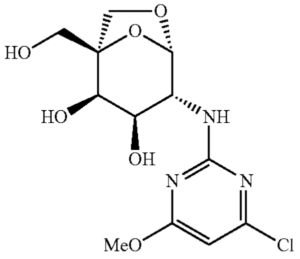 A292 | Yield: 16 mg, 25%, white solid. LC-MS (ESI) found: 334 $[M + H]^+$. $^1H$ NMR (400 MHz, MeOD): δ 6.06 (s, 1H), 5.39 (s, 1H), 4.15 (d, J = 9.2 Hz, 1H), 3.96-3.91 (m, 2H), 3.85-3.76 (m, 3H), 3.70 (d, J = 7.9 Hz, 1H), 3.35 (s, 3H). | 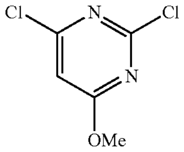 |

-continued

| ID | Characterization data | Starting Material |
|---|---|---|
| 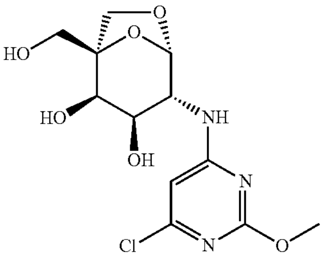 A293 | Yield: 2 mg, 6%, white solid. LC-MS (ESI) found: 334 $[M + H]^+$. $^1H$ NMR (400 MHz, MeOD): δ 6.23 (s, 1H), 5.35 (s, 1H), 4.30 (d, J = 9.9 Hz, 1H), 3.98-3.88 (m, 5H), 3.85-3.75 (m, 3H), 3.70 (d, J = 7.9 Hz, 1H). | 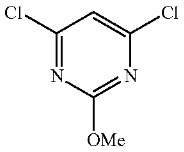 |

Preparation of 2-(((1S,2R,3R,4R,5S)-2,3-dihydroxy-1-(hydroxymethyl)-6,8-dioxabicyclo[3.2.1]octan-4-yl)amino)-6-methoxypyrimidine-4-carbonitrile (Compound A294)

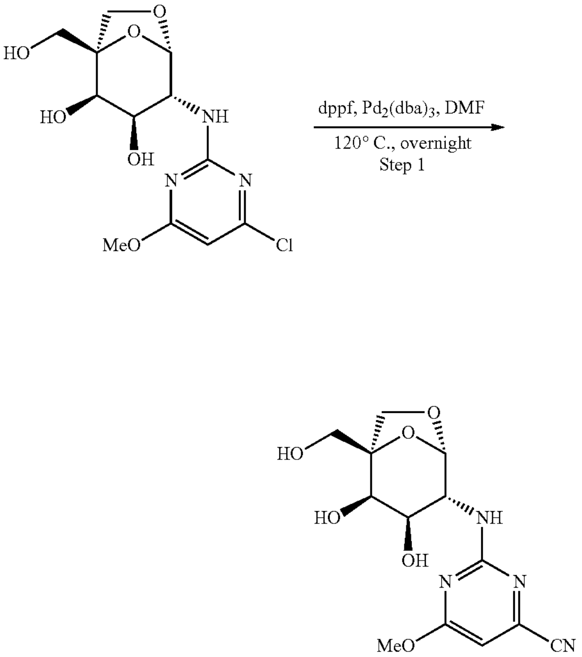

Step 1: To a solution of (1S,2R,3R,4R,5S)-4-((4-chloro-6-methoxypyrimidin-2-yl)amino)-1-(hydroxymethyl)-6,8-dioxabicyclo[3.2.1]octane-2,3-diol (A292, 30 mg, 0.09 mmol) in DMF (2 mL) was added dppf (14 mg, 0.024 mmol), $Pd_2(dba)_3$ (6 mg, 0.006 mmol) and $Zn(CN)_2$ (14 mg, 0.12 mmol) at rt. After the addition was complete, the mixture was stirred at 120° C. under $N_2$ atmosphere overnight. On consumption of starting material (LCMS monitoring), the mixture was filtered, concentrated, and purified by flash chromatography (silica gel, 0-10% MeOH in DCM) to give 2-(((1S,2R,3R,4R,5S)-2,3-dihydroxy-1-(hydroxymethyl)-6,8-dioxabicyclo[3.2.1]octan-4-yl)amino)-6-methoxypyrimidine-4-carbonitrile (2.7 mg, 9% yield) as white solid. LC-MS (ESI) found: 325 $[M+H]^+$. $^1H$ NMR (400 MHz, MeOD): δ 6.46 (s, 1H), 5.35 (s, 1H), 4.17 (d, J=8.6 Hz, 1H), 3.94 (d, J=11.3 Hz, 5H), 3.87-3.76 (m, 3H), 3.70 (d, J=7.9 Hz, 1H).

Reduced Galactose Series:

Preparation of (2R,3R,4R,5S)-2-(hydroxymethyl)-5-((4-(trifluoromethyl)pyrimidin-2-yl)amino)tetrahydro-2H-pyran-3,4-diol (Compound A295)

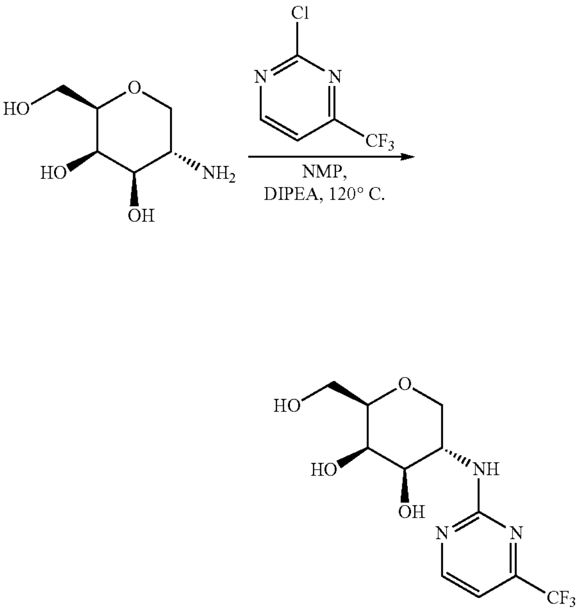

To a mixture of (2R,3R,4R,5S)-5-amino-2-(hydroxymethyl)tetrahydro-2H-pyran-3,4-diol hydrochloride (50 mg, 0.25 mmol) in NMP (2.0 mL) was added 2-chloro-4-(trifluoromethyl)pyrimidine (168 mg, 0.92 mmol) and TEA (124 mg, 1.2 mmol) at rt under $N_2$. After stirring at 120° C. overnight, the mixture was concentrated and purified by prep-TLC to give (2R,3R,4R,5S)-2-(hydroxymethyl)-5-((4-(trifluoromethyl)pyrimidin-2-yl)amino)tetrahydro-2H-pyran-3,4-diol (3 mg, 3.2% yield) as white solid. LC-MS (ESI) found: 310 $[M+H]^+$. $^1H$ NMR (400 MHz, $CD_3OD$): δ 8.51 (d, J=4.8 Hz, 1H), 6.89 (d, J=4.9 Hz, 1H), 4.36 (td, J=10.6, 5.3 Hz, 1H), 4.11 (dd, J=10.9, 5.2 Hz, 1H), 3.91 (d, J=2.6 Hz, 1H), 3.78-3.65 (m, 3H), 3.45 (ddd, J=6.9, 5.0, 1.0 Hz, 1H), 3.16 (t, J=10.9 Hz, 1H).

The following compounds below were made using the method described for A295:

| ID | Characterization data | Starting material |
|---|---|---|
| 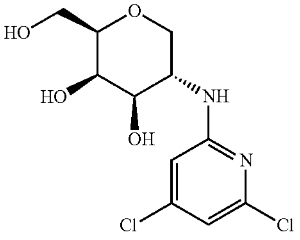 A296 | Yield: 2.3 mg, 5%, white solid. LC-MS (ESI) found: 309 $[M + H]^+$. $^1H$ NMR (400 MHz, MeOD): δ 6.56 (d, J = 1.4 Hz, 1H), 6.48 (d, J = 1.4 Hz, 1H), 4.23 (td, J = 10.5, 5.2 Hz, 1H), 4.08 (dd, J = 11.0, 5.2 Hz, 1H), 3.89 (d, J = 2.8 Hz, 1H), 3.71 (dt, J = 11.4, 5.3 Hz, 2H), 3.55 (dd, J = 10.5, 3.2 Hz, 1H), 3.46-3.42 (m, 1H), 3.08 (t, J = 10.8 Hz, 1H). | 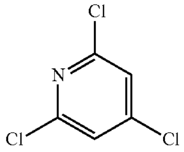 |
| 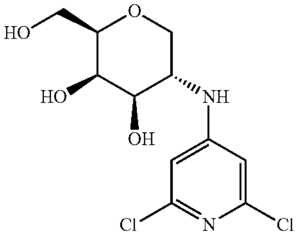 A297 | Yield: 1.4 mg, 3%, white solid LC-MS (ESI) found: 309 $[M + H]^+$. $^1H$ NMR (400 MHz, MeOD): δ 6.62 (s, 2H), 3.95 (dd, J= 11.3, 5.1 Hz, 1H), 3.89 (d, J = 2.9 Hz, 1H), 3.85-3.77 (m, 1H), 3.77-3.66 (m, 2H), 3.51 (dd, J = 10.0, 3.2 Hz, 1H), 3.44-3.40 (m, 1H), 3.10 (t, J = 11.0 Hz, 1H). | 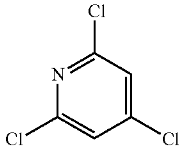 |
| 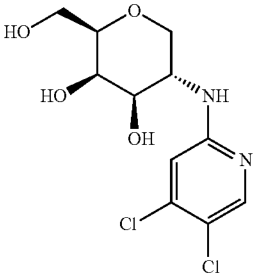 A298 | Yield: 2.7 mg, 5%, white solid. LC-MS (ESI) found: 309 $[M + H]^+$. $^1H$ NMR (400 MHz, MeOD): δ 7.93 (s, 1H), 6.90 (s, 1H), 3.99-3.91 (m, 3H), 3.76-3.68 (m, 3H), 3.48-3.45 (m, 1H), 3.28-3.23 (m, 1H). | 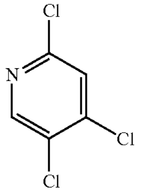 |
| 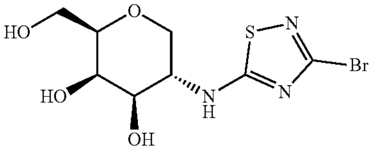 A299 | Yield: 65 mg, 66%, oil. LC-MS (ESI) found: 326 $[M + H]^+$. $^1H$ NMR (400 MHz, $D_2O$): δ 4.10-4.02 (m, 1H), 3.92 (d, J = 1.4 Hz, 1H), 3.80-3.59 (m, 4H), 3.57-3.50 (m, 1H), 3.23 (t, J = 11.0 Hz, 1H). | 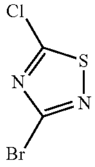 |
| 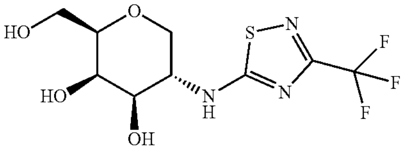 A300 | Yield: 15.3 mg, 32%, white solid. LC-MS (ESI) found: 316 $[M + H]^+$. $^1H$ NMR (400 MHz, MeOD): δ 4.15 (dd, J = 11.0, 5.1 Hz, 1H), 4.02 (s, 1H), 3.90 (d, J = 2.5 Hz, 1H), 3.71 (ddd, J = 1H 16.4, 11.4, 6.0 Hz, 2H), 3.61 (dd, J = 10.3, 3.2 Hz, 1H), 3.47-3.41 (m, 1H), 3.20 (t, J = 10.9 | 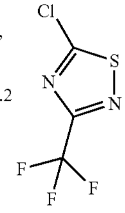 |
| 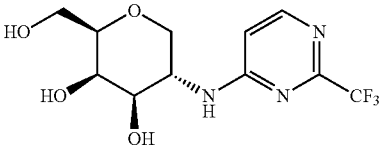 A301 | Yield: 6.7 mg, 7%, orange solid. LC-MS (ESI) found: 310 $[M + H]^+$. $^1H$ NMR (400 MHz, MeOD): δ 8.00 (s, 1H), 6.55 (s, 1H), 4.38 (s, 1H), 4.02 (s, 1H), 3.82 (d, J = 2.7 Hz, 1H), 3.63 (ddd, J = 16.4, 11.4, 6.0 Hz, 2H), 3.54 (dd, J = 10.5, 3.0 Hz, 1H), 3.38-3.33 (m, 1H), 3.03 (t, J = 9.8 Hz, 1H). | 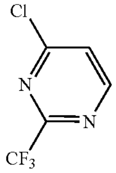 [SMILES: FC(F)(F)c1nccc(Cl)n1] |

-continued

| ID | Characterization data | Starting material |
|---|---|---|
| 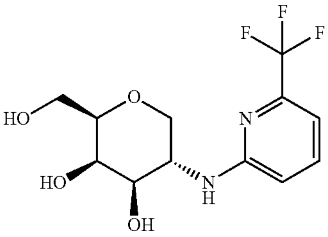 A302 | Yield: 2.9 mg, 3.4%, solid. LC/MS ESI(m/z): 309 [M + H]$^+$. $^1$H NMR (400 MHz, MeOD) δ 7.52 (t, J = 7.9 Hz, 1H), 6.88 (d, J = 7.2 Hz, 1H), 6.72 (d, J = 8.5 Hz, 1H), 4.29 (td, J = 10.5, 5.2 Hz, 1H), 4.18 (dd, J = 10.9, 5.2 Hz, 1H), 3.90 (d, J = 2.9 Hz, 1H), 3.72 (ddd, J = 16.3, 11.4, 6.0 Hz, 2H), 3.60 (dd, J = 10.4, 3.2 Hz, 1H), 3.49-3.42 (m, 1H), 3.11 (t, J = 10.7 Hz, 1H). | 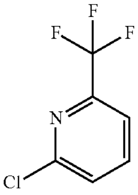 [SMILES: FC(F)(F)c1cccc(Cl)n1] |
| 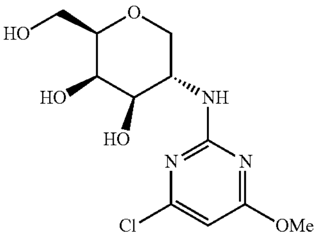 A303 | Yield: 8.9 mg, 30%, white solid. LC/MS ESI(m/z): 306 [M + H]$^+$. $^1$H NMR (400 MHz, MeOD): δ 6.04 (s, 1H), 4.31 (td, J = 10.6, 5.2 Hz, 1H), 4.11 (dd, J = 10.9, 5.1 Hz, 1H), 3.90 (d, J = 2.9 Hz, 4H), 3.73 (d, J = 7.0 Hz, 1H), 3.68 (dd, J = 11.4, 5.0 Hz, 1H), 3.61 (dd, J = 10.5, 2.7 Hz, 1H), 3.46-3.41 (m, 1H), 3.13 (t, J = 10.8 Hz, 1H). | 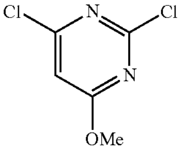 |
| 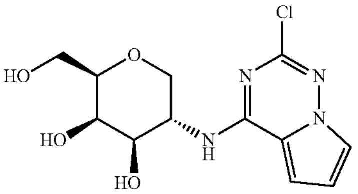 A304 | Yield: 5 mg, 5%, solid. LC/MS ESI(m/z): 315 [M + H]$^+$. $^1$H NMR (400 MHz, MeOD): δ 7.47 (dd, J = 2.6, 1.5 Hz, 1H), 6.90 (dd, J = 4.4, 1.4 Hz, 1H), 6.61 (dd, J = 4.4, 2.6 Hz, 1H), 4.69 (td, J = 10.8, 5.3 Hz, 1H), 4.11 (dd, J = 11.0, 5.3 Hz, 1H), 3.93 (d, J = 2.8 Hz, 1H), 3.79-3.68 (m, 3H), 3.47 (ddd, J = 6.8, 5.0, 0.9 Hz, 1H), 3.24 (t, J = 10.9 Hz, 1H). | 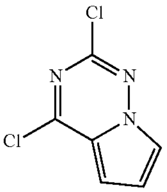 [SMILES: Clc1nc(Cl)c2cccn2n1] |
| 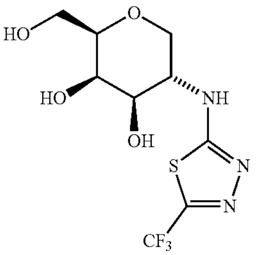 305 | Yield: 6.0 mg, 7%, a white solid. LC-MS (ESI) found: 316 [M + H]$^+$. $^1$H NMR (400 MHz, MeOD) δ 4.20 (dd, J = 11.0, 5.2 Hz, 1H), 4.07 (td, J = 10.5, 5.2 Hz, 1H), 3.90 (d, J = 2.9 Hz, 1H), 3.75 (dd, J = 11.4, 7.1 Hz, 1H), 3.68 (dd, J = 11.4, 5.0 Hz, 1H), 3.61 (dd, J = 10.3, 3.1 Hz, 1H), 3.47-3.43 (m, 1H), 3.20 (t, J = 10.9 Hz, 1H). | 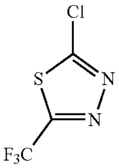 |
| 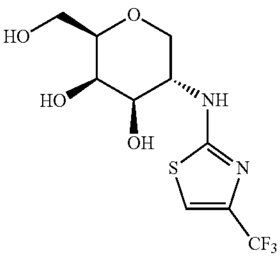 A306 | Yield: 62.8 mg, 68%, oil. LC-MS (ESI) found: 315 [M + H]$^+$. $^1$H NMR (400 MHz, MeOD): δ 7.08 (s, 1H), 4.16 (dd, J = 11.0, 5.2 Hz, 1H), 4.04 (m, 1H), 3.89 (d, J = 2.9 Hz, 1H), 3.74 (dd, J = 11.4, 7.0 Hz, 1H), 3.67 (dd, J = 11.3, 4.9 Hz, 1H), 3.57 (dd, J = 10.8, 3.6 Hz, 1H), 3.46-3.40 (m, 1H), 3.14 (t, J = 10.8 Hz, 1H). | 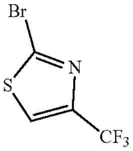 |

-continued

| ID | Characterization data | Starting material |
|---|---|---|
| 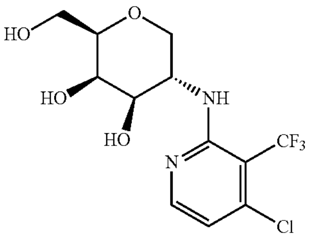<br>A307 | Yield: 3.8 mg, 11%, white solid. LC-MS (ESI) found: 343 [M + H]$^+$. $^1$H NMR (400 MHz, MeOD): δ 7.98 (d, J = 6.2 Hz, 1H), 6.98 (d, J = 6.2 Hz, 1H), 4.07-3.98 (m, 2H), 3.91 (dd, J = 3.1, 0.8 Hz, 1H), 3.78-3.65 (m, 3H), 3.50-3.44 (m, 1H), 3.23 (s, 1H). | 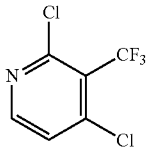 [SMILES: FC(F)(F)c1c(Cl)ccnc1Cl] |
| 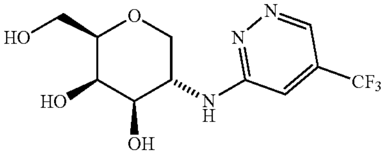<br>A308 | Yield: 5.3 mg, 6.9%, white solid. LC-MS (ESI) found: 310 [M + H]$^+$. $^1$H NMR (400 MHz, MeOD): δ 8.10 (s, 1H), 8.02 (s, 1H), 4.34 (td, J = 10.6, 5.1 Hz, 1H), 4.09 (dd, J = 11.0, 5.2 Hz, 1H), 3.91 (d, J = 2.9 Hz, 1H), 3.76 (dd, J = 11.4, 7.1 Hz, 1H), 3.69 (dd, J = 11.4, 5.0 Hz, 1H), 3.61 (dd, J = 10.5, 3.2 Hz, 1H), 3.50-3.40 (m, 1H), 3.11 (t, J = 10.9 Hz, 1H). | 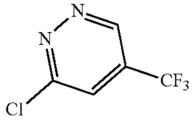 [SMILES: FC(F)(F)c1cnnc(Cl)c1] |
| 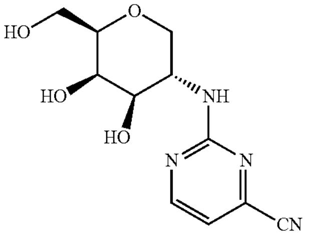<br>A309 | Yield: 8.1 mg, 31%, yellow solid. LC-MS (ESI) found: 267 [M + H]$^+$. $^1$H NMR (400 MHz, MeOD): δ 8.46 (t, J = 7.1 Hz, 1H), 6.94 (d, J = 4.7 Hz, 1H), 4.44-4.18 (m, 1H), 4.06 (dd, J = 11.0, 5.2 Hz, 1H), 3.91 (d, J = 3.0 Hz, 1H), 3.79-3.73 (m, 1H), 3.72-3.68 (m, 1H), 3.65 (dd, J = 10.5, 3.2 Hz, 1H), 3.48-3.43 (m, 1H), 3.16 (t, J = 10.9 Hz, 1H). | 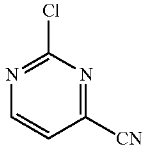 |
| 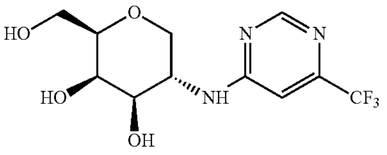<br>A310 | Yield: 50 mg, 65%, white solid. LC-MS(ESI) found 310 [M + H]$^+$. $^1$H NMR (400 MHz, MeOD): δ 8.50 (s, 1H), 6.84 (s, 1H), 4.53 (s, 1H), 4.10 (s, 1H), 3.91 (d, J = 2.7 Hz, 1H), 3.76 (dd, J = 11.4, 7.0 Hz, 1H), 3.69 (dd, J = 11.4, 5.0 Hz, 1H), 3.62 (dd, J = 10.5, 3.2 Hz, 1H), 3.47-3.43 (m, 1H), 3.14 (d, J = 10.7 Hz, 1H). | 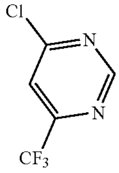 [SMILES: FC(F)(F)c1cc(Cl)ncn1] |
| 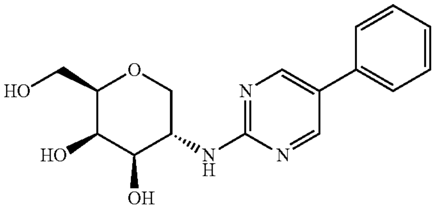<br>A311 | Yield: 2.1 mg, 1%, white solid. LC-MS (ESI) found: 318 [M + H]$^+$. $^1$H NMR (400 MHz, $CD_3OD$): δ 8.29 (d, J = 5.3 Hz, 1H), 8.20-8.05 (m, 2H), 7.47 (dd, J = 5.1, 1.9 Hz, 3H), 7.13 (d, J = 5.3 Hz, 1H), 4.44 (s, 1H), 4.23 (dd, J = 11.0, 5.2 Hz, 1H), 3.93 (d, J = 2.7 Hz, 1H), 3.82-3.66 (m, 3H), 3.52-3.45 (m, 1H), 3.20 (t, J = 10.8 Hz, 1H). | 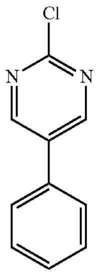 [SMILES: Clc1ncc(-c2ccccc2)cn1] |
| 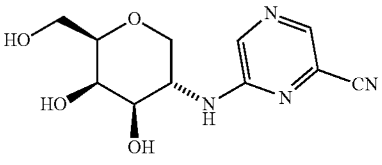<br>A312 | Yield: 3.3 mg, 5.1%, white solid. LC-MS (ESI) found: 267 [M + H]$^+$. $^1$H NMR (400 MHz, MeOD): δ 8.10 (s, 1H), 8.02 (s, 1H), 4.34 (td, J = 10.6, 5.1 Hz, 1H), 4.09 (dd, J = 11.0, 5.2 Hz, 1H), 3.91 (d, J = 2.9 Hz, 1H), 3.76 (dd, J = 11.4, 7.1 Hz, 1H), 3.69 (dd, J = 11.4, 5.0 Hz, 1H), 3.61 (dd, J = 10.5, 3.2 Hz, 1H), 3.50-3.40 (m, 1H), 3.11 (t, J = 10.9 Hz, 1H). | 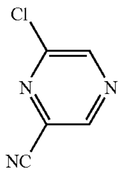 |

-continued

| ID | Characterization data | Starting material |
|---|---|---|
| 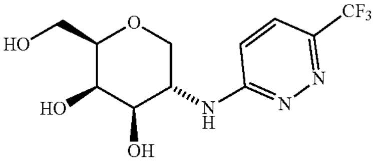 A313 | Yield: 8.7 mg, 11%, white solid. LC-MS (ESI) found: 310 $[M+H]^+$. $^1H$ NMR (400 MHz, MeOD): δ 7.58 (d, J = 9.4 Hz, 1H), 7.02 (d, J = 9.4 Hz, 1H), 4.44 (d, J = 4.4 Hz, 1H), 4.18 (dd, J = 11.0, 5.2 Hz, 1H), 3.92 (d, J = 2.8 Hz, 1H), 3.77 (dd, J = 11.4, 7.1 Hz, 1H), 3.70 (dd, J = 11.4, 5.0 Hz, 1H), 3.66 (dd, J = 10.4, 3.2 Hz, 1H), 3.51-3.44 (m, 1H), 3.18 (t, J = 10.9 Hz, 1H). | 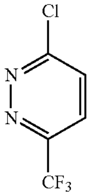 |
| 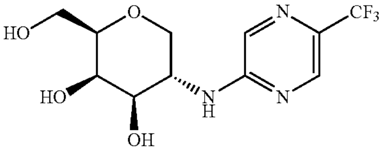 A314 | Yield: 9.1 mg, 12.8%, white solid. LC-MS (ESI) found: 310 $[M+H]^+$. $^1H$ NMR (400 MHz, MeOD): δ 8.27 (s, 1H), 7.94 (d, J = 1.0 Hz, 1H), 4.40 (td, J = 10.6, 5.1 Hz, 1H), 4.10 (dd, J = 11.0, 5.2 Hz, 1H), 3.91 (d, J = 2.8 Hz, 1H), 3.72 (ddd, J = 16.3, 11.4, 6.0 Hz, 2H), 3.63 (dd, J = 10.5, 3.2 Hz, 1H), 3.51-3.40 (m, 1H), 3.14 (t, J = 10.9 Hz, 1H). | 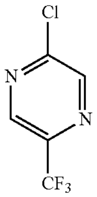 [SMILES: FC(F)(F)c1cnc(Cl)cn1] |
| 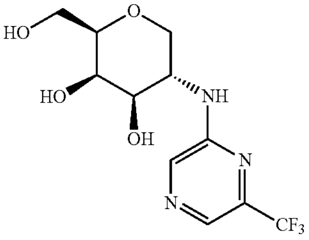 A315 | Yield: 10.1 mg, 13%, white solid. LC-MS (ESI) found: 310 $[M+H]^+$. $^1H$ NMR (400 MHz, MeOD): δ 8.11 (s, 1H), 7.99 (s, 1H), 4.34 (td, J = 10.5, 5.2 Hz, 1H), 4.14 (dd, J = 11.0, 5.2 Hz, 1H), 3.92 (d, J = 3.1 Hz, 1H), 3.76 (dd, J = 11.4, 7.1 Hz, 1H), 3.71-3.62 (m, 2H), 3.49-3.44 (m, 1H), 3.12 (t, J = 10.8 Hz, 1H). | 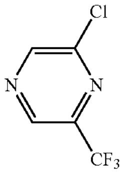 [SMILES: FC(F)(F)c1cncc(Cl)n1] |
| 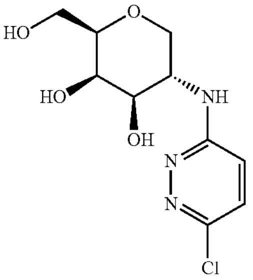 A316 | Yield: 10 mg, 38%, yellow solid. LC-MS (ESI) found: 276$[M+H]^+$ $^1H$ NMR (400 MHz, MeOD): δ 7.57 (d, J = 9.3 Hz, 1H), 7.15 (d, J = 9.3 Hz, 1H), 4.41 (ddd, J = 19.4, 11.3, 5.9 Hz, 2H), 3.97-3.72 (m, 3H), 3.39 (dd, J = 10.1, 3.3 Hz, 1H), 3.15-3.05 (m, 1H), 2.97 (td, J = 10.6, 5.1 Hz, 1H) | 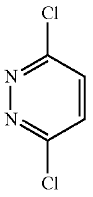 |
| 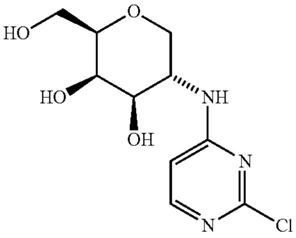 A317 | Yield: 4.1 mg, 6%, white solid. LC-MS (ESI) found: 276 $[M+H]^+$. $^1H$ NMR (400 MHz, MeOD): δ 7.85 (d, J = 2.3 Hz, 1H), 6.43 (d, J = 3.5 Hz, 1H), 4.44 (dd, J = 16.4, 9.5 Hz, 1H), 4.07 (dd, J = 6.9, 3.8 Hz, 1H), 3.90 (d, J = 2.8 Hz, 1H), 3.75 (dd, J = 11.4, 7.1 Hz, 1H), 3.68 (dd, J = 11.4, 5.0 Hz, 1H), 3.58 (dd, J = 10.5, 3.2 Hz, 1H), 3.46-3.39 (m, 1H), 3.10 (t, J = 10.6 Hz, 1H). | 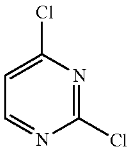 |
| 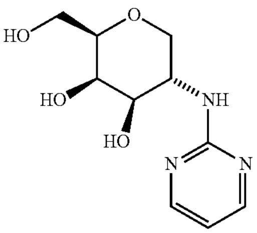 A318 | Yield: 9.8 mg, 16%, white solid. LC-MS (ESI) found: 242 $[M+H]^+$. $^1H$ NMR (400 MHz, MeOD): δ 8.26 (d, J = 4.7 Hz, 2H), 6.61 (t, J = 4.8 Hz, 1H), 4.30 (td, J = 10.6, 5.2 Hz, 1H), 4.11 (dd, J = 11.0, 5.2 Hz, 1H), 3.90 (d, J = 2.7 Hz, 1H), 3.76 (dd, J = 11.4, 7.0 Hz, 1H), 3.69 (dd, J = 11.4, 5.0 Hz, 1H), 3.63 (dd, J = 10.5, 3.2 Hz, 1H), 3.45 (dd, J = 6.5, 5.4 Hz, 1H), 3.15 (t, J = 10.8 Hz, 1H). | 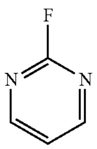 |

-continued

| ID | Characterization data | Starting material |
|---|---|---|
| 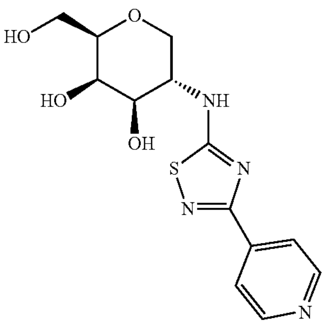 A319 | Yield: 0.7 mg, 2.4%, white solid. LC-MS (ESI) found: 325 $[M + H]^+$. $^1H$ NMR (400 MHz, MeOD): δ 8.62 (d, J = 6.1 Hz, 2H), 8.11 (d, J = 6.2 Hz, 2H), 4.23 (dd, J = 11.0, 5.2 Hz, 1H), 4.16-4.06 (m, 1H), 3.92 (d, J = 3.0 Hz, 1H), 3.77 (dd, J = 11.4, 7.0 Hz, 1H), 3.70 (dd, J = 11.4, 5.1 Hz, 1H), 3.65 (dd, J = 10.3, 3.1 Hz, 1H), 3.51-3.44 (m, 1H), 3.23 (t, J = 10.9 Hz, 1H). | |
| 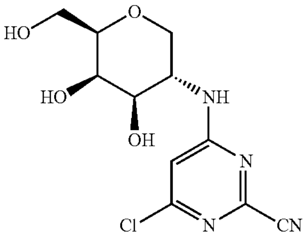 A320 | Yield: 3.1 mg, 4.1%, white solid. LC-MS (ESI) found: 301 $[M + H]^+$. $^1H$ NMR (400 MHz, MeOD): δ 6.67 (s, 1H), 4.45 (dd, J = 10.5, 5.1 Hz, 1H), 4.05 (dd, J = 11.0, 5.1 Hz, 1H), 3.90 (d, J = 2.9 Hz, 2H), 3.75 (dd, J = 11.4, 7.1 Hz, 1H), 3.68 (dd, J = 11.4, 5.0 Hz, 1H), 3.58 (dd, J = 10.5, 3.2 Hz, 1H), 3.48-3.40 (m, 1H), 3.11 (t, J = 10.9 Hz, 1H). | 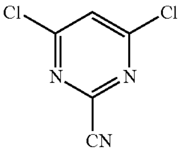 |
| 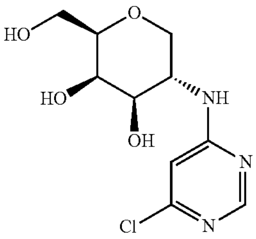 A321 | Yield: 19.1 mg, 28%, white solid. LC-MS (ESI) found: 276 $[M + H]^+$. $^1H$ NMR (400 MHz, MeOD): δ 8.22 (s, 1H), 6.55 (s, 1H), 4.44 (dd, J = 12.1, 4.9 Hz, 1H), 4.05 (dd, J = 6.1, 2.4 Hz, 1H), 3.90 (d, J = 3.1 Hz, 1H), 3.75 (dd, J = 11.4, 7.0 Hz, 1H), 3.68 (dd, J = 11.4, 5.0 Hz, 1H), 3.58 (dd, J = 10.4, 3.0 Hz, 1H), 3.44 (dd, J = 6.5, 5.5 Hz, 1H), 3.12 (t, J = 10.0 Hz, 1H). | 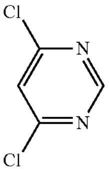 |
| 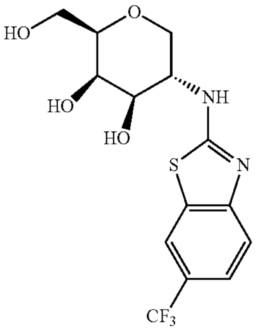 A322 | Yield: 3.7 mg, 9%, white solid. LC-MS (ESI) found: 365$[M + H]^+$. $^1H$ NMR (400 MHz, MeOD): δ 7.92 (s, 1H), 7.51 (s, 2H), 4.23 (ddd, J = 15.7, 11.7, 5.3 Hz, 2H), 3.92 (d, J = 2.5 Hz, 1H), 3.73 (ddd, J = 16.3, 11.4, 6.0 Hz, 2H), 3.62 (dd, J = 10.1, 3.2 Hz, 1H), 3.46 (ddd, J = 7.1, 5.3, 3.8 Hz, 1H), 3.24-3.15 (m, 1H). | 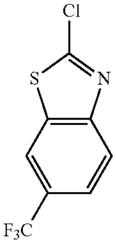 [SMILES: FC(F)(F)c1ccc2nc(Cl)sc2c1] |
| 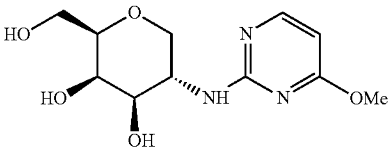 A323 | Yield: 8.3 mg, 20%, white solid. LC-MS (ESI) found: 272 $[M + H]^+$. $^1H$ NMR (400 MHz, MeOD): δ 7.93 (d, J = 5.9 Hz, 1H), 6.06 (d, J = 5.9 Hz, 1H), 4.29 (td, J = 10.5, 5.1 Hz, 1H), 4.14 (dd, J = 10.9, 5.2 Hz, 1H), 3.91 (s, 3H), 3.90 (s, 1H), 3.76 (dd, J = 11.4, 7.0 Hz, 1H), 3.69 (dd, J = 11.4, 5.0 Hz, 1H), 3.63 (dd, J = 10.5, 3.2 Hz, 1H), 3.47-3.41 (m, 1H), 3.15 (t, J = 10.8 Hz, 1H). | 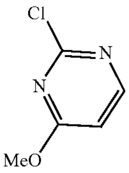 |

-continued

| ID | Characterization data | Starting material |
|---|---|---|
| 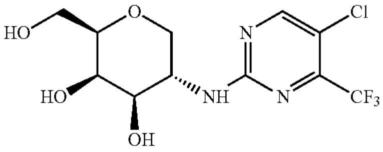 A324 | Yield: 5.4 mg, 10%, white solid. LC-MS (ESI) found: 344 $[M + H]^+$. $^1H$ NMR (400 MHz, MeOD): δ 8.46 (s, 1H), 4.32 (s, 1H), 4.07 (dd, J = 10.9, 5.1 Hz, 1H), 3.90 (d, J = 2.8 Hz, 1H), 3.75 (dd, J = 11.4, 7.1 Hz, 1H), 3.71-3.67 (m, 1H), 3.65 (d, J = 8.5 Hz, 1H), 3.47-3.41 (m, 1H), 3.16 (t, J = 10.9 Hz, 1H). | 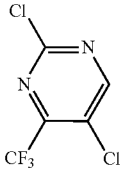 [SMILES: FC(F)(F)c1nc(Cl)ncc1Cl] |
| 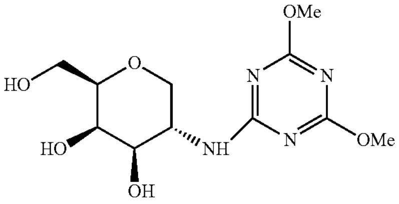 A325 | Yield: 8.3 mg, 11%, white solid. LC-MS (ESI) found: 303 $[M + H]^+$. $^1H$ NMR (400 MHz, MeOD): δ 4.39 (td, J = 10.7, 5.3 Hz, 1H), 4.08 (dd, J = 11.0, 5.3 Hz, 1H), 4.08 (dd, J = 11.0, 5.3 Hz, 1H), , 4.01 (s, 1H), 3.95 (s, 3H, 3.90 (s, 3H), 3.75 (dd, J = 11.4, 7.0 Hz, 1H), 3.71-3.66 (m, 1H), 3.63 (dd, J = 10.6, 3.2 Hz, 1H), 3.47-3.40 (m, 1H), 3.16 (t, J = 10.9 Hz, 1H). | 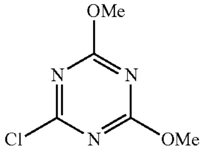 [SMILES: COc1nc(Cl)nc(OC)n1] |
| 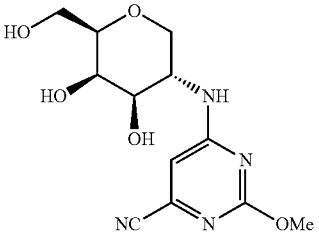 A326 | Yield: 3.0 mg, 10%, white solid. LC-MS (ESI) found: 297 $[M + H]^+$. $^1H$ NMR (400 MHz, MeOD): δ 6.55 (s, 1H), 4.53-4.40 (m, 1H), 4.12 (dd, J = 10.9, 5.3 Hz, 1H), 3.91 (dd, J = 8.4, 4.7 Hz, 6H), 3.75 (dd, J = 11.4, 7.1 Hz, 1H), 3.68 (dd, J = 11.4, 5.0 Hz, 1H), 3.60 (dd, J = 9.9, 2.4 Hz, 1H), 3.44 (dd, J = 8.7, 3.3 Hz, 2H), 3.11 (t, J = 10.7 Hz, 1H). | |
| 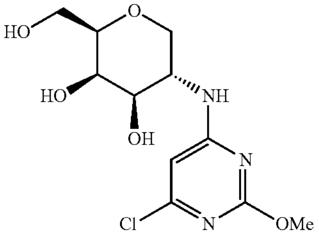 A327 | Yield: 3.0 mg, 1%, white solid. $^1H$ NMR (400 MHz, MeOD): δ 6.55 (s, 1H), 4.53-4.40 (m, 1H), 4.12 (dd, J = 10.9, 5.3 Hz, 1H), 3.91 (dd, J = 8.4, 4.7 Hz, 6H), 3.75 (dd, J = 11.4, 7.1 Hz, 1H), 3.68 (dd, J = 11.4, 5.0 Hz, 1H), 3.60 (dd, J = 9.9, 2.4 Hz, 1H), 3.44 (dd, J = 8.7, 3.3 Hz, 2H), 3.11 (t, J = 10.7 Hz, 1H). | 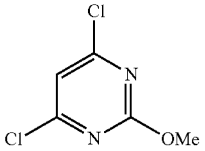 |
| 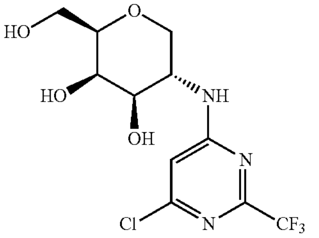 A328 | Yield: 5.0 mg, 21%, white solid. LC-MS (ESI) found: 344 $[M + H]^+$. $^1H$ NMR (400 MHz, MeOD): δ 6.76 (s, 1H), 4.49 (td, J = 10.7, 5.2 Hz, 1H), 4.09 (dd, J = 11.0, 5.2 Hz, 1H), 3.91 (d, J = 2.8 Hz, 1H), 3.76 (dd, J = 11.4, 7.1 Hz, 1H), 3.68 (dd, J = 11.4, 5.0 Hz, 1H), 3.61 (dd, J = 10.6, 3.1 Hz, 1H), 3.49-3.42 (m, 1H), 3.12 (t, J = 10.9 Hz, 1H). | 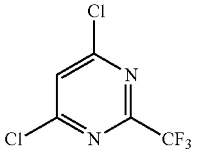 [SMILES: FC(F)(F)c1nc(Cl)cc(Cl)n1] |
| 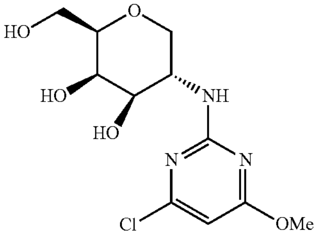 A329 | Yield: 3.1 mg, 4%, white solid. LC-MS (ESI) found: 306 $[M + H]^+$. $^1H$ NMR (400 MHz, MeOD): δ 6.04 (s, 1H), 4.31 (td, J = 10.5, 5.3 Hz, 1H), 4.11 (dd, J = 10.9, 5.1 Hz, 1H), 3.90 (d, J = 2.8 Hz, 4H), 3.75 (dd, J = 11.4, 7.0 Hz, 1H), 3.68 (dd, J = 11.3, 5.0 Hz, 1H), 3.61 (dd, J = 10.2, 3.2 Hz, 1H), 3.46-3.40 (m, 1H), 3.13 (t, J = 10.8 Hz, 1H). | 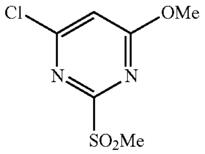 [SMILES: COc1cc(Cl)nc(S(C)(=O)=O)n1] |

-continued

| ID | Characterization data | Starting material |
|---|---|---|
| 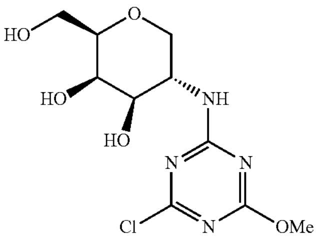 A330 | Yield: 8.0 mg, 6%, white solid. LC-MS (ESI) found: 307 [M + H]+. $^1$H NMR (400 MHz, MeOD): δ 4.48-4.37 (m, 1H), 4.10-4.03 (m, 1H), 4.02-3.95 (m, 3H), 3.92 (t, J = 3.3 Hz, 1H), 3.79-3.61 (m, 3H), 3.48-3.42 (m, 1H), 3.19 (td, J = 11.0, 5.8 Hz, 1H). | 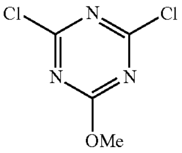 |
| 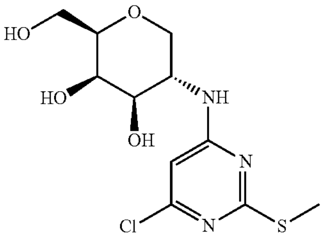 A331 | Yield: 4.5 mg, 5%, white solid. LC-MS (ESI) found: 322 [M + H]+. $^1$H NMR (400 MHz, MeOD): δ 6.20 (s, 1H), 4.44 (dd, J = 27.9, 14.4 Hz, 1H), 4.10 (dd, J = 15.2, 7.8 Hz, 1H), 3.90 (d, J = 2.6 Hz, 1H), 3.75 (dd, J = 11.3, 7.1 Hz, 1H), 3.68 (dd, J = 11.4, 5.0 Hz, 1H), 3.58 (dd, J = 10.5, 3.2 Hz, 1H), 3.43 (dd, J = 6.6, 5.5 Hz, 1H), 3.12 (t, 1H), 2.50 (s, 3H). | 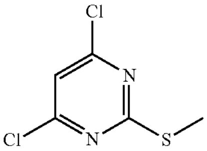 |
| 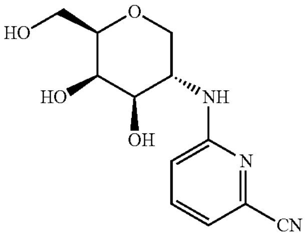 A332 | Yield: 2.0 mg, 3%, white solid. LC-MS (ESI) found: 266 [M + H]+. $^1$H NMR (400 MHz, MeOD): δ 7.47 (dd, J = 8.7, 7.2 Hz, 1H), 6.96 (dd, J = 7.1, 0.6 Hz, 1H), 6.76 (d, J = 8.7 Hz, 1H), 4.32 (td, J = 10.6, 5.2 Hz, 1H), 4.12 (dd, J = 11.0, 5.2 Hz, 1H), 3.90 (d, J = 2.7 Hz, 1H), 3.76 (dd, J = 11.4, 7.1 Hz, 1H), 3.68 (dd, J = 11.4, 5.0 Hz, 1H), 3.58 (dd, J = 10.5, 3.2 Hz, 1H), 3.44 (dd, J = 6.6, 5.5 # Hz, 1H), 3.08 (t, J = 10.8 Hz, 1H). | 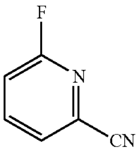 |
| 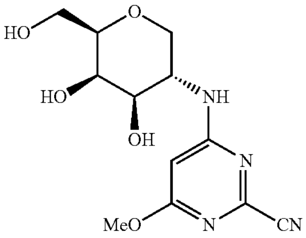 A333 | Yield: 6.0 mg, 8%, white solid. LC-MS (ESI) found: 297 [M + H]+. $^1$H NMR (400 MHz, $CD_3OD$): δ 5.97 (s, 1H), 4.36 (dd, J = 30.8, 19.2 Hz, 1H), 4.03 (dd, J = 10.9, 4.6 Hz, 1H), 3.89 (d, J = 3.3 Hz, 4H), 3.75 (dd, J = 11.4, 7.1 Hz, 1H), 3.67 (dd, J = 11.4, 5.0 Hz, 1H), 3.56 (dd, J = 10.4, 3.1 Hz, 1H), 3.43 (dd, J = 6.6, 5.5 Hz, 1H), 3.10 (t, J = 10.8 Hz, 1H). | 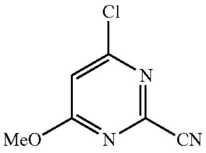 [SMILES: COc1cc(Cl)nc(C#N)n1] |
| 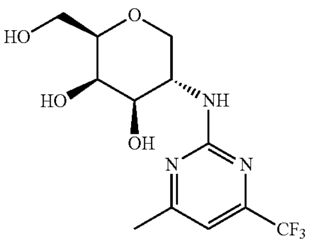 A334 | Yield: 8.0 mg, 8%, white solid. LC-MS (ESI) found: 324 [M + H]+. $^1$H NMR (400 MHz, MeOD): δ 6.82 (s, 1H), 4.36 (s, 1H), 4.12 (dd, J = 11.0, 5.2 Hz, 1H), 3.90 (d, J = 2.9 Hz, 1H), 3.75 (dd, J = 11.4, 7.1 Hz, 1H), 3.71-3.61 (m, 2H), 3.47-3.42 (m, 1H), 3.15 (t, J = 10.8 Hz, 1H), 2.40 (s, 3H). | 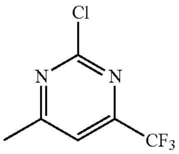 |

-continued

| ID | Characterization data | Starting material |
|---|---|---|
| 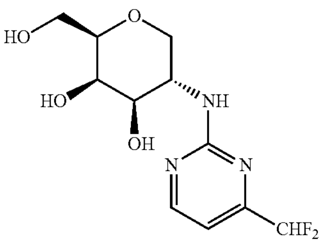 A335 | Yield: 26 mg, 36%, white solid. LC-MS (ESI) found: 292 [M + H]$^+$. $^1$H NMR (400 MHz, $CD_3OD$): δ 8.42 (d, J = 4.9 Hz, 1H), 6.81 (d, J = 4.9 Hz, 1H), 6.42 (t, J = 55.0 Hz, 1H), 4.36 (td, J = 10.6, 5.2 Hz, 1H), 4.11 (dd, J = 11.0, 5.2 Hz, 1H), 3.91 (d, J = 2.9 Hz, 1H), 3.75 (dd, J = 11.4, 7.0 Hz, 1H), 3.71-3.60 (m, 2H), 3.50-3.40 (m, 1H), 3.16 (t, J = 10.9 Hz, 1H). | 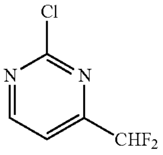 |
| 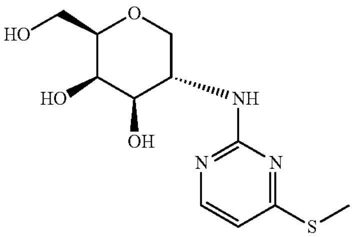 A336 | Yield: 2.3 mg, 9%, white solid. LC-MS (ESI) found: 288 [M + H]$^+$. $^1$H NMR (400 MHz, $CD_3OD$): δ 7.87 (d, J = 3.7 Hz, 1H), 6.51 (d, J = 5.4 Hz, 1H), 4.46-4.26 (m, 1H), 4.14 (dd, J = 11.0, 5.2 Hz, 1H), 3.90 (d, J = 2.8 Hz, 1H), 3.76 (dd, J = 11.4, 7.1 Hz, 1H), 3.69 (dd, J = 11.4, 5.0 Hz, 1H), 3.63 (dd, J = 10.5, 3.2 Hz, 1H), 3.50-3.42 (m, 1H), 3.15 (t, J = 10.8 Hz, 1H), 2.51 (s, 3H). | 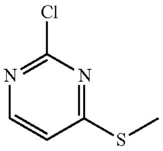 |

Preparation of 6-(((3S,4R,5R,6R)-4,5-dihydroxy-6-(hydroxymethyl)tetrahydro-2H-pyran-3-yl)amino)-1,3,5-triazine-2,4(1H,3H)-dione (Compound A337)

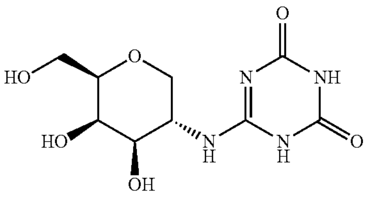 [SMILES: O=c1nc(N[C@H]2CO[C@H](CO)[C@H](O)[C@@H]2O)[nH]c(=O)[nH]1]

It was prepared according to the procedure same as that for A112. Yield: 1.5 mg, 2%, white solid. $^1$H NMR (400 MHz, $D_2O$): δ 4.73 (d, J=3.1 Hz, 2H), 4.42 (dt, J=9.6, 3.2 Hz, 1H), 4.21 (dd, J=12.7, 3.0 Hz, 1H), 4.06 (td, J=6.7, 2.5 Hz, 1H), 3.76-3.66 (m, 3H).

Preparation of (2R,3R,4R,5S)-2-(hydroxymethyl)-5-((3-(4-methylpiperazin-1-yl)-1,2,4-thiadiazol-5-yl)amino)tetrahydro-2H-pyran-3,4-diol (Compound A338)

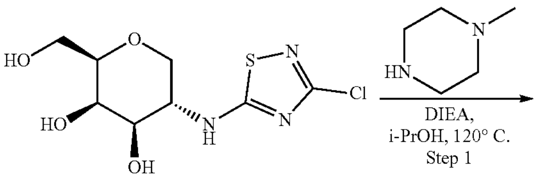

-continued

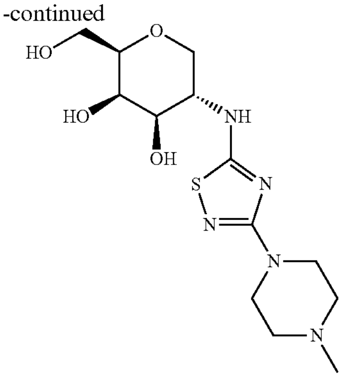

Step 1: To a mixture of (2R,3R,4R,5S)-5-((3-chloro-1,2,4-thiadiazol-5-yl)amino)-2-(hydroxymethyl)tetrahydro-2H-pyran-3,4-diol (A104, 100 mg, 0.36 mmol) in i-PrOH (3.0 mL) was added 1-methylpiperazine (107 mg, 1.07 mmol) and DIEA (0.25 mL, 1.44 mmol) at rt under $N_2$. After stirring at 120° C. overnight, the mixture was concentrated and purified by prep-TLC to give (2R,3R,4R,5S)-2-(hydroxymethyl)-5-((3-(4-methylpiperazin-1-yl)-1,2,4-thiadiazol-5-yl)amino)tetrahydro-2H-pyran-3,4-diol (1.8 mg, 6% yield) as a white solid. LC-MS (ESI) found: 346 [M+H]$^+$. $^1$H NMR (400 MHz, MeOD): δ 8.47 (s, 1H), 4.13 (dd, J=11.0, 5.2 Hz, 1H), 3.91 (t, J=13.4 Hz, 2H), 3.75-3.65 (m, 6H), 3.59 (dd, J=10.4, 3.2 Hz, 1H), 3.43 (dd, J=6.1, 5.1 Hz, 1H), 3.15 (t, J=10.9 Hz, 1H), 2.94 (t, J=5.0 Hz, 4H), 2.64 (s, 3H).

Preparation of (2R,3R,4R,5S)-5-((3-(dimethylamino)-1,2,4-thiadiazol-5-yl)amino)-2-(hydroxymethyl)tetrahydro-2H-pyran-3,4-diol (Compound A339)

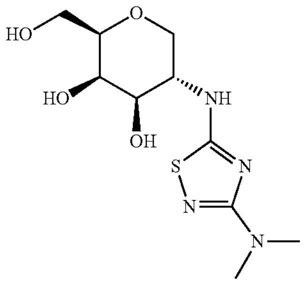 [SMILES: CN(C)c1nsc(N[C@H]2CO[C@H](CO)[C@H](O)[C@@H]2O)n1]

It was prepared according to the procedure same as that for A338. Yield: 0.9 mg, 7%, white solid. LC-MS (ESI) found: 291 $[M+H]^+$. $^1H$ NMR (400 MHz, MeOD): δ 4.16 (dd, J=11.0, 5.2 Hz, 1H), 3.90 (t, J=7.7 Hz, 2H), 3.76-3.67 (m, 2H), 3.59 (dd, J=10.4, 3.2 Hz, 1H), 3.45-3.41 (m, 1H), 3.16 (t, J=10.9 Hz, 1H), 3.04 (s, 6H).

Preparation of (2R,3R,4R,5S)-2-(hydroxymethyl)-5-((3-morpholino-1,2,4-thiadiazol-5-yl)amino)tetrahydro-2H-pyran-3,4-diol (Compound A340)

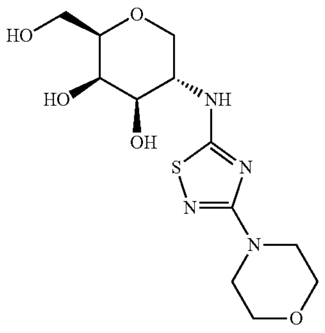 [SMILES: OC[C@H]1OC[C@H](Nc2nc(N3CCOCC3)ns2)[C@@H](O)[C@H]1O]

It was prepared according to the procedure same as that for A338. Yield: 0.8 mg, 5%, white solid. LC-MS (ESI) found: 333 $[M+H]^+$. $^1H$ NMR (400 MHz, MeOD): δ 4.14 (dd, J=11.0, 5.2 Hz, 1H), 3.90 (t, J=12.4 Hz, 2H), 3.77-3.63 (m, 6H), 3.58 (dd, J=10.4, 3.2 Hz, 1H), 3.51 (dd, J=12.3, 7.7 Hz, 4H), 3.45-3.39 (m, 1H), 3.16 (t, J=10.9 Hz, 1H).

Preparation of (2R,3R,4R,5S)-5-((3-amino-1,2,4-thiadiazol-5-yl)amino)-2-(hydroxymethyl)tetrahydro-2H-pyran-3,4-diol (Compound A341)

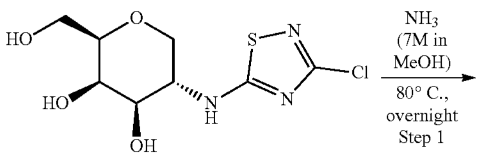

-continued

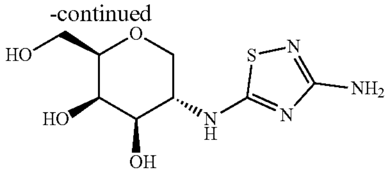

Step 1: A mixture of (2R,3R,4R,5S)-5-((3-chloro-1,2,4-thiadiazol-5-yl)amino)-2-(hydroxymethyl)tetrahydro-2H-pyran-3,4-diol (A104, 30 mg, 0.11 mmol) in $NH_3$-MeOH solution (2.0 mL, 7 M) was stirring at 80° C. overnight. The mixture was concentrated and purified by prep-TLC to give (2R,3R,4R,5S)-5-((3-amino-1,2,4-thiadiazol-5-yl)amino)-2-(hydroxymethyl)tetrahydro-2H-pyran-3,4-diol (2.1 mg, 7% yield) as a white solid. LC-MS (ESI) found: 263 $[M+H]^+$. $^1H$ NMR (400 MHz, MeOD): δ 4.11 (dd, J=11.1, 5.2 Hz, 1H), 3.87 (dd, J=11.0, 2.6 Hz, 2H), 3.77-3.63 (m, 2H), 3.57 (dd, J=10.3, 3.3 Hz, 1H), 3.44 (dd, J=16.8, 11.7 Hz, 1H), 3.16 (t, J=10.9 Hz, 1H).

Preparation of N-((3S,4R,5R,6R)-4,5-dihydroxy-6-(hydroxymethyl)tetrahydro-2H-pyran-3-yl)benzamide (Compound A342)

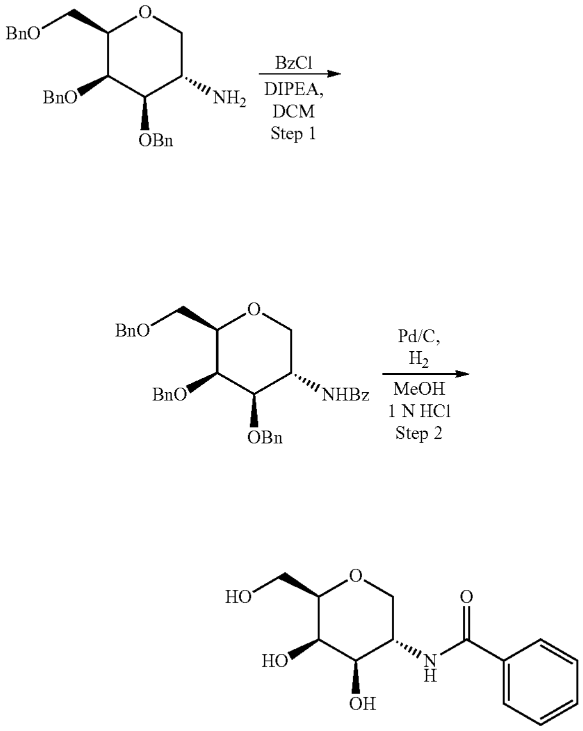

Step 1: To a mixture of (4R,5R,6R)-4,5-bis(benzyloxy)-6-((benzyloxy)methyl)tetrahydro-2H-pyran-3-amine (200 mg, 0.46 mmol) in DCM (5 mL) was added TEA (0.13 mL, 0.923 mmol) and BzCl (98 mg, 0.69 mmol). Then the mixture was stirred reaction at room temperature. After 2 h, the reaction was diluted with EA and water. The organic layer was separated, and concentrated in vacuo. The residue was purified by silica gel column to give N-((3S,4R,5R,6R)-4,5-bis(benzyloxy)-6-((benzyloxy)methyl)tetrahydro-2H-pyran-3-yl)benzamide (40 mg, 16% yield). LC-MS (ESI) found: 538 $[M+H]^+$.

Step 2: To a solution of N-[(3S,4R,5R,6R)-4,5-bis(benzyloxy)-6-[(benzyloxy)methyl]oxan-3-yl]benzamide (30 mg, 0.056 mmol) in MeOH (5 mL) were added Pd/C (3 mg, 10% wt, 60% wet) and HCl (1 mL, 1 M in $H_2O$) at rt. The mixture was stirred at rt 2 h under a $H_2$ balloon. The mixture was filtered through a Celite pad, and the filtrate was concentrated to give product N-((3S,4R,5R,6R)-4,5-dihydroxy-6-(hydroxymethyl)tetrahydro-2H-pyran-3-yl)benzamide. LC-MS (ESI) found: 268 $[M+H]^+$. $^1H$ NMR (400 MHz, MeOD): δ 7.86-7.79 (m, 2H), 7.56-7.48 (m, 1H), 7.45 (t, J=7.4 Hz, 2H), 4.39 (td, J=10.7, 5.3 Hz, 1H), 4.04 (dd, J=11.0, 5.3 Hz, 1H), 3.91 (d, J=2.9 Hz, 1H), 3.80-3.65 (m, 3H), 3.45 (dd, J=11.8, 6.5 Hz, 1H), 3.23 (t, J=10.9 Hz, 1H).

The following compounds below were prepared according to the procedure same as A342:

Step 1: To a solution of (2R,3R,4R,5S)-5-amino-2-(hydroxymethyl)tetrahydro-2H-pyran-3,4-diol hydrochloride (A92, 100 mg, 0.61 mmol) and 4H-pyran-4-one (59 mg, 0.61 mmol) in MeOH (2 mL) was added NaOH (24 mg, 0.61 mmol) in $H_2O$ (1 mL). The mixture was stirred at 60° C. overnight, then purified by prep-HPLC (Method A) to give 1-((3S,4R,5R,6R)-4,5-dihydroxy-6-(hydroxymethyl)tetrahydro-2H-pyran-3-yl)pyridin-4(1H)-one (3.5 mg, 2% yield) as colorless oil. LC-MS (ESI) found: 242 $[M+H]^+$. $^1H$ NMR (400 MHz, MeOD): δ 8.08-7.56 (m, 2H), 6.61-5.93 (m, 2H), 4.26 (td, J=10.9, 5.0 Hz, 1H), 4.10 (dd, J=11.0, 5.0 Hz, 1H), 4.03 (dt, J=4.8, 3.3 Hz, 2H), 3.79 (dd, J=11.4, 7.0 Hz, 1H), 3.75-3.71 (m, 1H), 3.68 (t, J=7.9 Hz, 1H), 3.63-3.59 (m, 1H).

| ID | Characterization data |
|---|---|
| 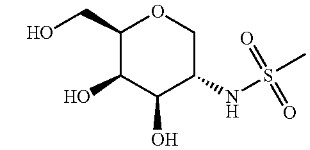 A343 | Yield: 21 mg, 63%, white solid. LC-MS (ESI) found: 242 $[M + H]^+$. $^1H$ NMR (400 MHz, MeOD): δ 3.98 (dd, J = 11.2, 5.3 Hz, 1H), 3.86 (d, J = 2.6 Hz, 1H), 3.68 (ddd, J = 16.4, 11.4, 6.0 Hz, 2H), 3.54 (td, J = 10.6, 5.3 Hz, 1H), 3.42 (dd, J = 10.4, 3.2 Hz, 1H), 3.39-3.35 (m, 1H), 3.13 (t, J = 11.0 Hz, 1H), 3.03 (s, 3H). |
| 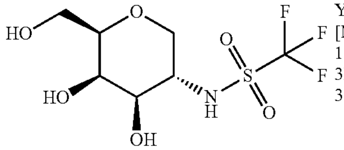 A344 | Yield: 50 mg, 77%, colorless oil. LC-MS (ESI) found: 318 [M + Na]+ . $^1H$ NMR (400 MHz, $CD_3OD$): δ 3.97 (dd, J = 11.1, 5.3 Hz, 1H), 3.88 (d, J = 2.8 Hz, 1H), 3.73-3.62 (m, 3H), 3.45 (dd, J = 10.3, 3.2 Hz, 1H), 3.41-3.37 (m, 1H), 3.19 (t, J = 11.1 Hz, 1H). |

Preparation of 1-((3S,4R,5R,6R)-4,5-dihydroxy-6-(hydroxymethyl)tetrahydro-2H-pyran-3-yl)pyridin-4(1H)-one (Compound A345)

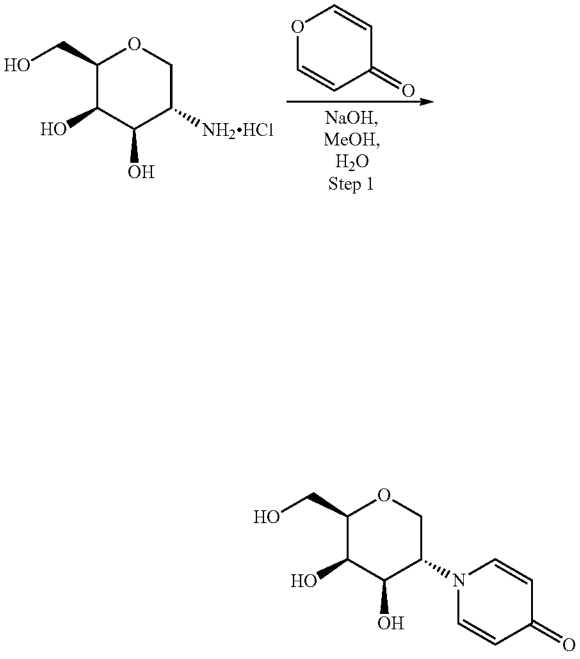

Preparation of 2-(((3S,4R,5R,6R)-4,5-dihydroxy-6-(hydroxymethyl)tetrahydro-2H-pyran-3-yl)amino)-6-methoxypyrimidine-4-carbonitrile (Compound A346)

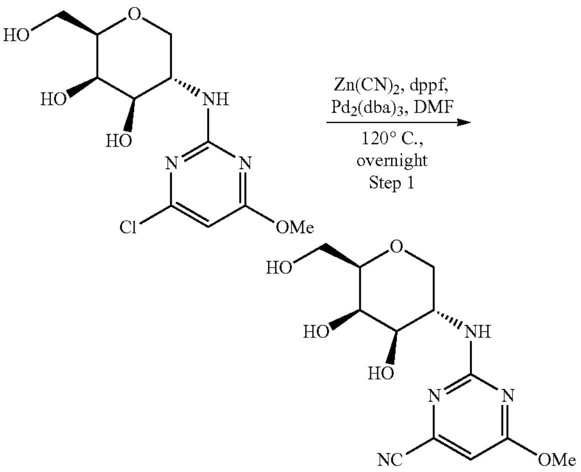

Step 1: To a solution of (2R,3R,4R,5S)-5-((4-chloro-6-methoxypyrimidin-2-yl)amino)-2-(hydroxymethyl)tetrahydro-2H-pyran-3,4-diol (A303, 20 mg, 0.06 mmol) in DMF (2 mL) was added dppf (7 mg, 0.012 mmol), $Pd_2(dba)_3$ (6 mg, 0.006 mmol) and $Zn(CN)_2$ (7 mg, 0.06 mmol) at rt. After the addition was complete, the mixture was stirred at 120° C. under $N_2$ atmosphere overnight. On consumption of starting material (LCMS monitoring), the mixture was filtered, concentrated, and purified by flash chromatography (silica gel, 0-10% MeOH in DCM) to give 4-(((3S,4R,5R,6R)-4,5-dihydroxy-6-(hydroxymethyl)tetrahydro-2H-pyran-3-yl)amino)-6-methoxypyrimidine-2-carbonitrile as a colorless oil (5 mg, 26% yield) as white solid. LC-MS (ESI) found: 297 $[M+H]^+$. $^1H$ NMR (400 MHz, MeOD): δ 6.44 (s, 1H), 4.34 (td, J=10.6, 5.3 Hz, 1H), 4.08 (dd, J=10.9, 5.2 Hz, 1H), 3.91 (s, 3H), 3.90 (d, J=2.7 Hz, 1H), 3.72 (ddd, J=16.4, 11.4, 6.0 Hz, 2H), 3.62 (d, J=8.4 Hz, 1H), 3.47-3.39 (m, 1H), 3.20-3.07 (m, 1H).

Preparation of 6-(((3S,4R,5R,6R)-4,5-dihydroxy-6-(hydroxymethyl)tetrahydro-2H-pyran-3-yl)amino)-2-methoxypyrimidine-4-carbonitrile (Compound A347)

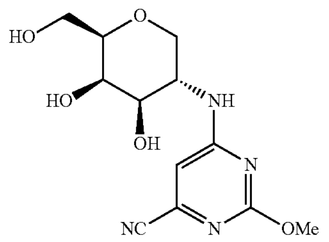 [SMILES: COc1nc(C#N)cc(N[C@H]2CO[C@H](CO)[C@H](O)[C@@H]2O)n1]

It was prepared according to the procedure same as that for A346 by using A327 as the starting material. LC-MS (ESI) found: 297 $[M+H]^+$. H NMR (400 MHz, MeOD): δ 6.17 (s, 1H), 4.43 (dd, J=17.9, 8.3 Hz, 1H), 4.10 (dd, J=13.5, 7.8 Hz, 1H), 3.96-3.85 (m, 5H), 3.75 (dd, J=11.4, 7.1 Hz, 1H), 3.68 (dd, J=11.4, 5.0 Hz, 1H), 3.58 (dd, J=10.5, 3.2 Hz, 1H), 3.46-3.41 (m, 1H), 3.10 (t, 1H).

Preparation of 6-(((3S,4R,5R,6R)-4,5-dihydroxy-6-(hydroxymethyl)tetrahydro-2H-pyran-3-yl)amino) pyrimidine-2,4-dicarbonitrile (Compound A348)

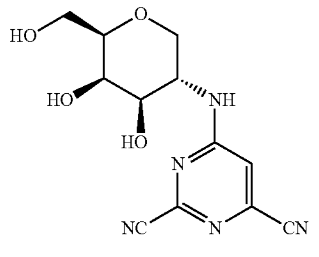 [SMILES: N#Cc1cc(N[C@H]2CO[C@H](CO)[C@H](O)[C@@H]2O)nc(C#N)n1]

It was prepared according to the procedure same as that for A346 by using A320 as the starting material. LC-MS (ESI) found: 292 $[M+H]^+$. 1 H NMR (400 MHz, MeOD): δ7.03 (s, 1H), 4.49 (td, J=10.6, 5.1 Hz, 1H), 4.06 (dd, J=11.0, 5.2 Hz, 1H), 3.91 (d, J=2.9 Hz, 1H), 3.75 (dd, J=11.4, 7.1 Hz, 1H), 3.68 (dd, J=11.4, 5.0 Hz, 1H), 3.61 (dd, J=10.6, 3.2 Hz, 1H), 3.48-3.39 (m, 1H), 3.12 (t, J=10.9 Hz, 1H).

Preparation of 4-(((3S,4R,5R,6R)-4,5-dihydroxy-6-(hydroxymethyl)tetrahydro-2H-pyran-3-yl)amino)-6-methoxy-1,3,5-triazine-2-carbonitrile (Compound A349)

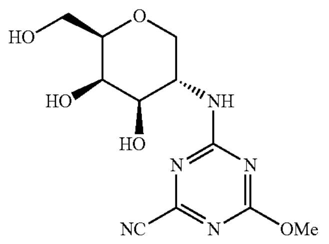 [SMILES: COc1nc(C#N)nc(N[C@H]2CO[C@H](CO)[C@H](O)[C@@H]2O)n1]

It was prepared according to the procedure same as that for A346 by using A330 as the starting material. $^1H$ NMR (400 MHz, DMSO-$d_6$): δ 8.58 (dd, J=26.3, 8.7 Hz, 1H), 4.19-4.12 (m, 1H), 3.90 (d, J=10.2 Hz, 3H), 3.86-3.83 (m, 1H), 3.81 (d, J=5.2 Hz, 1H), 3.77 (d, J=5.2 Hz, 1H), 3.73 (d, J=6.0 Hz, 2H), 3.55-3.51 (m, 1H), 3.48 (dd, J=6.1, 1.3 Hz, 2H), 3.24 (dd, J=10.9, 5.5 Hz, 1H), 3.01 (td, J=10.9, 6.5 Hz, 1H).

Preparation of (2R,3R,4R,5S)-2-(hydroxymethyl)-5-((4-methoxy-6-(4-methylpiperazin-1-yl)pyrimidin-2-yl)amino)tetrahydro-2H-pyran-3,4-diol (Compound A350)

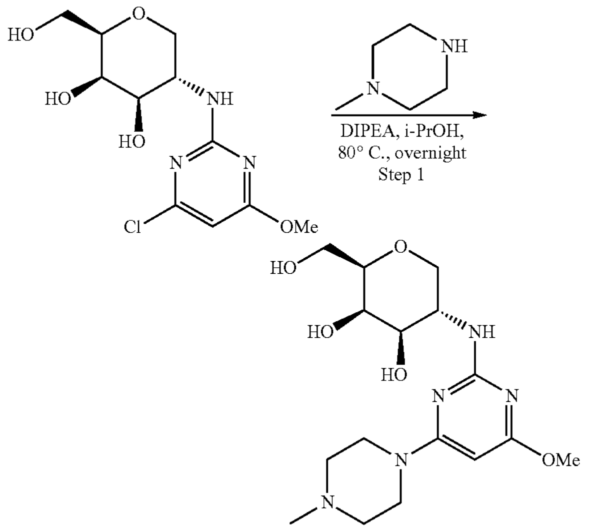

Step 1: To a solution of (2R,3R,4R,5S)-5-((4-chloro-6-methoxypyrimidin-2-yl)amino)-2-(hydroxymethyl)tetrahydro-2H-pyran-3,4-diol (A303, 20 mg, 0.065 mmol) and DIPEA (25 mg, 0.195 mmol) in dry i-PrOH (2 mL) at rt under $N_2$ atmosphere was added 1-methylpiperazine (17 mg, 0.13 mmol). After the addition was complete, the reaction was stirred at 80° C. overnight. On consumption of starting material (TLC monitoring), the reaction vessel was again cooled to rt. The mixture was concentrated in vacuo. The crude product was purified by flash chromatography (silica gel, 0-10% MeOH in DCM) to give (2R,3R,4R,5S)-2-(hydroxymethyl)-5-((4-methoxy-6-(4-methylpiperazin-1- yl)pyrimidin-2-yl)amino)tetrahydro-2H-pyran-3,4-diol as a yellow solid (12 mg, 50% yield). LC-MS (ESI) found: 370[M+H]$^+$. $^1$H NMR (400 MHz, MeOD): δ 5.38 (s, 1H), 4.24 (td, J=10.5, 5.2 Hz, 1H), 4.16 (dd, J=10.7, 5.2 Hz, 1H), 3.89 (d, J=2.7 Hz, 1H), 3.75 (dd, J=11.3, 7.0 Hz, 1H), 3.68 (dd, J=11.4, 5.0 Hz, 1H), 3.63-3.57 (m, 4H), 3.56 (d, J=3.2 Hz, 1H), 3.44 (dt, J=5.9, 5.4 Hz, 1H), 3.09 (dd, J=20.7, 10.1 Hz, 1H), 2.54 (t, J=5.1 Hz, 4H), 2.36 (s, 3H).

Preparation of 4-(((3S,4R,5R,6R)-4,5-dihydroxy-6-(hydroxymethyl)tetrahydro-2H-pyran-3-yl)amino)-6-(methylthio)pyrimidine-2-carbonitrile (Compound A351) and 4-(((3S,4R,5R,6R)-4,5-dihydroxy-6-(hydroxymethyl)tetrahydro-2H-pyran-3-yl)amino)-6-(methylthio)pyrimidine-2-carboxamide (Compound A352)

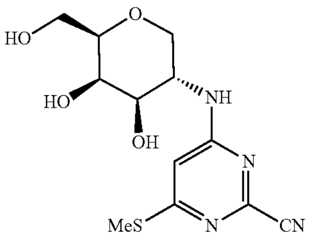

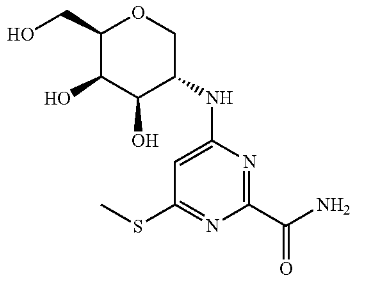

Was prepared according to the procedure same as that for A350 by using A320 as the starting material. A351: Yield: 2.0 mg, 4%, white solid. LC-MS (ESI) found: 313 [M+H]$^+$. $^1$H NMR (400 MHz, $CD_3OD$): δ 6.46 (s, 1H), 4.41 (dd, J=12.3, 7.5 Hz, 1H), 4.05 (dd, J=12.4, 5.3 Hz, 1H), 3.89 (d, J=2.7 Hz, 1H), 3.75 (dd, J=11.4, 7.1 Hz, 1H), 3.68 (dd, J=11.4, 5.0 Hz, 1H), 3.56 (dd, J=10.5, 3.2 Hz, 1H), 3.47-3.40 (m, 1H), 3.10 (t, 1H), 2.49 (s, 3H). A352: Yield: 3.0 mg, 3%, white solid. LC-MS (ESI) found: 331 [M+H]$^+$. $^1$H NMR (400 MHz, $CD_3OD$): δ 6.42 (s, 1H), 4.57 (dd, J=21.4, 17.8 Hz, 1H), 4.03 (dd, J=10.9, 4.8 Hz, 1H), 3.91 (d, J=2.9 Hz, 1H), 3.75 (dd, J=11.3, 7.1 Hz, 1H), 3.69 (dd, J=11.4, 5.0 Hz, 1H), 3.55 (dd, J=10.5, 3.0 Hz, 1H), 3.45 (dd, J=12.6, 6.9 Hz, 1H), 3.13 (t, J=10.7 Hz, 1H), 2.52 (s, 3H).

Preparation of 4-(((3S,4R,5R,6R)-4,5-dihydroxy-6-(hydroxymethyl)tetrahydro-2H-pyran-3-yl)amino)-6-(4-methylpiperazin-1-yl)pyrimidine-2-carbonitrile (Compound A353)

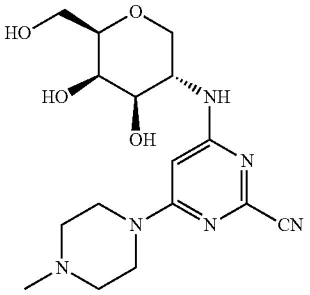 [SMILES: CN1CCN(c2cc(N[C@H]3CO[C@H](CO)[C@H](O)[C@@H]3O)nc(C#N)n2)CC1]

It was prepared according to the procedure same as that for A350 by using A320 as the starting material. Yield: 2.0 mg, 3%, white solid. $^1$H NMR (400 MHz, $CD_3OD$): δ 5.79 (s, 1H), 4.21 (dd, J=21.2, 12.1 Hz, 1H), 4.03 (dd, J=11.0, 5.0 Hz, 1H), 3.89 (d, J=2.9 Hz, 1H), 3.74 (dd, J=11.4, 7.1 Hz, 1H), 3.67 (dd, J=11.4, 5.0 Hz, 1H), 3.61-3.51 (m, 5H), 3.45-3.39 (m, 1H), 3.09 (t, J=10.9 Hz, 1H), 2.53-2.45 (m, 4H), 2.32 (s, 3H).

Preparation of (2R,3R,4R,5S)-5-(benzo[d]thiazol-2-ylamino)-2-(hydroxymethyl)tetrahydro-2H-pyran-3,4-diol (Compound A354)

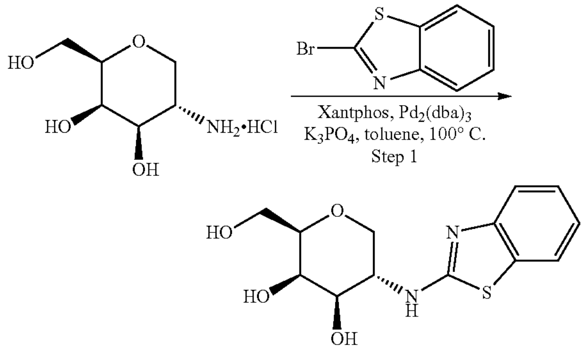

Step 1: A solution of (2R,3R,4R,5S)-5-amino-2-(hydroxymethyl)tetrahydro-2H-pyran-3,4-diol (A92, 20 mg, 0.12 mmol), 2-bromobenzo[d]thiazole (31 mg, 0.15 mmol), $K_3PO_4$ (78 mg, 0.37 mmol), $Pd_2(dba)_3$ (11 mg, 0.01 mmol) and Xantphos (14 mg, 0.02 mmol) in toluene (2 mL) was stirred at 100° C. overnight. The mixture was concentrated and the residue was purified by prep-TLC to give (2R,3R,4R,5S)-5-(benzo[d]thiazol-2-ylamino)-2-(hydroxymethyl)tetrahydro-2H-pyran-3,4-diol (4 mg, 9% yield) as white solid. LC-MS (ESI) found: 297 [M+H]$^+$. $^1$H NMR (400 MHz, MeOD): δ 7.61-7.52 (m, 1H), 7.41 (d, J=7.6 Hz, 1H), 7.28-7.18 (m, 1H), 7.10-6.88 (m, 1H), 4.25-4.06 (m, 2H), 3.91 (d, J=2.5 Hz, 1H), 3.77 (dd, J=11.4, 7.0 Hz, 1H), 3.70 (dd, J=11.4, 5.0 Hz, 1H), 3.60 (dd, J=10.0, 3.2 Hz, 1H), 3.48-3.42 (m, 1H), 3.20 (d, J=12.0 Hz, 1H).

Preparation of (2R,3R,4R,5S)-2-(hydroxymethyl)-5-((3-(trifluoromethyl)phenyl)amino) tetrahydro-2H-pyran-3,4-diol (Compound A355)

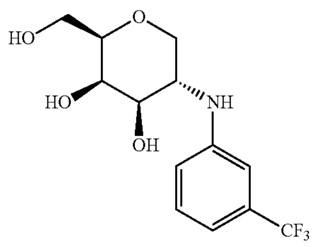 [SMILES: OC[C@H]1OC[C@H](Nc2cccc(C(F)(F)F)c2)[C@@H](O)[C@H]1O]

It was prepared according to the procedure same as that for A354. LC-MS (ESI) found: 308 [M+H]$^+$. $^1$H NMR (400 MHz, MeOD): δ 8.49 (s, 1H), 7.23 (t, J=7.9 Hz, 1H), 6.98-6.86 (m, 2H), 6.81 (d, J=7.6 Hz, 1H), 4.03 (dd, J=11.4, 5.0 Hz, 1H), 3.91 (d, J=2.9 Hz, 2H), 3.82 (dd, J=10.4, 4.9 Hz, 1H), 3.77 (dd, J=11.2, 4.3 Hz, 1H), 3.69 (dd, J=11.4, 5.0 Hz, 1H), 3.54 (dd, J=10.1, 3.1 Hz, 1H), 3.47-3.40 (m, 1H), 3.05 (t, J=11.0 Hz, 1H).

Preparation of (2R,3R,4R,5S)-2-(hydroxymethyl)-5-((4-(trifluoromethyl)pyridin-2-yl)amino)tetrahydro-2H-pyran-3,4-diol (Compound A356)

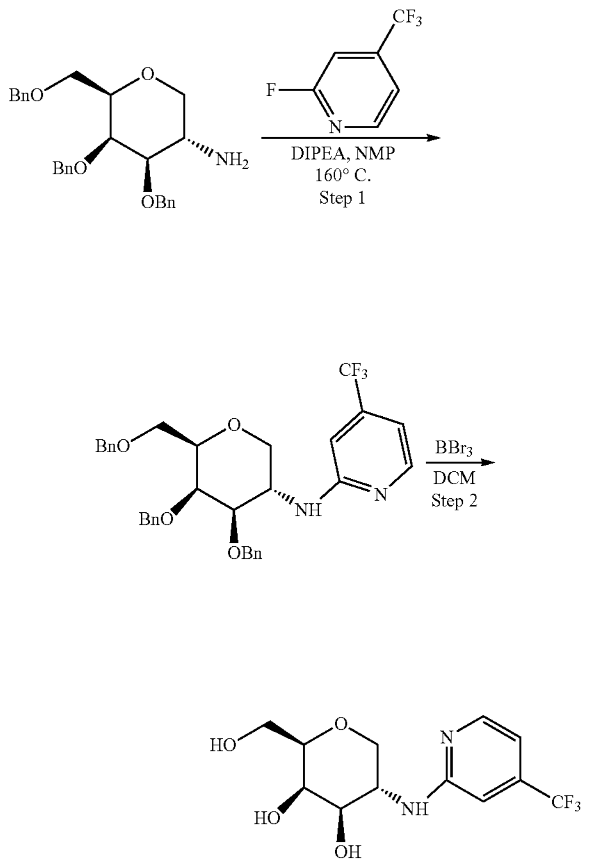

Step 1: To the solution of (3S,4R,5R,6R)-4,5-bis(benzyloxy)-6-[(benzyloxy)methyl]oxan-3-amine (100 mg, 0.23 mmol) in NMP (1 mL) were added 2-fluoro-4-(trifluoromethyl)pyridine (0.042 mL, 0.35 mmol) and DIPEA (0.12 mL, 0.69 mmol). The mixture was stirred at 80° C. overnight. The mixture was then concentrated and purified by flash to get N-((3S,4R,5R,6R)-4,5-bis(benzyloxy)-6-((benzyloxy)methyl)tetrahydro-2H-pyran-3-yl)-4-(trifluoromethyl)pyridin-2-amine (104 mg, 78% yield) as white solid. LC-MS (ESI) found: 579 [M+H]$^+$.

Step 2: To the solution of N-[(3S,5R,6R)-4,5-bis(benzyloxy)-6-[(benzyloxy)methyl]oxan-3-yl]-4-(trifluoromethyl)pyridin-2-amine (80 mg, 0.14 mmol) in DCM (1 mL) was added $BBr_3$ (122 μL, 1 M in DCM) at −40° C. The mixture was stirred for 4 h to completion. MeOH was added and then concentrated, the solid was filtered and washed by DCM. It was purified by prep-TLC to get (2R,3R,4R,5S)-2-(hydroxymethyl)-5-((4-(trifluoromethyl)pyridin-2-yl)amino) tetrahydro-2H-pyran-3,4-diol (7 mg, 15% yield) as white solid. LC-MS(ESI) found 309 [M+H]$^+$. $^1$H NMR (400 MHz, MeOD): δ 8.12 (d, J=5.4 Hz, 1H), 6.78 (s, 1H), 6.71 (d, J=5.4 Hz, 1H), 4.28 (td, J=10.6, 5.1 Hz, 1H), 4.11 (dd, J=11.0, 5.2 Hz, 1H), 3.90 (d, J=2.7 Hz, 1H), 3.76 (dd, J=11.4, 7.1 Hz, 1H), 3.69 (dd, J=11.4, 5.0 Hz, 1H), 3.58 (dd, J=10.4, 3.2 Hz, 1H), 3.45 (dd, J=12.4, 6.4 Hz, 1H), 3.12 (t, J=10.9 Hz, 1H).

Preparation of (2R,3R,4R,5S)-2-(hydroxymethyl)-5-((3-(pyridin-4-yl)-1,2,4-thiadiazol-5-yl)amino)tetrahydro-2H-pyran-3,4-diol (Compound A357)

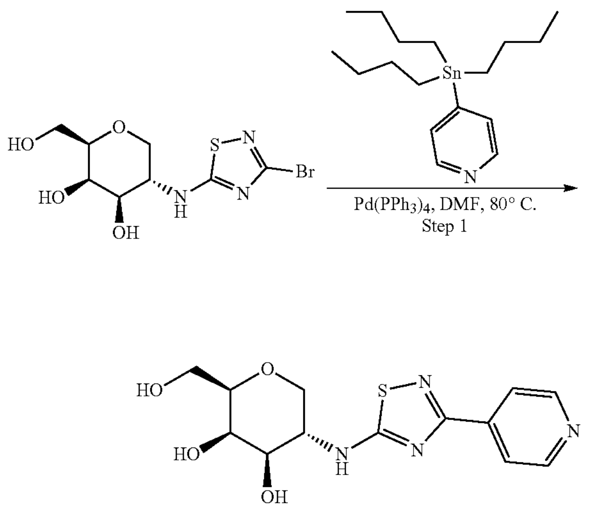 [SMILES: OC[C@H]1OC[C@H](Nc2nc(Br)ns2)[C@@H](O)[C@H]1O ; CCC[CH2][Sn]([CH2]CCC)([CH2]CCC)[c]1ccncc1 ; OC[C@H]1OC[C@H](Nc2nc(-c3ccncc3)ns2)[C@@H](O)[C@H]1O]

Step 1: A mixture of (2R,3R,4R,5S)-5-[(3-bromo-1,2,4-thiadiazol-5-yl)amino]-2-(hydroxymethyl)oxane-3,4-diol (A299, 10 mg, 0.03 mmol), 4-(tributylstannyl)pyridine (23 mg, 0.06 mmol), $Pd(PPh_3)_4$ (18 mg, 0.02 mmol) in toluene (1 ml) was stirred under $N_2$ at 80° C. for 12 h. The mixture was concentrated and purified by prep-HPLC (Method A) to give (2R,3R,4R,5S)-2-(hydroxymethyl)-5-((3-(pyridin-4-yl)-1,2,4-thiadiazol-5-yl)amino)tetrahydro-2H-pyran-3,4-diol (0.7 mg, 2% yield) as a white solid. LC-MS (ESI) found: 325 [M+H]$^+$. $^1$H NMR (400 MHz, MeOD): δ 8.62 (d, J=6.1 Hz, 2H), 8.11 (d, J=6.2 Hz, 2H), 4.23 (dd, J=11.0, 5.2 Hz, 1H), 4.16-4.06 (m, 1H), 3.92 (d, J=3.0 Hz, 1H), 3.77 (dd, J=11.4, 7.0 Hz, 1H), 3.70 (dd, J=11.4, 5.1 Hz, 1H), 3.65 (dd, J=10.3, 3.1 Hz, 1H), 3.51-3.44 (m, 1H), 3.23 (t, J=10.9 Hz, 1H).

Preparation of (2R,3R,4R,5S)-2-(hydroxymethyl)-5-((3-(pyridin-3-yl)-1,2,4-thiadiazol-5-yl)amino)tetrahydro-2H-pyran-3,4-diol (Compound A358)

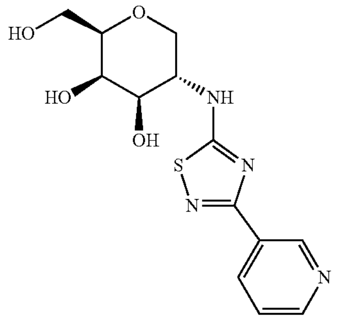 [SMILES: OC[C@H]1OC[C@H](Nc2nc(-c3cccnc3)ns2)[C@@H](O)[C@H]1O]

It was prepared according to the procedure same as that for A357. LC-MS (ESI) found: 325 $[M+H]^+$. $^1H$ NMR (400 MHz, MeOD): δ 9.26 (d, J=1.4 Hz, 1H), 8.58 (dd, J=4.9, 1.6 Hz, 1H), 8.52 (dt, J=8.0, 1.9 Hz, 1H), 7.54-7.49 (m, 1H), 4.23 (dd, J=11.0, 5.2 Hz, 1H), 4.12 (dd, J=10.9, 5.0 Hz, 1H), 3.93 (d, J=2.8 Hz, 1H), 3.77 (dd, J=11.4, 7.1 Hz, 1H), 3.68 (ddd, J=13.5, 10.8, 4.1 Hz, 2H), 3.48 (dd, J=6.5, 5.5 Hz, 1H), 3.23 (t, J=10.8 Hz, 1H).

Preparation of (2R,3R,4R,5S)-2-(hydroxymethyl)-5-((6-methoxy-2-(trifluoromethyl)pyrimidin-4-yl)amino)tetrahydro-2H-pyran-3,4-diol (Compound A359)

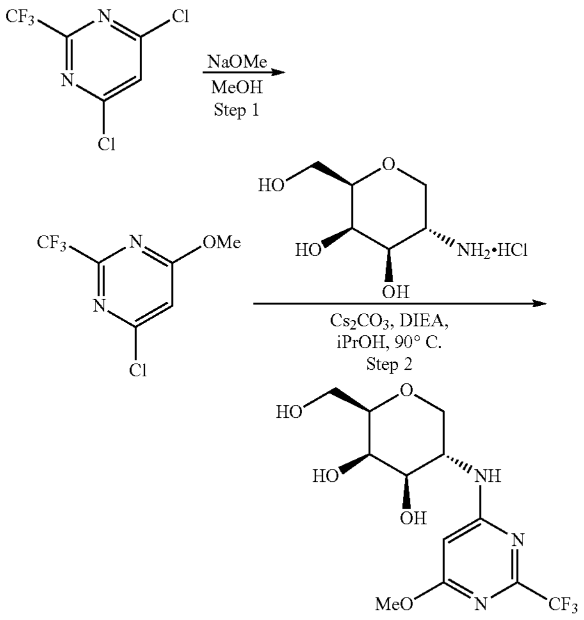

Step 1: To a solution of 4,6-dichloro-2-(trifluoromethyl)pyrimidine (1.0 g, 4.63 mmol) in MeOH (30 mL) was added NaOMe (750 mg, 13.89 mmol). The mixture was stirred at the room temperature for 16 h. The mixture was diluted ethyl acetate (40 mL) and washed water (50 mL×3), the organic layer was dried over sodium sulfate, filtered, concentrated under reduced pressure to give 4-chloro-6-methoxy-2-(trifluoromethyl)pyrimidine. Note the purification of this reagent is missing (424 mg, 43% yield). LC-MS (ESI) found: 213 $[M+H]^+$.

Step 2: To a solution of 4-chloro-6-methoxy-2-(trifluoromethyl)pyrimidine (42.0 mg, 0.20 mmol) in iPrOH (10 mL) was added $Cs_2CO_3$ (32.5 mg, 0.10 mmol), DIEA (79.0 mg, 0.60 mmol), (2R,3R,4R,5S)-5-amino-2-(hydroxymethyl)tetrahydro-2H-pyran-3,4-diol (A92, 32.6 mg, 0.20 mmol). The mixture was stirred at 90° C. for 16 h. The mixture was concentrated under reduced pressure to give a crude product, which was purified by column to give (2R,3R,4R,5S)-2-(hydroxymethyl)-5-((6-methoxy-2-(trifluoromethyl)pyrimidin-4-yl)amino)tetrahydro-2H-pyran-3,4-diol (15 mg, 21% yield). LC-MS (ESI) found: 340 $[M+H]^+$. $^1H$ NMR (400 MHz, MeOD) δ 6.26 (s, 1H), 4.29 (d, J=5.4 Hz, 1H), 4.07 (dd, J=10.9, 5.3 Hz, 1H), 3.96-3.79 (m, 4H), 3.74-3.52 (m, 3H), 3.39 (dd, J=12.2, 6.8 Hz, 1H), 3.08 (t, J=10.8 Hz, 1H).

Preparation of 6-(((3S,4R,5R,6R)-4,5-dihydroxy-6-(hydroxymethyl)tetrahydro-2H-pyran-3-yl)amino)-2-methoxypyrimidine-4-carboxamide (Compound A360)

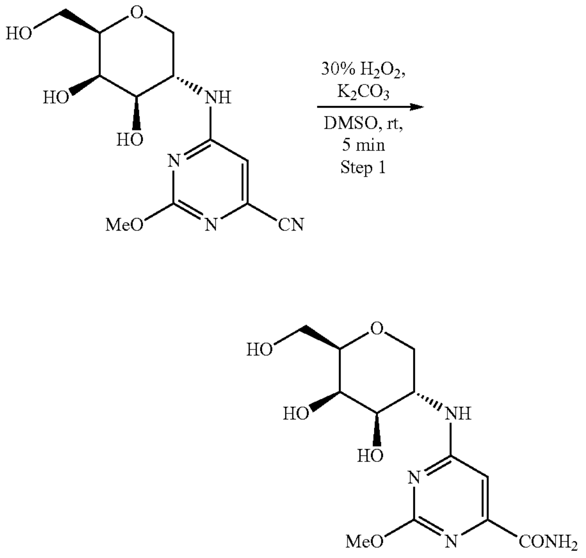

Step 1: A stirred solution of 6-(((3S,4R,5R,6R)-4,5-dihydroxy-6-(hydroxymethyl)tetrahydro-2H-pyran-3-yl)amino)-2-methoxypyrimidine-4-carbonitrile (A346, 30 mg, 0.01 mol) in DMSO (2 mL), cooled in an ice bath, was added 30% $H_2O_2$ (0.2 mL) and $K_2CO_3$ (10 mg, 0.001 mol), the reaction was allowed to warm up to rt (strong exothermic effect was observed). After 5 min, distilled water (50 mL) was added, cooling applied. The mixture was concentrated in vacuo. The crude product was purified by pre-HPLC (Method A) to give 6-(((3S,4R,5R,6R)-4,5-dihydroxy-6-(hydroxymethyl)tetrahydro-2H-pyran-3-yl)amino)-2-methoxypyrimidine-4-carboxamide as a white solid (5.2 mg, 16% yield). LC-MS (ESI) found: 315 $[M+H]^+$. $^1H$ NMR (400 MHz, MeOD): δ 6.62 (s, 1H), 4.47 (s, 1H), 4.10 (s, 1H), 3.92 (d, J=2.6 Hz, 4H), 3.72 (ddd, J=16.4, 11.4, 6.1 Hz, 2H), 3.62 (dd, J=10.7, 3.1 Hz, 1H), 3.51-3.39 (m, 1H), 3.13 (t, J=10.9 Hz, 1H).

Preparation of (2R,3R,4R,5S)-2-(hydroxymethyl)-5-((6-methoxy-2-(1H-tetrazol-5-yl)pyrimidin-4-yl) amino)tetrahydro-2H-pyran-3,4-diol (Compound A361)

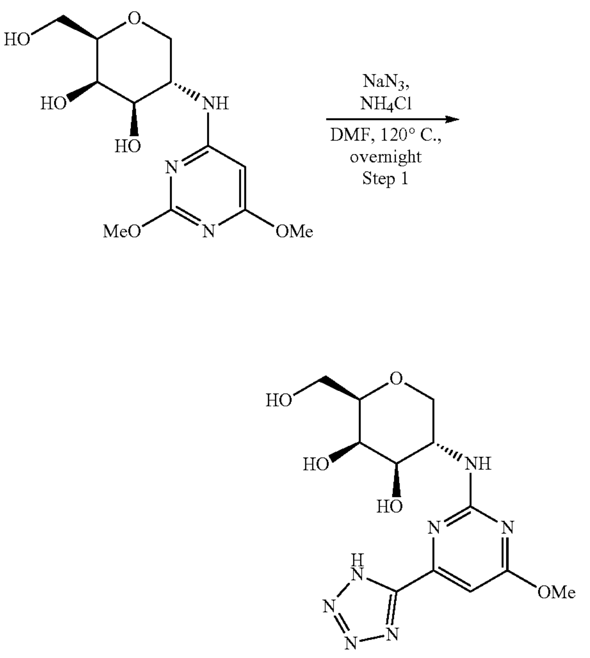 [SMILES: COc1cc(N[C@H]2CO[C@H](CO)[C@H](O)[C@@H]2O)nc(OC)n1 ; COc1cc(-c2nnn[nH]2)nc(N[C@H]2CO[C@H](CO)[C@H](O)[C@@H]2O)n1]

Step 1: A stirred solution of 4-(((3S,4R,5R,6R)-4,5-dihydroxy-6-(hydroxymethyl)tetrahydro-2H-pyran-3-yl)amino)-6-methoxypyrimidine-2-carbonitrile (A346, 30 mg, 0.01 mol) and $NH_4Cl$ (38.3 mg, 0.3 mmol) in DMF (2 mL) at rt under $N_2$ atmosphere was added $NaN_3$ (35.8 mg, 0.2 mmol). After the addition was complete, the reaction was stirred at 120° C. for overnight. On consumption of starting material (LCMS monitoring), the reaction vessel was again cooled to rt. The mixture was concentrated in vacuo. The crude product was purified by pre-HPLC (Method A) to give (2R,3R,4R,5S)-2-(hydroxymethyl)-5-((6-methoxy-2-(1H-tetrazol-5-yl)pyrimidin-4-yl)amino)tetrahydro-2H-pyran-3,4-diol as a yellow solid (6.5 mg, 16% yield). LC-MS (ESI) found: 340 $[M+H]^+$. $^1H$ NMR (400 MHz, MeOD): δ 6.81 (s, 1H), 4.56 (s, 1H), 4.12 (s, 1H), 3.95 (d, J=2.8 Hz, 4H), 3.75 (ddd, J=16.3, 11.3, 6.0 Hz, 2H), 3.65 (d, J=8.0 Hz, 1H), 3.48 (dd, J=6.9, 5.3 Hz, 1H), 3.20 (t, J=10.9 Hz, 1H).

Preparation of (2R,3R,4R,5S)-2-(hydroxymethyl)-5-((6-methoxy-2-(trifluoromethyl)pyrimidin-4-yl) amino)tetrahydro-2H-pyran-3,4-diol (Compound A362)

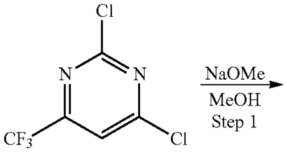

-continued

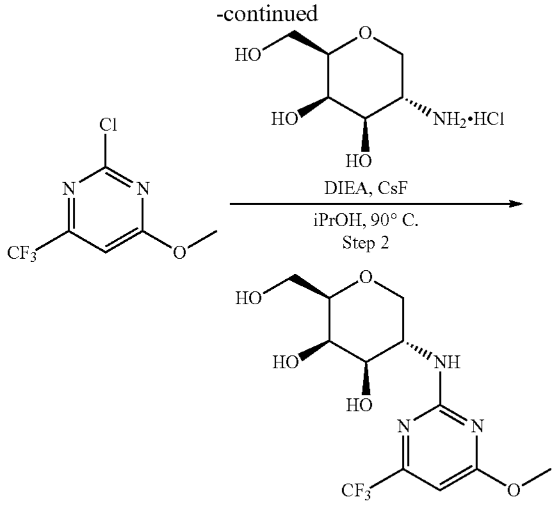

Step 1: To a solution of 2,4-dichloro-6-(trifluoromethyl) pyrimidine (300 mg, 1.39 mmol) in MeOH (10 mL) was added NaOMe (187 mg, 3.47 mmol). The mixture was stirred at 25° C. for 16 h. The mixture was concentrated under reduced pressure to give a crude product, which was purified by column to give 2-chloro-4-methoxy-6-(trifluoromethyl)pyrimidine (200 mg, 68% yield). LC-MS (ESI) found: 213 $[M+H]^+$.

Step 2: To a solution of 2-chloro-4-methoxy-6-(trifluoromethyl)pyrimidine (200 mg, 0.943 mmol) in iPrOH (10 mL) was added DIEA (371 mg, 2.83 mmol) and CsF (72 mg, 0.47 mmol). The mixture was stirred at 90° C. for 16 h. The mixture was concentrated under reduced pressure to give a crude product, which was purified by column to give (2R, 3R,4R,5S)-2-(hydroxymethyl)-5-((4-methoxy-6-(trifluoromethyl)pyrimidin-2-yl)amino)tetrahydro-2H-pyran-3,4-(12 mg, 4% yield). LC-MS (ESI) found: 340 $[M+H]^+$. $^1H$ NMR (400 MHz, MeOD): δ 6.32 (s, 1H), 4.35 (d, J=5.1 Hz, 1H), 4.14 (dd, J=11.0, 5.3 Hz, 1H), 3.95 (s, 3H), 3.90 (d, J=2.9 Hz, 1H), 3.75 (dd, J=11.4, 7.0 Hz, 1H), 3.69 (t, J=5.7 Hz, 1H), 3.64 (dd, J=10.6, 3.2 Hz, 1H), 3.47-3.42 (m, 1H), 3.15 (t, J=10.8 Hz, 1H)

Preparation of (2R,3R,4R,5S)-5-((2,6-dimethoxypyrimidin-4-yl)amino)-2-(hydroxy methyl)tetrahydro-2H-pyran-3,4-diol (Compound A363)

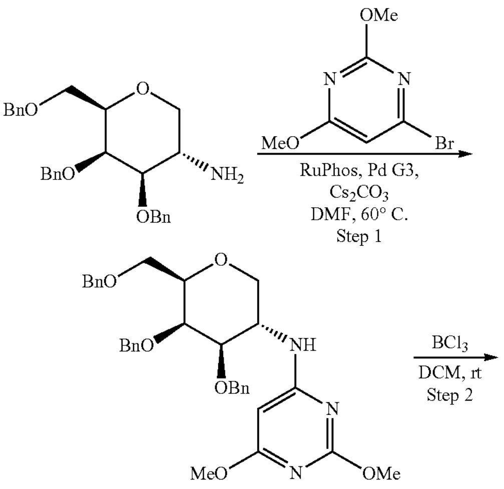

-continued

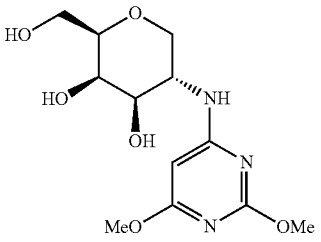

Step 1: To a solution of (3S,4S,5R,6S)-5-benzyl-4-(benzyloxy)-6-((benzyloxy)methyl)tetrahydro-2H-pyran-3-amine (400 mg, 0.96 mmol) in DMF (20 mL) was added 4-bromo-2,6-dimethoxypyrimidine (209 mg, 0.96 mmol), Ruphos.Pd.G3 (80 mg, 0.10 mmol), Ruphos (45 mg, 0.10 mmol), $Cs_2CO_3$ (94 mg, 0.29 mmol). The mixture was stirred at 100° C. for 16 h under $N_2$. The mixture was diluted with water (40 mL), the organic layer was dried over sodium sulfate, filtered, concentrated, and purified by flash column to give N-((3S,4R,5R,6R)-4,5-bis(benzyloxy)-6-((benzyloxy)methyl)tetrahydro-2H-pyran-3-yl)-2,6-dimethoxypyrimidin-4-amine (200 mg, 37% yield). LC-MS (ESI) found: 572 $[M+H]^+$.

Step 2: To a solution of N-((3S,4R,5R,6R)-4,5-bis(benzyloxy)-6-((benzyloxy)methyl)tetrahydro-2H-pyran-3-yl)-2,6-dimethoxypyrimidin-4-amine (200 mg, 0.35 mmol) in DCM (30 mL) was added $BCl_3$ (0.58 mL, 1 M in DCM). The mixture was stirred at 25° C. under $N_2$ for 16 h. $NH_3H_2O$ was added to the mixture until pH was adjusted to 9. The mixture was concentrated under reduced pressure to give a crude product, which was purified by column to give (2R,3R,4R,5S)-5-((2,6-dimethoxypyrimidin-4-yl)amino)-2-(hydroxymethyl)tetrahydro-2H-pyran-3,4-diol (16 mg, 15% yield). LC-MS (ESI) found: 302 $[M+H]^+$. $^1H$ NMR (400 MHz, MeOD): δ: 5.47 (s, 1H), 4.18 (s, 1H), 4.04 (dd, J=11.0, 4.9 Hz, 1H), 3.85 (s, 1H), 3.85 (s, 3H), 3.78 (s, 3H), 3.71 (dd, J=11.3, 7.1 Hz, 1H), 3.64 (dd, J=11.4, 5.0 Hz, 1H), 3.51 (dd, J=10.4, 3.2 Hz, 1H), 3.41-3.36 (m, 1H), 3.06 (t, J=10.9 Hz, 1H).

Preparation of 2-(((3S,4R,5R,6R)-4,5-dihydroxy-6-(hydroxymethyl)tetrahydro-2H-pyran-3-yl)amino)-6-methoxyisonicotinonitrile (Compound A364)

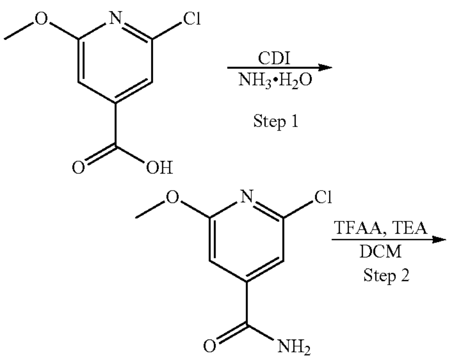

-continued

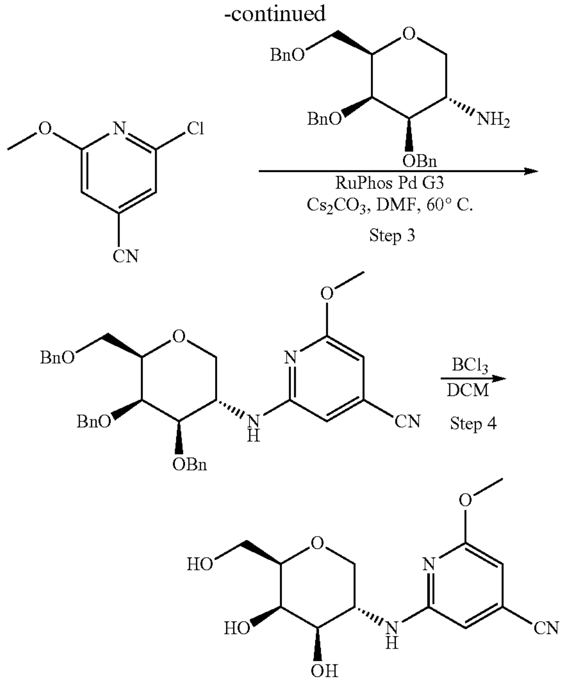

Step 1: To a solution of 2-chloro-6-methoxyisonicotinic acid (400 mg, 2.139 mmol) in DMF (30 mL) was added 1,1'-carbonyldiimidazole (381 mg, 2.353 mmol). The mixture was stirred at 45° C. for 1 h. Then $NH_3H_2O$ (3 mL) was added to the mixture. The mixture was stirred at the room temperature for 2 h. The mixture was concentrated under reduced pressure to give a crude product, which was purified by column to give 2-chloro-6-methoxyisonicotinamide (400 mg, 90% yield). LC-MS (ESI) found: 187 $[M+H]^+$.

Step 2: To a solution of 2-chloro-6-methoxyisonicotinamide (350 mg, 1.872 mmol) in DCM (50 mL) in 0° C. was added TEA (567 mg, 5.616 mmol) and TFAA (472 mg, 2.246 mmol). The mixture was stirred at the room temperature for 2 h. The mixture was concentrated under reduced pressure to give a crude product, which was purified by column to give 2-chloro-6-methoxyisonicotinonitrile (200 mg, 64% yield). LC-MS (ESI) found: 169 $[M+H]^+$.

Step 3: To a solution of 2-chloro-6-methoxyisonicotinonitrile (200 mg, 1.190 mmol) in DMF (3 mL) was added Ruphos Pd G3 (99 mg, 0.119 mmol), Ruphos (57 mg, 0.119 mmol), $Cs_2CO_3$ (1.2 g, 3.57 mmol). The mixture was stirred at 100° C. under $N_2$ for 3 h. The mixture was concentrated under reduced pressure to give a crude product, which was purified by column to give 2-(((3S,4R,5R,6R)-4,5-bis(benzyloxy)-6-((benzyloxy)methyl)tetrahydro-2H-pyran-3-yl)amino)-6-methoxyisonicotinonitrile (160 mg, 24% yield). LC-MS (ESI) found: 566 $[M+H]^+$.

Step 4: To a solution of 2-(((3S,4R,5R,6R)-4,5-bis(benzyloxy)-6-((benzyloxy)methyl)tetrahydro-2H-pyran-3-yl)amino)-6-methoxyisonicotinonitrile (160 mg, 0.283 mmol) in DCM (10 mL) was added $BCl_3$ (0.566 mL, 1 M in DCM). The mixture was stirred at the room temperature for 16 h. The mixture was concentrated under reduced pressure to give a crude product, which was purified by column to give 2-(((3S,4R,5R,6R)-4,5-dihydroxy-6-(hydroxymethyl)tetrahydro-2H-pyran-3-yl)amino)-6-methoxyisonicotinonitrile (20 mg, 24% yield). LC-MS (ESI) found: 296 $[M+H]^+$. $^1H$ NMR (400 MHz, MeOD): δ 6.29 (d, J=0.9 Hz, 1H), 6.12 (d, J=0.9 Hz, 1H), 4.27 (d, J=5.6 Hz, 1H), 4.15 (dd, J=11.0, 5.3

Hz, 1H), 3.90 (d, J=2.6 Hz, 1H), 3.88 (s, 3H), 3.75 (dd, J=11.3, 7.1 Hz, 1H), 3.69 (dd, J=11.4, 5.1 Hz, 1H), 3.58 (dd, J=10.4, 3.2 Hz, 1H), 3.47-3.42 (m, 1H), 3.09 (t, J=10.8 Hz, 1H).

Preparation of 2-(((3S,4R,5R,6R)-4,5-dihydroxy-6-(hydroxymethyl)tetrahydro-2H-pyran-3-yl)amino)-6-methoxyisonicotinamide (Compound A365)

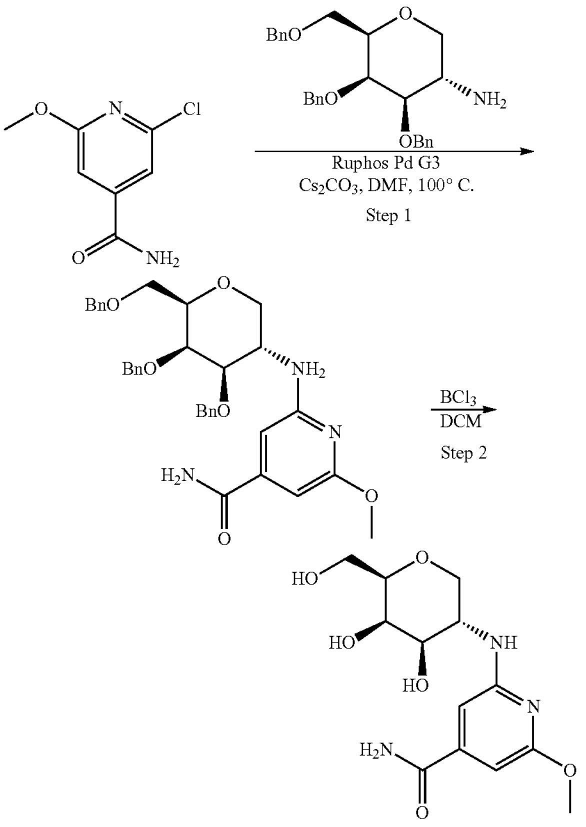

Step 1: To a solution of 2-chloro-6-methoxyisonicotinonitrile (221 mg, 1.190 mmol) in DMF (5 mL) was added Ruphos Pd G3 (99 mg, 0.119 mmol), Ruphos (56 mg, 0.119 mmol), $Cs_2CO_3$ (1.2 g, 3.57 mmol). The mixture was stirred at 100° C. under $N_2$ for 3 h. The mixture was concentrated under reduced pressure to give a crude product, which was purified by column to give 2-(((3S,4R,5R,6R)-4,5-bis(benzyloxy)-6-((benzyloxy)methyl)tetrahydro-2H-pyran-3-yl)amino)-6-methoxyisonicotinamide (80 mg, 12% yield). LC-MS (ESI) found: 584 $[M+H]^+$.

Step 2: To a solution of 2-(((3S,4R,5R,6R)-4,5-bis(benzyloxy)-6-((benzyloxy)methyl)tetrahydro-2H-pyran-3-yl)amino)-6-methoxyisonicotinamide (80 mg, 0.137 mmol) in DCM (10 mL) was added $BCl_3$ (0.274 mL, 1 M in DCM). The mixture was stirred at the room temperature for 16 h. The mixture was concentrated under reduced pressure to give a crude product, which was purified by column to give 2-(((3S,4R,5R,6R)-4,5-dihydroxy-6-(hydroxymethyl)tetrahydro-2H-pyran-3-yl)amino)-6-methoxyisonicotinonitrile (10 mg, 23% yield). LC-MS (ESI) found: 314 $[M+H]^+$. $^1H$ NMR (400 MHz, MeOD): δ 6.44 (d, J=1.2 Hz, 1H), 6.28 (d, J=1.1 Hz, 1H), 4.28-4.14 (m, 2H), 3.91 (d, J=2.6 Hz, 1H), 3.87 (s, 3H), 3.73 (ddd, J=16.3, 11.3, 6.0 Hz, 2H), 3.59 (dd, J=10.1, 3.2 Hz, 1H), 3.45 (dd, J=6.6, 5.5 Hz, 1H), 3.11 (t, J=10.4 Hz, 1H).

Preparation of 4-(((3S,4R,5R,6R)-4,5-dihydroxy-6-(hydroxymethyl)tetrahydro-2H-pyran-3-yl)(methyl)amino)-6-methoxypyrimidine-2-carbonitrile (Compound A366)

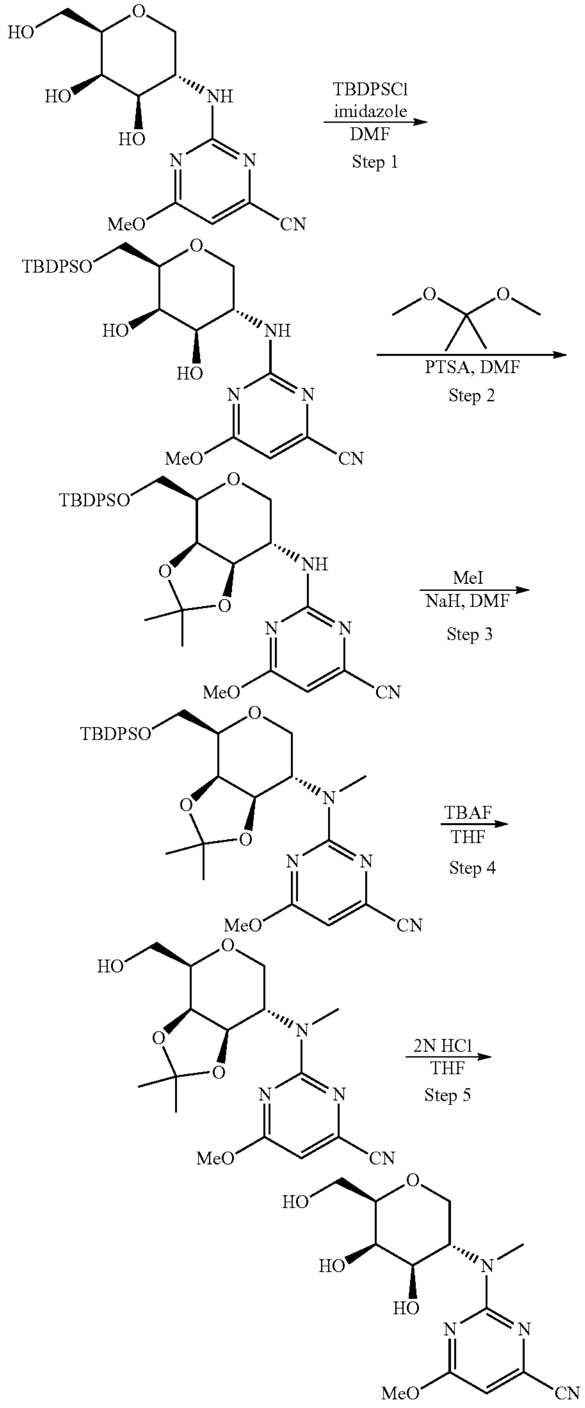

Step 1: To a solution of 4-(((3S,4R,5R,6R)-4,5-dihydroxy-6-(hydroxymethyl)tetrahydro-2H-pyran-3-yl)amino)-

6-methoxypyrimidine-2-carbonitrile (A346, 150 mg, 0.507 mmol) in DMF (10 mL) was added imidazole (69 mg, 1.014 mmol) and TBDPSCl (279 mg, 1.014 mmol). The mixture was stirred at 25° C. for 16 h. The mixture was concentrated under reduced pressure to give a crude product, which was purified by column to give 4-(((3S,4R,5R,6R)-6-(((tert-butyldiphenylsilyl)oxy)methyl)-4,5-dihydroxytetrahydro-2H-pyran-3-yl)amino)-6-methoxypyrimidine-2-carbonitrile (100 mg, 37% yield). LC-MS (ESI) found: 535 $[M+H]^+$.

Step 2: To a solution of 4-(((3S,4R,5R,6R)-6-(((tert-butyldiphenylsilyl)oxy)methyl)-4,5-dihydroxytetrahydro-2H-pyran-3-yl)amino)-6-methoxypyrimidine-2-carbonitrile (100 mg, 0.187 mmol) in 2,2-dimethoxypropane (10 mL) in was added TsOH (4 mg, 0.018 mmol). The mixture was stirred at the room temperature for 16 h. The mixture was concentrated under reduced pressure to give a crude product, which was purified by column to 4-(((3aR,4R,7S,7aR)-4-(((tert-butyldiphenylsilyl)oxy)methyl)-2,2-dimethyltetrahydro-4H-[1,3]dioxolo[4,5-c]pyran-7-yl)amino)-6-methoxypyrimidine-2-carbonitrile (70 mg, 65% yield). LC-MS (ESI) found: 575 $[M+H]^+$.

Step 3: To a solution of 4-(((3aR,4R,7S,7aR)-4-(((tert-butyldiphenylsilyl)oxy)methyl)-2,2-dimethyltetrahydro-4H-[1,3]dioxolo[4,5-c]pyran-7-yl)amino)-6-methoxypyrimidine-2-carbonitrile (70 mg, 0.122 mmol) in DMF (10 mL) was added NaH (9.4 mg, 0.235 mmol, 60% wt. in mineral oil). The mixture was stirred at 0° C. under $N_2$ for 1 h, then MeI (34.6 mg, 0.244 mmol) was added. The mixture was stirred at the room temperature under $N_2$ for 1 h. The mixture was added drops of saturated aqueous $NH_4Cl$ and concentrated under reduced pressure to give a crude product, which was purified by column to give 4-(((3aR,4R,7S,7aR)-4-(((tert-butyldiphenylsilyl)oxy)methyl)-2,2-dimethyltetrahydro-4H-[1,3]dioxolo[4,5-c]pyran-7-yl)(methyl)amino)-6-methoxypyrimidine-2-carbonitrile (25 mg, 35% yield). LC-MS (ESI) found: 589 $[M+H]^+$.

Step 4: To a solution of 4-(((3aR,4R,7S,7aR)-4-(((tert-butyldiphenylsilyl)oxy)methyl)-2,2-dimethyltetrahydro-4H-[1,3]dioxolo[4,5-c]pyran-7-yl)(methyl)amino)-6-methoxypyrimidine-2-carbonitrile (15 mg, 0.043 mmol) in THF (1 mL) was added TBAF (0.086 mL, 1 M in THF). The mixture was stirred at the room temperature for 16 h. The mixture was concentrated under reduced pressure to give a crude product, which was purified by column to give 4-(((3aR,4R,7S,7aR)-4-(hydroxymethyl)-2,2-dimethyltetrahydro-4H-[1,3]dioxolo[4,5-c]pyran-7-yl)(methyl)amino)-6-methoxypyrimidine-2-carbonitrile (10 mg, 67% yield). LC-MS (ESI) found: 351 $[M+H]^+$.

Step 5: To a solution of 4-(((3aR,4R,7S,7aR)-4-(hydroxymethyl)-2,2-dimethyltetrahydro-4H-[1,3]dioxolo[4,5-c]pyran-7-yl)(methyl)amino)-6-methoxypyrimidine-2-carbonitrile (10 mg, 0.029 mmol) in THF (1 mL) was added drops of HCl (1N in $H_2O$). The mixture was stirred at the room temperature for 16 h. The mixture was concentrated under reduced pressure to give 4-(((3S,4R,5R,6R)-4,5-dihydroxy-6-(hydroxymethyl)tetrahydro-2H-pyran-3-yl)(methyl)amino)-6-methoxypyrimidine-2-carbonitrile (1.5 mg, 17% yield). LC-MS (ESI) found: 311 $[M+H]^+$. $^1H$ NMR (400 MHz, MeOD): δ 6.43 (s, 1H), 3.97 (s, 2H), 3.97 (s, 3H), 3.86 (dd, J=10.8, 5.2 Hz, 1H), 3.76 (dd, J=11.3, 7.1 Hz, 1H), 3.69 (dd, J=11.3, 5.0 Hz, 1H), 3.49 (dd, J=6.6, 5.4 Hz, 2H), 3.13 (m, 4H).

Preparation of (2R,3R,4R,5S)-5-((4-chloro-6-ethoxypyrimidin-2-yl)amino)-2-(hydroxymethyl)tetrahydro-2H-pyran-3,4-diol (Compound A367) and 2-(((3S,4R,5R,6R)-4,5-dihydroxy-6-(hydroxymethyl)tetrahydro-2H-pyran-3-yl)amino)-6-ethoxypyrimidine-4-carbonitrile (Compound A368)

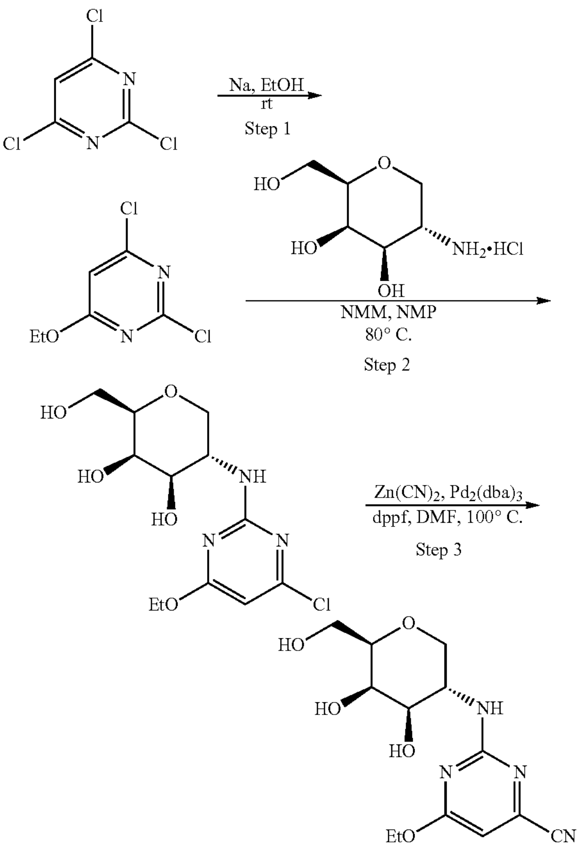

Step 1: A mixture of Na (110 mg, 4.8 mmol) in EtOH (10.0 mL) was stirring at rt for 1 h, 2,4,6-trichloropyrimidine (0.56 mL, 4.8 mmol) was added and the mixture was further stirred for 1 h. Then the reaction mixture was concentrated and purified by chromatography on (silica gel, 0-10% ethyl acetate in petroleum) to give 2,4-dichloro-6-ethoxypyrimidine (630 mg, 68% yield) as a white solid. LC-MS (ESI) found: 193 $[M+H]^+$.

Step 2: To a mixture of 2,4-dichloro-6-ethoxypyrimidine (416 mg, 2.2 mmol) in NMP (5.0 mL) was added A92, (200 mg, 1.2 mmol) and NMM (0.71 mL, 4.3 mmol) at rt under $N_2$. After stirring at 120° C. overnight, the mixture was concentrated and purified by chromatography on (silica gel, 0-50% ethyl acetate in petroleum) to give (2R,3R,4R,5S)-5-((4-chloro-6-ethoxypyrimidin-2-yl)amino)-2-(hydroxymethyl)tetrahydro-2H-pyran-3,4-diol (A367, 200 mg, 44% yield) as a yellow solid. LC-MS (ESI) found: 320 $[M+1]^+$. $^1H$ NMR (400 MHz, MeOD): δ 6.02 (s, 1H), 4.45-4.22 (m, 3H), 4.10 (dd, J=10.8, 5.2 Hz, 1H), 3.90 (d, J=2.8 Hz, 1H), 3.77-3.58 (m, 3H), 3.47-3.39 (m, 1H), 3.13 (t, J=10.8 Hz, 1H), 1.34 (t, J=7.1 Hz, 3H).

Step 3: To a mixture of (2R,3R,4R,5S)-5-((4-chloro-6-ethoxypyrimidin-2-yl)amino)-2-(hydroxymethyl)tetrahydro-2H-pyran-3,4-diol (A367, 60 mg, 0.19 mmol) in DMF (3.0 mL) was added $Zn(CN)_2$ (26 mg, 0.23 mmol), dppf (10.4 mg, 0.02 mmol) and $Pd_2(dba)_3$ (17.2 mg, 0.02 mmol) at rt under $N_2$. After stirring at 120° C. overnight, the reaction mixture was concentrated and purified by prep-TLC to give 2-(((3S,4R,5R,6R)-4,5-dihydroxy-6-(hydroxymethyl)tetrahydro-2H-pyran-3-yl)amino)-6-ethoxypyrimidine-4-carbonitrile (4.3 mg, 7% yield) as a white solid. LC-MS (ESI) found: 311 $[M+H]^+$. $^1H$ NMR (400 MHz, MeOD): δ 6.41 (s, 1H), 4.55-4.20 (m, 3H), 4.08 (dd, J=11.0, 5.3 Hz, 1H), 3.90 (d, J=2.9 Hz, 1H), 3.79-3.57 (m, 3H), 3.48-3.39 (m, 1H), 3.13 (t, J=10.9 Hz, 1H), 1.35 (t, J=6.9 Hz, 3H).

Preparation of 2-(((3S,4R,5R,6R)-4,5-dihydroxy-6-(hydroxymethyl)tetrahydro-2H-pyran-3-yl)amino)-4-(trifluoromethyl)thiazole-5-carbonitrile (Compound A369)

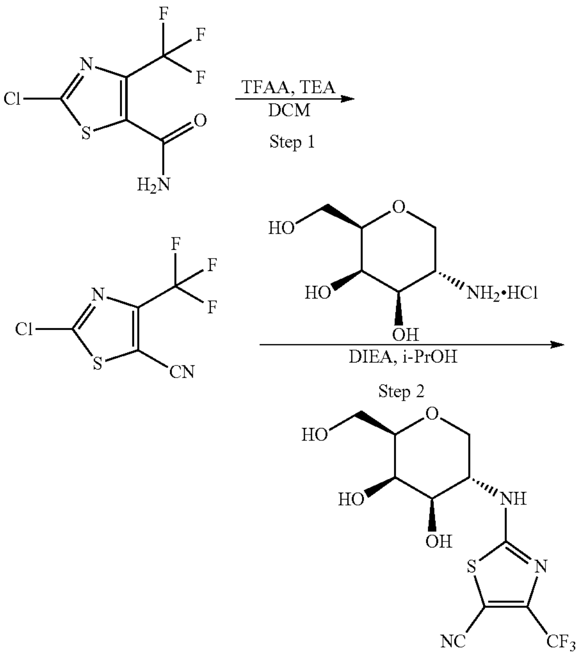

Step 1: 2-chloro-4-(trifluoromethyl)-1,3-thiazole-5-carboxamide (200 mg, 0.87 mmol) in DCM (10 ml) was added TEA (184 mg, 1.82 mmol) and TFAA (305 mg, 1.45 mmol) at 0° C., the mixture was stirred at rt for 3 h. The mixture was neutralized by $NaHCO_3$, extracted with DCM, purified by Silica (silica gel, 0-100% EA in PE) to give 2-chloro-4-(trifluoromethyl)-1,3-thiazole-5-carbonitrile (70 mg, 38% yield) as solid. LC-MS (ESI) found: 212 $[M+H]^+$.

Step 2: (2R,3R,4R)-5-amino-2-(hydroxymethyl)oxane-3,4-diol (A92, 50 mg, 0.31 mmol), 2-chloro-4-(trifluoromethyl)-1,3-thiazole-5-carbonitrile (68 mg, 0.32 mmol) and DIPEA (119 mg, 0.92 mmol) in i-PrOH (3 mL) were stirred at 120° C. for 12 h. The mixture was concentrated and purified by to give 2-(((3S,4R,5R,6R)-4,5-dihydroxy-6-(hydroxymethyl)tetrahydro-2H-pyran-3-yl)amino)-4-(trifluoromethyl)thiazole-5-carbonitrile (18 mg, 17% yield) as solid. LC-MS (ESI) found: 315 $[M+H]^+$. $^1H$ NMR (400 MHz, $CD_3OD$): δ 7.08 (s, 1H), 4.16 (dd, J=11.0, 5.2 Hz, 1H), 4.04 (td, J=10.5, 5.2 Hz, 1H), 3.89 (d, J=2.9 Hz, 1H), 3.74 (dd, J=11.4, 7.1 Hz, 1H), 3.67 (dd, J=11.4, 5.0 Hz, 1H), 3.57 (dd, J=10.3, 3.2 Hz, 1H), 3.43 (dd, J=6.5, 5.5 Hz, 1H), 3.14 (t, J=10.8 Hz, 1H).

Preparation of (2R,3R,4R,5S)-5-((6-chloro-2-(methylsulfonyl)pyrimidin-4-yl)amino)-2-(hydroxymethyl)tetrahydro-2H-pyran-3,4-diol (Compound A370)

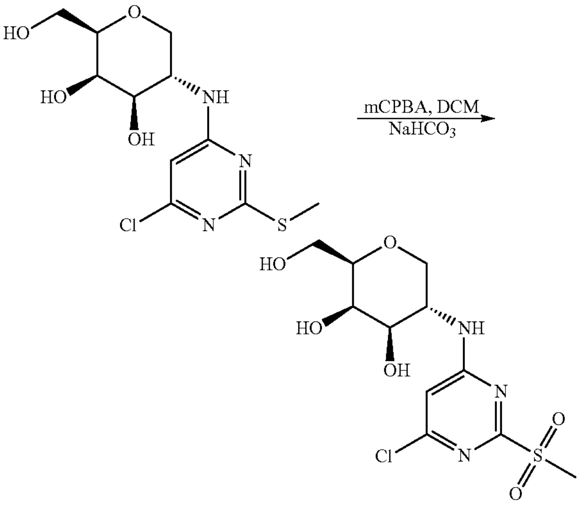

Step 1: A solution of (2R,3R,4R,5S)-5-((6-chloro-2-(methylthio)pyrimidin-4-yl)amino)-2-(hydroxymethyl)tetrahydro-2H-pyran-3,4-diol (A331, 30 mg, 0.09 mmol), mCPBA (48 mg, 0.28 mmol) in DCM (5 mL) was stirred at rt for 12 h. The mixture was concentrated and purified by C18 column to give (2R,3R,4R,5S)-5-((6-chloro-2-(methylsulfonyl)pyrimidin-4-yl)amino)-2-(hydroxymethyl)tetrahydro-2H-pyran-3,4-diol (2.2 mg, 6% yield) as white solid. LC-MS (ESI) found: 354 $[M+H]^+$. $^1H$ NMR (400 MHz, $CD_3OD$): δ 6.65 (s, 1H), 4.49 (td, J=10.7, 5.3 Hz, 1H), 4.09 (dd, J=10.9, 5.2 Hz, 1H), 3.90 (d, J=2.6 Hz, 1H), 3.75 (dd, J=11.4, 7.1 Hz, 1H), 3.68 (dd, J=11.4, 5.0 Hz, 1H), 3.60 (dd, J=10.6, 3.2 Hz, 1H), 3.49-3.39 (m, 2H), 3.13 (t, J=10.9 Hz, 1H).

Preparation of (2R,3R,4R,5S)-2-(hydroxymethyl)-5-((4-(methylsulfonyl)pyrimidin-2-yl)amino)tetrahydro-2H-pyran-3,4-diol (Compound A371)

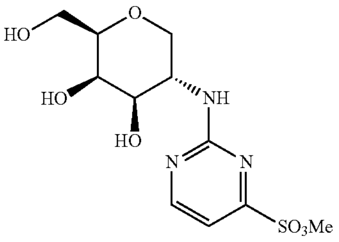

It was prepared according to the procedure same as that for A370 by using A336 as the starting material. Yield: 8.1 mg, 25%, white solid. LC-MS (ESI) found: 320 $[M+H]^+$. $^1H$ NMR (400 MHz, $CD_3OD$): δ 8.59 (d, J=4.3 Hz, 1H), 7.10

(d, J=4.8 Hz, 1H), 4.39 (td, J=10.2, 4.8 Hz, 1H), 4.09 (dd, J=11.0, 5.2 Hz, 1H), 3.91 (d, J=2.7 Hz, 1H), 3.76 (dd, J=11.4, 7.1 Hz, 1H), 3.72-3.63 (m, 2H), 3.50-3.42 (m, 1H), 3.27-3.12 (m, 4H).

Preparation of 2-(((3S,4R,5R,6R)-4,5-dihydroxy-6-(hydroxymethyl)tetrahydro-2H-pyran-3-yl)amino)thiazole-5-carbonitrile (Compound A372)

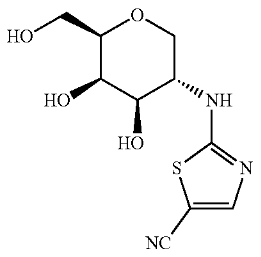 [SMILES: N#Cc1cnc(N[C@H]2CO[C@H](CO)[C@H](O)[C@@H]2O)s1]

It was prepared according to the procedure same as that for A363 using 2-chlorothiazole-5-carbonitrile. LC-MS (ESI) found: 272 $[M+H]^+$. 1H NMR (400 MHz, MeOD): δ 7.68 (s, 1H), 4.12 (dd, J=10.7, 5.2 Hz, 1H), 4.06 (m, 1H), 3.89 (d, J=2.6 Hz, 1H), 3.74 (dd, J=11.4, 7.0 Hz, 1H), 3.67 (dd, J=11.4, 5.0 Hz, 1H), 3.58 (dd, J=10.1, 3.2 Hz, 1H), 3.46-3.40 (m, 1H), 3.16 (t, J=10.6 Hz, 1H).

Preparation of 4-(((3S,4R,5R,6R)-4,5-dihydroxy-6-(hydroxymethyl)tetrahydro-2H-pyran-3-yl)amino)pyrrolo[2,1-f][1,2,4]triazine-2-carbonitrile (Compound A373)

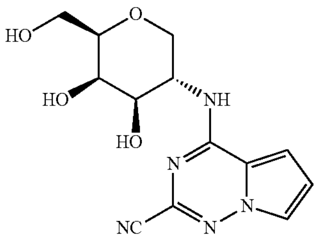 [SMILES: N#Cc1nc(N[C@H]2CO[C@H](CO)[C@H](O)[C@@H]2O)c2cccn2n1]

It was prepared according to the procedure same as that for A346 by using A304 as the starting material. Yield: 6.4 mg, 13%, white solid. $^1H$ NMR (400 MHz, $CD_3OD$): δ 7.63 (dd, J=2.7, 1.5 Hz, 1H), 6.99 (dd, J=4.4, 1.4 Hz, 1H), 6.77 (dd, J=4.4, 2.7 Hz, 1H), 4.73 (td, J=10.7, 5.2 Hz, 1H), 4.11 (dd, J=11.0, 5.3 Hz, 1H), 3.94 (d, J=2.7 Hz, 1H), 3.78 (dd, J=6.2, 5.2 Hz, 1H), 3.75 (d, J=3.5 Hz, 1H), 3.70 (dd, J=11.4, 5.0 Hz, 1H), 3.50-3.44 (m, 1H), 3.25 (t, J=10.9 Hz, 1H).

Preparation of methyl 2-(((3S,4R,5R,6R)-4,5-dihydroxy-6-(hydroxymethyl)tetrahydro-2H-pyran-3-yl)amino)-6-methoxypyrimidine-4-carboxylate (Compound A374)

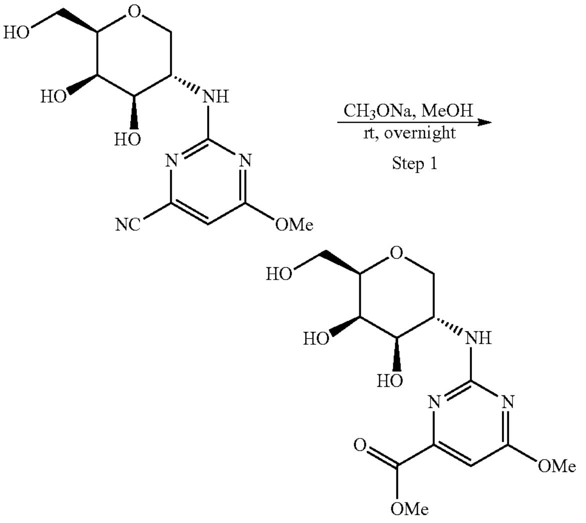

To a stirred solution of 2-(((3S,4R,5R,6R)-4,5-dihydroxy-6-(hydroxymethyl)tetrahydro-2H-pyran-3-yl)amino)-6-methoxypyrimidine-4-carbonitrile (A346, 30 mg, 0.01 mol) in MeOH (5 mL) at rt under $N_2$ atmosphere was added $CH_3ONa$ (0.1 mL, 5 M in MeOH). After the addition was complete, the reaction was stirred at rt overnight. On consumption of starting material (LCMS monitoring), the mixture was adjusted pH to 5 and concentrated in vacuo. The crude product was purified by pre-HPLC (Method A) to give methyl 2-(((3S,4R,5R,6R)-4,5-dihydroxy-6-(hydroxymethyl)tetrahydro-2H-pyran-3-yl)amino)-6-methoxypyrimidine-4-carboxylate as a white solid (1.5 mg, 5% yield). LC-MS (ESI) found: 330$[M+H]^+$. $^1H$ NMR (400 MHz, MeOD): δ 6.62 (s, 1H), 4.36 (d, J=5.8 Hz, 1H), 4.13 (s, 1H), 3.93 (d, J=23.1 Hz, 4H), 3.72 (ddd, J=16.3, 11.4, 6.1 Hz, 2H), 3.65-3.59 (m, 1H), 3.46 (dd, J=11.5, 5.3 Hz, 1H), 3.31 (dd, J=3.1, 1.5 Hz, 3H), 3.16 (dd, J=18.2, 7.3 Hz, 1H).

Preparation of methyl 2-(((3S,4R,5R,6R)-4,5-dihydroxy-6-(hydroxymethyl)tetrahydro-2H-pyran-3-yl)amino)-6-methoxypyrimidine-4-carbimidate (Compound A375)

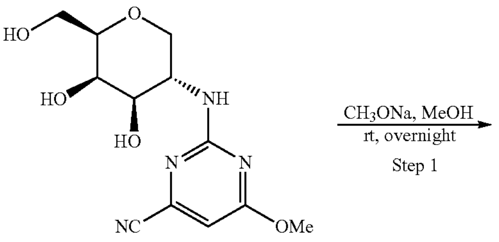

-continued

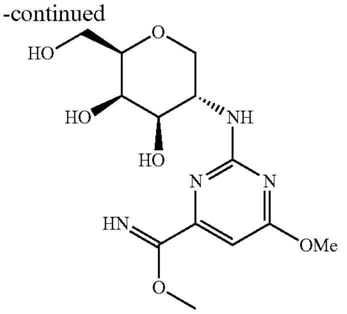

To a stirred solution of 2-(((3S,4R,5R,6R)-4,5-dihydroxy-6-(hydroxymethyl)tetrahydro-2H-pyran-3-yl)amino)-6-methoxypyrimidine-4-carbonitrile (A346, 30 mg, 0.01 mol) in MeOH (5 mL) at rt under $N_2$ atmosphere was added $CH_3ONa$ (36 mg, 0.2 mmol). After the addition was complete, the reaction was stirred at rt overnight. On consumption of starting material (LCMS monitoring), the mixture was concentrated in vacuo. The crude product was directly purified by pre-HPLC under basic condition to give methyl 2-(((3S,4R,5R,6R)-4,5-dihydroxy-6-(hydroxymethyl)tetrahydro-2H-pyran-3-yl)amino)-6-methoxypyrimidine-4-carboxylate as a white solid (1.5 mg, 5% yield). LC-MS (ESI) found: 329[M+H]$^+$. $^1$H NMR (400 MHz, MeOD): δ 6.43 (s, 1H), 4.42 (s, 1H), 4.13 (dd, J=11.0, 5.3 Hz, 1H), 3.94 (d, J=23.7 Hz, 4H), 3.73 (ddd, J=16.4, 11.4, 6.1 Hz, 2H), 3.63 (dd, J=10.6, 3.2 Hz, 1H), 3.51-3.40 (m, 1H), 3.36-3.30 (m, 3H), 3.14 (dd, J=12.8, 9.0 Hz, 1H).

1-OMe-α-galactose Series

Preparation of (2R,3R,4R,5R,6S)-5-((5-chloro-3-fluoropyridin-2-yl)amino)-2-(hydroxymethyl)-6-methoxytetrahydro-2H-pyran-3,4-diol (Compound A376)

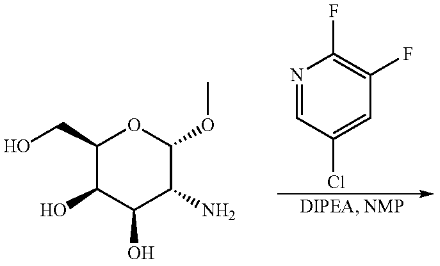

-continued

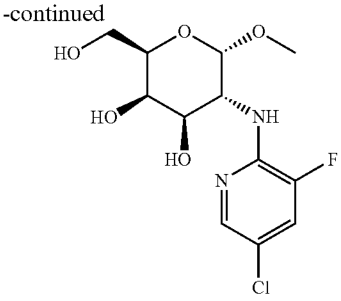

Step 1: To a mixture of (2R,3R,4R,5R,6S)-5-amino-2-(hydroxymethyl)-6-methoxytetrahydro-2H-pyran-3,4-diol (A91, 50 mg, 0.25 mmol) in NMP (2 mL) were added 5-chloro-2,3-difluoropyridine (116 mg, 0.75 mmol) and DIEA (0.17 mL, 1.0 mmol) at rt under $N_2$. After stirring at 120° C. overnight, the mixture was concentrated and purified by prep-HPLC (Method A) to give (2R,3R,4R,5R,6S)-5-((5-chloro-3-fluoropyridin-2-yl)amino)-2-(hydroxymethyl)-6-methoxytetrahydro-2H-pyran-3,4-diol (3.9 mg, 7.8% yield) as a white solid. No LCMS. $^1$H NMR (400 MHz, MeOD): δ 8.51 (s, 1H), 7.79 (d, J=2.1 Hz, 1H), 7.37 (dd, J=10.7, 2.1 Hz, 1H), 4.83 (s, 1H), 4.56 (d, J=3.7 Hz, 1H), 3.93 (d, J=3.1 Hz, 1H), 3.86 (dd, J=10.8, 3.2 Hz, 1H), 3.82-3.79 (m, 1H), 3.77-3.71 (m, 2H), 3.37 (s, 3H).

The following compounds below were prepared according to the procedure same as A376:

| ID | Characterization data | Starting Material |
|---|---|---|
| 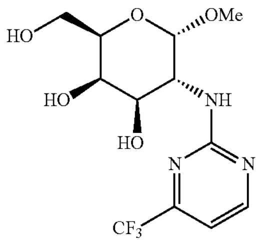 A377 | Yield: 4.1 mg, 7.8%, white solid. LC-MS (ESI) found: 340 [M + H]$^+$. $^1$H NMR (400 MHz, MeOD): δ 8.51 (d, J = 4.8 Hz, 1H), 6.90 (d, J = 4.9 Hz, 1H), 4.81 (s, 1H), 4.52 (s, 1H), 3.93 (d, J = 2.8 Hz, 1H), 3.88-3.79 (m, 2H), 3.78-3.70 (m, 2H), 3.38 (s, 3H). | 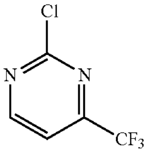 [SMILES: FC(F)(F)c1ccnc(Cl)n1] |

-continued

| ID | Characterization data | Starting Material |
|---|---|---|
| 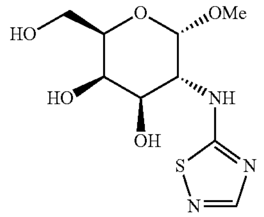 A378 | Yield: 0.8 mg, 1.9%, white solid. LC-MS (ESI) found: 278 [M + H]$^+$. $^1$H NMR (400 MHz, MeOD): δ 7.82 (s, 1H), 4.83-4.82 (m, 1H), 4.17 (t, J = 4.9 Hz, 1H), 3.91 (d, J = 2.9 Hz, 1H), 3.85-3.79 (m, 2H), 3.76-3.73 (m, 2H), 3.40 (s, 3H). | 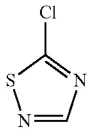 |
| 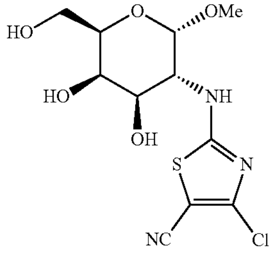 A379 | Yield: 1.2 mg, 1.4%, white solid. LC-MS (ESI) found: 336 [M + H]$^+$. $^1$H NMR (400 MHz, MeOD): δ 4.82 (d, J = 3.7 Hz, 1H), 4.26 (s, 1H), 3.90 (d, J = 3.1 Hz, 1H), 3.80 (dd, J = 10.6, 3.0 Hz, 2H), 3.73 (dd, J = 6.9, 5.9 Hz, 2H), 3.39 (s, 3H). | 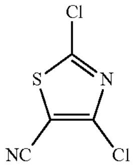 |
| 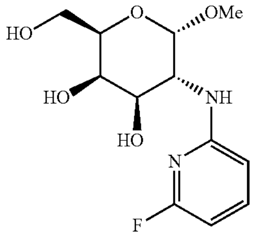 A380 | Yield: 3.2 mg, 7.2%, white solid. LC-MS (ESI) found: 289 [M + H]$^+$. $^1$H NMR (400 MHz, MeOD): δ 7.46 (dd, J = 16.3, 8.1 Hz, 1H), 6.43 (dd, J = 8.1, 2.2 Hz, 1H), 6.06 (dd, J = 7.6, 1.9 Hz, 1H), 4.79 (d, J = 3.6 Hz, 1H), 4.33 (dd, J = 10.8, 3.6 Hz, 1H), 3.91 (d, J = 3.0 Hz, 1H), 3.83-3.72 (m, 4H), 3.37 (s, 3H). | 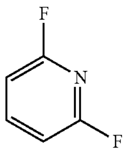 |
| 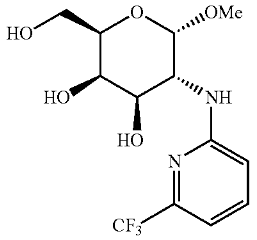 A381 | Yield: δ mg, 8.6%, white solid. LC-MS (ESI) found: 339 [M + H]$^+$. $^1$H NMR (400 MHz, MeOD): δ 7.53 (t, J = 7.9 Hz, 1H), 6.88 (d, J = 7.2 Hz, 1H), 6.80 (d, J = 8.6 Hz, 1H), 4.87 (s, 1H), 4.44 (dd, J = 10.8, 3.6 Hz, 1H), 3.92 (d, J = 3.0 Hz, 1H), 3.86-3.71 (m, 4H), 3.37 (s, 3H) | 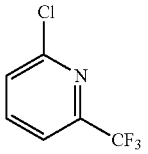 |

Preparation of (2R,3R,4R,5R,6S)-5-((3-(dimethylamino)-1,2,4-thiadiazol-5-yl)amino)-2-(hydroxymethyl)-6-methoxytetrahydro-2H-pyran-3,4-diol (Compound A114)

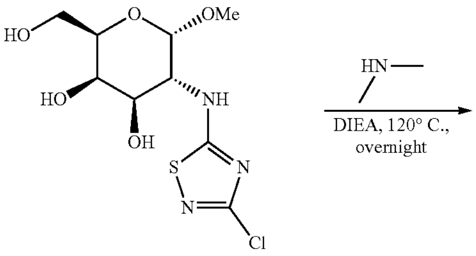

-continued

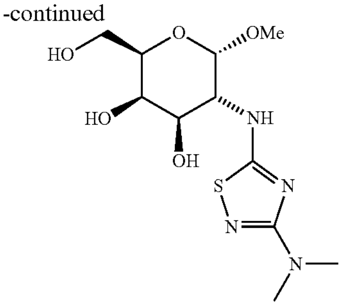

A solution of (2R,3R,4R,5R,6S)-5-((3-chloro-1,2,4-thiadiazol-5-yl)amino)-2-(hydroxymethyl)-6-methoxytetrahydro-2H-pyran-3,4-diol (10 mg, 0.03 mmol), dimethylamine (2.2 mg, 0.05 mmol) and DIEA (11.6 mg, 0.09 mmol) in i-PrOH (4 mL) was stirred at 120° C. overnight. The mixture was concentrated in vacuo. The crude product was purified by prep-HPLC (Method A) to give (2R,3R,4R,5R,6S)-5-((3-

(dimethylamino)-1,2,4-thiadiazol-5-yl)amino)-2-(hydroxymethyl)-6-methoxytetrahydro-2H-pyran-3,4-diol (0.8 mg, 8% yield) as white solid. LC-MS (ESI) found: 321 $[M+H]^+$. $^1H$ NMR (400 MHz, Methanol-$d_4$): δ 4.85-4.81 (m, 1H), 4.12 (d, J=13.7 Hz, 1H), 3.90 (d, J=3.2 Hz, 1H), 3.81 (ddd, J=11.4, 7.8, 3.3 Hz, 2H), 3.77-3.67 (m, 2H), 3.39 (s, 3H), 3.04 (s, 6H).

The following compound below was prepared according to the procedure same as A114.

| | |
|---|---|
| 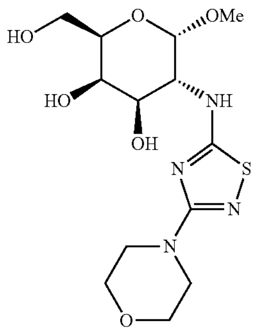 A382 | Yield: 0.5 mg, 0.1%, white solid. LC-MS (ESI) found: 363 $[M + H]^+$. $^1H$ NMR (400 MHz, MeOD): δ 4.78 (d, J = 9.0 Hz, 1H), 4.21-4.09 (m, 1H), 3.90 (d, J = 2.4 Hz, 1H), 3.85-3.76 (m, 2H), 3.76-3.67 (m, 6H), 3.56-3.46 (m, 4H), 3.39 (s, 3H). |

1-OMe-β-galactose Series

Preparation of (2R,3R,4R,5R,6R)-5-((3,5-difluoropyridin-2-yl)amino)-2-(hydroxymethyl)-6-methoxytetrahydro-2H-pyran-3,4-diol (Compound A383)

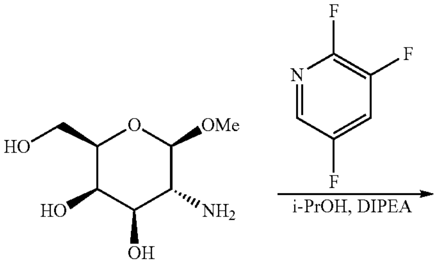

-continued

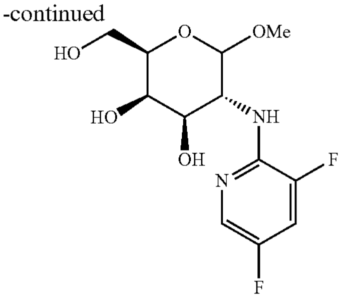

A solution of (2R,3R,4R,5R,6R)-5-amino-2-(hydroxymethyl)-6-methoxytetrahydro-2H-pyran-3,4-diol (30 mg, 0.16 mmol), DIPEA (91 mg, 0.70 mmol) and 2,3,5-trifluoropyridine (93 mg, 0.70 mmol) in i-PrOH (2 mL) was stirred at 120° C. overnight. The mixture was concentrated and the residue was purified by prep-HPLC (Method A) to give (2R,3R,4R,5R,6R)-5-((3,5-difluoropyridin-2-yl)amino)-2-(hydroxymethyl)-6-methoxytetrahydro-2H-pyran-3,4-diol (1.2 mg, 2% yield) as a white solid. LC-MS (ESI) found: 307 $[M+H]^+$. $^1H$ NMR (400 MHz, MeOD): δ 7.12 (dd, J=4.7, 2.5 Hz, 2H), 4.25 (d, J=8.1 Hz, 1H), 3.88 (d, J=3.0 Hz, 1H), 3.81-3.75 (m, 2H), 3.65 (dd, J=10.5, 3.5 Hz, 2H), 3.53 (t, J=6.1 Hz, 1H), 3.45 (s, 3H).

The following compounds below were prepared according to the procedure same as A383:

| ID | Characterization data | Starting Material |
|---|---|---|
| 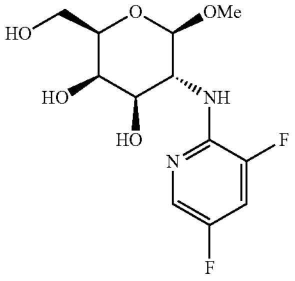 A383 | Yield: 1.2 mg, 2%, white solid. LC-MS (ESI) found: 307 $[M + H]^+$. $^1H$ NMR (400 MHz, MeOD): δ 7.12 (dd, J = 4.7, 2.5 Hz, 2H), 4.25 (d, J = 8.1 Hz, 1H), 3.88 (d, J = 3.0 Hz, 1H), 3.81-3.75 (m, 2H), 3.65 (dd, J = 10.5, 3.5 Hz, 2H), 3.53 (t, J = 6.1 Hz, 1H), 3.45 (s, 3H). | 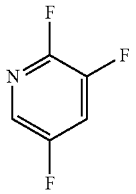 |

-continued

| ID | Characterization data | Starting Material |
|---|---|---|
| 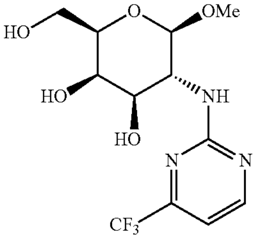 A384 | Yield: 12.1 mg, 14%, white solid. LC-MS (ESI) found: 340 $[M + H]^+$. $^1H$ NMR (400 MHz, MeOD): δ 8.48 (d, J = 4.9 Hz, 1H), 6.86 (d, J = 4.9 Hz, 1H), 4.42 (d, J = 8.4 Hz, 1H), 4.32 - 4.23 (m, 1H), 3.88 (d, J = 3.0 Hz, 1H), 3.76 (dt, J = 12.4, 7.1 Hz, 3H), 3.54 (t, J = 6.1 Hz, 1H), 3.44 (s, 3H). | 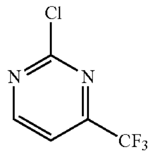 [SMILES: FC(F)(F)c1ccnc(Cl)n1] |
| 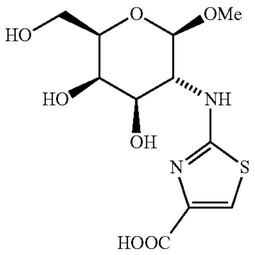 A385 | Yield: 32.3 mg, 33%, white solid. LC-MS (ESI) found: 321 $[M + H]^+$. $^1H$ NMR (400 MHz, MeOD): δ 8.22 (m, 1H), 8.18(s, 1H), 4.71-4.59 (m, 2H), 4.58-4.50 (m, 1H), 4.44-4.33 (dd, J = 11.4, 7.2 Hz, 1H), 4.04-3.96 (d, 1H), 3.78-3.63(m, 3H), 3.61-3.55 (m, 2H), 3.30 (s,3H). | 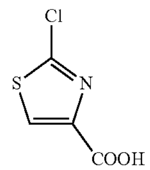 |
| 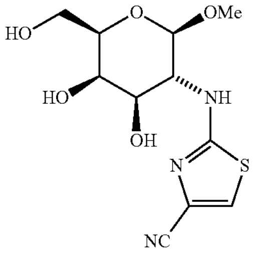 A386 | Yield: 30.4 mg, 39.0%, colorless oil. LC-MS (ESI) found: 302$[M + H]^+$. $^1H$ NMR (400 MHz, $D_2O$): δ 7.52 (s, 1H), 4.39 (d, J = 8.2 Hz, 1H), 3.92 (d, J = 3.0 Hz, 1H), 3.74 (m, 3H), 3.64 (m, 2H), 3.45 (s, 3H). | 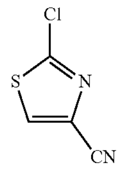 |

Preparation of (2R,3R,4R,5R,6R)-5-((1,2,4-thiadiazol-5-yl)amino)-2-(hydroxymethyl)-6-methoxytetrahydro-211-pyran-3,4-diol (Compound A110)

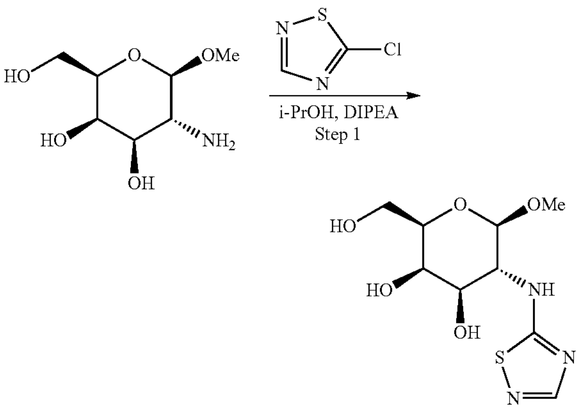

Step 1: A solution of (2R,3R,4R,5R,6R)-5-amino-2-(hydroxymethyl)-6-methoxytetrahydro-2H-pyran-3,4-diol (A90, 30 mg, 0.16 mmol), DIPEA (40 mg, 0.31 mmol) and 5-chloro-1,2,4-thiadiazole (22.4 mg, 0.19 mmol) in i-PrOH (1 mL) was stirred at 120° C. overnight. The mixture was concentrated and the residue was purified by prep-HPLC (Method A) to give (2R,3R,4R,5R,6R)-5-((1,2,4-thiadiazol-5-yl)amino)-2-(hydroxymethyl)-6-methoxytetrahydro-2H-pyran-3,4-diol (6.8 mg, 16% yield) as a white solid. LC-MS (ESI) found: 277 $[M+H]^+$. $^1H$ NMR (400 MHz, $CD_3OD$): δ 7.82 (s, 1H), 4.34 (d, J=8.1 Hz, 1H), 3.87 (d, J=3.1 Hz, 1H), 3.83-3.68 (m, 4H), 3.55-3.51 (m, 1H), 3.47 (s, 3H).

Preparation of 6-(((2R,3R,4R,5R,6R)-4,5-dihydroxy-6-(hydroxymethyl)-2-methoxy tetrahydro-2H-pyran-3-yl)amino)-1,3,5-triazine-2,4(1H,3H)-dione (Compound A112)

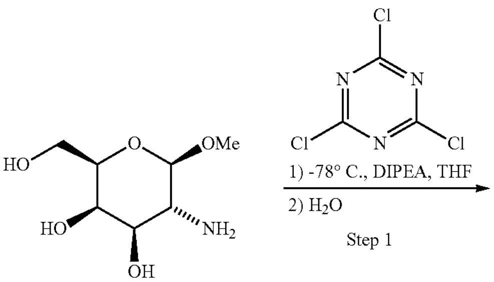

-continued

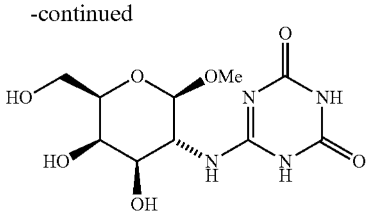

Step 1: To a solution of 2,4,6-trichloro-1,3,5-triazine (187 mg 1.03 mmol) in THF (5 mL) was added DIPEA (200 mg, 1.55 mmol) at −78° C. (2R,3R,4R,5R,6R)-5-amino-2-(hydroxymethyl)-6-methoxytetrahydro-2H-pyran-3,4-diol (100 mg, 0.51 mmol) was then added at −78° C. The mixture was further stirred for 2 h at −78° C. Then it was quenched by adding $H_2O$ (5 mL). The mixture was warmed to rt and stirred for another 2 h. The solvent was evaporated and the residual was purified by prep-HPLC (Method A) to give 6-(((2R,3R,4R,5R,6R)-4,5-dihydroxy-6-(hydroxymethyl)-2-methoxytetrahydro-2H-pyran-3-yl)amino)-1,3,5-triazine-2,4(1H,3H)-dione (6.1 mg, 4% yield) as white solid. LC-MS (ESI) found: 305 $[M+H]^+$. $^1H$ NMR (400 MHz, $D_2O$): δ 4.39 (d, J=8.4 Hz, 1H), 4.02 (dd, J=10.7, 8.5 Hz, 1H), 3.88 (d, J=3.2 Hz, 1H), 3.81-3.67 (m, 3H), 3.63 (dd, J=7.8, 4.3 Hz, 1H).

Preparation of (2R,3R,4R,5R,6S)-5-((3-chloro-1,2,4-thiadiazol-5-yl)amino)-2-(hydroxy methyl)-6-methoxytetrahydro-2H-pyran-3,4-diol (Compound A105) and (2R,3R,4R,5R,6R)-5-((3-chloro-1,2,4-thiadiazol-5-yl)amino)-2-(hydroxymethyl)-6-methoxytetrahydro-2H-pyran-3,4-diol (Compound A106)

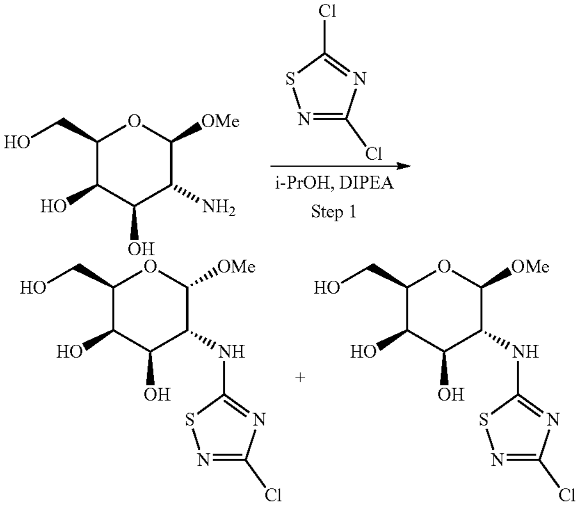

Step 1: A solution of (2R,3R,4R,5R,6R)-5-amino-2-(hydroxymethyl)-6-methoxytetrahydro-2H-pyran-3,4-diol (224.0 mg, 1.2 mmol), 3,5-dichloro-1,2,4-thiadiazole (372.0 mg, 2.4 mmol) and DIEA (464.4 mg, 3.6 mmol) in i-PrOH (10 mL) was stirred at rt overnight. The mixture was concentrated in vacuo. The crude product was purified by flash chromatography (silica gel, 0-10% MeOH in DCM) and pre-HPLC (Method B) to give (2R,3R,4R,5R,6S)-5-((3-chloro-1,2,4-thiadiazol-5-yl)amino)-2-(hydroxymethyl)-6-methoxytetrahydro-2H-pyran-3,4-diol (0.8 mg, 0.2% yield) as a white solid and (2R,3R,4R,5R,6R)-5-((3-chloro-1,2,4-thiadiazol-5-yl)amino)-2-(hydroxymethyl)-6-methoxytetrahydro-2H-pyran-3,4-diol (3.7 mg, 1% yield) as white solid. A105: LC-MS (ESI) found: 312 $[M+H]^+$. $^1H$ NMR (400 MHz, Methanol-$d_4$): δ 4.85-4.80 (m, 1H), 4.23-4.11 (m, 1H), 3.91 (d, J=3.1 Hz, 1H), 3.85-3.77 (m, 2H), 3.76-3.69 (m, 2H), 3.40 (s, 3H). A106: LC-MS (ESI) found: 312 $[M+H]^+$. $^1H$ NMR (400 MHz, Methanol-$d_4$): δ 4.33 (d, J=8.1 Hz, 1H), 3.87 (d, J=3.2 Hz, 1H), 3.84-3.70 (m, 2H), 3.68 (dd, J=10.4, 3.3 Hz, 1H), 3.53 (ddd, J=6.7, 5.4, 1.1 Hz, 1H), 3.48 (s, 3H), 3.46-3.40 (m, 1H).

Talose Series

Preparation of (2R,3R,4R,5R)-2-(hydroxymethyl)-5-((4-(trifluoromethyl)pyrimidin-2-yl)amino)tetrahydro-2H-pyran-3,4-diol (Compound A387)

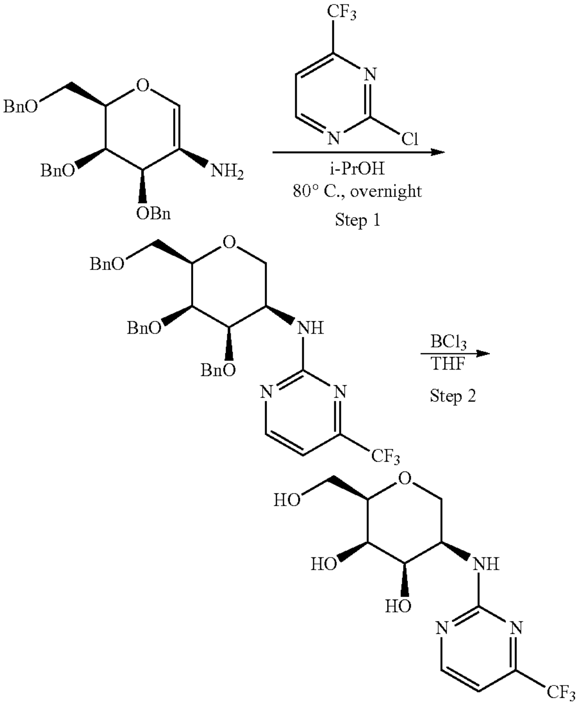

Step 1: A solution of (3R,4R,5R,6R)-4,5-bis(benzyloxy)-6-((benzyloxy)methyl)tetrahydro-2H-pyran-3-amine (50 mg, 0.12 mmol), 2-chloro-4-(trifluoromethyl)pyrimidine (32 mg, 0.17 mmol) and DIPEA (30 mg, 0.23 mmol) in i-PrOH (2 mL) was stirred at 80° C. overnight. The mixture was concentrated and the residue was purified by flash to give N-((3R,4R,5R,6R)-4,5-bis(benzyloxy)-6-((benzyloxy)methyl)tetrahydro-2H-pyran-3-yl)-4-(trifluoromethyl)pyrimidin-2-amine (50 mg, 75% yield) as a colorless oil. LC-MS (ESI) found: 580 $[M+H]^+$.

Step 2: To a solution of N-((3R,4R,5R,6R)-4,5-bis(benzyloxy)-6-((benzyloxy)methyl)tetrahydro-2H-pyran-3-yl)-4-(trifluoromethyl)pyrimidin-2-amine (25 mg, 0.043 mmol) in DCE (2 mL) was added $BCl_3$ (0.43 mL, 1 M in THF) at −78° C. After stirring at −78° C. for 1 h, the mixture was quenched with MeOH. The mixture was concentrated and the residue was purified by prep-TLC (Method A) to give (2R,3R,4R,5R)-2-(hydroxymethyl)-5-((4-(trifluoromethyl)pyrimidin-2-yl)amino)tetrahydro-2H-pyran-3,4-diol (2.7 mg, 20% yield) as a colorless oil. LC-MS (ESI) found: 310

[M+H]$^+$. $^1$H NMR (400 MHz, MeOD): δ 8.50 (s, 1H), 6.89 (d, J=4.9 Hz, 1H), 4.32 (d, J=3.2 Hz, 1H), 4.02 (dd, J=12.0, 1.9 Hz, 1H), 3.95-3.92 (m, 1H), 3.86-3.76 (m, 2H), 3.70 (dd, J=11.5, 4.8 Hz, 1H), 3.58 (dd, J=12.0, 1.6 Hz, 1H), 3.44 (ddd, J=6.9, 4.8, 1.2 Hz, 1H).

The following compounds below were prepared according to the procedure same as A387:

| ID | Characterization data | Starting Material |
|---|---|---|
| 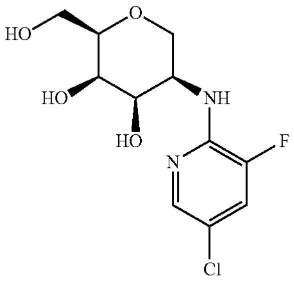 A388 | Yield: 13.4 mg, 59%, white solid. LC-MS(ESI) found 293 [M + H]$^+$. $^1$H NMR (400 MHz, MeOD): δ 7.77 (d, J = 2.1 Hz, 1H), 7.34 (dd, J = 10.7, 2.1 Hz, 1H), 4.35 (d, J = 3.4 Hz, 1H), 4.02 (dd, J = 11.9, 1.9 Hz, 1H), 3.94-3.91 (m, 1H), 3.81 (ddd, J = 18.5, 8.0, 5.1 Hz, 2H), 3.69 (dd, J = 11.5, 4.8 Hz, 1H), 3.55 (dd, J = 12.0, 1.6 Hz, 1H), 3.47-3.41 (m, 1H). | 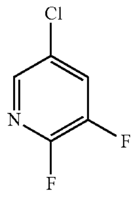 |
| 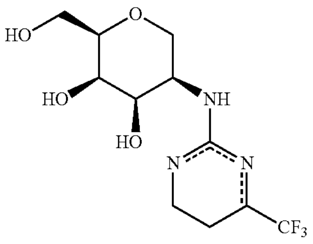 A389 | Yield: 5.0 mg, 37%, colorless oil. LC-MS (ESI) found: 314 [M + H]$^+$. $^1$H NMR (400 MHz, MeOD): δ 4.26 (d, J = 6.1 Hz, 1H), 3.99-3.89 (m, 2H), 3.78 (ddd, J = 10.3, 9.1, 5.6 Hz, 3H), 3.68 (dd, J = 11.5, 4.6 Hz, 1H), 3.60 (d, J = 12.3 Hz, 1H), 3.50-3.37 (m, 3H), 2.19 (d, J = 5.1 Hz, 2H). | 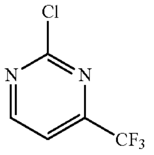 [SMILES: FC(F)(F)c1ccnc(Cl)n1] |

Preparation of N-((3R,4R,5R,6R)-4,5-dihydroxy-6-(hydroxymethyl)tetrahydro-2H-pyran-3-yl)benzamide (Compound A136)

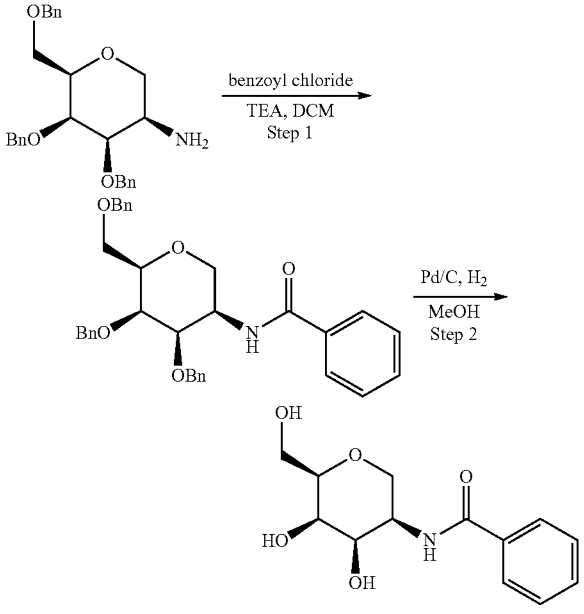

A136

Step 1: To a solution of (3R,4R,5R,6R)-4,5-bis(benzyloxy)-6-((benzyloxy)methyl)tetrahydro-2H-pyran-3-amine (80 mg, 0.19 mmol) and TEA (0.03 mL, 0.19 mmol) in dry DCM(3 mL) at 0° C. under $N_2$ atmosphere was added dropwise benzoyl chloride (27.1 mg, 0.19 mmol). The reaction mixture was stirred for 1 h. The resulting mixture was diluted with DCM (30 mL), washed with $H_2O$ (20 mL×2) and brine (30 mL), dried over $Na_2SO_4$. The organic layer was separated and concentrated in vacuo. The crude product was purified by flash chromatography (silica gel, 0~80% EA in PE) to give N-((3R,4R,5R,6R)-4,5-bis(benzyloxy)-6-((benzyloxy)methyl)tetrahydro-2H-pyran-3-yl) benzamide (70 mg, 71% yield) as a colorless oil. LC-MS (ESI) found: 538 [M+H]$^+$.

Step 2: To a solution of N-((3R,4R,5R,6R)-4,5-bis(benzyloxy)-6-((benzyloxy)methyl)tetrahydro-2H-pyran-3-yl) benzamide (35 mg, 0.07 mmol) in MeOH (3 mL) was added Pd/C (5 mg, 10% wt, 60% wet) and HCl (1 mL, 1 M in $H_2O$) at rt under a $H_2$ balloon. The reaction was stirred at rt for 3 h. The resulting mixture was filtered and concentrated in vacuo. The crude product was purified by prep-HPLC (Method A) to give N-((3R,4R,5R,6R)-4,5-dihydroxy-6-(hydroxymethyl)tetrahydro-2H-pyran-3-yl)benzamide (9.6 mg, 55%) as a colorless oil. LC-MS (ESI) found: 268 [M+H]$^+$. $^1$H NMR (400 MHz, MeOD): δ 7.86-7.80 (m, 2H), 7.58-7.51 (m, 1H), 7.49-7.44 (m, 2H), 4.31-4.27 (m, 1H), 4.04 (dd, J=12.0, 1.9 Hz, 1H), 3.98-3.95 (m, 1H), 3.86 (dd, J=4.4, 3.2 Hz, 1H), 3.80 (dd, J=11.4, 7.0 Hz, 1H), 3.70 (dd, J=11.5, 4.8 Hz, 1H), 3.62 (dd, J=12.0, 1.6 Hz, 1H), 3.46 (ddd, J=6.9, 4.8, 1.1 Hz, 1H).

Additional ASGPR Ligands

Preparation of N-(((3R,4R,5R,6R)-4,5-dihydroxy-6-(hydroxymethyl)tetrahydro-2H-pyran-3-yl)methyl) acetamide (Compound A183)

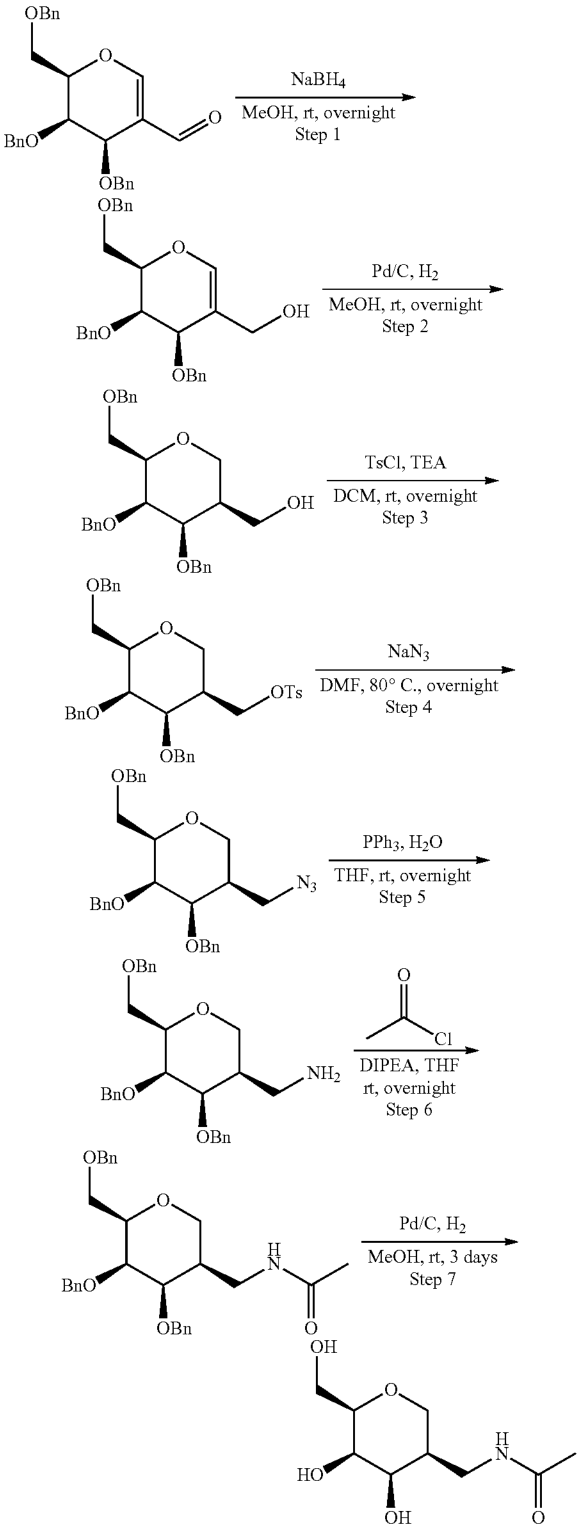

Step 1: To a solution of (2R,3R,4R)-3,4-bis(benzyloxy)-2-((benzyloxy)methyl)-3,4-dihydro-2H-pyran-5-carbaldehyde (1.2 g, 2.7 mmol) in dry MeOH (10 mL) at 0° C. under $N_2$ atmosphere was added $NaBH_4$ (230 mg, 6.05 mmol) in portions. After the addition was complete, the reaction was stirred at rt overnight. On consumption of starting material (TLC monitoring), the reaction vessel was again cooled to 0° C. The reaction mixture was quenched with 1 mL ice water. The mixture was concentrated in vacuo. The crude product was purified by flash chromatography (silica gel, 0-20% MeOH in DCM) to give ((2R,3R,4R)-3,4-bis(benzyloxy)-2-((benzyloxy)methyl)-3,4-dihydro-2H-pyran-5-yl)methanol (1 g, 83% yield) as a colorless oil. LC-MS (ESI) found: 447 $[M+H]^+$. $^1H$ NMR (400 MHz, $CDCl_3$): δ 7.37-7.26 (m, 15H), 6.39 (s, 1H), 4.82 (dd, J=11.7, 7.4 Hz, 2H), 4.68-4.40 (m, 4H), 4.33 (d, J=3.7 Hz, 1H), 4.21 (t, J=4.5 Hz, 1H), 4.02 (ddd, J=20.7, 16.4, 11.9 Hz, 3H), 3.74 (ddd, J=15.5, 10.2, 6.2 Hz, 2H).

Step 2: To a solution of ((2R,3R,4R)-3,4-bis(benzyloxy)-2-((benzyloxy)methyl)-3,4-dihydro-2H-pyran-5-yl)methanol (1 g, 2.24 mmol) in MeOH (40 mL) was added Pd/C (100 mg, 10% wt, 60% wet). The reaction mixture was stirred at rt under a $H_2$ balloon for 2 h. The mixture was filtered and concentrated in vacuo. The crude product was purified by flash chromatography (silica gel, 0-20% MeOH in DCM) to give ((4R,5R,6R)-4,5-bis(benzyloxy)-6-((benzyloxy)methyl)tetrahydro-2H-pyran-3-yl)methanol (350 mg, 35% yield) as a colorless oil. LC-MS (ESI) found: 449 $[M+H]^+$. $^1H$ NMR (400 MHz, $CDCl_3$): δ 7.38-7.25 (m, 15H), 4.88 (dd, J=13.5, 11.6 Hz, 1H), 4.69-4.50 (m, 4H), 4.44 (dd, J=11.9, 8.1 Hz, 1H), 4.01 (d, J=5.0 Hz, 1H), 3.87-3.72 (m, 3H), 3.63-3.45 (m, 3H), 2.04 (dd, J=7.0, 4.0 Hz, 1H), 1.17 (d, J=7.1 Hz, 2H).

Step 3: To a solution of ((4R,5R,6R)-4,5-bis(benzyloxy)-6-((benzyloxy)methyl)tetrahydro-2H-pyran-3-yl)methanol (350 mg, 0.78 mmol) and TEA (394 mg, 3.90 mmol) in DCM (10 mL) was added TsCl (446 mg, 2.34 mmol) slowly at 0° C. The reaction mixture was stirred at rt overnight. The resulting mixture was extracted with EA (50 mL), washed with $H_2O$ (40 mL×2) and brine (40 mL), dried over $Na_2SO_4$, filtered. The organic layer was separated and concentrated in vacuo. The crude product was purified by flash chromatography (silica gel, 0-50% EA in PE) to give ((4R,5R,6R)-4,5-bis(benzyloxy)-6-((benzyloxy)methyl)tetrahydro-2H-pyran-3-yl)methyl 4-methylbenzenesulfonate (180 mg, 38% yield) as a yellow oil. LC-MS (ESI) found: 603 $[M+H]^+$.

Step 4: To a solution of (2R,3R,4R)-5-(azidomethyl)-3,4-bis(benzyloxy)-2-((benzyloxy)methyl)tetrahydro-2H-pyran (185 mg, 0.31 mmol) in dry DMF (10 mL) was added $NaN_3$ (180 mg, 3.10 mmol). The reaction mixture was stirred at 80° C. overnight. The mixture was extracted with EA (20 mL), washed with $H_2O$ (20 mL×2) and brine (20 mL), dried over $Na_2SO_4$, filtered. The organic layer was separated and concentrated in vacuo. The crude product was purified by flash chromatography (silica gel, 0~50% EA in PE) to give (2R,3R,4R)-5-(azidomethyl)-3,4-bis(benzyloxy)-2-((benzyloxy)methyl)tetrahydro-2H-pyran (65 mg, 45% yield) as a colorless oil. LC-MS (ESI) found: 496 $[M+Na]^+$.

Step 5: To a solution of ((3R,4R,5R,6R)-4,5-bis(benzyloxy)-6-((benzyloxy)methyl)tetrahydro-2H-pyran-3-yl) methanamine (65 mg, 0.14 mmol) in THF (5 mL) was added $PPh_3$ (72 mg, 0.27 mmol) and water (5 mL). The reaction mixture was stirred at rt overnight. The mixture was concentrated in vacuo. The crude product was purified by flash chromatography (silica gel, 0-10% MeOH in DCM) to give ((3R,4R,5R,6R)-4,5-bis(benzyloxy)-6-((benzyloxy)methyl)

tetrahydro-2H-pyran-3-yl)methanamine (60 mg, 98% yield) as a colorless oil. LC-MS (ESI) found: 448 $[M+H]^+$.

Step 6: To a solution of N-(((3R,4R,5R,6R)-4,5-bis(benzyloxy)-6-((benzyloxy)methyl)tetrahydro-2H-pyran-3-yl)methyl)acetamide (30 mg, 0.067 mmol) in dry DCM (5 mL) was added DIPEA (30 mg, 0.07 mmol) and acetyl chloride (11 mg, 0.14 mmol) dropwise at 0° C. under $N_2$ atmosphere. The reaction mixture was stirred at rt for 8 h. The reaction was cooled to 0° C. and quenched with saturated sodium bicarbonate solution. The mixture was extracted with EA (10 mL), washed with $H_2O$ (10 mL×2) and brine (10 mL), dried over $Na_2SO_4$, filtered. The organic layer was separated and concentrated in vacuo. The crude product was purified by flash chromatography (silica gel, 0~50% EA in PE) to give N-(((3R,4R,5R,6R)-4,5-bis(benzyloxy)-6-((benzyloxy)methyl)tetrahydro-2H-pyran-3-yl)methyl)acetamide (14 mg, 44% yield) as a colorless oil. LC-MS (ESI) found: 490 $[M+H]^+$.

Step 7: To a solution of N-(((3R,4R,5R,6R)-4,5-bis(benzyloxy)-6-((benzyloxy)methyl)tetrahydro-2H-pyran-3-yl)methyl)acetamide (14 mg, 0.03 mmol) in dry MeOH (5 mL) was added Pd/C (10 mg, 10% wt, 60% wet). The reaction mixture was charged with $H_2$ and stirred at rt for 3 days with a $H_2$ balloon. The mixture was filtered and concentrated in vacuo to give N-(((3R,4R,5R,6R)-4,5-dihydroxy-6-(hydroxymethyl)tetrahydro-2H-pyran-3-yl)methyl)acetamide (1 mg, 16% yield) as a colorless oil. LC-MS (ESI) found: 220 $[M+H]^+$. $^1H$ NMR (400 MHz, $CD_3OD$): δ 3.91 (dd, J=11.9, 2.8 Hz, 1H), 3.85-3.72 (m, 3H), 3.66 (dd, J=11.7, 4.3 Hz, 1H), 3.58 (dd, J=13.9, 4.3 Hz, 1H), 3.48-3.40 (m, 3H), 1.93 (s, 3H), 1.92-1.84 (m, 1H).

General Procedure for the Mitsunobu Reaction

To a solution of ((2R,3R,4R)-3,4-bis(benzyloxy)-2-((benzyloxy)methyl)-3,4-dihydro-2H-pyran-5-yl)methanol (A182-2, 100 mg, 0.224 mmol, 1.0 eq), $PPh_3$ (88 mg, 0.336 mmol, 1.5 eq) and nucleophiles (1.0 eq) in dry DCM (1.1 mL) was added DIAD (0.053 mL, 0.269 mmol, 1.2 eq) dropwise at ice-bath under $N_2$ atmosphere. Then the reaction was allowed to warm to rt. The resulting reaction mixture was stirred at the same temperature for another 40 min, at which time TLC showed the disappearance of all starting material. The mixture was evaporated. The crude product was further purified by silica gel column chromatography to give desired products.

General Procedure for the Hydrogenation Reaction

A suspension of substrate (1.0 eq) and Pd/C (0.2 eq, 10% wt, 60% wet) in MeOH was charged with $H_2$ and stirred under a $H_2$ balloon. The reaction was stirred at rt and monitored by TLC. When TLC showed the disappearance of all starting material, the mixture was filtered and evaporated. The crude product was further purified by silica gel column chromatography to give desired products.

Preparation of (2R,3R,4R,5R,6S)-2-(hydroxymethyl)-5-methyl-6-phenoxytetrahydro-2H-pyran-3,4-diol (Compound A192), (2R,3R,4R,5S,6S)-2-(hydroxymethyl)-5-methyl-6-phenoxytetrahydro-2H-pyran-3,4-diol (Compound A191) and (2R,3R,4R,5S)-2-(hydroxymethyl)-5-(phenoxymethyl)tetrahydro-2H-pyran-3,4-diol (Compound A193)

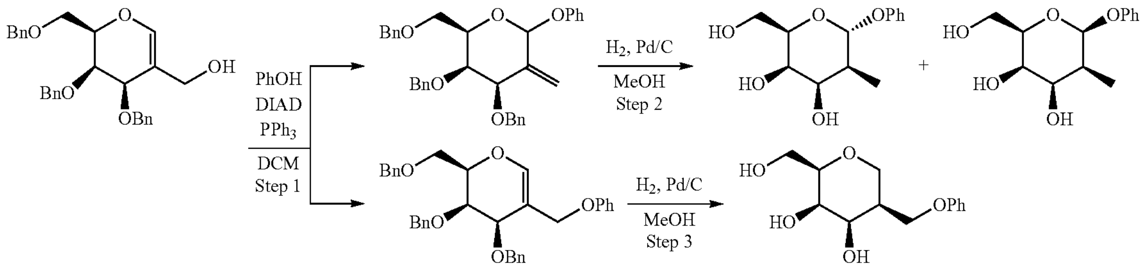

Step 1: They were synthesized according to the general procedure. Yield for (2R,3R,4R)-3,4-bis(benzyloxy)-2-((benzyloxy)methyl)-5-methylene-6-phenoxytetrahydro-2H-pyran: 30 mg, 26%. LC-MS (ESI) found: 545 [M+Na]+. Yield for (2R,3R,4R)-3,4-bis(benzyloxy)-2-((benzyloxy)methyl)-5-(phenoxymethyl)-3,4-dihydro-2H-pyran: 70 mg, 60%. LC-MS (ESI) found: 545 [M+Na]+.

Step 2: They were synthesized from 100 mg of (2R,3R,4R)-3,4-bis(benzyloxy)-2-((benzyloxy)methyl)-5-methylene-6-phenoxytetrahydro-2H-pyran according to the general procedure. Yield (A192): 0.5 mg, 1%. Yield (A191): 7 mg, 14%. LC-MS (ESI) found: 277 [M+Na]+. $^1$H NMR (400 MHz, CD3OD) δ 7.30-7.22 (m, 2H), 7.13-7.06 (m, 2H), 6.96 (tt, J=7.4, 1.1 Hz, 1H), 5.44 (d, J=1.8 Hz, 1H), 4.11 (dd, J=5.5, 3.5 Hz, 1H), 3.89 (d, J=2.2 Hz, 2H), 3.75-3.68 (m, 2H), 2.20 (ddd, J=7.4, 5.3, 1.8 Hz, 1H), 1.23 (d, J=7.4 Hz, 3H).

Step 3: 9.8 mg of (2R,3R,4R,5S)-2-(hydroxymethyl)-5-(phenoxymethyl)tetrahydro-2H-pyran-3,4-diol was obtained from 100 mg of (2R,3R,4R)-3,4-bis(benzyloxy)-2-((benzyloxy)methyl)-5-(phenoxymethyl)-3,4-dihydro-2H-pyran according to the general procedure. Yield: 20%. LC-MS (ESI) found: 277 [M+Na]+. $^1$H NMR (400 MHz, $CD_3OD$): δ 7.30-7.19 (m, 2H), 6.95-6.84 (m, 3H), 4.37 (t, J=10.0 Hz, 1H), 4.24 (ddd, J=9.7, 3.0, 1.4 Hz, 1H), 4.14 (dd, J=11.7, 1.9 Hz, 1H), 3.91 (dd, J=5.6, 3.2 Hz, 1H), 3.81-3.74 (m, 2H), 3.66 (dd, J=11.5, 4.6 Hz, 1H), 3.51 (ddd, J=11.7, 2.6, 1.4 Hz, 1H), 3.41 (ddd, J=7.2, 4.6, 1.7 Hz, 1H), 2.22 (ddd, J=10.2, 5.4, 2.7 Hz, 1H).

Synthesis 5-38. Preparation of (2R,3R,4R,5R)-2-(hydroxymethyl)-5-(3-hydroxypropyl)tetrahydro-2H-pyran-3,4-diol (Compound A162)

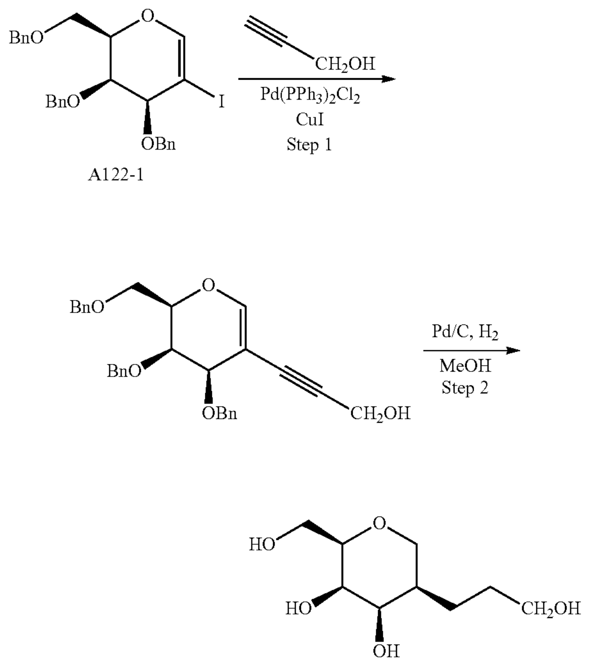

Step 1: To a solution of (2R,3S,4S)-3,4-bis(benzyloxy)-2-((benzyloxy)methyl)-5-iodo-3,4-dihydro-2H-pyran (A122-1, 100 mg, 0.18 mmol) in dioxane (5 mL) under $N_2$ were added $Pd(PPh_3)_2Cl_2$ (12.9 mg, 0.018 mmol), CuI (3.5 mg, 0.018 mmol), TEA (0.03 mL, 0.55 mmol). The mixture was stirred at 100° C. under $N_2$ for 16 h. The mixture was filtered, the filtrate was concentrated under reduced pressure to give crude product, which was purified by flash chromatography (silica gel, 10-50% EtOAc in PE) to give 3-((2R,3R,4R)-3,4-bis(benzyloxy)-2-((benzyloxy)methyl)-3,4-dihydro-2H-pyran-5-yl)prop-2-yn-1-ol (30 mg, 35% yield) as colorless oil. LC-MS (ESI) found: 493 [M+Na]+.

Step 2: To a solution of 3-((2R,3R,4R)-3,4-bis(benzyloxy)-2-((benzyloxy)methyl)-3,4-dihydro-2H-pyran-5-yl)prop-2-yn-1-ol (20 mg, 0.043 mmol) in MeOH (10 mL) was added Pd/C (5 mg, 10% wt, 60% wet), the mixture was stirred at rt under a $H_2$ balloon for 12 h. The mixture was filtered, the filtrate was concentrated to give a crude product, which was purified by prep-HPLC (Method A) to give (2R,3R,4R,5R)-2-(hydroxymethyl)-5-(3-hydroxypropyl)tetrahydro-2H-pyran-3,4-diol (5 mg, 57% yield). $^1$H NMR (400 MHz, MeOD): δ 3.96-3.73 (m, 3H), 3.67 (dd, J=11.8, 3.9 Hz, 1H), 3.54 (dt, J=7.4, 5.1 Hz, 2H), 3.42 (dd, J=11.8, 3.2 Hz, 1H), 1.73-1.41 (m, 4H), 1.40-1.29 (m, 2H), 0.91 (dd, J=14.5, 7.2 Hz, 1H).

Preparation of (2R,3R,4R,5R)-2-(hydroxymethyl)-5-((4-methylpiperazin-1-yl)methyl)tetrahydro-2H-pyran-3,4-diol (Compound A390)

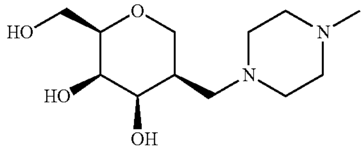 [SMILES: CN1CCN(C[C@@H]2CO[C@H](CO)[C@H](O)[C@@H]2O)CC1]

It was prepared according to the procedure same as that for A209. LC-MS (ESI) found: 261 [M+H]+. $^1$H NMR (400 MHz, MeOD): δ 4.06-3.54 (m, 16H), 3.46-3.41 (m, 1H), 3.03 (s, 3H), 2.51-2.42 (m, 1H).

Preparation of ((2R,3R,4R,5R)-2-(hydroxymethyl)-5-(piperidin-1-yl)tetrahydro-2H-pyran-3,4-diol (Compound A391)

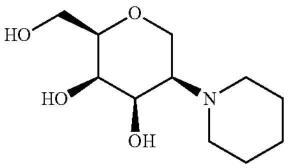 [SMILES: OC[C@H]1OC[C@@H](N2CCCCC2)[C@@H](O)[C@H]1O]

It was prepared according to the procedure same as that for A222. LC-MS (ESI) found: 232 [M+H]+. $^1$H NMR (400 MHz, MeOD): δ 4.47 (dd, J=14.3, 1.6 Hz, 1H), 4.10 (dd, J=10.9, 7.9 Hz, 2H), 4.03-3.93 (m, 2H), 3.75 (dd, J=11.4, 7.0 Hz, 1H), 3.71-3.65 (m, 2H), 3.61-3.53 (m, 2H), 3.26-3.18 (m, 2H), 2.07 (d, J=12.7 Hz, 1H), 2.02-1.93 (m, 1H), 1.86-1.76 (m, 2H), 1.73-1.56 (m, 2H).

Preparation of 1-((3R,4R,5R,6R)-4,5-dihydroxy-6-(hydroxymethyl)tetrahydro-2H-pyran-3-yl)-3-methylimidazolidin-2-one (Compound A392)

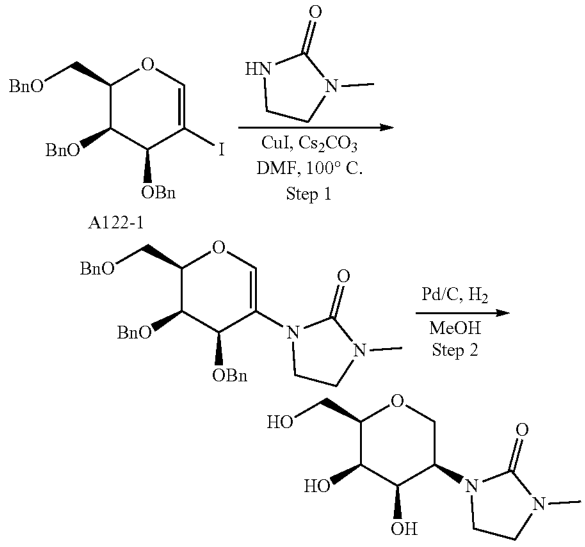

A122-1

Step 1: To a solution of (2R,3S,4S)-3,4-bis(benzyloxy)-2-((benzyloxy)methyl)-5-iodo-3,4-dihydro-2H-pyran (200 mg, 0.369 mmol) in DMF (10 mL) was added 1-methylimidazolidin-2-one (37 mg, 0.37 mmol), CuI (7 mg, 0.37 mmol), $Cs_2CO_3$ (360 mg, 1.12 mmol). The mixture was stirred at 100° C. for 16 h. The mixture was concentrated under reduced pressure to give a crude product, which was purified by column to give 1-((2R,3R,4R)-3,4-bis(benzyloxy)-2-((benzyloxy)methyl)-3,4-dihydro-2H-pyran-5-yl)-3-methylimidazolidin-2-one (103 mg). LC-MS (ESI) found: 515 $[M+H]^+$.

Step 2: To a solution of 1-((2R,3R,4R)-3,4-bis(benzyloxy)-2-((benzyloxy)methyl)-3,4-dihydro-2H-pyran-5-yl)-3-methylimidazolidin-2-one (103 mg, 0.20 mmol) in MeOH (10 mL) was added Pd/C (10 mg, 10% wt, 60% wet). The mixture was stirred at the room temperature at rt under a $H_2$ balloon for 16 h. The mixture was filtered, the filtrate was concentrated under reduced pressure to give 1-((3R,4R,5R,6R)-4,5-dihydroxy-6-(hydroxymethyl)tetrahydro-2H-pyran-3-yl)-3-methylimidazolidin-2-one (25 mg, 50% yield). LC-MS (ESI) found: 247 $[M+H]^+$. $^1$H NMR (400 MHz, MeOD): δ 4.17-4.04 (m, 2H), 3.99 (s, 1H), 3.89-3.77 (m, 3H), 3.72-3.62 (m, 2H), 3.47 (dd, J=11.4, 7.2 Hz, 2H), 3.38-3.33 (m, 1H), 3.26 (d, J=8.5 Hz, 1H), 2.76 (s, 3H).

Preparation of (2R,3R,4R,5R)-5-(dimethylamino)-2-(hydroxymethyl)tetrahydro-2H-pyran-3,4-diol (Compound A393)

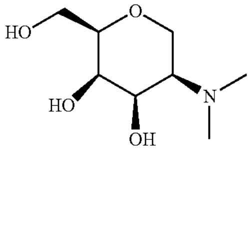

It was prepared according to the procedure same as that for A222. LC-MS (ESI) found: 192 $[M+H]^+$. $^1$H NMR (400 MHz, MeOD): δ 4.42 (dd, J=14.3, 2.0 Hz, 1H), 4.08-4.01 (m, 1H), 3.98-3.94 (m, 1H), 3.77 (dd, J=11.5, 7.0 Hz, 1H), 3.66 (ddd, J=14.3, 11.9, 3.1 Hz, 2H), 3.55-3.51 (m, 1H), 3.42 (d, J=1.8 Hz, 1H), 3.13 (s, 3H), 3.01 (s, 3H).

Preparation of (2R,3R,4R,5R)-2-(hydroxymethyl)-5-(1-methyl-1H-pyrazol-4-yl)tetrahydro-2H-pyran-3,4-diol (Compound A394)

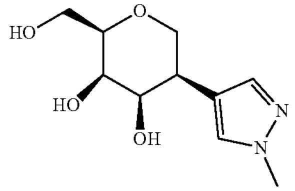 [SMILES: Cn1cc([C@@H]2CO[C@H](CO)[C@H](O)[C@@H]2O)cn1]

It was prepared according to the procedure same as that for A164. LC-MS (ESI) found: 229 $[M+H]^+$. $^1$H NMR (400 MHz, MeOD): δ 7.58 (s, 1H), 7.48 (s, 1H), 4.06 (dd, J=11.6, 5.1 Hz, 1H), 3.96 (dd, J=11.8, 7.7 Hz, 1H), 3.89 (dd, J=4.6, 3.5 Hz, 1H), 3.86-3.80 (m, 4H), 3.71 (dd, J=11.9, 3.9 Hz, 1H), 3.65 (m, 2H), 2.95 (dd, J=8.7, 4.6 Hz, 1H).

Preparation of (2R,3R,4R,5R)-2-(hydroxymethyl)-5-(pyrimidin-5-yl)tetrahydro-2H-pyran-3,4-diol (Compound A395)

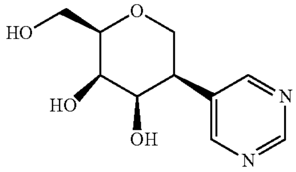 [SMILES: OC[C@H]1OC[C@@H](c2cncnc2)[C@@H](O)[C@H]1O]

It was prepared according to the procedure same as that for A164. LC-MS (ESI) found: 227$[M+H]^+$. $^1$H NMR (400 MHz, MeOD): δ 8.98 (s, 2H), 8.92 (s, 1H), 4.36 (dd, J=12.3, 2.1 Hz, 1H), 4.01 (dd, J=6.0, 3.2 Hz, 1H), 3.94-3.80 (m, 3H), 3.71 (dd, J=11.6, 4.3 Hz, 1H), 3.59 (m, 1H), 3.00 (m, 1H).

Preparation of N-((3R,4R,5R,6R)-4,5-dihydroxy-6-(hydroxymethyl)tetrahydro-2H-pyran-3-yl)-N-methylacetamide (Compound A396)

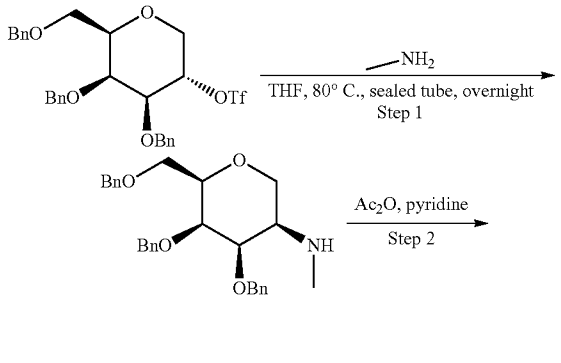

-continued

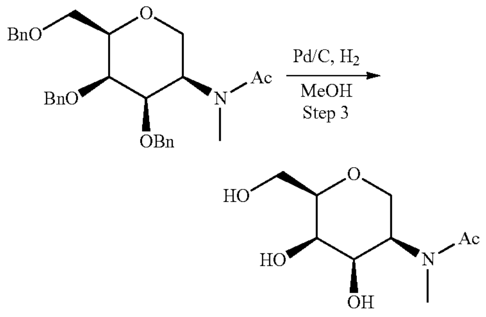

Step 1: A solution of (3S,4S,5S,6R)-4,5-bis(benzyloxy)-6-((benzyloxy)methyl)tetrahydro-2H-pyran-3-yl trifluoromethanesulfonate (100 mg, 0.18 mmol) in methanamine (0.88 mL, 1.76 mmol) was stirred at 80° C. overnight. The mixture was purified by flash to give (3R,4R,5R,6R)-4,5-bis(benzyloxy)-6-((benzyloxy)methyl)-N-methyltetrahydro-2H-pyran-3-amine (60 mg, 76% yield) as a colorless oil. LC-MS (ESI) found: 448 $[M+H]^+$.

Step 2: To a solution of (3R,4R,5R,6R)-4,5-bis(benzyloxy)-6-((benzyloxy)methyl)-N-methyltetrahydro-2H-pyran-3-amine (60 mg, 0.13 mmol) in pyridine (1 mL) was added $Ac_2O$ (68 mg, 0.67 mmol). After stirring at rt for 3 h, the mixture was concentrated and the residue was purified by prep-HPLC (Method B) to give N-((3R,4R,5R,6R)-4,5-bis(benzyloxy)-6-((benzyloxy)methyl)tetrahydro-2H-pyran-3-yl)-N-methylacetamide (40 mg, 60.9%) as a colorless oil. LC-MS (ESI) found: 490 $[M+H]^+$.

Step 3: A solution of N-((3R,4R,5R,6R)-4,5-bis(benzyloxy)-6-((benzyloxy)methyl)tetrahydro-2H-pyran-3-yl)-N-methylacetamide (20 mg, 0.04 mmol) in MeOH (2 mL) was added Pd/C (3 mg, 10% wt, 60% wet). The mixture was stirred at rt under a $H_2$ balloon overnight. The mixture was filtered through a Celite pad, and the filtrate was concentrated to give N-((3R,4R,5R,6R)-4,5-dihydroxy-6-(hydroxymethyl)tetrahydro-2H-pyran-3-yl)-N-methylacetamide (4 mg, 44.7%) as a brown oil. LC-MS (ESI) found: 220 $[M+H]^+$. $^1H$ NMR (400 MHz, MeOD): δ 4.34 (d, J=1.8 Hz, 1H), 4.14-4.08 (m, 1H), 3.81-3.75 (m, 2H), 3.70 (dd, J=4.9, 3.2 Hz, 2H), 3.64-3.58 (m, 1H), 3.40-3.35 (m, 1H), 2.80 (s, 3H), 2.21 (s, 3H).

Preparation of (1S,3R,4R,5R,6R)-7,7-dichloro-3-(hydroxymethyl)-2-oxabicyclo[4.1.0]heptane-4,5-diol (Compound A397)

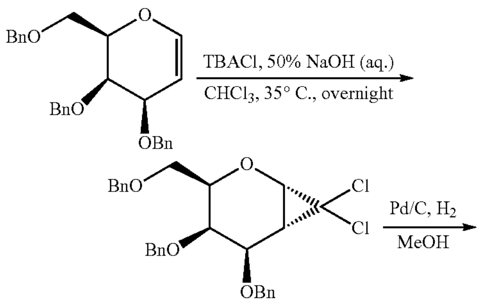

-continued

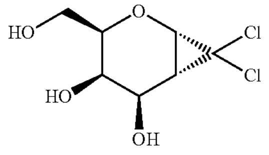

Step 1: To a solution of (2R,3R,4R)-3,4-bis(benzyloxy)-2-((benzyloxy)methyl)-3,4-dihydro-2H-pyran (5 g, 12.0 mmol) in $CHCl_3$ (20 mL) were added TBACl (90 mg, 0.24 mmol) and NaOH aq (8 mL, 50% wt in $H_2O$). After stirring at 35° C. overnight, the mixture was washed with $H_2O$, the organic layer was concentrated. The residue was purified by flash to give (1S,3R,4R,5R,6R)-4,5-bis(benzyloxy)-3-((benzyloxy)methyl)-7,7-dichloro-2-oxabicyclo[4.1.0]heptane (5 g, 83% yield) as a colorless oil. LC-MS (ESI) found: 499 $[M+H]^+$.

Step 2: A solution of (1S,3R,4R,5R,6R)-4,5-bis(benzyloxy)-3-((benzyloxy)methyl)-7,7-dichloro-2-oxabicyclo[4.1.0]heptane (100 mg, 0.44 mmol) in MeOH (2 mL) was added Pd/C (10 mg, 10% wt, 60% wet). The mixture was stirred at rt under a $H_2$ balloon overnight. The mixture was filtered through a Celite pad, and the filtrate was concentrated to give (1S,3R,4R,5R,6R)-7,7-dichloro-3-(hydroxymethyl)-2-oxabicyclo[4.1.0]heptane-4,5-diol (40 mg, 40% yield) as a brown oil. LC-MS (ESI) found: 251 $[M+Na]^+$. $^1H$ NMR (400 MHz, MeOD): δ 3.89 (d, J=9.0 Hz, 1H), 3.82-3.78 (m, 1H), 3.74 (t, J=3.1 Hz, 1H), 3.69 (d, J=1.4 Hz, 1H), 3.68 (s, 1H), 3.62 (dd, J=5.1, 1.8 Hz, 1H), 1.82 (dd, J=9.0, 3.3 Hz, 1H).

Preparation of (3R,4R,5R,6R)-4,5-dihydroxy-6-(hydroxymethyl)-N'-(2,2,2-trifluoroacetyl)tetrahydro-2H-pyran-3-carbohydrazide (Compound A398)

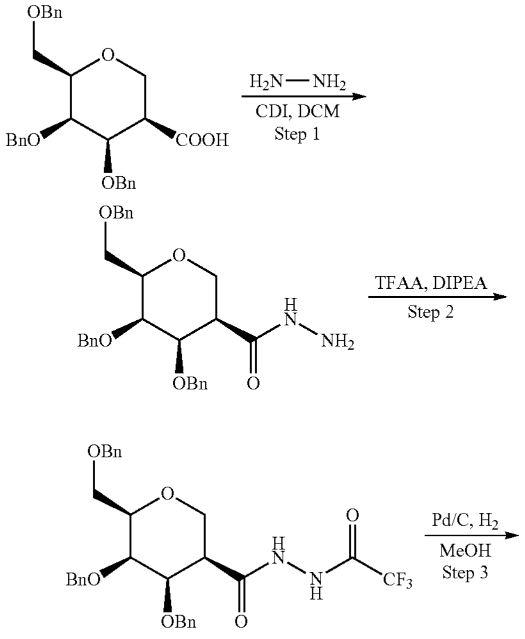

-continued

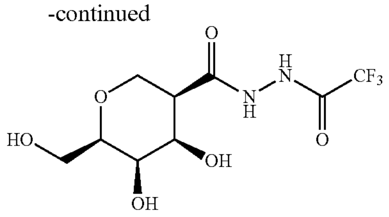

Step 1: To a solution of (4R,5R,6R)-4,5-bis(benzyloxy)-6-[(benzyloxy)methyl]oxane-3-carboxylic acid(400 mg, 0.865 mmol) and CDI (0.12 mL, 0.951 mmol) in DCM (20 mL) was added hydrazine hydrate (4.2 mL, 86.5 mmol) at 0° C. The mixture was stirred at rt for 12 h. the mixture was concentrated and purified by column to give (3R,4R,5R,6R)-4,5-bis(benzyloxy)-6-((benzyloxy)methyl)tetrahydro-2H-pyran-3-carbohydrazide (140 mg, 34% yield) as yellow solid. LC-MS (ESI) found: 477 $[M+H]^+$.

Step 2: To a solution of (4R,5R,6R)-4,5-bis(benzyloxy)-6-[(benzyloxy)methyl]oxane-3-carbohydrazide (140 mg, 0.30 mmol) and TFAA (0.08 mL, 0.60 mmol) in MeCN (10 mL) was added DIPEA (46 mg, 0.353 mmol) at 0° C. The mixture was stirred at rt for 2 h. The mixture was concentrated and purified by column to give (3R,4R,5R,6R)-4,5-bis(benzyloxy)-6-((benzyloxy)methyl)-N'-(2,2,2-trifluoroacetyl)tetrahydro-2H-pyran-3-carbohydrazide (135 mg, 80% yield) as yellow oil. LC-MS (ESI) found: 573 $[M+H]^+$.

Step 3: To a solution of (4R,5R,6R)-4,5-bis(benzyloxy)-6-[(benzyloxy)methyl]-N'-(trifluoroacetyl)oxane-3-carbohydrazide (10.0 mg, 0.017 mmol) in MeOH (2 mL) was added Pd/C (5 mg, 10% wt, 60% wet). The mixture was stirred at rt for 0.5 h under a $H_2$ balloon. The mixture was filtered and concentrated to give (3R,4R,5R,6R)-4,5-dihydroxy-6-(hydroxymethyl)-N'-(2,2,2-trifluoroacetyl)tetrahydro-2H-pyran-3-carbohydrazide (5.1 mg, 95% yield) as white solid. LC-MS (ESI) found: 303 $[M+H]^+$. $^1$H NMR (400 MHz, MeOD): δ 4.21 (dd, J=12.2, 0.9 Hz, 1H), 4.00 (dd, J=6.3, 3.7 Hz, 1H), 3.79-3.62 (m, 4H), 3.42-3.34 (m, 1H), 2.90 (dd, J=6.2, 2.6 Hz, 1H).

Preparation of 2-((3R,4R,5R,6R)-4,5-dihydroxy-6-(hydroxymethyl)tetrahydro-2H-pyran-3-yl)acetamide (Compound A399)

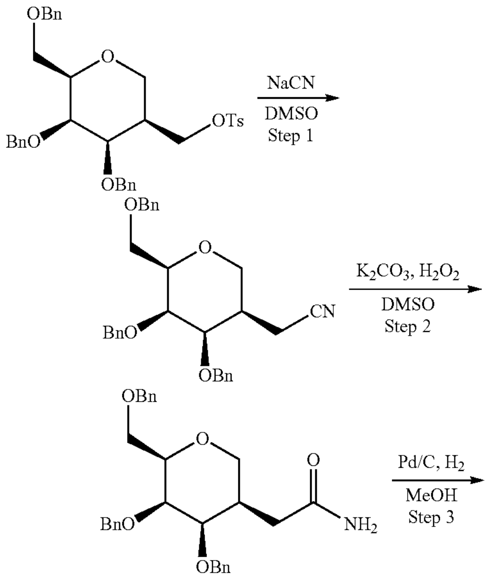

-continued

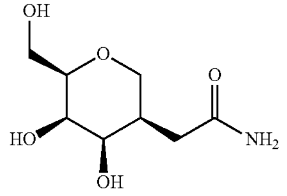

Step 1: To a solution of ((3S,4R,5R,6R)-4,5-bis(benzyloxy)-6-((benzyloxy)methyl)tetrahydro-2H-pyran-3-yl) methyl 4-methylbenzenesulfonate (400 mg, 0.66 mmol) in DMSO (3 mL) was added NaCN (98 mg, 1.99 mmol), and the reaction was stirred at room temperature for 18 h. The reaction was diluted with EA and water. The organic layer was separated, concentrated in vacuo. The residue was purified with pre-HPLC (Method A) to give 2-((3R,4R,5R,6R)-4,5-bis(benzyloxy)-6-((benzyloxy)methyl)tetrahydro-2H-pyran-3-yl)acetonitrile (60 mg, 20% yield). LC-MS (ESI) found: 458 $[M+H]^+$. $^1$H NMR (400 MHz, MeOD): δ 7.48-7.20 (m, 15H), 4.81 (d, J=11.1 Hz, 2H), 4.68 (q, J=11.8 Hz, 2H), 4.48 (dt, J=13.7, 11.8 Hz, 3H), 3.99 (dd, J=12.3, 1.8 Hz, 1H), 3.90-3.84 (m, 1H), 3.80 (dd, J=4.9, 3.1 Hz, 1H), 3.64-3.52 (m, 4H), 2.91 (qd, J=17.4, 7.2 Hz, 2H).

Step 2: To a solution of 2-((3R,4R,5R,6R)-4,5-bis(benzyloxy)-6-((benzyloxy)methyl)tetrahydro-2H-pyran-3-yl)acetonitrile (22 mg, 0.048 mmol) in DMSO (4 mL) was added $K_2CO_3$ (14 mg, 0.096 mmol) and $H_2O_2$ (2 mL). The reaction was stirred at rt for 2 h. The solvent was removed, distilled water (10 ml) was added, extracted with EA and the solvent was removed, purified by flash to give 2-((3R,4R,5R,6R)-4,5-bis(benzyloxy)-6-((benzyloxy)methyl)tetrahydro-2H-pyran-3-yl)acetamide (16 mg, 70% yield). LC-MS (ESI) found: 476 $[M+H]^+$.

Step 3: To a solution of 2-((3R,4R,5R,6R)-4,5-bis(benzyloxy)-6-((benzyloxy)methyl)tetrahydro-2H-pyran-3-yl)acetamide (20 mg, 0.042 mmol) in MeOH (5 mL) was added Pd/C (3 mg, 10% wt., 60% wet) and HCl (2 mL, 2 M in $H_2O$). The mixture was stirred at rt 2 h under a $H_2$ balloon. The mixture was filtered through a Celite pad, and the filtrate was concentrated to give crude 2-((3R,4R,5R,6R)-4,5-dihydroxy-6-(hydroxymethyl)tetrahydro-2H-pyran-3-yl)acetamide (8 mg, 93% yield). LC-MS (ESI) found: 206$[M+H]^+$. $^1$H NMR (400 MHz, MeOD): δ 4.62 (dd, J=7.4, 4.5 Hz, 1H), 3.94-3.89 (m, 1H), 3.80-3.73 (m, 2H), 3.68-3.61 (m, 2H), 3.52-3.48 (m, 1H), 3.36-3.33 (m, 1H), 2.93 (dd, J=18.3, 6.6 Hz, 1H), 2.83-2.75 (m, 1H).

Preparation of (3R,4R,5R,6R)-4,5-dihydroxy-6-(hydroxymethy1681)-N-methyltetrahydro-2H-pyran-3-carboxamide (Compound A400)

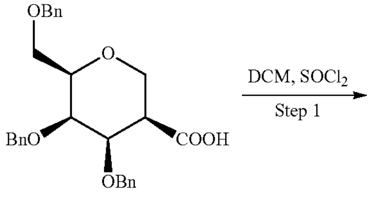

-continued

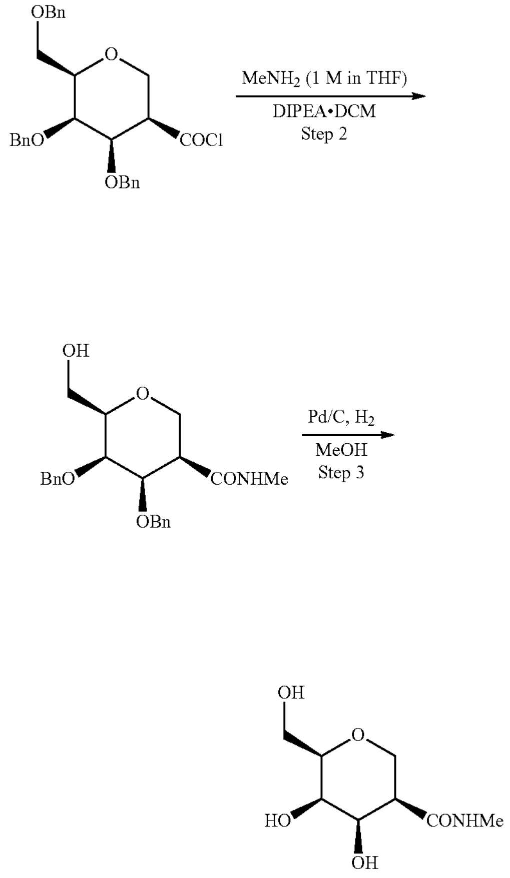

Step 1: To a solution of (3R,4R,5R,6R)-4,5-bis(benzyloxy)-6-((benzyloxy)methyl)tetrahydro-2H-pyran-3-carboxylic acid (200 mg, 0.432 mmol) in DCM (5 mL) was added $SOCl_2$ (3 mL, 43 mmol) at rt. The mixture was stirred at 50° C. for 6 h. The mixture was concentrated to give crude (3R,4R,5R,6R)-4,5-bis(benzyloxy)-6-((benzyloxy)methyl)tetrahydro-2H-pyran-3-carbonyl chloride which was used for next step directly.

Step 2: To a solution of (3R,4R,5R,6R)-4,5-bis(benzyloxy)-6-((benzyloxy)methyl)tetrahydro-2H-pyran-3-carbonyl chloride (100 mg, 0.208 mmol) in DCM (2 mL). Methanamine (2.1 mL, 2 M in THF) was added and the mixture was stirred at rt for 2 h. The mixture was quenched with $H_2O$ and extracted with DCM, concentrated, purified by prep-HPLC (Method A) to give (4R,5R,6R)-4,5-bis(benzyloxy)-6-(hydroxymethyl)-N-methyloxane-3-carboxamide (20 mg, 25%) as colorless oil. LC-MS (ESI) found: 386 $[M+H]^+$.

Step 3: To a solution of (3R,4R,5R,6R)-4,5-bis(benzyloxy)-6-(hydroxymethyl)-N-methyltetrahydro-2H-pyran-3-carboxamide (10 mg, 0.026 mmol) in MeOH (2 mL) was added Pd/C (3 mg, 10% wt., 60% wet). The mixture was stirred at rt for 0.5 h under a $H_2$ balloon. The mixture was filtered and concentrated to give (3R,4R,5R,6R)-4,5-dihydroxy-6-(hydroxymethyl)-N-methyltetrahydro-2H-pyran-3-carboxamide (3 mg, 58% yield) as white solid. LC-MS (ESI) found: 206 $[M+H]^+$. $^1H$ NMR (400 MHz, MeOD): δ 4.08 (dd, J=12.2, 1.0 Hz, 1H), 3.93 (dd, J=6.3, 3.7 Hz, 1H), 3.71 (tdd, J=16.0, 11.9, 5.2 Hz, 4H), 3.38-3.34 (m, 1H), 2.79 (dd, J=6.2, 2.9 Hz, 1H), 2.75 (s, 3H).

Preparation of methyl (3R,4R,5R,6R)-4,5-dihydroxy-6-(hydroxymethyl)tetrahydro-2H-pyran-3-carboxylate (Compound A401)

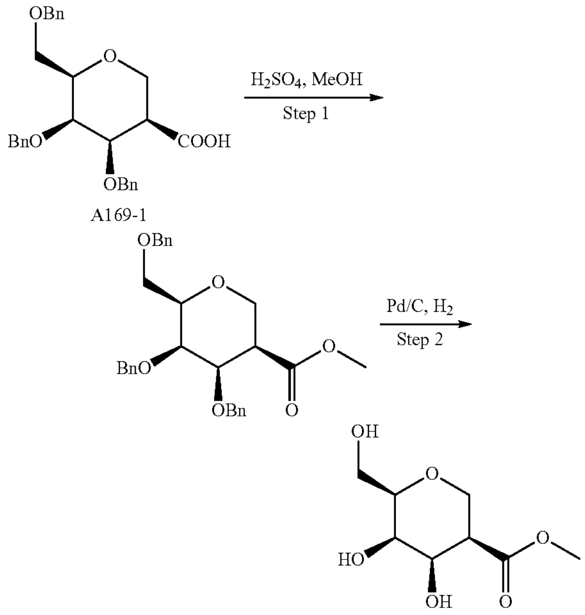

A169-1

Step 1: To a solution of (3R,4R,5R,6R)-4,5-bis(benzyloxy)-6-((benzyloxy)methyl)tetrahydro-2H-pyran-3-carboxylic acid (A169-1, 100 mg, 0.217 mmol) in MeOH (15 mL) was added $H_2SO_4$ (19.3 mg, 0.108 mmol). The mixture was stirred 60° C. rt for 5 h. The mixture was concentrated and purified by prep-HPLC (Method A) to give (3R,4R,5R,6R)-4,5-bis(benzyloxy)-6-((benzyloxy)methyl)tetrahydro-2H-pyran-3-carboxylate (55 mg, 53% yield) as yellow oil. LC-MS (ESI) found: 477 $[M+H]^+$.

Step 2: To a solution of (3R,4R,5R,6R)-4,5-bis(benzyloxy)-6-((benzyloxy)methyl)tetrahydro-2H-pyran-3-carboxylate (15 mg, 0.031 mmol) in MeOH (2 mL) was added Pd/C (4 mg, 10% wt., 60% wet). The mixture was stirred at rt for 0.5 h under a $H_2$ balloon The mixture was filtered and concentrated to give (3R,4R,5R,6R)-4,5-dihydroxy-6-(hydroxymethyl)tetrahydro-2H-pyran-3-carboxylate (6 mg, 92% yield) as yellow oil. LC-MS (ESI) found: 207 $[M+H]^+$. $^1H$ NMR (400 MHz, MeOD): δ 4.18 (dd, J=12.2, 2.9 Hz, 1H), 3.98 (dd, J=5.6, 3.5 Hz, 1H), 3.84-3.75 (m, 2H), 3.74 (s, 3H), 3.71-3.58 (m, 2H), 3.48-3.38 (m, 1H), 2.95-2.85 (m, 1H).

Preparation of N-(2-((((3R,4R,5R,6R)-4,5-dihydroxy-6-(hydroxymethyl)tetrahydro-2H-pyran-3-yl)methyl)amino)ethyl)acetamide (Compound A402)

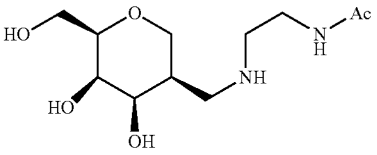 [SMILES: CC(=O)NCCNC[C@@H]1CO[C@H](CO)[C@H](O)[C@@H]1O]

It was prepared according to the procedure same as that for A209. LC-MS (ESI) found: 263 $[M+H]^+$. $^1H$ NMR (400 MHz, MeOD): δ 4.05 (d, J=12.4 Hz, 1H), 3.96 (dd, J=5.7, 3.3 Hz, 1H), 3.87-3.83 (m, 1H), 3.75 (dd, J=11.5, 7.2 Hz, 1H), 3.68-3.62 (m, 2H), 3.59-3.38 (m, 4H), 3.25 (dd, J=12.7, 3.2 Hz, 1H), 3.16-3.06 (m, 2H), 2.24-2.15 (m, 1H), 2.00 (s, 3H).

Preparation of 1-(((3R,4R,5R,6R)-4,5-dihydroxy-6-(hydroxymethyl)tetrahydro-2H-pyran-3-yl)methyl)urea (Compound A403)

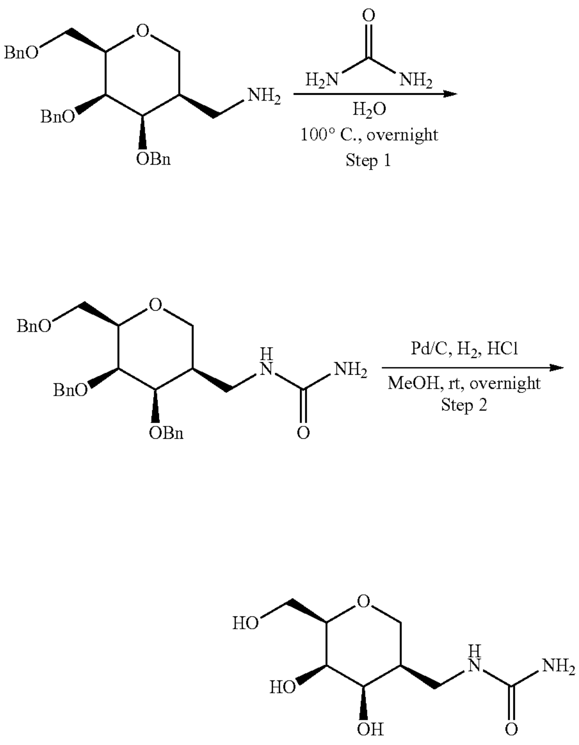

Step 1: To a solution of ((3R,4R,5R,6R)-4,5-bis(benzyloxy)-6-((benzyloxy)methyl)tetrahydro-2H-pyran-3-yl)methanamine (40 mg, 0.089 mmol) in $H_2O$ (10 mL) was added urea (8 mg, 0.13 mmol). The reaction mixture was stirred at 100° C. overnight. The resulting mixture was separated and concentrated in vacuo. The crude product was purified by flash chromatography (silica gel, 0~20% MeOH in DCM) to give 1-(((3R,4R,5R,6R)-4,5-bis(benzyloxy)-6-((benzyloxy)methyl)tetrahydro-2H-pyran-3-yl)methyl)urea (40 mg, 91% yield) as yellow oil. LC-MS (ESI) found: 491 $[M+H]^+$.

Step 2: To a solution of 1-(((3R,4R,5R,6R)-4,5-bis(benzyloxy)-6-((benzyloxy)methyl)tetrahydro-2H-pyran-3-yl)methyl)urea (40 mg, 0.082 mmol) in MeOH (10 mL) were added Pd/C (10 mg, 10% wt., 60% wet) and HCl (0.1 mL, 1 M in $H_2O$). The reaction mixture was stirred at rt overnight under a $H_2$ balloon. The mixture was filtered, the filtrate was concentrated to give 1-(((3R,4R,5R,6R)-4,5-dihydroxy-6-(hydroxymethyl)tetrahydro-2H-pyran-3-yl)methyl)urea (2 mg, 11% yield) as colorless oil. LC-MS (ESI) found: 221 $[M+H]^+$. 1H NMR (400 MHz, MeOD): δ 3.96-3.90 (m, 1H), 3.89-3.84 (m, 1H), 3.84-3.77 (m, 2H), 3.68 (dd, J=11.6, 4.4 Hz, 1H), 3.58-3.41 (m, 4H), 1.97-1.83 (m, 1H).

Allyl Alcohols

Preparation of N-((2S,3R,4R,5R,6R)-2-(allyloxy)-4,5-dihydroxy-6-(hydroxymethyl)tetrahydro-2H-pyran-3-yl)-2,2,2-trifluoroacetamide (Compound A404)

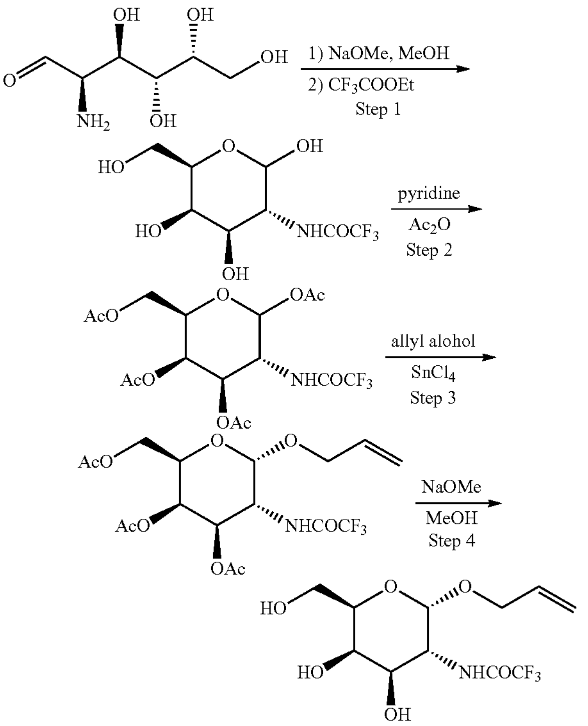

Step 1: To a solution of (2R,3R,4R,5R)-2-amino-3,4,5,6-tetrahydroxyhexanal hydrochloride (20 g, 92 mmol) in MeOH (200 mL) was added NaOMe (20.5 ml, 5 M in MeOH) at 0° C., then $CF_3COOEt$ (15 g, 102 mmol) was added. The mixture was stirred at rt for overnight. The mixture was concentrated and washed with i-PrOH to give 2,2,2-trifluoro-N-((3R,4R,5R,6R)-2,4,5-trihydroxy-6-(hydroxymethyl)tetrahydro-2H-pyran-3-yl)acetamide (20 g, 78% yield) as solid. LC-MS (ESI) found: 298 $[M+Na]^+$.

Step 2: To the solution of 2,2,2-trifluoro-N-((3R,4R,5R,6R)-2,4,5-trihydroxy-6-(hydroxymethyl)tetrahydro-2H-pyran-3-yl)acetamide (20 g, 73 mmol) in pyridine (60 mL) was added $Ac_2O$ (44 g, 434 mmol) at 0° C., then DMAP (1.2 g, 10 mmol) was added at 0° C. The mixture was stirred at rt overnight. The mixture was concentrated and washed with i-PrOH to give (3R,4R,5R,6R)-6-(acetoxymethyl)-3-(2,2,2-trifluoroacetamido)tetrahydro-2H-pyran-2,4,5-triyl triacetate (20 g, 62% yield) as solid. LC-MS (ESI) found: 442 $[M-H]^-$.

Step 3: To the solution of (3R,4R,5R,6R)-6-(acetoxymethyl)-3-(2,2,2-trifluoroacetamido)tetrahydro-2H-pyran-2,4,5-triyl triacetate (5 g, 11.28 mmol) in DCM (50 mL) was added allyl alcohol (2 g, 37.76 mmol), then $SnCl_4$ (7 g, 28.19 mmol) was added at 0° C. The mixture was stirred at rt overnight. the mixture was slowly poured into ice-cold water, the organic layer was separated and washed with $NaHCO_3$. The organic phase was then dried and concentrated. The residual was purified by silica gel column to give (2R,3R,4R,5R,6S)-2-(acetoxymethyl)-6-(allyloxy)-5-(2,2,2-trifluoroacetamido)tetrahydro-2H-pyran-3,4-diyl diacetate (2.6 g, 52% yield) as solid. LC-MS (ESI) found: 440 $[M-H]^-$.

Step 4: To a solution of (2R,3R,4R,5R,6S)-2-(acetoxymethyl)-6-(allyloxy)-5-(2,2,2-trifluoroacetamido)tetrahydro-2H-pyran-3,4-diyl diacetate (2.6 g, 30.18 mmol) in MeOH (30 mL) was added NaOMe (6 mL, 5 M in MeOH) at 0° C., the mixture was stirred at rt for 3 h. The mixture was acidified with Amberlite IR120 ($H^+$) form and filtered. The filtrate was concentrated to give N-((2S,3R,4R,5R,6R)-2-(allyloxy)-4,5-dihydroxy-6-(hydroxymethyl)tetrahydro-2H-pyran-3-yl)-2,2,2-trifluoroacetamide (1.4 g, 78% yield) as white solid. LC-MS (ESI) found: 316 $[M+H]^+$. $^1H$ NMR (400 MHz, $CD_3OD$): δ 5.98-5.82 (m, 1H), 5.30 (ddd, J=17.3, 3.3, 1.6 Hz, 1H), 5.17 (ddd, J=10.5, 2.8, 1.3 Hz, 1H), 4.92 (d, J=3.7 Hz, 1H), 4.29 (dd, J=10.9, 3.7 Hz, 1H), 4.24-4.13 (m, 1H), 4.01 (ddt, J=13.2, 6.2, 1.3 Hz, 1H), 3.95 (dd, J=10.9, 3.2 Hz, 1H), 3.91 (d, J=2.7 Hz, 1H), 3.85 (t, J=6.1 Hz, 1H), 3.78-3.67 (m, 2H).

Preparation of (2R,3R,4R,5R,6S)-6-(allyloxy)-5-((3-chloro-1,2,4-thiadiazol-5-yl)amino)-2-(hydroxymethyl)tetrahydro-2H-pyran-3,4-diol (Compound A405)

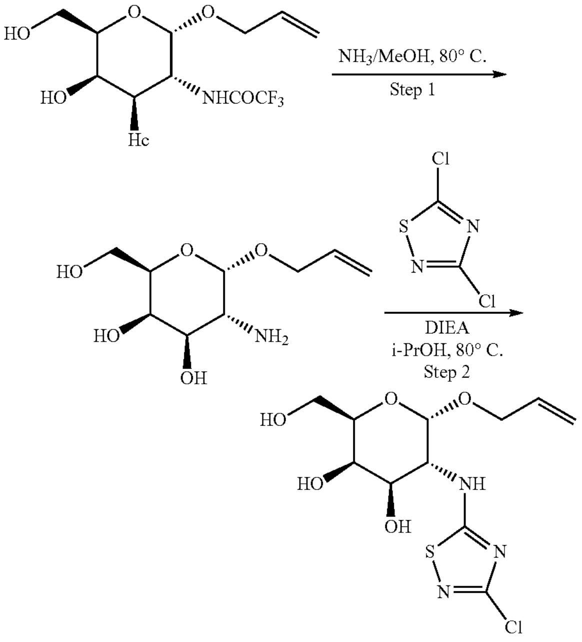

Step 1: A solution of N-((2S,3R,4R,5R,6R)-2-(allyloxy)-4,5-dihydroxy-6-(hydroxymethyl)tetrahydro-2H-pyran-3-yl)-2,2,2-trifluoroacetamide (A404, 200 mg, 0.6 mmol) in $NH_3$/MeOH (6 mL, 7 M) was stirred at 80° C. overnight in a sealed tube. The mixture was concentrated and purified by C18 column to give (2R,3R,4R,5R,6S)-6-(allyloxy)-5-amino-2-(hydroxymethyl)tetrahydro-2H-pyran-3,4-diol (50 mg, 36% yield) as a white solid. LC-MS (ESI) found: 220 $[M+H]^+$.

Step 2: A mixture of (2R,3R,4R,5R,6S)-6-(allyloxy)-5-amino-2-(hydroxymethyl)tetrahydro-2H-pyran-3,4-diol (30 mg, 0.1 mmol), 3,5-dichloro-1,2,4-thiadiazole (31 mg, 0.2 mmol) and DIEA (39 mg, 0.3 mmol) in isopropanol (3 mL) was stirred at 80° C. overnight in a sealed tube. The mixture was concentrated and purified by silica gel column (0-20% methanol in methylene chloride) to give (2R,3R,4R,5R,6S)-6-(allyloxy)-5-((3-chloro-1,2,4-thiadiazol-5-yl)amino)-2-(hydroxymethyl)tetrahydro-2H-pyran-3,4-diol (1.1 mg, 2% yield) as a white solid. LC-MS (ESI) found: 338 $[M+H]^+$. $^1H$ NMR (400 MHz, $CD_3OD$): δ 5.93 (ddd, J=21.9, 10.8, 5.7 Hz, 1H), 5.30 (dd, J=17.2, 1.7 Hz, 1H), 5.16 (dd, J=10.4, 1.6 Hz, 1H), 5.01 (d, J=3.6 Hz, 1H), 4.22 (dd, J=13.1, 5.1 Hz, 2H), 4.02 (dd, J=13.0, 6.2 Hz, 1H), 3.92 (d, J=2.8 Hz, 1H), 3.89-3.83 (m, 2H), 3.78-3.68 (m, 2H).

Preparation of (2R,3R,4R,5R,6S)-6-(allyloxy)-2-(hydroxymethyl)-5-((4-(trifluoromethyl)pyrimidin-2-yl)amino)tetrahydro-2H-pyran-3,4-diol (Compound A406)

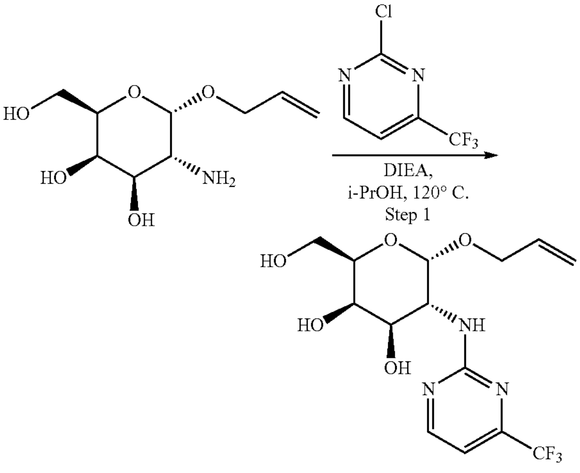

Step 1: To a mixture of (2R,3R,4R,5R,6S)-6-(allyloxy)-5-amino-2-(hydroxymethyl)tetrahydro-2H-pyran-3,4-diol (30 mg, 0.14 mmol) in i-PrOH (2 mL) was added 2-chloro-4-(trifluoromethyl)pyrimidine (0.03 mL, 0.27 mmol) and DIEA (0.06 mL, 0.41 mmol) at rt under $N_2$. After stirring at 120° C. overnight, the reaction mixture was concentrated and purified by prep-TLC to afford (2R,3R,4R,5R,6S)-6-(allyloxy)-2-(hydroxymethyl)-5-((4-(trifluoromethyl)pyrimidin-2-yl)amino)tetrahydro-2H-pyran-3,4-diol (21 mg, 41% yield) as a white solid. LC-MS (ESI) found: 366 $[M+H]^+$. $^1H$ NMR (400 MHz, $CD_3OD$): δ 8.52 (d, J=4.7 Hz, 1H), 6.91 (d, J=4.9 Hz, 1H), 5.88 (s, 1H), 5.27 (d, J=16.9 Hz, 1H), 5.10 (d, J=10.6 Hz, 1H), 5.02 (s, 1H), 4.53 (s, 1H), 4.21 (dd, J=13.1, 5.0 Hz, 1H), 4.01-3.86 (m, 4H), 3.79-3.70 (m, 2H).

Preparation of (2R,3R,4R,5R)-5-(aminomethyl)-2-(hydroxymethyl)tetrahydro-2H-pyran-3,4-diol (Compound A425)

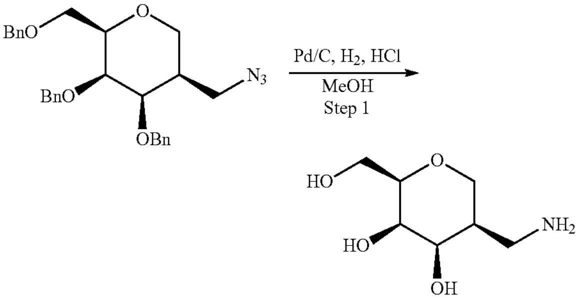

Step 1: To a solution of (2R,3R,4R,5R)-5-(azidomethyl)-3,4-bis(benzyloxy)-2-((benzyloxy)methyl)tetrahydro-2H-pyran (50 mg, 0.11 mmol) in MeOH (5 mL) were added Pd/C (5 mg, 10% wt, 60% wet) and HCl (0.1 mL, 1N in $H_2O$). The reaction mixture was stirred at rt overnight under a balloon of $H_2$. The mixture was filtered and concentrated in vacuo to give (2R,3R,4R,5R)-5-(aminomethyl)-2-(hydroxymethyl)tetrahydro-2H-pyran-3,4-diol (16 mg, 86 yield) as yellow oil. LC-MS (ESI) found: 178 $[M+H]^+$. $^1H$ NMR (400 MHz, $CD_3OD$): δ 4.09-4.02 (m, 1H), 3.96 (dd, J=5.7, 3.3 Hz, 1H), 3.85 (d, J=2.7 Hz, 1H), 3.76-3.70 (m, 1H), 3.69-3.61 (m, 2H), 3.43-3.33 (m, 2H), 3.26 (dd, J=13.0, 3.7 Hz, 1H), 2.22-2.05 (n, 1H).

The following compounds below were prepared according to the procedure same as A287:

| ID | Characterization data | Starting Material |
|---|---|---|
| 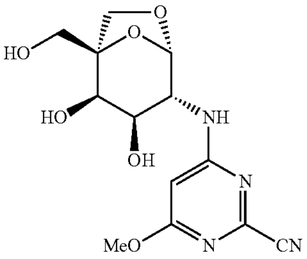 A426 | Yield: 2.6 mg, 3%, white solid. LC-MS (ESI) found: 325 $[M + H]^+$. $^1H$ NMR (400 MHz, $CD_3OD$): δ 6.00 (s, 1H), 5.29 (d, J = 0.9 Hz, 1H), 4.25 (dd, J = 17.2, 7.1 Hz, 1H), 3.93 (d, J = 11.4 Hz, 1H), 3.90 (d, J = 4.3 Hz, 1H), 3.89 (s, 3H), 3.83 (d, J = 11.4 Hz, 1H), 3.77 (dd, J = 8.8, 4.5 Hz, 2H), 3.70 (d, J = 7.9 Hz, 1H). | 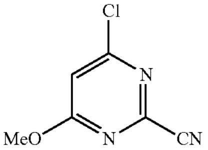 [SMILES: COc1cc(Cl)nc(C#N)n1] |
| 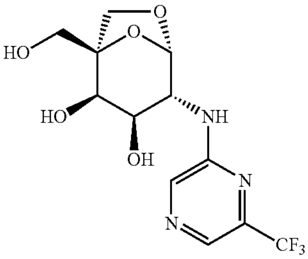 A427 | Yield: 1.4 mg, 2%, white solid. LC-MS (ESI) found: 338 $[M + H]^+$. $^1H$ NMR (400 MHz, $CD_3OD$): δ 8.16 (s, 1H), 8.01 (s, 1H), 5.35 (d, J = 1.4 Hz, 1H), 4.21 (dd, J = 9.9, 1.2 Hz, 1H), 3.94 (d, J = 10.2 Hz, 1H), 3.92 (d, J = 3.0 Hz, 1H), 3.84 (dd, J = 9.6, 4.5 Hz, 2H), 3.81 (d, J = 9.0 Hz, 1H), 3.72 (d, J = 7.9 Hz, 1H). | 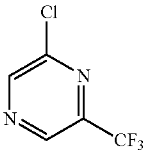 [SMILES: FC(F)(F)c1cncc(Cl)n1] |

Linkers:

Preparation of N-((1S,2R,3R,4R,5S)-1-(13-azido-2,5,8,11-tetraoxatridecyl)-2,3-dihydroxy-6,8-dioxabicyclo[3.2.1]octan-4-yl)-2,2,2-trifluoroacetamide (Compound A407)

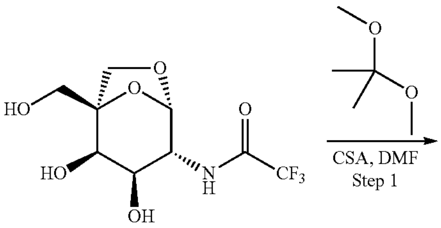

-continued

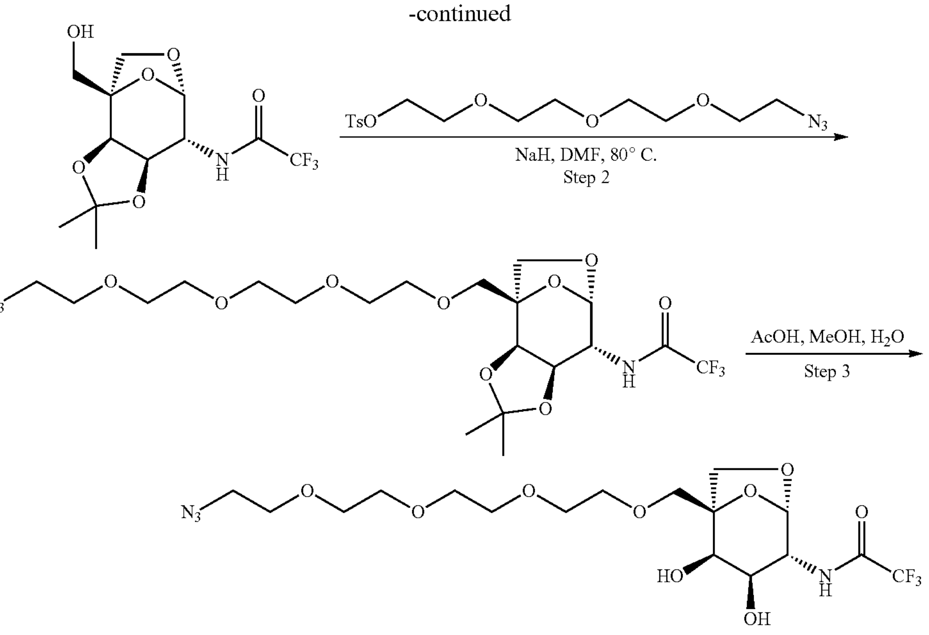

Step 1: The solution of N-((1S,2R,3R,4R,5S)-2,3-dihydroxy-1-(hydroxymethyl)-6,8-dioxabicyclo[3.2.1]octan-4-yl)-2,2,2-trifluoroacetamide in DMF (20 mL) was added CSA (0.81 g, 3.48 mmol) and 2,2-dimethoxypropane (7.54 g, 72.43 mmol). The reaction mixture was stirred at 80° C. overnight and quenched with TEA. Then the solvent was removed under vacuum. The residue was purified by flash chromatography (DCM:MeOH=10:1) to give 2,2,2-trifluoro-N-((3aR,4S,7S,8R,8aR)-4-(hydroxymethyl)-2,2-dimethylhexahydro-4,7-epoxy[1,3]dioxolo[4,5-d]oxepin-8-yl) acetamide (2 g, 68% yield) as a colorless oil. LC-MS (ESI) found: 328 $[M+H]^+$.

Step 2: To a suspension of 2,2,2-trifluoro-N-((3aR,4S,7S,8R,8aR)-4-(hydroxymethyl)-2,2-dimethylhexahydro-4,7-epoxy[1,3]dioxolo[4,5-d]oxepin-8-yl)acetamide (2.27 g, 6.94 mmol) in dry DMF (30 mL) was added NaH (0.33 g, 8.32 mmol, 60% weight in mineral oil) was added. After stirring at rt for 1.5 h, 2-(2-(2-(2-azidoethoxy)ethoxy)ethoxy)ethyl 4-methylbenzenesulfonate (2.85 g, 7.63 mmol) was added. The mixture was stirred at 60° C. for 16 h, $NH_4Cl$ (aq) was added, the solvent was removed, and purified by prep-HPLC (Method B) to give N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)-2,2,2-trifluoroacetamide (650 mg, 18% yield). LC-MS (ESI) found: 529 $[M+H]^+$.

Step 3: A solution of N-((3aR,4S,7S,8R,8aR)-4-(13-azido-2,5,8,11-tetraoxatridecyl)-2,2-dimethylhexahydro-4,7-epoxy[1,3]dioxolo[4,5-d]oxepin-8-yl)-2,2,2-trifluoroacetamide (30 mg, 0.057 mmol) in AcOH (3.2 mL), MeOH (1 mL) and $H_2O$ (1 mL) was stirred at 70° C. for 14 h. Solvent was evaporated and the residue was co-evaporated twice with toluene. The residue was purified by prep-HPLC (Method B) to give N-((1S,2R,3R,4R,5S)-1-(13-azido-2,5,8,11-tetraoxatridecyl)-2,3-dihydroxy-6,8-dioxabicyclo[3.2.1]octan-4-yl)-2,2,2-trifluoroacetamide (10 mg, 39% yield). LC-MS (ESI) found: 489 $[M+H]^+$. $^1H$ NMR (400 MHz, $CDCl_3$): δ 6.51 (d, J=8.5 Hz, 1H), 5.38 (d, J=1.3 Hz, 1H), 4.81 (d, J=4.7 Hz, 1H), 4.18-4.05 (m, 3H), 3.81 (d, J=8.2 Hz, 1H), 3.76-3.63 (m, 16H), 3.58 (s, 1H), 3.42 (td, J=4.7, 1.9 Hz, 2H), 3.18 (d, J=10.1 Hz, 1H)

Preparation of 13,13-bis((2-carboxyethoxy)methyl)-1-((2,4-dinitrophenyl)amino)-11-oxo-3,6,9,15-tetraoxa-12-azaoctadecan-18-oic Acid (Compound A408)

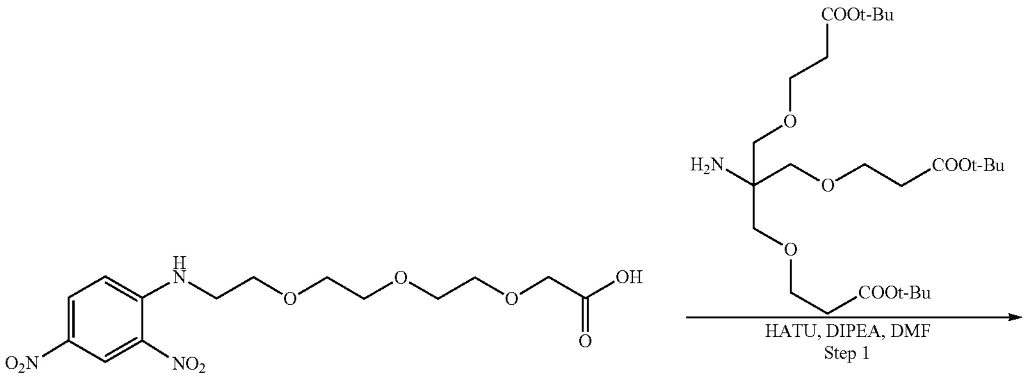

-continued

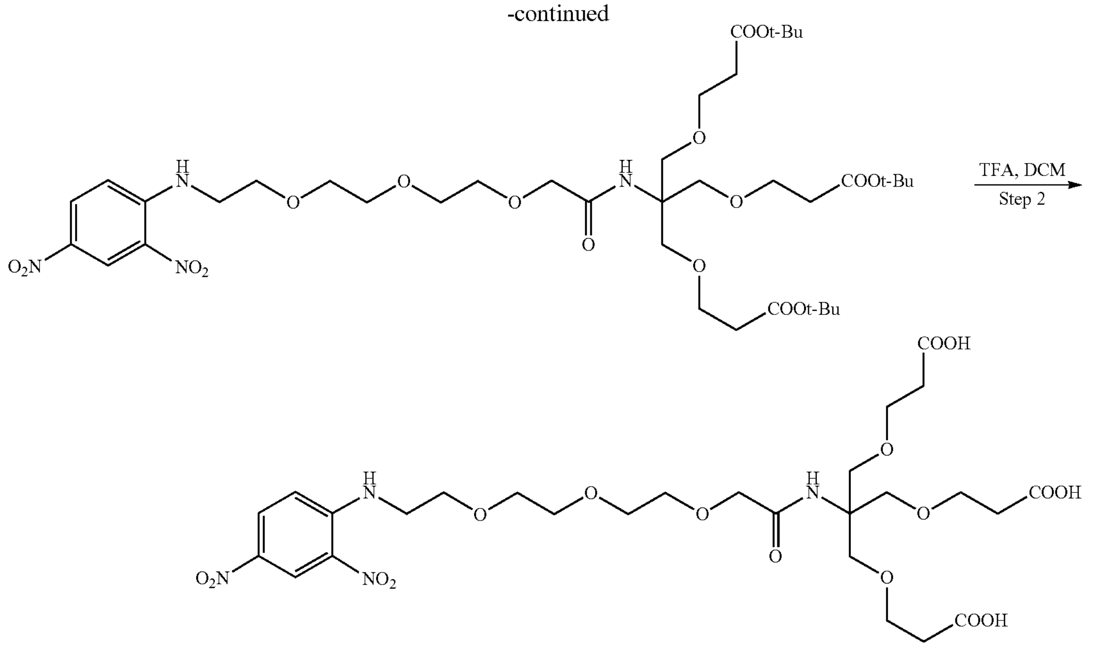

Step 1: To a solution of 2-[2-(2-{2-[(2,4-dinitrophenyl)amino]ethoxy}ethoxy)ethoxy]acetic acid (3 g, 8.04 mmol) in DMF (30 mL) were added HATU (3.97 g, 10.45 mmol) and DIEA (3.98 mL, 24.11 mmol). The reaction mixture was stirred at ice water for 0.5 hours, then di-tert-butyl 3,3'-((2-amino-2-((3-(tert-butoxy)-3-oxopropoxy)methyl)propane-1,3-diyl)bis(oxy))dipropionate (4.47 g, 8.84 mmol) was added. The reaction mixture was stirred at rt for 16 h and purified by prep-HPLC (Method B) to give tert-butyl 13,13-bis((3-(tert-butoxy)-3-oxopropoxy)methyl)-1-((2,4-dinitrophenyl)amino)-11-oxo-3,6,9,15-tetraoxa-12-azaoctadecan-18-oate (4 g, 89%). LC-MS (ESI) found: 861 $[M+H]^+$.

Step 2: To a solution of tert-butyl 13,13-bis((3-(tert-butoxy)-3-oxopropoxy)methyl)-1-((2,4-dinitrophenyl)amino)-11-oxo-3,6,9,15-tetraoxa-12-azaoctadecan-18-oate (500 mg, 0.58 mmol) in DCM (8 mL) was added TFA (0.8 mL). The reaction was stirred at rt for 18 h. The reaction was concentrated in vacuo and the residue was purified by flash (C18)(water/$CH_3CN$) to give 13,13-bis((2-carboxyethoxy)methyl)-1-((2,4-dinitrophenyl)amino)-11-oxo-3,6,9,15-tetraoxa-12-azaoctadecan-18-oic acid (110 mg, 75%). LC-MS (ESI) found: 693 $[M+H]^+$. $^1H$ NMR (400 MHz, MeOD): δ 9.04 (d, J=2.7 Hz, 1H), 8.29 (dd, J=9.6, 2.7 Hz, 1H), 7.23 (d, J=9.6 Hz, 1H), 3.88 (s, 2H), 3.82 (t, J=5.3 Hz, 2H), 3.74-3.64 (m, 22H), 2.51 (t, J=6.1 Hz, 6H).

Preparation of (2S,3R,4R,5R)—N-(2-(2-(2-(2-((2,4-dinitrophenyl)amino)ethoxy)ethoxy)ethoxy)ethyl)-3,4-dihydroxy-5-(1-methyl-1H-pyrazol-4-yl)tetrahydro-2H-pyran-2-carboxamide (Compound A409)

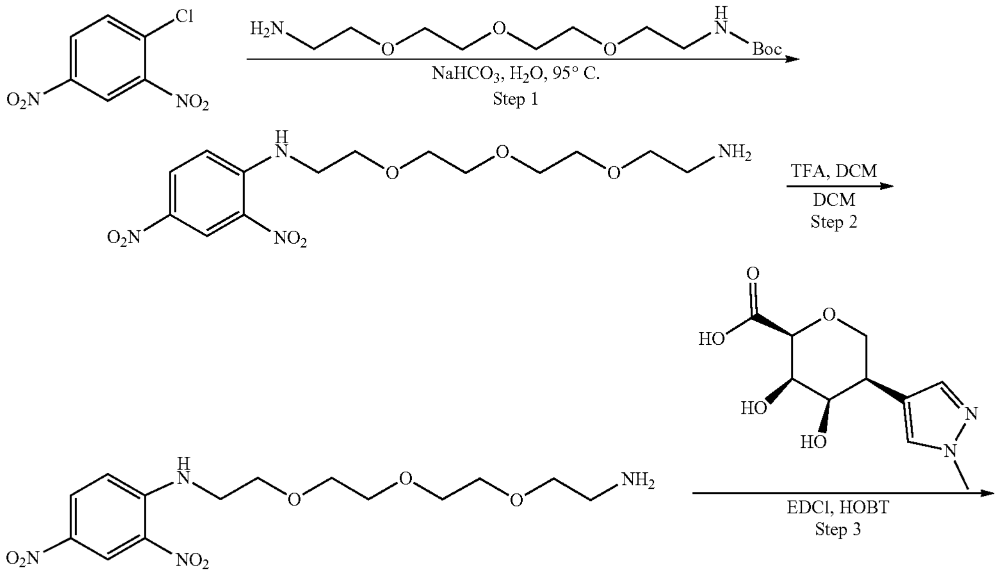

-continued

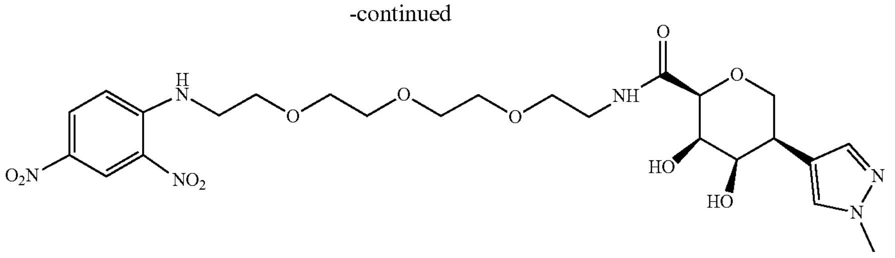

Step 1: To a solution of 1-chloro-2,4-dinitrobenzene (1.0 g, 4.94 mmol) in $H_2O$ (20 mL) was added $NaHCO_3$ (0.4 g, 5.13 mmol) and tert-butyl (2-(2-(2-(2-aminoethoxy)ethoxy) ethoxy)ethyl)carbamate (0.5 g, 1.71 mmol) at 0° C. in portions. The mixture was stirred at 95° C. for 2 h. The mixture was adjust pH to 6 and extracted with DCM, washed with brine, concentrated and purified by silica column to give (2-(2-(2-(2-((2,4-dinitrophenyl)amino)ethoxy)ethoxy) ethoxy)ethyl)carbamate (710 mg, 90% yield) as a yellow oil. LC-MS (ESI) found: 459 $[M+H]^+$.

Step 2: To a solution of tert-butyl (2-(2-(2-(2-((2,4-dinitrophenyl)amino)ethoxy)ethoxy)ethoxy)ethyl)carbamate (100 mg, 0.22 mmol) in DCM (5 mL) was added TFA (0.8 mL, 10.9 mmol) and stirred at rt for 2 h. The mixture was concentrated to give crude N-(2-(2-(2-(2-aminoethoxy) ethoxy)ethoxy)ethyl)-2,4-dinitroaniline (75 mg, 96% yield) as a yellow oil. LC-MS (ESI) found: 359 $[M+H]^+$.

Step 3: To a solution of N-(2-(2-(2-(2-aminoethoxy) ethoxy)ethoxy)ethyl)-2,4-dinitroaniline and (2S,3R,4R,5R)-3,4-dihydroxy-5-(1-methyl-1H-pyrazol-4-yl)tetrahydro-2H-pyran-2-carboxylic acid in DCM is added EDCI, HOBt, NMM at 0° C. The mixture is stirred at rt for 2 h. The mixture is purified by prep-HPLC (Method A) to give (2S,3R,4R,5R)—N-(2-(2-(2-(2-((2,4-dinitrophenyl)amino) ethoxy)ethoxy)ethoxy)ethyl)-3,4-dihydroxy-5-(1-methyl-1H-pyrazol-4-yl)tetrahydro-2H-pyran-2-carboxamide.

Preparation of 6-(2-(2-(2-(2-((2,4-dinitrophenyl) amino)ethoxy)ethoxy)ethoxy)ethoxy)benzo[d]thiazole-2-carbonitrile (Compound A410)

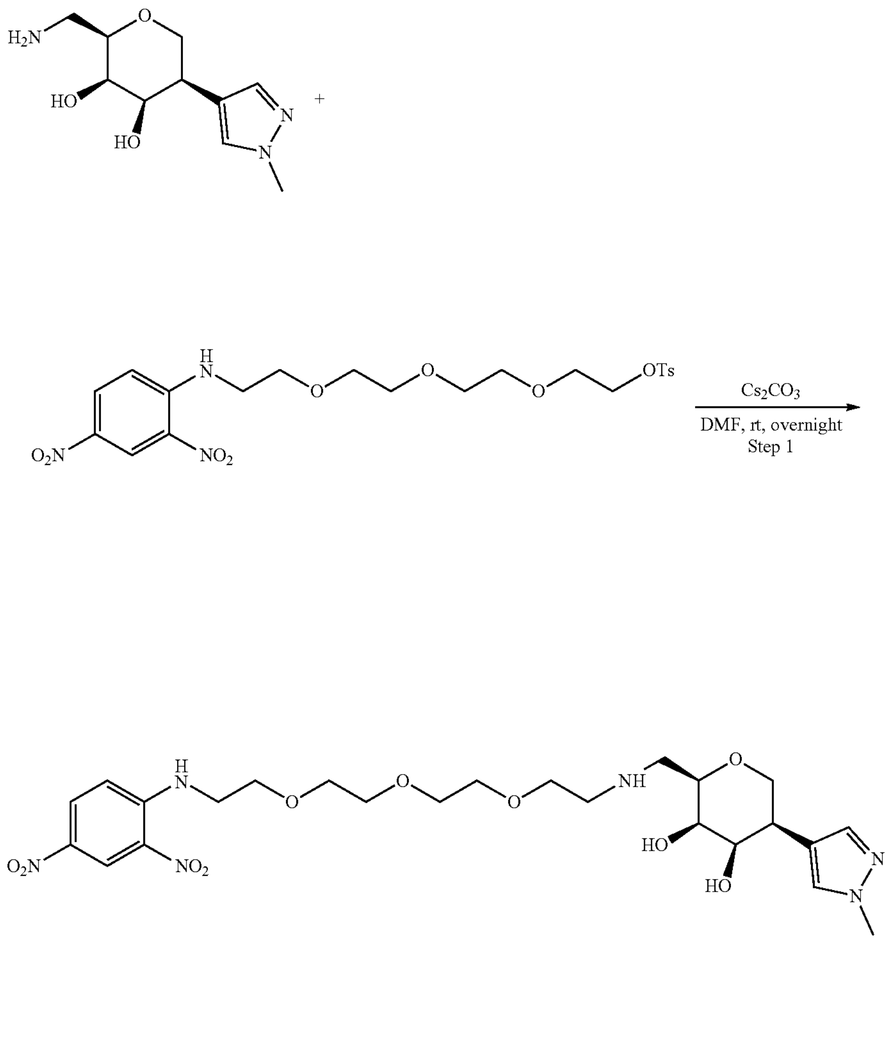

Step 1: To a solution of (2R,3R,4R,5R)-2-(aminomethyl)-5-(1-methyl-1H-pyrazol-4-yl)tetrahydro-2H-pyran-3,4-diol in DMF is added 2-(2-(2-(2-((2,4-dinitrophenyl)amino)ethoxy)ethoxy)ethoxy)ethyl 4-methylbenzenesulfonate and $Cs_2CO_3$. The reaction mixture is stirred at rt overnight. The resulting mixture is extracted with EA, washed with $H_2O$ and brine, and dried over $Na_2SO_4$. The organic layer is separated and concentrated in vacuo. The crude product is purified by flash chromatography (silica gel, 0-50% EA in PE) to give (2R,3R,4R,5R)-2-(13-((2,4-dinitrophenyl)amino)-5,8,11-trioxa-2-azatridecyl)-5-(1-methyl-1H-pyrazol-4-yl)tetrahydro-2H-pyran-3,4-diol.

Preparation of N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)but-3-ynamide (Compound A411)

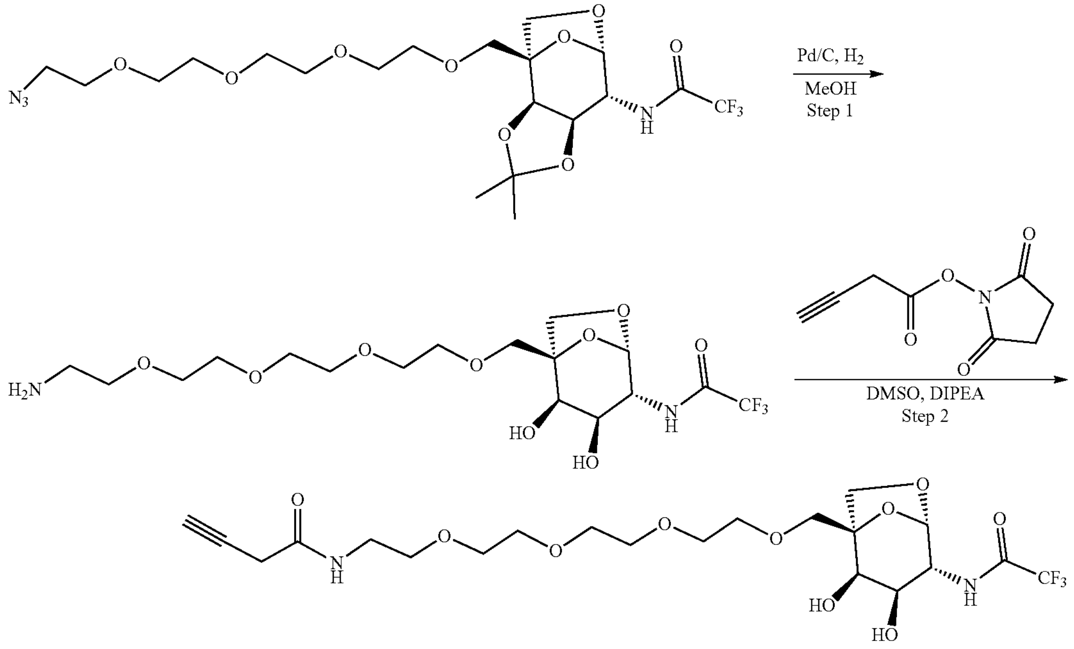

Preparation of (2R,3R,4R,5S)-5-((2-chloropyrrolo[2,1-f][1,2,4]triazin-4-yl)amino)-2-(13-((2,4-dinitrophenyl)amino)-5,8,11-trioxa-2-azatridecyl)tetrahydro-2H-pyran-3,4-diol (Compound A412)

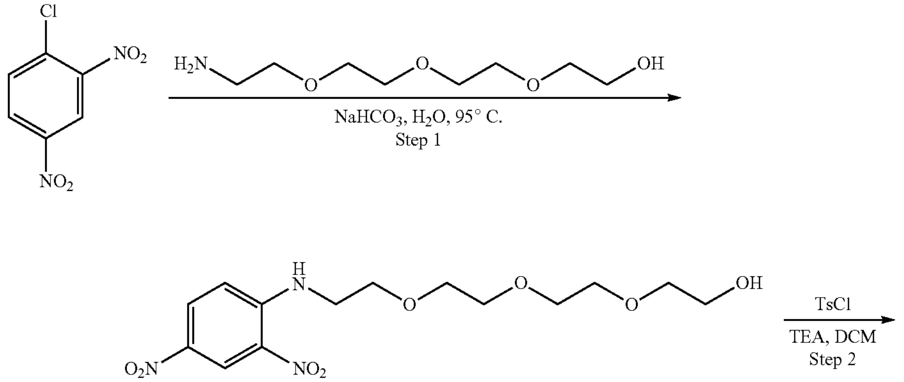

-continued

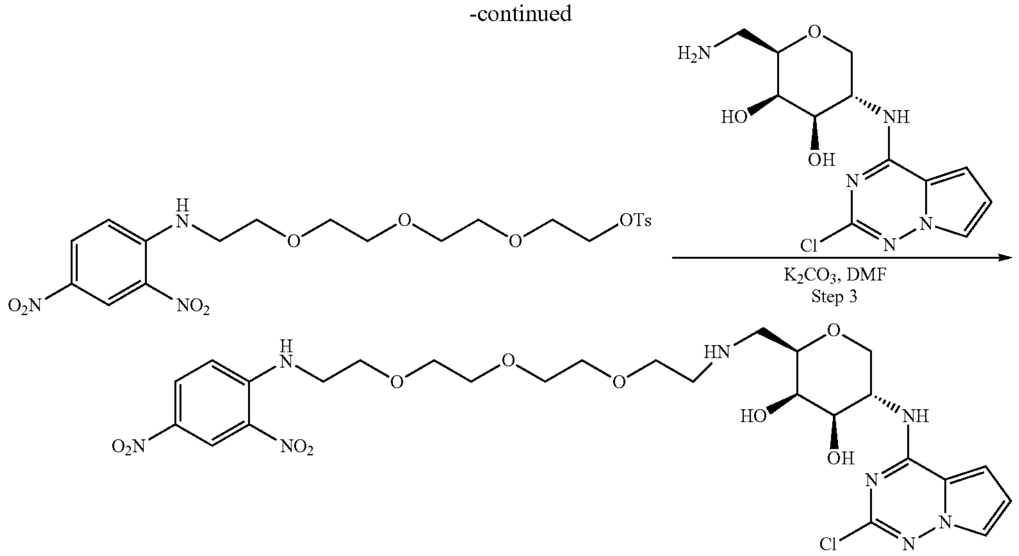

Step 1: To a solution of 2-(2-(2-(2-aminoethoxy)ethoxy) ethoxy)ethan-1-ol (1.2 g, 6.21 mmol) in $H_2O$ (20 mL) was added $NaHCO_3$ (1.6 g, 18.63 mmol) and 1-chloro-2,4-dinitrobenzene (2.5 g, 12.42 mmol) at 0° C. The mixture was stirred at 95° C. for 2 h. The mixture was adjust PH to 6 and extracted with DCM, washed with brine, concentrated and purified by silica gel column to give 2-2-(2-(2-(2-((2,4-dinitrophenyl)amino)ethoxy)ethoxy)ethoxy)ethan-1-ol (2.1 g, 941%) as a yellow oil. LC-MS (ESI) found: 360 $[M+H]^+$.

Step 2: To a solution of 2-(2-(2-(2-((2,4-dinitrophenyl) amino)ethoxy)ethoxy)ethoxy)ethan-1-ol (1.0 g, 2.78 mmol) in DCM (20 mL) was added TsCl (635 mg, 3.340 mmol) and TEA (1.16 mL, 8.35 mmol) at 0° C. in portions. The mixture was stirred at rt for 2 h. The mixture was concentrated and purified by silica gel column to give 2-(2-(2-(2-((2,4-dinitrophenyl)amino)ethoxy)ethoxy)ethoxy)ethyl 4-methylbenzenesulfonate (1.2 g, 87%) as a yellow oil. LC-MS (ESI) found: 514 $[M+H]^+$.

Step 3: To a solution of 2-(2-(2-(2-((2,4-dinitrophenyl) amino)ethoxy)ethoxy)ethoxy)ethyl 4-methylbenzenesulfonate in DMF is added (2R,3R,4R,5S)-2-(aminomethyl)-5-((2-chloropyrrolo[2,1-f][1,2,4]triazin-4-yl)amino) tetrahydro-2H-pyran-3,4-diol and $K_2CO_3$ at 0° C. The mixture is stirred at 100° C. for 12 h. The mixture is concentrated and purified by silica gel column to give (2R,3R,4R,5S)-5-((2-chloropyrrolo[2,1-f][1,2,4]triazin-4-yl)amino)-2-(13-((2,4-dinitrophenyl)amino)-5,8,11-trioxa-2-azatridecyl)tetrahydro-2H-pyran-3,4-diol.

Preparation of (2R,3R,4R,5S)-2-(13-azido-2,5,8,11-tetraoxatridecyl)-5-(methyl(4-(trifluoromethyl)pyrimidin-2-yl)amino)tetrahydro-2H-pyran-3,4-diol (Compound A413)

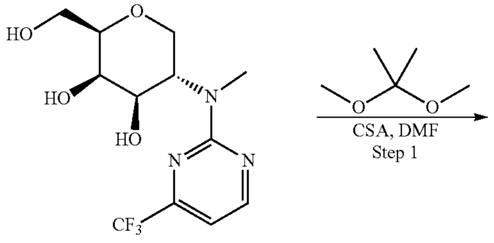

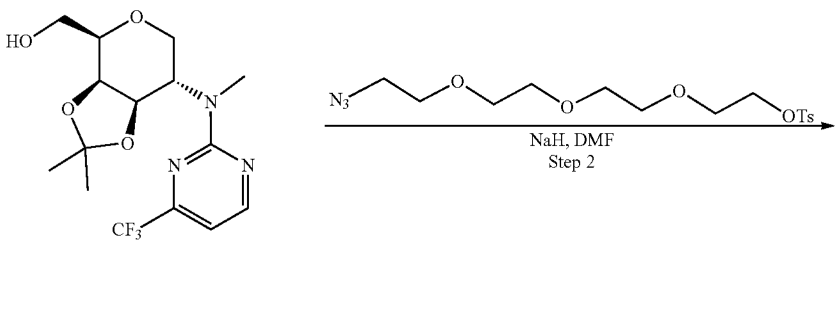

-continued
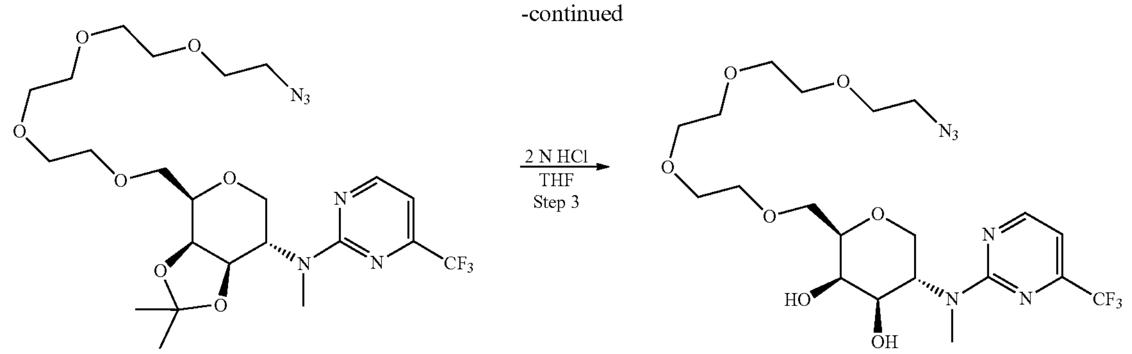
Preparation of 3,3'-((2-(2-(2-(2-(2-((2,4-dinitrophenyl)amino)ethoxy)ethoxy)ethoxy)acetamido)propane-1,3-diyl)bis(oxy))bis(N-(((2R,3R,4R,5S)-5-((3-amino-1,2,4-thiadiazol-5-yl)amino)-3,4-dihydroxytetrahydro-2H-pyran-2-yl)methyl)propanamide)(Compound A414)
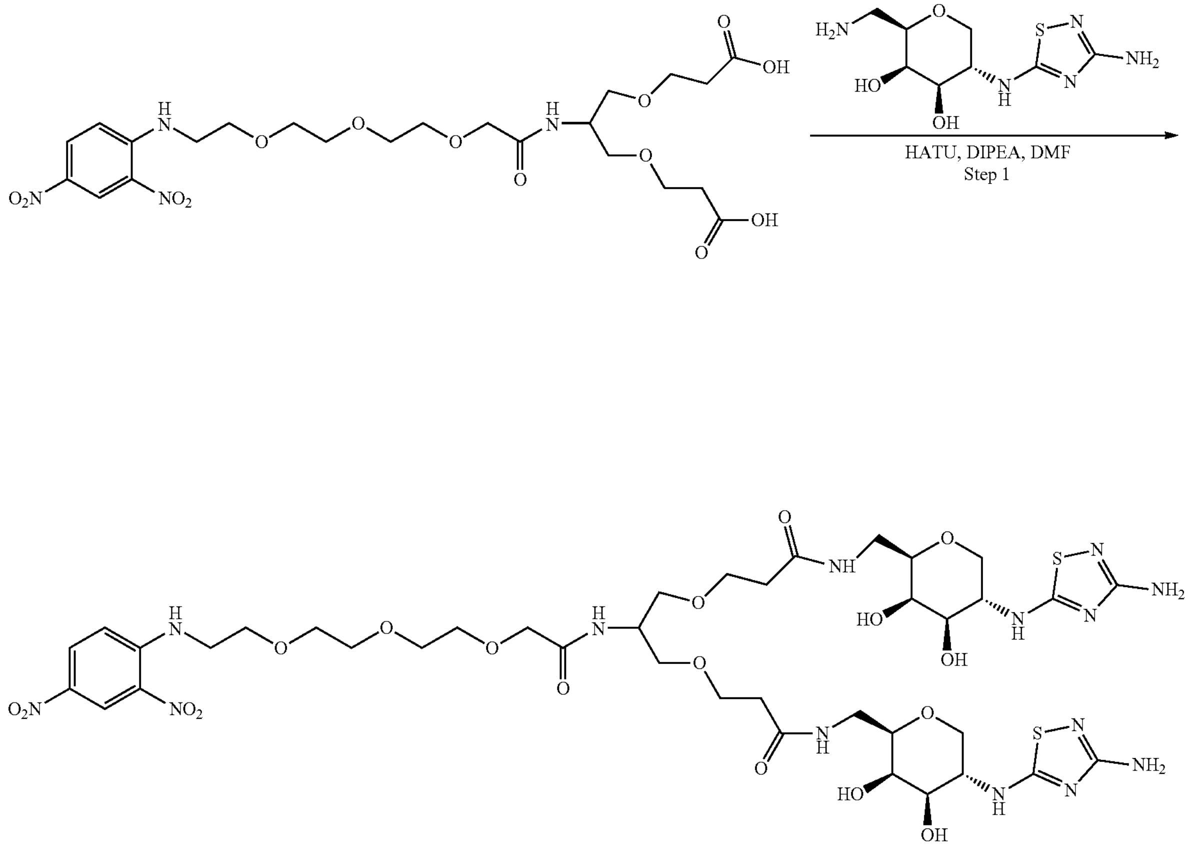

Preparation of 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)(Compound A415)
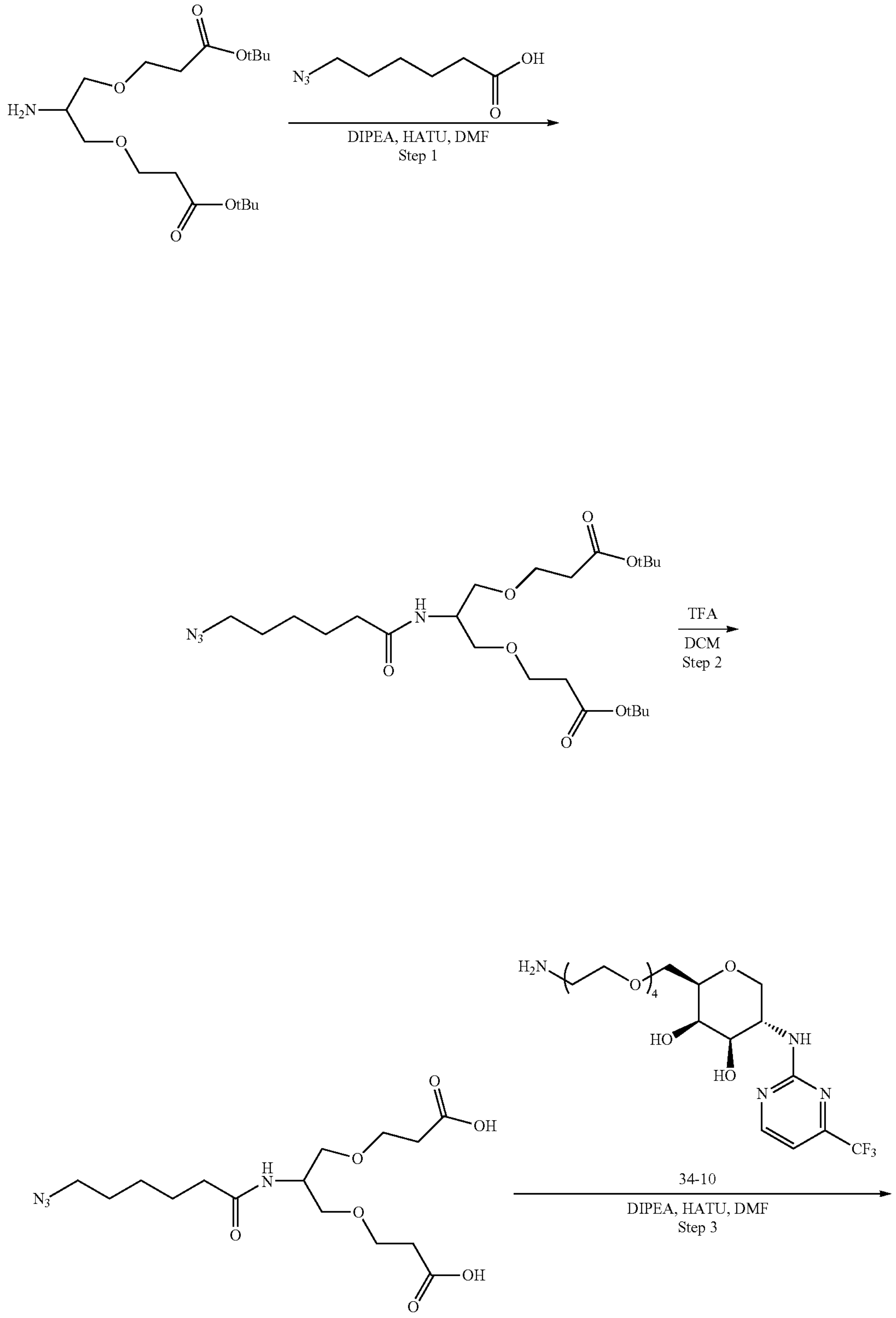

-continued

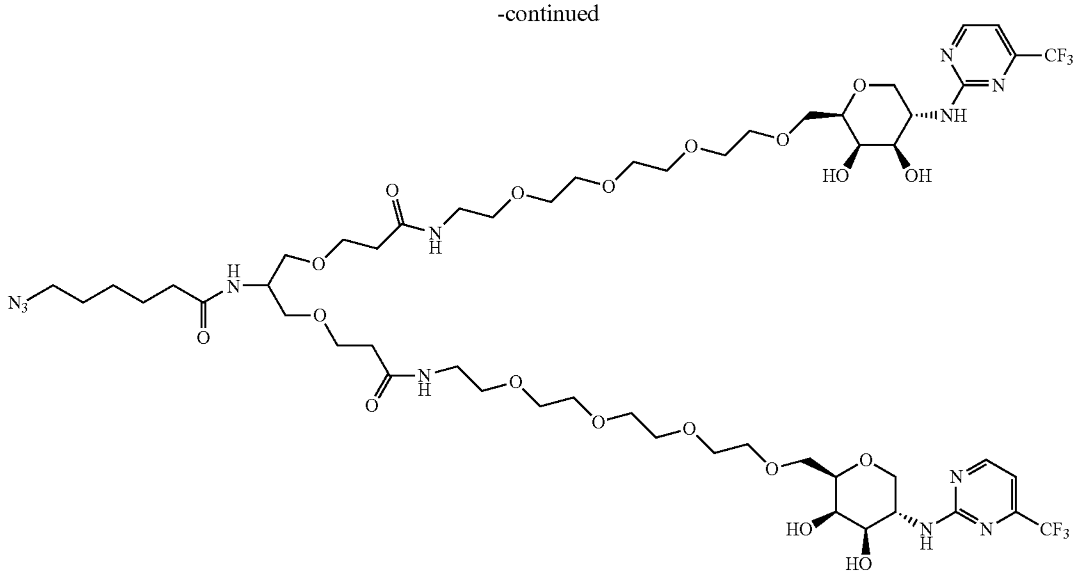

Step 1: A solution of 6-azidohexanoic acid (0.54 g, 3.45 mmol) and HATU (1.3 g, 3.45 mmol) in DMF (10 mL) was stirred at rt for 30 min. Di-tert-butyl 3,3'-((2-aminopropane-1,3-diyl)bis(oxy))dipropionate (1 g, 2.88 mmol) and DIPEA (0.95 mL, 5.76 mmol) were added at rt. The reaction was stirred overnight. The resulting mixture was diluted with DCM (100 mL), washed with $H_2O$ (50 mL×2) and brine (20 mL), dried over $Na_2SO_4$. The organic layer was separated and concentrated in vacuo. The crude product was purified by flash chromatography (silica gel, 0-80% EA in PE) to give di-tert-butyl 3,3'-((2-(6-azidohexanamido)propane-1,3-diyl)bis(oxy))dipropionate (800 mg, 93% yield) as colorless oil. LC-MS (ESI) found: 487 $[M+H]^+$. $^1H$ NMR (400 MHz, $CDCl_3$): δ 6.28 (d, J=8.2 Hz, 1H), 4.19-4.11 (m, 1H), 3.74-3.62 (m, 4H), 3.58 (dd, J=9.6, 4.0 Hz, 2H), 3.40 (dd, J=9.6, 6.1 Hz, 2H), 3.26 (t, J=6.9 Hz, 2H), 2.52-2.38 (m, 4H), 2.20 (t, J=7.5 Hz, 2H), 1.67-1.63 (m, 4H), 1.47-1.37 (m, 20H).

Step 2: A solution of 3,3'-((2-(6-azidohexanamido)propane-1,3-diyl)bis(oxy))dipropionate (800 mg, 1.64 mmol) in DCM (6 mL) was added TFA (2 mL, 26.93 mmol) dropwise at 0° C. The reaction was stirred at rt for 3 h. The resulting mixture was filtered and concentrated in vacuo. The crude 3,3'-((2-(6-azidohexanamido)propane-1,3-diyl)bis(oxy))dipropionic acid (470 mg, 76% yield) was used to next step with no further purification. LC-MS (ESI) found: 375 $[M+H]^+$. $^1H$ NMR (400 MHz, DMSO-$d_6$): δ 12.14 (s, 2H), 7.64 (d, J=8.2 Hz, 1H), 4.00-3.86 (m, 1H), 3.57 (t, J=6.3 Hz, 4H), 3.34 (d, J=5.8 Hz, 4H), 3.29 (d, J=6.9 Hz, 2H), 2.43 (t, J=6.3 Hz, 4H), 2.07 (t, J=7.3 Hz, 2H), 1.56-1.43 (m, 4H), 1.33-1.23 (m, 2H).

Step 3: A solution of 3,3'-((2-(6-azidohexanamido)propane-1,3-diyl)bis(oxy))dipropionic acid (70 mg, 0.19 mmol) and HATU (163 mg, 0.43 mmol) in DMF (5 mL) was stirred at rt for 30 min. (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (208 mg, 0.43 mmol) and DIPEA (73 mg, 0.56 mmol) were added at rt. The reaction was stirred overnight. The resulting mixture was concentrated in vacuo. The crude product was purified by flash chromatography (silica gel, 0~10% MeOH in DCM) to give 3,3'-((2-(6-azidohexanamido)propane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)(65 mg, 28% yield) as white solid. LC-MS (ESI) found: 654 $[M+2H]^{2+}$. $^1H$ NMR (400 MHz, MeOD): δ 8.51 (d, J=4.8 Hz, 2H), 6.90 (d, J=4.9 Hz, 2H), 4.36 (td, J=10.6, 5.3 Hz, 2H), 4.16-4.04 (m, 3H), 3.92 (d, J=2.9 Hz, 2H), 3.73-3.60 (m, 36H), 3.56 (dt, J=10.6, 3.0 Hz, 6H), 3.51-3.43 (m, 4H), 3.38 (t, J=5.5 Hz, 4H), 3.17 (t, J=10.9 Hz, 2H), 2.45 (dd, J=6.7, 5.4 Hz, 4H), 2.23 (t, J=7.5 Hz, 2H), 1.67-1.57 (m, 4H), 1.44-1.36 (m, 2H). $^{19}F$ NMR (377 MHz, MeOD): δ-72.30 (s).

Preparation of 2-(2-(2-(2-((2,4-dinitrophenyl)amino)ethoxy)ethoxy)ethoxy)acetic Acid (Compound A416)

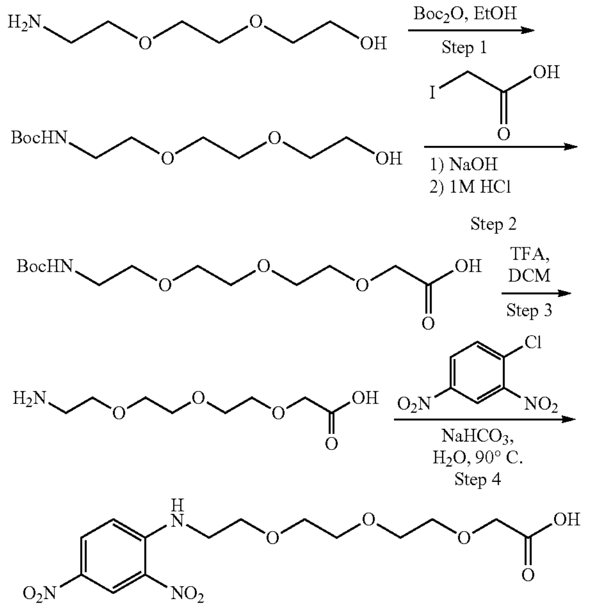

Step 1: To a solution of 2-(2-(2-aminoethoxy)ethoxy)ethan-1-ol (5.0 g, 33 mmol) in EtOH (60 mL) was added TEA (61.5 mL, 442 mmol) and di-tert-butyl dicarbonate (8.6 mL, 40 mmol) at 0° C. in portions. The mixture was vigorously stirred and allowed to warm up to room temperature slowly overnight (16 h). The solvents were evaporated under vacuum and the residue was purified by column chromatography ($SiO_2$, solvent gradient: DCM to 1:9 MeOH/DCM) to give tert-butyl (2-(2-(2-hydroxyethoxy)ethoxy)ethyl)carbamate as a colorless oil (4.5 g, 55% yield). LC-MS (ESI) found: 250 $[M+H]^+$.

Step 2: To a solution of tert-butyl (2-(2-(2-hydroxyethoxy)ethoxy)ethyl)carbamate as a colorless oil (72 g, 288 mmol) in THF (100 mL) was added 2-iodoacetic acid (160 g, 866 mmol) and NaOH (69 g, 1.7 mol) at 0° C. in portions. The mixture was stirred at rt for 2 days. The solvent was removed under vacuum, and then a solution of NaOH in water was added. DCM was used to wash the mixture. The aqueous phase was then acidified with 3N HCl solution with vigorous stirring until pH 4. Extraction with DCM and concentration give 2,2-dimethyl-4-oxo-3,8,11,14-tetraoxa-5-azahexadecan-16-oic acid as a yellowish oil (80 g, 90% yield). LC-MS (ESI) found: 308 $[M+H]^+$.

Step 3: To a solution of 2,2-dimethyl-4-oxo-3,8,11,14-tetraoxa-5-azahexadecan-16-oic acid as a yellowish oil (42 g, 136 mmol) in DCM (250 mL) was added TFA (51 mL, 683 mmol) at 0° C. The mixture was stirred at rt for 2 h. The mixture was concentrated to give crude 2-(2-(2-(2-aminoethoxy)ethoxy)ethoxy)acetic acid (28 g, 99% yield) as a white solid. LC-MS (ESI) found: 208 $[M+H]^+$.

Step 4: To a solution of 2-(2-(2-(2-aminoethoxy)ethoxy)ethoxy)acetic acid (28 g, 135 mmol) in $H_2O$ (300 mL) was added $NaHCO_3$ (34 g, 405 mmol) and 1-chloro-2,4-dinitrobenzene (41 g, 203 mmol) at 0° C. in portions. The mixture was stirred at 90° C. overnight. The mixture was adjust pH to 6, extracted with DCM, washed with brine, concentrated and purified by silica gel column to give 2-(2-(2-(2-((2,4-dinitrophenyl)amino)ethoxy)ethoxy)ethoxy)acetic acid (20 g, 40% yield) as a yellow oil. LC-MS (ESI) found: 374 $[M+H]^+$. $^1H$ NMR (400 MHz, MeOD): δ 9.03 (d, J=2.7 Hz, 1H), 8.28 (dd, J=9.6, 2.7 Hz, 1H), 7.22 (d, J=9.6 Hz, 1H), 4.10 (s, 2H), 3.81 (t, J=5.3 Hz, 2H), 3.75-3.61 (m, 10H).

Preparation of 6-azido-N-(1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)hexanamide (Compound A417)

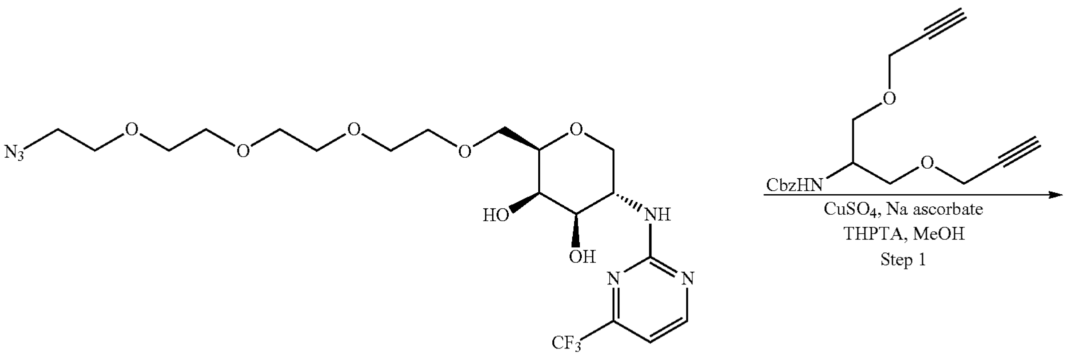

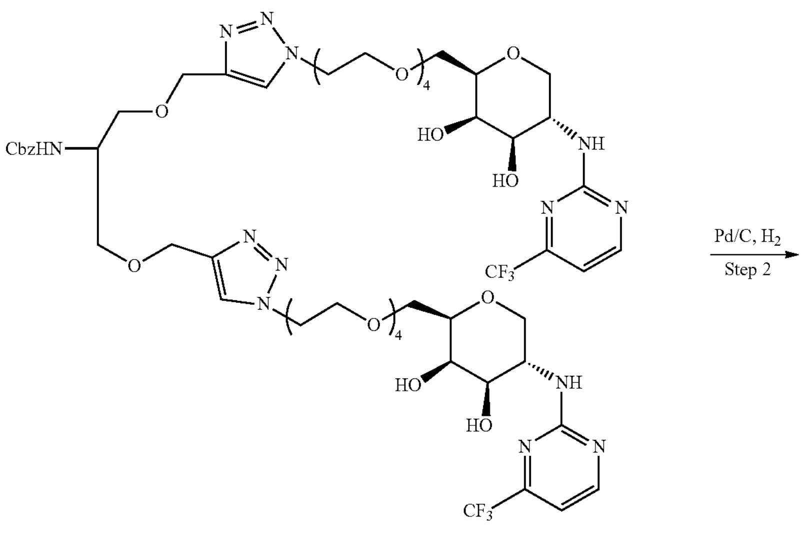

-continued

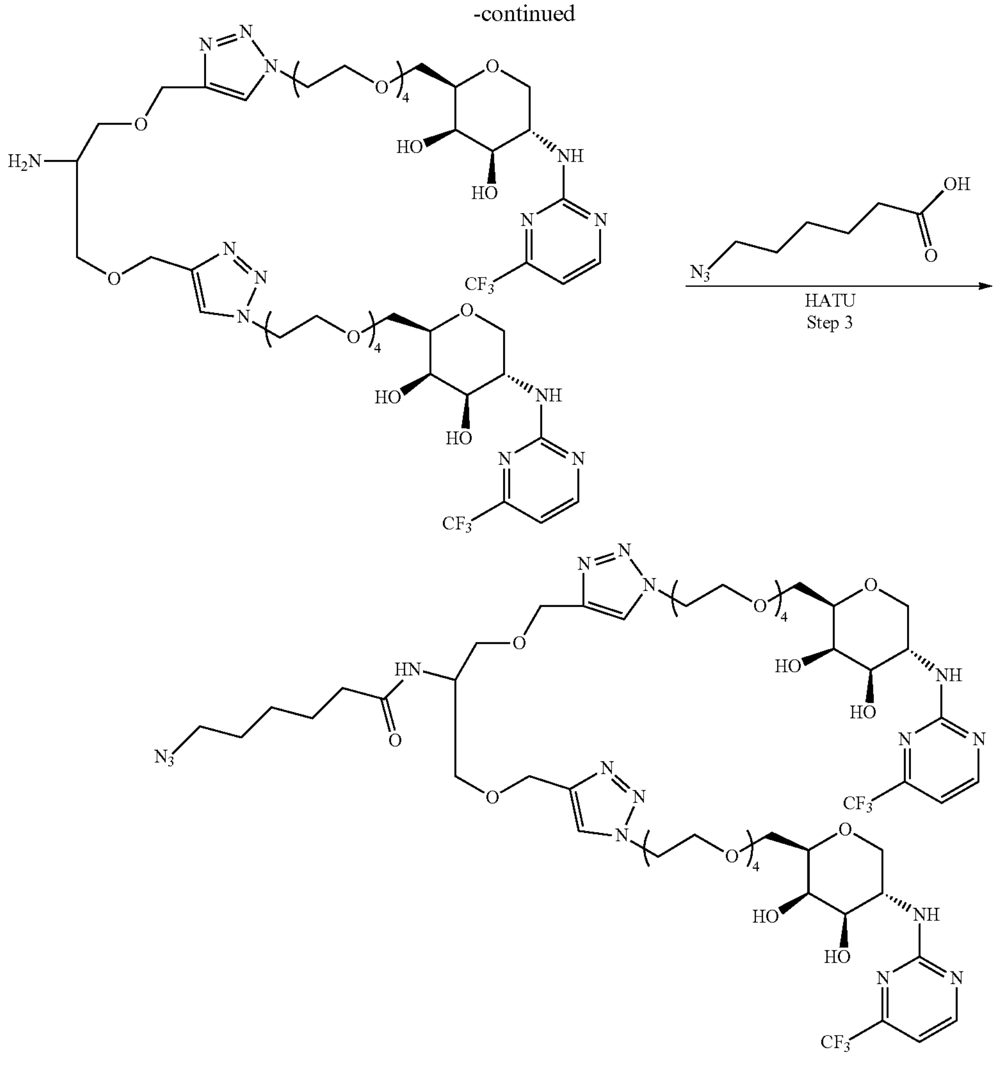

Step 1: To a solution of benzyl (1,3-bis(prop-2-yn-1-yloxy)propan-2-yl)carbamate (80 mg, 0.27 mmol) and (2R,3R,4R,5S)-2-(13-azido-2,5,8,11-tetraoxatridecyl)-5-((4-(trifluoromethyl)pyrimidin-2-yl)amino)tetrahydro-2H-pyran-3,4-diol (A419, 300 mg, 0.58 mmol) in MeOH (3 mL) were added $CuSO_4$ (4.2 mg, 0.03 mmol) and THPTA (20 mg, 0.004 mmol) in $H_2O$ (0.5 mL) and Na ascorbate (11 mg, 0.05 mmol) in $H_2O$ (0.5 mL). The mixture was stirred at rt overnight and concentrated. The residue was purified by flash to give benzyl (1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)carbamate (A420, 320 mg, 91% yield) as colorless oil. LC-MS (ESI) found: 1322 $[M+H]^+$. $^1H$ NMR (400 MHz, MeOD): δ 8.49 (d, J=4.8 Hz, 2H), 8.01 (s, 2H), 7.47-7.19 (m, 5H), 6.88 (d, J=4.9 Hz, 2H), 5.07 (s, 2H), 4.57 (dd, J=9.5, 4.6 Hz, 8H), 4.35 (d, J=5.1 Hz, 2H), 4.06 (dd, J=10.9, 5.2 Hz, 2H), 3.95-3.85 (m, 7H), 3.69-3.63 (m, 6H), 3.62-3.51 (m, 30H), 3.13 (t, J=10.9 Hz, 2H).

Step 2: A solution of benzyl (1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)carbamate (300 mg, 0.23 mmol) and Pd/C (30 mg, 10% wt, 60% wet) in MeOH (5 mL) was stirred at rt under a $H_2$ balloon overnight. The mixture was filtered through a Celite pad, and the filtrate was concentrated to give (2R,2'R,3R,3'R,4R,4'R,5S,5'S)-2,2'-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(5-((4-(trifluoromethyl)pyrimidin-2-yl)amino)tetrahydro-2H-pyran-3,4-diol)(160 mg, 60% yield) as colorless oil. LC-MS (ESI) found: 1188 $[M+H]^+$.

Step 3: To a solution of 6-azidohexanoic acid (13 mg, 0.08 mmol) in DMF (3 mL) was added HATU (35 mg, 0.09 mmol) and DIPEA (22 mg, 0.17 mmol). After stirring at rt for 30 min, (2R,2'R,3R,3'R,4R,4'R,5S,5'S)-2,2'-(((((2-aminopropane-1,3-diyl)bis(oxy))bis(methylene))bis(1H-1,2,3-triazole-4,1-diyl))bis(2,5,8,11-tetraoxatridecane-13,1-diyl))bis(5-((4-(trifluoromethyl)pyrimidin-2-yl)amino)tetrahydro-2H-pyran-3,4-diol)(147 mg, 0.12 mmol) was added. The mixture was stirred at rt under $N_2$ overnight. The mixture was concentrated and the residue was purified by prep-HPLC (Method A) to give 6-azido-N-(1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)

propan-2-yl)hexanamide (36 mg, 33% yield) as white solid. LC-MS (ESI) found: 1327 $[M+H]^+$. $^1H$ NMR (400 MHz, MeOD): δ 8.50 (d, J=4.8 Hz, 2H), 8.02 (s, 2H), 6.89 (d, J=4.9 Hz, 2H), 4.67-4.53 (m, 8H), 4.35 (td, J=10.4, 5.2 Hz, 2H), 4.19 (p, J=5.5 Hz, 1H), 4.07 (dd, J=10.9, 5.2 Hz, 2H), 3.89 (t, J=4.9 Hz, 5H), 3.69-3.50 (m, 37H), 3.26 (t, J=6.8 Hz, 2H), 3.14 (t, J=10.9 Hz, 2H), 2.21 (t, J=7.4 Hz, 2H), 1.66-1.52 (m, 4H), 1.45-1.27 (m, 2H).

Preparation of 3,3'-((2-(2-(2-(2-(2-(4-((2-phenylpiperidin-1-yl)methyl)-1H-indol-1-yl)ethoxy)ethoxy)ethoxy)acetamido)propane-1,3-diyl)bis(oxy))bis(N-(1-((1S,2R,3R,4R,5S)-2,3-dihydroxy-4-(2,2,2-trifluoroacetamido)-6,8-dioxabicyclo[3.2.1]octan-1-yl)-2,5,8,11-tetraoxatridecan-13-yl)propanamide) (Compound A421)

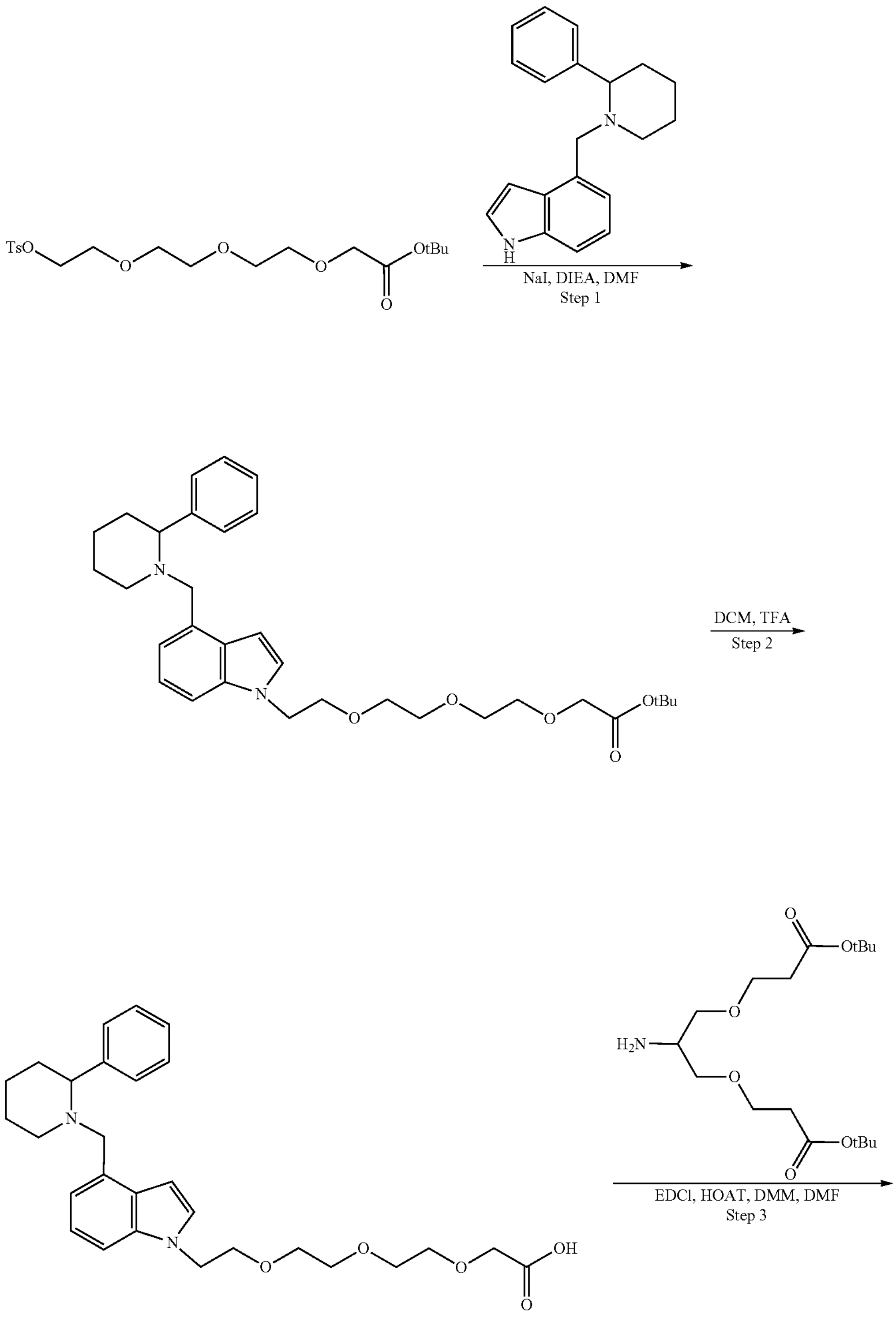

-continued
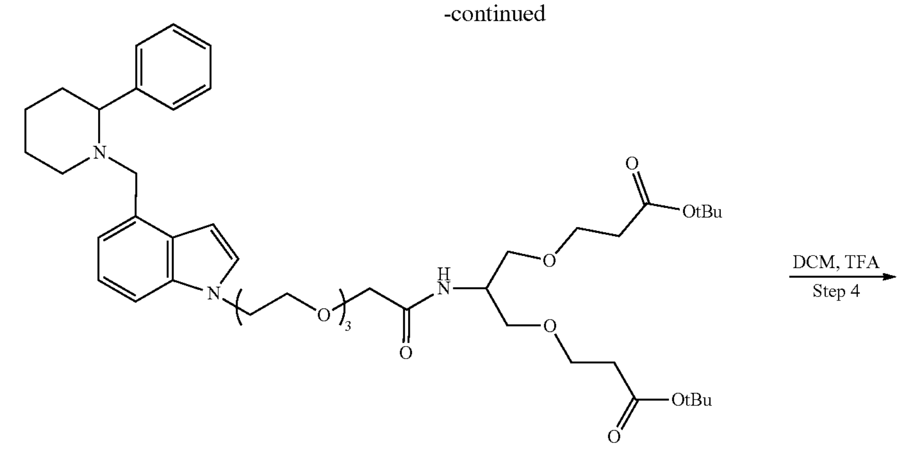
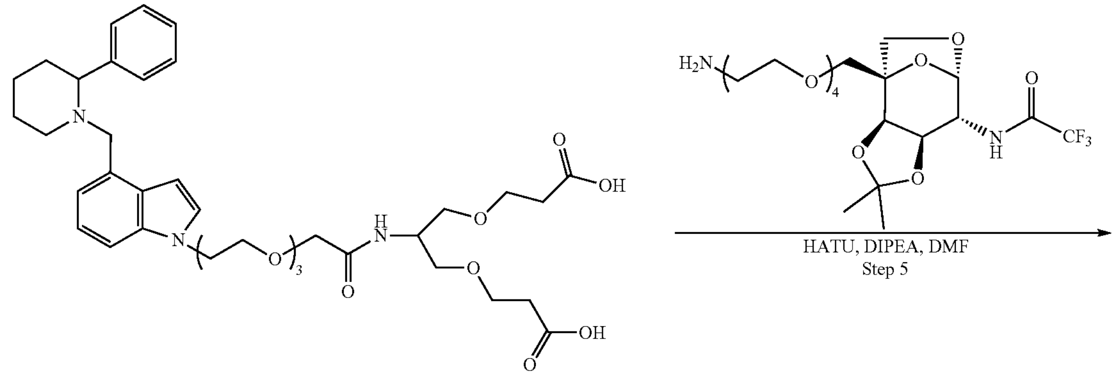
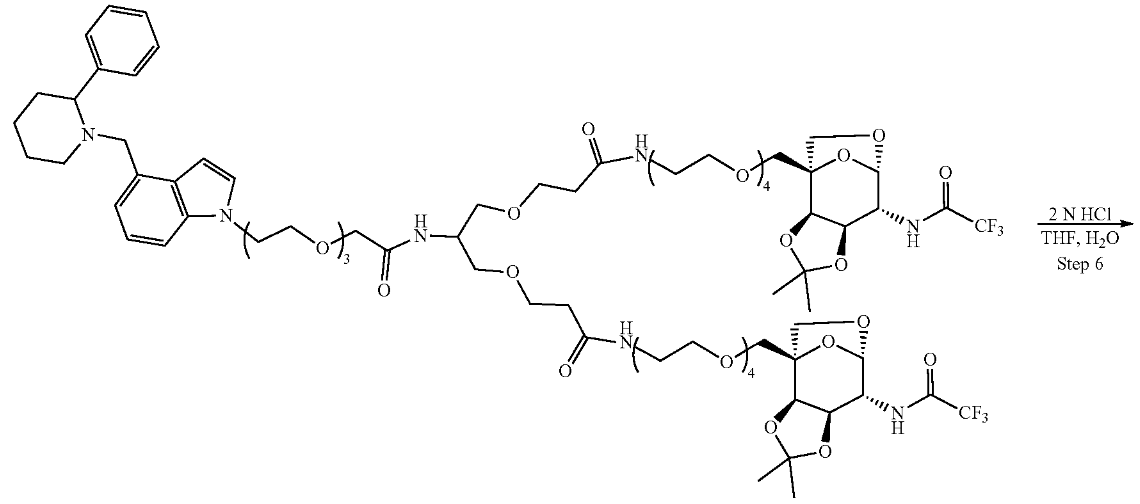

-continued
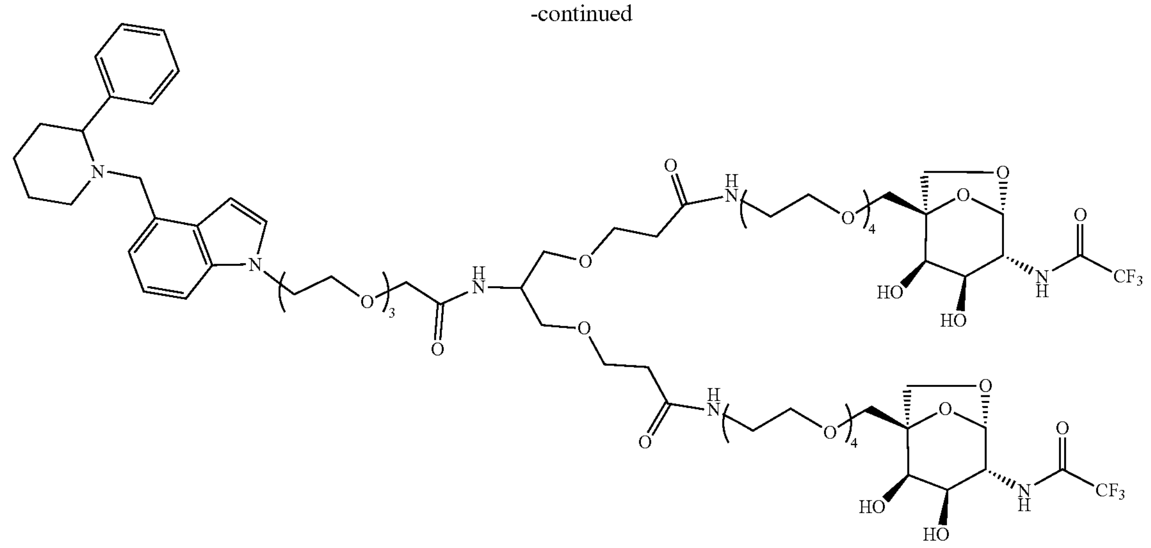
Preparation of 3,3'-((2-aminopropane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)(Compound A 422)
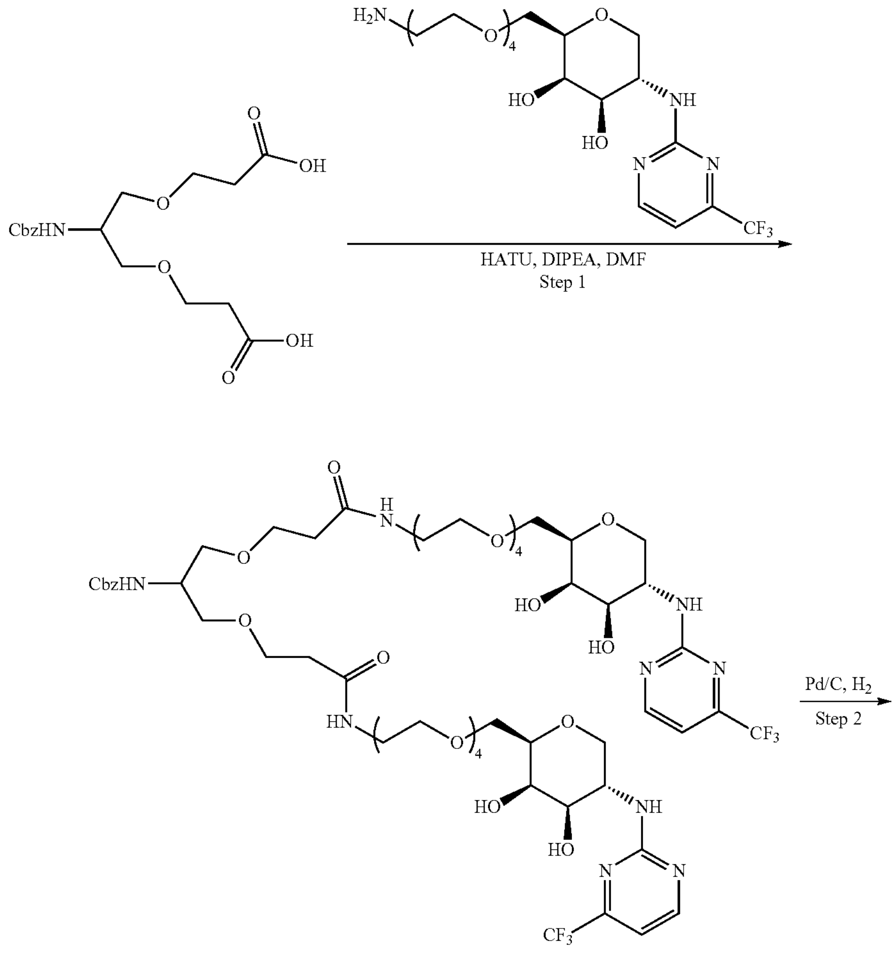

-continued

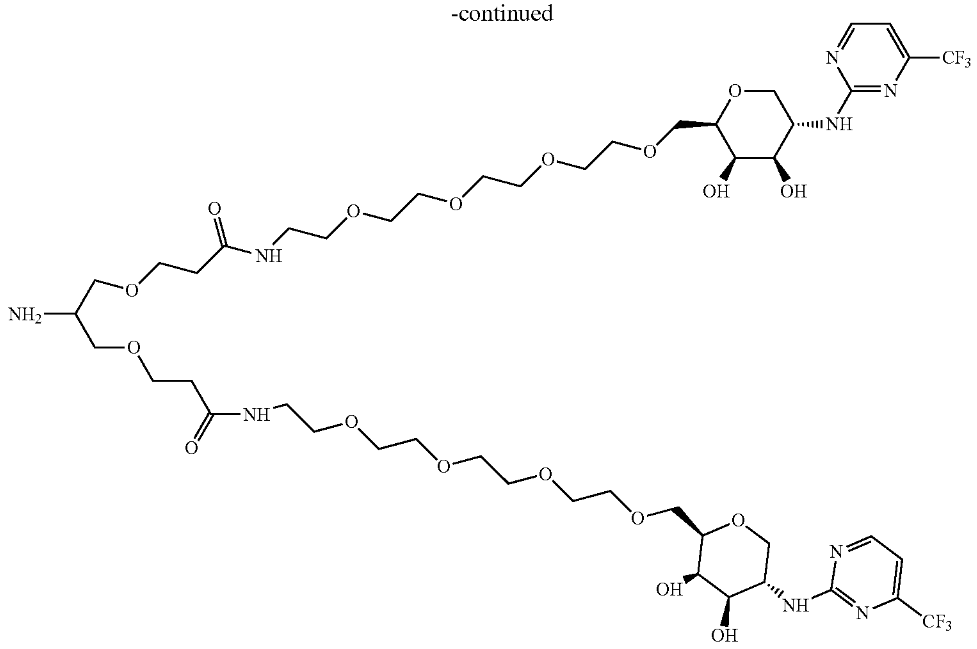

Step 1: To a solution of 3,3'-((2-(((benzyloxy)carbonyl)amino)propane-1,3-diyl)bis(oxy))dipropionic acid (0.72 g, 1.96 mmol) and HATU (2.23 g, 5.88 mmol) in DMF (20 mL) was added DIPEA (1.0 g, 7.84 mmol) and (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (2.1 g, 4.33 mmol) at rt. The reaction mixture was stirred at rt for overnight. The resulting mixture was separated and concentrated in vacuo. The crude product was purified by flash chromatography (C18, 0~80%, MeOH in $H_2O$) to give benzyl (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)carbamate (A423, 1.2 g, 48% yield) as white solid. LC-MS (ESI) found: 1303[M+H]$^+$. $^1$H NMR (400 MHz, MeOD): δ 8.50 (d, J=4.8 Hz, 2H), 7.41-7.25 (m, 5H), 6.89 (d, J=4.9 Hz, 2H), 5.07 (s, 2H), 4.43-4.27 (m, 2H), 4.08 (dd, J=10.9, 5.2 Hz, 2H), 3.91 (d, J=3.0 Hz, 2H), 3.88-3.82 (m, 1H), 3.72-3.55 (m, 36H), 3.55-3.42 (m, 8H), 3.35 (t, J=5.5 Hz, 4H), 3.15 (t, J=10.9 Hz, 2H), 2.43 (t, J=6.1, 4H).

Step 2: To a solution of benzyl (1,39-bis((2R,3R,4R,5S)-3,4-dihydroxy-5-((4-(trifluoromethyl)pyrimidin-2-yl)amino)tetrahydro-2H-pyran-2-yl)-15,25-dioxo-2,5,8,11,18,22,29,32,35,38-decaoxa-14,26-diazanonatriacontan-20-yl)carbamate (1.2 g, 0.92 mmol) in MeOH (10 mL) was added Pd/C (120 mg, 10% wt, 60% wet) at rt. The reaction mixture was stirred at rt under a $H_2$ balloon overnight. The resulting mixture was separated and concentrated in vacuo. The crude product was purified by flash chromatography (C18, 0~40%, MeOH in $H_2O$) to give 3,3'-((2-aminopropane-1,3-diyl)bis(oxy))bis(N-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)propanamide)(800 mg, 74% yield) as white solid. LC-MS (ESI) found: 1169[M+H]$^+$. $^1$H NMR (400 MHz, MeOD): δ 8.51 (d, J=4.7 Hz, 2H), 6.89 (d, J=4.9 Hz, 2H), 4.36 (d, J=5.0 Hz, 2H), 4.08 (dd, J=11.0, 5.1 Hz, 2H), 3.89 (t, J=17.0 Hz, 2H), 3.79-3.52 (m, 40H), 3.46 (dt, J=20.7, 10.3 Hz, 2H), 3.37 (td, J=8.5, 4.9 Hz, 6H), 3.13 (dt, J=10.3, 8.0 Hz, 3H), 2.46 (t, J=6.0 Hz, 4H).

Preparation of 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide)(Compound A424)

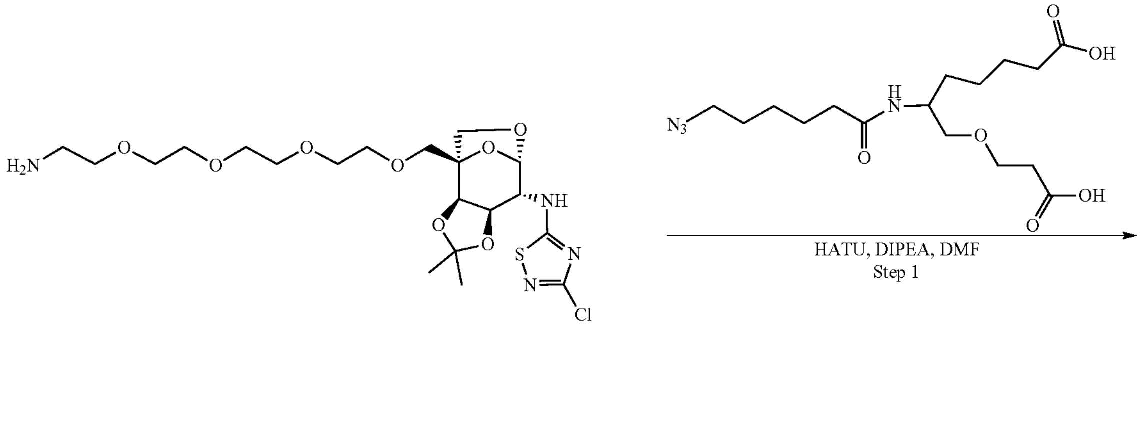

-continued

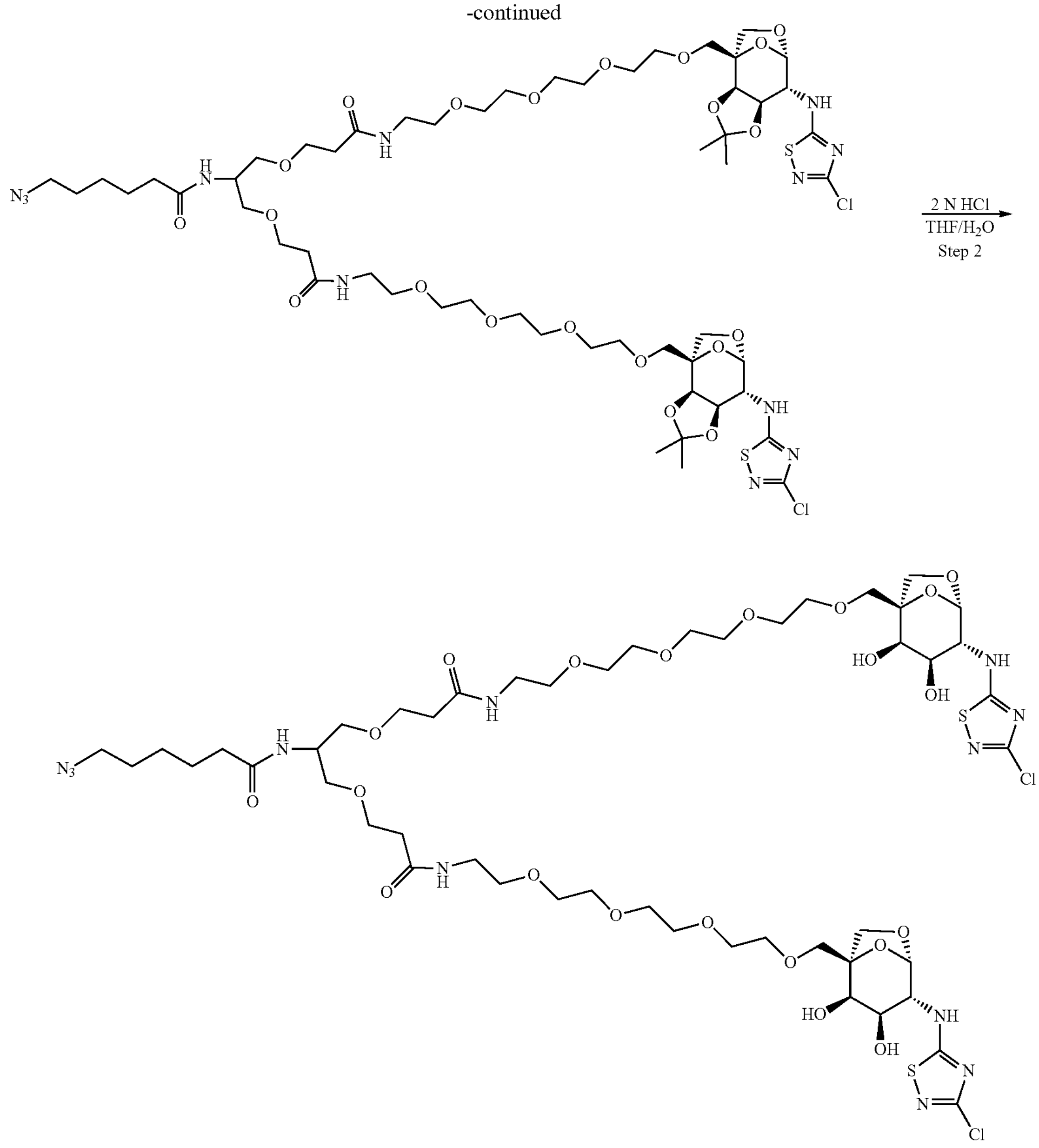

Step 1: A solution of 3,3'-((2-(6-azidohexanamido)propane-1,3-diyl)bis(oxy))dipropionic acid (28 mg, 0.08 mmol) and HATU (62.7 mg, 0.17 mmol) in DMF (3 mL) was stirred at rt for 30 min. N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-3-chloro-1,2,4-thiadiazol-5-amine (98 mg, 0.19 mmol) and DIPEA (0.05 mL, 0.3 mmol) were added at rt. The reaction was stirred overnight. The resulting mixture was concentrated in vacuo. The crude product was purified by flash chromatography (silica gel, 0~10% MeOH in DCM) to give 3,3'-((2-(6-azidohexanamido)propane-1,3-diyl)bis(oxy))bis(N-(1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-yl)propanamide)(50 mg, 48% yield) as a colorless oil. LC-MS (ESI) found: 1389 $[M+H]^+$.

Step 2: To a solution of 3,3'-((2-(6-azidohexanamido)propane-1,3-diyl)bis(oxy))bis(N-(1-((3aR,4S,7S,8R,8aR)-8-((3-chloro-1,2,4-thiadiazol-5-yl)amino)-2,2-dimethyltetrahydro-4,7-epoxy[1,3]dioxolo[4,5-d]oxepin-4(5H)-yl)-2,5,8,11-tetraoxatridecan-13-yl)propanamide)(50 mg, 0.04 mmol) in THF (3 mL) was added HCl (1 mL, 2 M in $H_2O$). The reaction was stirred at rt overnight. The crude product was purified by flash chromatography (silica gel, 0-10% MeOH in DCM) to give 3,3'-((2-(6-azidohexanamido)propane-1,3-diyl)bis(oxy))bis(N-(1-((1S,2R,3R,4R,5S)-4-((3-chloro-1,2,4-thiadiazol-5-yl)amino)-2,3-dihydroxy-6,8-dioxabicyclo[3.2.1]octan-1-yl)-2,5,8,11-tetraoxatridecan-13-yl)propanamide)(30 mg, 64% yield) as a white solid. LC-MS (ESI) found: 1309 $[M+H]^+$. $^1H$ NMR (400 MHz, MeOD): δ 5.39 (s, 2H), 4.14-4.09 (m, 1H), 4.00 (d, J=9.6 Hz, 2H), 3.93 (d, J=4.1 Hz, 2H), 3.83 (d, J=8.0 Hz, 2H), 3.77 (dd, J=9.6, 4.2 Hz, 2H), 3.73-3.60 (m, 35H), 3.56 (t, J=5.5 Hz, 4H), 3.52-3.45 (m, 4H), 3.39 (t, J=5.5 Hz, 4H), 3.28 (s, 1H), 2.46 (dd, J=6.6, 5.4 Hz, 4H), 2.23 (t, J=7.4 Hz, 2H), 1.67-1.57 (m, 4H), 1.44-1.36 (m, 2H).

Degraders

Preparation of Compound 28 ((S)-2-((S)-33-((1H-imidazol-5-yl)methyl)-1-((2R,3R,4R,5R,6R)-5-acetamido-3,4-dihydroxy-6-methoxytetrahydro-2H-pyran-2-yl)-20,20-bis(1-((2R,3R,4R,5R,6R)-5-acetamido-3,4-dihydroxy-6-methoxytetrahydro-2H-pyran-2-yl)-15-oxo-2,5,8,11,18-pentaoxa-14-azanonadecan-19-yl)-15,22,31-trioxo-2,5,8,11,18,25,28-heptaoxa-14,21,32-triazatetratriacontan-34-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide)

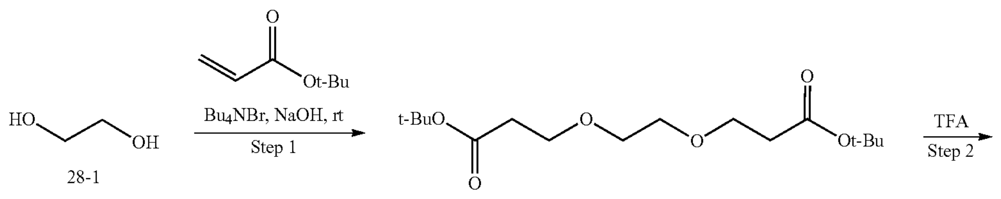

28-1

28-2

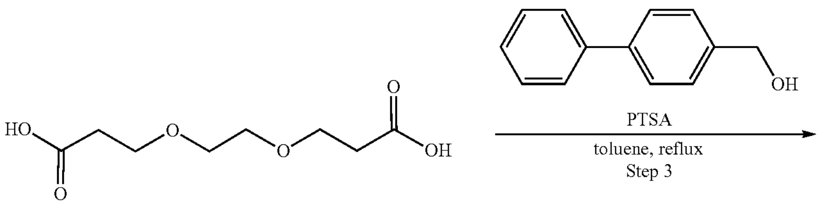

28-3

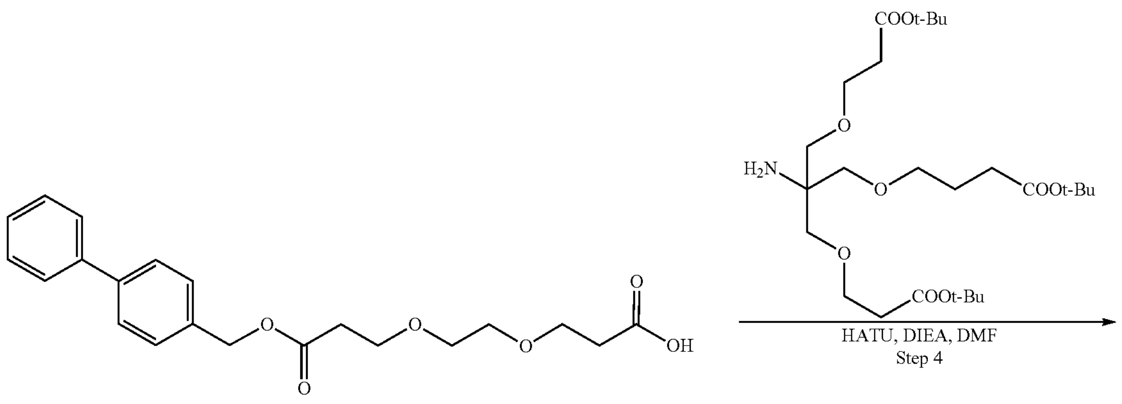

28-4

-continued
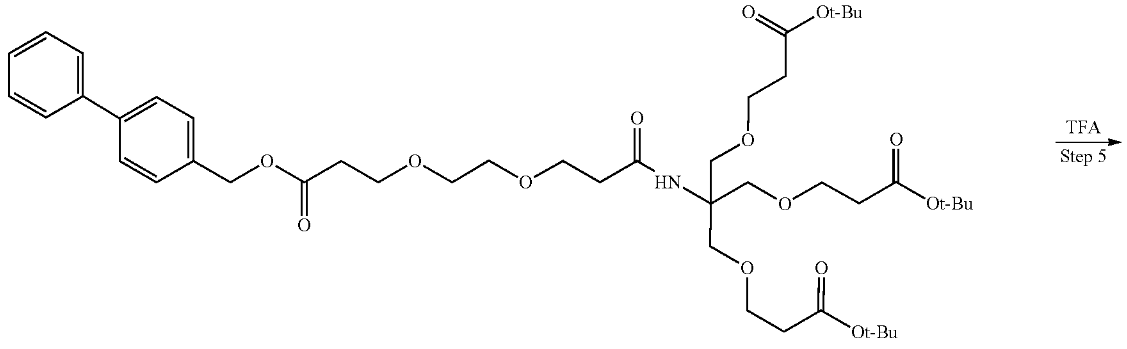
28-5
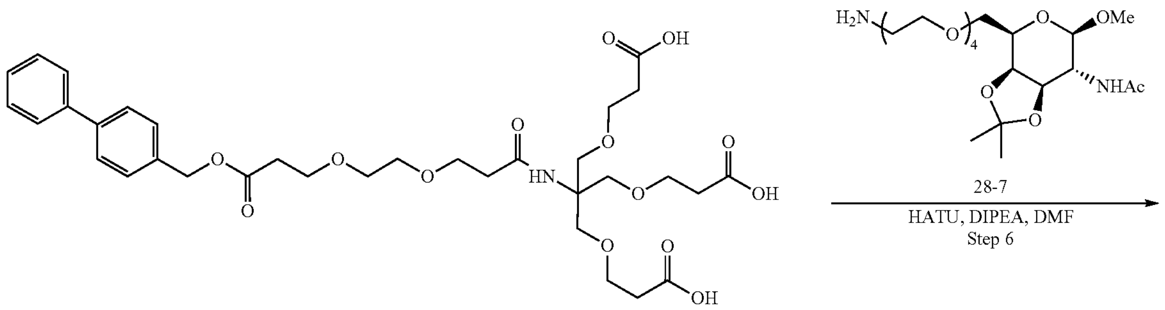
28-6
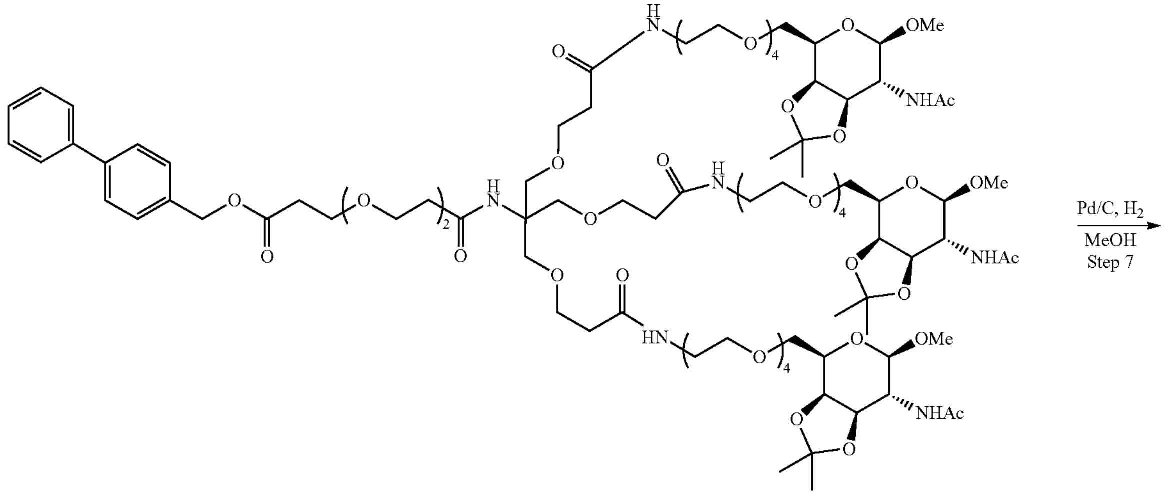
28-9

-continued
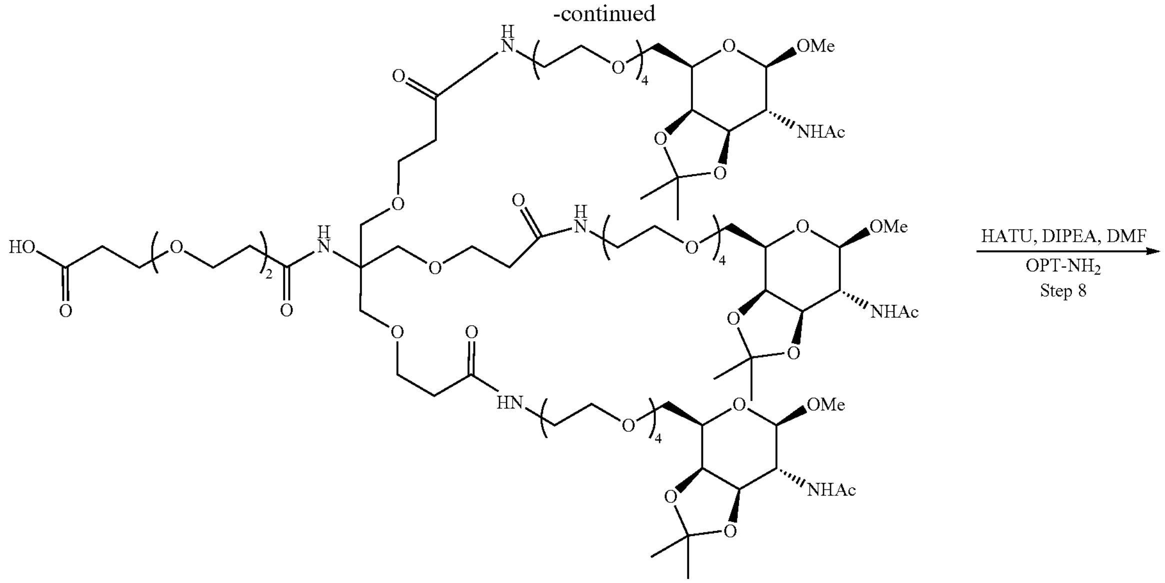
28-10
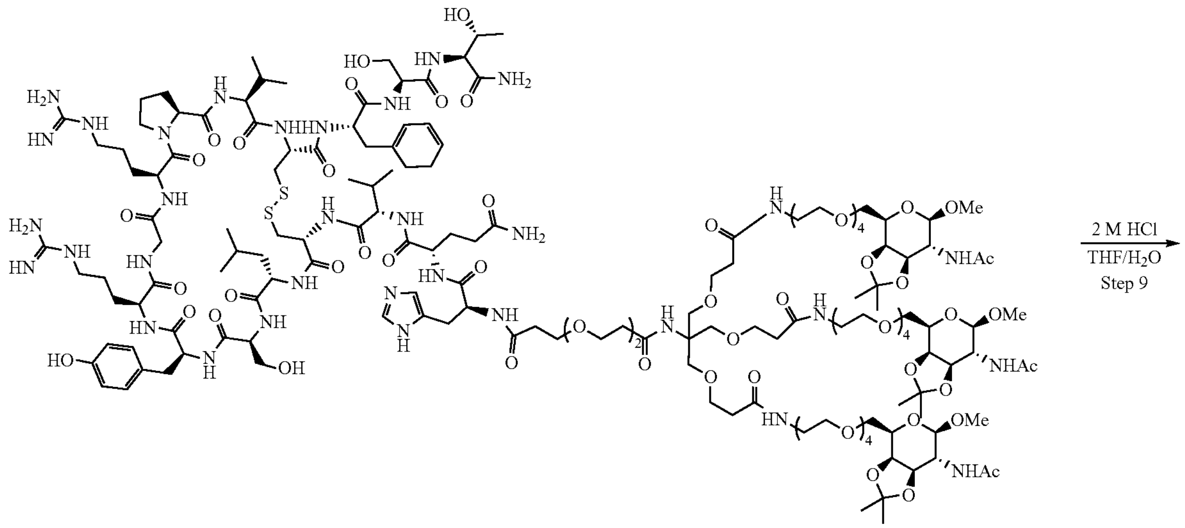
28-11

-continued

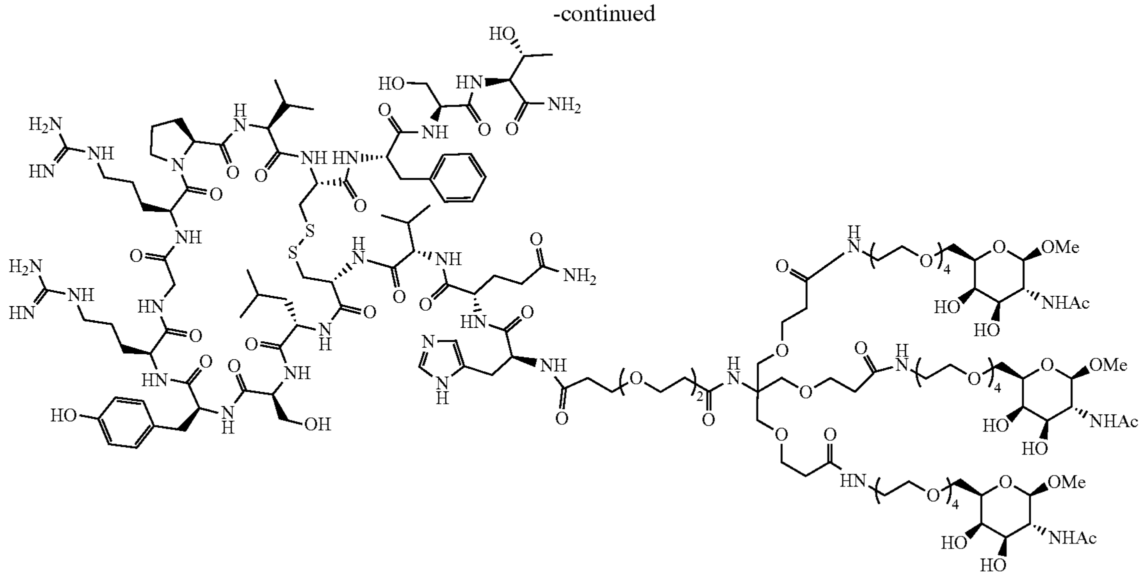

Compound 28

Step 1: To a solution of ethane-1,2-diol (1.8 mL, 32.2 mmol) and tert-butyl prop-2-enoate (11.7 mL, 80.6 mmol) in DCM (65 mL) and $H_2O$ (2.6 mL) was added $Bu_4NBr$ (6.2 g, 19.3 mmol) and sodium hydroxide (2.6 g, 65.0 mmol) at room temperature. The mixture was stirred at room temperature for 12 h. Then the mixture was extracted by DCM and the organic phase was concentrated. The residual was then purified by flash chromatography (silica gel, 0-15% PE in EA) to give di-tert-butyl 3,3'-(ethane-1,2-diylbis(oxy)) dipropionate (4.3 g, 42% yield). LC-MS (ESI) found: 319 $[M+H]^+$.

Step 2: To a mixture of di-tert-butyl 3,3'-(ethane-1,2-diylbis(oxy))dipropionate (4.3 g, 13.51 mmol) in DCM (28 mL) was added TFA (5.6 mL). The mixture was stirred for 4 h at room temperature. The mixture was concentrated to give crude 3,3'-(ethane-1,2-diylbis(oxy))dipropionic acid (2.8 g, 94% yield). LC-MS (ESI) found: 207 $[M+H]^+$.

Step 3: To a solution of 3,3'-(ethane-1,2-diylbis(oxy)) dipropionic acid (2.8 g, 13.6 mmol) and (4-phenylphenyl) methanol (2.50 g, 13.58 mmol) were added PTSA (0.02 g, 0.14 mmol) under $N_2$. The mixture was stirred at 140° C. for 3 h. Then $NaHCO_3$ was added, and the mixture was extracted by DCM and the organic phase was concentrated. The residual was then purified by flash chromatography (silica gel, 0~50% methanol in dichloromethane) to give 3-(2-(3-([1,1'-biphenyl]-4-ylmethoxy)-3-oxopropoxy) ethoxy)propanoic acid (0.88 g, 17% yield). LC-MS (ESI) found: 373 $[M+H]^+$.

Step 4: To a solution of 3-(2-(3-([1,1'-biphenyl]-4-yl-methoxy)-3-oxopropoxy)ethoxy)propanoic acid (500 mg, 1.34 mmol) and di-tert-butyl 3,3'-((2-amino-2-((3-(tert-butoxy)-3-oxopropoxy)methyl)propane-1,3-diyl)bis(oxy))dipropionate (792 mg, 1.61 mmol) in DMF (5 mL) was added HATU (765 mg, 2.01 mmol) and DIPEA (0.7 mL, 4.02 mmol) at room temperature. The mixture was stirred at room temperature for 12 h. Then the mixture was extracted by DCM and the organic phase was concentrated. The residual was then purified by flash chromatography (silica gel, 0~48% ethyl acetate in petroleum ether) to give 17-([1,1'-biphenyl]-4-ylmethyl) 1-(tert-butyl) 6,6-bis((3-(tert-butoxy)-3-oxopropoxy)methyl)-8-oxo-4,11,14-trioxa-7-aza-heptadecanedioate (1 g, 87% yield) as a solid. LC-MS (ESI) found: 860 $[M+H]^+$.

Step 5: To a mixture of 17-([1,1'-biphenyl]-4-ylmethyl) 1-(tert-butyl) 6,6-bis((3-(tert-butoxy)-3-oxopropoxy) methyl)-8-oxo-4,11,14-trioxa-7-azaheptadecanedioate (1 g, 1.16 mmol) in DCM (10 mL) was added TFA (2 mL). The mixture was stirred for 4 h at room temperature. The mixture was concentrated to give crude 1-([1,1'-biphenyl]-4-yl)-14,14-bis((2-carboxyethoxy)methyl)-3,12-dioxo-2,6,9,16-tetraoxa-13-azanonadecan-19-oic acid (620 mg, 77%). LC-MS (ESI) found: 692 $[M+H]^+$.

Step 6: To a solution of 1-([1,1'-biphenyl]-4-yl)-14,14-bis ((2-carboxyethoxy)methyl)-3,12-dioxo-2,6,9,16-tetraoxa-13-azanonadecan-19-oic acid (40 mg, 0.060 mmol) in DMF (5 mL) was added HATU (102 mg, 0.27 mmol). After stirring at rt for 30 min, N-((3aR,4R,6R,7R,7aR)-4-(13-amino-2,5,8,11-tetraoxatridecyl)-6-methoxy-2,2-dimethyl-tetrahydro-4H-[1,3]dioxolo[4,5-c]pyran-7-yl)acetamide (103 mg, 0.23 mmol) and DIPEA (77 mg, 0.60 mmol) were added. The mixture was stirred at rt for 8 h, then diluted with ethyl acetate and washed with water. The organic layer was dried over sodium sulfate, filtered, concentrated under reduced pressure to give a crude product, which was purified by column to give [1,1'-biphenyl]-4-ylmethyl 1-((3aR,4R,6R,7R,7aR)-7-acetamido-6-methoxy-2,2-dimethyltetra-hydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,25,28-heptaoxa-14,21-diazahentriacontan-31-oate (60 mg, 50% yield). LC-MS (ESI) found: 1989 $[M+H]^+$.

Step 7: To a solution of [1,1'-biphenyl]-4-ylmethyl 1-((3aR,4R,6R,7R,7aR)-7-acetamido-6-methoxy-2,2-dim-ethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,25,28-heptaoxa-14,21-diazahentriacontan-31-oate (60 mg, 0.030 mmol) in MeOH (5 mL), Pd/C (10 mg, 10% wt, 60% wet) was added. The reaction mixture was stirred at rt overnight under a $H_2$ balloon. The mixture was filtered and concentrated to give 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,25,28-heptaoxa-14,21-diazahentriacontan-31-oic acid (14 mg, 26% yield) as yellow oil. LC-MS (ESI) found: 1822 $[M+H]^+$.

Step 8: To a solution of 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,25,28-heptaoxa-14,21-diazahentriacontan-31-oic acid (14 mg, 0.008 mmol) in DMF (1 mL) was added HATU (3.8 mg, 0.010 mmol). After stirring at rt for 30 min, (S)-2-((S)-2-amino-3-(1H-imidazol-5-yl)propanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (15 mg, 0.008 mmol) and DIPEA (2 mg, 0.015 mmol) were added. The mixture was stirred at rt for 8 h, then the mixture was purified by pre-HPLC (Method B) to give 28-11 (20 mg, 71% yield). LC-MS (ESI) found: 1219 $[M+3H]^{3+}$.

Step 9: To a solution of 28-11 (20 mg, 0.014 mmol) in THF (0.5 mL) was added HCl (0.1 mL, 2N in $H_2O$). The reaction was stirred at rt for 16 h. The reaction was concentrated in vacuo. The residue was purified with prep-HPLC (Method B) to give (S)-2-((S)-33-((1H-imidazol-5-yl)methyl)-1-((2R,3R,4R,5R,6R)-5-acetamido-3,4-dihydroxy-6-methoxytetrahydro-2H-pyran-2-yl)-20,20-bis(1-((2R,3R,4R,5R,6R)-5-acetamido-3,4-dihydroxy-6-methoxytetrahydro-2H-pyran-2-yl)-15-oxo-2,5,8,11,18-pentaoxa-14-azanonadecan-19-yl)-15,22,31-trioxo-2,5,8,11,18,25,28-heptaoxa-14,21,32-triazatetratriacontan-34-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 28, 8.2 mg, 40% yield). LC-MS (ESI) found: 1179 $[M+3H]^{3+}$.

Preparation of Compound 29: N-(1-((2R,3R,4R,5S)-3,4-dihydroxy-5-((3-(pyridin-4-yl)-1,2,4-thiadiazol-5-yl)amino)tetrahydro-2H-pyran-2-yl)-2,5,8,11-tetraoxatridecan-13-yl)-3-((14-((2,4-dinitrophenyl)amino)-4-oxo-6,9,12-trioxa-3-azatetradecyl)oxy)propanamide

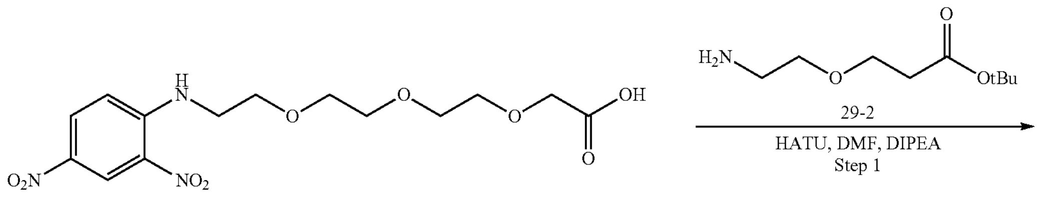

29-1

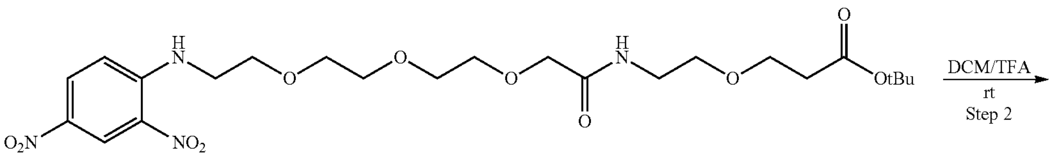

29-3

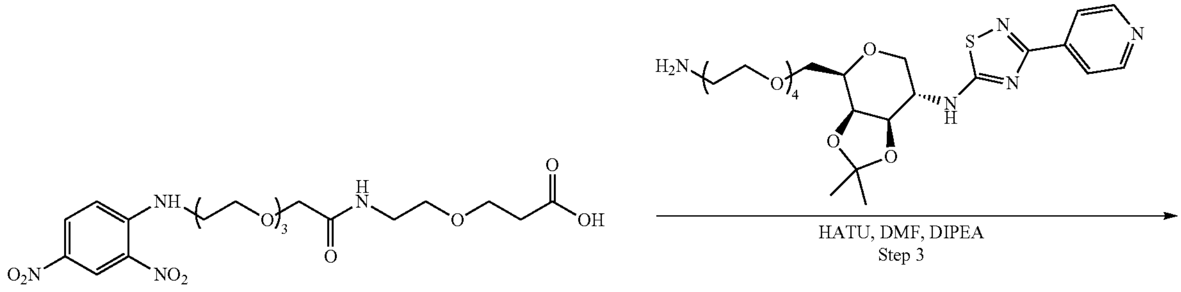

29-4

-continued

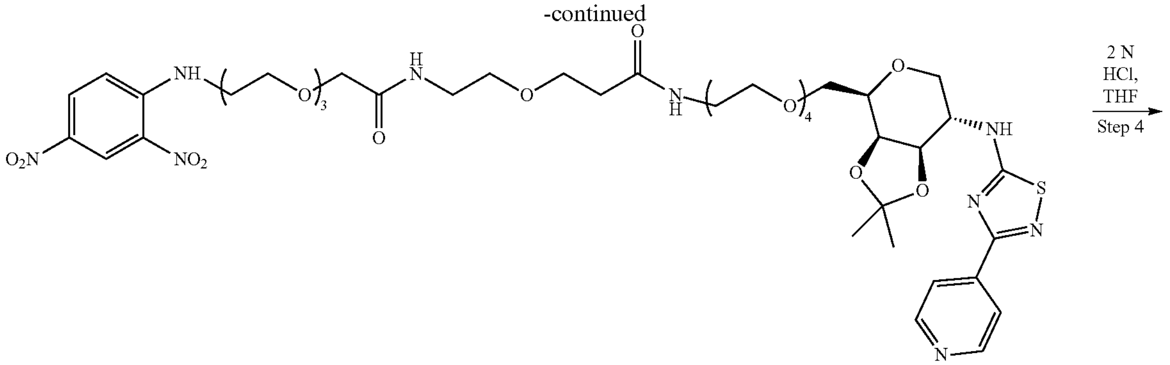

29-5

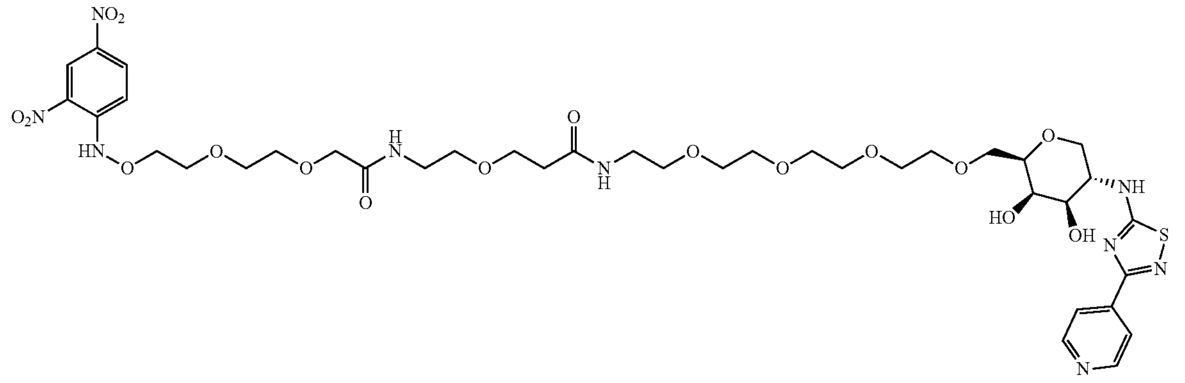

Compound 29

Step 1: To a solution of 2-(2-(2-(2-((2,4-dinitrophenyl)amino)ethoxy)ethoxy)ethoxy)acetic acid (200 mg, 0.54 mmol) in DCM (5 mL) were added HATU (306 mg, 0.81 mmol) and DIPEA (207 mg, 1.61 mmol) at 0° C. in portions. After stirring at 0° C. for 30 min, tert-butyl 3-(2-aminoethoxy)propanoate (152 mg, 0.81 mmol) was added. The mixture was stirred at rt for 12 h. The mixture was extracted with DCM and washed with brine and concentrated and purified by silica gel column to give tert-butyl 1-((2,4-dinitrophenyl)amino)-11-oxo-3,6,9,15-tetraoxa-12-azaoctadecan-18-oate (280 mg, 96% yield) as yellow oil. LC-MS (ESI) found: 545 $[M+H]^+$.

Step 2: To a solution of tert-butyl 1-((2,4-dinitrophenyl)amino)-11-oxo-3,6,9,15-tetraoxa-12-azaoctadecan-18-oate (100 mg, 0.18 mmol) in DCM (3 mL) was added TFA (0.5 mL) at 0° C. The mixture was stirred at rt for 12 h. The mixture was concentrated to give 1-((2,4-dinitrophenyl)amino)-11-oxo-3,6,9,15-tetraoxa-12-azaoctadecan-18-oic acid (88 mg, 98% yield) as yellow oil. LC-MS (ESI) found: 489 $[M+H]^+$.

Step 3: To a solution of 1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and N-((3aR,4R,7S,7aR)-4-(13-amino-2,5,8,11-tetraoxatridecyl)-2,2-dimethyltetrahydro-4H-[1,3]dioxolo[4,5-c]pyran-7-yl)-3-(pyridin-4-yl)-1,2,4-thiadiazol-5-amine (1 equiv.) at 0° C. The mixture is stirred at rt for 2 h. The mixture is quenched with $H_2O$, extracted with DCM and washed with brine. The organic phase is dried and concentrated. The residual is purified by flash column to give N-(1-((3aR,4R,7S,7aR)-2,2-dimethyl-7-((3-(pyridin-4-yl)-1,2,4-thiadiazol-5-yl)amino)tetrahydro-4H-[1,3]dioxolo[4,5-c]pyran-4-yl)-2,5,8,11-tetraoxatridecan-13-yl)-3-((14-((2,4-dinitrophenyl)amino)-4-oxo-6,9,12-trioxa-3-azatetradecyl)oxy)propenamide.

Step 4: To a solution of N-(1-((3aR,4R,7S,7aR)-2,2-dimethyl-7-((3-(pyridin-4-yl)-1,2,4-thiadiazol-5-yl)amino)tetrahydro-4H-[1,3]dioxolo[4,5-c]pyran-4-yl)-2,5,8,11-tetraoxatridecan-13-yl)-3-((14-((2,4-dinitrophenyl)amino)-4-oxo-6,9,12-trioxa-3-azatetradecyl)oxy)propenamide (0.01 mmol) in THF (3 mL) is added HCl (0.5 mL, 2N in $H_2O$) at 0° C. The mixture is stirred at rt for 2 h. The mixture is concentrated and purified by prep-HPLC (Method A) to give N-(1-((2R,3R,4R,5S)-3,4-dihydroxy-5-((3-(pyridin-4-yl)-1,2,4-thiadiazol-5-yl)amino)tetrahydro-2H-pyran-2-yl)-2,5,8,11-tetraoxatridecan-13-yl)-3-((14-((2,4-dinitrophenyl)amino)-4-oxo-6,9,12-trioxa-3-azatetradecyl)oxy)propanamide (Compound 29).

Preparation of Compound 30 (((S)-2-((S)-34-((1H-imidazol-5-yl)methyl)-1-((2R,3R,4R,5R,6R)-5-acetamido-3,4-dihydroxy-6-methoxytetrahydro-2H-pyran-2-yl)-20,20-bis(1-((2R,3R,4R,5R,6R)-5-acetamido-3,4-dihydroxy-6-methoxytetrahydro-2H-pyran-2-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide)

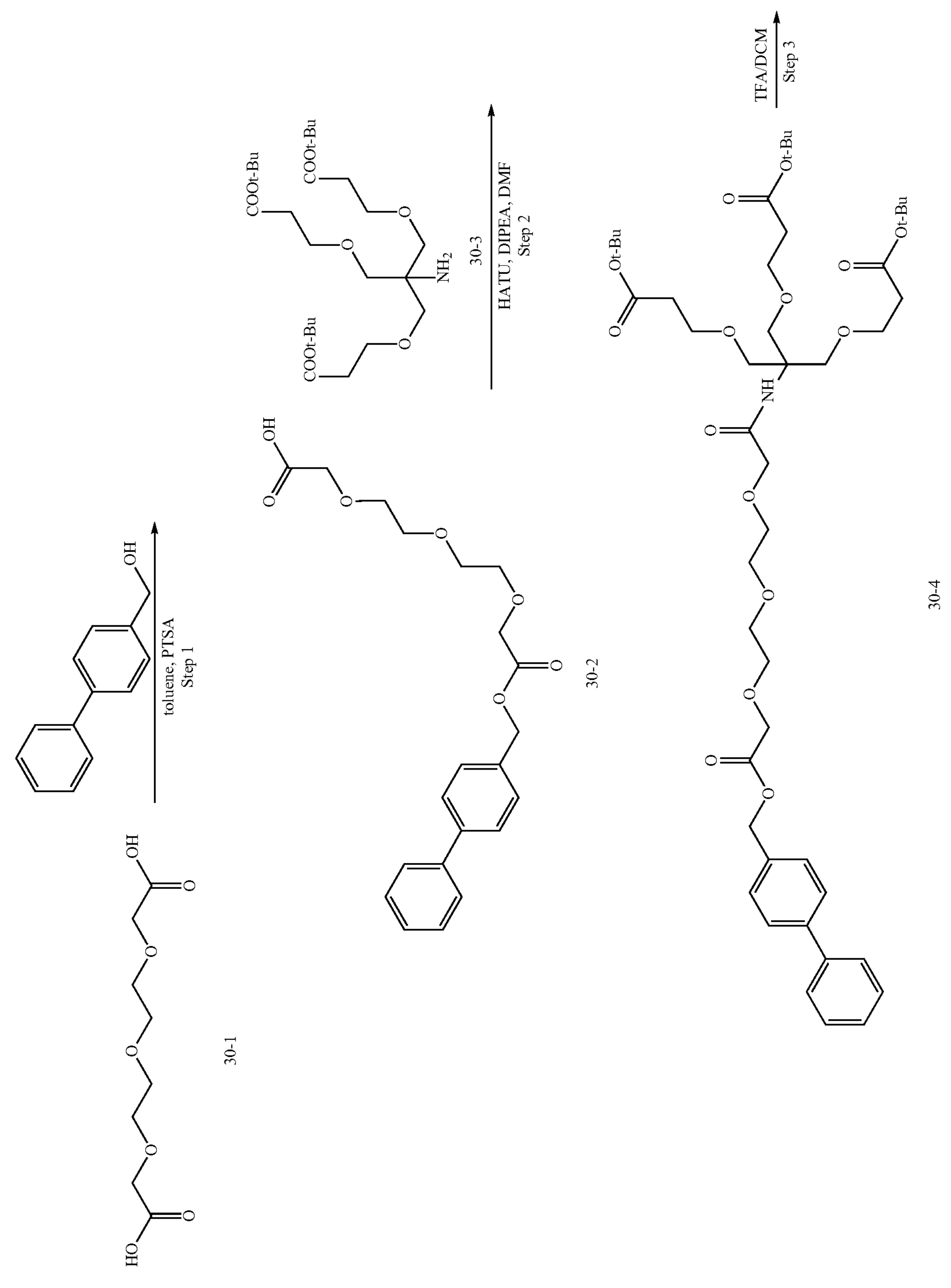
30-1
30-2
30-4

-continued
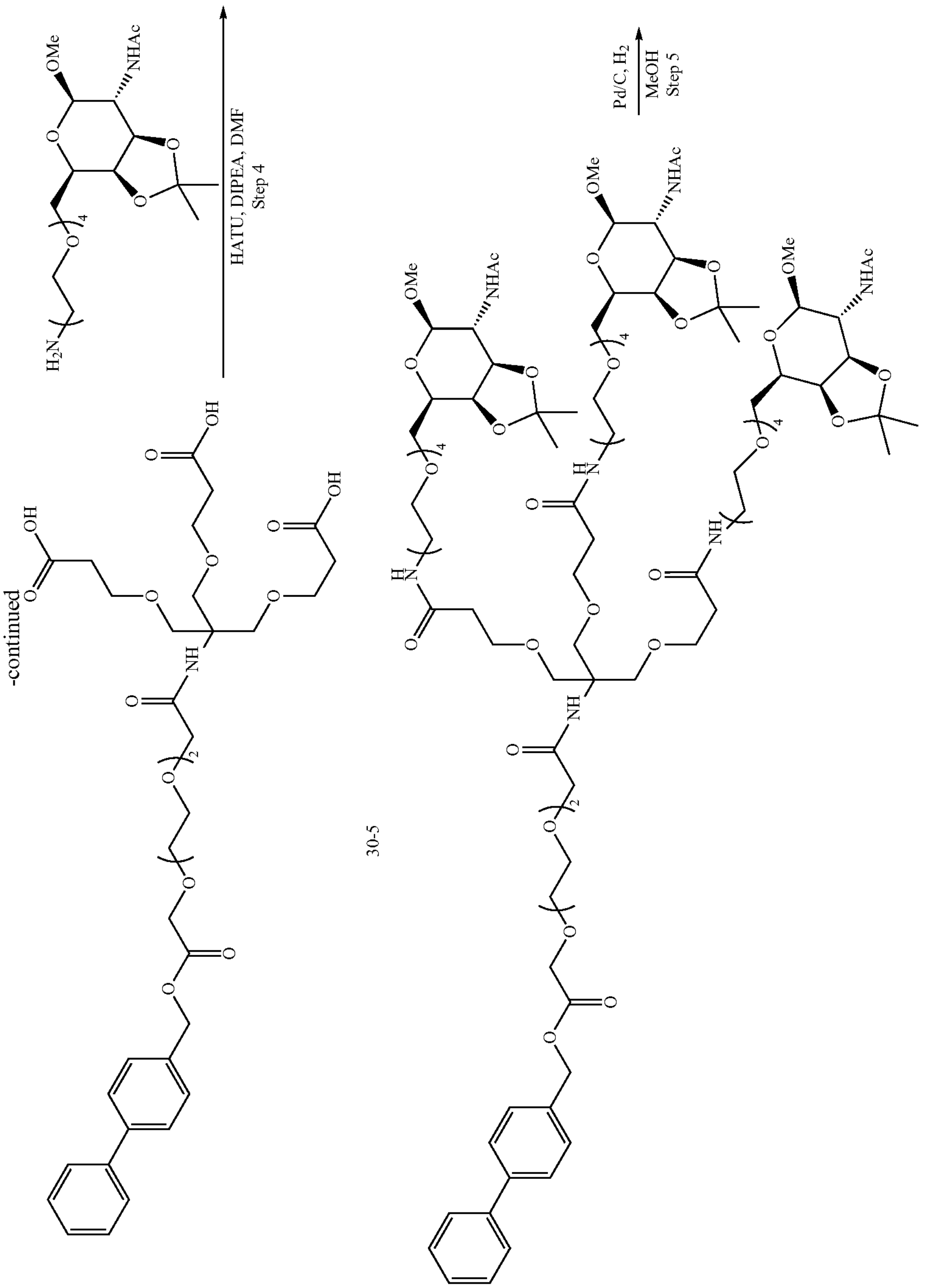
30-5
30-6

-continued
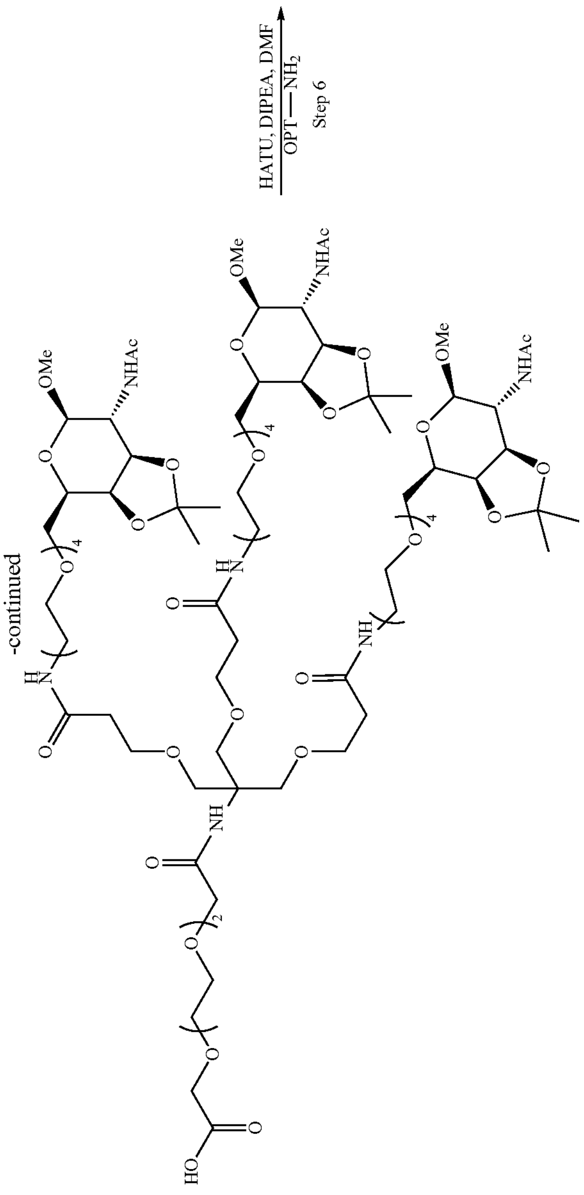
30-7

-continued
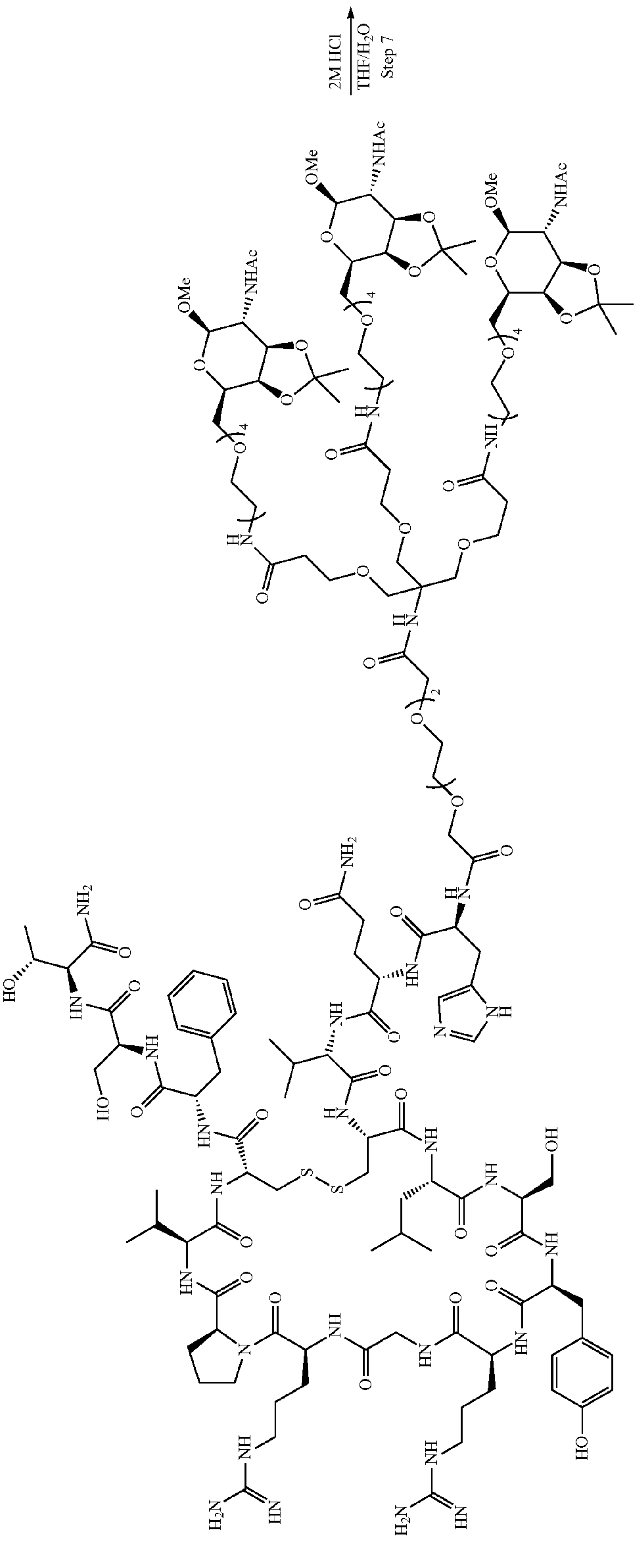
30-8

-continued
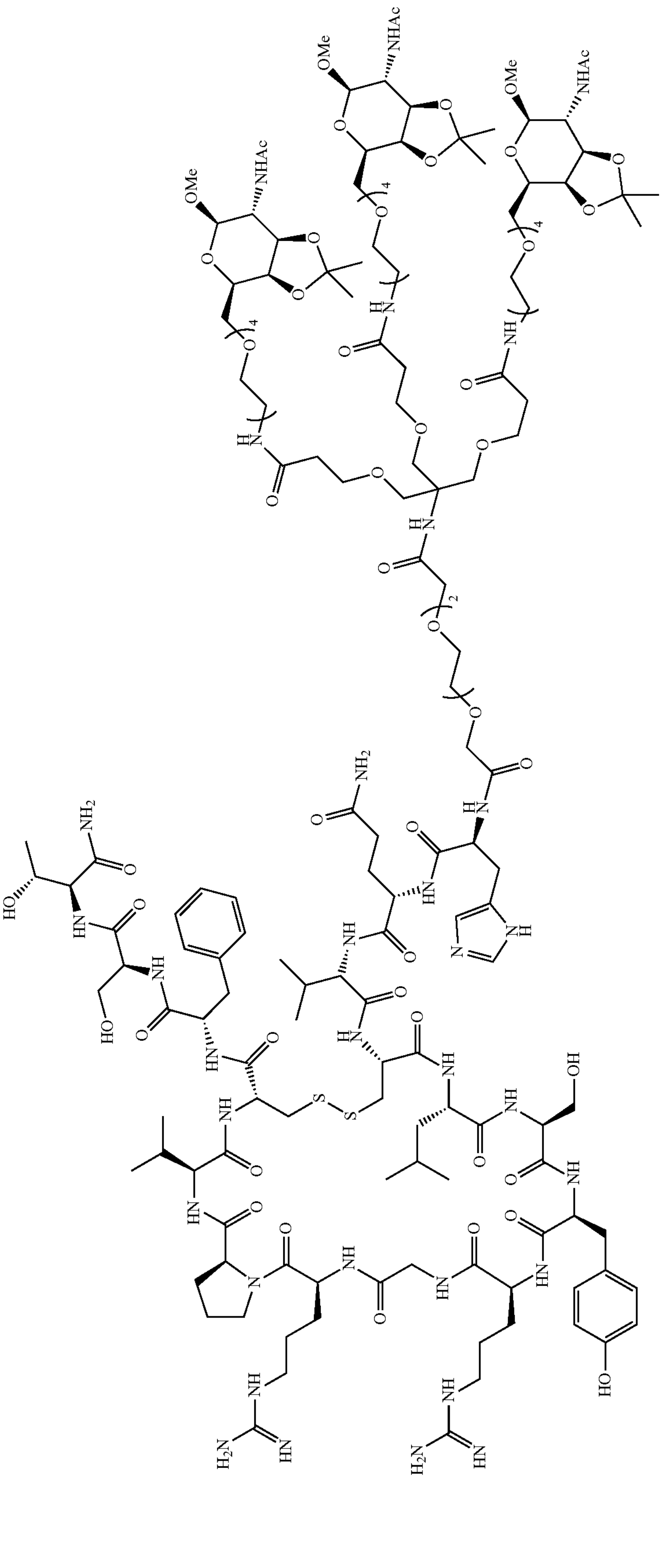
Compound 30

Step 1: A solution of 2,2'-((oxybis(ethane-2,1-diyl))bis(oxy))diacetic acid (5 g, 22.5 mmol), (4-phenylphenyl)methanol (4.2 g, 22.5 mmol) and PTSA (400 mg, 0.22 mmol) in toluene (70 mL) was stirred at 130° C. for 3 h. The mixture was quenched with $NaHCO_3$(aq., 10% wt.) was added and extracted with EA. The aqueous phase was extracted with EA three times, then the aqueous phase was adjusted to pH=3 with con. HCl. The aqueous phase was extracted with EA, the organic layer was concentrated to give 1-([1,1'-biphenyl]-4-yl)-3-oxo-2,5,8,11-tetraoxatridecan-13-oic acid (1.4 g, 16% yield) as a colorless oil. LC-MS (ESI) found: 389 $[M+H]^+$.

Step 2: A solution of 1-([1,1'-biphenyl]-4-yl)-3-oxo-2,5,8,11-tetraoxatridecan-13-oic acid (1.4 g, 3.6 mmol), DIPEA (1.4 g, 10.8 mmol) and HATU (2.0 g, 5.4 mmol) in DMF (10 mL) was stirred at rt for 30 min, then di-tert-butyl 3,3'-((2-amino-2-((3-(tert-butoxy)-3-oxopropoxy)methyl)propane-1,3-diyl)bis(oxy))dipropionate (2.2 g, 4.3 mmol) was added. The mixture was stirred at rt overnight, then extracted with EA. The organic layer was concentrated and the residue was purified by flash to give [1,1'-biphenyl]-4-ylmethyl 13,13-bis(((4,4-dimethyl-3-oxopentyl)oxy)methyl)-19,19-dimethyl-11,18-dioxo-3,6,9,15-tetraoxa-12-azaicosanoate (2.7 g, 86% yield) as a colorless oil. LC-MS (ESI) found: 828 $[M+H]^+$.

Step 3: To a solution of [1,1'-biphenyl]-4-ylmethyl 13,13-bis(((4,4-dimethyl-3-oxopentyl)oxy)methyl)-19,19-dimethyl-11,18-dioxo-3,6,9,15-tetraoxa-12-azaicosanoate (1 g, 1.1 mmol) in DCM (10 mL) was added TFA (1 mL). The mixture was stirred at rt overnight, then purified by Prep-HPLC (Method A) to give 1-([1,1'-biphenyl]-4-yl)-15,15-bis((2-carboxyethoxy)methyl)-3,13-dioxo-2,5,8,11,17-pentaoxa-14-azaicosan-20-oic acid (600 mg, 74% yield) as a colorless oil. LC-MS (ESI) found: 707 $[M+H]^+$.

Step 4: A solution of 1-([1,1'-biphenyl]-4-yl)-15,15-bis((2-carboxyethoxy)methyl)-3,13-dioxo-2,5,8,11,17-pentaoxa-14-azaicosan-20-oic acid (70 mg, 0.1 mmol), DIPEA (38 mg, 0.3 mmol) and HATU (169 mg, 0.35 mmol) in DMF (2 mL) was stirred at rt for 30 min, then N-((3aR,4R,6R,7R,7aR)-4-(13-amino-2,5,8,11-tetraoxatridecyl)-6-methoxy-2,2-dimethyltetrahydro-4H-[1,3]dioxolo[4,5-c]pyran-7-yl)acetamide (155 mg, 0.35 mmol) was added. The mixture was stirred at rt for 3 h, then extracted with EA. The organic layer was concentrated and the residue was purified by flash followed by prep-HPLC to give [1,1'-biphenyl]-4-ylmethyl 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (60 mg, 30% yield) as a colorless oil. LC-MS (ESI) found: 1003 $[M+2H]^{2+}$.

Step 5: A solution of [1,1'-biphenyl]-4-ylmethyl 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oate (60 mg, 0.03 mmol) in MeOH (4 mL) was added Pd/C (10 mg, 10% wt, 60% wet). The mixture was stirred at rt under $H_2$ for 2 h. The mixture was filtered through a Celite pad, and the filtrate was concentrated, then purified by prep-HPLC (Method B) to give 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (40 mg, 73% yield) as a colorless oil. LC-MS (ESI) found: 1837 $[M+H]^+$.

Step 6: A solution of 1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22-dioxo-2,5,8,11,18,24,27,30-octaoxa-14,21-diazadotriacontan-32-oic acid (40 mg, 0.022 mmol), DIPEA (8.4 mg, 0.065 mmol) and HATU (12.4 mg, 0.033 mmol) in DMF (2 mL) was stirred at rt for 30 min, then OPT-$NH_2$ (42 mg, 0.023 mmol) was added. The mixture was stirred at rt overnight and purified by prep-HPLC (Method B) to give (S)-2-((S)-34-((1H-imidazol-5-yl)methyl)-1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (40 mg, 50% yield) as a colorless oil. LC-MS (ESI) found: 919 $[M+4H]^{4+}$.

Step 7: To a solution of (S)-2-((S)-34-((1H-imidazol-5-yl)methyl)-1-((3aR,4R,6R,7R,7aR)-7-acetamido-6-methoxy-2,2-dimethyltetrahydro-4H-[1,3]dioxolo[4,5-c]pyran-4-yl)-20,20-bis(1-((3aR,4R,6R,7R,7aR)-7-acetamido-6-methoxy-2,2-dimethyltetrahydro-4H-[1,3]dioxolo[4,5-c]pyran-4-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (20 mg, 0.005 mmol) in THF (2 mL) was added HCl (0.1 mL, 2N in $H_2O$). The mixture was stirred at rt for 2 h, purified by prep-HPLC (Method A) to give ((S)-2-((S)-34-((1H-imidazol-5-yl)methyl)-1-((2R,3R,4R,5R,6R)-5-acetamido-3,4-dihydroxy-6-methoxytetrahydro-2H-pyran-2-yl)-20,20-bis(1-((2R,3R,4R,5R,6R)-5-acetamido-3,4-dihydroxy-6-methoxytetrahydro-2H-pyran-2-yl)-15-oxo-2,5,8,11,18-pentaoxa-14-azanonadecan-19-yl)-15,22,32-trioxo-2,5,8,11,18,24,27,30-octaoxa-14,21,33-triazapentatriacontan-35-amido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 30, 8 mg, 41% yield) as a white solid. LC-MS (ESI) found: 711 $[M+5H]^{5+}$.

Preparation of Compound 31 ((S)—N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)-2-((S)-2-(3-((1r,3S)-3-((20,20-bis(1-((1S,2R,3R,4R,5S)-2,3-dihydroxy-4-(2,2,2-trifluoroacetamido)-6,8-dioxabicyclo[3.2.1]octan-1-yl)-15-oxo-2,5,8,11,18-pentaoxa-14-azanonadecan-19-yl)-1-((1S,2R,3R,4R,5S)-2,3-dihydroxy-4-(2,2,2-trifluoroacetamido)-6,8-dioxabicyclo[3.2.1]octan-1-yl)-15,22-dioxo-2,5,8,11,18-pentaoxa-14,21-diazatetracosan-24-yl)oxy)cyclobutoxy)propanamido)-3-(1H-imidazol-5-yl)propanamido)pentanediamide)

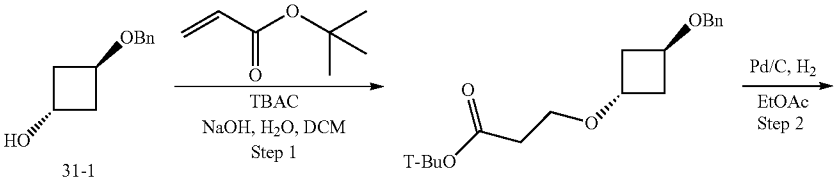

31-1

31-2

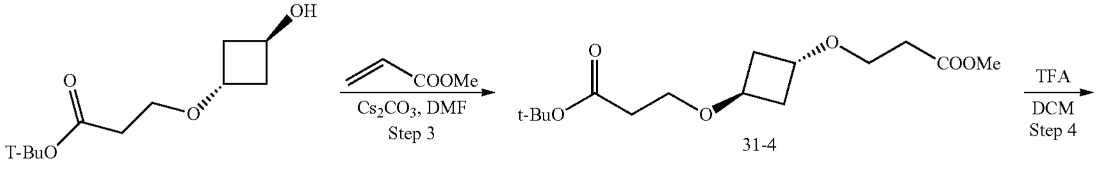

31-3

31-4

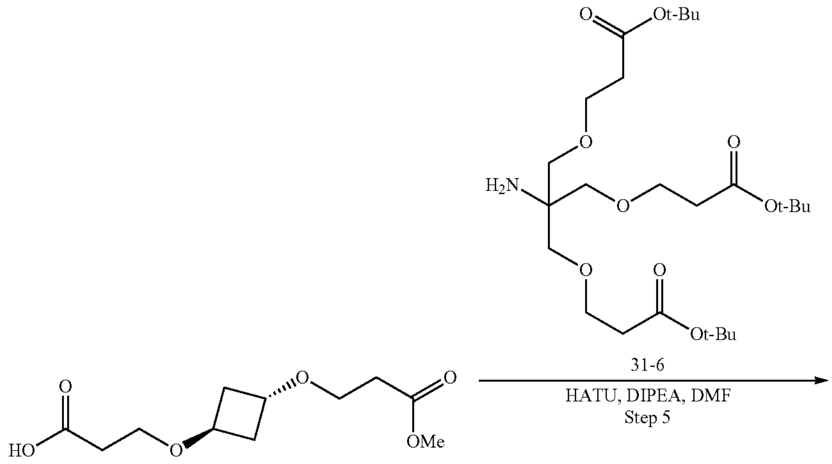

31-6

31-5

-continued
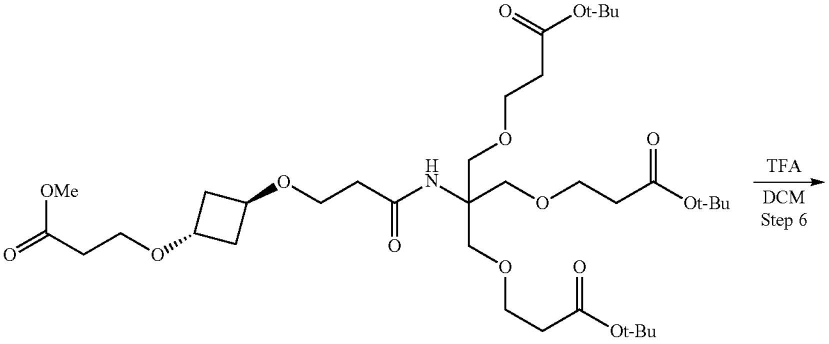
31-7
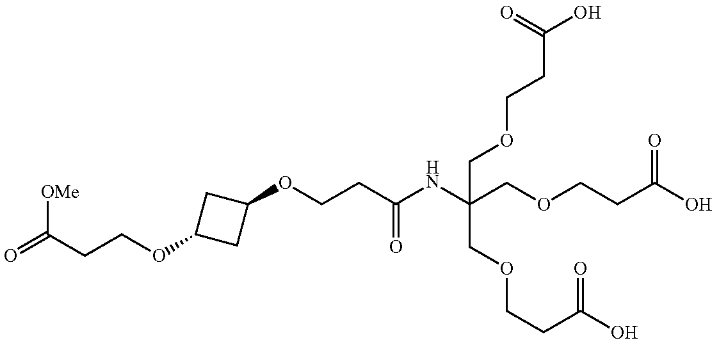
31-8
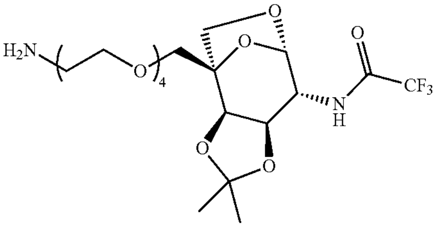
31-9
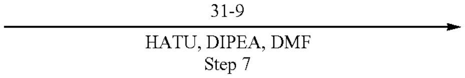
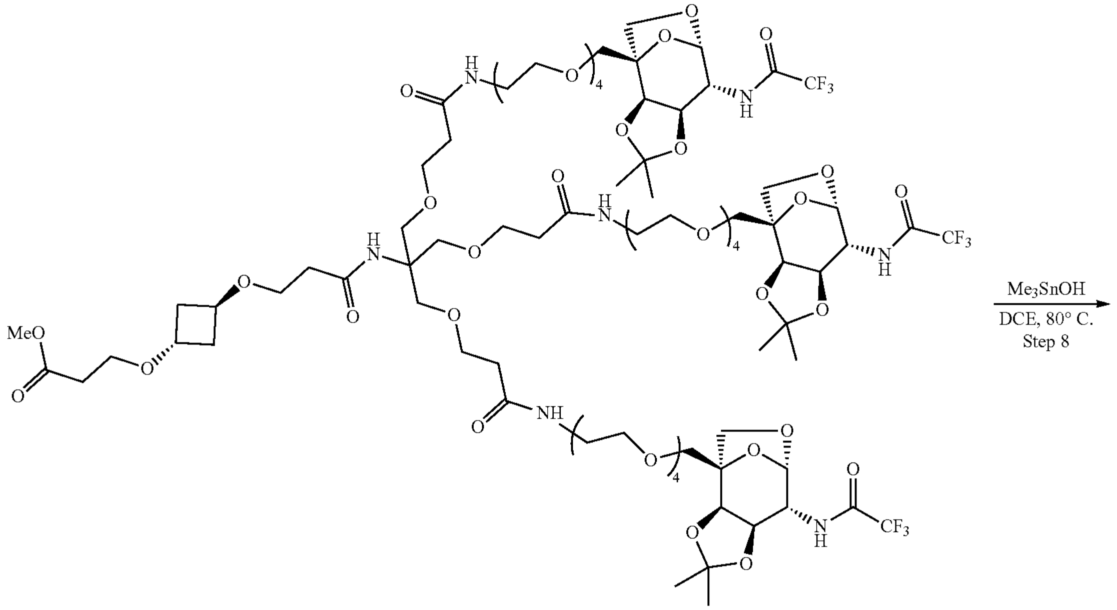
31-10

-continued
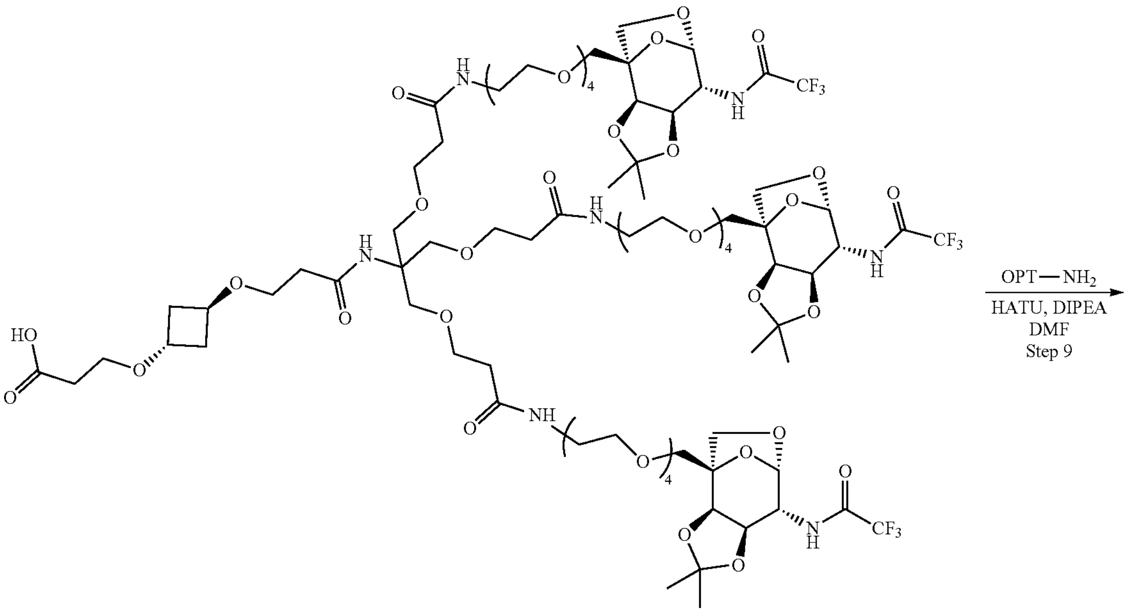
31-11
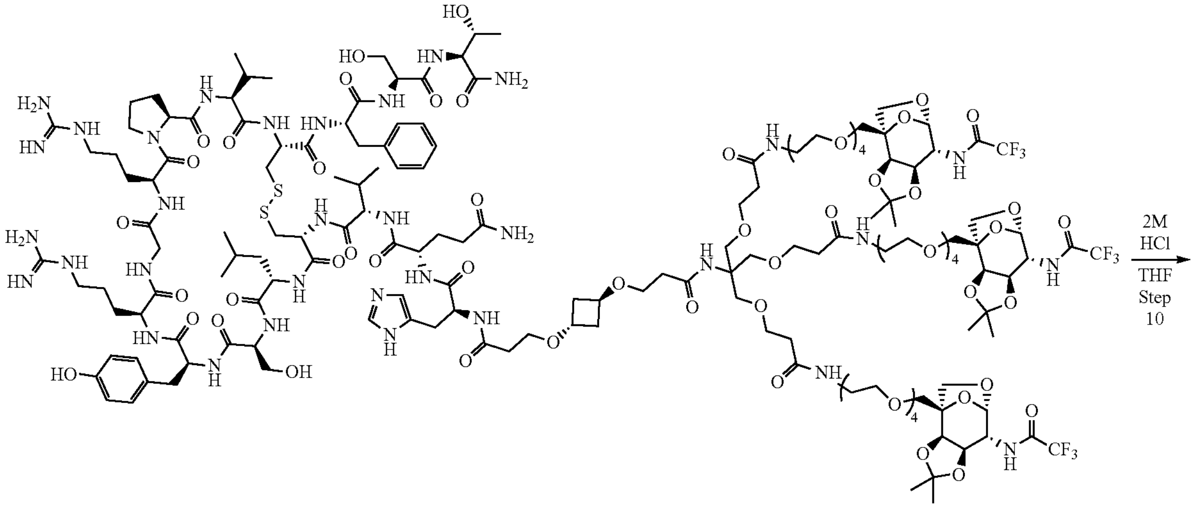
31-12

-continued

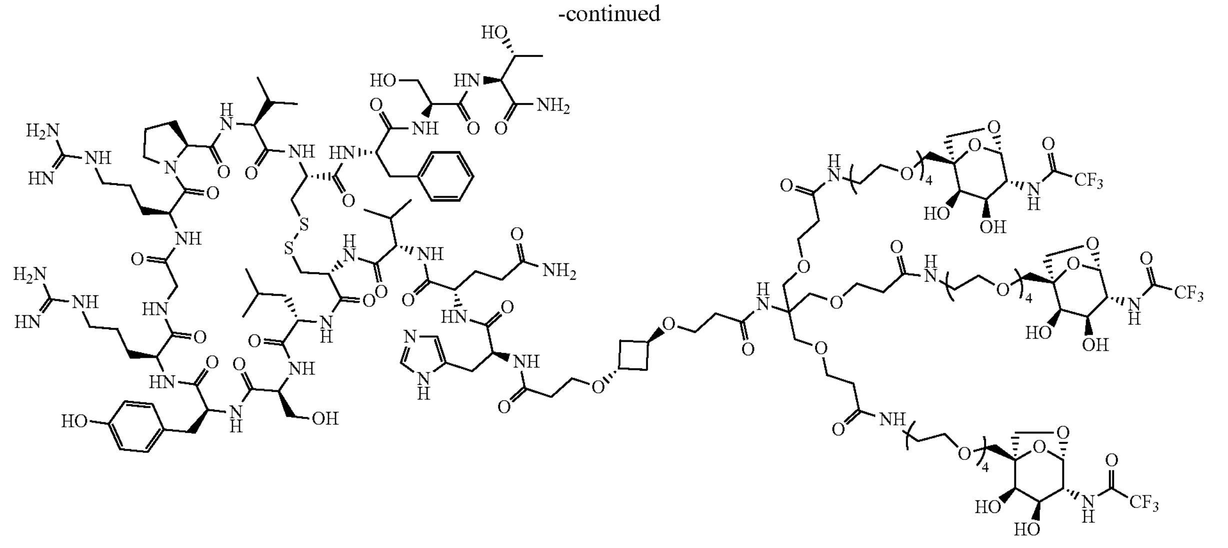

Compound 31

Step 1: To a solution of (1r,3r)-3-(benzyloxy)cyclobutanol (1.3 g, 7.29 mmol) and tetrabutylammonium chloride (0.67 g, 2.41 mmol) in DCM (20 mL). NaOH (1.22 g, 30.63 mmol) in $H_2O$ (3.5 mL) was added. The mixture was stirred for 10 min. The reaction cooled to 0° C., tert-Butyl acrylate (2.8 g, 21.88 mmol) was added dropwise over 1 h. The reaction was stirred at rt overnight and concentrated in vacuo. The crude product was purified by flash chromatography (silica gel, 0~10% EtOAc in PE) to give tert-butyl 3-((1r,3r)-3-(benzyloxy)cyclobutoxy)propanoate (1.6 g, 5.22 mmol, 72% yield) as a colorless oil. LC-MS (ESI) found: 329 $[M+Na]^+$. $^1$H NMR (400 MHz, $CDCl_3$): δ 7.36-7.26 (m, 5H), 4.41 (d, J=4.7 Hz, 2H), 4.27-4.11 (m, 2H), 3.56 (t, J=6.5 Hz, 2H), 2.46 (t, J=6.5 Hz, 2H), 2.31-2.18 (m, 4H), 1.45 (s, 9H).

Step 2: To a solution of tert-butyl 3-((1r,3r)-3-(benzyloxy) cyclobutoxy)propanoate (1.8 g, 5.88 mmol) in EtOAc (25 mL) was added Pd/C (60 mg, 10% wt, 60% wet) at rt under $H_2$(15 Psi). The reaction was stirred at rt for 2 h. The resulting mixture was filtered and concentrated in vacuo. The crude product tert-butyl 3-((1r,3r)-3-hydroxycyclobutoxy)propanoate (1.1 g) was used to next step with no further purification. LC-MS (ESI) found: 217 $[M+H]^+$.

Step 3: To a solution of tert-butyl 3-((1r,3r)-3-hydroxycyclobutoxy)propanoate (1.1 g, crude) and $Cs_2CO_3$ (3.31 g, 10.17 mmol) in DMF (15 mL) was added methyl acrylate (1.83 mL, 20.34 mmol) at rt. The mixture was stirred overnight. The resulting mixture was filtered and concentrated in vacuo. The crude product was purified by flash chromatography (silica gel, 0~10% EtOAc in PE) to give tert-butyl 3-((1r,3r)-3-(3-methoxy-3-oxopropoxy)cyclobutoxy)propanoate (400 mg, 26% yield) as a colorless oil. LC-MS (ESI) found: 303 $[M+H]^+$. $^1$H NMR (400 MHz, $CDCl_3$): δ 4.14-4.05 (m, 2H), 3.69 (s, 3H), 3.59 (t, J=6.4 Hz, 2H), 3.54 (t, J=6.5 Hz, 2H), 2.56 (t, J=6.4 Hz, 2H), 2.46 (t, J=6.5 Hz, 2H), 2.20 (t, J=5.7 Hz, 4H), 1.45 (s, 9H).

Step 4: To a solution of tert-butyl 3-((1r,3r)-3-(3-methoxy-3-oxopropoxy)cyclobutoxy)propanoate (100 mg, 0.33 mmol) in DCM (3 mL) was added TFA (1 mL, 13.5 mmol) dropwise at 0° C. under $N_2$. The reaction was stirred at rt for 1 h. The resulting mixture was filtered and concentrated in vacuo. The crude product 3-((1r,3r)-3-(3-methoxy-3-oxopropoxy)cyclobutoxy) propanoic acid (80 mg) was used to next step with no further purification. LC-MS (ESI) found: 247 $[M+H]^+$.

Step 5: To a solution of 3-((1r,3r)-3-(3-methoxy-3-oxopropoxy)cyclobutoxy)propanoic acid (200 mg, 0.81 mmol) and HATU (401 mg, 1.1 mmol) in DMF (5 mL) was stirred at rt for 30 min, and then added di-tert-butyl 3,3'-((2-amino-2-((3-(tert-butoxy)-3-oxopropoxy)methyl)propane-1,3-diyl) bis(oxy))dipropanoate (492.8 mg, 0.97 mmol) and N,N-Diisopropylethylamine (0.4 mL, 2.4 mmol) at rt. The reaction was stirred overnight. The resulting mixture was diluted with DCM (100 mL), washed with $H_2O$ (50 mL×2) and brine (50 mL), dried over $Na_2SO_4$. The organic layer was separated and concentrated in vacuo. The crude product was purified by flash chromatography (silica gel, 0~80% EA in PE) to give di-tert-butyl 3,3'-((2-((3-(tert-butoxy)-3-oxopropoxy)methyl)-2-(3-((1r,3r)-3-(3-methoxy-3-oxopropoxy)cyclobutoxy)propanamido)propane-1,3-diyl)bis (oxy))dipropanoate (300 mg, 50% yield) as a colorless oil. LC-MS (ESI) found: 734 $[M+H]^+$.

Step 6: To a solution of di-tert-butyl 3,3'-((2-((3-(tert-butoxy)-3-oxopropoxy)methyl)-2-(3-((1r,3r)-3-(3-methoxy-3-oxopropoxy)cyclobutoxy)propanamido)propane-1,3-diyl) bis(oxy))dipropanoate (300 mg, 0.41 mmol) in DCM (4 mL) was added TFA (1 mL, 13.5 mmol) dropwise at 0° C. under $N_2$. The reaction was stirred at rt for 2 h. The resulting mixture was filtered and concentrated in vacuo. The crude product was purified by prep-HPLC (Method A) to give 3,3'-((2-((2-carboxyethoxy)methyl)-2-(3-((1r,3r)-3-(3-methoxy-3-oxopropoxy)cyclobutoxy)propanamido)propane-1,3-diyl)bis(oxy))dipropanoic acid (200 mg, 86%) as a colorless oil. LC-MS (ESI) found: 566 $[M+H]^+$. $^1$H NMR (400 MHz, $CDCl_3$): δ 6.52 (s, 1H), 4.13 (dd, J=11.1, 6.0 Hz, 2H), 3.71 (dd, J=7.6, 3.8 Hz, 15H), 3.60 (t, J=6.3 Hz, 2H), 3.56 (t, J=5.9 Hz, 2H), 2.57 (t, J=6.0 Hz, 8H), 2.43 (t, J=5.8 Hz, 2H), 2.22 (t, J=5.7 Hz, 4H).

Step 7: A solution of 3,3'-((2-((2-carboxyethoxy)methyl)-2-(3-((1r,3r)-3-(3-methoxy-3-oxopropoxy)cyclobutoxy)propanamido)propane-1,3-diyl)bis(oxy))dipropanoic acid (15 mg, 0.03 mmol) and HATU (35.9 mg, 0.09 mmol) in DMF (1 mL) was stirred at rt for 30 min, then N-((3aR,4S,7S,8R,8aR)-4-(13-amino-2,5,8,11-tetraoxatridecyl)-2,2-dimethylhexahydro-4,7-epoxy[1,3]dioxolo[4,5-d]oxepin-8-yl)-2,2,2-trifluoroacetamide (47.5 mg, 0.09 mmol) and N,N-Diisopropylethylamine (0.02 mL, 0.14 mmol) were added at rt. The reaction was stirred for 2.5 h. The residue was purified by prep-HPLC (Method A) to give methyl 3-((1r,3r)-3-((1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-20,20-bis(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-15-oxo-2,5,8,11,18-pentaoxa-14-azanonadecan-19-yl)-15,22-dioxo-2,5,8,11,18-pentaoxa-14,21-diazatetracosan-24-yl)oxy)cyclobutoxy)propanoate (6 mg, 11% yield) as a colorless oil. LC-MS (ESI) found: 1010 $[M+2]^{2+}$. $^1$H NMR (400 MHz, MeOD): δ 5.29 (d, J=1.7 Hz, 3H), 4.35 (q, J=5.9 Hz, 6H), 4.10 (dd, J=9.8, 5.6 Hz, 2H), 3.97-3.88 (m, 9H), 3.80 (dd, J=9.0, 4.6 Hz, 6H), 3.71-3.61 (m, 53H), 3.57-3.53 (m, 8H), 3.38 (t, J=5.5 Hz, 6H), 2.55 (t, J=6.1 Hz, 2H), 2.44 (q, J=6.1 Hz, 8H), 2.19 (t, J=5.6 Hz, 4H), 1.50 (s, 9H), 1.35 (s, 9H).

Step 8: To a solution of methyl 3-((1r,3r)-3-((1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-20,20-bis(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-15-oxo-2,5,8,11,18-pentaoxa-14-azanonadecan-19-yl)-15,22-dioxo-2,5,8,11,18-pentaoxa-14,21-diazatetracosan-24-yl)oxy)cyclobutoxy)propanoate (6 mg) in DCM (2 mL) was added $Me_3SnOH$ (0.45 mg, 0.002 mmol) at rt under $N_2$. The reaction was stirred at 80° C. for 3 days. The resulting mixture was filtered and concentrated in vacuo. The crude product 3-((1r,3r)-3-((1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-20,20-bis(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-15-oxo-2,5,8,11,18-pentaoxa-14-azanonadecan-19-yl)-15,22-dioxo-2,5,8,11,18-pentaoxa-14,21-diazatetracosan-24-yl)oxy)cyclobutoxy)propanoic acid (3 mg) was used to next step with no further purification. LC-MS (ESI) found: 1003 $[M+2H]^{2+}$.

Step 9: A solution of 3-((1r,3r)-3-((1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-20,20-bis(1-((3aR,4S,7S,8R,8aR)-2,2-dimethyl-8-(2,2,2-trifluoroacetamido)hexahydro-4,7-epoxy[1,3]dioxolo[4,5-d]oxepin-4-yl)-15-oxo-2,5,8,11,18-pentaoxa-14-azanonadecan-19-yl)-15,22-dioxo-2,5,8,11,18-pentaoxa-14,21-diazatetracosan-24-yl)oxy)cyclobutoxy)propanoic acid (3 mg, 0.001 mmol) and HATU (0.85 mg, 0.002 mmol) in DMF (1 mL) was stirred at rt for 30 min, then OPT-$NH_2$ (3.05 mg, 0.002 mmol) and N,N-Diisopropylethylamine (0.05 mL) were added at rt. The reaction was stirred for 2.5 h. The residue was purified by prep-HPLC (Method A) to give target (1 mg) as a colorless oil. LC-MS (ESI) found: 1280 $[M+3H]^{3+}$ Step 10: To a solution of product from Step 9 (1 mg) in THF (3 mL) was added HCl (0.1 mL, 1 M in $H_2O$). The reaction was stirred at rt for 3 h. The crude product was purified by prep-HPLC (Method A) to give (S)—N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)-2-((S)-2-(3-((1r,3S)-3-((20,20-bis(1-((1S,2R,3R,4R,5S)-2,3-dihydroxy-4-(2,2,2-trifluoroacetamido)-6,8-dioxabicyclo[3.2.1]octan-1-yl)-15-oxo-2,5,8,11,18-pentaoxa-14-azanonadecan-19-yl)-1-((1S,2R,3R,4R,5S)-2,3-dihydroxy-4-(2,2,2-trifluoroacetamido)-6,8-dioxabicyclo[3.2.1]octan-1-yl)-15,22-dioxo-2,5,8,11,18-pentaoxa-14,21-diazatetracosan-24-yl)oxy)cyclobutoxy)propanamido)-3-(1H-imidazol-5-yl)propanamido)pentanediamide (Compound 31, 0.9 mg) as a colorless oil. LC-MS (ESI) found: 1240 $[M+3H]^{3+}$.

Preparation of Compound 32: 3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5R)-5-((2,6-dimethoxypyrimidin-4-yl)amino)-3,4-dihydroxytetrahydro-2H-pyran-2-yl)-2,5,8,11-tetraoxatridecan-13-yl)propanamide)

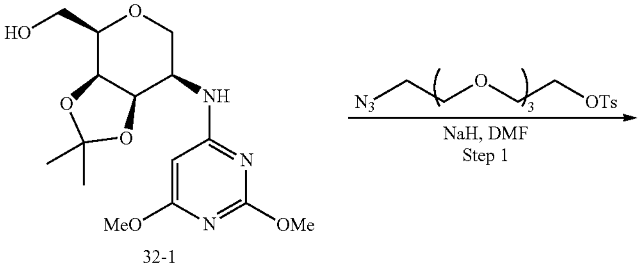

32-1

-continued

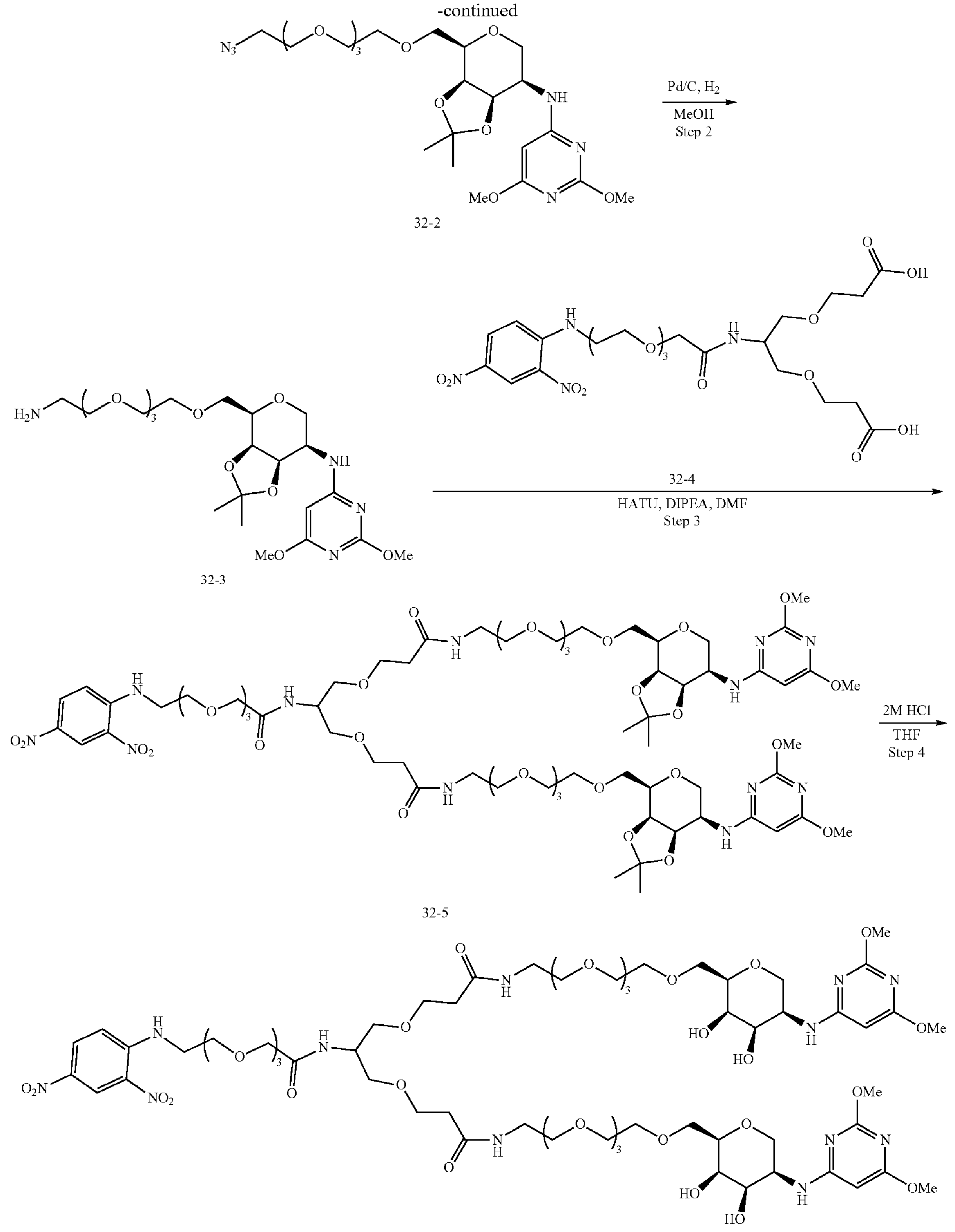

32-2

32-3

32-5

Compound 32

Step 1: To a solution of ((3aR,4R,7R,7aR)-7-((2,6-dimethoxypyrimidin-4-yl)amino)-2,2-dimethyltetrahydro-4H-[1,3]dioxolo[4,5-c]pyran-4-yl)methanol in DMF is added NaH at 0° C. and stirred for 1 h under $N_2$. Then 2-(2-(2-(2-azidoethoxy)ethoxy)ethoxy)ethyl 4-methylbenzenesulfonate is added at 0° C. and stirred at rt for 2 h under $N_2$. The resulting mixture is diluted with DCM and water. The aqueous phase is extracted with DCM. The organic layer is separated, dried over $Na_2SO_4$ and concentrated in vacuo. The crude product is purified by flash chromatography (silica gel, 0~10% MeOH in DCM) to give N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-2,6-dimethoxypyrimidin-4-amine.

Step 2: To a solution N-((3aR,4R,7R,7aR)-4-(13-azido-2,5,8,11-tetraoxatridecyl)-2,2-dimethyltetrahydro-4H-[1,3]dioxolo[4,5-c]pyran-7-yl)-2,6-dimethoxypyrimidin-4-amine in MeOH is added Pd/C at rt under a $H_2$ balloon. The reaction is stirred at rt for 1.5 h. The resulting mixture is filtered and concentrated in vacuo. The crude product N-((3aR,4R,7R,7aR)-4-(13-amino-2,5,8,11-tetraoxatridecyl)-2,2-dimethyltetrahydro-4H-[1,3]dioxolo[4,5-c]pyran-7-yl)-2,6-dimethoxypyrimidin-4-amine is used to next step with no further purification.

Step 3: To a solution of 13-((2-carboxyethoxy)methyl)-1-((2,4-dinitrophenyl)amino)-11-oxo-3,6,9,15-tetraoxa-12-azaoctadecan-18-oic acid and HATU in DMF is stirred at rt for 30 min, then N-((3aR,4R,7R,7aR)-4-(13-amino-2,5,8,11-tetraoxatridecyl)-2,2-dimethyltetrahydro-4H-[1,3]dioxolo[4,5-c]pyran-7-yl)-2,6-dimethoxypyrimidin-4-amine and N,N-Diisopropylethylamine are added at rt. The reaction is stirred overnight. The residue is purified by prep-HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((3aR,4R,7R,7aR)-7-((2,6-dimethoxypyrimidin-4-yl)amino)-2,2-dimethyltetrahydro-4H-[1,3]dioxolo[4,5-c]pyran-4-yl)-2,5,8,11-tetraoxatridecan-13-yl)propanamide) as a yellow oil.

Step 4: To a solution of 3,3'-((2-(2-(2-(2-(2-((2,4-dinitrophenyl)amino)ethoxy)ethoxy)ethoxy)acetamido)propane-1,3-diyl)bis(oxy))bis(N-(1-((3aR,4R,7R,7aR)-7-((2,6-dimethoxypyrimidin-4-yl)amino)-2,2-dimethyltetrahydro-4H-[1,3]dioxolo[4,5-c]pyran-4-yl)-2,5,8,11-tetraoxatridecan-13-yl)propanamide) in THF is added HCl (1 M in $H_2O$). The reaction is stirred at rt for 3 h. The crude product is purified by prep-HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-(1-((2R,3R,4R,5R)-5-((2,6-dimethoxypyrimidin-4-yl)amino)-3,4-dihydroxytetrahydro-2H-pyran-2-yl)-2,5,8,11-tetraoxatridecan-13-yl)propanamide)(Compound 32).

Preparation of Compound 33 3,3'-((2-(2-(2-(2-(2-((2,4-dinitrophenyl)amino)ethoxy)ethoxy)ethoxy)acetamido)propane-1,3-diyl)tris(oxy))tris(N-(1-((2R,3R,4R,5R)-5-acetamido-3,4-dihydroxytetrahydro-2H-pyran-2-yl)-2,5,8,11-tetraoxatridecan-13-yl)propanamide)

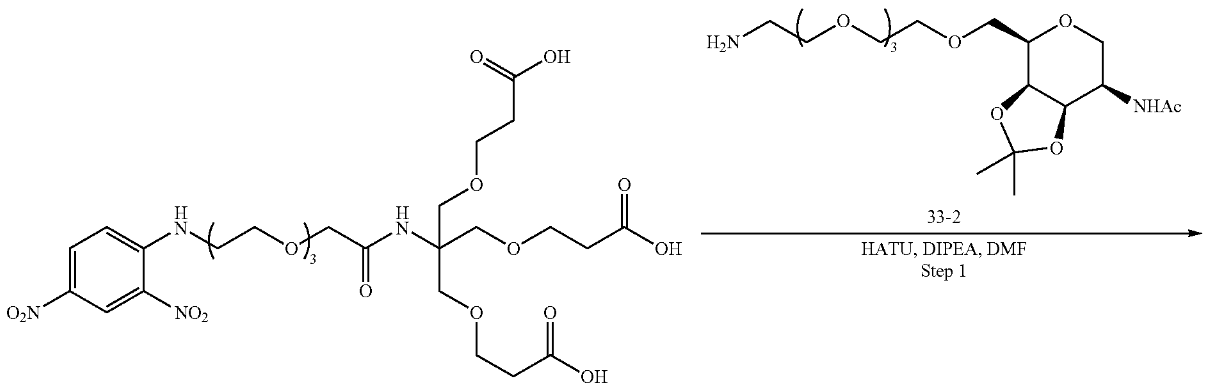

33-1

-continued

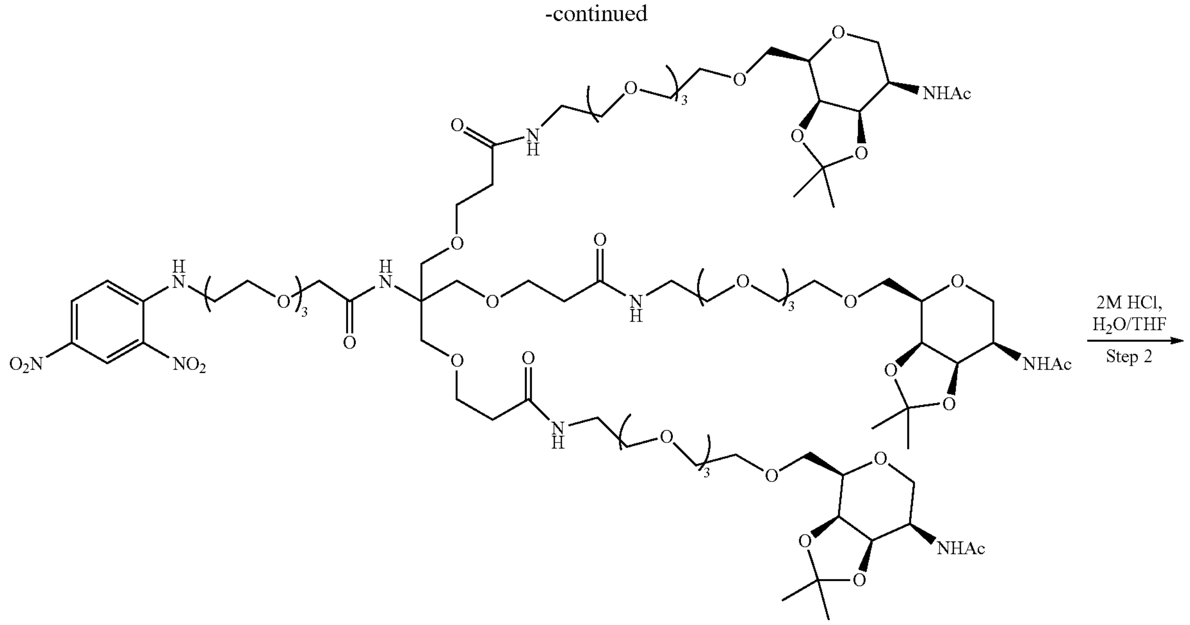

33-3

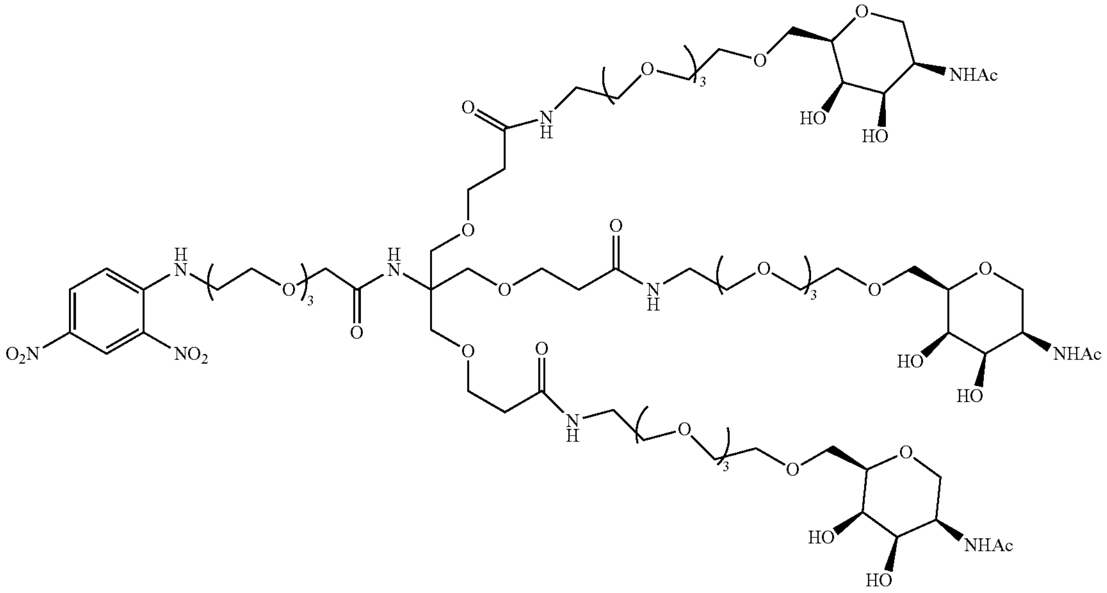

Compound 33

Step 1: To a solution of 13,13-bis((2-carboxyethoxy) methyl)-1-((2,4-dinitrophenyl)amino)-11-oxo-3,6,9,15-tetraoxa-12-azaoctadecan-18-oic acid (10 mg, 0.014 mmol) and HATU (19.2 mg, 0.05 mmol) in DMF (2 mL) was stirred at rt for 30 min, then N-((3aR,4R,7R,7aR)-4-(13-amino-2,5,8,11-tetraoxatridecyl)-2,2-dimethyltetrahydro-3aH-[1,3]dioxolo[4,5-c]pyran-7-yl)acetamide (24.3 mg, 0.06 mmol) and DIPEA (0.01 mL, 0.07 mmol) were added at rt. The reaction was stirred overnight. The residue was purified by prep-HPLC (Method A) to give product (10 mg, 37% yield) as yellow oil. LC-MS (ESI) found: 1900 $[M+H]^+$. $^1H$ NMR (400 MHz, $CDCl_3$) δ 9.13 (d, J=2.6 Hz, 1H), 8.81 (s, 1H), 8.27 (dd, J=9.5, 2.6 Hz, 1H), 8.08 (s, 1H), 7.00-6.97 (m, 3H), 6.84 (d, J=7.6 Hz, 1H), 5.91 (d, J=8.5 Hz, 3H), 4.39 (d, J=5.8 Hz, 6H), 4.26 (dd, J=7.1, 2.0 Hz, 3H), 3.92-3.81 (m, 9H), 3.72-3.68 (m, 28H), 3.64 (dd, J=8.6, 4.3 Hz, 40H), 3.55 (t, J=5.3 Hz, 6H), 3.45-3.40 (m, 6H), 2.43 (t, J=5.7 Hz, 6H), 2.01 (s, 9H), 1.50 (s, 9H), 1.34 (s, 9H).

Step 2: To a solution of material from step 1 (10 mg, 0.005 mmol) in THF (3 mL) was added HCl (0.5 mL, 1 M in $H_2O$). The reaction was stirred at rt for 3 h. The crude product was purified by prep-HPLC (Method A) to give 3,3'-((2-(2-(2-(2-(2-((2,4-dinitrophenyl)amino)ethoxy)ethoxy)ethoxy)acetamido)propane-1,3-diyl)tris(oxy))tris(N-(1-((2R,3R,4R,5R)-5-acetamido-3,4-dihydroxytetrahydro-2H-pyran-2-yl)-2,5,8,11-tetraoxatridecan-13-yl)propanamide)(Compound 33, 0.7 mg, 7.5% yield) as a yellow oil. LC-MS (ESI) found: 1780 $[M+H]^+$. $^1$H NMR (400 MHz, MeOD): δ 9.05 (d, J=2.7 Hz, 1H), 8.31 (dd, J=9.6, 2.7 Hz, 1H), 7.25 (d, J=9.7 Hz, 1H), 4.07 (s, 3H), 3.91-3.86 (m, 8H), 3.82 (t, J=5.2 Hz, 3H), 3.76-3.74 (m, 3H), 3.71-3.66 (m, 24H), 3.65-3.62 (m, 36H), 3.57-3.47 (m, 15H), 3.37 (t, J=5.5 Hz, 6H), 2.44 (t, J=6.1 Hz, 6H), 2.00 (s, 9H).

Preparation of Compound 34: 3,3'-((2-(2-(2-(2-(2-((2,4-dinitrophenyl)amino)ethoxy)ethoxy)ethoxy)acetamido)propane-1,3-diyl)bis(oxy))bis(N-((1-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-1H-1,2,3-triazol-4-yl)methyl)propanamide)

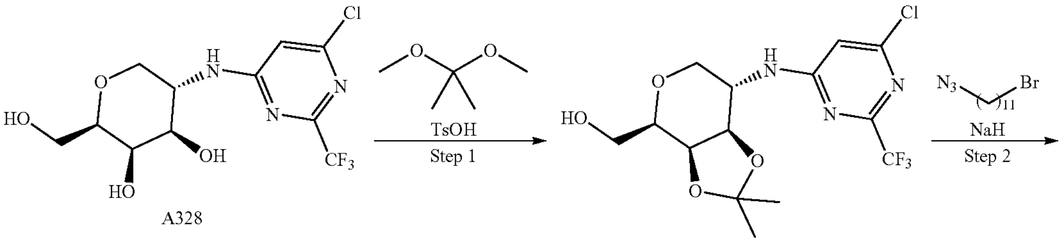

A328

34-1

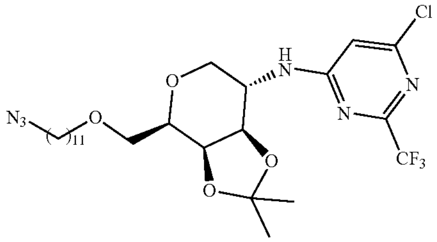

34-2

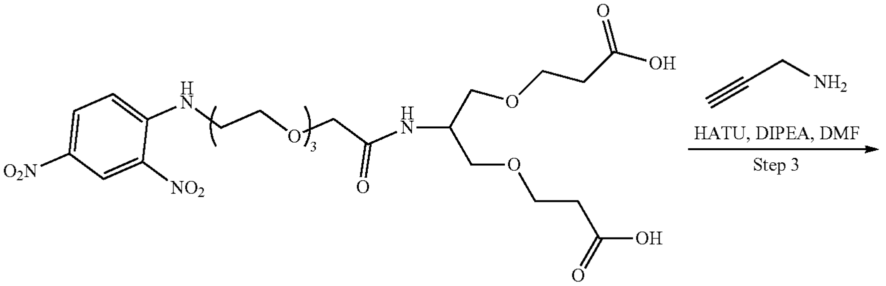

34-3

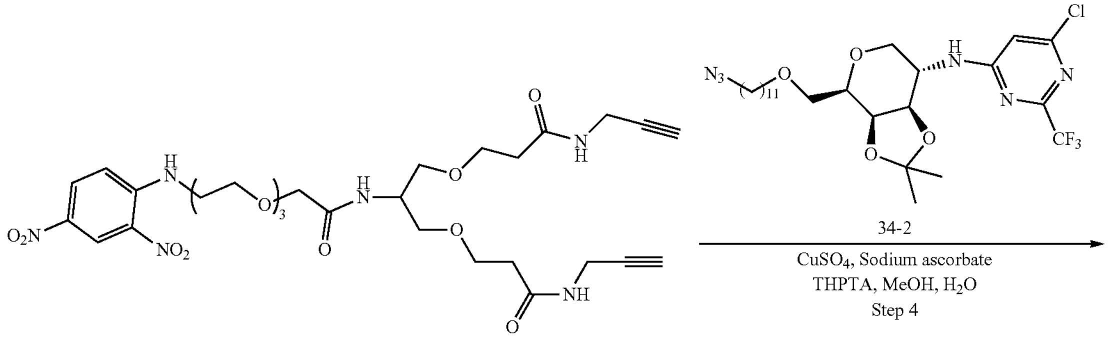

34-4

-continued

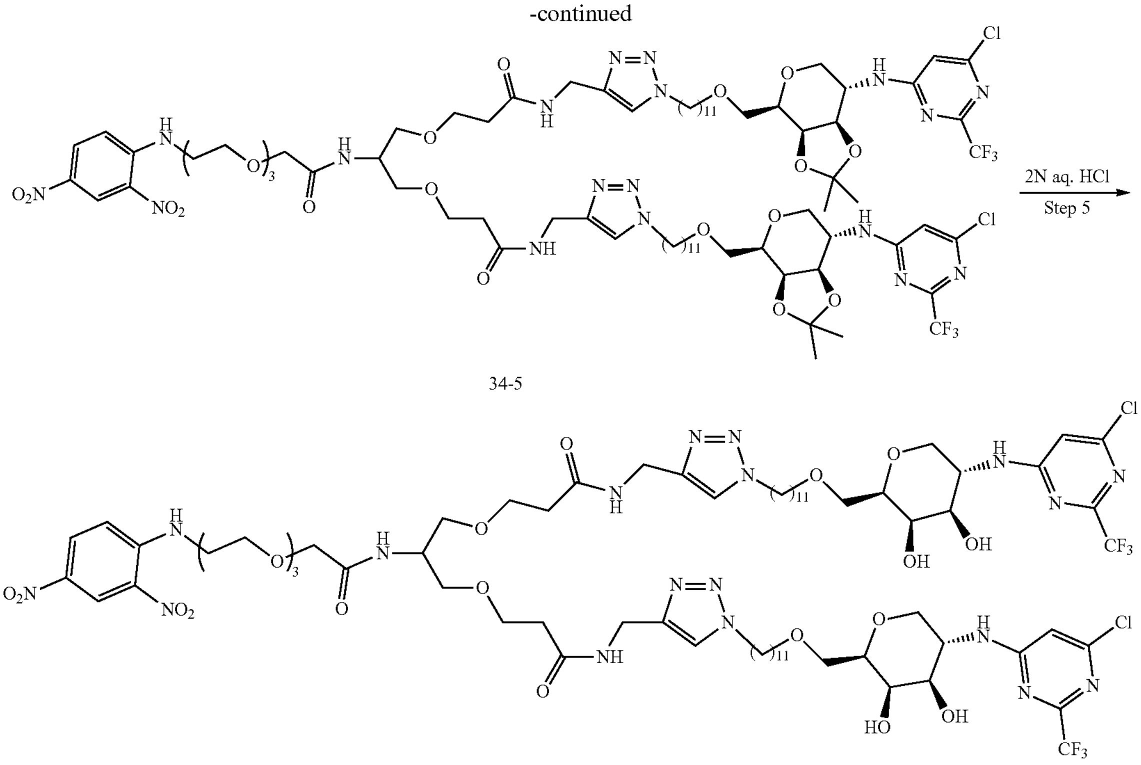

34-5

Compound 34

Step 1: To a solution of (2R,3R,4R,5S)-5-((6-chloro-2-(trifluoromethyl)pyrimidin-4-yl)amino)-2-(hydroxymethyl)tetrahydro-2H-pyran-3,4-diol (1 equiv.) in 2,2-dimethoxypropane is added TsOH (0.1 equiv.), and the reaction is stirred at room temperature overnight. The mixture is concentrated under reduced pressure to give a crude product ((3aR,4R,7S,7aR)-7-((6-chloro-2-(trifluoromethyl)pyrimidin-4-yl)amino)-2,2-dimethyltetrahydro-4H-[1,3]dioxolo[4,5-c]pyran-4-yl)methanol.

Step 2: To a solution of ((3aR,4R,7S,7aR)-7-((6-chloro-2-(trifluoromethyl)pyrimidin-4-yl)amino)-2,2-dimethyltetrahydro-4H-[1,3]dioxolo[4,5-c]pyran-4-yl)methanol in DMF at 0° C. is added NaH (60% wt. in mineral oil) and 1-azido-11-bromoundecane, then the mixture is stirred at the room temperature overnight. On consumption of starting material (LCMS monitoring), the reaction vessel is again cooled to 0° C., water slowly added, and the reaction mixture is stirred for 15 min. The mixture is diluted with ethyl acetate and washed with water. The organic layer is dried over sodium sulfate, concentrated under reduced pressure to give a crude product, which is purified by flash chromatography to give N-((3aR,4R,7S,7aR)-4-(((11-azidoundecyl)oxy)methyl)-2,2-dimethyltetrahydro-4H-[1,3]dioxolo[4,5-c]pyran-7-yl)-6-chloro-2-(trifluoromethyl)pyrimidin-4-amine.

Step 3: To a solution of 13-((2-carboxyethoxy)methyl)-1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and propargylamine (2 equiv.) at 0° C. The mixture is stirred at rt for 2 h. The mixture is quenched with $H_2O$, extracted with DCM and washed with brine. The organic phase is dried and concentrated. The residual is purified by flash column to give 3,3'-((2-(2-(2-(2-(2-((2,4-dinitrophenyl)amino)ethoxy)ethoxy)ethoxy)acetamido)propane-1,3-diyl)bis(oxy))bis(N-(prop-2-yn-1-yl)propanamide).

Step 4: THPTA and $CuSO_4$ are dissolved in water. The mixture is added to a solution of N-((3aR,4R,7S,7aR)-4-(((11-azidoundecyl)oxy)methyl)-2,2-dimethyltetrahydro-4H-[1,3]dioxolo[4,5-c]pyran-7-yl)-6-chloro-2-(trifluoromethyl)pyrimidin-4-amine and 3,3'-((2-(2-(2-(2-(2-((2,4-dinitrophenyl)amino)ethoxy)ethoxy)ethoxy)acetamido)propane-1,3-diyl)bis(oxy))bis(N-(prop-2-yn-1-yl)propanamide) in MeOH. A solution of Na ascorbate in water is added. The reaction is stirred overnight. The resulting mixture is filtered. The crude product is purified by prep-HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-((1-(11-(((3aR,4R,7S,7aR)-7-((6-chloro-2-(trifluoromethyl)pyrimidin-4-yl)amino)-2,2-dimethyltetrahydro-4H-[1,3]dioxolo[4,5-c]pyran-4-yl)methoxy)undecyl)-1H-1,2,3-triazol-4-yl)methyl)propanamide).

Step 5: To a solution of 3,3'-((2-(2-(2-(2-(2-((2,4-dinitrophenyl)amino)ethoxy)ethoxy)ethoxy)acetamido)propane-1,3-diyl)bis(oxy))bis(N-((1-(11-(((3aR,4R,7S,7aR)-7-((6-chloro-2-(trifluoromethyl)pyrimidin-4-yl)amino)-2,2-dimethyltetrahydro-4H-[1,3]dioxolo[4,5-c]pyran-4-yl)methoxy)undecyl)-1H-1,2,3-triazol-4-yl)methyl)propanamide) in THF is added HCl (2N in $H_2O$) at 0° C. The mixture is stirred at rt for 2 h. The mixture is concentrated and purified by prep-HPLC (Method A) to give 3,3'-((2-(2-(2-(2-(2-((2,4-dinitrophenyl)amino)ethoxy)ethoxy)ethoxy)acetamido)propane-1,3-diyl)bis(oxy))bis(N-((1-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-1H-1,2,3-triazol-4-yl)methyl)propanamide) (Compound 34).

Preparation of Compound 35 ((2R,3R,4R,5S)-2-(13-((2,4-dinitrophenyl)amino)-2,5,8,11-tetraoxatridecyl)-5-((4-(trifluoromethyl)pyrimidin-2-yl)amino)tetrahydro-2H-pyran-3,4-diol)

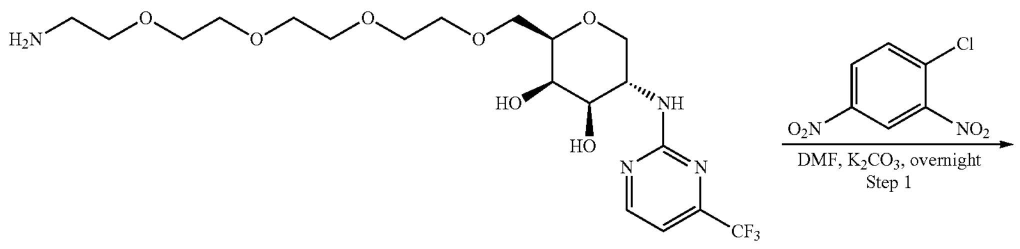

34-10

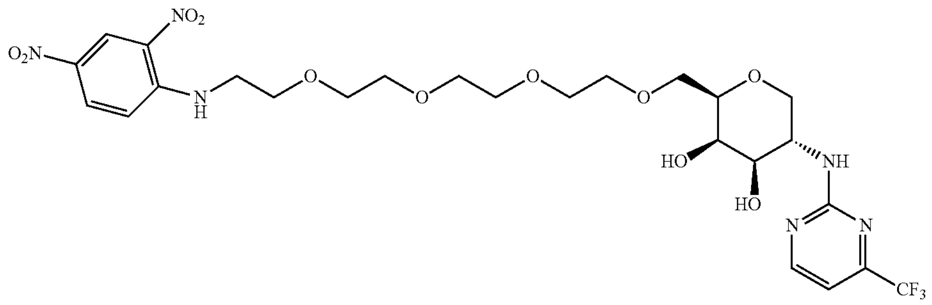

Compound 35

Step 1: To a solution of (2R,3R,4R,5S)-2-(13-amino-2,5,8,11-tetraoxatridecyl)-5-((4-(trifluoromethyl)pyrimidin-2-yl)amino)tetrahydro-2H-pyran-3,4-diol (72 mg, 0.149 mmol) in DMF (3 mL) was added $K_2CO_3$ (62 mg, 0.446 mmol) and 1-chloro-2,4-dinitrobenzene (30 mg, 0.149 mmol). The mixture was stirred at 80° C. for 16 h. The mixture was filtered, concentrated and purified by prep-HPLC (Method A) to give (2R,3R,4R,5S)-2-(13-((2,4-dinitrophenyl)amino)-2,5,8,11-tetraoxatridecyl)-5-((4-(trifluoromethyl)pyrimidin-2-yl)amino)tetrahydro-2H-pyran-3,4-diol (Compound 35, 7.0 mg, 7% yield) as yellow solid. LC-MS (ESI) found: 651 $[M+H]^+$. $^1H$ NMR (400 MHz, MeOD): δ 9.02 (d, J=2.7 Hz, 1H), 8.50 (d, J=4.8 Hz, 1H), 8.28 (dd, J=9.6, 2.7 Hz, 1H), 7.22 (d, J=9.6 Hz, 1H), 6.89 (d, J=4.9 Hz, 1H), 4.34 (td, J=10.5, 5.2 Hz, 1H), 4.07 (dd, J=10.9, 5.2 Hz, 1H), 3.90 (d, J=2.9 Hz, 1H), 3.81 (t, J=5.2 Hz, 2H), 3.71-3.61 (m, 18H), 3.15 (t, J=10.9 Hz, 1H).

Preparation of Compound 36: N-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((2-((3-((2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propanamide

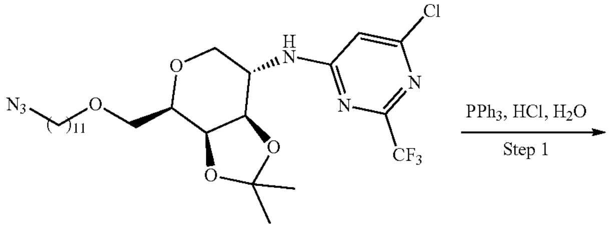

34-2

-continued

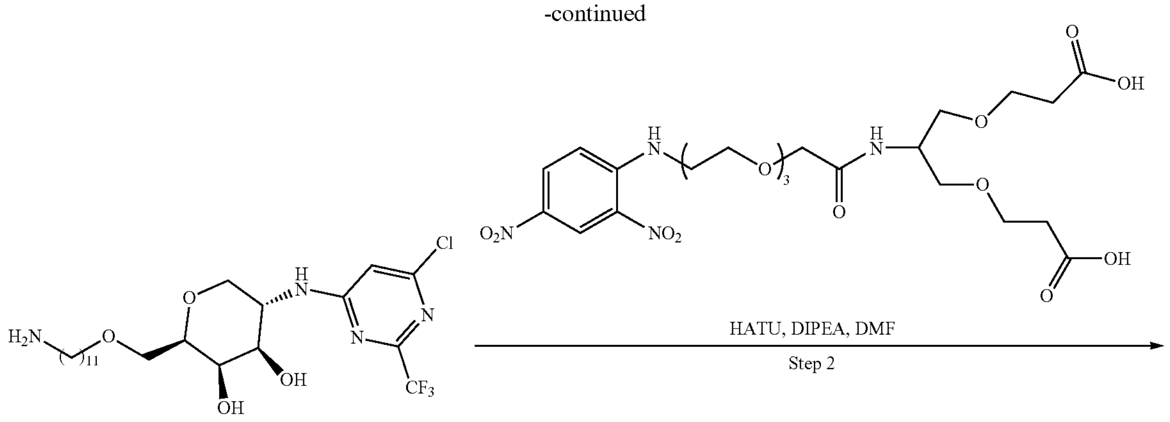

36-1

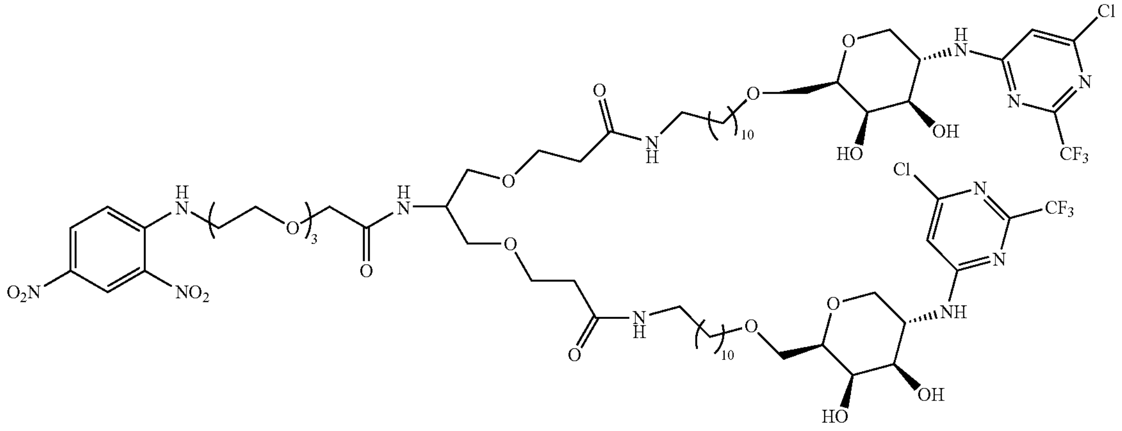

Compound 36

Step 1: To a solution of N-((3aR,4R,7S,7aR)-4-(((11-azidoundecyl)oxy)methyl)-2,2-dimethyltetrahydro-4H-[1,3]dioxolo[4,5-c]pyran-7-yl)-6-chloro-2-(trifluoromethyl)pyrimidin-4-amine in THF is added $PPh_3$ and water. The reaction mixture is stirred at rt overnight. The mixture is concentrated in vacuo. The crude product is purified by flash chromatography (silica gel, 0-10% MeOH in DCM) to give (2R,3R,4R,5S)-2-(((11-aminododecyl)oxy)methyl)-5-((6-chloro-2-(trifluoromethyl)pyrimidin-4-yl)amino)tetrahydro-2H-pyran-3,4-diol.

Step 2: To a solution of 13-((2-carboxyethoxy)methyl)-1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and (2R,3R,4R,5S)-2-(((11-aminododecyl)oxy)methyl)-5-((6-chloro-2-(trifluoromethyl)pyrimidin-4-yl)amino)tetrahydro-2H-pyran-3,4-diol (2 equiv.) at 0° C. The mixture is stirred at rt for 2 h. The mixture is quenched with $H_2O$, extracted with DCM and washed with brine. The organic phase is dried and concentrated. The residual is purified by flash column to give N-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((2-((3-((2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propenamide (Compound 36).

Preparation of Compound 37: 3,3'-((2-((3-((11-(((2R,3R,4R,5R)-5-((1,2,4-thiadiazol-5-yl)amino)-3,4-dihydroxytetrahydro-2H-pyran-2-yl)methoxy)undecyl)amino)-3-oxopropoxy)methyl)-2-(2-(2-(2-(2-((2,4-dinitrophenyl)amino)ethoxy)ethoxy)ethoxy)acetamido)propane-1,3-diyl)bis(oxy))bis(N-(11-(((2R,3R,4R,5R)-5-((1,2,4-thiadiazol-5-yl)amino)-3,4-dihydroxytetrahydro-2H-pyran-2-yl)methoxy)undecyl)propanamide)

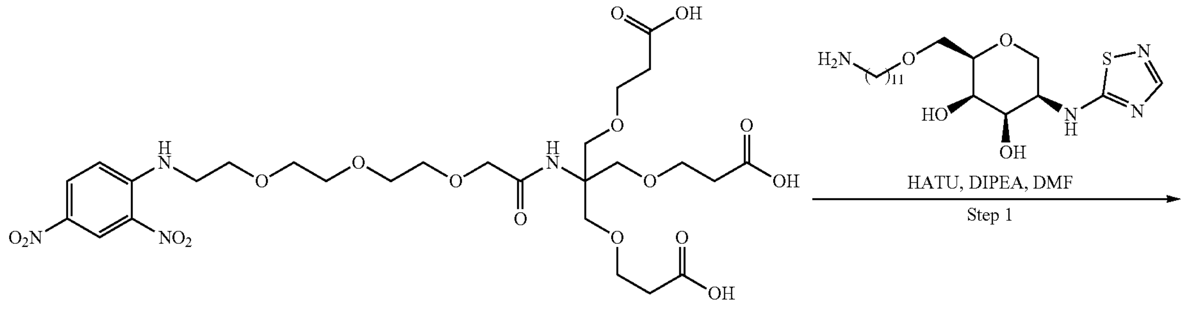

37-1

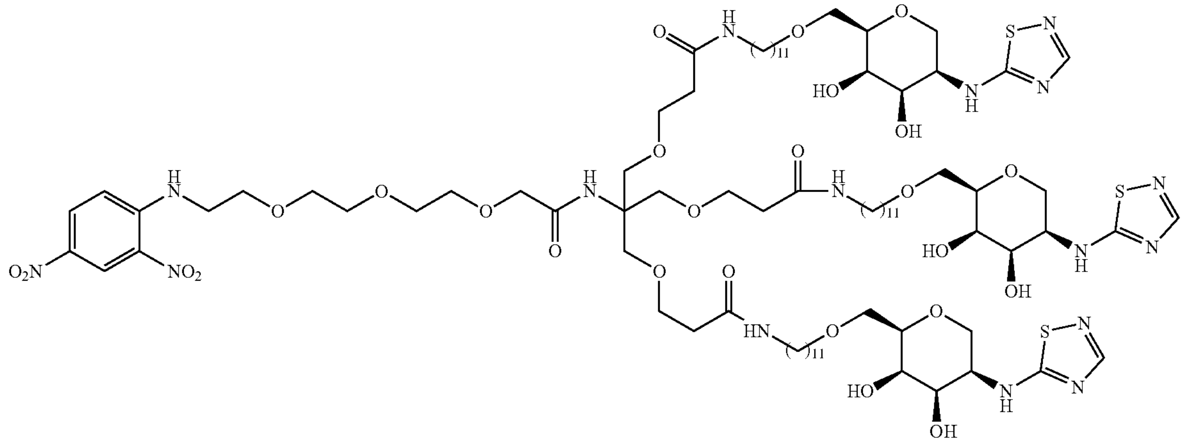

Compound 37

Step 1: To a solution of 13,13-bis((2-carboxyethoxy)methyl)-1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and (2R,3R,4R,5R)-5-((1,2,4-thiadiazol-5-yl)amino)-2-(((11-aminododecyl)oxy)methyl)tetrahydro-2H-pyran-3,4-diol (3 equiv.) at 0° C. The mixture is stirred at rt for 2 h. The mixture is quenched with $H_2O$, extracted with DCM and washed with brine. The organic phase is dried and concentrated. The residual is purified by flash column to give 3,3'-((2-((3-((11-(((2R,3R,4R,5R)-5-((1,2,4-thiadiazol-5-yl)amino)-3,4-dihydroxytetrahydro-2H-pyran-2-yl)methoxy)undecyl)amino)-3-oxopropoxy)methyl)-2-(2-(2-(2-(2-((2,4-dinitrophenyl)amino)ethoxy)ethoxy)ethoxy)acetamido)propane-1,3-diyl)bis(oxy))bis(N-(11-(((2R,3R,4R,5R)-5-((1,2,4-thiadiazol-5-yl)amino)-3,4-dihydroxytetrahydro-2H-pyran-2-yl)methoxy)undecyl)propanamide)(Compound 37).

Preparation of Compound 38: N-(2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((14-((2,4-dinitrophenyl)amino)-4-oxo-6,9,12-trioxa-3-azatetradecyl)oxy)propanamide

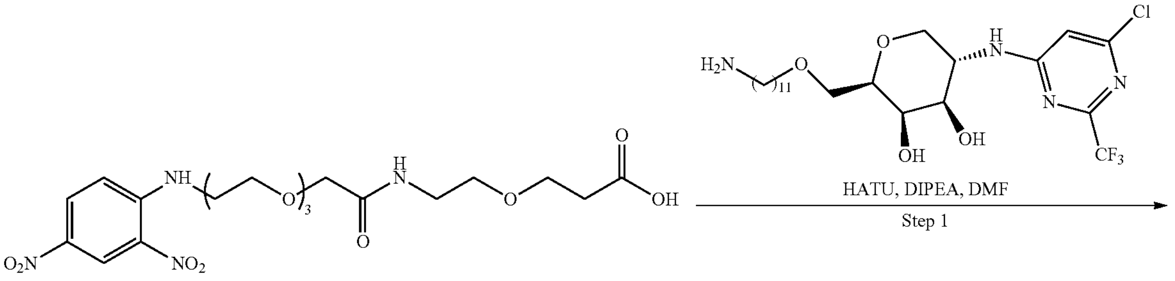

38-1

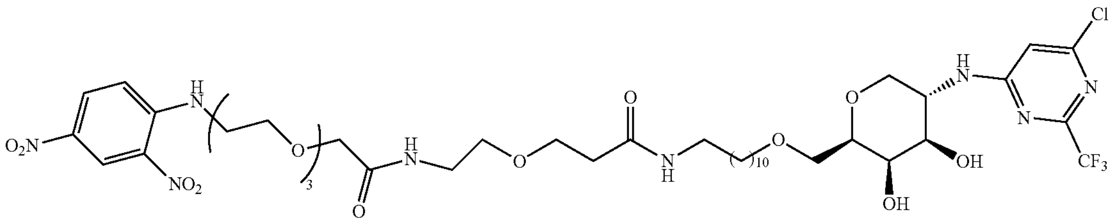

Compound 38

Step 1: To a solution of 1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and (2R,3R,4R,5S)-2-(((11-aminododecyl)oxy)methyl)-5-((6-chloro-2-(trifluoromethyl)pyrimidin-4-yl)amino)tetrahydro-2H-pyran-3,4-diol (1 equiv.) at 0° C. The mixture is stirred at rt for 2 h. The mixture is quenched with $H_2O$, extracted with DCM and washed with brine. The organic phase is dried and concentrated. The residual is purified by flash column to give N-(2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((14-((2,4-dinitrophenyl)amino)-4-oxo-6,9,12-trioxa-3-azatetradecyl)oxy)propanamide (Compound 38).

Preparation of Compound 39 (S)-2-((S)-2-((1H-imidazol-5-yl)methyl)-23-(1-(1-((2R,3R,4R,5S)-5-((6-chloro-2-(trifluoromethyl)pyrimidin-4-yl)amino)-3,4-dihydroxytetrahydro-2H-pyran-2-yl)-20-((3-((11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-15,22-dioxo-2,18-dioxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide

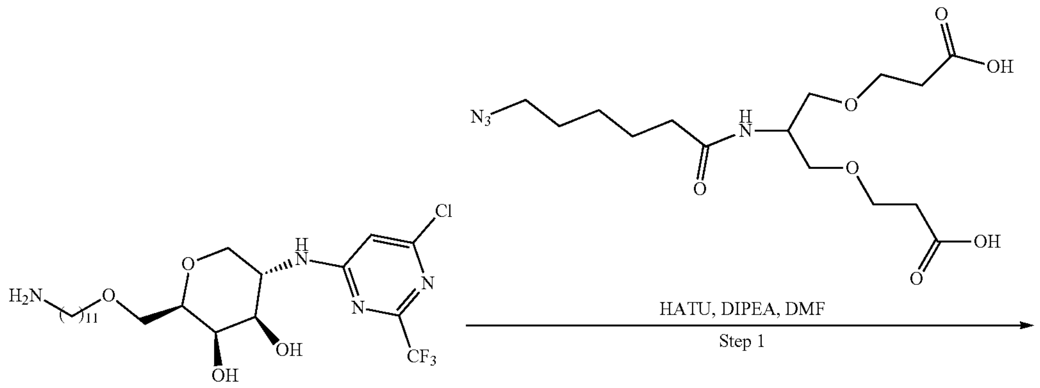

36-1

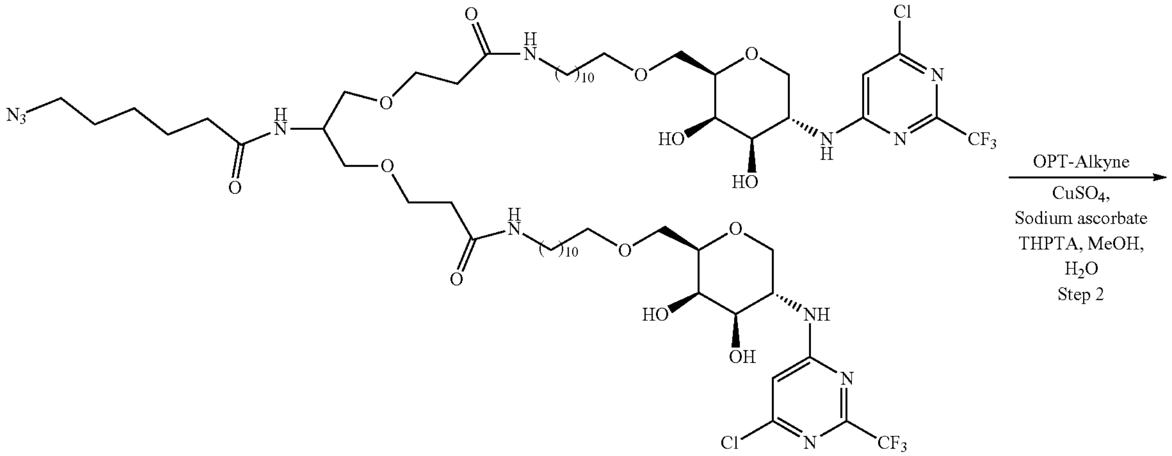

39-1

-continued

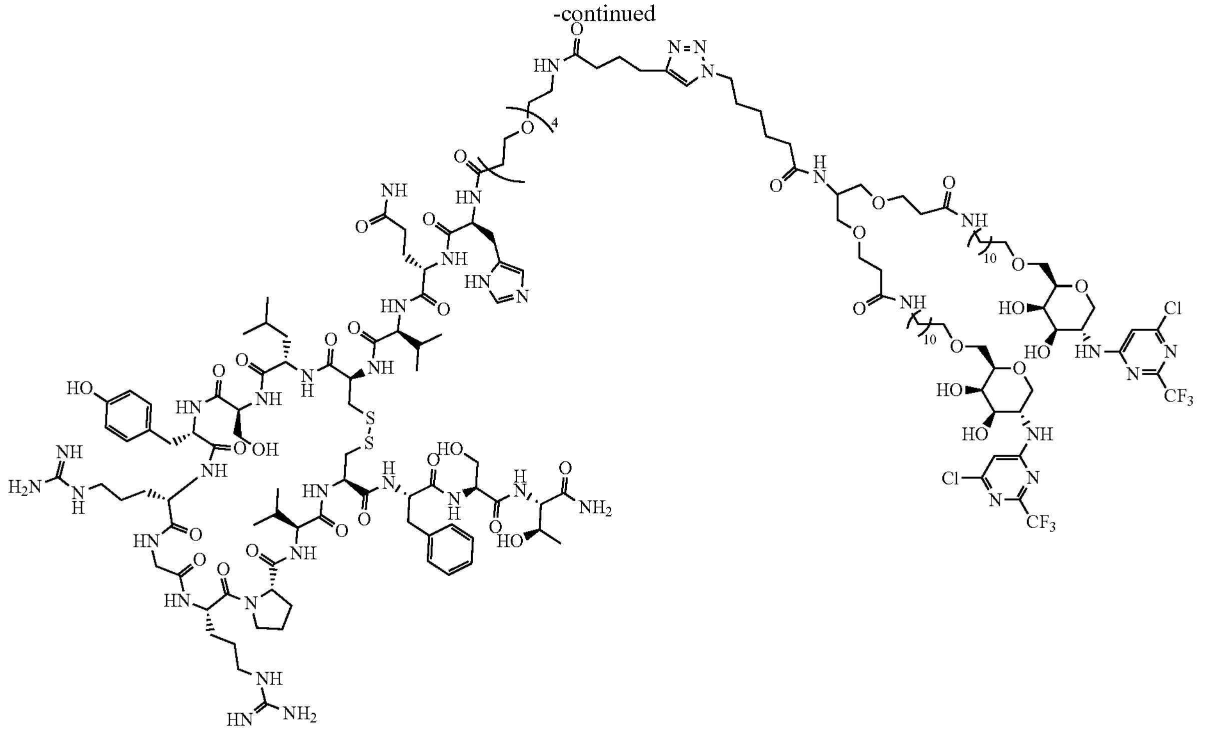

Compound 39

Step 1: To a solution of 3,3'-((2-(6-azidohexanamido)propane-1,3-diyl)bis(oxy))dipropionic acid (1 equiv.) in DMF (2 mL) is added HATU (1.5 equiv.), DIPEA (3 equiv.) and (2R,3R,4R,5S)-2-(((11-aminododecyl)oxy)methyl)-5-((6-chloro-2-(trifluoromethyl)pyrimidin-4-yl)amino)tetrahydro-2H-pyran-3,4-diol (2 equiv.) at 0° C. The mixture is stirred at rt for 2 h. The mixture is quenched with $H_2O$, extracted with DCM and washed with brine. The organic phase is dried and concentrated. The residual is purified by flash column to give N-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((2-((3-((2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propenamide.

Step 2: THPTA and $CuSO_4$ are dissolved in water. The mixture is added to a solution of N-(11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)-3-((2-((3-((2-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propenamide and OPT-Alkyne in MeOH. A solution of Na ascorbate in water is added. The reaction is stirred overnight. The resulting mixture is filtered. The crude product is purified by prep-HPLC (Method A) to give (S)-2-((S)-2-((1H-imidazol-5-yl)methyl)-23-(1-(1-((2R,3R,4R,5S)-5-((6-chloro-2-(trifluoromethyl)pyrimidin-4-yl)amino)-3,4-dihydroxytetrahydro-2H-pyran-2-yl)-20-((3-((11-(((2R,3R,4R,5S)-5-((6-chloro-2-(trifluoromethyl)pyrimidin-4-yl)amino)-3,4-dihydroxytetrahydro-2H-pyran-2-yl)methoxy)undecyl)amino)-3-oxopropoxy)methyl)-15,22-dioxo-2,18-dioxa-14,21-diazaheptacosan-27-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (Compound 39).

Preparation of Compound 48: (2R,3R,4R,5S)-5-((3-bromo-1,2,4-thiadiazol-5-yl)amino)-2-(13-((2,4-dinitrophenyl)amino)-2,5,8,11-tetraoxatridecyl)tetrahydro-2H-pyran-3,4-diol

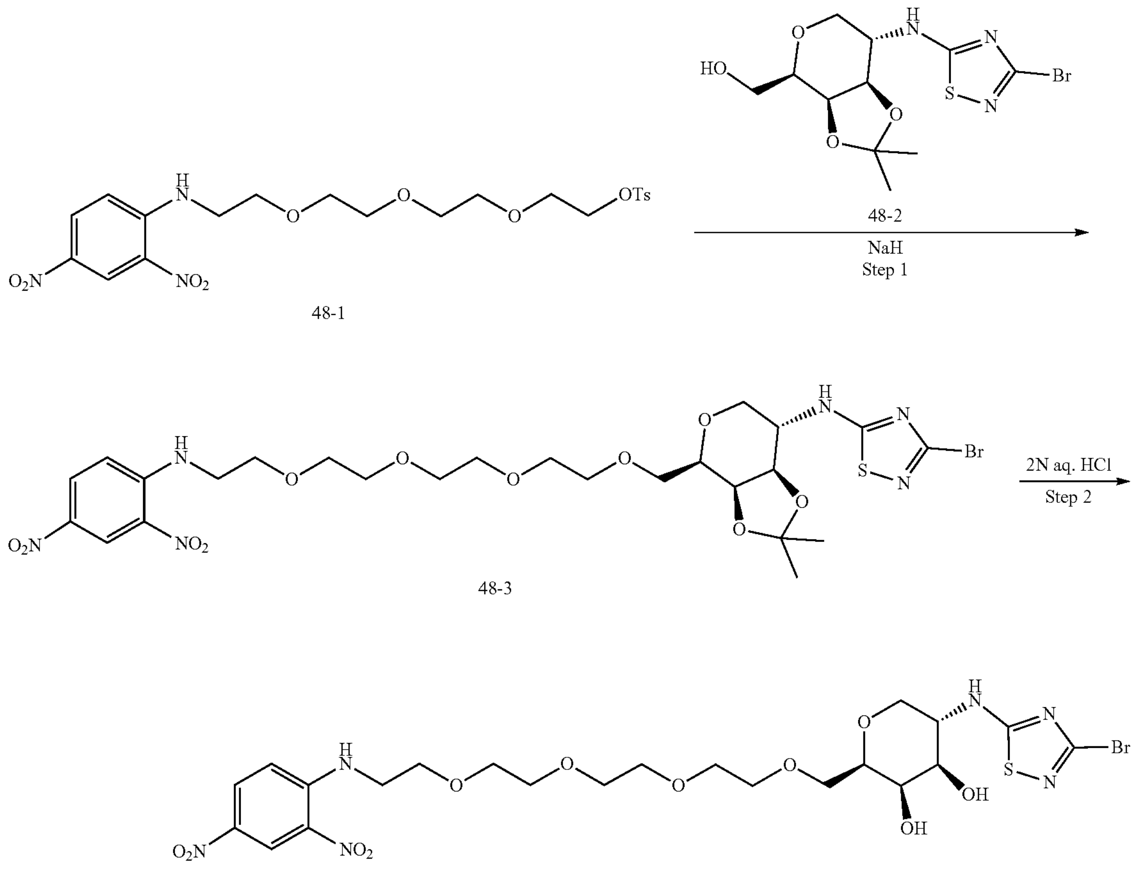

48-1

48-2

48-3

Compound 48

Step 1: NaH is added to a suspension of ((3aR,4R,7S,7aR)-7-((3-bromo-1,2,4-thiadiazol-5-yl)amino)-2,2-dimethyltetrahydro-4H-[1,3]dioxolo[4,5-c]pyran-4-yl)methanol in dry DMF. The mixture is stirred at rt for 1.5 h. Then 2-(2-(2-(2-((2,4-dinitrophenyl)amino)ethoxy)ethoxy)ethoxy)ethyl 4-methylbenzenesulfonate is added to the above solution. The mixture is further stirred at rt for 16 h. To the mixture is added $NH_4Cl$ (aq) and the solvent removed. Then the residual is purified by flash (DCM: MeOH=15:1) to give 3-bromo-N-((3aR,4R,7S,7aR)-4-(13-((2,4-dinitrophenyl)amino)-2,5,8,11-tetraoxatridecyl)-2,2-dimethyltetrahydro-4H-[1,3]dioxolo[4,5-c]pyran-7-yl)-1,2,4-thiadiazol-5-amine.

Step 2: To a solution of 3,3'-((2-(2-(2-(2-(2-((2,4-dinitrophenyl)amino)ethoxy)ethoxy)ethoxy)acetamido)propane-1,3-diyl)bis(oxy))bis(N-((1-(11-(((3aR,4R,7S,7aR)-7-((6-chloro-2-(trifluoromethyl)pyrimidin-4-yl)amino)-2,2-dimethyltetrahydro-4H-[1,3]dioxolo[4,5-c]pyran-4-yl)methoxy)undecyl)-1H-1,2,3-triazol-4-yl)methyl)propanamide) in THF is added HCl (2N in $H_2O$) at 0° C. The mixture is stirred at rt for 2 h. The mixture is concentrated and purified by prep-HPLC (Method A) to give (2R,3R,4R,5S)-5-((3-bromo-1,2,4-thiadiazol-5-yl)amino)-2-(13-((2,4-dinitrophenyl)amino)-2,5,8,11-tetraoxatridecyl)tetrahydro-2H-pyran-3,4-diol (Compound 48).

Preparation of Compound 49: (2R,3R,4R,5S)-5-((3-bromo-1,2,4-thiadiazol-5-yl)amino)-2-(22-((2,4-dinitrophenyl)amino)-2,5,8,11,14,17,20-heptaoxadocosyl)tetrahydro-2H-pyran-3,4-diol Compound 49

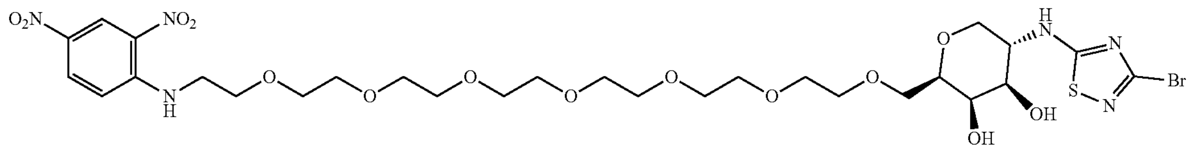

It is prepared according to the procedures same as that for Compound 48 by using 20-((2,4-dinitrophenyl)amino)-3,6,9,12,15,18-hexaoxaicosyl 4-methylbenzenesulfonate as the starting material.

Preparation of Compound 50: (2R,3R,4R,5S)-2-(22-((2,4-dinitrophenyl)amino)-2,5,8,11,14,17,20-heptaoxadocosyl)-5-((3-(pyridin-4-yl)-1,2,4-thiadiazol-5-yl)amino)tetrahydro-2H-pyran-3,4-diol Compound 50

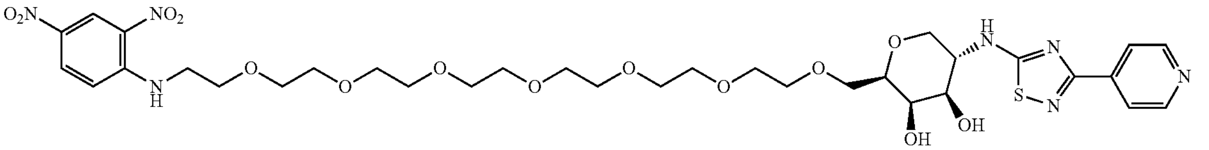

It is prepared according to the procedures same as that for A357 by using Compound 49 as the starting material.

Preparation of Compound 51

(S)-2-((S)-2-((1H-imidazol-5-yl)methyl)-23-(1-(1-((2R,3R,4R,5S)-3,4-dihydroxy-5-((4-(trifluoromethyl)pyrimidin-2-yl)amino)tetrahydro-2H-pyr

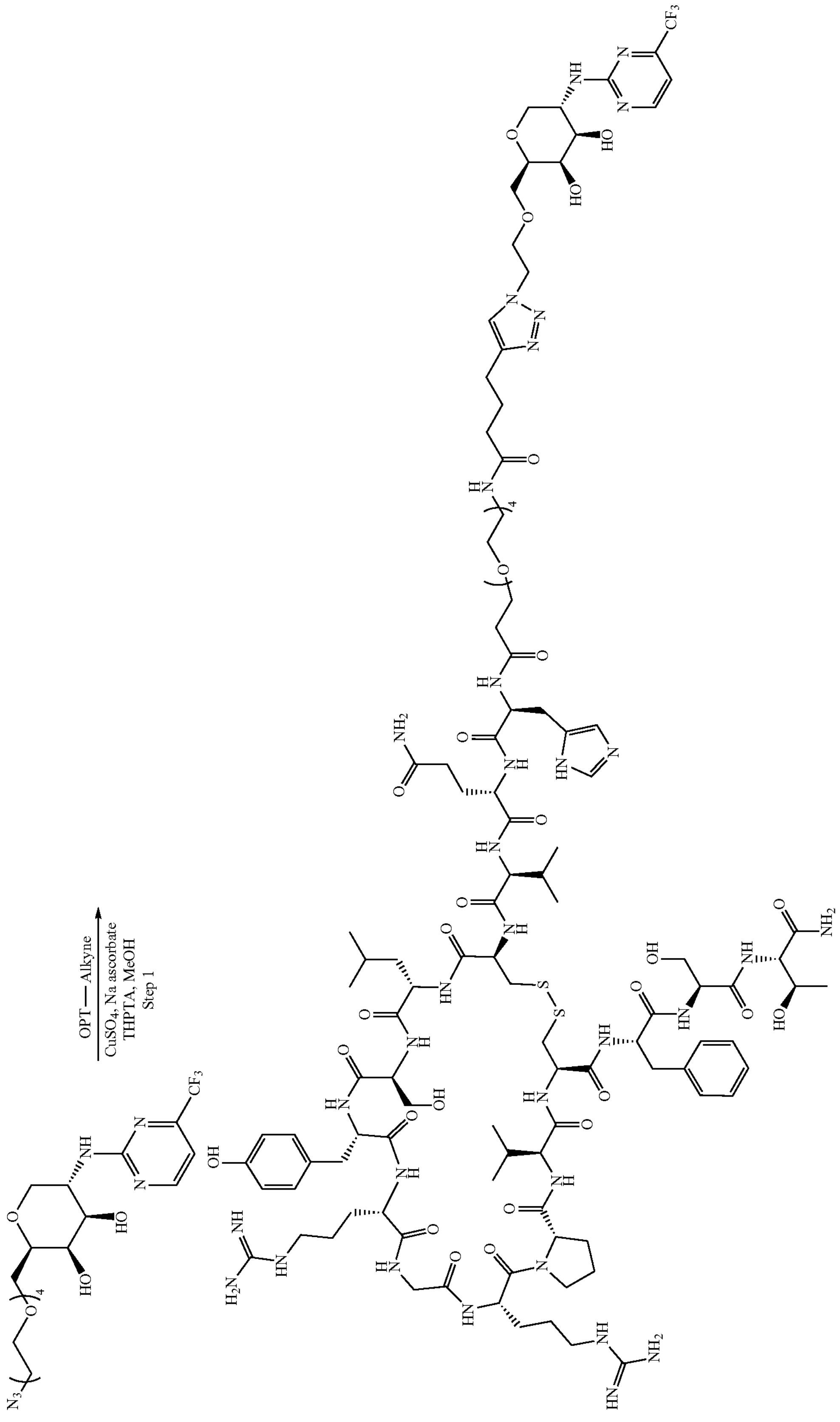
Compound 51

Step 1: THPTA (2.97 mg, 0.007 mmol) and $Cu_2SO_4$ (0.22 mg, 0.001 mmol) were dissolved in water (0.5 mL). Then a solution of (2R,3R,4R,5S)-2-(13-azido-2,5,8,11-tetraoxatridecyl)-5-((4-(trifluoromethyl)pyrimidin-2-yl)amino)tetrahydro-2H-pyran-3,4-diol (A419, 7.69 mg, 0.015 mmol) and OPT-Alkyne (30 mg, 0.014 mmol) in MeOH (2 mL) was added to the above mixture. Then a freshly-prepared solution of Na ascorbate (0.54 mg, 0.003 mmol) in water (0.5 mL) was added and the reaction mixture was stirred at room temperature for 24 hours. The mixture was filtered and the residue was purified by pre-HPLC (Method A) to afford (S)-2-((S)-2-((1H-imidazol-5-yl)methyl)-23-(1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (14 mg, 36% yield). LC-MS (ESI) found: 676 $[M+4H]^{4+}$. $^1H$ NMR (400 MHz, $D_2O$): δ 8.43 (d, J=4.6 Hz, 1H), 8.37 (s, 1H), 7.74 (s, 1H), 7.08 (d, J=8.3 Hz, 2H), 6.98 (s, 1H), 6.93-6.84 (m, 4H), 6.83-6.73 (m, 4H), 4.52-4.44 (m, 5H), 4.40-4.31 (m, 4H), 4.28-4.18 (m, 3H), 4.15-4.04 (m, 4H), 3.97 (dd, J=10.9, 5.0 Hz, 2H), 3.91 (d, J=3.2 Hz, 2H), 3.79 (ddd, J=30.0, 10.0, 4.0 Hz, 10H), 3.56 (ddd, J=19.4, 12.8, 7.5 Hz, 46H), 3.28 (d, J=5.4 Hz, 3H), 3.17 (dd, J=14.4, 8.8 Hz, 5H), 3.07-2.95 (m, 4H), 2.83 (d, J=38.1 Hz, 8H), 2.63 (dd, J=17.2, 9.6 Hz, 6H), 2.45 (dd, J=10.1, 5.2 Hz, 3H), 2.19 (t, J=7.3 Hz, 4H), 2.14-2.00 (m, 6H), 1.94-1.76 (m, 11H), 1.59 (dd, J=7.7, 2.6 Hz, 6H), 1.40 (d, J=10.1 Hz, 2H), 1.11-0.97 (m, 5H), 0.88-0.52 (m, 24H).

Preparation of Compound 52 (S)-2-((S)-2-((1H-imidazol-5-yl)methyl)-23-(1-(6-((1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)amino)-6-oxohexyl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide

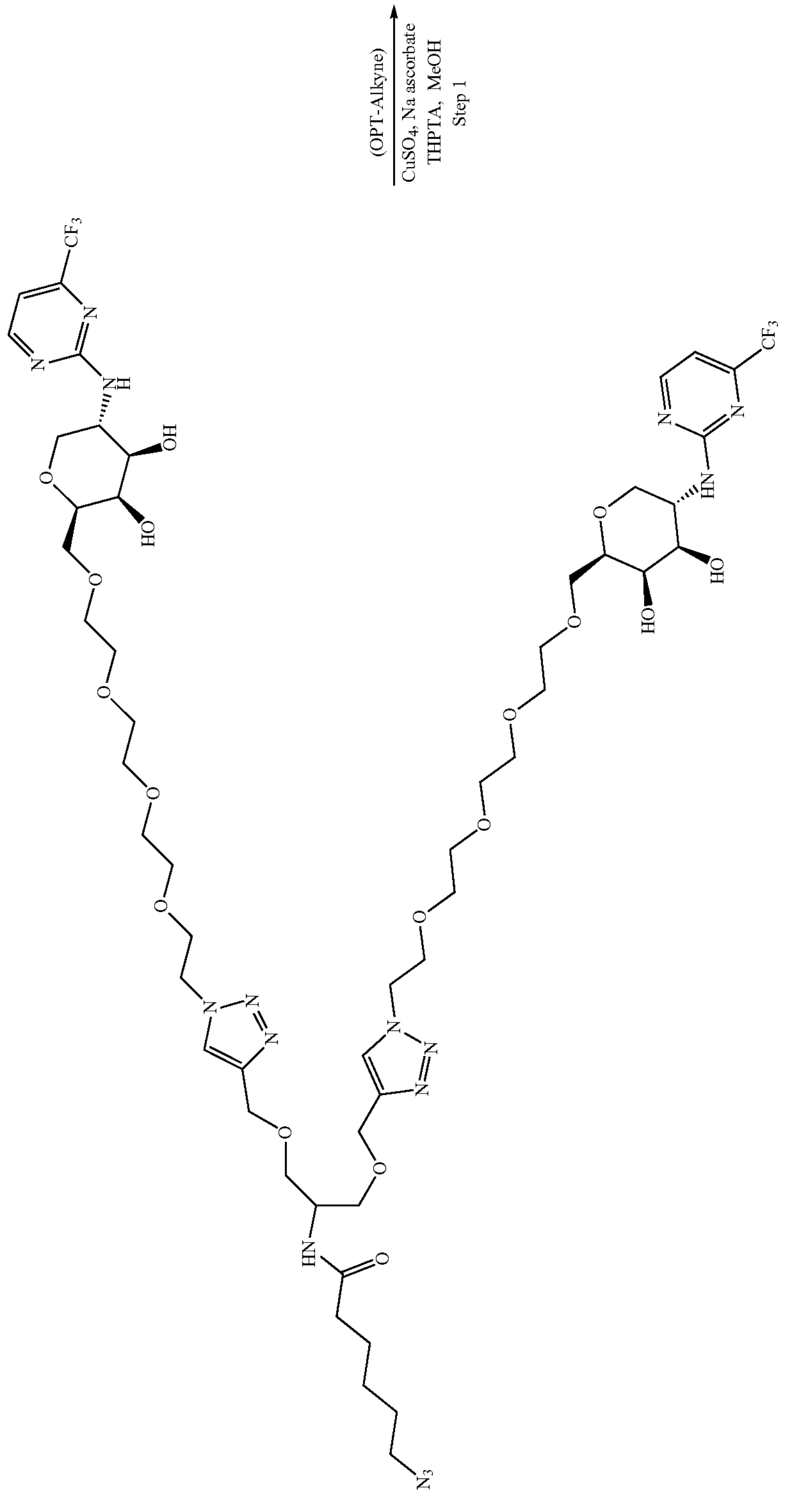
(OPT-Alkyne)
CuSO$_4$, Na ascorbate
THPTA, MeOH
Step 1

-continued
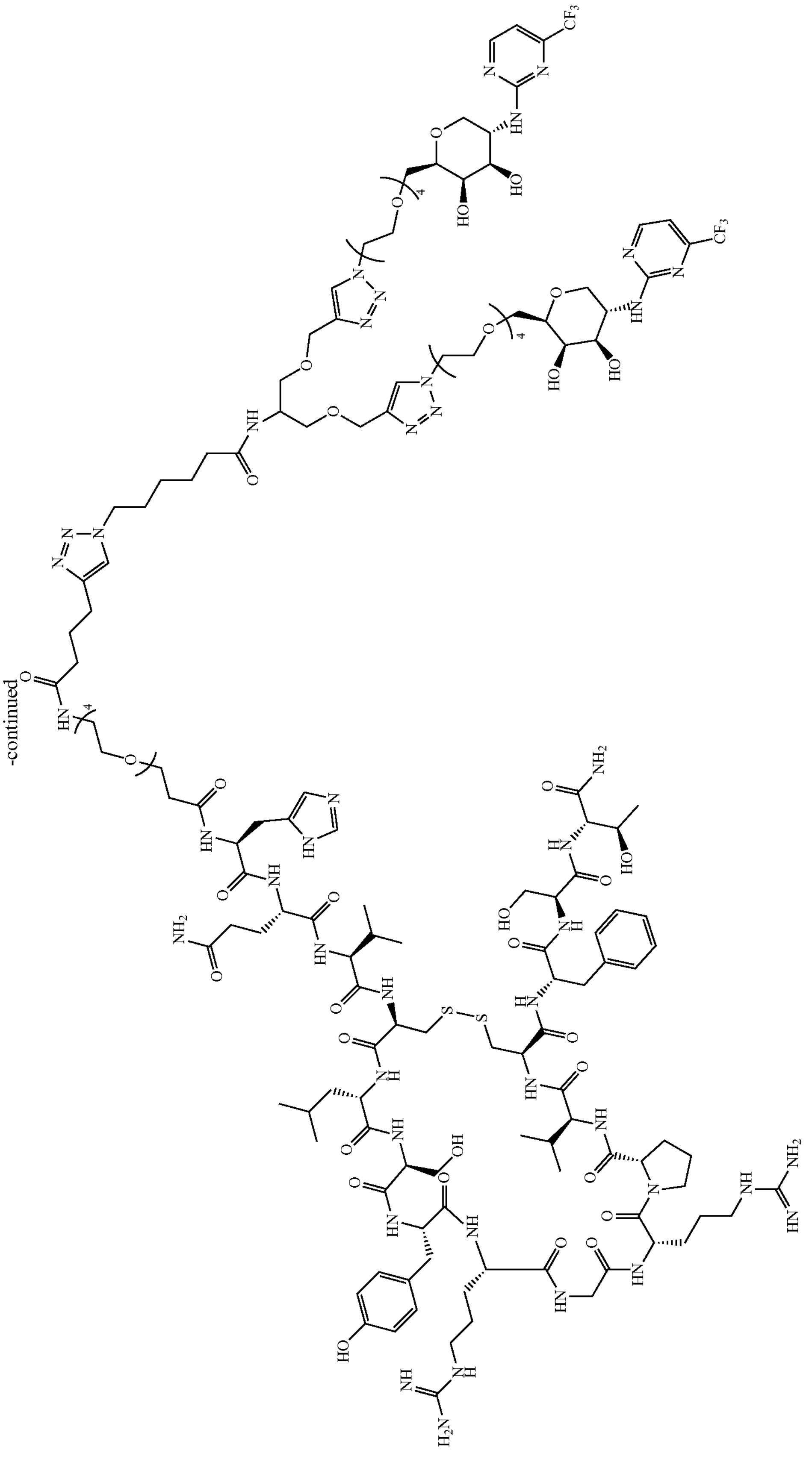

Step 1: THPTA (3.91 mg, 0.009 mmol) and $Cu_2SO_4$ (0.29 mg, 0.002 mmol) were dissolved in water (0.5 mL). Then a solution of 6-azido-N-(1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)hexanamide (A417, 25.96 mg, 0.020 mmol) and OPT-Alkyne (39 mg, 0.018 mmol) in MeOH (3 mL) was added into the above mixture. A freshly-prepared solution of Na ascorbate (0.71 mg, 0.004 mmol) in water (0.5 mL) was then added and the reaction mixture was stirred at room temperature for 24 hours. Solvent was evaporated and the crude material was purified by pre-HPLC (Method A) to afford (S)-2-((S)-2-((1H-imidazol-5-yl)methyl)-23-(1-(6-((1,3-bis((1-(1-((2R,3R,4R,5S)-3,4-dihydroxy-5-((4-(trifluoromethyl)pyrimidin-2-yl)amino)tetrahydro-2H-pyran-2-yl)-2,5,8,11-tetraoxatridecan-13-yl)-1H-1,2,3-triazol-4-yl)methoxy)propan-2-yl)amino)-6-oxohexyl)-1H-1,2,3-triazol-4-yl)-4,20-dioxo-7,10,13,16-tetraoxa-3,19-diazatricosanamido)-N1-((S)-1-(((3S,6R,11R,14S,17S,20S,23S,29S,34aS)-6-(((S)-1-(((S)-1-(((2S,3R)-1-amino-3-hydroxy-1-oxobutan-2-yl)amino)-3-hydroxy-1-oxopropan-2-yl)amino)-1-oxo-3-phenylpropan-2-yl)carbamoyl)-23,29-bis(3-guanidinopropyl)-20-(4-hydroxybenzyl)-17-(hydroxymethyl)-14-isobutyl-3-isopropyl-1,4,12,15,18,21,24,27,30-nonaoxotriacontahydro-1H,10H-pyrrolo[2,1-j][1,2]dithia[5,8,11,14,17,20,23,26,29]nonaazacyclodotriacontin-11-yl)amino)-3-methyl-1-oxobutan-2-yl)pentanediamide (10 mg, 17% yield). LC-MS (ESI) found: 705 $[M+5H]^{5+}$. $^1H$ NMR (400 MHz, MeOD): δ 8.79 (s, 1H), 8.50 (d, J=4.9 Hz, 2H), 8.03 (s, 2H), 7.78 (s, 1H), 7.36 (s, 1H), 7.17-7.02 (m, 7H), 6.89 (d, J=4.9 Hz, 2H), 6.74 (d, J=8.4 Hz, 2H), 5.78 (dt, J=22.6, 11.6 Hz, 2H), 5.24-5.10 (m, 3H), 5.05 (d, J=4.7 Hz, 2H), 4.79-4.69 (m, 2H), 4.57 (d, J=6.9 Hz, 8H), 4.52 (d, J=2.7 Hz, 1H), 4.43-4.29 (m, 7H), 4.19 (dd, J=10.4, 4.8 Hz, 2H), 4.06 (dd, J=10.9, 5.1 Hz, 2H), 3.89 (dd, J=10.0, 4.3 Hz, 7H), 3.78-3.47 (m, 59H), 3.34 (d, J=5.6 Hz, 3H), 3.23 (t, J=7.1 Hz, 2H), 3.14 (t, J=10.9 Hz, 4H), 3.06-2.88 (m, 6H), 2.81 (dd, J=17.6, 9.7 Hz, 2H), 2.70 (dd, J=17.5, 8.4 Hz, 3H), 2.61-2.34 (m, 3H), 2.22 (dt, J=21.7, 7.3 Hz, 7H), 2.09-1.80 (m, 14H), 1.77-1.69 (m, 4H), 1.69-1.52 (m, 4H), 1.39-1.13 (m, 7H), 1.06-0.93 (m, 10H), 0.85 (t, J=6.2 Hz, 9H).

Compound 40

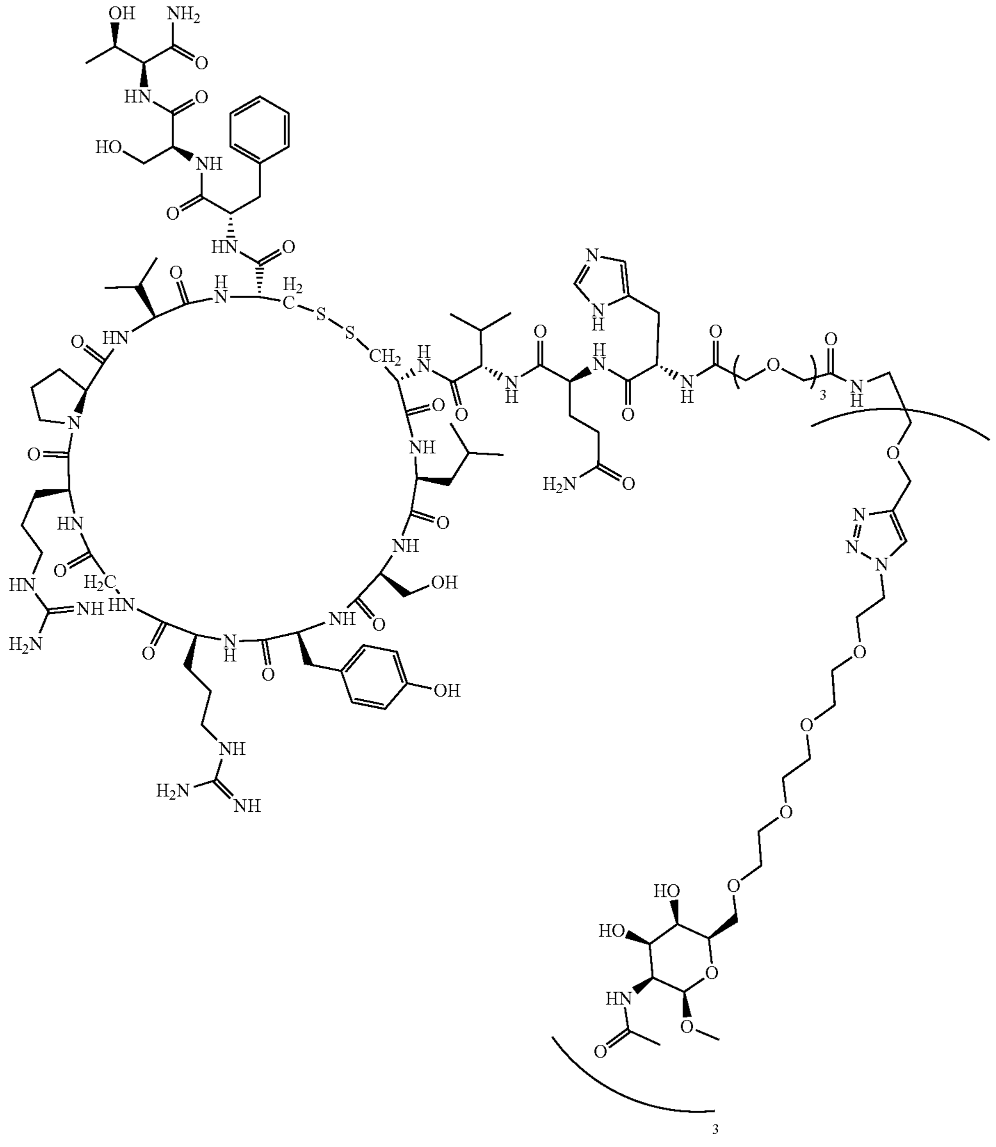

-continued
Compound 41
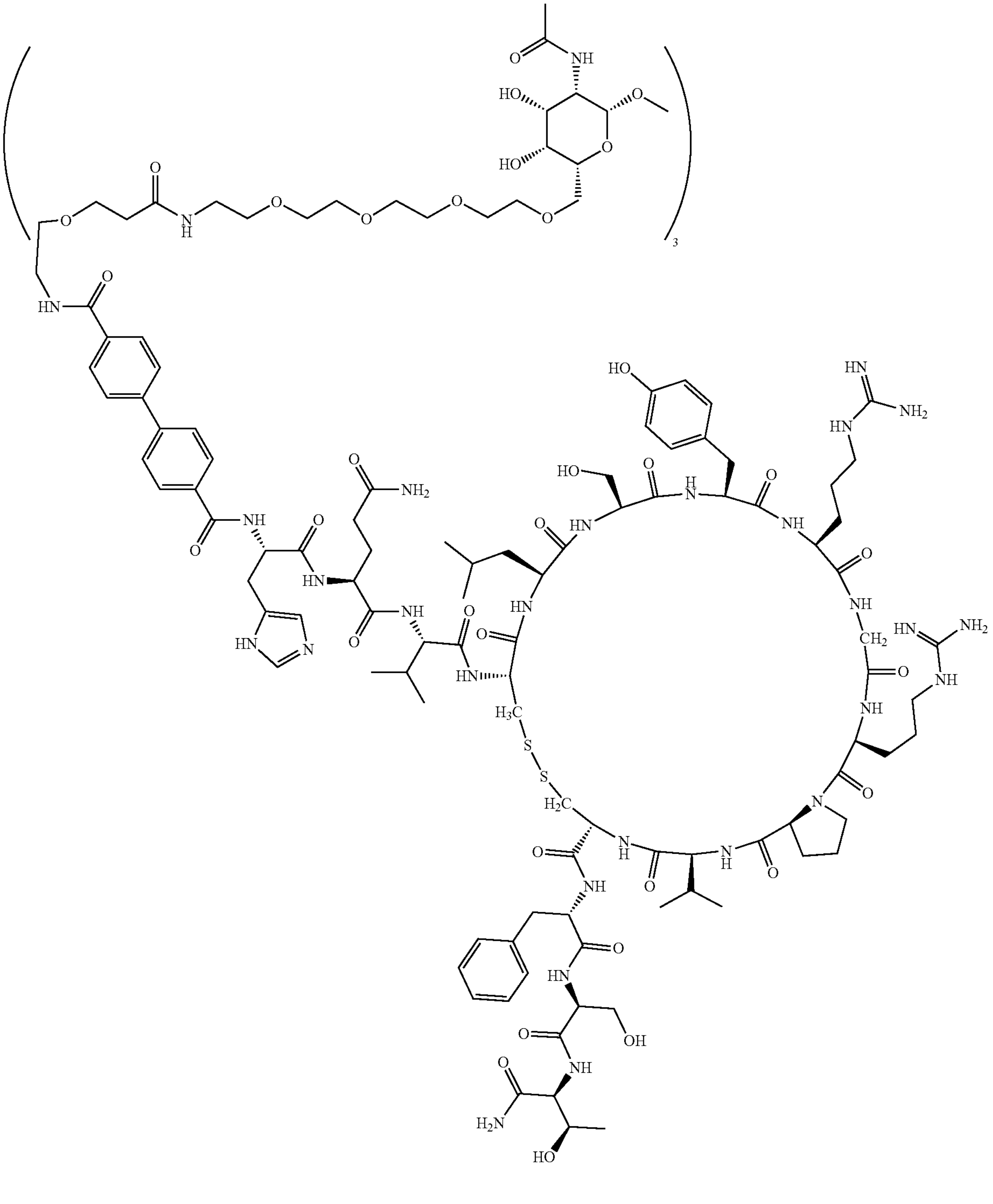

-continued
Compound 42
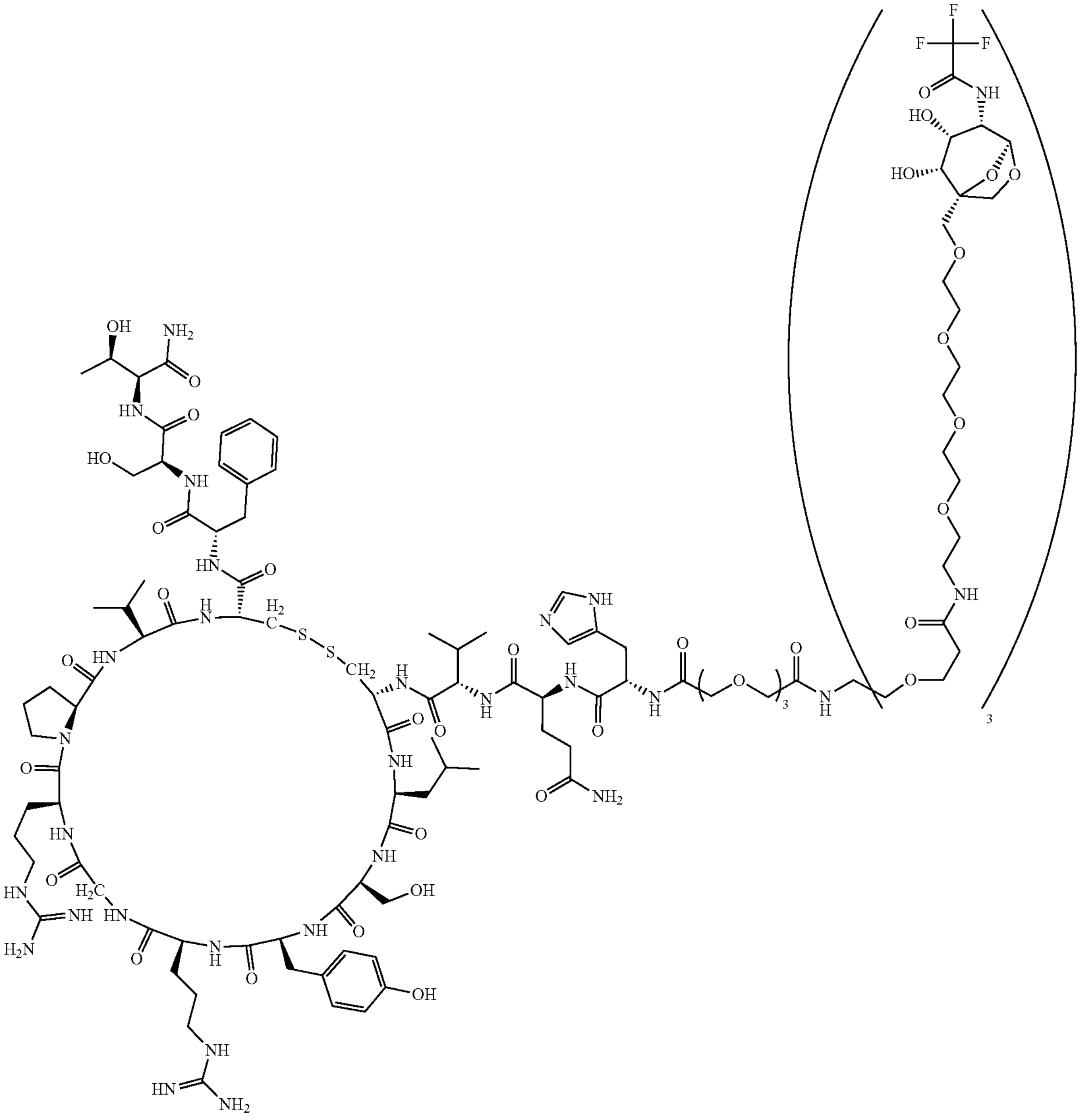

-continued
Compound 43
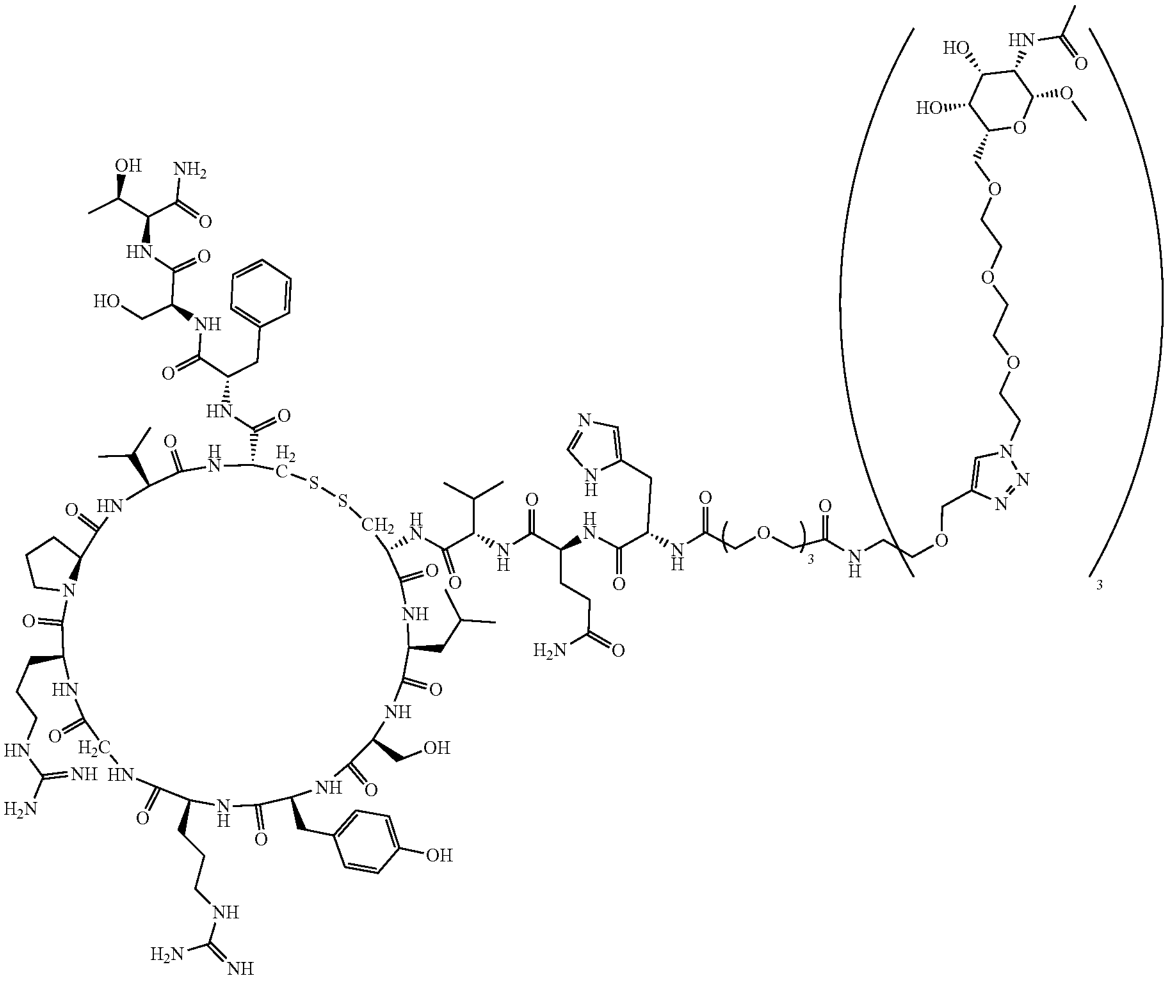

-continued
Compound 44
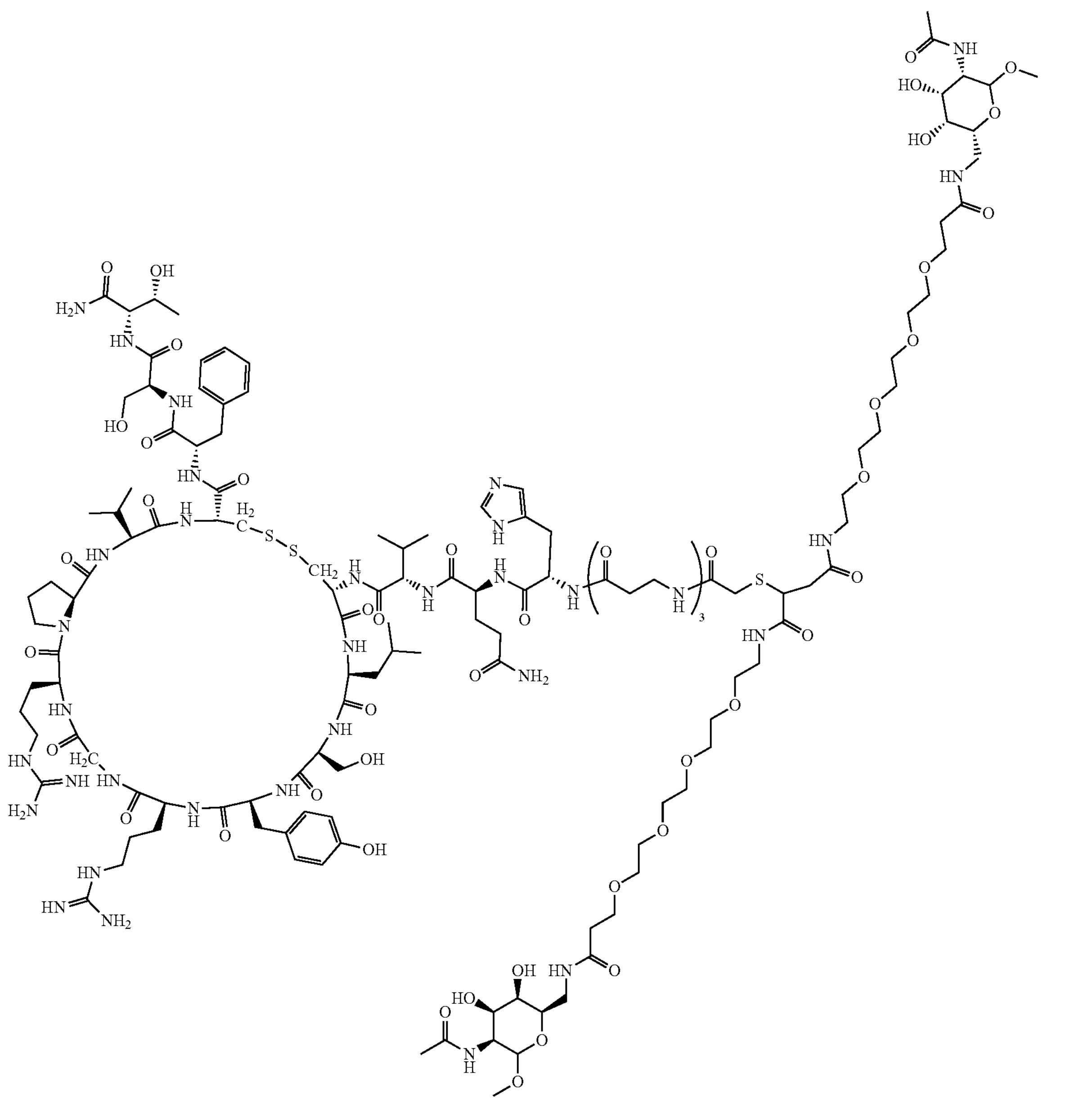

-continued
Compound 45
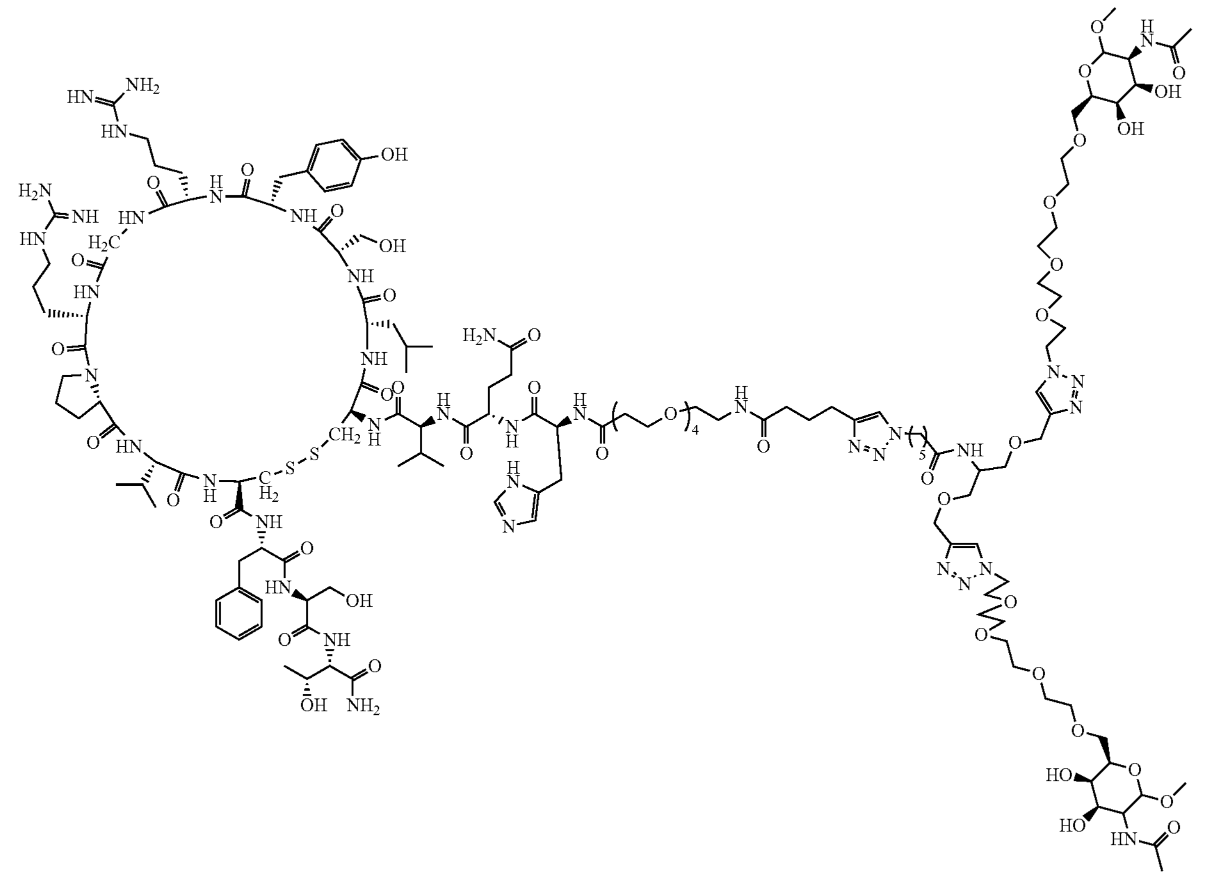

Compound 46
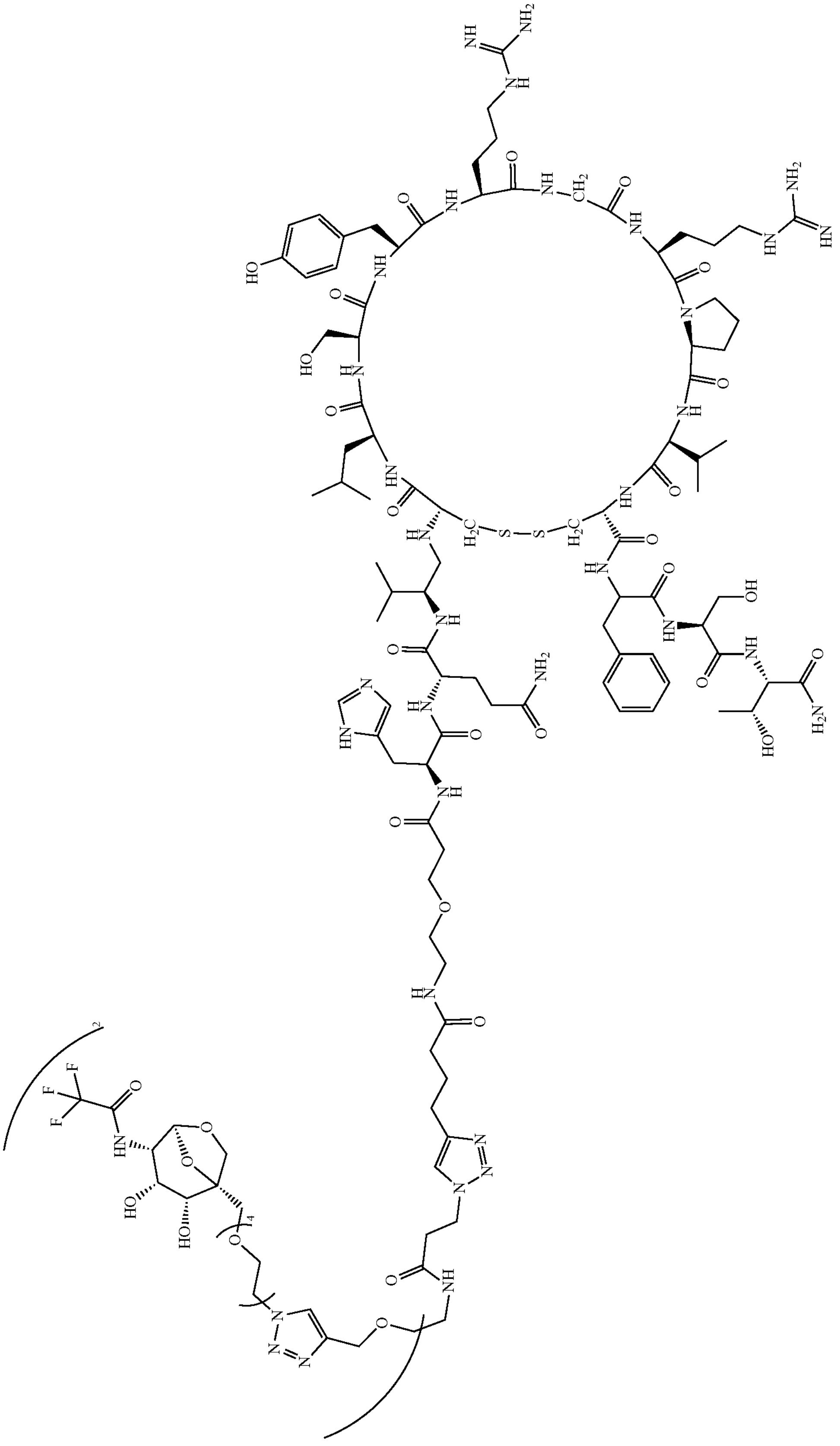

-continued
Compound 47
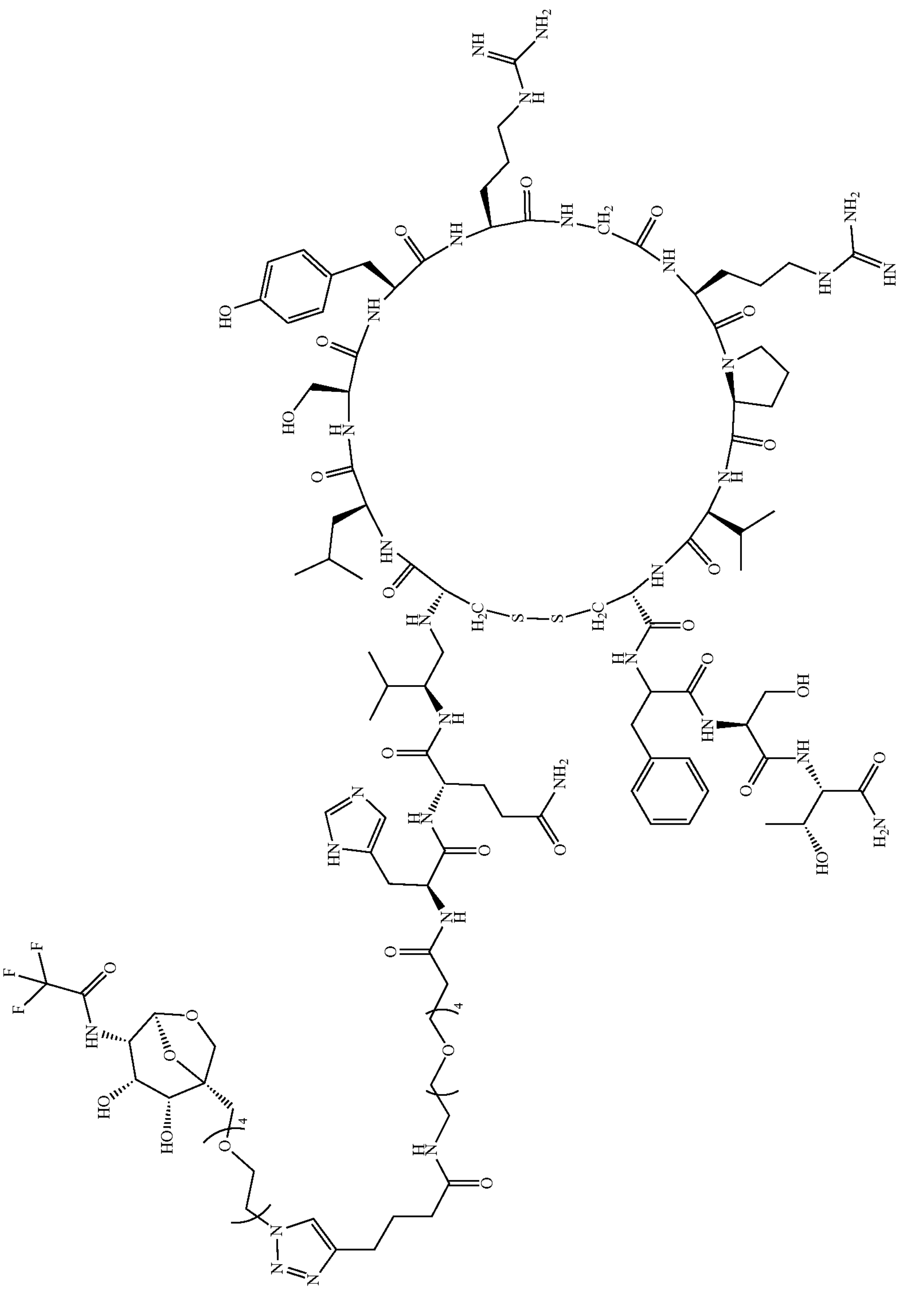

Preparation of Compound 53 3-(2-(2-(2-(3-(1-(4-amino-6,7-dimethoxyquinazolin-2-yl)-4-((R)-3-(ethylamino)-3-(4-fluorophenyl)propanoyl)piperazin-2-yl)phenoxy)ethoxy)ethoxy)ethoxy)-N-(1,31-bis((2R,3R,4R,5R)-3,4-dihydroxy-5-(2-oxooxazolidin-3-yl)tetrahydro-2H-pyran-2-yl)-16-(15-((2R,3R,4R,5R)-3,4-dihydroxy-5-(2-oxooxazolidin-3-yl)tetrahydro-2H-pyran-2-yl)-2,5,8,11,14-pentaoxapentadecyl)-2,5,8,11,14,18,21,24,27,30-decaoxahentriacontan-16-yl)propanamide
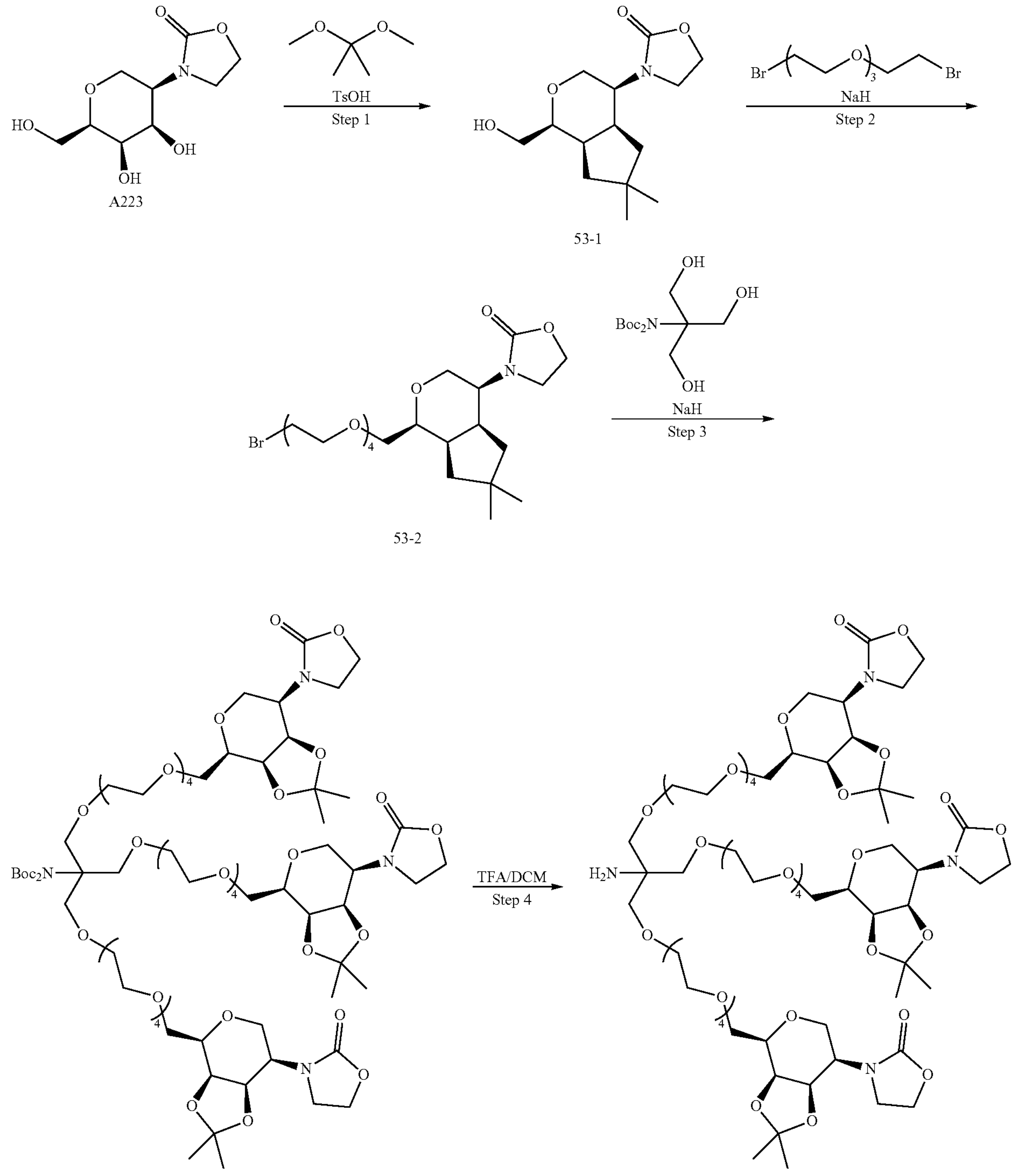
A223
53-1
53-2
53-3
53-4

-continued
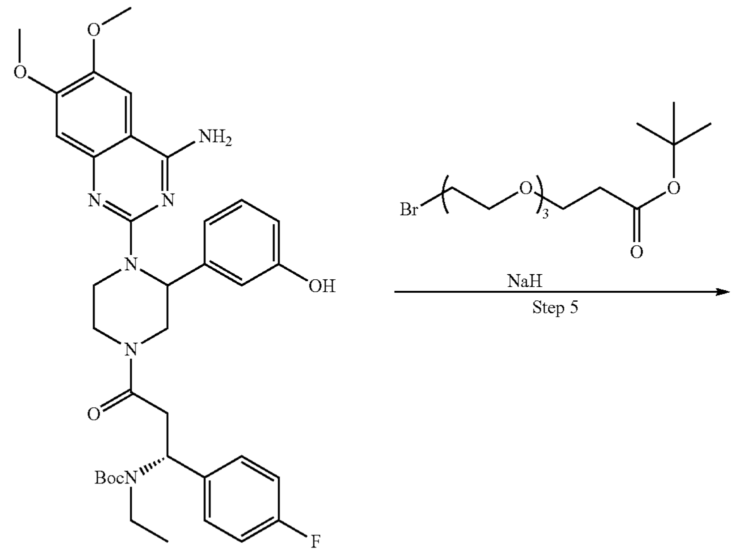
53-5
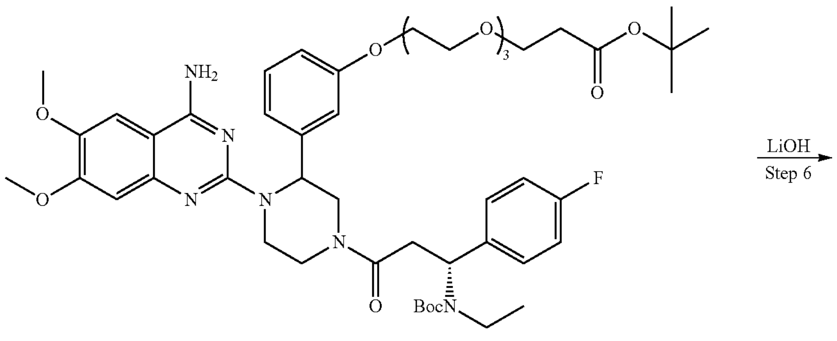
53-6

-continued
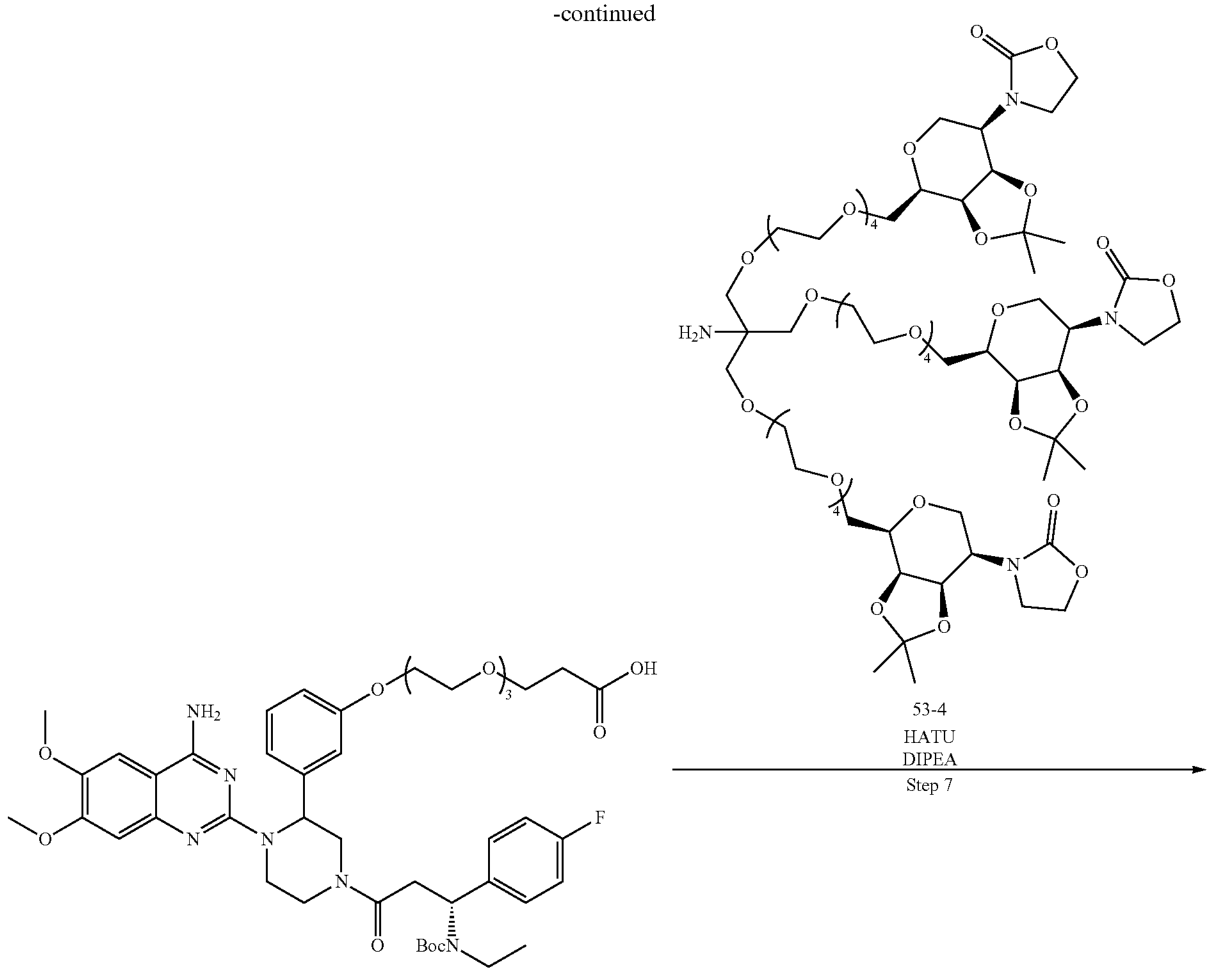
53-4
53-7
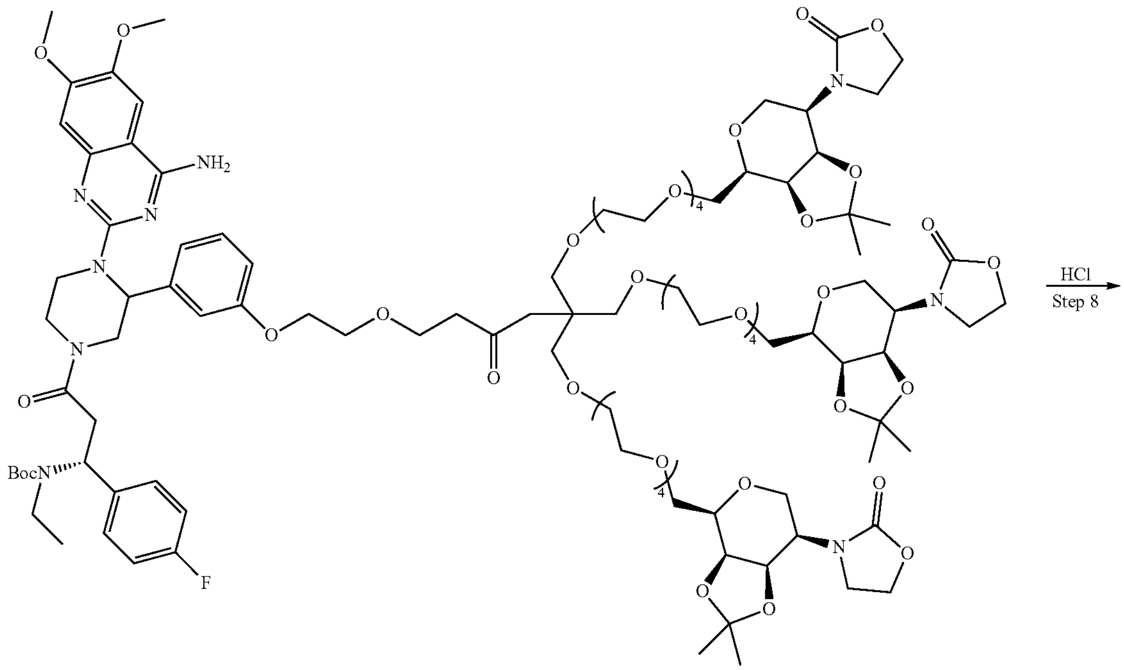
53-9

-continued

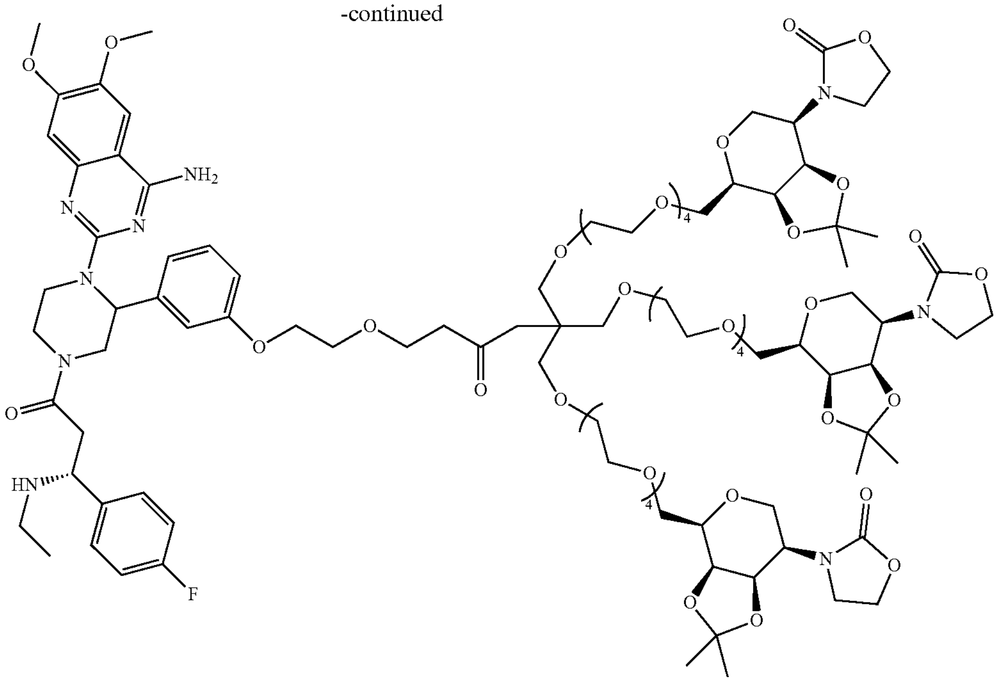

Compound 53

Step 1: To a solution of 3-((3R,4R,5R,6R)-4,5-dihydroxy-6-(hydroxymethyl)tetrahydro-2H-pyran-3-yl)oxazolidin-2-one (1 equiv.) in 2,2-dimethoxypropane is added TsOH (0.1 equiv.), and the reaction is stirred at room temperature overnight. The mixture is concentrated under reduced pressure to give a crude product 3-((3aR,4R,7R,7aR)-4-(hydroxymethyl)-2,2-dimethyltetrahydro-4H-[1,3]dioxolo[4,5-c]pyran-7-yl)oxazolidin-2-one.

Step 2: To a solution of 3-((3aR,4R,7R,7aR)-4-(hydroxymethyl)-2,2-dimethyltetrahydro-4H-[1,3]dioxolo[4,5-c]pyran-7-yl)oxazolidin-2-one in DMF at 0° C. is added NaH (60% wt. in mineral oil) and 1-bromo-2-(2-(2-(2-bromoethoxy)ethoxy)ethoxy)ethane, then the mixture is stirred at the room temperature overnight. On consumption of starting material (LCMS monitoring), the reaction vessel is again cooled to 0° C., water slowly added, and the reaction mixture is stirred for 15 min. The mixture is diluted with ethyl acetate and washed with water. The organic layer is dried over sodium sulfate, concentrated under reduced pressure to give a crude product, which is purified by flash chromatography to give 3-((3aR,4R,7R,7aR)-4-(13-bromo-2,5,8,11-tetraoxatridecyl)-2,2-dimethyltetrahydro-4H-[1,3]dioxolo[4,5-c]pyran-7-yl)oxazolidin-2-one.

Step 3: To a solution of tert-butyl (tert-butoxycarbonyl)(1,3-dihydroxy-2-(hydroxymethyl)propan-2-yl)carbamate in DMF is added NaH at 0° C. and stirred for 1 h under $N_2$. Then 3-((3aR,4R,7R,7aR)-4-(13-bromo-2,5,8,11-tetraoxatridecyl)-2,2-dimethyltetrahydro-4H-[1,3]dioxolo[4,5-c]pyran-7-yl)oxazolidin-2-one is added at 0° C. and stirred at rt for 2 h under $N_2$. The resulting mixture is diluted with DCM and water. The aqueous phase is extracted with DCM. The organic layer is separated, dried over $Na_2SO_4$ and concentrated in vacuo. The crude product is purified by flash chromatography (silica gel, 0-10% MeOH in DCM) to give tert-butyl (1,31-bis((3aR,4R,7R,7aR)-2,2-dimethyl-7-(2-oxooxazolidin-3-yl)tetrahydro-4H-[1,3]dioxolo[4,5-c]pyran-4-yl)-16-(15-((3aR,4R,7R,7aR)-2,2-dimethyl-7-(2-oxooxazolidin-3-yl)tetrahydro-4H-[1,3]dioxolo[4,5-c]pyran-4-yl)-2,5,8,11,14-pentaoxapentadecyl)-2,5,8,11,14,18,21,24,27,30-decaoxahentriacontan-16-yl)(tert-butoxycarbonyl)carbamate.

Step 4: To a solution of tert-butyl (1,31-bis((3aR,4R,7R,7aR)-2,2-dimethyl-7-(2-oxooxazolidin-3-yl)tetrahydro-4H-[1,3]dioxolo[4,5-c]pyran-4-yl)-16-(15-((3aR,4R,7R,7aR)-2,2-dimethyl-7-(2-oxooxazolidin-3-yl)tetrahydro-4H-[1,3]dioxolo[4,5-c]pyran-4-yl)-2,5,8,11,14-pentaoxapentadecyl)-2,5,8,11,14,18,21,24,27,30-decaoxahentriacontan-16-yl)(tert-butoxycarbonyl)carbamate in DCM is added TFA at rt under $N_2$. After stirring for 2 h, the mixture is quenched with $NaHCO_3$(aq) and extracted with EA. The combined organic layer is washed with brine, dried over anhydrous $Na_2SO_4$. The residue is concentrated and purified by chromatography on silica gel (0-50% ethyl acetate in petroleum) to give 53-4.

Step 5: To a solution of tert-butyl ((1R)-3-(4-(4-amino-6,7-dimethoxyquinazolin-2-yl)-3-(3-hydroxyphenyl)piperazin-1-yl)-1-(4-fluorophenyl)-3-oxopropyl)(ethyl)carbamate in DMF at 0° C. is added NaH (60% wt. in mineral oil) and tert-butyl 3-(2-(2-(2-bromoethoxy)ethoxy)ethoxy)propanoate, then the mixture is stirred at the room temperature overnight. On consumption of starting material (LCMS monitoring), the reaction vessel is again cooled to 0° C., water slowly added, and the reaction mixture is stirred for 15 min. The mixture is diluted with ethyl acetate and washed with water. The organic layer is dried over sodium sulfate, concentrated under reduced pressure to give a crude product, which is purified by flash chromatography to give tert-butyl 3-(2-(2-(2-(3-(1-(4-amino-6,7-dimethoxyquinazolin-2-yl)-4-((R)-3-((tert-butoxycarbonyl)(ethyl)amino)-3-(4-fluorophenyl)propanoyl)piperazin-2-yl)phenoxy)ethoxy)ethoxy)ethoxy)propanoate.

Step 6: To a solution of tert-butyl 3-(2-(2-(2-(3-(1-(4-amino-6,7-dimethoxyquinazolin-2-yl)-4-((R)-3-((tert-butoxycarbonyl)(ethyl)amino)-3-(4-fluorophenyl)propanoyl)

piperazin-2-yl)phenoxy)ethoxy)ethoxy)ethoxy)propanoate in THF at room temperature is added LiOH (5 M in water) and stirred overnight. On consumption of starting material, the mixture is diluted with ethyl acetate and washed with water. The organic layer is dried over sodium sulfate, concentrated under reduced pressure to give a crude product, which is purified by flash chromatography to give 3-(2-(2-(2-(3-(1-(4-amino-6,7-dimethoxyquinazolin-2-yl)-4-((R)-3-((tert-butoxycarbonyl)(ethyl)amino)-3-(4-fluorophenyl)propanoyl)piperazin-2-yl)phenoxy)ethoxy)ethoxy)ethoxy)propanoic acid.

Step 7: To a solution of 3-(2-(2-(2-(3-(1-(4-amino-6,7-dimethoxyquinazolin-2-yl)-4-((R)-3-((tert-butoxycarbonyl)(ethyl)amino)-3-(4-fluorophenyl)propanoyl)piperazin-2-yl)phenoxy)ethoxy)ethoxy)ethoxy)propanoic acid (1 equiv.) in DMF is added HATU (1.5 equiv.), DIPEA (3 equiv.) and 53-4 (1 equiv.) at 0° C. The mixture is stirred at rt for 2 h. The mixture is quenched with $H_2O$, extracted with DCM and washed with brine. The organic phase is dried and concentrated. The residual is purified by flash column to give tert-butyl ((1R)-3-(4-(4-amino-6,7-dimethoxyquinazolin-2-yl)-3-(3-((1-((3aR,4R,7R,7aR)-2,2-dimethyl-7-(2-oxooxazolidin-3-yl)tetrahydro-4H-[1,3]dioxolo[4,5-c]pyran-4-yl)-16,16-bis(15-((3aR,4R,7R,7aR)-2,2-dimethyl-7-(2-oxooxazolidin-3-yl)tetrahydro-4H-[1,3]dioxolo[4,5-c]pyran-4-yl)-2,5,8,11,14-pentaoxapentadecyl)-18-oxo-2,5,8,11,14,21,24,27-octaoxa-17-azanonacosan-29-yl)oxy)phenyl)piperazin-1-yl)-1-(4-fluorophenyl)-3-oxopropyl)(ethyl)carbamate.

Step 8: To a solution of tert-butyl ((1R)-3-(4-(4-amino-6,7-dimethoxyquinazolin-2-yl)-3-(3-((1-((3aR,4R,7R,7aR)-2,2-dimethyl-7-(2-oxooxazolidin-3-yl)tetrahydro-4H-[1,3]dioxolo[4,5-c]pyran-4-yl)-16,16-bis(15-((3aR,4R,7R,7aR)-2,2-dimethyl-7-(2-oxooxazolidin-3-yl)tetrahydro-4H-[1,3]dioxolo[4,5-c]pyran-4-yl)-2,5,8,11,14-pentaoxapentadecyl)-18-oxo-2,5,8,11,14,21,24,27-octaoxa-17-azanonacosan-29-yl)oxy)phenyl)piperazin-1-yl)-1-(4-fluorophenyl)-3-oxopropyl)(ethyl)carbamate in THF is added HCl (2N in $H_2O$) at 0° C. The mixture is stirred at rt for 2 h. The mixture is concentrated and purified by prep-HPLC (Method A) to give 3-(2-(2-(2-(3-(1-(4-amino-6,7-dimethoxyquinazolin-2-yl)-4-((R)-3-(ethylamino)-3-(4-fluorophenyl)propanoyl)piperazin-2-yl)phenoxy)ethoxy)ethoxy)ethoxy)-N-(1,31-bis((2R,3R,4R,5R)-3,4-dihydroxy-5-(2-oxooxazolidin-3-yl)tetrahydro-2H-pyran-2-yl)-16-(15-((2R,3R,4R,5R)-3,4-dihydroxy-5-(2-oxooxazolidin-3-yl)tetrahydro-2H-pyran-2-yl)-2,5,8,11,14-pentaoxapentadecyl)-2,5,8,11,14,18,21,24,27,30-decaoxahentriacontan-16-yl)propanamide (Compound 53).

Preparation of Compound 54: (2S,4R)-1-(2-(3-acetyl-5-(2-((2-((2-((2-((((2R,3R,4R,5R)-3,4-dihydroxy-5-(1-methyl-1H-pyrazol-4-yl)tetrahydro-2H-pyran-2-yl)methyl)amino)-2-oxoethyl)amino)-2-oxoethyl)amino)-2-oxoethyl)amino)pyrimidin-5-yl)-1H-indazol-1-yl)acetyl)-N-(6-bromopyridin-2-yl)-4-fluoropyrrolidine-2-carboxamide

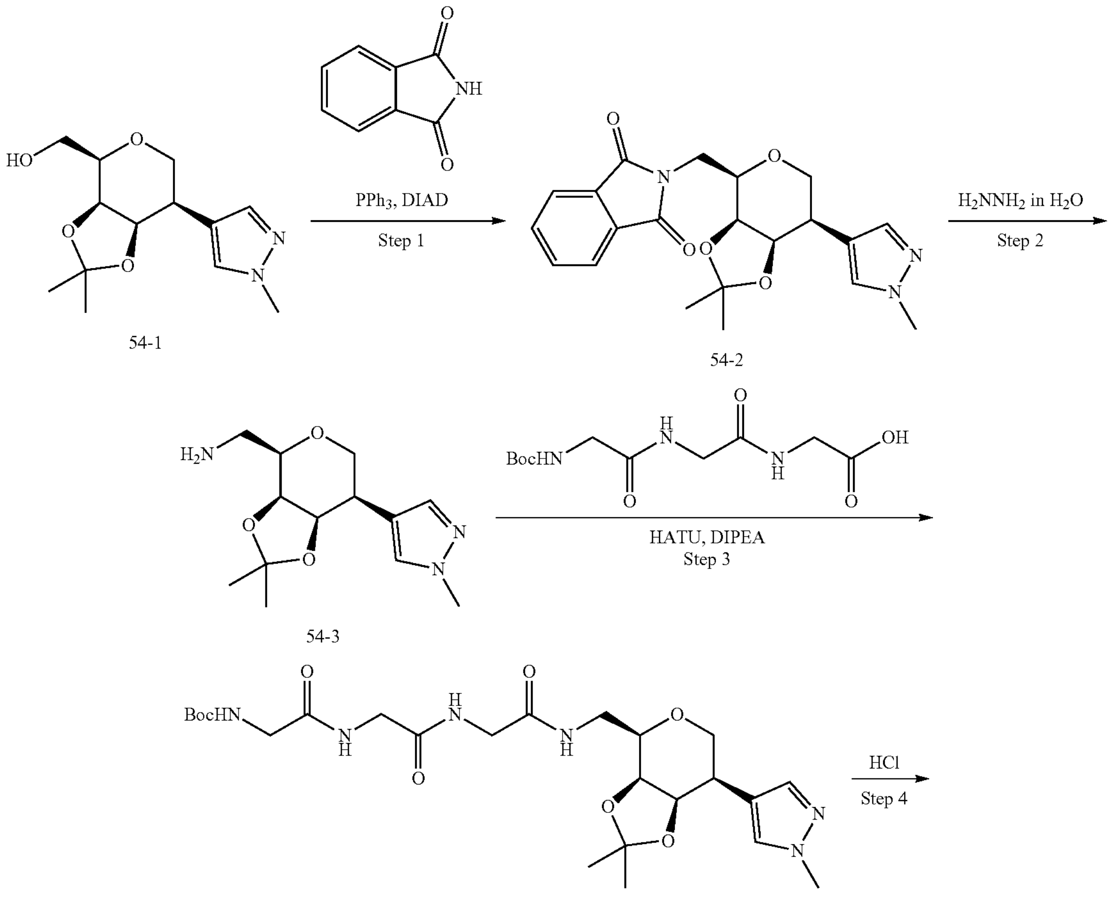

54-1

54-2

54-3

54-4

-continued

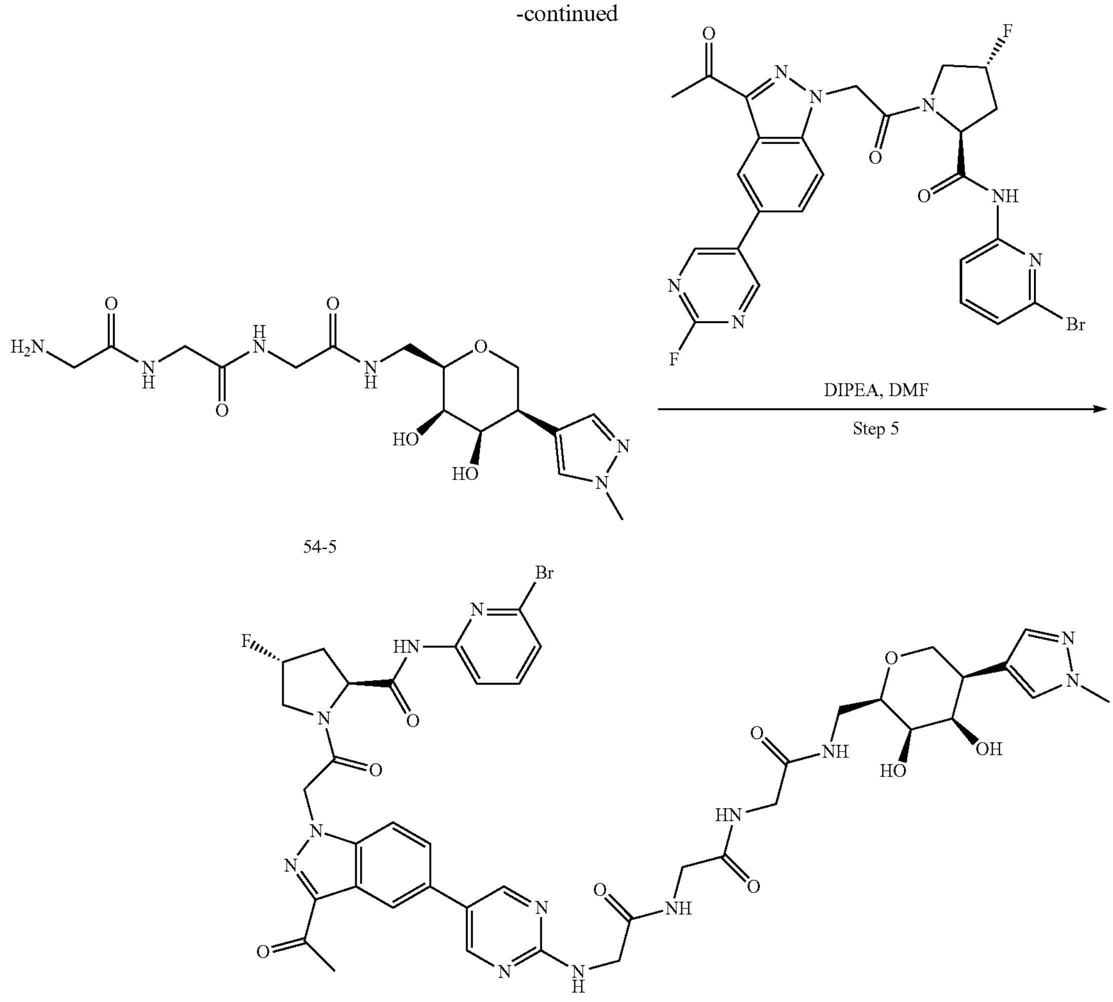

54-5

Compound 54

Step 1: To a solution ((3aR,4R,7R,7aR)-2,2-dimethyl-7-(1-methyl-1H-pyrazol-4-yl)tetrahydro-4H-[1,3]dioxolo[4,5-c]pyran-4-yl)methanol (1.0 equiv.), $PPh_3$ (1.5 equiv.) and phthalimide (1.0 eq) in dry DCM is added DIAD (1.2 eq) dropwise at ice-bath under $N_2$ atmosphere. Then the reaction is allowed to warm to rt. The resulting reaction mixture is stirred at the same temperature until starting material is consumed. The mixture is evaporated. The crude product is further purified by silica gel column chromatography to give 2-(((3aR,4R,7R,7aR)-2,2-dimethyl-7-(1-methyl-1H-pyrazol-4-yl)tetrahydro-4H-[1,3]dioxolo[4,5-c]pyran-4-yl)methyl)isoindoline-1,3-dione.

Step 2: To a solution of 2-(((3aR,4R,7R,7aR)-2,2-dimethyl-7-(1-methyl-1H-pyrazol-4-yl)tetrahydro-4H-[1,3]dioxolo[4,5-c]pyran-4-yl)methyl)isoindoline-1,3-dione in DMF is added hydrazine (35% wt. in $H_2O$) and stirred with heating as necessary overnight. On consumption of starting material (LCMS monitoring), the reaction vessel is again cooled to room temperature. The mixture is diluted with ethyl acetate and washed with water. The organic layer is dried over sodium sulfate, concentrated under reduced pressure to give a crude product, which is purified by flash chromatography to give ((3aR,4R,7R,7aR)-2,2-dimethyl-7-(1-methyl-1H-pyrazol-4-yl)tetrahydro-4H-[1,3]dioxolo[4,5-c]pyran-4-yl)methanamine.

Step 3: To a solution of ((3aR,4R,7R,7aR)-2,2-dimethyl-7-(1-methyl-1H-pyrazol-4-yl)tetrahydro-4H-[1,3]dioxolo[4,5-c]pyran-4-yl)methanamine (1 equiv.) in DMF is added HATU (1.5 equiv.), DIPEA (3 equiv.) and (tert-butoxycarbonyl)glycylglycylglycine (1 equiv.) at 0° C. The mixture is stirred at rt for 2 h. The mixture is quenched with $H_2O$, extracted with DCM and washed with brine. The organic phase is dried and concentrated. The residual is purified by flash column to give tert-butyl (2-((2-((2-((((3aR,4R,7R,7aR)-2,2-dimethyl-7-(1-methyl-1H-pyrazol-4-yl)tetrahydro-4H-[1,3]dioxolo[4,5-c]pyran-4-yl)methyl)amino)-2-oxoethyl)amino)-2-oxoethyl)amino)-2-oxoethyl)carbamate.

Step 4: To a solution of tert-butyl (2-((2-((2-((((3aR,4R,7R,7aR)-2,2-dimethyl-7-(1-methyl-1H-pyrazol-4-yl)tetrahydro-4H-[1,3]dioxolo[4,5-c]pyran-4-yl)methyl)amino)-2-oxoethyl)amino)-2-oxoethyl)amino)-2-oxoethyl)carbamate in DCM is added HCl (6 M in $H_2O$) at rt under $N_2$. After stirring for 2 h, the mixture is quenched with $NaHCO_3$(aq) and extracted with EA. The combined organic layer is washed with brine, dried over anhydrous $Na_2SO_4$. The residue is concentrated and purified by chromatography on silica gel (0-50% ethyl acetate in petroleum) to give 2-amino-N-(2-((2-((((2R,3R,4R,5R)-3,4-dihydroxy-5-(1-methyl-1H-pyrazol-4-yl)tetrahydro-2H-pyran-2-yl)methyl)amino)-2-oxoethyl)amino)-2-oxoethyl)acetamide.

Step 5: To a solution of 2-amino-N-(2-((2-((((2R,3R,4R,5R)-3,4-dihydroxy-5-(1-methyl-1H-pyrazol-4-yl)tetrahydro-2H-pyran-2-yl)methyl)amino)-2-oxoethyl)amino)-2-oxoethyl)acetamide in DMF is added DIPEA and (2S,4R)-1-(2-(3-acetyl-5-(2-fluoropyrimidin-5-yl)-1H-indazol-1-yl)acetyl)-N-(6-bromopyridin-2-yl)-4-fluoropyrrolidine-2-carboxamide, then the mixture is stirred at reflux overnight. On consumption of starting material (LCMS monitoring), the reaction vessel is again cooled to room temperature. The mixture is diluted with ethyl acetate and washed with water. The organic layer is dried over sodium sulfate, concentrated under reduced pressure to give a crude product, which is purified by flash chromatography to give (2S,4R)-1-(2-(3-acetyl-5-(2-((2-((2-((2-((((2R,3R,4R,5R)-3,4-dihydroxy-5-(1-methyl-1H-pyrazol-4-yl)tetrahydro-2H-pyran-2-yl)methyl)amino)-2-oxoethyl)amino)-2-oxoethyl)amino)-2-oxoethyl)amino)pyrimidin-5-yl)-1H-indazol-1-yl)acetyl)-N-(6-bromopyridin-2-yl)-4-fluoropyrrolidine-2-carboxamide (Compound 54).

Preparation of Compound 55: 2-(2-(2-((2R,3S)-2-(4-(cyclopentylamino)phenyl)-1-(2-fluoro-6-methylbenzoyl)piperidine-3-carboxamido)-3-hydroxypropanamido)-3-(1H-indol-3-yl)propanamido)-N1-(1-((((2R,3R,4R,5R)-3,4-dihydroxy-5-(1-methyl-1H-pyrazol-4-yl)tetrahydro-2H-pyran-2-yl)methyl)amino)-4-(methylthio)-1-oxobutan-2-yl)succinamide

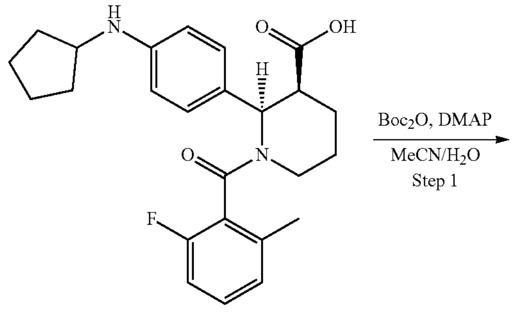

55-1

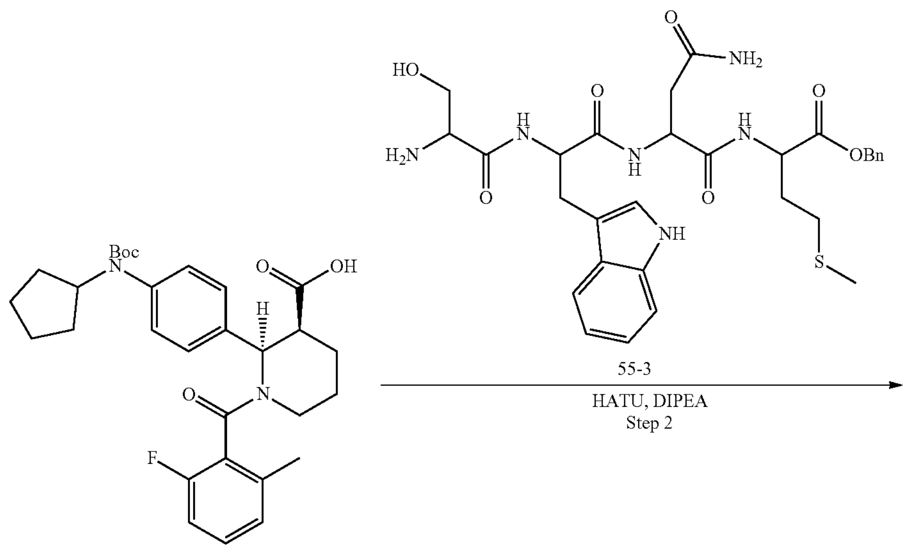

55-3

55-2

-continued
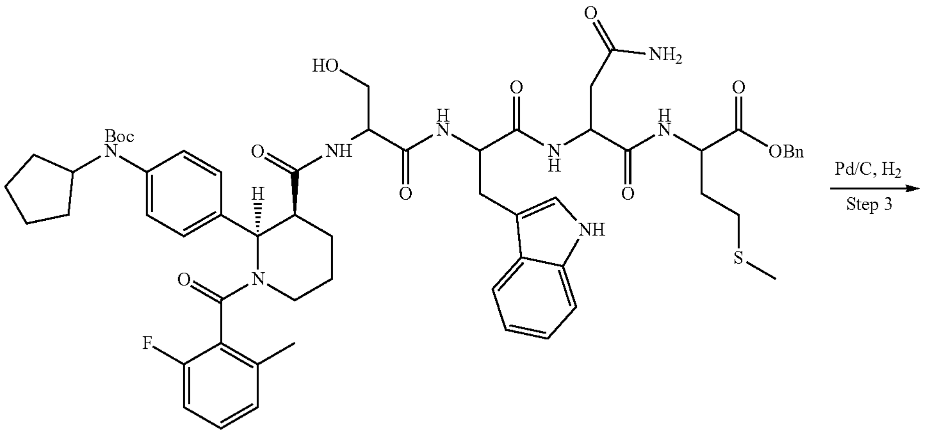
55-4
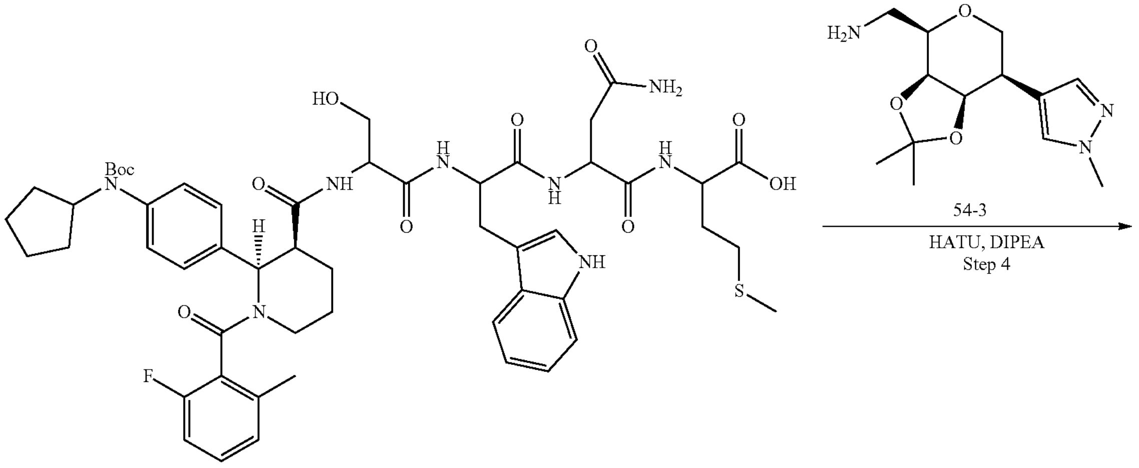
55-5
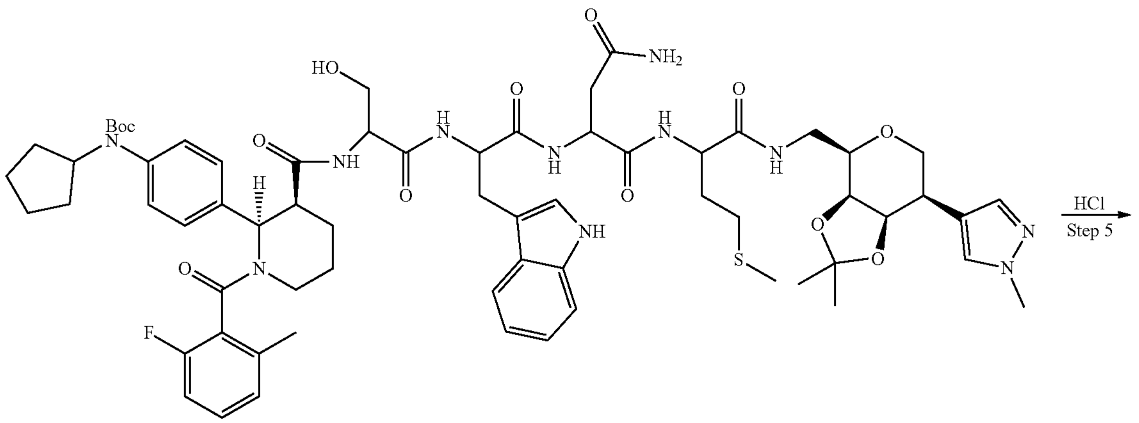
55-6

-continued

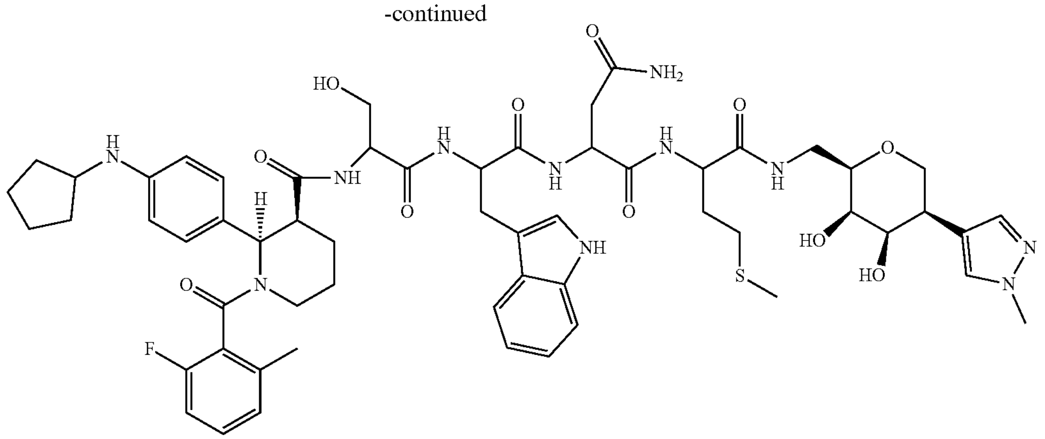

Compound 55

Step 1: To a solution of (2R,3S)-2-(4-(cyclopentylamino)phenyl)-1-(2-fluoro-6-methylbenzoyl)piperidine-3-carboxylic acid in EtOH is added DMAP and di-tert-butyl dicarbonate at 0° C. in portions. The mixture is vigorously stirred and allowed to warm up to room temperature slowly overnight (16 h). The solvents are evaporated under vacuum and the residue is purified by column chromatography ($SiO_2$, solvent gradient: DCM to 1:9 MeOH/DCM) to give (2R,3S)-2-(4-((tert-butoxycarbonyl)(cyclopentyl)amino)phenyl)-1-(2-fluoro-6-methylbenzoyl)piperidine-3-carboxylic acid.

Step 2: To a solution of benzyl seryltryptophylasparaginylmethioninate (1 equiv.) in DMF is added HATU (1.5 equiv.), DIPEA (3 equiv.) and (2R,3S)-2-(4-((tert-butoxycarbonyl)(cyclopentyl)amino)phenyl)-1-(2-fluoro-6-methylbenzoyl)piperidine-3-carboxylic acid (1 equiv.) at 0° C. The mixture is stirred at rt for 2 h. The mixture is quenched with $H_2O$, extracted with DCM and washed with brine. The organic phase is dried and concentrated. The residual is purified by flash column to give benzyl ((2R,3S)-2-(4-((tert-butoxycarbonyl)(cyclopentyl)amino)phenyl)-1-(2-fluoro-6-methylbenzoyl)piperidine-3-carbonyl)seryltryptophylasparaginylmethioninate.

Step 3: To a solution of benzyl ((2R,3S)-2-(4-((tert-butoxycarbonyl)(cyclopentyl)amino)phenyl)-1-(2-fluoro-6-methylbenzoyl)piperidine-3-carbonyl)seryltryptophylasparaginylmethioninate in MeOH is added Pd/C at rt under a $H_2$ balloon. The reaction is stirred at rt for 1.5 h. The resulting mixture is filtered and concentrated in vacuo. The crude product ((2R,3S)-2-(4-((tert-butoxycarbonyl)(cyclopentyl)amino)phenyl)-1-(2-fluoro-6-methylbenzoyl)piperidine-3-carbonyl)seryltryptophylasparaginylmethionine is used to next step with no further purification.

Step 4: To a solution of ((3aR,4R,7R,7aR)-2,2-dimethyl-7-(1-methyl-1H-pyrazol-4-yl)tetrahydro-4H-[1,3]dioxolo[4,5-c]pyran-4-yl)methanamine (1 equiv.) in DMF is added HATU (1.5 equiv.), DIPEA (3 equiv.) and (((2R,3S)-2-(4-((tert-butoxycarbonyl)(cyclopentyl)amino)phenyl)-1-(2-fluoro-6-methylbenzoyl)piperidine-3-carbonyl)seryltryptophylasparaginylmethionine (1 equiv.) at 0° C. The mixture is stirred at rt for 2 h. The mixture is quenched with $H_2O$, extracted with DCM and washed with brine. The organic phase is dried and concentrated. The residual is purified by flash column to give tert-butyl (4-((2R,3S)-3-((11-((1H-indol-3-yl)methyl)-8-(2-amino-2-oxoethyl)-5-((((3aR,4R,7R,7aR)-2,2-dimethyl-7-(1-methyl-1H-pyrazol-4-yl)tetrahydro-4H-[1,3]dioxolo[4,5-c]pyran-4-yl)methyl)carbamoyl)-15-hydroxy-7,10,13-trioxo-2-thia-6,9,12-triazapentadecane-14-yl)carbamoyl)-1-(2-fluoro-6-methylbenzoyl)piperidin-2-yl)phenyl)(cyclopentyl)carbamate.

Step 8: To a solution of tert-butyl (4-((2R,3S)-3-((11-((1H-indol-3-yl)methyl)-8-(2-amino-2-oxoethyl)-5-((((3aR,4R,7R,7aR)-2,2-dimethyl-7-(1-methyl-1H-pyrazol-4-yl)tetrahydro-4H-[1,3]dioxolo[4,5-c]pyran-4-yl)methyl)carbamoyl)-15-hydroxy-7,10,13-trioxo-2-thia-6,9,12-triazapentadecan-14-yl)carbamoyl)-1-(2-fluoro-6-methylbenzoyl)piperidin-2-yl)phenyl)(cyclopentyl)carbamate in THF is added HCl (2N in $H_2O$) at 0° C. The mixture is stirred at rt for 2 h. The mixture is concentrated and purified by prep-HPLC (Method A) to give 2-(2-(2-((2R,3S)-2-(4-(cyclopentylamino)phenyl)-1-(2-fluoro-6-methylbenzoyl)piperidine-3-carboxamido)-3-hydroxypropanamido)-3-(1H-indol-3-yl)propanamido)-N1-(1-((((2R,3R,4R,5R)-3,4-dihydroxy-5-(1-methyl-1H-pyrazol-4-yl)tetrahydro-2H-pyran-2-yl)methyl)amino)-4-(methylthio)-1-oxobutan-2-yl)succinamide (Compound 55).

Preparation of Compound 56: N-(11-(((2R,3R,4R,5S)-5-((4-chloro-3-(trifluoromethyl)pyridin-2-yl)amino)-3,4-dihydroxytetrahydro-2H-pyran-2-yl)methoxy)undecyl)-3-((2-((3-((2-(((2R,3R,4R,5S)-5-((4-chloro-3-(trifluoromethyl)pyridin-2-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propanamide

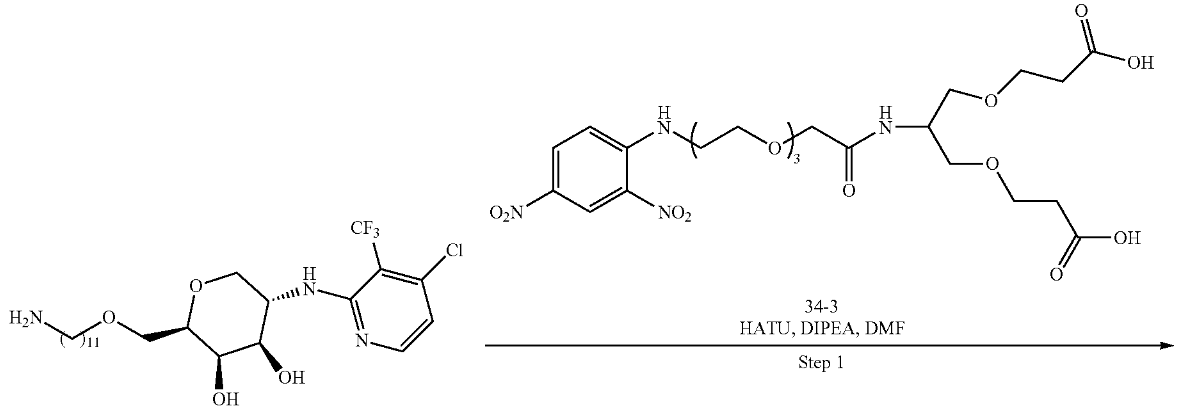

56-1

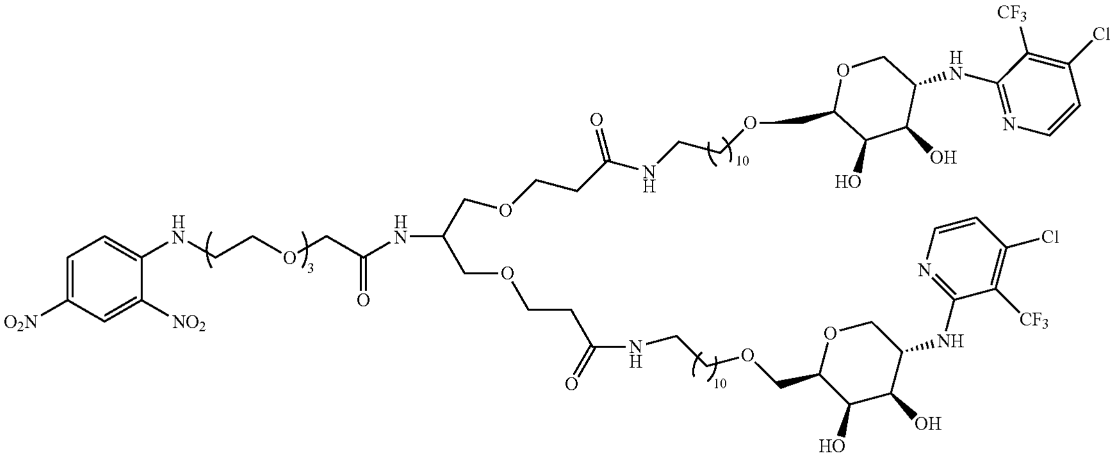

Compound 56

Step 1: To a solution of 13-((2-carboxyethoxy)methyl)-1-((2,4-dinitrophenyl)amino)-11-oxo-3,6,9,15-tetraoxa-12-azaoctadecan-18-oic acid (1 equiv.) in DMF (2 mL) is added HATU (1.5 equiv.), DIPEA (3 equiv.) and (2R,3R,4R,5S)-2-(((11-aminododecyl)oxy)methyl)-5-((4-chloro-3-(trifluoromethyl)pyridin-2-yl)amino)tetrahydro-2H-pyran-3,4-diol (1 equiv.) at 0° C. The mixture is stirred at rt for 2 h. The mixture is quenched with $H_2O$, extracted with DCM and washed with brine. The organic phase is dried and concentrated. The residual is purified by flash column to give N-(11-(((2R,3R,4R,5S)-5-((4-chloro-3-(trifluoromethyl)pyridin-2-yl)amino)-3,4-dihydroxytetrahydro-2H-pyran-2-yl)methoxy)undecyl)-3-((2-((3-((2-(((2R,3R,4R,5S)-5-((4-chloro-3-(trifluoromethyl)pyridin-2-yl)amino)-3,4-dihydroxytetrahydro-2H-pyran-2-yl)methoxy)undecyl)amino)-3-oxopropoxy)methyl)-14-((2,4-dinitrophenyl)amino)-4-oxo-6,9,12-trioxa-3-azatetradecyl)oxy)propanamide (Compound 56).

Example 9. Non-Limiting Exemplary Compounds of the Present Invention
TABLE 1
| Degraders | |
|---|---|
| # | Compound |
| 1 | 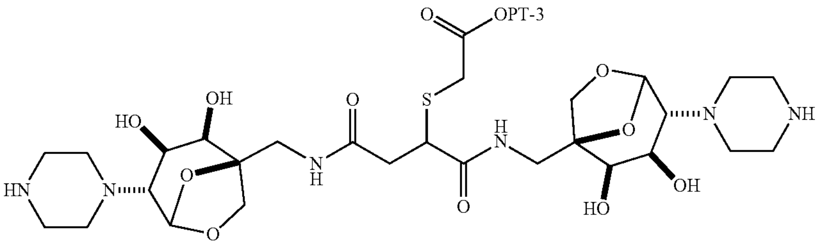 |
| 2 | 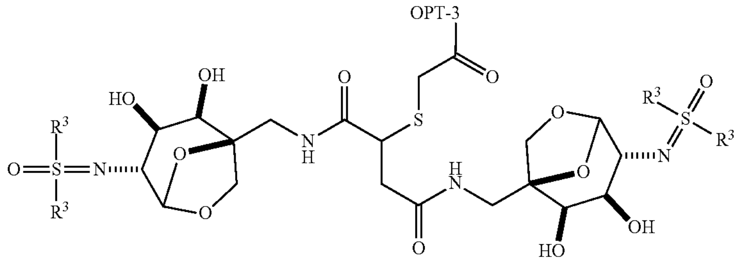 |
| 3 | 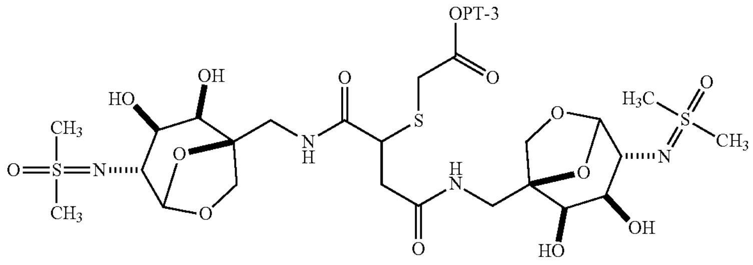 |
| 4 | 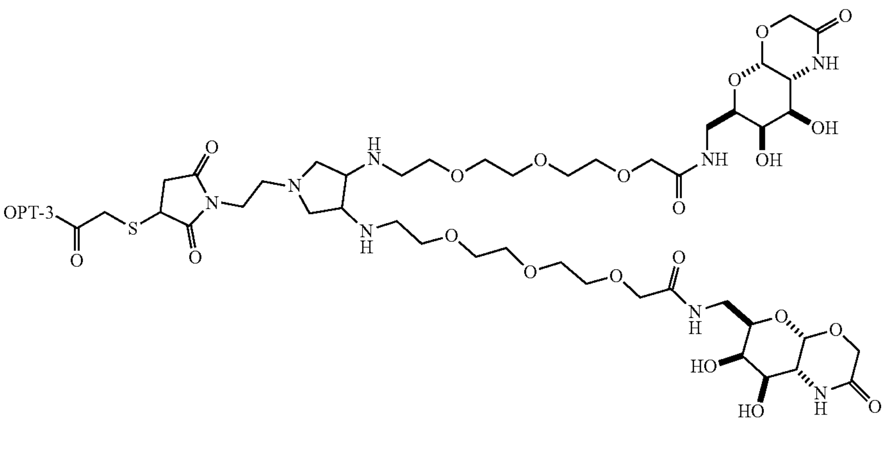 |

TABLE 1-continued
| Degraders | |
|---|---|
| # | Compound |
| 5 | 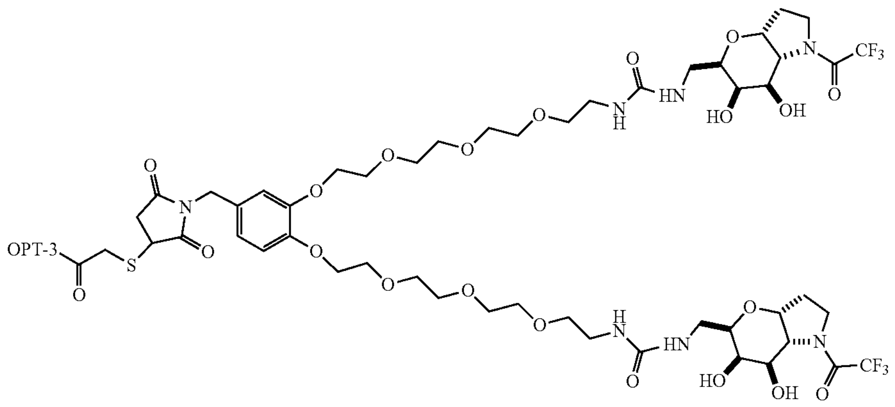 |
| 6 | 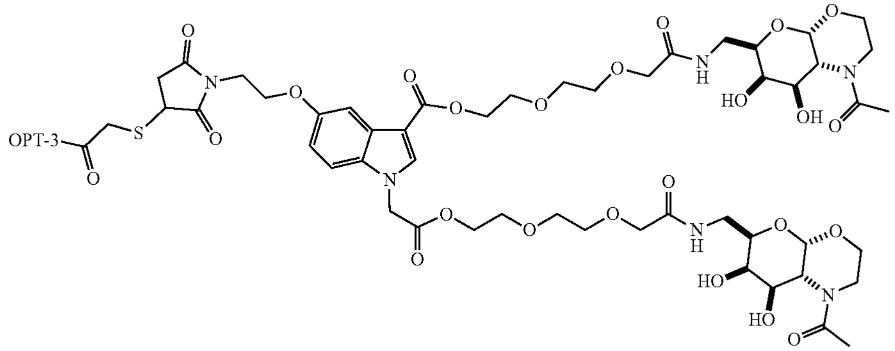 |
| 7 | 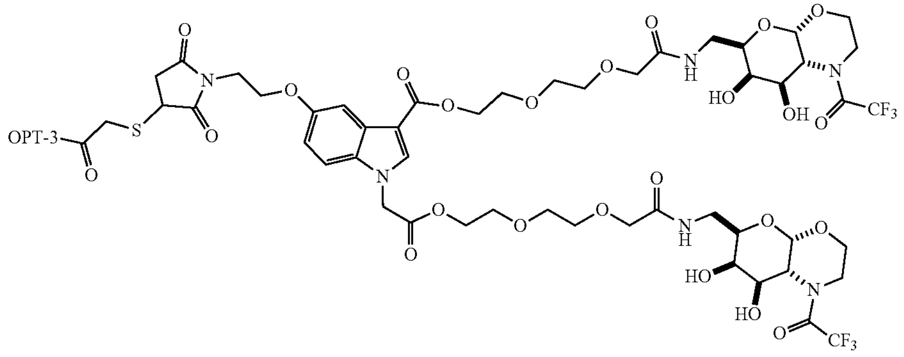 |
| 8 | 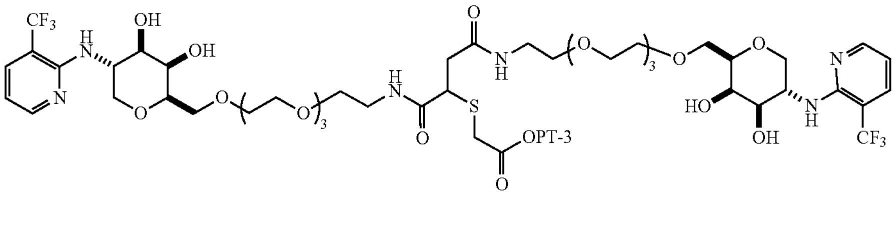 |

TABLE 1-continued
| Degraders | |
|---|---|
| # | Compound |
| 9 | 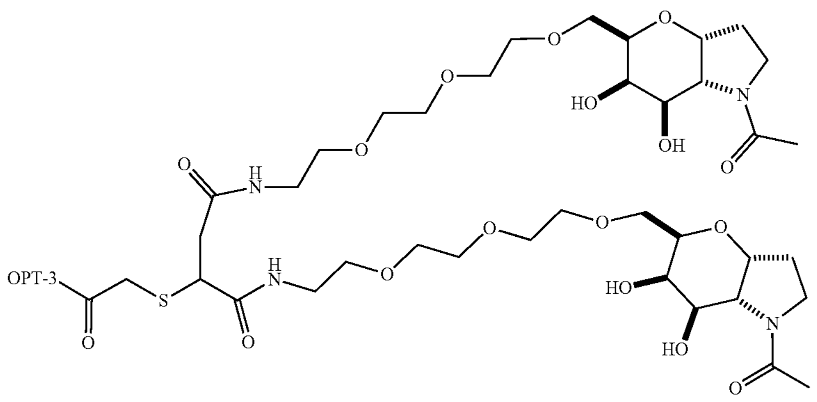 |
| 10 | 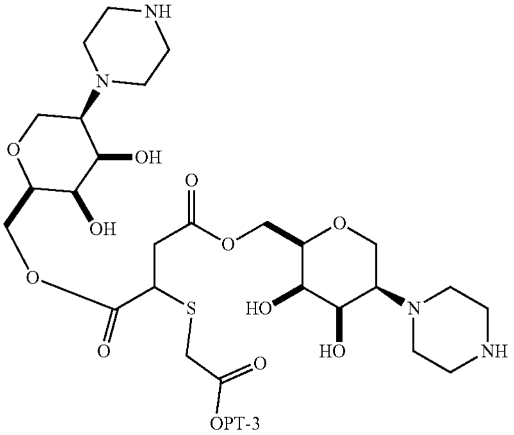 |
| 11 | 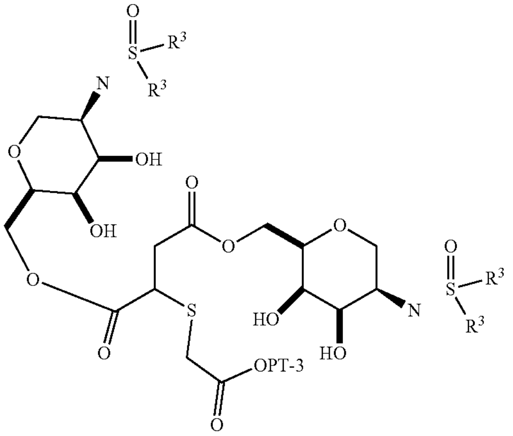 |

TABLE 1-continued
| Degraders | |
|---|---|
| # | Compound |
| 12 | 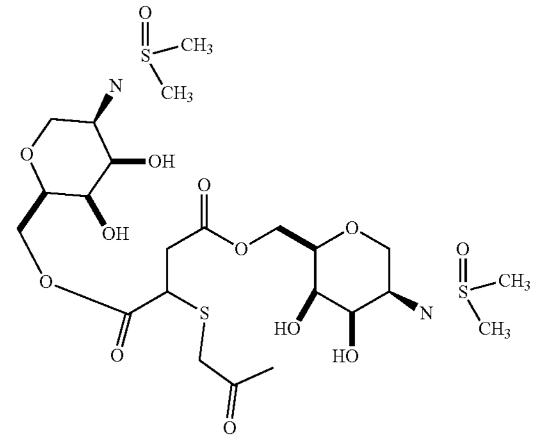 |
| 13 | 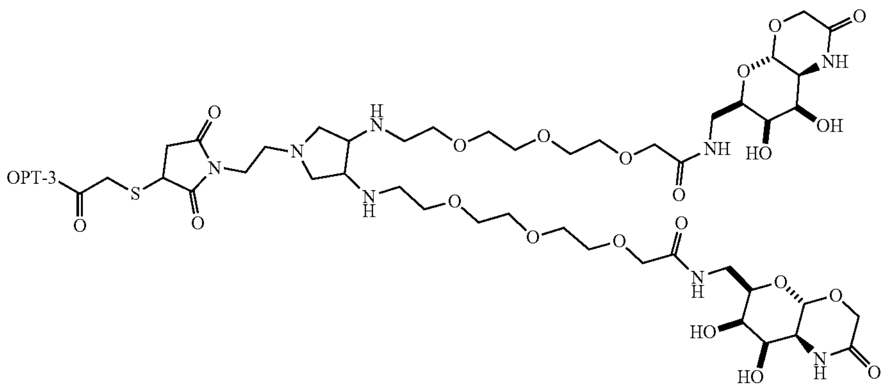 |
| 14 | 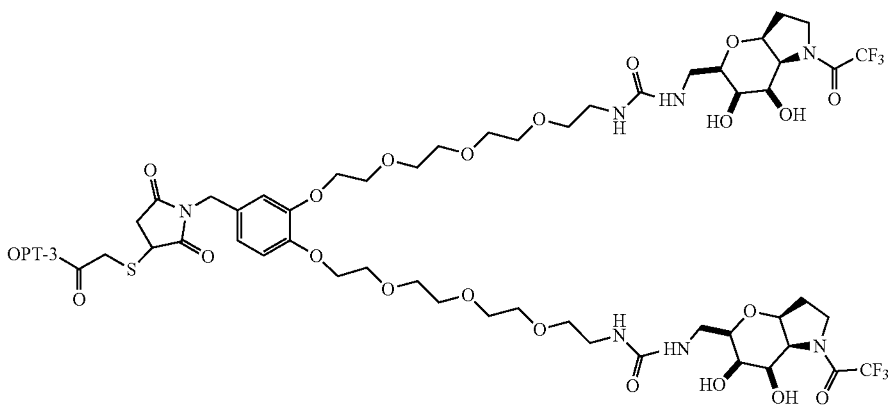 |

TABLE 1-continued
| Degraders | |
|---|---|
| # | Compound |
| 15 | 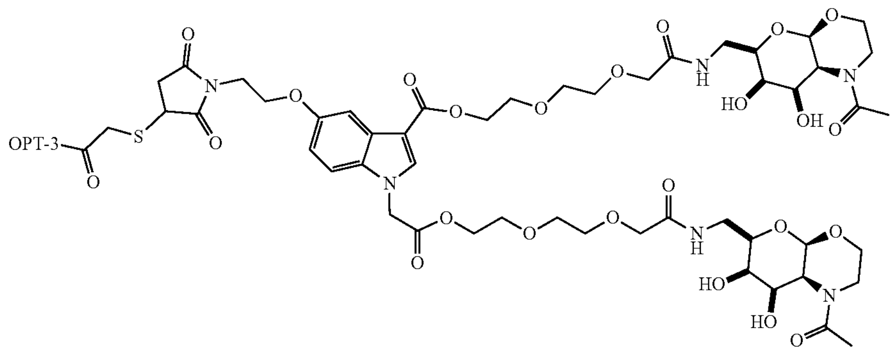 |
| 16 | 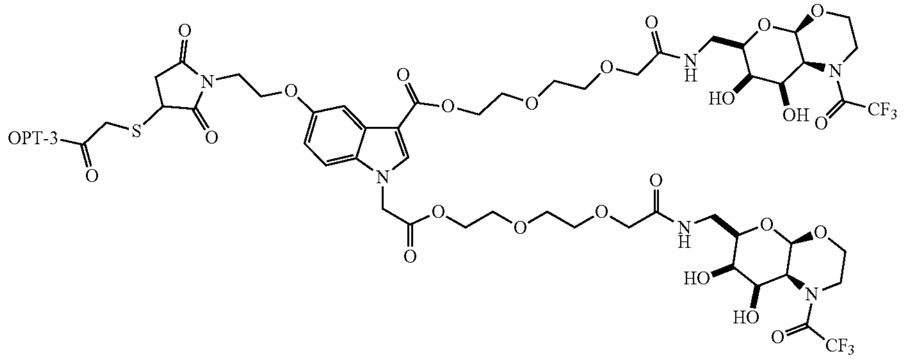 |
| 17 | 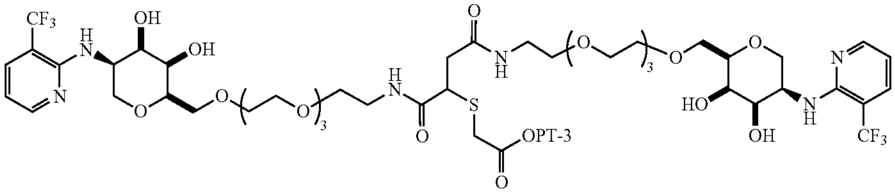 |
| 18 | 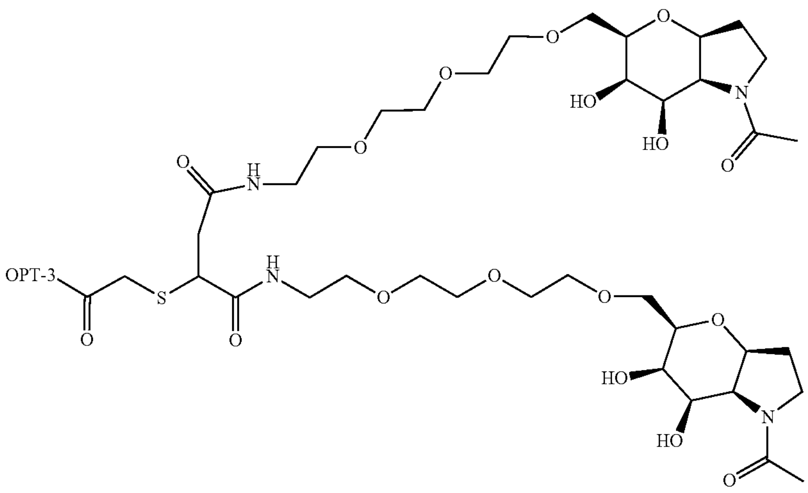 |

TABLE 2
ASGPR Ligands of the Present Invention
| Cmpd # | Structure | SPR Binding External Calculation: KD (uM) |
|---|---|---|
| A90 | 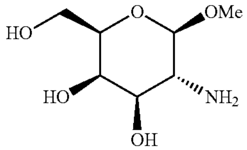 [SMILES: CO[C@@H]1O[C@H](CO)[C@H](O)[C@H](O)[C@H]1N] | +++ |
| A92 | 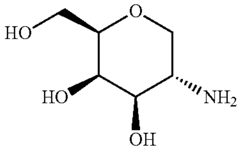 [SMILES: N[C@H]1CO[C@H](CO)[C@H](O)[C@@H]1O] | + |
| A95 | 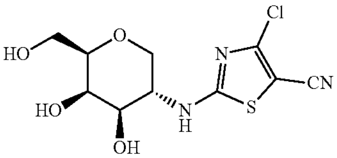 [SMILES: N#Cc1sc(N[C@H]2CO[C@H](CO)[C@H](O)[C@@H]2O)nc1Cl] | ++++ |
| A96 | 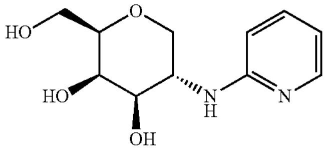 [SMILES: OC[C@H]1OC[C@H](Nc2ccccn2)[C@@H](O)[C@H]1O] | |
| A97 | 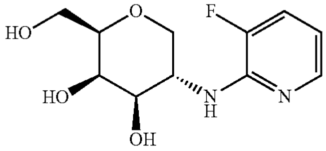 [SMILES: OC[C@H]1OC[C@H](Nc2ncccc2F)[C@@H](O)[C@H]1O] | |
| A98 | 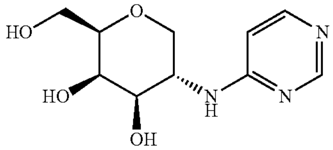 [SMILES: OC[C@H]1OC[C@H](Nc2ccncn2)[C@@H](O)[C@H]1O] | |
| A99 | 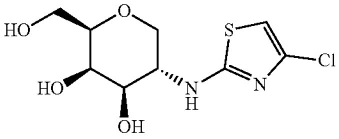 [SMILES: OC[C@H]1OC[C@H](Nc2nc(Cl)cs2)[C@@H](O)[C@H]1O] | + |
| A100 | 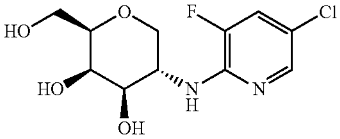 [SMILES: OC[C@H]1OC[C@H](Nc2ncc(Cl)cc2F)[C@@H](O)[C@H]1O] | ++++ |
| A101 | 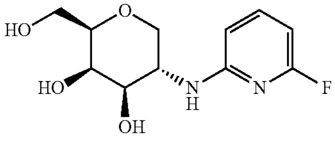 [SMILES: OC[C@H]1OC[C@H](Nc2cccc(F)n2)[C@@H](O)[C@H]1O] | |
TABLE 2-continued
ASGPR Ligands of the Present Invention
| Cmpd # | Structure | SPR Binding External Calculation: KD (uM) |
|---|---|---|
| A102 | 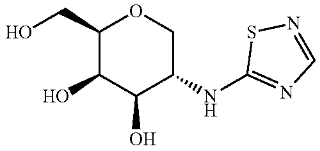 [SMILES: OC[C@H]1OC[C@H](Nc2ncns2)[C@@H](O)[C@H]1O] | |
| A103 | 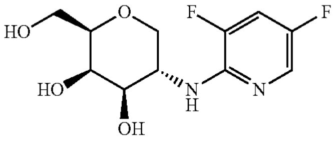 [SMILES: OC[C@H]1OC[C@H](Nc2ncc(F)cc2F)[C@@H](O)[C@H]1O] | +++ |
| A104 | 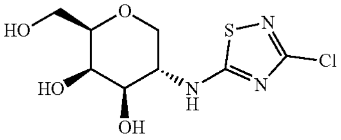 [SMILES: OC[C@H]1OC[C@H](Nc2nc(Cl)ns2)[C@@H](O)[C@H]1O] | |
| A105 | 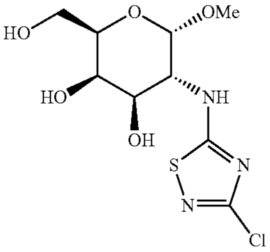 [SMILES: CO[C@H]1O[C@H](CO)[C@H](O)[C@H](O)[C@H]1Nc1nc(Cl)ns1] | ++++ |
| A106 | 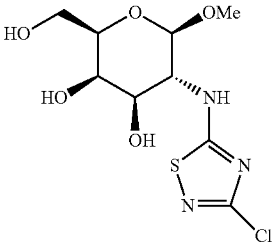 [SMILES: CO[C@@H]1O[C@H](CO)[C@H](O)[C@H](O)[C@H]1Nc1nc(Cl)ns1] | ++++ |
| A107 | 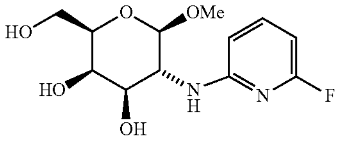 [SMILES: CO[C@@H]1O[C@H](CO)[C@H](O)[C@H](O)[C@H]1Nc1cccc(F)n1] | + |
| A108 | 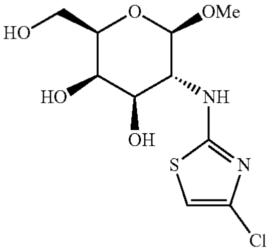 [SMILES: CO[C@@H]1O[C@H](CO)[C@H](O)[C@H](O)[C@H]1Nc1nc(Cl)cs1] | ++++ |

TABLE 2-continued
ASGPR Ligands of the Present Invention
| Cmpd # | Structure | SPR Binding External Calculation: KD (uM) |
|---|---|---|
| A109 | 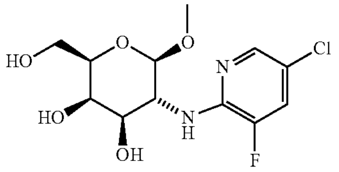 [SMILES: CO[C@@H]1O[C@H](CO)[C@H](O)[C@H](O)[C@H]1Nc1ncc(Cl)cc1F] | ++++ |
| A110 | 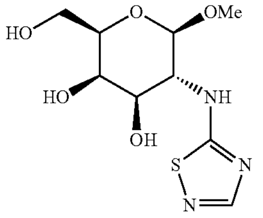 [SMILES: CO[C@@H]1O[C@H](CO)[C@H](O)[C@H](O)[C@H]1Nc1ncns1] | ++++ |
| A111 | 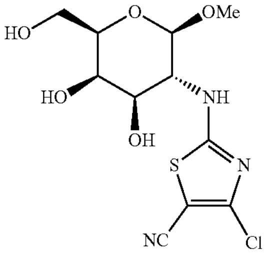 [SMILES: CO[C@@H]1O[C@H](CO)[C@H](O)[C@H](O)[C@H]1Nc1nc(Cl)c(C#N)s1] | |
| A112 | 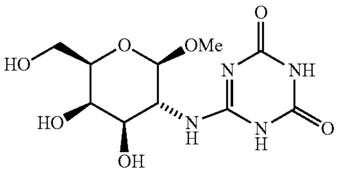 [SMILES: CO[C@@H]1O[C@H](CO)[C@H](O)[C@H](O)[C@H]1Nc1nc(=O)[nH]c(=O)[nH]1] | ++++ |
| A113 | 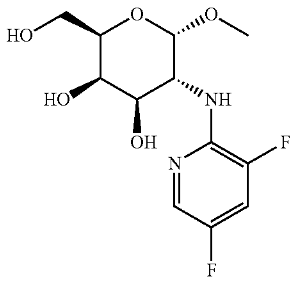 [SMILES: CO[C@H]1O[C@H](CO)[C@H](O)[C@H](O)[C@H]1Nc1ncc(F)cc1F] | ++++ |
| A114 | 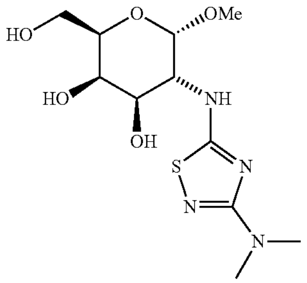 [SMILES: CO[C@H]1O[C@H](CO)[C@H](O)[C@H](O)[C@H]1Nc1nc(N(C)C)ns1] | ++++ |
| A115 | 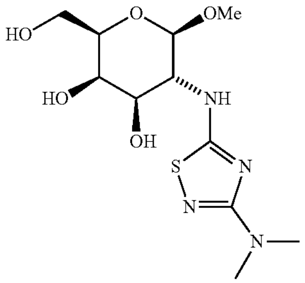 [SMILES: CO[C@@H]1O[C@H](CO)[C@H](O)[C@H](O)[C@H]1Nc1nc(N(C)C)ns1] | |
| A116 | 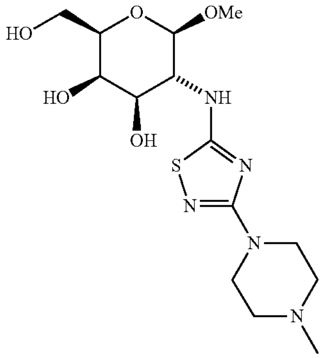 [SMILES: CO[C@@H]1O[C@H](CO)[C@H](O)[C@H](O)[C@H]1Nc1nc(N2CCN(C)CC2)ns1] | ++++ |
| A117 | 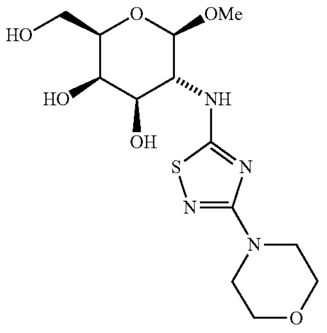 [SMILES: CO[C@@H]1O[C@H](CO)[C@H](O)[C@H](O)[C@H]1Nc1nc(N2CCOCC2)ns1] | +++ |
| A118 | 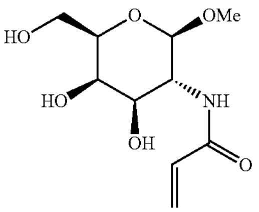 [SMILES: C=CC(=O)N[C@H]1[C@H](OC)O[C@H](CO)[C@H](O)[C@@H]1O] | ++++ |
| A119 | 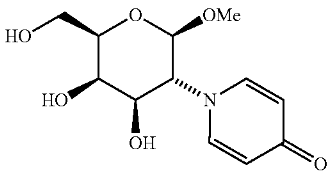 [SMILES: CO[C@@H]1O[C@H](CO)[C@H](O)[C@H](O)[C@H]1n1ccc(=O)cc1] | ++++ |

TABLE 2-continued
ASGPR Ligands of the Present Invention
| Cmpd # | Structure | SPR Binding External Calculation: KD (uM) |
|---|---|---|
| A120 | 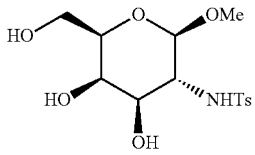 | +++ |
| A121 | 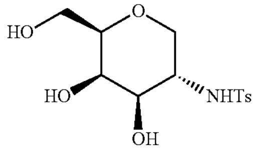 | +++ |
| A127 | 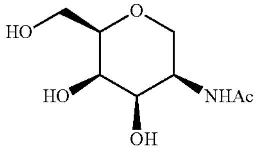 [SMILES: CC(=O)N[C@@H]1CO[C@H](CO)[C@H](O)[C@@H]1O] | ++++ |
| A128 | 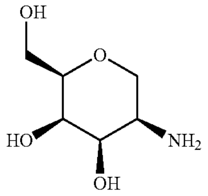 [SMILES: N[C@@H]1CO[C@H](CO)[C@H](O)[C@@H]1O] | + |
| A129 | 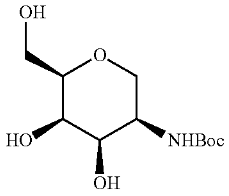 [SMILES: CC(C)(C)OC(=O)N[C@@H]1CO[C@H](CO)[C@H](O)[C@@H]1O] | |
| A134 | 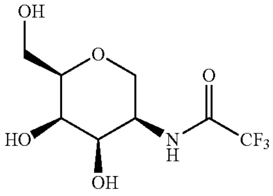 [SMILES: O=C(N[C@@H]1CO[C@H](CO)[C@H](O)[C@@H]1O)C(F)(F)F] | |
| A160 | 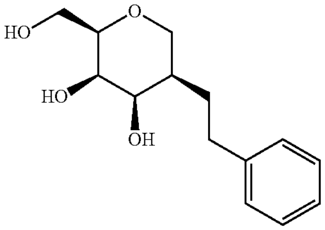 [SMILES: OC[C@H]1OC[C@@H](CCc2ccccc2)[C@@H](O)[C@H]1O] | + |
TABLE 2-continued
ASGPR Ligands of the Present Invention
| Cmpd # | Structure | SPR Binding External Calculation: KD (uM) |
|---|---|---|
| A162 | 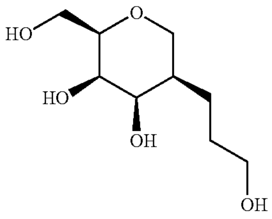 [SMILES: OCCC[C@@H]1CO[C@H](CO)[C@H](O)[C@@H]1O] | + |
| A164 | 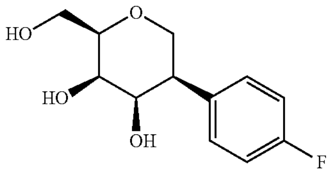 [SMILES: OC[C@H]1OC[C@@H](c2ccc(F)cc2)[C@@H](O)[C@H]1O] | ++ |
| A169 | 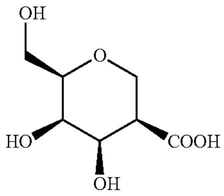 [SMILES: O=C(O)[C@@H]1CO[C@H](CO)[C@H](O)[C@@H]1O] | |
| A181 | 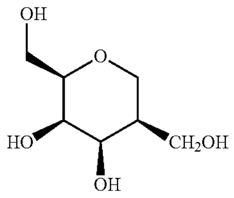 [SMILES: OC[C@@H]1CO[C@H](CO)[C@H](O)[C@@H]1O] | +++ |
| A182 | 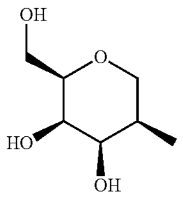 | + |
| A183 | 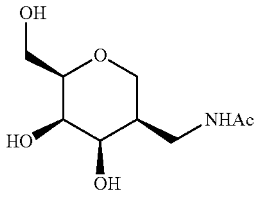 [SMILES: CC(=O)NC[C@@H]1CO[C@H](CO)[C@H](O)[C@@H]1O] | +++ |
| A184 | 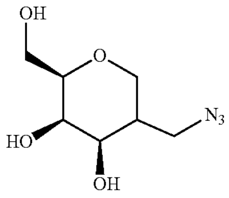 [SMILES: [N-]=[N+]=NCC1CO[C@H](CO)[C@H](O)[C@@H]1O] | ++++ |

TABLE 2-continued

ASGPR Ligands of the Present Invention

| Cmpd # | Structure | SPR Binding External Calculation: KD (uM) |
|---|---|---|
| A187 | 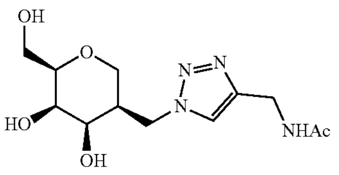 [SMILES: CC(=O)NCc1cn(C[C@@H]2CO[C@H](CO)[C@H](O)[C@@H]2O)nn1] | ++++ |
| A191 | 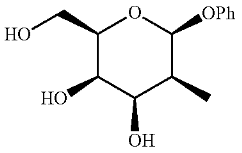 [SMILES: C[C@@H]1[C@H](Oc2ccccc2)O[C@H](CO)[C@H](O)[C@@H]1O] | + |
| A192 | 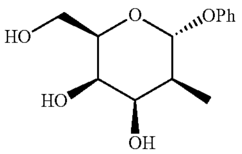 [SMILES: C[C@@H]1[C@@H](Oc2ccccc2)O[C@H](CO)[C@H](O)[C@@H]1O] | + |
| A193 | 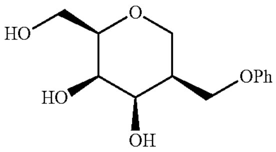 [SMILES: OC[C@H]1OC[C@@H](COc2ccccc2)[C@@H](O)[C@H]1O] | +++ |
| A196 | 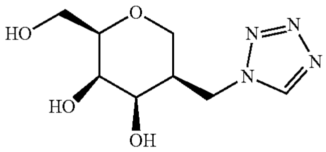 [SMILES: OC[C@H]1OC[C@@H](Cn2cnnn2)[C@@H](O)[C@H]1O] | ++++ |
| A209 | 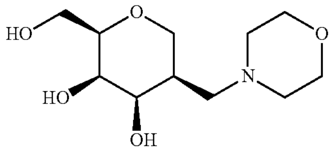 | + |
| A217 | 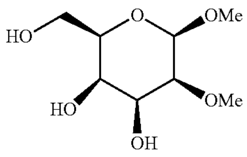 [SMILES: CO[C@@H]1O[C@H](CO)[C@H](O)[C@H](O)[C@@H]1OC] | + |
| A283 | 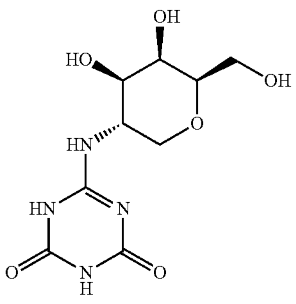 [SMILES: O=c1nc(N[C@H]2CO[C@H](CO)[C@H](O)[C@@H]2O)[nH]c(=O)[nH]1] | +++ |
| A284 | 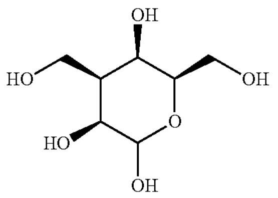 [SMILES: OC[C@H]1[C@@H](O)[C@@H](CO)OC(O)[C@H]1O] | +++ |
| A285 | 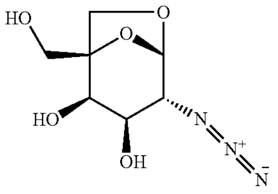 [SMILES: [N-]=[N+]=N[C@H]1[C@H]2OC[C@](CO)(O2)[C@H](O)[C@@H]1O] | ++++ |
| A286 | 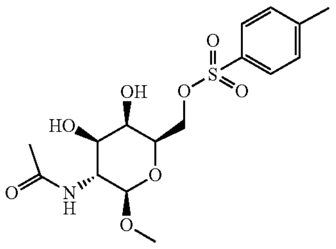 [SMILES: CO[C@@H]1O[C@H](COS(=O)(=O)c2ccc(C)cc2)[C@H](O)[C@H](O)[C@H]1NC(C)=O] | ++++ |

In the table above $K_D$ values that are >= 1000 uM = +, <1000 uM = ++, <500 uM = +++, and <100 uM = ++++

Example 10. Affinity of Compounds to ASGPR Measured Using Surface Plasmon Resonance (SPR)

The dissociation constants ($K_D$) of compounds described herein to the ASGP receptor are measured in SPR experiments using a Biacore 8K instrument (GE Healthcare) at 25° C. Recombinant ASGPR protein is first biotinylated using Maleimide-PEG2-biotin reagent (Pierce, 19-fold molar excess) in phosphate-buffered saline (PBS) solution overnight at 4° C. Excess amount of biotin in the reaction mixture is removed by Zeba desalting columns (Thermo). Biotinylation is confirmed by mass spectroscopic analysis of ASGPR. Biotinylated ASGPR is then immobilized on SA sensor chips (GE Healthcare) with an immobilization level ranging from 1500-3000 resonance units (RU). The running buffer is 50 mM Tris, pH7.5, 150 mM NaCl, 50 mM $CaCl_2$), 0.01% P20, 3% DMSO. The concentration of compounds sometimes vary from 2 mM to 50 M depending on KD values. The compounds are diluted 3 folds with total 8 concentration points. Solutions containing serially diluted compounds are injected at a flow rate of 50 μL/min for 60 sec followed by a 180 sec dissociation phase for each concentration. Data is processed using the analysis software in Biacore 8K to perform background subtraction, double referencing and solvent correction. Values of affinity expressed as the dissociation constants (KD) were determined by fitting the steady state binding responses (RUss) as a function of the concentration ([Compound]) using the following equation: RUss=RUmax/(KD+[Compound]), where RUmax is the calculated maximal response.

TABLE 3

Biological Data for Extracellular Protein Degrading Compounds

| Compound # | SPR Binding External Calculation: KD (uM) ASGPR | SPR Binding External Calculation: KD (uM) Additional Targets |
|---|---|---|
| Compound 20 | ++++ | ++++ hIgA1-FL |
| Compound 21 | ++++ | ++++ hIgA1-FL |
| Compound 22 | ++++ | ++++ hIgA1-FL |
| Compound 23 | ++++ | ++++ hIgA1-Fc |
| Compound 24 | ++++ | ++++ hIgA1-Fc |
| Compound 25 | ++++ | ++++ hIgA1-Fc |
| Compound 26 | ++++ | |
| Compound 27 | | ++++ hIgA1-Fc |

In the table above KD values that are >=1000 uM = +, <1000 uM = ++, <500 uM = +++, and <100 uM = ++++

TABLE 4

Biological Data for ASGPR Ligands

| Compound ID | Structure | ASGPR_SPR Binding $K_D$ (μM) |
|---|---|---|
| A127-2c | 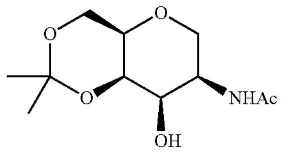 [SMILES: CC(=O)N[C@@H]1CO[C@@H]2COC(C)(C)O[C@@H]2[C@@H]1O] | >200 |
| A131 | 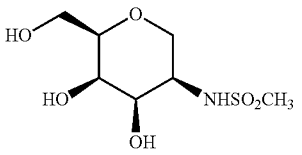 | +++ |
| A136 | 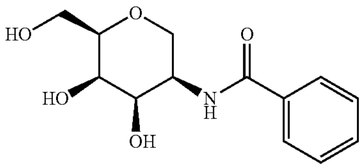 [SMILES: O=C(N[C@@H]1CO[C@H](CO)[C@H](O)[C@@H]1O)c1ccccc1] | +++ |
| A146 | 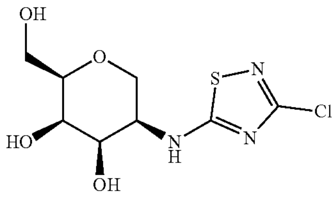 [SMILES: OC[C@H]1OC[C@@H](Nc2nc(Cl)ns2)[C@@H](O)[C@H]1O] | ++++ |
| A147 | 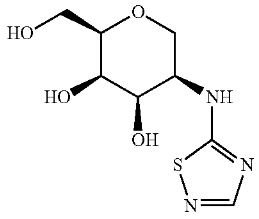 [SMILES: OC[C@H]1OC[C@@H](Nc2ncns2)[C@@H](O)[C@H]1O] | ++++ |

TABLE 4-continued

Biological Data for ASGPR Ligands

| Compound ID | Structure | ASGPR_SPR Binding $K_D$ (μM) |
|---|---|---|
| A148 | 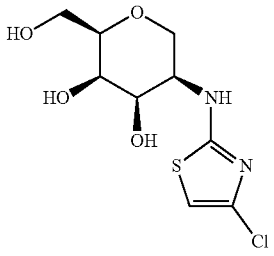 [SMILES: OC[C@H]1OC[C@@H](Nc2nc(Cl)cs2)[C@@H](O)[C@H]1O] | >20 |
| A149 | 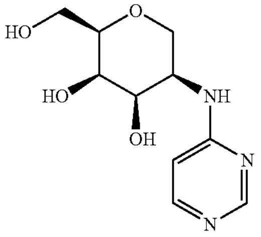 [SMILES: OC[C@H]1OC[C@@H](Nc2ccncn2)[C@@H](O)[C@H]1O] | >20 |
| A153 | 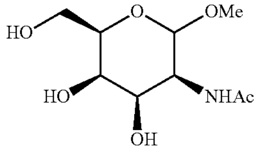 [SMILES: COC1O[C@H](CO)[C@H](O)[C@H](O)[C@@H]1NC(C)=O] | +++ |
| A157 | 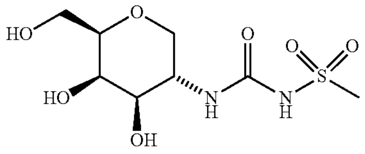 [SMILES: CS(=O)(=O)NC(=O)N[C@H]1CO[C@H](CO)[C@H](O)[C@@H]1O] | >20 |
| A163 | 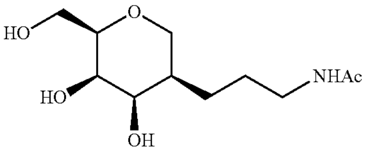 [SMILES: CC(=O)NCCC[C@@H]1CO[C@H](CO)[C@H](O)[C@@H]1O] | >200 |
| A170 | 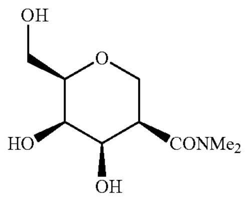 | >200 |
| A174 | 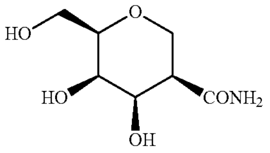 [SMILES: NC(=O)[C@@H]1CO[C@H](CO)[C@H](O)[C@@H]1O] | ++++ |

TABLE 4-continued
| Biological Data for ASGPR Ligands | | |
|---|---|---|
| Compound ID | Structure | ASGPR_SPR Binding $K_D$ (μM) |
| A180 | 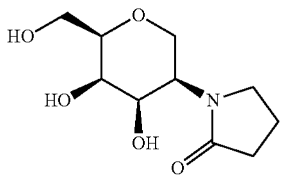 [SMILES: O=C1CCCN1[C@@H]1CO[C@H](CO)[C@H](O)[C@@H]1O] | ++++ |
| A186 | 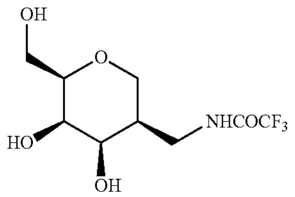 | + |
| A188 | 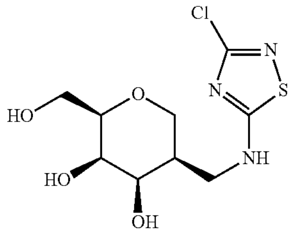 [SMILES: OC[C@H]1OC[C@@H](CNc2nc(Cl)ns2)[C@@H](O)[C@H]1O] | +++ |
| A212 | 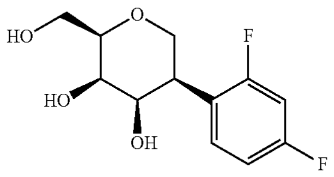 [SMILES: OC[C@H]1OC[C@@H](c2ccc(F)cc2F)[C@@H](O)[C@H]1O] | +++ |
| A213 | 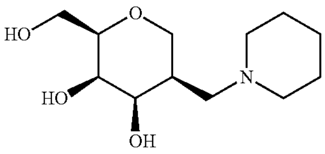 [SMILES: OC[C@H]1OC[C@@H](CN2CCCCC2)[C@@H](O)[C@H]1O] | +++ |
| A218 | 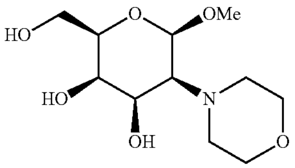 [SMILES: CO[C@@H]1O[C@H](CO)[C@H](O)[C@H](O)[C@@H]1N1CCOCC1] | + |
| A221-2 | 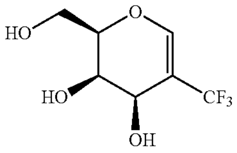 [SMILES: OC[C@H]1OC=C(C(F)(F)F)[C@@H](O)[C@H]1O] | >200 |
| A222 | 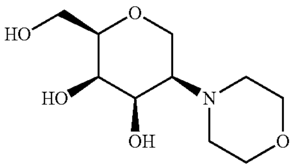 [SMILES: OC[C@H]1OC[C@@H](N2CCOCC2)[C@@H](O)[C@H]1O] | +++ |
TABLE 4-continued
| Biological Data for ASGPR Ligands | | |
|---|---|---|
| Compound ID | Structure | ASGPR_SPR Binding $K_D$ (μM) |
| A223 | 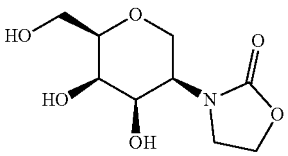 [SMILES: O=C1OCCN1[C@@H]1CO[C@H](CO)[C@H](O)[C@@H]1O] | ++++ |
| A287 | 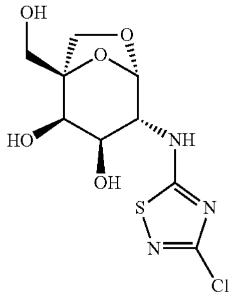 [SMILES: OC[C@@]12CO[C@@H](O1)[C@H](Nc1nc(Cl)ns1)[C@@H](O)[C@H]2O] | ++++ |
| A288 | 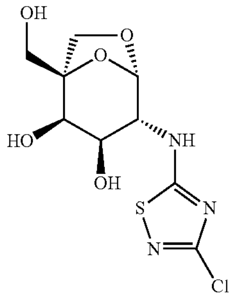 [SMILES: OC[C@@]12CO[C@@H](O1)[C@H](Nc1nc(Cl)ns1)[C@@H](O)[C@H]2O] | ++++ |
| A289 | 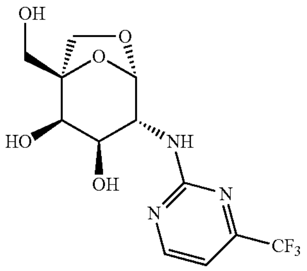 [SMILES: OC[C@@]12CO[C@@H](O1)[C@H](Nc1nccc(C(F)(F)F)n1)[C@@H](O)[C@H]2O] | ++++ |
| A290 | 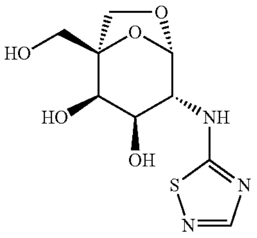 [SMILES: OC[C@@]12CO[C@@H](O1)[C@H](Nc1ncns1)[C@@H](O)[C@H]2O] | ++++ |

TABLE 4-continued
Biological Data for ASGPR Ligands
| Compound ID | Structure | ASGPR_SPR Binding $K_D$ (μM) |
|---|---|---|
| A291 | 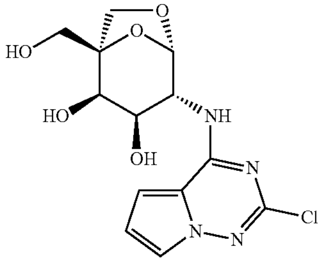 [SMILES: OC[C@@]12CO[C@@H](O1)[C@H](Nc1nc(Cl)nn3cccc13)[C@@H](O)[C@H]2O] | ++++ |
| A292 | 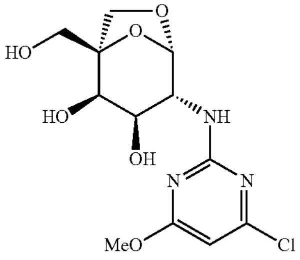 [SMILES: COc1cc(Cl)nc(N[C@H]2[C@H]3OC[C@](CO)(O3)[C@H](O)[C@@H]2O)n1] | ++++ |
| A293 | 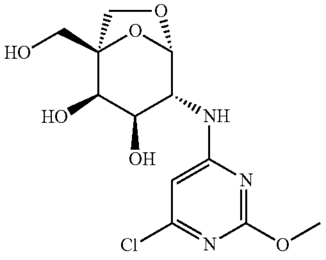 [SMILES: COc1nc(Cl)cc(N[C@H]2[C@H]3OC[C@](CO)(O3)[C@H](O)[C@@H]2O)n1] | ++++ |
| A294 | 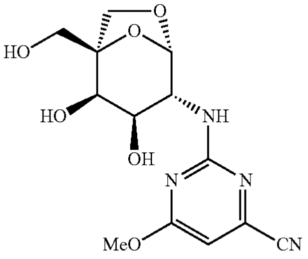 | ++++ |
| A295 | 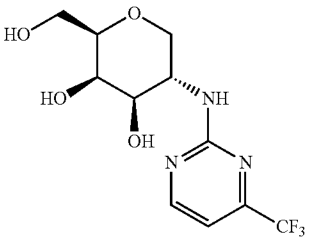 | ++++ |
TABLE 4-continued
Biological Data for ASGPR Ligands
| Compound ID | Structure | ASGPR_SPR Binding $K_D$ (μM) |
|---|---|---|
| A296 | 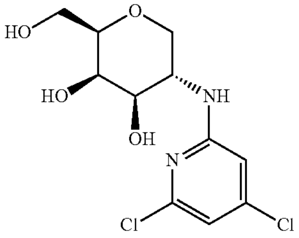 [SMILES: OC[C@H]1OC[C@H](Nc2cc(Cl)cc(Cl)n2)[C@@H](O)[C@H]1O] | ++++ |
| A298 | 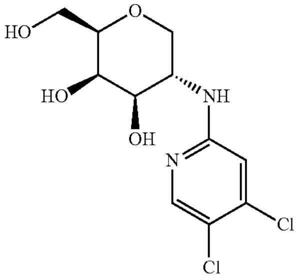 [SMILES: OC[C@H]1OC[C@H](Nc2cc(Cl)c(Cl)cn2)[C@@H](O)[C@H]1O] | ++++ |
| A299 | 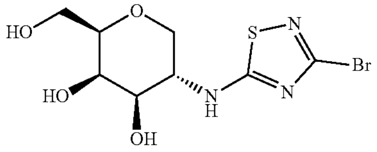 | ++++ |
| A300 | 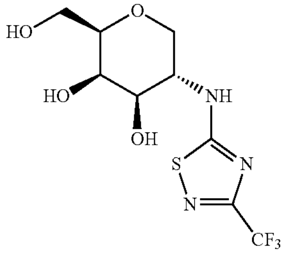 [SMILES: OC[C@H]1OC[C@H](Nc2nc(C(F)(F)F)ns2)[C@@H](O)[C@H]1O] | ++++ |
| A301 | 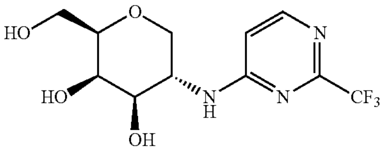 [SMILES: OC[C@H]1OC[C@H](Nc2ccnc(C(F)(F)F)n2)[C@@H](O)[C@H]1O] | ++++ |
| A302 | 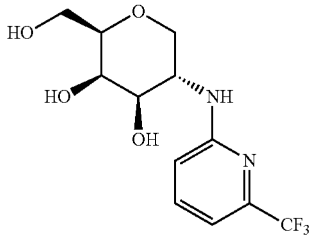 [SMILES: OC[C@H]1OC[C@H](Nc2cccc(C(F)(F)F)n2)[C@@H](O)[C@H]1O] | ++++ |

TABLE 4-continued
Biological Data for ASGPR Ligands
| Compound ID | Structure | ASGPR_SPR Binding $K_D$ (μM) |
|---|---|---|
| A304 | 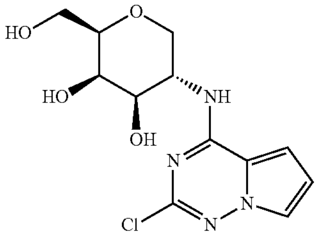 [SMILES: OC[C@H]1OC[C@H](Nc2nc(Cl)nn3cccc23)[C@@H](O)[C@H]1O] | ++++ |
| A305 | 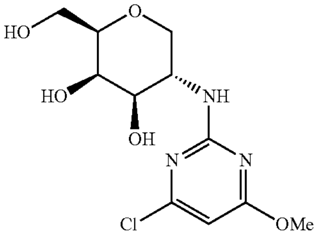 [SMILES: COc1cc(Cl)nc(N[C@H]2CO[C@H](CO)[C@H](O)[C@@H]2O)n1] | ++++ |
| A305 | 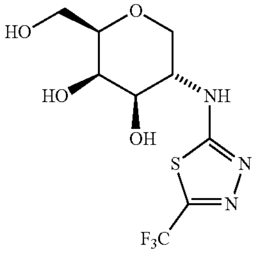 [SMILES: OC[C@H]1OC[C@H](Nc2nnc(C(F)(F)F)s2)[C@@H](O)[C@H]1O] | >20 |
| A306 | 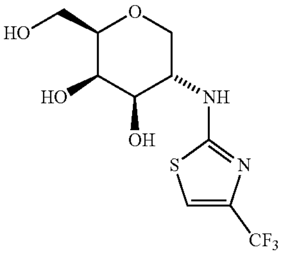 | ++++ |
| A307 | 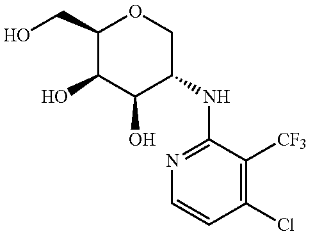 [SMILES: OC[C@H]1OC[C@H](Nc2nccc(Cl)c2C(F)(F)F)[C@@H](O)[C@H]1O] | ++++ |
| A308 | 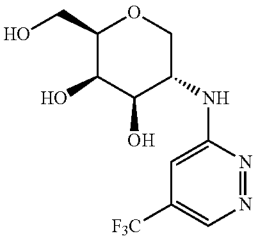 [SMILES: OC[C@H]1OC[C@H](Nc2cc(C(F)(F)F)cnn2)[C@@H](O)[C@H]1O] | >20 |
| A309 | 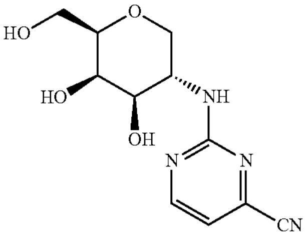 | ++++ |
| A310 | 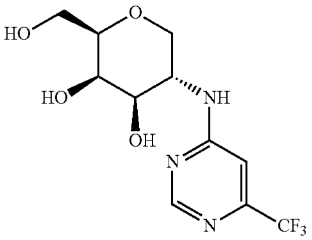 | >20 |
| A311 | 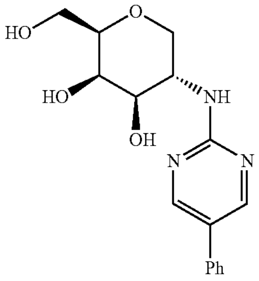 [SMILES: OC[C@H]1OC[C@H](Nc2ncc(-c3ccccc3)cn2)[C@@H](O)[C@H]1O] | >20 |
| A312 | 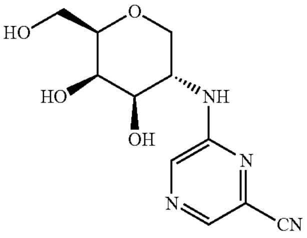 | ++++ |
| A313 | 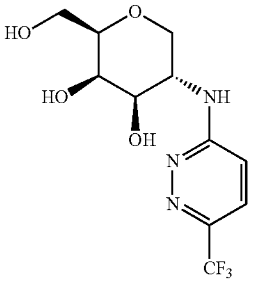 [SMILES: OC[C@H]1OC[C@H](Nc2ccc(C(F)(F)F)nn2)[C@@H](O)[C@H]1O] | >20 |

TABLE 4-continued
Biological Data for ASGPR Ligands
| Compound ID | Structure | ASGPR_SPR Binding $K_D$ (μM) |
|---|---|---|
| A314 | 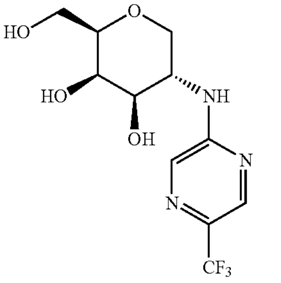 [SMILES: OC[C@H]1OC[C@H](Nc2cnc(C(F)(F)F)cn2)[C@@H](O)[C@H]1O] | >20 |
| A315 | 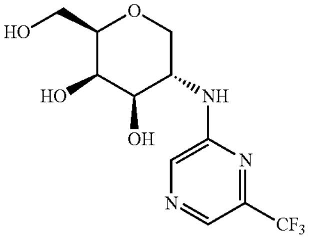 [SMILES: OC[C@H]1OC[C@H](Nc2cncc(C(F)(F)F)n2)[C@@H](O)[C@H]1O] | ++++ |
| A316 | 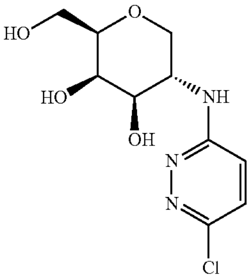 [SMILES: OC[C@H]1OC[C@H](Nc2ccc(Cl)nn2)[C@@H](O)[C@H]1O] | >20 |
| A317 | 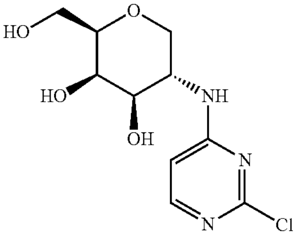 [SMILES: OC[C@H]1OC[C@H](Nc2ccnc(Cl)n2)[C@@H](O)[C@H]1O] | ++++ |
| A318 | 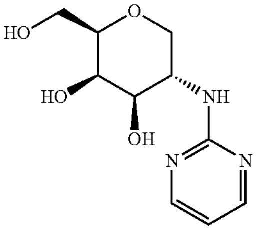 [SMILES: OC[C@H]1OC[C@H](Nc2ncccn2)[C@@H](O)[C@H]1O] | ++++ |
| A319 | 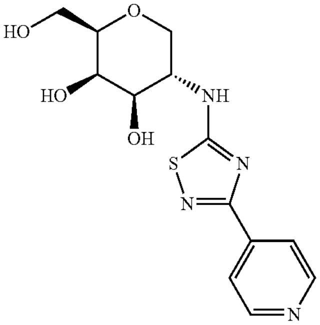 [SMILES: OC[C@H]1OC[C@H](Nc2nc(-c3ccncc3)ns2)[C@@H](O)[C@H]1O] | ++++ |
| A320 | 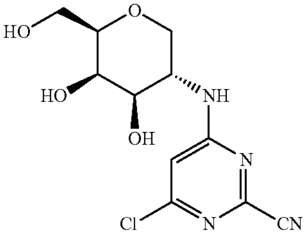 | ++++ |
| A321 | 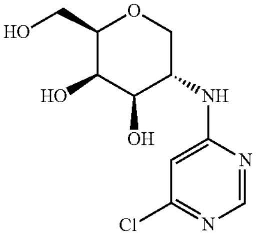 [SMILES: OC[C@H]1OC[C@H](Nc2cc(Cl)ncn2)[C@@H](O)[C@H]1O] | ++++ |
| A322 | 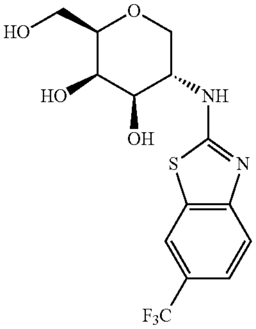 [SMILES: OC[C@H]1OC[C@H](Nc2nc3ccc(C(F)(F)F)cc3s2)[C@@H](O)[C@H]1O] | >20 |
| A323 | 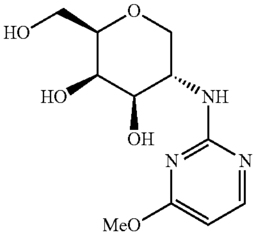 [SMILES: COc1ccnc(N[C@H]2CO[C@H](CO)[C@H](O)[C@@H]2O)n1] | ++++ |

TABLE 4-continued
| Biological Data for ASGPR Ligands | | |
|---|---|---|
| Compound ID | Structure | ASGPR_SPR Binding $K_D$ (μM) |
| A324 | 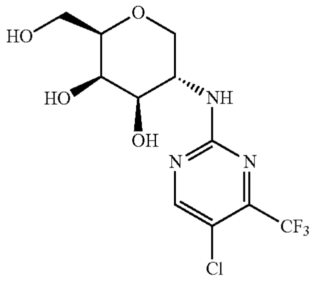 [SMILES: OC[C@H]1OC[C@H](Nc2ncc(Cl)c(C(F)(F)F)n2)[C@@H](O)[C@H]1O] | ++++ |
| A325 | 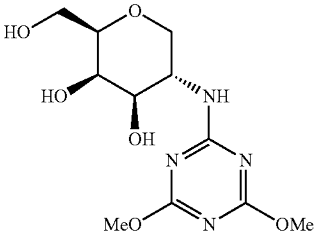 [SMILES: COc1nc(N[C@H]2CO[C@H](CO)[C@H](O)[C@@H]2O)nc(OC)n1] | ++++ |
| A326 | 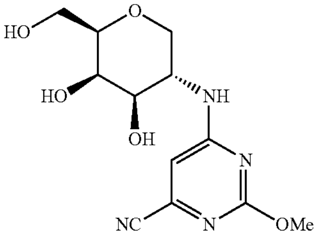 [SMILES: COc1nc(C#N)cc(N[C@H]2CO[C@H](CO)[C@H](O)[C@@H]2O)n1] | ++++ |
| A327 | 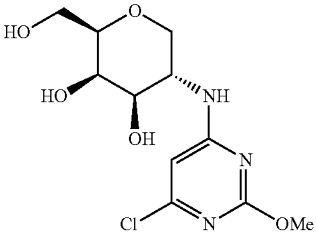 [SMILES: COc1nc(Cl)cc(N[C@H]2CO[C@H](CO)[C@H](O)[C@@H]2O)n1] | ++++ |
| A328 | 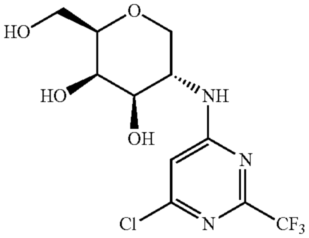 [SMILES: OC[C@H]1OC[C@H](Nc2cc(Cl)nc(C(F)(F)F)n2)[C@@H](O)[C@H]1O] | >20 |
| A330 | 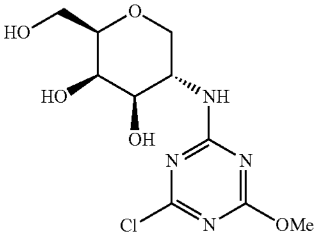 | ++++ |
| A331 | 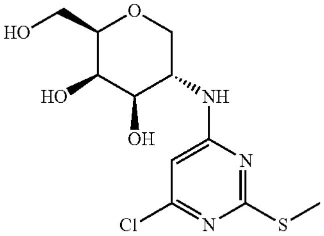 [SMILES: CSc1nc(Cl)cc(N[C@H]2CO[C@H](CO)[C@H](O)[C@@H]2O)n1] | ++++ |
| A332 | 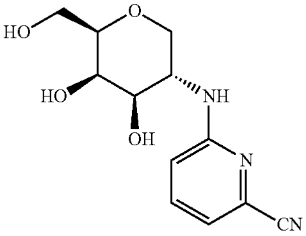 [SMILES: N#Cc1cccc(N[C@H]2CO[C@H](CO)[C@H](O)[C@@H]2O)n1] | ++++ |
| A333 | 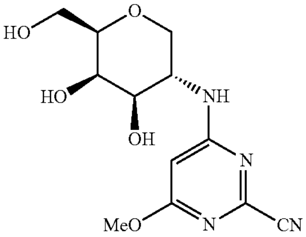 [SMILES: COc1cc(N[C@H]2CO[C@H](CO)[C@H](O)[C@@H]2O)nc(C#N)n1] | >10 |
| A334 | 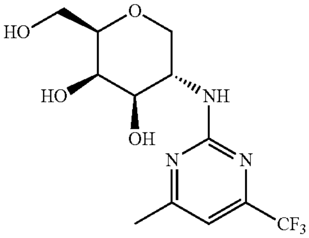 [SMILES: Cc1cc(C(F)(F)F)nc(N[C@H]2CO[C@H](CO)[C@H](O)[C@@H]2O)n1] | ++++ |
| A335 | 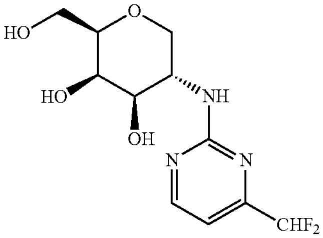 [SMILES: OC[C@H]1OC[C@H](Nc2nccc(C(F)F)n2)[C@@H](O)[C@H]1O] | ++++ |
| A336 | 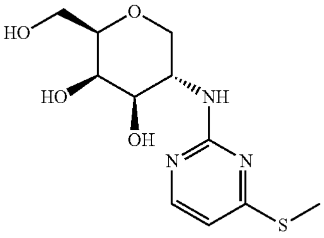 [SMILES: CSc1ccnc(N[C@H]2CO[C@H](CO)[C@H](O)[C@@H]2O)n1] | ++++ |

TABLE 4-continued
| Biological Data for ASGPR Ligands | | |
|---|---|---|
| Compound ID | Structure | ASGPR_SPR Binding $K_D$ (μM) |
| A338 | 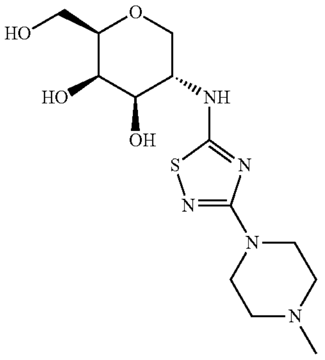 [SMILES: CN1CCN(c2nsc(N[C@H]3CO[C@H](CO)[C@H](O)[C@@H]3O)n2)CC1] | ++++ |
| A339 | 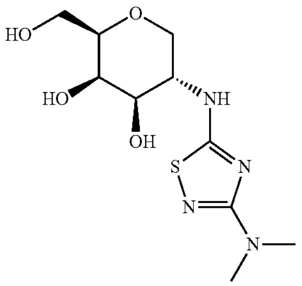 [SMILES: CN(C)c1nsc(N[C@H]2CO[C@H](CO)[C@H](O)[C@@H]2O)n1] | ++++ |
| A340 | 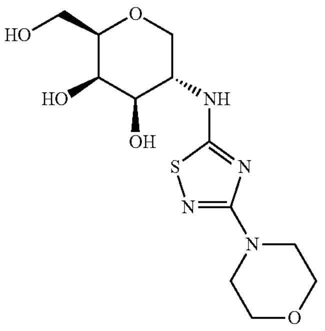 [SMILES: OC[C@H]1OC[C@H](Nc2nc(N3CCOCC3)ns2)[C@@H](O)[C@H]1O] | ++++ |
| A341 | 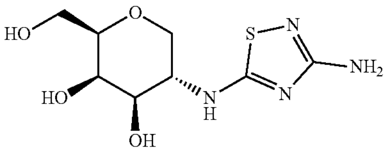 [SMILES: Nc1nsc(N[C@H]2CO[C@H](CO)[C@H](O)[C@@H]2O)n1] | ++++ |
| A342 | 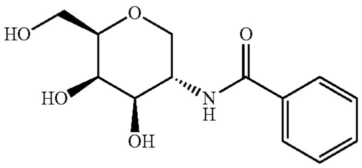 [SMILES: O=C(N[C@H]1CO[C@H](CO)[C@H](O)[C@@H]1O)c1ccccc1] | ++++ |
| A344 | 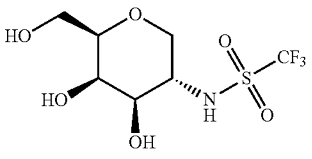 [SMILES: O=S(=O)(N[C@H]1CO[C@H](CO)[C@H](O)[C@@H]1O)C(F)(F)F] | ++++ |
TABLE 4-continued
| Biological Data for ASGPR Ligands | | |
|---|---|---|
| Compound ID | Structure | ASGPR_SPR Binding $K_D$ (μM) |
| A345 | 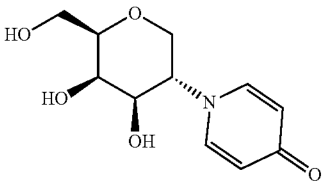 [SMILES: O=c1ccn([C@H]2CO[C@H](CO)[C@H](O)[C@@H]2O)cc1] | ++++ |
| A346 | 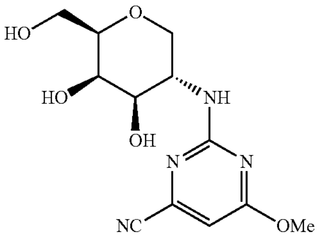 | ++++ |
| A348 | 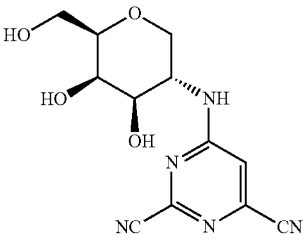 [SMILES: N#Cc1cc(N[C@H]2CO[C@H](CO)[C@H](O)[C@@H]2O)nc(C#N)n1] | >20 |
| A349 | 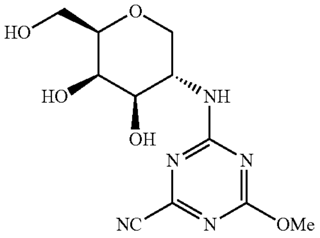 | ++++ |
| A350 | 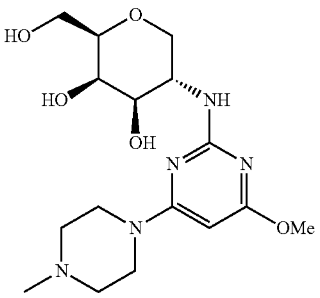 [SMILES: COc1cc(N2CCN(C)CC2)nc(N[C@H]2CO[C@H](CO)[C@H](O)[C@@H]2O)n1] | >20 |
| A351 | 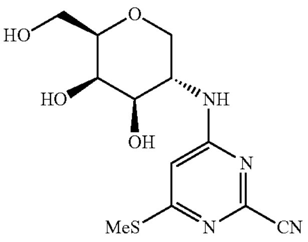 [SMILES: CSc1cc(N[C@H]2CO[C@H](CO)[C@H](O)[C@@H]2O)nc(C#N)n1] | >20 |

TABLE 4-continued
Biological Data for ASGPR Ligands
| Compound ID | Structure | ASGPR_SPR Binding $K_D$ (μM) |
|---|---|---|
| A352 | 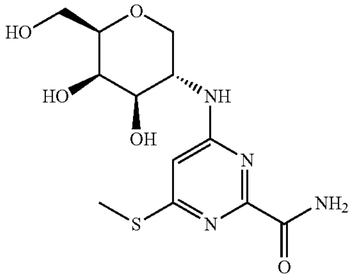 [SMILES: CSc1cc(N[C@H]2CO[C@H](CO)[C@H](O)[C@@H]2O)nc(C(N)=O)n1] | >20 |
| A353 | 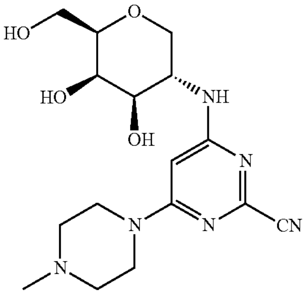 [SMILES: CN1CCN(c2cc(N[C@H]3CO[C@H](CO)[C@H](O)[C@@H]3O)nc(C#N)n2)CC1] | |
| A354 | 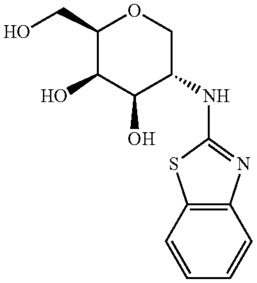 [SMILES: OC[C@H]1OC[C@H](Nc2nc3ccccc3s2)[C@@H](O)[C@H]1O] | ++++ |
| A355 | 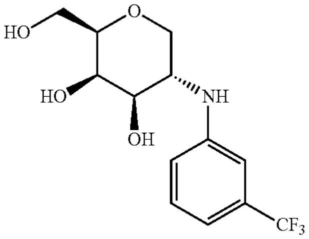 [SMILES: OC[C@H]1OC[C@H](Nc2cccc(C(F)(F)F)c2)[C@@H](O)[C@H]1O] | ++++ |
| A356 | 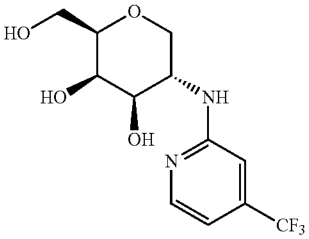 | >20 |
| A358 | 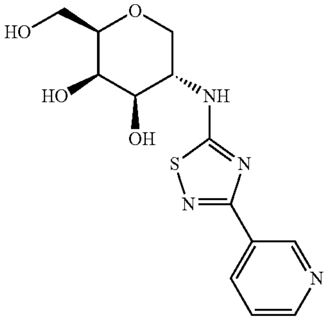 [SMILES: OC[C@H]1OC[C@H](Nc2nc(-c3cccnc3)ns2)[C@@H](O)[C@H]1O] | ++++ |
| A359 | 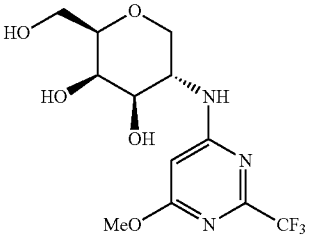 [SMILES: COc1cc(N[C@H]2CO[C@H](CO)[C@H](O)[C@@H]2O)nc(C(F)(F)F)n1] | ++++ |
| A360 | 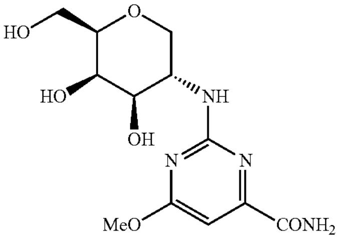 [SMILES: COc1cc(C(N)=O)nc(N[C@H]2CO[C@H](CO)[C@H](O)[C@@H]2O)n1] | ++++ |
| A361 | 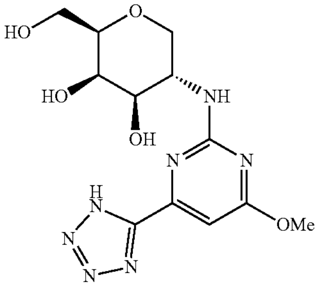 [SMILES: COc1cc(-c2nnn[nH]2)nc(N[C@H]2CO[C@H](CO)[C@H](O)[C@@H]2O)n1] | >20 |
| A362 | 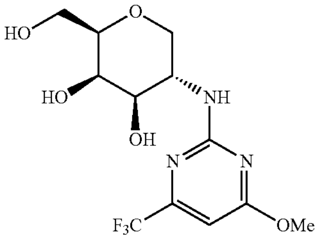 [SMILES: COc1cc(C(F)(F)F)nc(N[C@H]2CO[C@H](CO)[C@H](O)[C@@H]2O)n1] | ++++ |

TABLE 4-continued
| Biological Data for ASGPR Ligands | | |
|---|---|---|
| Compound ID | Structure | ASGPR_SPR Binding $K_D$ (μM) |
| A363 | 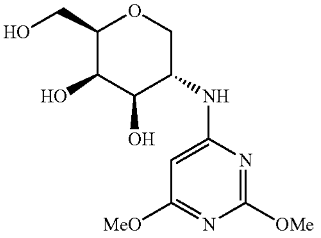 [SMILES: COc1cc(N[C@H]2CO[C@H](CO)[C@H](O)[C@@H]2O)nc(OC)n1] | ++++ |
| A364 | 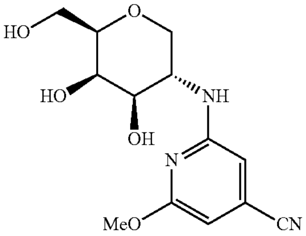 [SMILES: COc1cc(C#N)cc(N[C@H]2CO[C@H](CO)[C@H](O)[C@@H]2O)n1] | ++++ |
| A365 | 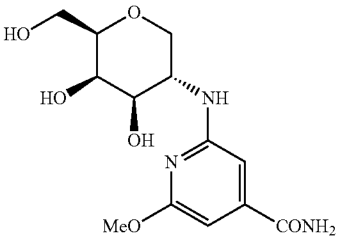 [SMILES: COc1cc(C(N)=O)cc(N[C@H]2CO[C@H](CO)[C@H](O)[C@@H]2O)n1] | >20 |
| A366 | 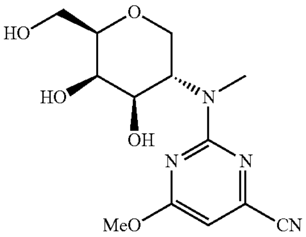 [SMILES: COc1cc(C#N)nc(N(C)[C@H]2CO[C@H](CO)[C@H](O)[C@@H]2O)n1] | ++++ |
| A367 | 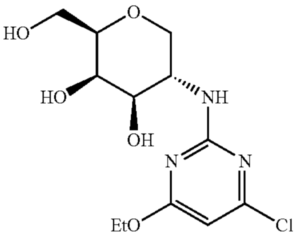 [SMILES: CCOc1cc(Cl)nc(N[C@H]2CO[C@H](CO)[C@H](O)[C@@H]2O)n1] | ++++ |
| A368 | 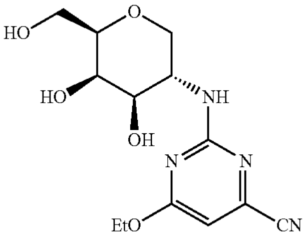 [SMILES: CCOc1cc(C#N)nc(N[C@H]2CO[C@H](CO)[C@H](O)[C@@H]2O)n1] | >20 |
TABLE 4-continued
| Biological Data for ASGPR Ligands | | |
|---|---|---|
| Compound ID | Structure | ASGPR_SPR Binding $K_D$ (μM) |
| A369 | 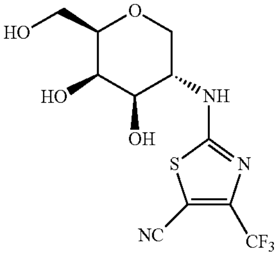 [SMILES: N#Cc1sc(N[C@H]2CO[C@H](CO)[C@H](O)[C@@H]2O)nc1C(F)(F)F] | >20 |
| A370 | 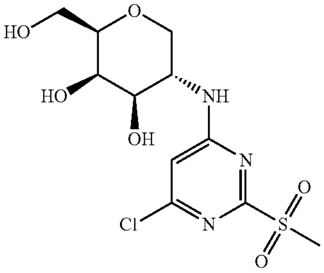 [SMILES: CS(=O)(=O)c1nc(Cl)cc(N[C@H]2CO[C@H](CO)[C@H](O)[C@@H]2O)n1] | >10 |
| A371 | 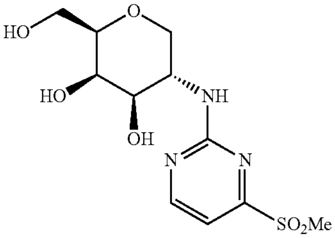 [SMILES: CS(=O)(=O)c1ccnc(N[C@H]2CO[C@H](CO)[C@H](O)[C@@H]2O)n1] | ++++ |
| A372 | 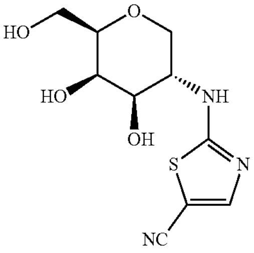 [SMILES: N#Cc1cnc(N[C@H]2CO[C@H](CO)[C@H](O)[C@@H]2O)s1] | >20 |
| A373 | 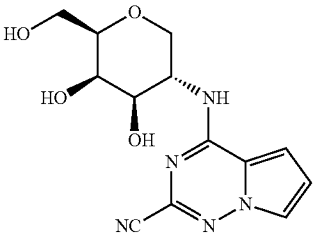 [SMILES: N#Cc1nc(N[C@H]2CO[C@H](CO)[C@H](O)[C@@H]2O)c2cccn2n1] | ++++ |

TABLE 4-continued
Biological Data for ASGPR Ligands
| Compound ID | Structure | ASGPR_SPR Binding $K_D$ (μM) |
|---|---|---|
| A374 | 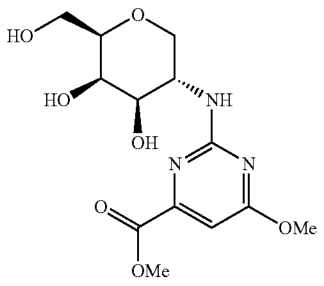 [SMILES: COC(=O)c1cc(OC)nc(N[C@H]2CO[C@H](CO)[C@H](O)[C@@H]2O)n1] | >20 |
| A377 | 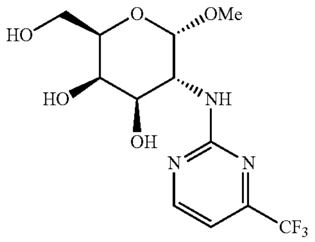 [SMILES: CO[C@H]1O[C@H](CO)[C@H](O)[C@H](O)[C@H]1Nc1nccc(C(F)(F)F)n1] | ++++ |
| A378 | 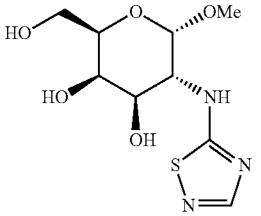 [SMILES: CO[C@H]1O[C@H](CO)[C@H](O)[C@H](O)[C@H]1Nc1ncns1] | ++++ |
| A379 | 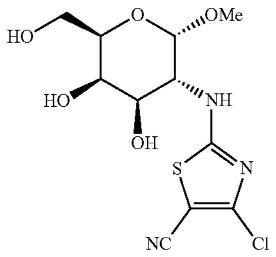 [SMILES: CO[C@H]1O[C@H](CO)[C@H](O)[C@H](O)[C@H]1Nc1nc(Cl)c(C#N)s1] | ++++ |
| A380 | 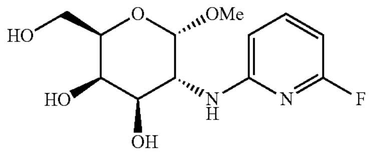 [SMILES: CO[C@H]1O[C@H](CO)[C@H](O)[C@H](O)[C@H]1Nc1cccc(F)n1] | ++++ |
| A381 | 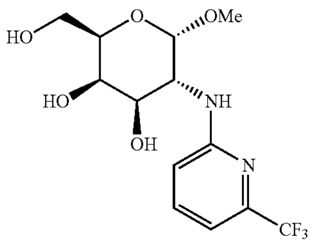 [SMILES: CO[C@H]1O[C@H](CO)[C@H](O)[C@H](O)[C@H]1Nc1cccc(C(F)(F)F)n1] | ++++ |
TABLE 4-continued
Biological Data for ASGPR Ligands
| Compound ID | Structure | ASGPR_SPR Binding $K_D$ (μM) |
|---|---|---|
| A382 | 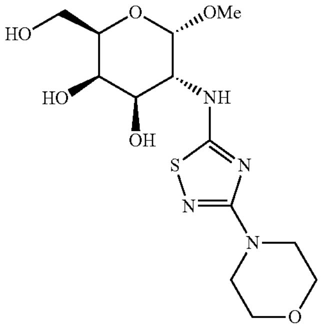 [SMILES: CO[C@H]1O[C@H](CO)[C@H](O)[C@H](O)[C@H]1Nc1nc(N2CCOCC2)ns1] | ++++ |
| A383 | 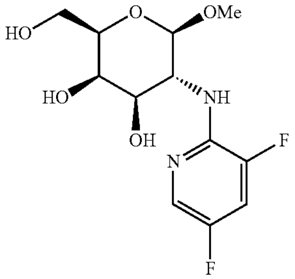 [SMILES: CO[C@@H]1O[C@H](CO)[C@H](O)[C@H](O)[C@H]1Nc1ncc(F)cc1F] | ++++ |
| A384 | 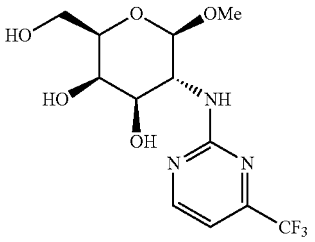 [SMILES: CO[C@@H]1O[C@H](CO)[C@H](O)[C@H](O)[C@H]1Nc1nccc(C(F)(F)F)n1] | ++++ |
| A385 | 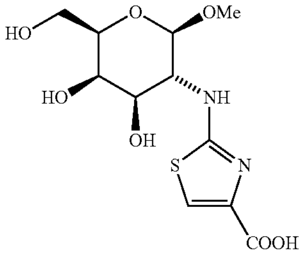 [SMILES: CO[C@@H]1O[C@H](CO)[C@H](O)[C@H](O)[C@H]1Nc1nc(C(=O)O)cs1] | >200 |
| A386 | 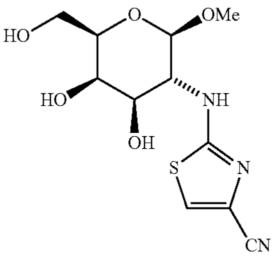 [SMILES: CO[C@@H]1O[C@H](CO)[C@H](O)[C@H](O)[C@H]1Nc1nc(C#N)cs1] | >20 |

TABLE 4-continued
| Biological Data for ASGPR Ligands | | |
|---|---|---|
| Compound ID | Structure | ASGPR_SPR Binding $K_D$ (μM) |
| A387 | 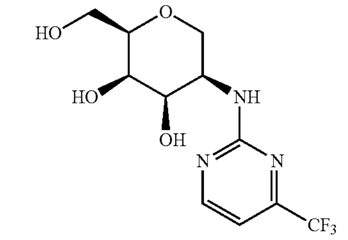 [SMILES: OC[C@H]1OC[C@@H](Nc2nccc(C(F)(F)F)n2)[C@@H](O)[C@H]1O] | >20 |
| A388 | 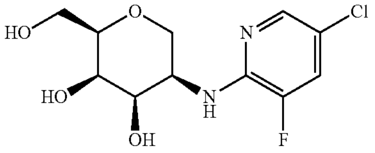 [SMILES: OC[C@H]1OC[C@@H](Nc2ncc(Cl)cc2F)[C@@H](O)[C@H]1O] | >20 |
| A389 | 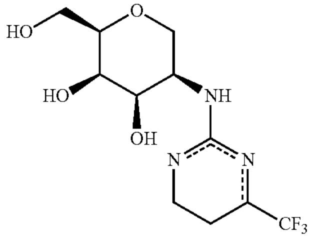 | >20 |
| A390 | 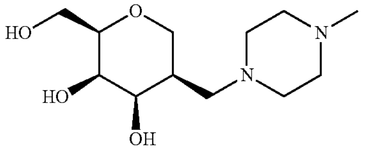 [SMILES: CN1CCN(C[C@@H]2CO[C@H](CO)[C@H](O)[C@@H]2O)CC1] | >200 |
| A392 | 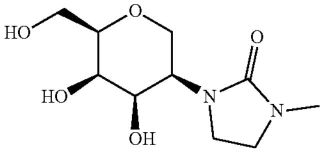 [SMILES: CN1CCN([C@@H]2CO[C@H](CO)[C@H](O)[C@@H]2O)C1=O] | +++ |
| A393 | 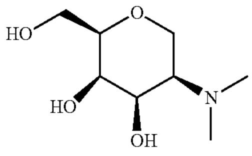 | +++ |
| A394 | 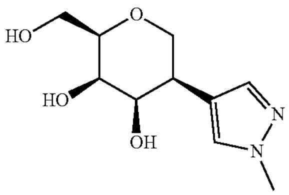 [SMILES: Cn1cc([C@@H]2CO[C@H](CO)[C@H](O)[C@@H]2O)cn1] | >200 |
TABLE 4-continued
| Biological Data for ASGPR Ligands | | |
|---|---|---|
| Compound ID | Structure | ASGPR_SPR Binding $K_D$ (μM) |
| A395 | 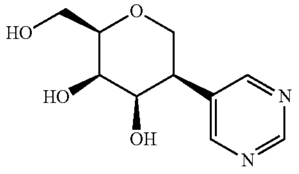 [SMILES: OC[C@H]1OC[C@@H](c2cncnc2)[C@@H](O)[C@H]1O] | >200 |
| A397 | 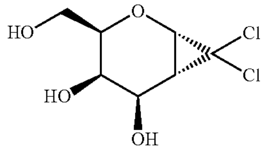 [SMILES: OC[C@H]1O[C@H]2[C@@H]([C@@H](O)[C@H]1O)C2(Cl)Cl] | +++ |
| A399 | 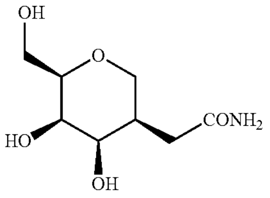 [SMILES: NC(=O)C[C@@H]1CO[C@H](CO)[C@H](O)[C@@H]1O] | >200 |
| A400 | 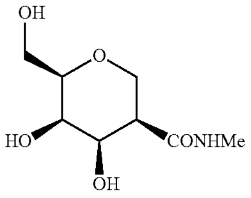 | >200 |
| A401 | 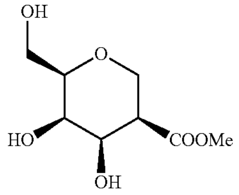 [SMILES: COC(=O)[C@@H]1CO[C@H](CO)[C@H](O)[C@@H]1O] | >200 |
| A402 | 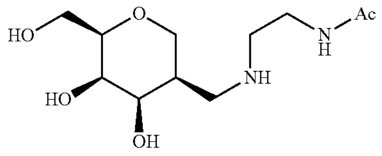 [SMILES: CC(=O)NCCNC[C@@H]1CO[C@H](CO)[C@H](O)[C@@H]1O] | >200 |
| A403 | 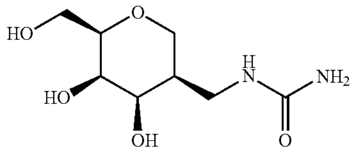 [SMILES: NC(=O)NC[C@@H]1CO[C@H](CO)[C@H](O)[C@@H]1O] | >20 |
| A404 | 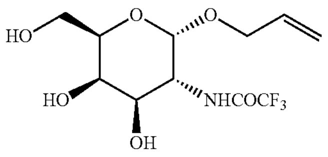 | ++++ |

TABLE 4-continued
Biological Data for ASGPR Ligands
| Compound ID | Structure | ASGPR_SPR Binding $K_D$ (μM) |
|---|---|---|
| A405 | 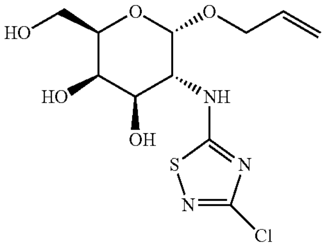 [SMILES: C=CCO[C@H]1O[C@H](CO)[C@H](O)[C@H](O)[C@H]1Nc1nc(Cl)ns1] | ++++ |
| A406 | 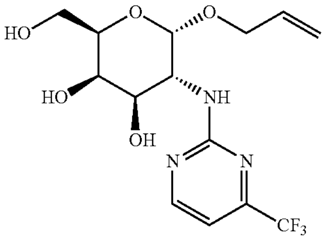 [SMILES: C=CCO[C@H]1O[C@H](CO)[C@H](O)[C@H](O)[C@H]1Nc1nccc(C(F)(F)F)n1] | ++++ |
| A425 | 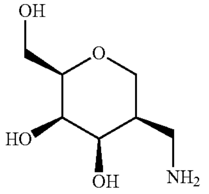 [SMILES: NC[C@@H]1CO[C@H](CO)[C@H](O)[C@@H]1O] | + |
| A426 | 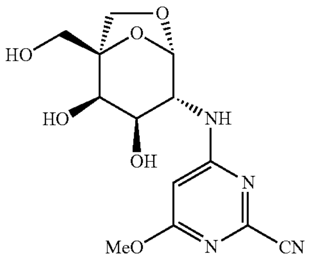 [SMILES: COc1cc(N[C@H]2[C@H]3OC[C@](CO)(O3)[C@H](O)[C@@H]2O)nc(C#N)n1] | ++++ |
| A427 | 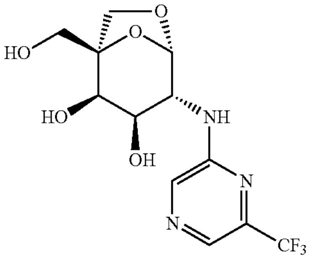 [SMILES: OC[C@@]12CO[C@@H](O1)[C@H](Nc1cncc(C(F)(F)F)n1)[C@@H](O)[C@H]2O] | ++++ |
| A91 | 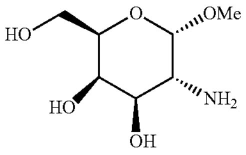 [SMILES: CO[C@H]1O[C@H](CO)[C@H](O)[C@H](O)[C@H]1N] | ++++ |
In the table above KD values that are >=1000 uM = +, <1000 uM = ++, <500 uM = +++, and <100 uM = ++++

TABLE 5
Biological Data for ASGPR Ligands with Linker
| Compound ID | Structure | ASGPR_SPR Binding $K_D$ (μM) |
|---|---|---|
| Compound 29 | 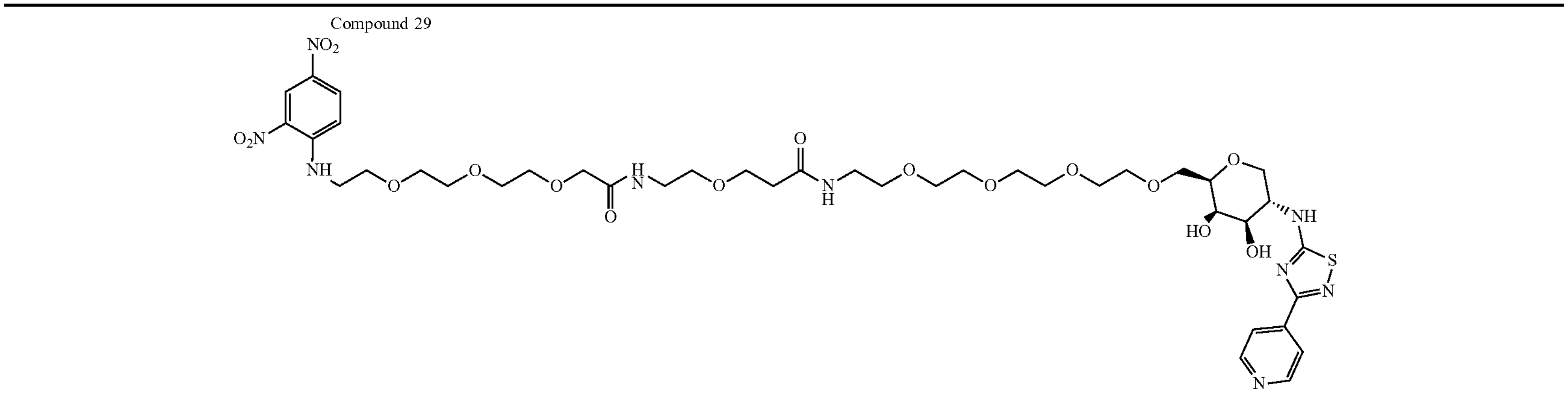 | |
| Compound 30 | | ++++ |

TABLE 5-continued
| Biological Data for ASGPR Ligands with Linker | |
|---|---|
| Compound ID<br>Structure | ASGPR_SPR Binding $K_D$ (μM) |
| 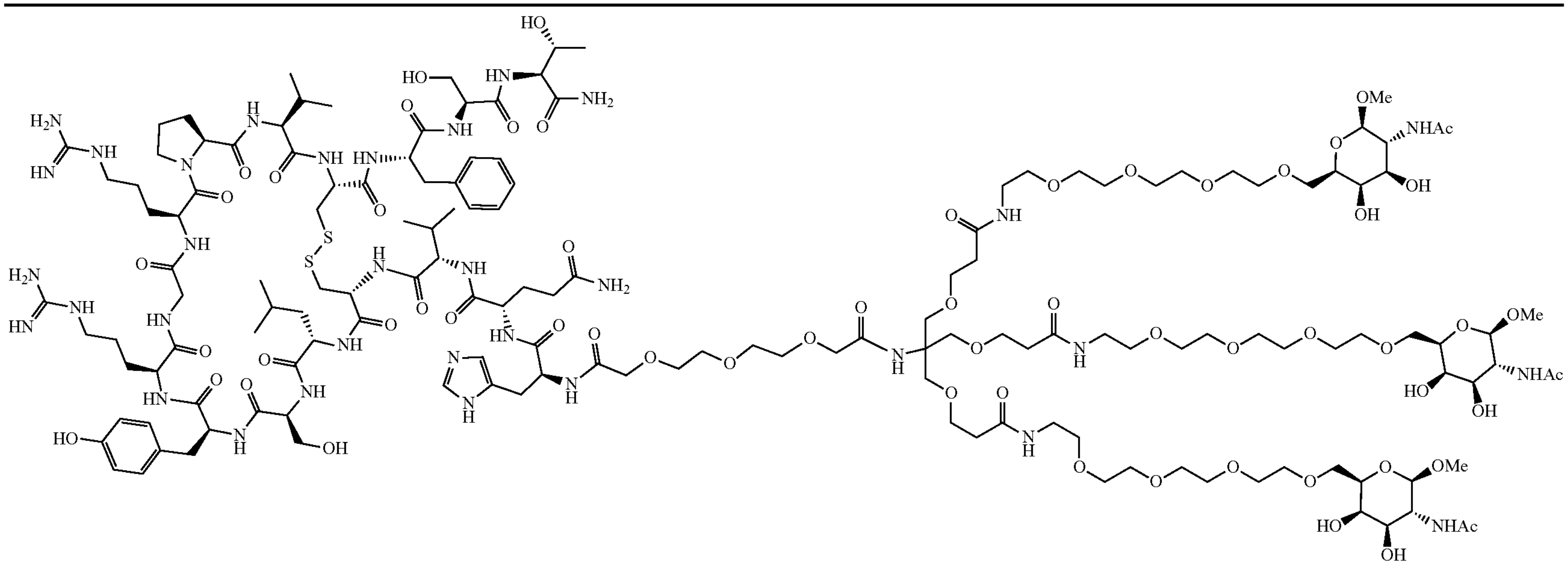<br>Compound 31 | |

TABLE 5-continued
| Biological Data for ASGPR Ligands with Linker | |
|---|---|
| Compound ID | ASGPR_SPR Binding $K_D$ (μM) |
| Structure | |
| 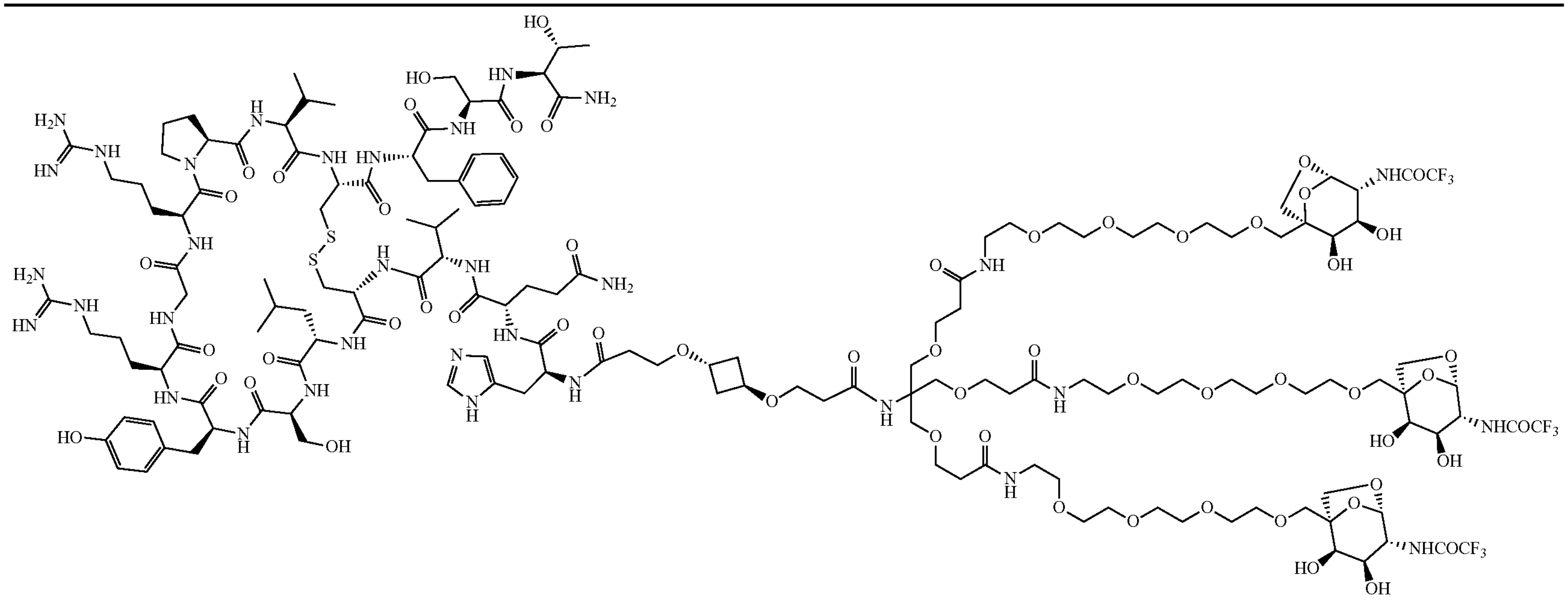 | |
| Compound 32 | |

TABLE 5-continued
| Biological Data for ASGPR Ligands with Linker | | |
|---|---|---|
| Compound ID | Structure | ASGPR_SPR Binding $K_D$ (μM) |
| Compound 33 | 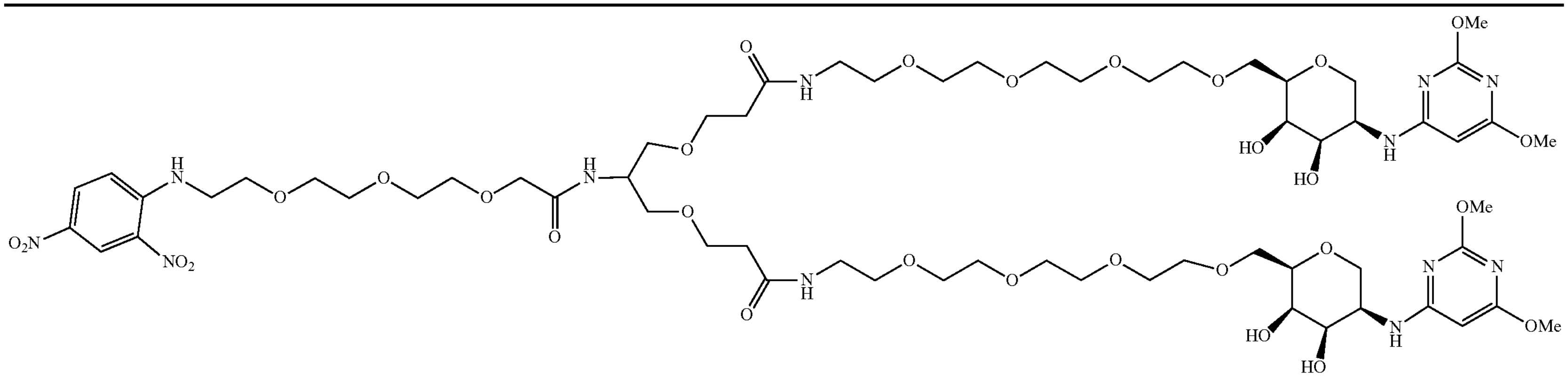 | ++++ |

TABLE 5-continued
| Biological Data for ASGPR Ligands with Linker | | |
|---|---|---|
| Compound ID | Structure | ASGPR_SPR Binding $K_D$ (μM) |
| Compound 34 | 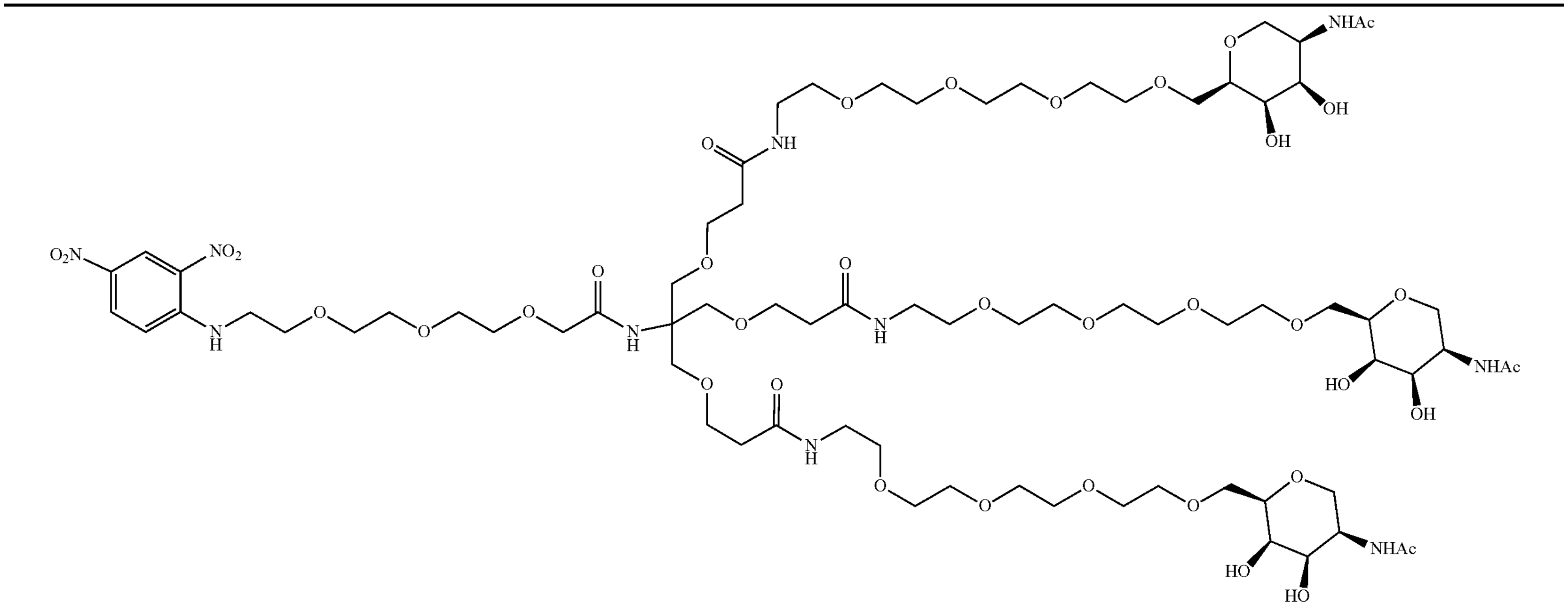 | |

TABLE 5-continued
| Biological Data for ASGPR Ligands with Linker | | |
|---|---|---|
| Compound ID | Structure | ASGPR_SPR Binding $K_D$ (μM) |
| A413 | 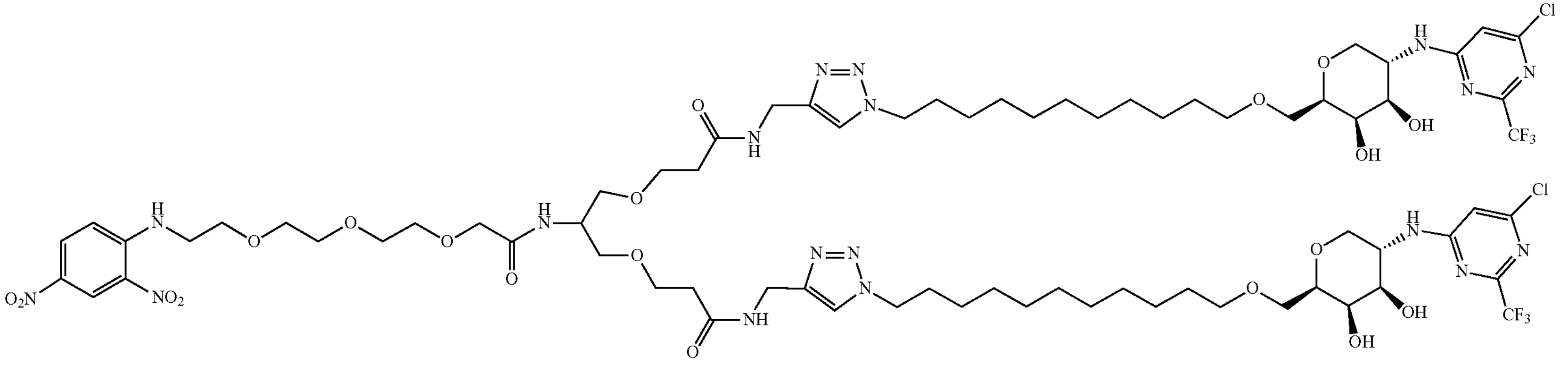 [SMILES: O=C(CCOCC(COCCC(=O)NCc1cn(CCCCCCCCCCCOC[C@H]2OC[C@H](Nc3cc(Cl)nc(C(F)(F)F)n3)[C@@H](O)[C@H]2O)nn1)NC(=O)COCCOCCOCCNc1ccc([N+](=O)[O-])cc1[N+](=O)[O-])NCc1cn(CCCCCCCCCCCOC[C@H]2OC[C@H](Nc3cc(Cl)nc(C(F)(F)F)n3)[C@@H](O)[C@H]2O)nn1] | ++++ |
| Compound 35 | 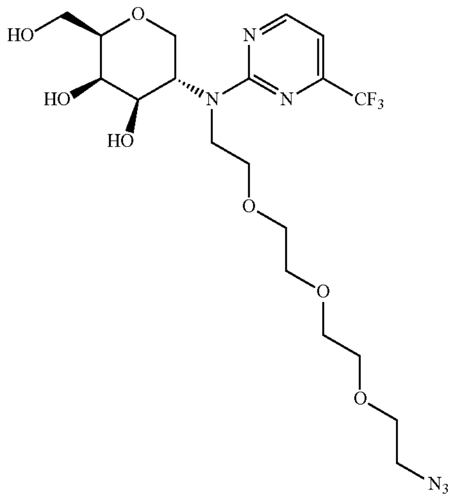 [SMILES: [N-]=[N+]=NCCOCCOCCOCCN(c1nccc(C(F)(F)F)n1)[C@H]1CO[C@H](CO)[C@H](O)[C@@H]1O] | ++++ |

TABLE 5-continued
| Biological Data for ASGPR Ligands with Linker | | |
|---|---|---|
| Compound ID | Structure | ASGPR_SPR Binding $K_D$ (μM) |
| | 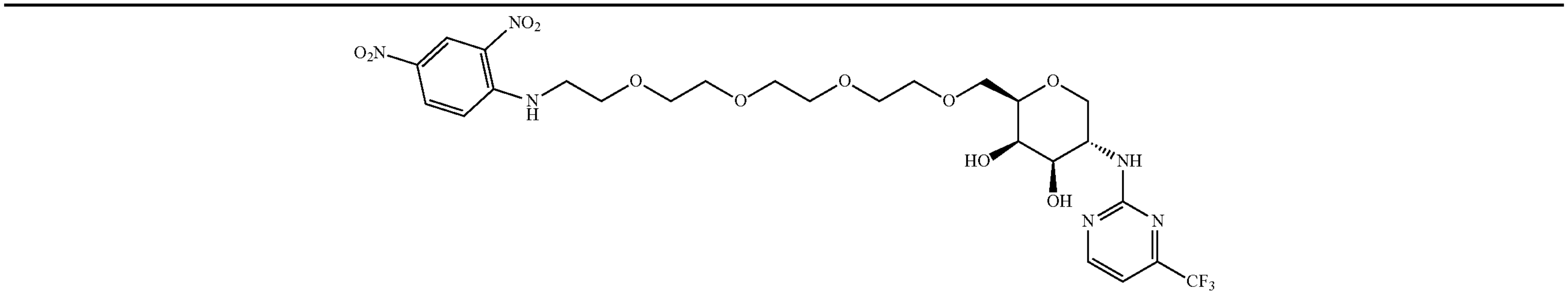 | |
| Compound 36 | | |

TABLE 5-continued
| Biological Data for ASGPR Ligands with Linker | | |
|---|---|---|
| Compound ID | Structure | ASGPR_SPR Binding $K_D$ (μM) |
| Compound 37 | 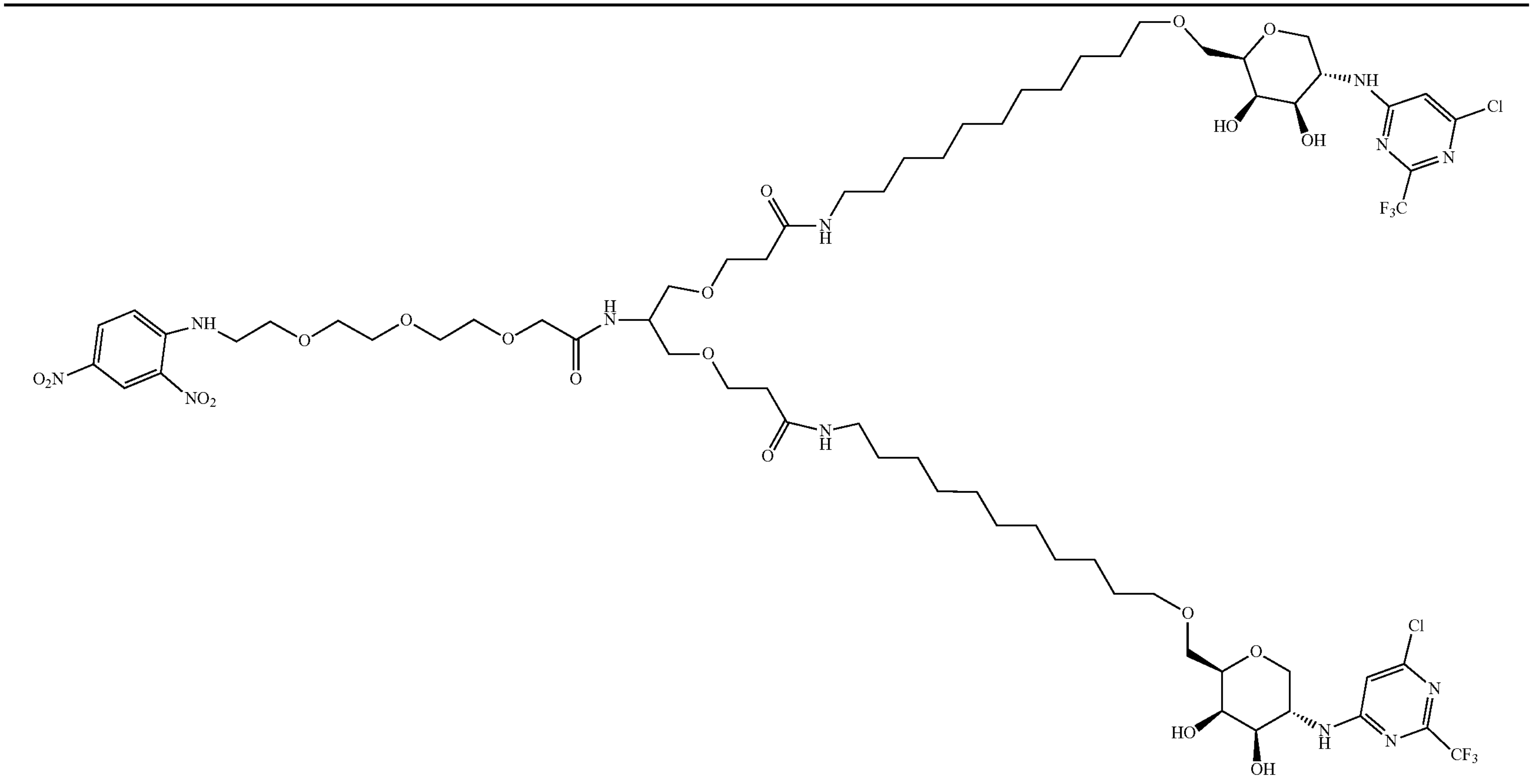 | |

TABLE 5-continued
| Biological Data for ASGPR Ligands with Linker | | |
|---|---|---|
| Compound ID | Structure | ASGPR_SPR Binding $K_D$ (μM) |
| Compound 38 | 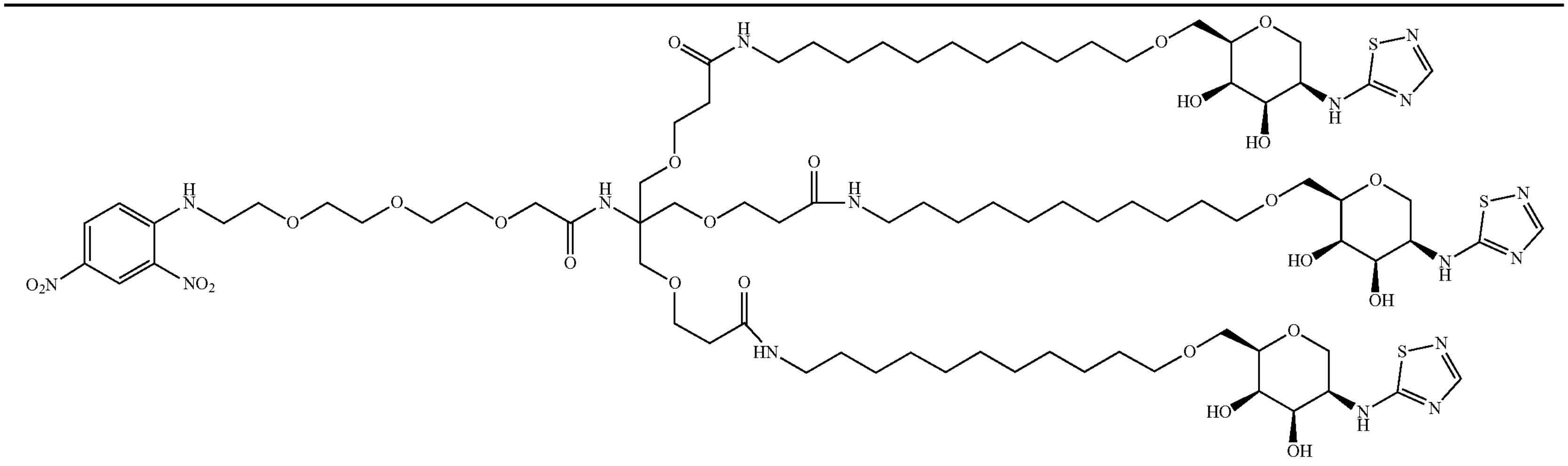 | |
| Compound 39 | 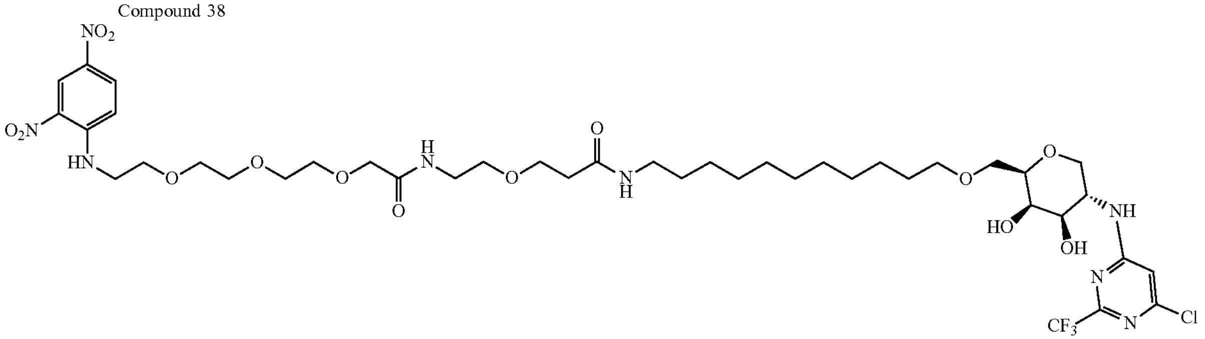 | |

TABLE 5-continued
Biological Data for ASGPR Ligands with Linker
| Compound ID | Structure | ASGPR_SPR Binding $K_D$ (μM) |
|---|---|---|
| Compound 56 | 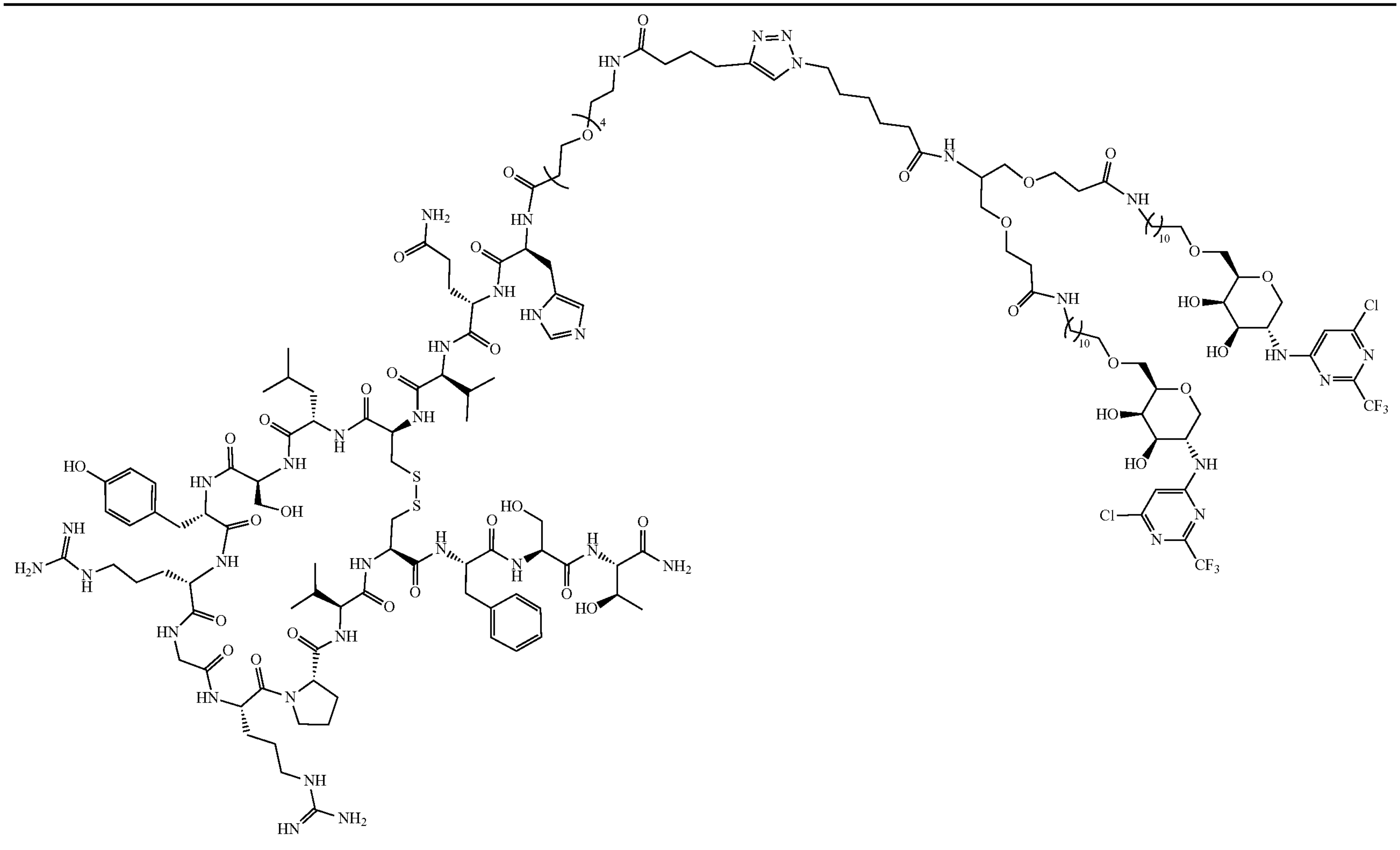 | |

TABLE 5-continued
| Biological Data for ASGPR Ligands with Linker | | |
|---|---|---|
| Compound ID | Structure | ASGPR_SPR Binding $K_D$ (μM) |
| A420 | 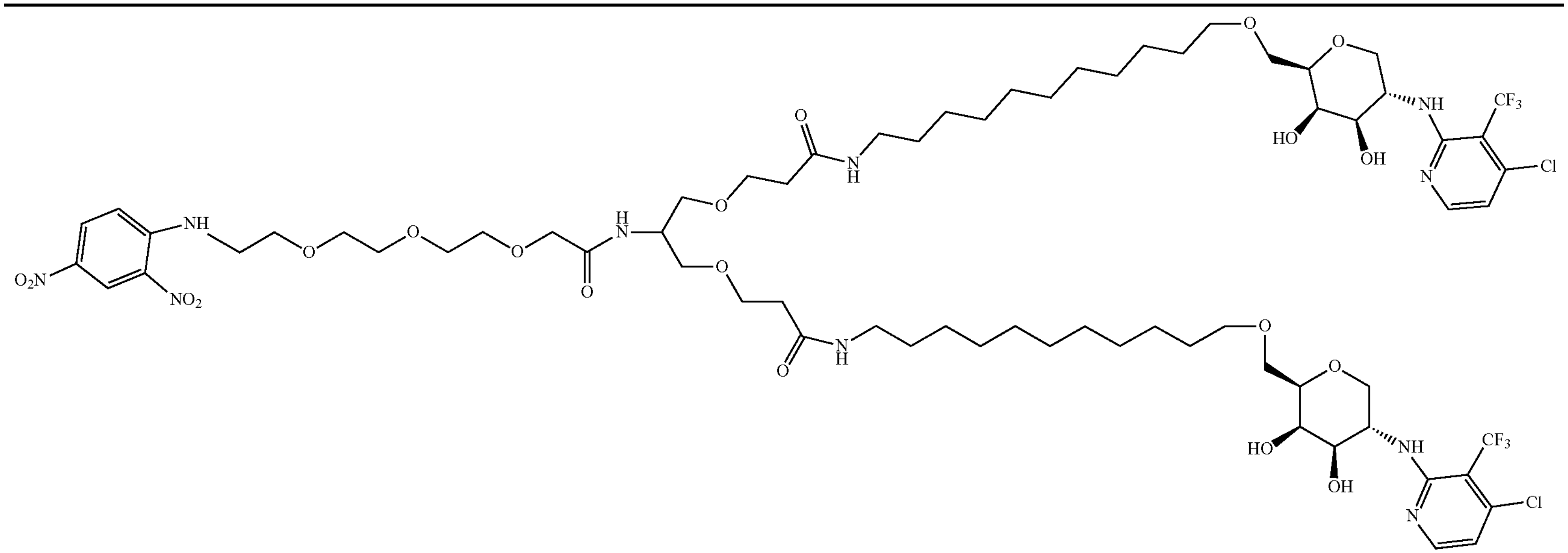 | |

TABLE 5-continued
| Biological Data for ASGPR Ligands with Linker | | |
|---|---|---|
| Compound ID | Structure | ASGPR_SPR Binding $K_D$ (μM) |
| A421 | 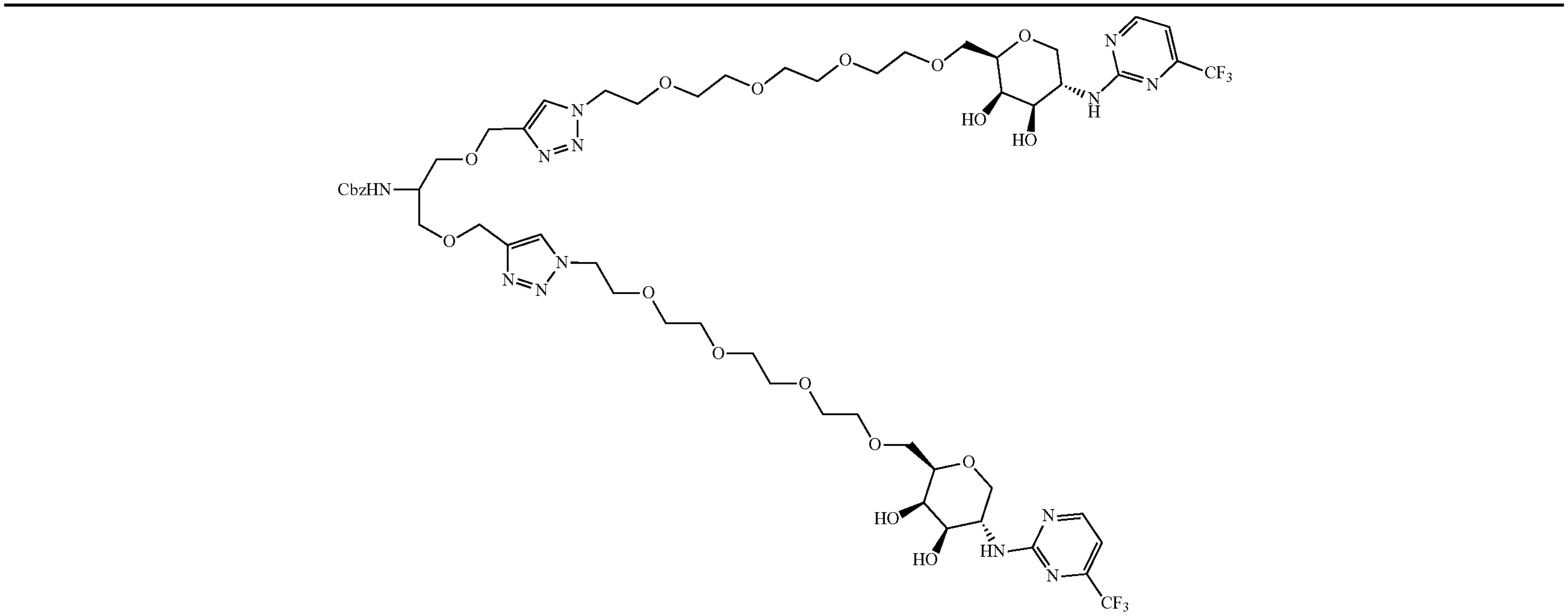 | |

TABLE 5-continued
| Biological Data for ASGPR Ligands with Linker | | |
|---|---|---|
| Compound ID | Structure | ASGPR_SPR Binding $K_D$ (μM) |
| A423 | 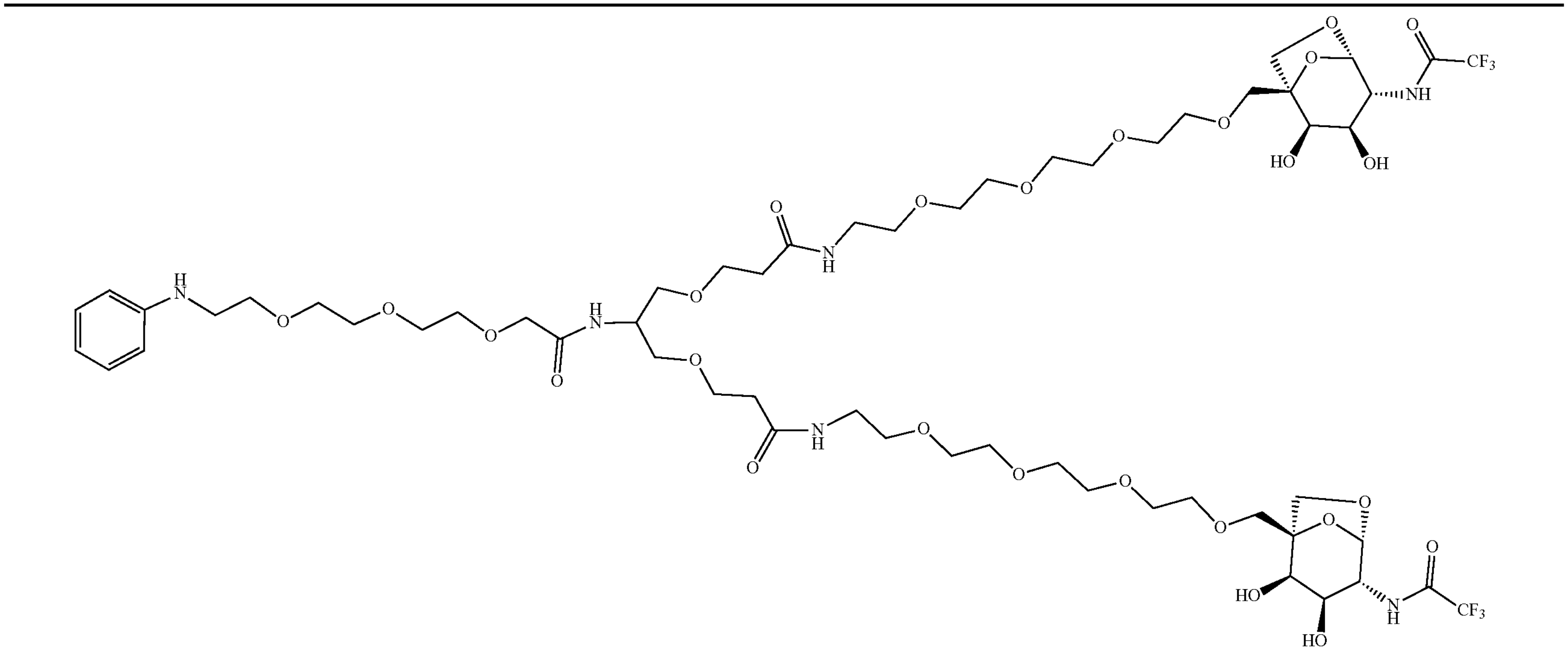 | |

TABLE 5-continued
| Biological Data for ASGPR Ligands with Linker | | |
|---|---|---|
| Compound ID | Structure | ASGPR_SPR Binding $K_D$ (μM) |
| Compound 48 | 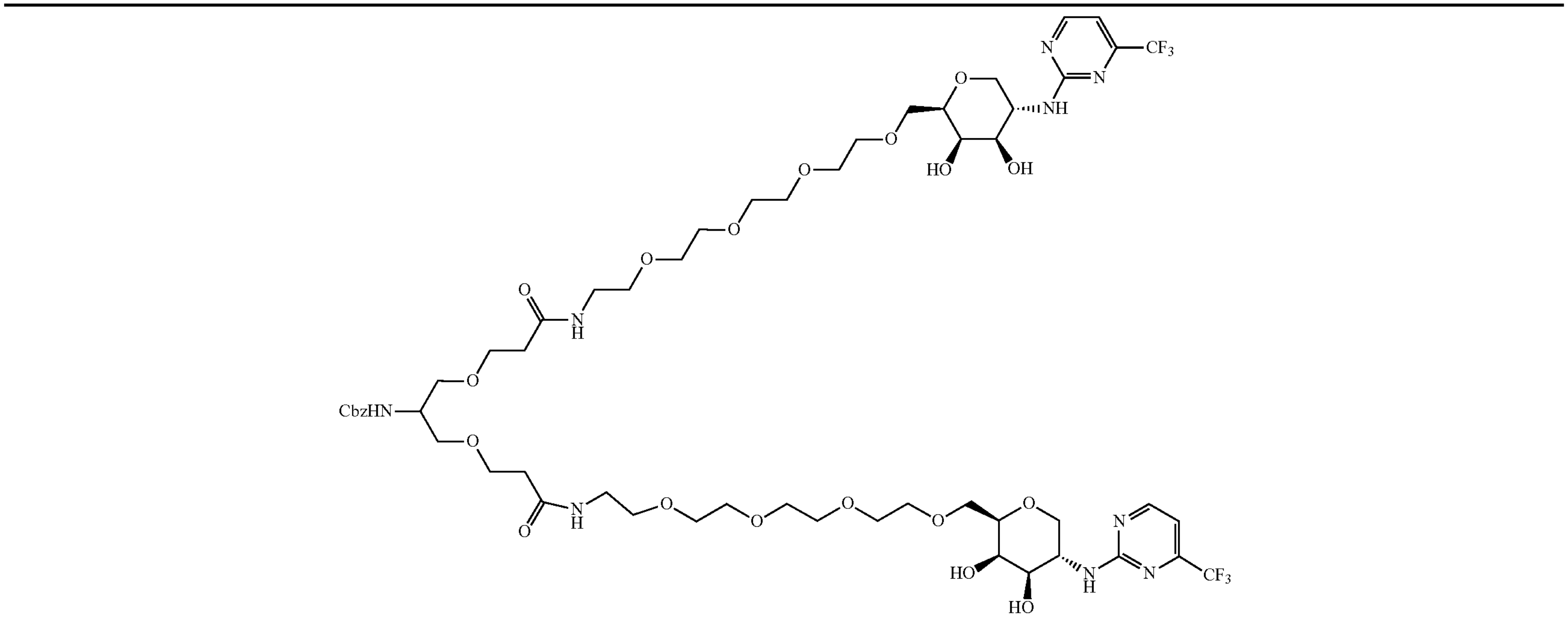 | |
| Compound 49 | 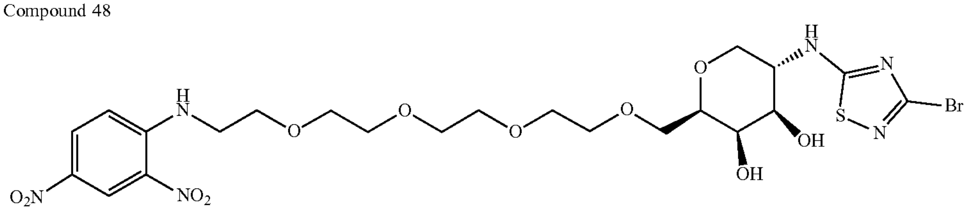 | |

TABLE 5-continued
Biological Data for ASGPR Ligands with Linker
| Compound ID | Structure | ASGPR_SPR Binding $K_D$ (μM) |
|---|---|---|
| Compound 50 | 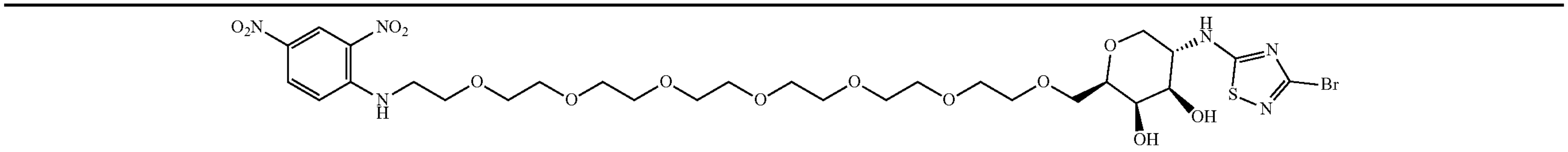 | |
| A417 | 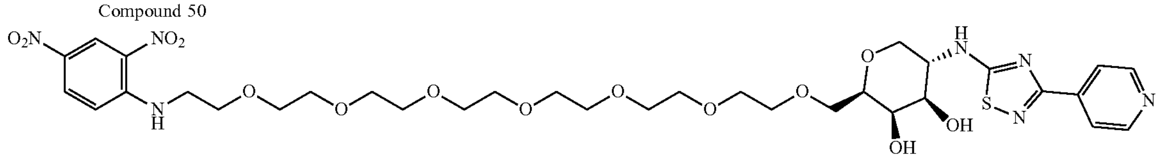 | ++++ |
| A424 | 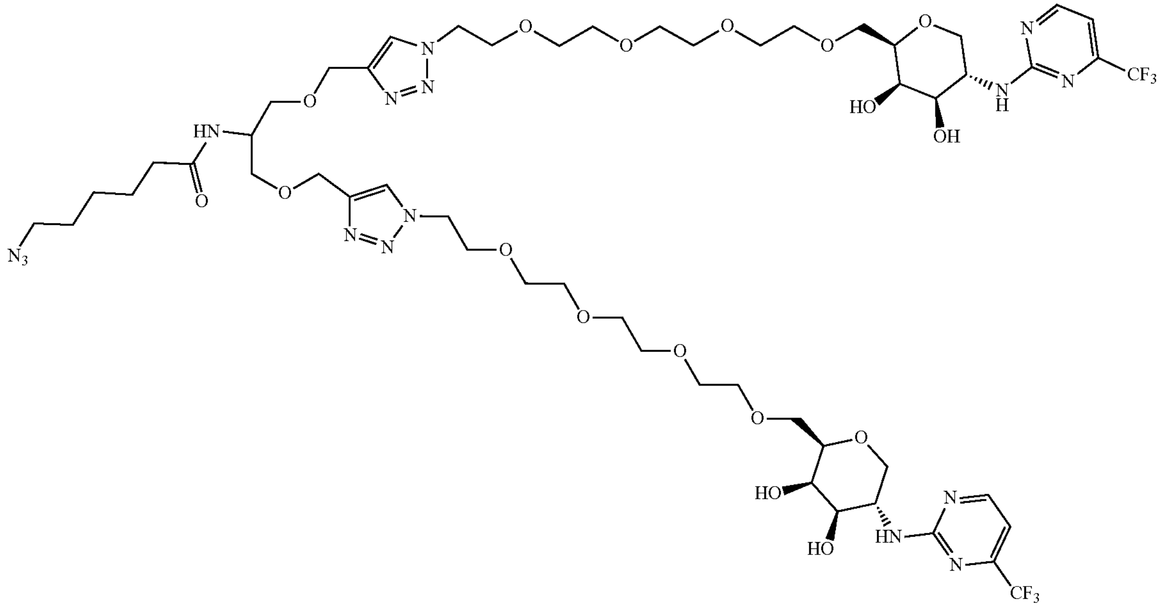 [SMILES: [N-]=[N+]=NCCCCCC(=O)NC(COCc1cn(CCOCCOCCOCCOC[C@H]2OC[C@H](Nc3nccc(C(F)(F)F)n3)[C@@H](O)[C@H]2O)nn1)COCc1cn(CCOCCOCCOCCOC[C@H]2OC[C@H](Nc3nccc(C(F)(F)F)n3)[C@@H](O)[C@H]2O)nn1] | |

TABLE 5-continued
| Biological Data for ASGPR Ligands with Linker | | |
|---|---|---|
| Compound ID | Structure | ASGPR_SPR Binding $K_D$ (μM) |
| A422 | 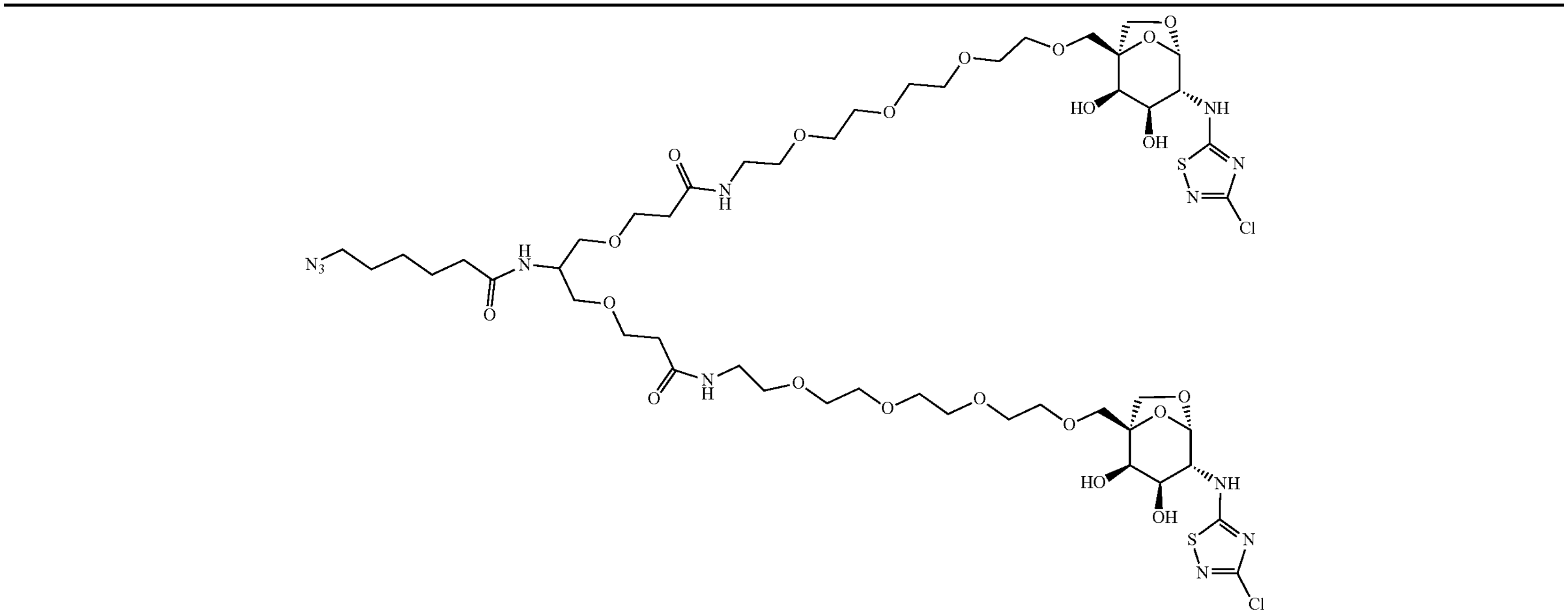 | ++++ |

TABLE 5-continued
| Biological Data for ASGPR Ligands with Linker | | |
|---|---|---|
| Compound ID | Structure | ASGPR_SPR Binding $K_D$ (μM) |
| | 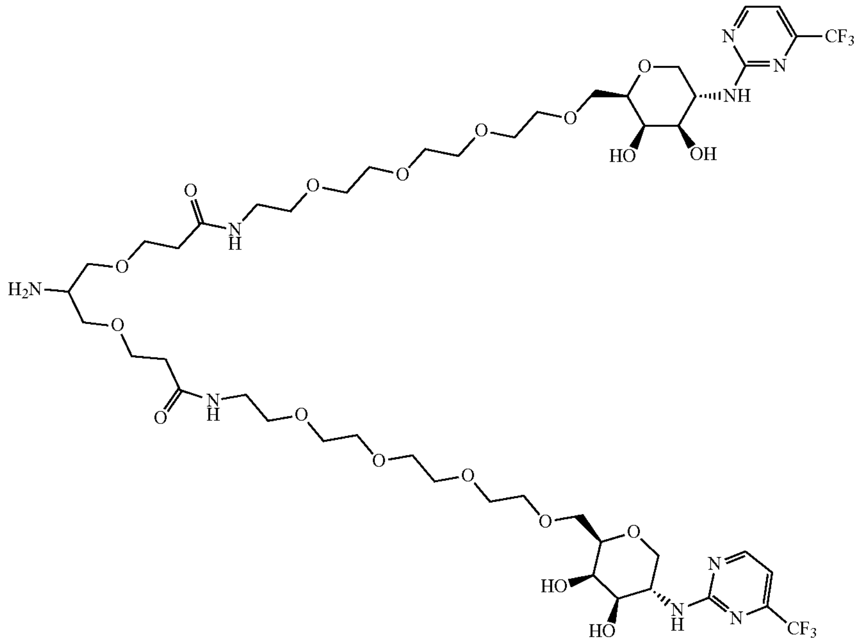 [SMILES: NC(COCCC(=O)NCCOCCOCCOCCOC[C@H]1OC[C@H](Nc2nccc(C(F)(F)F)n2)[C@@H](O)[C@H]1O)COCCC(=O)NCCOCCOCCOCCOC[C@H]1OC[C@H](Nc2nccc(C(F)(F)F)n2)[C@@H](O)[C@H]1O] | |
In the table above KD values that are >= 1000 uM = +, <1000 uM = ++, <500 uM = +++, and <100 uM = ++++

Example 11: Cellular Degradation of an Extracellular Protein by ASGPR-Binding Extracellular Protein Targeting Ligand Degrader Compounds as Described Herein The selected Extracellular Target Protein (typically 80 uM to 1 mM) is added to cell culture media in the presence or absence of the bifunctional degrader as described herein. The assay is performed with human hepatic cell line HepG2 in 96-well plates. HepG2 cells is cultured to 70-80% confluency in RPMI media (ThermoFisher/Gibco). The cells are washed two times with PBS solution and then treated with serum-free media containing human IgA or other target proteins. The bifunctional degrader is then added to the cell culture media with the top concentration of 20 μM in a 2-fold dilution series. The cells are then incubated for 24 h at 37° C. An aliquot of the supernatant is then removed, diluted (10 to 100-fold dilution) and the concentration of the target protein analyzed with a sandwiched ELISA assay using a commercial kit (MyBioSource or equivalent) in a 96-well plate. Dose-dependent depletion of the target protein is analyzed by GraphPad Prism software and the data were fitted to a sigmoidal curve to obtain IC50 values.

Example 12. Cellular Degradation of IgA by Bifunctional Molecules Containing ASGPR and Target Protein-Binding Moieties Human IgA (Sigma) protein (80 uM to 1 mM) was added to the cell culture media in the presence or absence of Compound A below that includes IgA binding peptide OPT-3. The studies were performed with human hepatic cell line HepG2 in 96-well plates. HepG2 cells were cultured to 70-80% confluency in RPMI media (ThermoFisher/Gibco). The cells were washed 2 times with PBS solution and were then treated with serum-free media containing human IgA or other target proteins. The bifunctional compounds were then added to the cell culture media with the top concentration of 20 M in a 2-fold dilution series. The cells were then incubated for 24 h at 37° C. An aliquot of the supernatant was then removed, diluted (10 to 100-fold dilution) and the concentration of the target protein was analyzed by a sandwiched ELISA assay using a commercial kit (MyBioSource or equivalent) in a 96-well plate. Dose-dependent depletion of the target protein was analyzed by GraphPad Prism software and the data were fitted to a sigmoidal curve to obtain IC50 values.

All publications and patent applications cited in this specification are herein incorporated by reference as if each individual publication or patent application were specifically and individually indicated to be incorporated by reference.

Although the foregoing invention has been described in some detail by way of illustration and example for the purpose of clarity of understanding, it will be readily apparent to one of ordinary skill in the art in light of the teaching of this invention that certain changes or modifications may be made thereto without departing from the spirit or scope of the invention as defined in the appended claims. Additionally, those skilled in the art will recognize, or be able to ascertain using no more than routine experimentation, many equivalents to the specific embodiments and methods described herein. Such equivalents are intended to be encompassed by the scope of the present application.

SEQUENCE LISTING

```
Sequence total quantity: 85
SEQ ID NO: 1            moltype = AA  length = 6
FEATURE                 Location/Qualifiers
source                  1..6
                        mol_type = protein
                        organism = synthetic construct
SEQUENCE: 1
MLKKIE                                                          6

SEQ ID NO: 2            moltype = AA  length = 16
FEATURE                 Location/Qualifiers
source                  1..16
                        mol_type = protein
                        organism = synthetic construct
SEQUENCE: 2
HMVCLAYRGR PVCFAL                                               16

SEQ ID NO: 3            moltype = AA  length = 16
FEATURE                 Location/Qualifiers
source                  1..16
                        mol_type = protein
                        organism = synthetic construct
SEQUENCE: 3
HMVCLSYRGR PVCFSL                                               16

SEQ ID NO: 4            moltype = AA  length = 16
FEATURE                 Location/Qualifiers
source                  1..16
                        mol_type = protein
                        organism = synthetic construct
SEQUENCE: 4
HQVCLSYRGR PVCFST                                               16

SEQ ID NO: 5            moltype = AA  length = 16
FEATURE                 Location/Qualifiers
source                  1..16
                        mol_type = protein
```

-continued

```
                         organism = synthetic construct
SEQUENCE: 5
QMRCLSYKGR RVCLWL                                                      16

SEQ ID NO: 6             moltype = AA  length = 16
FEATURE                  Location/Qualifiers
source                   1..16
                         mol_type = protein
                         organism = synthetic construct
SEQUENCE: 6
KRLCLQYKGS KVCFRL                                                      16

SEQ ID NO: 7             moltype = AA  length = 16
FEATURE                  Location/Qualifiers
source                   1..16
                         mol_type = protein
                         organism = synthetic construct
SEQUENCE: 7
RMRCLTYRGR RVCLEL                                                      16

SEQ ID NO: 8             moltype = AA  length = 16
FEATURE                  Location/Qualifiers
source                   1..16
                         mol_type = protein
                         organism = synthetic construct
SEQUENCE: 8
SMRCLQYRGS RVCLTL                                                      16

SEQ ID NO: 9             moltype = AA  length = 16
FEATURE                  Location/Qualifiers
source                   1..16
                         mol_type = protein
                         organism = synthetic construct
SEQUENCE: 9
HLRCLRYKGT RVCFSL                                                      16

SEQ ID NO: 10            moltype = AA  length = 16
FEATURE                  Location/Qualifiers
source                   1..16
                         mol_type = protein
                         organism = synthetic construct
SEQUENCE: 10
HVRCLSYKGR EVCVQL                                                      16

SEQ ID NO: 11            moltype = AA  length = 16
FEATURE                  Location/Qualifiers
source                   1..16
                         mol_type = protein
                         organism = synthetic construct
SEQUENCE: 11
PRMCLFIYKG RRVCIP                                                      16

SEQ ID NO: 12            moltype = AA  length = 16
FEATURE                  Location/Qualifiers
source                   1..16
                         mol_type = protein
                         organism = synthetic construct
SEQUENCE: 12
HMRCLHYKGR RVCFLL                                                      16

SEQ ID NO: 13            moltype = AA  length = 16
FEATURE                  Location/Qualifiers
source                   1..16
                         mol_type = protein
                         organism = synthetic construct
SEQUENCE: 13
HKRCLHYRGR MVCFLI                                                      16

SEQ ID NO: 14            moltype = AA  length = 16
FEATURE                  Location/Qualifiers
source                   1..16
                         mol_type = protein
                         organism = synthetic construct
SEQUENCE: 14
QKRCLKYKGS RVCFFL                                                      16

SEQ ID NO: 15            moltype = AA  length = 16
FEATURE                  Location/Qualifiers
source                   1..16
```

-continued

```
                        mol_type = protein
                        organism = synthetic construct
SEQUENCE: 15
HVRCLRYRGK NVCFLL                                                    16

SEQ ID NO: 16           moltype = AA  length = 16
FEATURE                 Location/Qualifiers
source                  1..16
                        mol_type = protein
                        organism = synthetic construct
SEQUENCE: 16
SDVCLRYRGR PVCFQV                                                    16

SEQ ID NO: 17           moltype = AA  length = 16
FEATURE                 Location/Qualifiers
source                  1..16
                        mol_type = protein
                        organism = synthetic construct
SEQUENCE: 17
RDVCLRYRGR PVCFQV                                                    16

SEQ ID NO: 18           moltype = AA  length = 16
FEATURE                 Location/Qualifiers
source                  1..16
                        mol_type = protein
                        organism = synthetic construct
SEQUENCE: 18
HDVCLRYRGR PVCFQV                                                    16

SEQ ID NO: 19           moltype = AA  length = 16
FEATURE                 Location/Qualifiers
source                  1..16
                        mol_type = protein
                        organism = synthetic construct
SEQUENCE: 19
SMVCLRYRGR PVCFQV                                                    16

SEQ ID NO: 20           moltype = AA  length = 16
FEATURE                 Location/Qualifiers
source                  1..16
                        mol_type = protein
                        organism = synthetic construct
SEQUENCE: 20
SAVCLRYRGR PVCFQV                                                    16

SEQ ID NO: 21           moltype = AA  length = 16
FEATURE                 Location/Qualifiers
source                  1..16
                        mol_type = protein
                        organism = synthetic construct
SEQUENCE: 21
SDVCLNYRGR PVCFQV                                                    16

SEQ ID NO: 22           moltype = AA  length = 16
FEATURE                 Location/Qualifiers
source                  1..16
                        mol_type = protein
                        organism = synthetic construct
SEQUENCE: 22
SDVCLHYRGR PVCFQV                                                    16

SEQ ID NO: 23           moltype = AA  length = 16
FEATURE                 Location/Qualifiers
source                  1..16
                        mol_type = protein
                        organism = synthetic construct
SEQUENCE: 23
SDVCLAYRGR PVCFQV                                                    16

SEQ ID NO: 24           moltype = AA  length = 16
FEATURE                 Location/Qualifiers
source                  1..16
                        mol_type = protein
                        organism = synthetic construct
SEQUENCE: 24
SDVCLRYRGR PVCFAV                                                    16

SEQ ID NO: 25           moltype = AA  length = 16
FEATURE                 Location/Qualifiers
```

-continued

```
source                  1..16
                        mol_type = protein
                        organism = synthetic construct
SEQUENCE: 25
SDVCLRYRGR PVCFQL                                                   16

SEQ ID NO: 26           moltype = AA  length = 16
FEATURE                 Location/Qualifiers
source                  1..16
                        mol_type = protein
                        organism = synthetic construct
SEQUENCE: 26
SDVCLRYRGR PVCFQA                                                   16

SEQ ID NO: 27           moltype = AA  length = 14
FEATURE                 Location/Qualifiers
source                  1..14
                        mol_type = protein
                        organism = synthetic construct
SEQUENCE: 27
HMVCLSYRGR PVCF                                                     14

SEQ ID NO: 28           moltype = AA  length = 15
FEATURE                 Location/Qualifiers
source                  1..15
                        mol_type = protein
                        organism = synthetic construct
SEQUENCE: 28
HMVCLSYRGR PVCFS                                                    15

SEQ ID NO: 29           moltype = AA  length = 16
FEATURE                 Location/Qualifiers
source                  1..16
                        mol_type = protein
                        organism = synthetic construct
SEQUENCE: 29
HQVCLSYRGQ PVCFSL                                                   16

SEQ ID NO: 30           moltype = AA  length = 16
FEATURE                 Location/Qualifiers
source                  1..16
                        mol_type = protein
                        organism = synthetic construct
SEQUENCE: 30
HQVCLSYRGR PTCFSL                                                   16

SEQ ID NO: 31           moltype = AA  length = 16
FEATURE                 Location/Qualifiers
source                  1..16
                        mol_type = protein
                        organism = synthetic construct
SEQUENCE: 31
HQVCLSYRGR PVCYSL                                                   16

SEQ ID NO: 32           moltype = AA  length = 16
FEATURE                 Location/Qualifiers
source                  1..16
                        mol_type = protein
                        organism = synthetic construct
SEQUENCE: 32
HQVCLSYRGQ PVCFST                                                   16

SEQ ID NO: 33           moltype = AA  length = 16
FEATURE                 Location/Qualifiers
source                  1..16
                        mol_type = protein
                        organism = synthetic construct
SEQUENCE: 33
HQVCLSYRGR PTCFST                                                   16

SEQ ID NO: 34           moltype = AA  length = 16
FEATURE                 Location/Qualifiers
source                  1..16
                        mol_type = protein
                        organism = synthetic construct
SEQUENCE: 34
HQVCLSYRGQ PTCFST                                                   16

SEQ ID NO: 35           moltype = AA  length = 16
```

-continued

```
FEATURE                Location/Qualifiers
source                 1..16
                       mol_type = protein
                       organism = synthetic construct
SEQUENCE: 35
RTYRTYRTYR TYKKKG                                                   16

SEQ ID NO: 36          moltype = AA  length = 16
FEATURE                Location/Qualifiers
source                 1..16
                       mol_type = protein
                       organism = synthetic construct
SITE                   1..16
                       note = D-Amino Acids
SEQUENCE: 36
RTYRTYRTYR TYKKKG                                                   16

SEQ ID NO: 37          moltype = AA  length = 16
FEATURE                Location/Qualifiers
source                 1..16
                       mol_type = protein
                       organism = synthetic construct
REGION                 1..16
                       note = D-Amino Acids
MOD_RES                1
                       note = Phenylacetic acid
MOD_RES                4
                       note = Phenylacetic acid
MOD_RES                7
                       note = Phenylacetic acid
MOD_RES                10
                       note = Phenylacetic acid
SEQUENCE: 37
RTYRTYRTYR TYKKKG                                                   16

SEQ ID NO: 38          moltype = AA  length = 9
FEATURE                Location/Qualifiers
source                 1..9
                       mol_type = protein
                       organism = synthetic construct
SEQUENCE: 38
TWKTSRISF                                                           9

SEQ ID NO: 39          moltype = AA  length = 10
FEATURE                Location/Qualifiers
source                 1..10
                       mol_type = protein
                       organism = synthetic construct
SEQUENCE: 39
FGRLVSSIRY                                                          10

SEQ ID NO: 40          moltype = AA  length = 13
FEATURE                Location/Qualifiers
source                 1..13
                       mol_type = protein
                       organism = synthetic construct
SEQUENCE: 40
DCAWHLGELV WCT                                                      13

SEQ ID NO: 41          moltype = AA  length = 12
FEATURE                Location/Qualifiers
source                 1..12
                       mol_type = protein
                       organism = synthetic construct
SEQUENCE: 41
DSAWHLGELW ST                                                       12

SEQ ID NO: 42          moltype = AA  length = 13
FEATURE                Location/Qualifiers
source                 1..13
                       mol_type = protein
                       organism = synthetic construct
SEQUENCE: 42
DCHKRSFWAD NCT                                                      13

SEQ ID NO: 43          moltype = AA  length = 13
FEATURE                Location/Qualifiers
source                 1..13
                       mol_type = protein
```

```
                        organism = synthetic construct
SEQUENCE: 43
DCRTQFRPNQ TCT                                                      13

SEQ ID NO: 44           moltype = AA  length = 13
FEATURE                 Location/Qualifiers
source                  1..13
                        mol_type = protein
                        organism = synthetic construct
SEQUENCE: 44
DCQLCDFWRT RCT                                                      13

SEQ ID NO: 45           moltype = AA  length = 13
FEATURE                 Location/Qualifiers
source                  1..13
                        mol_type = protein
                        organism = synthetic construct
SEQUENCE: 45
DCFEDFNEQR TCT                                                      13

SEQ ID NO: 46           moltype = AA  length = 13
FEATURE                 Location/Qualifiers
source                  1..13
                        mol_type = protein
                        organism = synthetic construct
SEQUENCE: 46
DCLAKFLKGK DCT                                                      13

SEQ ID NO: 47           moltype = AA  length = 13
FEATURE                 Location/Qualifiers
source                  1..13
                        mol_type = protein
                        organism = synthetic construct
SEQUENCE: 47
DCWHRRTHKT FCT                                                      13

SEQ ID NO: 48           moltype = AA  length = 11
FEATURE                 Location/Qualifiers
source                  1..11
                        mol_type = protein
                        organism = synthetic construct
SEQUENCE: 48
DCRTIQTRSC T                                                        11

SEQ ID NO: 49           moltype = AA  length = 13
FEATURE                 Location/Qualifiers
source                  1..13
                        mol_type = protein
                        organism = synthetic construct
SEQUENCE: 49
DCIKLAQLHS VCT                                                      13

SEQ ID NO: 50           moltype = AA  length = 13
FEATURE                 Location/Qualifiers
source                  1..13
                        mol_type = protein
                        organism = synthetic construct
SEQUENCE: 50
DCWRHRNATE WCT                                                      13

SEQ ID NO: 51           moltype = AA  length = 13
FEATURE                 Location/Qualifiers
source                  1..13
                        mol_type = protein
                        organism = synthetic construct
SEQUENCE: 51
DCQNWIKDVH KCT                                                      13

SEQ ID NO: 52           moltype = AA  length = 13
FEATURE                 Location/Qualifiers
source                  1..13
                        mol_type = protein
                        organism = synthetic construct
SEQUENCE: 52
DCAWHLGELV WCT                                                      13

SEQ ID NO: 53           moltype = AA  length = 13
FEATURE                 Location/Qualifiers
source                  1..13
```

```
                        mol_type = protein
                        organism = synthetic construct
SEQUENCE: 53
DCAFHLGELV WCT                                                   13

SEQ ID NO: 54           moltype = AA  length = 13
FEATURE                 Location/Qualifiers
source                  1..13
                        mol_type = protein
                        organism = synthetic construct
SEQUENCE: 54
DCAYHLGELV WCT                                                   13

SEQ ID NO: 55           moltype = AA  length = 11
FEATURE                 Location/Qualifiers
source                  1..11
                        mol_type = protein
                        organism = synthetic construct
MOD_RES                 11
                        note = D-Amino Acid
SEQUENCE: 55
PAWHLGELVW P                                                     11

SEQ ID NO: 56           moltype = AA  length = 15
FEATURE                 Location/Qualifiers
source                  1..15
                        mol_type = protein
                        organism = synthetic construct
MOD_RES                 15
                        note = D-Amino Acid
SEQUENCE: 56
PDCAWHLGEL VWCTP                                                 15

SEQ ID NO: 57           moltype = AA  length = 15
FEATURE                 Location/Qualifiers
source                  1..15
                        mol_type = protein
                        organism = synthetic construct
SEQUENCE: 57
CDCAWHLGEL VWCTC                                                 15

SEQ ID NO: 58           moltype = AA  length = 12
FEATURE                 Location/Qualifiers
source                  1..12
                        mol_type = protein
                        organism = synthetic construct
SEQUENCE: 58
EPIHRSTLTA LL                                                    12

SEQ ID NO: 59           moltype = AA  length = 4
FEATURE                 Location/Qualifiers
source                  1..4
                        mol_type = protein
                        organism = synthetic construct
SEQUENCE: 59
APAR                                                             4

SEQ ID NO: 60           moltype = AA  length = 10
FEATURE                 Location/Qualifiers
source                  1..10
                        mol_type = protein
                        organism = synthetic construct
SEQUENCE: 60
CFHHCFHHKG                                                       10

SEQ ID NO: 61           moltype = AA  length = 6
FEATURE                 Location/Qualifiers
source                  1..6
                        mol_type = protein
                        organism = synthetic construct
SEQUENCE: 61
HWRGWV                                                           6

SEQ ID NO: 62           moltype = AA  length = 6
FEATURE                 Location/Qualifiers
source                  1..6
                        mol_type = protein
                        organism = synthetic construct
SEQUENCE: 62
```

-continued

```
HYFKFD                                                            6

SEQ ID NO: 63          moltype = AA  length = 6
FEATURE                Location/Qualifiers
source                 1..6
                       mol_type = protein
                       organism = synthetic construct
SEQUENCE: 63
HFRRHL                                                            6

SEQ ID NO: 64          moltype = AA  length = 6
FEATURE                Location/Qualifiers
source                 1..6
                       mol_type = protein
                       organism = synthetic construct
SITE                   3
                       note = Citrulline
SEQUENCE: 64
HWXGWV                                                            6

SEQ ID NO: 65          moltype = AA  length = 6
FEATURE                Location/Qualifiers
source                 1..6
                       mol_type = protein
                       organism = synthetic construct
MOD_RES                3
                       note = Citrulline
MOD_RES                2
                       note = METHYLATION
MOD_RES                5
                       note = METHYLATION
SEQUENCE: 65
HWXGWV                                                            6

SEQ ID NO: 66          moltype = AA  length = 5
FEATURE                Location/Qualifiers
source                 1..5
                       mol_type = protein
                       organism = synthetic construct
SEQUENCE: 66
DDAAG                                                             5

SEQ ID NO: 67          moltype = AA  length = 4
FEATURE                Location/Qualifiers
source                 1..4
                       mol_type = protein
                       organism = synthetic construct
SEQUENCE: 67
DAAG                                                              4

SEQ ID NO: 68          moltype = AA  length = 9
FEATURE                Location/Qualifiers
source                 1..9
                       mol_type = protein
                       organism = synthetic construct
CROSSLNK               1..9
                       note = N(alpha)acetyl Linker (Ser-Glu)
CROSSLNK               8..9
                       note = Lactic acid Linker (Lys-Glu)
SEQUENCE: 68
SARWHYFKE                                                         9

SEQ ID NO: 69          moltype = AA  length = 9
FEATURE                Location/Qualifiers
source                 1..9
                       mol_type = protein
                       organism = synthetic construct
MOD_RES                1
                       note = Dpr
CROSSLNK               1..9
                       note = N(alpha)acetyl Linker (Dpr-Glu)
CROSSLNK               8..9
                       note = Lactic acid Linker (Lys-Glu)
SEQUENCE: 69
XARWHYFKE                                                         9

SEQ ID NO: 70          moltype = AA  length = 7
FEATURE                Location/Qualifiers
source                 1..7
```

```
                        mol_type = protein
                        organism = synthetic construct
SEQUENCE: 70
MWFRHYK                                                     7

SEQ ID NO: 71           moltype = AA  length = 8
FEATURE                 Location/Qualifiers
source                  1..8
                        mol_type = protein
                        organism = synthetic construct
SEQUENCE: 71
NKFRGKYK                                                    8

SEQ ID NO: 72           moltype = AA  length = 8
FEATURE                 Location/Qualifiers
source                  1..8
                        mol_type = protein
                        organism = synthetic construct
SEQUENCE: 72
NARKFYKG                                                    8

SEQ ID NO: 73           moltype = AA  length = 8
FEATURE                 Location/Qualifiers
source                  1..8
                        mol_type = protein
                        organism = synthetic construct
SEQUENCE: 73
FYWHCLDE                                                    8

SEQ ID NO: 74           moltype = AA  length = 8
FEATURE                 Location/Qualifiers
source                  1..8
                        mol_type = protein
                        organism = synthetic construct
SEQUENCE: 74
FYCHWALE                                                    8

SEQ ID NO: 75           moltype = AA  length = 8
FEATURE                 Location/Qualifiers
source                  1..8
                        mol_type = protein
                        organism = synthetic construct
SEQUENCE: 75
FYCHTIDE                                                    8

SEQ ID NO: 76           moltype = AA  length = 16
FEATURE                 Location/Qualifiers
source                  1..16
                        mol_type = protein
                        organism = synthetic construct
SEQUENCE: 76
FYWHCLDEFY CHTIDE                                           16

SEQ ID NO: 77           moltype = AA  length = 4
FEATURE                 Location/Qualifiers
source                  1..4
                        mol_type = protein
                        organism = synthetic construct
SEQUENCE: 77
RRGW                                                        4

SEQ ID NO: 78           moltype = AA  length = 7
FEATURE                 Location/Qualifiers
source                  1..7
                        mol_type = protein
                        organism = synthetic construct
SEQUENCE: 78
KHRFNKD                                                     7

SEQ ID NO: 79           moltype = AA  length = 7
FEATURE                 Location/Qualifiers
source                  1..7
                        mol_type = protein
                        organism = synthetic construct
SEQUENCE: 79
CPSTHWK                                                     7

SEQ ID NO: 80           moltype = AA  length = 7
FEATURE                 Location/Qualifiers
```

-continued

```
source              1..7
                    mol_type = protein
                    organism = synthetic construct
SEQUENCE: 80
NVQYFAV                                                              7

SEQ ID NO: 81       moltype = AA  length = 7
FEATURE             Location/Qualifiers
source              1..7
                    mol_type = protein
                    organism = synthetic construct
SEQUENCE: 81
ASHTQKS                                                              7

SEQ ID NO: 82       moltype = AA  length = 7
FEATURE             Location/Qualifiers
source              1..7
                    mol_type = protein
                    organism = synthetic construct
SEQUENCE: 82
QPQMSHM                                                              7

SEQ ID NO: 83       moltype = AA  length = 7
FEATURE             Location/Qualifiers
source              1..7
                    mol_type = protein
                    organism = synthetic construct
SEQUENCE: 83
TNIESLK                                                              7

SEQ ID NO: 84       moltype = AA  length = 7
FEATURE             Location/Qualifiers
source              1..7
                    mol_type = protein
                    organism = synthetic construct
SEQUENCE: 84
NCHKCWN                                                              7

SEQ ID NO: 85       moltype = AA  length = 7
FEATURE             Location/Qualifiers
source              1..7
                    mol_type = protein
                    organism = synthetic construct
SEQUENCE: 85
SHLSKNF                                                              7
```

We claim:

1. A compound of formula:

(I)

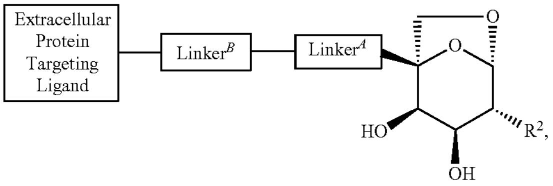

(V)

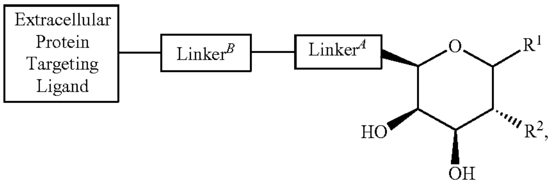

-continued (I-Bi)

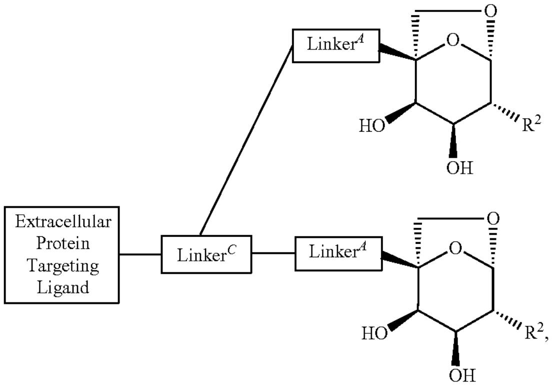

-continued (V-Bi)

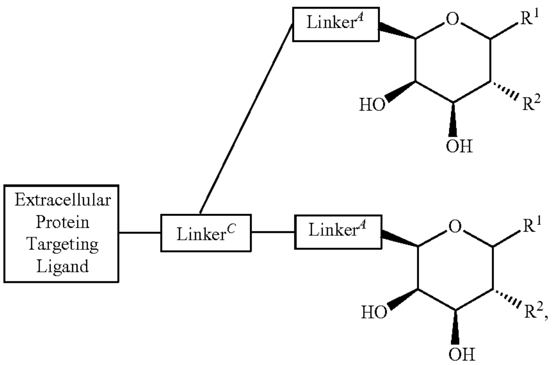

(I-Tri)

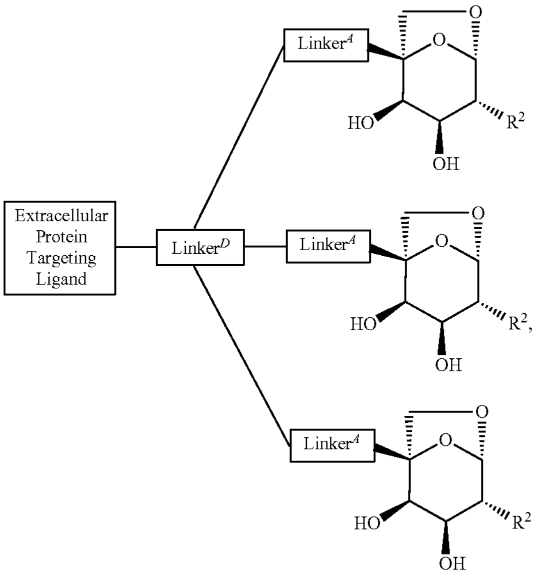

or (V-Tri)

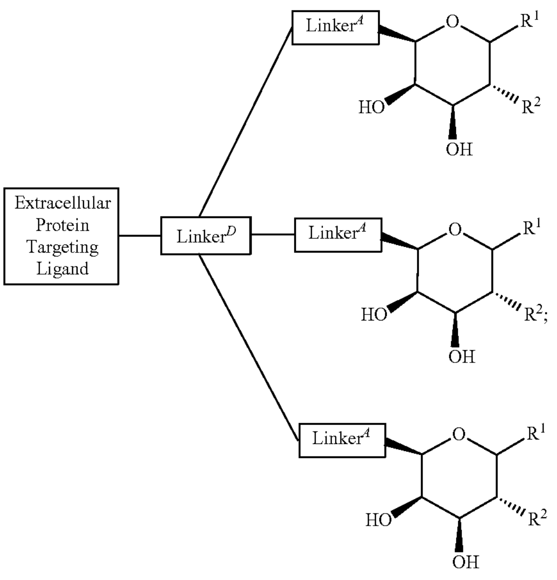

or a pharmaceutically acceptable salt thereof;

wherein:

$R^1$ is selected from the group consisting of hydrogen, alkyl, alkenyl, and haloalkyl;

$R^2$ is selected from the group consisting of —$NR^6$-heteroaryl and —$NR^6$-aryl, each of which $R^2$ is optionally substituted with 1, 2, 3, or 4 substituents independently selected from the group consisting of alkyl, alkenyl, haloalkyl, —$OR^6$, F, Cl, Br, I, —$NR^6R^7$, cyano, nitro, and C(O) $R^3$;

$R^3$ at each occurrence is independently selected from the group consisting of hydrogen, alkyl, haloalkyl, arylalkyl, alkenyl, aryl, heteroaryl, heterocycle, —$OR^8$, and —$NR^8R^9$; $R^6$ and $R^7$ are independently selected at each occurrence from the group consisting of hydrogen, alkyl, arylalkyl, alkenyl, aryl, haloalkyl, heteroaryl, heterocycle, and C(O) $R^3$;

$R^8$ and $R^{10}$ are independently selected at each occurrence from the group consisting of hydrogen, alkyl, arylalkyl, alkenyl, aryl, heteroaryl, and heterocycle;

Linker$^A$ is bond;

Linker$^B$ is

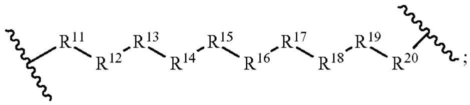

;

$R^{11}$, $R^{12}$, $R^{13}$, $R^{14}$, $R^{15}$, $R^{16}$, $R^{17}$, $R^{18}$, $R^{19}$, and $R^{20}$ are independently at each occurrence selected from the group consisting of a bond, alkyl, —C(O)—, —C(O)O—, —OC(O)—, —$SO_2$—, —S(O)—, —C(S)—, —C(O)$NR^6$—, —$NR^6$C(O)—, —O—, —S—, —$NR^6$—, —C($R^{21}R^{21}$)—, —P(O)($R^3$)O—, —P(O)($R^3$)—, alkenyl, alkynyl, haloalkyl, alkoxy, aryl, heterocycle, heteroaryl, —$CH_2CH_2$—[O—$(CH_2)_2]_n$—O—, —$CH_2CH_2$—[O—$(CH_2)_2]_n$—$NR^6$—, —$CH_2CH_2$—[O—$(CH_2)_2]_n$—, —[—$(CH_2)_2$—O-$]_n$—, —[O—$(CH_2)_2]_n$—, —[O—$CH(CH_3)C(O)]_n$—, —[C(O)—$CH(CH_3)$—$O]_n$—, —[O—$CH_2C(O)]_n$—, and —[C(O)—$CH_2$—$O]_n$—, each of which is optionally substituted with 1, 2, 3, or 4 substituents independently selected from $R^{21}$;

n is independently selected at each instance from 0, 1, 2, 3, 4, 5, 6, 7, 8, 9, or 10;

$R^{21}$ is independently at each occurrence selected from the group consisting of hydrogen, alkyl, alkenyl, F, Cl, Br, I, hydroxyl, alkoxy, azide, amino, cyano, —$NR^6R^7$, —$NR^8SO_2R^3$, —$NR^8$S (O) $R^3$, haloalkyl, aryl, heteroaryl, and heterocycle;

Linker$^C$ is selected from:

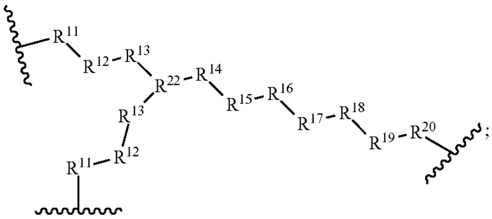

;

$R^{22}$ is selected from the group consisting of alkyl, —C(O)N—, —NC(O)—, —N—, —C($R^{21}$)—, —P(O)—, alkenyl, haloalkyl, aryl, heterocycle, and heteroaryl, each of which is optionally substituted with 1, 2, 3, or 4 substituents independently selected from $R^{21}$;

$Linker^D$ is selected from:

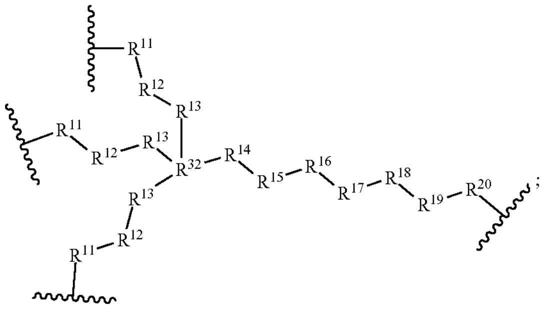

;

$R^{32}$ is selected from the group consisting of alkyl, $N^+X^-$, —C—, alkenyl, haloalkyl, aryl, heterocycle, and heteroaryl, each of which is optionally substituted with 1, 2, 3, or 4 substituents independently selected from $R^{21}$;

$X^-$ is an anionic group; and

Extracellular Protein Targeting Ligand is an IgE Targeting Ligand that binds IgE.

2. The compound of claim 1, wherein $R^2$ is —$NR^6$-heteroaryl optionally substituted with 1, 2, or 3 substituents independently selected from the group consisting of alkyl, alkenyl, haloalkyl, —$OR^6$, F, Cl, Br, —$NR^6R^7$, cyano, nitro, and C(O) $R^3$.

3. The compound of claim 2, wherein $R^6$ is hydrogen.

4. The compound of claim 3, wherein $R^1$ is hydrogen.

5. The compound of claim 1, wherein $R^2$ is —$NR^6$-heteroaryl substituted with 1 or 2 substituents independently selected from the group consisting of alkyl, haloalkyl, —$OR^6$, halogen, and —$NR^6R^7$.

6. The compound of claim 5, wherein $R^6$ is hydrogen.

7. The compound of claim 6, wherein the heteroaryl which is substituted with 1 or 2 substituents is selected from the group consisting of

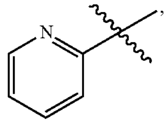
,
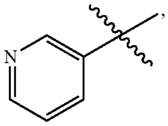
,
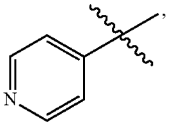
,
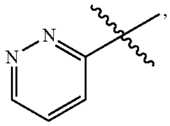
,
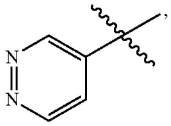
,
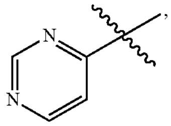
,
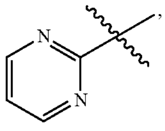
,
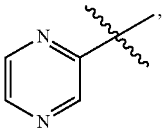
, and
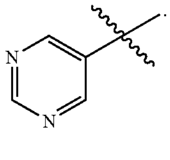
.

8. The compound of claim 7, wherein the 1 or 2 substituents are independently selected from the group consisting of haloalkyl and halogen.

9. The compound of claim 8, wherein haloalkyl is trifluoromethyl.

10. The compound of claim 8, wherein halogen is F.

11. The compound of claim 6, wherein heteroaryl which is substituted with 1 or 2 substituents is selected from the group consisting of

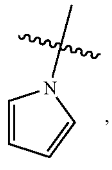
,
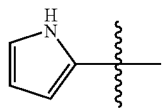
,
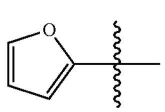
,
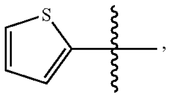
,
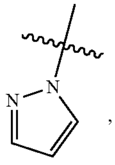
,
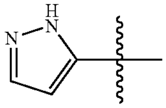
,
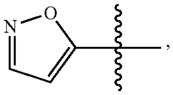
,
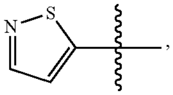
,
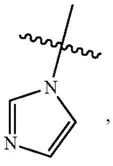
,
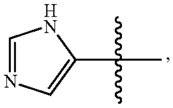
,
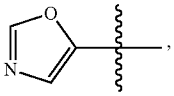
,
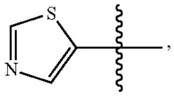
,
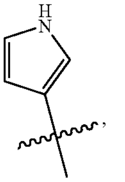
,
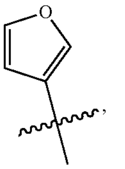
,
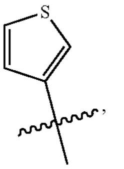
,
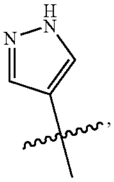
,
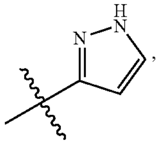
,
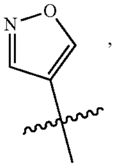
,
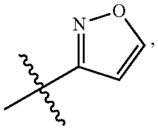
,
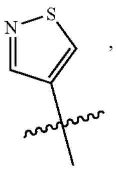
,
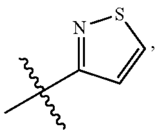
,
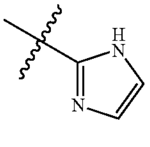
,
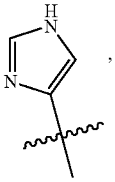
,
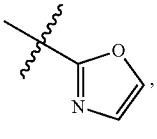
,
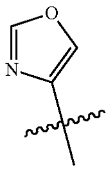
, -continued

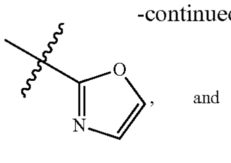

and

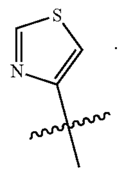

12. The compound of claim 11, wherein the 1 or 2 substituents are independently selected from the group consisting of haloalkyl and halogen.

13. The compound of claim 1, wherein $R^2$ is —$NR^6$-aryl.

14. The compound of claim 1 of Formula:

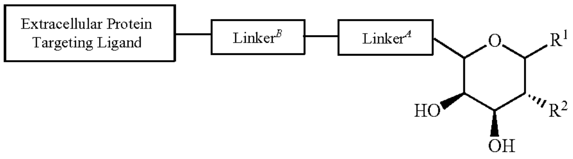

or a pharmaceutically acceptable salt thereof.

15. The compound of claim 14, wherein $R^2$ is —$NR^6$-(6-membered heteroaryl) optionally substituted with 1, 2, or 3 substituents independently selected from the group consisting of alkyl, alkenyl, haloalkyl, —$OR^6$, F, Cl, Br, —$NR^6R^7$, cyano, nitro, and C(O) $R^3$.

16. The compound of claim 15, wherein Linker$^B$ is selected from the group consisting of

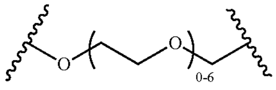

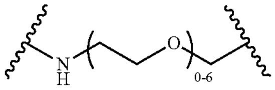

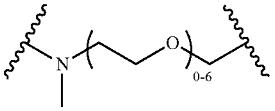

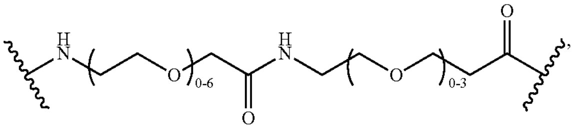

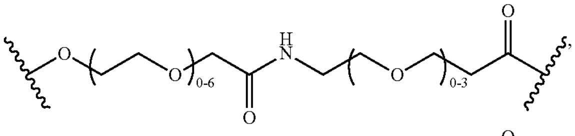

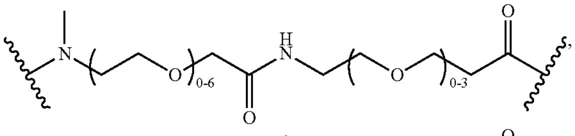

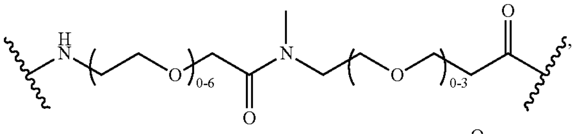

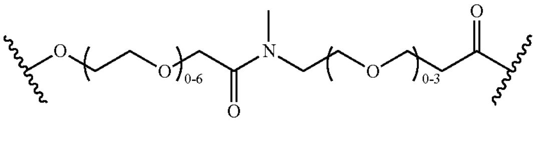

and

-continued

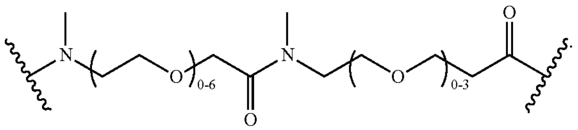

17. The compound of claim 15, wherein Linker$^B$ is selected from the group consisting of

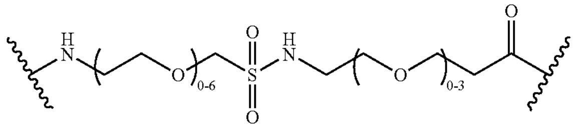

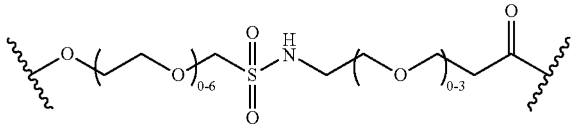

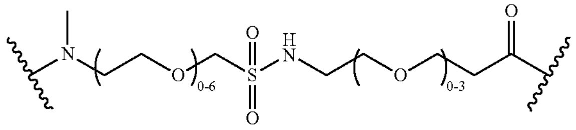

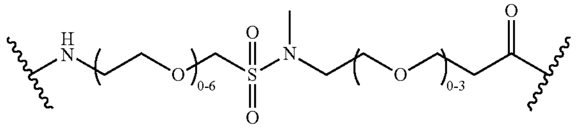

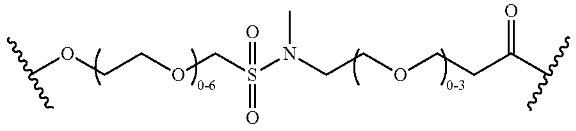

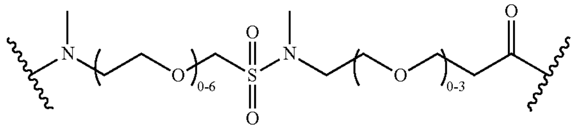

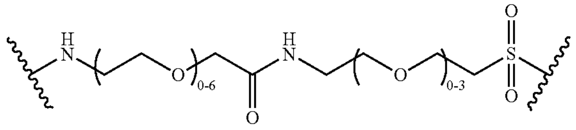

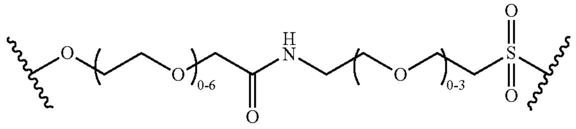

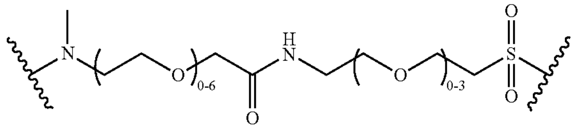

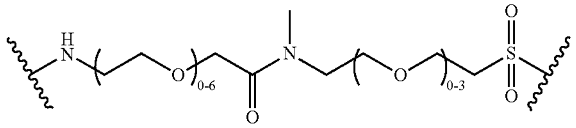

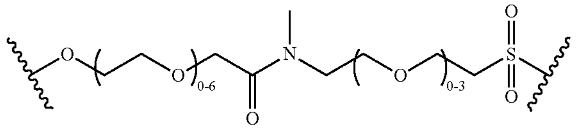

-continued

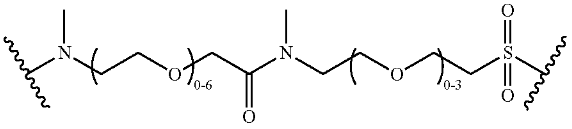

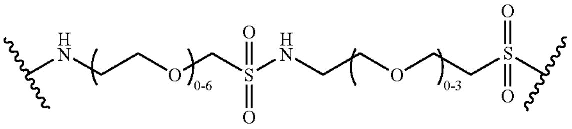

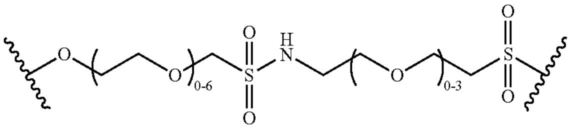

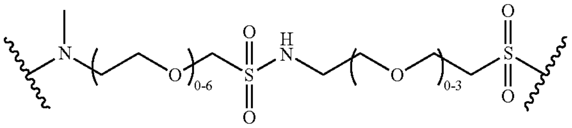

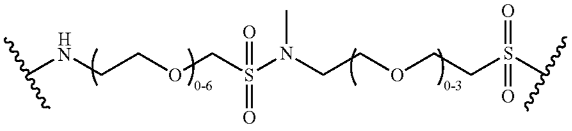

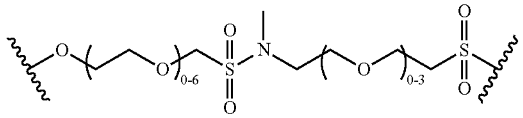

and

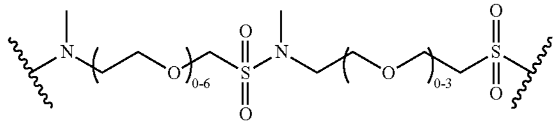

.

18. The compound of claim 1 of Formula:

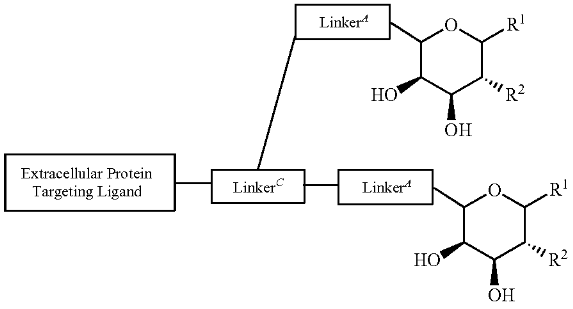

or a pharmaceutically acceptable salt thereof.

19. The compound of claim 18, wherein $R^2$ is —$NR^6$-(6-membered heteroaryl) optionally substituted with 1, 2, or 3 substituents independently selected from the group consisting of alkyl, alkenyl, haloalkyl, —$OR^6$, F, Cl, Br, I, —$NR^6R^7$, cyano, nitro, and C(O) $R^3$.

20. The compound of claim 18, wherein $Linker^C$ is selected from the group consisting of:

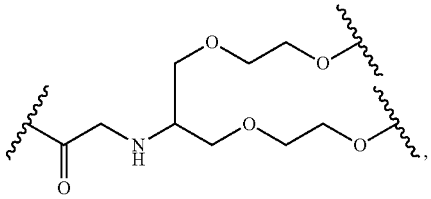

,

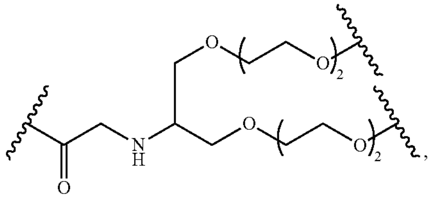

,

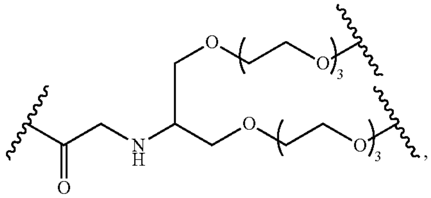

,

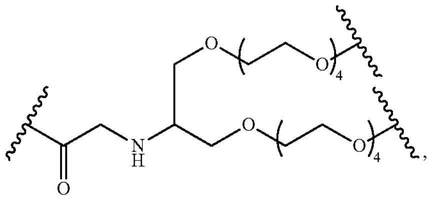

, and

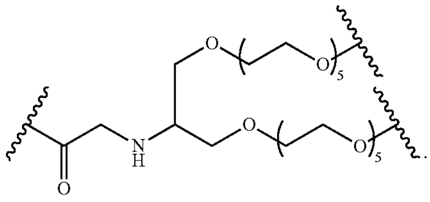

.

21. The compound of claim 18, wherein $Linker^C$ is selected from the group consisting of:

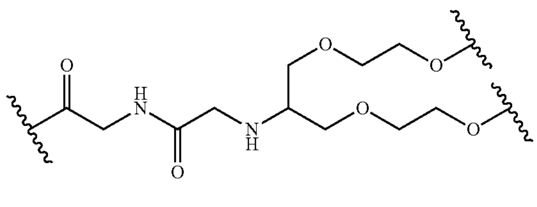

,

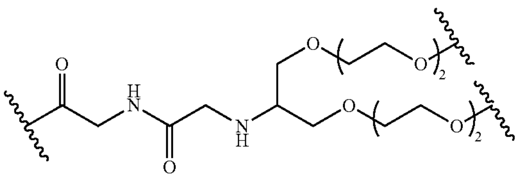

, and

-continued

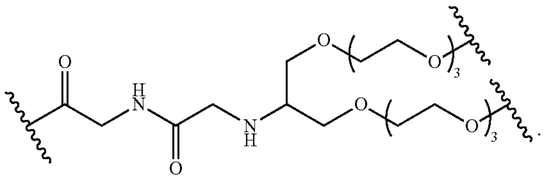

22. The compound of claim 1 of Formula:

(I-Tri)

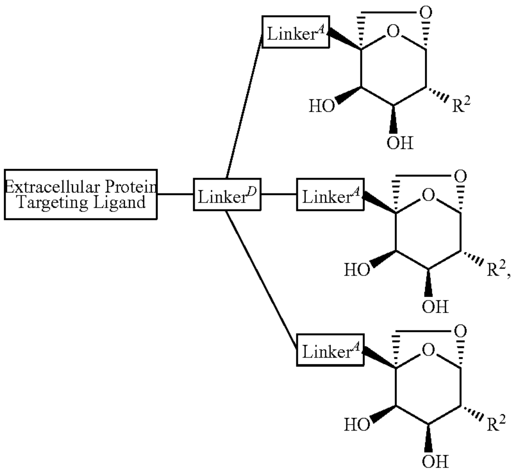

or

-continued (V-Tri)

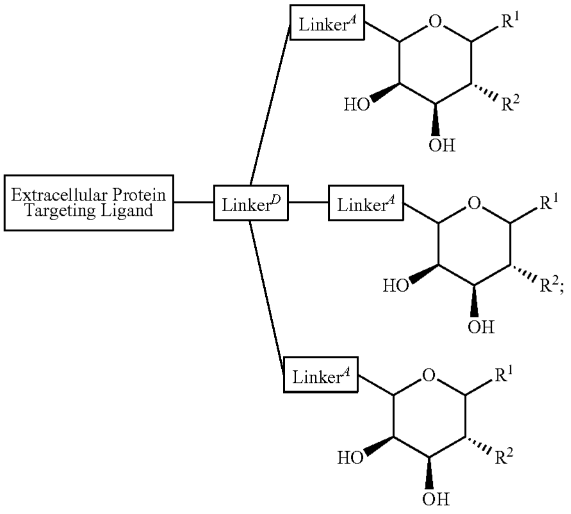

or a pharmaceutically acceptable salt thereof.

23. The compound of claim 1, wherein the Extracellular Protein Targeting Ligand is a peptide.

24. The compound of claim 1, wherein the Extracellular Protein Targeting Ligand is an antibody.

25. The compound of claim 1, wherein the Extracellular Protein Targeting Ligand is

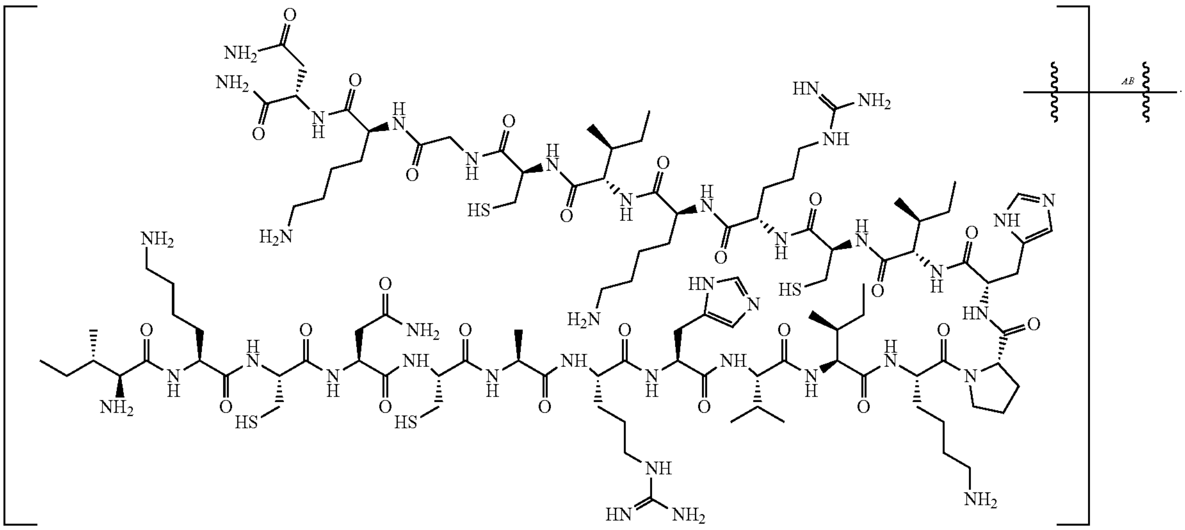

26. The compound of claim 1, wherein the Extracellular Protein Targeting Ligand is

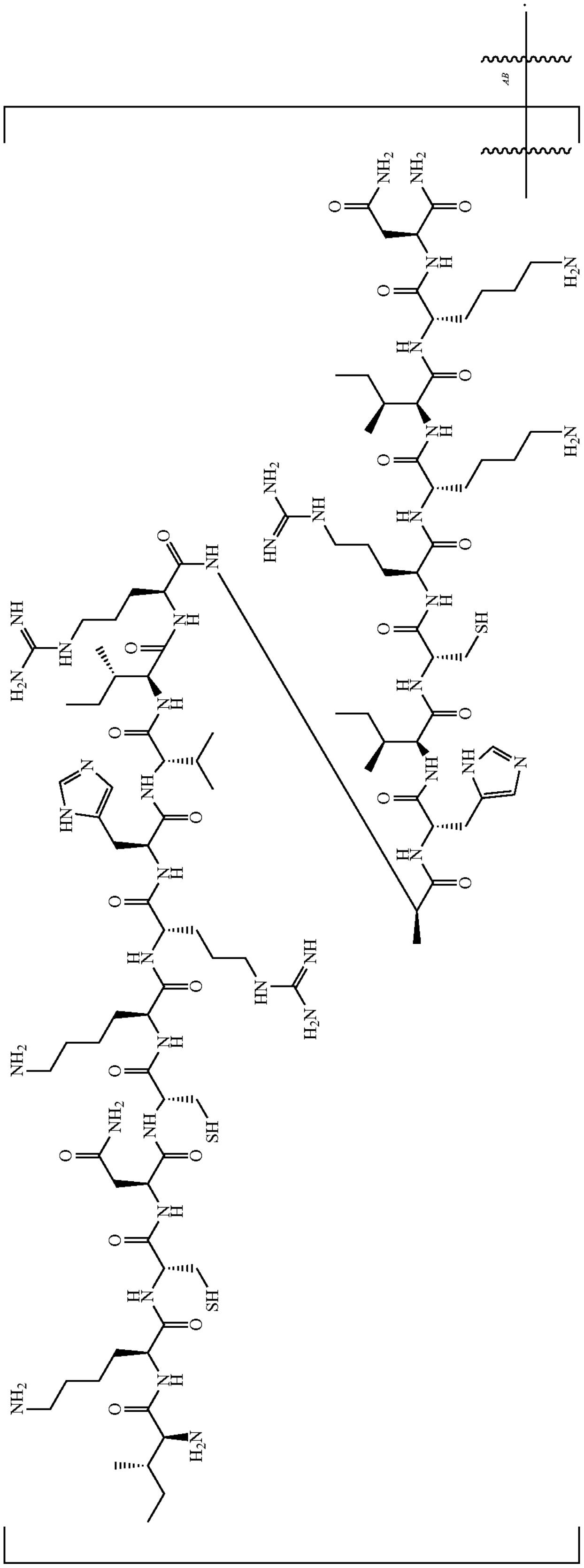

27. The compound of claim 1, wherein the Extracellular Protein Targeting Ligand is
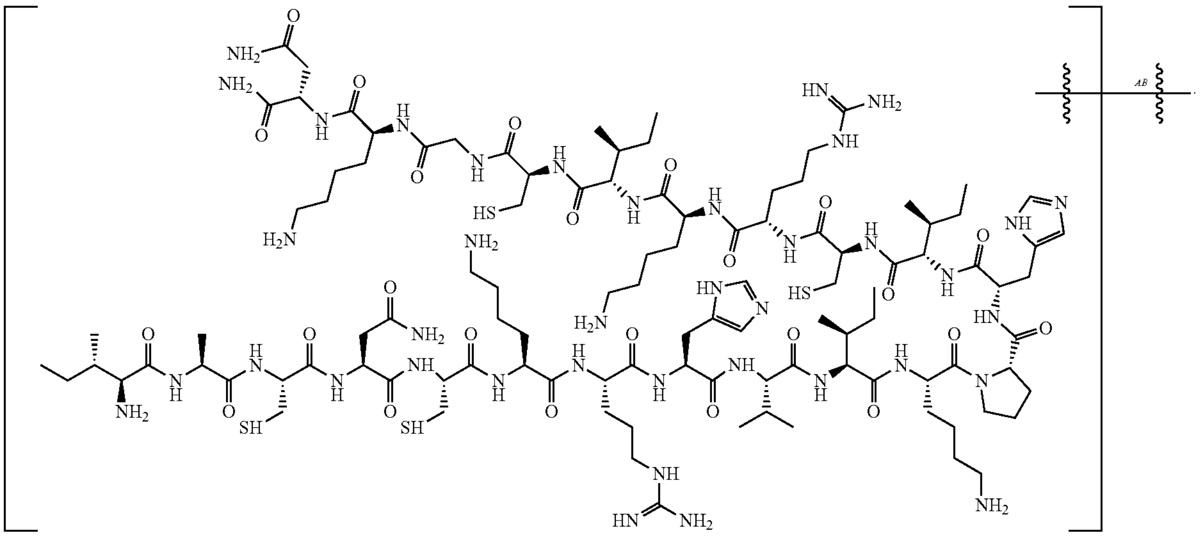
28. The compound of claim 1, wherein the Extracellular Protein Targeting Ligand is

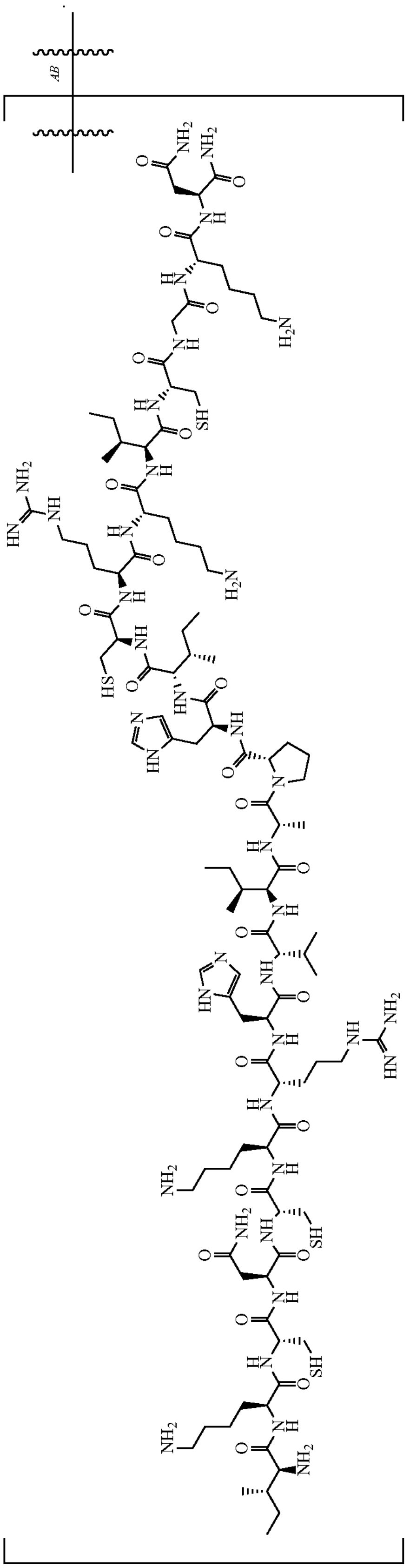

29. The compound of claim 1, wherein the Extracellular Protein Targeting Ligand is
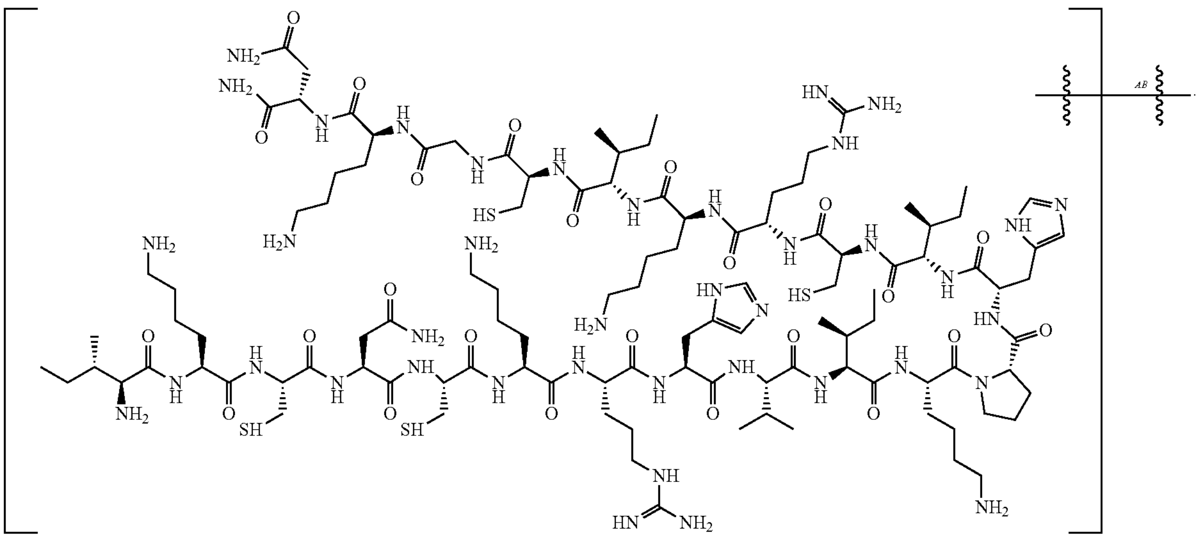
30. The compound of claim 1, wherein the Extracellular Protein Targeting Ligand is
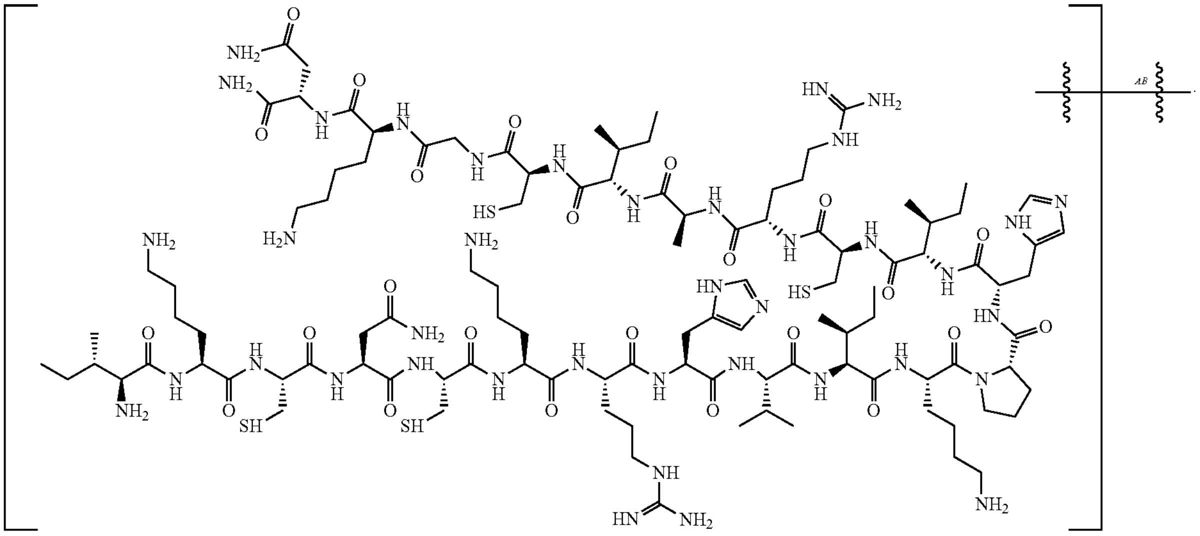
* * * * *